US012134625B2

(12) United States Patent
Mittapalli et al.

(10) Patent No.: US 12,134,625 B2
(45) Date of Patent: Nov. 5, 2024

(54) PYRROLO[2,1-F][1,2,4]TRIAZINES AND PREPARATION AND USES THEREOF

(71) Applicant: BioSplice Therapeutics, Inc., San Diego, CA (US)

(72) Inventors: Gopi Kumar Mittapalli, San Diego, CA (US); Sunil Kumar K C, San Diego, CA (US); Chi Ching Mak, San Diego, CA (US); Brian Joseph Hofilena, San Diego, CA (US); Lewis Daniel Turner, San Diego, CA (US); Brian Walter Eastman, San Diego, CA (US); Ramkrishna Reddy Vakiti, San Diego, CA (US); Joseph Timothy Marakovits, Encinitas, CA (US)

(73) Assignee: BioSplice Therapeutics, Inc., San Diego, CA (US)

( * ) Notice: Subject to any disclaimer, the term of this patent is extended or adjusted under 35 U.S.C. 154(b) by 0 days.

(21) Appl. No.: 17/964,489

(22) Filed: Oct. 12, 2022

(65) Prior Publication Data

US 2023/0312605 A1 Oct. 5, 2023

Related U.S. Application Data

(60) Provisional application No. 63/347,757, filed on Jun. 1, 2022, provisional application No. 63/254,733, filed on Oct. 12, 2021.

(51) Int. Cl.
*C07D 519/00* (2006.01)
*C07D 487/04* (2006.01)

(52) U.S. Cl.
CPC ......... *C07D 519/00* (2013.01); *C07D 487/04* (2013.01); *C07B 2200/05* (2013.01)

(58) Field of Classification Search
CPC ............................ C07D 487/04; C07D 519/00
See application file for complete search history.

(56) References Cited

U.S. PATENT DOCUMENTS

| | | | |
|---|---|---|---|
| 4,164,559 | A | 8/1979 | Miyata et al. |
| 4,474,752 | A | 10/1984 | Haslam et al. |
| 6,120,484 | A | 9/2000 | Silverstein |
| 6,377,849 | B1 | 4/2002 | Lenarz et al. |
| 6,440,102 | B1 | 8/2002 | Arenberg |
| 6,648,873 | B2 | 11/2003 | Arenberg |
| 6,911,211 | B2 | 6/2005 | Eini et al. |
| 2006/0264897 | A1 | 11/2006 | Lobl et al. |
| 2016/0008365 | A1 | 1/2016 | Zhu et al. |
| 2018/0273538 | A1 | 9/2018 | Fiumana et al. |
| 2020/0039989 | A1 | 2/2020 | Hulme et al. |
| 2022/0062240 | A1 | 3/2022 | Tam et al. |
| 2023/0000842 | A1 | 1/2023 | Deshmukh et al. |
| 2023/0167133 | A1 | 6/2023 | Mittapalli et al. |
| 2023/0192686 | A1 | 6/2023 | Mittapalli et al. |
| 2024/0002391 | A1 | 1/2024 | Mittapalli et al. |

FOREIGN PATENT DOCUMENTS

| | | | |
|---|---|---|---|
| WO | WO 1987/005297 A1 | | 9/1987 |
| WO | WO 2005/095400 | | 10/2005 |
| WO | WO 2010/003133 | | 1/2010 |
| WO | WO 2011/018894 | | 2/2011 |
| WO | WO 2014/093383 | | 6/2014 |
| WO | WO 2014/100620 | | 6/2014 |
| WO | WO 2017/040993 | | 3/2017 |
| WO | WO2019/074962 A1 | * | 4/2019 |
| WO | WO 2019/169306 | | 9/2019 |
| WO | WO 2020/006115 | | 1/2020 |
| WO | WO 2020/081689 | | 4/2020 |
| WO | WO 2020/150552 | | 7/2020 |
| WO | WO2021/257863 A1 | * | 12/2021 |
| WO | WO 2022/020342 | | 1/2022 |
| WO | WO 2023/064361 A1 | | 4/2023 |

OTHER PUBLICATIONS

Abbassi et al., "DYRK1A in neurodegeneration and cancer: Molecular basis and clinical implications," Pharmacology & Therapeutics, Jul. 1, 2015, 151: 87-98.
Ackeifi et al., "GLP-1 receptor agonists synergize with DYRK1A inhibitors to potentiate functional human β cell regeneration," Science Translational Medicine, Feb. 12, 2020, 12(530): 13 pages.
Ackeifi et al., "Pharmacologic and genetic approaches define human pancreatic β cell mitogenic targets of DYRK1A inhibitors," JCI Insight, Jan. 1, 2020, 5(1): 17 pages.
Arbones et al., "DYRK1A and cognition: A lifelong relationship," Pharmacology & Therapeutics, Feb. 1, 2019, 194: 78 pages.
Bai et al., "The USP22 promotes the growth of cancer cells through the DYRK1A in pancreatic ductal adenocarcinoma," Gene, Oct. 20, 2020, 758(144960).
Becker et al., "Activation, regulation, and inhibition of DYRK1A," The FEBS Journal, Jan. 2011, 278(2):246-256.
Bhansali et al., "DYRK1A regulates B cell acute lymphoblastic leukemia through phosphorylation of FOXO1 and STAT3," The Journal of Clinical Investigation, Jan. 4, 2021, 131(1): 19 pages.
Boni et al., "The DYRK family of kinases in cancer: molecular functions and therapeutic opportunities," Cancers, Jul. 29, 2020, 12(8):2106, 26 pages.
Booiman et al., "DYRK1A controls HIV-1 replication at a transcriptional level in an NFAT dependent manner," PloS One, Dec. 7, 2015, 10(12):e0144229, 16 pages.
Chou et al., "Quantitative analysis of dose-effect relationships: the combined effects of multiple drugs or enzyme inhibitors," Advances in Enzyme Regulation, Jan. 1, 1984, 22: 27-55.
Dirice et al., "Inhibition of DYRK1A stimulates human β-cell proliferation," Diabetes, Jun. 1, 2016, 65(6):1660-1671.
Feki et al., "DYRK1A protein, a promising therapeutic target to improve cognitive deficits in Down syndrome," Brain Sciences, Oct. 16, 2018, 8(10):187, 13 pages.
Fernandez-Martinez et al., "DYRK1A: the double-edged kinase as a protagonist in cell growth and tumorigenesis," Molecular & Cellular Oncology, Jan. 2, 2015, 2(1):e970048, 12 pages.

(Continued)

*Primary Examiner* — Samantha L Shterengarts
*Assistant Examiner* — Karen Cheng
(74) *Attorney, Agent, or Firm* — Fish & Richardson P.C.

(57) ABSTRACT

Pyrrolo[2,1-f][1,2,4]triazine compounds for treating various diseases and pathologies are disclosed. More particularly, the present disclosure concerns the use of pyrrolo[2,1-f][1,2,4]triazine compounds or analogs thereof, in the treatment of disorders characterized by overexpression of DYRK1A (e.g., cancer, Down syndrome, Alzheimer's disease, diabetes, viral infections, and osteoarthritis).

12 Claims, No Drawings

(56) References Cited

OTHER PUBLICATIONS

Ferrer et al., "Constitutive Dyrk1A is abnormally expressed in Alzheimer disease, Down syndrome, Pick disease, and related transgenic models," Neurobiology of Disease, Nov. 1, 2005, 20(2):392-400.
GenBank Accession No. NM_001396, "*Homo sapiens* dual specificity tyrosine phosphorylation regulated kinase 1A (DYRK1A), transcript variant 1, mRNA," Sep. 20, 2020, 10 pages.
GenBank Accession No. NM_005910, "*Homo sapiens* microtubule associated protein tau (MAPT), transcript variant 2, mRNA," Sep. 26, 2021, 6 pages.
Guard et al., "The nuclear interactome of DYRK1A reveals a functional role in DNA damage repair," Scientific Reports, Apr. 25, 2019, 9(1):6539, 12 pages.
Hadigal et al., "Heparanase-regulated syndecan-1 shedding facilitates herpes simplex virus 1 egress," Journal of Virology, Feb. 28, 2020, 94(6):e01672-19, 12 pages.
Iness et al., "Oncogenic B-Myb is associated with deregulation of the DREAM-mediated cell cycle gene expression program in high grade serous ovarian carcinoma clinical tumor samples," Frontiers in Oncology, Mar. 4, 2021, 11(637193): 14 pages.
International Search Report and Written Opinion in International Appln. No. PCT/US2022/046395, mailed on Mar. 27, 2023, 22 pages.
International Search Report and Written Opinion in International Appln. No. PCT/US2022/046409, mailed on Mar. 30, 2023, 20 pages.
International Search Report and Written Opinion in International Appln. No. PCT/US2022/046416, mailed on Jan. 24, 2023, 14 pages.
Jin et al., "Truncation and activation of dual 0161001 specificity tyrosine phosphorylation-regulated kinase 1A by calpain I: A molecular mechanism linked to tau pathology in Alzheimer disease," Journal of Biological Chemistry, Jun. 12, 2015, 290(24):15219-15237.
Kovacs, "Tauopathies," Handbook of Clinical Neurology, Jan. 1, 2018, 145: 355-368.
Kumar et al., "DYRK1A inhibitors as potential therapeutics for β-cell regeneration for diabetes," Journal of Medicinal Chemistry, Mar. 8, 2021, 64(6): 2901-2922.
Laham et al., "DYRK1A: A down syndrome-related dual protein kinase with a versatile role in tumorigenesis," Cellular and Molecular Life Sciences, Jan. 2021, 78: 44 pages.
Lee et al., "An ID2-dependent mechanism for VHL inactivation in cancer," Nature, Jan. 14, 2016, 529(7585): 33 pages.
Li et al., "TROAP switches DYRK1 activity to drive hepatocellular carcinoma progression," Cell Death & Disease, Jan. 26, 2021, 12(125): 15 pages.
Lindberg et al., "Dual-specificity, tyrosine phosphorylation-regulated kinases (DYRKs) and cdc2-like kinases (CLKs) in human disease, an overview," International Journal of Molecular Sciences, Jun. 3, 2021, 22(11):6047, 25 pages.
Luna et al., "DYRK1A modulates c-MET in pancreatic ductal adenocarcinoma to drive tumour growth," Gut, Aug. 1, 2019, 68(8):1465-1476.
Malinge et al., "Increased dosage of the chromosome 21 ortholog Dyrk1a promotes megakaryoblastic leukemia in a murine model of Down syndrome," The Journal of Clinical Investigation, Mar. 1, 2012, 122(3):948-962.
Marcotte et al., "Functional genomic landscape of human breast cancer drivers, vulnerabilities, and resistance," Cell, Jan. 14, 2016, 164(1-2): 18 pages.
Melchior et al., "Tau pathology reduction with SM07883, a novel, potent, and selective oral DYRK1A inhibitor: A potential therapeutic for Alzheimer's disease," Aging Cell, Oct. 2019, 18(5):e13000, 14 pages.
Nalls et al., "Identification of novel risk loci, causal insights, and heritable risk for Parkinson's disease: a meta-analysis of genome-wide association studies," The Lancet Neurology, Dec. 1, 2019, 18(12): 61 pages.
Pathak et al., "DYRK1A kinase inhibition with emphasis on neurodegeneration: A comprehensive evolution story-cum-perspective," European Journal of Medicinal Chemistry, Oct. 5, 2018, 158: Abstract 2 pages.
Pozo et al., "Inhibition of DYRK1A destabilizes EGFR and reduces EGFR-dependent glioblastoma growth," The Journal of Clinical Investigation, Jun. 3, 2013, 123(6): 14 pages.
Pucelik et al., "Diabetic kinome inhibitors—a new opportunity for β-cells restoration," International Journal of Molecular Sciences, Aug. 23, 2021, 22(16):9083, 53 pages.
Radhakrishnan et al., "A dual specificity kinase, DYRK1A, as a potential therapeutic target for head and neck squamous cell carcinoma," Scientific Reports, Oct. 31, 2016, 6(36132): 15 pages.
Roewenstrunk et al., "A comprehensive proteomics-based interaction screen that links DYRK1A to RNF169 and to the DNA damage response," Scientific Reports, Apr. 12, 2019, 9(1):6014, 14 pages.
Shen et al., "Inhibition of DYRK1A and GSK3B induces human β-cell proliferation," Nature Communications, Oct. 26, 2015, 6(8372): 11 pages.
Stotani et al., "DYRK1A inhibition as potential treatment for Alzheimer's disease," Future Medicinal Chemistry, Apr. 2016, 8(6): 681-696.
Xu et al., "Inhibition of DYRK1A-EGFR axis by p53-MDM2 cascade mediates the induction of cellular senescence," Cell Death & Disease, Mar. 25, 2019, 10(4):18 pages.
Gurbatri et al., "Engineered Probiotics for Local Tumor Delivery of Checkpoint Blockade Nanobodies," Science Translational Medicine, Feb. 12, 2020, 12(530):eaax0876.
International Search Report and Written Opinion in International Appln. No. PCT/US2023/026100, mailed on Sep. 13, 2023, 13 pages.
MacDonald et al., "A Systematic Analysis of Negative Growth Control Implicates the DREAM Complex in Cancer Cell Dormancy," Molecular Cancer Research, Apr. 1, 2017, 15(4):371-381.
U.S. Appl. No. 17/964,423, filed Oct. 12, 2022, Gopi Kumar Mittapalli.
U.S. Appl. No. 17/964,470, filed Oct. 12, 2022, Gopi Kumar Mittapalli.
U.S. Appl. No. 18/340,543, filed Jun. 23, 2023, Gopi Kumar Mittapalli.

* cited by examiner

PYRROLO[2,1-F][1,2,4]TRIAZINES AND PREPARATION AND USES THEREOF

RELATED APPLICATIONS

This application claims the benefit of U.S. Provisional Application Nos. 63/254,733, filed Oct. 12, 2021, and 63/347,757, filed Jun. 1, 2022, which are incorporated herein by reference in its entirety.

BACKGROUND

Technical Field

This disclosure relates to inhibitors of dual-specificity tyrosine phosphorylation-regulated 1A kinase, and compositions comprising the same. More particularly, it concerns the use of a pyrrolo[2,1-f][1,2,4]triazine compound or salts or analogs thereof, in the treatment of disorders characterized by the abnormal expression and/or activity of DYRK1A (e.g., cancer, Down syndrome, Alzheimer's disease, diabetes, viral infections, and osteoarthritis).

Background

Dual-specificity tyrosine phosphorylation-regulated kinases (DYRK1A, 1B, 2-4) comprise a family of protein kinases within the CMGC group of the eukaryotic kinome. These protein kinases are involved in multiple cellular functions, including intracellular signaling, mRNA splicing, chromatin transcription, DNA damage repair, cell survival, cell cycle control, differentiation, homocysteine/methionine/folate regulation, body temperature regulation, endocytosis, neuronal development, synaptic plasticity, etc. Abnormal expression and/or activity of some of these kinases, DYRK1A in particular, is seen in many human nervous system diseases, such as cognitive deficits associated with Down syndrome, Alzheimer's disease, and related diseases, tauopathies, dementia, Pick's disease, Parkinson's disease, and other neurodegenerative diseases, Phelan-McDermid syndrome, autism, and CDKL5 deficiency disorder. DYRKs are also involved in diabetes, abnormal folate/methionine metabolism, osteoarthritis, several solid cancers (glioblastoma, breast, and pancreatic cancers) and leukemias (acute lymphoblastic leukemia, acute megakaryoblastic leukemia), viral infections (influenza, HIV-1, HCMV, HCV, CMV, HPV), as well as infections caused by unicellular parasites (*Leishmania, Trypanosoma, Plasmodium*) (*International Journal of Molecular Sciences* (2021), 22(11), 6047). DYRK1A has also been identified as a critical stabilizer of EGFR (*Cell Death & Disease* (2019), 10, 282) which is a crucial factor contributing to the keratinization, cell hyperproliferation, abnormal differentiation and inflammatory infiltration during the progress of psoriasis.

SUMMARY

The present disclosure provides methods and reagents, involving contacting a cell with an agent, such as a pyrrolo[2,1-f][1,2,4]triazine compound, in a sufficient amount to antagonize DYRK1A activity, e.g., reduced the proliferation of head and neck squamous cell carcinoma, luminal/HER2 breast cancer (*Cell* (2016), 164(1-2), 293-309) or pancreatic adenocarcinoma, as well as impaired the self-renewal capacity of glioblastoma and compromised ovarian cancer spheroid cell viability (*Molecular Cancer Research* (2017), 15(4), 371-381).

The present disclosure also provides methods and reagents, involving contacting a cell with an agent, such as a pyrrolo[2,1-f][1,2,4]triazine compound, in a sufficient amount to antagonize DYRK1A activity, e.g., i) to normalize prenatal and early postnatal brain development; ii) to improve cognitive function in youth and adulthood; and/or iii) to attenuate Alzheimer's-type neurodegeneration.

Some embodiments disclosed herein include DYRK1A inhibitors containing a pyrrolo[2,1-f][1,2,4]triazine core. Other embodiments disclosed herein include pharmaceutical compositions and methods of treatment using these compounds.

One embodiment disclosed herein includes a compound having the structure of Formula I.

I

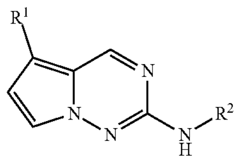

or a pharmaceutically acceptable salt thereof, wherein, $R^1$ is heteroaryl optionally substituted with 1-10 $R^3$;

$R^2$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-3}$ alkylene)$_p$OR$^4$, —($C_{1-5}$ alkylene)$_p$heterocyclyl optionally substituted with 1-10 $R^5$, -heteroaryl optionally substituted with 1-10 $R^6$, and —($C_{1-5}$ alkylene)$_p$carbocyclyl optionally substituted with 1-12 $R^7$, wherein each —($C_{1-5}$ alkylene) is, independently, optionally substituted with 1-5 halide and/or 1-3 unsubstituted —($C_{1-3}$ alkyl);

each $R^3$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR, -heterocyclyl optionally substituted with 1-10 $R^9$, -carbocyclyl optionally substituted with 1-12 $R^{10}$, —C(═O)N($R^{11}$)$_2$, and —C(═O)$R^{12}$, wherein the —($C_{1-5}$ alkylene) is optionally substituted with 1-5 halide and/or 1-3 unsubstituted —($C_{1-3}$ alkyl); each $R^4$ is independently selected from the group consisting of unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl); each $R^5$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —OMe;

each $R^6$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —OMe;

each $R^7$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —N($R^{13}$)$_2$, —($C_{1-5}$ alkylene)$_p$OR$^{14}$, and -heterocyclyl optionally substituted with 1-10 $R^{15}$, wherein the —($C_{1-5}$ alkylene) is optionally substituted with 1-5 halide and/or 1-3 unsubstituted —($C_{1-3}$ alkyl);

each $R^8$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^9$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{10}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{11}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$-carbocyclyl optionally substituted with 1-12 $R^{16}$, -heterocyclyl optionally substituted with 1-10 $R^{17}$, and -heteroaryl optionally substituted with 1-10 $R^{18}$, wherein the —($C_{1-5}$ alkylene) is optionally substituted with 1-5 halide and/or 1-3 unsubstituted —($C_{1-3}$ alkyl);

each $R^{12}$ is -heterocyclyl optionally substituted with 1-10 $R^{17}$;

each $R^{13}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{14}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{15}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{16}$ is independently selected from the group consisting of halide, —OMe, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{17}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{18}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each p is independently 0 or 1; and wherein each H atom is optionally, independently replaced by $^2H$ (D) (deuterium).

In another embodiment disclosed herein includes a compound having the structure of Formula I.

I

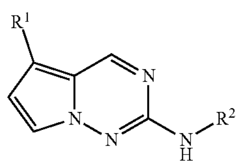

or a pharmaceutically acceptable salt thereof, wherein, $R^1$ is heteroaryl optionally substituted with 1-10 $R^3$;

$R^2$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR$^4$, —($C_{1-5}$ alkylene)$_p$heterocyclyl optionally substituted with 1-10 $R^5$, -heteroaryl optionally substituted with 1-10 $R^6$, and —($C_{1-5}$ alkylene)$_p$carbocyclyl optionally substituted with 1-12 $R^7$, wherein each —($C_{1-5}$ alkylene) is, independently, optionally substituted with 1-5 halide and/or 1-3 unsubstituted —($C_{1-3}$ alkyl);

each $R^3$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR$^8$, —($C_{1-5}$ alkylene)CN, —($C_{1-5}$ alkylene)$_p$heterocyclyl optionally substituted with 1-10 $R^9$, -carbocyclyl optionally substituted with 1-12 $R^{10}$, —($C_{1-5}$ alkylene)$_p$heteroaryl optionally substituted with 1-10 $R^{19}$, —($C_{1-5}$ alkylene)$_p$C(═O)N($R^{11}$)$_2$, and —C(═O)$R^{12}$, wherein each —($C_{1-5}$ alkylene) is, independently, optionally substituted with 1-5 halide and/or 1-3 unsubstituted —($C_{1-3}$ alkyl);

each $R^4$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^5$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), -heterocyclyl optionally substituted with 1-10 $R^{15}$, —($C_{1-5}$ alkylene)$_p$OR$^{20}$, —SO$_2$R$^{22}$, and —C(═O)$R^{23}$, wherein the —($C_{1-5}$ alkylene) is optionally substituted with 1-5 halide and/or 1-3 unsubstituted —($C_{1-3}$ alkyl);

alternatively, two $R^5$ attached to the same carbon atom are taken together to form a carbonyl group;

each $R^6$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —OMe;

each $R^7$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —N($R^{13}$)$_2$, —($C_{1-5}$ alkylene)$_p$OR$^{14}$, —($C_{1-5}$ alkylene)$_p$heterocyclyl optionally substituted with 1-10 $R^{15}$, —C(═O)$R^{21}$, and —NHC(═O)$R^{22}$, wherein each —($C_{1-5}$ alkylene) is, independently, optionally substituted with 1-5 halide and/or 1-3 unsubstituted —($C_{1-3}$ alkyl);

each $R^8$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^9$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{10}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{11}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$-carbocyclyl optionally substituted with 1-12 $R^{16}$, -heterocyclyl optionally substituted with 1-10 $R^{17}$, and -heteroaryl optionally substituted with 1-10 $R^{18}$, wherein the —($C_{1-5}$ alkylene) is optionally substituted with 1-5 halide and/or 1-3 unsubstituted —($C_{1-3}$ alkyl); each $R^{12}$ is -heterocyclyl optionally substituted with 1-10 $R^{17}$;

each $R^{13}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^4$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —($C_{1-5}$ alkylene)$_p$OR$^{20}$;

each $R^{15}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{16}$ is independently selected from the group consisting of halide, —OMe, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{17}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{18}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{19}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{20}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{21}$ is independently selected from the group consisting of -heterocyclyl optionally substituted with 1-10 $R^{11}$, —N($R^{11}$)$_2$ and —OR$^{20}$;

each $R^{22}$ is independently selected from the group consisting of unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl); each $R^{23}$ is independently selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and -carbocyclyl optionally substituted with 1-12 $R^{24}$;

each $R^{24}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each p is independently 0 or 1; and wherein each H atom is optionally, independently replaced by $^2$H (D) (deuterium).

In another embodiment disclosed herein includes a compound having the structure of Formula I:

$R^1$ is heteroaryl optionally substituted with 1-10 $R^3$;

$R^2$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR$^4$, —($C_{1-5}$ alkylene)$_p$heterocyclyl optionally substituted with 1-10 $R^5$, -heteroaryl optionally substituted with 1-10 $R^6$, and —($C_{1-5}$ alkylene)$_p$carbocyclyl optionally substituted with 1-12 $R^7$, wherein each —($C_{1-5}$ alkylene) is, independently, optionally substituted with 1-5 halide and/or 1-3 unsubstituted —($C_{1-3}$ alkyl);

each $R^3$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR$^8$, —($C_{1-5}$ alkylene)CN, —($C_{1-5}$ alkylene)$_p$heterocyclyl optionally substituted with 1-10 $R^9$, -carbocyclyl optionally substituted with 1-12 $R^{10}$, —($C_{1-5}$ alkylene)$_p$heteroaryl optionally substituted with 1-10 $R^{19}$, —($C_{1-5}$ alkylene)$_p$C(=O)N($R^{11}$)$_2$, and —C(=O)R$^{12}$, wherein each —($C_{1-5}$ alkylene) is, independently, optionally substituted with 1-5 halide and/or 1-3 unsubstituted —($C_{1-3}$ alkyl);

each $R^4$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^5$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), -heterocyclyl optionally substituted with 1-10 $R^{15}$, —($C_{1-5}$ alkylene)$_p$OR$^{20}$, —SO$_2$R$^{22}$, and —C(=O)R$^{23}$ wherein the —($C_{1-5}$ alkylene) is optionally substituted with 1-5 halide and/or 1-3 unsubstituted —($C_{1-3}$ alkyl);

alternatively, two R attached to the same carbon atom are taken together to form a carbonyl group;

each $R^6$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —OMe;

each $R^7$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —N($R^{13}$)$_2$, —($C_{1-5}$ alkylene)$_p$OR$^{14}$, —($C_{1-5}$ alkylene)$_p$heterocyclyl optionally substituted with 1-10 $R^{11}$, —C(=O)R$^{21}$, and —NH(=O)R$^{22}$, wherein each —($C_{1-5}$ alkylene) is, independently, optionally substituted with 1-5 halide and/or 1-3 unsubstituted —($C_{1-3}$ alkyl);

each $R^8$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^9$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{10}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{11}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$-carbocyclyl optionally substituted with 1-12 $R^{16}$, -heterocyclyl optionally substituted with 1-10 $R^{17}$, and -heteroaryl optionally substituted with 1-10 $R^{18}$, wherein the —($C_{1-5}$ alkylene) is optionally substituted with 1-5 halide and/or 1-3 unsubstituted —($C_{1-3}$ alkyl);

each $R^{12}$ is -heterocyclyl optionally substituted with 1-10 $R^{17}$;

each $R^{13}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{14}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —($C_{1-5}$ alkylene)$_p$OR$^{20}$;

each $R^{15}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

alternatively, two $R^{15}$ attached to the same carbon atom are taken together to form a carbonyl group;

each $R^{16}$ is independently selected from the group consisting of halide, —OMe, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{17}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{18}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{19}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{20}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{21}$ is independently selected from the group consisting of -heterocyclyl optionally substituted with 1-10 $R^{17}$, —N($R^{11}$)$_2$ and —OR$^{20}$;

each $R^{22}$ is independently selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —($C_{1-5}$ alkylene)$_p$OR$^{20}$;

each $R^{23}$ is independently selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and -carbocyclyl optionally substituted with 1-12 $R^{24}$;

each $R^{24}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each p is independently 0 or 1; and wherein each H atom is optionally, independently replaced by $^2$H (D) (deuterium).

Some embodiments include stereoisomers and pharmaceutically acceptable salts of a compound of Formula (I). Some embodiments include pharmaceutically acceptable salts of a compound of Formula (I).

Some embodiments include pro-drugs of a compound of Formula (I).

Some embodiments of the present disclosure include pharmaceutical compositions comprising a compound of Formula (I) and a pharmaceutically acceptable carrier, diluent, or excipient.

Other embodiments disclosed herein include methods of inhibiting DYRK1A by administering to a patient affected by a disorder or disease in which DYRK1A overexpression is implicated, such as Alzheimer's Disease, Amyotrophic Lateral Sclerosis, CDKL5 Deficiency Disorder, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor and Stroke.

Inhibitors of DYRK1A can also be used to treat tauopathies. Tauopathies are neurodegenerative disorders characterized by the deposition of abnormal tau protein in the brain. The spectrum of tau pathologies expands beyond the traditionally discussed disease forms like Pick's disease, progressive supranuclear palsy, corticobasal degeneration, and argyrophilic grain disease. Emerging entities and pathologies include globular glial tauopathies, primary age-related tauopathy, which includes neurofibrillary tangle dementia, chronic traumatic encephalopathy (CTE), frontotemporal lobar degeneration with tau inclusions (FTLD-tau), and aging-related tau astrogliopathy. Clinical symptoms include frontotemporal dementia, corticobasal syndrome, Richardson syndrome, parkinsonism, pure akinesia with gait freezing and, rarely, motor neuron symptoms or cerebellar ataxia (*Handbook of Clinical Neurology* (2018), 145, 355-368 and *Aging Cell* (2019), 18(5), e13000).

Inhibitors of DYRK1A can also be used to treat disorders associated with abnormal folate/methionine metabolism.

Non-limiting examples of diseases which can be treated with the compounds and compositions provided herein include a variety of cancers, diabetes, psoriasis, knee osteoarthritis, tendinopathy, human immunodeficiency virus type 1 (HIV-1), human cytomegalovirus (HCMV), hepatitis C virus (HCV), and herpes simplex virus 1 (HSV-1).

Some embodiments of the present disclosure include methods to prepare compounds of Formula (I).

It is to be understood that both the foregoing general description and the following detailed description are exemplary and explanatory only and are not restrictive of the disclosure, as claimed.

DETAILED DESCRIPTION

Provided herein are compositions and methods for inhibiting DYRK1A.

Some embodiments provided herein relate to a method for treating a disease including, but not limited to, neurological diseases or disorders, cancers, cognitive deficits, knee osteoarthritis, tendinopathy, viral infections, unicellular parasite infections, and motor deficits.

In some embodiments, non-limiting examples of a neurological disease or disorder which can be treated with the compounds and compositions provided herein include, but are not limited to, Alzheimer's disease, amyotrophic lateral sclerosis, Down Syndrome, frontotemporal dementia with Parkinsonism-17 (FTDP-17), Lewy body dementia, Parkinson's disease, Pick's disease tauopathies, and additional diseases with pronounced neurodegeneration such as autism, dementia, epilepsy, Huntington's disease, multiple sclerosis; diseases and disorders associated with acquired brain injury such as Chronic Traumatic Encephalopathy, Traumatic Brain Injury, Tumor, and Stroke.

In some embodiments, non-limiting examples of cancers which can be treated with the compounds and compositions provided herein include solid cancers (e.g., glioblastoma, ovarian, breast, and pancreatic cancers) and leukemias (e.g., acute lymphoblastic leukemia, acute megakaryoblastic leukemia, and chronic myeloid leukemia).

In some embodiments, pharmaceutical compositions are provided that are effective for treatment of a disease of an animal, e.g., a mammal, caused by DYRK1A overexpression. The composition includes a pharmaceutically acceptable carrier and a compound as described herein.

Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, "alkyl" means a branched, or straight chain chemical group containing only carbon and hydrogen, such as methyl, ethyl, n-propyl, iso-propyl, n-butyl, iso-butyl, sec-butyl, tert-butyl, n-pentyl, iso-pentyl, sec-pentyl and neo-pentyl. Alkyl groups can either be unsubstituted or substituted with one or more substituents. In some embodiments, alkyl groups include 1 to 9 carbon atoms (for example, 1 to 6 carbon atoms, 1 to 4 carbon atoms, or 1 to 2 carbon atoms).

As used herein, "alkenyl" means a straight or branched chain chemical group containing only carbon and hydrogen and containing at least one carbon-carbon double bond, such as ethenyl, 1-propenyl, 2-propenyl, 2-methyl-1-propenyl, 1-butenyl, 2-butenyl, and the like. In various embodiments, alkenyl groups can either be unsubstituted or substituted with one or more substituents. Typically, alkenyl groups will comprise 2 to 9 carbon atoms (for example, 2 to 6 carbon atoms, 2 to 4 carbon atoms, or 2 carbon atoms).

As used herein, "alkynyl" means a straight or branched chain chemical group containing only carbon and hydrogen and containing at least one carbon-carbon triple bond, such as ethynyl, 1-propynyl, 1-butynyl, 2-butynyl, and the like. In various embodiments, alkynyl groups can either be unsubstituted or substituted with one or more substituents. Typically, alkynyl groups will comprise 2 to 9 carbon atoms (for example, 2 to 6 carbon atoms, 2 to 4 carbon atoms, or 2 carbon atoms).

As used herein, "alkylene" means a bivalent branched or straight chain chemical group containing only carbon and hydrogen, such as methylene, ethylene, n-propylene, iso-propylene, n-butylene, iso-butylene, sec-butylene, tert-butylene, n-pentylene, iso-pentylene, sec-pentylene and neo-pentylene. Alkylene groups can either be unsubstituted or substituted with one or more substituents. In some embodiments, alkylene groups include 1 to 9 carbon atoms (for example, 1 to 6 carbon atoms, 1 to 4 carbon atoms, or 1 to 2 carbon atoms).

As used herein, "alkenylene" means a bivalent branched or straight chain chemical group containing only carbon and hydrogen and containing at least one carbon-carbon double bond, such as ethenylene, 1-propenylene, 2-propenylene, 2-methyl-1-propenylene, 1-butenylene, 2-butenylene, and the like. In various embodiments, alkenylene groups can either be unsubstituted or substituted with one or more substituents. Typically, alkenylene groups will comprise 2 to 9 carbon atoms (for example, 2 to 6 carbon atoms, 2 to 4 carbon atoms, or 2 carbon atoms).

As used herein, "alkynylene" means a bivalent branched or straight chain chemical group containing only carbon and hydrogen and containing at least one carbon-carbon triple bond, such as ethynylene, 1-propynylene, 1-butynylene, 2-butynylene, and the like. In various embodiments, alkynylene groups can either be unsubstituted or substituted with one or more substituents. Typically, alkynylene groups will comprise 2 to 9 carbon atoms (for example, 2 to 6 carbon atoms, 2 to 4 carbon atoms, or 2 carbon atoms).

As used herein, "alkoxy" means an alkyl-O— group in which the alkyl group is as described herein. Exemplary alkoxy groups include methoxy, ethoxy, n-propoxy, i-propoxy, n-butoxy, s-butoxy, t-butoxy, pentoxy, hexoxy and heptoxy, and also the linear or branched positional isomers thereof.

As used herein, "haloalkoxy" means a haloalkyl-O— group in which the haloalkyl group is as described herein. Exemplary haloalkoxy groups include fluoromethoxy, difluoromethoxy, trifluoromethoxy, and also the linear or branched positional isomers thereof.

As used herein, "carbocyclyl" means a cyclic ring system containing only carbon atoms in the ring system backbone, such as cyclopropyl, cyclobutyl, cyclopentyl, cyclohexyl, and cyclohexenyl. Carbocyclyls may include multiple fused rings. Carbocyclyls may have any degree of saturation provided that none of the rings in the ring system are aromatic. Carbocyclyl groups can either be unsubstituted or substituted with one or more substituents. In some embodiments, carbocyclyl groups include 3 to 10 carbon atoms, for example, 3 to 6 carbon atoms.

As used herein, "aryl" means a mono-, bi-, tri- or polycyclic group with only carbon atoms present in the ring backbone having 5 to 14 ring atoms, alternatively 5, 6, 9, or 10 ring atoms; and having 6, 10, or 14 pi electrons shared in a cyclic array; wherein at least one ring in the system is aromatic. Aryl groups can either be unsubstituted or substituted with one or more substituents. Examples of aryl include phenyl, naphthyl, tetrahydronaphthyl, 2,3-dihydro-1H-indenyl, and others. In some embodiments, the aryl is phenyl.

As used herein, "arylalkylene" means an aryl-alkylene-group in which the aryl and alkylene moieties are as previously described. In some embodiments, arylalkylene groups contain a $C_{1-4}$alkylene moiety. Exemplary arylalkylene groups include benzyl and 2-phenethyl.

As used herein, the term "heteroaryl" means a mono-, bi-, tri- or polycyclic group having 5 to 14 ring atoms, alternatively 5, 6, 9, or 10 ring atoms; and having 6, 10, or 14 pi electrons shared in a cyclic array; wherein at least one ring in the system is aromatic, and at least one ring in the system contains one or more heteroatoms independently selected from the group consisting of N, O, and S. Heteroaryl groups can either be unsubstituted or substituted with one or more substituents. Examples of heteroaryl include thienyl, pyridinyl, furyl, oxazolyl, oxadiazolyl, pyrrolyl, imidazolyl, triazolyl, thiodiazolyl, pyrazolyl, isoxazolyl, thiadiazolyl, pyranyl, pyrazinyl, pyrimidinyl, pyridazinyl, triazinyl, thiazolyl benzothienyl, benzoxadiazolyl, benzofuranyl, benzimidazolyl, benzotriazolyl, cinnolinyl, indazolyl, indolyl, isoquinolinyl, isothiazolyl, naphthyridinyl, purinyl, thienopyridinyl, pyrido[2,3-d]pyrimidinyl, pyrrolo[2,3-b]pyridinyl, quinazolinyl, quinolinyl, thieno[2,3-c]pyridinyl, pyrazolo[3,4-b]pyridinyl, pyrazolo[3,4-c]pyridinyl, pyrazolo[4,3-c]pyridine, pyrazolo[4,3-b]pyridinyl, tetrazolyl, chromane, 2,3-dihydrobenzo[b][1,4]dioxine, benzo[d][1,3]dioxole, 2,3-dihydrobenzofuran, tetrahydroquinoline, 2,3-dihydrobenzo[b][1,4]oxathiine, isoindoline, and others. In some embodiments, the heteroaryl is selected from thienyl, pyridinyl, furyl, pyrazolyl, imidazolyl, isoindolinyl, pyranyl, pyrazinyl, and pyrimidinyl.

As used herein, "halo", "halide" or "halogen" is a chloro, bromo, fluoro, or iodo atom radical. In some embodiments, a halo is a chloro, bromo or fluoro. For example, a halide can be fluoro.

As used herein, "haloalkyl" means a hydrocarbon substituent, which is a linear or branched alkyl, alkenyl or alkynyl substituted with one or more chloro, bromo, fluoro, and/or iodo atom(s). In some embodiments, a haloalkyl is a fluoroalkyl, wherein one or more of the hydrogen atoms have been substituted by fluoro. In some embodiments, haloalkyls are 1 to 3 carbons in length (e.g., 1 to 2 carbons in length or 1 carbon in length). The term "haloalkylene" means a diradical variant of haloalkyl, and such diradicals may act as spacers between radicals, other atoms, or between a ring and another functional group.

As used herein, "heterocyclyl" means a nonaromatic cyclic ring system comprising at least one heteroatom in the ring system backbone. Heterocyclyls may include multiple fused rings such as bicyclic and spirocyclic heterocyclyls. Heterocyclyls may be substituted or unsubstituted with one or more substituents. In some embodiments, heterocycles have 3-11 members. In six membered monocyclic heterocycles, the heteroatom(s) are selected from one to three of O, N and S, and wherein when the heterocycle is five membered, it can have one or two heteroatoms selected from O, N, and S. Examples of heterocyclyl include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others. In some embodiments, the heterocyclyl is selected from azetidinyl, morpholinyl, piperazinyl, pyrrolidinyl, and tetrahydropyridinyl.

As used herein, "monocyclic heterocyclyl" means a single nonaromatic cyclic ring comprising at least one heteroatom in the ring system backbone. Heterocyclyls may be substituted or unsubstituted with one or more substituents. In some embodiments, heterocycles have 3-7 members. In six membered monocyclic heterocycles, the heteroatom(s) are selected from one to three of O, N and S, and wherein when the heterocycle is five membered, it can have one or two heteroatoms selected from O, N, and S. Examples of monocyclic heterocyclyls include azirinyl, aziridinyl, azetidinyl, oxetanyl, thietanyl, 1,4,2-dithiazolyl, dihydropyridinyl, 1,3-dioxanyl, 1,4-dioxanyl, 1,3-dioxolanyl, morpholinyl, thiomorpholinyl, piperazinyl, pyranyl, pyrrolidinyl, tetrahydrofuryl, tetrahydropyridinyl, oxazinyl, thiazinyl, thiinyl, thiazolidinyl, isothiazolidinyl, oxazolidinyl, isoxazolidinyl, piperidinyl, pyrazolidinyl imidazolidinyl, thiomorpholinyl, and others.

As used herein, "bicyclic heterocyclyl" means a nonaromatic bicyclic ring system comprising at least one heteroatom in the ring system backbone. Bicyclic heterocyclyls may be substituted or unsubstituted with one or more substituents. In some embodiments, bicyclic heterocycles have 4-11 members with the heteroatom(s) being selected from one to five of O, N and S. Examples of bicyclic heterocyclyls include 2-azabicyclo[1.1.0]butane, 2-azabicyclo[2.1.0]pentane, 2-azabicyclo[1.1.1]pentane, 3-azabicyclo[3.1.0]hexane, 5-azabicyclo[2.1.1]hexane, 3-azabicyclo[3.2.0]heptane, octahydrocyclopenta[c]pyrrole, 3-azabicyclo[4.1.0]heptane, 7-azabicyclo[2.2.1]heptane, 6-azabicyclo[3.1.1]heptane, 7-azabicyclo[4.2.0]octane, 2-azabicyclo[2.2.2]octane, and the like.

As used herein, "spirocyclic heterocyclyl" means a nonaromatic bicyclic ring system comprising at least one heteroatom in the ring system backbone and with the rings connected through just one atom. Spirocyclic heterocyclyls may be substituted or unsubstituted with one or more substituents. In some embodiments, spirocyclic heterocycles have 5-11 members with the heteroatom(s) being selected from one to five of O, N and S. Examples of spirocyclic heterocyclyls include 2-azaspiro[2.2]pentane, 4-azaspiro[2.5]octane, 1-azaspiro[3.5]nonane, 2-azaspiro[3.5]nonane, 7-azaspiro[3.5]nonane, 2-azaspiro[4.4]nonane, 6-azaspiro[2.6]nonane, 1,7-diazaspiro[4.5]decane, 2,5-diazaspiro[3.6]decane, and the like.

The term "substituted" refers to moieties having substituents replacing a hydrogen on one or more non-hydrogen atoms of the molecule. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. Substituents can include, for example, —($C_{1-9}$ alkyl) optionally substituted with one or more of hydroxyl, —$NH_2$, —NH($C_{1-3}$ alkyl), and —N($C_{1-3}$ alkyl)$_2$; —($C_{1-9}$ haloalkyl); a halide; a hydroxyl; a carbonyl [such as —C(O)OR, and —C(O)R]; a thiocarbonyl [such as —C(S)OR, —C(O)SR, and —C(S)R]; —($C_{1-9}$ alkoxy) optionally substituted with one or more of halide, hydroxyl, —$NH_2$, —NH($C_{1-3}$ alkyl), and —N($C_{1-3}$ alkyl)$_2$; —$OPO(OH)_2$; a phosphonate [such as —$PO(OH)_2$ and —$PO(OR')_2$]; —$OPO(OR')R^{11}$; —NRR'; —C(O)NRR'; —C(NR)NR'R"; —C(NR')R"; a cyano; a nitro; an azido; —SH; —S—R; —$OSO_2(OR)$; a sulfonate [such as —$SO_2(OH)$ and —$SO_2(OR)$]; —$SO_2NR'R"$; and —$SO_2R$; in which each occurrence of R, R' and R" are independently selected from H; —($C_{1-9}$ alkyl); $C_{6-10}$ aryl optionally substituted with 1-3 R'"; 5-10 membered heteroaryl having from 1-4 heteroatoms independently selected from N, O, and S and optionally substituted with 1-3 R'"; $C_{3-7}$ carbocyclyl optionally substituted with 1-3 R'"; and 3-8 membered heterocyclyl having from 1-4 heteroatoms independently selected from N, O, and S and optionally substituted with 1-3 R'"; wherein each R'" is independently selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl). In some embodiments, the substituent is selected from —($C_{1-6}$ alkyl), —($C_{1-6}$ haloalkyl), a halide (e.g., F), a hydroxyl, —C(O)OR, —C(O)R, —($C_{1-6}$ alkoxyl), —NRR', —C(O)NRR', and a cyano, in which each occurrence of R and R' is independently selected from H and —($C_{1-6}$ alkyl).

As used herein, when two groups are indicated to be "linked" or "bonded" to form a "ring", it is to be understood that a bond is formed between the two groups and may involve replacement of a hydrogen atom on one or both groups with the bond, thereby forming a carbocyclyl, heterocyclyl, aryl, or heteroaryl ring. The skilled artisan will recognize that such rings can and are readily formed by routine chemical reactions. In some embodiments, such rings have from 3-7 members, for example, 5 or 6 members.

The skilled artisan will recognize that some chemical structures described herein may be represented on paper by one or more other resonance forms; or may exist in one or more other tautomeric forms, even when kinetically, the artisan recognizes that such tautomeric forms represent only a very small portion of a sample of such compound(s). Such compounds are clearly contemplated within the scope of this disclosure, though such resonance forms or tautomers are not explicitly represented herein.

The compounds provided herein may encompass various stereochemical forms. The compounds also encompass diastereomers as well as optical isomers, e.g., mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art. Unless otherwise indicated, when a disclosed compound is named or depicted by a structure without specifying the stereochemistry and has one or more chiral centers, it is understood to represent all possible stereoisomers of the compound.

The present disclosure includes all pharmaceutically acceptable isotopically labeled compounds of Formula I wherein one or more atoms are replaced by atoms having the same atomic number, but an atomic mass or mass number different from the atomic mass or mass number which predominates in nature. Examples of isotopes suitable for inclusion in the compounds of the disclosure include, but are not limited to, isotopes of hydrogen, such as $^{2}H$ (deuterium) and $^{3}H$ (tritium), isotopes of carbon, such as $^{11}C$, $^{13}C$ and $^{14}C$, isotopes of chlorine, such as $^{36}Cl$, isotopes of fluorine, such as $^{18}F$, isotopes of iodine, such as $^{123}I$ and $^{125}I$, isotopes of nitrogen, such as 13N and $^{15}N$, isotopes of oxygen, such as $^{15}O$, $^{17}O$ and $^{18}O$, isotopes of phosphorus, such as $^{32}P$, and isotopes of sulfur, such as $^{35}S$.

The term “administration” or “administering” refers to a method of providing a dosage of a compound or pharmaceutical composition to a vertebrate or invertebrate, including a mammal, a bird, a fish, or an amphibian, where the method of administration is, e.g., orally, subcutaneously, intravenously, intralymphatic, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic device. The method of administration can vary depending on various factors, e.g., the components of the pharmaceutical composition, the site of the disease, the disease involved, and the severity of the disease.

A “diagnostic” as used herein is a compound, method, system, or device that assists in the identification or characterization of a health or disease state. The diagnostic can be used in standard assays as is known in the art.

The term “mammal” is used in its usual biological sense. Thus, it specifically includes humans, cattle, horses, monkeys, dogs, cats, mice, rats, cows, sheep, pigs, goats, and non-human primates, but also includes many other species.

The terms “pharmaceutically acceptable carrier”, “pharmaceutically acceptable diluent” and “pharmaceutically acceptable excipient” include any and all solvents, cosolvents, complexing agents, dispersion media, coatings, isotonic and absorption delaying agents and the like which are not biologically or otherwise undesirable. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, NJ. Considerations for the inclusion of various components in pharmaceutical compositions are described, e.g., in Gilman et al. (Eds.) (2010); *Goodman and Gilman's: The Pharmacological Basis of Therapeutics,* 12th Ed., The McGraw-Hill Companies.

The term “pharmaceutically acceptable salt” refers to salts that retain the biological effectiveness and properties of the compounds provided herein and, which are not biologically or otherwise undesirable. In many cases, the compounds provided herein are capable of forming acid and/or base salts by virtue of the presence of amino and/or carboxyl groups or groups similar thereto. Many such salts are known in the art, for example, as described in WO 87/05297. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium, and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine.

“Patient” as used herein, means a human or a non-human mammal, e.g., a dog, a cat, a mouse, a rat, a cow, a sheep, a pig, a goat, a non-human primate, or a bird, e.g., a chicken, as well as any other vertebrate or invertebrate. In some embodiments, the patient is a human.

A “therapeutically effective amount” of a compound as provided herein is one which is sufficient to achieve the desired physiological effect and may vary according to the nature and severity of the disease condition, and the potency of the compound. “Therapeutically effective amount” is also intended to include one or more of the compounds of Formula I in combination with one or more other agents that are effective to treat the diseases and/or conditions described herein. The combination of compounds can be a synergistic combination. Synergy, as described, for example, by Chou and Talalay, Advances in Enzyme Regulation (1984), 22, 27-55, occurs when the effect of the compounds when administered in combination is greater than the additive effect of the compounds when administered alone as a single agent. In general, a synergistic effect is most clearly demonstrated at sub-optimal concentrations of the compounds. It will be appreciated that different concentrations may be employed for prophylaxis than for treatment of an active disease. This amount can further depend upon the patient's height, weight, sex, age, and medical history.

A therapeutic effect relieves, to some extent, one or more of the symptoms of the disease.

"Treat," "treatment," or "treating," as used herein refers to administering a compound or pharmaceutical composition as provided herein for therapeutic purposes. The term "therapeutic treatment" refers to administering treatment to a patient already suffering from a disease thus causing a therapeutically beneficial effect, such as ameliorating existing symptoms, ameliorating the underlying metabolic causes of symptoms, postponing, or preventing the further development of a disorder, and/or reducing the severity of symptoms that will or are expected to develop.

"Drug-eluting" and/or controlled release as used herein refers to any and all mechanisms, e.g., diffusion, migration, permeation, and/or desorption by which the drug(s) incorporated in the drug-eluting material pass therefrom overtime into the surrounding body tissue.

"Drug-eluting material" and/or controlled release material as used herein refers to any natural, synthetic, or semi-synthetic material capable of acquiring and retaining a desired shape or configuration and into which one or more drugs can be incorporated and from which incorporated drug(s) are capable of eluting over time.

"Elutable drug" as used herein refers to any drug or combination of drugs having the ability to pass over time from the drug-eluting material in which it is incorporated into the surrounding areas of the body.

Compounds

The compounds and compositions described herein can be used to inhibit DYRK1A for treating a disorder or disease in which DYRK1A overexpression is implicated, such as in neurological diseases or disorders, cancers, cognitive deficits, knee osteoarthritis, tendinopathy, viral infections, unicellular parasite infections, and motor deficits.

Some embodiments of the present disclosure include compounds of Formula I:

I

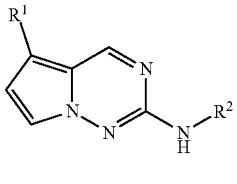

or salts, pharmaceutically acceptable salts, or prodrugs thereof.

In some embodiments of Formula I, $R^1$ is heteroaryl optionally substituted with 1-10 $R^3$. In some embodiments, $R^1$ is heteroaryl optionally substituted with 1-10, 1-9, 1-8, 1-7, 1-6, 1-5, 1-4, 1-3, 1-2, or 1 $R^3$.

In some embodiments of Formula I, $R^1$ is selected from the heteroaryl group consisting of:

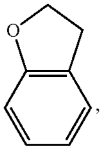, 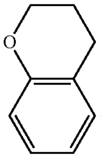, 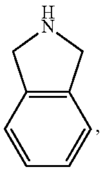, 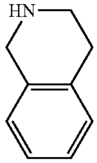,

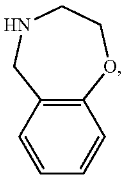 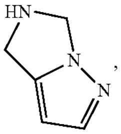, 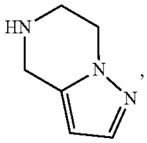,

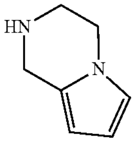, 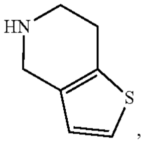, 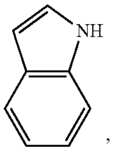,

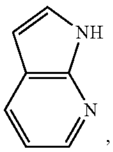, 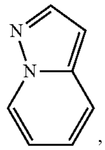, 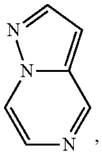, 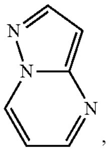,

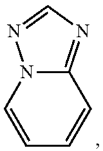, 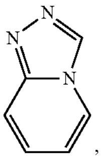, 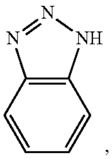, 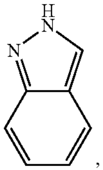,

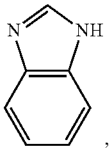, 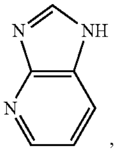, 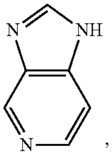, 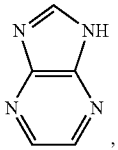,

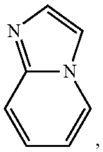, 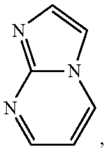, 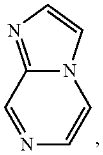, 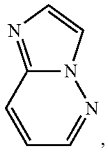,

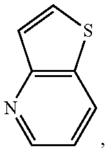, 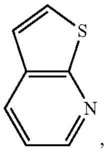, 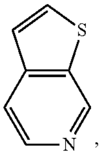, 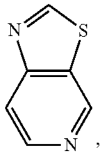,

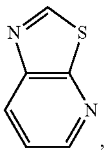, 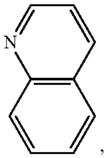, 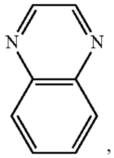, 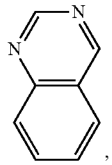,

-continued

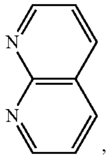 , 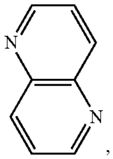 , and 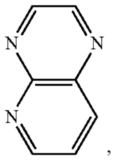 , optionally substituted with 1-10 (e.g., 1-9, 1-8, 1-7, 1-6, 1-5, 1-4, 1-3, 1-2, 1) $R^3$.

In some embodiments of Formula I, $R^1$ is selected from the heteroaryl group consisting of:

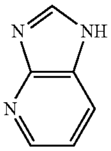 , 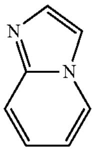 , 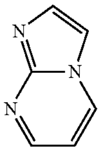 ,

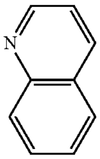 , 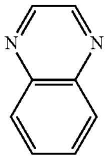 , and 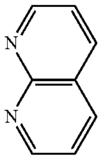 , optionally substituted with 1-10 (e.g., 1-9, 1-8, 1-7, 1-6, 1-5, 1-4, 1-3, 1-2, 1) $R^3$.

In some embodiments of Formula I, $R^1$ is selected from the heteroaryl group consisting of:

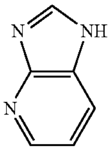 , 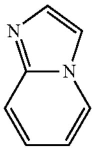 , 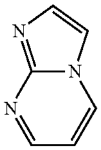 ,

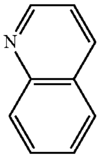 , 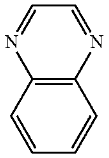 , and 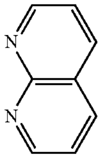 , optionally substituted with 1-3 (e.g., 1-2, 1) $R^3$.

In some embodiments of Formula I, $R^1$ is selected from the group consisting of:

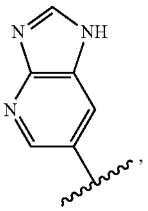 , 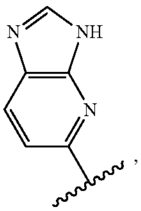 , 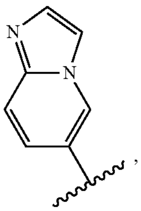 ,

-continued

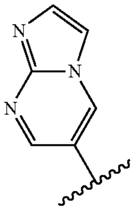 , 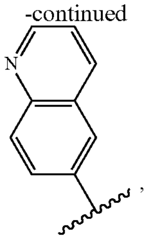 , 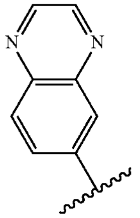 , and

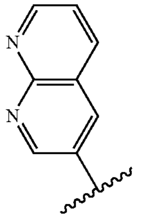 , optionally substituted with 1-3 $R^3$.

The compound according to any one of claims 1-3, wherein $R^1$ is selected from the group consisting of: unsubstituted

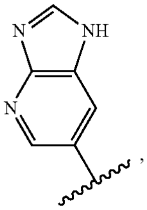 , 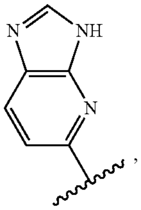 , 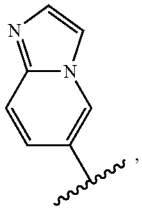 ,

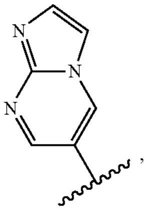 , 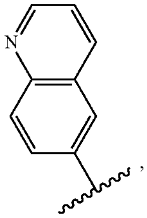 , 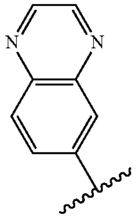 , and

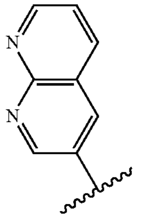

In some embodiments of Formula I, $R^2$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-3}$ alkylene)$_p$OR$^4$, —($C_{1-5}$ alkylene)$_p$heterocyclyl optionally substituted with 1-10 (e.g., 1-9, 1-8, 1-7, 1-6, 1-5, 1-4, 1-3, 1-2, 1) $R^5$, -heteroaryl optionally substituted with 1-10 (e.g., 1-9, 1-8, 1-7, 1-6, 1-5, 1-4, 1-3, 1-2, 1)R, and —($C_{1-5}$ alkylene)$_p$ carbocyclyl optionally substituted with 1-12 (e.g., 1-11, 1-10, 1-9, 1-8, 1-7, 1-6, 1-5, 1-4, 1-3, 1-2, 1) $R^7$, wherein each —($C_{1-5}$ alkylene) is, independently, optionally substituted with 1-5 (e.g., 1-4, 1-3, 1-2, 1) halide (e.g., F, Cl, Br, I) and/or 1-3 (e.g., 1-2, 1) unsubstituted —($C_{1-3}$ alkyl).

In some embodiments of Formula I, $R^2$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR$^4$, —($C_{1-5}$ alkylene)$_p$heterocyclyl optionally substituted with 1-10 $R^5$, -heteroaryl optionally substituted with 1-10 $R^6$, and —($C_{1-5}$ alkylene)$_p$carbocyclyl optionally substituted with 1-12 $R^7$, wherein each —($C_{1-5}$ alkylene) is, independently, optionally substituted with 1-5 halide and/or 1-3 unsubstituted —($C_{1-3}$ alkyl).

In some embodiments of Formula I, $R^2$ is selected from the group consisting of unsubstituted —($C_{1-9}$ alkyl), unsubstituted —($C_{1-9}$ haloalkyl), —($C_{1-5}$ alkylene)$_p$heterocyclyl optionally substituted with 1-10 (e.g., 1-9, 1-8, 1-7, 1-6, 1-5, 1-4, 1-3, 1-2, 1) $R^5$, -heteroaryl optionally substituted with 1-10 $R^6$, and —($C_{1-5}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^7$, wherein each —($C_{1-5}$ alkylene) is, independently, optionally substituted with 1-5 (e.g., 1-4, 1-3, 1-2, 1) halide (e.g., F, Cl, Br, I) and/or 1-3 (e.g., 1-2, 1) unsubstituted —($C_{1-3}$ alkyl).

In some embodiments of Formula I, $R^2$ is selected from the group consisting of unsubstituted —($C_{1-5}$ alkyl), unsubstituted —($C_{1-5}$ haloalkyl), —($C_{1-2}$ alkylene)$_p$heterocyclyl optionally substituted with 1-3 (e.g., 1-2, 1) $R^5$, and —($C_{1-2}$ alkylene)$_p$carbocyclyl optionally substituted with 1-3 (e.g., 1-2, 1) $R^{17}$, wherein each —($C_{1-5}$ alkylene) is, independently, optionally substituted with 1-2 halide.

In some embodiments of Formula I, $R^2$ is selected from the group consisting of unsubstituted —($C_{1-5}$ alkyl), unsubstituted —($C_{2-5}$ alkenyl), unsubstituted —($C_{2-5}$ alkynyl), unsubstituted —($C_{1-5}$ haloalkyl), —($C_{1-2}$ alkylene)$_p$OR$^4$, —($C_{1-2}$ alkylene)$_p$heterocyclyl optionally substituted with 1-3 $R^5$, -heteroaryl optionally substituted with 1-3 $R^6$, and —($C_{1-2}$ alkylene)$_p$carbocyclyl optionally substituted with 1-3 $R^7$, wherein each —($C_{1-2}$ alkylene) is, independently, optionally substituted with 1-2 halide.

In some embodiments of Formula I, $R^2$ is —($C_{1-2}$ alkylene)$_p$heterocyclyl optionally substituted with 1-3 $R^5$, wherein the —($C_{1-5}$ alkylene) is optionally substituted with 1-2 halide and wherein the heterocyclyl is selected from the group consisting of oxetanyl, tetrahydrofuranyl, tetrahydropyranyl, azetidinyl, pyrrolidinyl, piperidinyl, morpholinyl, piperazinyl, oxaspiro[3.3]heptanyl, and oxaspiro[3.3]heptanyl.

In some embodiments of Formula I, $R^2$ is selected from the group consisting of:

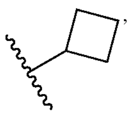 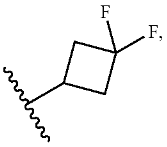 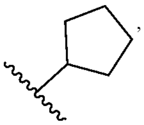

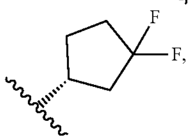 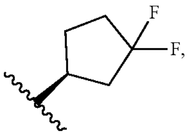

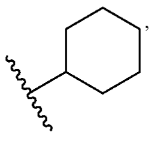 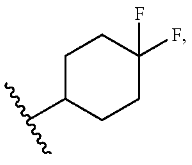 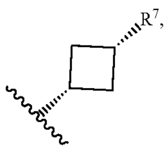

-continued

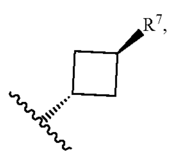 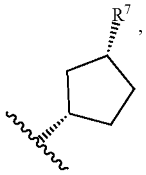 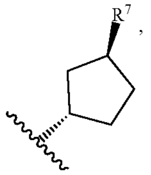

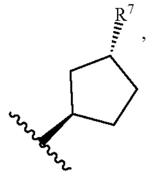 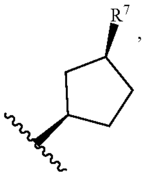 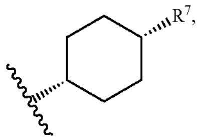

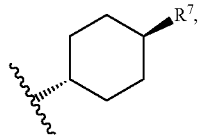 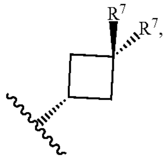 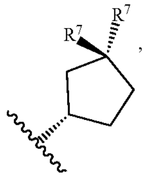

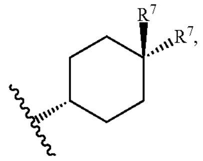 and 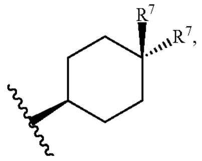

wherein each $R^7$ is independently selected from the group consisting of F, Me, —$CH_2F$, —$CHF_2$, —$CF_3$, —$CH_2OH$, —$CH_2OMe$, —OH, —OMe, —OEt, —$OCD_3$, —$OCF_3$, —$OCH_2CH_2F$, —$OCH_2CHF_2$, —$OCH_2CF_3$, —$OCH_2CH_2OMe$, —$OCH_2CH_2OH$, —$NH_2$, —NHMe, and —$NMe_2$.

In some embodiments of Formula I, $R^2$ is selected from the group consisting of:

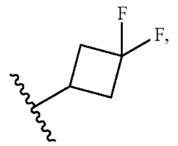 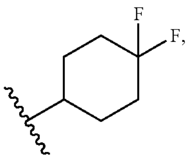

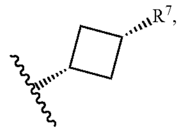 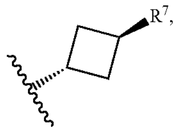

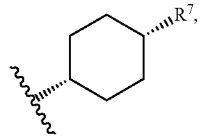 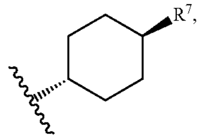

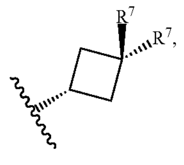 and 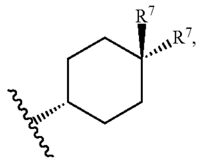

-continued

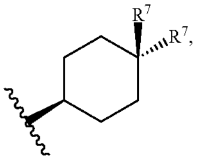

wherein each $R^7$ is independently selected from the group consisting of F, Me, —$CHF_2$, —$CH_2OMe$, —OH, —OMe, —$OCD_3$, —$OCH_2CHF_2$, and —$OCH_2CH_2OMe$.

In some embodiments of Formula I, $R^2$ is selected from the group consisting of:

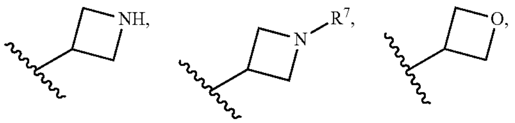

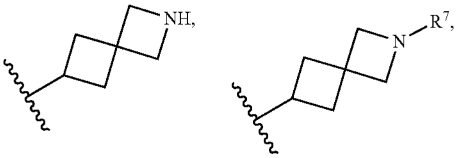

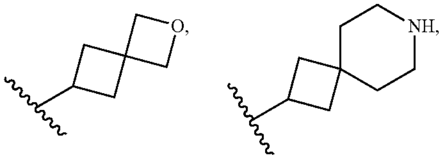

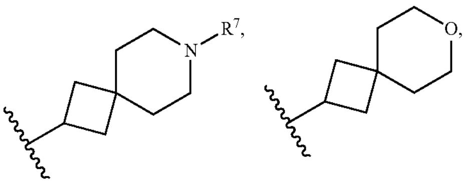

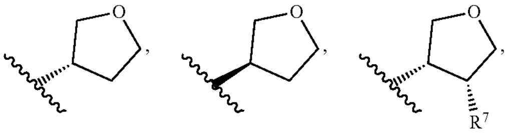

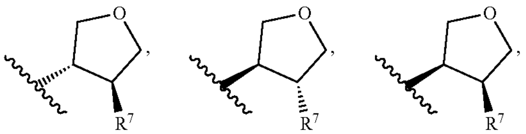

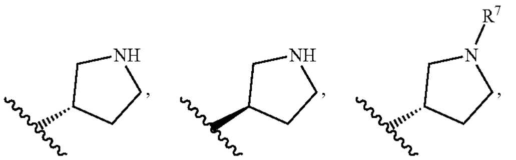

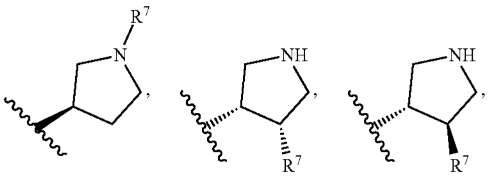

-continued

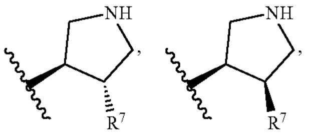

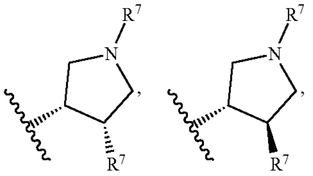

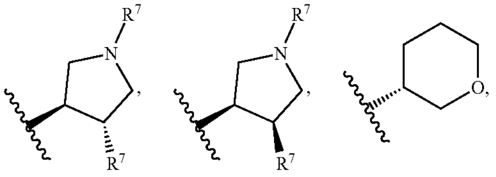

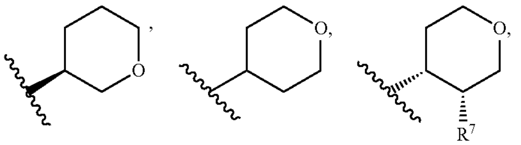

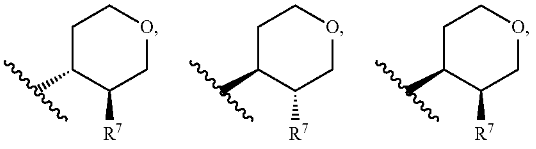

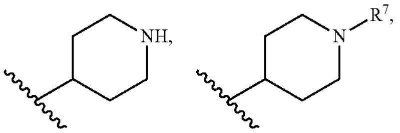

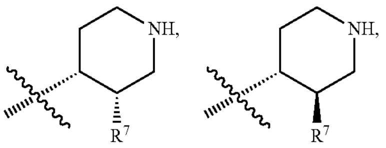

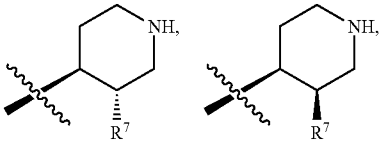

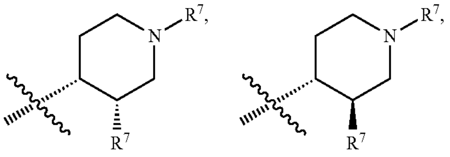

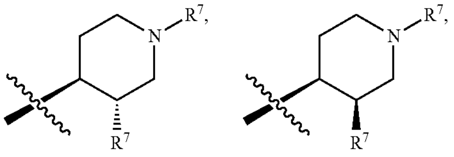

wherein each $R^7$ is independently selected from the group consisting of F, Me, Et, iPr, iBu, —$CH_2F$, —$CHF_2$, —$CF_3$, —$CH_2OH$, —$CH_2OMe$, —OH, —OMe, —OEt, —$OCD_3$, —$OCF_3$, —$CH_2CH_2F$, —$CH_2CHF_2$, —$CH_2CF_3$, —$CH_2CH_2CF_3$, —$CH_2CH_2OMe$, —$CH_2CH_2OH$, —C(═O)Me, —C(═O)Et, —C(═O)iPr,

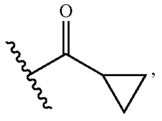 [SMILES: *C(=O)C1CC1]
, and $-SO_2Me$; with the proviso that F, —OH, —OMe, —OEt, $-OCD_3$, and $-OCF_3$ are not attached to N.

In some embodiments of Formula I, $R^2$ is selected from the group consisting of:

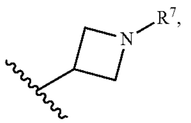
, 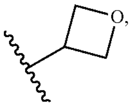
, 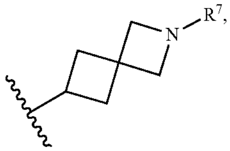
, 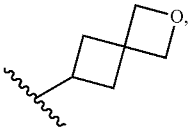
, 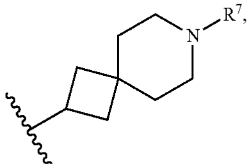
, 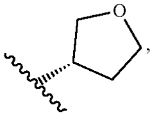
, 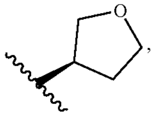
, 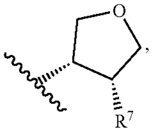
, 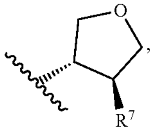
, 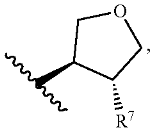
, 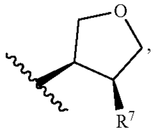
, 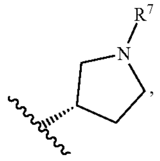
, 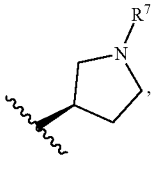
, 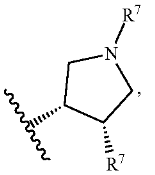
, 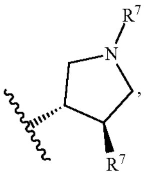
, 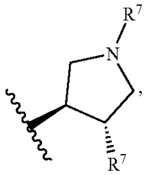
, 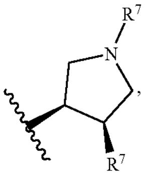
, 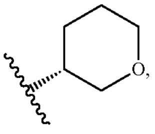
, 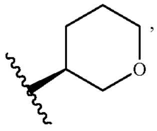
, 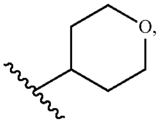
, 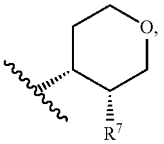
, 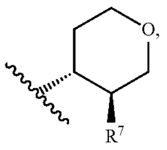
, 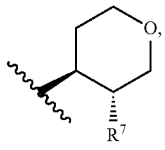
, 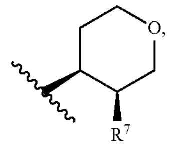
, -continued

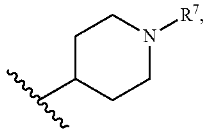
, 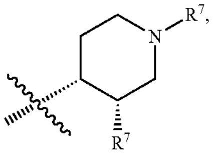
, 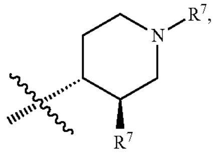
, 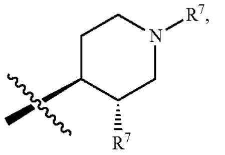
, 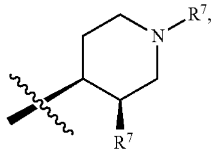
, wherein each $R^7$ is independently selected from the group consisting of F, Me, iBu, —OH, —OMe, $-CH_2CH_2F$, $-CH_2CHF_2$, $-CH_2CF_3$, $-CH_2CH_2CF_3$, $-CH_2CH_2OMe$, $-CH_2CH_2OH$, —C(═O)Me, —C(═O)Et, and —C(═O)iPr; with the proviso that F, —OH, —OMe are not attached to N.

In some embodiments of Formula I, $R^2$ is -heteroaryl optionally substituted with 1-2 $R^6$, wherein the heteroaryl is pyrazolyl.

In some embodiments of Formula I, $R^2$ is $-(C_{1-2}$ alkylene$)_p$carbocyclyl optionally substituted with 1-3 $R^7$, wherein the $-(C_{1-5}$ alkylene) is optionally substituted with 1-2 halide and wherein the carbocyclyl is selected from the group consisting of cyclopropyl, cyclobutyl, cyclopentyl, cyclohexyl, and spiro[3.3]heptanyl.

In some embodiments of Formula I, each $R^3$ is independently selected from the group consisting of halide (e.g., F, Cl, Br, I), unsubstituted $-(C_{1-9}$ alkyl), unsubstituted $-(C_{2-9}$ alkenyl), unsubstituted $-(C_{2-9}$ alkynyl), unsubstituted $-(C_{1-9}$ haloalkyl), $-(C_{1-5}$ alkylene$)_p$OR, -heterocyclyl optionally substituted with 1-10 (e.g., 1-9, 1-8, 1-7, 1-6, 1-5, 1-4, 1-3, 1-2, 1) $R^9$, -carbocyclyl optionally substituted with 1-12 (e.g., 1-11, 1-10, 1-9, 1-8, 1-7, 1-6, 1-5, 1-4, 1-3, 1-2, 1) $R^{10}$, $-C(=O)N(R^{11})_2$, and $-C(=O)R^{12}$, wherein the $-(C_{1-5}$ alkylene) is optionally substituted with 1-5 (e.g., 1-4, 1-3, 1-2, 1) halide (e.g., F, Cl, Br, I) and/or 1-3 (e.g., 1-2, 1) unsubstituted $-(C_{1-3}$ alkyl).

In some embodiments of Formula I, each $R^3$ is independently selected from the group consisting of halide, unsubstituted $-(C_{1-9}$ alkyl), unsubstituted $-(C_{2-9}$ alkenyl), unsubstituted $-(C_{2-9}$ alkynyl), unsubstituted $-(C_{1-9}$ haloalkyl), $-(C_{1-5}$ alkylene$)_p$OR, $-(C_{1-5}$ alkylene)CN, $-(C_{1-5}$ alkylene$)_p$heterocyclyl optionally substituted with 1-10 $R^9$, -carbocyclyl optionally substituted with 1-12 $R^{10}$, $-(C_{1-5}$ alkylene$)_p$heteroaryl optionally substituted with 1-10 $R^{19}$, $-(C_{1-5}$ alkylene$)_p$C(═O)N$(R^{11})_2$, and $-C(=O)R^{12}$, wherein each $-(C_{1-5}$ alkylene) is, independently, optionally substituted with 1-5 halide and/or 1-3 unsubstituted $-(C_{1-3}$ alkyl).

In some embodiments of Formula I, each $R^3$ is independently selected from the group consisting of halide (e.g., F, Cl, Br, I), unsubstituted $-(C_{1-9}$ alkyl), unsubstituted $-(C_{1-9}$ haloalkyl), $-(C_{1-5}$ alkylene$)_p$OR$^8$, -heterocyclyl optionally substituted with 1-10 (e.g., 1-9, 1-8, 1-7, 1-6, 1-5, 1-4, 1-3, 1-2, 1) $R^9$, -carbocyclyl optionally substituted with 1-12 (e.g., 1-11, 1-10, 1-9, 1-8, 1-7, 1-6, 1-5, 1-4, 1-3, 1-2, 1) $R^{10}$, and $-C(=O)R^{12}$, wherein the $-(C_{1-5}$ alkylene) is optionally substituted with 1-5 (e.g., 1-4, 1-3, 1-2, 1) halide (e.g., F, Cl, Br, I) and/or 1-3 (e.g., 1-2, 1) unsubstituted —($C_{1-3}$ alkyl).

In some embodiments of Formula I, each $R^3$ is independently selected from the group consisting of halide, unsubstituted —($C_{1-5}$ alkyl), unsubstituted —($C_{2-9}$ alkenyl), unsubstituted —($C_{2-5}$ alkynyl), unsubstituted —($C_{1-5}$ haloalkyl), —($C_{1-4}$ alkylene)$_p$OR, —($C_{1-2}$ alkylene)$_p$OR, —($C_{1-4}$ alkylene)CN, —($C_{1-2}$ alkylene)CN, —($C_{1-2}$ alkylene)$_p$heterocyclyl optionally substituted with 1-2 $R^9$, -carbocyclyl optionally substituted with 1-2 $R^{10}$, —($C_{1-2}$ alkylene)$_p$heteroaryl optionally substituted with 1-2 $R^{19}$, —($C_{1-2}$ alkylene)$_p$C(═O)N($R^{11}$)$_2$, and —C(═O)$R^{12}$, wherein each —($C_{1-2}$ alkylene) or —($C_{1-4}$ alkylene) is, independently, optionally substituted with 1-2 halide.

In some embodiments of Formula I, each $R^3$ is independently selected from the group consisting of F, Cl, unsubstituted —($C_{1-5}$ alkyl), unsubstituted —($C_{1-5}$ haloalkyl), —($C_{1-4}$ alkylene)$_p$OH, —($C_{1-2}$alkylene)$_p$OMe, —($C_{1-4}$ alkylene)CN, —($C_{1-2}$alkylene)CN, —($CH_2$)$_p$heterocyclyl optionally substituted with 1-2 $R^9$, -carbocyclyl optionally substituted with 1-2 $R^{10}$, —($CH_2$)$_p$heteroaryl optionally substituted with 1-2 $R^{19}$, —($CH_2$)C(═O)N(Me)$_2$, and —C(═O)$R^{12}$, wherein each —($C_{1-2}$ alkylene) or —($C_{1-4}$ alkylene) is, independently, optionally substituted with 1-2 halide.

In some embodiments of Formula I, each $R^3$ is independently selected from the group consisting of halide (e.g., F, Cl, Br, I), unsubstituted —($C_{1-4}$ alkyl), unsubstituted —($C_{1-4}$ haloalkyl), -heterocyclyl optionally substituted with 1-3 (e.g., 1-2, 1) $R^9$, and -carbocyclyl optionally substituted with 1-3 (e.g., 1-2, 1) $R^{10}$.

In some embodiments of Formula I, each $R^3$ is independently selected from the group consisting of halide, unsubstituted —($C_{1-3}$ alkyl), unsubstituted —($C_{1-3}$ haloalkyl), —($C_{1-3}$ alkylene)$_p$O$R^8$, -heterocyclyl optionally substituted with 1-2 $R^9$, -carbocyclyl optionally substituted with 1-2 $R^{10}$, and —C(═O)$R^{12}$.

In some embodiments of Formula I, each $R^3$ is independently selected from the group consisting of chloro, methyl, ethyl, isopropyl, 2-fluoroethyl, 2,2-difluoroethyl, methoxy, methoxymethyl, tetrahydropyranyl, difluorocyclobutyl, and (pyrrolidin-1-yl)methanone.

In some embodiments of Formula I, each $R^4$ is independently selected from the group consisting of unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, each $R^4$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, each $R^4$ is independently selected from the group consisting of H, unsubstituted —($C_{1-5}$ alkyl), unsubstituted —($C_{2-5}$ alkenyl), unsubstituted —($C_{2-5}$ alkynyl), and unsubstituted —($C_{1-5}$ haloalkyl).

In some embodiments of Formula I, each $R^4$ is independently selected from the group consisting of H, unsubstituted —($C_{1-3}$ alkyl), and unsubstituted —($C_{1-3}$ haloalkyl).

In some embodiments of Formula I, each $R^5$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —OMe.

In some embodiments of Formula I, each $R^5$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), -heterocyclyl optionally substituted with 1-10 (e.g., 1-9, 1-8, 1-7, 1-6, 1-5, 1-4, 1-3, 1-2, 1) $R^{15}$, —($C_{1-5}$ alkylene)$_p$O$R^{20}$, —$SO_2R^{22}$, and —C(═O)$R^{23}$, wherein the —($C_{1-5}$ alkylene) is optionally substituted with 1-5 halide and/or 1-3 unsubstituted —($C_{1-3}$ alkyl).

In some embodiments of Formula I, each $R^5$ is independently selected from the group consisting of F, Cl, unsubstituted —($C_{1-5}$ alkyl), unsubstituted —($C_{1-5}$ haloalkyl), -heterocyclyl optionally substituted with 1-2 $R^{15}$, —($C_{1-2}$ alkylene)$_p$O$R^{20}$, —$SO_2R^{22}$, and —C(═O)$R^{23}$, wherein the —($C_{1-2}$ alkylene) is optionally substituted with 1-2 halide.

In some embodiments of Formula I, each $R^5$ is independently selected from the group consisting of F, Cl, unsubstituted —($C_{1-5}$ alkyl), unsubstituted —($C_{1-5}$ haloalkyl), -heterocyclyl optionally substituted with 1-2 $R^{15}$, —OH, —OMe, —$SO_2$Me, and —C(═O)$R^{23}$.

In some embodiments of Formula I, two $R^5$ attached to the same carbon atom are taken together to form a carbonyl group.

In some embodiments of Formula I, each $R^6$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —OMe.

In some embodiments of Formula I, each $R^6$ is independently selected from the group consisting of F, Cl, Me, $CF_3$, and —OMe.

In some embodiments of Formula I, each $R^7$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —N($R^{13}$)$_2$, —($C_{1-5}$ alkylene)$_p$O$R^{14}$, and -heterocyclyl optionally substituted with 1-10 (e.g., 1-9, 1-8, 1-7, 1-6, 1-5, 1-4, 1-3, 1-2, 1) $R^{15}$, wherein —($C_{1-5}$ alkylene) is optionally substituted with 1-5 (e.g., 1-4, 1-3, 1-2, 1) halide (e.g., F, Cl, Br, I) and/or 1-3 (e.g., 1-2, 1) unsubstituted —($C_{1-3}$ alkyl).

In some embodiments of Formula I, each $R^7$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —N($R^{13}$)$_2$, —($C_{1-5}$ alkylene)$_p$O$R^{14}$, —($C_{1-5}$ alkylene)$_p$heterocyclyl optionally substituted with 1-10 $R^{15}$, —C(═O)$R^{21}$, and —NHC(═O)$R^{22}$, wherein each —($C_{1-5}$ alkylene) is, independently, optionally substituted with 1-5 halide and/or 1-3 unsubstituted —($C_{1-3}$ alkyl).

In some embodiments of Formula I, each $R^7$ is independently selected from the group consisting of halide, unsubstituted —($C_{1-5}$ alkyl), unsubstituted —($C_{2-5}$ alkenyl), unsubstituted —($C_2$_s alkynyl), unsubstituted —($C_{1-5}$ haloalkyl), —N($R^{13}$)$_2$, —($C_{1-2}$ alkylene)$_p$O$R^{14}$, —($C_{1-2}$ alkylene)$_p$heterocyclyl optionally substituted with 1-2 $R^{15}$, —C(═O)$R^{21}$, and —NHC(═O)$R^{22}$, wherein each —($C_{1-2}$ alkylene) is, independently, optionally substituted with 1-2 halide.

In some embodiments of Formula I, each $R^8$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, each $R^9$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, each $R^{10}$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, each $R^{11}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl), —($C_{1-5}$ alkylene)$_p$carbocyclyl optionally substituted with 1-12 (e.g., 1-11, 1-10, 1-9, 1-8, 1-7, 1-6, 1-5, 1-4, 1-3, 1-2, 1) $R^{16}$, -heterocyclyl optionally substituted with 1-10 (e.g., 1-9, 1-8, 1-7, 1-6, 1-5, 1-4, 1-3, 1-2, 1) $R^{17}$, and -heteroaryl optionally substituted with 1-10 (e.g., 1-9, 1-8, 1-7, 1-6, 1-5, 1-4, 1-3, 1-2, 1) $R^{18}$, wherein —($C_{1-5}$ alkylene) is optionally substituted with 1-5 (e.g., 1-4, 1-3, 1-2, 1) halide (e.g., F, Cl, Br, I) and/or 1-3 (e.g., 1-2, 1) unsubstituted —($C_{1-3}$ alkyl).

In some embodiments of Formula I, each $R^{12}$ is -heterocyclyl optionally substituted with 1-10 (e.g., 1-9, 1-8, 1-7, 1-6, 1-5, 1-4, 1-3, 1-2, 1) $R^{17}$.

In some embodiments of Formula I, each $R^{13}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, each $R^{14}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, each $R^{14}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —($C_{1-5}$ alkylene)$_p$OR$^{20}$.

In some embodiments of Formula I, each $R^{15}$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, two $R^{15}$ attached to the same carbon atom are taken together to form a carbonyl group.

In some embodiments of Formula I, each $R^{16}$ is independently selected from the group consisting of halide (e.g., F, Cl, Br, I), —OMe, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, each $R^{17}$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, each $R^{18}$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, each $R^{19}$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, each $R^{20}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, each $R^{21}$ is independently selected from the group consisting of -heterocyclyl optionally substituted with 1-10 (e.g., 1-9, 1-8, 1-7, 1-6, 1-5, 1-4, 1-3, 1-2, 1) $R^{17}$, —N($R^{11}$)$_2$ and —OR$^{20}$.

In some embodiments of Formula I, each $R^{22}$ is independently selected from the group consisting of unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, each $R^{22}$ is independently selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —($C_{1-5}$ alkylene)$_p$OR$^{20}$.

In some embodiments of Formula I, each $R^{23}$ is independently selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and -carbocyclyl optionally substituted with 1-12 (e.g., 1-11, 1-10, 1-9, 1-8, 1-7, 1-6, 1-5, 1-4, 1-3, 1-2, 1) $R^{24}$.

In some embodiments of Formula I, each $R^{24}$ is independently selected from the group consisting of halide (e.g., F, Cl, Br, I), unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl).

In some embodiments of Formula I, each p is independently 0 or 1.

In some embodiments of Formula I, each H atom is optionally, independently replaced by $^2$H (D) (deuterium).

Illustrative compounds of Formula I are shown in Table 1.

TABLE 1

1

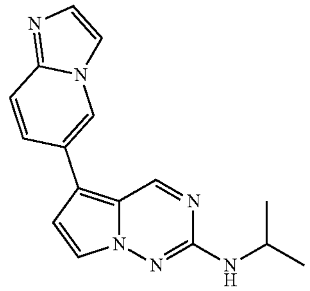 [SMILES: CC(C)Nc1ncc2c(-c3ccc4nccn4c3)ccn2n1]

TABLE 1-continued
2
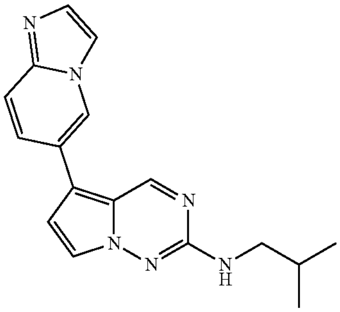 [SMILES: CC(C)CNc1ncc2c(-c3ccc4nccn4c3)ccn2n1]
3
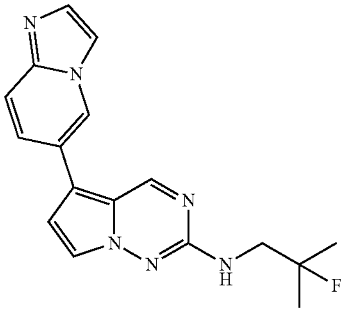 [SMILES: CC(C)(F)CNc1ncc2c(-c3ccc4nccn4c3)ccn2n1]
4
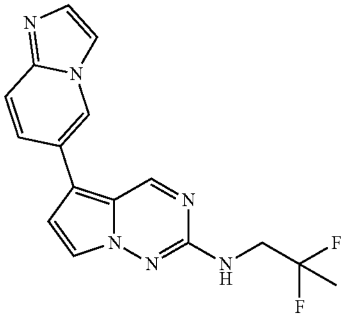 [SMILES: CC(F)(F)CNc1ncc2c(-c3ccc4nccn4c3)ccn2n1]
5
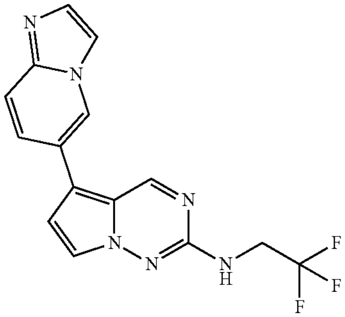 [SMILES: FC(F)(F)CNc1ncc2c(-c3ccc4nccn4c3)ccn2n1]
6
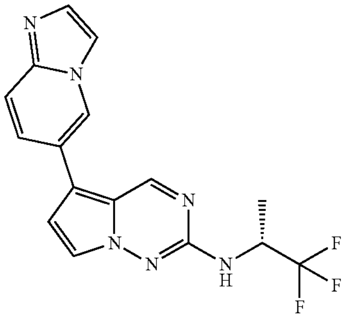 [SMILES: C[C@@H](Nc1ncc2c(-c3ccc4nccn4c3)ccn2n1)C(F)(F)F]

TABLE 1-continued
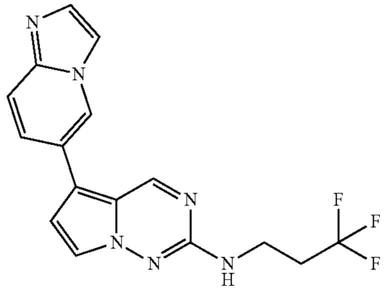 [SMILES: FC(F)(F)CCNc1ncc2c(-c3ccc4nccn4c3)ccn2n1]
7
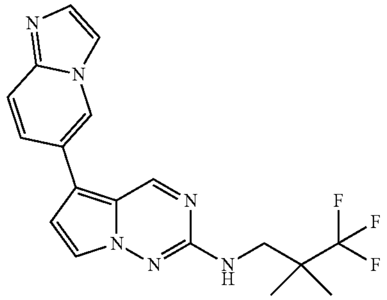 [SMILES: CC(C)(CNc1ncc2c(-c3ccc4nccn4c3)ccn2n1)C(F)(F)F]
8
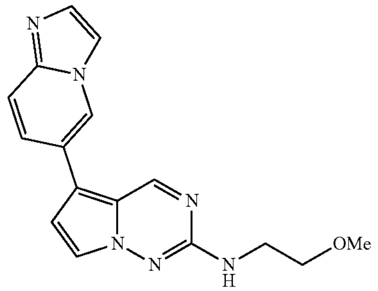 [SMILES: COCCNc1ncc2c(-c3ccc4nccn4c3)ccn2n1]
9
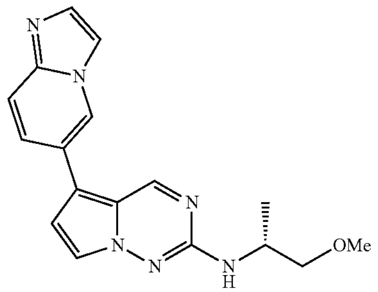 [SMILES: COC[C@@H](C)Nc1ncc2c(-c3ccc4nccn4c3)ccn2n1]
10
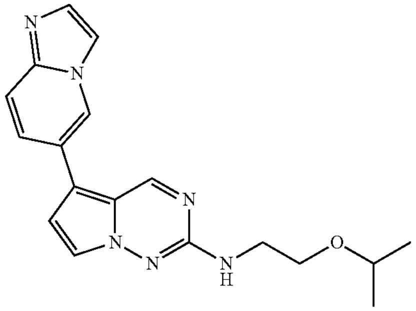 [SMILES: CC(C)OCCNc1ncc2c(-c3ccc4nccn4c3)ccn2n1]
11

TABLE 1-continued
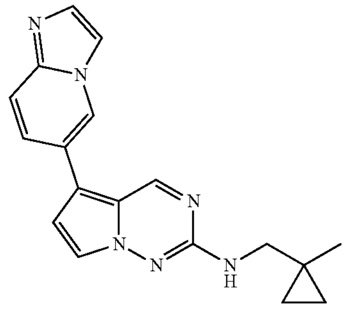 [SMILES: CC1(CNc2ncc3c(-c4ccc5nccn5c4)ccn3n2)CC1]
12
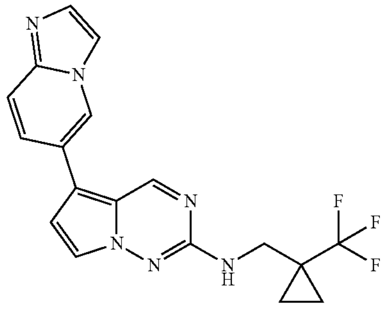 [SMILES: FC(F)(F)C1(CNc2ncc3c(-c4ccc5nccn5c4)ccn3n2)CC1]
13
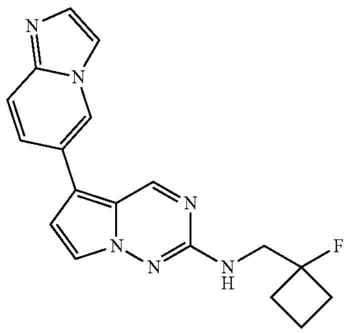 [SMILES: FC1(CNc2ncc3c(-c4ccc5nccn5c4)ccn3n2)CCC1]
14
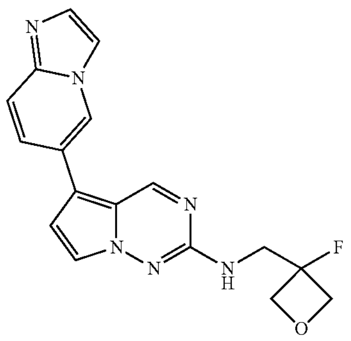 [SMILES: FC1(CNc2ncc3c(-c4ccc5nccn5c4)ccn3n2)COC1]
15
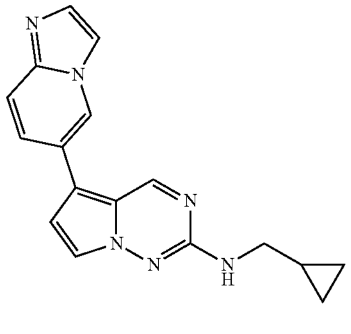 [SMILES: c1cn2cc(-c3ccn4nc(NCC5CC5)ncc34)ccc2n1]
16

TABLE 1-continued
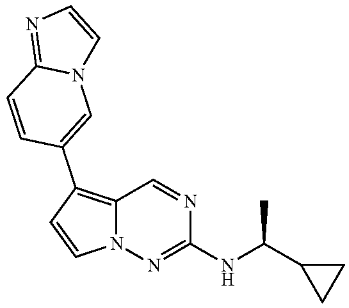 [SMILES: C[C@H](Nc1ncc2c(-c3ccc4nccn4c3)ccn2n1)C1CC1]
17
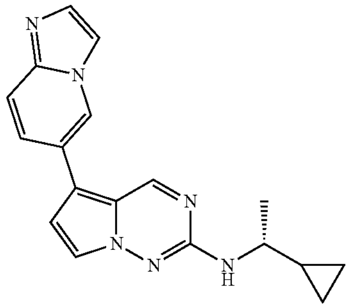 [SMILES: C[C@@H](Nc1ncc2c(-c3ccc4nccn4c3)ccn2n1)C1CC1]
18
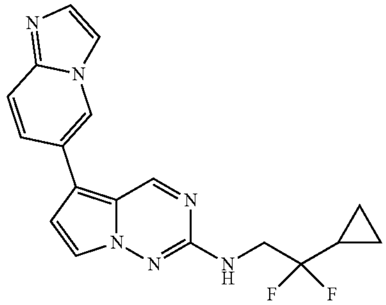 [SMILES: FC(F)(CNc1ncc2c(-c3ccc4nccn4c3)ccn2n1)C1CC1]
19
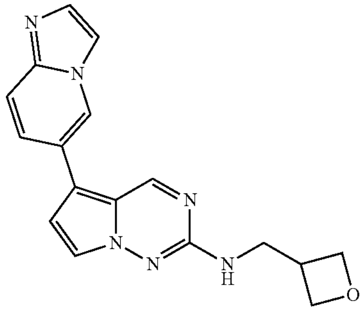 [SMILES: c1cn2cc(-c3ccn4nc(NCC5COC5)ncc34)ccc2n1]
20
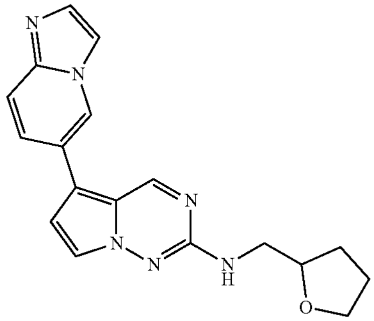 [SMILES: c1cn2cc(-c3ccn4nc(NCC5CCCO5)ncc34)ccc2n1]
21

TABLE 1-continued
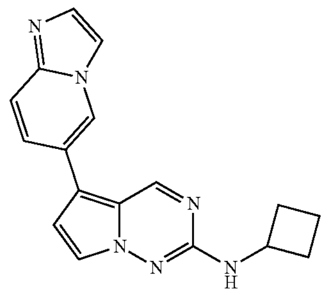 [SMILES: c1cn2cc(-c3ccn4nc(NC5CCC5)ncc34)ccc2n1]
22
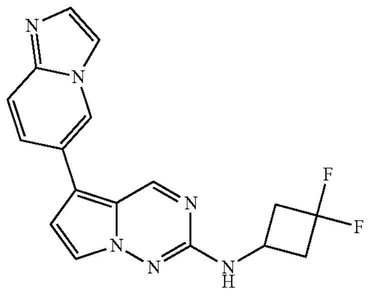 [SMILES: FC1(F)CC(Nc2ncc3c(-c4ccc5nccn5c4)ccn3n2)C1]
23
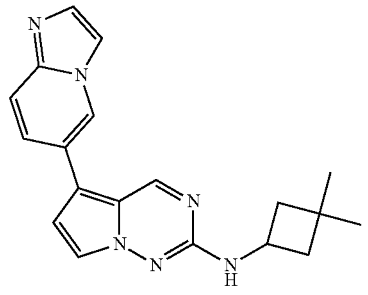 [SMILES: CC1(C)CC(Nc2ncc3c(-c4ccc5nccn5c4)ccn3n2)C1]
24
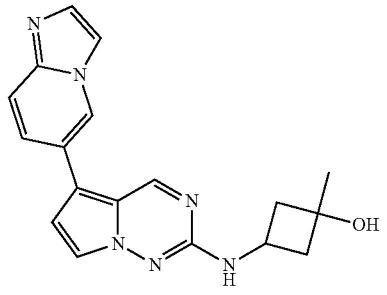 [SMILES: CC1(O)CC(Nc2ncc3c(-c4ccc5nccn5c4)ccn3n2)C1]
25
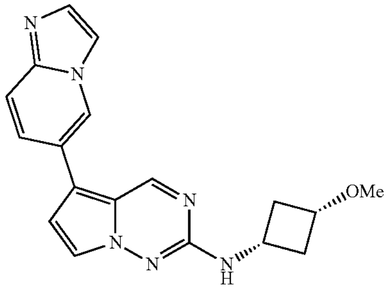 [SMILES: CO[C@H]1C[C@@H](Nc2ncc3c(-c4ccc5nccn5c4)ccn3n2)C1]
26

TABLE 1-continued
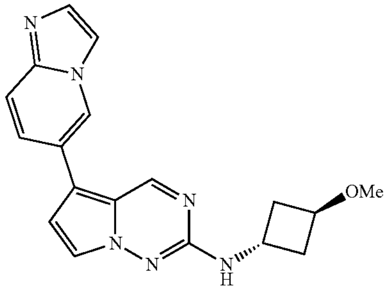 [SMILES: CO[C@H]1C[C@H](Nc2ncc3c(-c4ccc5nccn5c4)ccn3n2)C1]
27
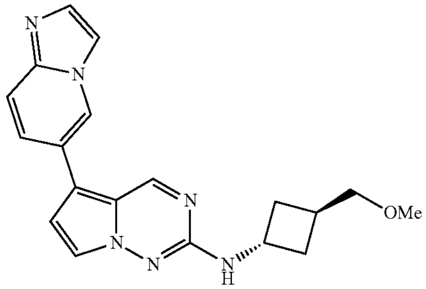 [SMILES: COC[C@H]1C[C@H](Nc2ncc3c(-c4ccc5nccn5c4)ccn3n2)C1]
28
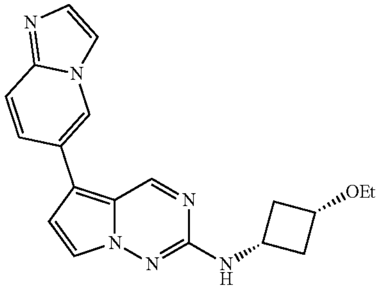 [SMILES: CCO[C@H]1C[C@@H](Nc2ncc3c(-c4ccc5nccn5c4)ccn3n2)C1]
29
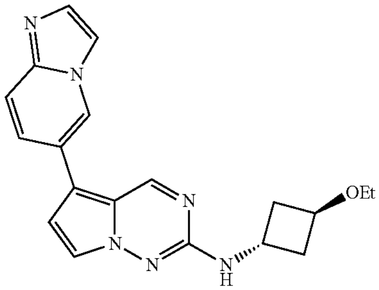 [SMILES: CCO[C@H]1C[C@H](Nc2ncc3c(-c4ccc5nccn5c4)ccn3n2)C1]
30
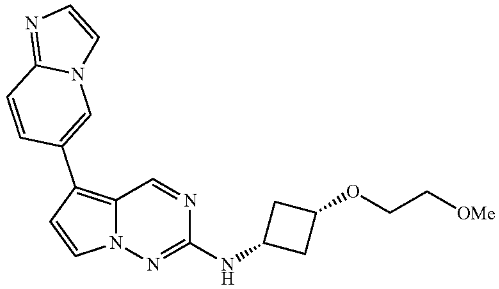 [SMILES: COCCO[C@H]1C[C@@H](Nc2ncc3c(-c4ccc5nccn5c4)ccn3n2)C1]
31

TABLE 1-continued
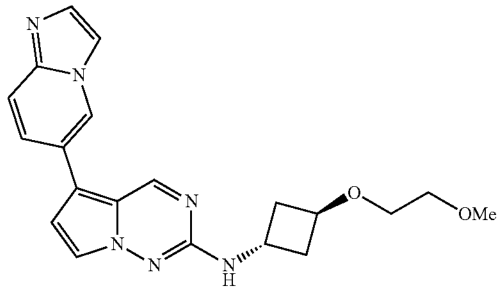 [SMILES: COCCO[C@H]1C[C@H](Nc2ncc3c(-c4ccc5nccn5c4)ccn3n2)C1]
32
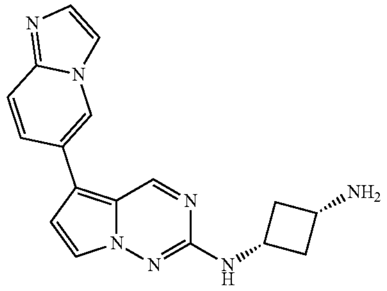 [SMILES: N[C@H]1C[C@@H](Nc2ncc3c(-c4ccc5nccn5c4)ccn3n2)C1]
33
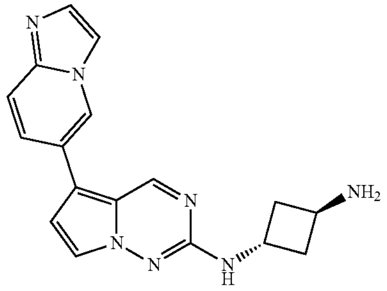 [SMILES: N[C@H]1C[C@H](Nc2ncc3c(-c4ccc5nccn5c4)ccn3n2)C1]
34
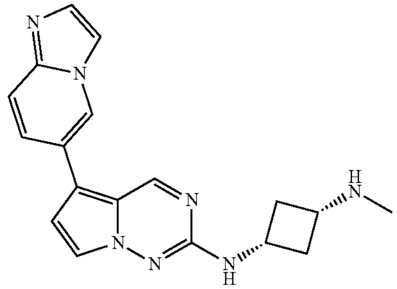 [SMILES: CN[C@H]1C[C@@H](Nc2ncc3c(-c4ccc5nccn5c4)ccn3n2)C1]
35
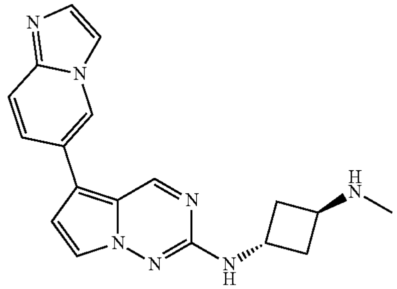 [SMILES: CN[C@H]1C[C@H](Nc2ncc3c(-c4ccc5nccn5c4)ccn3n2)C1]
36

TABLE 1-continued
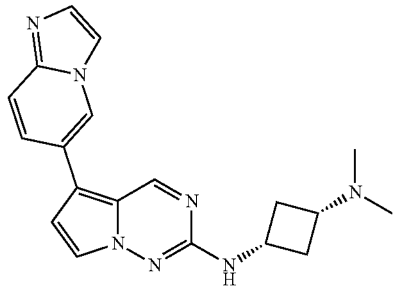 [SMILES: CN(C)[C@H]1C[C@@H](Nc2ncc3c(-c4ccc5nccn5c4)ccn3n2)C1]
37
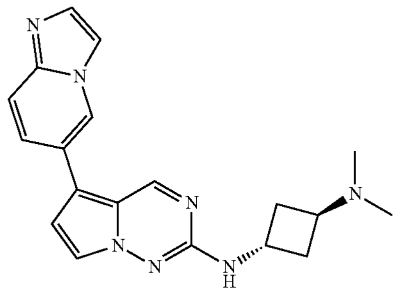 [SMILES: CN(C)[C@H]1C[C@H](Nc2ncc3c(-c4ccc5nccn5c4)ccn3n2)C1]
38
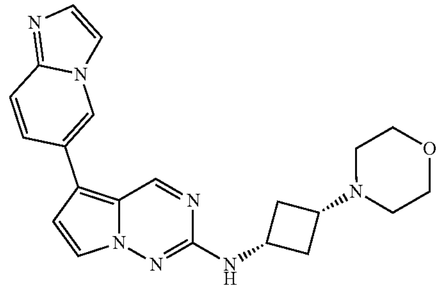 [SMILES: c1cn2cc(-c3ccn4nc(N[C@H]5C[C@@H](N6CCOCC6)C5)ncc34)ccc2n1]
39
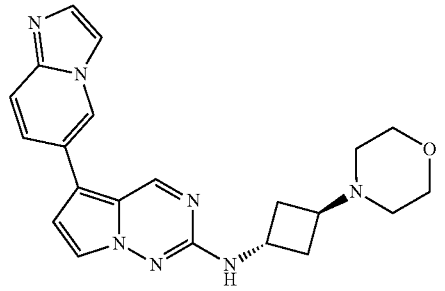 [SMILES: c1cn2cc(-c3ccn4nc(N[C@H]5C[C@H](N6CCOCC6)C5)ncc34)ccc2n1]
40
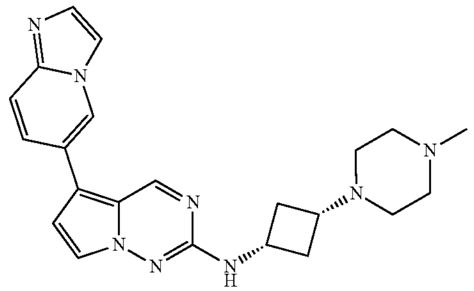 [SMILES: CN1CCN([C@H]2C[C@@H](Nc3ncc4c(-c5ccc6nccn6c5)ccn4n3)C2)CC1]
41

TABLE 1-continued
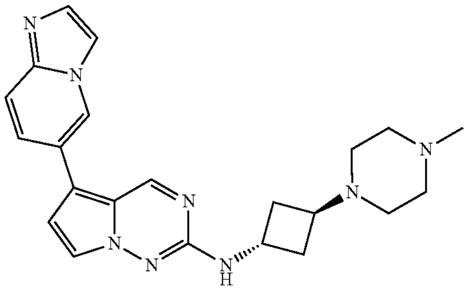 [SMILES: CN1CCN([C@H]2C[C@H](Nc3ncc4c(-c5ccc6nccn6c5)ccn4n3)C2)CC1]
42
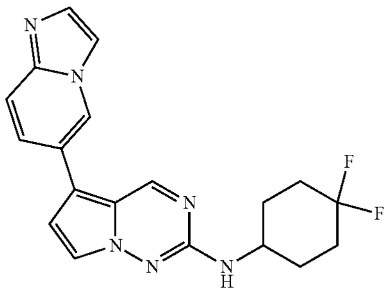 [SMILES: FC1(F)CCC(Nc2ncc3c(-c4ccc5nccn5c4)ccn3n2)CC1]
43
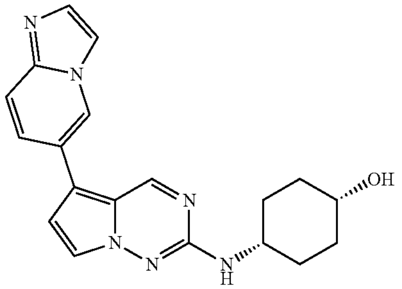 [SMILES: O[C@H]1CC[C@@H](Nc2ncc3c(-c4ccc5nccn5c4)ccn3n2)CC1]
44
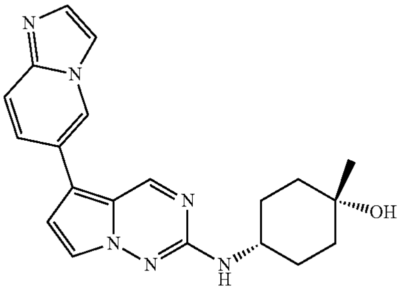 [SMILES: C[C@]1(O)CC[C@@H](Nc2ncc3c(-c4ccc5nccn5c4)ccn3n2)CC1]
45
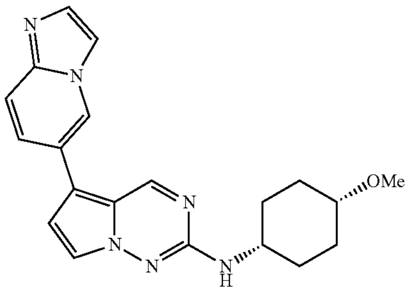 [SMILES: CO[C@H]1CC[C@@H](Nc2ncc3c(-c4ccc5nccn5c4)ccn3n2)CC1]
46

TABLE 1-continued
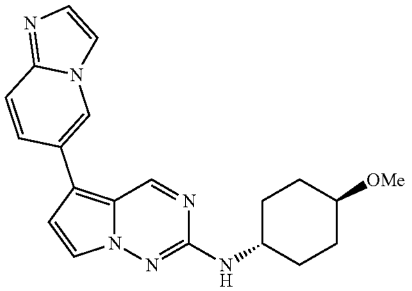 [SMILES: CO[C@H]1CC[C@H](Nc2ncc3c(-c4ccc5nccn5c4)ccn3n2)CC1]
47
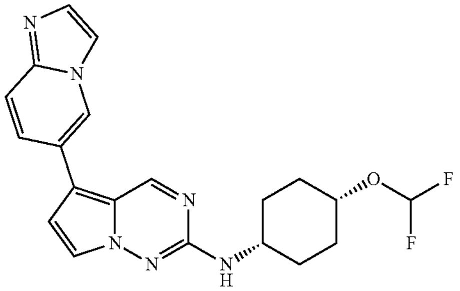 [SMILES: FC(F)O[C@H]1CC[C@@H](Nc2ncc3c(-c4ccc5nccn5c4)ccn3n2)CC1]
48
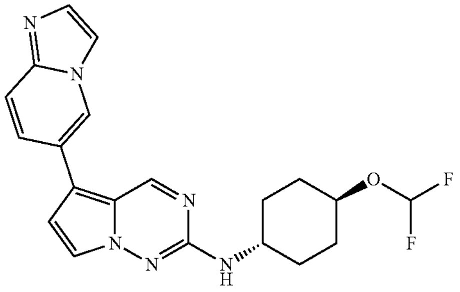 [SMILES: FC(F)O[C@H]1CC[C@H](Nc2ncc3c(-c4ccc5nccn5c4)ccn3n2)CC1]
49
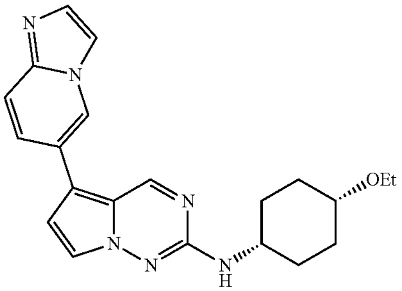 [SMILES: CCO[C@H]1CC[C@@H](Nc2ncc3c(-c4ccc5nccn5c4)ccn3n2)CC1]
50
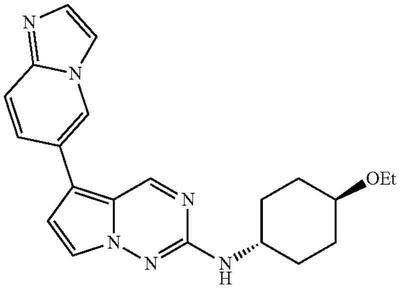 [SMILES: CCO[C@H]1CC[C@H](Nc2ncc3c(-c4ccc5nccn5c4)ccn3n2)CC1]
51

TABLE 1-continued
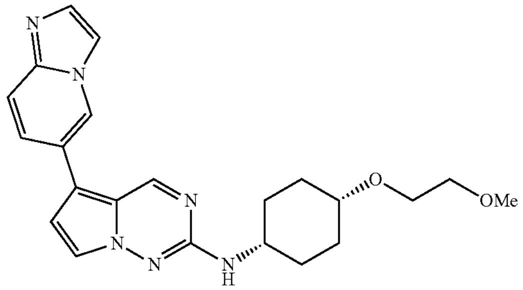
52
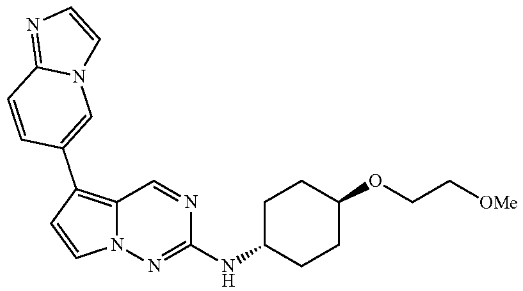 [SMILES: COCCO[C@H]1CC[C@H](Nc2ncc3c(-c4ccc5nccn5c4)ccn3n2)CC1]
53
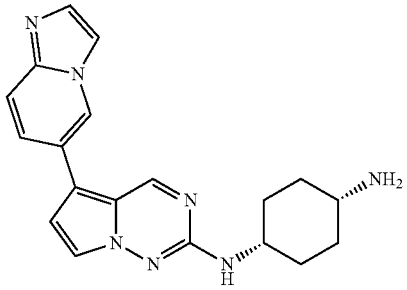 [SMILES: N[C@H]1CC[C@@H](Nc2ncc3c(-c4ccc5nccn5c4)ccn3n2)CC1]
54
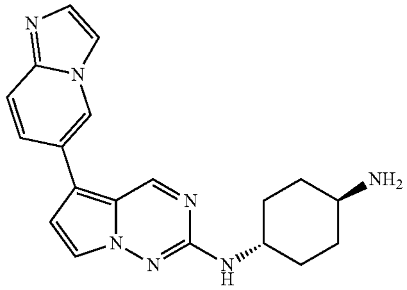 [SMILES: N[C@H]1CC[C@H](Nc2ncc3c(-c4ccc5nccn5c4)ccn3n2)CC1]
55
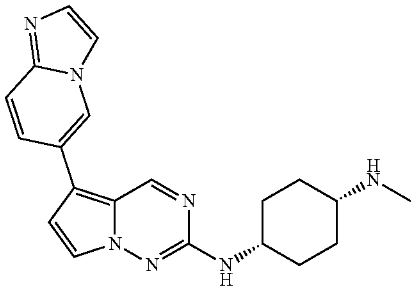 [SMILES: CN[C@H]1CC[C@@H](Nc2ncc3c(-c4ccc5nccn5c4)ccn3n2)CC1]
56

TABLE 1-continued
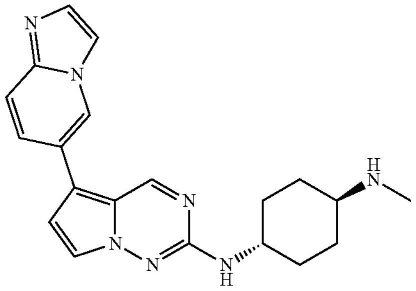 [SMILES: CN[C@H]1CC[C@H](Nc2ncc3c(-c4ccc5nccn5c4)ccn3n2)CC1]
57
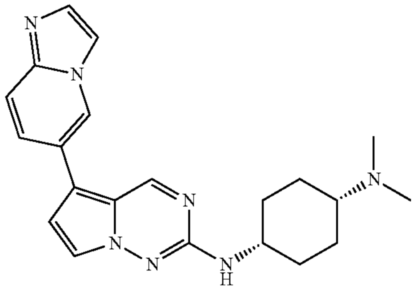 [SMILES: CN(C)[C@H]1CC[C@@H](Nc2ncc3c(-c4ccc5nccn5c4)ccn3n2)CC1]
58
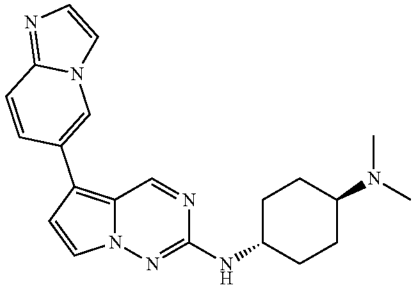 [SMILES: CN(C)[C@H]1CC[C@H](Nc2ncc3c(-c4ccc5nccn5c4)ccn3n2)CC1]
59
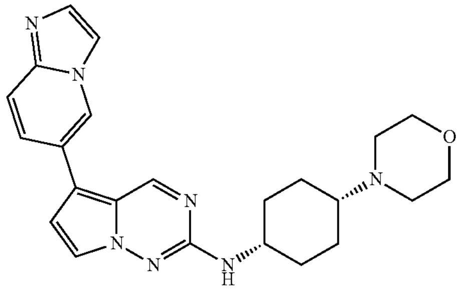 [SMILES: c1cn2cc(-c3ccn4nc(N[C@H]5CC[C@@H](N6CCOCC6)CC5)ncc34)ccc2n1]
60
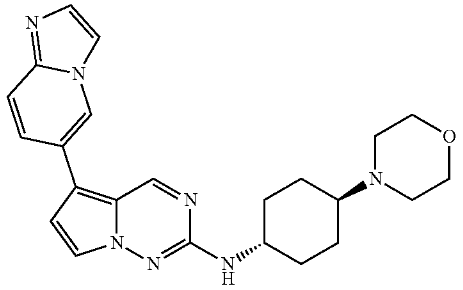
61

TABLE 1-continued
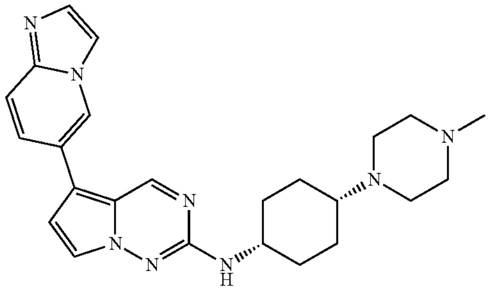 [SMILES: CN1CCN([C@H]2CC[C@@H](Nc3ncc4c(-c5ccc6nccn6c5)ccn4n3)CC2)CC1]
62
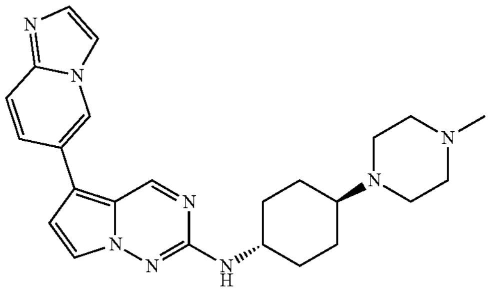 [SMILES: CN1CCN([C@H]2CC[C@H](Nc3ncc4c(-c5ccc6nccn6c5)ccn4n3)CC2)CC1]
63
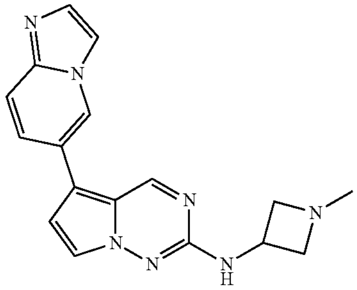 [SMILES: CN1CC(Nc2ncc3c(-c4ccc5nccn5c4)ccn3n2)C1]
64
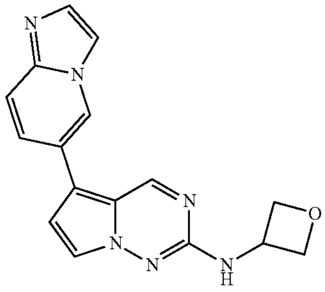 [SMILES: c1cn2cc(-c3ccn4nc(NC5COC5)ncc34)ccc2n1]
65
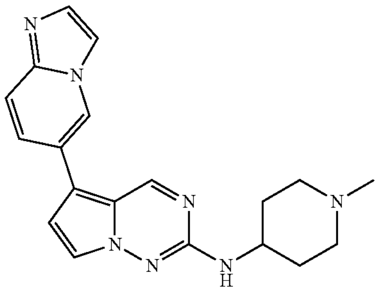
66

TABLE 1-continued
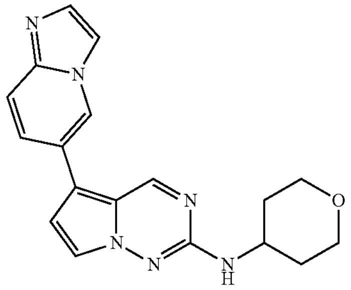
67
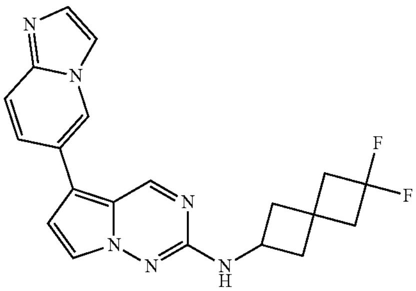
68
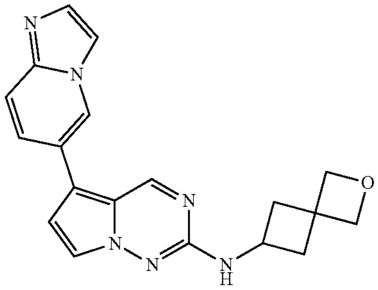 [SMILES: c1cn2cc(-c3ccn4nc(NC5CC6(COC6)C5)ncc34)ccc2n1]
69
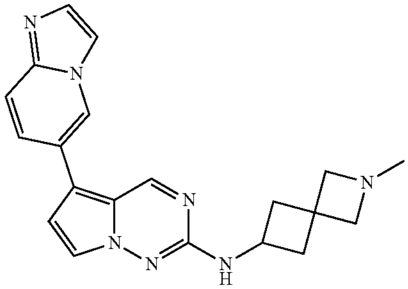 [SMILES: CN1CC2(CC(Nc3ncc4c(-c5ccc6nccn6c5)ccn4n3)C2)C1]
70
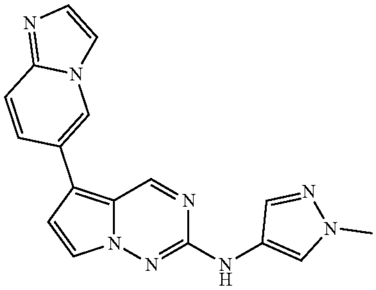
71

TABLE 1-continued
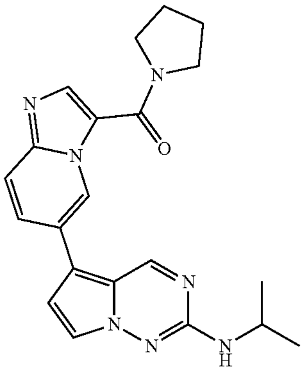 [SMILES: CC(C)Nc1ncc2c(-c3ccc4ncc(C(=O)N5CCCC5)n4c3)ccn2n1]
72
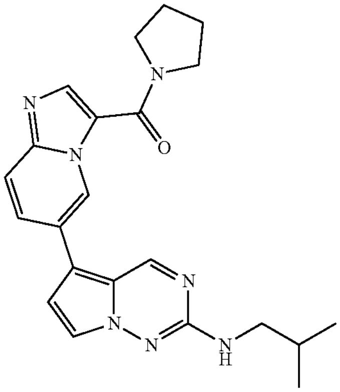 [SMILES: CC(C)CNc1ncc2c(-c3ccc4ncc(C(=O)N5CCCC5)n4c3)ccn2n1]
73
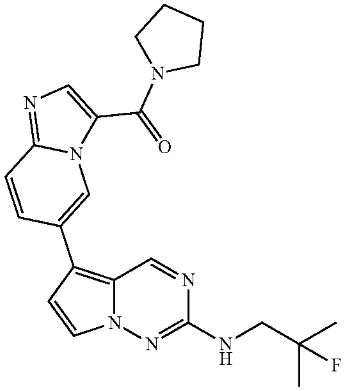 [SMILES: CC(C)(F)CNc1ncc2c(-c3ccc4ncc(C(=O)N5CCCC5)n4c3)ccn2n1]
74
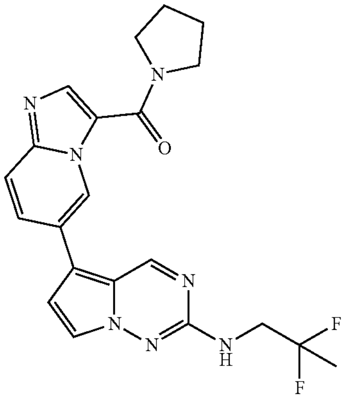 [SMILES: CC(F)(F)CNc1ncc2c(-c3ccc4ncc(C(=O)N5CCCC5)n4c3)ccn2n1]
75

TABLE 1-continued
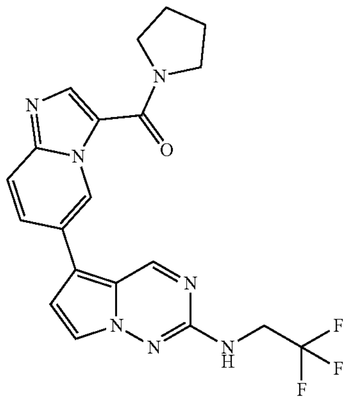 [SMILES: O=C(c1cnc2ccc(-c3ccn4nc(NCC(F)(F)F)ncc34)cn12)N1CCCC1]
76
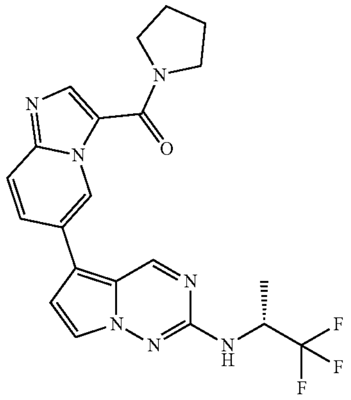 [SMILES: C[C@@H](Nc1ncc2c(-c3ccc4ncc(C(=O)N5CCCC5)n4c3)ccn2n1)C(F)(F)F]
77
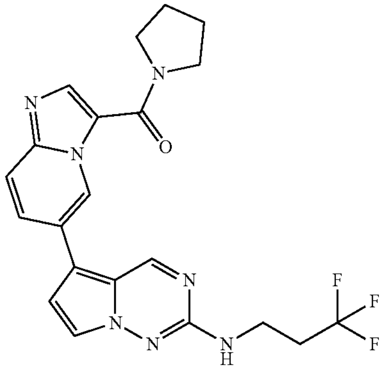 [SMILES: O=C(c1cnc2ccc(-c3ccn4nc(NCCC(F)(F)F)ncc34)cn12)N1CCCC1]
78
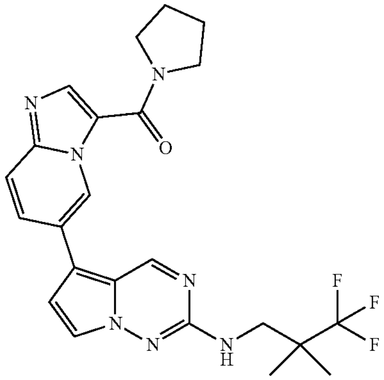 [SMILES: CC(C)(CNc1ncc2c(-c3ccc4ncc(C(=O)N5CCCC5)n4c3)ccn2n1)C(F)(F)F]
79

TABLE 1-continued
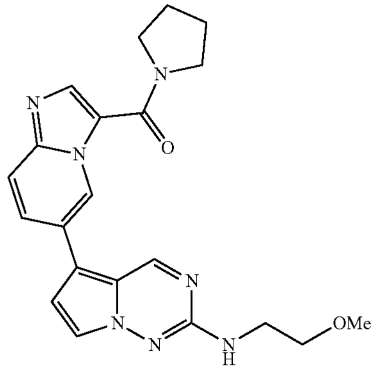 [SMILES: COCCNc1ncc2c(-c3ccc4ncc(C(=O)N5CCCC5)n4c3)ccn2n1]
80
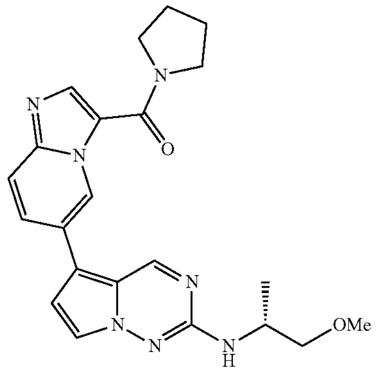 [SMILES: COC[C@@H](C)Nc1ncc2c(-c3ccc4ncc(C(=O)N5CCCC5)n4c3)ccn2n1]
81
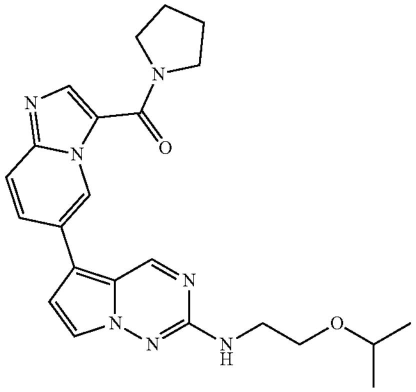 [SMILES: CC(C)OCCNc1ncc2c(-c3ccc4ncc(C(=O)N5CCCC5)n4c3)ccn2n1]
82
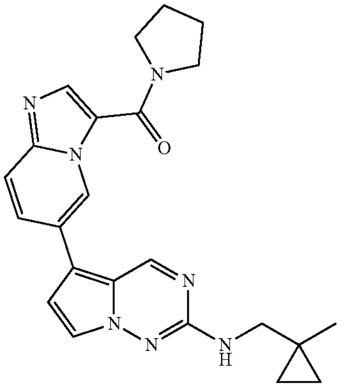 [SMILES: CC1(CNc2ncc3c(-c4ccc5ncc(C(=O)N6CCCC6)n5c4)ccn3n2)CC1]
83

TABLE 1-continued
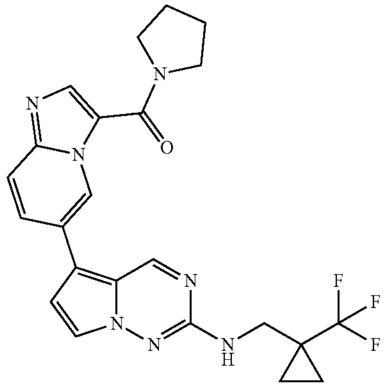 [SMILES: O=C(c1cnc2ccc(-c3ccn4nc(NCC5(C(F)(F)F)CC5)ncc34)cn12)N1CCCC1]
84
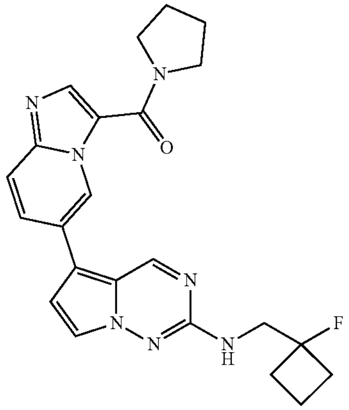 [SMILES: O=C(c1cnc2ccc(-c3ccn4nc(NCC5(F)CCC5)ncc34)cn12)N1CCCC1]
85
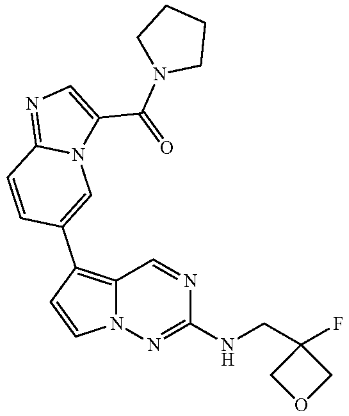 [SMILES: O=C(c1cnc2ccc(-c3ccn4nc(NCC5(F)COC5)ncc34)cn12)N1CCCC1]
86
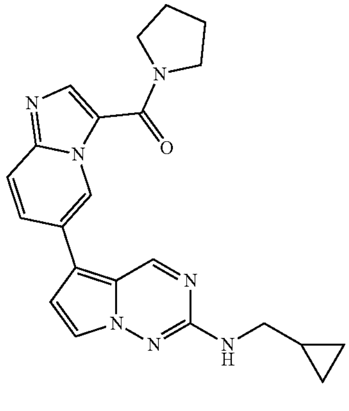 [SMILES: O=C(c1cnc2ccc(-c3ccn4nc(NCC5CC5)ncc34)cn12)N1CCCC1]
87

TABLE 1-continued
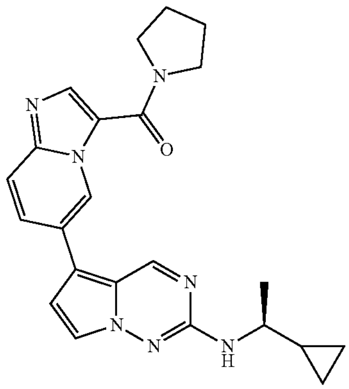 [SMILES: C[C@H](Nc1ncc2c(-c3ccc4ncc(C(=O)N5CCCC5)n4c3)ccn2n1)C1CC1]
88
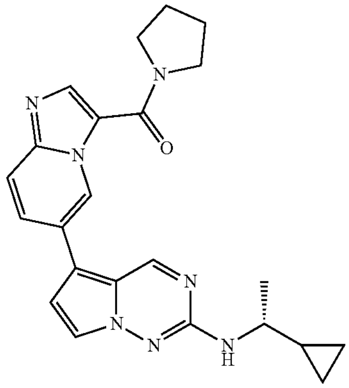 [SMILES: C[C@@H](Nc1ncc2c(-c3ccc4ncc(C(=O)N5CCCC5)n4c3)ccn2n1)C1CC1]
89
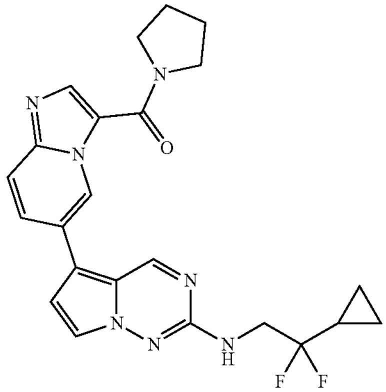 [SMILES: O=C(c1cnc2ccc(-c3ccn4nc(NCC(F)(F)C5CC5)ncc34)cn12)N1CCCC1]
90
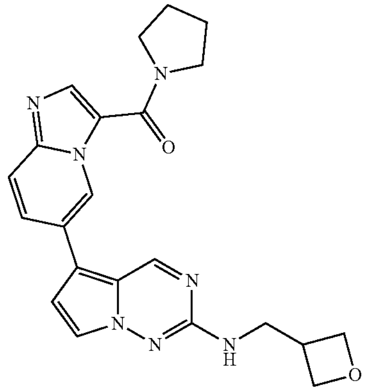 [SMILES: O=C(c1cnc2ccc(-c3ccn4nc(NCC5COC5)ncc34)cn12)N1CCCC1]
91

TABLE 1-continued
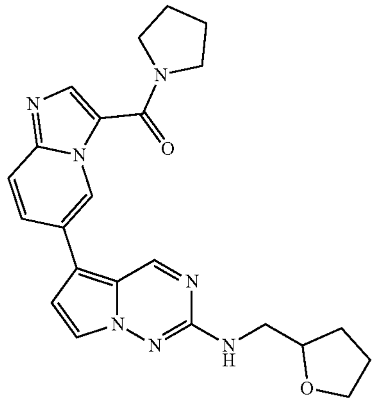 [SMILES: O=C(c1cnc2ccc(-c3ccn4nc(NCC5CCCO5)ncc34)cn12)N1CCCC1]
92
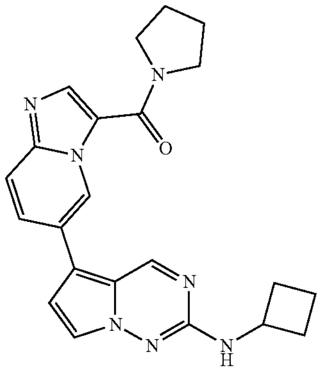 [SMILES: O=C(c1cnc2ccc(-c3ccn4nc(NC5CCC5)ncc34)cn12)N1CCCC1]
93
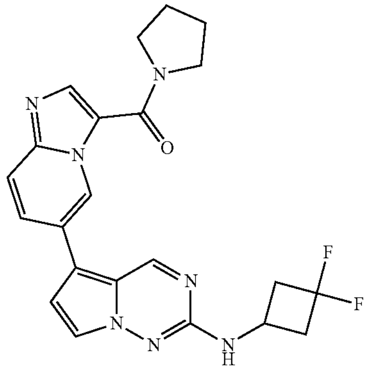 [SMILES: O=C(c1cnc2ccc(-c3ccn4nc(NC5CC(F)(F)C5)ncc34)cn12)N1CCCC1]
94
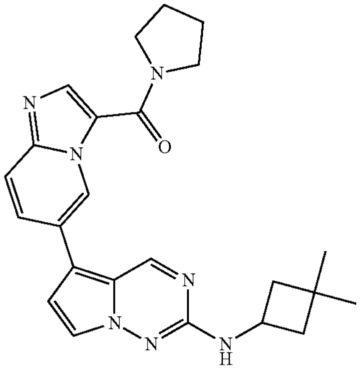 [SMILES: CC1(C)CC(Nc2ncc3c(-c4ccc5ncc(C(=O)N6CCCC6)n5c4)ccn3n2)C1]
95

TABLE 1-continued
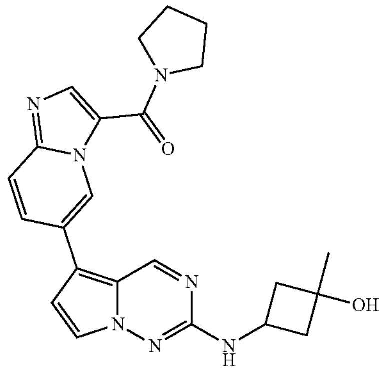 [SMILES: CC1(O)CC(Nc2ncc3c(-c4ccc5ncc(C(=O)N6CCCC6)n5c4)ccn3n2)C1]
96
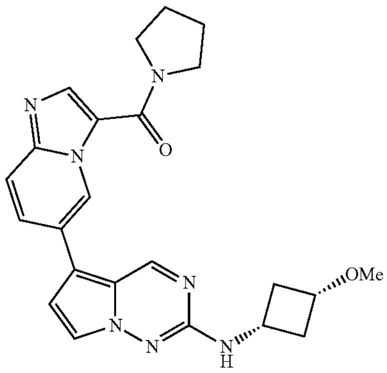 [SMILES: CO[C@H]1C[C@@H](Nc2ncc3c(-c4ccc5ncc(C(=O)N6CCCC6)n5c4)ccn3n2)C1]
97
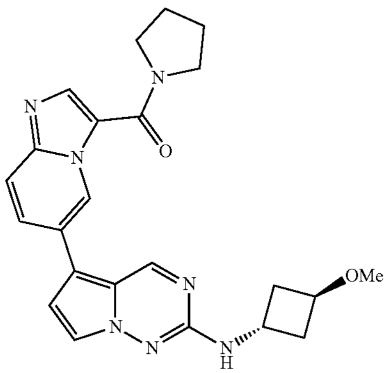 [SMILES: CO[C@H]1C[C@H](Nc2ncc3c(-c4ccc5ncc(C(=O)N6CCCC6)n5c4)ccn3n2)C1]
98
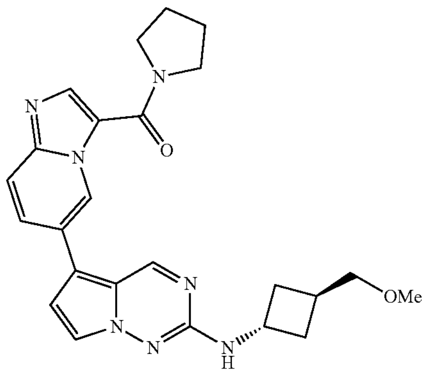 [SMILES: COC[C@H]1C[C@H](Nc2ncc3c(-c4ccc5ncc(C(=O)N6CCCC6)n5c4)ccn3n2)C1]
99

TABLE 1-continued
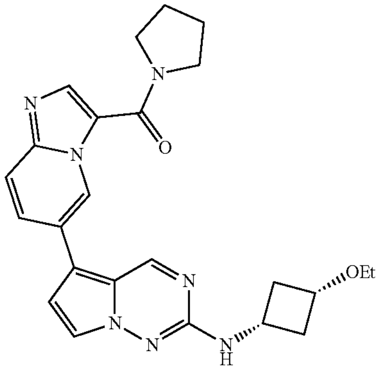 [SMILES: CCO[C@H]1C[C@@H](Nc2ncc3c(-c4ccc5ncc(C(=O)N6CCCC6)n5c4)ccn3n2)C1]
100
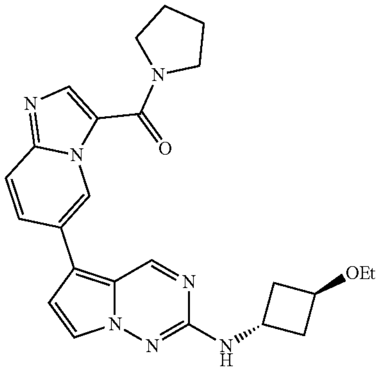 [SMILES: CCO[C@H]1C[C@H](Nc2ncc3c(-c4ccc5ncc(C(=O)N6CCCC6)n5c4)ccn3n2)C1]
101
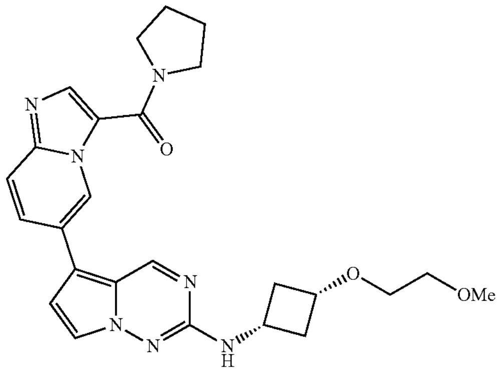 [SMILES: COCCO[C@H]1C[C@@H](Nc2ncc3c(-c4ccc5ncc(C(=O)N6CCCC6)n5c4)ccn3n2)C1]
102
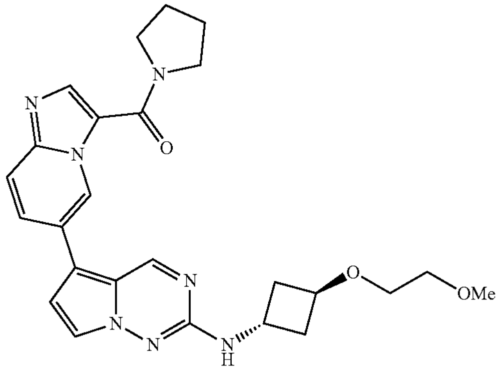 [SMILES: COCCO[C@H]1C[C@H](Nc2ncc3c(-c4ccc5ncc(C(=O)N6CCCC6)n5c4)ccn3n2)C1]
103

TABLE 1-continued
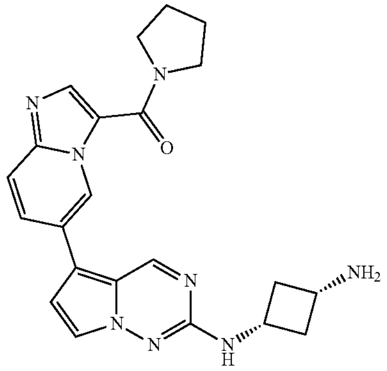 [SMILES: N[C@H]1C[C@@H](Nc2ncc3c(-c4ccc5ncc(C(=O)N6CCCC6)n5c4)ccn3n2)C1]
104
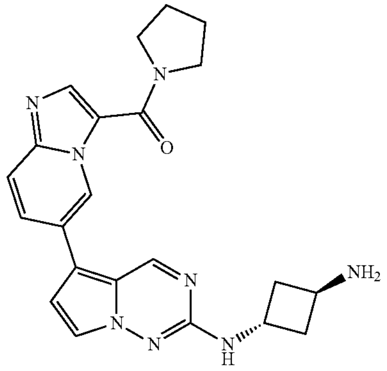 [SMILES: N[C@H]1C[C@H](Nc2ncc3c(-c4ccc5ncc(C(=O)N6CCCC6)n5c4)ccn3n2)C1]
105
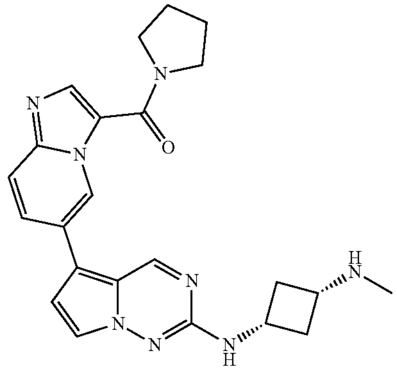
106
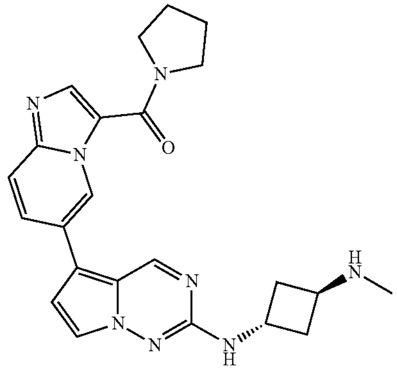 [SMILES: CN[C@H]1C[C@H](Nc2ncc3c(-c4ccc5ncc(C(=O)N6CCCC6)n5c4)ccn3n2)C1]
107

TABLE 1-continued
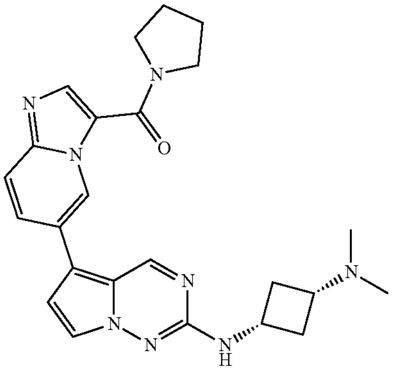 [SMILES: CN(C)[C@H]1C[C@@H](Nc2ncc3c(-c4ccc5ncc(C(=O)N6CCCC6)n5c4)ccn3n2)C1]
108
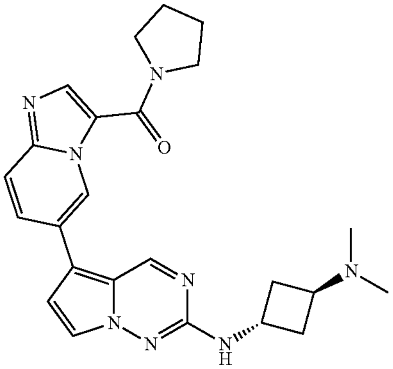 [SMILES: CN(C)[C@H]1C[C@H](Nc2ncc3c(-c4ccc5ncc(C(=O)N6CCCC6)n5c4)ccn3n2)C1]
109
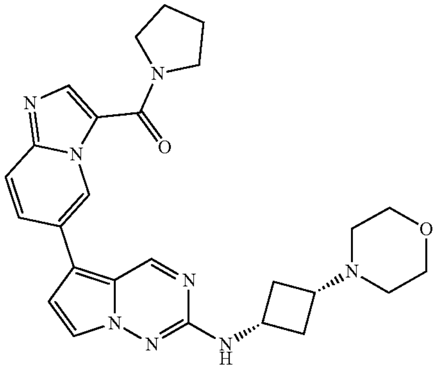 [SMILES: O=C(c1cnc2ccc(-c3ccn4nc(N[C@H]5C[C@@H](N6CCOCC6)C5)ncc34)cn12)N1CCCC1]
110
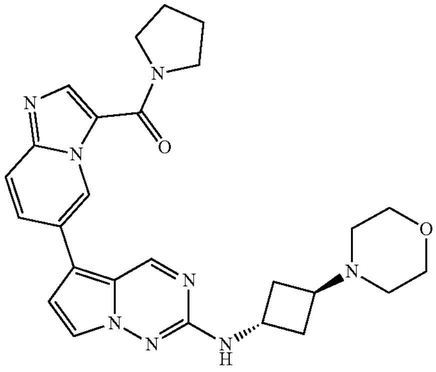 [SMILES: O=C(c1cnc2ccc(-c3ccn4nc(N[C@H]5C[C@H](N6CCOCC6)C5)ncc34)cn12)N1CCCC1]
111

TABLE 1-continued
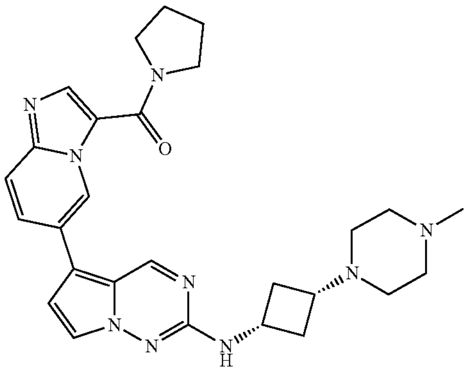 [SMILES: CN1CCN([C@H]2C[C@@H](Nc3ncc4c(-c5ccc6ncc(C(=O)N7CCCC7)n6c5)ccn4n3)C2)CC1]
112
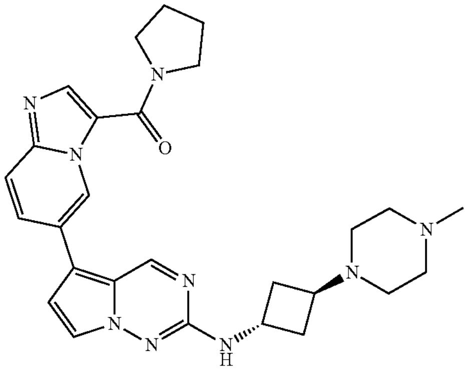 [SMILES: CN1CCN([C@H]2C[C@H](Nc3ncc4c(-c5ccc6ncc(C(=O)N7CCCC7)n6c5)ccn4n3)C2)CC1]
113
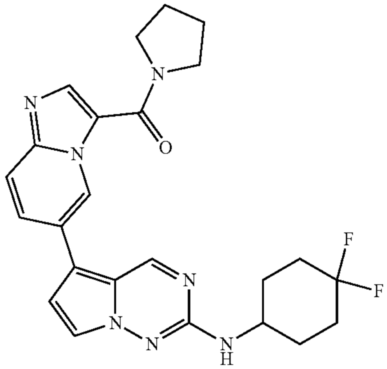 [SMILES: O=C(c1cnc2ccc(-c3ccn4nc(NC5CCC(F)(F)CC5)ncc34)cn12)N1CCCC1]
114
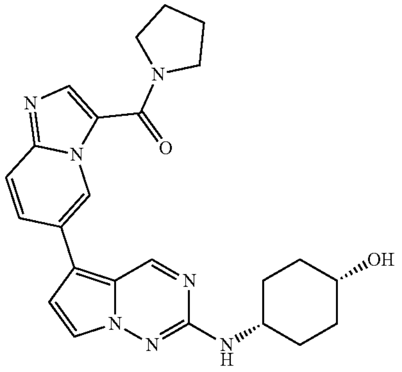 [SMILES: O=C(c1cnc2ccc(-c3ccn4nc(N[C@H]5CC[C@@H](O)CC5)ncc34)cn12)N1CCCC1]
115

TABLE 1-continued
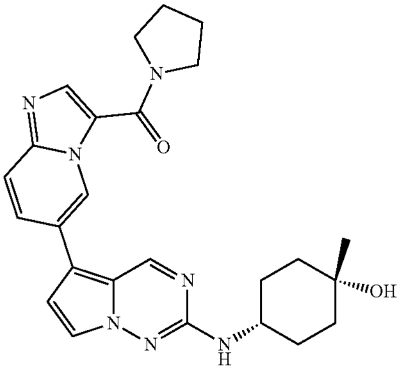 [SMILES: C[C@]1(O)CC[C@@H](Nc2ncc3c(-c4ccc5ncc(C(=O)N6CCCC6)n5c4)ccn3n2)CC1]
116
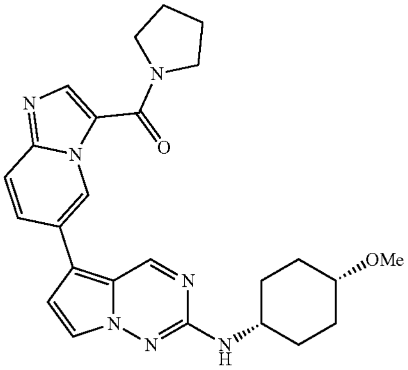 [SMILES: CO[C@H]1CC[C@@H](Nc2ncc3c(-c4ccc5ncc(C(=O)N6CCCC6)n5c4)ccn3n2)CC1]
117
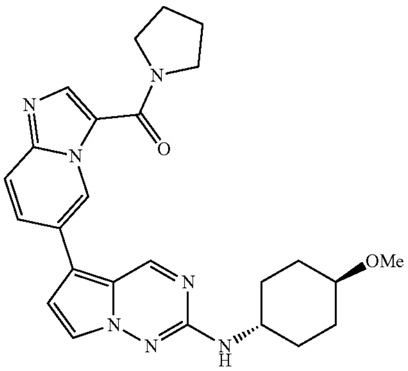 [SMILES: CO[C@H]1CC[C@H](Nc2ncc3c(-c4ccc5ncc(C(=O)N6CCCC6)n5c4)ccn3n2)CC1]
118
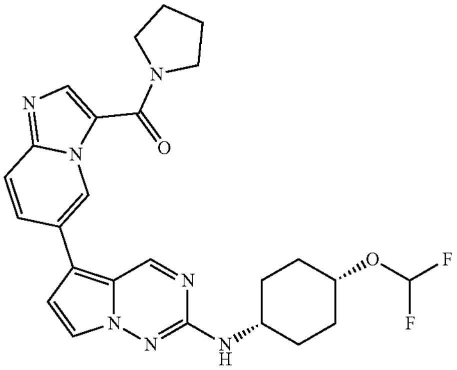 [SMILES: O=C(c1cnc2ccc(-c3ccn4nc(N[C@H]5CC[C@@H](OC(F)F)CC5)ncc34)cn12)N1CCCC1]
119

TABLE 1-continued
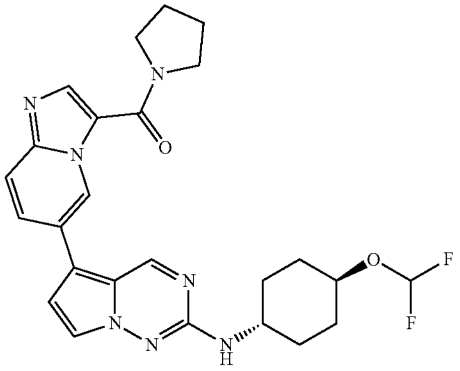 [SMILES: O=C(c1cnc2ccc(-c3ccn4nc(N[C@H]5CC[C@H](OC(F)F)CC5)ncc34)cn12)N1CCCC1]
120
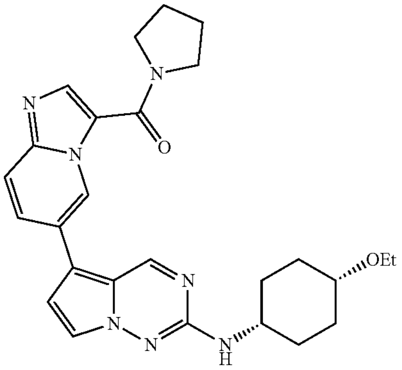 [SMILES: CCO[C@H]1CC[C@@H](Nc2ncc3c(-c4ccc5ncc(C(=O)N6CCCC6)n5c4)ccn3n2)CC1]
121
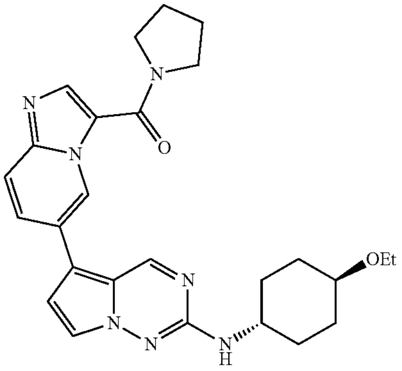 [SMILES: CCO[C@H]1CC[C@H](Nc2ncc3c(-c4ccc5ncc(C(=O)N6CCCC6)n5c4)ccn3n2)CC1]
122
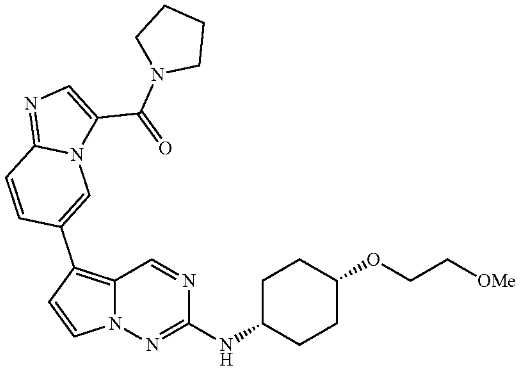 [SMILES: COCCO[C@H]1CC[C@@H](Nc2ncc3c(-c4ccc5ncc(C(=O)N6CCCC6)n5c4)ccn3n2)CC1]
123

TABLE 1-continued
124
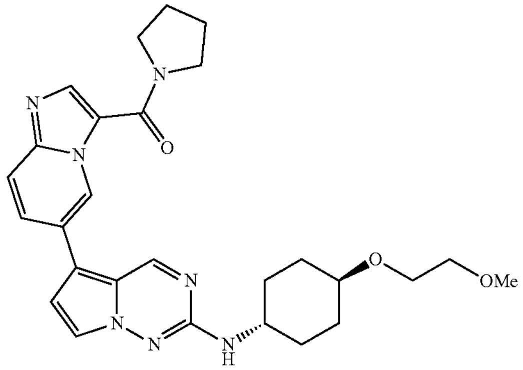 [SMILES: COCCO[C@H]1CC[C@H](Nc2ncc3c(-c4ccc5ncc(C(=O)N6CCCC6)n5c4)ccn3n2)CC1]
125
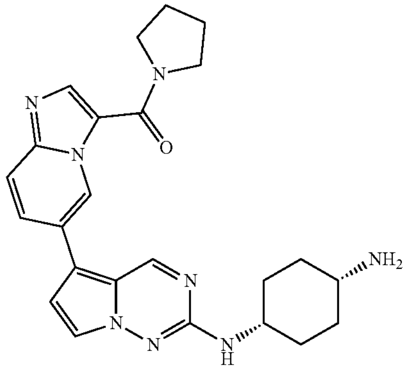 [SMILES: N[C@H]1CC[C@@H](Nc2ncc3c(-c4ccc5ncc(C(=O)N6CCCC6)n5c4)ccn3n2)CC1]
126
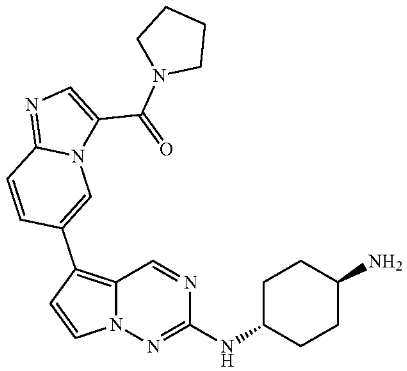 [SMILES: N[C@H]1CC[C@H](Nc2ncc3c(-c4ccc5ncc(C(=O)N6CCCC6)n5c4)ccn3n2)CC1]
127
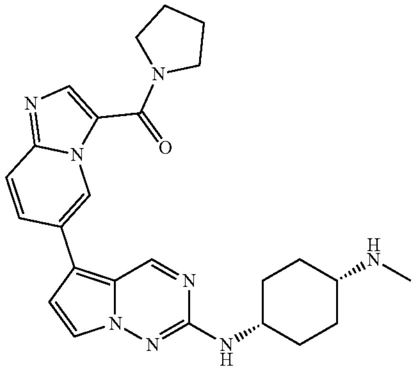 [SMILES: CN[C@H]1CC[C@@H](Nc2ncc3c(-c4ccc5ncc(C(=O)N6CCCC6)n5c4)ccn3n2)CC1]

TABLE 1-continued
128
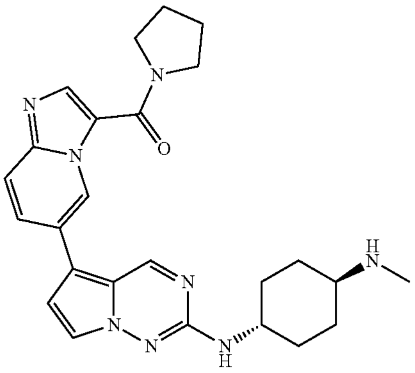 [SMILES: CN[C@H]1CC[C@H](Nc2ncc3c(-c4ccc5ncc(C(=O)N6CCCC6)n5c4)ccn3n2)CC1]
129
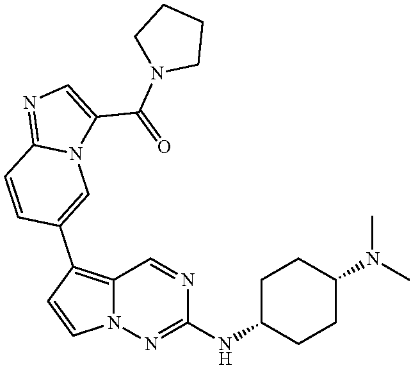 [SMILES: CN(C)[C@H]1CC[C@@H](Nc2ncc3c(-c4ccc5ncc(C(=O)N6CCCC6)n5c4)ccn3n2)CC1]
130
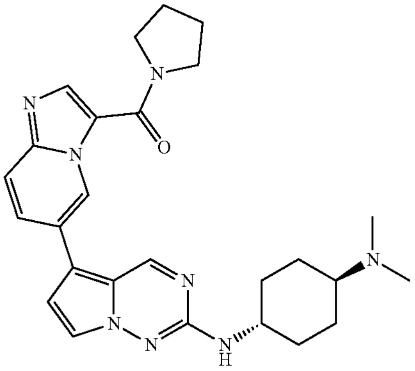 [SMILES: CN(C)[C@H]1CC[C@H](Nc2ncc3c(-c4ccc5ncc(C(=O)N6CCCC6)n5c4)ccn3n2)CC1]
131
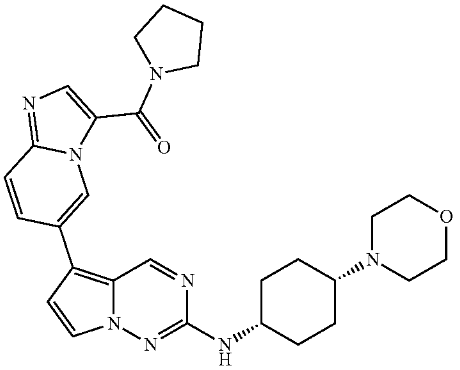 [SMILES: O=C(c1cnc2ccc(-c3ccn4nc(N[C@H]5CC[C@@H](N6CCOCC6)CC5)ncc34)cn12)N1CCCC1]

TABLE 1-continued
132
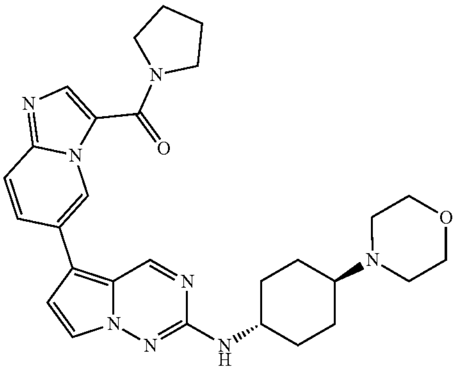 [SMILES: O=C(c1cnc2ccc(-c3ccn4nc(N[C@H]5CC[C@H](N6CCOCC6)CC5)ncc34)cn12)N1CCCC1]
133
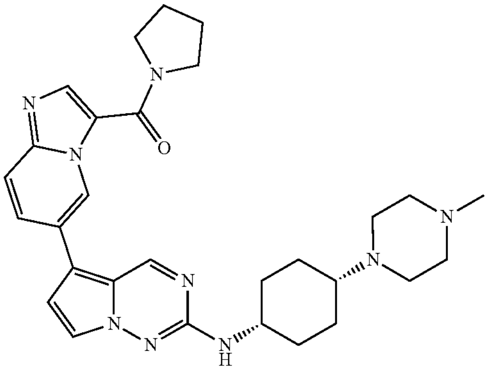 [SMILES: CN1CCN([C@H]2CC[C@@H](Nc3ncc4c(-c5ccc6ncc(C(=O)N7CCCC7)n6c5)ccn4n3)CC2)CC1]
134
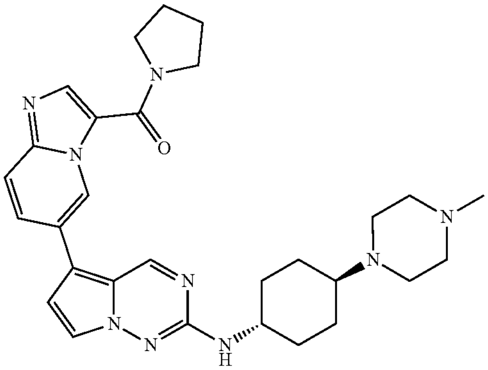 [SMILES: CN1CCN([C@H]2CC[C@H](Nc3ncc4c(-c5ccc6ncc(C(=O)N7CCCC7)n6c5)ccn4n3)CC2)CC1]
135
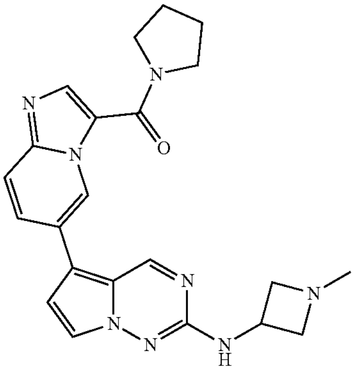 [SMILES: CN1CC(Nc2ncc3c(-c4ccc5ncc(C(=O)N6CCCC6)n5c4)ccn3n2)C1]

TABLE 1-continued
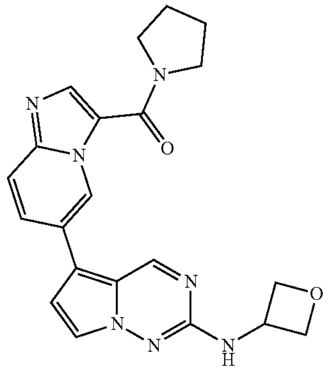 [SMILES: O=C(c1cnc2ccc(-c3ccn4nc(NC5COC5)ncc34)cn12)N1CCCC1]
136
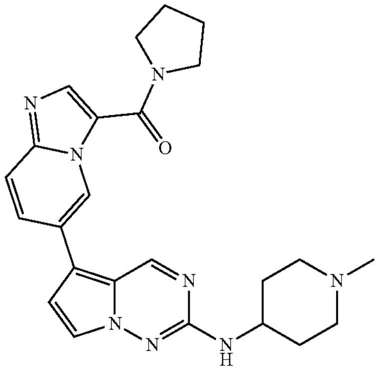 [SMILES: CN1CCC(Nc2ncc3c(-c4ccc5ncc(C(=O)N6CCCC6)n5c4)ccn3n2)CC1]
137
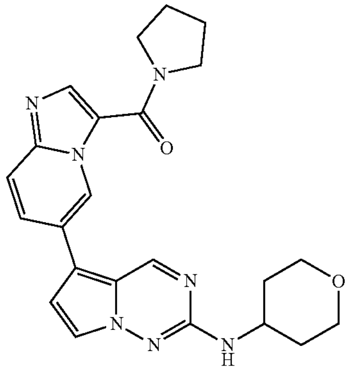 [SMILES: O=C(c1cnc2ccc(-c3ccn4nc(NC5CCOCC5)ncc34)cn12)N1CCCC1]
138
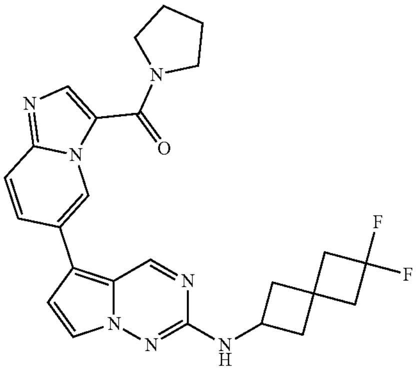 [SMILES: O=C(c1cnc2ccc(-c3ccn4nc(NC5CC6(C5)CC(F)(F)C6)ncc34)cn12)N1CCCC1]
139

TABLE 1-continued
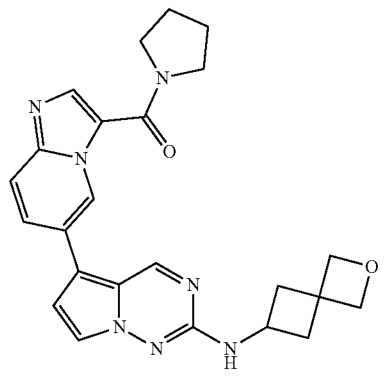 [SMILES: O=C(c1cnc2ccc(-c3ccn4nc(NC5CC6(COC6)C5)ncc34)cn12)N1CCCC1]
140
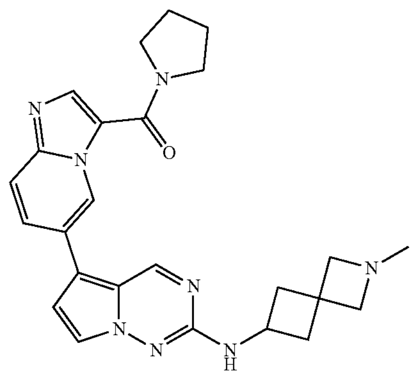 [SMILES: CN1CC2(CC(Nc3ncc4c(-c5ccc6ncc(C(=O)N7CCCC7)n6c5)ccn4n3)C2)C1]
141
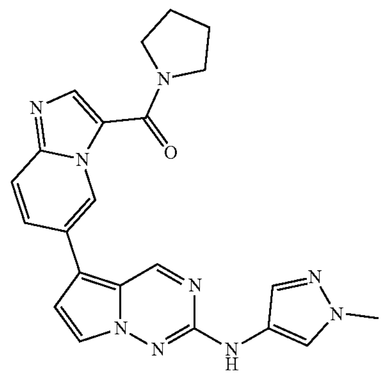 [SMILES: Cn1cc(Nc2ncc3c(-c4ccc5ncc(C(=O)N6CCCC6)n5c4)ccn3n2)cn1]
142
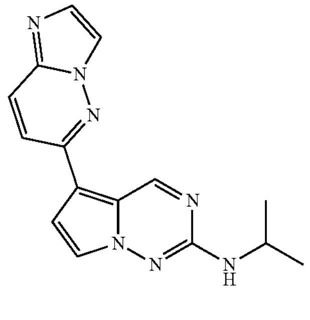 [SMILES: CC(C)Nc1ncc2c(-c3ccc4nccn4n3)ccn2n1]
143

TABLE 1-continued
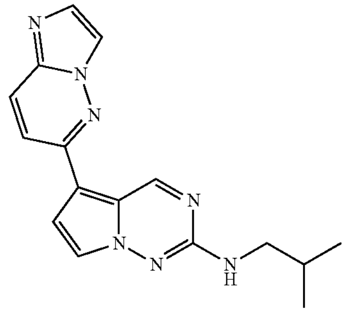 [SMILES: CC(C)CNc1ncc2c(-c3ccc4nccn4n3)ccn2n1]
144
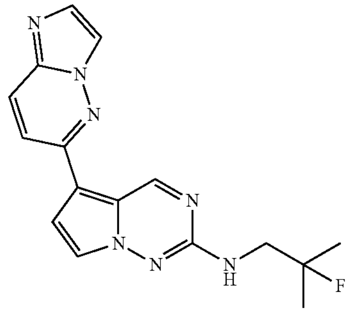 [SMILES: CC(C)(F)CNc1ncc2c(-c3ccc4nccn4n3)ccn2n1]
145
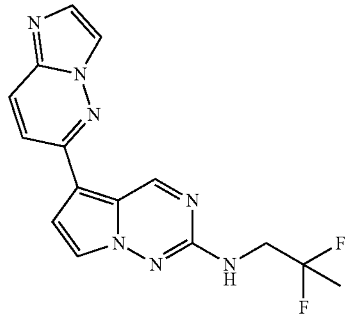 [SMILES: CC(F)(F)CNc1ncc2c(-c3ccc4nccn4n3)ccn2n1]
146
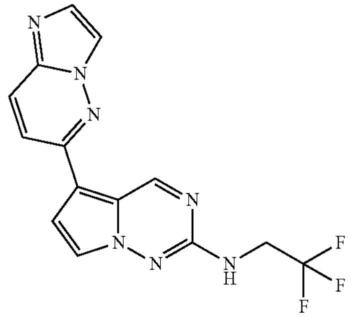 [SMILES: FC(F)(F)CNc1ncc2c(-c3ccc4nccn4n3)ccn2n1]
147
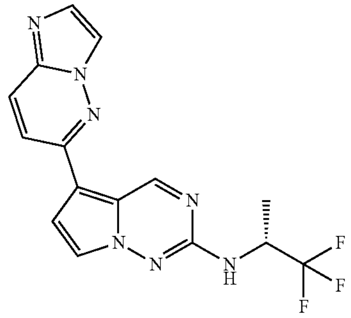 [SMILES: C[C@@H](Nc1ncc2c(-c3ccc4nccn4n3)ccn2n1)C(F)(F)F]
148

TABLE 1-continued
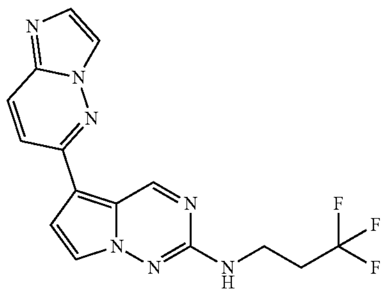 [SMILES: FC(F)(F)CCNc1ncc2c(-c3ccc4nccn4n3)ccn2n1]
149
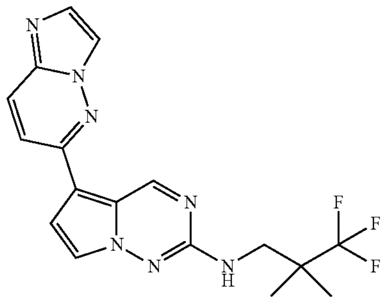 [SMILES: CC(C)(CNc1ncc2c(-c3ccc4nccn4n3)ccn2n1)C(F)(F)F]
150
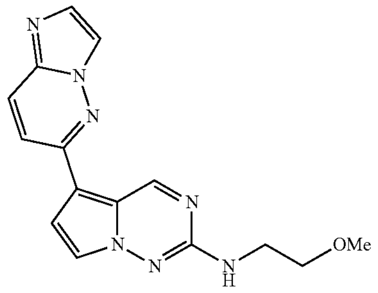 [SMILES: COCCNc1ncc2c(-c3ccc4nccn4n3)ccn2n1]
151
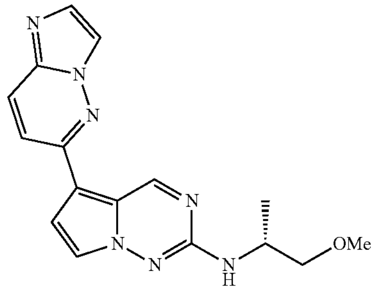
152
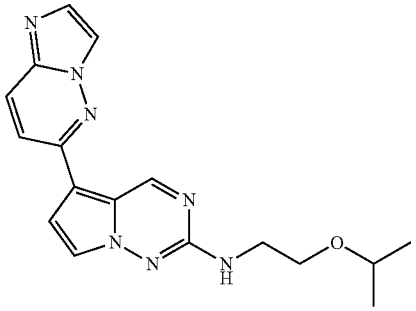 [SMILES: CC(C)OCCNc1ncc2c(-c3ccc4nccn4n3)ccn2n1]
153

TABLE 1-continued
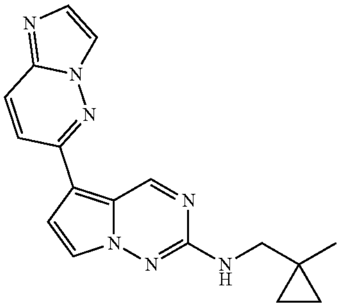 [SMILES: CC1(CNc2ncc3c(-c4ccc5nccn5n4)ccn3n2)CC1]
154
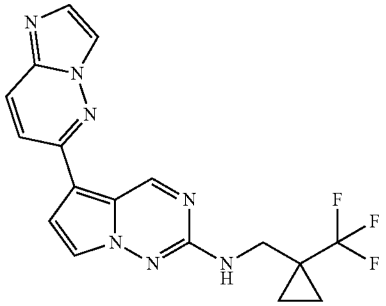 [SMILES: FC(F)(F)C1(CNc2ncc3c(-c4ccc5nccn5n4)ccn3n2)CC1]
155
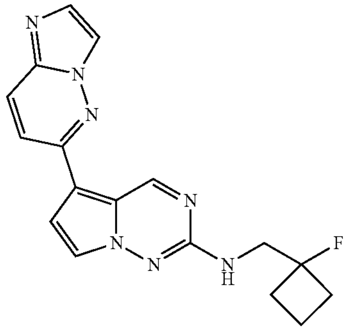 [SMILES: FC1(CNc2ncc3c(-c4ccc5nccn5n4)ccn3n2)CCC1]
156
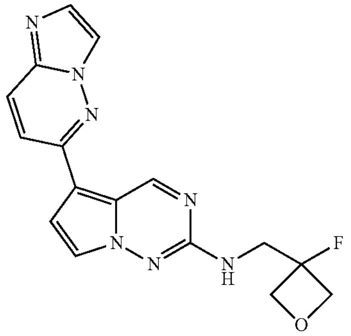 [SMILES: FC1(CNc2ncc3c(-c4ccc5nccn5n4)ccn3n2)COC1]
157
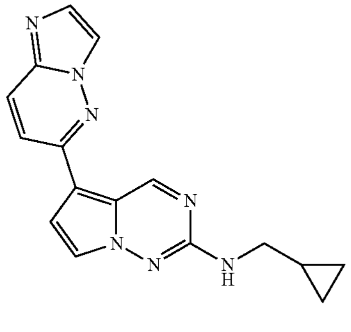 [SMILES: c1cn2nc(-c3ccn4nc(NCC5CC5)ncc34)ccc2n1]
158

TABLE 1-continued
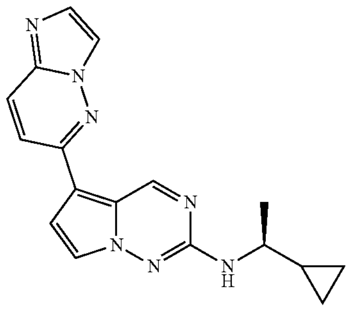 [SMILES: C[C@H](Nc1ncc2c(-c3ccc4nccn4n3)ccn2n1)C1CC1]
159
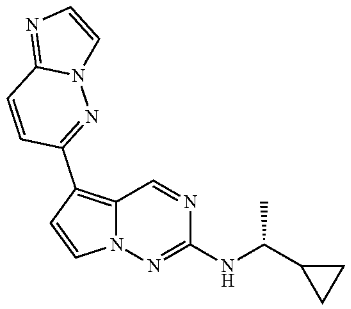 [SMILES: C[C@@H](Nc1ncc2c(-c3ccc4nccn4n3)ccn2n1)C1CC1]
160
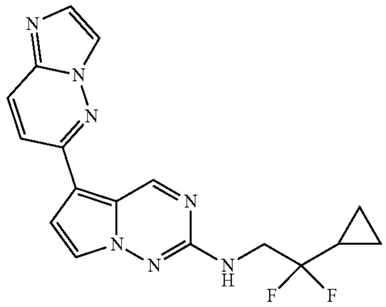 [SMILES: FC(F)(CNc1ncc2c(-c3ccc4nccn4n3)ccn2n1)C1CC1]
161
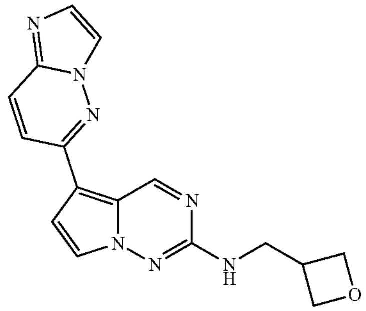 [SMILES: c1cn2nc(-c3ccn4nc(NCC5COC5)ncc34)ccc2n1]
162
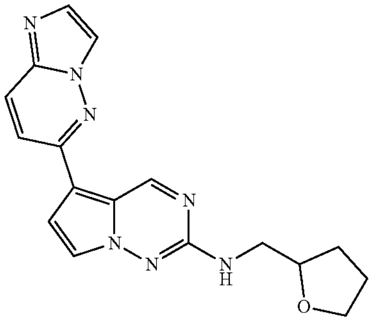
163

TABLE 1-continued
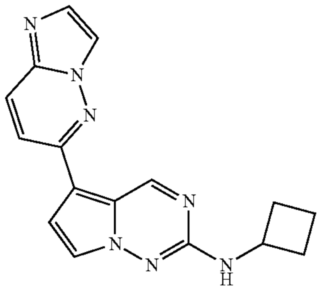 [SMILES: c1cn2nc(-c3ccn4nc(NC5CCC5)ncc34)ccc2n1]
164
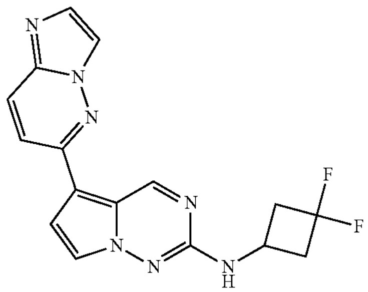 [SMILES: FC1(F)CC(Nc2ncc3c(-c4ccc5nccn5n4)ccn3n2)C1]
165
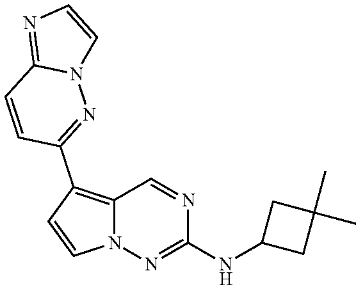 [SMILES: CC1(C)CC(Nc2ncc3c(-c4ccc5nccn5n4)ccn3n2)C1]
166
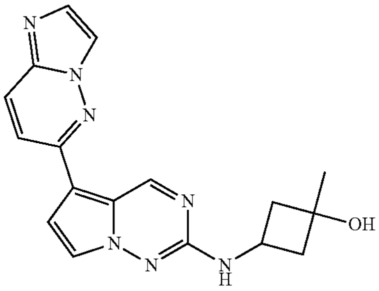 [SMILES: CC1(O)CC(Nc2ncc3c(-c4ccc5nccn5n4)ccn3n2)C1]
167
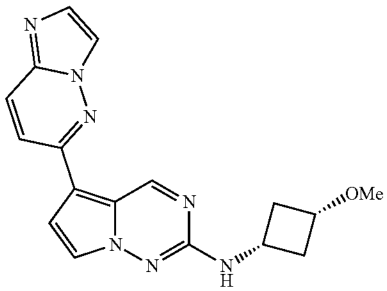 [SMILES: CO[C@H]1C[C@@H](Nc2ncc3c(-c4ccc5nccn5n4)ccn3n2)C1]
168

TABLE 1-continued
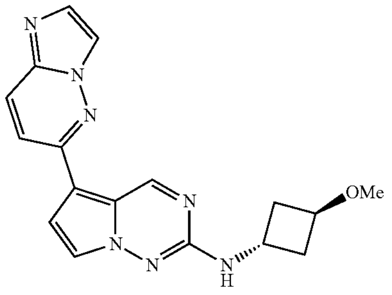 [SMILES: CO[C@H]1C[C@H](Nc2ncc3c(-c4ccc5nccn5n4)ccn3n2)C1]
169
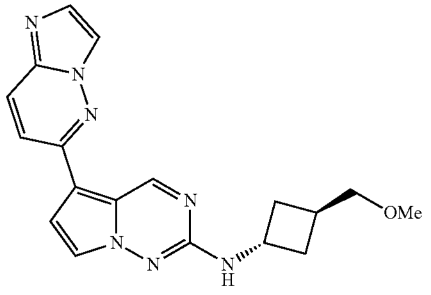 [SMILES: COC[C@H]1C[C@H](Nc2ncc3c(-c4ccc5nccn5n4)ccn3n2)C1]
170
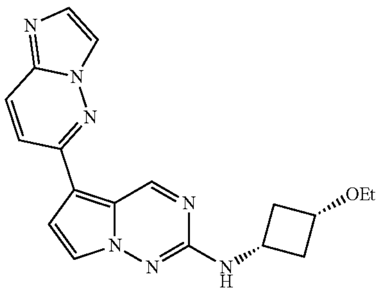 [SMILES: CCO[C@H]1C[C@@H](Nc2ncc3c(-c4ccc5nccn5n4)ccn3n2)C1]
171
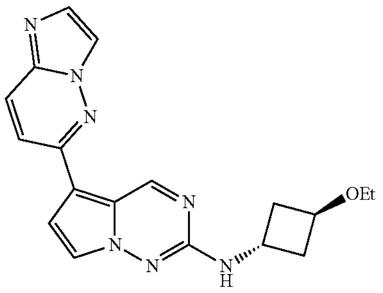 [SMILES: CCO[C@H]1C[C@H](Nc2ncc3c(-c4ccc5nccn5n4)ccn3n2)C1]
172
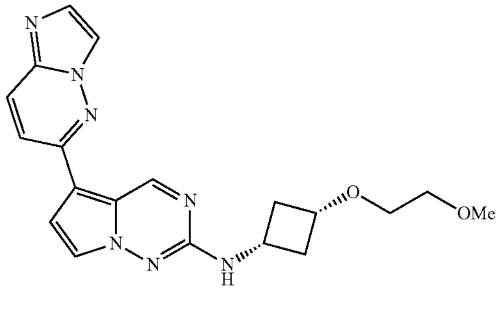 [SMILES: COCCO[C@H]1C[C@@H](Nc2ncc3c(-c4ccc5nccn5n4)ccn3n2)C1]
173

TABLE 1-continued
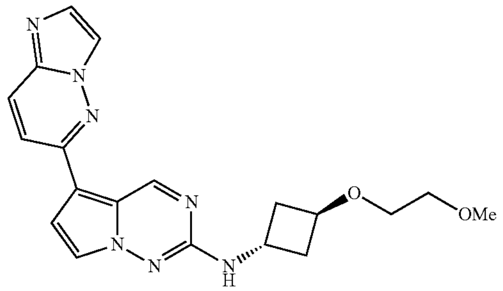 [SMILES: COCCO[C@H]1C[C@H](Nc2ncc3c(-c4ccc5nccn5n4)ccn3n2)C1]
174
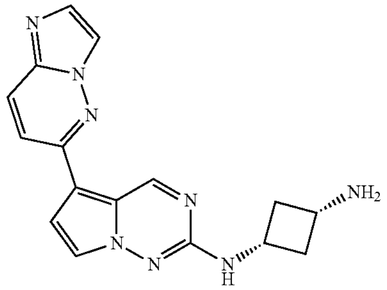 [SMILES: N[C@H]1C[C@@H](Nc2ncc3c(-c4ccc5nccn5n4)ccn3n2)C1]
175
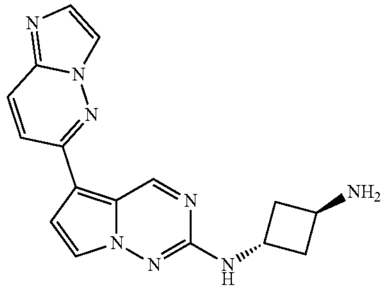 [SMILES: N[C@H]1C[C@H](Nc2ncc3c(-c4ccc5nccn5n4)ccn3n2)C1]
176
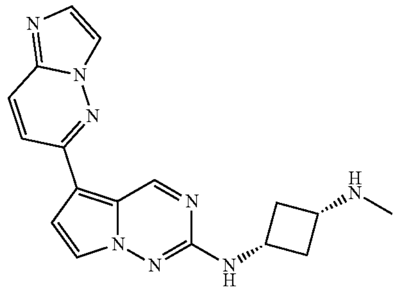 [SMILES: CN[C@H]1C[C@@H](Nc2ncc3c(-c4ccc5nccn5n4)ccn3n2)C1]
177
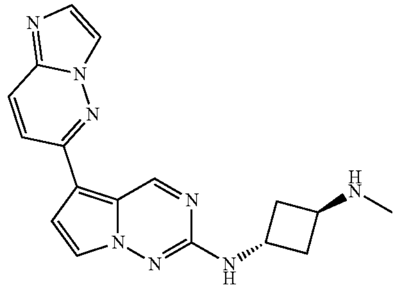 [SMILES: CN[C@H]1C[C@H](Nc2ncc3c(-c4ccc5nccn5n4)ccn3n2)C1]
178

TABLE 1-continued
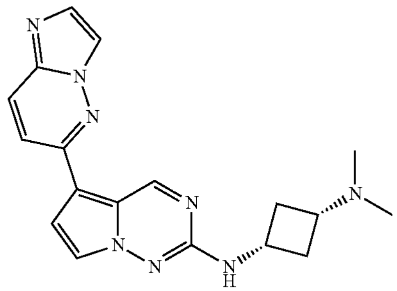 [SMILES: CN(C)[C@H]1C[C@@H](Nc2ncc3c(-c4ccc5nccn5n4)ccn3n2)C1]
179
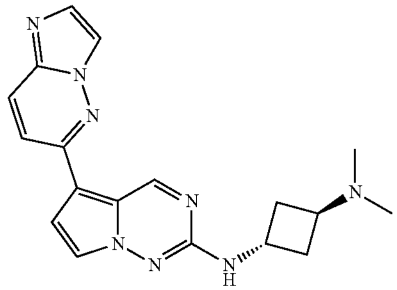 [SMILES: CN(C)[C@H]1C[C@H](Nc2ncc3c(-c4ccc5nccn5n4)ccn3n2)C1]
180
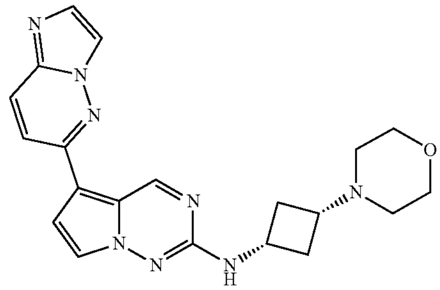 [SMILES: c1cn2nc(-c3ccn4nc(N[C@H]5C[C@@H](N6CCOCC6)C5)ncc34)ccc2n1]
181
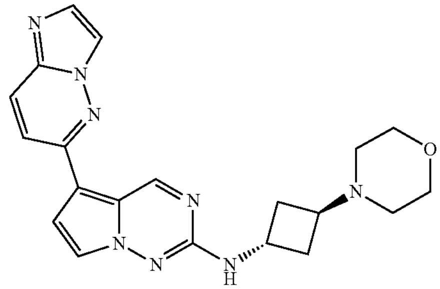 [SMILES: c1cn2nc(-c3ccn4nc(N[C@H]5C[C@H](N6CCOCC6)C5)ncc34)ccc2n1]
182
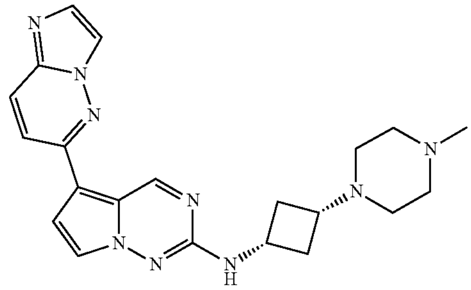 [SMILES: CN1CCN([C@H]2C[C@@H](Nc3ncc4c(-c5ccc6nccn6n5)ccn4n3)C2)CC1]
183

TABLE 1-continued
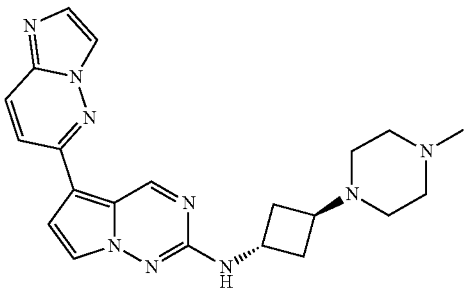 [SMILES: CN1CCN([C@H]2C[C@H](Nc3ncc4c(-c5ccc6nccn6n5)ccn4n3)C2)CC1]
184
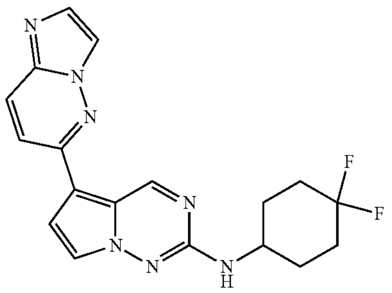 [SMILES: FC1(F)CCC(Nc2ncc3c(-c4ccc5nccn5n4)ccn3n2)CC1]
185
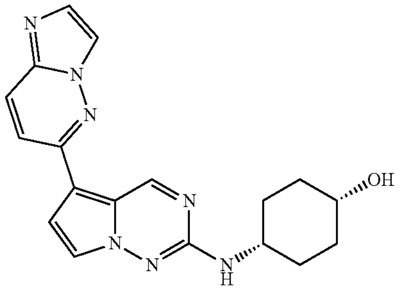 [SMILES: O[C@H]1CC[C@@H](Nc2ncc3c(-c4ccc5nccn5n4)ccn3n2)CC1]
186
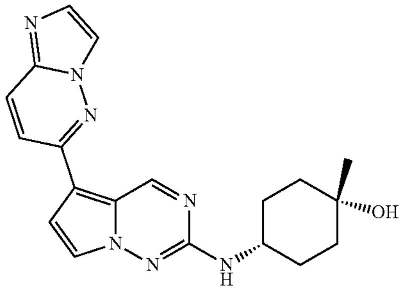 [SMILES: C[C@]1(O)CC[C@@H](Nc2ncc3c(-c4ccc5nccn5n4)ccn3n2)CC1]
187
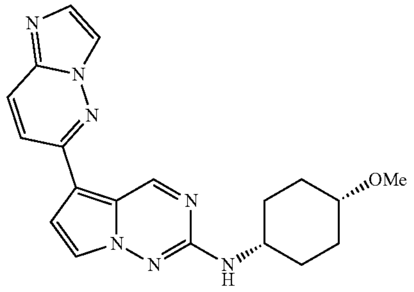 [SMILES: CO[C@H]1CC[C@@H](Nc2ncc3c(-c4ccc5nccn5n4)ccn3n2)CC1]
188

TABLE 1-continued
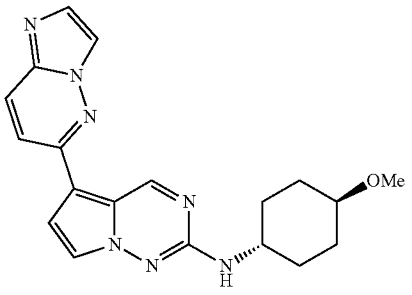 [SMILES: CO[C@H]1CC[C@H](Nc2ncc3c(-c4ccc5nccn5n4)ccn3n2)CC1]
189
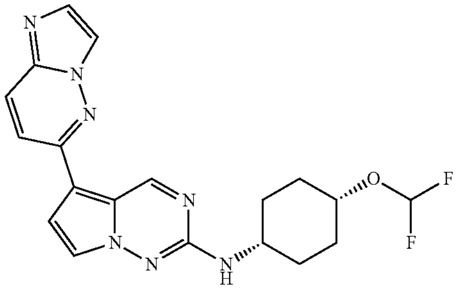 [SMILES: FC(F)O[C@H]1CC[C@@H](Nc2ncc3c(-c4ccc5nccn5n4)ccn3n2)CC1]
190
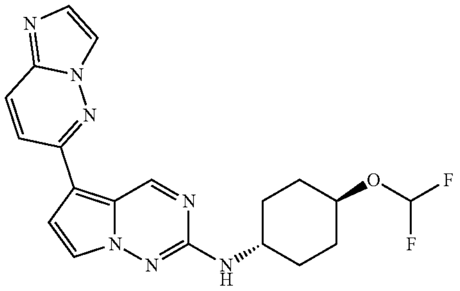 [SMILES: FC(F)O[C@H]1CC[C@H](Nc2ncc3c(-c4ccc5nccn5n4)ccn3n2)CC1]
191
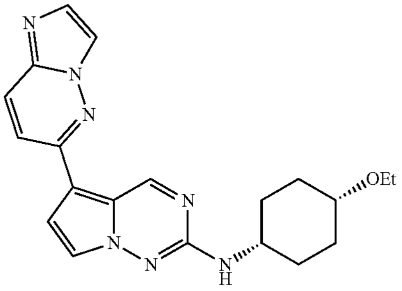 [SMILES: CCO[C@H]1CC[C@@H](Nc2ncc3c(-c4ccc5nccn5n4)ccn3n2)CC1]
192
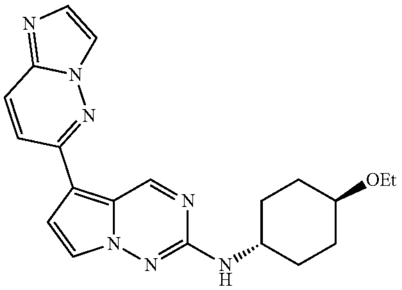 [SMILES: CCO[C@H]1CC[C@H](Nc2ncc3c(-c4ccc5nccn5n4)ccn3n2)CC1]
193

TABLE 1-continued
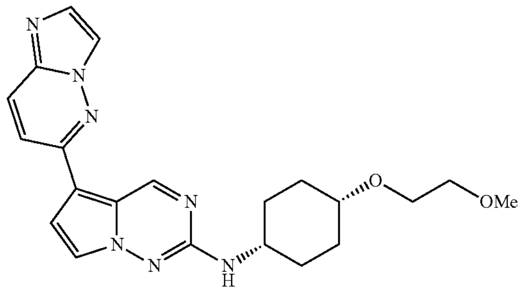 [SMILES: COCCO[C@H]1CC[C@@H](Nc2ncc3c(-c4ccc5nccn5n4)ccn3n2)CC1]
194
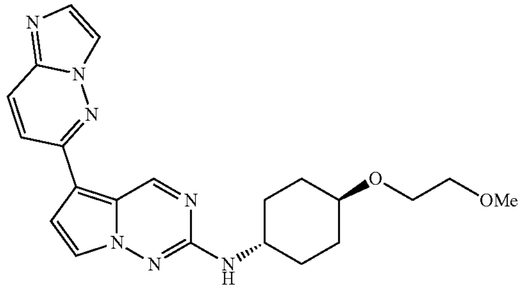 [SMILES: COCCO[C@H]1CC[C@H](Nc2ncc3c(-c4ccc5nccn5n4)ccn3n2)CC1]
195
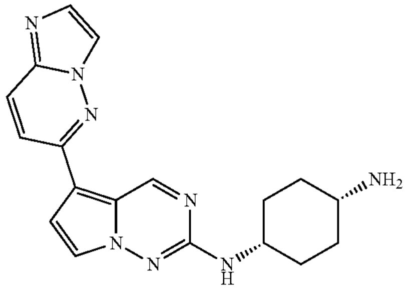 [SMILES: N[C@H]1CC[C@@H](Nc2ncc3c(-c4ccc5nccn5n4)ccn3n2)CC1]
196
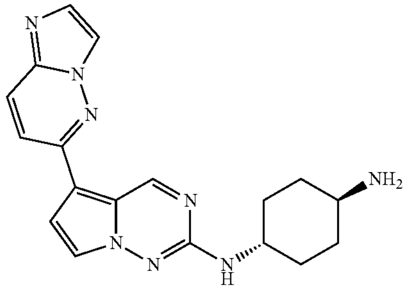 [SMILES: N[C@H]1CC[C@H](Nc2ncc3c(-c4ccc5nccn5n4)ccn3n2)CC1]
197
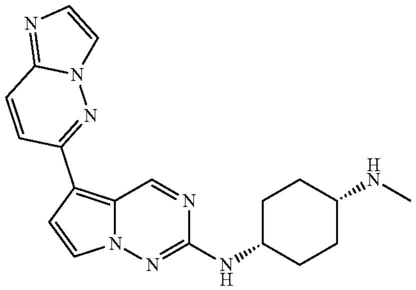 [SMILES: CN[C@H]1CC[C@@H](Nc2ncc3c(-c4ccc5nccn5n4)ccn3n2)CC1]
198

TABLE 1-continued
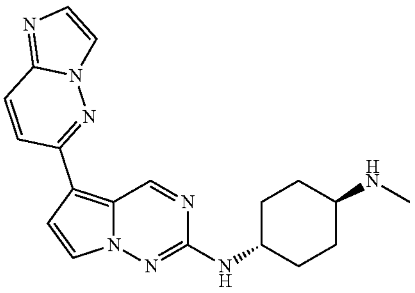 [SMILES: CN[C@H]1CC[C@H](Nc2ncc3c(-c4ccc5nccn5n4)ccn3n2)CC1]
199
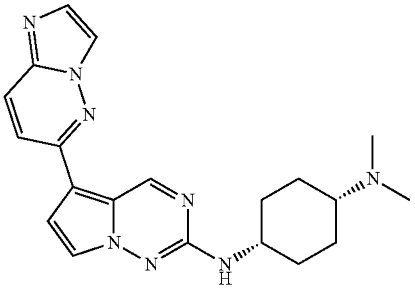 [SMILES: CN(C)[C@H]1CC[C@@H](Nc2ncc3c(-c4ccc5nccn5n4)ccn3n2)CC1]
200
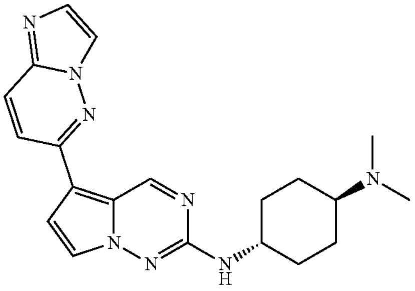 [SMILES: CN(C)[C@H]1CC[C@H](Nc2ncc3c(-c4ccc5nccn5n4)ccn3n2)CC1]
201
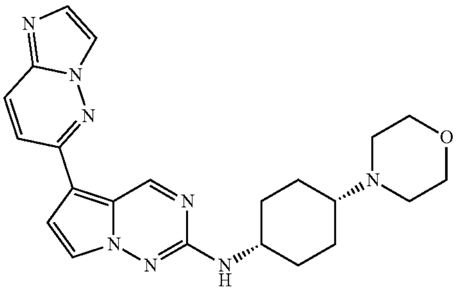 [SMILES: c1cn2nc(-c3ccn4nc(N[C@H]5CC[C@@H](N6CCOCC6)CC5)ncc34)ccc2n1]
202
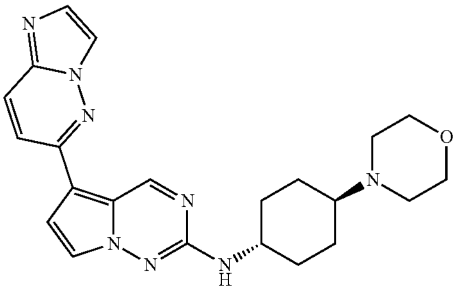 [SMILES: c1cn2nc(-c3ccn4nc(N[C@H]5CC[C@H](N6CCOCC6)CC5)ncc34)ccc2n1]
203

TABLE 1-continued
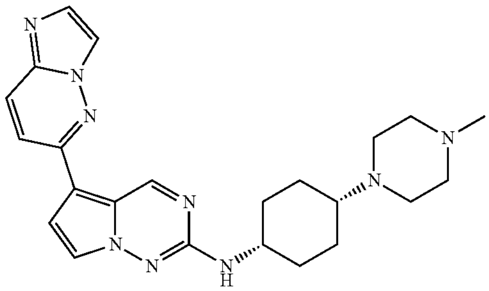 [SMILES: CN1CCN([C@H]2CC[C@@H](Nc3ncc4c(-c5ccc6nccn6n5)ccn4n3)CC2)CC1]
204
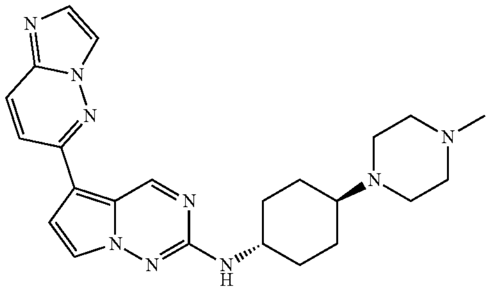
205
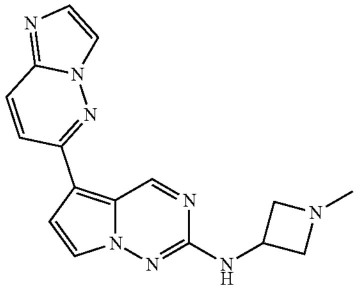 [SMILES: CN1CC(Nc2ncc3c(-c4ccc5nccn5n4)ccn3n2)C1]
206
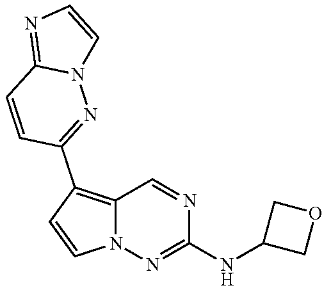 [SMILES: c1cn2nc(-c3ccn4nc(NC5COC5)ncc34)ccc2n1]
207
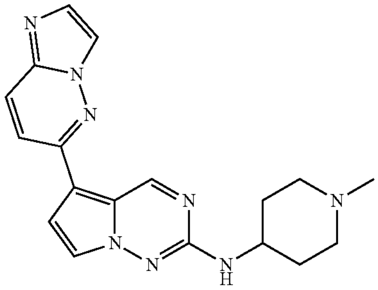 [SMILES: CN1CCC(Nc2ncc3c(-c4ccc5nccn5n4)ccn3n2)CC1]
208

TABLE 1-continued
209
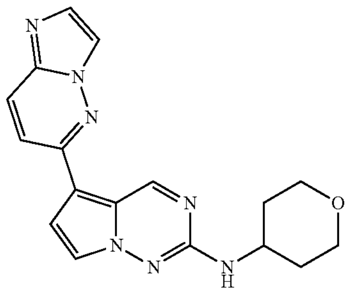 [SMILES: c1cn2nc(-c3ccn4nc(NC5CCOCC5)ncc34)ccc2n1]
210
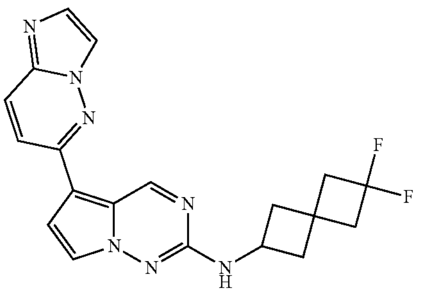 [SMILES: FC1(F)CC2(CC(Nc3ncc4c(-c5ccc6nccn6n5)ccn4n3)C2)C1]
211
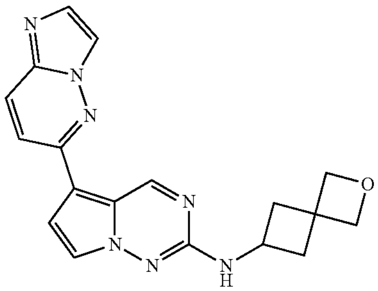 [SMILES: c1cn2nc(-c3ccn4nc(NC5CC6(COC6)C5)ncc34)ccc2n1]
212
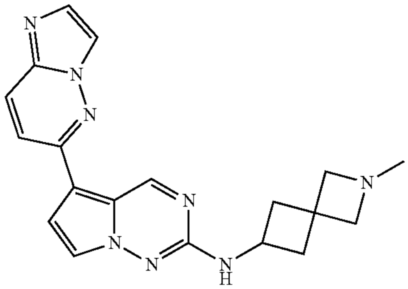 [SMILES: CN1CC2(CC(Nc3ncc4c(-c5ccc6nccn6n5)ccn4n3)C2)C1]
213
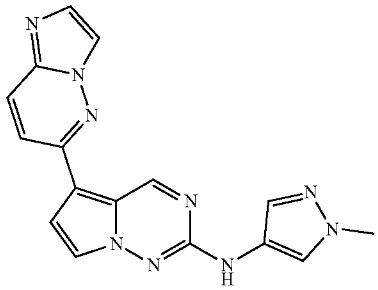 [SMILES: Cn1cc(Nc2ncc3c(-c4ccc5nccn5n4)ccn3n2)cn1]

TABLE 1-continued
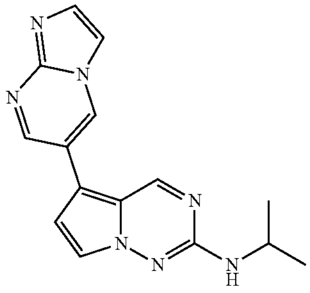 [SMILES: CC(C)Nc1ncc2c(-c3cnc4nccn4c3)ccn2n1]
214
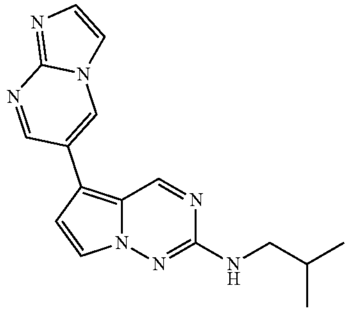 [SMILES: CC(C)CNc1ncc2c(-c3cnc4nccn4c3)ccn2n1]
215
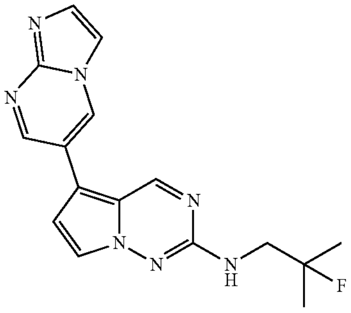 [SMILES: CC(C)(F)CNc1ncc2c(-c3cnc4nccn4c3)ccn2n1]
216
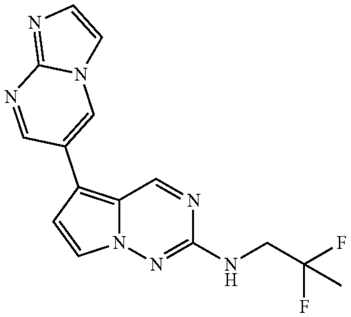 [SMILES: CC(F)(F)CNc1ncc2c(-c3cnc4nccn4c3)ccn2n1]
217
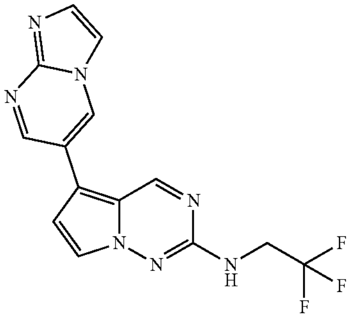 [SMILES: FC(F)(F)CNc1ncc2c(-c3cnc4nccn4c3)ccn2n1]
218

TABLE 1-continued
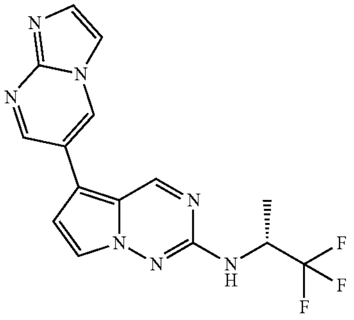 [SMILES: C[C@@H](Nc1ncc2c(-c3cnc4nccn4c3)ccn2n1)C(F)(F)F]
219
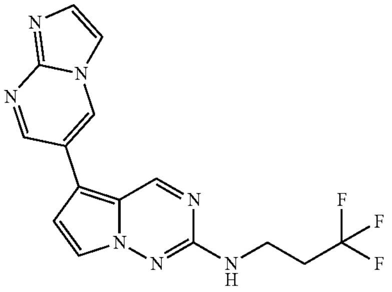 [SMILES: FC(F)(F)CCNc1ncc2c(-c3cnc4nccn4c3)ccn2n1]
220
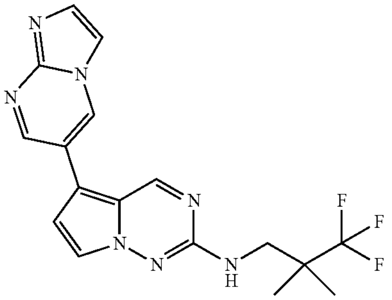 [SMILES: CC(C)(CNc1ncc2c(-c3cnc4nccn4c3)ccn2n1)C(F)(F)F]
221
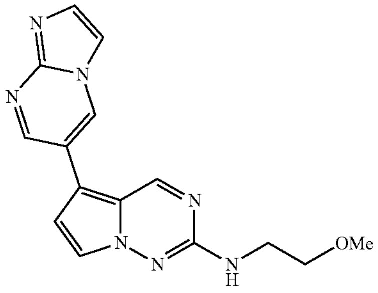 [SMILES: COCCNc1ncc2c(-c3cnc4nccn4c3)ccn2n1]
222
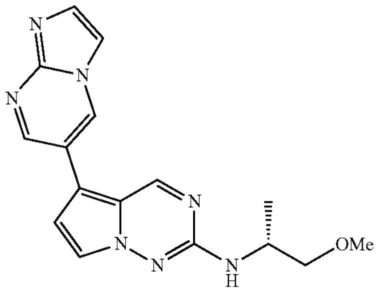 [SMILES: COC[C@@H](C)Nc1ncc2c(-c3cnc4nccn4c3)ccn2n1]
223

TABLE 1-continued
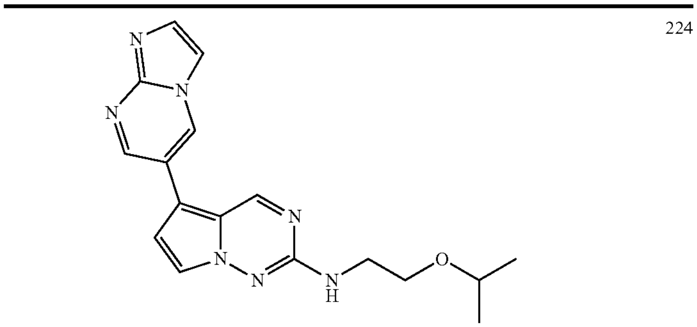
224
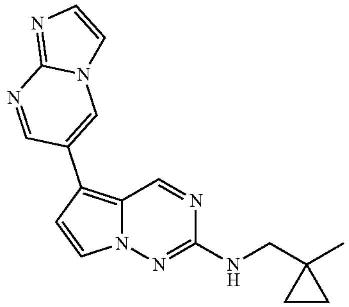 [SMILES: CC1(CNc2ncc3c(-c4cnc5nccn5c4)ccn3n2)CC1]
225
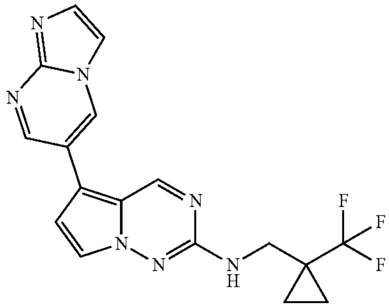 [SMILES: FC(F)(F)C1(CNc2ncc3c(-c4cnc5nccn5c4)ccn3n2)CC1]
226
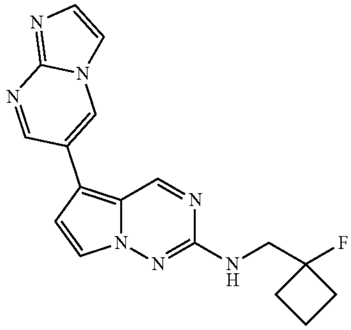 [SMILES: FC1(CNc2ncc3c(-c4cnc5nccn5c4)ccn3n2)CCC1]
227
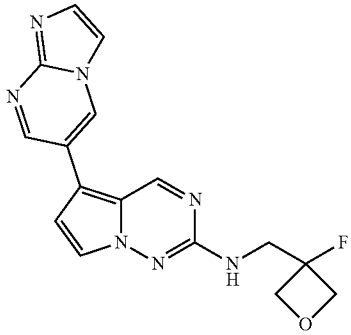 [SMILES: FC1(CNc2ncc3c(-c4cnc5nccn5c4)ccn3n2)COC1]
228

TABLE 1-continued
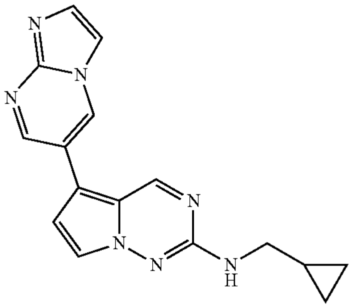 [SMILES: c1cn2cc(-c3ccn4nc(NCC5CC5)ncc34)cnc2n1]
229
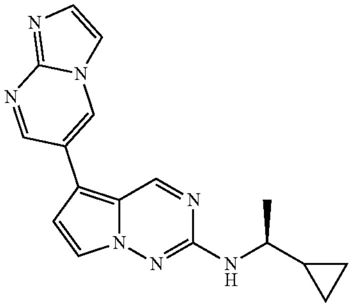 [SMILES: C[C@H](Nc1ncc2c(-c3cnc4nccn4c3)ccn2n1)C1CC1]
230
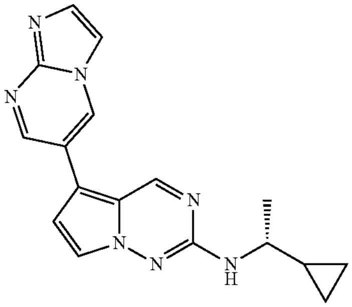 [SMILES: C[C@@H](Nc1ncc2c(-c3cnc4nccn4c3)ccn2n1)C1CC1]
231
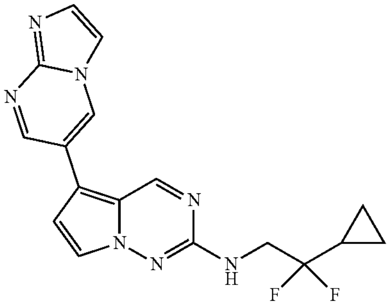 [SMILES: FC(F)(CNc1ncc2c(-c3cnc4nccn4c3)ccn2n1)C1CC1]
232
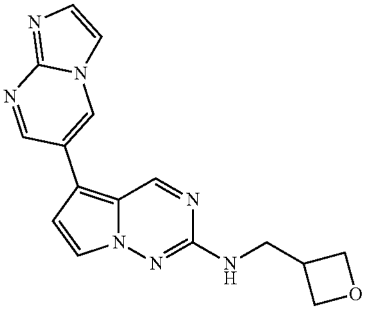 [SMILES: c1cn2cc(-c3ccn4nc(NCC5COC5)ncc34)cnc2n1]
233

TABLE 1-continued
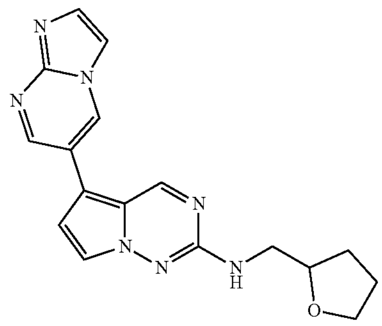 [SMILES: c1cn2cc(-c3ccn4nc(NCC5CCCO5)ncc34)cnc2n1]
234
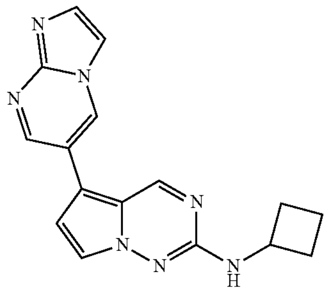 [SMILES: c1cn2cc(-c3ccn4nc(NC5CCC5)ncc34)cnc2n1]
235
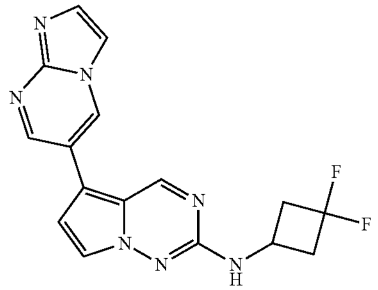 [SMILES: FC1(F)CC(Nc2ncc3c(-c4cnc5nccn5c4)ccn3n2)C1]
236
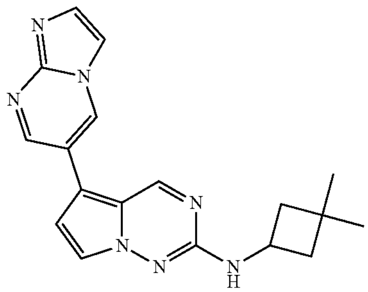 [SMILES: CC1(C)CC(Nc2ncc3c(-c4cnc5nccn5c4)ccn3n2)C1]
237
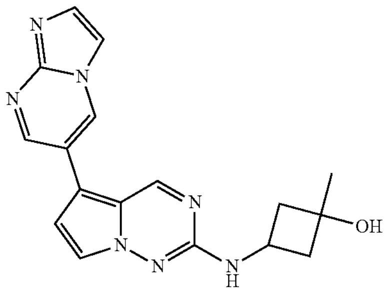 [SMILES: CC1(O)CC(Nc2ncc3c(-c4cnc5nccn5c4)ccn3n2)C1]
238

TABLE 1-continued
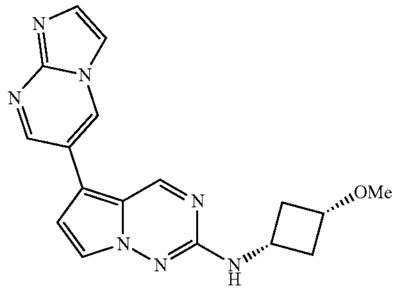 [SMILES: CO[C@H]1C[C@@H](Nc2ncc3c(-c4cnc5nccn5c4)ccn3n2)C1]
239
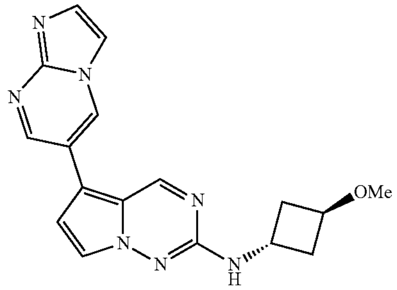 [SMILES: CO[C@H]1C[C@H](Nc2ncc3c(-c4cnc5nccn5c4)ccn3n2)C1]
240
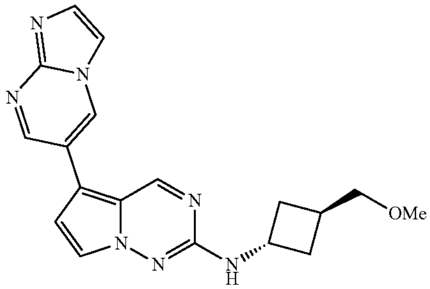 [SMILES: COC[C@H]1C[C@H](Nc2ncc3c(-c4cnc5nccn5c4)ccn3n2)C1]
241
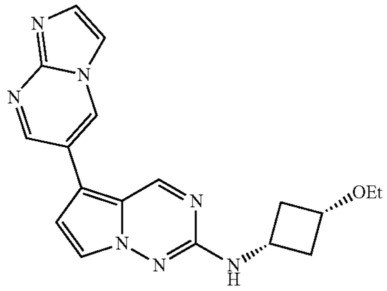 [SMILES: CCO[C@H]1C[C@@H](Nc2ncc3c(-c4cnc5nccn5c4)ccn3n2)C1]
242
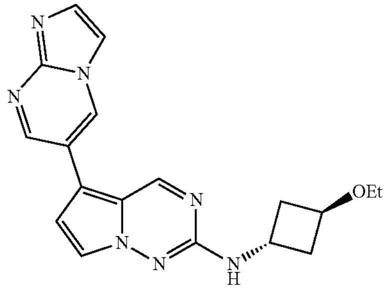 [SMILES: CCO[C@H]1C[C@H](Nc2ncc3c(-c4cnc5nccn5c4)ccn3n2)C1]
243

TABLE 1-continued
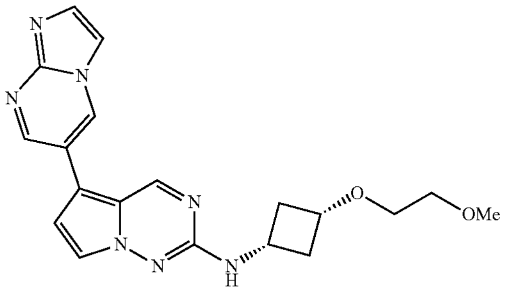 [SMILES: COCCO[C@H]1C[C@@H](Nc2ncc3c(-c4cnc5nccn5c4)ccn3n2)C1]
244
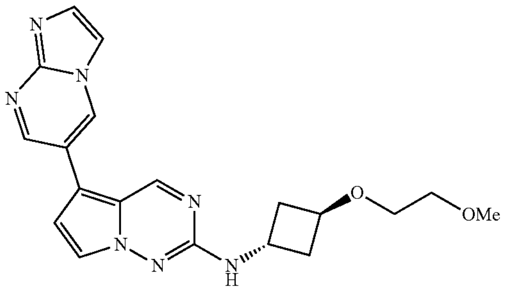 [SMILES: COCCO[C@H]1C[C@H](Nc2ncc3c(-c4cnc5nccn5c4)ccn3n2)C1]
245
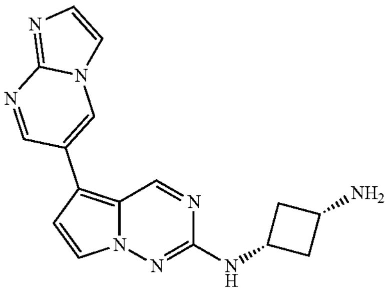 [SMILES: N[C@H]1C[C@@H](Nc2ncc3c(-c4cnc5nccn5c4)ccn3n2)C1]
246
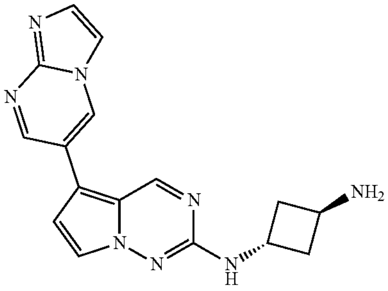 [SMILES: N[C@H]1C[C@H](Nc2ncc3c(-c4cnc5nccn5c4)ccn3n2)C1]
247
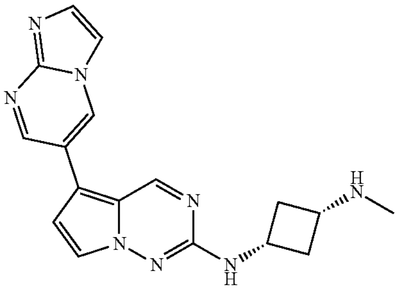 [SMILES: CN[C@H]1C[C@@H](Nc2ncc3c(-c4cnc5nccn5c4)ccn3n2)C1]
248

TABLE 1-continued
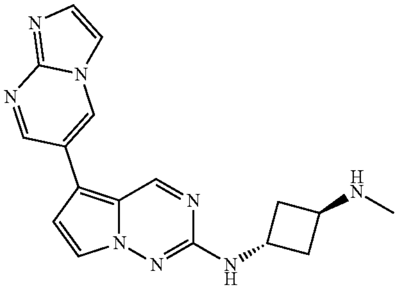 [SMILES: CN[C@H]1C[C@H](Nc2ncc3c(-c4cnc5nccn5c4)ccn3n2)C1]
249
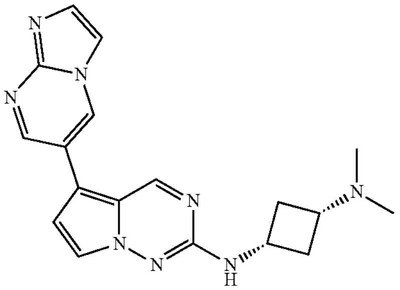 [SMILES: CN(C)[C@H]1C[C@@H](Nc2ncc3c(-c4cnc5nccn5c4)ccn3n2)C1]
250
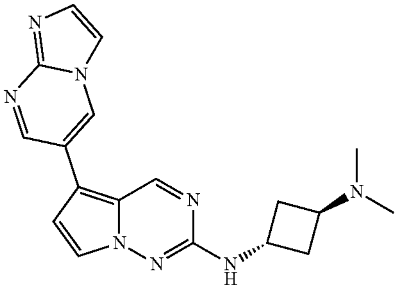 [SMILES: CN(C)[C@H]1C[C@H](Nc2ncc3c(-c4cnc5nccn5c4)ccn3n2)C1]
251
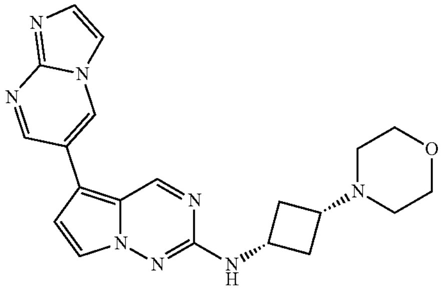 [SMILES: c1cn2cc(-c3ccn4nc(N[C@H]5C[C@@H](N6CCOCC6)C5)ncc34)cnc2n1]
252
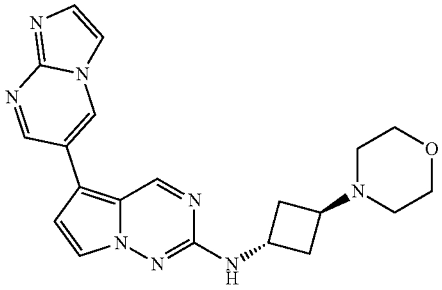 [SMILES: c1cn2cc(-c3ccn4nc(N[C@H]5C[C@H](N6CCOCC6)C5)ncc34)cnc2n1]
253

TABLE 1-continued
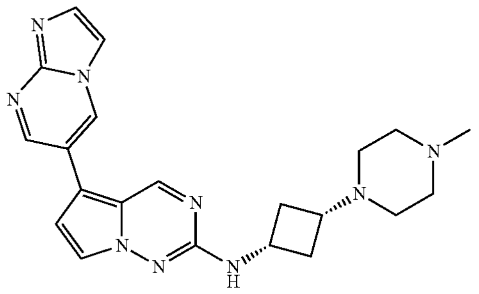 [SMILES: CN1CCN([C@H]2C[C@@H](Nc3ncc4c(-c5cnc6nccn6c5)ccn4n3)C2)CC1]
254
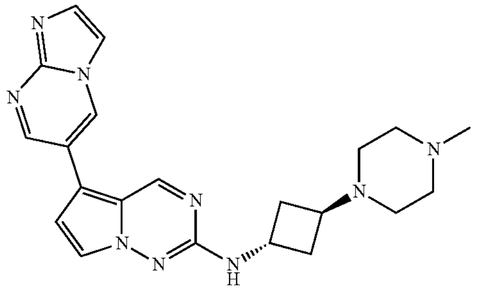 [SMILES: CN1CCN([C@H]2C[C@H](Nc3ncc4c(-c5cnc6nccn6c5)ccn4n3)C2)CC1]
255
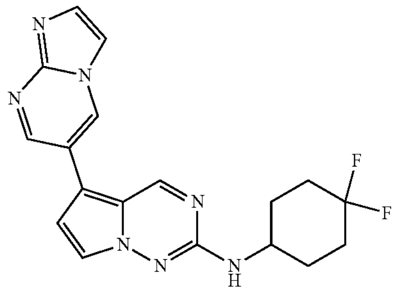 [SMILES: FC1(F)CCC(Nc2ncc3c(-c4cnc5nccn5c4)ccn3n2)CC1]
256
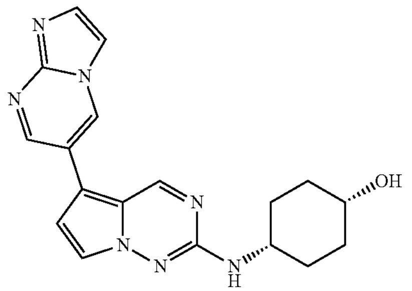 [SMILES: O[C@H]1CC[C@@H](Nc2ncc3c(-c4cnc5nccn5c4)ccn3n2)CC1]
257
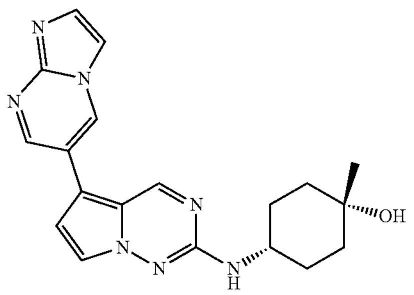 [SMILES: C[C@]1(O)CC[C@@H](Nc2ncc3c(-c4cnc5nccn5c4)ccn3n2)CC1]
258

TABLE 1-continued
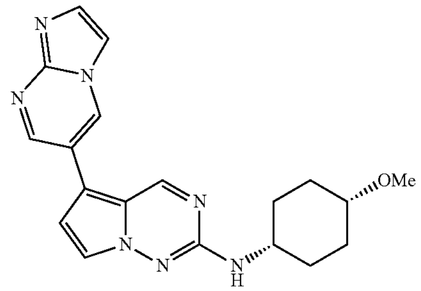 [SMILES: CO[C@H]1CC[C@@H](Nc2ncc3c(-c4cnc5nccn5c4)ccn3n2)CC1]
259
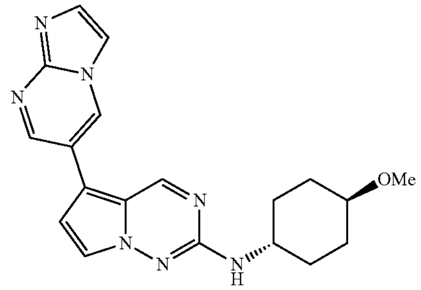 [SMILES: CO[C@H]1CC[C@H](Nc2ncc3c(-c4cnc5nccn5c4)ccn3n2)CC1]
260
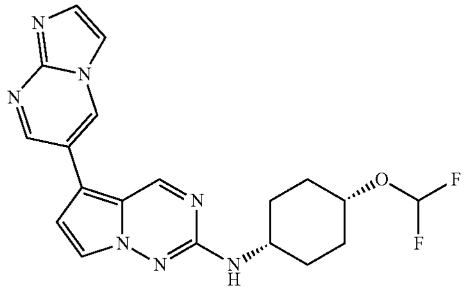 [SMILES: FC(F)O[C@H]1CC[C@@H](Nc2ncc3c(-c4cnc5nccn5c4)ccn3n2)CC1]
261
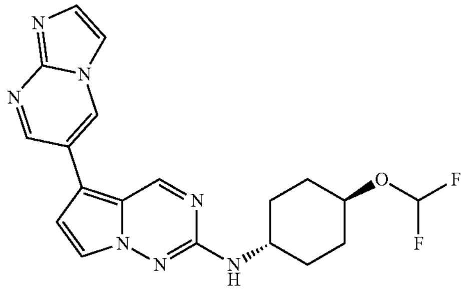 [SMILES: FC(F)O[C@H]1CC[C@H](Nc2ncc3c(-c4cnc5nccn5c4)ccn3n2)CC1]
262
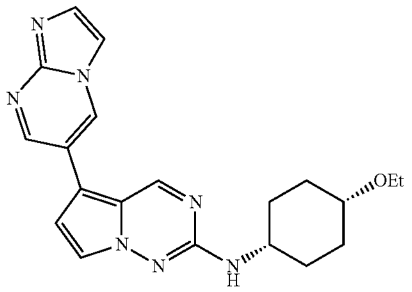 [SMILES: CCO[C@H]1CC[C@@H](Nc2ncc3c(-c4cnc5nccn5c4)ccn3n2)CC1]
263

TABLE 1-continued
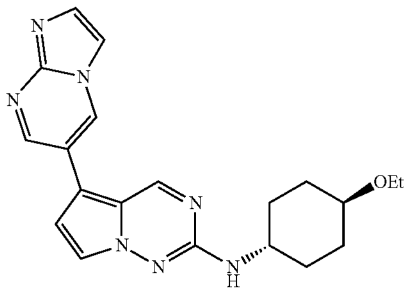 [SMILES: CCO[C@H]1CC[C@H](Nc2ncc3c(-c4cnc5nccn5c4)ccn3n2)CC1]
264
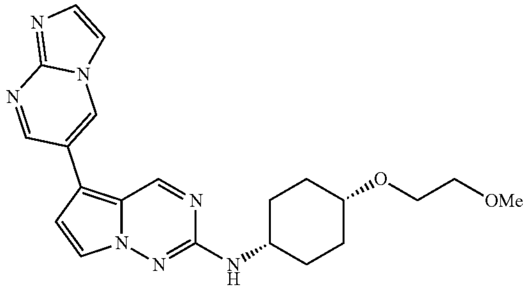 [SMILES: COCCO[C@H]1CC[C@@H](Nc2ncc3c(-c4cnc5nccn5c4)ccn3n2)CC1]
265
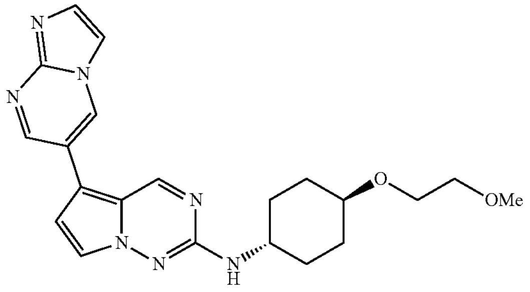 [SMILES: COCCO[C@H]1CC[C@H](Nc2ncc3c(-c4cnc5nccn5c4)ccn3n2)CC1]
266
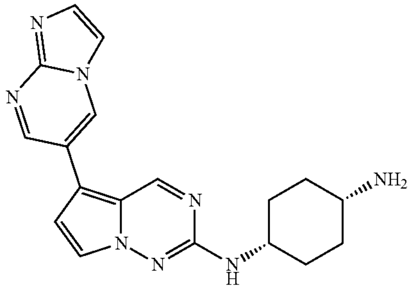 [SMILES: N[C@H]1CC[C@@H](Nc2ncc3c(-c4cnc5nccn5c4)ccn3n2)CC1]
267
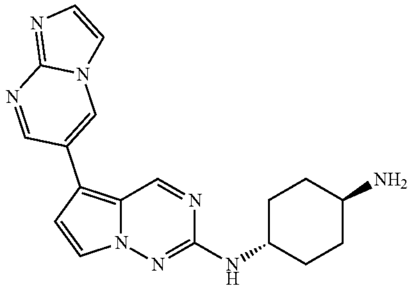 [SMILES: N[C@H]1CC[C@H](Nc2ncc3c(-c4cnc5nccn5c4)ccn3n2)CC1]
268

TABLE 1-continued
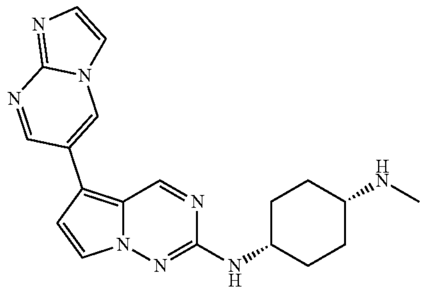 [SMILES: CN[C@H]1CC[C@@H](Nc2ncc3c(-c4cnc5nccn5c4)ccn3n2)CC1]
269
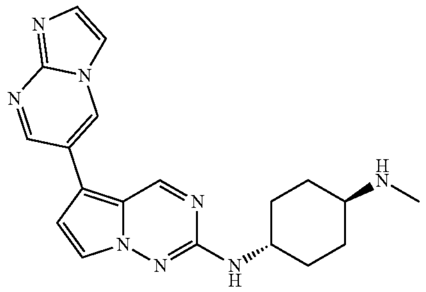 [SMILES: CN[C@H]1CC[C@H](Nc2ncc3c(-c4cnc5nccn5c4)ccn3n2)CC1]
270
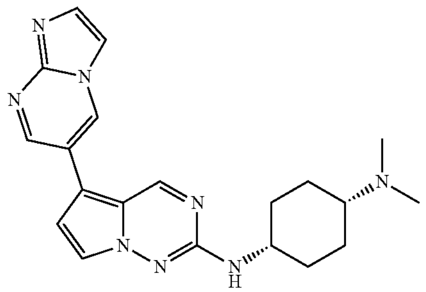 [SMILES: CN(C)[C@H]1CC[C@@H](Nc2ncc3c(-c4cnc5nccn5c4)ccn3n2)CC1]
271
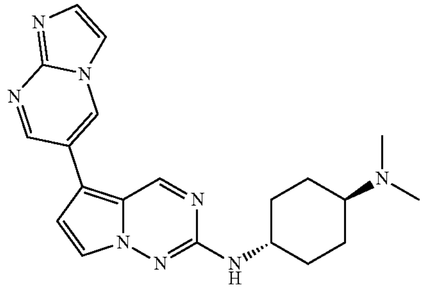 [SMILES: CN(C)[C@H]1CC[C@H](Nc2ncc3c(-c4cnc5nccn5c4)ccn3n2)CC1]
272
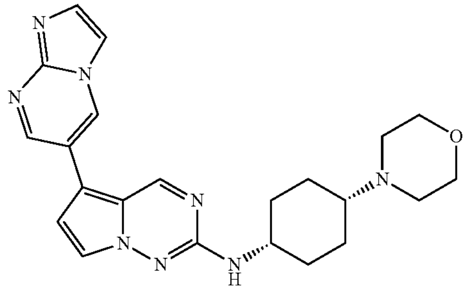 [SMILES: c1cn2cc(-c3ccn4nc(N[C@H]5CC[C@@H](N6CCOCC6)CC5)ncc34)cnc2n1]
273

TABLE 1-continued
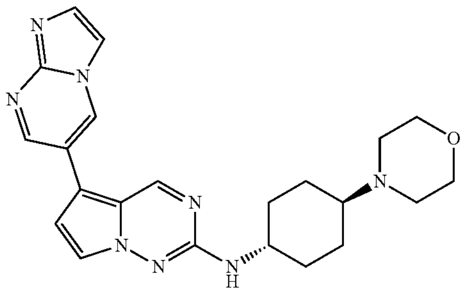 [SMILES: c1cn2cc(-c3ccn4nc(N[C@H]5CC[C@H](N6CCOCC6)CC5)ncc34)cnc2n1]
274
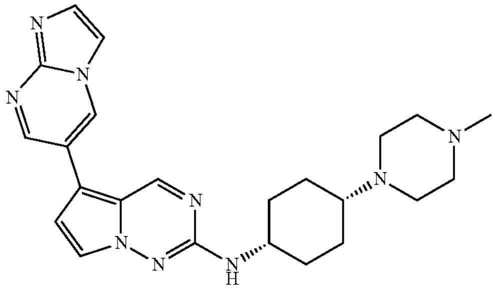 [SMILES: CN1CCN([C@H]2CC[C@@H](Nc3ncc4c(-c5cnc6nccn6c5)ccn4n3)CC2)CC1]
275
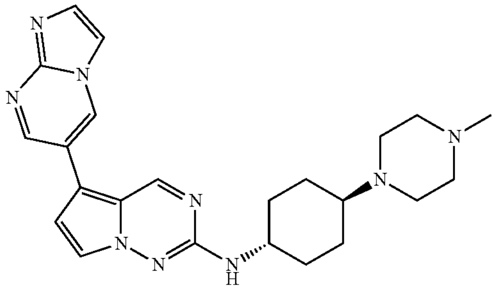 [SMILES: CN1CCN([C@H]2CC[C@H](Nc3ncc4c(-c5cnc6nccn6c5)ccn4n3)CC2)CC1]
276
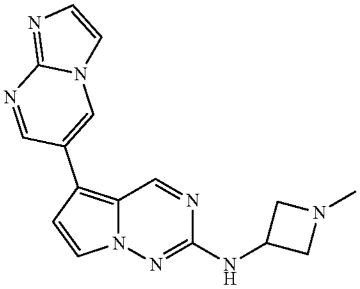 [SMILES: CN1CC(Nc2ncc3c(-c4cnc5nccn5c4)ccn3n2)C1]
277
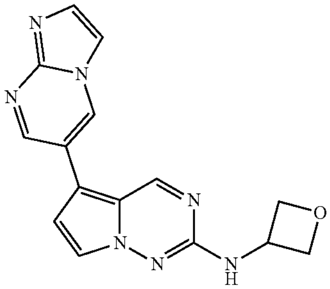 [SMILES: c1cn2cc(-c3ccn4nc(NC5COC5)ncc34)cnc2n1]
278

TABLE 1-continued
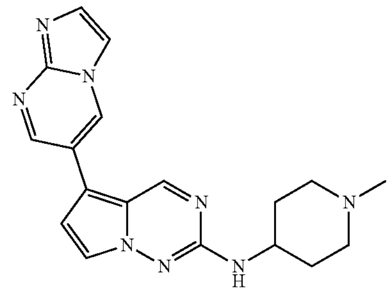 [SMILES: CN1CCC(Nc2ncc3c(-c4cnc5nccn5c4)ccn3n2)CC1]
279
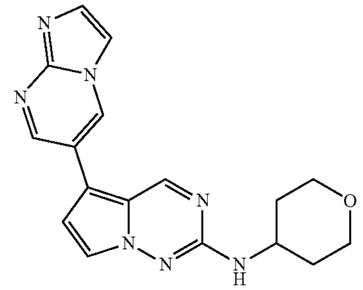 [SMILES: c1cn2cc(-c3ccn4nc(NC5CCOCC5)ncc34)cnc2n1]
280
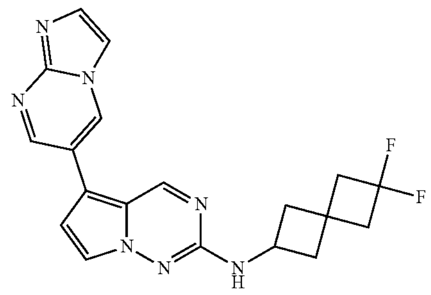 [SMILES: FC1(F)CC2(CC(Nc3ncc4c(-c5cnc6nccn6c5)ccn4n3)C2)C1]
281
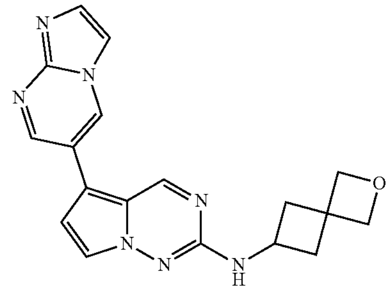 [SMILES: c1cn2cc(-c3ccn4nc(NC5CC6(COC6)C5)ncc34)cnc2n1]
282
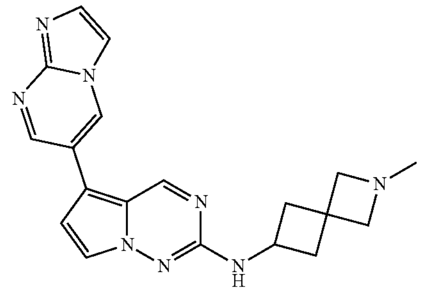 [SMILES: CN1CC2(CC(Nc3ncc4c(-c5cnc6nccn6c5)ccn4n3)C2)C1]
283

TABLE 1-continued
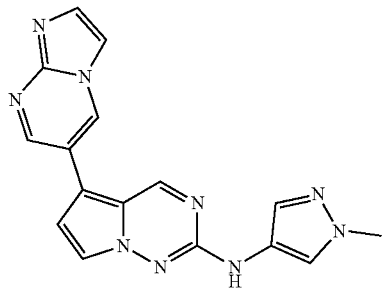 [SMILES: Cn1cc(Nc2ncc3c(-c4cnc5nccn5c4)ccn3n2)cn1]
284
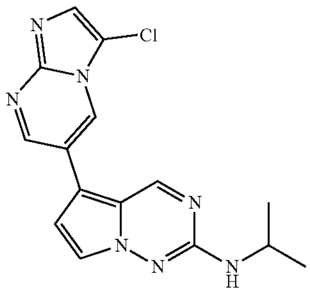 [SMILES: CC(C)Nc1ncc2c(-c3cnc4ncc(Cl)n4c3)ccn2n1]
285
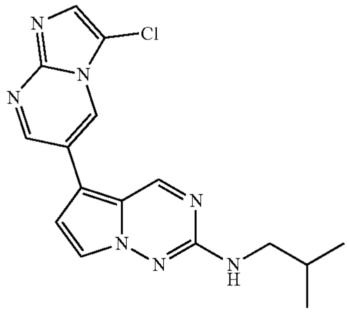 [SMILES: CC(C)CNc1ncc2c(-c3cnc4ncc(Cl)n4c3)ccn2n1]
286
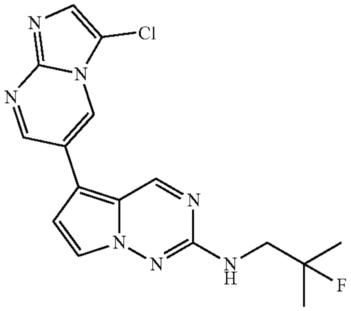 [SMILES: CC(C)(F)CNc1ncc2c(-c3cnc4ncc(Cl)n4c3)ccn2n1]
287
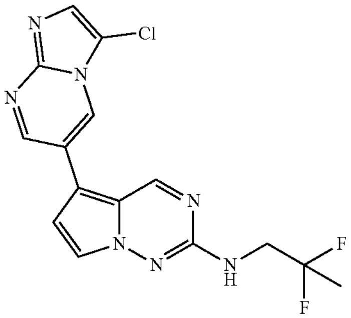 [SMILES: CC(F)(F)CNc1ncc2c(-c3cnc4ncc(Cl)n4c3)ccn2n1]
288

TABLE 1-continued
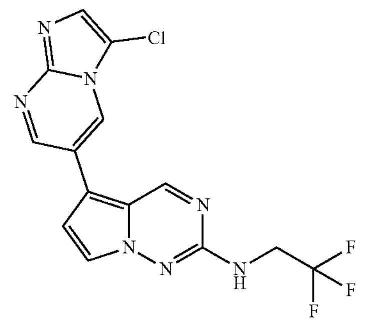 [SMILES: FC(F)(F)CNc1ncc2c(-c3cnc4ncc(Cl)n4c3)ccn2n1]
289
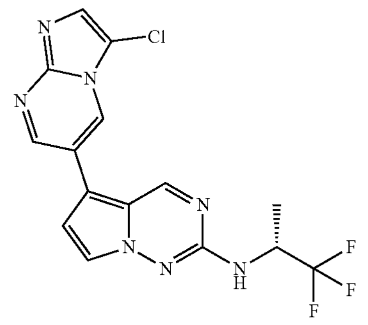 [SMILES: C[C@@H](Nc1ncc2c(-c3cnc4ncc(Cl)n4c3)ccn2n1)C(F)(F)F]
290
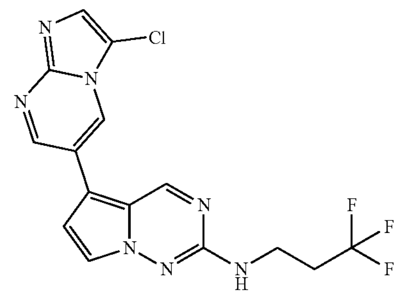 [SMILES: FC(F)(F)CCNc1ncc2c(-c3cnc4ncc(Cl)n4c3)ccn2n1]
291
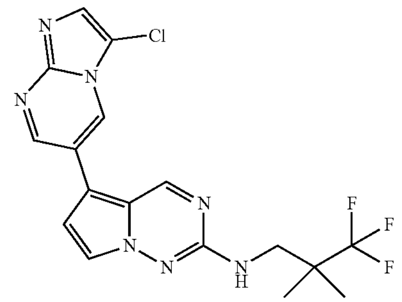 [SMILES: CC(C)(CNc1ncc2c(-c3cnc4ncc(Cl)n4c3)ccn2n1)C(F)(F)F]
292
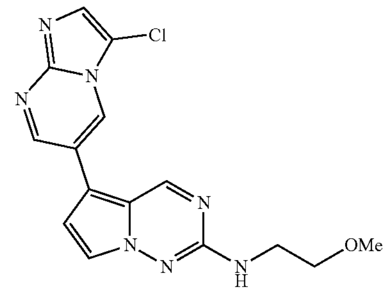 [SMILES: COCCNc1ncc2c(-c3cnc4ncc(Cl)n4c3)ccn2n1]
293

TABLE 1-continued
294
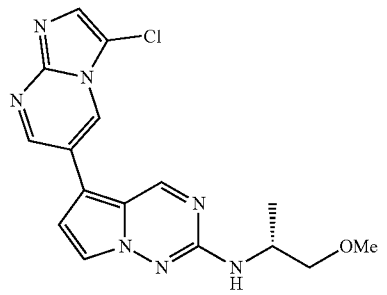
295
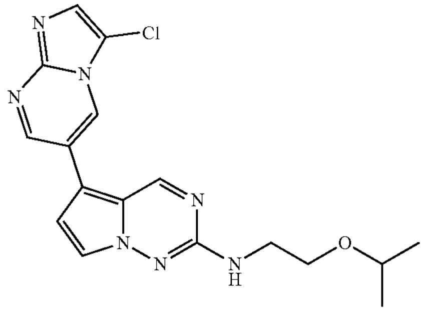 [SMILES: CC(C)OCCNc1ncc2c(-c3cnc4ncc(Cl)n4c3)ccn2n1]
296
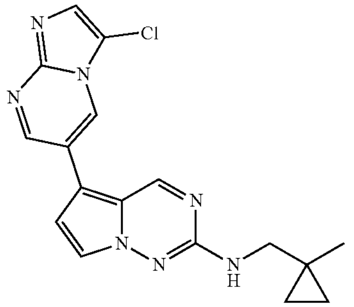 [SMILES: CC1(CNc2ncc3c(-c4cnc5ncc(Cl)n5c4)ccn3n2)CC1]
297
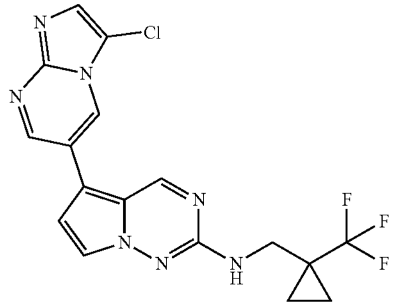 [SMILES: FC(F)(F)C1(CNc2ncc3c(-c4cnc5ncc(Cl)n5c4)ccn3n2)CC1]
298
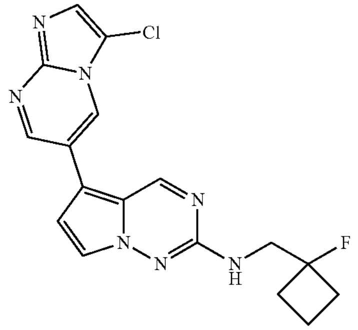

TABLE 1-continued
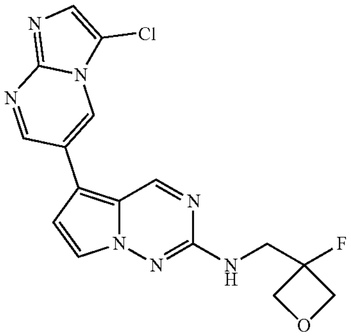
299
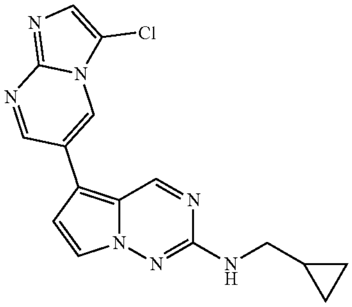 [SMILES: Clc1cnc2ncc(-c3ccn4nc(NCC5CC5)ncc34)cn12]
300
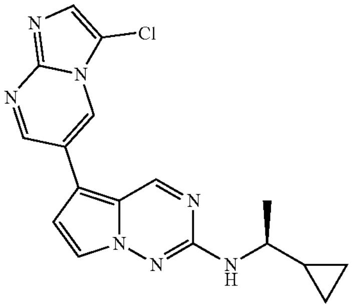 [SMILES: C[C@H](Nc1ncc2c(-c3cnc4ncc(Cl)n4c3)ccn2n1)C1CC1]
301
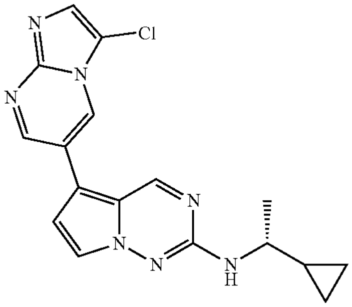 [SMILES: C[C@@H](Nc1ncc2c(-c3cnc4ncc(Cl)n4c3)ccn2n1)C1CC1]
302
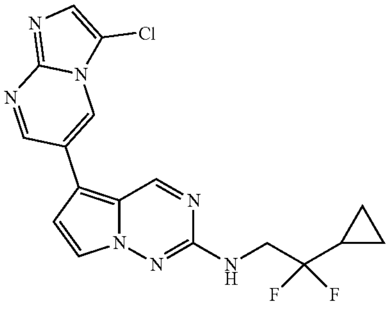 [SMILES: FC(F)(CNc1ncc2c(-c3cnc4ncc(Cl)n4c3)ccn2n1)C1CC1]
303

TABLE 1-continued
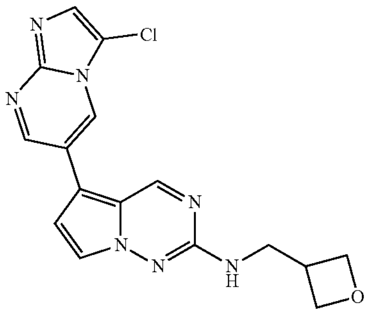 [SMILES: Clc1cnc2ncc(-c3ccn4nc(NCC5COC5)ncc34)cn12]
304
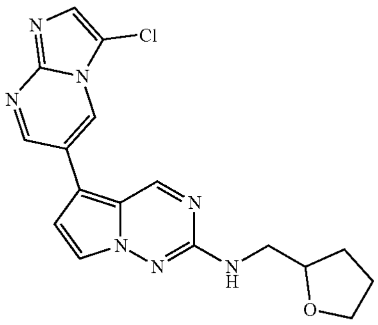 [SMILES: Clc1cnc2ncc(-c3ccn4nc(NCC5CCCO5)ncc34)cn12]
305
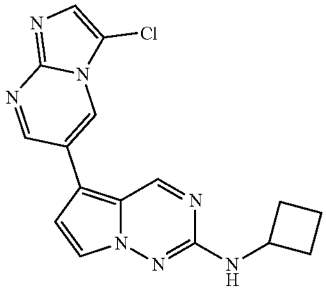 [SMILES: Clc1cnc2ncc(-c3ccn4nc(NC5CCC5)ncc34)cn12]
306
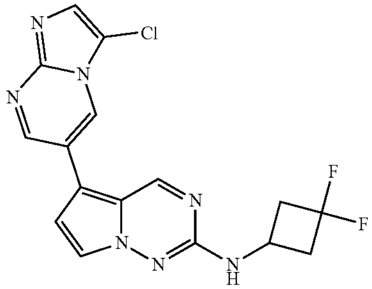 [SMILES: FC1(F)CC(Nc2ncc3c(-c4cnc5ncc(Cl)n5c4)ccn3n2)C1]
307
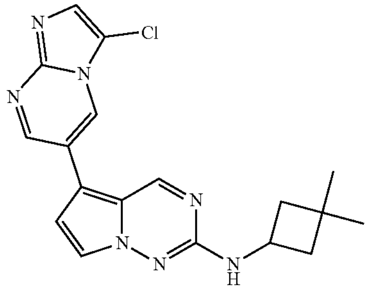 [SMILES: CC1(C)CC(Nc2ncc3c(-c4cnc5ncc(Cl)n5c4)ccn3n2)C1]
308

TABLE 1-continued
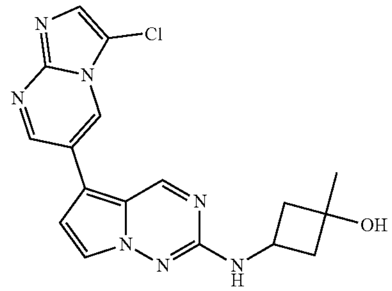 [SMILES: CC1(O)CC(Nc2ncc3c(-c4cnc5ncc(Cl)n5c4)ccn3n2)C1]
309
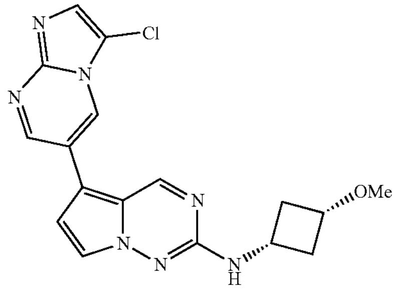 [SMILES: CO[C@H]1C[C@@H](Nc2ncc3c(-c4cnc5ncc(Cl)n5c4)ccn3n2)C1]
310
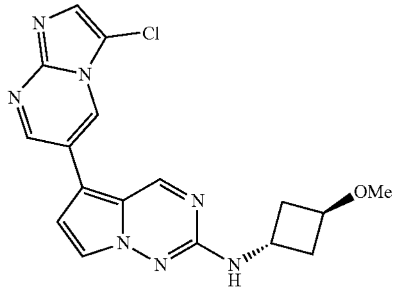 [SMILES: CO[C@H]1C[C@H](Nc2ncc3c(-c4cnc5ncc(Cl)n5c4)ccn3n2)C1]
311
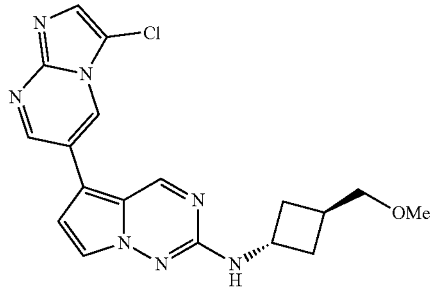
312
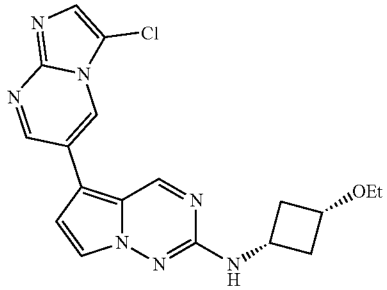 [SMILES: CCO[C@H]1C[C@@H](Nc2ncc3c(-c4cnc5ncc(Cl)n5c4)ccn3n2)C1]
313

TABLE 1-continued
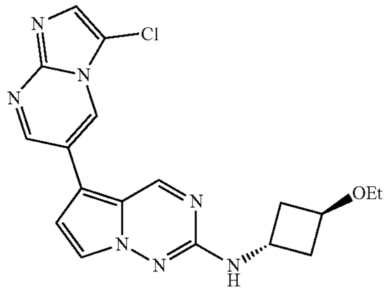 [SMILES: CCO[C@H]1C[C@H](Nc2ncc3c(-c4cnc5ncc(Cl)n5c4)ccn3n2)C1]
314
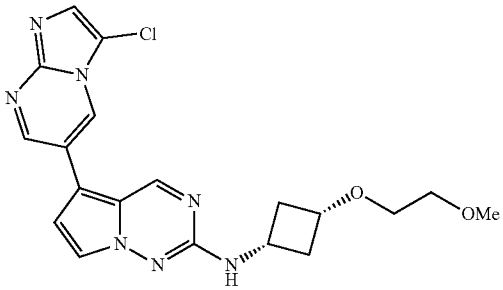 [SMILES: COCCO[C@H]1C[C@@H](Nc2ncc3c(-c4cnc5ncc(Cl)n5c4)ccn3n2)C1]
315
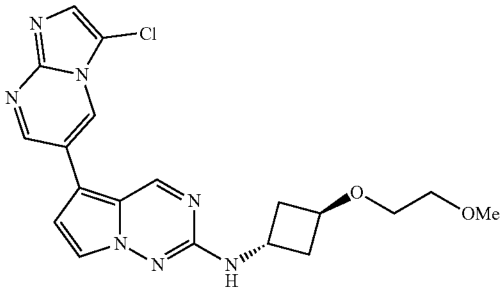 [SMILES: COCCO[C@H]1C[C@H](Nc2ncc3c(-c4cnc5ncc(Cl)n5c4)ccn3n2)C1]
316
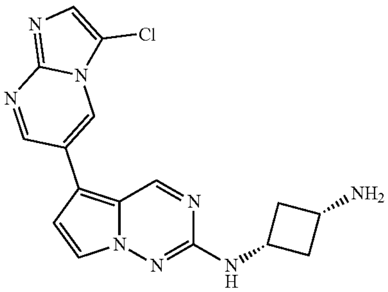 [SMILES: N[C@H]1C[C@@H](Nc2ncc3c(-c4cnc5ncc(Cl)n5c4)ccn3n2)C1]
317
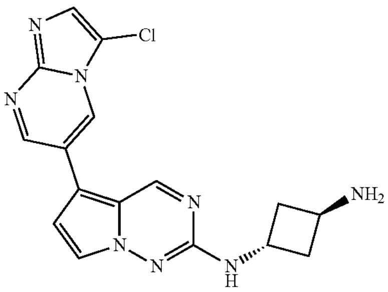 [SMILES: N[C@H]1C[C@H](Nc2ncc3c(-c4cnc5ncc(Cl)n5c4)ccn3n2)C1]
318

TABLE 1-continued
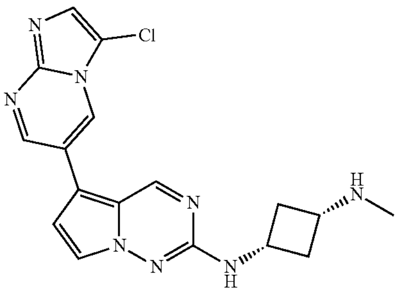 [SMILES: CN[C@H]1C[C@@H](Nc2ncc3c(-c4cnc5ncc(Cl)n5c4)ccn3n2)C1]
319
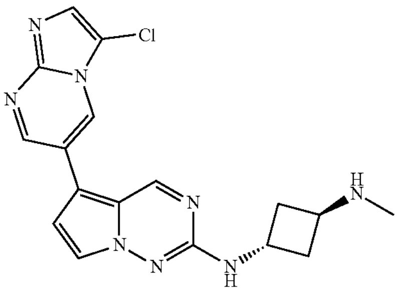 [SMILES: CN[C@H]1C[C@H](Nc2ncc3c(-c4cnc5ncc(Cl)n5c4)ccn3n2)C1]
320
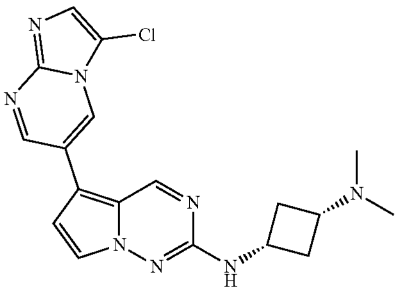 [SMILES: CN(C)[C@H]1C[C@@H](Nc2ncc3c(-c4cnc5ncc(Cl)n5c4)ccn3n2)C1]
321
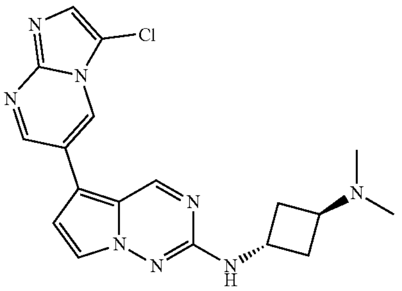
322
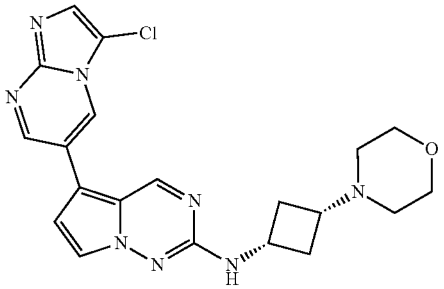
323

TABLE 1-continued
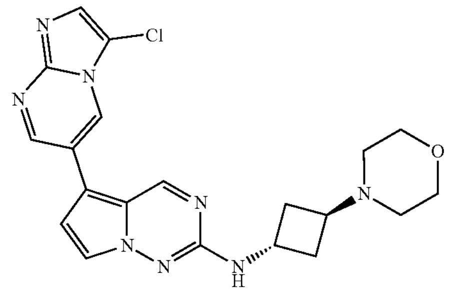
324
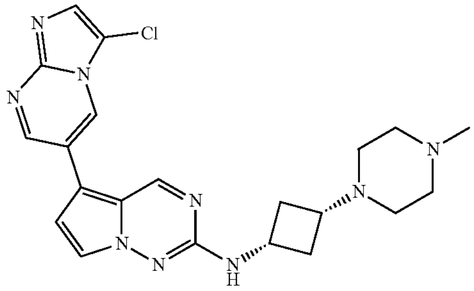 [SMILES: CN1CCN([C@H]2C[C@@H](Nc3ncc4c(-c5cnc6ncc(Cl)n6c5)ccn4n3)C2)CC1]
325
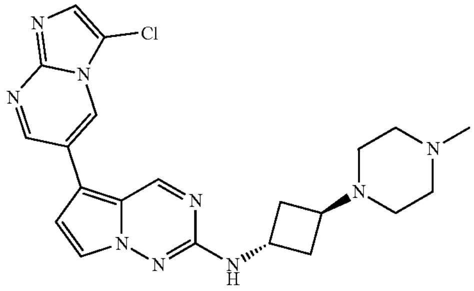 [SMILES: CN1CCN([C@H]2C[C@H](Nc3ncc4c(-c5cnc6ncc(Cl)n6c5)ccn4n3)C2)CC1]
326
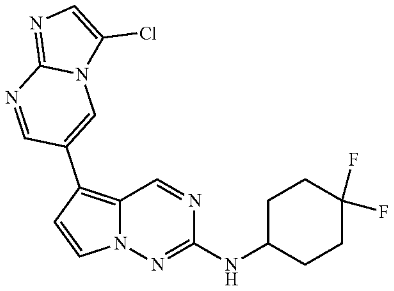 [SMILES: FC1(F)CCC(Nc2ncc3c(-c4cnc5ncc(Cl)n5c4)ccn3n2)CC1]
327
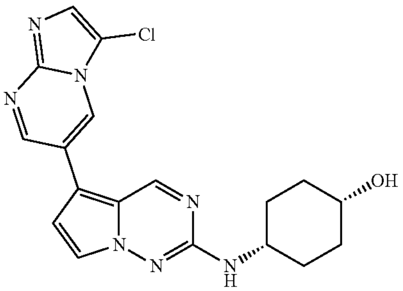 [SMILES: O[C@H]1CC[C@@H](Nc2ncc3c(-c4cnc5ncc(Cl)n5c4)ccn3n2)CC1]
328

TABLE 1-continued
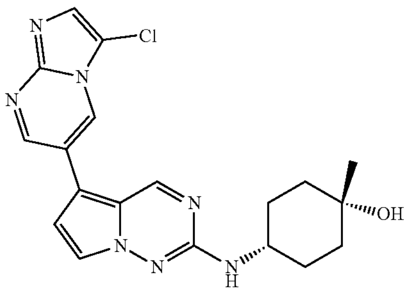 [SMILES: C[C@]1(O)CC[C@@H](Nc2ncc3c(-c4cnc5ncc(Cl)n5c4)ccn3n2)CC1]
329
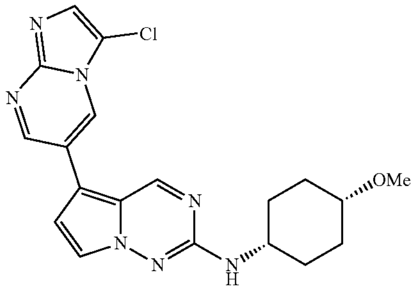
330
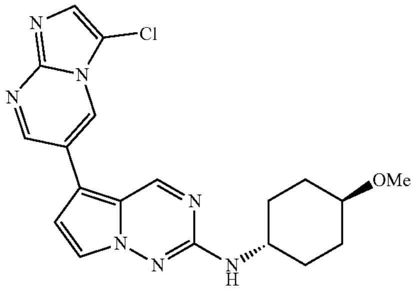 [SMILES: CO[C@H]1CC[C@H](Nc2ncc3c(-c4cnc5ncc(Cl)n5c4)ccn3n2)CC1]
331
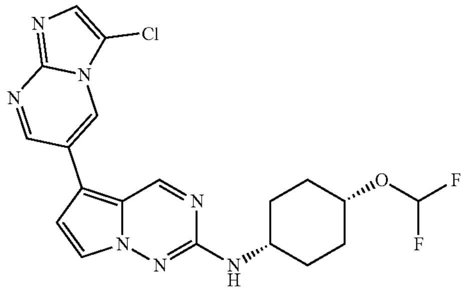
332
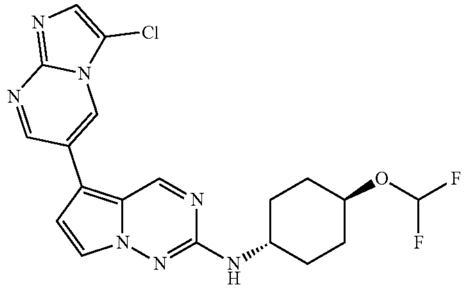 [SMILES: FC(F)O[C@H]1CC[C@H](Nc2ncc3c(-c4cnc5ncc(Cl)n5c4)ccn3n2)CC1]
333

TABLE 1-continued
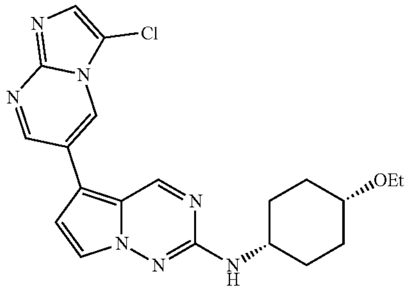 [SMILES: CCO[C@H]1CC[C@@H](Nc2ncc3c(-c4cnc5ncc(Cl)n5c4)ccn3n2)CC1]
334
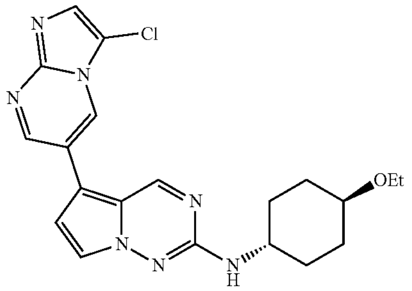 [SMILES: CCO[C@H]1CC[C@H](Nc2ncc3c(-c4cnc5ncc(Cl)n5c4)ccn3n2)CC1]
335
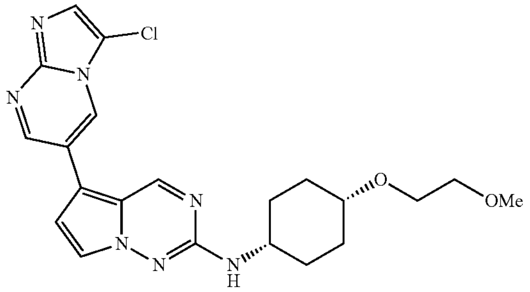 [SMILES: COCCO[C@H]1CC[C@@H](Nc2ncc3c(-c4cnc5ncc(Cl)n5c4)ccn3n2)CC1]
336
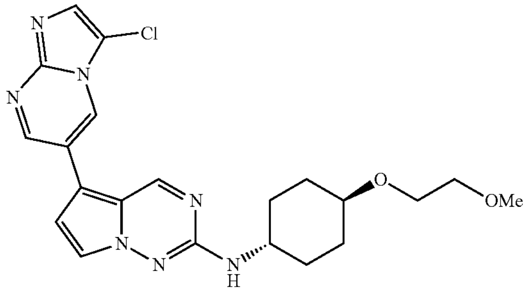 [SMILES: COCCO[C@H]1CC[C@H](Nc2ncc3c(-c4cnc5ncc(Cl)n5c4)ccn3n2)CC1]
337
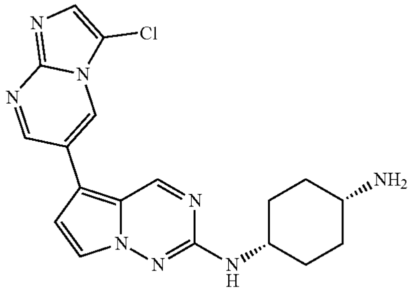 [SMILES: N[C@H]1CC[C@@H](Nc2ncc3c(-c4cnc5ncc(Cl)n5c4)ccn3n2)CC1]
338

TABLE 1-continued
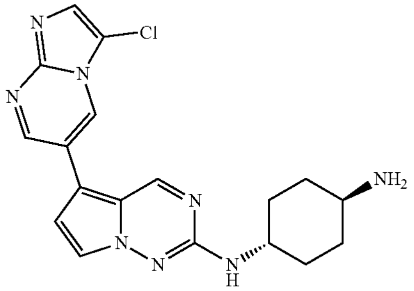 [SMILES: N[C@H]1CC[C@H](Nc2ncc3c(-c4cnc5ncc(Cl)n5c4)ccn3n2)CC1]
339
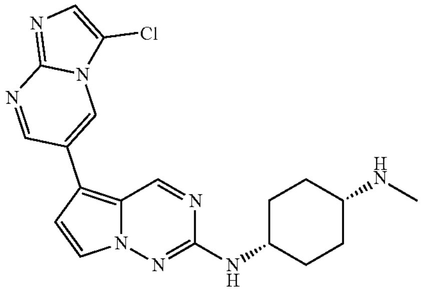 [SMILES: CN[C@H]1CC[C@@H](Nc2ncc3c(-c4cnc5ncc(Cl)n5c4)ccn3n2)CC1]
340
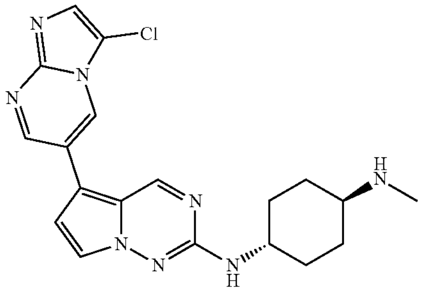 [SMILES: CN[C@H]1CC[C@H](Nc2ncc3c(-c4cnc5ncc(Cl)n5c4)ccn3n2)CC1]
341
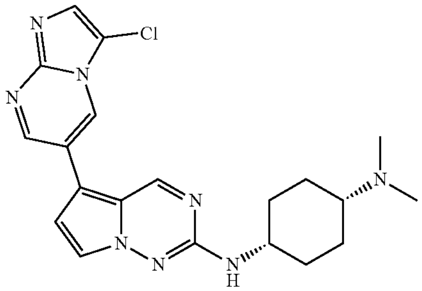 [SMILES: CN(C)[C@H]1CC[C@@H](Nc2ncc3c(-c4cnc5ncc(Cl)n5c4)ccn3n2)CC1]
342
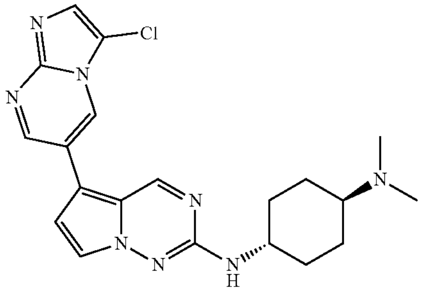 [SMILES: CN(C)[C@H]1CC[C@H](Nc2ncc3c(-c4cnc5ncc(Cl)n5c4)ccn3n2)CC1]
343

TABLE 1-continued
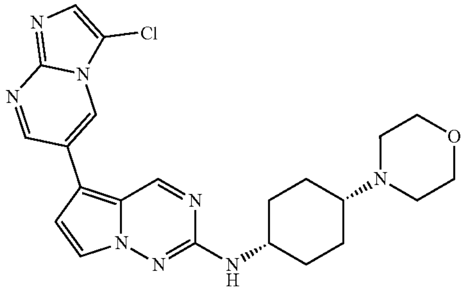 [SMILES: Clc1cnc2ncc(-c3ccn4nc(N[C@H]5CC[C@@H](N6CCOCC6)CC5)ncc34)cn12]
344
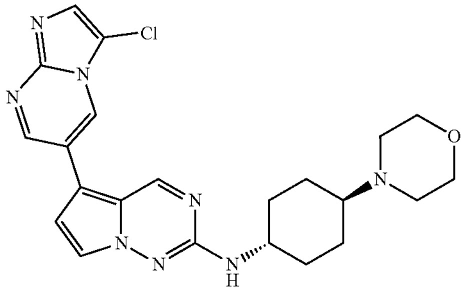 [SMILES: Clc1cnc2ncc(-c3ccn4nc(N[C@H]5CC[C@H](N6CCOCC6)CC5)ncc34)cn12]
345
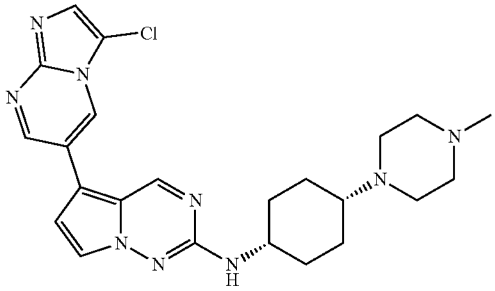 [SMILES: CN1CCN([C@H]2CC[C@@H](Nc3ncc4c(-c5cnc6ncc(Cl)n6c5)ccn4n3)CC2)CC1]
346
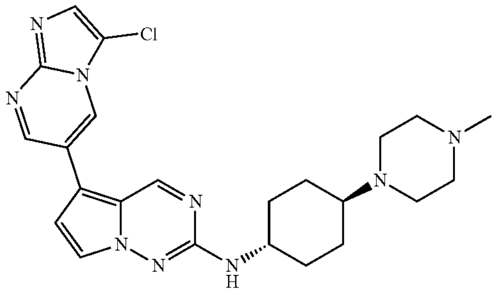 [SMILES: CN1CCN([C@H]2CC[C@H](Nc3ncc4c(-c5cnc6ncc(Cl)n6c5)ccn4n3)CC2)CC1]
347
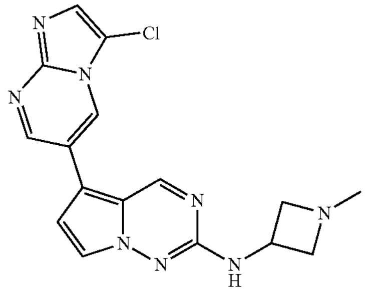 [SMILES: CN1CC(Nc2ncc3c(-c4cnc5ncc(Cl)n5c4)ccn3n2)C1]
348

TABLE 1-continued
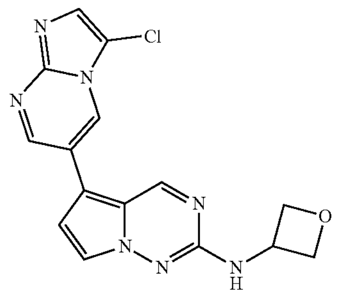 [SMILES: Clc1cnc2ncc(-c3ccn4nc(NC5COC5)ncc34)cn12]
349
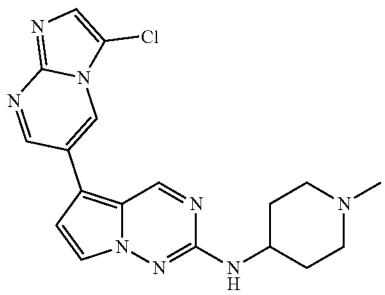 [SMILES: CN1CCC(Nc2ncc3c(-c4cnc5ncc(Cl)n5c4)ccn3n2)CC1]
350
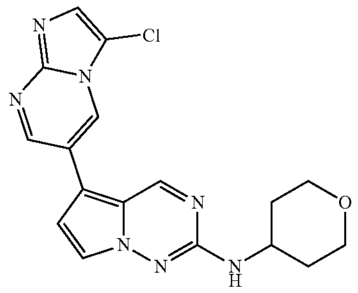 [SMILES: Clc1cnc2ncc(-c3ccn4nc(NC5CCOCC5)ncc34)cn12]
351
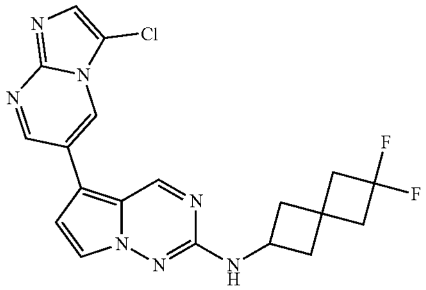 [SMILES: FC1(F)CC2(CC(Nc3ncc4c(-c5cnc6ncc(Cl)n6c5)ccn4n3)C2)C1]
352
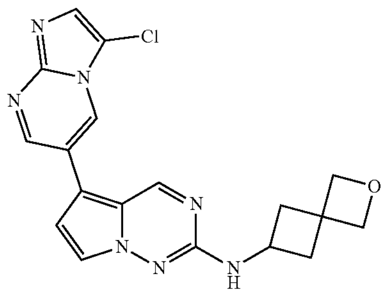 [SMILES: Clc1cnc2ncc(-c3ccn4nc(NC5CC6(COC6)C5)ncc34)cn12]
353

TABLE 1-continued
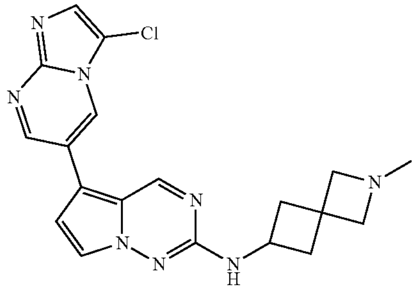 [SMILES: CN1CC2(CC(Nc3ncc4c(-c5cnc6ncc(Cl)n6c5)ccn4n3)C2)C1]
354
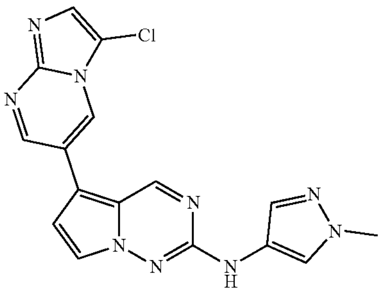 [SMILES: Cn1cc(Nc2ncc3c(-c4cnc5ncc(Cl)n5c4)ccn3n2)cn1]
355
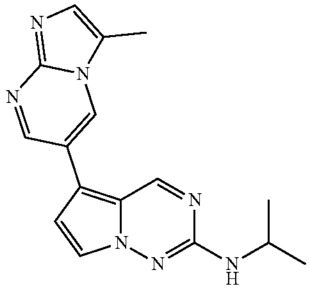 [SMILES: Cc1cnc2ncc(-c3ccn4nc(NC(C)C)ncc34)cn12]
356
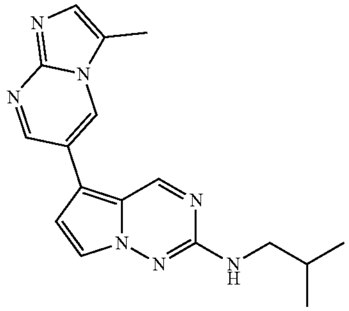 [SMILES: Cc1cnc2ncc(-c3ccn4nc(NCC(C)C)ncc34)cn12]
357
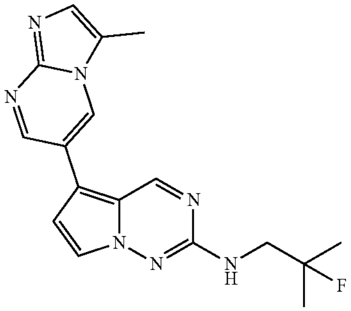 [SMILES: Cc1cnc2ncc(-c3ccn4nc(NCC(C)(C)F)ncc34)cn12]
358

TABLE 1-continued
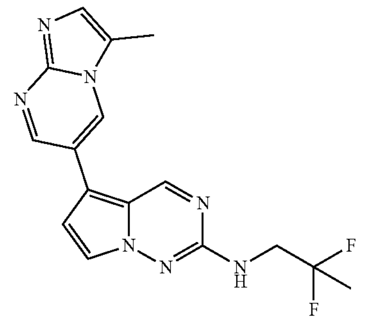 [SMILES: Cc1cnc2ncc(-c3ccn4nc(NCC(C)(F)F)ncc34)cn12]
359
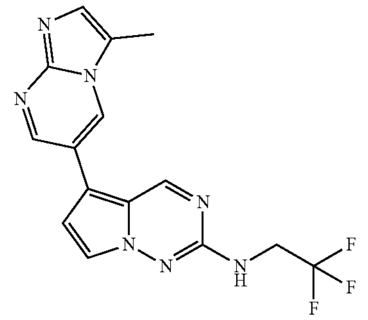 [SMILES: Cc1cnc2ncc(-c3ccn4nc(NCC(F)(F)F)ncc34)cn12]
360
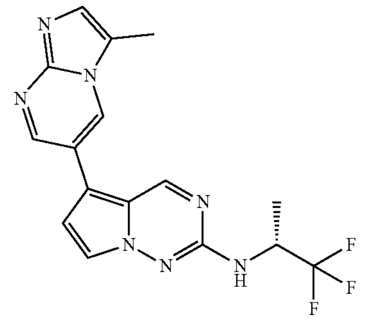 [SMILES: Cc1cnc2ncc(-c3ccn4nc(N[C@H](C)C(F)(F)F)ncc34)cn12]
361
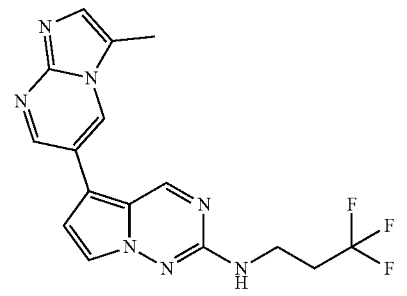 [SMILES: Cc1cnc2ncc(-c3ccn4nc(NCCC(F)(F)F)ncc34)cn12]
362
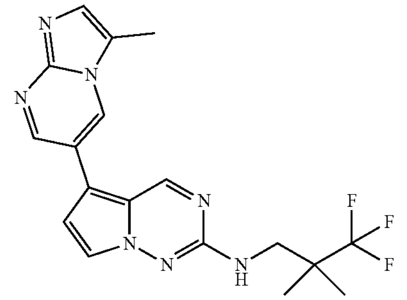 [SMILES: Cc1cnc2ncc(-c3ccn4nc(NCC(C)(C)C(F)(F)F)ncc34)cn12]
363

TABLE 1-continued
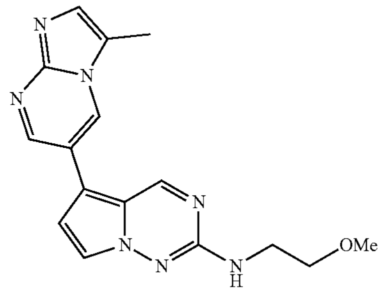 [SMILES: COCCNc1ncc2c(-c3cnc4ncc(C)n4c3)ccn2n1]
364
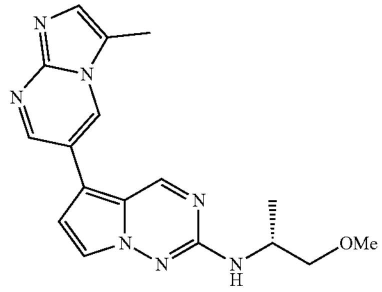 [SMILES: COC[C@@H](C)Nc1ncc2c(-c3cnc4ncc(C)n4c3)ccn2n1]
365
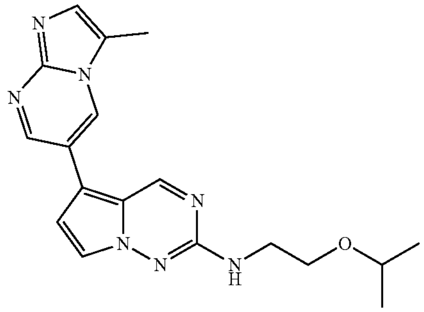 [SMILES: Cc1cnc2ncc(-c3ccn4nc(NCCOC(C)C)ncc34)cn12]
366
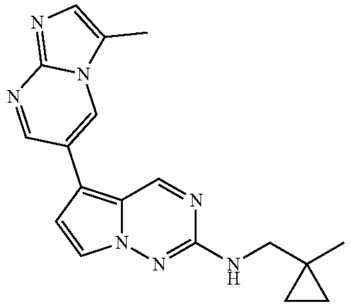 [SMILES: Cc1cnc2ncc(-c3ccn4nc(NCC5(C)CC5)ncc34)cn12]
367
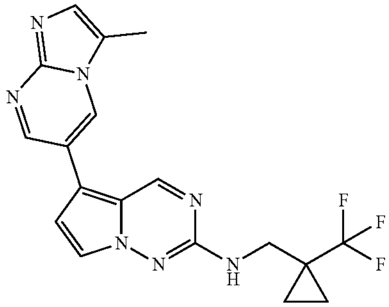 [SMILES: Cc1cnc2ncc(-c3ccn4nc(NCC5(C(F)(F)F)CC5)ncc34)cn12]
368

TABLE 1-continued
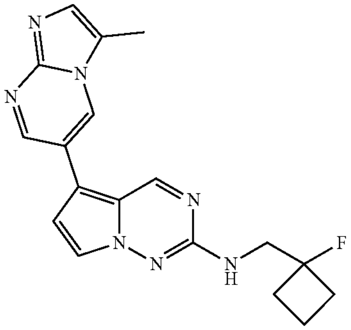 [SMILES: Cc1cnc2ncc(-c3ccn4nc(NCC5(F)CCC5)ncc34)cn12]
369
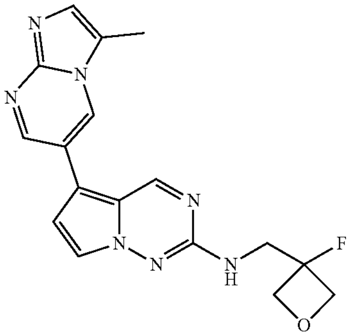 [SMILES: Cc1cnc2ncc(-c3ccn4nc(NCC5(F)COC5)ncc34)cn12]
370
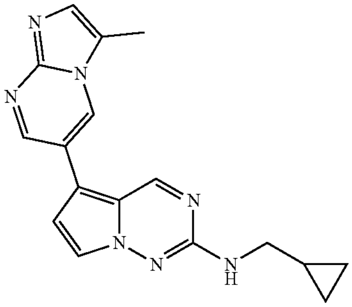 [SMILES: Cc1cnc2ncc(-c3ccn4nc(NCC5CC5)ncc34)cn12]
371
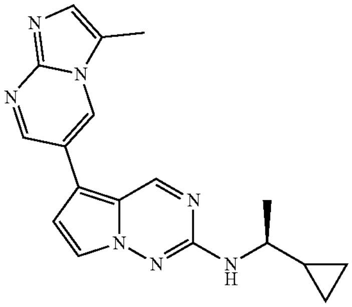 [SMILES: Cc1cnc2ncc(-c3ccn4nc(N[C@@H](C)C5CC5)ncc34)cn12]
372
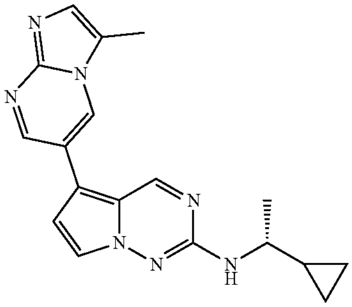 [SMILES: Cc1cnc2ncc(-c3ccn4nc(N[C@H](C)C5CC5)ncc34)cn12]
373

TABLE 1-continued
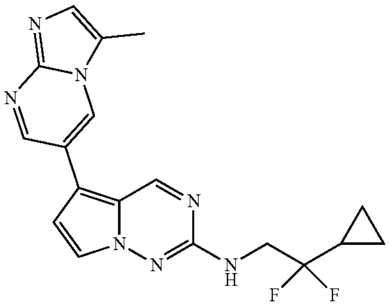 [SMILES: Cc1cnc2ncc(-c3ccn4nc(NCC(F)(F)C5CC5)ncc34)cn12]
374
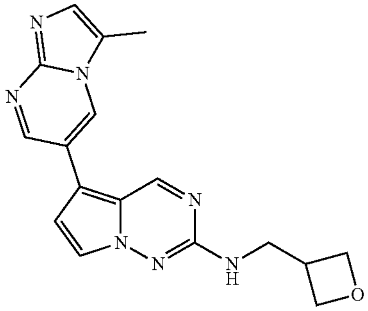 [SMILES: Cc1cnc2ncc(-c3ccn4nc(NCC5COC5)ncc34)cn12]
375
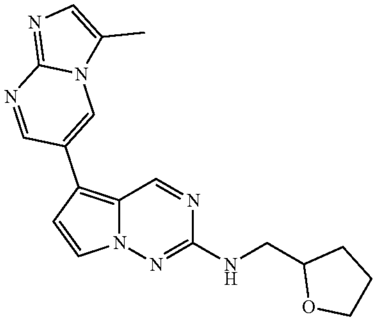 [SMILES: Cc1cnc2ncc(-c3ccn4nc(NCC5CCCO5)ncc34)cn12]
376
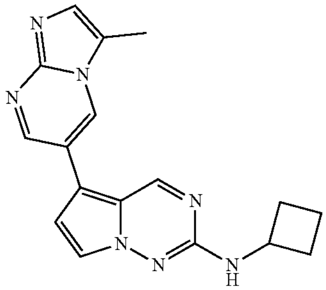 [SMILES: Cc1cnc2ncc(-c3ccn4nc(NC5CCC5)ncc34)cn12]
377
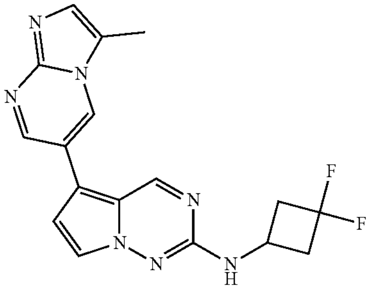 [SMILES: Cc1cnc2ncc(-c3ccn4nc(NC5CC(F)(F)C5)ncc34)cn12]
378

TABLE 1-continued
379
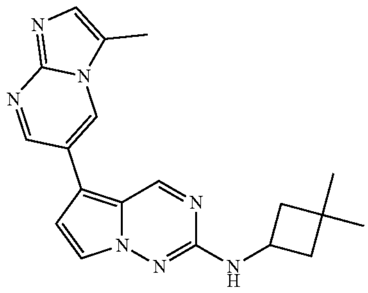 [SMILES: Cc1cnc2ncc(-c3ccn4nc(NC5CC(C)(C)C5)ncc34)cn12]
380
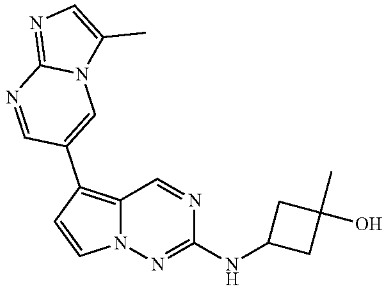
381
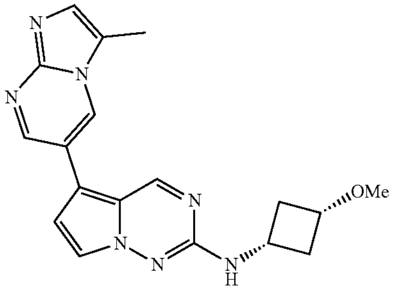 [SMILES: CO[C@H]1C[C@@H](Nc2ncc3c(-c4cnc5ncc(C)n5c4)ccn3n2)C1]
382
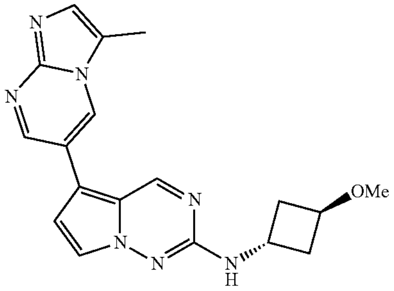 [SMILES: CO[C@H]1C[C@H](Nc2ncc3c(-c4cnc5ncc(C)n5c4)ccn3n2)C1]
383
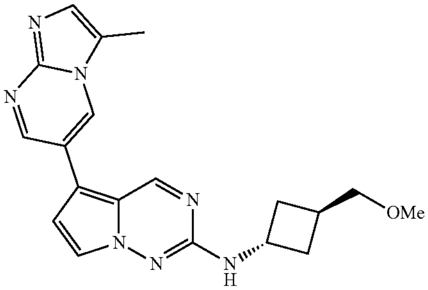 [SMILES: COC[C@H]1C[C@H](Nc2ncc3c(-c4cnc5ncc(C)n5c4)ccn3n2)C1]

TABLE 1-continued
384
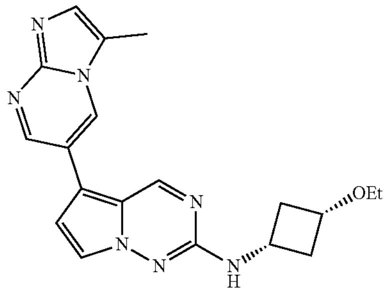 [SMILES: CCO[C@H]1C[C@@H](Nc2ncc3c(-c4cnc5ncc(C)n5c4)ccn3n2)C1]
385
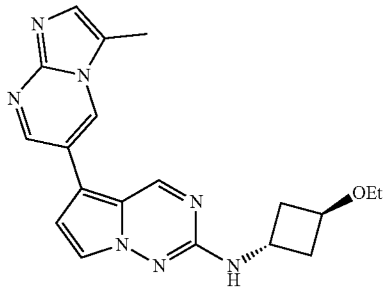 [SMILES: CCO[C@H]1C[C@H](Nc2ncc3c(-c4cnc5ncc(C)n5c4)ccn3n2)C1]
386
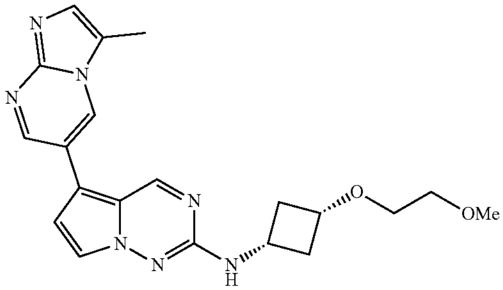 [SMILES: COCCO[C@H]1C[C@@H](Nc2ncc3c(-c4cnc5ncc(C)n5c4)ccn3n2)C1]
387
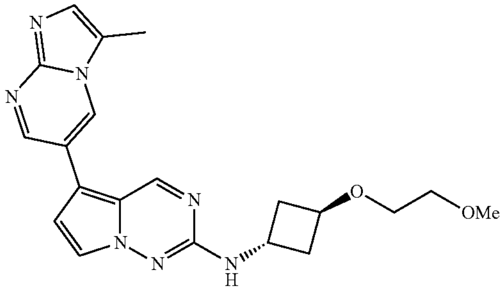
388
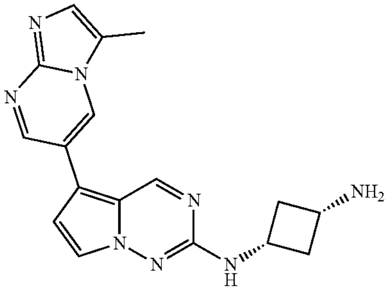 [SMILES: Cc1cnc2ncc(-c3ccn4nc(N[C@H]5C[C@@H](N)C5)ncc34)cn12]

TABLE 1-continued
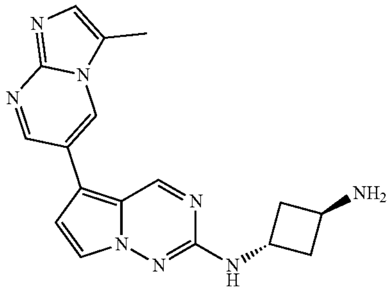 [SMILES: Cc1cnc2ncc(-c3ccn4nc(N[C@H]5C[C@H](N)C5)ncc34)cn12]
389
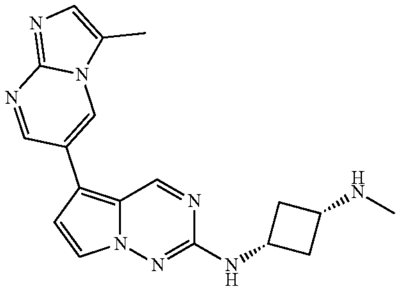 [SMILES: CN[C@H]1C[C@@H](Nc2ncc3c(-c4cnc5ncc(C)n5c4)ccn3n2)C1]
390
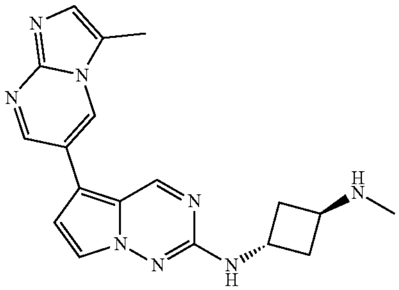 [SMILES: CN[C@H]1C[C@H](Nc2ncc3c(-c4cnc5ncc(C)n5c4)ccn3n2)C1]
391
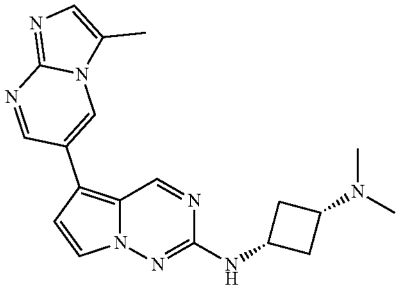 [SMILES: Cc1cnc2ncc(-c3ccn4nc(N[C@H]5C[C@@H](N(C)C)C5)ncc34)cn12]
392
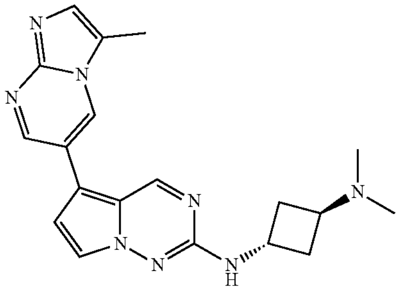 [SMILES: Cc1cnc2ncc(-c3ccn4nc(N[C@H]5C[C@H](N(C)C)C5)ncc34)cn12]
393

TABLE 1-continued
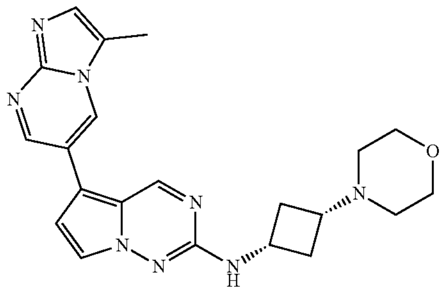 [SMILES: Cc1cnc2ncc(-c3ccn4nc(N[C@H]5C[C@@H](N6CCOCC6)C5)ncc34)cn12]
394
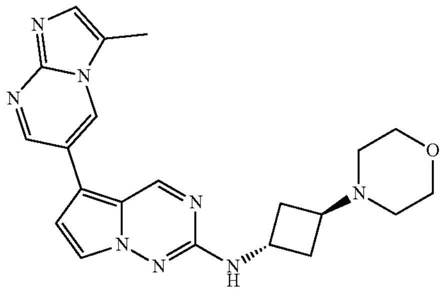 [SMILES: Cc1cnc2ncc(-c3ccn4nc(N[C@H]5C[C@H](N6CCOCC6)C5)ncc34)cn12]
395
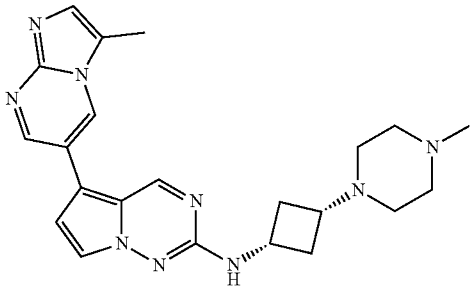 [SMILES: Cc1cnc2ncc(-c3ccn4nc(N[C@H]5C[C@@H](N6CCN(C)CC6)C5)ncc34)cn12]
396
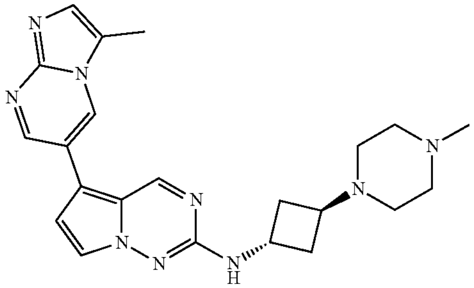 [SMILES: Cc1cnc2ncc(-c3ccn4nc(N[C@H]5C[C@H](N6CCN(C)CC6)C5)ncc34)cn12]
397
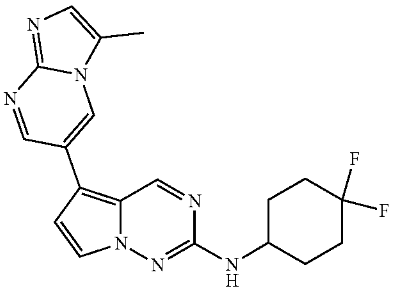 [SMILES: Cc1cnc2ncc(-c3ccn4nc(NC5CCC(F)(F)CC5)ncc34)cn12]
398

TABLE 1-continued
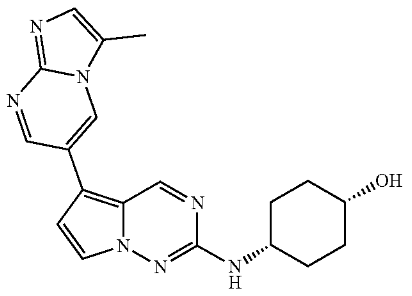 [SMILES: Cc1cnc2ncc(-c3ccn4nc(N[C@H]5CC[C@@H](O)CC5)ncc34)cn12]
399
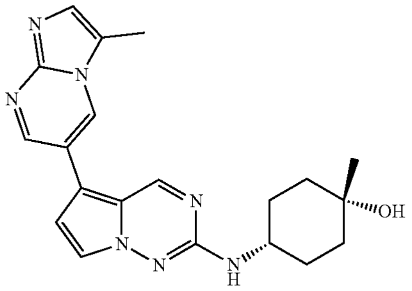 [SMILES: Cc1cnc2ncc(-c3ccn4nc(N[C@H]5CC[C@@](C)(O)CC5)ncc34)cn12]
400
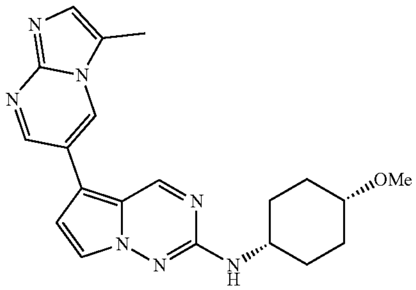 [SMILES: CO[C@H]1CC[C@@H](Nc2ncc3c(-c4cnc5ncc(C)n5c4)ccn3n2)CC1]
401
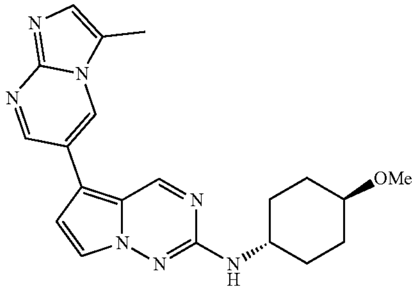 [SMILES: CO[C@H]1CC[C@H](Nc2ncc3c(-c4cnc5ncc(C)n5c4)ccn3n2)CC1]
402
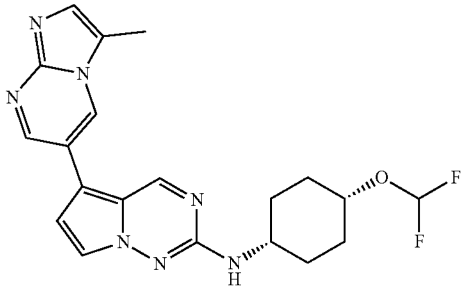 [SMILES: Cc1cnc2ncc(-c3ccn4nc(N[C@H]5CC[C@@H](OC(F)F)CC5)ncc34)cn12]
403

TABLE 1-continued
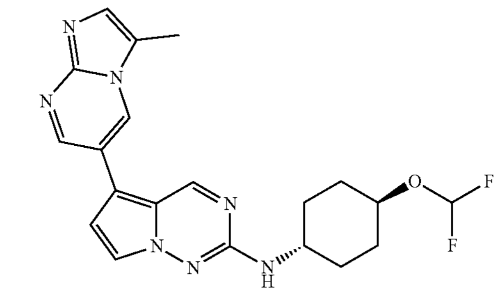 [SMILES: Cc1cnc2ncc(-c3ccn4nc(N[C@H]5CC[C@H](OC(F)F)CC5)ncc34)cn12]
404
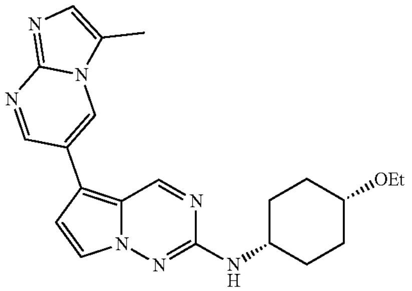 [SMILES: CCO[C@H]1CC[C@@H](Nc2ncc3c(-c4cnc5ncc(C)n5c4)ccn3n2)CC1]
405
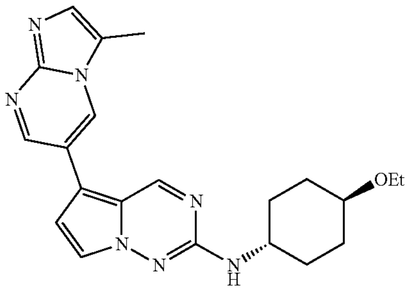 [SMILES: CCO[C@H]1CC[C@H](Nc2ncc3c(-c4cnc5ncc(C)n5c4)ccn3n2)CC1]
406
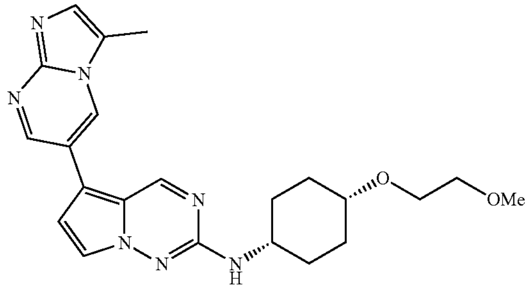 [SMILES: COCCO[C@H]1CC[C@@H](Nc2ncc3c(-c4cnc5ncc(C)n5c4)ccn3n2)CC1]
407
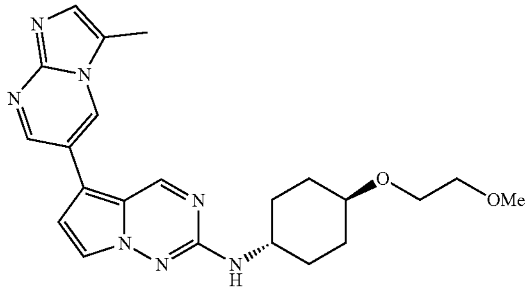 [SMILES: COCCO[C@H]1CC[C@H](Nc2ncc3c(-c4cnc5ncc(C)n5c4)ccn3n2)CC1]
408

TABLE 1-continued
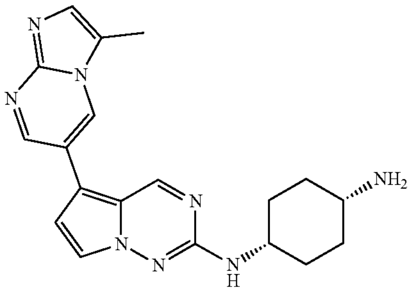 [SMILES: Cc1cnc2ncc(-c3ccn4nc(N[C@H]5CC[C@@H](N)CC5)ncc34)cn12]
409
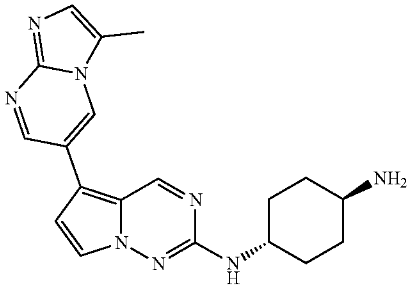 [SMILES: Cc1cnc2ncc(-c3ccn4nc(N[C@H]5CC[C@H](N)CC5)ncc34)cn12]
410
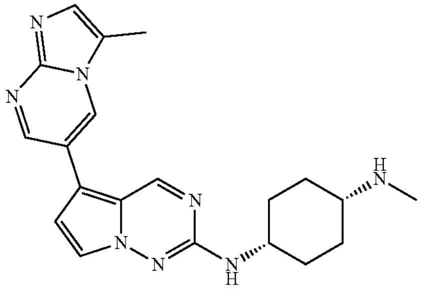 [SMILES: CN[C@H]1CC[C@@H](Nc2ncc3c(-c4cnc5ncc(C)n5c4)ccn3n2)CC1]
411
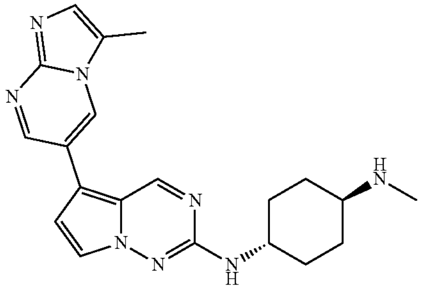 [SMILES: CN[C@H]1CC[C@H](Nc2ncc3c(-c4cnc5ncc(C)n5c4)ccn3n2)CC1]
412
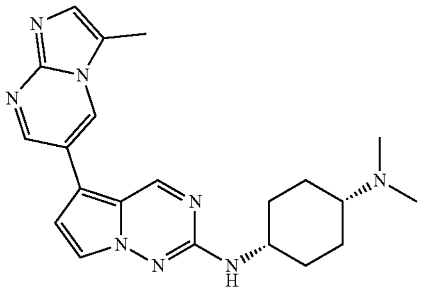 [SMILES: Cc1cnc2ncc(-c3ccn4nc(N[C@H]5CC[C@@H](N(C)C)CC5)ncc34)cn12]
413

TABLE 1-continued
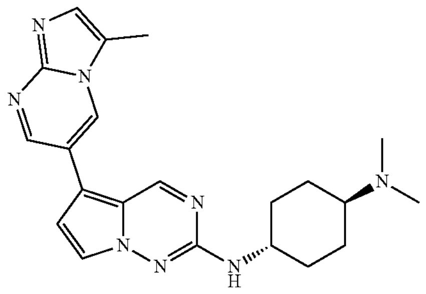 [SMILES: Cc1cnc2ncc(-c3ccn4nc(N[C@H]5CC[C@H](N(C)C)CC5)ncc34)cn12]
414
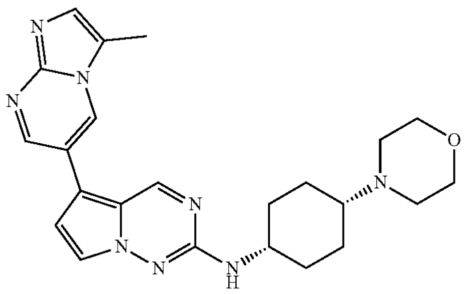 [SMILES: Cc1cnc2ncc(-c3ccn4nc(N[C@H]5CC[C@@H](N6CCOCC6)CC5)ncc34)cn12]
415
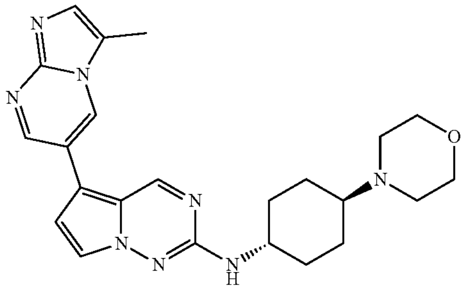 [SMILES: Cc1cnc2ncc(-c3ccn4nc(N[C@H]5CC[C@H](N6CCOCC6)CC5)ncc34)cn12]
416
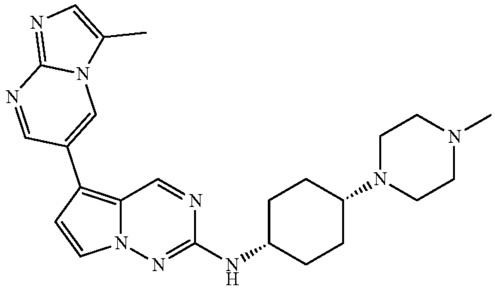 [SMILES: Cc1cnc2ncc(-c3ccn4nc(N[C@H]5CC[C@@H](N6CCN(C)CC6)CC5)ncc34)cn12]
417
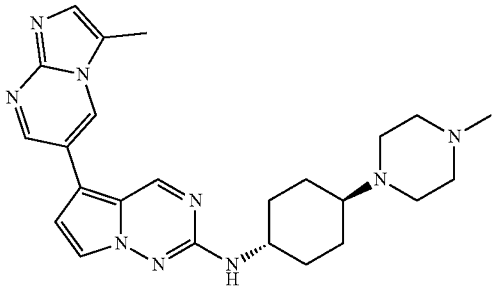
418

TABLE 1-continued
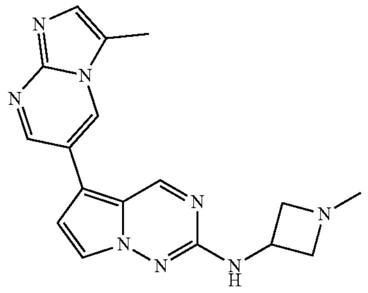 [SMILES: Cc1cnc2ncc(-c3ccn4nc(NC5CN(C)C5)ncc34)cn12]
419
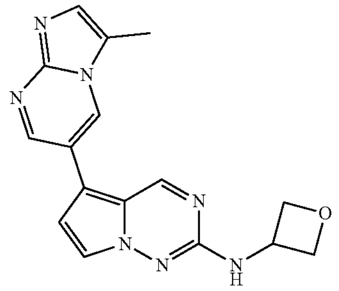 [SMILES: Cc1cnc2ncc(-c3ccn4nc(NC5COC5)ncc34)cn12]
420
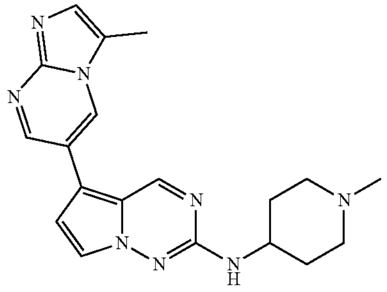 [SMILES: Cc1cnc2ncc(-c3ccn4nc(NC5CCN(C)CC5)ncc34)cn12]
421
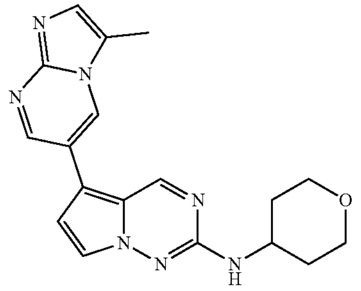 [SMILES: Cc1cnc2ncc(-c3ccn4nc(NC5CCOCC5)ncc34)cn12]
422
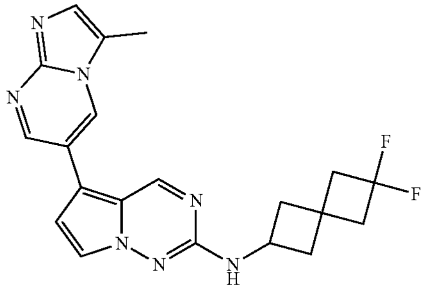 [SMILES: Cc1cnc2ncc(-c3ccn4nc(NC5CC6(C5)CC(F)(F)C6)ncc34)cn12]
423

TABLE 1-continued
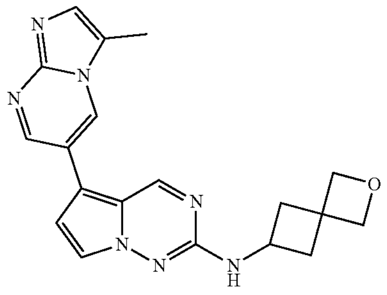 [SMILES: Cc1cnc2ncc(-c3ccn4nc(NC5CC6(COC6)C5)ncc34)cn12]
424
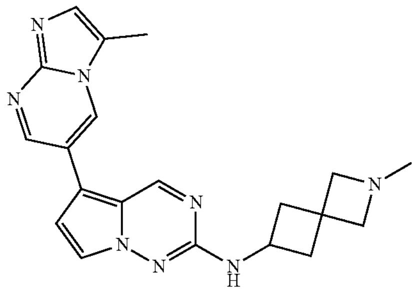 [SMILES: Cc1cnc2ncc(-c3ccn4nc(NC5CC6(C5)CN(C)C6)ncc34)cn12]
425
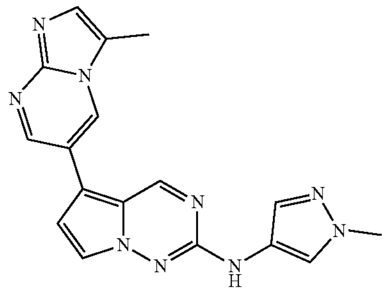 [SMILES: Cc1cnc2ncc(-c3ccn4nc(Nc5cnn(C)c5)ncc34)cn12]
426
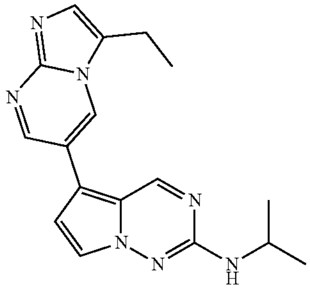 [SMILES: CCc1cnc2ncc(-c3ccn4nc(NC(C)C)ncc34)cn12]
427
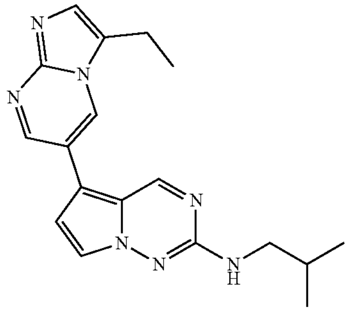 [SMILES: CCc1cnc2ncc(-c3ccn4nc(NCC(C)C)ncc34)cn12]
428

TABLE 1-continued
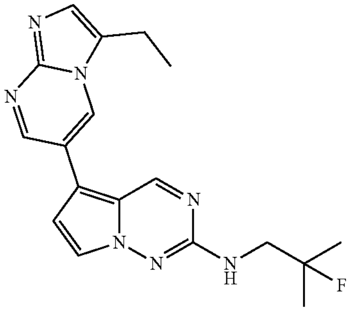 [SMILES: CCc1cnc2ncc(-c3ccn4nc(NCC(C)(C)F)ncc34)cn12]
429
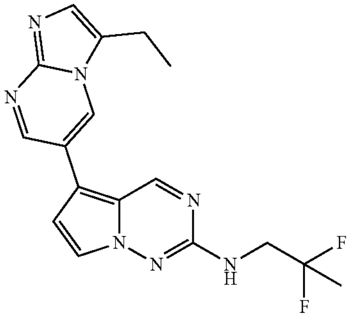 [SMILES: CCc1cnc2ncc(-c3ccn4nc(NCC(C)(F)F)ncc34)cn12]
430
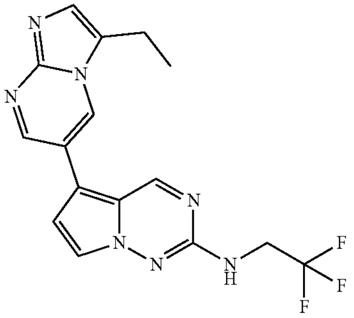 [SMILES: CCc1cnc2ncc(-c3ccn4nc(NCC(F)(F)F)ncc34)cn12]
431
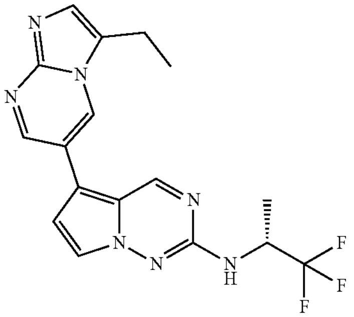 [SMILES: CCc1cnc2ncc(-c3ccn4nc(N[C@H](C)C(F)(F)F)ncc34)cn12]
432
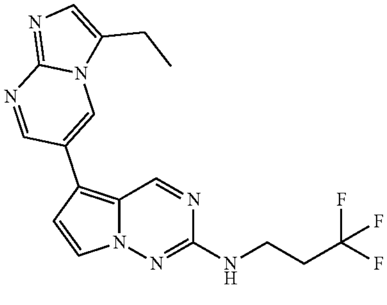 [SMILES: CCc1cnc2ncc(-c3ccn4nc(NCCC(F)(F)F)ncc34)cn12]
433

TABLE 1-continued
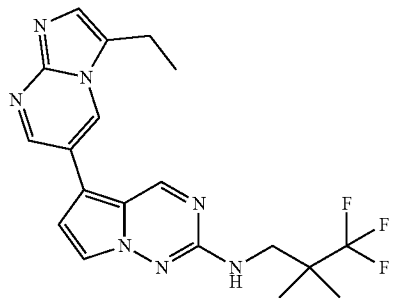 [SMILES: CCc1cnc2ncc(-c3ccn4nc(NCC(C)(C)C(F)(F)F)ncc34)cn12]
434
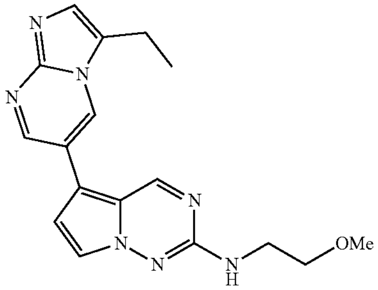 [SMILES: CCc1cnc2ncc(-c3ccn4nc(NCCOC)ncc34)cn12]
435
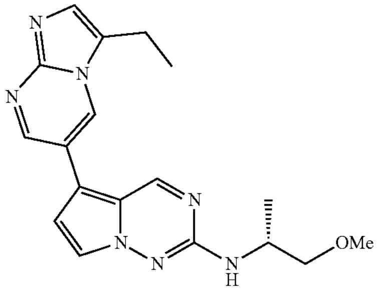 [SMILES: CCc1cnc2ncc(-c3ccn4nc(N[C@H](C)COC)ncc34)cn12]
436
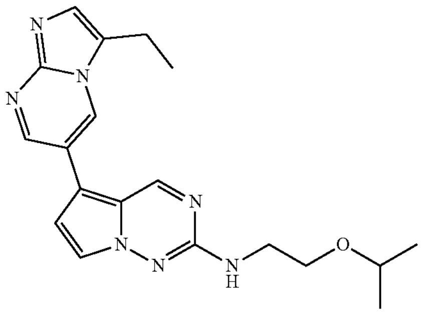 [SMILES: CCc1cnc2ncc(-c3ccn4nc(NCCOC(C)C)ncc34)cn12]
437
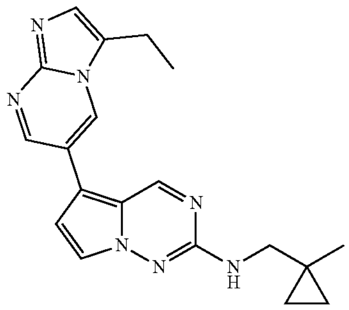 [SMILES: CCc1cnc2ncc(-c3ccn4nc(NCC5(C)CC5)ncc34)cn12]
438

TABLE 1-continued
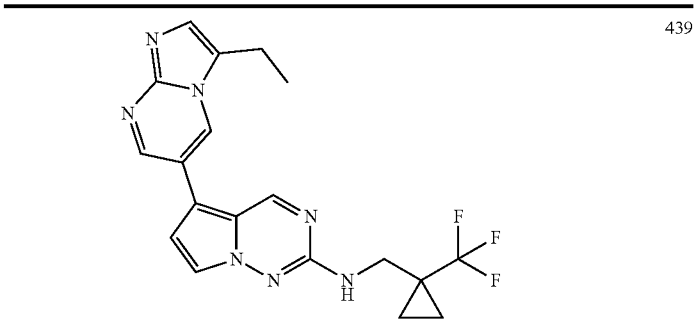
439
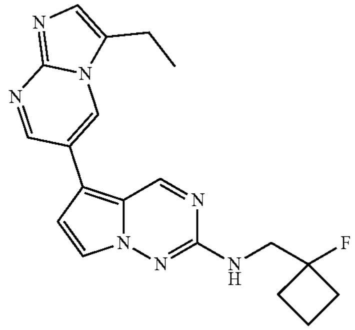 [SMILES: CCc1cnc2ncc(-c3ccn4nc(NCC5(F)CCC5)ncc34)cn12]
440
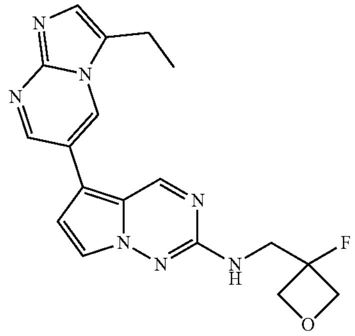 [SMILES: CCc1cnc2ncc(-c3ccn4nc(NCC5(F)COC5)ncc34)cn12]
441
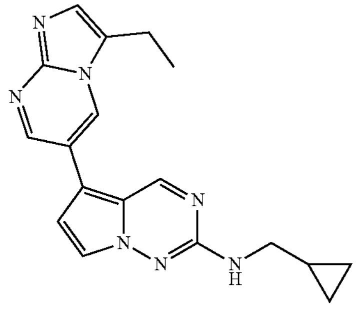 [SMILES: CCc1cnc2ncc(-c3ccn4nc(NCC5CC5)ncc34)cn12]
442
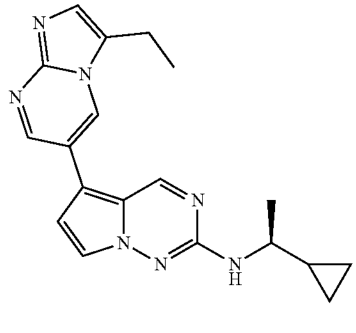 [SMILES: CCc1cnc2ncc(-c3ccn4nc(N[C@@H](C)C5CC5)ncc34)cn12]
443

TABLE 1-continued
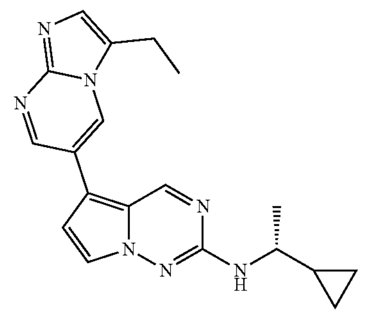 [SMILES: CCc1cnc2ncc(-c3ccn4nc(N[C@H](C)C5CC5)ncc34)cn12]
444
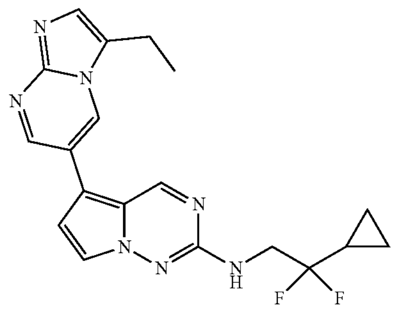 [SMILES: CCc1cnc2ncc(-c3ccn4nc(NCC(F)(F)C5CC5)ncc34)cn12]
445
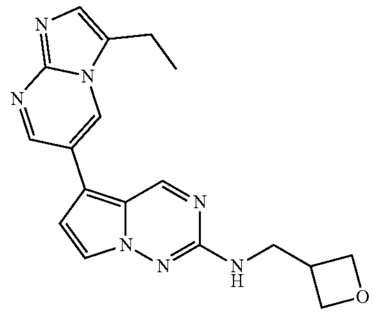 [SMILES: CCc1cnc2ncc(-c3ccn4nc(NCC5COC5)ncc34)cn12]
446
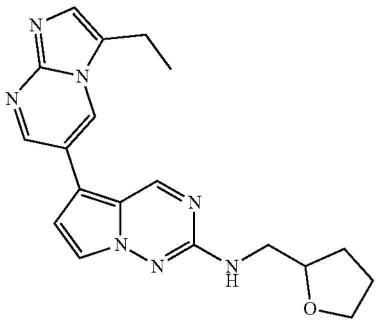 [SMILES: CCc1cnc2ncc(-c3ccn4nc(NCC5CCCO5)ncc34)cn12]
447
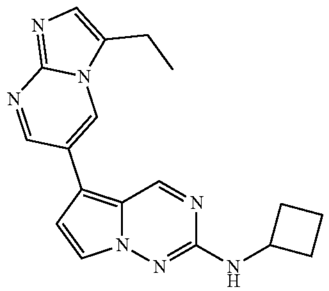 [SMILES: CCc1cnc2ncc(-c3ccn4nc(NC5CCC5)ncc34)cn12]
448

TABLE 1-continued
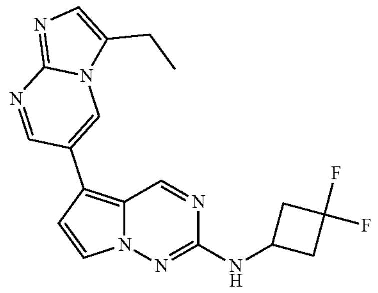 [SMILES: CCc1cnc2ncc(-c3ccn4nc(NC5CC(F)(F)C5)ncc34)cn12]
449
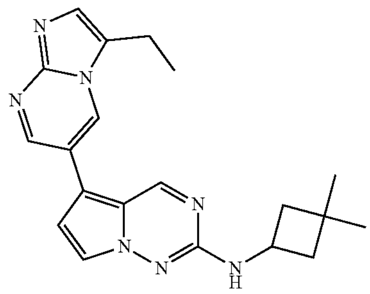 [SMILES: CCc1cnc2ncc(-c3ccn4nc(NC5CC(C)(C)C5)ncc34)cn12]
450
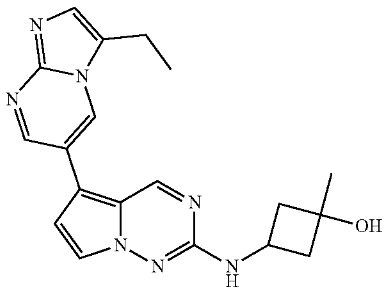 [SMILES: CCc1cnc2ncc(-c3ccn4nc(NC5CC(C)(O)C5)ncc34)cn12]
451
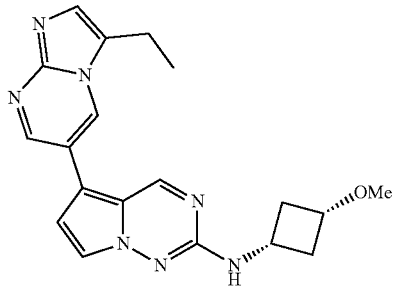 [SMILES: CCc1cnc2ncc(-c3ccn4nc(N[C@H]5C[C@@H](OC)C5)ncc34)cn12]
452
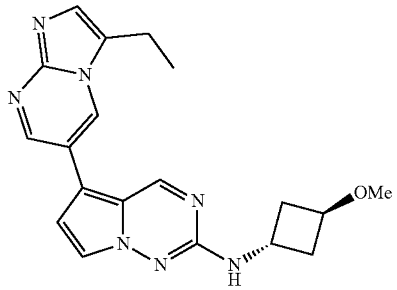 [SMILES: CCc1cnc2ncc(-c3ccn4nc(N[C@H]5C[C@H](OC)C5)ncc34)cn12]
453

TABLE 1-continued
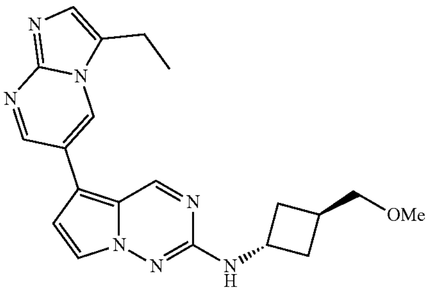 [SMILES: CCc1cnc2ncc(-c3ccn4nc(N[C@H]5C[C@H](COC)C5)ncc34)cn12]
454
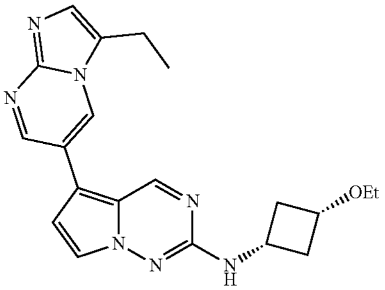
455
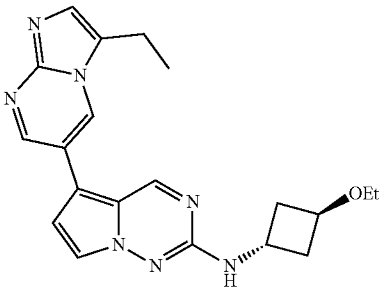 [SMILES: CCO[C@H]1C[C@H](Nc2ncc3c(-c4cnc5ncc(CC)n5c4)ccn3n2)C1]
456
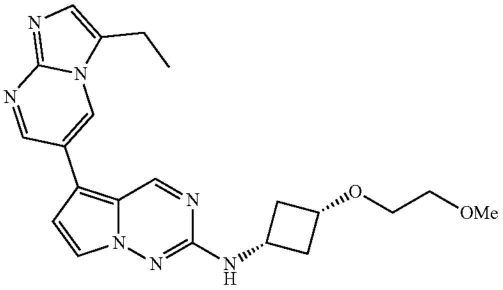 [SMILES: CCc1cnc2ncc(-c3ccn4nc(N[C@H]5C[C@@H](OCCOC)C5)ncc34)cn12]
457
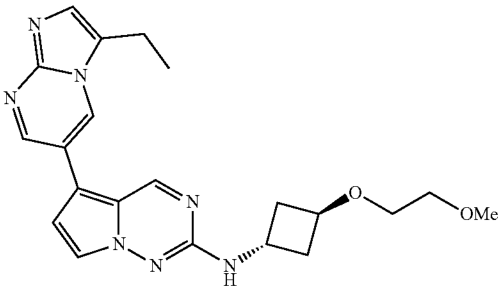 [SMILES: CCc1cnc2ncc(-c3ccn4nc(N[C@H]5C[C@H](OCCOC)C5)ncc34)cn12]
458

TABLE 1-continued
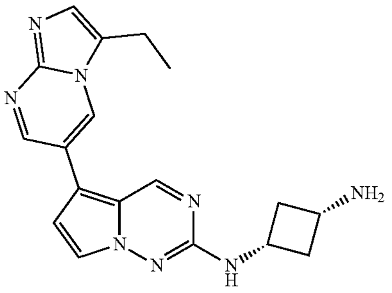 [SMILES: CCc1cnc2ncc(-c3ccn4nc(N[C@H]5C[C@@H](N)C5)ncc34)cn12]
459
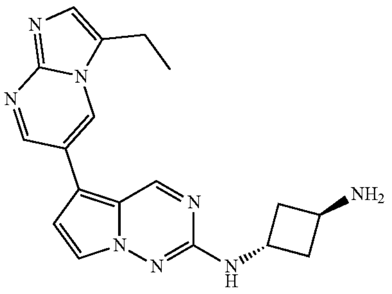 [SMILES: CCc1cnc2ncc(-c3ccn4nc(N[C@H]5C[C@H](N)C5)ncc34)cn12]
460
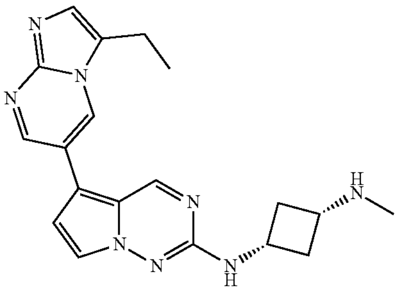 [SMILES: CCc1cnc2ncc(-c3ccn4nc(N[C@H]5C[C@@H](NC)C5)ncc34)cn12]
461
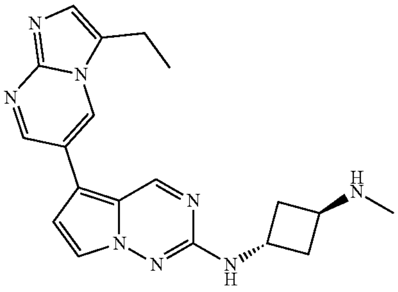 [SMILES: CCc1cnc2ncc(-c3ccn4nc(N[C@H]5C[C@H](NC)C5)ncc34)cn12]
462
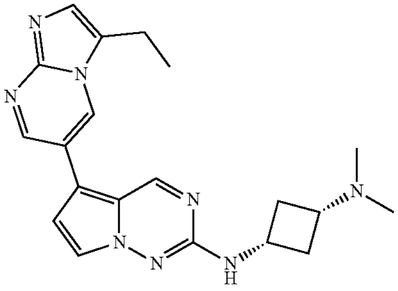 [SMILES: CCc1cnc2ncc(-c3ccn4nc(N[C@H]5C[C@@H](N(C)C)C5)ncc34)cn12]
463

TABLE 1-continued
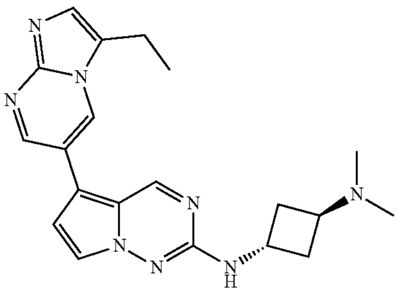 [SMILES: CCc1cnc2ncc(-c3ccn4nc(N[C@H]5C[C@H](N(C)C)C5)ncc34)cn12]
464
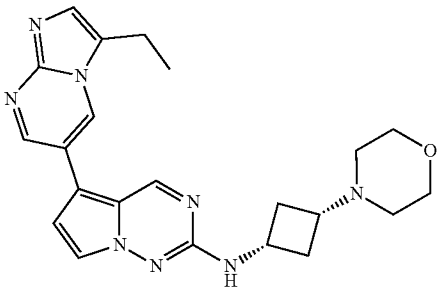 [SMILES: CCc1cnc2ncc(-c3ccn4nc(N[C@H]5C[C@@H](N6CCOCC6)C5)ncc34)cn12]
465
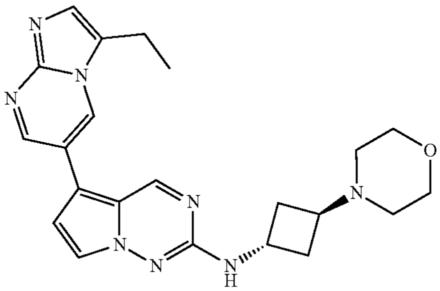 [SMILES: CCc1cnc2ncc(-c3ccn4nc(N[C@H]5C[C@H](N6CCOCC6)C5)ncc34)cn12]
466
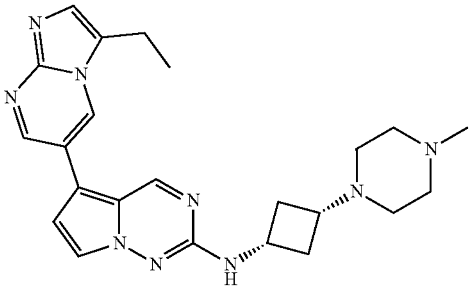 [SMILES: CCc1cnc2ncc(-c3ccn4nc(N[C@H]5C[C@@H](N6CCN(C)CC6)C5)ncc34)cn12]
467
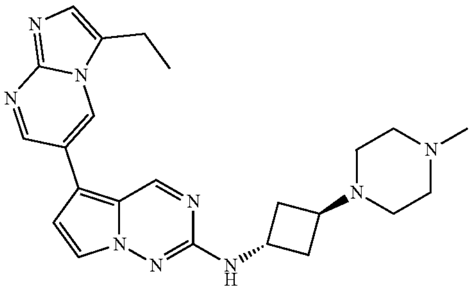 [SMILES: CCc1cnc2ncc(-c3ccn4nc(N[C@H]5C[C@H](N6CCN(C)CC6)C5)ncc34)cn12]
468

TABLE 1-continued
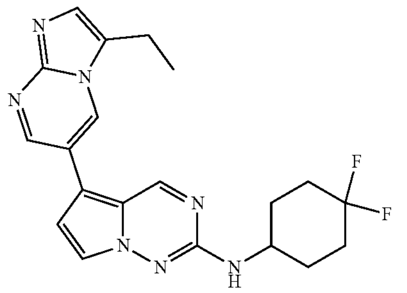 [SMILES: CCc1cnc2ncc(-c3ccn4nc(NC5CCC(F)(F)CC5)ncc34)cn12]
469
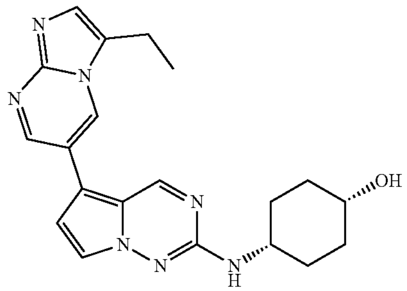 [SMILES: CCc1cnc2ncc(-c3ccn4nc(N[C@H]5CC[C@@H](O)CC5)ncc34)cn12]
470
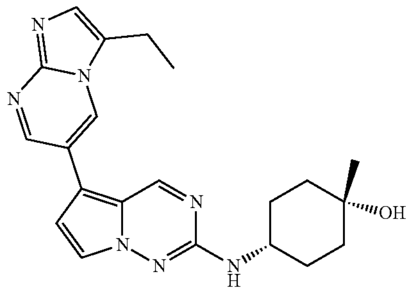 [SMILES: CCc1cnc2ncc(-c3ccn4nc(N[C@H]5CC[C@@](C)(O)CC5)ncc34)cn12]
471
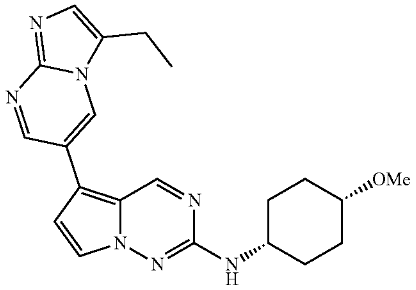 [SMILES: CCc1cnc2ncc(-c3ccn4nc(N[C@H]5CC[C@@H](OC)CC5)ncc34)cn12]
472
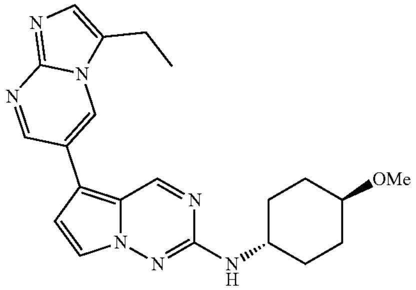 [SMILES: CCc1cnc2ncc(-c3ccn4nc(N[C@H]5CC[C@H](OC)CC5)ncc34)cn12]
473

TABLE 1-continued
474
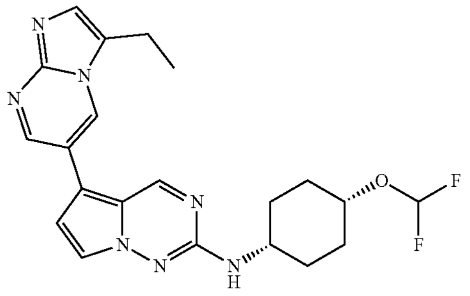 [SMILES: CCc1cnc2ncc(-c3ccn4nc(N[C@H]5CC[C@@H](OC(F)F)CC5)ncc34)cn12]
475
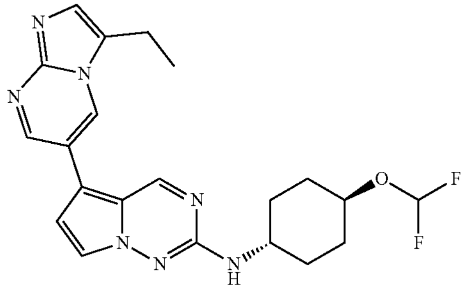 [SMILES: CCc1cnc2ncc(-c3ccn4nc(N[C@H]5CC[C@H](OC(F)F)CC5)ncc34)cn12]
476
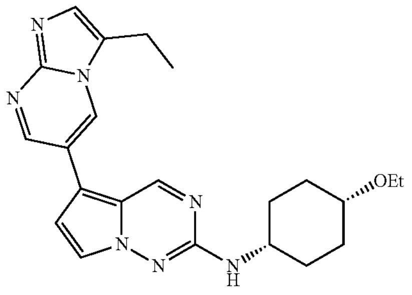 [SMILES: CCO[C@H]1CC[C@@H](Nc2ncc3c(-c4cnc5ncc(CC)n5c4)ccn3n2)CC1]
477
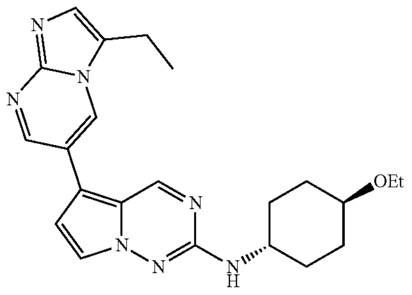 [SMILES: CCO[C@H]1CC[C@H](Nc2ncc3c(-c4cnc5ncc(CC)n5c4)ccn3n2)CC1]
478
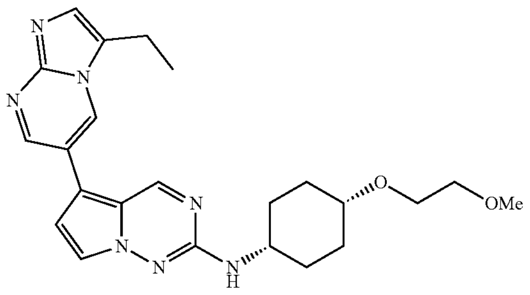 [SMILES: CCc1cnc2ncc(-c3ccn4nc(N[C@H]5CC[C@@H](OCCOC)CC5)ncc34)cn12]

TABLE 1-continued
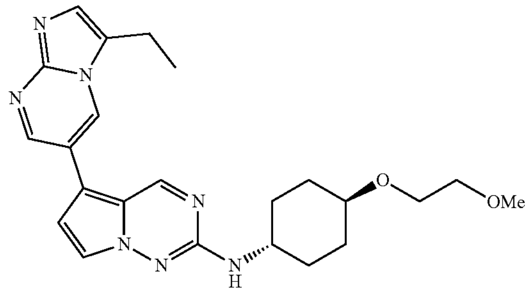 [SMILES: CCc1cnc2ncc(-c3ccn4nc(N[C@H]5CC[C@H](OCCOC)CC5)ncc34)cn12]
479
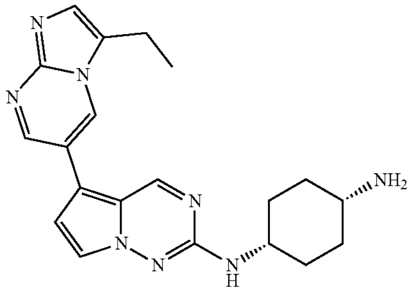 [SMILES: CCc1cnc2ncc(-c3ccn4nc(N[C@H]5CC[C@@H](N)CC5)ncc34)cn12]
480
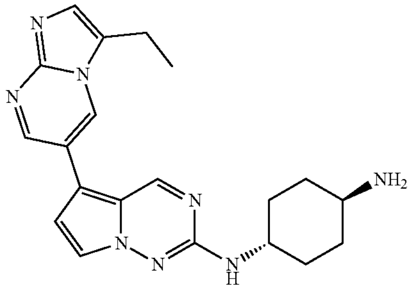 [SMILES: CCc1cnc2ncc(-c3ccn4nc(N[C@H]5CC[C@H](N)CC5)ncc34)cn12]
481
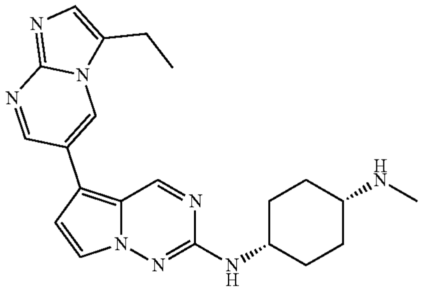 [SMILES: CCc1cnc2ncc(-c3ccn4nc(N[C@H]5CC[C@@H](NC)CC5)ncc34)cn12]
482
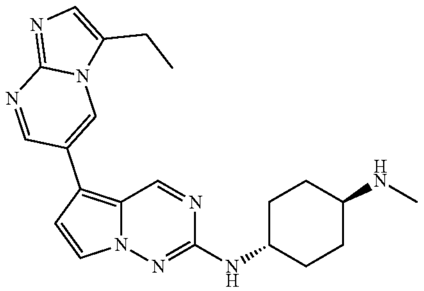 [SMILES: CCc1cnc2ncc(-c3ccn4nc(N[C@H]5CC[C@H](NC)CC5)ncc34)cn12]
483

TABLE 1-continued
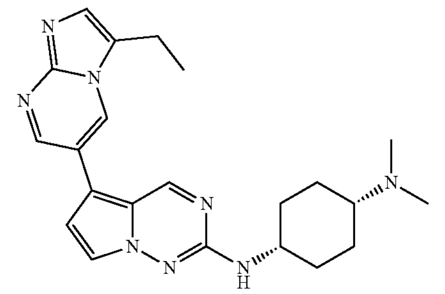 [SMILES: CCc1cnc2ncc(-c3ccn4nc(N[C@H]5CC[C@@H](N(C)C)CC5)ncc34)cn12]
484
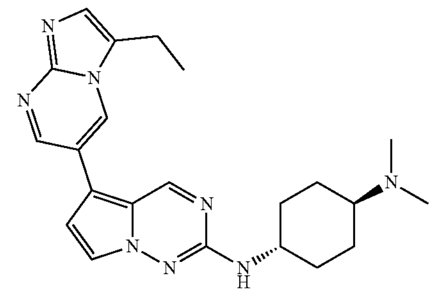 [SMILES: CCc1cnc2ncc(-c3ccn4nc(N[C@H]5CC[C@H](N(C)C)CC5)ncc34)cn12]
485
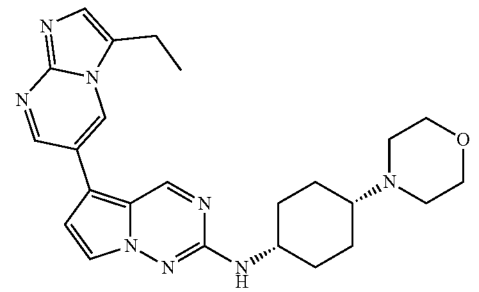 [SMILES: CCc1cnc2ncc(-c3ccn4nc(N[C@H]5CC[C@@H](N6CCOCC6)CC5)ncc34)cn12]
486
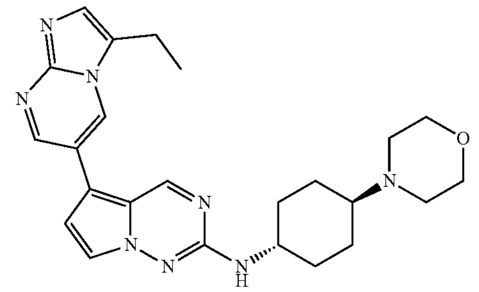 [SMILES: CCc1cnc2ncc(-c3ccn4nc(N[C@H]5CC[C@H](N6CCOCC6)CC5)ncc34)cn12]
487
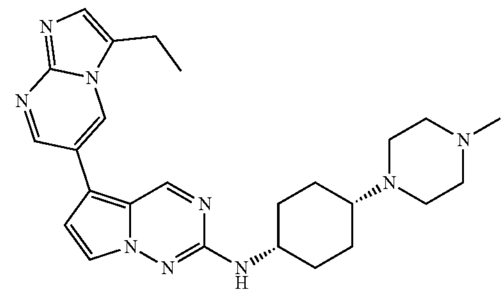 [SMILES: CCc1cnc2ncc(-c3ccn4nc(N[C@H]5CC[C@@H](N6CCN(C)CC6)CC5)ncc34)cn12]
488

TABLE 1-continued
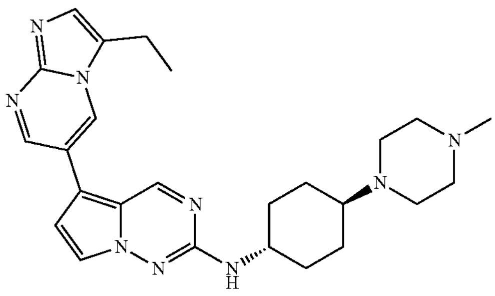 [SMILES: CCc1cnc2ncc(-c3ccn4nc(N[C@H]5CC[C@H](N6CCN(C)CC6)CC5)ncc34)cn12]
489
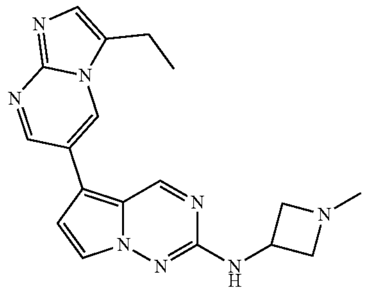 [SMILES: CCc1cnc2ncc(-c3ccn4nc(NC5CN(C)C5)ncc34)cn12]
490
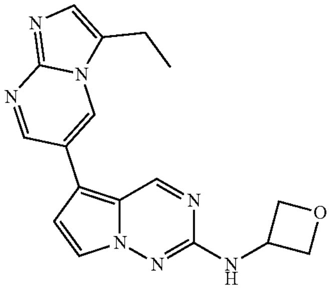 [SMILES: CCc1cnc2ncc(-c3ccn4nc(NC5COC5)ncc34)cn12]
491
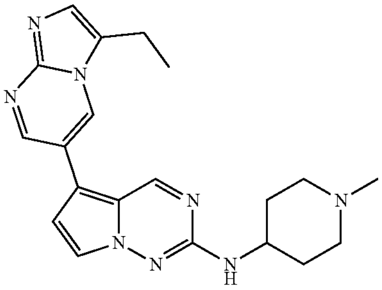 [SMILES: CCc1cnc2ncc(-c3ccn4nc(NC5CCN(C)CC5)ncc34)cn12]
492
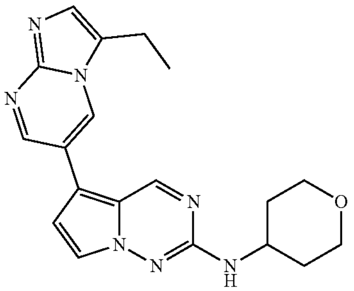 [SMILES: CCc1cnc2ncc(-c3ccn4nc(NC5CCOCC5)ncc34)cn12]
493

TABLE 1-continued
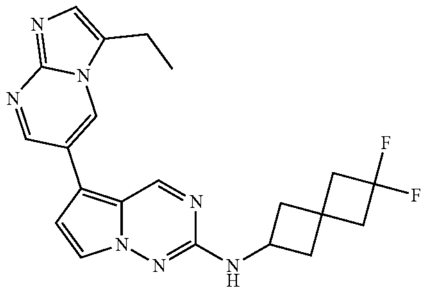 [SMILES: CCc1cnc2ncc(-c3ccn4nc(NC5CC6(C5)CC(F)(F)C6)ncc34)cn12]
494
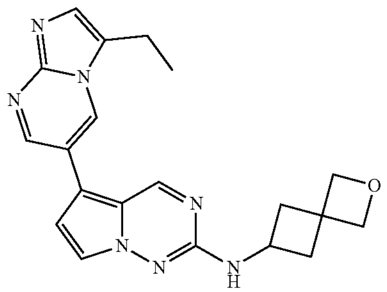 [SMILES: CCc1cnc2ncc(-c3ccn4nc(NC5CC6(COC6)C5)ncc34)cn12]
495
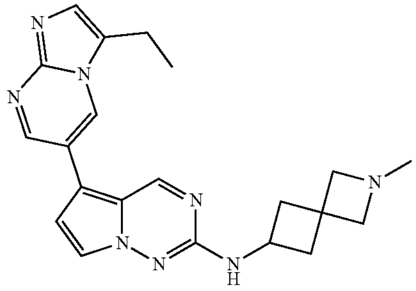 [SMILES: CCc1cnc2ncc(-c3ccn4nc(NC5CC6(C5)CN(C)C6)ncc34)cn12]
496
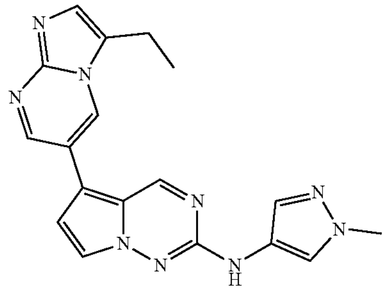 [SMILES: CCc1cnc2ncc(-c3ccn4nc(Nc5cnn(C)c5)ncc34)cn12]
497
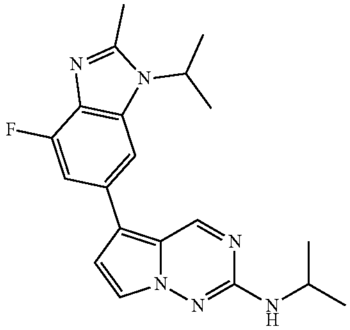 [SMILES: Cc1nc2c(F)cc(-c3ccn4nc(NC(C)C)ncc34)cc2n1C(C)C]
498

TABLE 1-continued
499
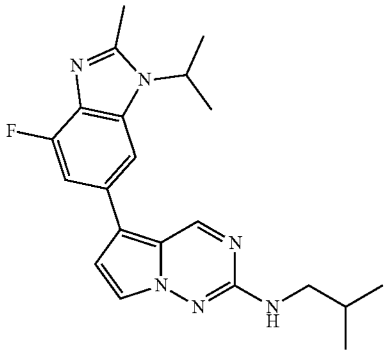 [SMILES: Cc1nc2c(F)cc(-c3ccn4nc(NCC(C)C)ncc34)cc2n1C(C)C]
500
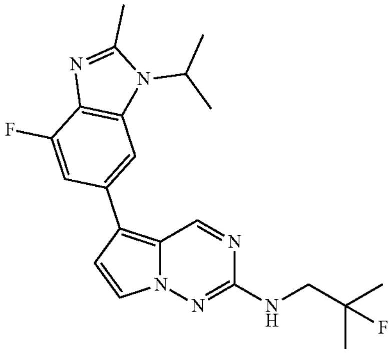 [SMILES: Cc1nc2c(F)cc(-c3ccn4nc(NCC(C)(C)F)ncc34)cc2n1C(C)C]
501
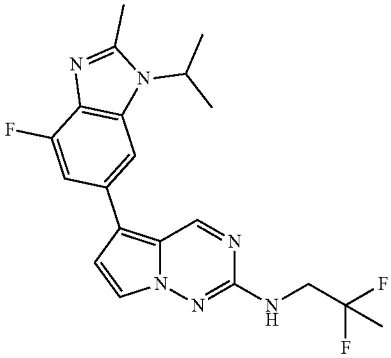 [SMILES: Cc1nc2c(F)cc(-c3ccn4nc(NCC(C)(F)F)ncc34)cc2n1C(C)C]
502
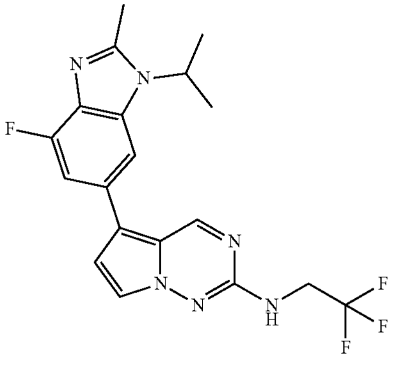 [SMILES: Cc1nc2c(F)cc(-c3ccn4nc(NCC(F)(F)F)ncc34)cc2n1C(C)C]

TABLE 1-continued
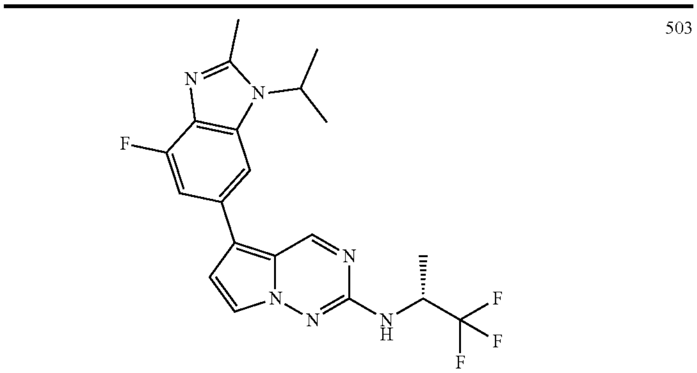
503
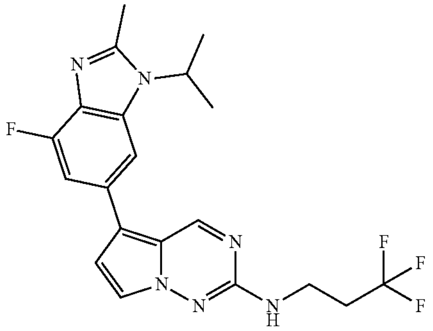 [SMILES: Cc1nc2c(F)cc(-c3ccn4nc(NCCC(F)(F)F)ncc34)cc2n1C(C)C]
504
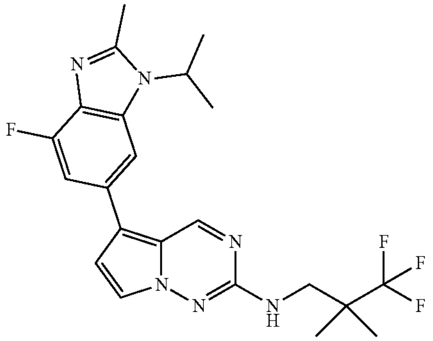 [SMILES: Cc1nc2c(F)cc(-c3ccn4nc(NCC(C)(C)C(F)(F)F)ncc34)cc2n1C(C)C]
505
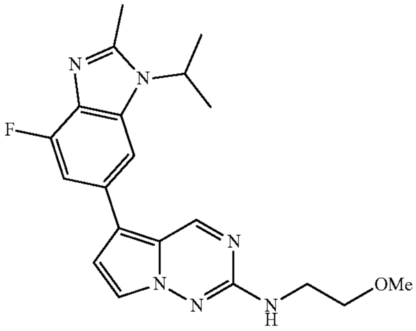 [SMILES: COCCNc1ncc2c(-c3cc(F)c4nc(C)n(C(C)C)c4c3)ccn2n1]
506

TABLE 1-continued
507
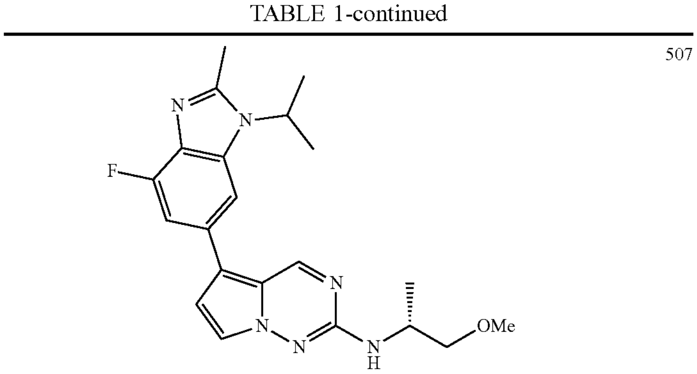
508
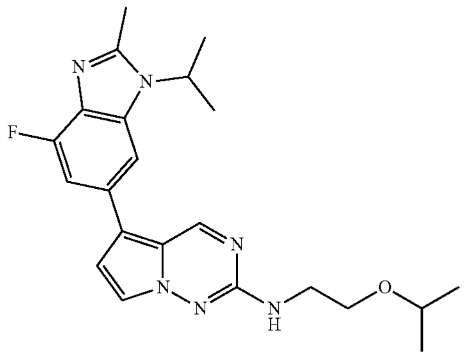 [SMILES: Cc1nc2c(F)cc(-c3ccn4nc(NCCOC(C)C)ncc34)cc2n1C(C)C]
509
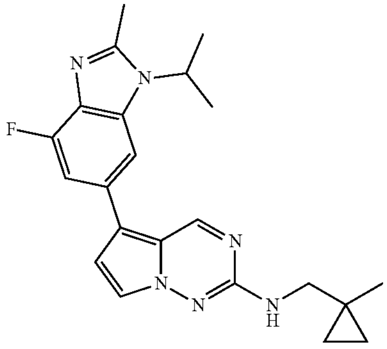 [SMILES: Cc1nc2c(F)cc(-c3ccn4nc(NCC5(C)CC5)ncc34)cc2n1C(C)C]
510
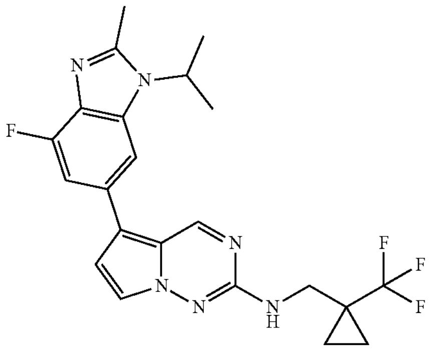 [SMILES: Cc1nc2c(F)cc(-c3ccn4nc(NCC5(C(F)(F)F)CC5)ncc34)cc2n1C(C)C]

TABLE 1-continued
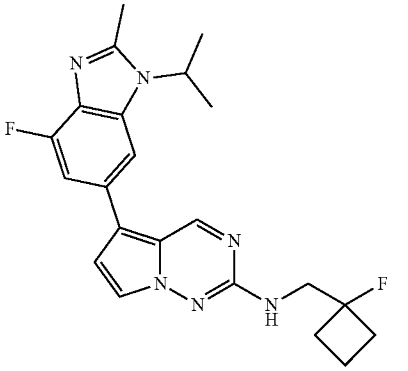 [SMILES: Cc1nc2c(F)cc(-c3ccn4nc(NCC5(F)CCC5)ncc34)cc2n1C(C)C]
511
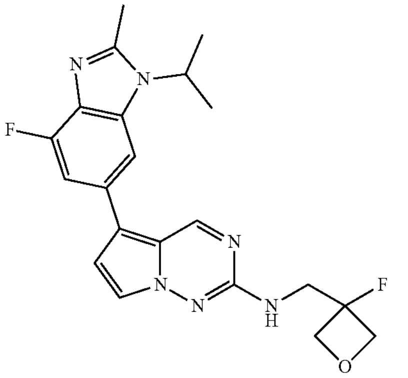 [SMILES: Cc1nc2c(F)cc(-c3ccn4nc(NCC5(F)COC5)ncc34)cc2n1C(C)C]
512
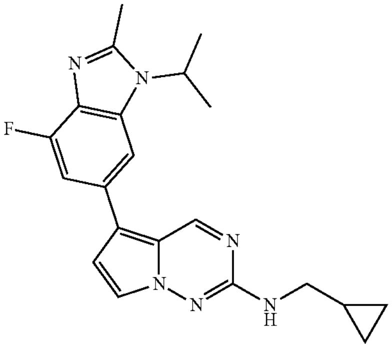 [SMILES: Cc1nc2c(F)cc(-c3ccn4nc(NCC5CC5)ncc34)cc2n1C(C)C]
513
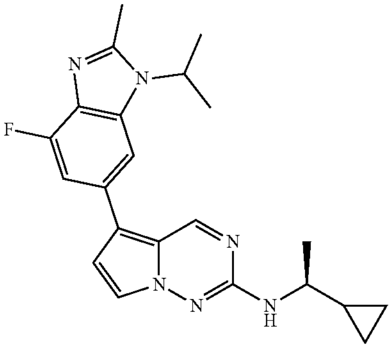
514

TABLE 1-continued
515
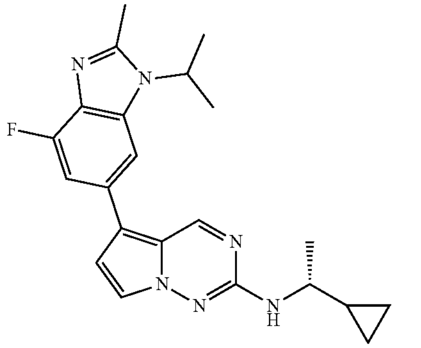 [SMILES: Cc1nc2c(F)cc(-c3ccn4nc(N[C@H](C)C5CC5)ncc34)cc2n1C(C)C]
516
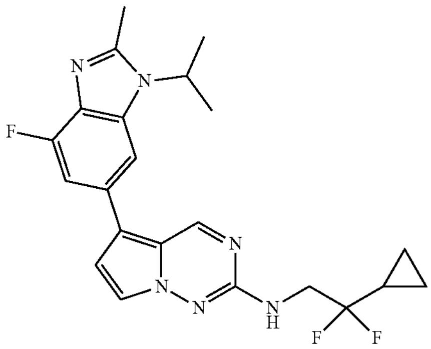 [SMILES: Cc1nc2c(F)cc(-c3ccn4nc(NCC(F)(F)C5CC5)ncc34)cc2n1C(C)C]
517
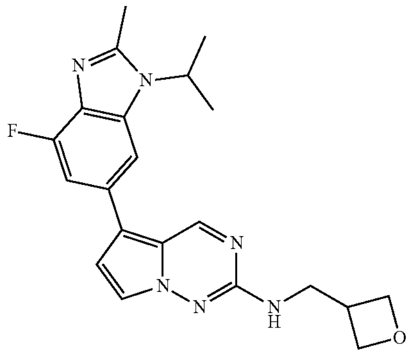 [SMILES: Cc1nc2c(F)cc(-c3ccn4nc(NCC5COC5)ncc34)cc2n1C(C)C]
518
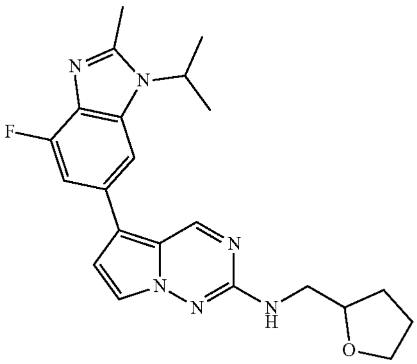 [SMILES: Cc1nc2c(F)cc(-c3ccn4nc(NCC5CCCO5)ncc34)cc2n1C(C)C]

TABLE 1-continued
519
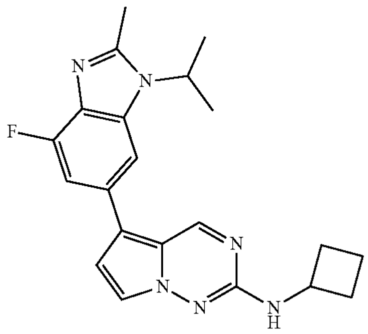 [SMILES: Cc1nc2c(F)cc(-c3ccn4nc(NC5CCC5)ncc34)cc2n1C(C)C]
520
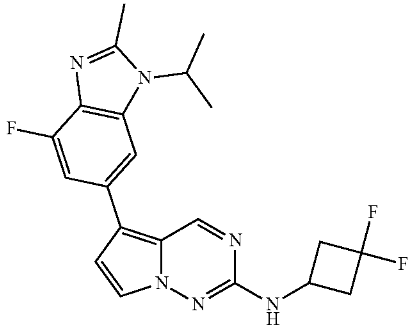 [SMILES: Cc1nc2c(F)cc(-c3ccn4nc(NC5CC(F)(F)C5)ncc34)cc2n1C(C)C]
521
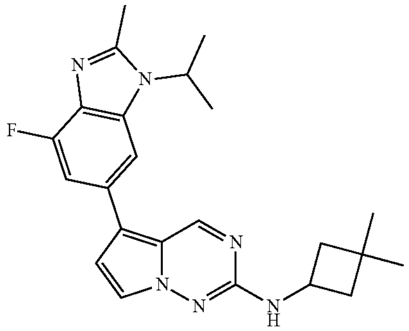 [SMILES: Cc1nc2c(F)cc(-c3ccn4nc(NC5CC(C)(C)C5)ncc34)cc2n1C(C)C]
522
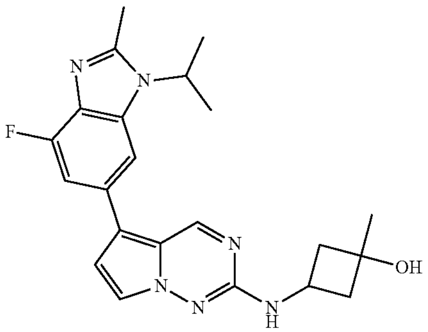 [SMILES: Cc1nc2c(F)cc(-c3ccn4nc(NC5CC(C)(O)C5)ncc34)cc2n1C(C)C]

TABLE 1-continued
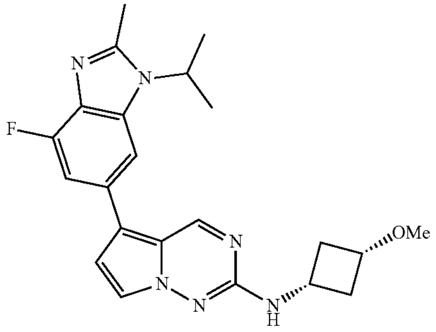 [SMILES: CO[C@H]1C[C@@H](Nc2ncc3c(-c4cc(F)c5nc(C)n(C(C)C)c5c4)ccn3n2)C1]
523
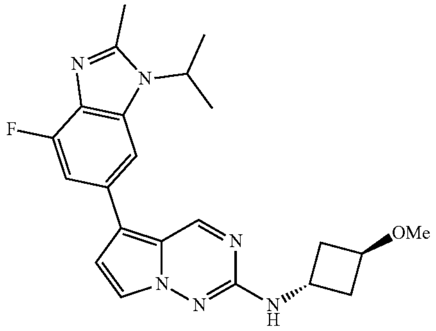 [SMILES: CO[C@H]1C[C@H](Nc2ncc3c(-c4cc(F)c5nc(C)n(C(C)C)c5c4)ccn3n2)C1]
524
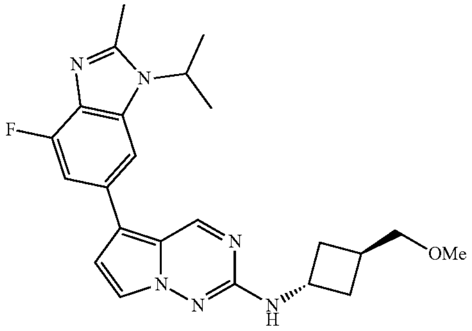 [SMILES: COC[C@H]1C[C@H](Nc2ncc3c(-c4cc(F)c5nc(C)n(C(C)C)c5c4)ccn3n2)C1]
525
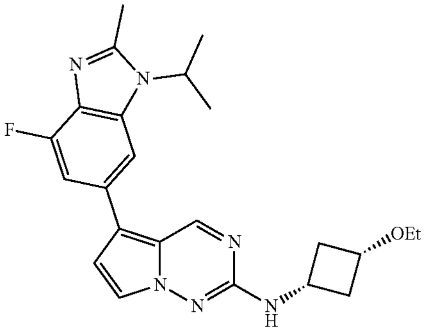 [SMILES: CCO[C@H]1C[C@@H](Nc2ncc3c(-c4cc(F)c5nc(C)n(C(C)C)c5c4)ccn3n2)C1]
526

TABLE 1-continued
527
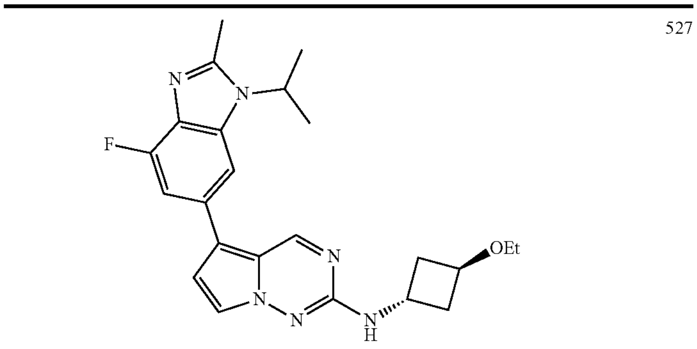
528
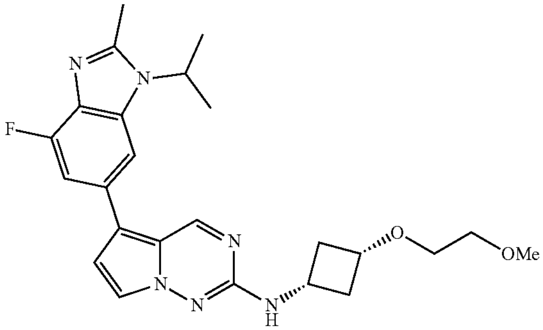 [SMILES: COCCO[C@H]1C[C@@H](Nc2ncc3c(-c4cc(F)c5nc(C)n(C(C)C)c5c4)ccn3n2)C1]
529
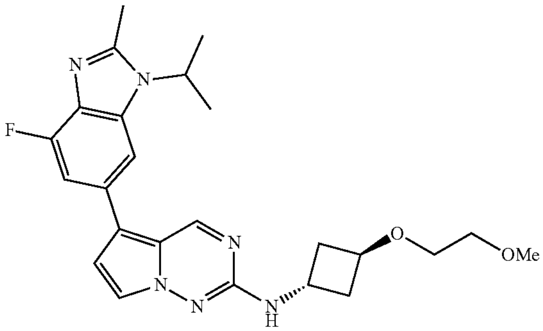 [SMILES: COCCO[C@H]1C[C@H](Nc2ncc3c(-c4cc(F)c5nc(C)n(C(C)C)c5c4)ccn3n2)C1]
530
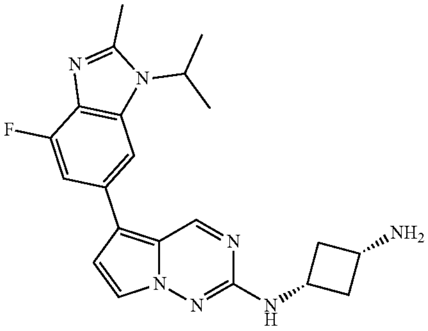 [SMILES: Cc1nc2c(F)cc(-c3ccn4nc(N[C@H]5C[C@@H](N)C5)ncc34)cc2n1C(C)C]

TABLE 1-continued
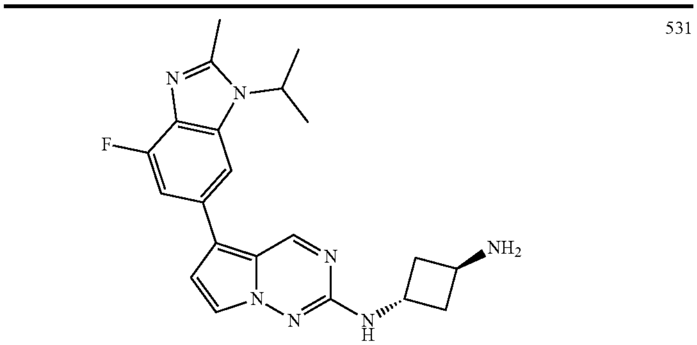
531
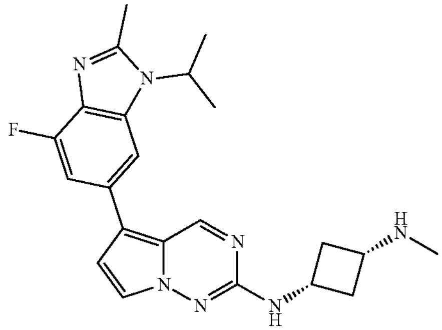 [SMILES: CN[C@H]1C[C@@H](Nc2ncc3c(-c4cc(F)c5nc(C)n(C(C)C)c5c4)ccn3n2)C1]
532
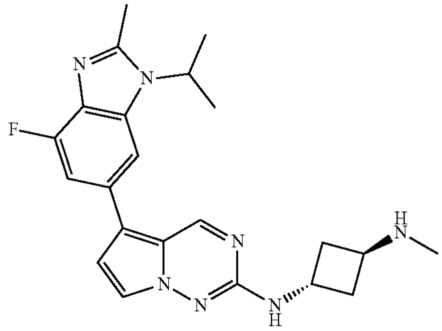 [SMILES: CN[C@H]1C[C@H](Nc2ncc3c(-c4cc(F)c5nc(C)n(C(C)C)c5c4)ccn3n2)C1]
533
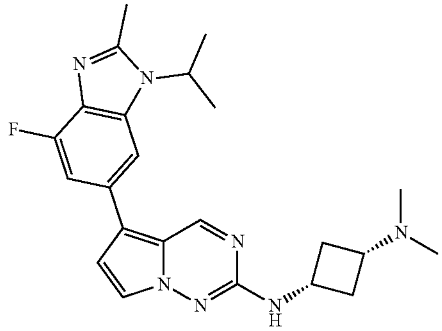 [SMILES: Cc1nc2c(F)cc(-c3ccn4nc(N[C@H]5C[C@@H](N(C)C)C5)ncc34)cc2n1C(C)C]
534

TABLE 1-continued
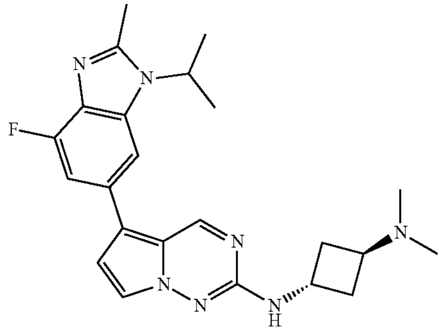 [SMILES: Cc1nc2c(F)cc(-c3ccn4nc(N[C@H]5C[C@H](N(C)C)C5)ncc34)cc2n1C(C)C]
535
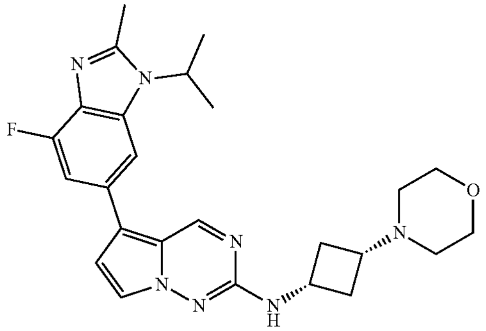 [SMILES: Cc1nc2c(F)cc(-c3ccn4nc(N[C@H]5C[C@@H](N6CCOCC6)C5)ncc34)cc2n1C(C)C]
536
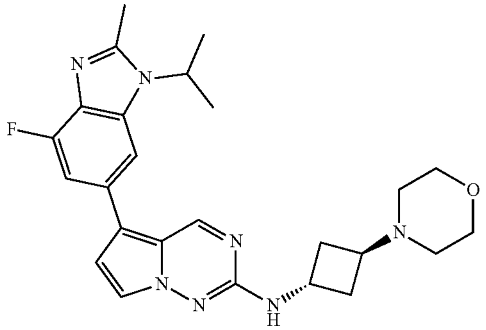 [SMILES: Cc1nc2c(F)cc(-c3ccn4nc(N[C@H]5C[C@H](N6CCOCC6)C5)ncc34)cc2n1C(C)C]
537
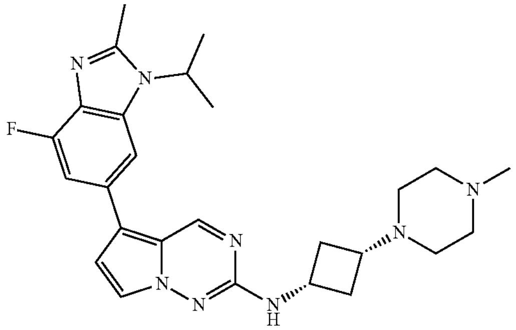 [SMILES: Cc1nc2c(F)cc(-c3ccn4nc(N[C@H]5C[C@@H](N6CCN(C)CC6)C5)ncc34)cc2n1C(C)C]
538

TABLE 1-continued
539
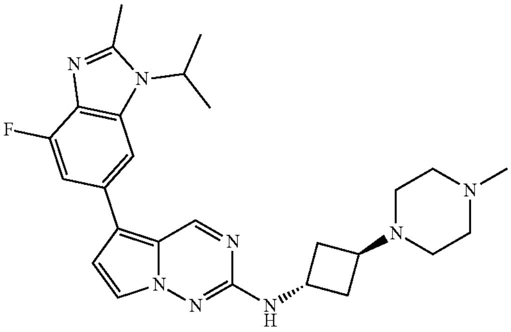 [SMILES: Cc1nc2c(F)cc(-c3ccn4nc(N[C@H]5C[C@H](N6CCN(C)CC6)C5)ncc34)cc2n1C(C)C]
540
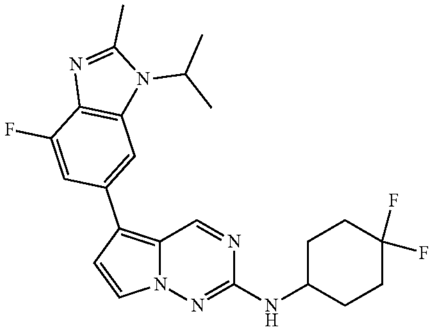 [SMILES: Cc1nc2c(F)cc(-c3ccn4nc(NC5CCC(F)(F)CC5)ncc34)cc2n1C(C)C]
541
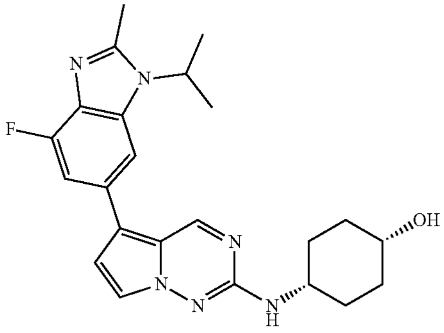 [SMILES: Cc1nc2c(F)cc(-c3ccn4nc(N[C@H]5CC[C@@H](O)CC5)ncc34)cc2n1C(C)C]
542
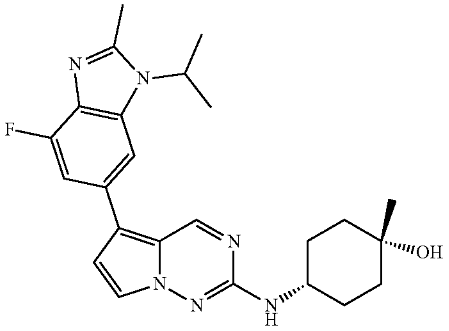 [SMILES: Cc1nc2c(F)cc(-c3ccn4nc(N[C@H]5CC[C@@](C)(O)CC5)ncc34)cc2n1C(C)C]

TABLE 1-continued
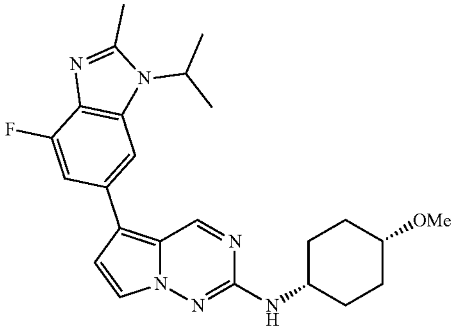 [SMILES: CO[C@H]1CC[C@@H](Nc2ncc3c(-c4cc(F)c5nc(C)n(C(C)C)c5c4)ccn3n2)CC1]
543
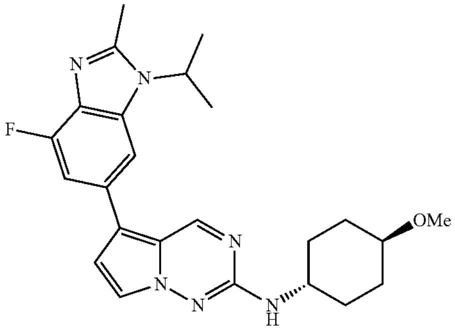 [SMILES: CO[C@H]1CC[C@H](Nc2ncc3c(-c4cc(F)c5nc(C)n(C(C)C)c5c4)ccn3n2)CC1]
544
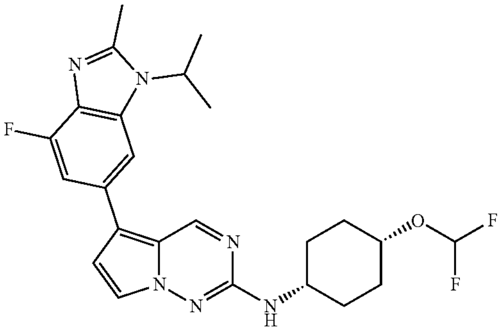 [SMILES: Cc1nc2c(F)cc(-c3ccn4nc(N[C@H]5CC[C@@H](OC(F)F)CC5)ncc34)cc2n1C(C)C]
545
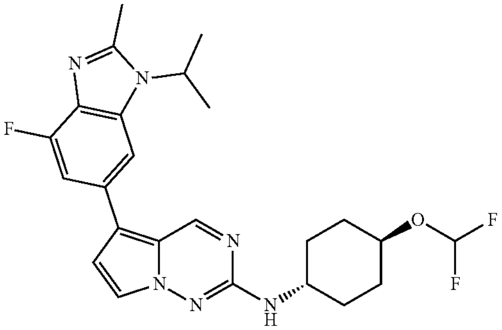 [SMILES: Cc1nc2c(F)cc(-c3ccn4nc(N[C@H]5CC[C@H](OC(F)F)CC5)ncc34)cc2n1C(C)C]
546

TABLE 1-continued
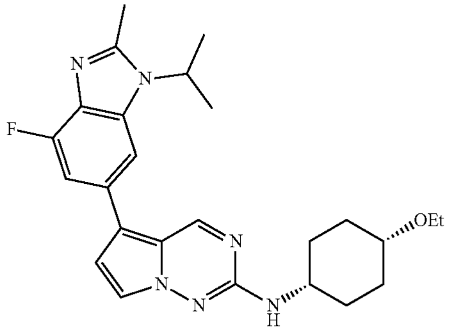 [SMILES: CCO[C@H]1CC[C@@H](Nc2ncc3c(-c4cc(F)c5nc(C)n(C(C)C)c5c4)ccn3n2)CC1]
547
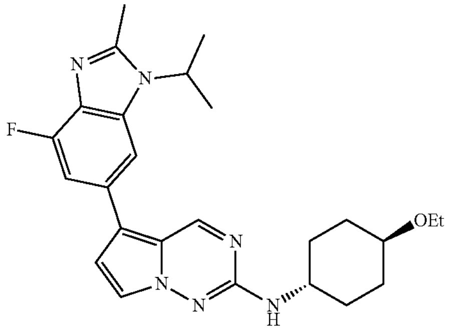 [SMILES: CCO[C@H]1CC[C@H](Nc2ncc3c(-c4cc(F)c5nc(C)n(C(C)C)c5c4)ccn3n2)CC1]
548
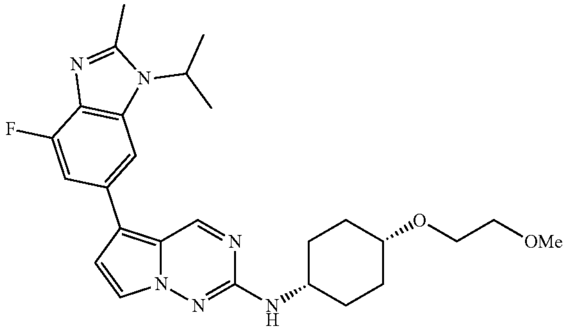 [SMILES: COCCO[C@H]1CC[C@@H](Nc2ncc3c(-c4cc(F)c5nc(C)n(C(C)C)c5c4)ccn3n2)CC1]
549
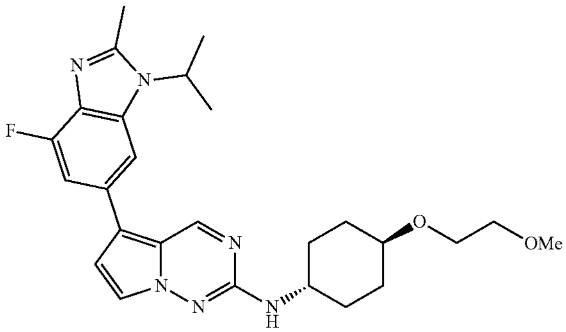 [SMILES: COCCO[C@H]1CC[C@H](Nc2ncc3c(-c4cc(F)c5nc(C)n(C(C)C)c5c4)ccn3n2)CC1]
550

TABLE 1-continued
551
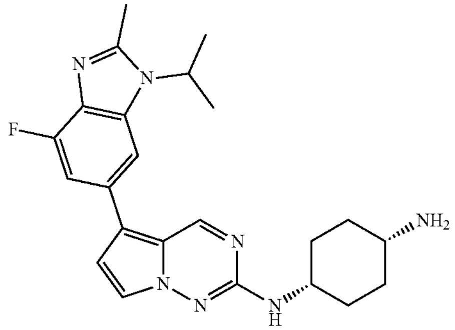 [SMILES: Cc1nc2c(F)cc(-c3ccn4nc(N[C@H]5CC[C@@H](N)CC5)ncc34)cc2n1C(C)C]
552
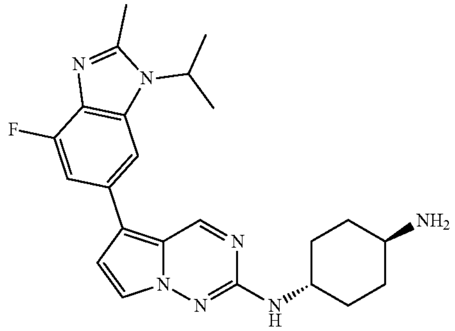 [SMILES: Cc1nc2c(F)cc(-c3ccn4nc(N[C@H]5CC[C@H](N)CC5)ncc34)cc2n1C(C)C]
553
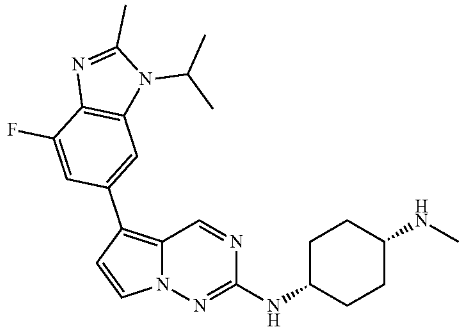 [SMILES: CN[C@H]1CC[C@@H](Nc2ncc3c(-c4cc(F)c5nc(C)n(C(C)C)c5c4)ccn3n2)CC1]
554
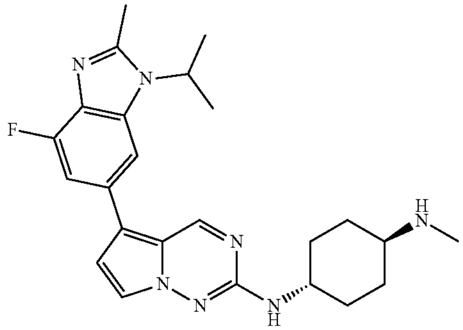

TABLE 1-continued
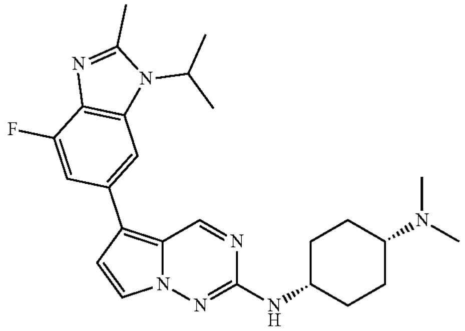 [SMILES: Cc1nc2c(F)cc(-c3ccn4nc(N[C@H]5CC[C@@H](N(C)C)CC5)ncc34)cc2n1C(C)C]
555
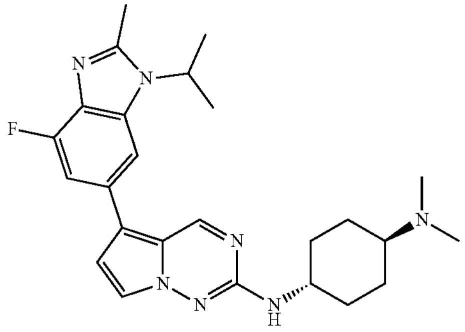 [SMILES: Cc1nc2c(F)cc(-c3ccn4nc(N[C@H]5CC[C@H](N(C)C)CC5)ncc34)cc2n1C(C)C]
556
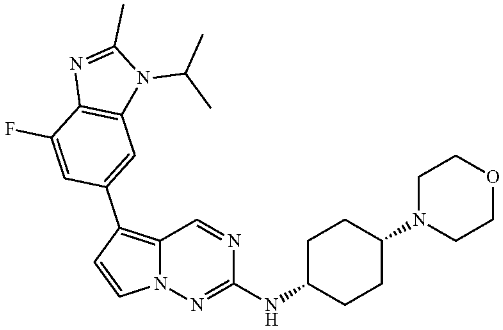 [SMILES: Cc1nc2c(F)cc(-c3ccn4nc(N[C@H]5CC[C@@H](N6CCOCC6)CC5)ncc34)cc2n1C(C)C]
557
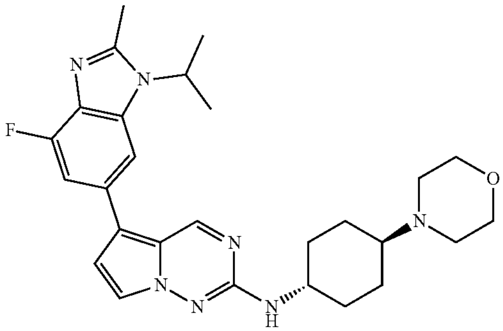 [SMILES: Cc1nc2c(F)cc(-c3ccn4nc(N[C@H]5CC[C@H](N6CCOCC6)CC5)ncc34)cc2n1C(C)C]
558

TABLE 1-continued
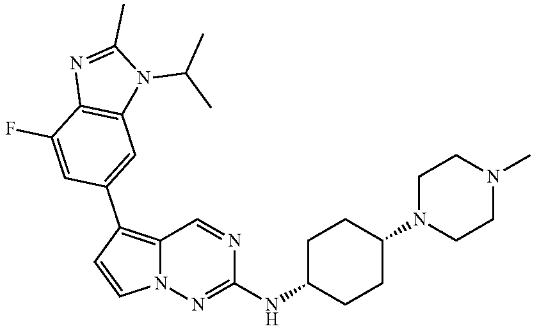 [SMILES: Cc1nc2c(F)cc(-c3ccn4nc(N[C@H]5CC[C@@H](N6CCN(C)CC6)CC5)ncc34)cc2n1C(C)C]
559
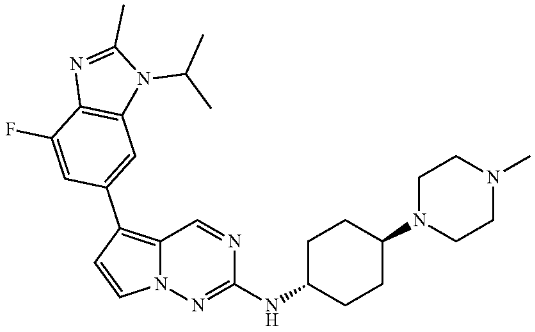 [SMILES: Cc1nc2c(F)cc(-c3ccn4nc(N[C@H]5CC[C@H](N6CCN(C)CC6)CC5)ncc34)cc2n1C(C)C]
560
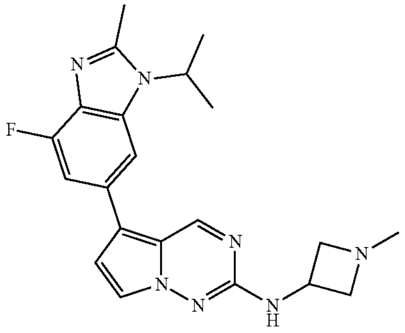 [SMILES: Cc1nc2c(F)cc(-c3ccn4nc(NC5CN(C)C5)ncc34)cc2n1C(C)C]
561
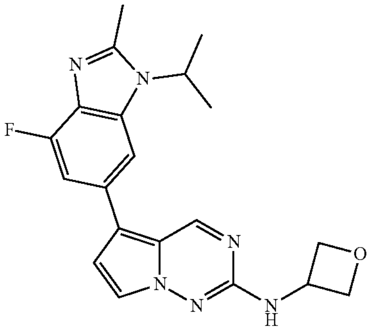 [SMILES: Cc1nc2c(F)cc(-c3ccn4nc(NC5COC5)ncc34)cc2n1C(C)C]
562

TABLE 1-continued
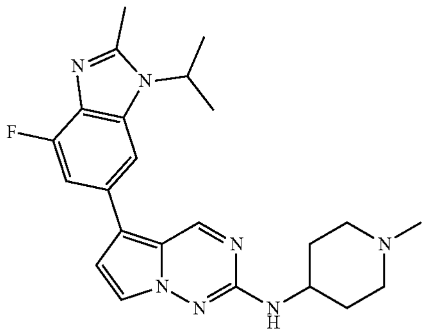 [SMILES: Cc1nc2c(F)cc(-c3ccn4nc(NC5CCN(C)CC5)ncc34)cc2n1C(C)C]
563
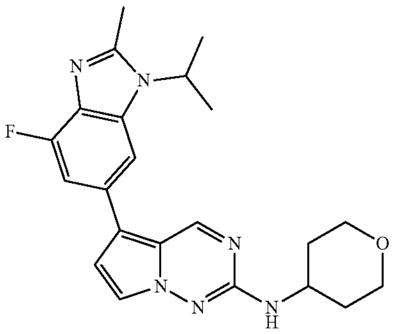 [SMILES: Cc1nc2c(F)cc(-c3ccn4nc(NC5CCOCC5)ncc34)cc2n1C(C)C]
564
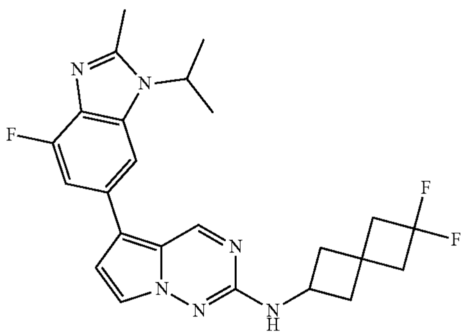 [SMILES: Cc1nc2c(F)cc(-c3ccn4nc(NC5CC6(C5)CC(F)(F)C6)ncc34)cc2n1C(C)C]
565
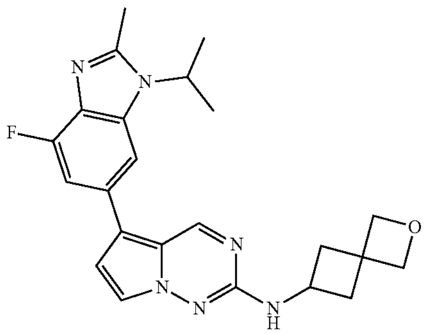 [SMILES: Cc1nc2c(F)cc(-c3ccn4nc(NC5CC6(COC6)C5)ncc34)cc2n1C(C)C]
566

TABLE 1-continued
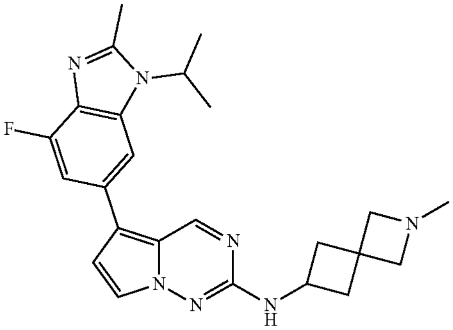 [SMILES: Cc1nc2c(F)cc(-c3ccn4nc(NC5CC6(C5)CN(C)C6)ncc34)cc2n1C(C)C]
567
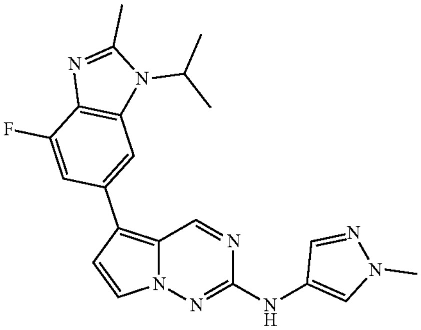 [SMILES: Cc1nc2c(F)cc(-c3ccn4nc(Nc5cnn(C)c5)ncc34)cc2n1C(C)C]
568
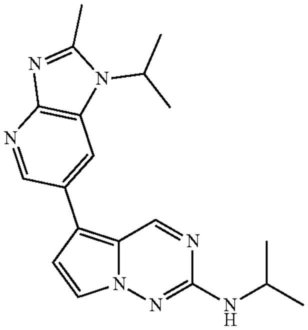 [SMILES: Cc1nc2ncc(-c3ccn4nc(NC(C)C)ncc34)cc2n1C(C)C]
569
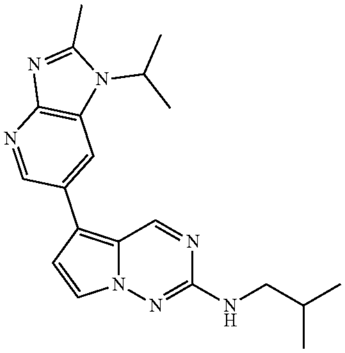 [SMILES: Cc1nc2ncc(-c3ccn4nc(NCC(C)C)ncc34)cc2n1C(C)C]
570

TABLE 1-continued
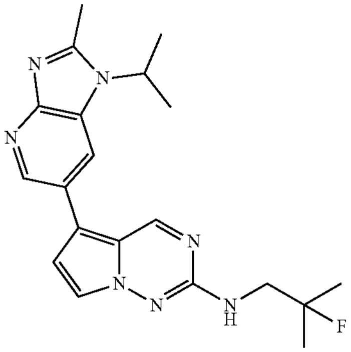 [SMILES: Cc1nc2ncc(-c3ccn4nc(NCC(C)(C)F)ncc34)cc2n1C(C)C]
571
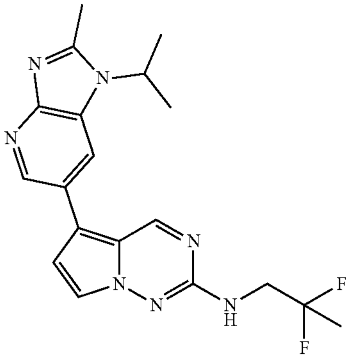 [SMILES: Cc1nc2ncc(-c3ccn4nc(NCC(C)(F)F)ncc34)cc2n1C(C)C]
572
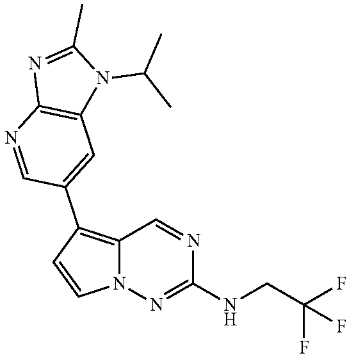 [SMILES: Cc1nc2ncc(-c3ccn4nc(NCC(F)(F)F)ncc34)cc2n1C(C)C]
573
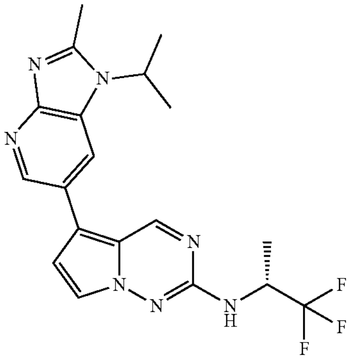 [SMILES: Cc1nc2ncc(-c3ccn4nc(N[C@H](C)C(F)(F)F)ncc34)cc2n1C(C)C]
574

TABLE 1-continued
575
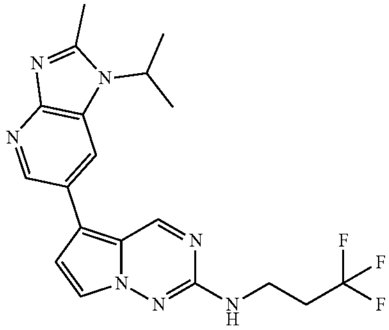 [SMILES: Cc1nc2ncc(-c3ccn4nc(NCCC(F)(F)F)ncc34)cc2n1C(C)C]
576
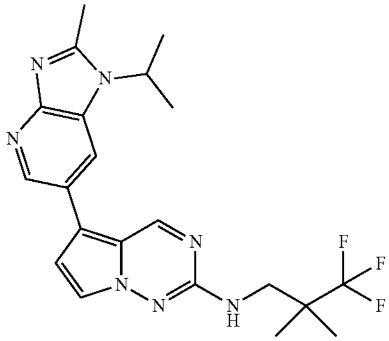 [SMILES: Cc1nc2ncc(-c3ccn4nc(NCC(C)(C)C(F)(F)F)ncc34)cc2n1C(C)C]
577
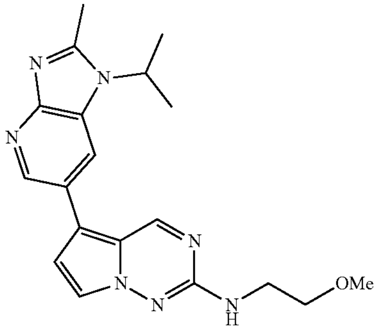 [SMILES: COCCNc1ncc2c(-c3cnc4nc(C)n(C(C)C)c4c3)ccn2n1]
578
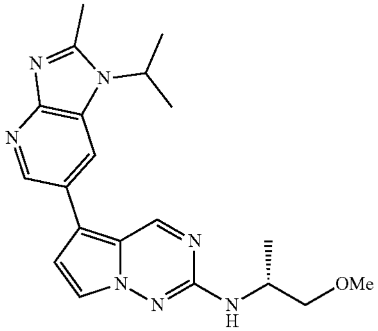 [SMILES: COC[C@@H](C)Nc1ncc2c(-c3cnc4nc(C)n(C(C)C)c4c3)ccn2n1]

TABLE 1-continued
579
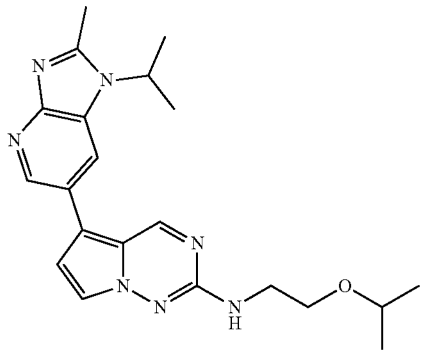 [SMILES: Cc1nc2ncc(-c3ccn4nc(NCCOC(C)C)ncc34)cc2n1C(C)C]
580
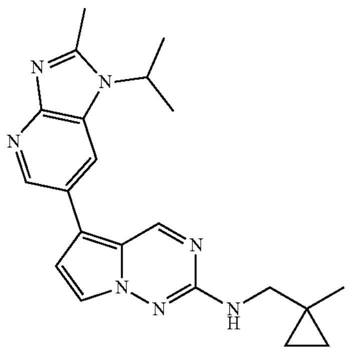 [SMILES: Cc1nc2ncc(-c3ccn4nc(NCC5(C)CC5)ncc34)cc2n1C(C)C]
581
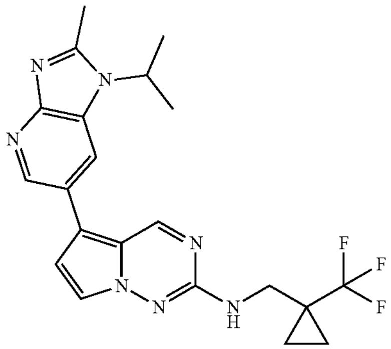 [SMILES: Cc1nc2ncc(-c3ccn4nc(NCC5(C(F)(F)F)CC5)ncc34)cc2n1C(C)C]
582
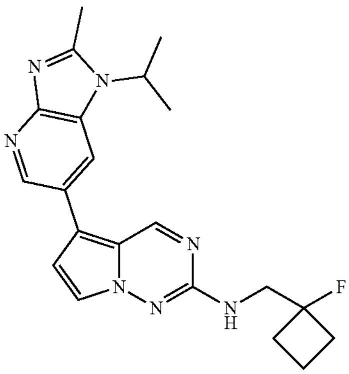 [SMILES: Cc1nc2ncc(-c3ccn4nc(NCC5(F)CCC5)ncc34)cc2n1C(C)C]

TABLE 1-continued
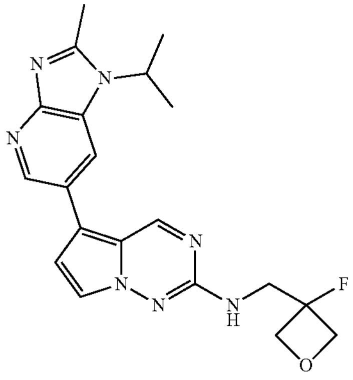 [SMILES: Cc1nc2ncc(-c3ccn4nc(NCC5(F)COC5)ncc34)cc2n1C(C)C]
583
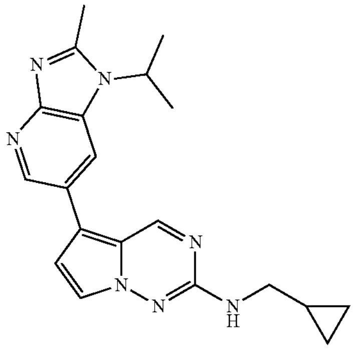 [SMILES: Cc1nc2ncc(-c3ccn4nc(NCC5CC5)ncc34)cc2n1C(C)C]
584
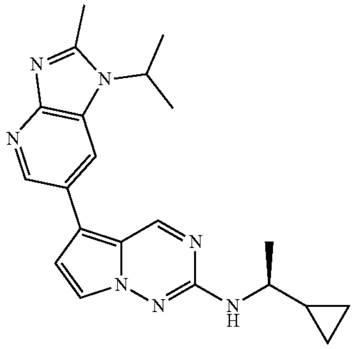 [SMILES: Cc1nc2ncc(-c3ccn4nc(N[C@@H](C)C5CC5)ncc34)cc2n1C(C)C]
585
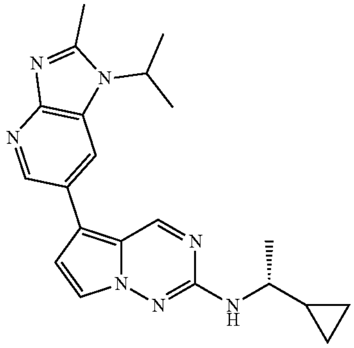 [SMILES: Cc1nc2ncc(-c3ccn4nc(N[C@H](C)C5CC5)ncc34)cc2n1C(C)C]
586

TABLE 1-continued
587
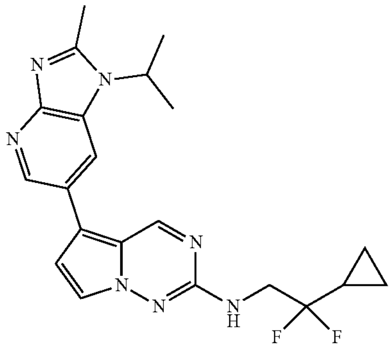 [SMILES: Cc1nc2ncc(-c3ccn4nc(NCC(F)(F)C5CC5)ncc34)cc2n1C(C)C]
588
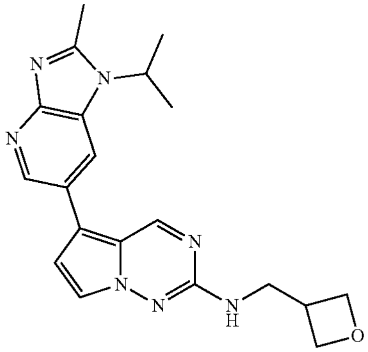 [SMILES: Cc1nc2ncc(-c3ccn4nc(NCC5COC5)ncc34)cc2n1C(C)C]
589
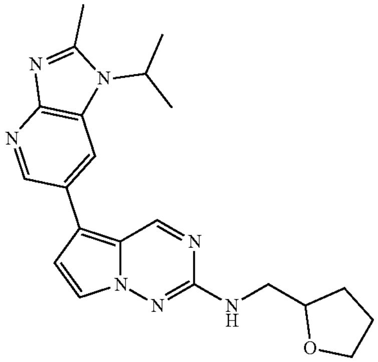 [SMILES: Cc1nc2ncc(-c3ccn4nc(NCC5CCCO5)ncc34)cc2n1C(C)C]
590
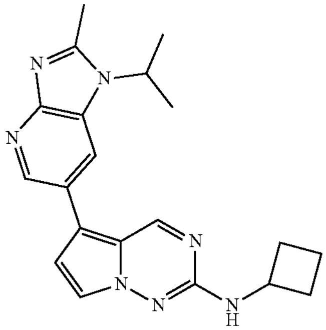 [SMILES: Cc1nc2ncc(-c3ccn4nc(NC5CCC5)ncc34)cc2n1C(C)C]

TABLE 1-continued
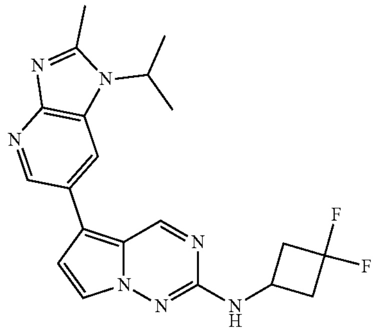 [SMILES: Cc1nc2ncc(-c3ccn4nc(NC5CC(F)(F)C5)ncc34)cc2n1C(C)C]
591
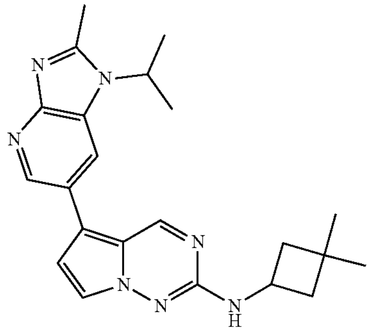 [SMILES: Cc1nc2ncc(-c3ccn4nc(NC5CC(C)(C)C5)ncc34)cc2n1C(C)C]
592
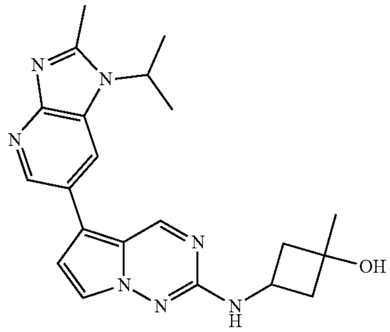 [SMILES: Cc1nc2ncc(-c3ccn4nc(NC5CC(C)(O)C5)ncc34)cc2n1C(C)C]
593
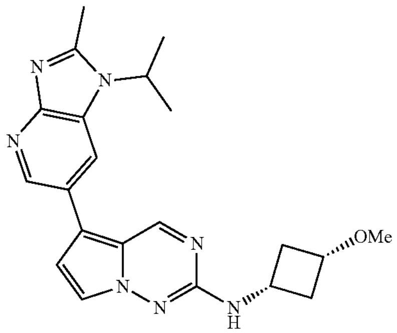 [SMILES: CO[C@H]1C[C@@H](Nc2ncc3c(-c4cnc5nc(C)n(C(C)C)c5c4)ccn3n2)C1]
594

TABLE 1-continued
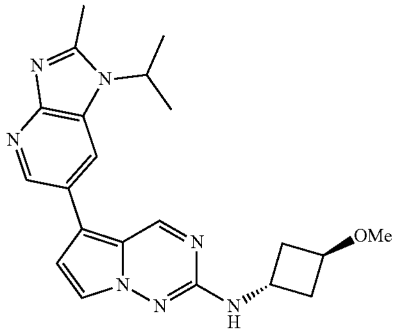 [SMILES: CO[C@H]1C[C@H](Nc2ncc3c(-c4cnc5nc(C)n(C(C)C)c5c4)ccn3n2)C1]
595
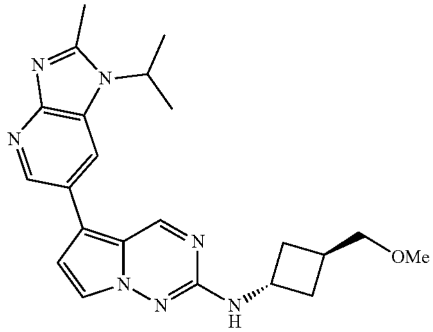 [SMILES: COC[C@H]1C[C@H](Nc2ncc3c(-c4cnc5nc(C)n(C(C)C)c5c4)ccn3n2)C1]
596
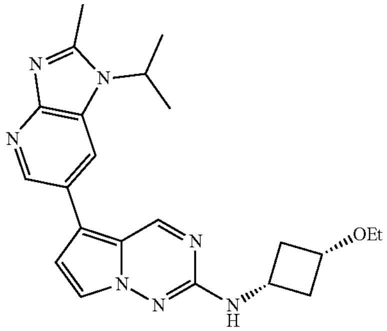 [SMILES: CCO[C@H]1C[C@@H](Nc2ncc3c(-c4cnc5nc(C)n(C(C)C)c5c4)ccn3n2)C1]
597
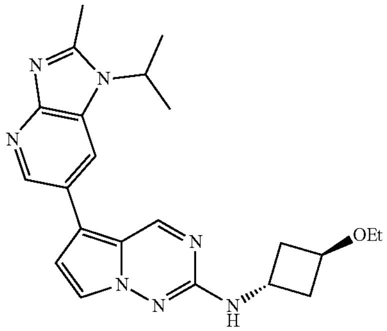 [SMILES: CCO[C@H]1C[C@H](Nc2ncc3c(-c4cnc5nc(C)n(C(C)C)c5c4)ccn3n2)C1]
598

TABLE 1-continued
599
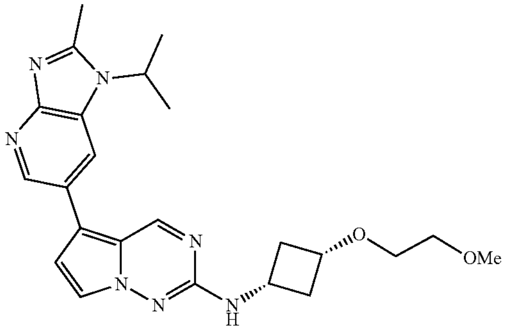 [SMILES: COCCO[C@H]1C[C@@H](Nc2ncc3c(-c4cnc5nc(C)n(C(C)C)c5c4)ccn3n2)C1]
600
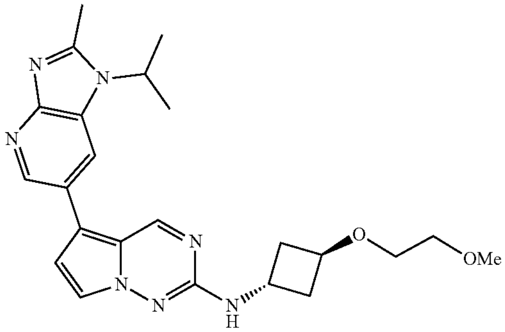 [SMILES: COCCO[C@H]1C[C@H](Nc2ncc3c(-c4cnc5nc(C)n(C(C)C)c5c4)ccn3n2)C1]
601
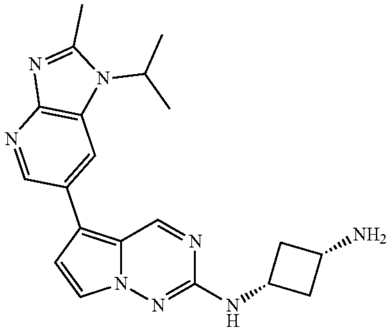 [SMILES: Cc1nc2ncc(-c3ccn4nc(N[C@H]5C[C@@H](N)C5)ncc34)cc2n1C(C)C]
602
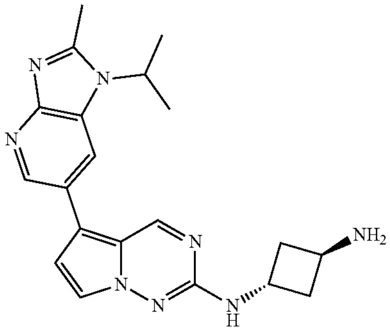 [SMILES: Cc1nc2ncc(-c3ccn4nc(N[C@H]5C[C@H](N)C5)ncc34)cc2n1C(C)C]

TABLE 1-continued
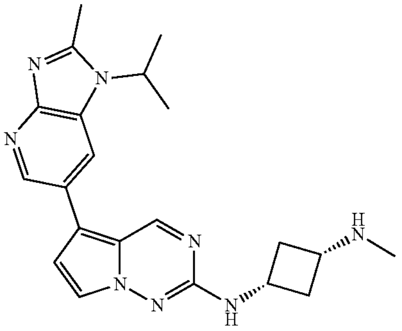 [SMILES: CN[C@H]1C[C@@H](Nc2ncc3c(-c4cnc5nc(C)n(C(C)C)c5c4)ccn3n2)C1]
603
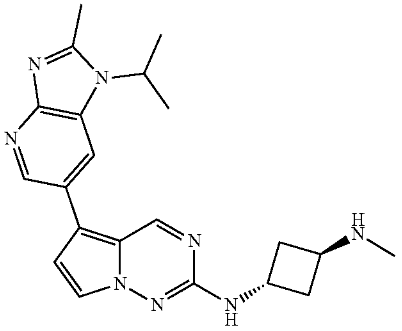 [SMILES: CN[C@H]1C[C@H](Nc2ncc3c(-c4cnc5nc(C)n(C(C)C)c5c4)ccn3n2)C1]
604
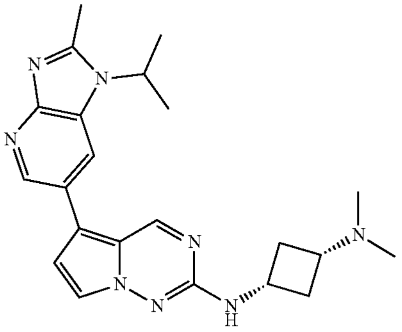 [SMILES: Cc1nc2ncc(-c3ccn4nc(N[C@H]5C[C@@H](N(C)C)C5)ncc34)cc2n1C(C)C]
605
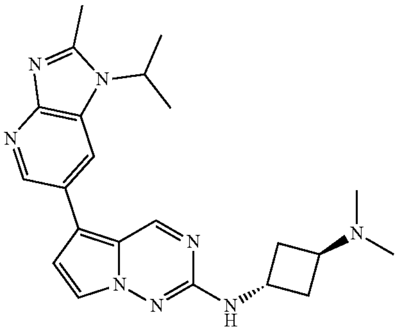 [SMILES: Cc1nc2ncc(-c3ccn4nc(N[C@H]5C[C@H](N(C)C)C5)ncc34)cc2n1C(C)C]
606

TABLE 1-continued
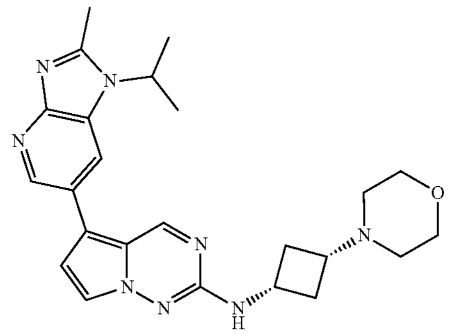 [SMILES: Cc1nc2ncc(-c3ccn4nc(N[C@H]5C[C@@H](N6CCOCC6)C5)ncc34)cc2n1C(C)C]
607
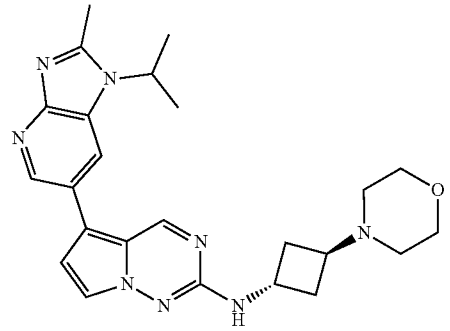 [SMILES: Cc1nc2ncc(-c3ccn4nc(N[C@H]5C[C@H](N6CCOCC6)C5)ncc34)cc2n1C(C)C]
608
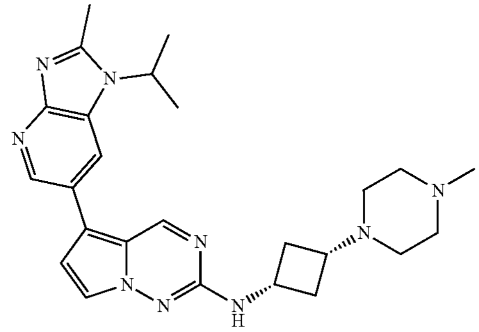 [SMILES: Cc1nc2ncc(-c3ccn4nc(N[C@H]5C[C@@H](N6CCN(C)CC6)C5)ncc34)cc2n1C(C)C]
609
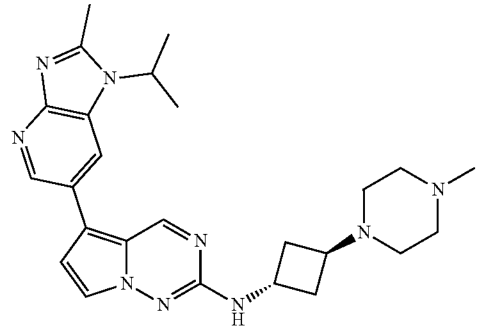 [SMILES: Cc1nc2ncc(-c3ccn4nc(N[C@H]5C[C@H](N6CCN(C)CC6)C5)ncc34)cc2n1C(C)C]
610

TABLE 1-continued
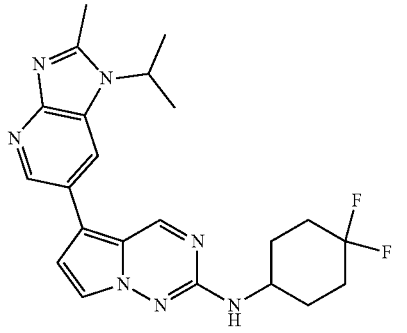 [SMILES: Cc1nc2ncc(-c3ccn4nc(NC5CCC(F)(F)CC5)ncc34)cc2n1C(C)C]
611
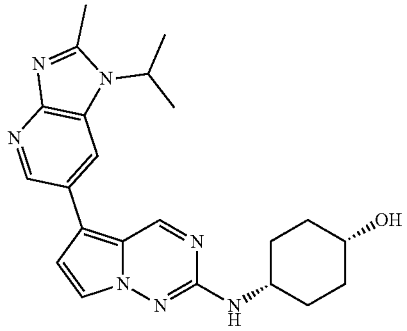 [SMILES: Cc1nc2ncc(-c3ccn4nc(N[C@H]5CC[C@@H](O)CC5)ncc34)cc2n1C(C)C]
612
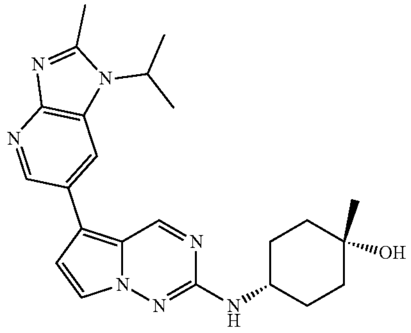 [SMILES: Cc1nc2ncc(-c3ccn4nc(N[C@H]5CC[C@@](C)(O)CC5)ncc34)cc2n1C(C)C]
613
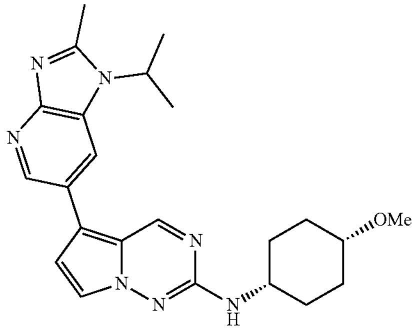 [SMILES: CO[C@H]1CC[C@@H](Nc2ncc3c(-c4cnc5nc(C)n(C(C)C)c5c4)ccn3n2)CC1]
614

TABLE 1-continued
615
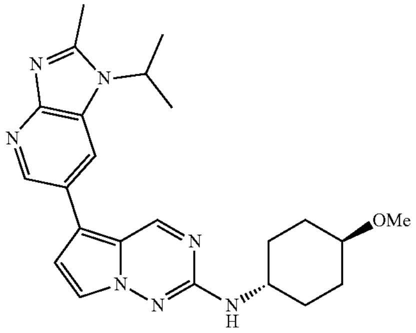 [SMILES: CO[C@H]1CC[C@H](Nc2ncc3c(-c4cnc5nc(C)n(C(C)C)c5c4)ccn3n2)CC1]
616
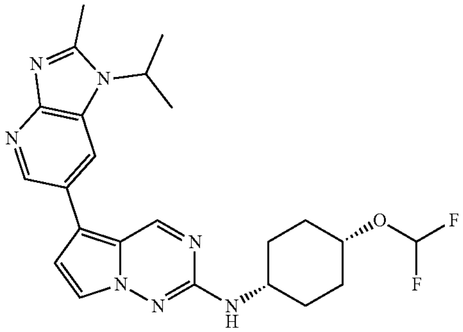 [SMILES: Cc1nc2ncc(-c3ccn4nc(N[C@H]5CC[C@@H](OC(F)F)CC5)ncc34)cc2n1C(C)C]
617
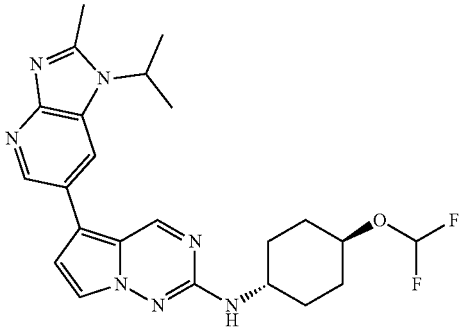 [SMILES: Cc1nc2ncc(-c3ccn4nc(N[C@H]5CC[C@H](OC(F)F)CC5)ncc34)cc2n1C(C)C]
618
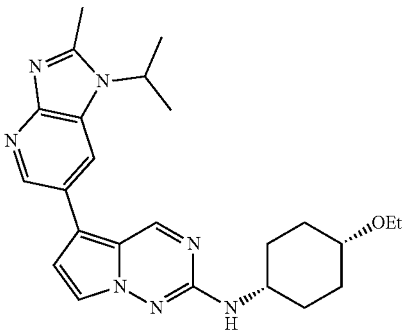 [SMILES: CCO[C@H]1CC[C@@H](Nc2ncc3c(-c4cnc5nc(C)n(C(C)C)c5c4)ccn3n2)CC1]

TABLE 1-continued
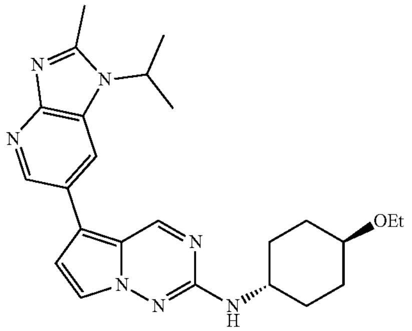 [SMILES: CCO[C@H]1CC[C@H](Nc2ncc3c(-c4cnc5nc(C)n(C(C)C)c5c4)ccn3n2)CC1]
619
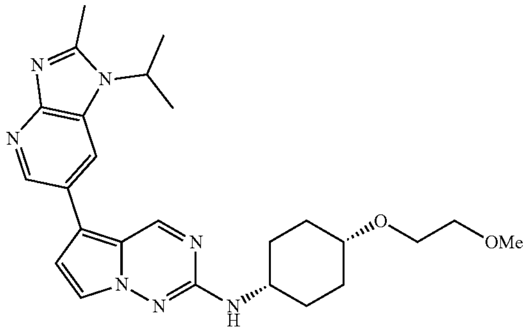 [SMILES: COCCO[C@H]1CC[C@@H](Nc2ncc3c(-c4cnc5nc(C)n(C(C)C)c5c4)ccn3n2)CC1]
620
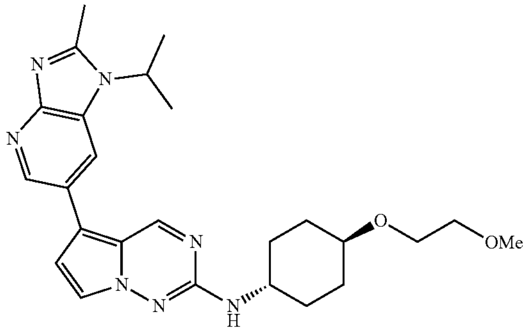 [SMILES: COCCO[C@H]1CC[C@H](Nc2ncc3c(-c4cnc5nc(C)n(C(C)C)c5c4)ccn3n2)CC1]
621
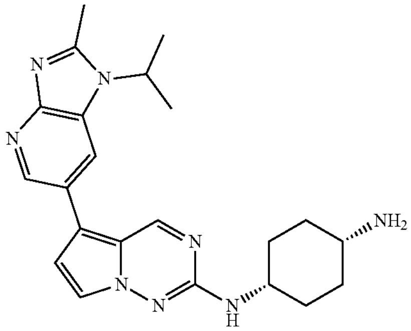 [SMILES: Cc1nc2ncc(-c3ccn4nc(N[C@H]5CC[C@@H](N)CC5)ncc34)cc2n1C(C)C]
622

TABLE 1-continued
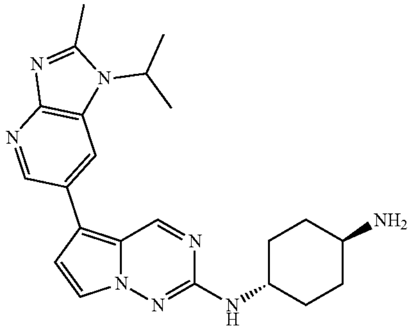 [SMILES: Cc1nc2ncc(-c3ccn4nc(N[C@H]5CC[C@H](N)CC5)ncc34)cc2n1C(C)C]
623
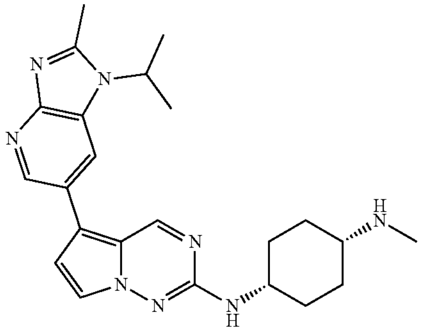 [SMILES: CN[C@H]1CC[C@@H](Nc2ncc3c(-c4cnc5nc(C)n(C(C)C)c5c4)ccn3n2)CC1]
624
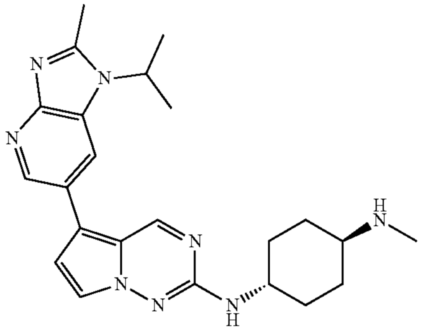 [SMILES: CN[C@H]1CC[C@H](Nc2ncc3c(-c4cnc5nc(C)n(C(C)C)c5c4)ccn3n2)CC1]
625
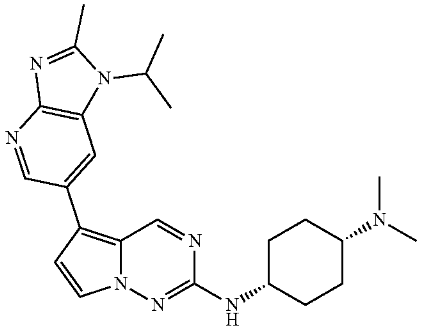 [SMILES: Cc1nc2ncc(-c3ccn4nc(N[C@H]5CC[C@@H](N(C)C)CC5)ncc34)cc2n1C(C)C]
626

TABLE 1-continued
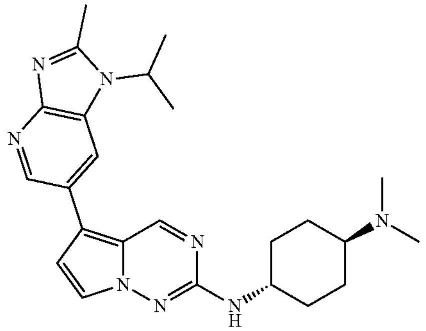 [SMILES: Cc1nc2ncc(-c3ccn4nc(N[C@H]5CC[C@H](N(C)C)CC5)ncc34)cc2n1C(C)C]
627
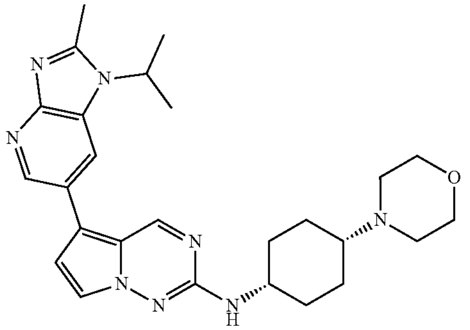 [SMILES: Cc1nc2ncc(-c3ccn4nc(N[C@H]5CC[C@@H](N6CCOCC6)CC5)ncc34)cc2n1C(C)C]
628
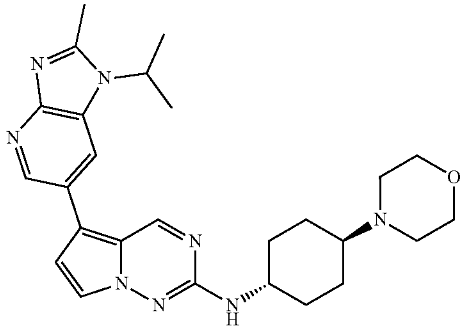 [SMILES: Cc1nc2ncc(-c3ccn4nc(N[C@H]5CC[C@H](N6CCOCC6)CC5)ncc34)cc2n1C(C)C]
629
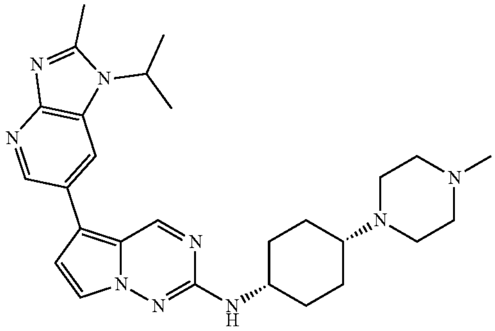 [SMILES: Cc1nc2ncc(-c3ccn4nc(N[C@H]5CC[C@@H](N6CCN(C)CC6)CC5)ncc34)cc2n1C(C)C]
630

TABLE 1-continued
631
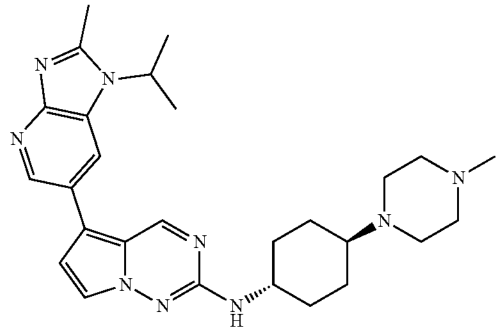 [SMILES: Cc1nc2ncc(-c3ccn4nc(N[C@H]5CC[C@H](N6CCN(C)CC6)CC5)ncc34)cc2n1C(C)C]
632
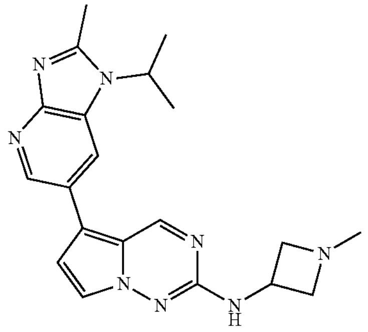 [SMILES: Cc1nc2ncc(-c3ccn4nc(NC5CN(C)C5)ncc34)cc2n1C(C)C]
633
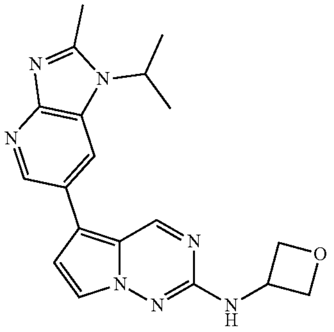 [SMILES: Cc1nc2ncc(-c3ccn4nc(NC5COC5)ncc34)cc2n1C(C)C]
634
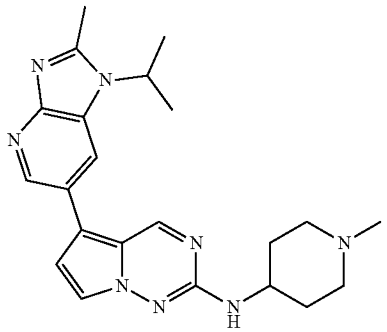 [SMILES: Cc1nc2ncc(-c3ccn4nc(NC5CCN(C)CC5)ncc34)cc2n1C(C)C]

TABLE 1-continued
635
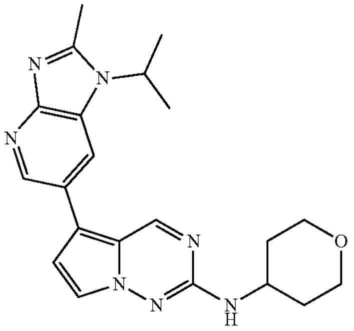 [SMILES: Cc1nc2ncc(-c3ccn4nc(NC5CCOCC5)ncc34)cc2n1C(C)C]
636
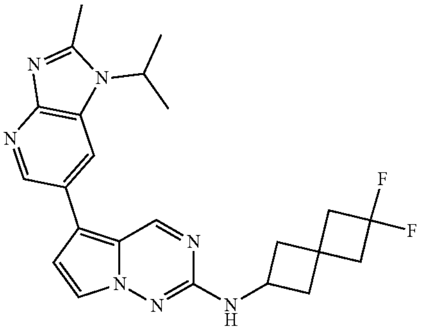 [SMILES: Cc1nc2ncc(-c3ccn4nc(NC5CC6(C5)CC(F)(F)C6)ncc34)cc2n1C(C)C]
637
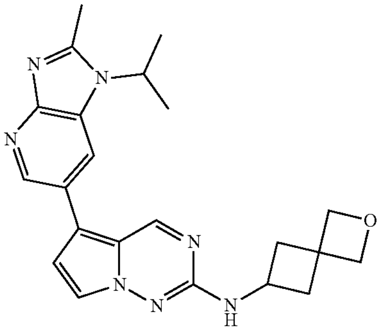 [SMILES: Cc1nc2ncc(-c3ccn4nc(NC5CC6(COC6)C5)ncc34)cc2n1C(C)C]
638
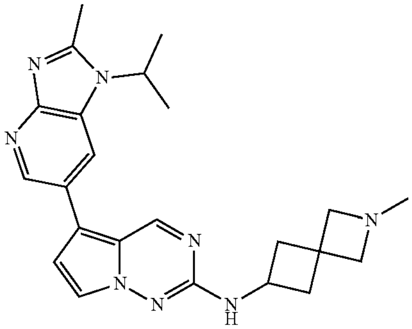

TABLE 1-continued
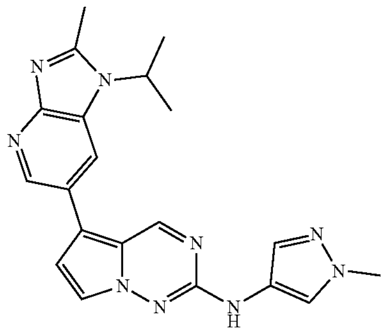 [SMILES: Cc1nc2ncc(-c3ccn4nc(Nc5cnn(C)c5)ncc34)cc2n1C(C)C]
639
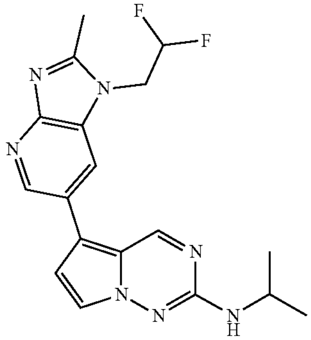 [SMILES: Cc1nc2ncc(-c3ccn4nc(NC(C)C)ncc34)cc2n1CC(F)F]
640
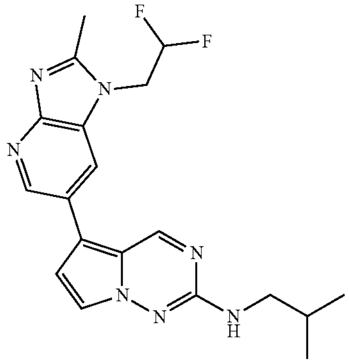 [SMILES: Cc1nc2ncc(-c3ccn4nc(NCC(C)C)ncc34)cc2n1CC(F)F]
641
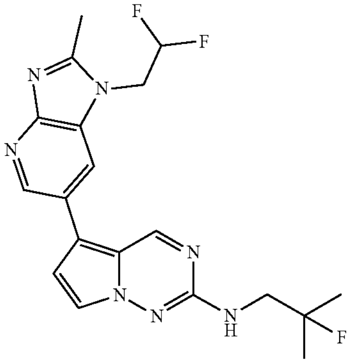 [SMILES: Cc1nc2ncc(-c3ccn4nc(NCC(C)(C)F)ncc34)cc2n1CC(F)F]
642

TABLE 1-continued
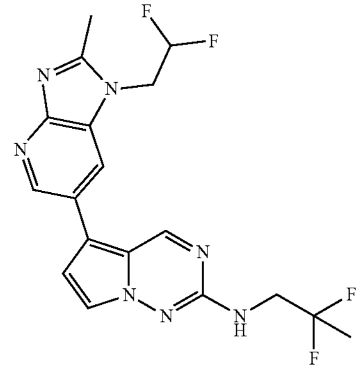 [SMILES: Cc1nc2ncc(-c3ccn4nc(NCC(C)(F)F)ncc34)cc2n1CC(F)F]
643
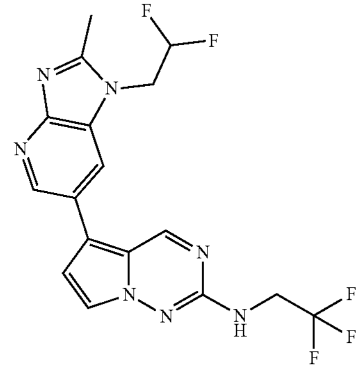 [SMILES: Cc1nc2ncc(-c3ccn4nc(NCC(F)(F)F)ncc34)cc2n1CC(F)F]
644
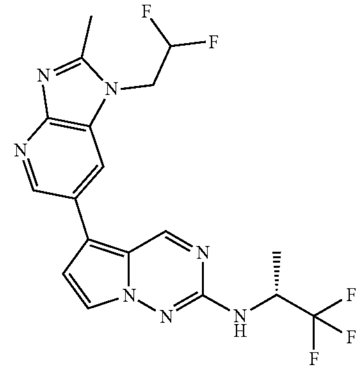 [SMILES: Cc1nc2ncc(-c3ccn4nc(N[C@H](C)C(F)(F)F)ncc34)cc2n1CC(F)F]
645
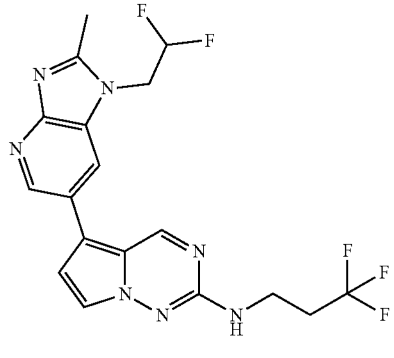 [SMILES: Cc1nc2ncc(-c3ccn4nc(NCCC(F)(F)F)ncc34)cc2n1CC(F)F]
646

TABLE 1-continued
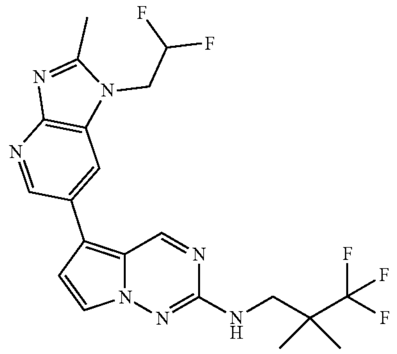 [SMILES: Cc1nc2ncc(-c3ccn4nc(NCC(C)(C)C(F)(F)F)ncc34)cc2n1CC(F)F]
647
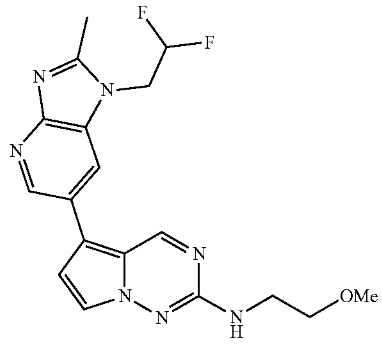 [SMILES: COCCNc1ncc2c(-c3cnc4nc(C)n(CC(F)F)c4c3)ccn2n1]
648
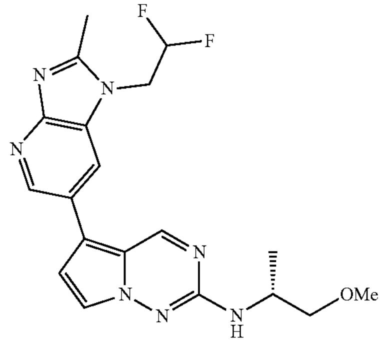 [SMILES: COC[C@@H](C)Nc1ncc2c(-c3cnc4nc(C)n(CC(F)F)c4c3)ccn2n1]
649
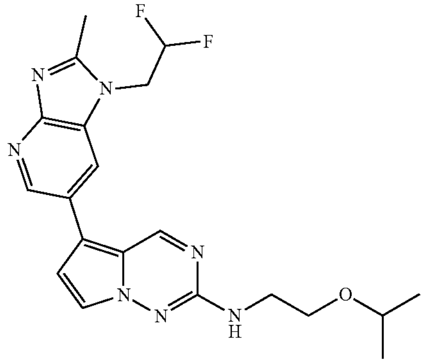 [SMILES: Cc1nc2ncc(-c3ccn4nc(NCCOC(C)C)ncc34)cc2n1CC(F)F]
650

TABLE 1-continued
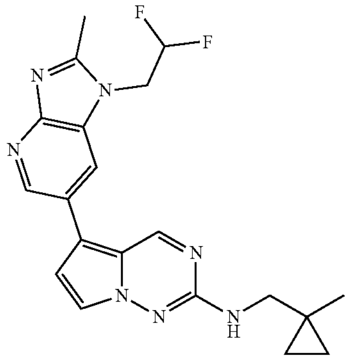 [SMILES: Cc1nc2ncc(-c3ccn4nc(NCC5(C)CC5)ncc34)cc2n1CC(F)F]
651
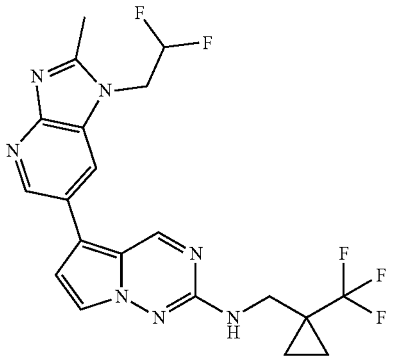 [SMILES: Cc1nc2ncc(-c3ccn4nc(NCC5(C(F)(F)F)CC5)ncc34)cc2n1CC(F)F]
652
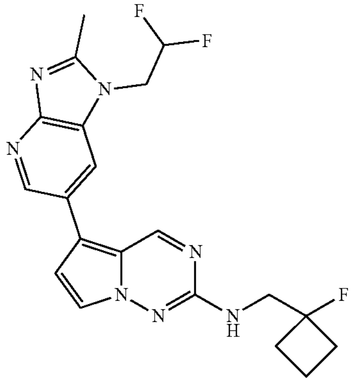 [SMILES: Cc1nc2ncc(-c3ccn4nc(NCC5(F)CCC5)ncc34)cc2n1CC(F)F]
653
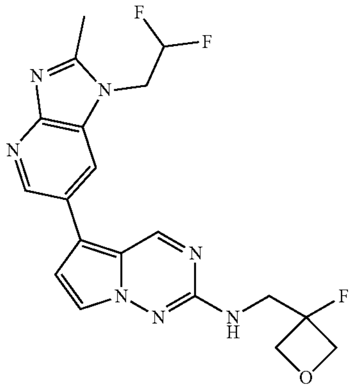 [SMILES: Cc1nc2ncc(-c3ccn4nc(NCC5(F)COC5)ncc34)cc2n1CC(F)F]
654

TABLE 1-continued
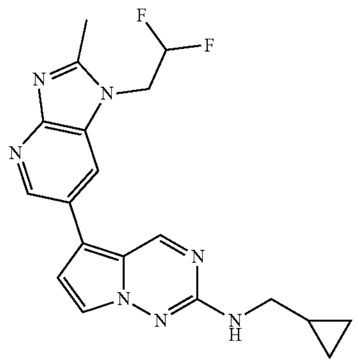 [SMILES: Cc1nc2ncc(-c3ccn4nc(NCC5CC5)ncc34)cc2n1CC(F)F]
655
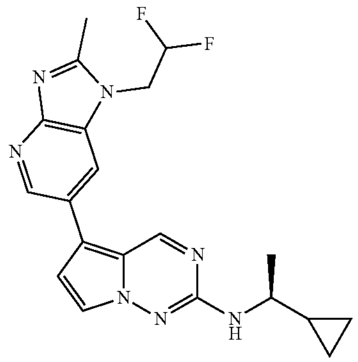 [SMILES: Cc1nc2ncc(-c3ccn4nc(N[C@@H](C)C5CC5)ncc34)cc2n1CC(F)F]
656
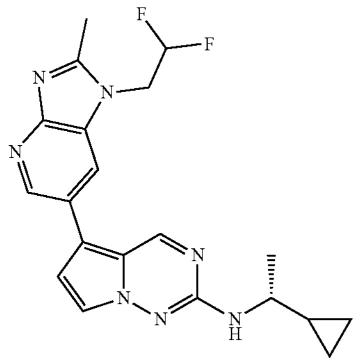 [SMILES: Cc1nc2ncc(-c3ccn4nc(N[C@H](C)C5CC5)ncc34)cc2n1CC(F)F]
657
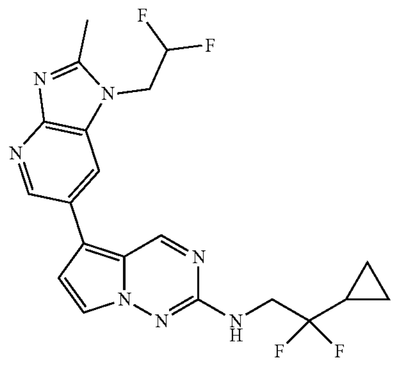 [SMILES: Cc1nc2ncc(-c3ccn4nc(NCC(F)(F)C5CC5)ncc34)cc2n1CC(F)F]
658

TABLE 1-continued
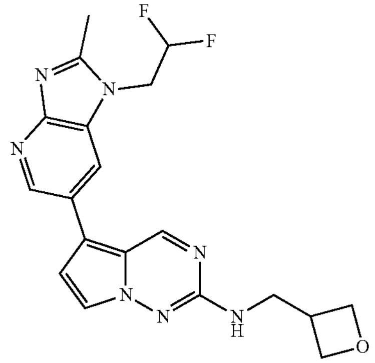 [SMILES: Cc1nc2ncc(-c3ccn4nc(NCC5COC5)ncc34)cc2n1CC(F)F]
659
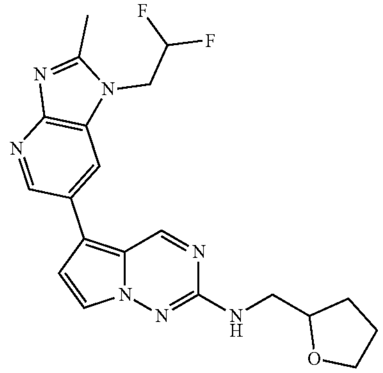 [SMILES: Cc1nc2ncc(-c3ccn4nc(NCC5CCCO5)ncc34)cc2n1CC(F)F]
660
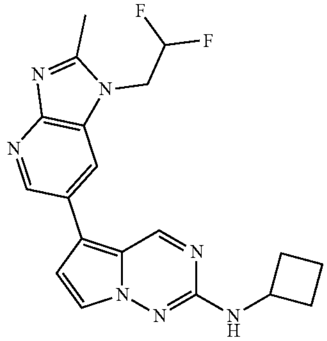 [SMILES: Cc1nc2ncc(-c3ccn4nc(NC5CCC5)ncc34)cc2n1CC(F)F]
661
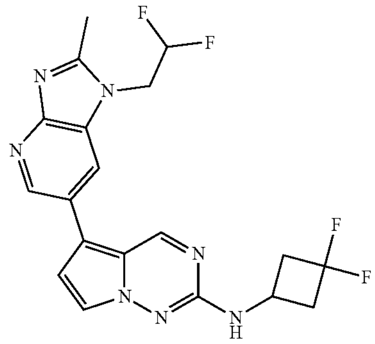 [SMILES: Cc1nc2ncc(-c3ccn4nc(NC5CC(F)(F)C5)ncc34)cc2n1CC(F)F]
662

TABLE 1-continued
663
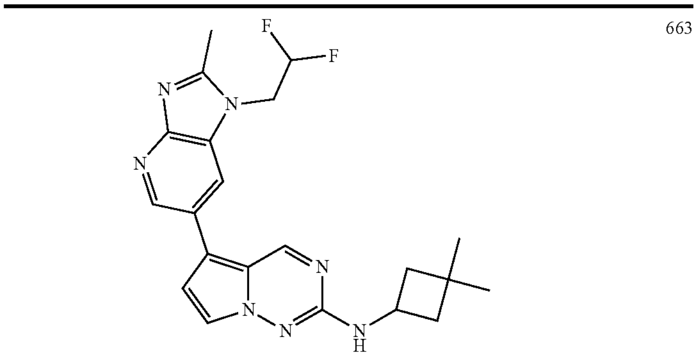
664
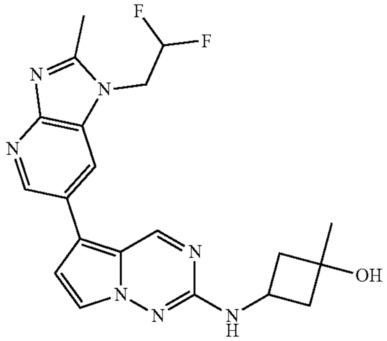 [SMILES: Cc1nc2ncc(-c3ccn4nc(NC5CC(C)(O)C5)ncc34)cc2n1CC(F)F]
665
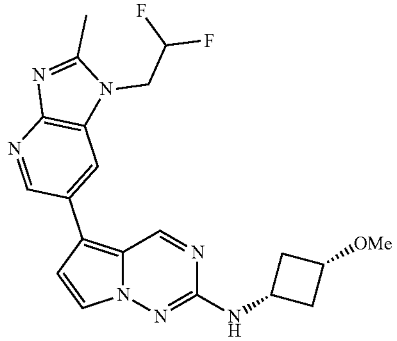 [SMILES: CO[C@H]1C[C@@H](Nc2ncc3c(-c4cnc5nc(C)n(CC(F)F)c5c4)ccn3n2)C1]
666
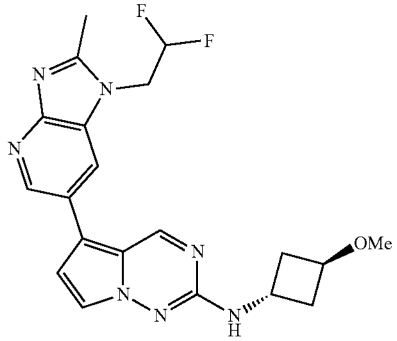 [SMILES: CO[C@H]1C[C@H](Nc2ncc3c(-c4cnc5nc(C)n(CC(F)F)c5c4)ccn3n2)C1]

TABLE 1-continued
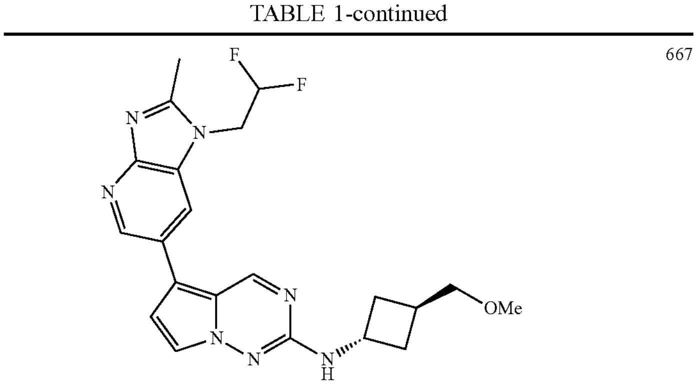
667
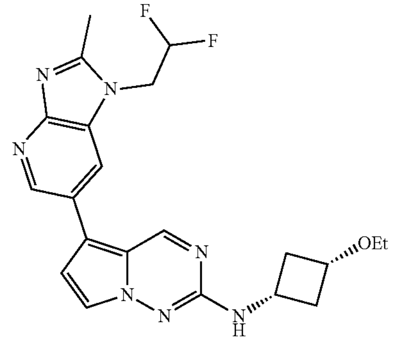 [SMILES: CCO[C@H]1C[C@@H](Nc2ncc3c(-c4cnc5nc(C)n(CC(F)F)c5c4)ccn3n2)C1]
668
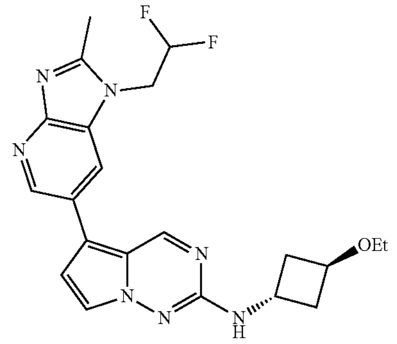 [SMILES: CCO[C@H]1C[C@H](Nc2ncc3c(-c4cnc5nc(C)n(CC(F)F)c5c4)ccn3n2)C1]
669
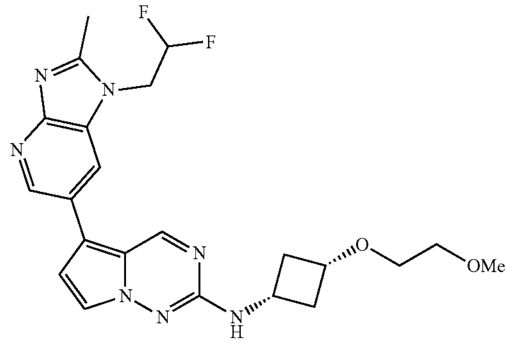 [SMILES: COCCO[C@H]1C[C@@H](Nc2ncc3c(-c4cnc5nc(C)n(CC(F)F)c5c4)ccn3n2)C1]
670

TABLE 1-continued
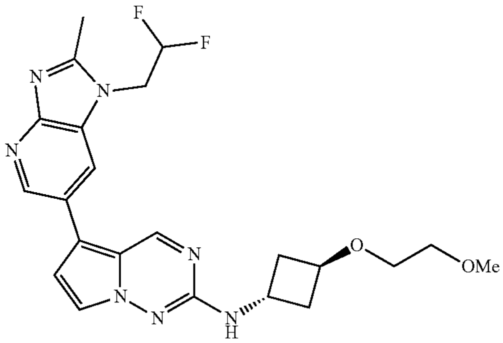 [SMILES: COCCO[C@H]1C[C@H](Nc2ncc3c(-c4cnc5nc(C)n(CC(F)F)c5c4)ccn3n2)C1]
671
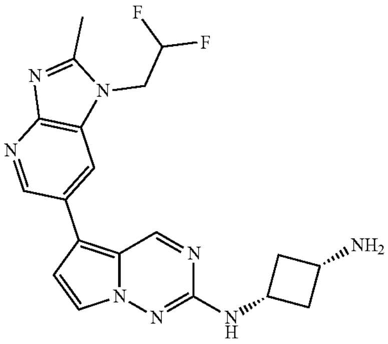 [SMILES: Cc1nc2ncc(-c3ccn4nc(N[C@H]5C[C@@H](N)C5)ncc34)cc2n1CC(F)F]
672
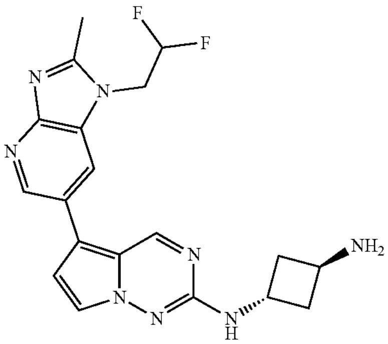 [SMILES: Cc1nc2ncc(-c3ccn4nc(N[C@H]5C[C@H](N)C5)ncc34)cc2n1CC(F)F]
673
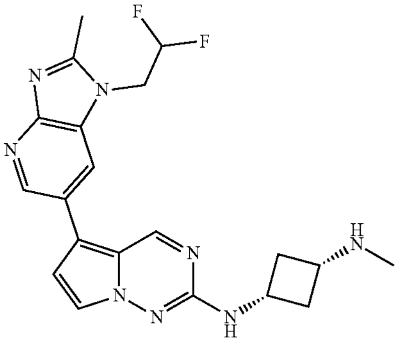 [SMILES: CN[C@H]1C[C@@H](Nc2ncc3c(-c4cnc5nc(C)n(CC(F)F)c5c4)ccn3n2)C1]
674

TABLE 1-continued
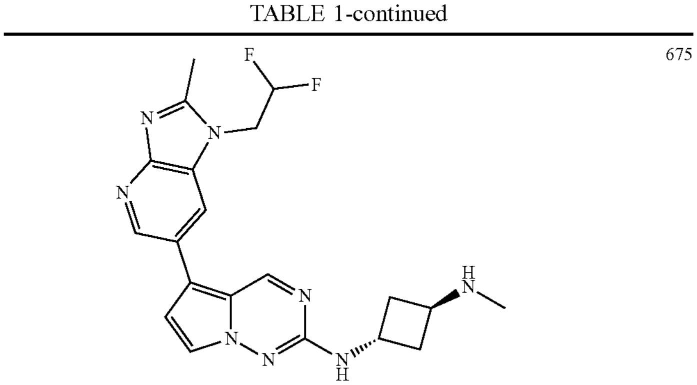
675
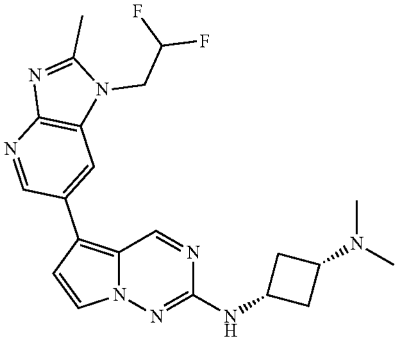 [SMILES: Cc1nc2ncc(-c3ccn4nc(N[C@H]5C[C@@H](N(C)C)C5)ncc34)cc2n1CC(F)F]
676
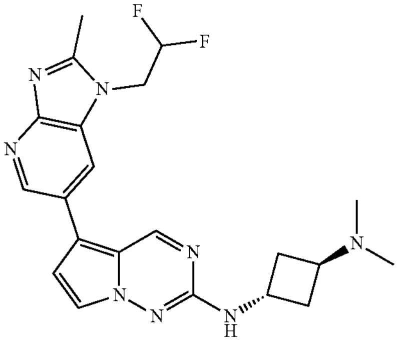 [SMILES: Cc1nc2ncc(-c3ccn4nc(N[C@H]5C[C@H](N(C)C)C5)ncc34)cc2n1CC(F)F]
677
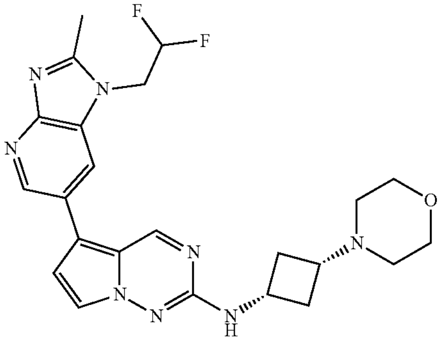 [SMILES: Cc1nc2ncc(-c3ccn4nc(N[C@H]5C[C@@H](N6CCOCC6)C5)ncc34)cc2n1CC(F)F]
678

TABLE 1-continued
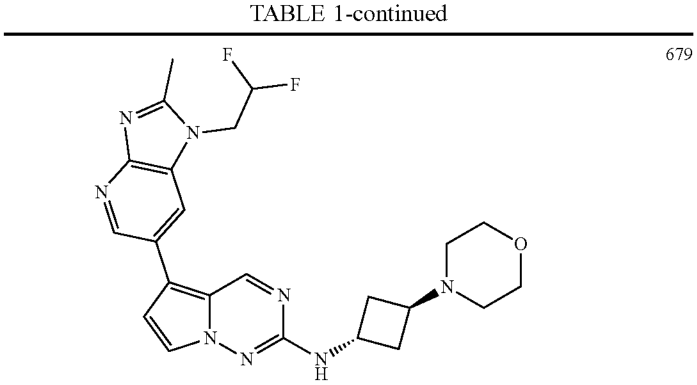
679
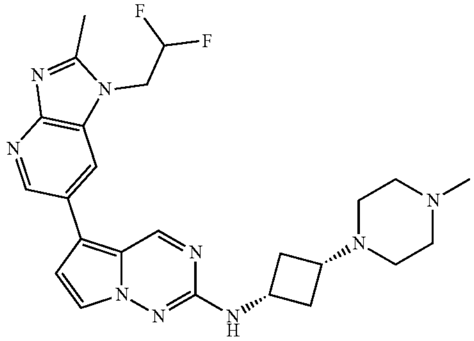 [SMILES: Cc1nc2ncc(-c3ccn4nc(N[C@H]5C[C@@H](N6CCN(C)CC6)C5)ncc34)cc2n1CC(F)F]
680
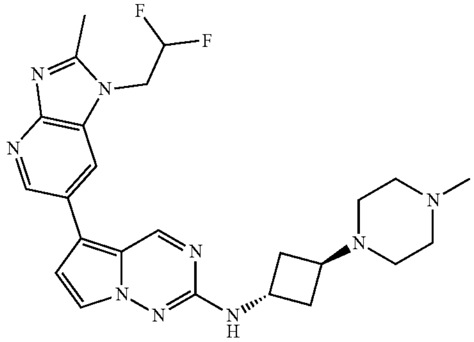 [SMILES: Cc1nc2ncc(-c3ccn4nc(N[C@H]5C[C@H](N6CCN(C)CC6)C5)ncc34)cc2n1CC(F)F]
681
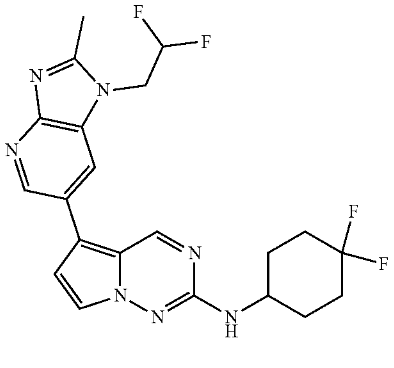 [SMILES: Cc1nc2ncc(-c3ccn4nc(NC5CCC(F)(F)CC5)ncc34)cc2n1CC(F)F]
682

TABLE 1-continued
683
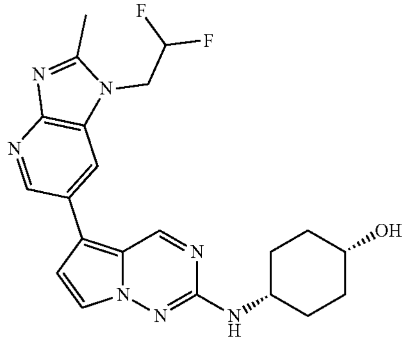 [SMILES: Cc1nc2ncc(-c3ccn4nc(N[C@H]5CC[C@@H](O)CC5)ncc34)cc2n1CC(F)F]
684
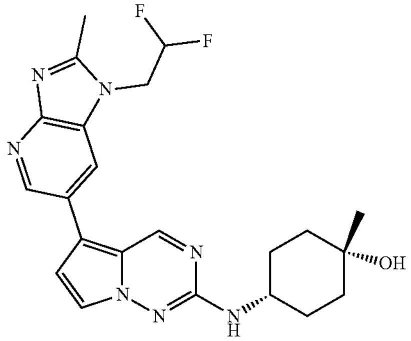 [SMILES: Cc1nc2ncc(-c3ccn4nc(N[C@H]5CC[C@@](C)(O)CC5)ncc34)cc2n1CC(F)F]
685
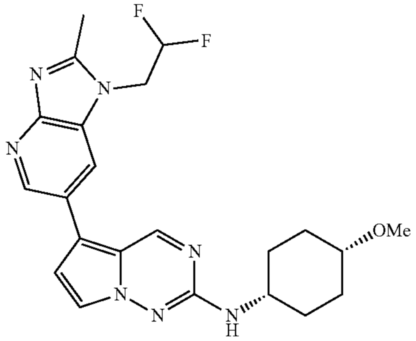 [SMILES: CO[C@H]1CC[C@@H](Nc2ncc3c(-c4cnc5nc(C)n(CC(F)F)c5c4)ccn3n2)CC1]
686
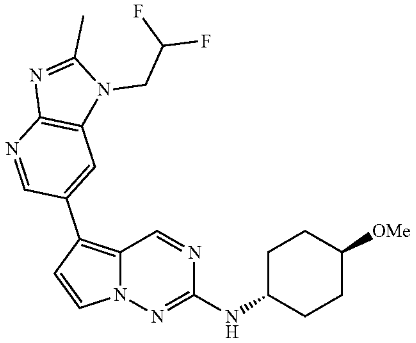 [SMILES: CO[C@H]1CC[C@H](Nc2ncc3c(-c4cnc5nc(C)n(CC(F)F)c5c4)ccn3n2)CC1]

TABLE 1-continued
687
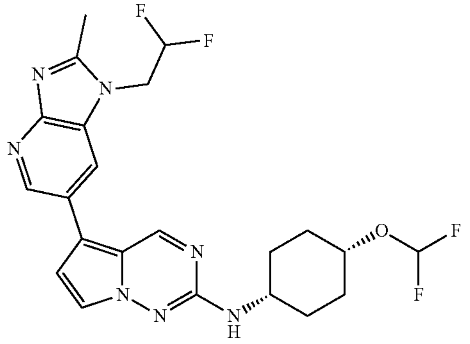 [SMILES: Cc1nc2ncc(-c3ccn4nc(N[C@H]5CC[C@@H](OC(F)F)CC5)ncc34)cc2n1CC(F)F]
688
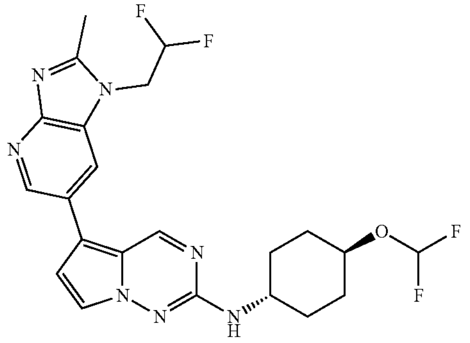 [SMILES: Cc1nc2ncc(-c3ccn4nc(N[C@H]5CC[C@H](OC(F)F)CC5)ncc34)cc2n1CC(F)F]
689
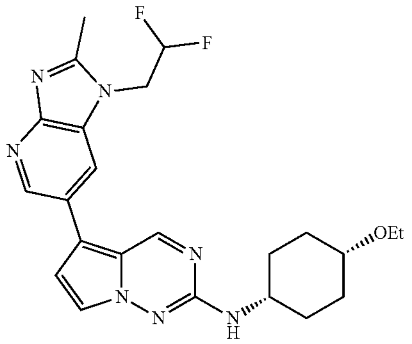 [SMILES: CCO[C@H]1CC[C@@H](Nc2ncc3c(-c4cnc5nc(C)n(CC(F)F)c5c4)ccn3n2)CC1]
690
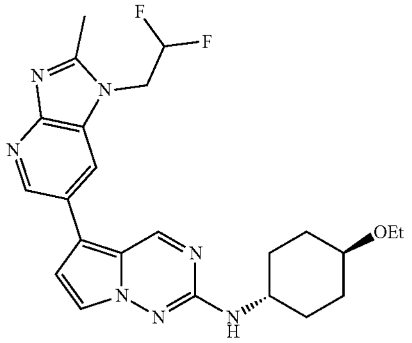 [SMILES: CCO[C@H]1CC[C@H](Nc2ncc3c(-c4cnc5nc(C)n(CC(F)F)c5c4)ccn3n2)CC1]

TABLE 1-continued
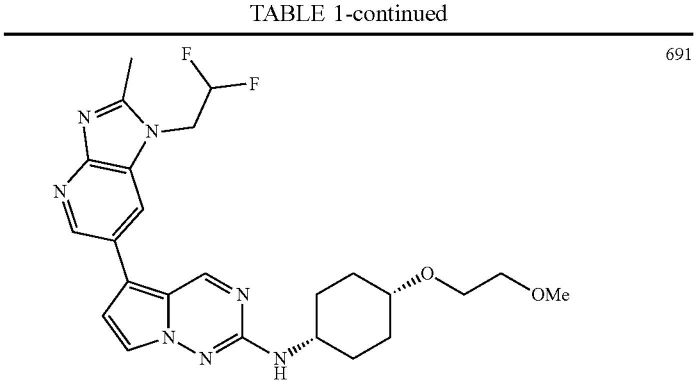
691
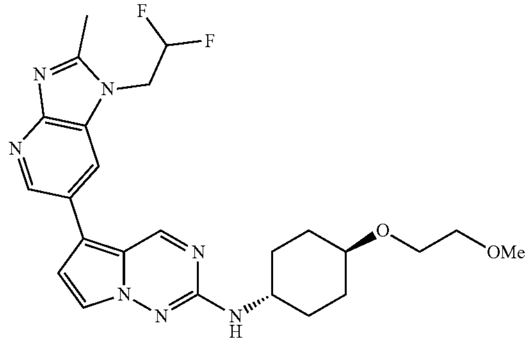 [SMILES: COCCO[C@H]1CC[C@H](Nc2ncc3c(-c4cnc5nc(C)n(CC(F)F)c5c4)ccn3n2)CC1]
692
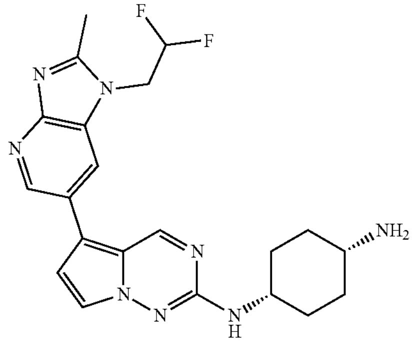 [SMILES: Cc1nc2ncc(-c3ccn4nc(N[C@H]5CC[C@@H](N)CC5)ncc34)cc2n1CC(F)F]
693
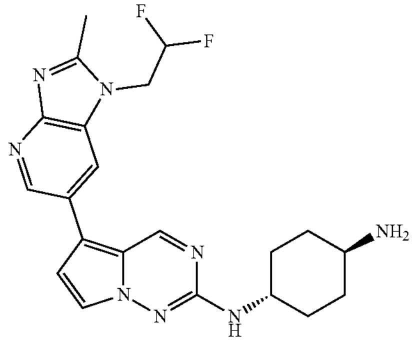 [SMILES: Cc1nc2ncc(-c3ccn4nc(N[C@H]5CC[C@H](N)CC5)ncc34)cc2n1CC(F)F]
694

TABLE 1-continued
695
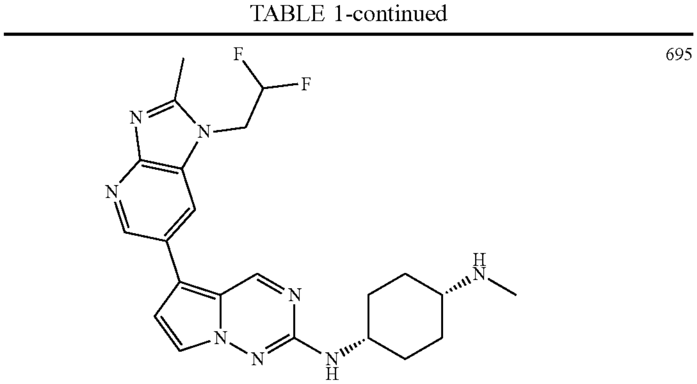
696
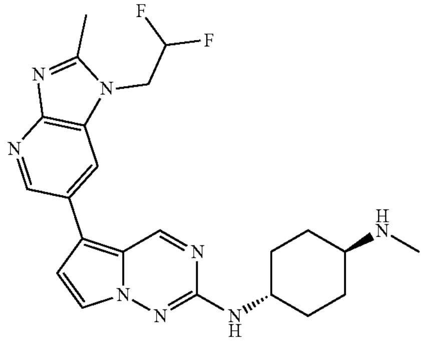
697
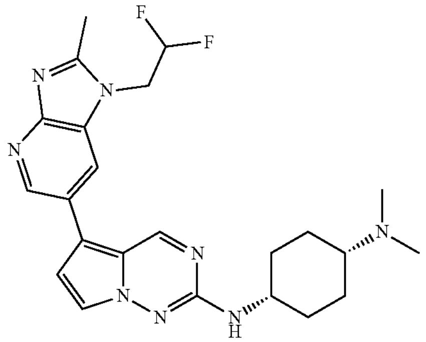 [SMILES: Cc1nc2ncc(-c3ccn4nc(N[C@H]5CC[C@@H](N(C)C)CC5)ncc34)cc2n1CC(F)F]
698
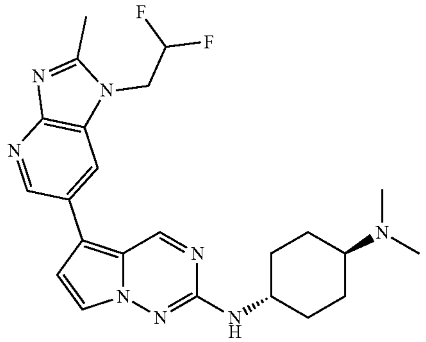 [SMILES: Cc1nc2ncc(-c3ccn4nc(N[C@H]5CC[C@H](N(C)C)CC5)ncc34)cc2n1CC(F)F]

TABLE 1-continued
699
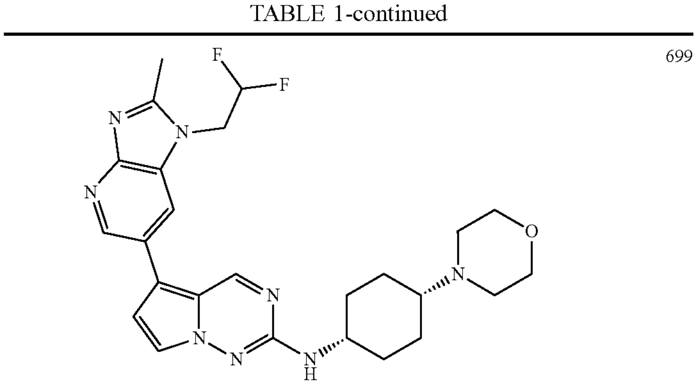
700
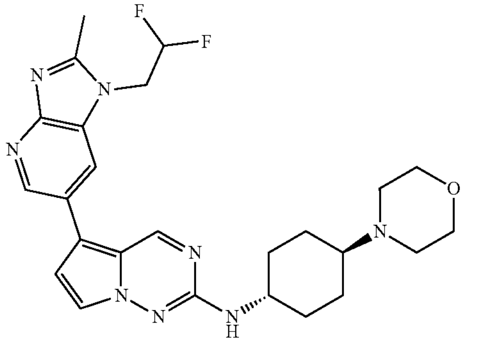 [SMILES: Cc1nc2ncc(-c3ccn4nc(N[C@H]5CC[C@H](N6CCOCC6)CC5)ncc34)cc2n1CC(F)F]
701
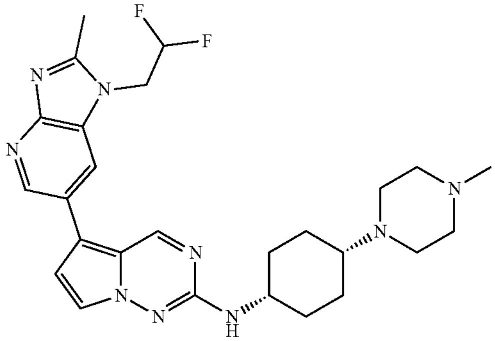 [SMILES: Cc1nc2ncc(-c3ccn4nc(N[C@H]5CC[C@@H](N6CCN(C)CC6)CC5)ncc34)cc2n1CC(F)F]
702
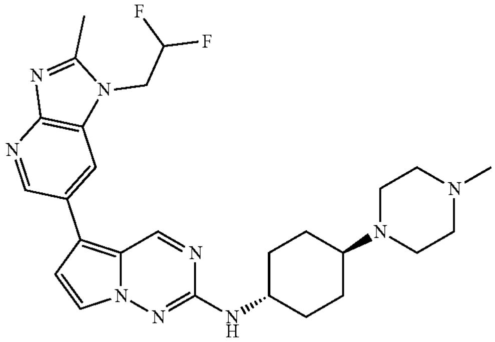 [SMILES: Cc1nc2ncc(-c3ccn4nc(N[C@H]5CC[C@H](N6CCN(C)CC6)CC5)ncc34)cc2n1CC(F)F]

TABLE 1-continued
703
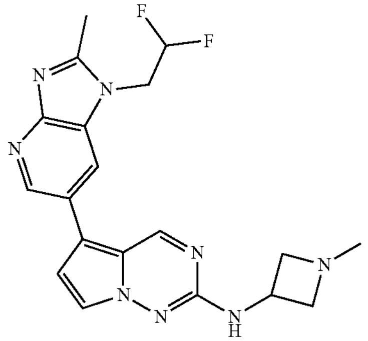 [SMILES: Cc1nc2ncc(-c3ccn4nc(NC5CN(C)C5)ncc34)cc2n1CC(F)F]
704
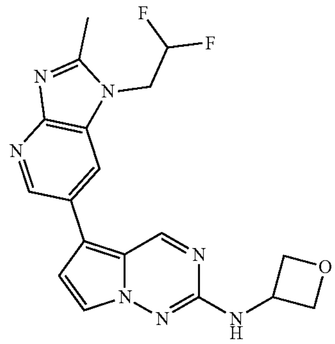 [SMILES: Cc1nc2ncc(-c3ccn4nc(NC5COC5)ncc34)cc2n1CC(F)F]
705
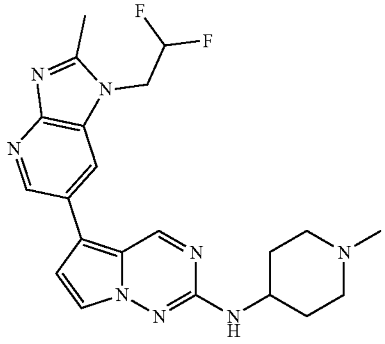 [SMILES: Cc1nc2ncc(-c3ccn4nc(NC5CCN(C)CC5)ncc34)cc2n1CC(F)F]
706
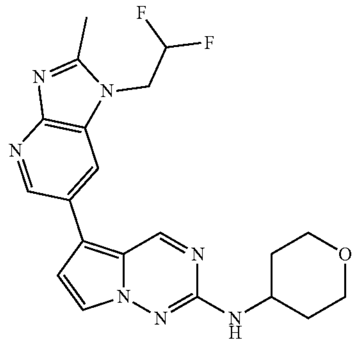 [SMILES: Cc1nc2ncc(-c3ccn4nc(NC5CCOCC5)ncc34)cc2n1CC(F)F]

TABLE 1-continued
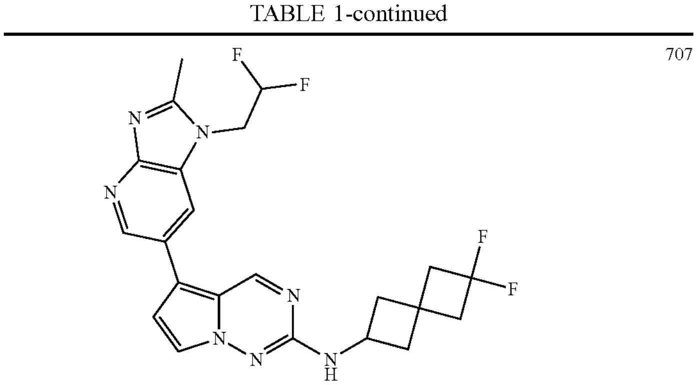
707
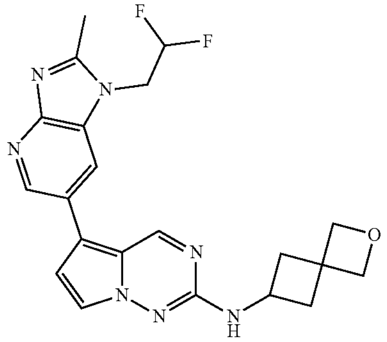 [SMILES: Cc1nc2ncc(-c3ccn4nc(NC5CC6(COC6)C5)ncc34)cc2n1CC(F)F]
708
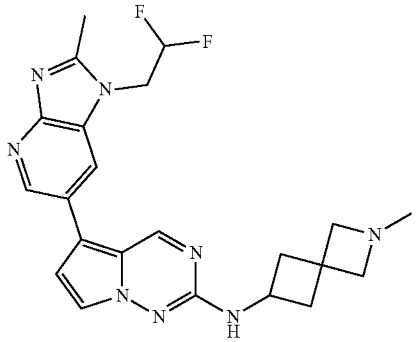 [SMILES: Cc1nc2ncc(-c3ccn4nc(NC5CC6(C5)CN(C)C6)ncc34)cc2n1CC(F)F]
709
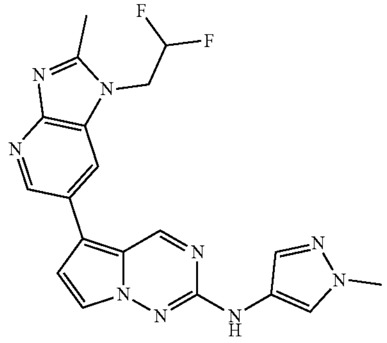 [SMILES: Cc1nc2ncc(-c3ccn4nc(Nc5cnn(C)c5)ncc34)cc2n1CC(F)F]
710

TABLE 1-continued
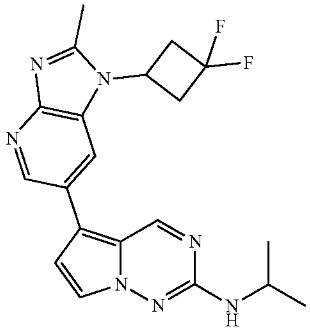 [SMILES: Cc1nc2ncc(-c3ccn4nc(NC(C)C)ncc34)cc2n1C1CC(F)(F)C1]
711
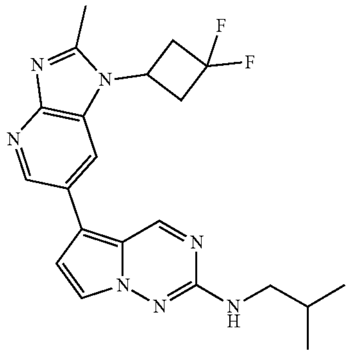 [SMILES: Cc1nc2ncc(-c3ccn4nc(NCC(C)C)ncc34)cc2n1C1CC(F)(F)C1]
712
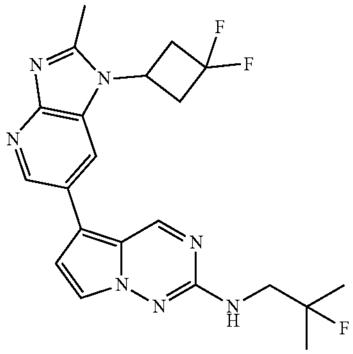 [SMILES: Cc1nc2ncc(-c3ccn4nc(NCC(C)(C)F)ncc34)cc2n1C1CC(F)(F)C1]
713
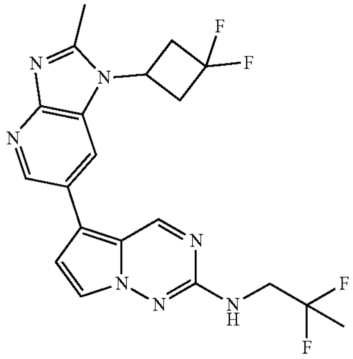 [SMILES: Cc1nc2ncc(-c3ccn4nc(NCC(C)(F)F)ncc34)cc2n1C1CC(F)(F)C1]
714

TABLE 1-continued
715
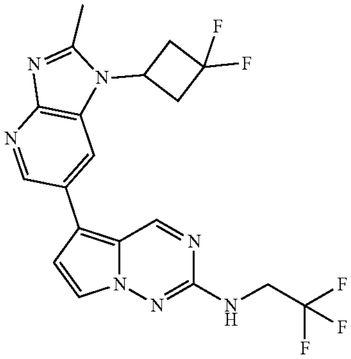 [SMILES: Cc1nc2ncc(-c3ccn4nc(NCC(F)(F)F)ncc34)cc2n1C1CC(F)(F)C1]
716
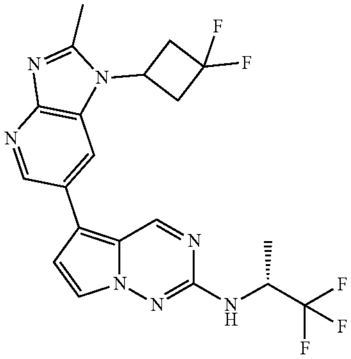 [SMILES: Cc1nc2ncc(-c3ccn4nc(N[C@H](C)C(F)(F)F)ncc34)cc2n1C1CC(F)(F)C1]
717
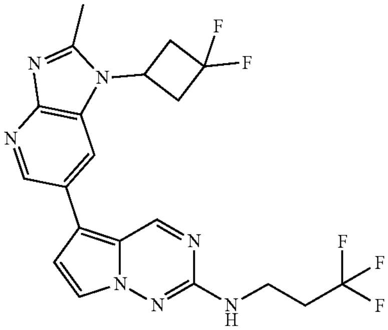 [SMILES: Cc1nc2ncc(-c3ccn4nc(NCCC(F)(F)F)ncc34)cc2n1C1CC(F)(F)C1]
718
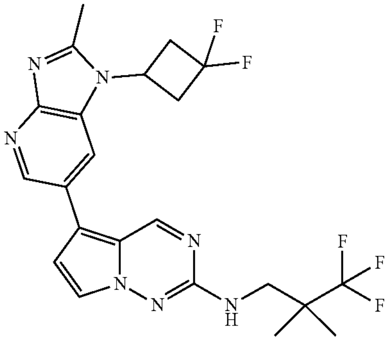 [SMILES: Cc1nc2ncc(-c3ccn4nc(NCC(C)(C)C(F)(F)F)ncc34)cc2n1C1CC(F)(F)C1]

TABLE 1-continued
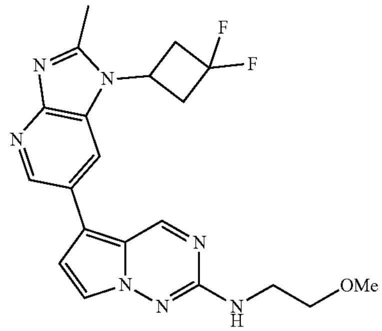 [SMILES: COCCNc1ncc2c(-c3cnc4nc(C)n(C5CC(F)(F)C5)c4c3)ccn2n1]
719
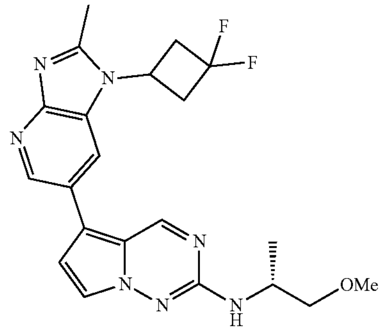 [SMILES: COC[C@@H](C)Nc1ncc2c(-c3cnc4nc(C)n(C5CC(F)(F)C5)c4c3)ccn2n1]
720
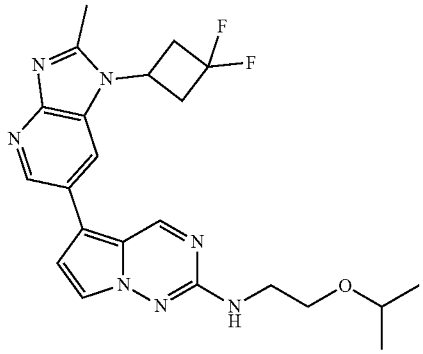 [SMILES: Cc1nc2ncc(-c3ccn4nc(NCCOC(C)C)ncc34)cc2n1C1CC(F)(F)C1]
721
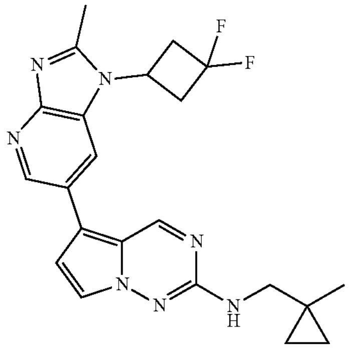 [SMILES: Cc1nc2ncc(-c3ccn4nc(NCC5(C)CC5)ncc34)cc2n1C1CC(F)(F)C1]
722

TABLE 1-continued
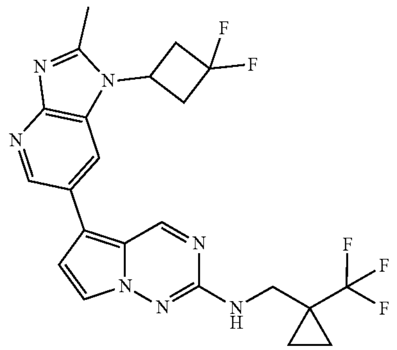 [SMILES: Cc1nc2ncc(-c3ccn4nc(NCC5(C(F)(F)F)CC5)ncc34)cc2n1C1CC(F)(F)C1]
723
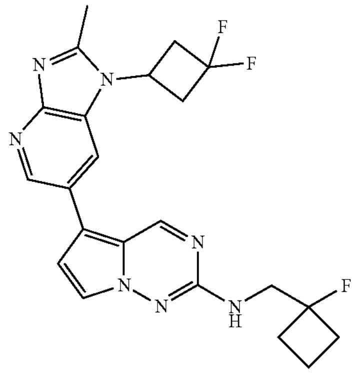 [SMILES: Cc1nc2ncc(-c3ccn4nc(NCC5(F)CCC5)ncc34)cc2n1C1CC(F)(F)C1]
724
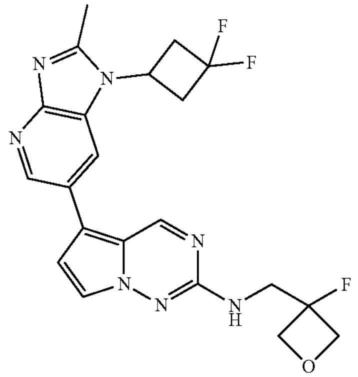 [SMILES: Cc1nc2ncc(-c3ccn4nc(NCC5(F)COC5)ncc34)cc2n1C1CC(F)(F)C1]
725
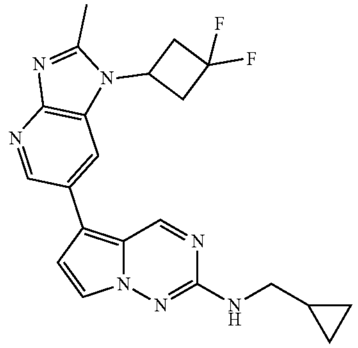 [SMILES: Cc1nc2ncc(-c3ccn4nc(NCC5CC5)ncc34)cc2n1C1CC(F)(F)C1]
726

TABLE 1-continued
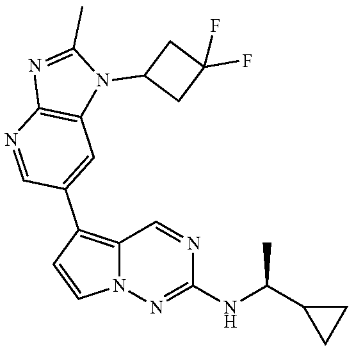 [SMILES: Cc1nc2ncc(-c3ccn4nc(N[C@@H](C)C5CC5)ncc34)cc2n1C1CC(F)(F)C1]
727
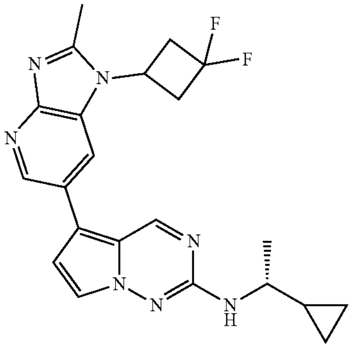 [SMILES: Cc1nc2ncc(-c3ccn4nc(N[C@H](C)C5CC5)ncc34)cc2n1C1CC(F)(F)C1]
728
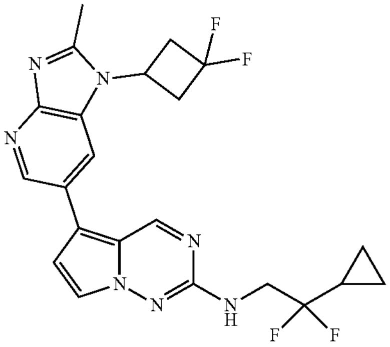 [SMILES: Cc1nc2ncc(-c3ccn4nc(NCC(F)(F)C5CC5)ncc34)cc2n1C1CC(F)(F)C1]
729
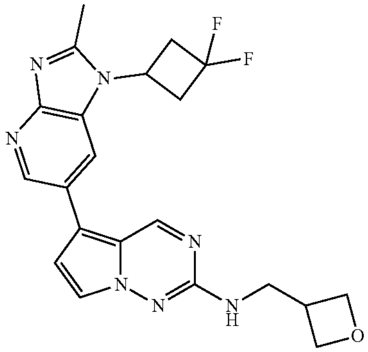 [SMILES: Cc1nc2ncc(-c3ccn4nc(NCC5COC5)ncc34)cc2n1C1CC(F)(F)C1]
730

TABLE 1-continued
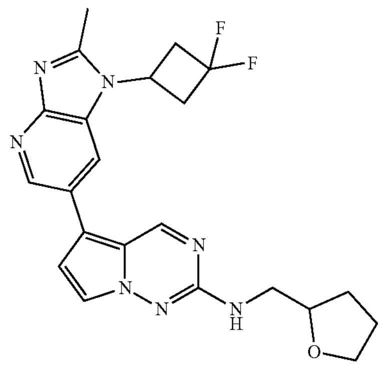 [SMILES: Cc1nc2ncc(-c3ccn4nc(NCC5CCCO5)ncc34)cc2n1C1CC(F)(F)C1]
731
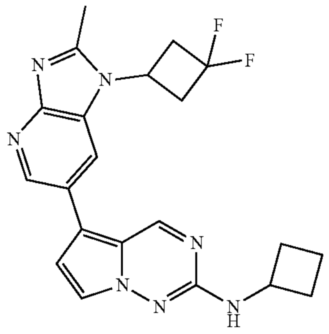 [SMILES: Cc1nc2ncc(-c3ccn4nc(NC5CCC5)ncc34)cc2n1C1CC(F)(F)C1]
732
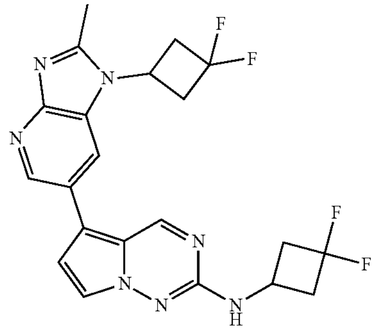 [SMILES: Cc1nc2ncc(-c3ccn4nc(NC5CC(F)(F)C5)ncc34)cc2n1C1CC(F)(F)C1]
733
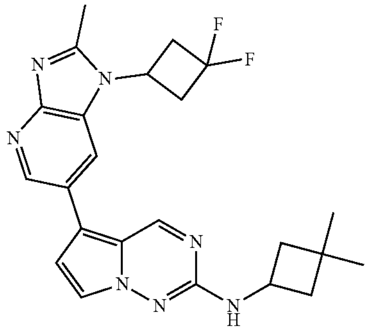 [SMILES: Cc1nc2ncc(-c3ccn4nc(NC5CC(C)(C)C5)ncc34)cc2n1C1CC(F)(F)C1]
734

TABLE 1-continued
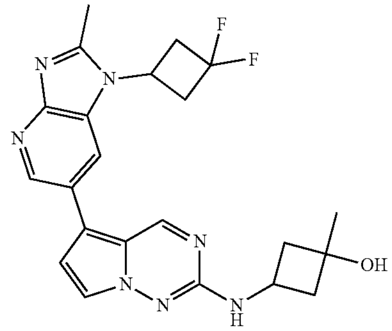 [SMILES: Cc1nc2ncc(-c3ccn4nc(NC5CC(C)(O)C5)ncc34)cc2n1C1CC(F)(F)C1]
735
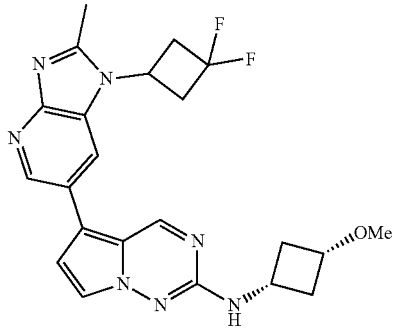 [SMILES: CO[C@H]1C[C@@H](Nc2ncc3c(-c4cnc5nc(C)n(C6CC(F)(F)C6)c5c4)ccn3n2)C1]
736
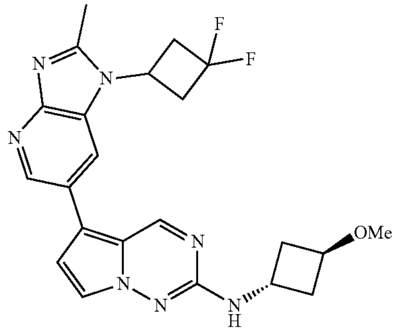 [SMILES: CO[C@H]1C[C@H](Nc2ncc3c(-c4cnc5nc(C)n(C6CC(F)(F)C6)c5c4)ccn3n2)C1]
737
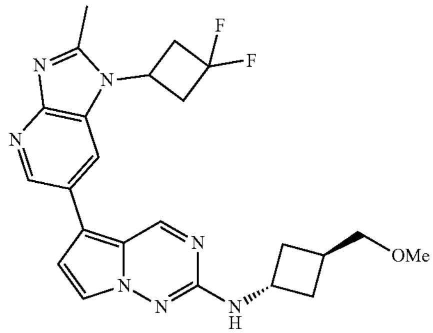 [SMILES: COC[C@H]1C[C@H](Nc2ncc3c(-c4cnc5nc(C)n(C6CC(F)(F)C6)c5c4)ccn3n2)C1]
738

TABLE 1-continued
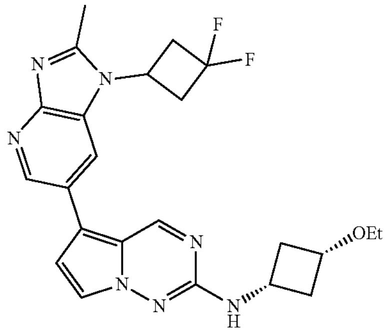 [SMILES: CCO[C@H]1C[C@@H](Nc2ncc3c(-c4cnc5nc(C)n(C6CC(F)(F)C6)c5c4)ccn3n2)C1]
739
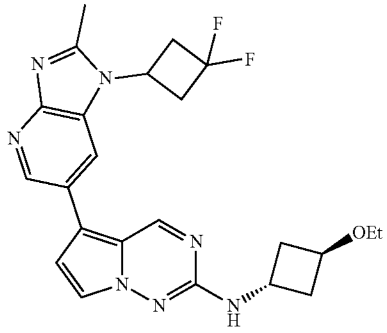 [SMILES: CCO[C@H]1C[C@H](Nc2ncc3c(-c4cnc5nc(C)n(C6CC(F)(F)C6)c5c4)ccn3n2)C1]
740
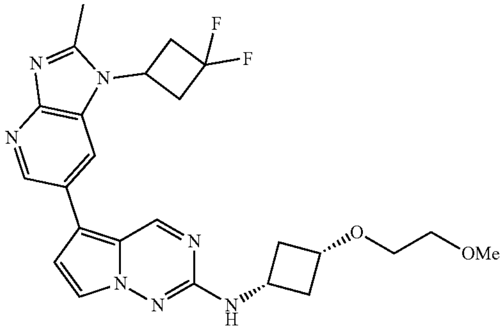 [SMILES: COCCO[C@H]1C[C@@H](Nc2ncc3c(-c4cnc5nc(C)n(C6CC(F)(F)C6)c5c4)ccn3n2)C1]
741
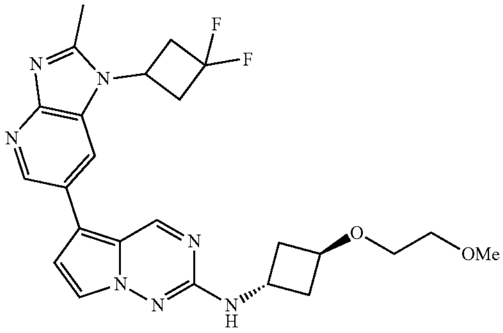 [SMILES: COCCO[C@H]1C[C@H](Nc2ncc3c(-c4cnc5nc(C)n(C6CC(F)(F)C6)c5c4)ccn3n2)C1]
742

TABLE 1-continued
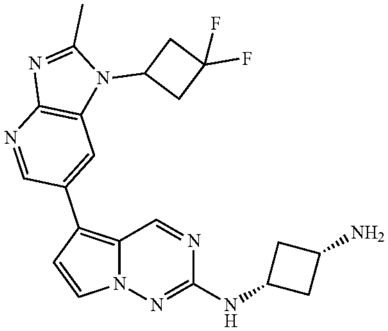 [SMILES: Cc1nc2ncc(-c3ccn4nc(N[C@H]5C[C@@H](N)C5)ncc34)cc2n1C1CC(F)(F)C1]
743
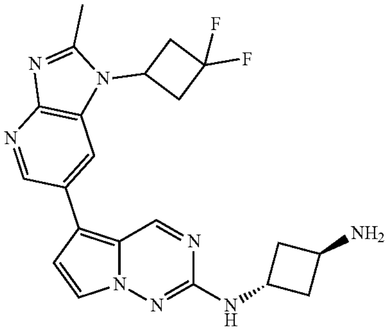 [SMILES: Cc1nc2ncc(-c3ccn4nc(N[C@H]5C[C@H](N)C5)ncc34)cc2n1C1CC(F)(F)C1]
744
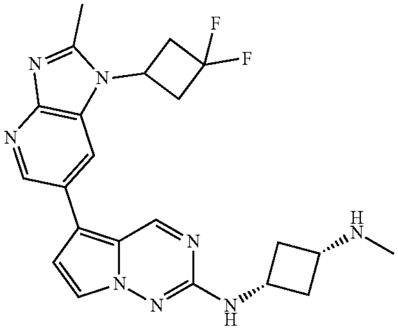 [SMILES: CN[C@H]1C[C@@H](Nc2ncc3c(-c4cnc5nc(C)n(C6CC(F)(F)C6)c5c4)ccn3n2)C1]
745
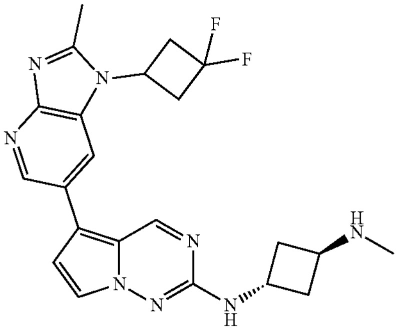 [SMILES: CN[C@H]1C[C@H](Nc2ncc3c(-c4cnc5nc(C)n(C6CC(F)(F)C6)c5c4)ccn3n2)C1]
746

TABLE 1-continued
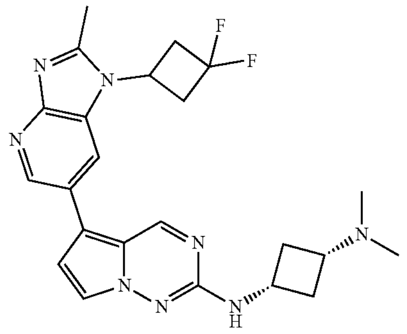 [SMILES: Cc1nc2ncc(-c3ccn4nc(N[C@H]5C[C@@H](N(C)C)C5)ncc34)cc2n1C1CC(F)(F)C1]
747
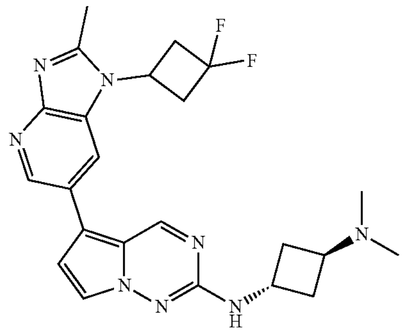 [SMILES: Cc1nc2ncc(-c3ccn4nc(N[C@H]5C[C@H](N(C)C)C5)ncc34)cc2n1C1CC(F)(F)C1]
748
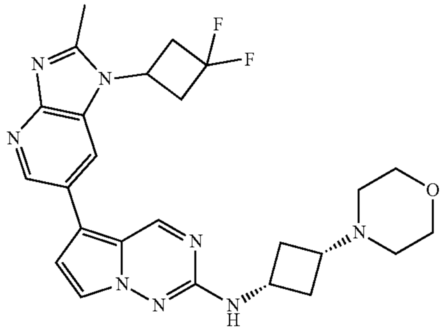 [SMILES: Cc1nc2ncc(-c3ccn4nc(N[C@H]5C[C@@H](N6CCOCC6)C5)ncc34)cc2n1C1CC(F)(F)C1]
749
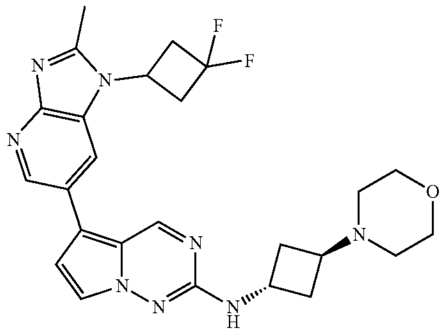 [SMILES: Cc1nc2ncc(-c3ccn4nc(N[C@H]5C[C@H](N6CCOCC6)C5)ncc34)cc2n1C1CC(F)(F)C1]
750

TABLE 1-continued
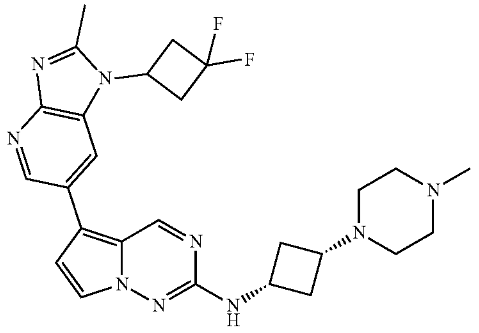 [SMILES: Cc1nc2ncc(-c3ccn4nc(N[C@H]5C[C@@H](N6CCN(C)CC6)C5)ncc34)cc2n1C1CC(F)(F)C1]
751
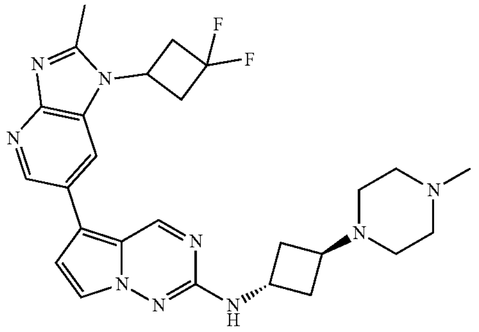 [SMILES: Cc1nc2ncc(-c3ccn4nc(N[C@H]5C[C@H](N6CCN(C)CC6)C5)ncc34)cc2n1C1CC(F)(F)C1]
752
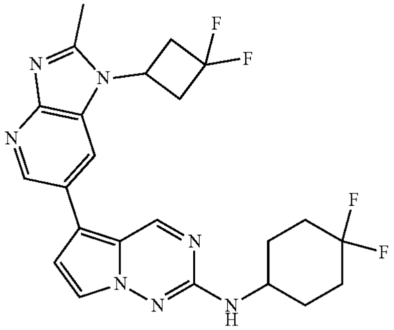 [SMILES: Cc1nc2ncc(-c3ccn4nc(NC5CCC(F)(F)CC5)ncc34)cc2n1C1CC(F)(F)C1]
753
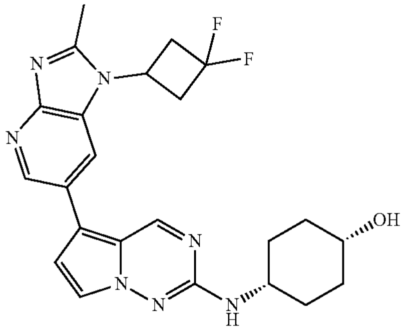 [SMILES: Cc1nc2ncc(-c3ccn4nc(N[C@H]5CC[C@@H](O)CC5)ncc34)cc2n1C1CC(F)(F)C1]
754

TABLE 1-continued
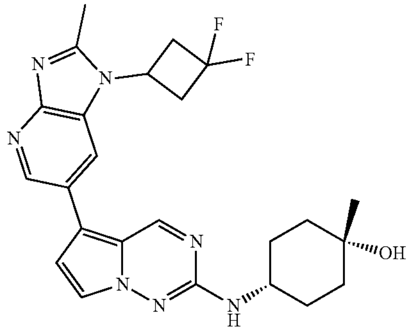 [SMILES: Cc1nc2ncc(-c3ccn4nc(N[C@H]5CC[C@@](C)(O)CC5)ncc34)cc2n1C1CC(F)(F)C1]
755
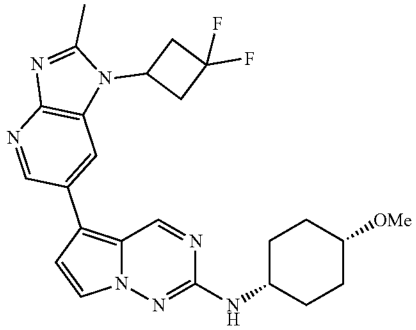 [SMILES: CO[C@H]1CC[C@@H](Nc2ncc3c(-c4cnc5nc(C)n(C6CC(F)(F)C6)c5c4)ccn3n2)CC1]
756
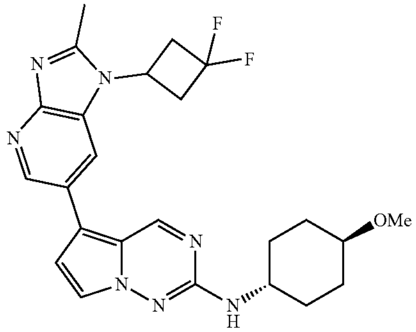 [SMILES: CO[C@H]1CC[C@H](Nc2ncc3c(-c4cnc5nc(C)n(C6CC(F)(F)C6)c5c4)ccn3n2)CC1]
757
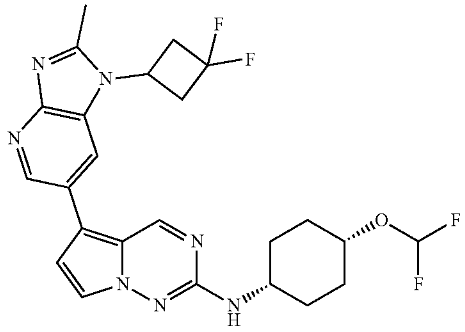 [SMILES: Cc1nc2ncc(-c3ccn4nc(N[C@H]5CC[C@@H](OC(F)F)CC5)ncc34)cc2n1C1CC(F)(F)C1]
758

TABLE 1-continued
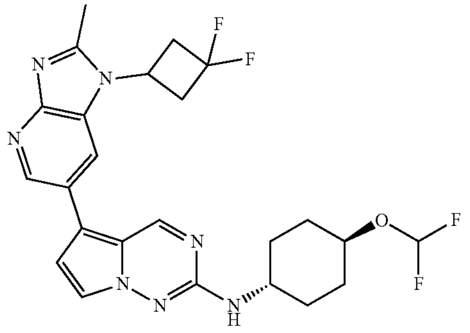 [SMILES: Cc1nc2ncc(-c3ccn4nc(N[C@H]5CC[C@H](OC(F)F)CC5)ncc34)cc2n1C1CC(F)(F)C1]
759
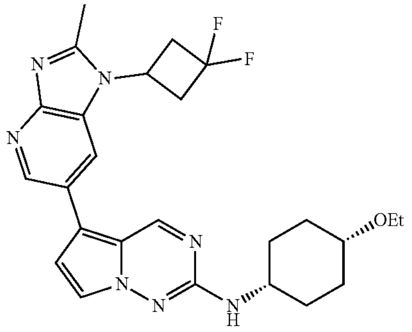 [SMILES: CCO[C@H]1CC[C@@H](Nc2ncc3c(-c4cnc5nc(C)n(C6CC(F)(F)C6)c5c4)ccn3n2)CC1]
760
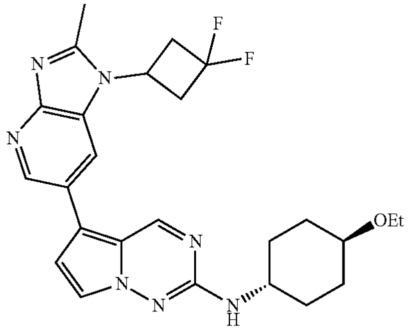 [SMILES: CCO[C@H]1CC[C@H](Nc2ncc3c(-c4cnc5nc(C)n(C6CC(F)(F)C6)c5c4)ccn3n2)CC1]
761
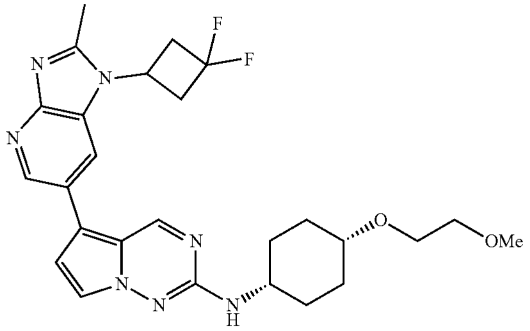 [SMILES: COCCO[C@H]1CC[C@@H](Nc2ncc3c(-c4cnc5nc(C)n(C6CC(F)(F)C6)c5c4)ccn3n2)CC1]
762

TABLE 1-continued
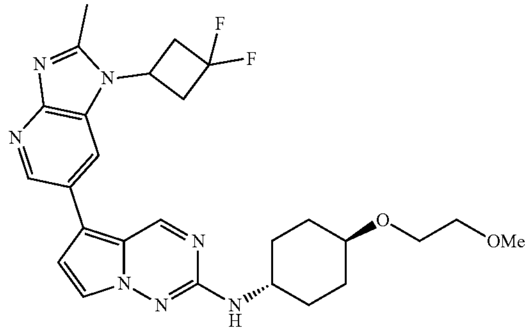 [SMILES: COCCO[C@H]1CC[C@H](Nc2ncc3c(-c4cnc5nc(C)n(C6CC(F)(F)C6)c5c4)ccn3n2)CC1]
763
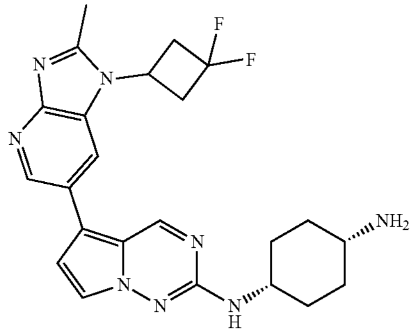 [SMILES: Cc1nc2ncc(-c3ccn4nc(N[C@H]5CC[C@@H](N)CC5)ncc34)cc2n1C1CC(F)(F)C1]
764
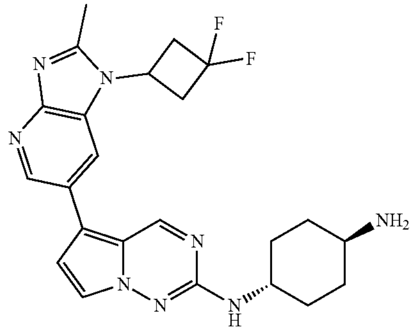 [SMILES: Cc1nc2ncc(-c3ccn4nc(N[C@H]5CC[C@H](N)CC5)ncc34)cc2n1C1CC(F)(F)C1]
765
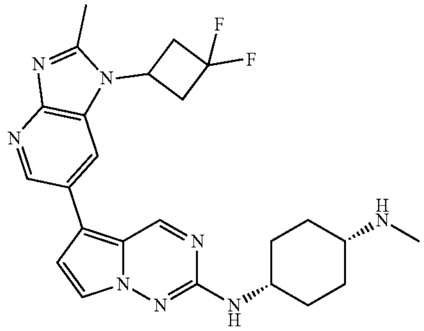 [SMILES: CN[C@H]1CC[C@@H](Nc2ncc3c(-c4cnc5nc(C)n(C6CC(F)(F)C6)c5c4)ccn3n2)CC1]
766

TABLE 1-continued
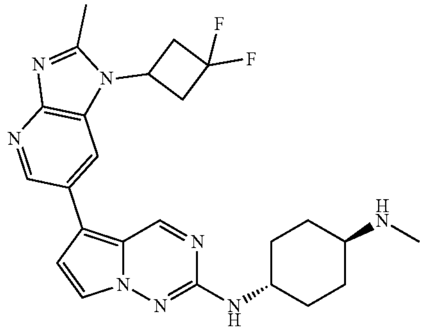 [SMILES: CN[C@H]1CC[C@H](Nc2ncc3c(-c4cnc5nc(C)n(C6CC(F)(F)C6)c5c4)ccn3n2)CC1]
767
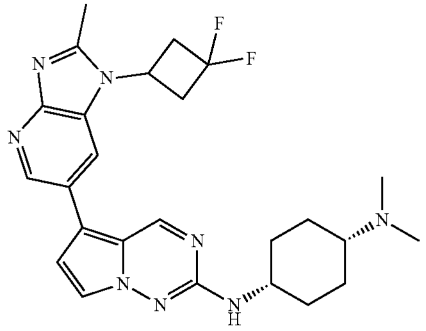 [SMILES: Cc1nc2ncc(-c3ccn4nc(N[C@H]5CC[C@@H](N(C)C)CC5)ncc34)cc2n1C1CC(F)(F)C1]
768
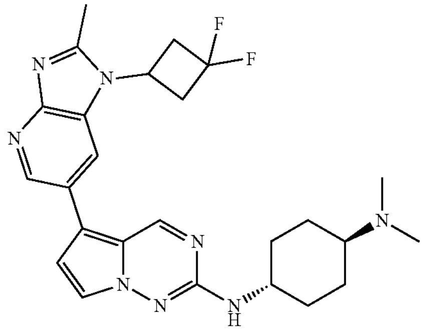 [SMILES: Cc1nc2ncc(-c3ccn4nc(N[C@H]5CC[C@H](N(C)C)CC5)ncc34)cc2n1C1CC(F)(F)C1]
769
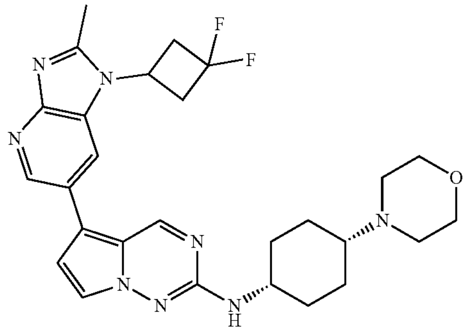 [SMILES: Cc1nc2ncc(-c3ccn4nc(N[C@H]5CC[C@@H](N6CCOCC6)CC5)ncc34)cc2n1C1CC(F)(F)C1]
770

TABLE 1-continued
771
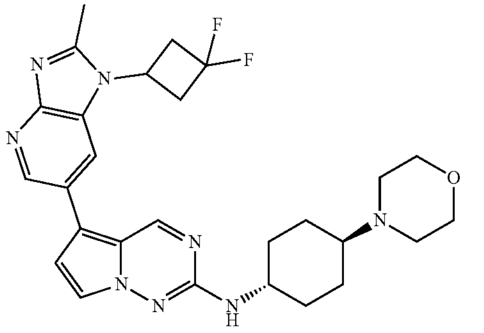 [SMILES: Cc1nc2ncc(-c3ccn4nc(N[C@H]5CC[C@H](N6CCOCC6)CC5)ncc34)cc2n1C1CC(F)(F)C1]
772
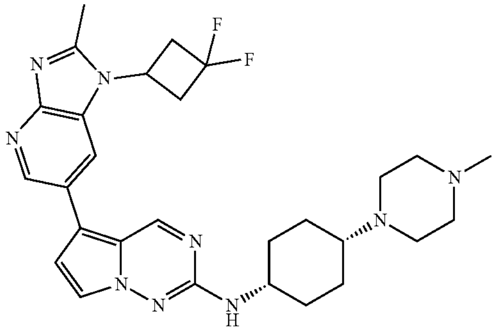 [SMILES: Cc1nc2ncc(-c3ccn4nc(N[C@H]5CC[C@@H](N6CCN(C)CC6)CC5)ncc34)cc2n1C1CC(F)(F)C1]
773
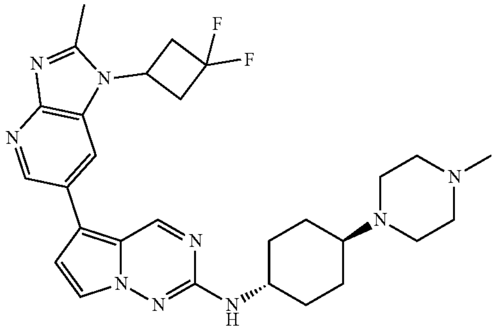 [SMILES: Cc1nc2ncc(-c3ccn4nc(N[C@H]5CC[C@H](N6CCN(C)CC6)CC5)ncc34)cc2n1C1CC(F)(F)C1]
774
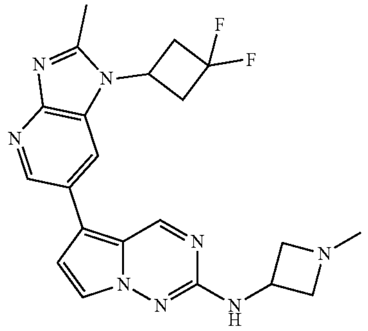 [SMILES: Cc1nc2ncc(-c3ccn4nc(NC5CN(C)C5)ncc34)cc2n1C1CC(F)(F)C1]

TABLE 1-continued
775
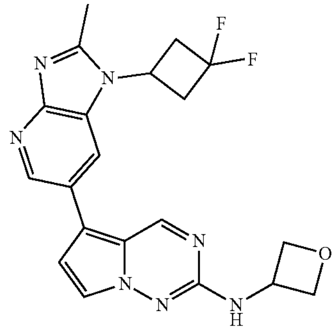 [SMILES: Cc1nc2ncc(-c3ccn4nc(NC5COC5)ncc34)cc2n1C1CC(F)(F)C1]
776
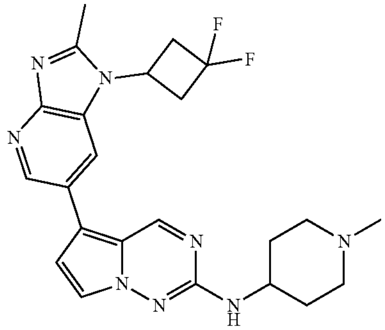 [SMILES: Cc1nc2ncc(-c3ccn4nc(NC5CCN(C)CC5)ncc34)cc2n1C1CC(F)(F)C1]
777
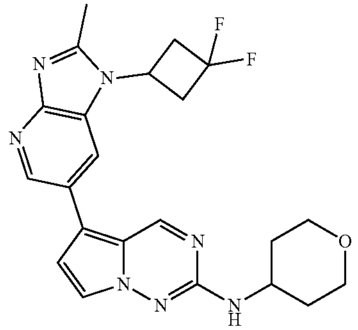 [SMILES: Cc1nc2ncc(-c3ccn4nc(NC5CCOCC5)ncc34)cc2n1C1CC(F)(F)C1]
778
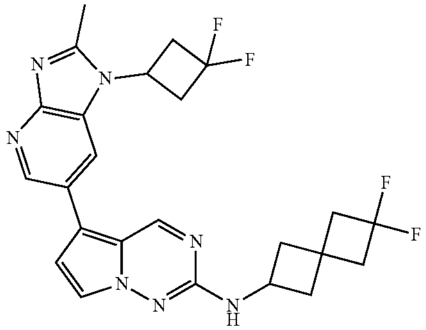 [SMILES: Cc1nc2ncc(-c3ccn4nc(NC5CC6(C5)CC(F)(F)C6)ncc34)cc2n1C1CC(F)(F)C1]

TABLE 1-continued
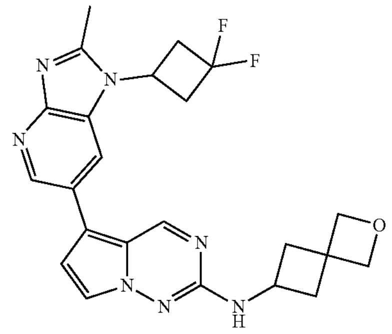 [SMILES: Cc1nc2ncc(-c3ccn4nc(NC5CC6(COC6)C5)ncc34)cc2n1C1CC(F)(F)C1]
779
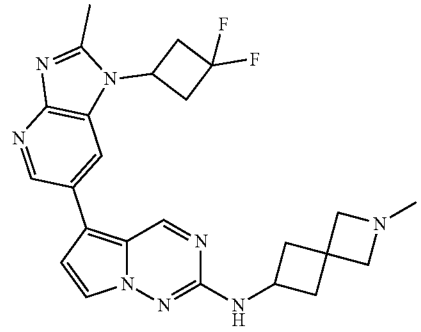 [SMILES: Cc1nc2ncc(-c3ccn4nc(NC5CC6(C5)CN(C)C6)ncc34)cc2n1C1CC(F)(F)C1]
780
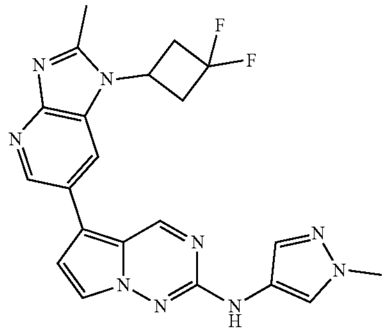 [SMILES: Cc1nc2ncc(-c3ccn4nc(Nc5cnn(C)c5)ncc34)cc2n1C1CC(F)(F)C1]
781
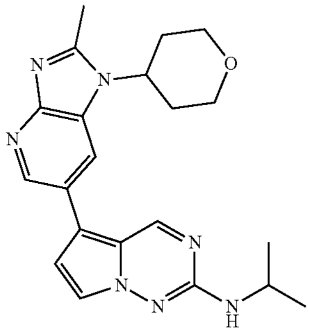 [SMILES: Cc1nc2ncc(-c3ccn4nc(NC(C)C)ncc34)cc2n1C1CCOCC1]
782

TABLE 1-continued
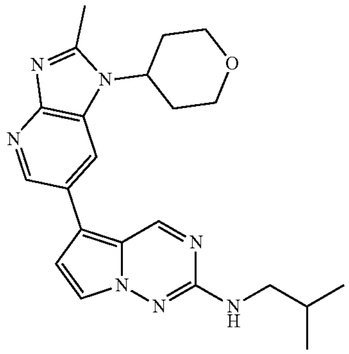 [SMILES: Cc1nc2ncc(-c3ccn4nc(NCC(C)C)ncc34)cc2n1C1CCOCC1]
783
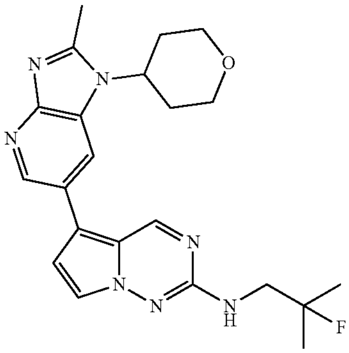 [SMILES: Cc1nc2ncc(-c3ccn4nc(NCC(C)(C)F)ncc34)cc2n1C1CCOCC1]
784
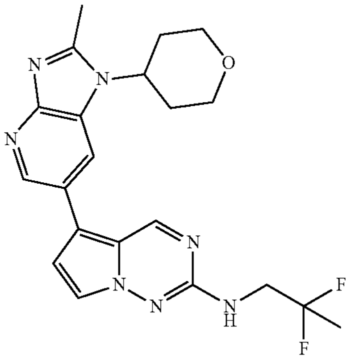 [SMILES: Cc1nc2ncc(-c3ccn4nc(NCC(C)(F)F)ncc34)cc2n1C1CCOCC1]
785
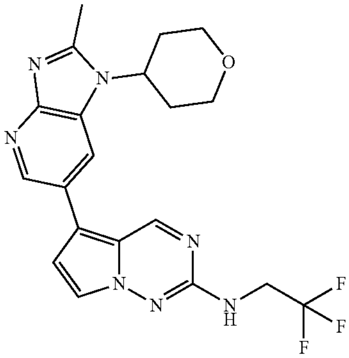 [SMILES: Cc1nc2ncc(-c3ccn4nc(NCC(F)(F)F)ncc34)cc2n1C1CCOCC1]
786

TABLE 1-continued
787
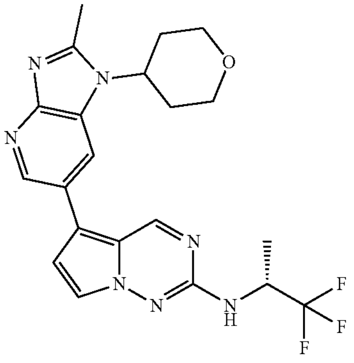 [SMILES: Cc1nc2ncc(-c3ccn4nc(N[C@H](C)C(F)(F)F)ncc34)cc2n1C1CCOCC1]
788
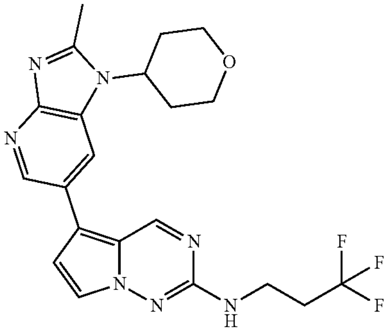 [SMILES: Cc1nc2ncc(-c3ccn4nc(NCCC(F)(F)F)ncc34)cc2n1C1CCOCC1]
789
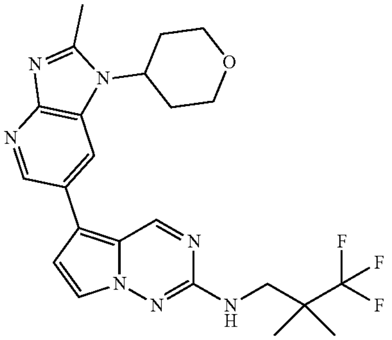 [SMILES: Cc1nc2ncc(-c3ccn4nc(NCC(C)(C)C(F)(F)F)ncc34)cc2n1C1CCOCC1]
790
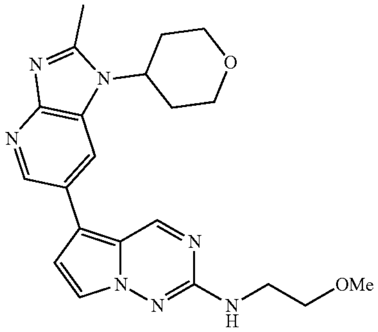 [SMILES: COCCNc1ncc2c(-c3cnc4nc(C)n(C5CCOCC5)c4c3)ccn2n1]

TABLE 1-continued
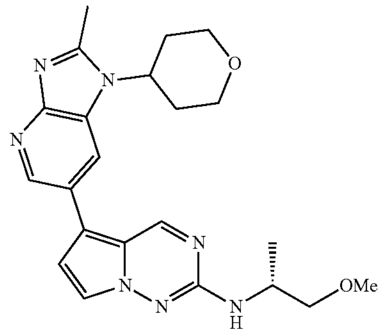 [SMILES: COC[C@@H](C)Nc1ncc2c(-c3cnc4nc(C)n(C5CCOCC5)c4c3)ccn2n1]
791
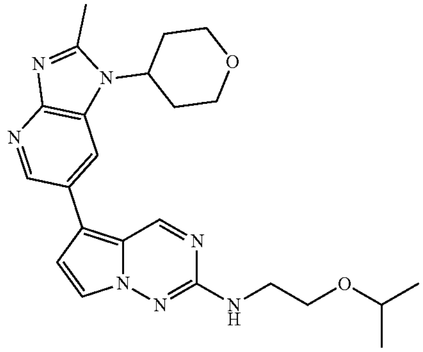 [SMILES: Cc1nc2ncc(-c3ccn4nc(NCCOC(C)C)ncc34)cc2n1C1CCOCC1]
792
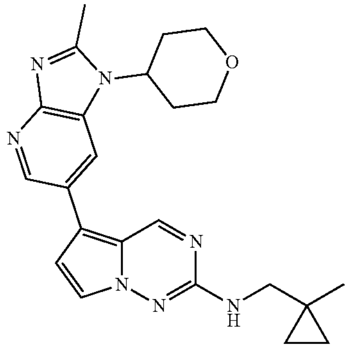 [SMILES: Cc1nc2ncc(-c3ccn4nc(NCC5(C)CC5)ncc34)cc2n1C1CCOCC1]
793
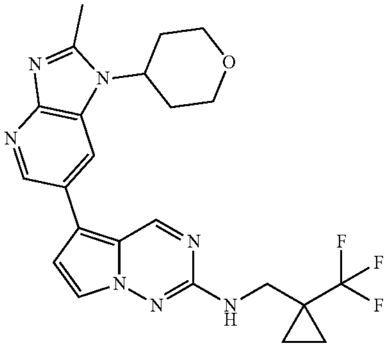 [SMILES: Cc1nc2ncc(-c3ccn4nc(NCC5(C(F)(F)F)CC5)ncc34)cc2n1C1CCOCC1]
794

TABLE 1-continued
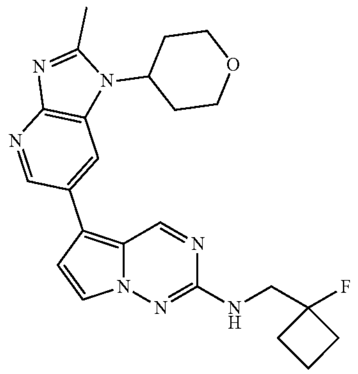 [SMILES: Cc1nc2ncc(-c3ccn4nc(NCC5(F)CCC5)ncc34)cc2n1C1CCOCC1]
795
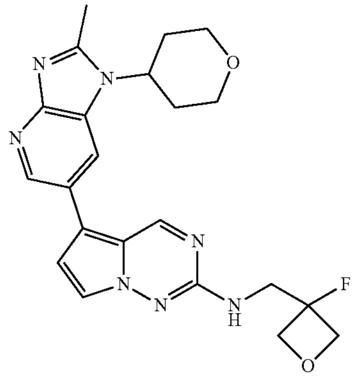 [SMILES: Cc1nc2ncc(-c3ccn4nc(NCC5(F)COC5)ncc34)cc2n1C1CCOCC1]
796
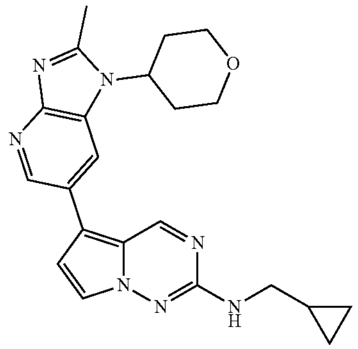 [SMILES: Cc1nc2ncc(-c3ccn4nc(NCC5CC5)ncc34)cc2n1C1CCOCC1]
797
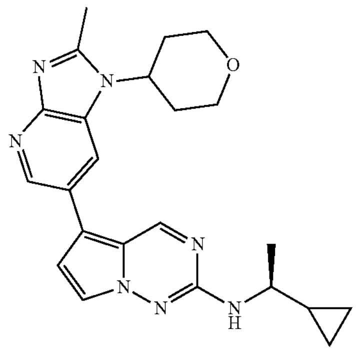 [SMILES: Cc1nc2ncc(-c3ccn4nc(N[C@@H](C)C5CC5)ncc34)cc2n1C1CCOCC1]
798

TABLE 1-continued
799
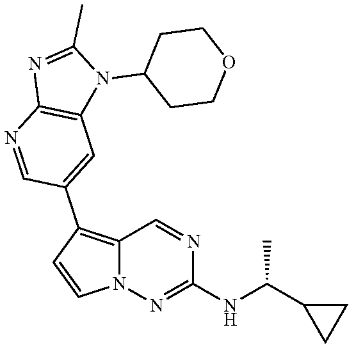 [SMILES: Cc1nc2ncc(-c3ccn4nc(N[C@H](C)C5CC5)ncc34)cc2n1C1CCOCC1]
800
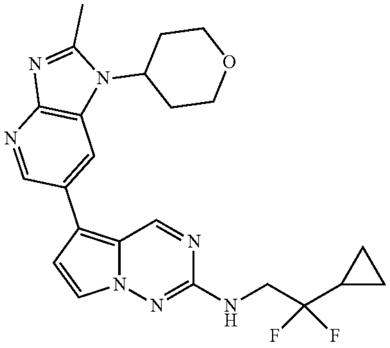 [SMILES: Cc1nc2ncc(-c3ccn4nc(NCC(F)(F)C5CC5)ncc34)cc2n1C1CCOCC1]
801
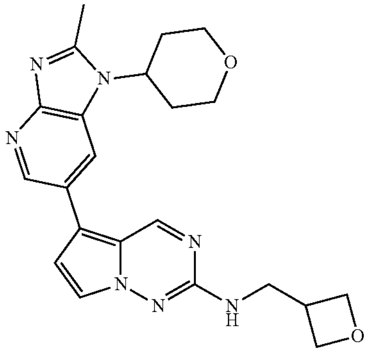 [SMILES: Cc1nc2ncc(-c3ccn4nc(NCC5COC5)ncc34)cc2n1C1CCOCC1]
802
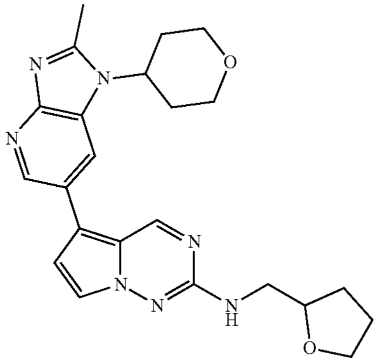 [SMILES: Cc1nc2ncc(-c3ccn4nc(NCC5CCCO5)ncc34)cc2n1C1CCOCC1]

TABLE 1-continued
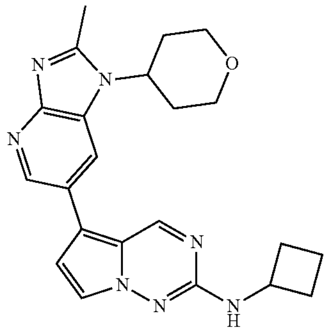 [SMILES: Cc1nc2ncc(-c3ccn4nc(NC5CCC5)ncc34)cc2n1C1CCOCC1]
803
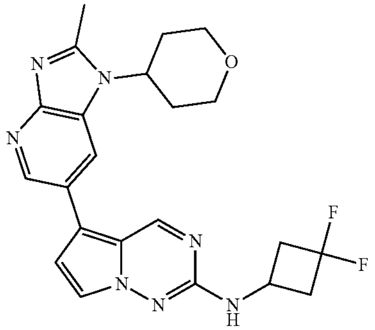 [SMILES: Cc1nc2ncc(-c3ccn4nc(NC5CC(F)(F)C5)ncc34)cc2n1C1CCOCC1]
804
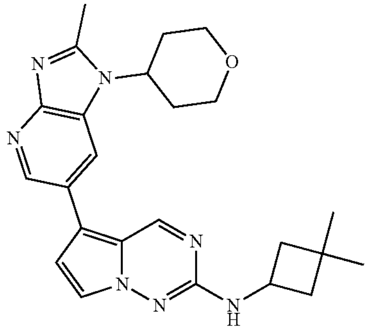 [SMILES: Cc1nc2ncc(-c3ccn4nc(NC5CC(C)(C)C5)ncc34)cc2n1C1CCOCC1]
805
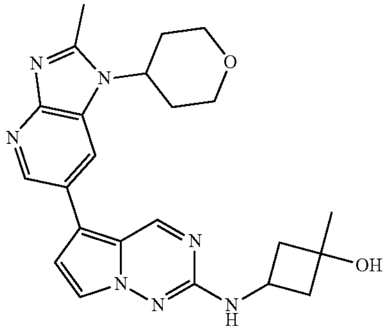 [SMILES: Cc1nc2ncc(-c3ccn4nc(NC5CC(C)(O)C5)ncc34)cc2n1C1CCOCC1]
806

TABLE 1-continued
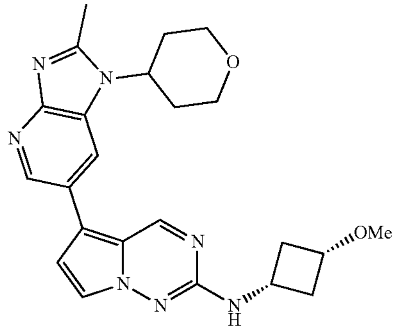 [SMILES: CO[C@H]1C[C@@H](Nc2ncc3c(-c4cnc5nc(C)n(C6CCOCC6)c5c4)ccn3n2)C1]
807
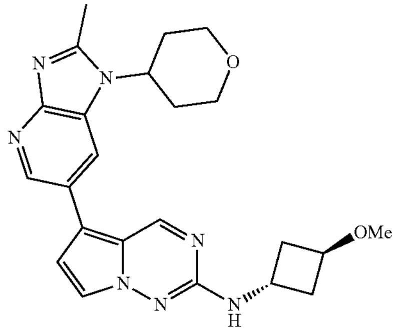 [SMILES: CO[C@H]1C[C@H](Nc2ncc3c(-c4cnc5nc(C)n(C6CCOCC6)c5c4)ccn3n2)C1]
808
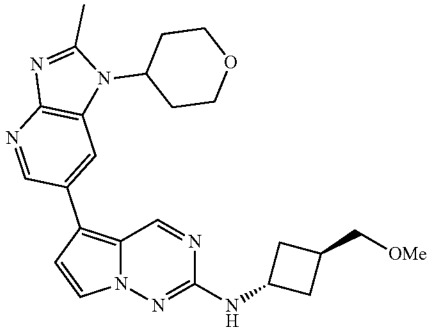 [SMILES: COC[C@H]1C[C@H](Nc2ncc3c(-c4cnc5nc(C)n(C6CCOCC6)c5c4)ccn3n2)C1]
809
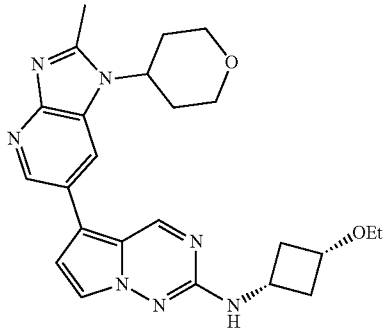 [SMILES: CCO[C@H]1C[C@@H](Nc2ncc3c(-c4cnc5nc(C)n(C6CCOCC6)c5c4)ccn3n2)C1]
810

TABLE 1-continued
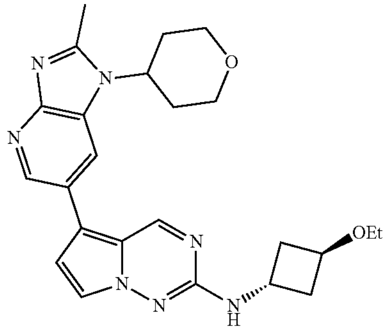 [SMILES: CCO[C@H]1C[C@H](Nc2ncc3c(-c4cnc5nc(C)n(C6CCOCC6)c5c4)ccn3n2)C1]
811
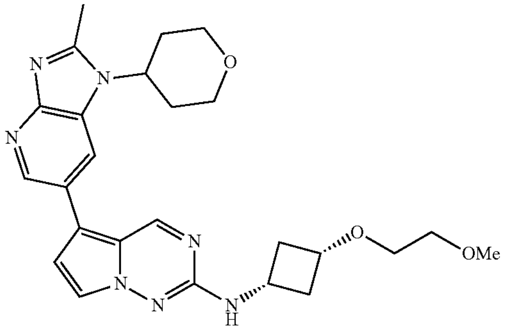 [SMILES: COCCO[C@H]1C[C@@H](Nc2ncc3c(-c4cnc5nc(C)n(C6CCOCC6)c5c4)ccn3n2)C1]
812
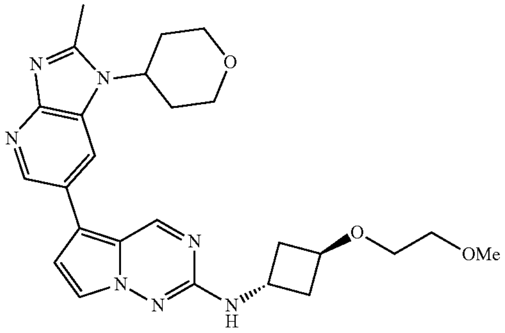 [SMILES: COCCO[C@H]1C[C@H](Nc2ncc3c(-c4cnc5nc(C)n(C6CCOCC6)c5c4)ccn3n2)C1]
813
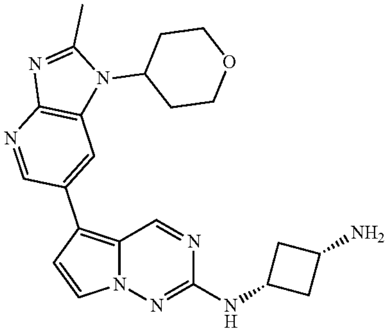 [SMILES: Cc1nc2ncc(-c3ccn4nc(N[C@H]5C[C@@H](N)C5)ncc34)cc2n1C1CCOCC1]
814

TABLE 1-continued
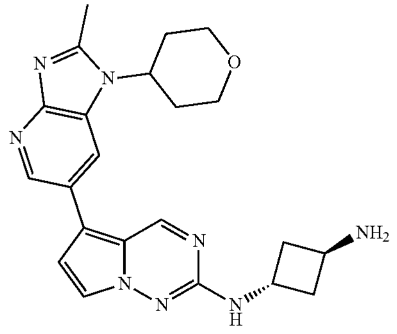 [SMILES: Cc1nc2ncc(-c3ccn4nc(N[C@H]5C[C@H](N)C5)ncc34)cc2n1C1CCOCC1]
815
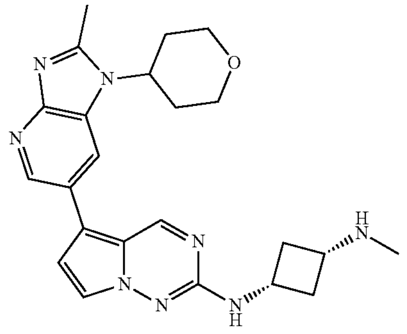 [SMILES: CN[C@H]1C[C@@H](Nc2ncc3c(-c4cnc5nc(C)n(C6CCOCC6)c5c4)ccn3n2)C1]
816
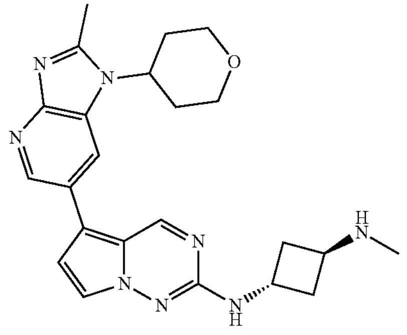 [SMILES: CN[C@H]1C[C@H](Nc2ncc3c(-c4cnc5nc(C)n(C6CCOCC6)c5c4)ccn3n2)C1]
817
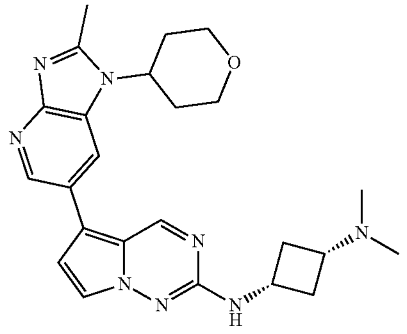 [SMILES: Cc1nc2ncc(-c3ccn4nc(N[C@H]5C[C@@H](N(C)C)C5)ncc34)cc2n1C1CCOCC1]
818

TABLE 1-continued
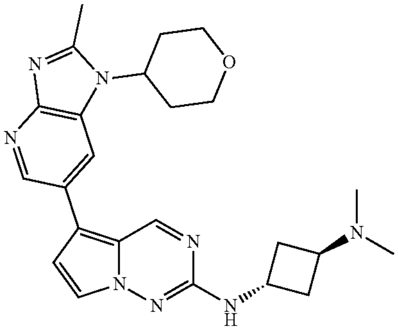 [SMILES: Cc1nc2ncc(-c3ccn4nc(N[C@H]5C[C@H](N(C)C)C5)ncc34)cc2n1C1CCOCC1]
819
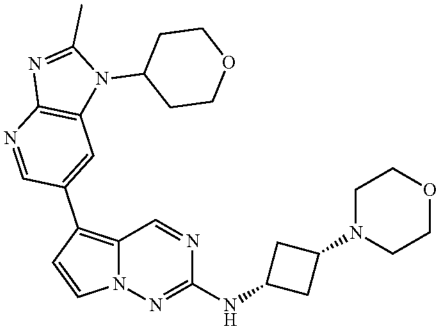 [SMILES: Cc1nc2ncc(-c3ccn4nc(N[C@H]5C[C@@H](N6CCOCC6)C5)ncc34)cc2n1C1CCOCC1]
820
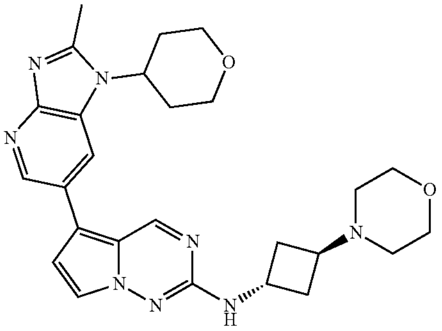 [SMILES: Cc1nc2ncc(-c3ccn4nc(N[C@H]5C[C@H](N6CCOCC6)C5)ncc34)cc2n1C1CCOCC1]
821
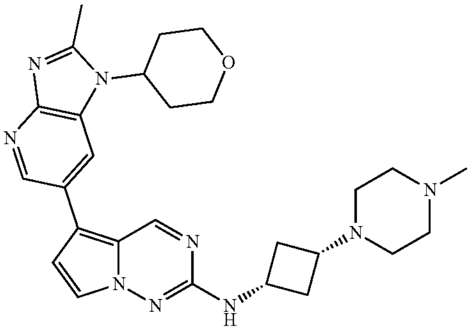 [SMILES: Cc1nc2ncc(-c3ccn4nc(N[C@H]5C[C@@H](N6CCN(C)CC6)C5)ncc34)cc2n1C1CCOCC1]
822

TABLE 1-continued
823
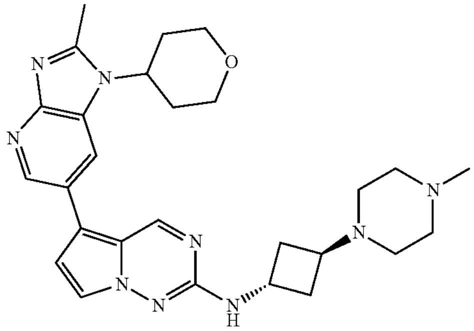 [SMILES: Cc1nc2ncc(-c3ccn4nc(N[C@H]5C[C@H](N6CCN(C)CC6)C5)ncc34)cc2n1C1CCOCC1]
824
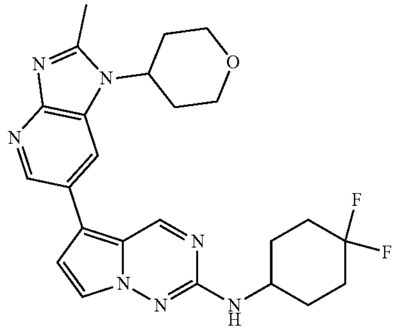 [SMILES: Cc1nc2ncc(-c3ccn4nc(NC5CCC(F)(F)CC5)ncc34)cc2n1C1CCOCC1]
825
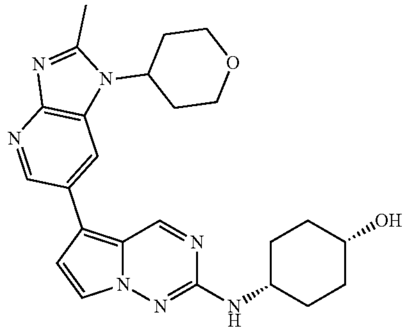 [SMILES: Cc1nc2ncc(-c3ccn4nc(N[C@H]5CC[C@@H](O)CC5)ncc34)cc2n1C1CCOCC1]
lp;2p
826
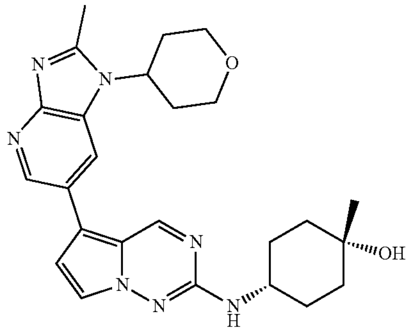 [SMILES: Cc1nc2ncc(-c3ccn4nc(N[C@H]5CC[C@@](C)(O)CC5)ncc34)cc2n1C1CCOCC1]

TABLE 1-continued
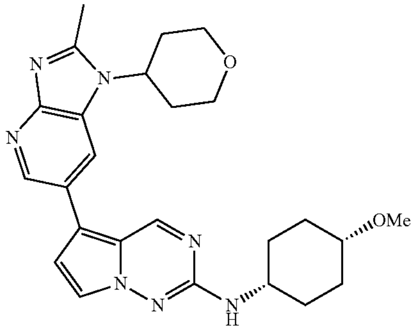 [SMILES: CO[C@H]1CC[C@@H](Nc2ncc3c(-c4cnc5nc(C)n(C6CCOCC6)c5c4)ccn3n2)CC1]
827
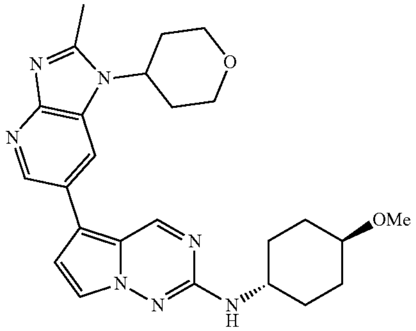 [SMILES: CO[C@H]1CC[C@H](Nc2ncc3c(-c4cnc5nc(C)n(C6CCOCC6)c5c4)ccn3n2)CC1]
828
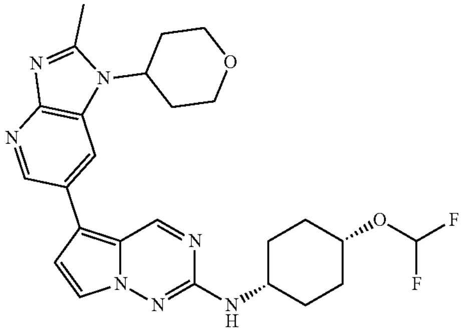 [SMILES: Cc1nc2ncc(-c3ccn4nc(N[C@H]5CC[C@@H](OC(F)F)CC5)ncc34)cc2n1C1CCOCC1]
829
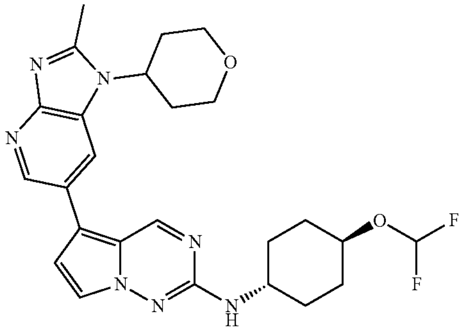 [SMILES: Cc1nc2ncc(-c3ccn4nc(N[C@H]5CC[C@H](OC(F)F)CC5)ncc34)cc2n1C1CCOCC1]
830

TABLE 1-continued
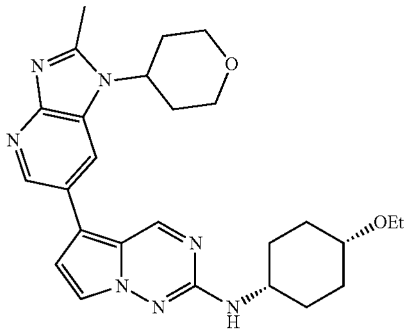 [SMILES: CCO[C@H]1CC[C@@H](Nc2ncc3c(-c4cnc5nc(C)n(C6CCOCC6)c5c4)ccn3n2)CC1]
831
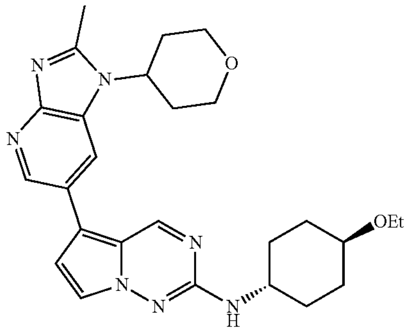 [SMILES: CCO[C@H]1CC[C@H](Nc2ncc3c(-c4cnc5nc(C)n(C6CCOCC6)c5c4)ccn3n2)CC1]
832
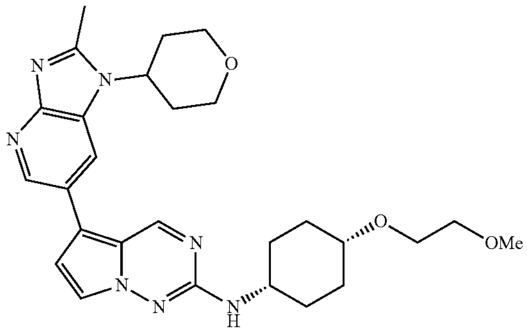 [SMILES: COCCO[C@H]1CC[C@@H](Nc2ncc3c(-c4cnc5nc(C)n(C6CCOCC6)c5c4)ccn3n2)CC1]
833
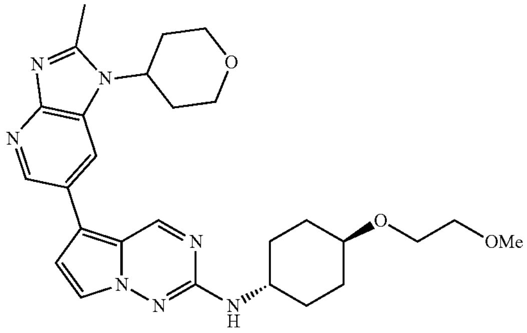 [SMILES: COCCO[C@H]1CC[C@H](Nc2ncc3c(-c4cnc5nc(C)n(C6CCOCC6)c5c4)ccn3n2)CC1]
834

TABLE 1-continued
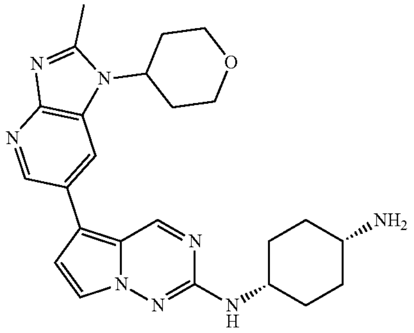 [SMILES: Cc1nc2ncc(-c3ccn4nc(N[C@H]5CC[C@@H](N)CC5)ncc34)cc2n1C1CCOCC1]
835
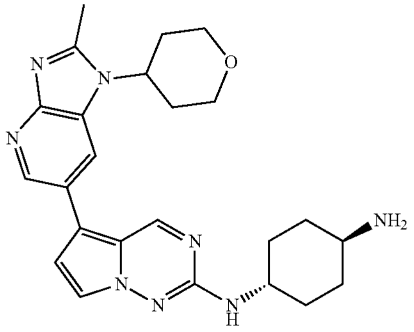 [SMILES: Cc1nc2ncc(-c3ccn4nc(N[C@H]5CC[C@H](N)CC5)ncc34)cc2n1C1CCOCC1]
836
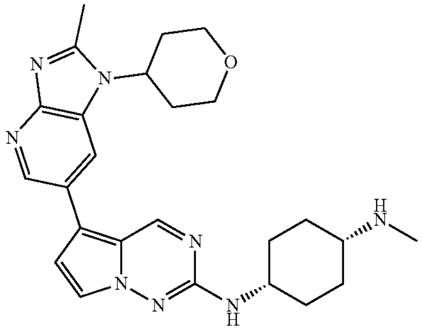 [SMILES: CN[C@H]1CC[C@@H](Nc2ncc3c(-c4cnc5nc(C)n(C6CCOCC6)c5c4)ccn3n2)CC1]
837
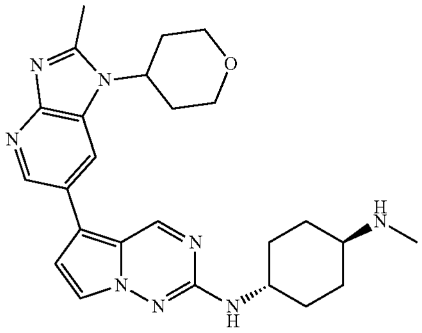 [SMILES: CN[C@H]1CC[C@H](Nc2ncc3c(-c4cnc5nc(C)n(C6CCOCC6)c5c4)ccn3n2)CC1]
838

TABLE 1-continued
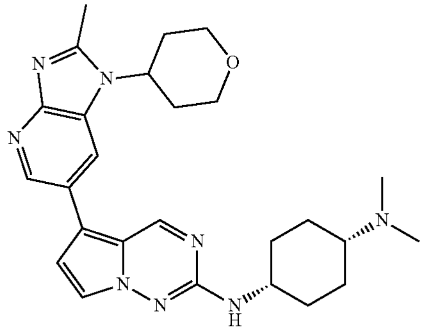 [SMILES: Cc1nc2ncc(-c3ccn4nc(N[C@H]5CC[C@@H](N(C)C)CC5)ncc34)cc2n1C1CCOCC1]
839
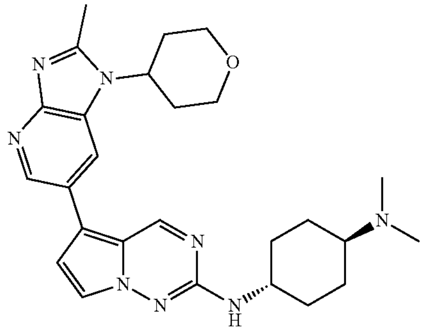 [SMILES: Cc1nc2ncc(-c3ccn4nc(N[C@H]5CC[C@H](N(C)C)CC5)ncc34)cc2n1C1CCOCC1]
840
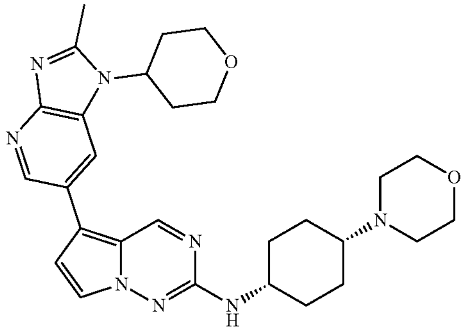 [SMILES: Cc1nc2ncc(-c3ccn4nc(N[C@H]5CC[C@@H](N6CCOCC6)CC5)ncc34)cc2n1C1CCOCC1]
841
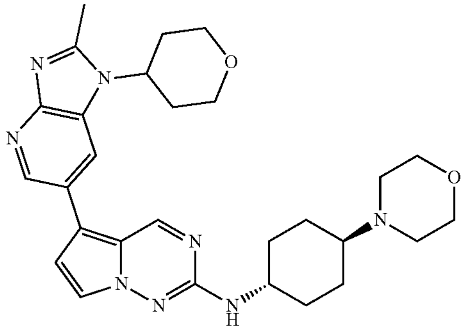 [SMILES: Cc1nc2ncc(-c3ccn4nc(N[C@H]5CC[C@H](N6CCOCC6)CC5)ncc34)cc2n1C1CCOCC1]
842

TABLE 1-continued
843
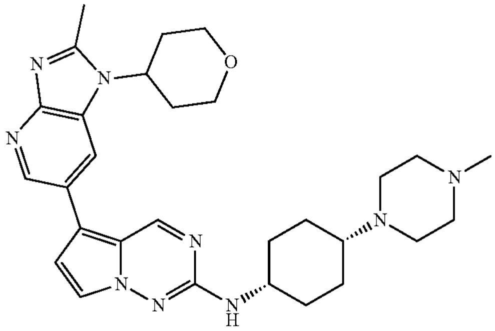 [SMILES: Cc1nc2ncc(-c3ccn4nc(N[C@H]5CC[C@@H](N6CCN(C)CC6)CC5)ncc34)cc2n1C1CCOCC1]
844
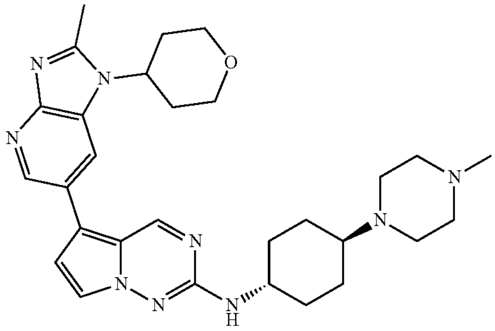 [SMILES: Cc1nc2ncc(-c3ccn4nc(N[C@H]5CC[C@H](N6CCN(C)CC6)CC5)ncc34)cc2n1C1CCOCC1]
845
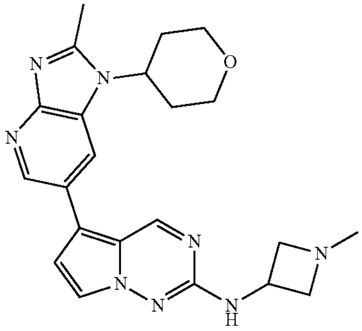 [SMILES: Cc1nc2ncc(-c3ccn4nc(NC5CN(C)C5)ncc34)cc2n1C1CCOCC1]
846
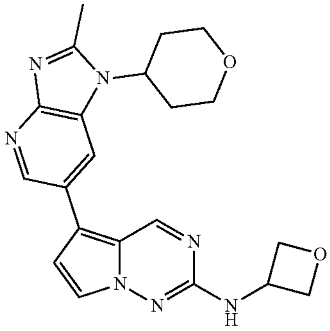 [SMILES: Cc1nc2ncc(-c3ccn4nc(NC5COC5)ncc34)cc2n1C1CCOCC1]

TABLE 1-continued
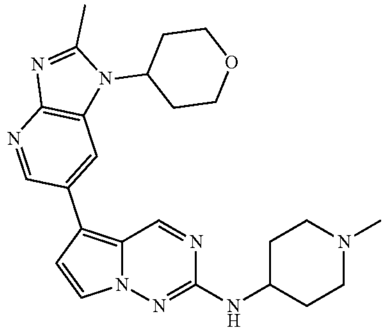 [SMILES: Cc1nc2ncc(-c3ccn4nc(NC5CCN(C)CC5)ncc34)cc2n1C1CCOCC1]
847
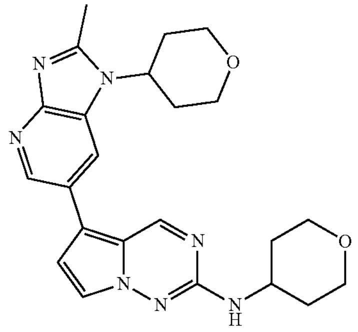 [SMILES: Cc1nc2ncc(-c3ccn4nc(NC5CCOCC5)ncc34)cc2n1C1CCOCC1]
848
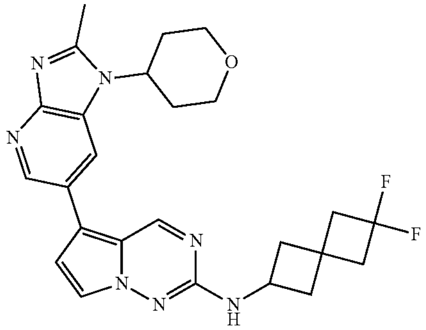 [SMILES: Cc1nc2ncc(-c3ccn4nc(NC5CC6(C5)CC(F)(F)C6)ncc34)cc2n1C1CCOCC1]
849
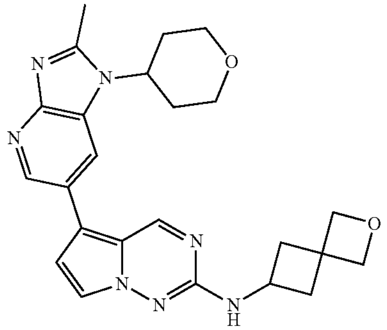 [SMILES: Cc1nc2ncc(-c3ccn4nc(NC5CC6(COC6)C5)ncc34)cc2n1C1CCOCC1]
850

TABLE 1-continued
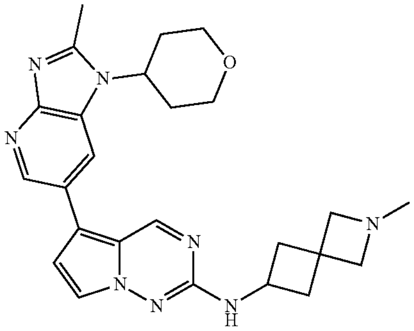 [SMILES: Cc1nc2ncc(-c3ccn4nc(NC5CC6(C5)CN(C)C6)ncc34)cc2n1C1CCOCC1]
851
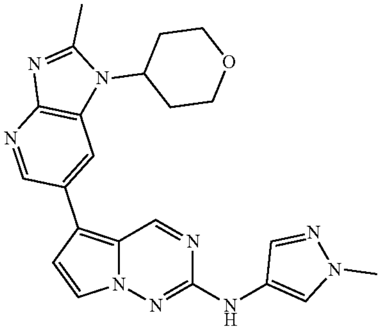 [SMILES: Cc1nc2ncc(-c3ccn4nc(Nc5cnn(C)c5)ncc34)cc2n1C1CCOCC1]
852
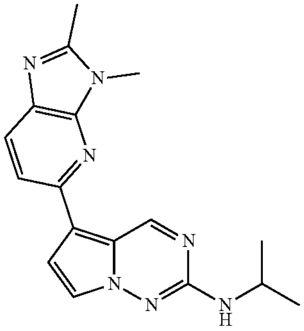 [SMILES: Cc1nc2ccc(-c3ccn4nc(NC(C)C)ncc34)nc2n1C]
853
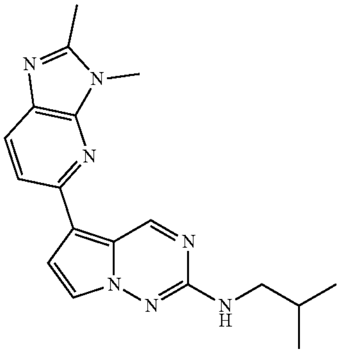 [SMILES: Cc1nc2ccc(-c3ccn4nc(NCC(C)C)ncc34)nc2n1C]
854

TABLE 1-continued
855
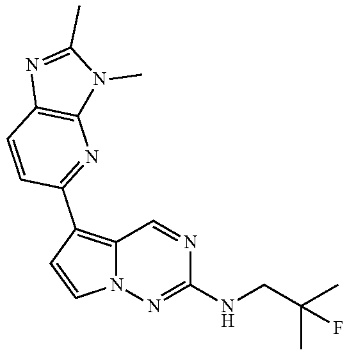 [SMILES: Cc1nc2ccc(-c3ccn4nc(NCC(C)(C)F)ncc34)nc2n1C]
856
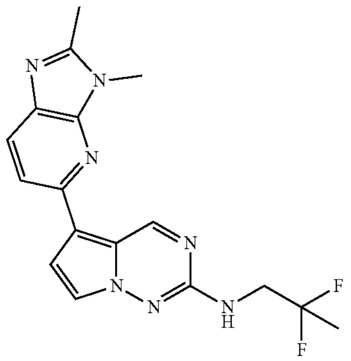 [SMILES: Cc1nc2ccc(-c3ccn4nc(NCC(C)(F)F)ncc34)nc2n1C]
857
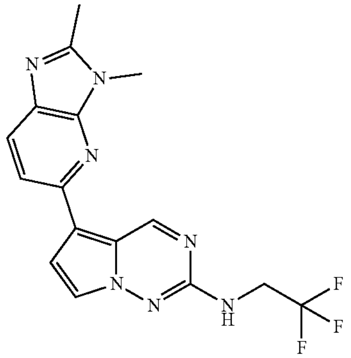 [SMILES: Cc1nc2ccc(-c3ccn4nc(NCC(F)(F)F)ncc34)nc2n1C]
858
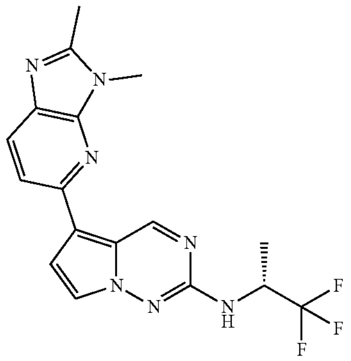 [SMILES: Cc1nc2ccc(-c3ccn4nc(N[C@H](C)C(F)(F)F)ncc34)nc2n1C]

TABLE 1-continued
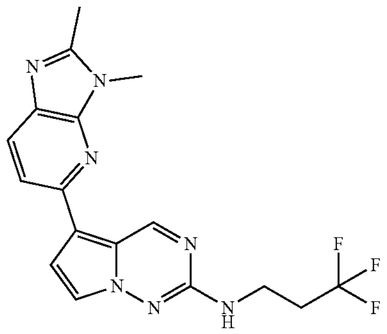 [SMILES: Cc1nc2ccc(-c3ccn4nc(NCCC(F)(F)F)ncc34)nc2n1C]
859
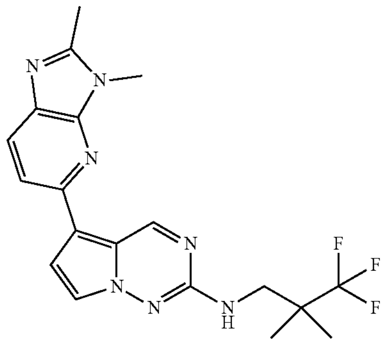 [SMILES: Cc1nc2ccc(-c3ccn4nc(NCC(C)(C)C(F)(F)F)ncc34)nc2n1C]
860
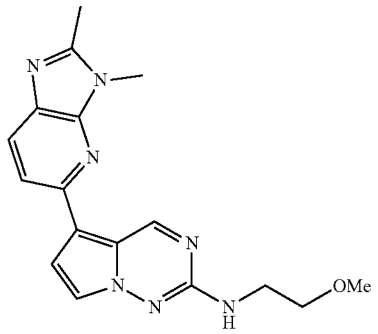 [SMILES: COCCNc1ncc2c(-c3ccc4nc(C)n(C)c4n3)ccn2n1]
861
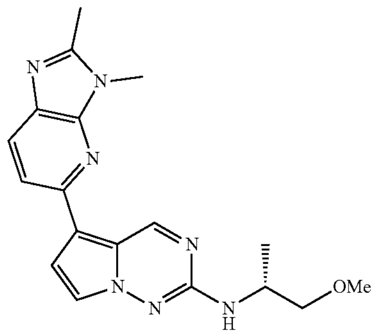 [SMILES: COC[C@@H](C)Nc1ncc2c(-c3ccc4nc(C)n(C)c4n3)ccn2n1]
862

TABLE 1-continued
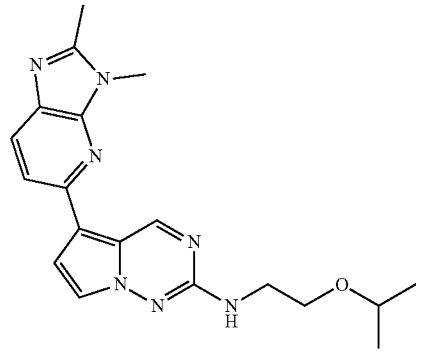 [SMILES: Cc1nc2ccc(-c3ccn4nc(NCCOC(C)C)ncc34)nc2n1C]
863
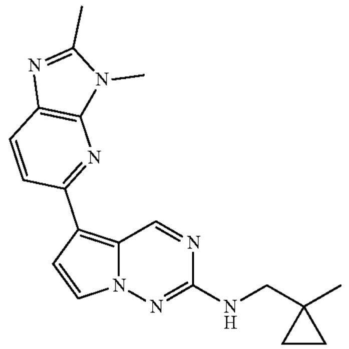 [SMILES: Cc1nc2ccc(-c3ccn4nc(NCC5(C)CC5)ncc34)nc2n1C]
864
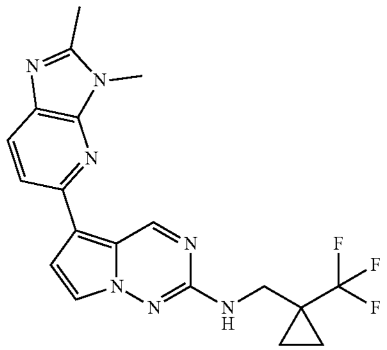 [SMILES: Cc1nc2ccc(-c3ccn4nc(NCC5(C(F)(F)F)CC5)ncc34)nc2n1C]
865
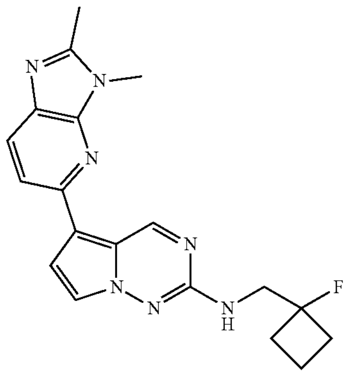 [SMILES: Cc1nc2ccc(-c3ccn4nc(NCC5(F)CCC5)ncc34)nc2n1C]
866

TABLE 1-continued
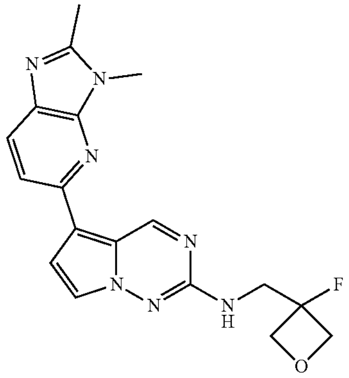 [SMILES: Cc1nc2ccc(-c3ccn4nc(NCC5(F)COC5)ncc34)nc2n1C]
867
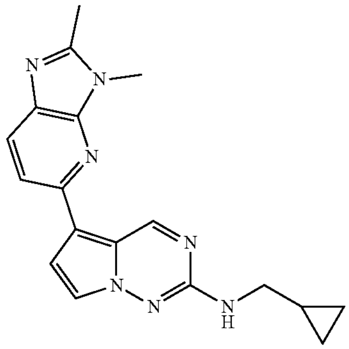 [SMILES: Cc1nc2ccc(-c3ccn4nc(NCC5CC5)ncc34)nc2n1C]
868
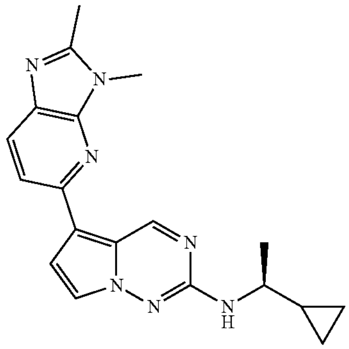 [SMILES: Cc1nc2ccc(-c3ccn4nc(N[C@@H](C)C5CC5)ncc34)nc2n1C]
869
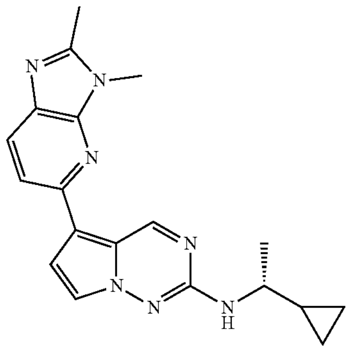 [SMILES: Cc1nc2ccc(-c3ccn4nc(N[C@H](C)C5CC5)ncc34)nc2n1C]
870

TABLE 1-continued
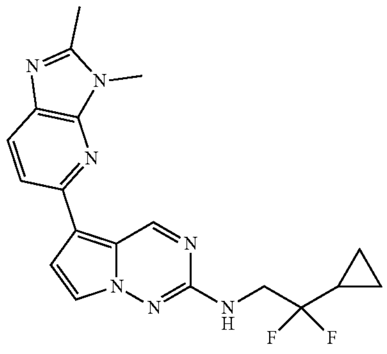 [SMILES: Cc1nc2ccc(-c3ccn4nc(NCC(F)(F)C5CC5)ncc34)nc2n1C]
871
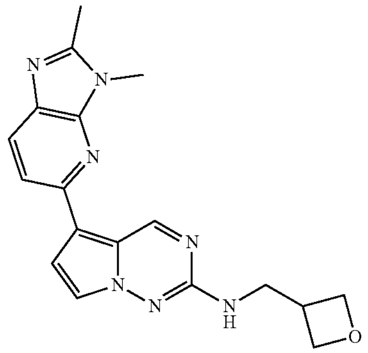 [SMILES: Cc1nc2ccc(-c3ccn4nc(NCC5COC5)ncc34)nc2n1C]
872
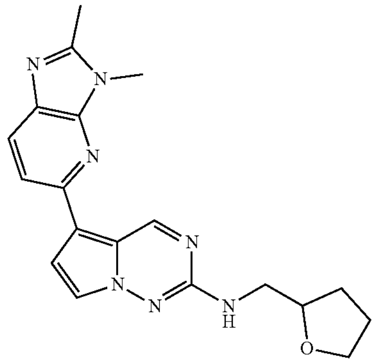 [SMILES: Cc1nc2ccc(-c3ccn4nc(NCC5CCCO5)ncc34)nc2n1C]
873
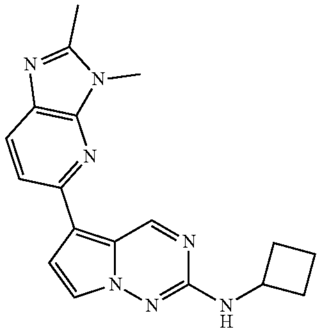 [SMILES: Cc1nc2ccc(-c3ccn4nc(NC5CCC5)ncc34)nc2n1C]
874

TABLE 1-continued
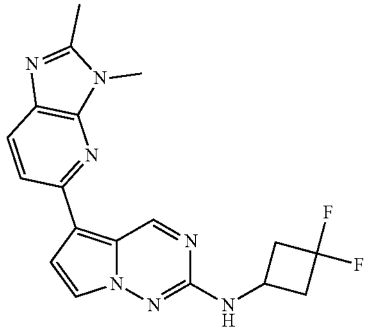 [SMILES: Cc1nc2ccc(-c3ccn4nc(NC5CC(F)(F)C5)ncc34)nc2n1C]
875
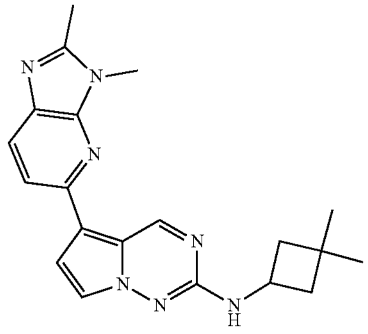 [SMILES: Cc1nc2ccc(-c3ccn4nc(NC5CC(C)(C)C5)ncc34)nc2n1C]
876
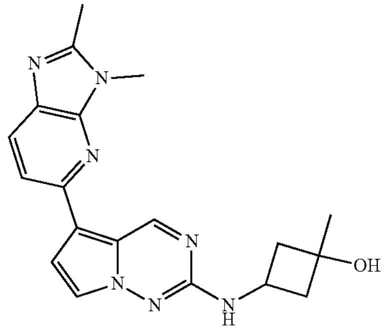 [SMILES: Cc1nc2ccc(-c3ccn4nc(NC5CC(C)(O)C5)ncc34)nc2n1C]
877
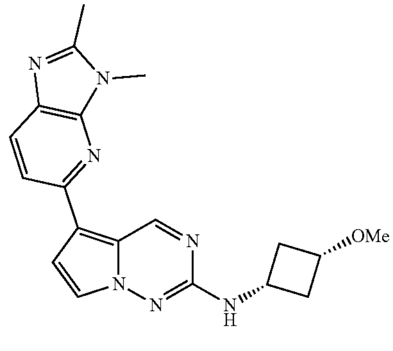 [SMILES: CO[C@H]1C[C@@H](Nc2ncc3c(-c4ccc5nc(C)n(C)c5n4)ccn3n2)C1]
878

TABLE 1-continued
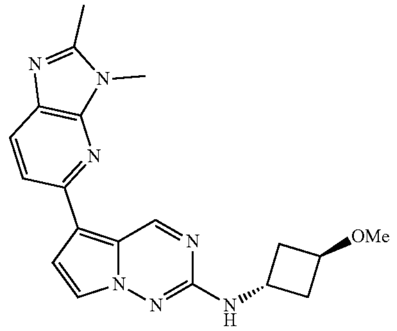 [SMILES: CO[C@H]1C[C@H](Nc2ncc3c(-c4ccc5nc(C)n(C)c5n4)ccn3n2)C1]
879
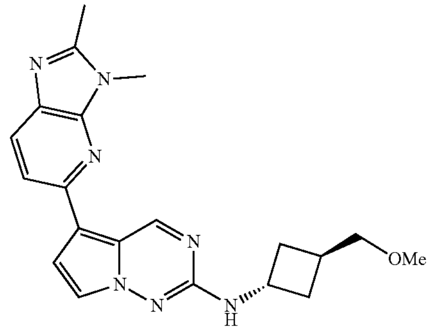 [SMILES: COC[C@H]1C[C@H](Nc2ncc3c(-c4ccc5nc(C)n(C)c5n4)ccn3n2)C1]
880
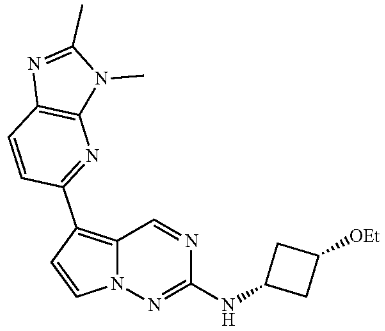 [SMILES: CCO[C@H]1C[C@@H](Nc2ncc3c(-c4ccc5nc(C)n(C)c5n4)ccn3n2)C1]
881
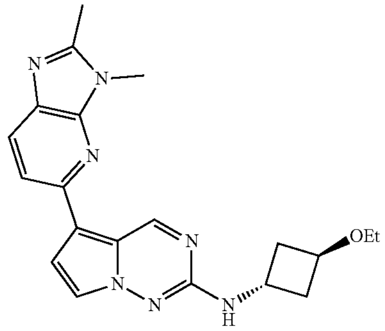 [SMILES: CCO[C@H]1C[C@H](Nc2ncc3c(-c4ccc5nc(C)n(C)c5n4)ccn3n2)C1]
882

TABLE 1-continued
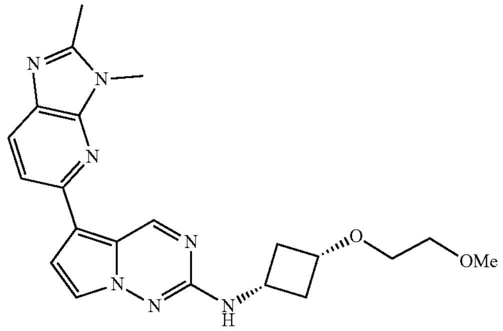 [SMILES: COCCO[C@H]1C[C@@H](Nc2ncc3c(-c4ccc5nc(C)n(C)c5n4)ccn3n2)C1]
883
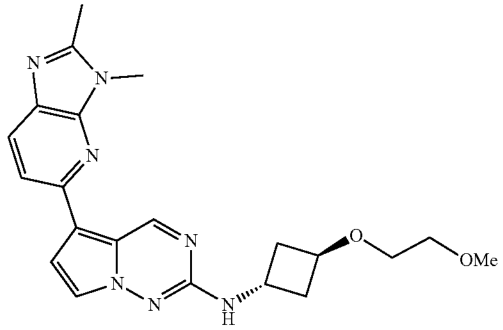 [SMILES: COCCO[C@H]1C[C@H](Nc2ncc3c(-c4ccc5nc(C)n(C)c5n4)ccn3n2)C1]
884
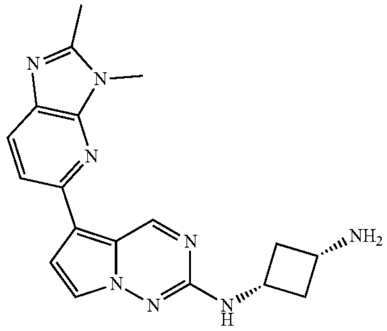 [SMILES: Cc1nc2ccc(-c3ccn4nc(N[C@H]5C[C@@H](N)C5)ncc34)nc2n1C]
885
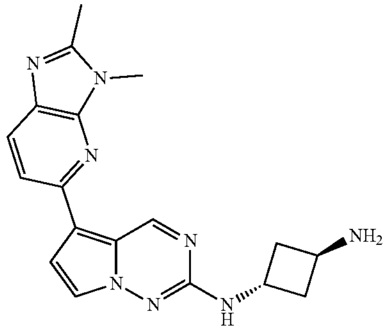 [SMILES: Cc1nc2ccc(-c3ccn4nc(N[C@H]5C[C@H](N)C5)ncc34)nc2n1C]
886

TABLE 1-continued
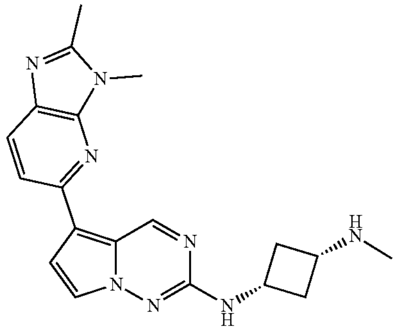 [SMILES: CN[C@H]1C[C@@H](Nc2ncc3c(-c4ccc5nc(C)n(C)c5n4)ccn3n2)C1]
887
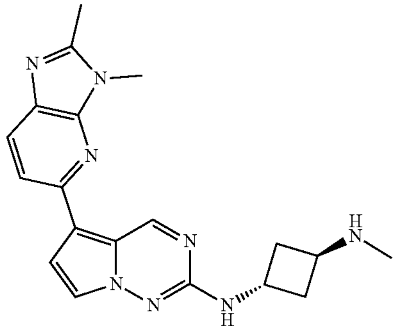 [SMILES: CN[C@H]1C[C@H](Nc2ncc3c(-c4ccc5nc(C)n(C)c5n4)ccn3n2)C1]
888
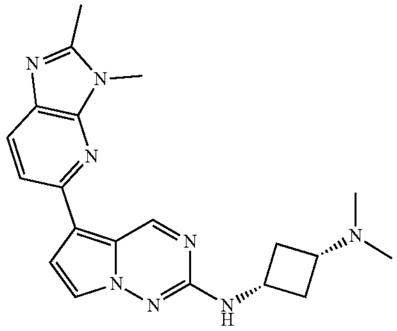 [SMILES: Cc1nc2ccc(-c3ccn4nc(N[C@H]5C[C@@H](N(C)C)C5)ncc34)nc2n1C]
889
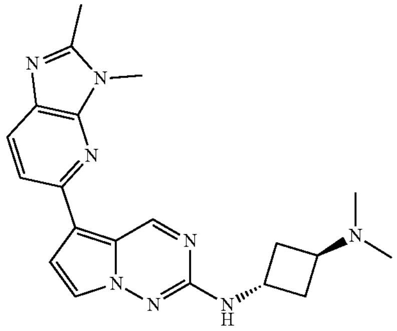 [SMILES: Cc1nc2ccc(-c3ccn4nc(N[C@H]5C[C@H](N(C)C)C5)ncc34)nc2n1C]
890

TABLE 1-continued
891
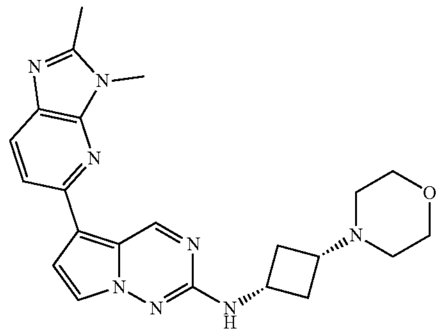 [SMILES: Cc1nc2ccc(-c3ccn4nc(N[C@H]5C[C@@H](N6CCOCC6)C5)ncc34)nc2n1C]
892
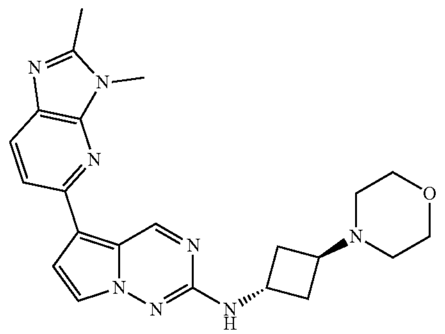 [SMILES: Cc1nc2ccc(-c3ccn4nc(N[C@H]5C[C@H](N6CCOCC6)C5)ncc34)nc2n1C]
893
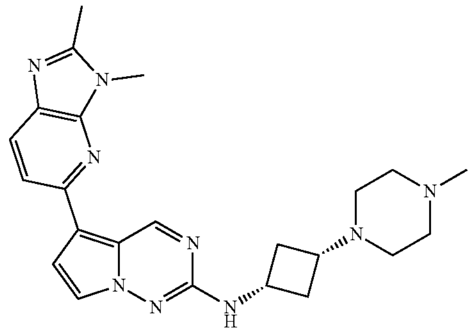 [SMILES: Cc1nc2ccc(-c3ccn4nc(N[C@H]5C[C@@H](N6CCN(C)CC6)C5)ncc34)nc2n1C]
894
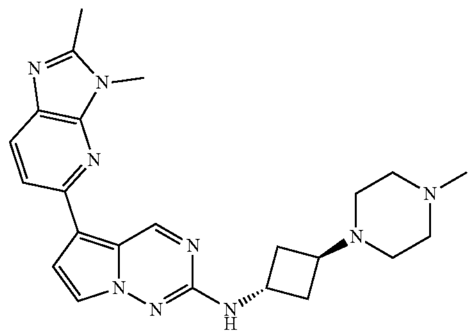 [SMILES: Cc1nc2ccc(-c3ccn4nc(N[C@H]5C[C@H](N6CCN(C)CC6)C5)ncc34)nc2n1C]

TABLE 1-continued
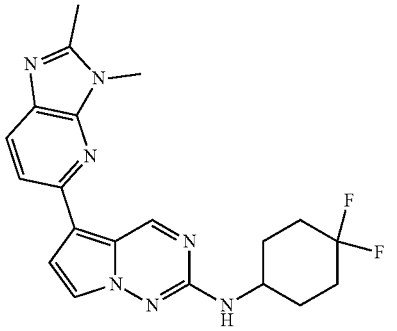 [SMILES: Cc1nc2ccc(-c3ccn4nc(NC5CCC(F)(F)CC5)ncc34)nc2n1C]
895
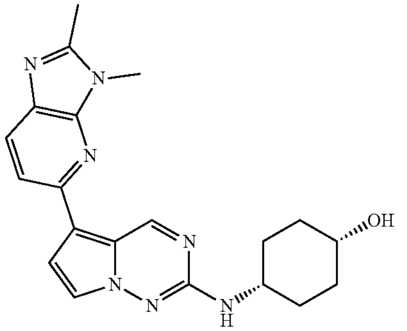 [SMILES: Cc1nc2ccc(-c3ccn4nc(N[C@H]5CC[C@@H](O)CC5)ncc34)nc2n1C]
896
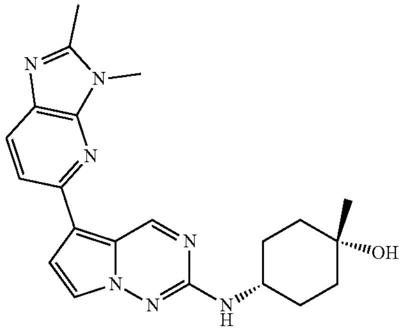 [SMILES: Cc1nc2ccc(-c3ccn4nc(N[C@H]5CC[C@@](C)(O)CC5)ncc34)nc2n1C]
897
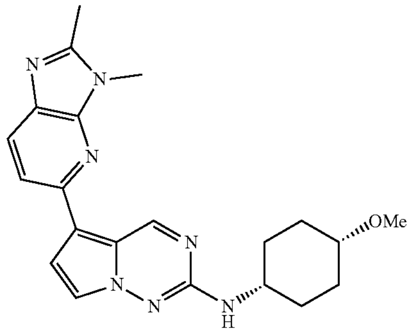 [SMILES: CO[C@H]1CC[C@@H](Nc2ncc3c(-c4ccc5nc(C)n(C)c5n4)ccn3n2)CC1]
898

TABLE 1-continued
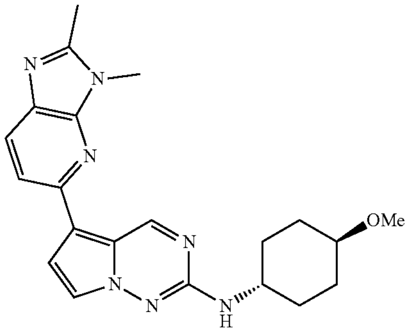 [SMILES: CO[C@H]1CC[C@H](Nc2ncc3c(-c4ccc5nc(C)n(C)c5n4)ccn3n2)CC1]
899
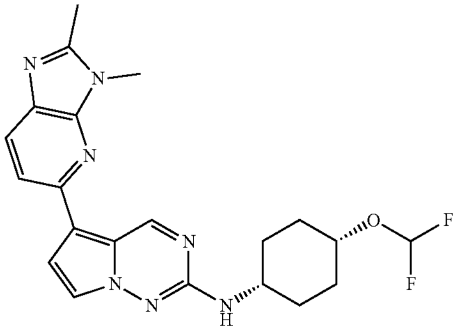 [SMILES: Cc1nc2ccc(-c3ccn4nc(N[C@H]5CC[C@@H](OC(F)F)CC5)ncc34)nc2n1C]
900
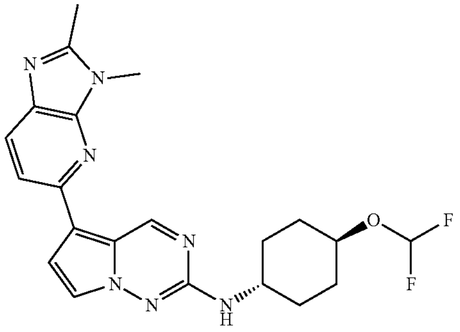 [SMILES: Cc1nc2ccc(-c3ccn4nc(N[C@H]5CC[C@H](OC(F)F)CC5)ncc34)nc2n1C]
901
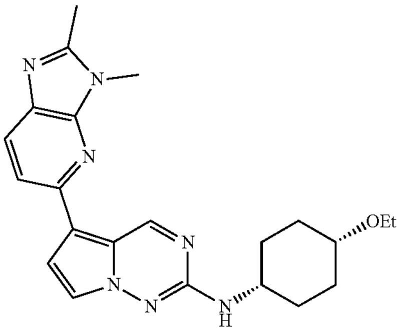 [SMILES: CCO[C@H]1CC[C@@H](Nc2ncc3c(-c4ccc5nc(C)n(C)c5n4)ccn3n2)CC1]
902

TABLE 1-continued
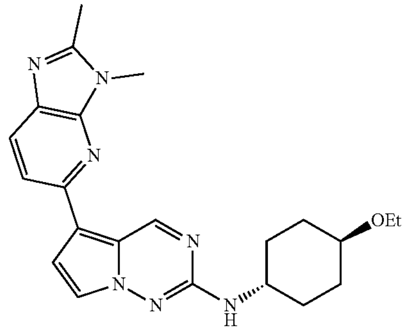 [SMILES: CCO[C@H]1CC[C@H](Nc2ncc3c(-c4ccc5nc(C)n(C)c5n4)ccn3n2)CC1]
903
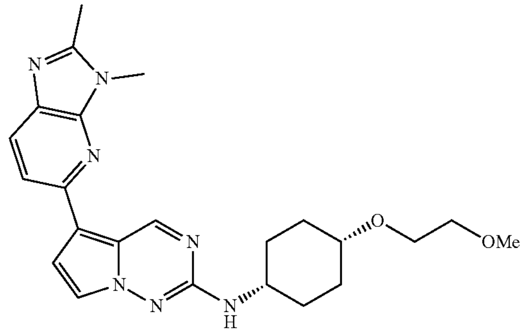 [SMILES: COCCO[C@H]1CC[C@@H](Nc2ncc3c(-c4ccc5nc(C)n(C)c5n4)ccn3n2)CC1]
904
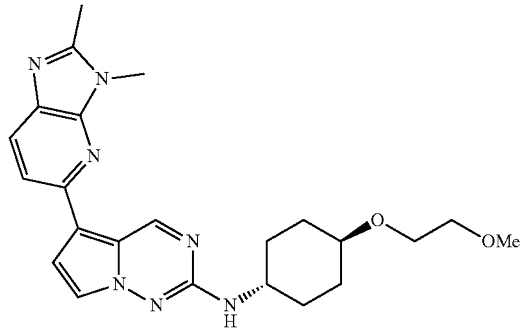
905
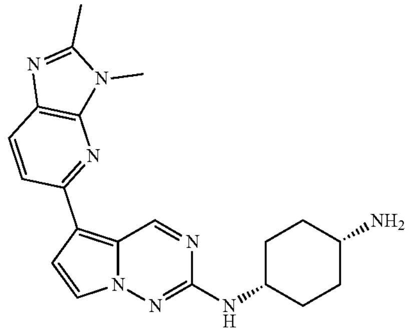 [SMILES: Cc1nc2ccc(-c3ccn4nc(N[C@H]5CC[C@@H](N)CC5)ncc34)nc2n1C]
906

TABLE 1-continued
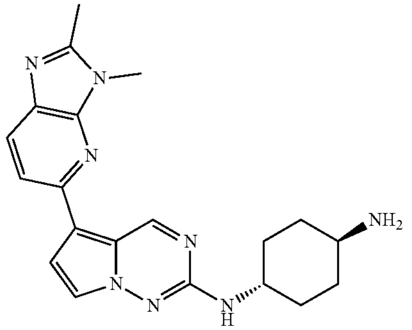 [SMILES: Cc1nc2ccc(-c3ccn4nc(N[C@H]5CC[C@H](N)CC5)ncc34)nc2n1C]
907
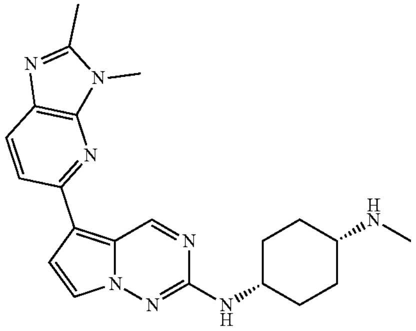 [SMILES: CN[C@H]1CC[C@@H](Nc2ncc3c(-c4ccc5nc(C)n(C)c5n4)ccn3n2)CC1]
908
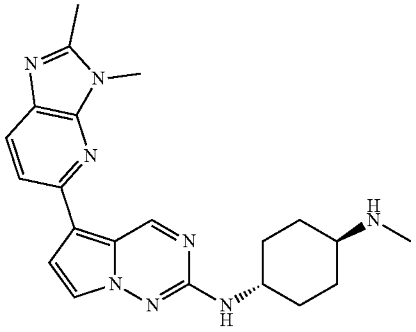 [SMILES: CN[C@H]1CC[C@H](Nc2ncc3c(-c4ccc5nc(C)n(C)c5n4)ccn3n2)CC1]
909
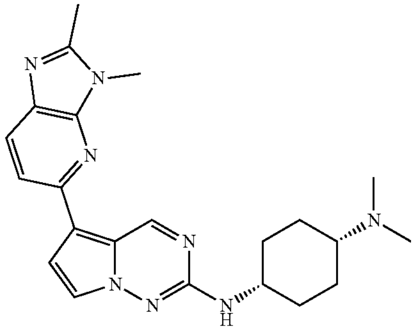 [SMILES: Cc1nc2ccc(-c3ccn4nc(N[C@H]5CC[C@@H](N(C)C)CC5)ncc34)nc2n1C]
910

TABLE 1-continued
911
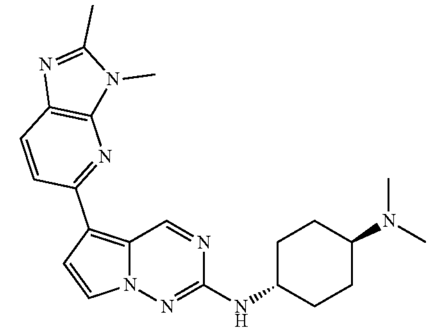 [SMILES: Cc1nc2ccc(-c3ccn4nc(N[C@H]5CC[C@H](N(C)C)CC5)ncc34)nc2n1C]
912
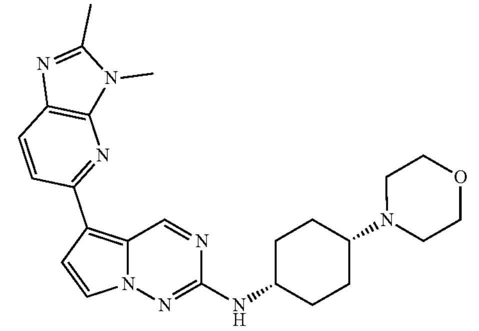 [SMILES: Cc1nc2ccc(-c3ccn4nc(N[C@H]5CC[C@@H](N6CCOCC6)CC5)ncc34)nc2n1C]
913
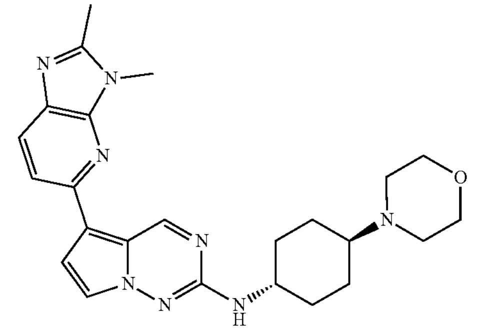 [SMILES: Cc1nc2ccc(-c3ccn4nc(N[C@H]5CC[C@H](N6CCOCC6)CC5)ncc34)nc2n1C]
914
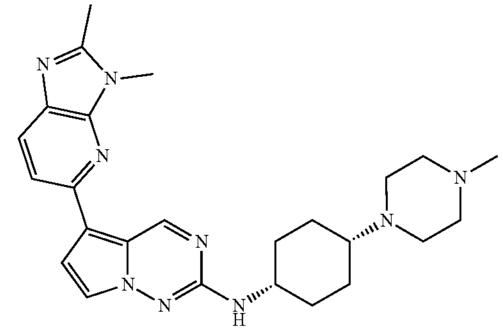 [SMILES: Cc1nc2ccc(-c3ccn4nc(N[C@H]5CC[C@@H](N6CCN(C)CC6)CC5)ncc34)nc2n1C]

TABLE 1-continued
915
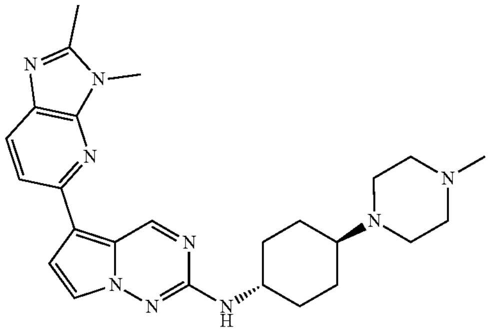 [SMILES: Cc1nc2ccc(-c3ccn4nc(N[C@H]5CC[C@H](N6CCN(C)CC6)CC5)ncc34)nc2n1C]
916
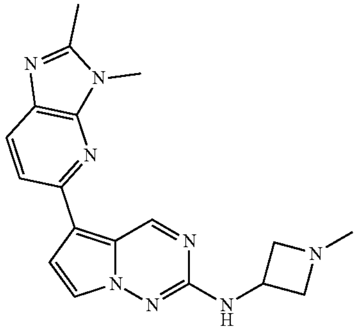 [SMILES: Cc1nc2ccc(-c3ccn4nc(NC5CN(C)C5)ncc34)nc2n1C]
917
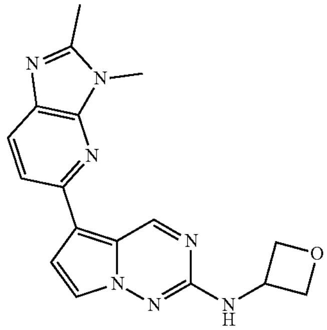 [SMILES: Cc1nc2ccc(-c3ccn4nc(NC5COC5)ncc34)nc2n1C]
918
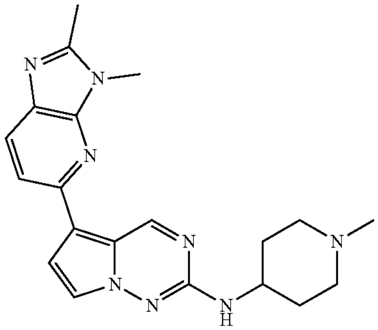 [SMILES: Cc1nc2ccc(-c3ccn4nc(NC5CCN(C)CC5)ncc34)nc2n1C]

TABLE 1-continued
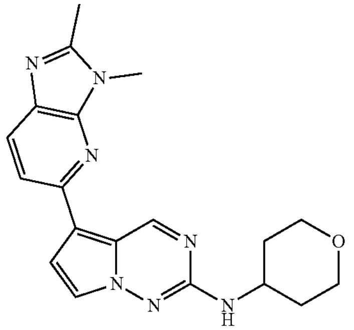 [SMILES: Cc1nc2ccc(-c3ccn4nc(NC5CCOCC5)ncc34)nc2n1C]
919
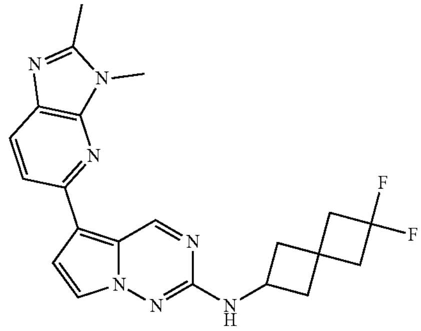 [SMILES: Cc1nc2ccc(-c3ccn4nc(NC5CC6(C5)CC(F)(F)C6)ncc34)nc2n1C]
920
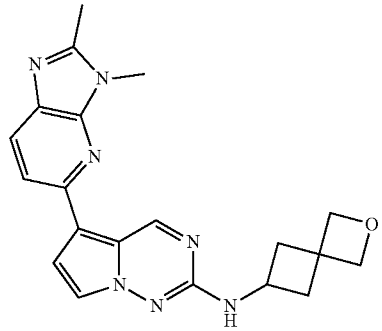 [SMILES: Cc1nc2ccc(-c3ccn4nc(NC5CC6(COC6)C5)ncc34)nc2n1C]
921
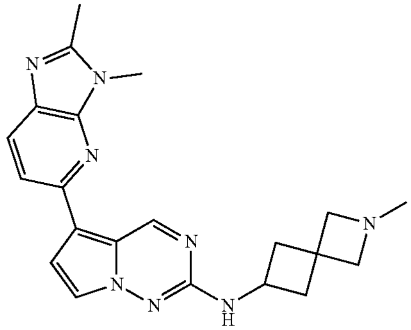 [SMILES: Cc1nc2ccc(-c3ccn4nc(NC5CC6(C5)CN(C)C6)ncc34)nc2n1C]
922

TABLE 1-continued
923
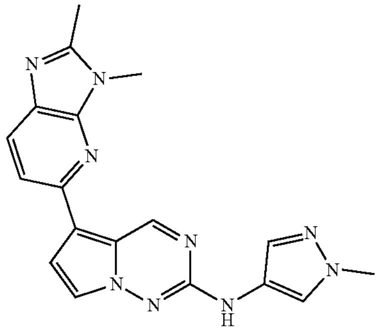 [SMILES: Cc1nc2ccc(-c3ccn4nc(Nc5cnn(C)c5)ncc34)nc2n1C]
924
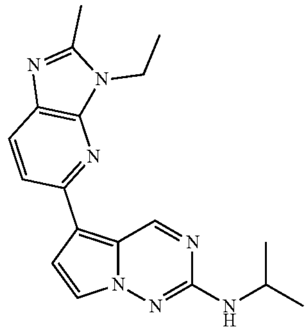 [SMILES: CCn1c(C)nc2ccc(-c3ccn4nc(NC(C)C)ncc34)nc21]
925
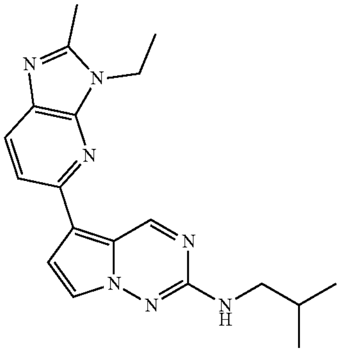 [SMILES: CCn1c(C)nc2ccc(-c3ccn4nc(NCC(C)C)ncc34)nc21]
926
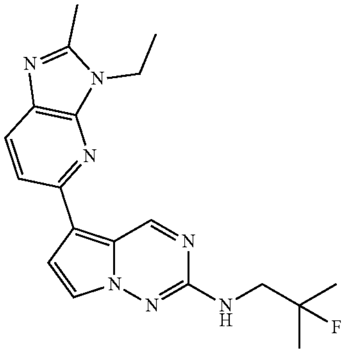 [SMILES: CCn1c(C)nc2ccc(-c3ccn4nc(NCC(C)(C)F)ncc34)nc21]

TABLE 1-continued
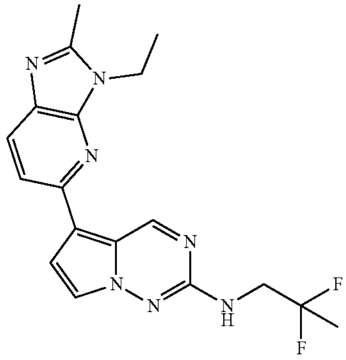 [SMILES: CCn1c(C)nc2ccc(-c3ccn4nc(NCC(C)(F)F)ncc34)nc21]
927
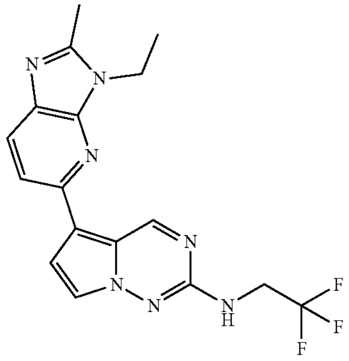 [SMILES: CCn1c(C)nc2ccc(-c3ccn4nc(NCC(F)(F)F)ncc34)nc21]
928
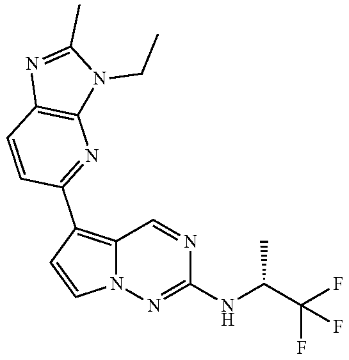 [SMILES: CCn1c(C)nc2ccc(-c3ccn4nc(N[C@H](C)C(F)(F)F)ncc34)nc21]
929
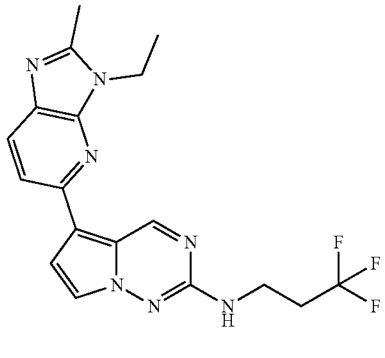 [SMILES: CCn1c(C)nc2ccc(-c3ccn4nc(NCCC(F)(F)F)ncc34)nc21]
930

TABLE 1-continued
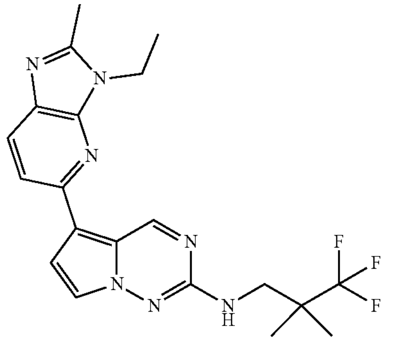 [SMILES: CCn1c(C)nc2ccc(-c3ccn4nc(NCC(C)(C)C(F)(F)F)ncc34)nc21]
931
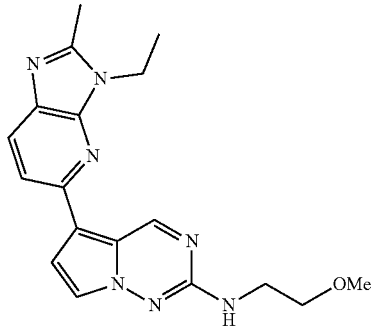 [SMILES: CCn1c(C)nc2ccc(-c3ccn4nc(NCCOC)ncc34)nc21]
932
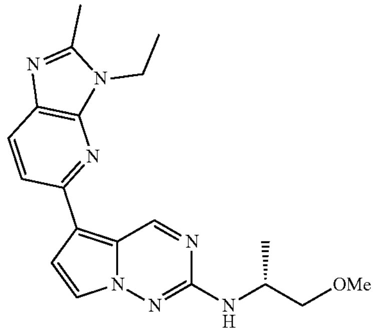 [SMILES: CCn1c(C)nc2ccc(-c3ccn4nc(N[C@H](C)COC)ncc34)nc21]
933
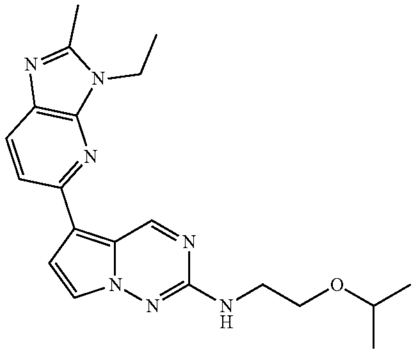 [SMILES: CCn1c(C)nc2ccc(-c3ccn4nc(NCCOC(C)C)ncc34)nc21]
934

TABLE 1-continued
935
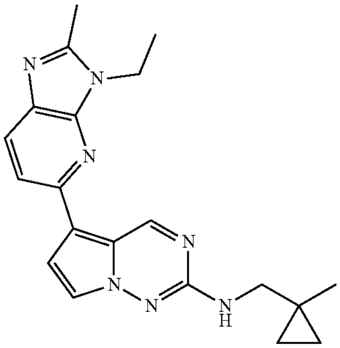 [SMILES: CCn1c(C)nc2ccc(-c3ccn4nc(NCC5(C)CC5)ncc34)nc21]
936
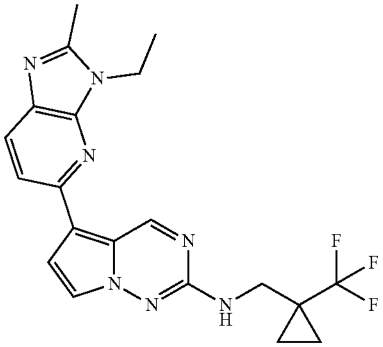 [SMILES: CCn1c(C)nc2ccc(-c3ccn4nc(NCC5(C(F)(F)F)CC5)ncc34)nc21]
937
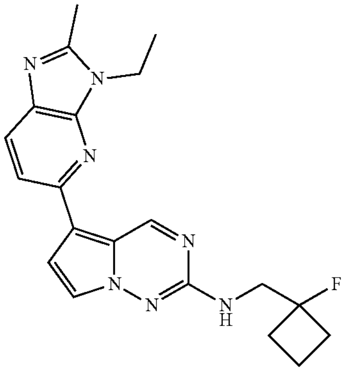 [SMILES: CCn1c(C)nc2ccc(-c3ccn4nc(NCC5(F)CCC5)ncc34)nc21]
938
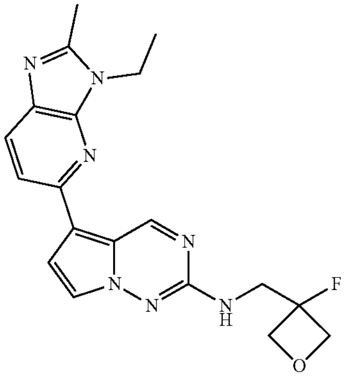 [SMILES: CCn1c(C)nc2ccc(-c3ccn4nc(NCC5(F)COC5)ncc34)nc21]

TABLE 1-continued
939
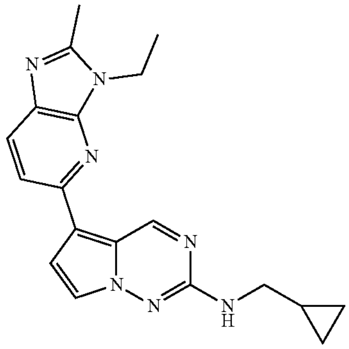 [SMILES: CCn1c(C)nc2ccc(-c3ccn4nc(NCC5CC5)ncc34)nc21]
940
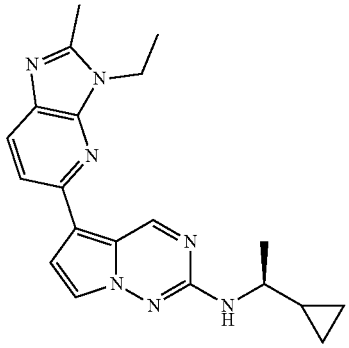 [SMILES: CCn1c(C)nc2ccc(-c3ccn4nc(N[C@@H](C)C5CC5)ncc34)nc21]
941
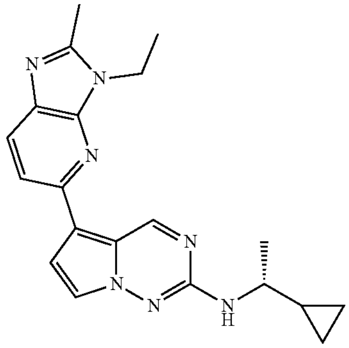 [SMILES: CCn1c(C)nc2ccc(-c3ccn4nc(N[C@H](C)C5CC5)ncc34)nc21]
942
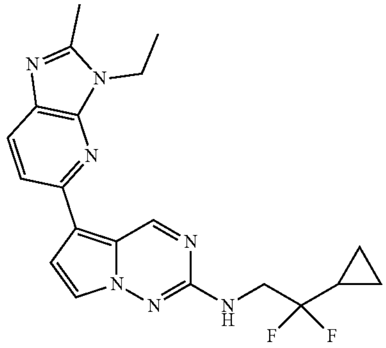 [SMILES: CCn1c(C)nc2ccc(-c3ccn4nc(NCC(F)(F)C5CC5)ncc34)nc21]

TABLE 1-continued
943
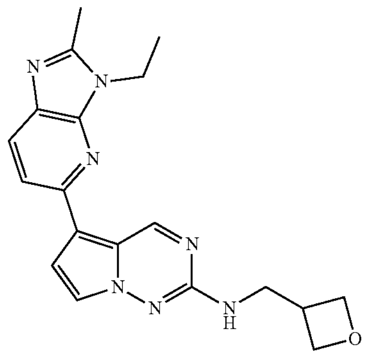 [SMILES: CCn1c(C)nc2ccc(-c3ccn4nc(NCC5COC5)ncc34)nc21]
944
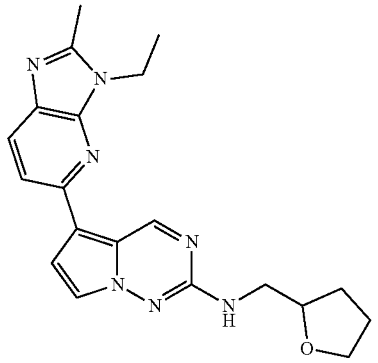 [SMILES: CCn1c(C)nc2ccc(-c3ccn4nc(NCC5CCCO5)ncc34)nc21]
945
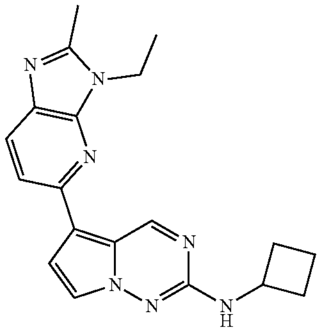 [SMILES: CCn1c(C)nc2ccc(-c3ccn4nc(NC5CCC5)ncc34)nc21]
946
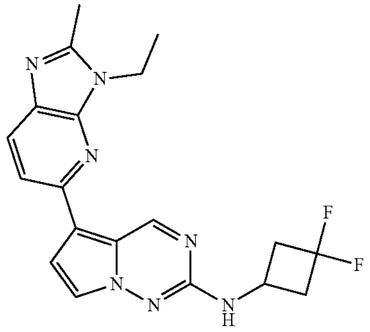 [SMILES: CCn1c(C)nc2ccc(-c3ccn4nc(NC5CC(F)(F)C5)ncc34)nc21]

TABLE 1-continued
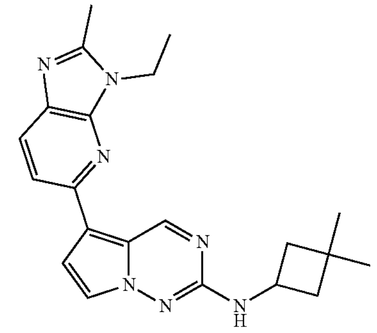 [SMILES: CCn1c(C)nc2ccc(-c3ccn4nc(NC5CC(C)(C)C5)ncc34)nc21]
947
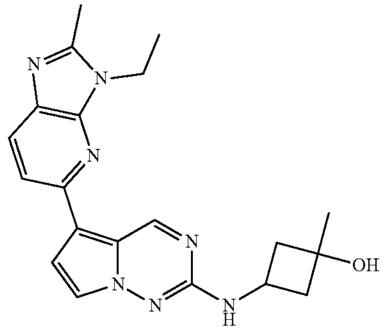 [SMILES: CCn1c(C)nc2ccc(-c3ccn4nc(NC5CC(C)(O)C5)ncc34)nc21]
948
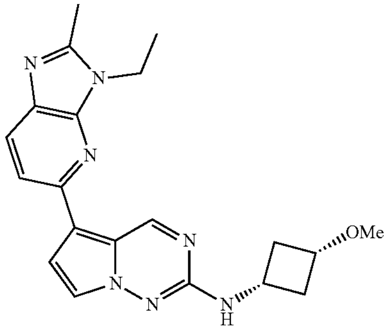 [SMILES: CCn1c(C)nc2ccc(-c3ccn4nc(N[C@H]5C[C@@H](OC)C5)ncc34)nc21]
949
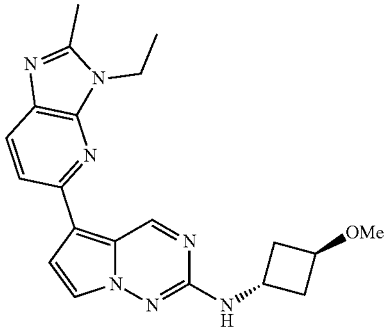 [SMILES: CCn1c(C)nc2ccc(-c3ccn4nc(N[C@H]5C[C@H](OC)C5)ncc34)nc21]
950

TABLE 1-continued
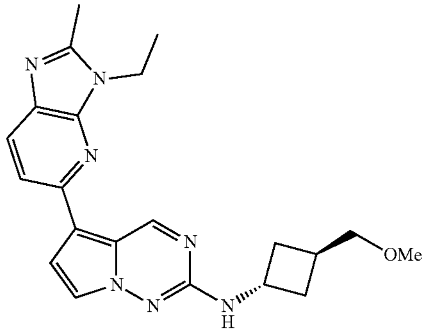 [SMILES: CCn1c(C)nc2ccc(-c3ccn4nc(N[C@H]5C[C@H](COC)C5)ncc34)nc21]
951
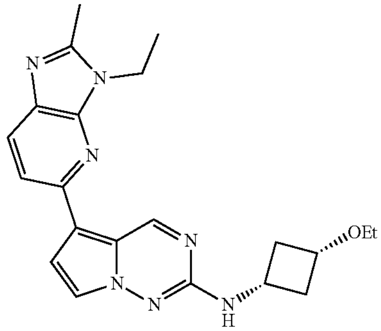 [SMILES: CCO[C@H]1C[C@@H](Nc2ncc3c(-c4ccc5nc(C)n(CC)c5n4)ccn3n2)C1]
952
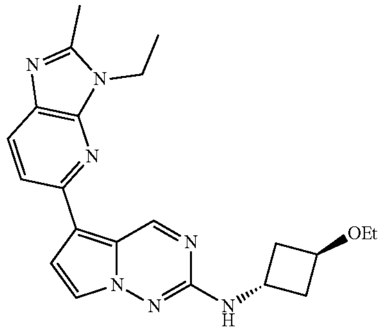 [SMILES: CCO[C@H]1C[C@H](Nc2ncc3c(-c4ccc5nc(C)n(CC)c5n4)ccn3n2)C1]
953
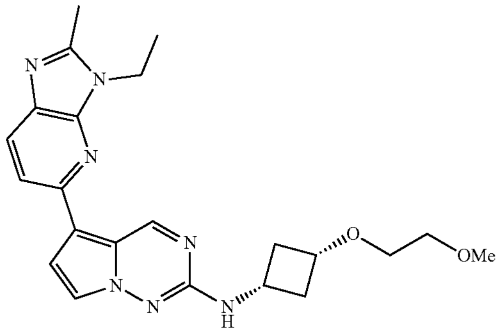 [SMILES: CCn1c(C)nc2ccc(-c3ccn4nc(N[C@H]5C[C@@H](OCCOC)C5)ncc34)nc21]
954

TABLE 1-continued
955
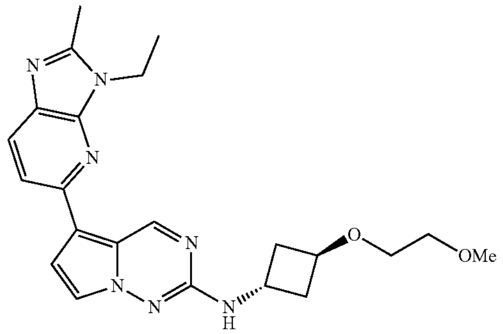 [SMILES: CCn1c(C)nc2ccc(-c3ccn4nc(N[C@H]5C[C@H](OCCOC)C5)ncc34)nc21]
956
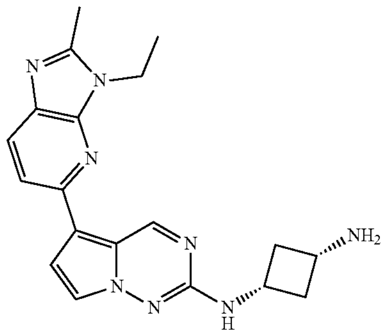 [SMILES: CCn1c(C)nc2ccc(-c3ccn4nc(N[C@H]5C[C@@H](N)C5)ncc34)nc21]
957
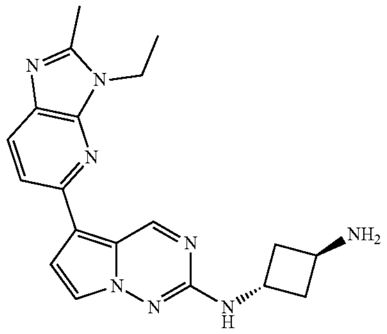 [SMILES: CCn1c(C)nc2ccc(-c3ccn4nc(N[C@H]5C[C@H](N)C5)ncc34)nc21]
958
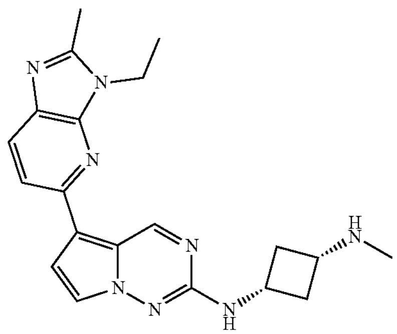 [SMILES: CCn1c(C)nc2ccc(-c3ccn4nc(N[C@H]5C[C@@H](NC)C5)ncc34)nc21]

TABLE 1-continued
959
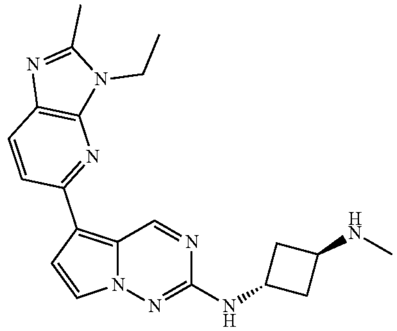 [SMILES: CCn1c(C)nc2ccc(-c3ccn4nc(N[C@H]5C[C@H](NC)C5)ncc34)nc21]
960
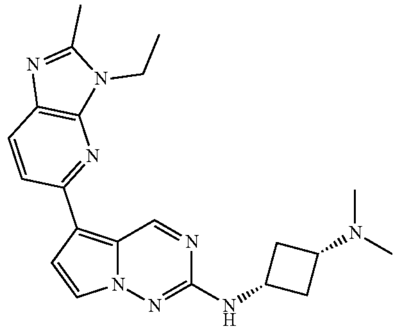 [SMILES: CCn1c(C)nc2ccc(-c3ccn4nc(N[C@H]5C[C@@H](N(C)C)C5)ncc34)nc21]
961
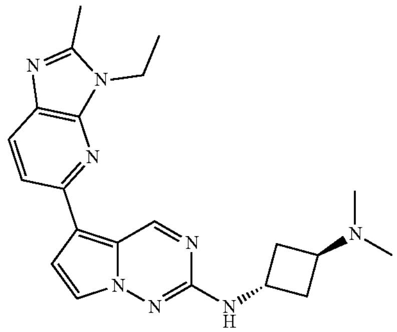 [SMILES: CCn1c(C)nc2ccc(-c3ccn4nc(N[C@H]5C[C@H](N(C)C)C5)ncc34)nc21]
962
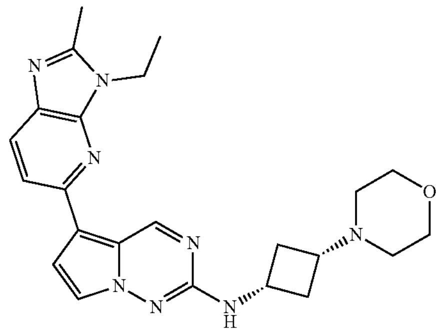 [SMILES: CCn1c(C)nc2ccc(-c3ccn4nc(N[C@H]5C[C@@H](N6CCOCC6)C5)ncc34)nc21]

TABLE 1-continued
963
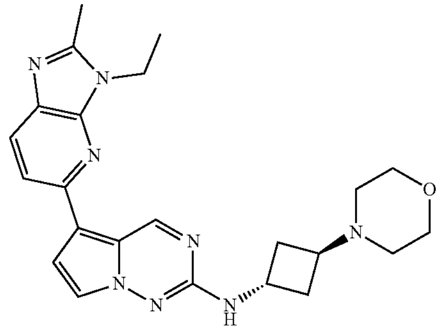 [SMILES: CCn1c(C)nc2ccc(-c3ccn4nc(N[C@H]5C[C@H](N6CCOCC6)C5)ncc34)nc21]
964
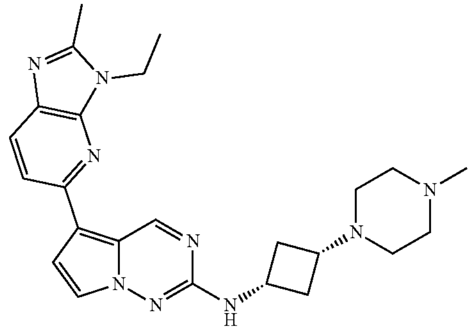 [SMILES: CCn1c(C)nc2ccc(-c3ccn4nc(N[C@H]5C[C@@H](N6CCN(C)CC6)C5)ncc34)nc21]
965
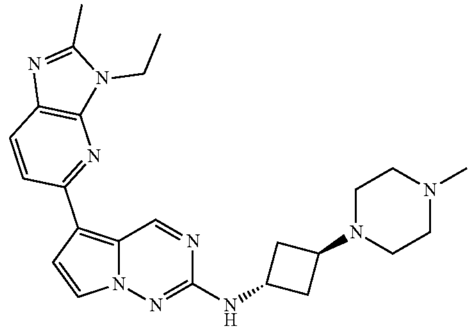 [SMILES: CCn1c(C)nc2ccc(-c3ccn4nc(N[C@H]5C[C@H](N6CCN(C)CC6)C5)ncc34)nc21]
966
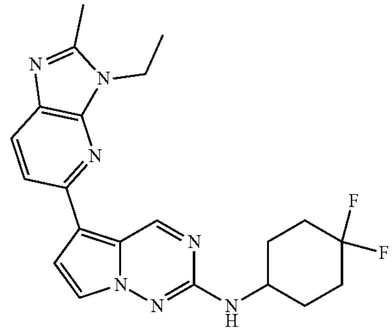 [SMILES: CCn1c(C)nc2ccc(-c3ccn4nc(NC5CCC(F)(F)CC5)ncc34)nc21]

TABLE 1-continued
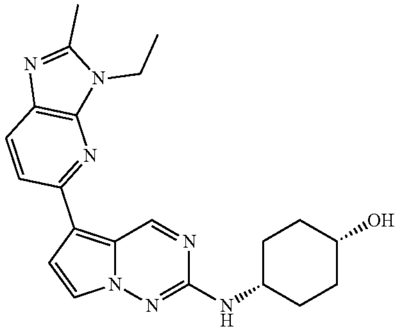 [SMILES: CCn1c(C)nc2ccc(-c3ccn4nc(N[C@H]5CC[C@@H](O)CC5)ncc34)nc21]
967
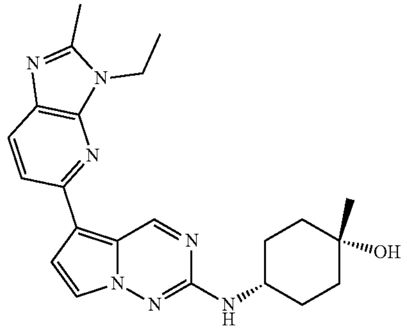 [SMILES: CCn1c(C)nc2ccc(-c3ccn4nc(N[C@H]5CC[C@@](C)(O)CC5)ncc34)nc21]
968
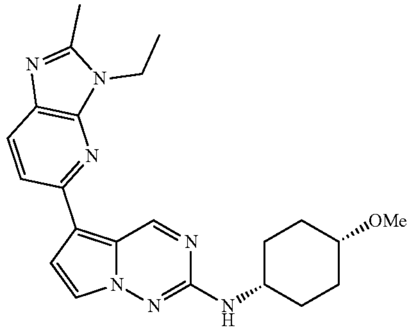 [SMILES: CCn1c(C)nc2ccc(-c3ccn4nc(N[C@H]5CC[C@@H](OC)CC5)ncc34)nc21]
969
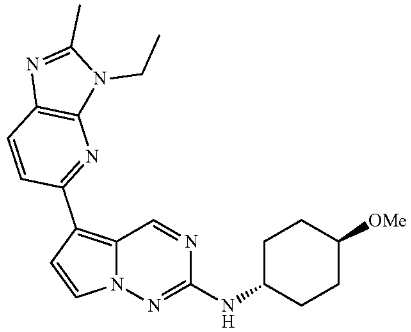 [SMILES: CCn1c(C)nc2ccc(-c3ccn4nc(N[C@H]5CC[C@H](OC)CC5)ncc34)nc21]
970

TABLE 1-continued
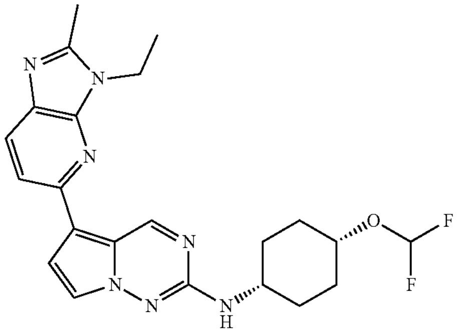 [SMILES: CCn1c(C)nc2ccc(-c3ccn4nc(N[C@H]5CC[C@@H](OC(F)F)CC5)ncc34)nc21]
971
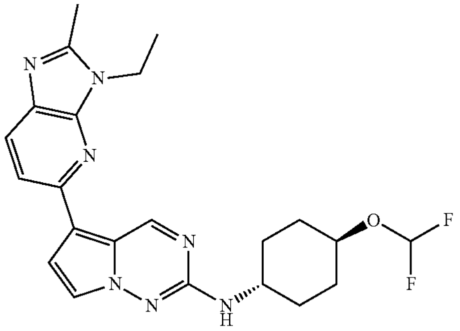 [SMILES: CCn1c(C)nc2ccc(-c3ccn4nc(N[C@H]5CC[C@H](OC(F)F)CC5)ncc34)nc21]
972
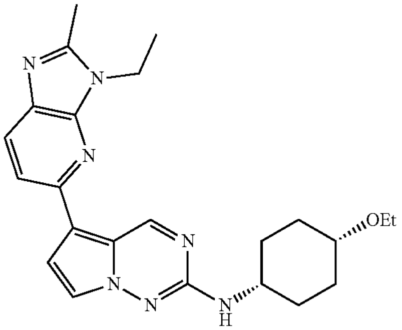 [SMILES: CCO[C@H]1CC[C@@H](Nc2ncc3c(-c4ccc5nc(C)n(CC)c5n4)ccn3n2)CC1]
973
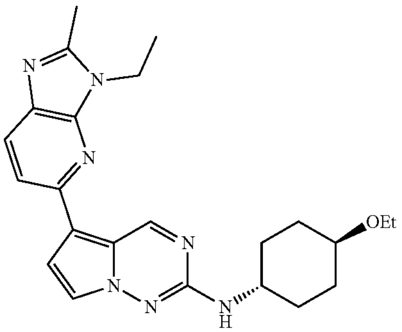 [SMILES: CCO[C@H]1CC[C@H](Nc2ncc3c(-c4ccc5nc(C)n(CC)c5n4)ccn3n2)CC1]
974

TABLE 1-continued
975
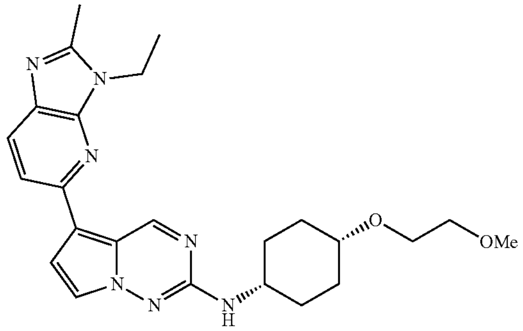 [SMILES: CCn1c(C)nc2ccc(-c3ccn4nc(N[C@H]5CC[C@@H](OCCOC)CC5)ncc34)nc21]
976
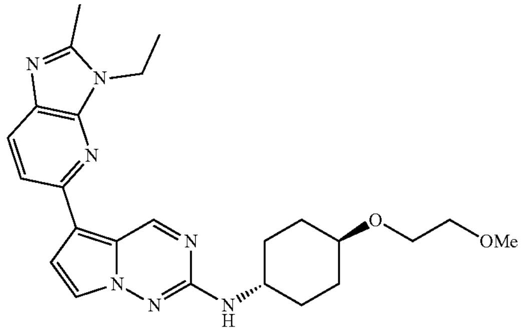 [SMILES: CCn1c(C)nc2ccc(-c3ccn4nc(N[C@H]5CC[C@H](OCCOC)CC5)ncc34)nc21]
977
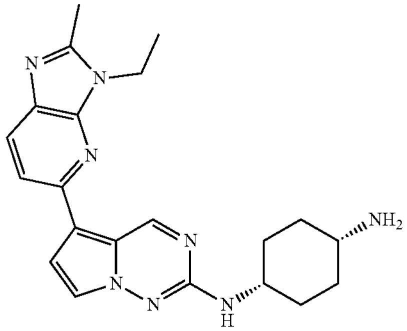 [SMILES: CCn1c(C)nc2ccc(-c3ccn4nc(N[C@H]5CC[C@@H](N)CC5)ncc34)nc21]
978
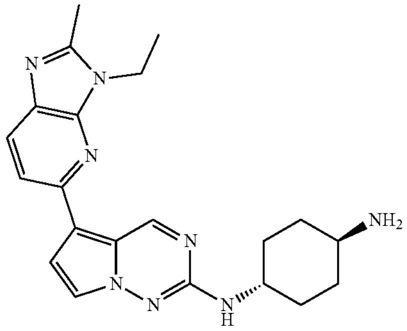 [SMILES: CCn1c(C)nc2ccc(-c3ccn4nc(N[C@H]5CC[C@H](N)CC5)ncc34)nc21]

TABLE 1-continued
979
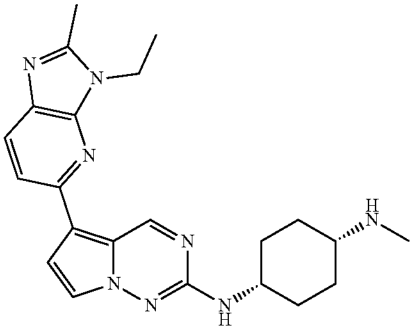 [SMILES: CCn1c(C)nc2ccc(-c3ccn4nc(N[C@H]5CC[C@@H](NC)CC5)ncc34)nc21]
980
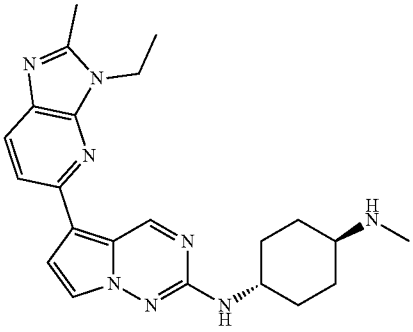 [SMILES: CCn1c(C)nc2ccc(-c3ccn4nc(N[C@H]5CC[C@H](NC)CC5)ncc34)nc21]
981
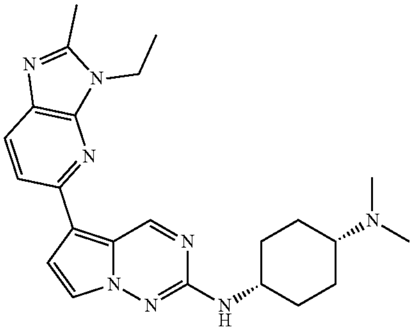 [SMILES: CCn1c(C)nc2ccc(-c3ccn4nc(N[C@H]5CC[C@@H](N(C)C)CC5)ncc34)nc21]
982
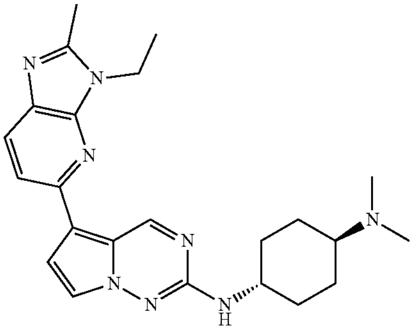

TABLE 1-continued
983
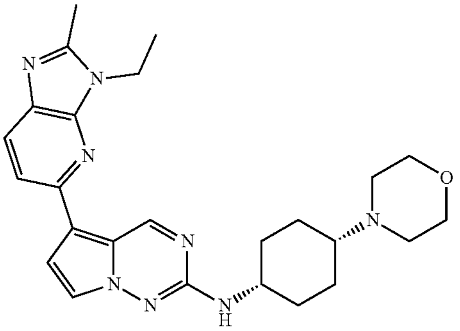 [SMILES: CCn1c(C)nc2ccc(-c3ccn4nc(N[C@H]5CC[C@@H](N6CCOCC6)CC5)ncc34)nc21]
984
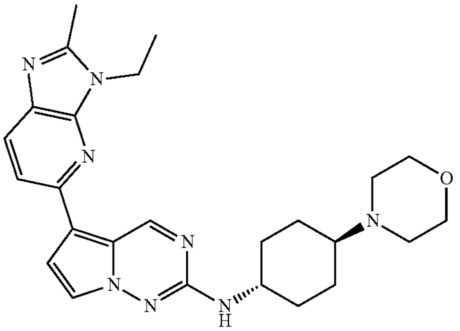
985
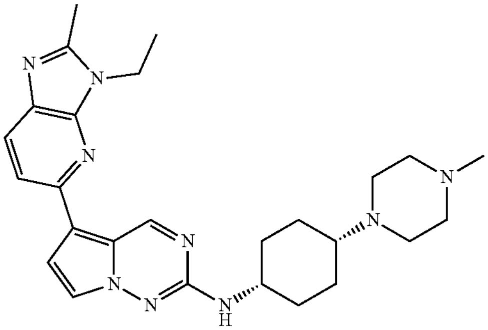 [SMILES: CCn1c(C)nc2ccc(-c3ccn4nc(N[C@H]5CC[C@@H](N6CCN(C)CC6)CC5)ncc34)nc21]
986
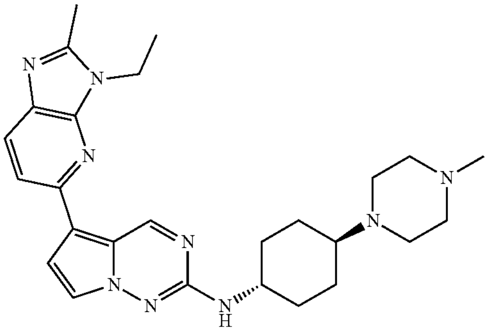

TABLE 1-continued
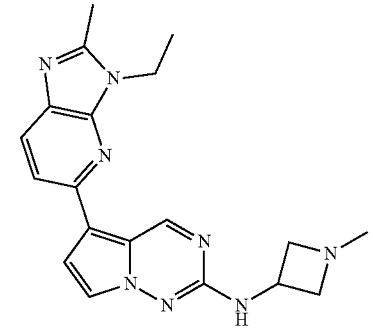 [SMILES: CCn1c(C)nc2ccc(-c3ccn4nc(NC5CN(C)C5)ncc34)nc21]
987
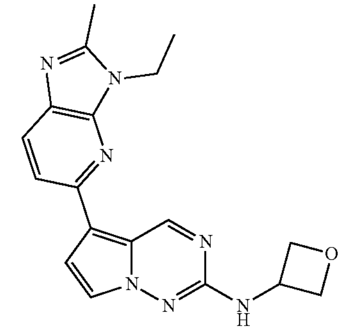 [SMILES: CCn1c(C)nc2ccc(-c3ccn4nc(NC5COC5)ncc34)nc21]
988
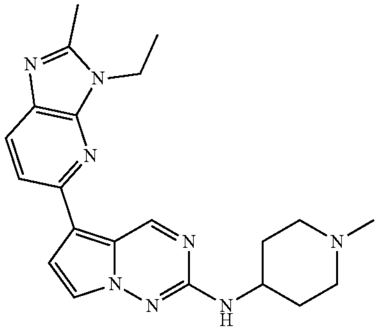 [SMILES: CCn1c(C)nc2ccc(-c3ccn4nc(NC5CCN(C)CC5)ncc34)nc21]
989
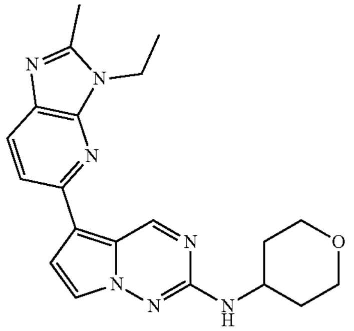 [SMILES: CCn1c(C)nc2ccc(-c3ccn4nc(NC5CCOCC5)ncc34)nc21]
990

TABLE 1-continued
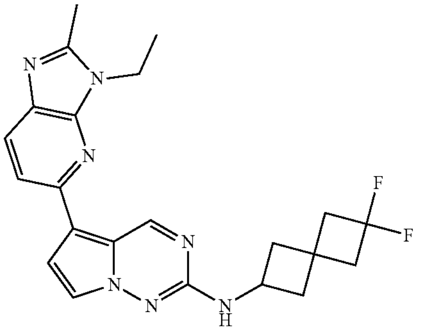 [SMILES: CCn1c(C)nc2ccc(-c3ccn4nc(NC5CC6(C5)CC(F)(F)C6)ncc34)nc21]
991
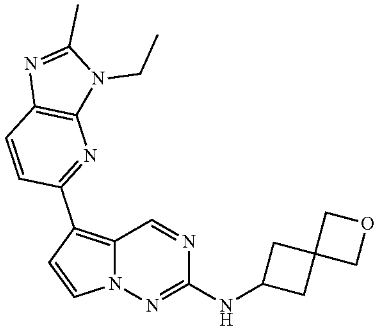 [SMILES: CCn1c(C)nc2ccc(-c3ccn4nc(NC5CC6(COC6)C5)ncc34)nc21]
992
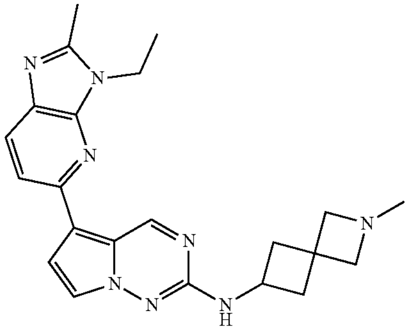 [SMILES: CCn1c(C)nc2ccc(-c3ccn4nc(NC5CC6(C5)CN(C)C6)ncc34)nc21]
993
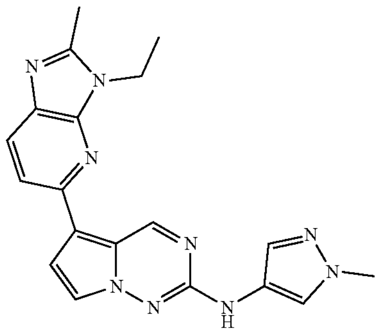 [SMILES: CCn1c(C)nc2ccc(-c3ccn4nc(Nc5cnn(C)c5)ncc34)nc21]
994

TABLE 1-continued
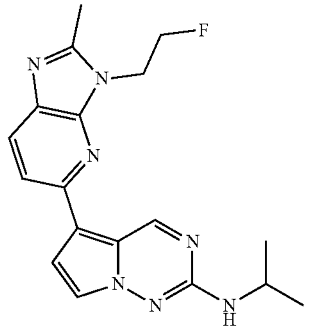 [SMILES: Cc1nc2ccc(-c3ccn4nc(NC(C)C)ncc34)nc2n1CCF]
995
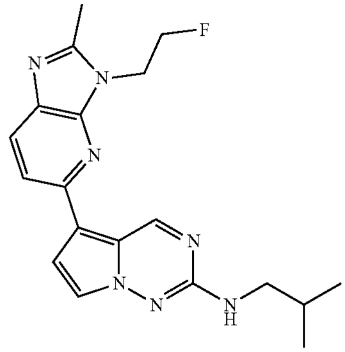 [SMILES: Cc1nc2ccc(-c3ccn4nc(NCC(C)C)ncc34)nc2n1CCF]
996
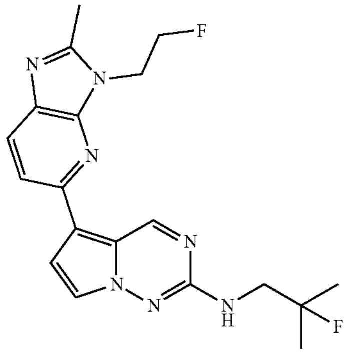 [SMILES: Cc1nc2ccc(-c3ccn4nc(NCC(C)(C)F)ncc34)nc2n1CCF]
997
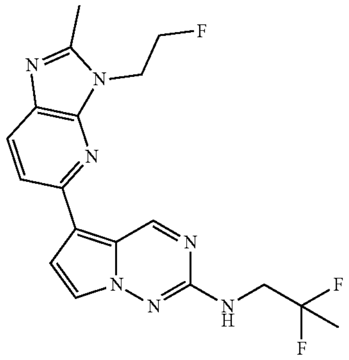 [SMILES: Cc1nc2ccc(-c3ccn4nc(NCC(C)(F)F)ncc34)nc2n1CCF]
998

TABLE 1-continued
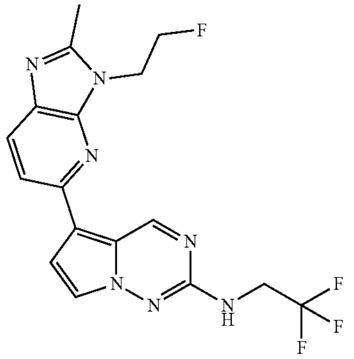 [SMILES: Cc1nc2ccc(-c3ccn4nc(NCC(F)(F)F)ncc34)nc2n1CCF]
999
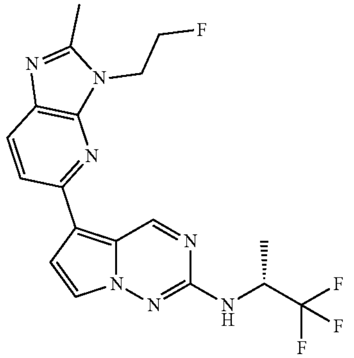 [SMILES: Cc1nc2ccc(-c3ccn4nc(N[C@H](C)C(F)(F)F)ncc34)nc2n1CCF]
1000
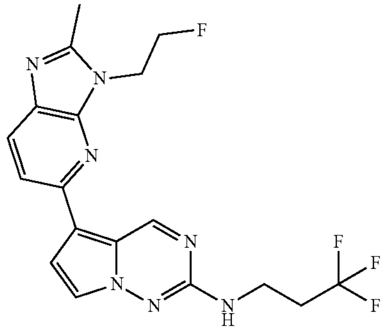 [SMILES: Cc1nc2ccc(-c3ccn4nc(NCCC(F)(F)F)ncc34)nc2n1CCF]
1001
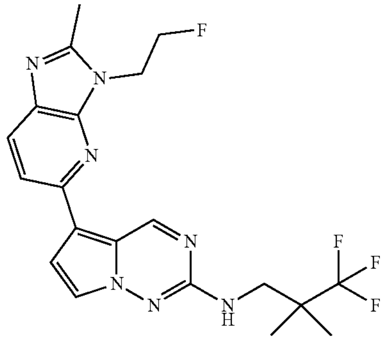 [SMILES: Cc1nc2ccc(-c3ccn4nc(NCC(C)(C)C(F)(F)F)ncc34)nc2n1CCF]
1002

TABLE 1-continued
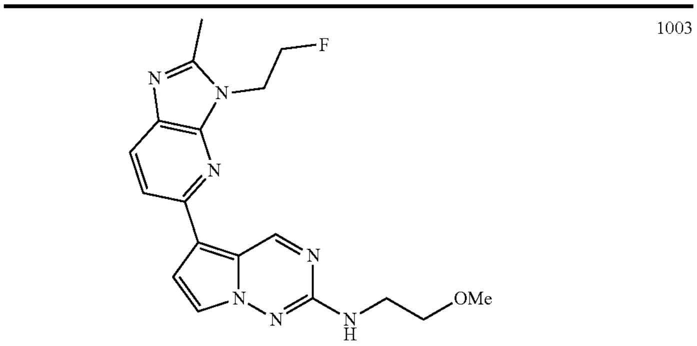
1003
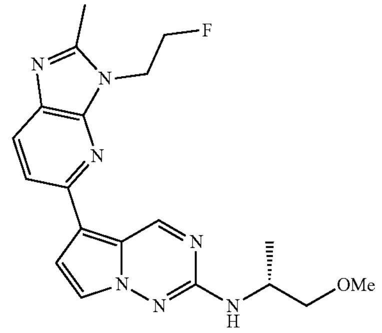 [SMILES: COC[C@@H](C)Nc1ncc2c(-c3ccc4nc(C)n(CCF)c4n3)ccn2n1]
1004
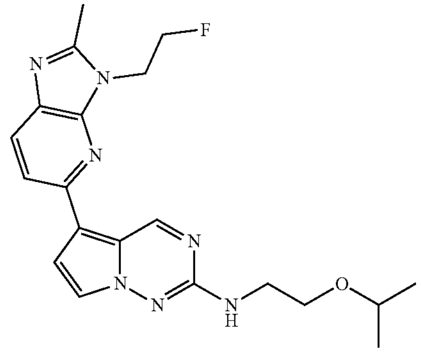 [SMILES: Cc1nc2ccc(-c3ccn4nc(NCCOC(C)C)ncc34)nc2n1CCF]
1005
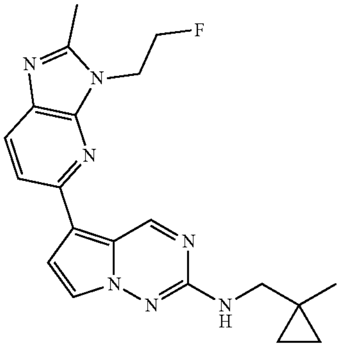 [SMILES: Cc1nc2ccc(-c3ccn4nc(NCC5(C)CC5)ncc34)nc2n1CCF]
1006

TABLE 1-continued
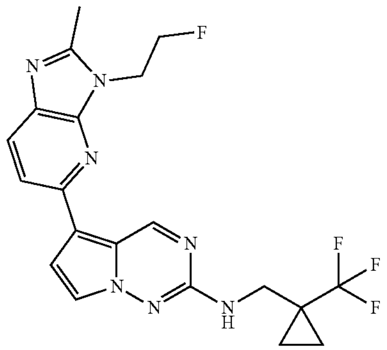 [SMILES: Cc1nc2ccc(-c3ccn4nc(NCC5(C(F)(F)F)CC5)ncc34)nc2n1CCF]
1007
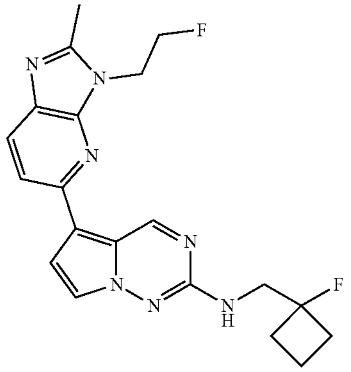 [SMILES: Cc1nc2ccc(-c3ccn4nc(NCC5(F)CCC5)ncc34)nc2n1CCF]
1008
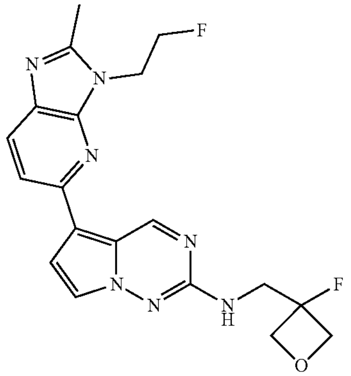 [SMILES: Cc1nc2ccc(-c3ccn4nc(NCC5(F)COC5)ncc34)nc2n1CCF]
1009
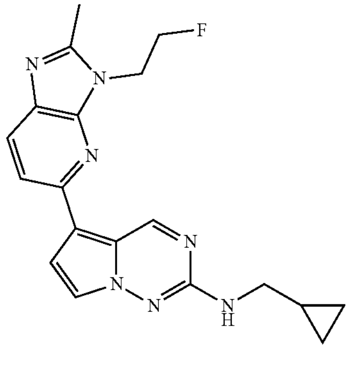 [SMILES: Cc1nc2ccc(-c3ccn4nc(NCC5CC5)ncc34)nc2n1CCF]
1010

TABLE 1-continued
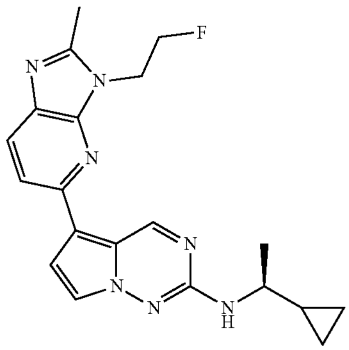 [SMILES: Cc1nc2ccc(-c3ccn4nc(N[C@@H](C)C5CC5)ncc34)nc2n1CCF]
1011
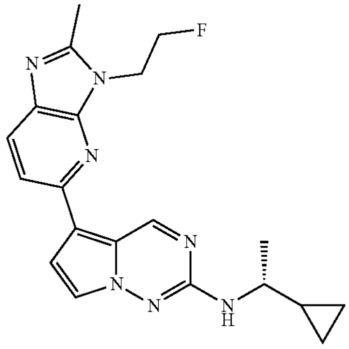 [SMILES: Cc1nc2ccc(-c3ccn4nc(N[C@H](C)C5CC5)ncc34)nc2n1CCF]
1012
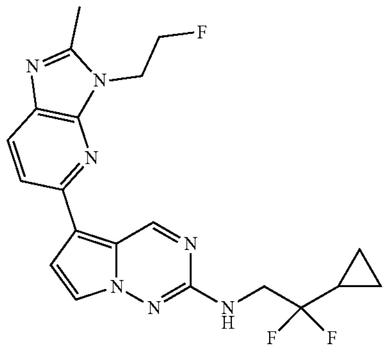 [SMILES: Cc1nc2ccc(-c3ccn4nc(NCC(F)(F)C5CC5)ncc34)nc2n1CCF]
1013
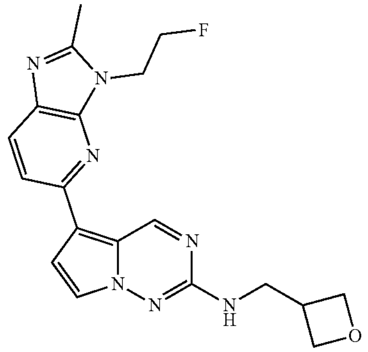 [SMILES: Cc1nc2ccc(-c3ccn4nc(NCC5COC5)ncc34)nc2n1CCF]
1014

TABLE 1-continued
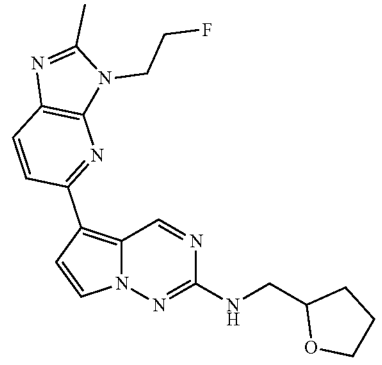 [SMILES: Cc1nc2ccc(-c3ccn4nc(NCC5CCCO5)ncc34)nc2n1CCF]
1015
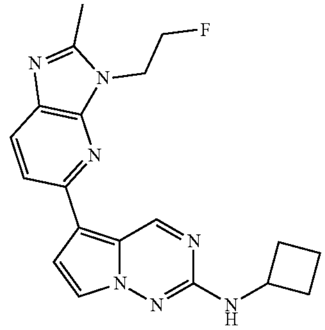 [SMILES: Cc1nc2ccc(-c3ccn4nc(NC5CCC5)ncc34)nc2n1CCF]
1016
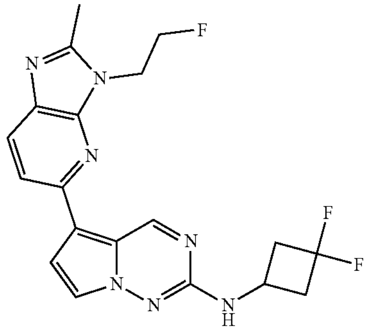 [SMILES: Cc1nc2ccc(-c3ccn4nc(NC5CC(F)(F)C5)ncc34)nc2n1CCF]
1017
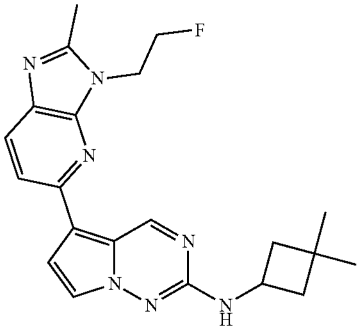 [SMILES: Cc1nc2ccc(-c3ccn4nc(NC5CC(C)(C)C5)ncc34)nc2n1CCF]
1018

TABLE 1-continued
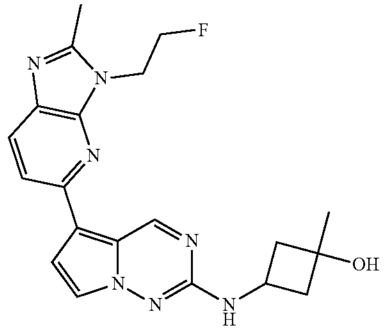 [SMILES: Cc1nc2ccc(-c3ccn4nc(NC5CC(C)(O)C5)ncc34)nc2n1CCF]
1019
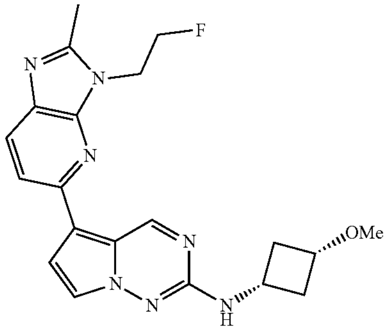 [SMILES: CO[C@H]1C[C@@H](Nc2ncc3c(-c4ccc5nc(C)n(CCF)c5n4)ccn3n2)C1]
1020
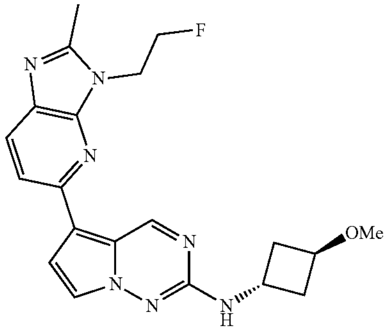 [SMILES: CO[C@H]1C[C@H](Nc2ncc3c(-c4ccc5nc(C)n(CCF)c5n4)ccn3n2)C1]
1021
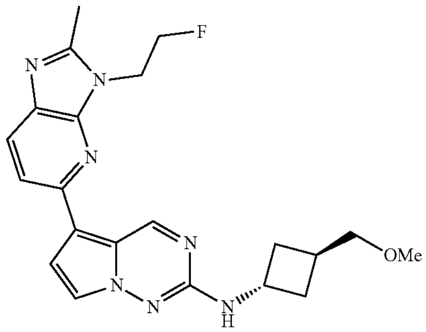 [SMILES: COC[C@H]1C[C@H](Nc2ncc3c(-c4ccc5nc(C)n(CCF)c5n4)ccn3n2)C1]
1022

TABLE 1-continued
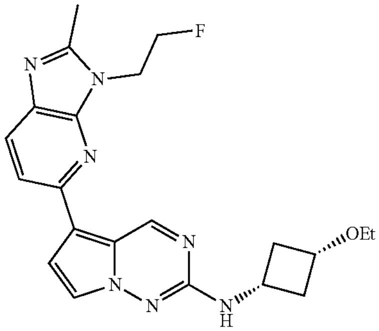 [SMILES: CCO[C@H]1C[C@@H](Nc2ncc3c(-c4ccc5nc(C)n(CCF)c5n4)ccn3n2)C1]
1023
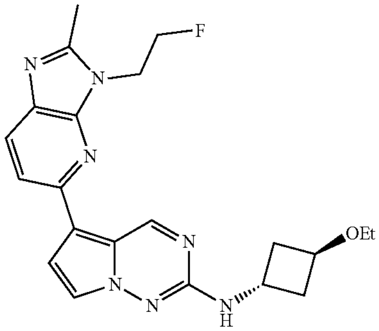 [SMILES: CCO[C@H]1C[C@H](Nc2ncc3c(-c4ccc5nc(C)n(CCF)c5n4)ccn3n2)C1]
1024
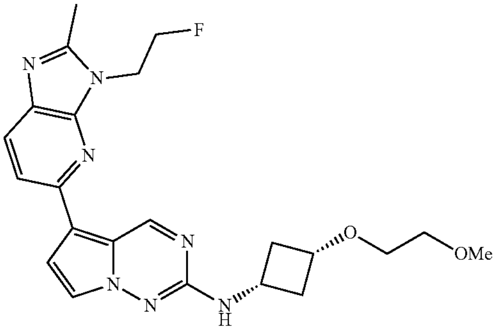 [SMILES: COCCO[C@H]1C[C@@H](Nc2ncc3c(-c4ccc5nc(C)n(CCF)c5n4)ccn3n2)C1]
1025
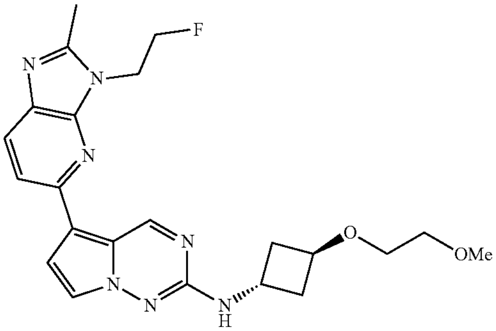 [SMILES: COCCO[C@H]1C[C@H](Nc2ncc3c(-c4ccc5nc(C)n(CCF)c5n4)ccn3n2)C1]
1026

TABLE 1-continued
1027
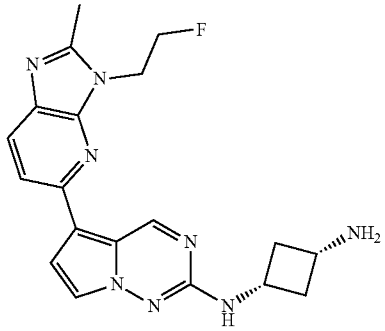 [SMILES: Cc1nc2ccc(-c3ccn4nc(N[C@H]5C[C@@H](N)C5)ncc34)nc2n1CCF]
1028
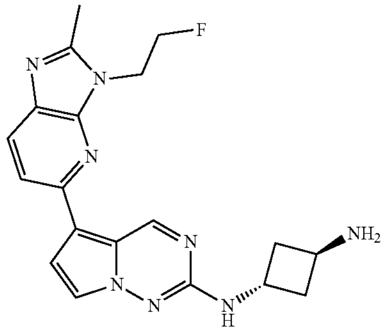 [SMILES: Cc1nc2ccc(-c3ccn4nc(N[C@H]5C[C@H](N)C5)ncc34)nc2n1CCF]
1029
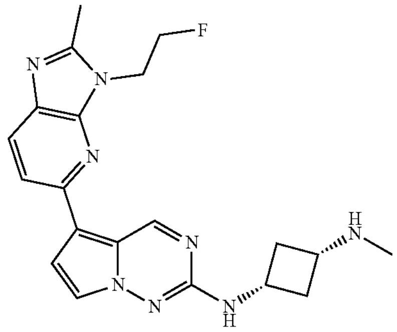 [SMILES: CN[C@H]1C[C@@H](Nc2ncc3c(-c4ccc5nc(C)n(CCF)c5n4)ccn3n2)C1]
1030
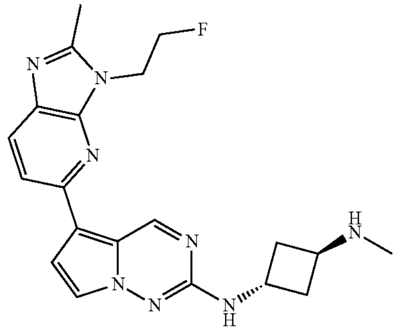 [SMILES: CN[C@H]1C[C@H](Nc2ncc3c(-c4ccc5nc(C)n(CCF)c5n4)ccn3n2)C1]

TABLE 1-continued
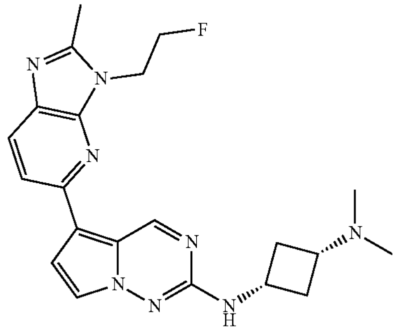 [SMILES: Cc1nc2ccc(-c3ccn4nc(N[C@H]5C[C@@H](N(C)C)C5)ncc34)nc2n1CCF]
1031
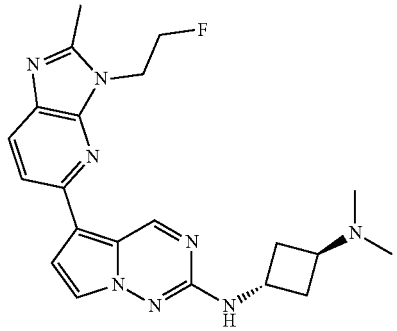 [SMILES: Cc1nc2ccc(-c3ccn4nc(N[C@H]5C[C@H](N(C)C)C5)ncc34)nc2n1CCF]
1032
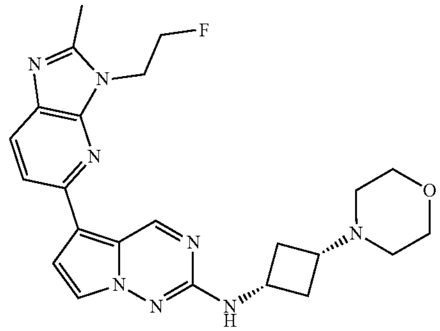 [SMILES: Cc1nc2ccc(-c3ccn4nc(N[C@H]5C[C@@H](N6CCOCC6)C5)ncc34)nc2n1CCF]
1033
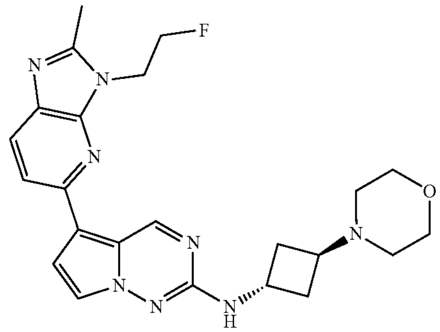 [SMILES: Cc1nc2ccc(-c3ccn4nc(N[C@H]5C[C@H](N6CCOCC6)C5)ncc34)nc2n1CCF]
1034

TABLE 1-continued
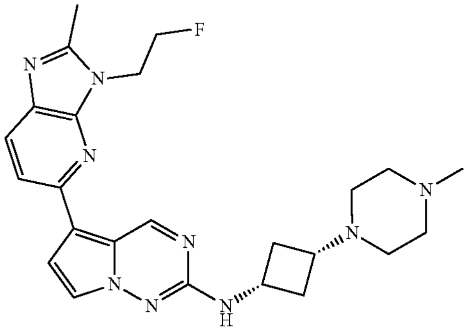 [SMILES: Cc1nc2ccc(-c3ccn4nc(N[C@H]5C[C@@H](N6CCN(C)CC6)C5)ncc34)nc2n1CCF]
1035
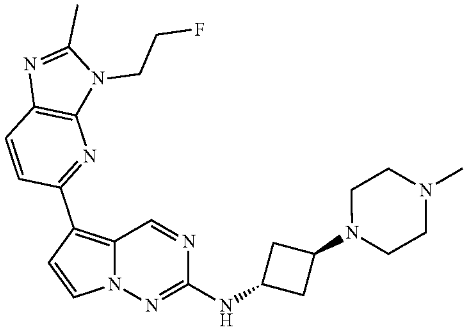 [SMILES: Cc1nc2ccc(-c3ccn4nc(N[C@H]5C[C@H](N6CCN(C)CC6)C5)ncc34)nc2n1CCF]
1036
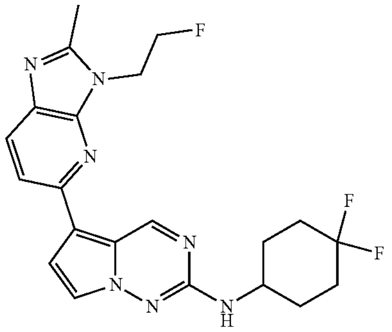 [SMILES: Cc1nc2ccc(-c3ccn4nc(NC5CCC(F)(F)CC5)ncc34)nc2n1CCF]
1037
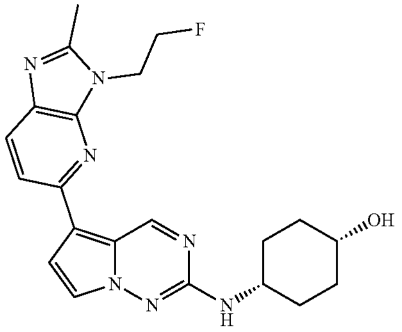 [SMILES: Cc1nc2ccc(-c3ccn4nc(N[C@H]5CC[C@@H](O)CC5)ncc34)nc2n1CCF]
1038

TABLE 1-continued
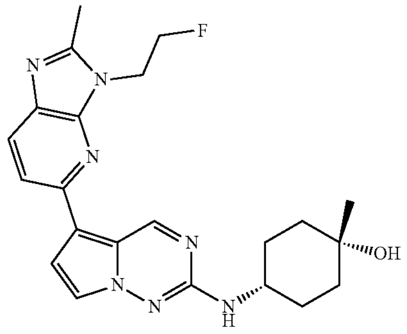 [SMILES: Cc1nc2ccc(-c3ccn4nc(N[C@H]5CC[C@@](C)(O)CC5)ncc34)nc2n1CCF]
1039
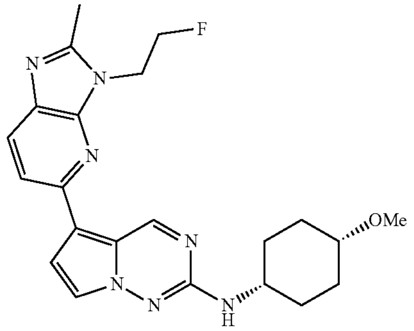 [SMILES: CO[C@H]1CC[C@@H](Nc2ncc3c(-c4ccc5nc(C)n(CCF)c5n4)ccn3n2)CC1]
1040
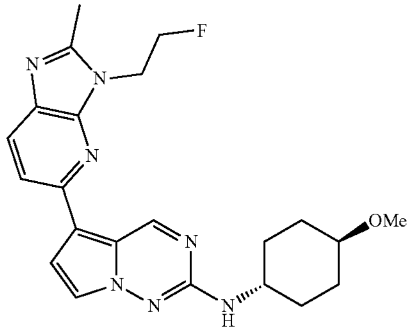 [SMILES: CO[C@H]1CC[C@H](Nc2ncc3c(-c4ccc5nc(C)n(CCF)c5n4)ccn3n2)CC1]
1041
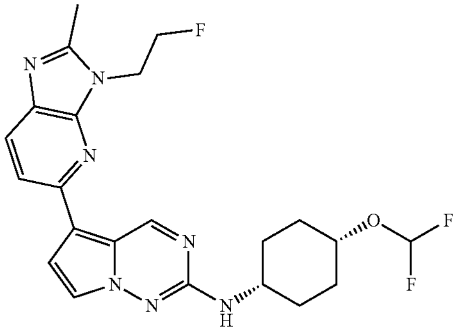 [SMILES: Cc1nc2ccc(-c3ccn4nc(N[C@H]5CC[C@@H](OC(F)F)CC5)ncc34)nc2n1CCF]
1042

TABLE 1-continued
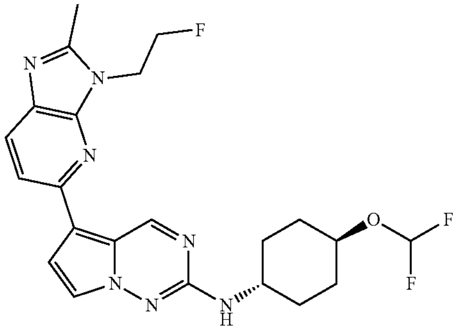 [SMILES: Cc1nc2ccc(-c3ccn4nc(N[C@H]5CC[C@H](OC(F)F)CC5)ncc34)nc2n1CCF]
1043
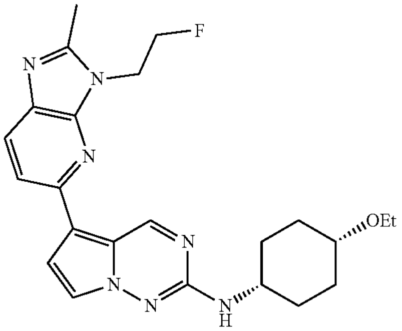 [SMILES: CCO[C@H]1CC[C@@H](Nc2ncc3c(-c4ccc5nc(C)n(CCF)c5n4)ccn3n2)CC1]
1044
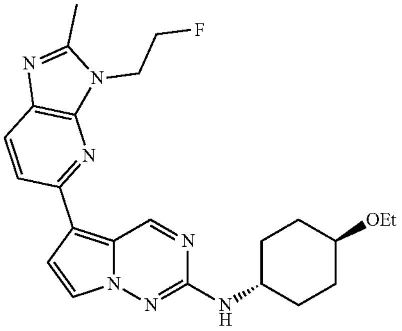 [SMILES: CCO[C@H]1CC[C@H](Nc2ncc3c(-c4ccc5nc(C)n(CCF)c5n4)ccn3n2)CC1]
1045
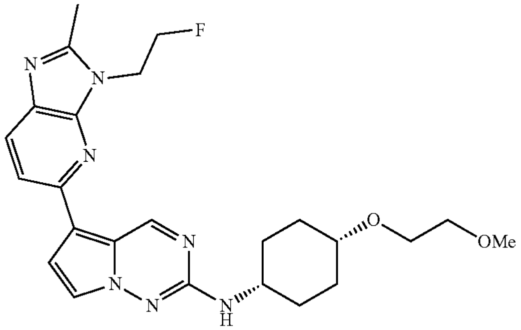 [SMILES: COCCO[C@H]1CC[C@@H](Nc2ncc3c(-c4ccc5nc(C)n(CCF)c5n4)ccn3n2)CC1]
1046

TABLE 1-continued
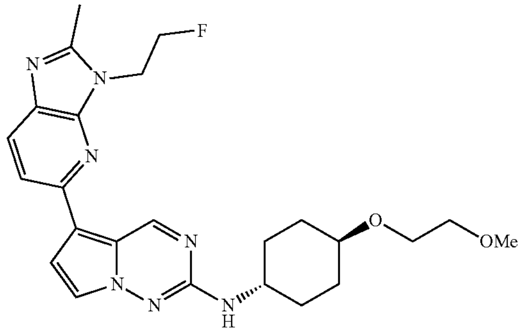 [SMILES: COCCO[C@H]1CC[C@H](Nc2ncc3c(-c4ccc5nc(C)n(CCF)c5n4)ccn3n2)CC1]
1047
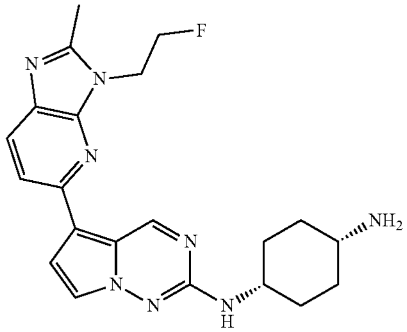 [SMILES: Cc1nc2ccc(-c3ccn4nc(N[C@H]5CC[C@@H](N)CC5)ncc34)nc2n1CCF]
1048
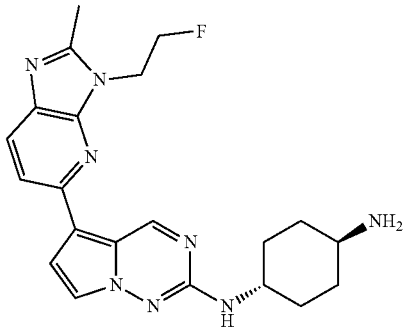 [SMILES: Cc1nc2ccc(-c3ccn4nc(N[C@H]5CC[C@H](N)CC5)ncc34)nc2n1CCF]
1049
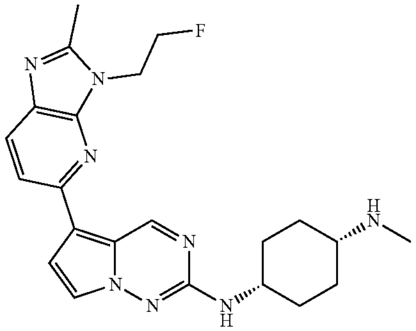 [SMILES: CN[C@H]1CC[C@@H](Nc2ncc3c(-c4ccc5nc(C)n(CCF)c5n4)ccn3n2)CC1]
1050

TABLE 1-continued
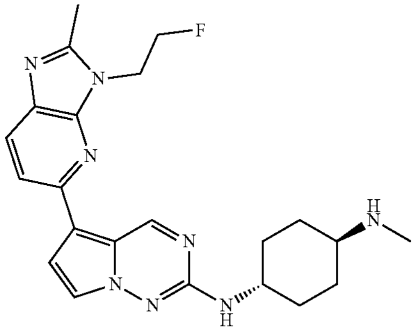 [SMILES: CN[C@H]1CC[C@H](Nc2ncc3c(-c4ccc5nc(C)n(CCF)c5n4)ccn3n2)CC1]
1051
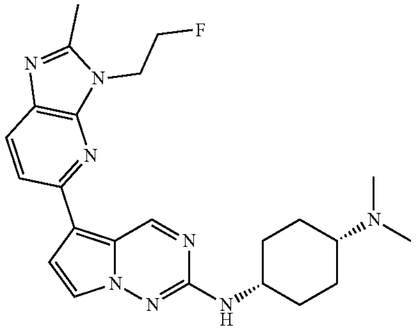 [SMILES: Cc1nc2ccc(-c3ccn4nc(N[C@H]5CC[C@@H](N(C)C)CC5)ncc34)nc2n1CCF]
1052
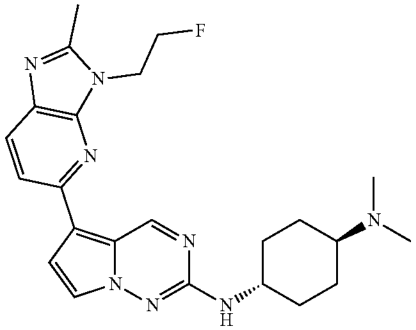 [SMILES: Cc1nc2ccc(-c3ccn4nc(N[C@H]5CC[C@H](N(C)C)CC5)ncc34)nc2n1CCF]
1053
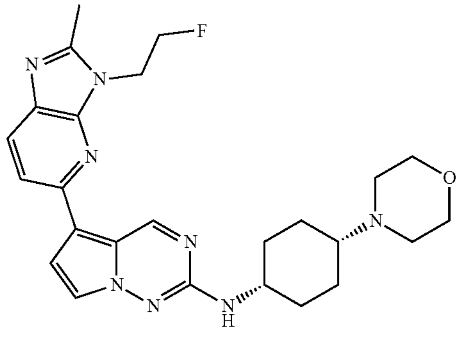 [SMILES: Cc1nc2ccc(-c3ccn4nc(N[C@H]5CC[C@@H](N6CCOCC6)CC5)ncc34)nc2n1CCF]
1054

TABLE 1-continued
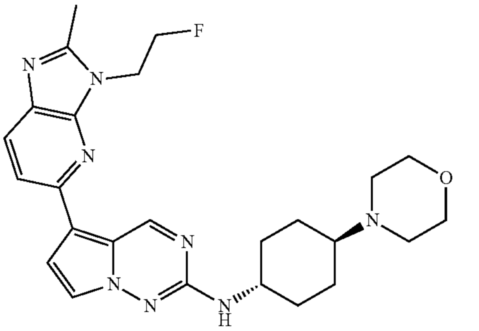 [SMILES: Cc1nc2ccc(-c3ccn4nc(N[C@H]5CC[C@H](N6CCOCC6)CC5)ncc34)nc2n1CCF]
1055
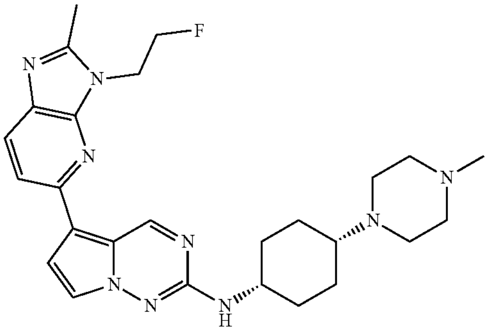 [SMILES: Cc1nc2ccc(-c3ccn4nc(N[C@H]5CC[C@@H](N6CCN(C)CC6)CC5)ncc34)nc2n1CCF]
1056
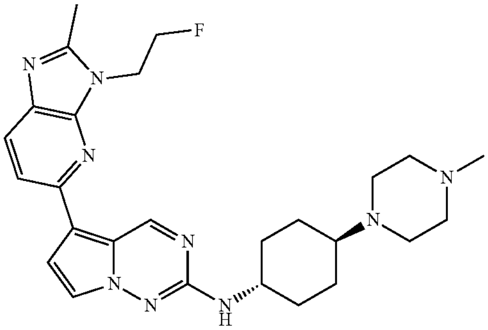 [SMILES: Cc1nc2ccc(-c3ccn4nc(N[C@H]5CC[C@H](N6CCN(C)CC6)CC5)ncc34)nc2n1CCF]
1057
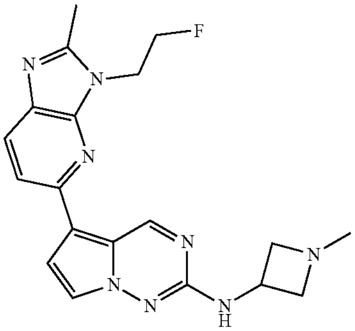 [SMILES: Cc1nc2ccc(-c3ccn4nc(NC5CN(C)C5)ncc34)nc2n1CCF]
1058

TABLE 1-continued
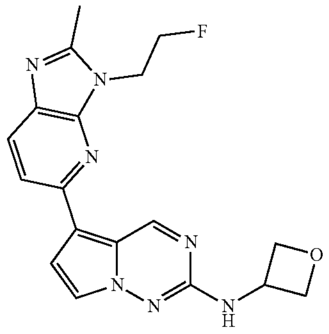 [SMILES: Cc1nc2ccc(-c3ccn4nc(NC5COC5)ncc34)nc2n1CCF]
1059
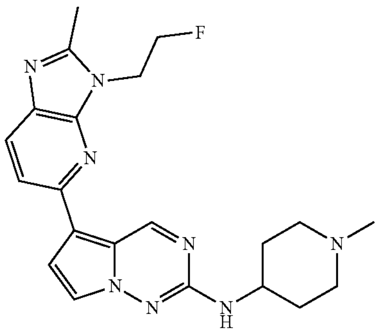 [SMILES: Cc1nc2ccc(-c3ccn4nc(NC5CCN(C)CC5)ncc34)nc2n1CCF]
1060
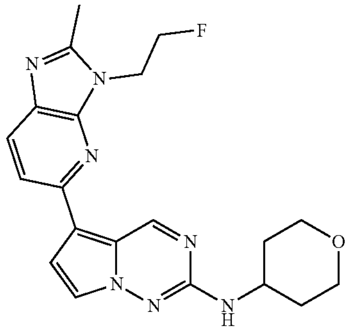 [SMILES: Cc1nc2ccc(-c3ccn4nc(NC5CCOCC5)ncc34)nc2n1CCF]
1061
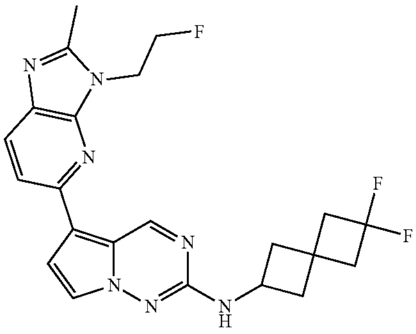 [SMILES: Cc1nc2ccc(-c3ccn4nc(NC5CC6(C5)CC(F)(F)C6)ncc34)nc2n1CCF]
1062

TABLE 1-continued
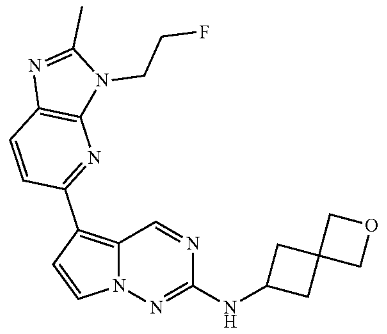 [SMILES: Cc1nc2ccc(-c3ccn4nc(NC5CC6(COC6)C5)ncc34)nc2n1CCF]
1063
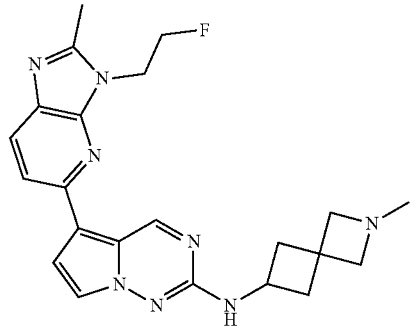 [SMILES: Cc1nc2ccc(-c3ccn4nc(NC5CC6(C5)CN(C)C6)ncc34)nc2n1CCF]
1064
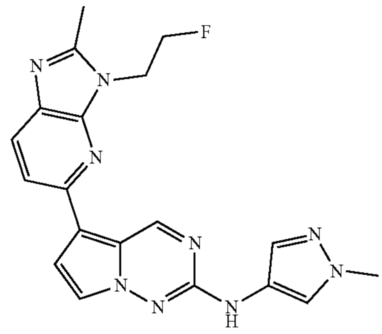 [SMILES: Cc1nc2ccc(-c3ccn4nc(Nc5cnn(C)c5)ncc34)nc2n1CCF]
1065
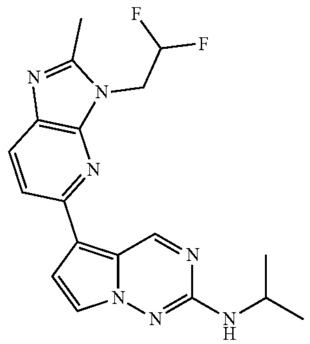 [SMILES: Cc1nc2ccc(-c3ccn4nc(NC(C)C)ncc34)nc2n1CC(F)F]
1066

TABLE 1-continued
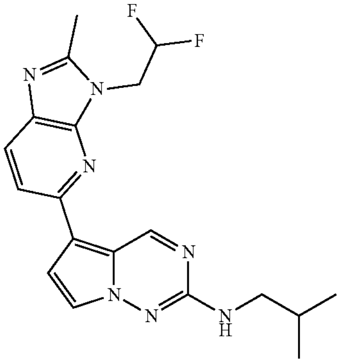 [SMILES: Cc1nc2ccc(-c3ccn4nc(NCC(C)C)ncc34)nc2n1CC(F)F]
1067
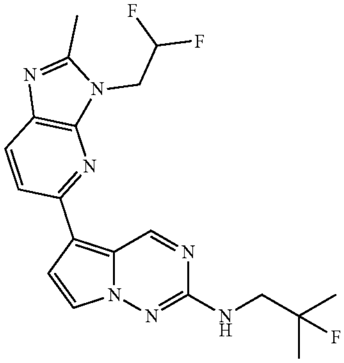 [SMILES: Cc1nc2ccc(-c3ccn4nc(NCC(C)(C)F)ncc34)nc2n1CC(F)F]
1068
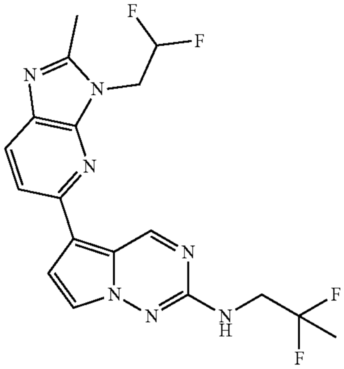 [SMILES: Cc1nc2ccc(-c3ccn4nc(NCC(C)(F)F)ncc34)nc2n1CC(F)F]
1069
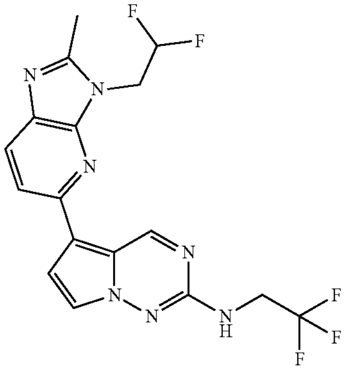
1070

TABLE 1-continued
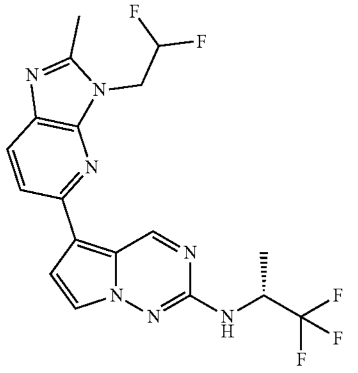 [SMILES: Cc1nc2ccc(-c3ccn4nc(N[C@H](C)C(F)(F)F)ncc34)nc2n1CC(F)F]
1071
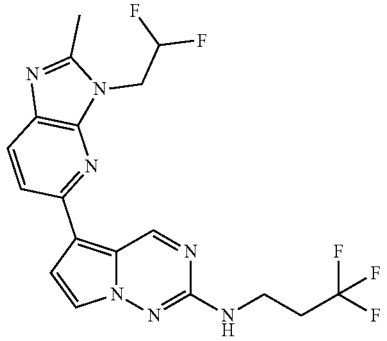 [SMILES: Cc1nc2ccc(-c3ccn4nc(NCCC(F)(F)F)ncc34)nc2n1CC(F)F]
1072
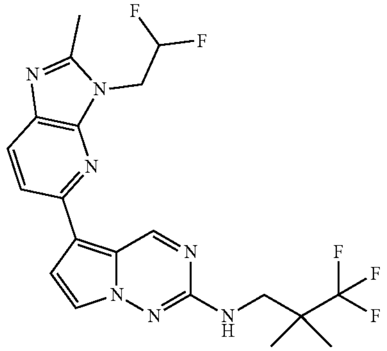 [SMILES: Cc1nc2ccc(-c3ccn4nc(NCC(C)(C)C(F)(F)F)ncc34)nc2n1CC(F)F]
1073
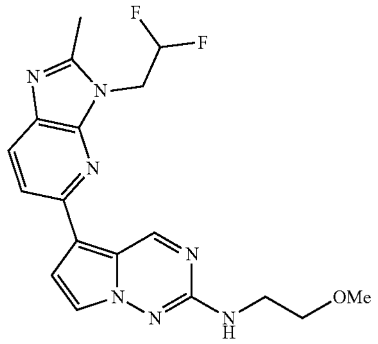 [SMILES: COCCNc1ncc2c(-c3ccc4nc(C)n(CC(F)F)c4n3)ccn2n1]
1074

TABLE 1-continued
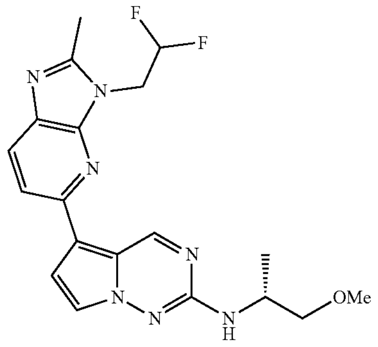 [SMILES: COC[C@@H](C)Nc1ncc2c(-c3ccc4nc(C)n(CC(F)F)c4n3)ccn2n1]
1075
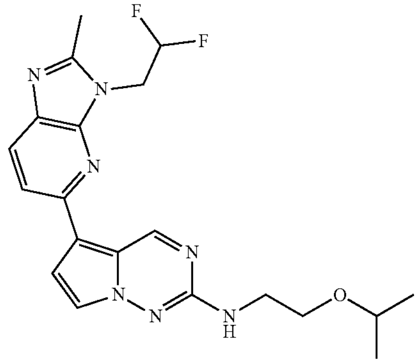 [SMILES: Cc1nc2ccc(-c3ccn4nc(NCCOC(C)C)ncc34)nc2n1CC(F)F]
1076
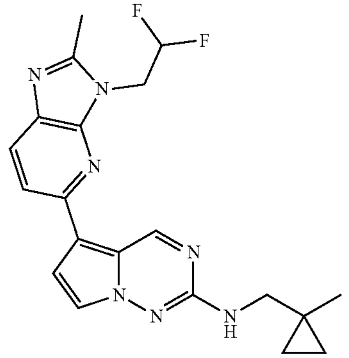 [SMILES: Cc1nc2ccc(-c3ccn4nc(NCC5(C)CC5)ncc34)nc2n1CC(F)F]
1077
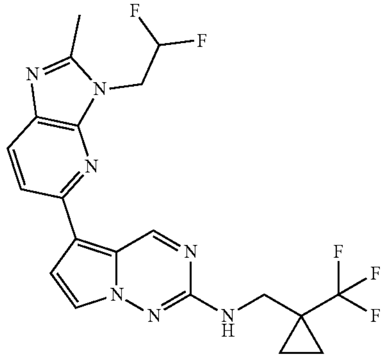 [SMILES: Cc1nc2ccc(-c3ccn4nc(NCC5(C(F)(F)F)CC5)ncc34)nc2n1CC(F)F]
1078

TABLE 1-continued
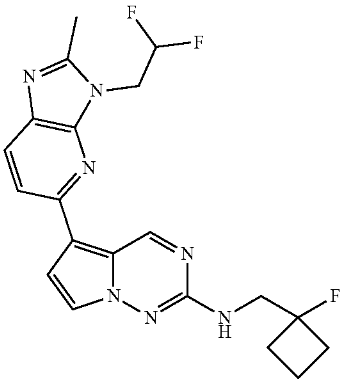 [SMILES: Cc1nc2ccc(-c3ccn4nc(NCC5(F)CCC5)ncc34)nc2n1CC(F)F]
1079
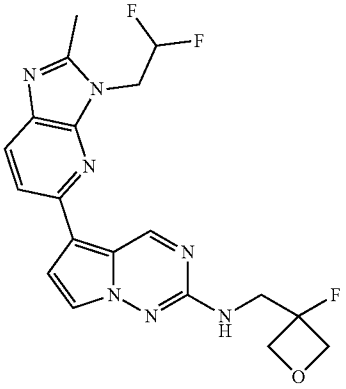 [SMILES: Cc1nc2ccc(-c3ccn4nc(NCC5(F)COC5)ncc34)nc2n1CC(F)F]
1080
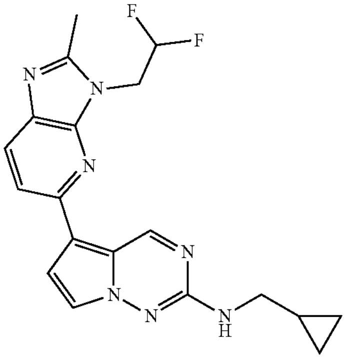 [SMILES: Cc1nc2ccc(-c3ccn4nc(NCC5CC5)ncc34)nc2n1CC(F)F]
1081
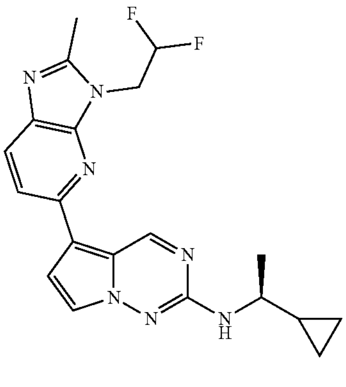 [SMILES: Cc1nc2ccc(-c3ccn4nc(N[C@@H](C)C5CC5)ncc34)nc2n1CC(F)F]
1082

TABLE 1-continued
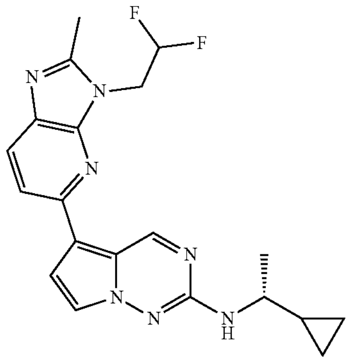 [SMILES: Cc1nc2ccc(-c3ccn4nc(N[C@H](C)C5CC5)ncc34)nc2n1CC(F)F]
1083
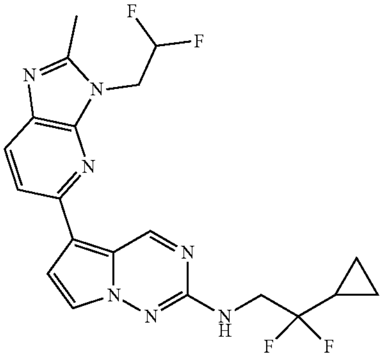 [SMILES: Cc1nc2ccc(-c3ccn4nc(NCC(F)(F)C5CC5)ncc34)nc2n1CC(F)F]
1084
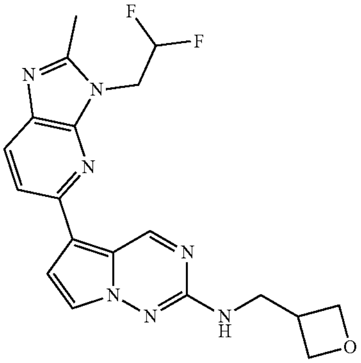 [SMILES: Cc1nc2ccc(-c3ccn4nc(NCC5COC5)ncc34)nc2n1CC(F)F]
1085
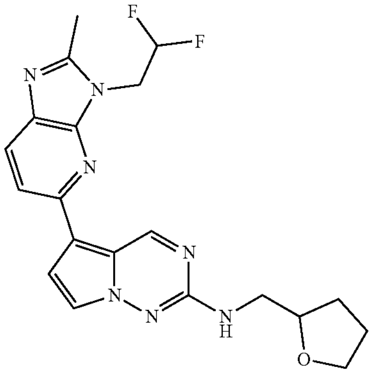 [SMILES: Cc1nc2ccc(-c3ccn4nc(NCC5CCCO5)ncc34)nc2n1CC(F)F]
1086

TABLE 1-continued
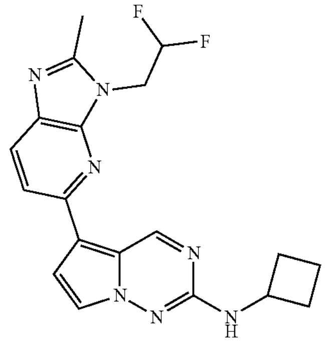 [SMILES: Cc1nc2ccc(-c3ccn4nc(NC5CCC5)ncc34)nc2n1CC(F)F]
1087
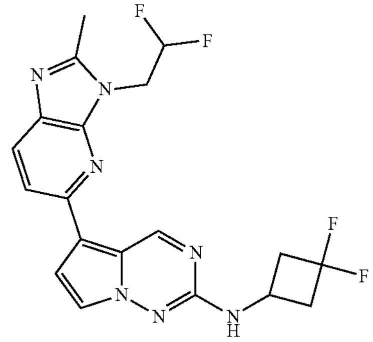 [SMILES: Cc1nc2ccc(-c3ccn4nc(NC5CC(F)(F)C5)ncc34)nc2n1CC(F)F]
1088
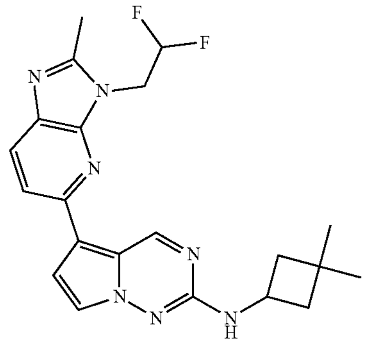 [SMILES: Cc1nc2ccc(-c3ccn4nc(NC5CC(C)(C)C5)ncc34)nc2n1CC(F)F]
1089
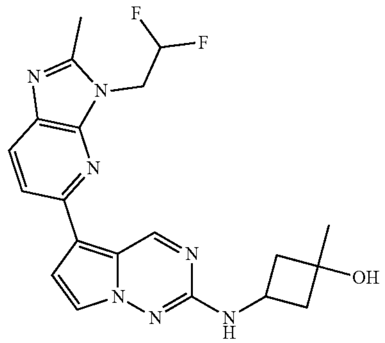 [SMILES: Cc1nc2ccc(-c3ccn4nc(NC5CC(C)(O)C5)ncc34)nc2n1CC(F)F]
1090

TABLE 1-continued
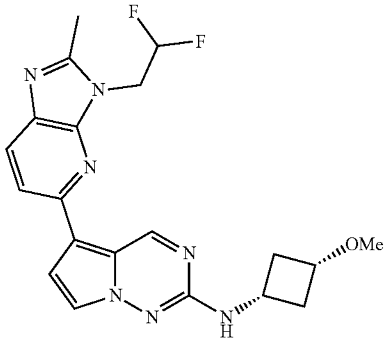 [SMILES: CO[C@H]1C[C@@H](Nc2ncc3c(-c4ccc5nc(C)n(CC(F)F)c5n4)ccn3n2)C1]
1091
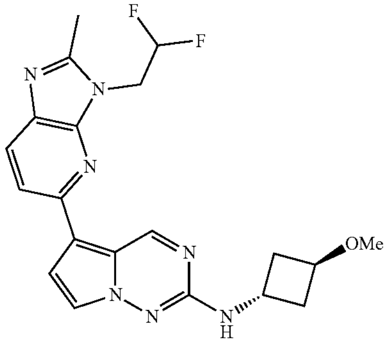 [SMILES: CO[C@H]1C[C@H](Nc2ncc3c(-c4ccc5nc(C)n(CC(F)F)c5n4)ccn3n2)C1]
1092
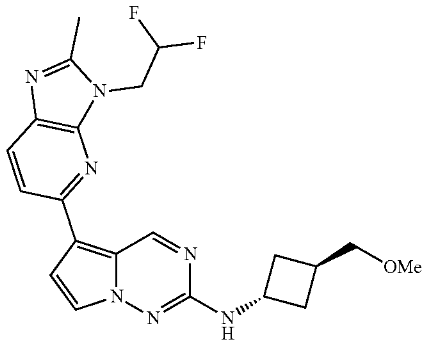 [SMILES: COC[C@H]1C[C@H](Nc2ncc3c(-c4ccc5nc(C)n(CC(F)F)c5n4)ccn3n2)C1]
1093
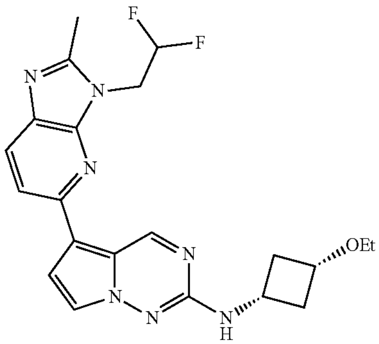 [SMILES: CCO[C@H]1C[C@@H](Nc2ncc3c(-c4ccc5nc(C)n(CC(F)F)c5n4)ccn3n2)C1]
1094

TABLE 1-continued
1095
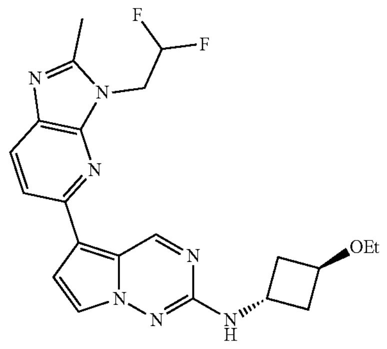 [SMILES: CCO[C@H]1C[C@H](Nc2ncc3c(-c4ccc5nc(C)n(CC(F)F)c5n4)ccn3n2)C1]
1096
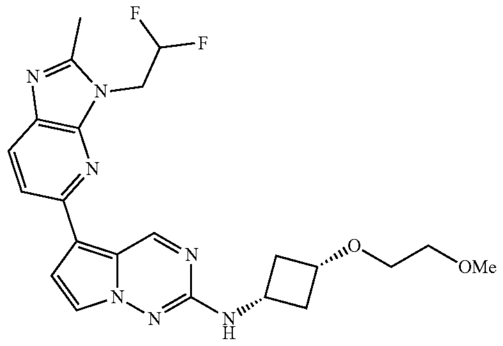 [SMILES: COCCO[C@H]1C[C@@H](Nc2ncc3c(-c4ccc5nc(C)n(CC(F)F)c5n4)ccn3n2)C1]
1097
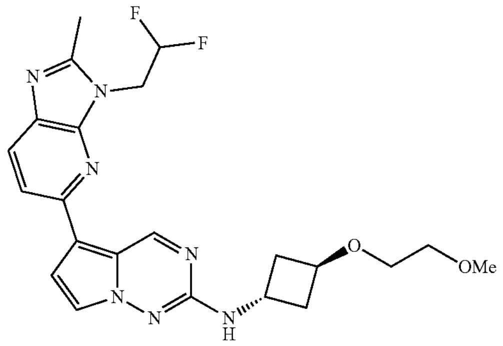 [SMILES: COCCO[C@H]1C[C@H](Nc2ncc3c(-c4ccc5nc(C)n(CC(F)F)c5n4)ccn3n2)C1]
1098
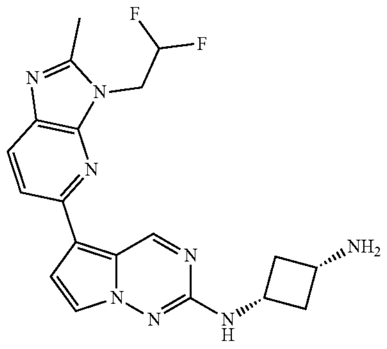 [SMILES: Cc1nc2ccc(-c3ccn4nc(N[C@H]5C[C@@H](N)C5)ncc34)nc2n1CC(F)F]

TABLE 1-continued
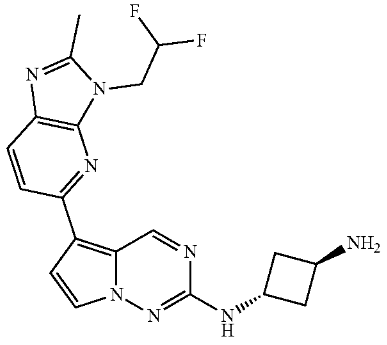 [SMILES: Cc1nc2ccc(-c3ccn4nc(N[C@H]5C[C@H](N)C5)ncc34)nc2n1CC(F)F]
1099
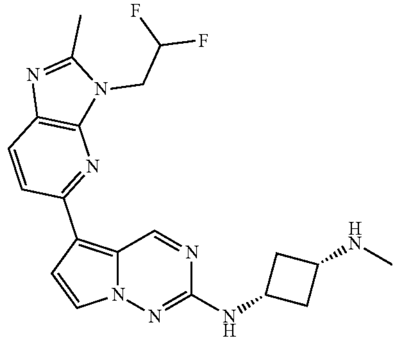 [SMILES: CN[C@H]1C[C@@H](Nc2ncc3c(-c4ccc5nc(C)n(CC(F)F)c5n4)ccn3n2)C1]
1100
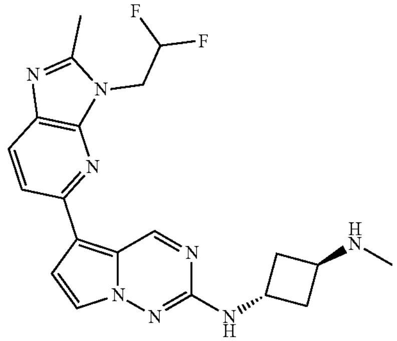 [SMILES: CN[C@H]1C[C@H](Nc2ncc3c(-c4ccc5nc(C)n(CC(F)F)c5n4)ccn3n2)C1]
1101
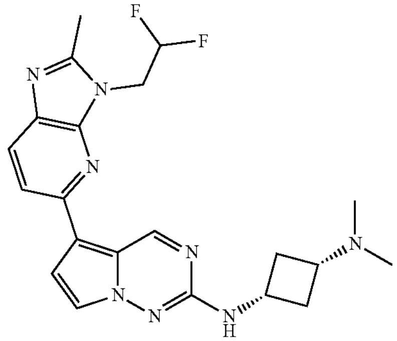 [SMILES: Cc1nc2ccc(-c3ccn4nc(N[C@H]5C[C@@H](N(C)C)C5)ncc34)nc2n1CC(F)F]
1102

TABLE 1-continued
1103
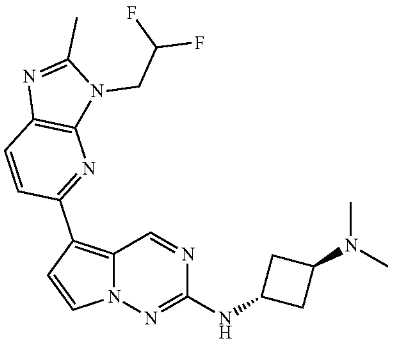 [SMILES: Cc1nc2ccc(-c3ccn4nc(N[C@H]5C[C@H](N(C)C)C5)ncc34)nc2n1CC(F)F]
1104
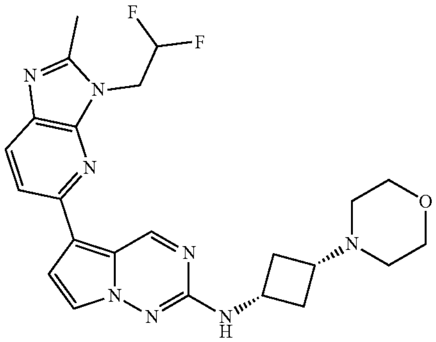 [SMILES: Cc1nc2ccc(-c3ccn4nc(N[C@H]5C[C@@H](N6CCOCC6)C5)ncc34)nc2n1CC(F)F]
1105
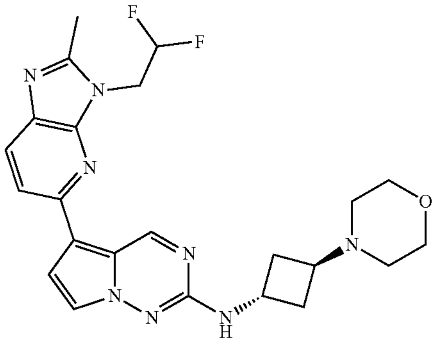 [SMILES: Cc1nc2ccc(-c3ccn4nc(N[C@H]5C[C@H](N6CCOCC6)C5)ncc34)nc2n1CC(F)F]
1106
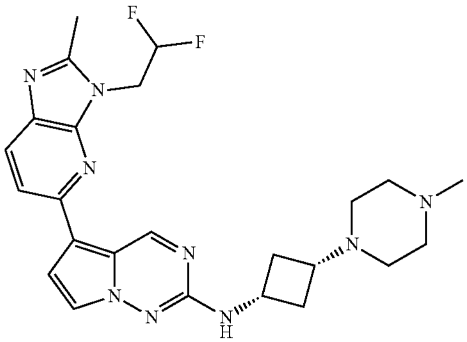 [SMILES: Cc1nc2ccc(-c3ccn4nc(N[C@H]5C[C@@H](N6CCN(C)CC6)C5)ncc34)nc2n1CC(F)F]

TABLE 1-continued
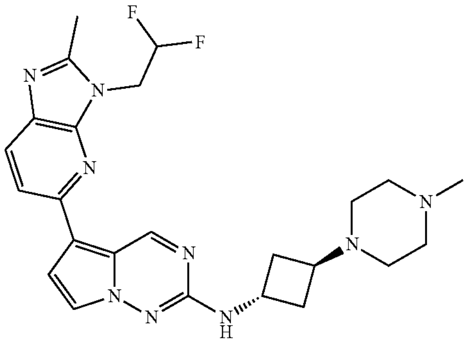 [SMILES: Cc1nc2ccc(-c3ccn4nc(N[C@H]5C[C@H](N6CCN(C)CC6)C5)ncc34)nc2n1CC(F)F]
1107
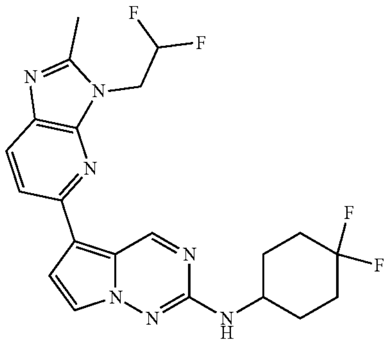 [SMILES: Cc1nc2ccc(-c3ccn4nc(NC5CCC(F)(F)CC5)ncc34)nc2n1CC(F)F]
1108
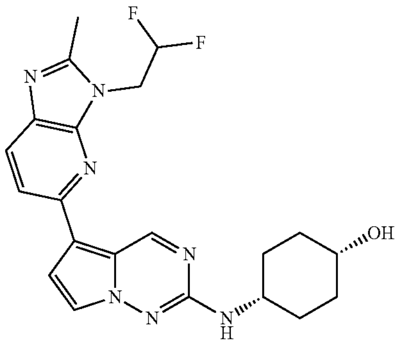 [SMILES: Cc1nc2ccc(-c3ccn4nc(N[C@H]5CC[C@@H](O)CC5)ncc34)nc2n1CC(F)F]
1109
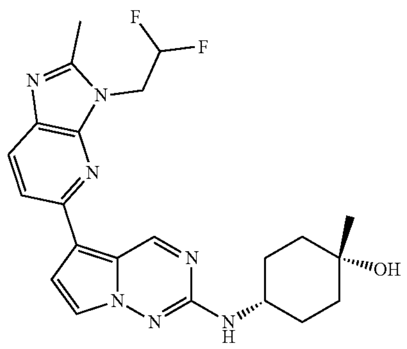 [SMILES: Cc1nc2ccc(-c3ccn4nc(N[C@H]5CC[C@@](C)(O)CC5)ncc34)nc2n1CC(F)F]
1110

TABLE 1-continued
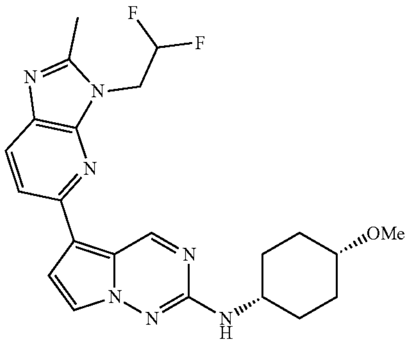 [SMILES: CO[C@H]1CC[C@@H](Nc2ncc3c(-c4ccc5nc(C)n(CC(F)F)c5n4)ccn3n2)CC1]
1111
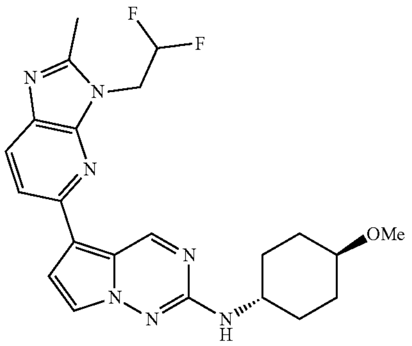 [SMILES: CO[C@H]1CC[C@H](Nc2ncc3c(-c4ccc5nc(C)n(CC(F)F)c5n4)ccn3n2)CC1]
1112
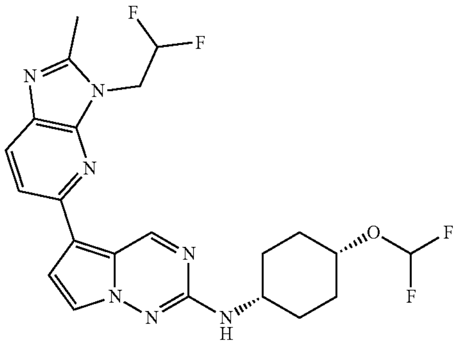 [SMILES: Cc1nc2ccc(-c3ccn4nc(N[C@H]5CC[C@@H](OC(F)F)CC5)ncc34)nc2n1CC(F)F]
1113
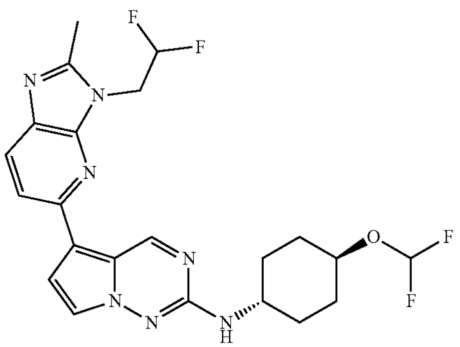 [SMILES: Cc1nc2ccc(-c3ccn4nc(N[C@H]5CC[C@H](OC(F)F)CC5)ncc34)nc2n1CC(F)F]
1114

TABLE 1-continued
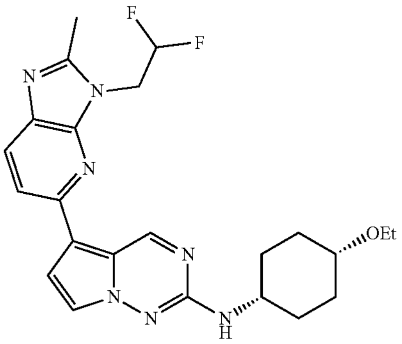 [SMILES: CCO[C@H]1CC[C@@H](Nc2ncc3c(-c4ccc5nc(C)n(CC(F)F)c5n4)ccn3n2)CC1]
1115
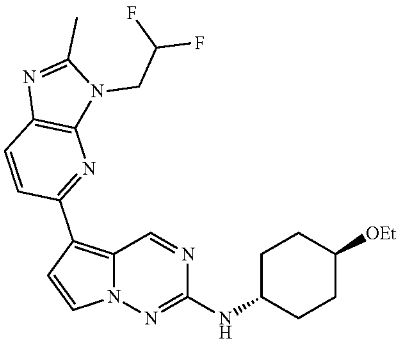 [SMILES: CCO[C@H]1CC[C@H](Nc2ncc3c(-c4ccc5nc(C)n(CC(F)F)c5n4)ccn3n2)CC1]
1116
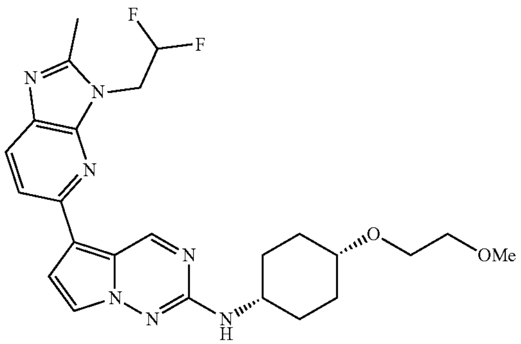 [SMILES: COCCO[C@H]1CC[C@@H](Nc2ncc3c(-c4ccc5nc(C)n(CC(F)F)c5n4)ccn3n2)CC1]
1117
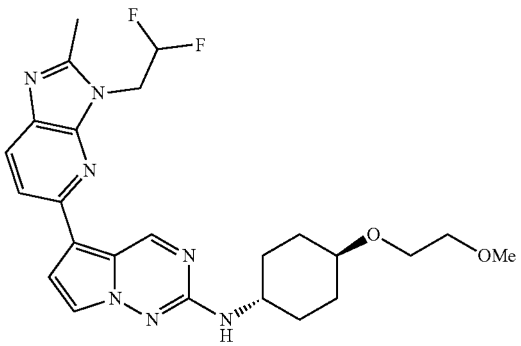 [SMILES: COCCO[C@H]1CC[C@H](Nc2ncc3c(-c4ccc5nc(C)n(CC(F)F)c5n4)ccn3n2)CC1]
1118

TABLE 1-continued
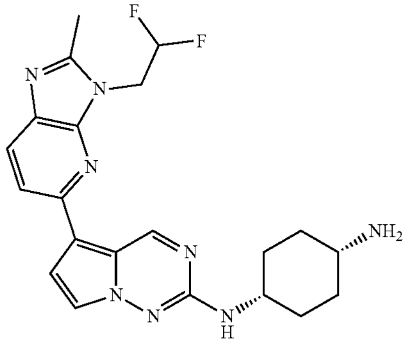 [SMILES: Cc1nc2ccc(-c3ccn4nc(N[C@H]5CC[C@@H](N)CC5)ncc34)nc2n1CC(F)F]
1119
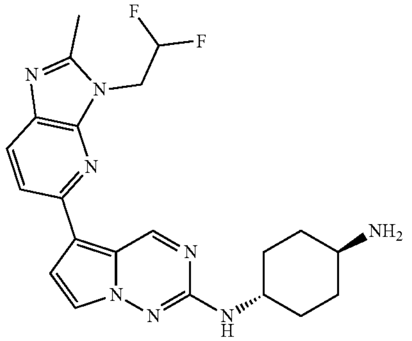 [SMILES: Cc1nc2ccc(-c3ccn4nc(N[C@H]5CC[C@H](N)CC5)ncc34)nc2n1CC(F)F]
1120
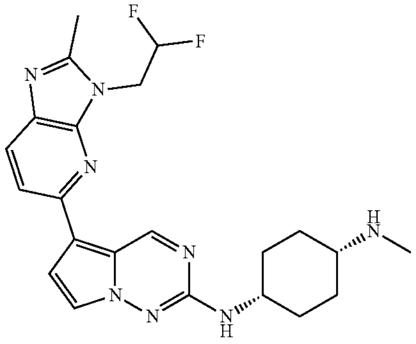 [SMILES: CN[C@H]1CC[C@@H](Nc2ncc3c(-c4ccc5nc(C)n(CC(F)F)c5n4)ccn3n2)CC1]
1121
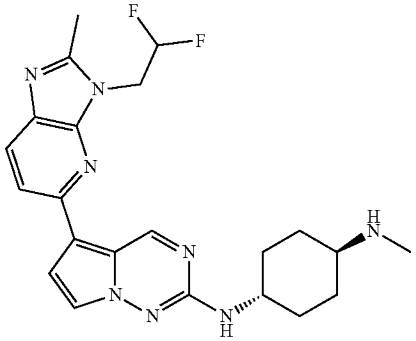 [SMILES: CN[C@H]1CC[C@H](Nc2ncc3c(-c4ccc5nc(C)n(CC(F)F)c5n4)ccn3n2)CC1]
1122

TABLE 1-continued
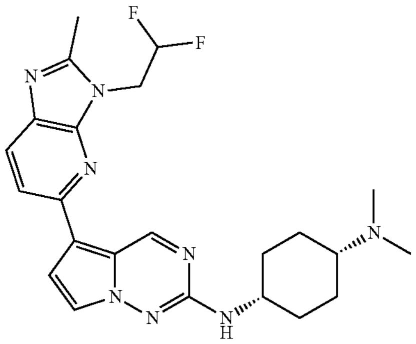 [SMILES: Cc1nc2ccc(-c3ccn4nc(N[C@H]5CC[C@@H](N(C)C)CC5)ncc34)nc2n1CC(F)F]
1123
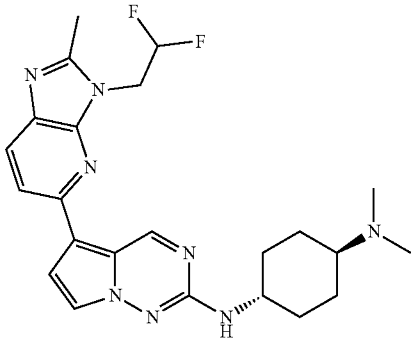 [SMILES: Cc1nc2ccc(-c3ccn4nc(N[C@H]5CC[C@H](N(C)C)CC5)ncc34)nc2n1CC(F)F]
1124
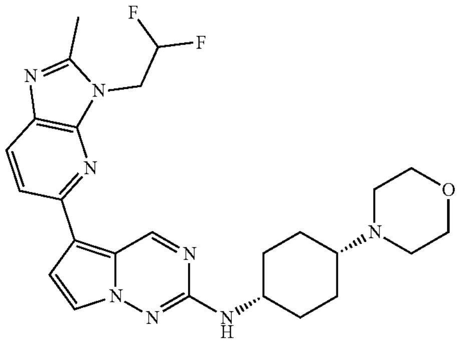 [SMILES: Cc1nc2ccc(-c3ccn4nc(N[C@H]5CC[C@@H](N6CCOCC6)CC5)ncc34)nc2n1CC(F)F]
1125
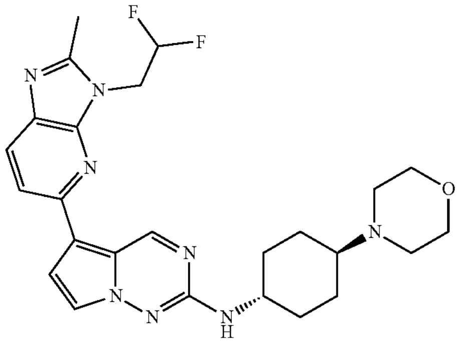 [SMILES: Cc1nc2ccc(-c3ccn4nc(N[C@H]5CC[C@H](N6CCOCC6)CC5)ncc34)nc2n1CC(F)F]
1126

TABLE 1-continued
1127
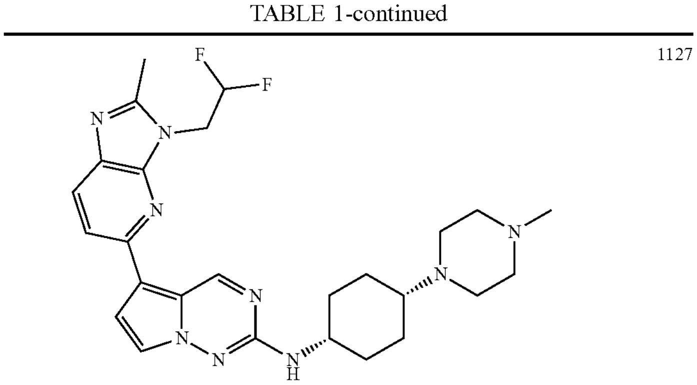
1128
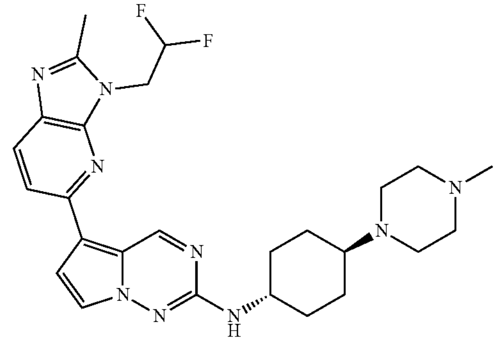 [SMILES: Cc1nc2ccc(-c3ccn4nc(N[C@H]5CC[C@H](N6CCN(C)CC6)CC5)ncc34)nc2n1CC(F)F]
1129
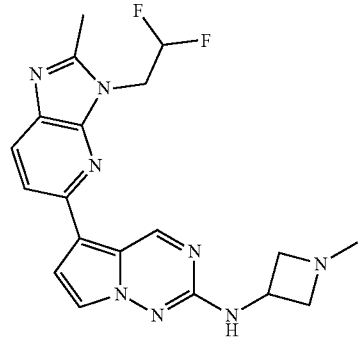 [SMILES: Cc1nc2ccc(-c3ccn4nc(NC5CN(C)C5)ncc34)nc2n1CC(F)F]
1130
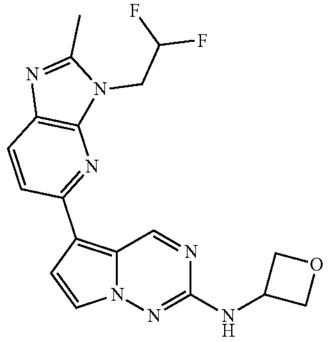 [SMILES: Cc1nc2ccc(-c3ccn4nc(NC5COC5)ncc34)nc2n1CC(F)F]

TABLE 1-continued
1131
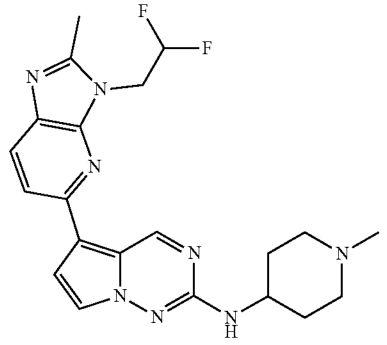 [SMILES: Cc1nc2ccc(-c3ccn4nc(NC5CCN(C)CC5)ncc34)nc2n1CC(F)F]
1132
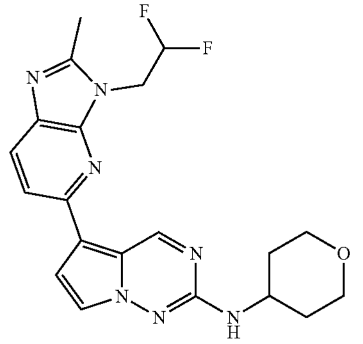 [SMILES: Cc1nc2ccc(-c3ccn4nc(NC5CCOCC5)ncc34)nc2n1CC(F)F]
1133
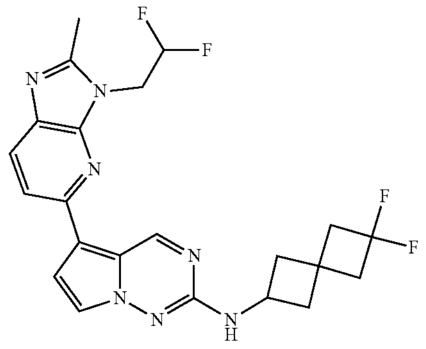 [SMILES: Cc1nc2ccc(-c3ccn4nc(NC5CC6(C5)CC(F)(F)C6)ncc34)nc2n1CC(F)F]
1134
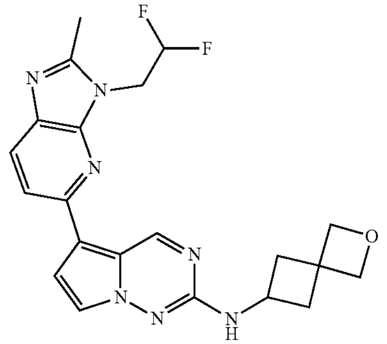 [SMILES: Cc1nc2ccc(-c3ccn4nc(NC5CC6(COC6)C5)ncc34)nc2n1CC(F)F]

TABLE 1-continued
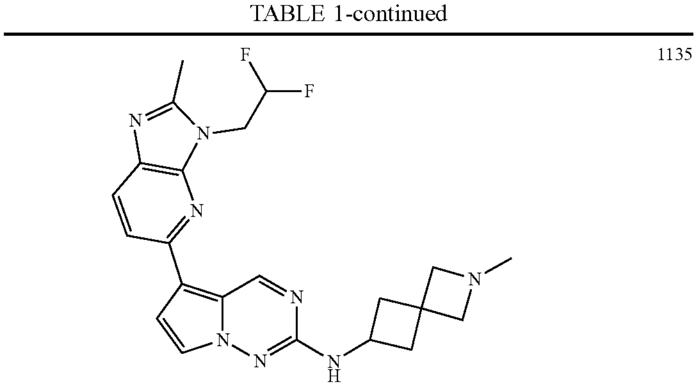
1135
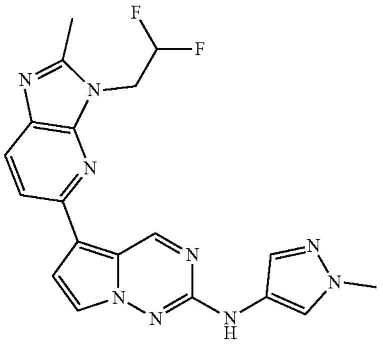 [SMILES: Cc1nc2ccc(-c3ccn4nc(Nc5cnn(C)c5)ncc34)nc2n1CC(F)F]
1136
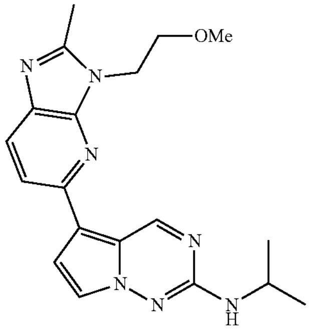 [SMILES: COCCn1c(C)nc2ccc(-c3ccn4nc(NC(C)C)ncc34)nc21]
1137
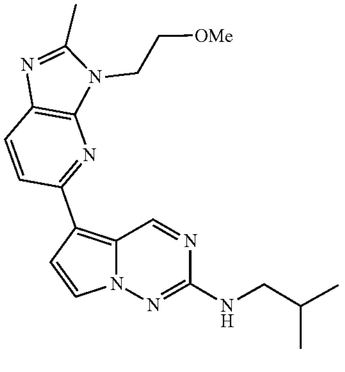 [SMILES: COCCn1c(C)nc2ccc(-c3ccn4nc(NCC(C)C)ncc34)nc21]
1138

TABLE 1-continued
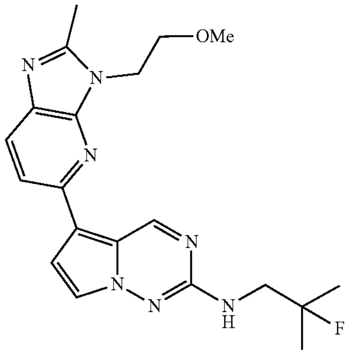 [SMILES: COCCn1c(C)nc2ccc(-c3ccn4nc(NCC(C)(C)F)ncc34)nc21]
1139
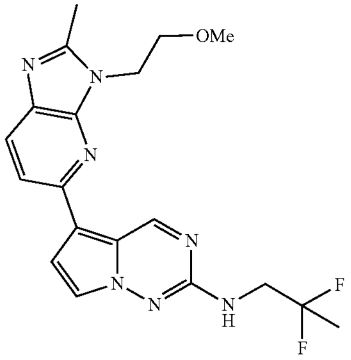 [SMILES: COCCn1c(C)nc2ccc(-c3ccn4nc(NCC(C)(F)F)ncc34)nc21]
1140
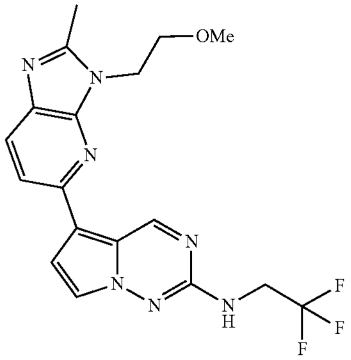 [SMILES: COCCn1c(C)nc2ccc(-c3ccn4nc(NCC(F)(F)F)ncc34)nc21]
1141
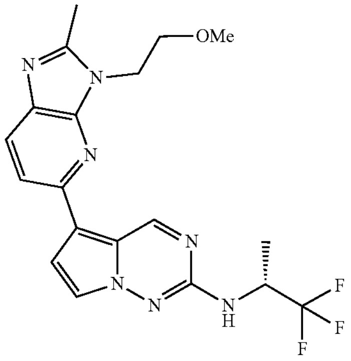 [SMILES: COCCn1c(C)nc2ccc(-c3ccn4nc(N[C@H](C)C(F)(F)F)ncc34)nc21]
1142

TABLE 1-continued
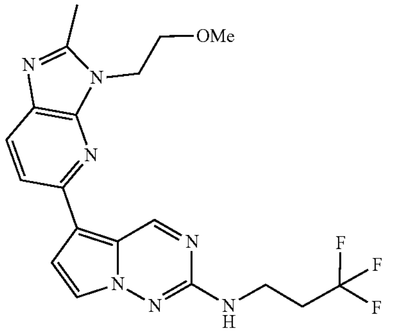 [SMILES: COCCn1c(C)nc2ccc(-c3ccn4nc(NCCC(F)(F)F)ncc34)nc21]
1143
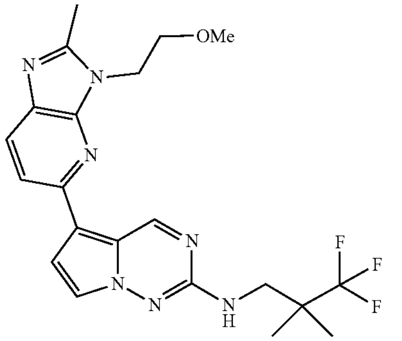 [SMILES: COCCn1c(C)nc2ccc(-c3ccn4nc(NCC(C)(C)C(F)(F)F)ncc34)nc21]
1144
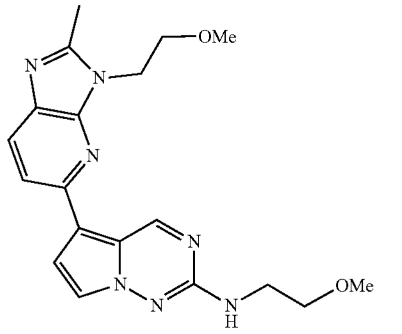 [SMILES: COCCNc1ncc2c(-c3ccc4nc(C)n(CCOC)c4n3)ccn2n1]
1145
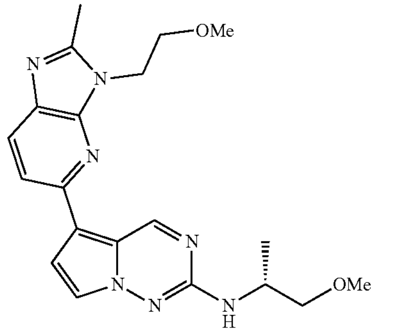 [SMILES: COCCn1c(C)nc2ccc(-c3ccn4nc(N[C@H](C)COC)ncc34)nc21]
1146

TABLE 1-continued
1147
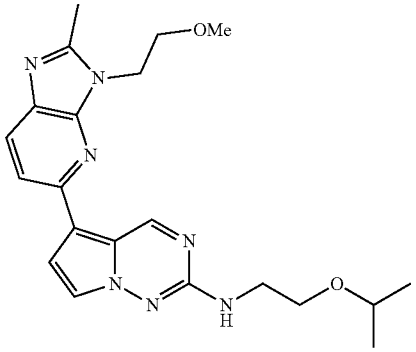 [SMILES: COCCn1c(C)nc2ccc(-c3ccn4nc(NCCOC(C)C)ncc34)nc21]
1148
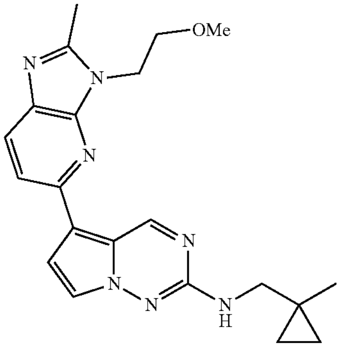 [SMILES: COCCn1c(C)nc2ccc(-c3ccn4nc(NCC5(C)CC5)ncc34)nc21]
1149
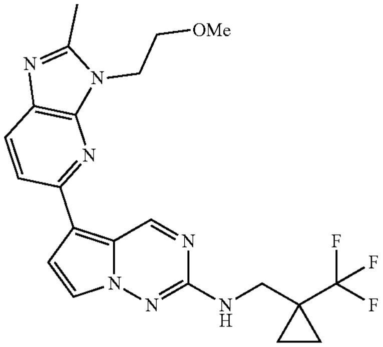 [SMILES: COCCn1c(C)nc2ccc(-c3ccn4nc(NCC5(C(F)(F)F)CC5)ncc34)nc21]
1150
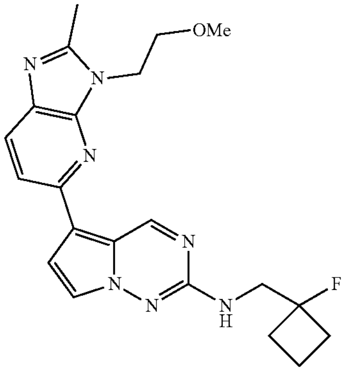 [SMILES: COCCn1c(C)nc2ccc(-c3ccn4nc(NCC5(F)CCC5)ncc34)nc21]

TABLE 1-continued
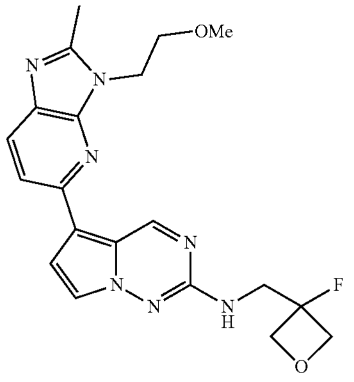 [SMILES: COCCn1c(C)nc2ccc(-c3ccn4nc(NCC5(F)COC5)ncc34)nc21]
1151
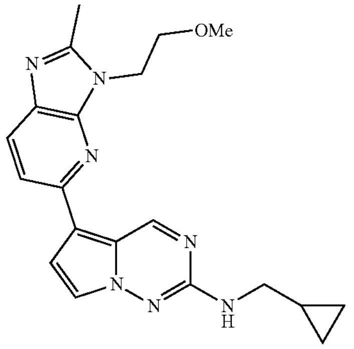 [SMILES: COCCn1c(C)nc2ccc(-c3ccn4nc(NCC5CC5)ncc34)nc21]
1152
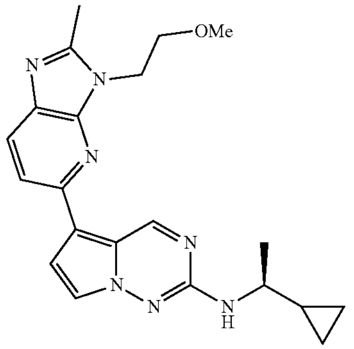 [SMILES: COCCn1c(C)nc2ccc(-c3ccn4nc(N[C@@H](C)C5CC5)ncc34)nc21]
1153
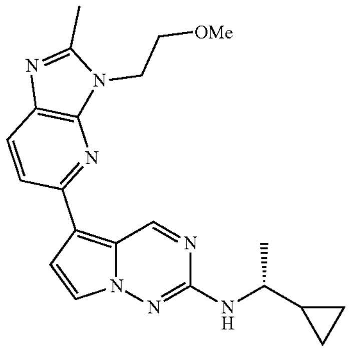 [SMILES: COCCn1c(C)nc2ccc(-c3ccn4nc(N[C@H](C)C5CC5)ncc34)nc21]
1154

TABLE 1-continued
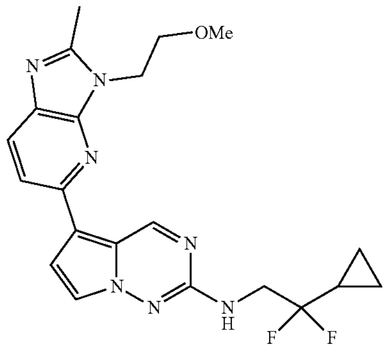 [SMILES: COCCn1c(C)nc2ccc(-c3ccn4nc(NCC(F)(F)C5CC5)ncc34)nc21]
1155
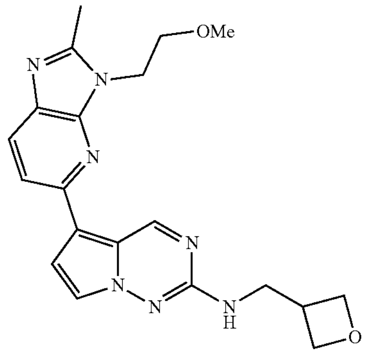 [SMILES: COCCn1c(C)nc2ccc(-c3ccn4nc(NCC5COC5)ncc34)nc21]
1156
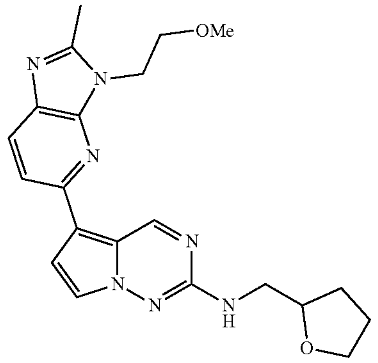 [SMILES: COCCn1c(C)nc2ccc(-c3ccn4nc(NCC5CCCO5)ncc34)nc21]
1157
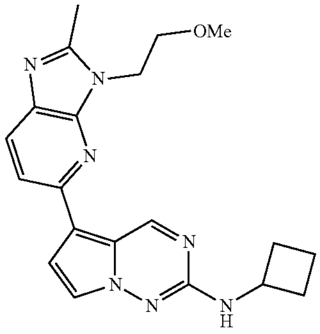 [SMILES: COCCn1c(C)nc2ccc(-c3ccn4nc(NC5CCC5)ncc34)nc21]
1158

TABLE 1-continued
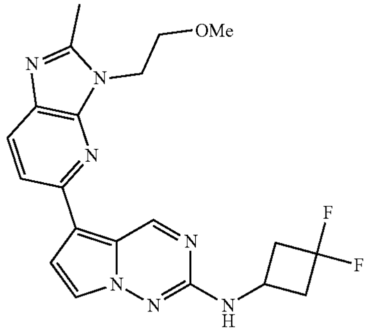 [SMILES: COCCn1c(C)nc2ccc(-c3ccn4nc(NC5CC(F)(F)C5)ncc34)nc21]
1159
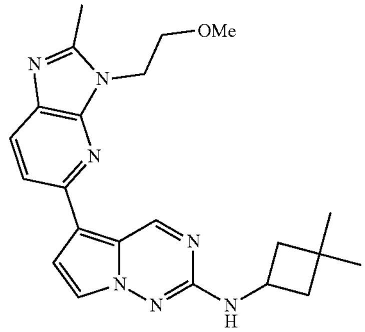 [SMILES: COCCn1c(C)nc2ccc(-c3ccn4nc(NC5CC(C)(C)C5)ncc34)nc21]
1160
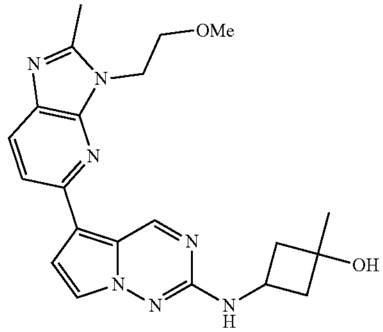 [SMILES: COCCn1c(C)nc2ccc(-c3ccn4nc(NC5CC(C)(O)C5)ncc34)nc21]
1161
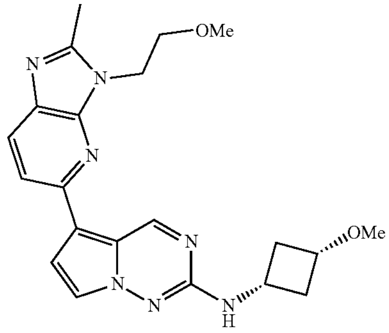 [SMILES: COCCn1c(C)nc2ccc(-c3ccn4nc(N[C@H]5C[C@@H](OC)C5)ncc34)nc21]
1162

TABLE 1-continued
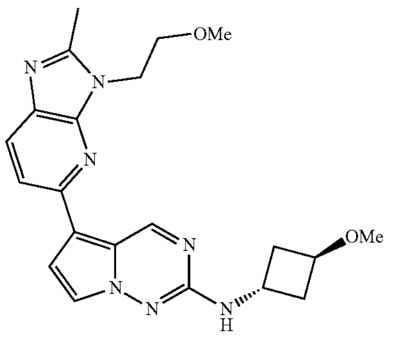 [SMILES: COCCn1c(C)nc2ccc(-c3ccn4nc(N[C@H]5C[C@H](OC)C5)ncc34)nc21]
1163
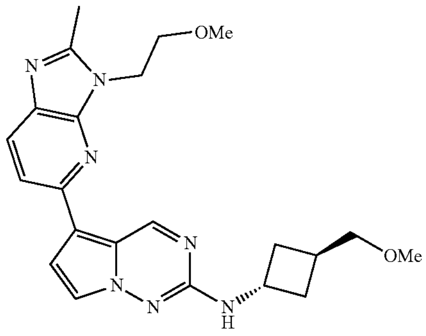 [SMILES: COCCn1c(C)nc2ccc(-c3ccn4nc(N[C@H]5C[C@H](COC)C5)ncc34)nc21]
1164
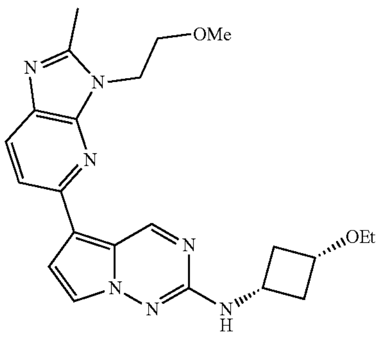 [SMILES: CCO[C@H]1C[C@@H](Nc2ncc3c(-c4ccc5nc(C)n(CCOC)c5n4)ccn3n2)C1]
1165
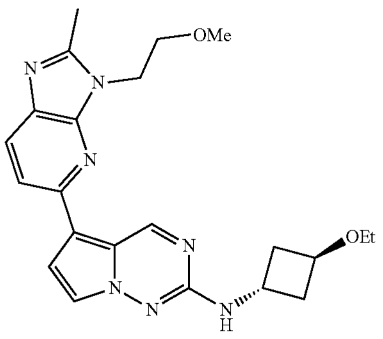 [SMILES: CCO[C@H]1C[C@H](Nc2ncc3c(-c4ccc5nc(C)n(CCOC)c5n4)ccn3n2)C1]
1166

TABLE 1-continued
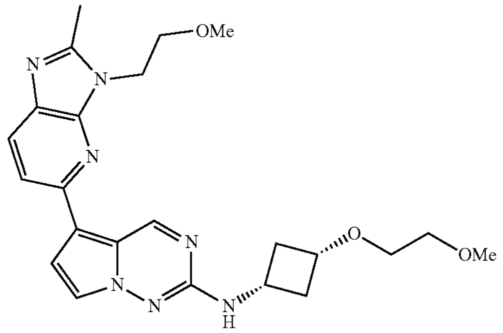 [SMILES: COCCO[C@H]1C[C@@H](Nc2ncc3c(-c4ccc5nc(C)n(CCOC)c5n4)ccn3n2)C1]
1167
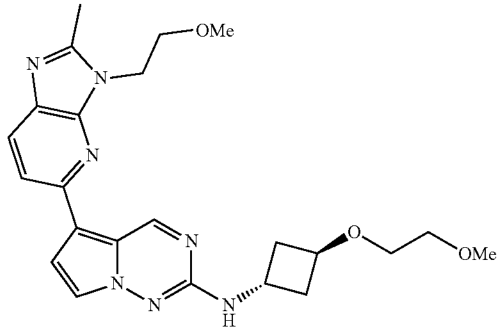 [SMILES: COCCO[C@H]1C[C@H](Nc2ncc3c(-c4ccc5nc(C)n(CCOC)c5n4)ccn3n2)C1]
1168
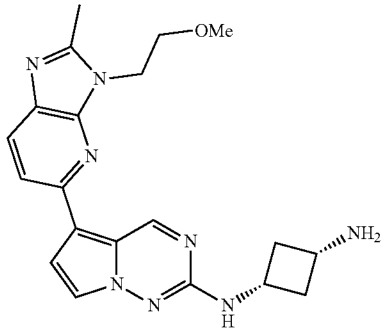 [SMILES: COCCn1c(C)nc2ccc(-c3ccn4nc(N[C@H]5C[C@@H](N)C5)ncc34)nc21]
1169
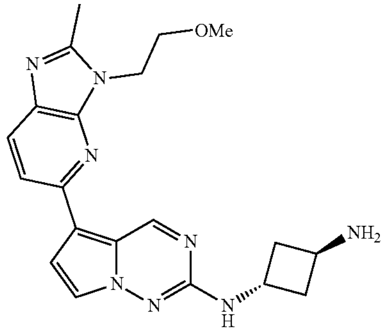 [SMILES: COCCn1c(C)nc2ccc(-c3ccn4nc(N[C@H]5C[C@H](N)C5)ncc34)nc21]
1170

TABLE 1-continued
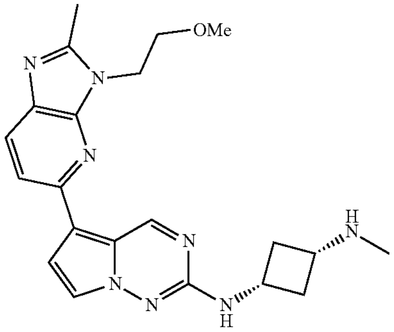 [SMILES: CN[C@H]1C[C@@H](Nc2ncc3c(-c4ccc5nc(C)n(CCOC)c5n4)ccn3n2)C1]
1171
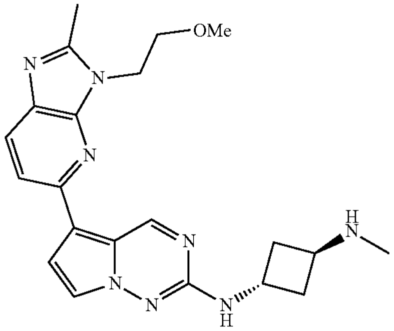 [SMILES: CN[C@H]1C[C@H](Nc2ncc3c(-c4ccc5nc(C)n(CCOC)c5n4)ccn3n2)C1]
1172
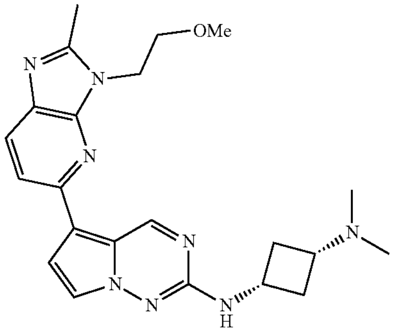 [SMILES: COCCn1c(C)nc2ccc(-c3ccn4nc(N[C@H]5C[C@@H](N(C)C)C5)ncc34)nc21]
1173
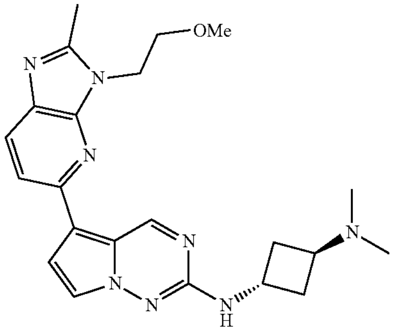 [SMILES: COCCn1c(C)nc2ccc(-c3ccn4nc(N[C@H]5C[C@H](N(C)C)C5)ncc34)nc21]
1174

TABLE 1-continued
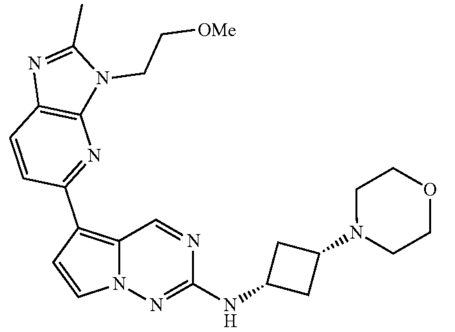 [SMILES: COCCn1c(C)nc2ccc(-c3ccn4nc(N[C@H]5C[C@@H](N6CCOCC6)C5)ncc34)nc21]
1175
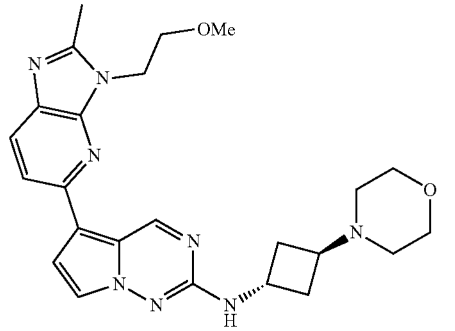 [SMILES: COCCn1c(C)nc2ccc(-c3ccn4nc(N[C@H]5C[C@H](N6CCOCC6)C5)ncc34)nc21]
1176
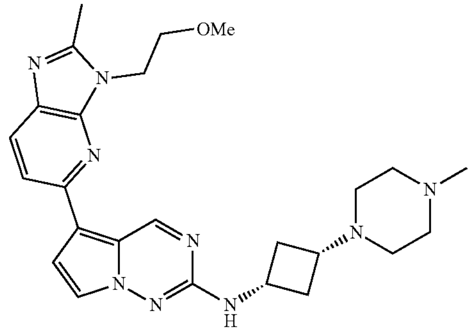 [SMILES: COCCn1c(C)nc2ccc(-c3ccn4nc(N[C@H]5C[C@@H](N6CCN(C)CC6)C5)ncc34)nc21]
1177
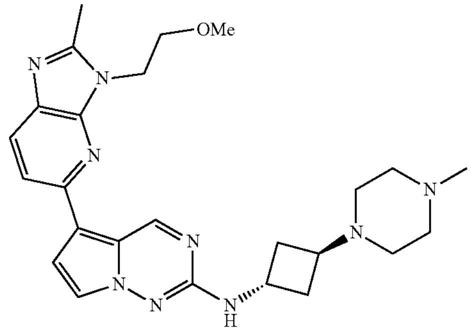 [SMILES: COCCn1c(C)nc2ccc(-c3ccn4nc(N[C@H]5C[C@H](N6CCN(C)CC6)C5)ncc34)nc21]
1178

TABLE 1-continued
1179
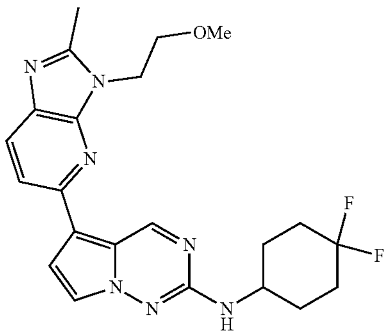 [SMILES: COCCn1c(C)nc2ccc(-c3ccn4nc(NC5CCC(F)(F)CC5)ncc34)nc21]
1180
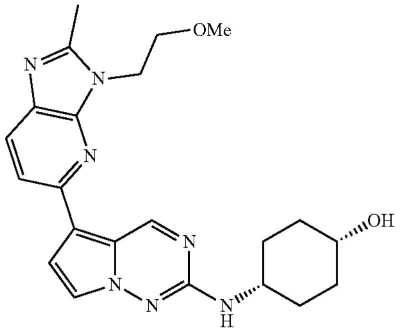 [SMILES: COCCn1c(C)nc2ccc(-c3ccn4nc(N[C@H]5CC[C@@H](O)CC5)ncc34)nc21]
1181
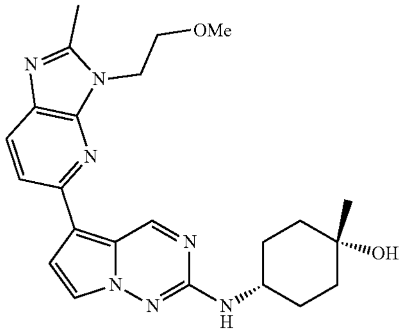 [SMILES: COCCn1c(C)nc2ccc(-c3ccn4nc(N[C@H]5CC[C@@](C)(O)CC5)ncc34)nc21]
1182
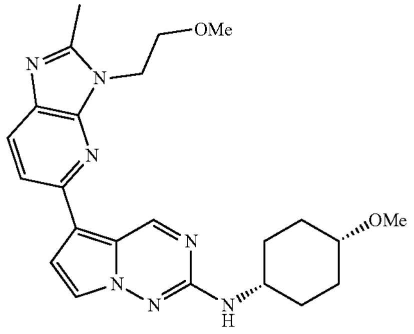 [SMILES: COCCn1c(C)nc2ccc(-c3ccn4nc(N[C@H]5CC[C@@H](OC)CC5)ncc34)nc21]

TABLE 1-continued
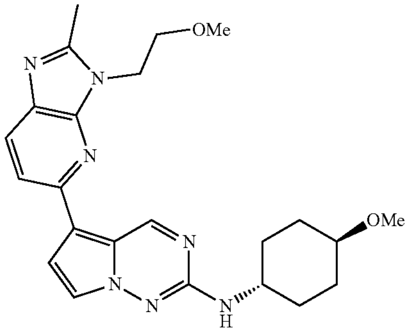 [SMILES: COCCn1c(C)nc2ccc(-c3ccn4nc(N[C@H]5CC[C@H](OC)CC5)ncc34)nc21]
1183
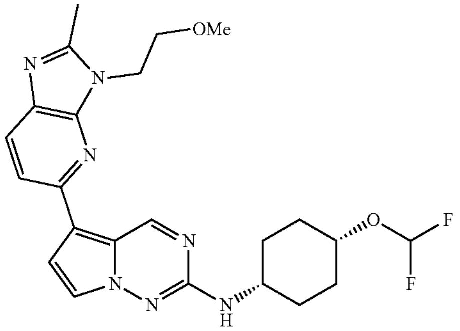 [SMILES: COCCn1c(C)nc2ccc(-c3ccn4nc(N[C@H]5CC[C@@H](OC(F)F)CC5)ncc34)nc21]
1184
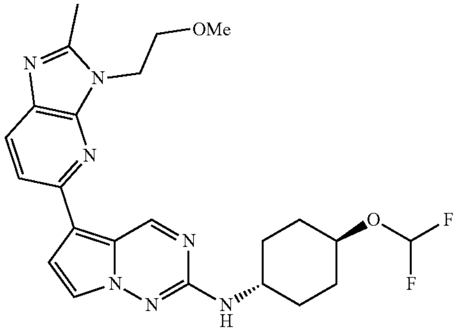 [SMILES: COCCn1c(C)nc2ccc(-c3ccn4nc(N[C@H]5CC[C@H](OC(F)F)CC5)ncc34)nc21]
1185
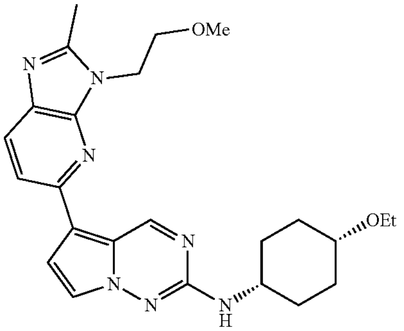 [SMILES: CCO[C@H]1CC[C@@H](Nc2ncc3c(-c4ccc5nc(C)n(CCOC)c5n4)ccn3n2)CC1]
1186

TABLE 1-continued
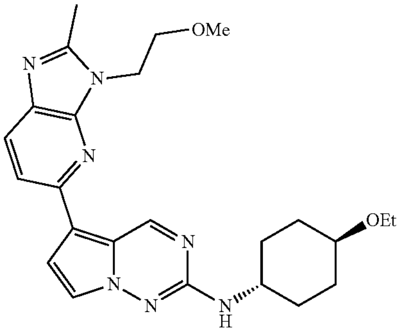 [SMILES: CCO[C@H]1CC[C@H](Nc2ncc3c(-c4ccc5nc(C)n(CCOC)c5n4)ccn3n2)CC1]
1187
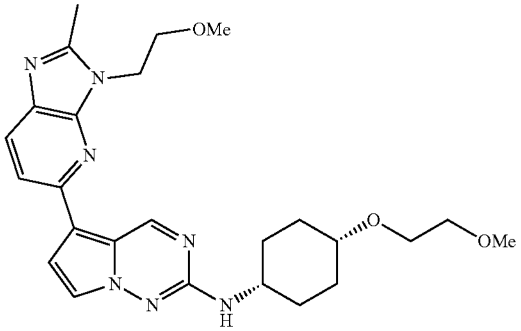 [SMILES: COCCO[C@H]1CC[C@@H](Nc2ncc3c(-c4ccc5nc(C)n(CCOC)c5n4)ccn3n2)CC1]
1188
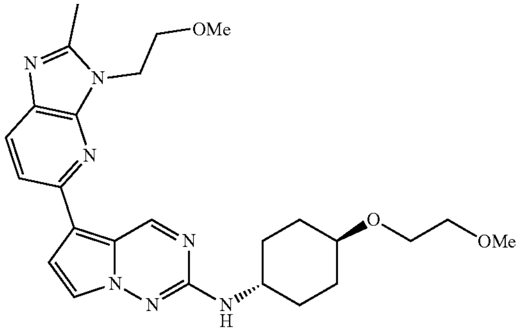 [SMILES: COCCO[C@H]1CC[C@H](Nc2ncc3c(-c4ccc5nc(C)n(CCOC)c5n4)ccn3n2)CC1]
1189
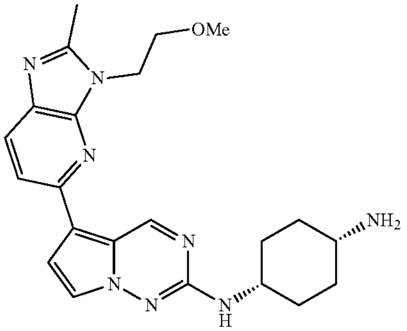 [SMILES: COCCn1c(C)nc2ccc(-c3ccn4nc(N[C@H]5CC[C@@H](N)CC5)ncc34)nc21]
1190

TABLE 1-continued
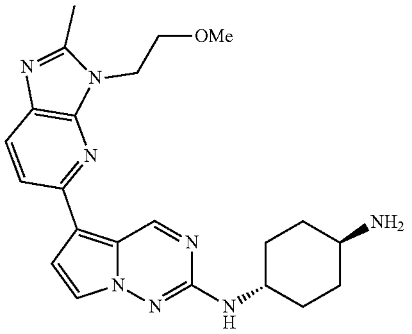 [SMILES: COCCn1c(C)nc2ccc(-c3ccn4nc(N[C@H]5CC[C@H](N)CC5)ncc34)nc21]
1191
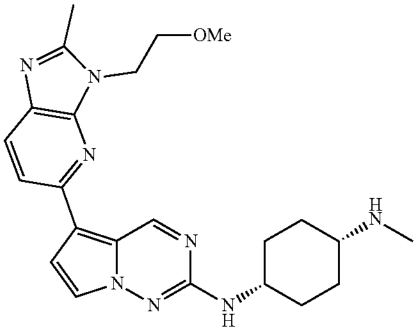
1192
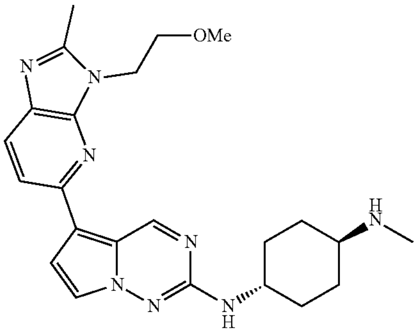
1193
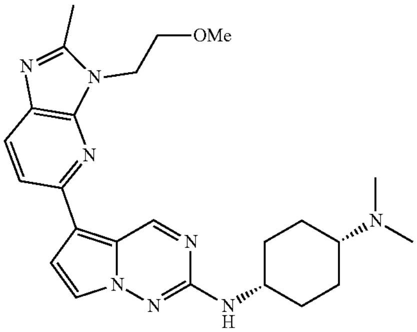 [SMILES: CN[C@H]1CC[C@@H](Nc2ncc3c(-c4ccc5nc(C)n(CCOC)c5n4)ccn3n2)CC1]
1194

TABLE 1-continued
1195
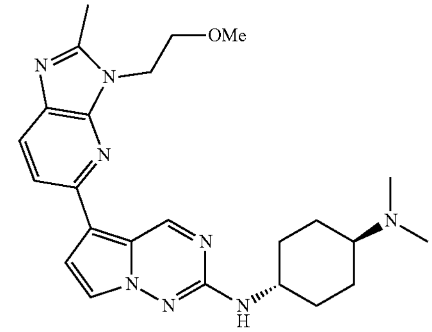 [SMILES: COCCn1c(C)nc2ccc(-c3ccn4nc(N[C@H]5CC[C@H](N(C)C)CC5)ncc34)nc21]
1196
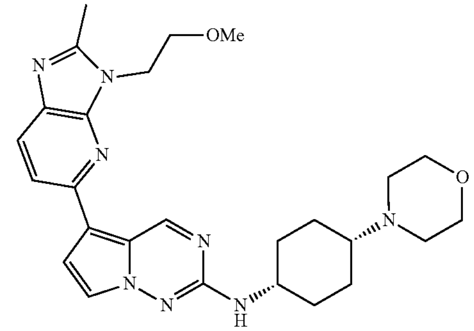 [SMILES: COCCn1c(C)nc2ccc(-c3ccn4nc(N[C@H]5CC[C@@H](N6CCOCC6)CC5)ncc34)nc21]
1197
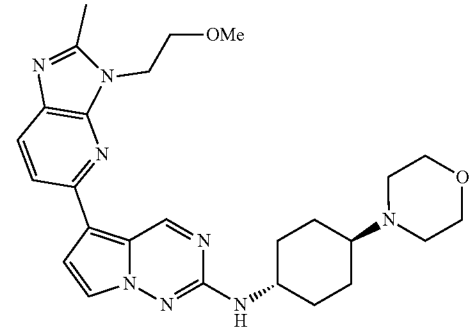 [SMILES: COCCn1c(C)nc2ccc(-c3ccn4nc(N[C@H]5CC[C@H](N6CCOCC6)CC5)ncc34)nc21]
1198
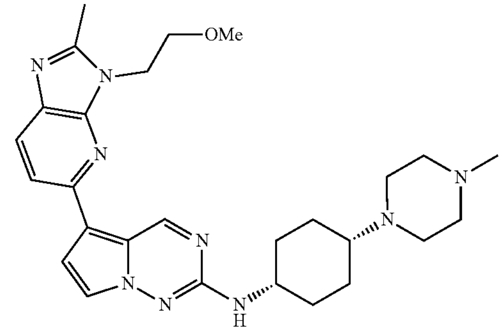 [SMILES: COCCn1c(C)nc2ccc(-c3ccn4nc(N[C@H]5CC[C@@H](N6CCN(C)CC6)CC5)ncc34)nc21]

TABLE 1-continued
1199
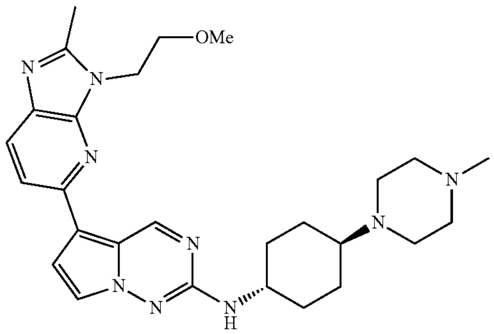 [SMILES: COCCn1c(C)nc2ccc(-c3ccn4nc(N[C@H]5CC[C@H](N6CCN(C)CC6)CC5)ncc34)nc21]
1200
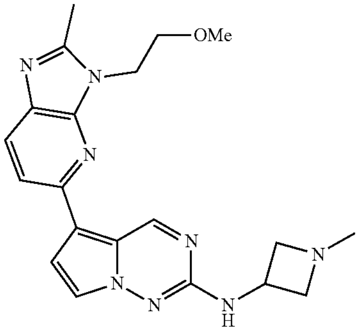 [SMILES: COCCn1c(C)nc2ccc(-c3ccn4nc(NC5CN(C)C5)ncc34)nc21]
1201
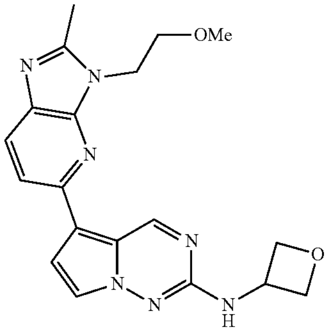 [SMILES: COCCn1c(C)nc2ccc(-c3ccn4nc(NC5COC5)ncc34)nc21]
1202
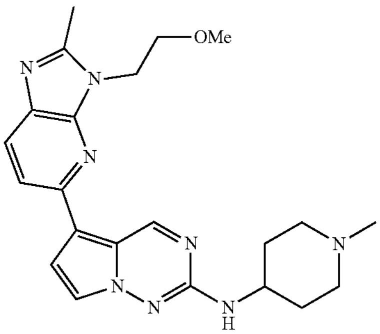 [SMILES: COCCn1c(C)nc2ccc(-c3ccn4nc(NC5CCN(C)CC5)ncc34)nc21]

TABLE 1-continued
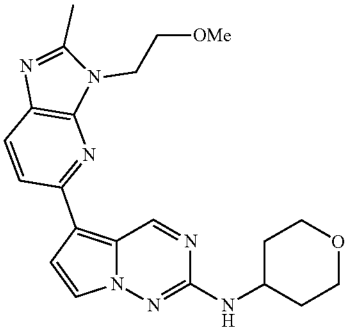 [SMILES: COCCn1c(C)nc2ccc(-c3ccn4nc(NC5CCOCC5)ncc34)nc21]
1203
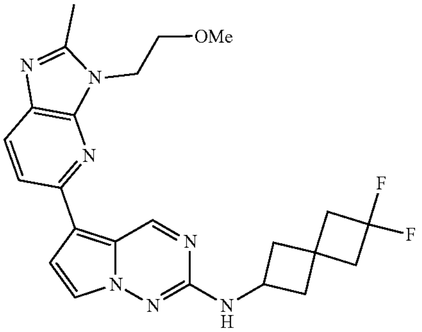 [SMILES: COCCn1c(C)nc2ccc(-c3ccn4nc(NC5CC6(C5)CC(F)(F)C6)ncc34)nc21]
1204
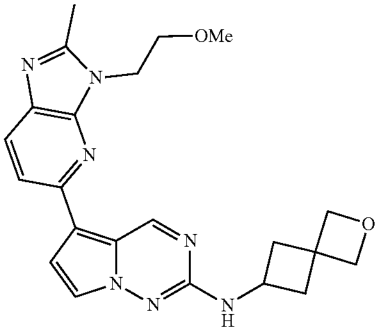 [SMILES: COCCn1c(C)nc2ccc(-c3ccn4nc(NC5CC6(COC6)C5)ncc34)nc21]
1205
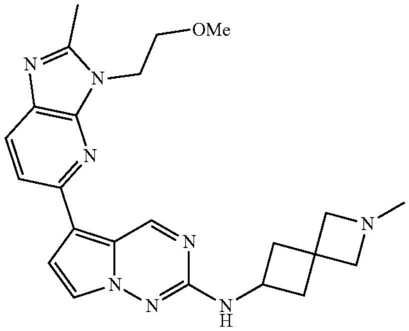 [SMILES: COCCn1c(C)nc2ccc(-c3ccn4nc(NC5CC6(C5)CN(C)C6)ncc34)nc21]
1206

TABLE 1-continued
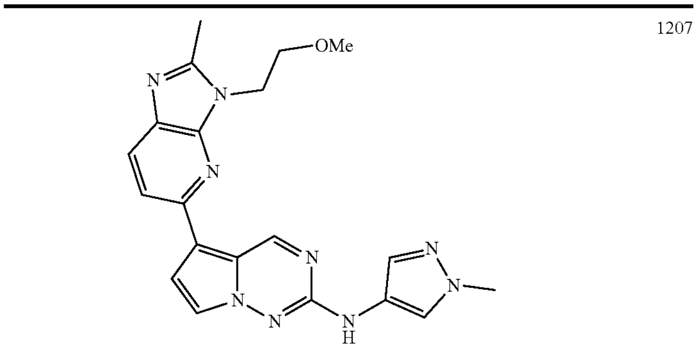
1207
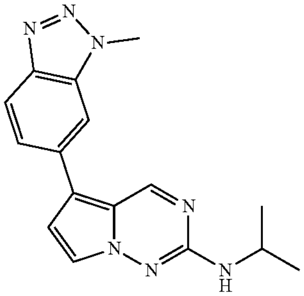 [SMILES: CC(C)Nc1ncc2c(-c3ccc4nnn(C)c4c3)ccn2n1]
1208
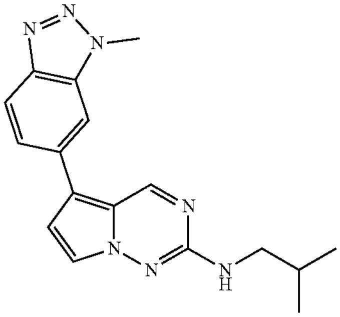 [SMILES: CC(C)CNc1ncc2c(-c3ccc4nnn(C)c4c3)ccn2n1]
1209
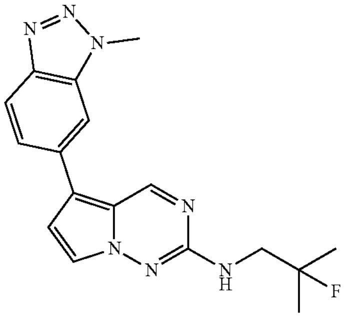 [SMILES: Cn1nnc2ccc(-c3ccn4nc(NCC(C)(C)F)ncc34)cc21]
1210
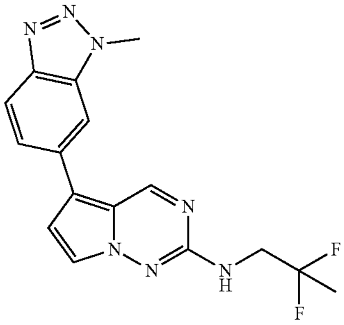 [SMILES: Cn1nnc2ccc(-c3ccn4nc(NCC(C)(F)F)ncc34)cc21]
1211

TABLE 1-continued
1212
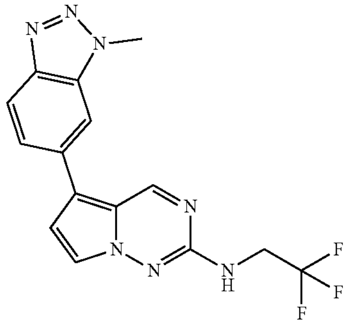 [SMILES: Cn1nnc2ccc(-c3ccn4nc(NCC(F)(F)F)ncc34)cc21]
1213
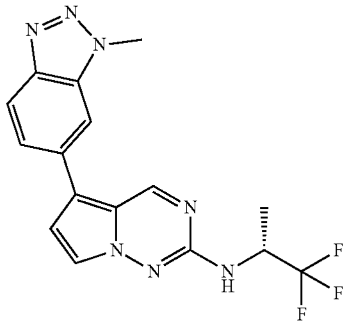 [SMILES: C[C@@H](Nc1ncc2c(-c3ccc4nnn(C)c4c3)ccn2n1)C(F)(F)F]
1214
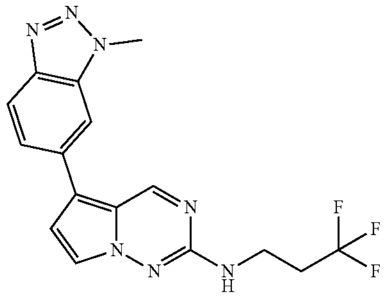 [SMILES: Cn1nnc2ccc(-c3ccn4nc(NCCC(F)(F)F)ncc34)cc21]
1215
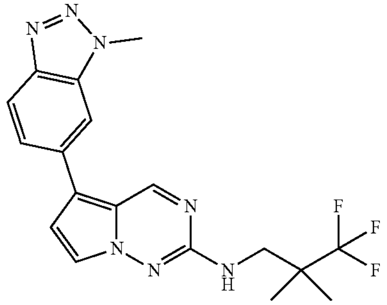 [SMILES: Cn1nnc2ccc(-c3ccn4nc(NCC(C)(C)C(F)(F)F)ncc34)cc21]
1216
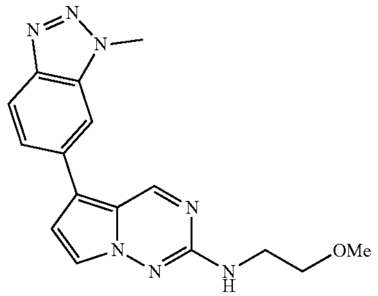 [SMILES: COCCNc1ncc2c(-c3ccc4nnn(C)c4c3)ccn2n1]

TABLE 1-continued
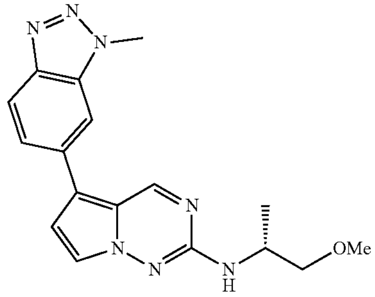 [SMILES: COC[C@@H](C)Nc1ncc2c(-c3ccc4nnn(C)c4c3)ccn2n1]
1217
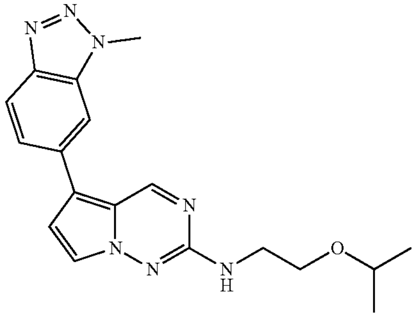 [SMILES: CC(C)OCCNc1ncc2c(-c3ccc4nnn(C)c4c3)ccn2n1]
1218
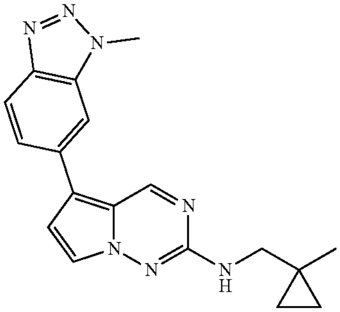 [SMILES: Cn1nnc2ccc(-c3ccn4nc(NCC5(C)CC5)ncc34)cc21]
1219
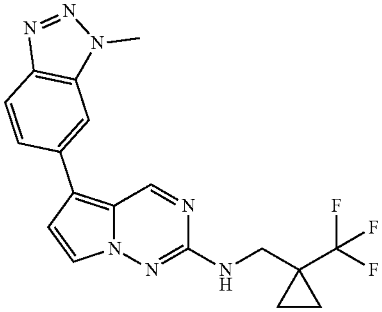 [SMILES: Cn1nnc2ccc(-c3ccn4nc(NCC5(C(F)(F)F)CC5)ncc34)cc21]
1220
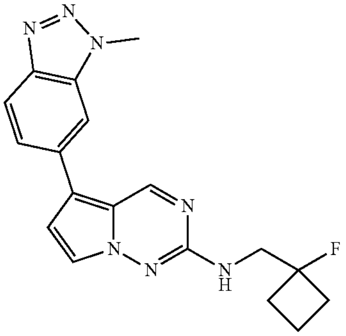 [SMILES: Cn1nnc2ccc(-c3ccn4nc(NCC5(F)CCC5)ncc34)cc21]
1221

TABLE 1-continued
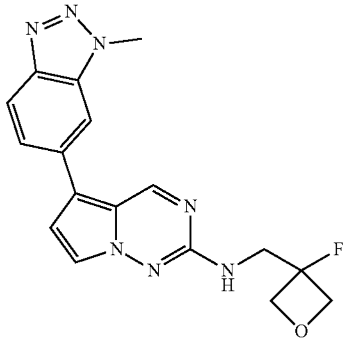 [SMILES: Cn1nnc2ccc(-c3ccn4nc(NCC5(F)COC5)ncc34)cc21]
1222
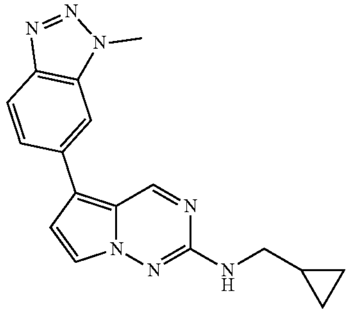 [SMILES: Cn1nnc2ccc(-c3ccn4nc(NCC5CC5)ncc34)cc21]
1223
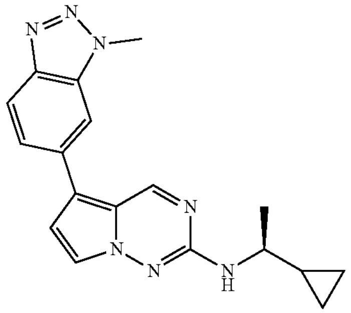 [SMILES: C[C@H](Nc1ncc2c(-c3ccc4nnn(C)c4c3)ccn2n1)C1CC1]
1224
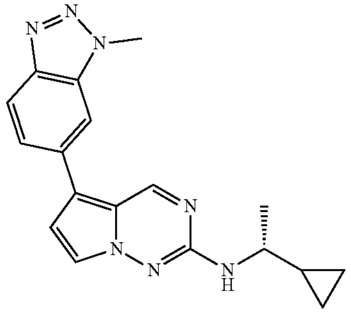 [SMILES: C[C@@H](Nc1ncc2c(-c3ccc4nnn(C)c4c3)ccn2n1)C1CC1]
1225
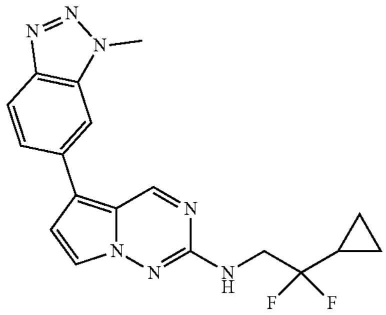 [SMILES: Cn1nnc2ccc(-c3ccn4nc(NCC(F)(F)C5CC5)ncc34)cc21]
1226

TABLE 1-continued
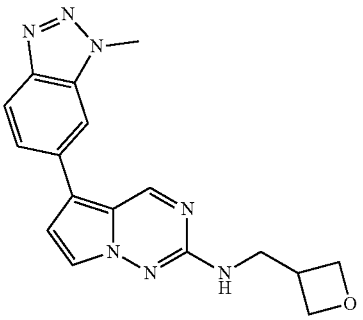 [SMILES: Cn1nnc2ccc(-c3ccn4nc(NCC5COC5)ncc34)cc21]
1227
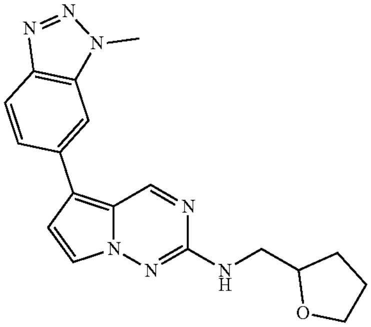 [SMILES: Cn1nnc2ccc(-c3ccn4nc(NCC5CCCO5)ncc34)cc21]
1228
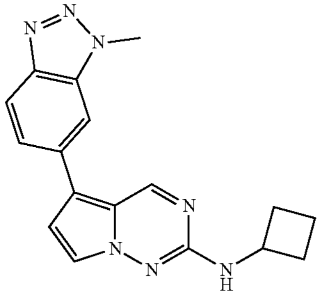 [SMILES: Cn1nnc2ccc(-c3ccn4nc(NC5CCC5)ncc34)cc21]
1229
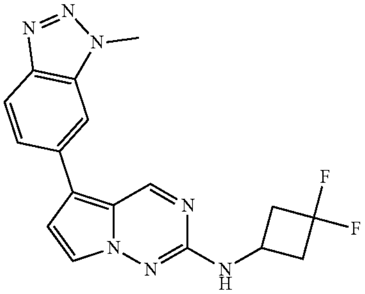 [SMILES: Cn1nnc2ccc(-c3ccn4nc(NC5CC(F)(F)C5)ncc34)cc21]
1230
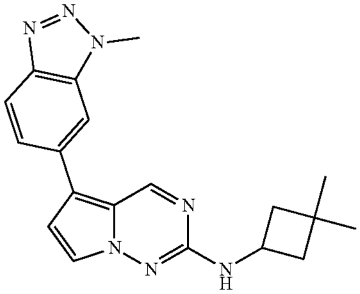 [SMILES: Cn1nnc2ccc(-c3ccn4nc(NC5CC(C)(C)C5)ncc34)cc21]
1231

TABLE 1-continued
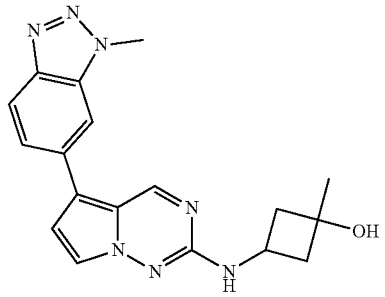 [SMILES: Cn1nnc2ccc(-c3ccn4nc(NC5CC(C)(O)C5)ncc34)cc21]
1232
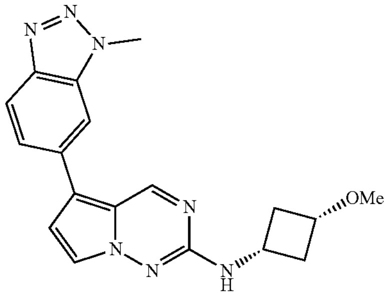 [SMILES: CO[C@H]1C[C@@H](Nc2ncc3c(-c4ccc5nnn(C)c5c4)ccn3n2)C1]
1233
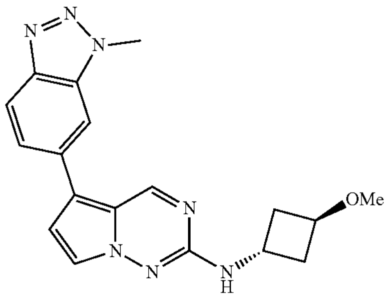 [SMILES: CO[C@H]1C[C@H](Nc2ncc3c(-c4ccc5nnn(C)c5c4)ccn3n2)C1]
1234
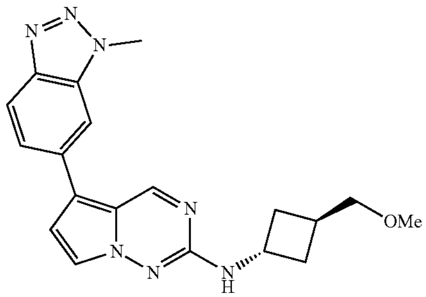 [SMILES: COC[C@H]1C[C@H](Nc2ncc3c(-c4ccc5nnn(C)c5c4)ccn3n2)C1]
1235
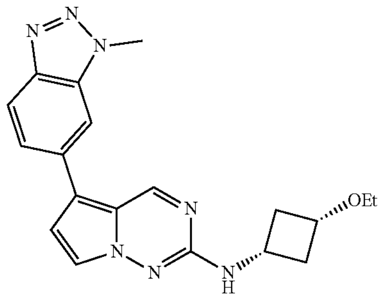 [SMILES: CCO[C@H]1C[C@@H](Nc2ncc3c(-c4ccc5nnn(C)c5c4)ccn3n2)C1]
1236

TABLE 1-continued
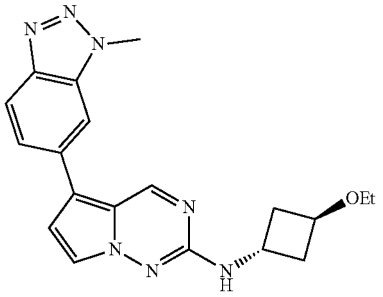 [SMILES: CCO[C@H]1C[C@H](Nc2ncc3c(-c4ccc5nnn(C)c5c4)ccn3n2)C1]
1237
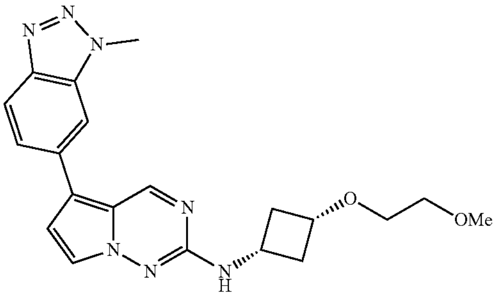 [SMILES: COCCO[C@H]1C[C@@H](Nc2ncc3c(-c4ccc5nnn(C)c5c4)ccn3n2)C1]
1238
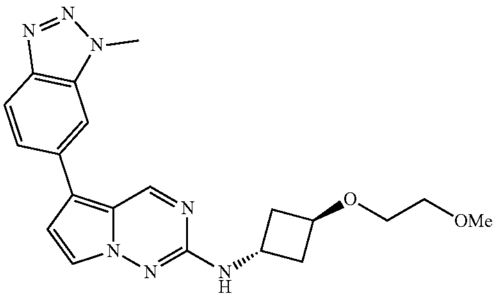 [SMILES: COCCO[C@H]1C[C@H](Nc2ncc3c(-c4ccc5nnn(C)c5c4)ccn3n2)C1]
1239
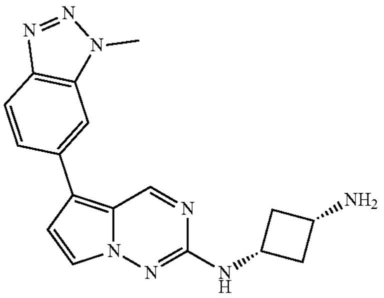 [SMILES: Cn1nnc2ccc(-c3ccn4nc(N[C@H]5C[C@@H](N)C5)ncc34)cc21]
1240
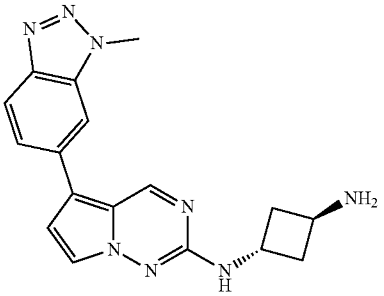 [SMILES: Cn1nnc2ccc(-c3ccn4nc(N[C@H]5C[C@H](N)C5)ncc34)cc21]
1241

TABLE 1-continued
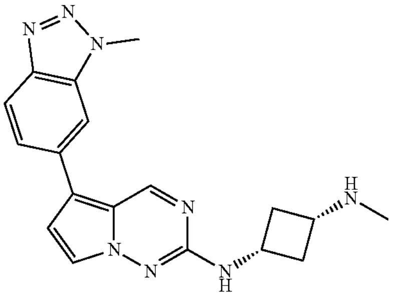 [SMILES: CN[C@H]1C[C@@H](Nc2ncc3c(-c4ccc5nnn(C)c5c4)ccn3n2)C1]
1242
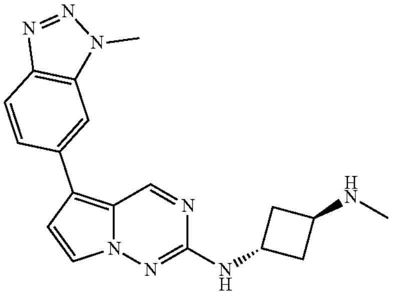 [SMILES: CN[C@H]1C[C@H](Nc2ncc3c(-c4ccc5nnn(C)c5c4)ccn3n2)C1]
1243
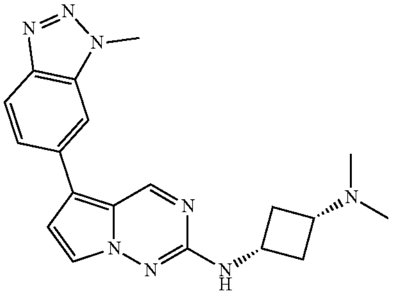 [SMILES: Cn1nnc2ccc(-c3ccn4nc(N[C@H]5C[C@@H](N(C)C)C5)ncc34)cc21]
1244
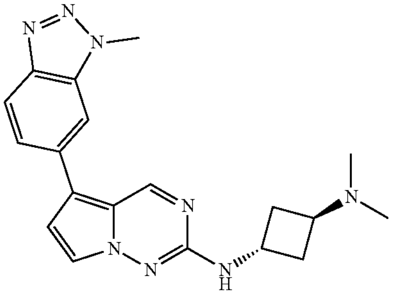 [SMILES: Cn1nnc2ccc(-c3ccn4nc(N[C@H]5C[C@H](N(C)C)C5)ncc34)cc21]
1245
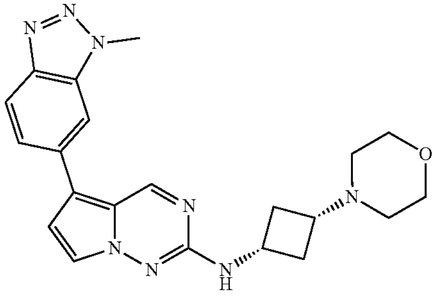 [SMILES: Cn1nnc2ccc(-c3ccn4nc(N[C@H]5C[C@@H](N6CCOCC6)C5)ncc34)cc21]
1246

TABLE 1-continued
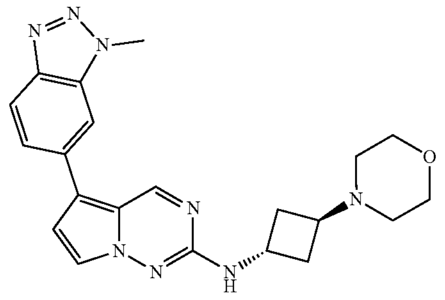 [SMILES: Cn1nnc2ccc(-c3ccn4nc(N[C@H]5C[C@H](N6CCOCC6)C5)ncc34)cc21]
1247
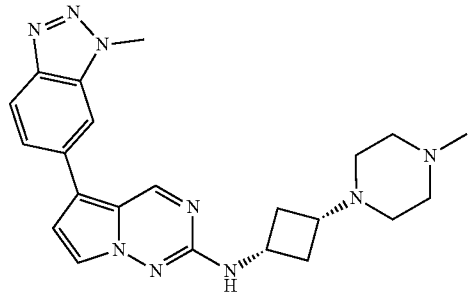 [SMILES: CN1CCN([C@H]2C[C@@H](Nc3ncc4c(-c5ccc6nnn(C)c6c5)ccn4n3)C2)CC1]
1248
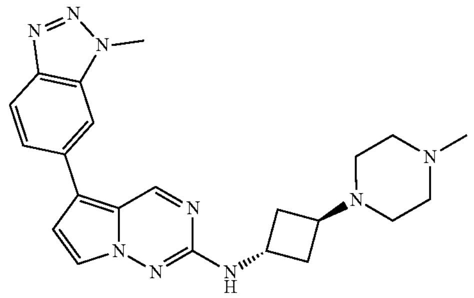 [SMILES: CN1CCN([C@H]2C[C@H](Nc3ncc4c(-c5ccc6nnn(C)c6c5)ccn4n3)C2)CC1]
1249
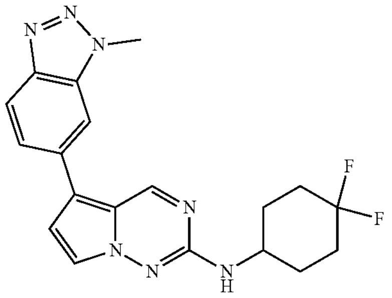 [SMILES: Cn1nnc2ccc(-c3ccn4nc(NC5CCC(F)(F)CC5)ncc34)cc21]
1250
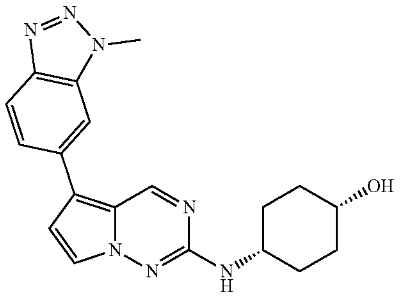 [SMILES: Cn1nnc2ccc(-c3ccn4nc(N[C@H]5CC[C@@H](O)CC5)ncc34)cc21]
1251

TABLE 1-continued
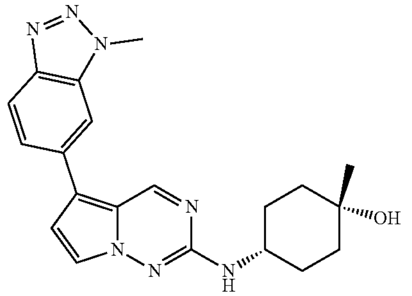 [SMILES: Cn1nnc2ccc(-c3ccn4nc(N[C@H]5CC[C@@](C)(O)CC5)ncc34)cc21]
1252
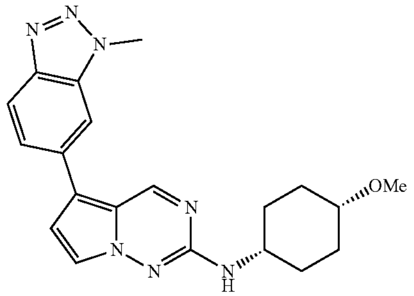 [SMILES: CO[C@H]1CC[C@@H](Nc2ncc3c(-c4ccc5nnn(C)c5c4)ccn3n2)CC1]
1253
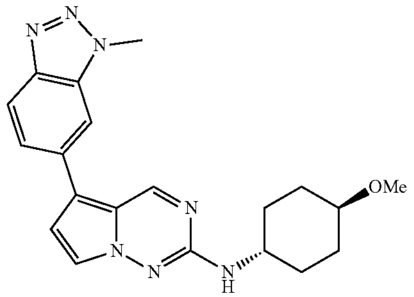 [SMILES: CO[C@H]1CC[C@H](Nc2ncc3c(-c4ccc5nnn(C)c5c4)ccn3n2)CC1]
1254
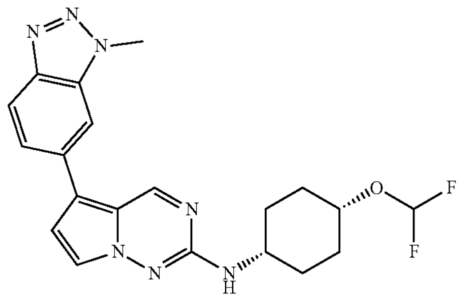 [SMILES: Cn1nnc2ccc(-c3ccn4nc(N[C@H]5CC[C@@H](OC(F)F)CC5)ncc34)cc21]
1255
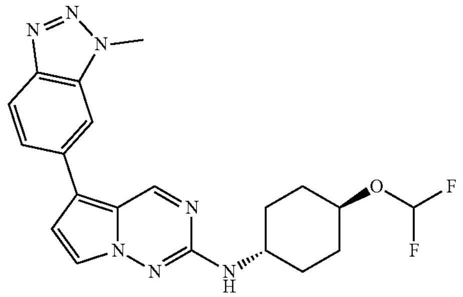 [SMILES: Cn1nnc2ccc(-c3ccn4nc(N[C@H]5CC[C@H](OC(F)F)CC5)ncc34)cc21]
1256

TABLE 1-continued
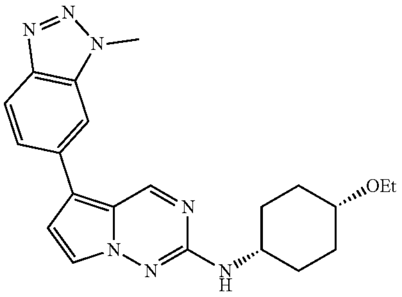 [SMILES: CCO[C@H]1CC[C@@H](Nc2ncc3c(-c4ccc5nnn(C)c5c4)ccn3n2)CC1]
1257
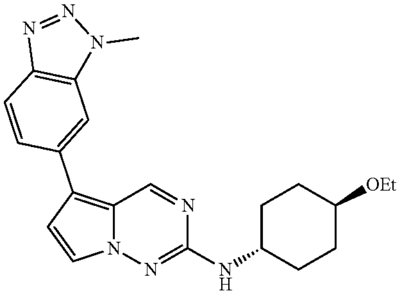 [SMILES: CCO[C@H]1CC[C@H](Nc2ncc3c(-c4ccc5nnn(C)c5c4)ccn3n2)CC1]
1258
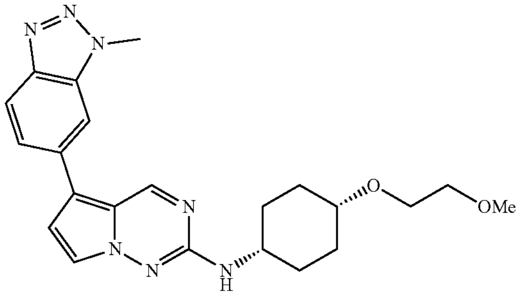 [SMILES: COCCO[C@H]1CC[C@@H](Nc2ncc3c(-c4ccc5nnn(C)c5c4)ccn3n2)CC1]
1259
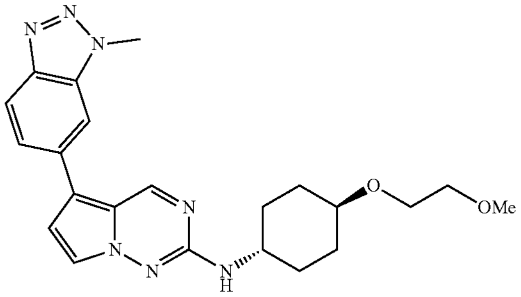 [SMILES: COCCO[C@H]1CC[C@H](Nc2ncc3c(-c4ccc5nnn(C)c5c4)ccn3n2)CC1]
1260
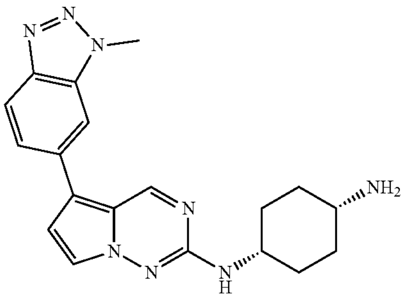 [SMILES: Cn1nnc2ccc(-c3ccn4nc(N[C@H]5CC[C@@H](N)CC5)ncc34)cc21]
1261

TABLE 1-continued
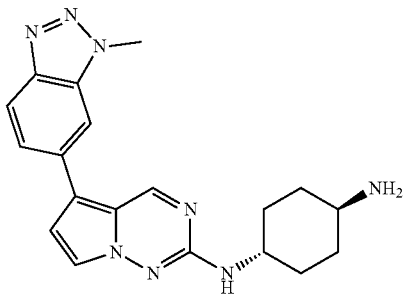 [SMILES: Cn1nnc2ccc(-c3ccn4nc(N[C@H]5CC[C@H](N)CC5)ncc34)cc21]
1262
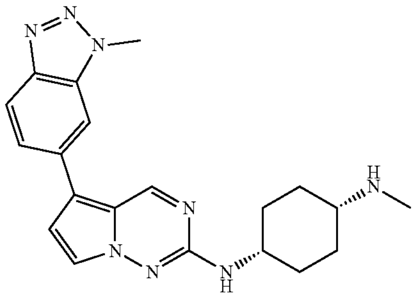 [SMILES: CN[C@H]1CC[C@@H](Nc2ncc3c(-c4ccc5nnn(C)c5c4)ccn3n2)CC1]
1263
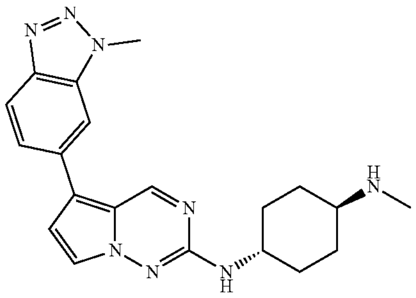 [SMILES: CN[C@H]1CC[C@H](Nc2ncc3c(-c4ccc5nnn(C)c5c4)ccn3n2)CC1]
1264
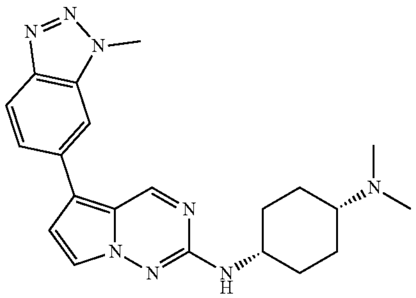 [SMILES: Cn1nnc2ccc(-c3ccn4nc(N[C@H]5CC[C@@H](N(C)C)CC5)ncc34)cc21]
1265
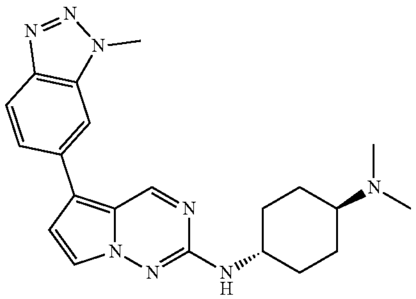 [SMILES: Cn1nnc2ccc(-c3ccn4nc(N[C@H]5CC[C@H](N(C)C)CC5)ncc34)cc21]
1266

TABLE 1-continued
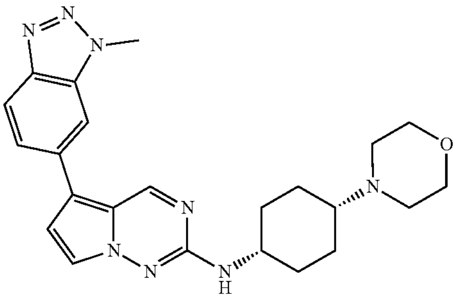 [SMILES: Cn1nnc2ccc(-c3ccn4nc(N[C@H]5CC[C@@H](N6CCOCC6)CC5)ncc34)cc21]
1267
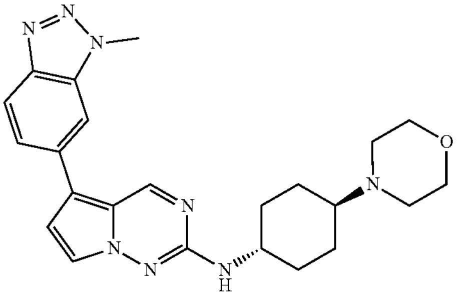 [SMILES: Cn1nnc2ccc(-c3ccn4nc(N[C@H]5CC[C@H](N6CCOCC6)CC5)ncc34)cc21]
1268
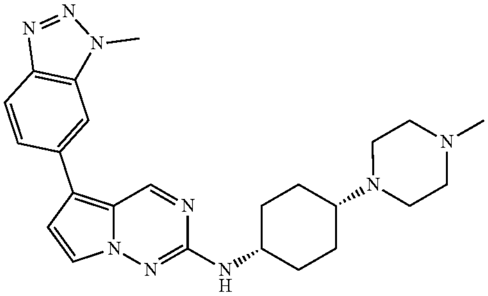 [SMILES: CN1CCN([C@H]2CC[C@@H](Nc3ncc4c(-c5ccc6nnn(C)c6c5)ccn4n3)CC2)CC1]
1269
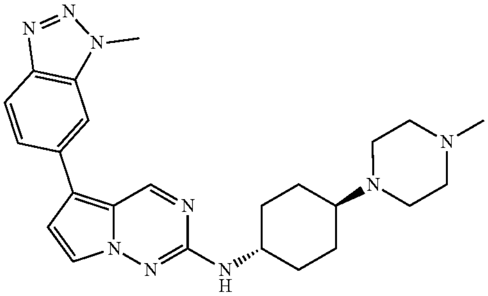 [SMILES: CN1CCN([C@H]2CC[C@H](Nc3ncc4c(-c5ccc6nnn(C)c6c5)ccn4n3)CC2)CC1]
1270
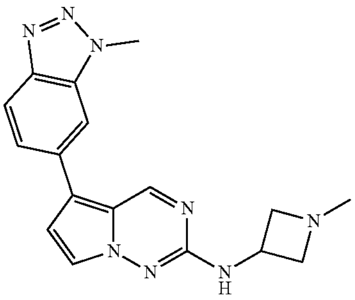 [SMILES: CN1CC(Nc2ncc3c(-c4ccc5nnn(C)c5c4)ccn3n2)C1]
1271

TABLE 1-continued
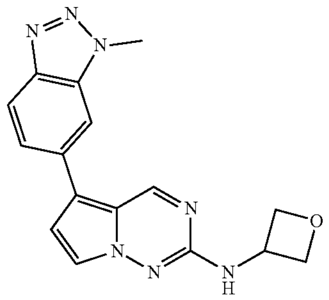 [SMILES: Cn1nnc2ccc(-c3ccn4nc(NC5COC5)ncc34)cc21]
1272
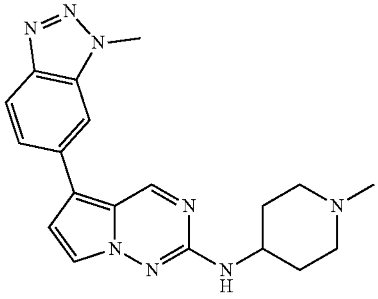 [SMILES: CN1CCC(Nc2ncc3c(-c4ccc5nnn(C)c5c4)ccn3n2)CC1]
1273
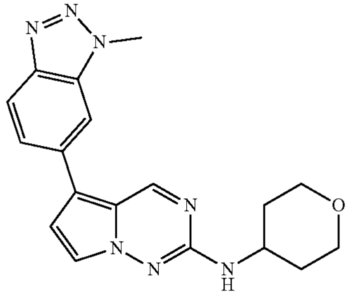 [SMILES: Cn1nnc2ccc(-c3ccn4nc(NC5CCOCC5)ncc34)cc21]
1274
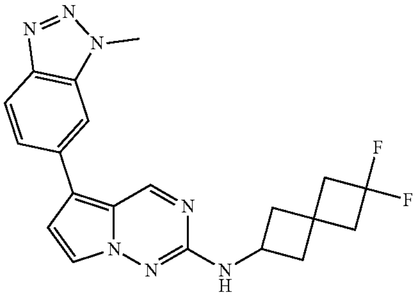 [SMILES: Cn1nnc2ccc(-c3ccn4nc(NC5CC6(C5)CC(F)(F)C6)ncc34)cc21]
1275
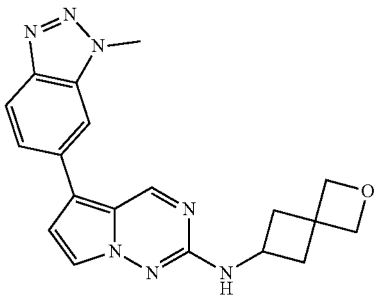 [SMILES: Cn1nnc2ccc(-c3ccn4nc(NC5CC6(COC6)C5)ncc34)cc21]
1276

TABLE 1-continued
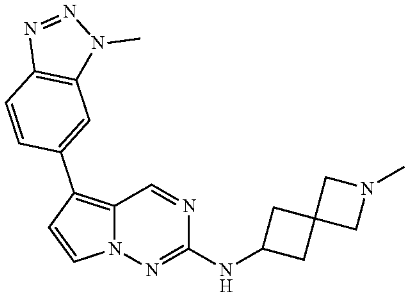 [SMILES: CN1CC2(CC(Nc3ncc4c(-c5ccc6nnn(C)c6c5)ccn4n3)C2)C1]
1277
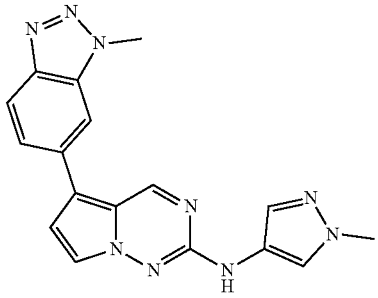 [SMILES: Cn1cc(Nc2ncc3c(-c4ccc5nnn(C)c5c4)ccn3n2)cn1]
1278
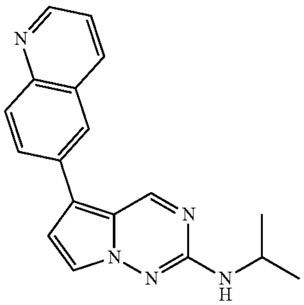 [SMILES: CC(C)Nc1ncc2c(-c3ccc4ncccc4c3)ccn2n1]
1279
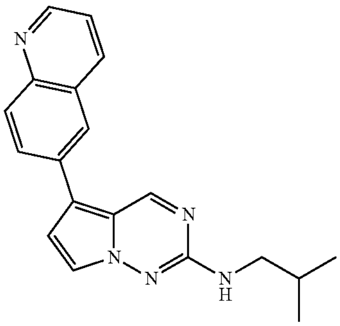
1280
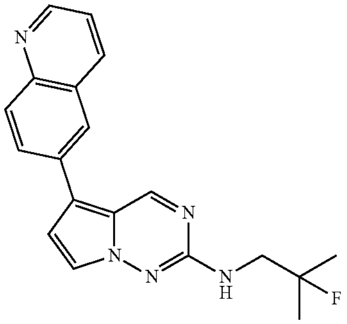
1281

TABLE 1-continued
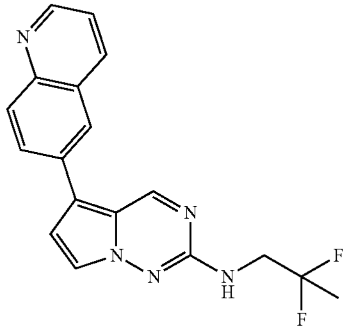
1282
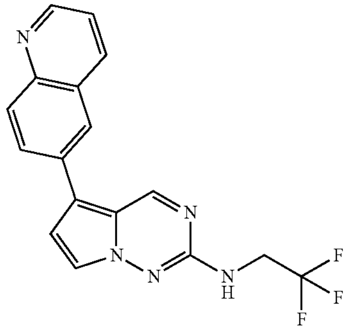
1283
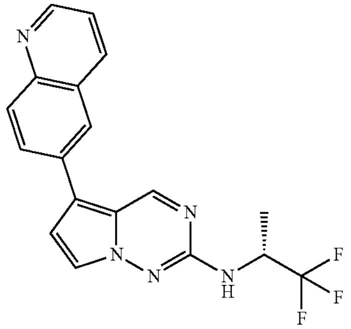
1284
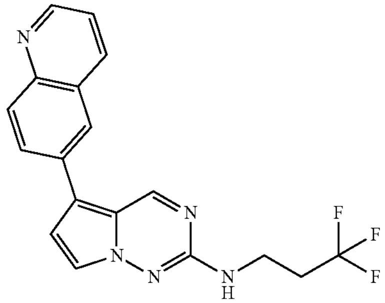 [SMILES: FC(F)(F)CCNc1ncc2c(-c3ccc4ncccc4c3)ccn2n1]
1285
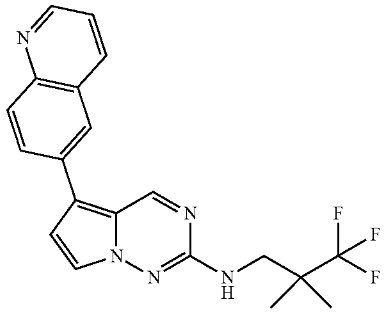
1286

TABLE 1-continued
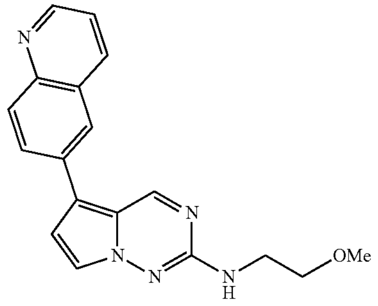 [SMILES: COCCNc1ncc2c(-c3ccc4ncccc4c3)ccn2n1]
1287
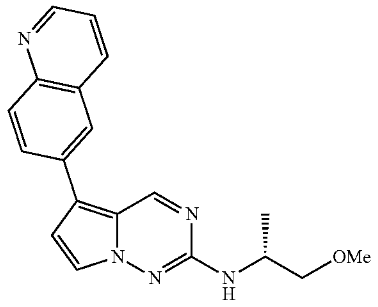 [SMILES: COC[C@@H](C)Nc1ncc2c(-c3ccc4ncccc4c3)ccn2n1]
1288
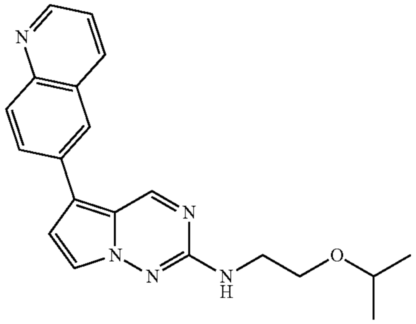 [SMILES: CC(C)OCCNc1ncc2c(-c3ccc4ncccc4c3)ccn2n1]
1289
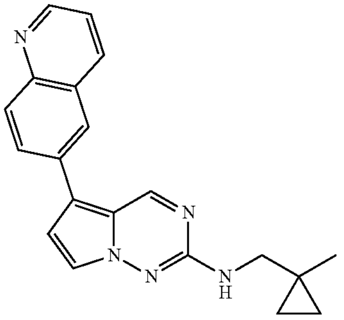
1290
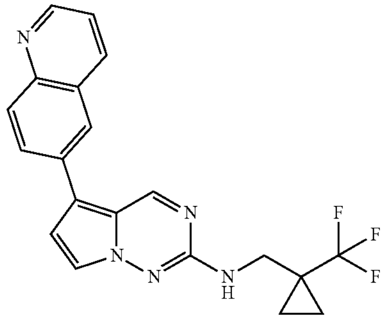 [SMILES: FC(F)(F)C1(CNc2ncc3c(-c4ccc5ncccc5c4)ccn3n2)CC1]
1291

TABLE 1-continued
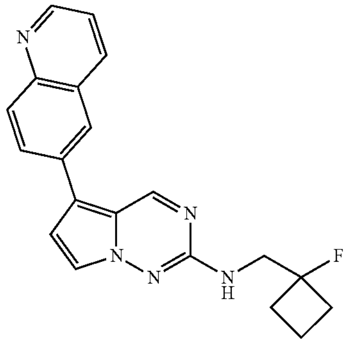
1292
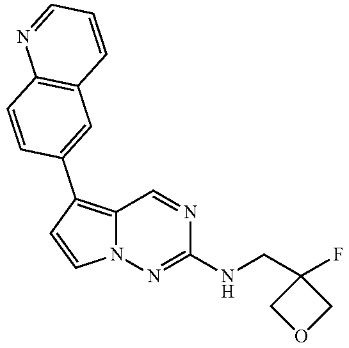
1293
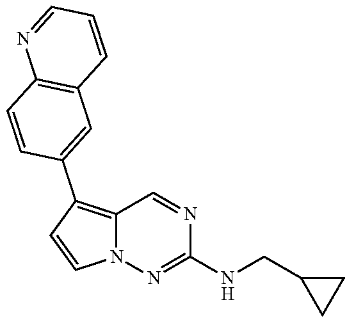 [SMILES: c1cnc2ccc(-c3ccn4nc(NCC5CC5)ncc34)cc2c1]
1294
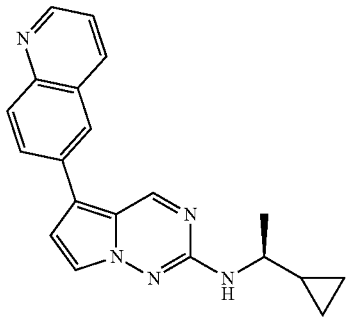 [SMILES: C[C@H](Nc1ncc2c(-c3ccc4ncccc4c3)ccn2n1)C1CC1]
1295

TABLE 1-continued
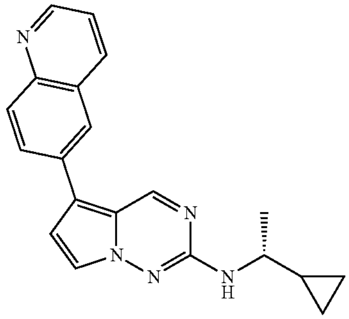 [SMILES: C[C@@H](Nc1ncc2c(-c3ccc4ncccc4c3)ccn2n1)C1CC1]
1296
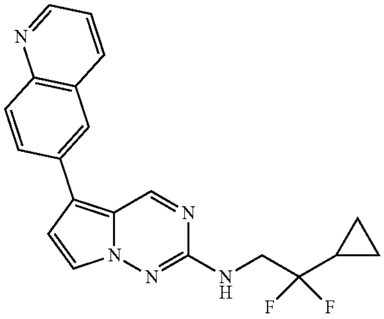 [SMILES: FC(F)(CNc1ncc2c(-c3ccc4ncccc4c3)ccn2n1)C1CC1]
1297
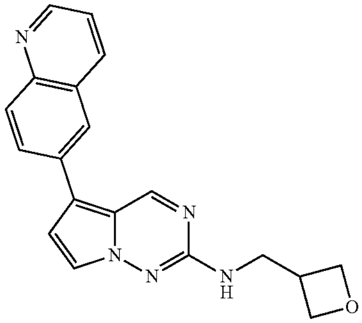 [SMILES: c1cnc2ccc(-c3ccn4nc(NCC5COC5)ncc34)cc2c1]
1298
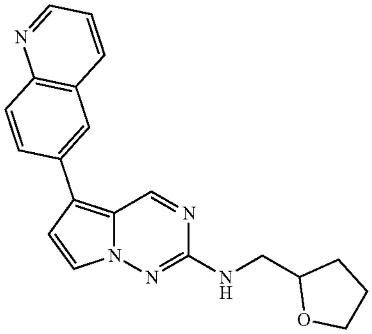
1299
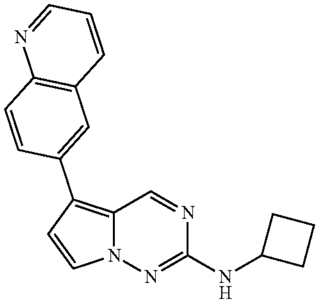 [SMILES: c1cnc2ccc(-c3ccn4nc(NC5CCC5)ncc34)cc2c1]
1300

TABLE 1-continued
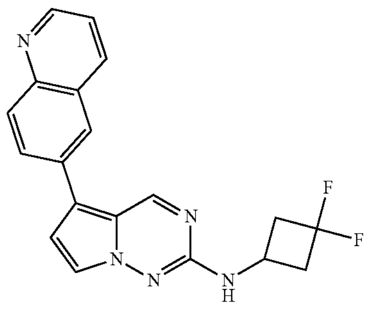 [SMILES: FC1(F)CC(Nc2ncc3c(-c4ccc5ncccc5c4)ccn3n2)C1]
1301
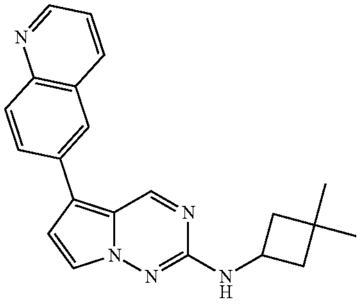 [SMILES: CC1(C)CC(Nc2ncc3c(-c4ccc5ncccc5c4)ccn3n2)C1]
1302
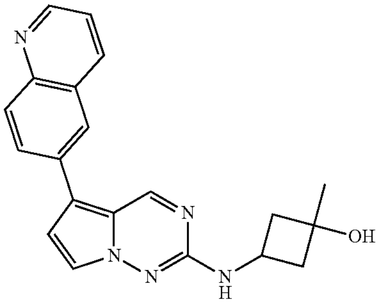 [SMILES: CC1(O)CC(Nc2ncc3c(-c4ccc5ncccc5c4)ccn3n2)C1]
1303
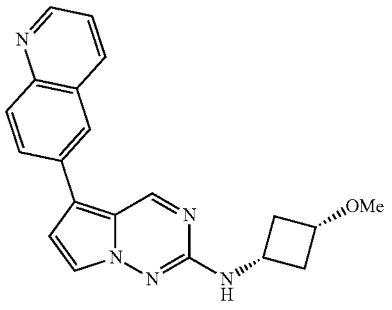 [SMILES: CO[C@H]1C[C@@H](Nc2ncc3c(-c4ccc5ncccc5c4)ccn3n2)C1]
1304
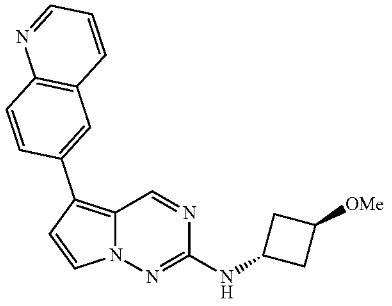 [SMILES: CO[C@H]1C[C@H](Nc2ncc3c(-c4ccc5ncccc5c4)ccn3n2)C1]
1305

TABLE 1-continued
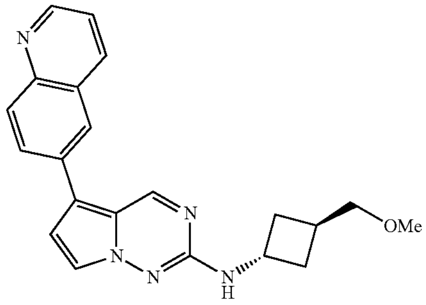 [SMILES: COC[C@H]1C[C@H](Nc2ncc3c(-c4ccc5ncccc5c4)ccn3n2)C1]
1306
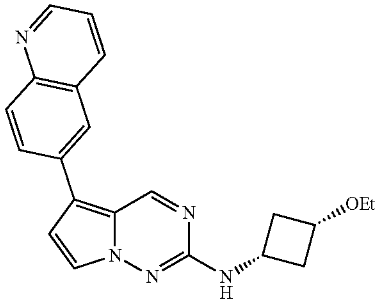 [SMILES: CCO[C@H]1C[C@@H](Nc2ncc3c(-c4ccc5ncccc5c4)ccn3n2)C1]
1307
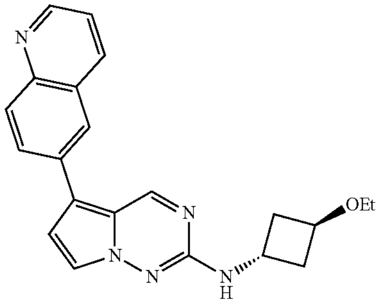 [SMILES: CCO[C@H]1C[C@H](Nc2ncc3c(-c4ccc5ncccc5c4)ccn3n2)C1]
1308
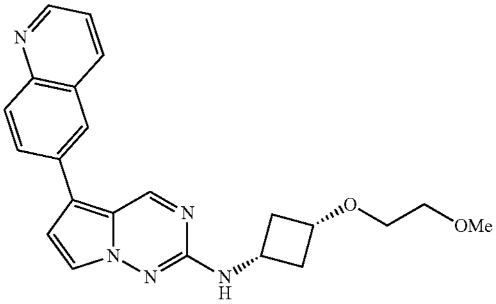 [SMILES: COCCO[C@H]1C[C@@H](Nc2ncc3c(-c4ccc5ncccc5c4)ccn3n2)C1]
1309
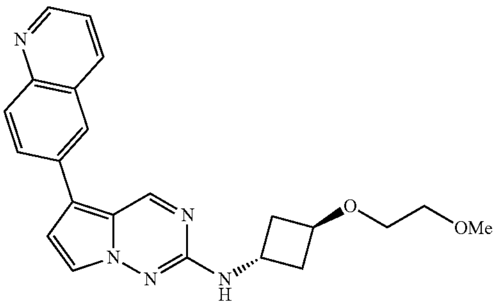 [SMILES: COCCO[C@H]1C[C@H](Nc2ncc3c(-c4ccc5ncccc5c4)ccn3n2)C1]
1310

TABLE 1-continued
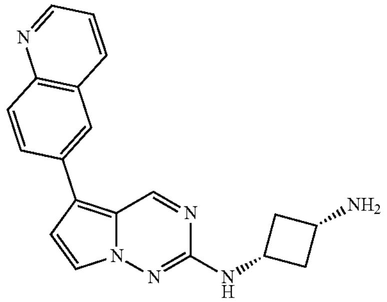 [SMILES: N[C@H]1C[C@@H](Nc2ncc3c(-c4ccc5ncccc5c4)ccn3n2)C1]
1311
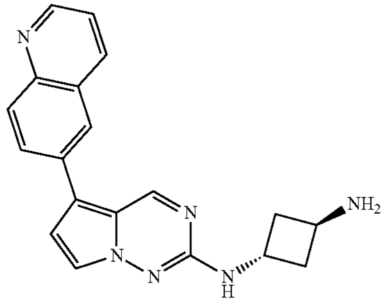 [SMILES: N[C@H]1C[C@H](Nc2ncc3c(-c4ccc5ncccc5c4)ccn3n2)C1]
1312
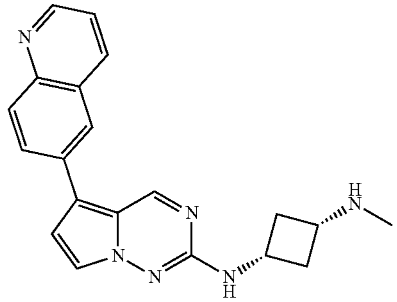 [SMILES: CN[C@H]1C[C@@H](Nc2ncc3c(-c4ccc5ncccc5c4)ccn3n2)C1]
1313
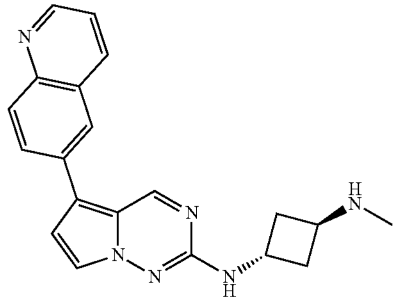 [SMILES: CN[C@H]1C[C@H](Nc2ncc3c(-c4ccc5ncccc5c4)ccn3n2)C1]
1314
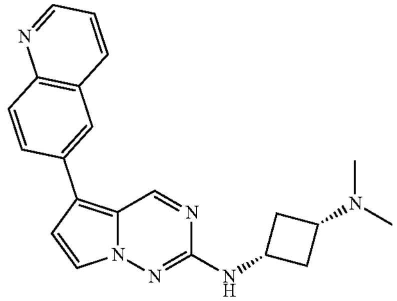 [SMILES: CN(C)[C@H]1C[C@@H](Nc2ncc3c(-c4ccc5ncccc5c4)ccn3n2)C1]
1315

TABLE 1-continued
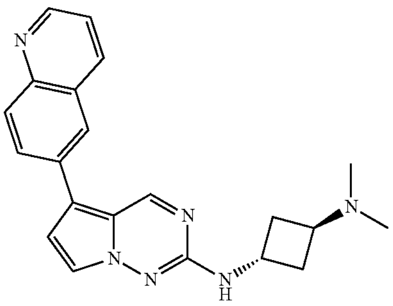 [SMILES: CN(C)[C@H]1C[C@H](Nc2ncc3c(-c4ccc5ncccc5c4)ccn3n2)C1]
1316
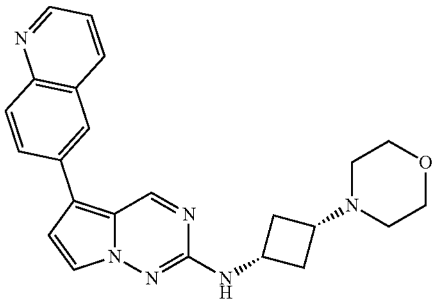 [SMILES: c1cnc2ccc(-c3ccn4nc(N[C@H]5C[C@@H](N6CCOCC6)C5)ncc34)cc2c1]
1317
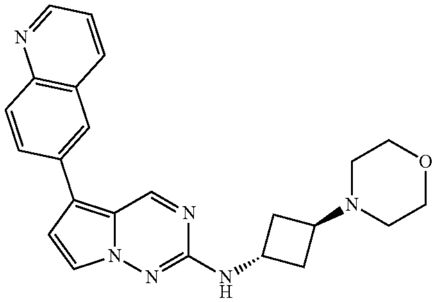 [SMILES: c1cnc2ccc(-c3ccn4nc(N[C@H]5C[C@H](N6CCOCC6)C5)ncc34)cc2c1]
1318
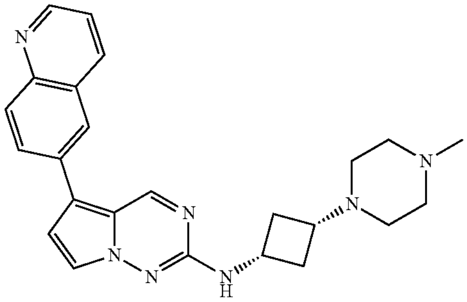 [SMILES: CN1CCN([C@H]2C[C@@H](Nc3ncc4c(-c5ccc6ncccc6c5)ccn4n3)C2)CC1]
1319
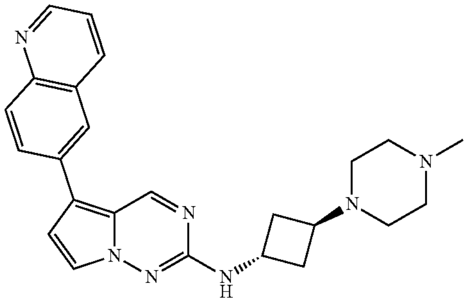 [SMILES: CN1CCN([C@H]2C[C@H](Nc3ncc4c(-c5ccc6ncccc6c5)ccn4n3)C2)CC1]
1320

TABLE 1-continued
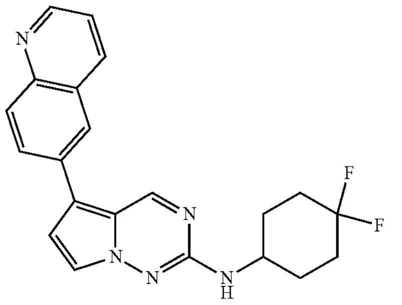 [SMILES: FC1(F)CCC(Nc2ncc3c(-c4ccc5ncccc5c4)ccn3n2)CC1]
1321
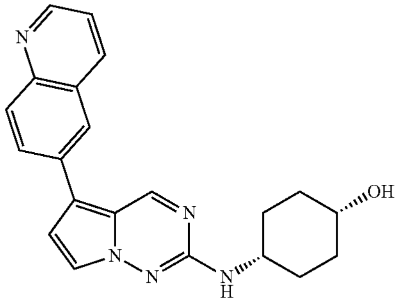 [SMILES: O[C@H]1CC[C@@H](Nc2ncc3c(-c4ccc5ncccc5c4)ccn3n2)CC1]
1322
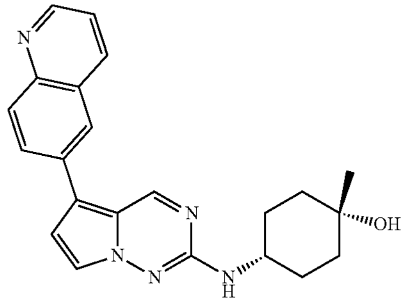 [SMILES: C[C@]1(O)CC[C@@H](Nc2ncc3c(-c4ccc5ncccc5c4)ccn3n2)CC1]
1323
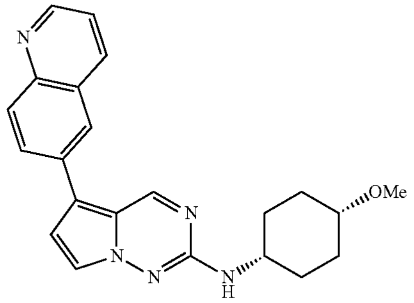 [SMILES: CO[C@H]1CC[C@@H](Nc2ncc3c(-c4ccc5ncccc5c4)ccn3n2)CC1]
1324
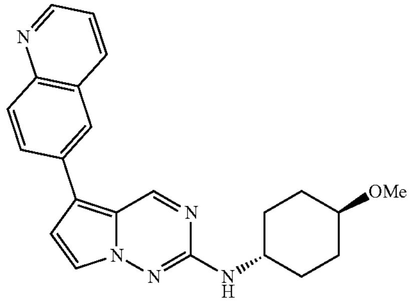 [SMILES: CO[C@H]1CC[C@H](Nc2ncc3c(-c4ccc5ncccc5c4)ccn3n2)CC1]
1325

TABLE 1-continued
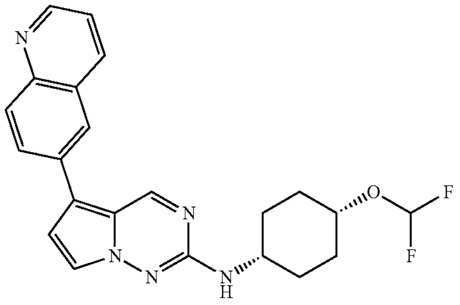 [SMILES: FC(F)O[C@H]1CC[C@@H](Nc2ncc3c(-c4ccc5ncccc5c4)ccn3n2)CC1]
1326
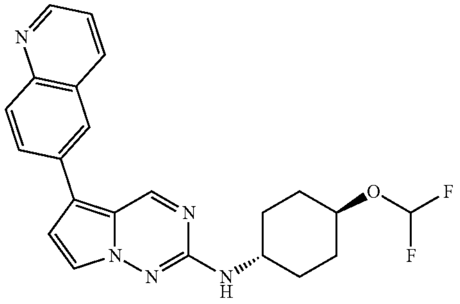 [SMILES: FC(F)O[C@H]1CC[C@H](Nc2ncc3c(-c4ccc5ncccc5c4)ccn3n2)CC1]
1327
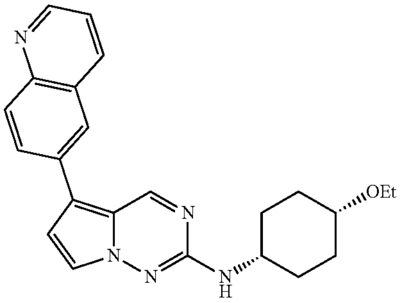 [SMILES: CCO[C@H]1CC[C@@H](Nc2ncc3c(-c4ccc5ncccc5c4)ccn3n2)CC1]
1328
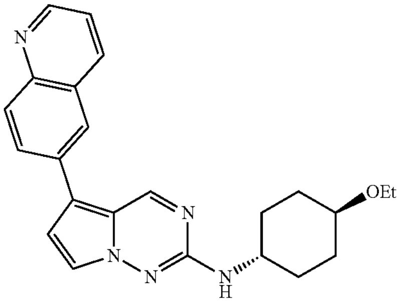 [SMILES: CCO[C@H]1CC[C@H](Nc2ncc3c(-c4ccc5ncccc5c4)ccn3n2)CC1]
1329
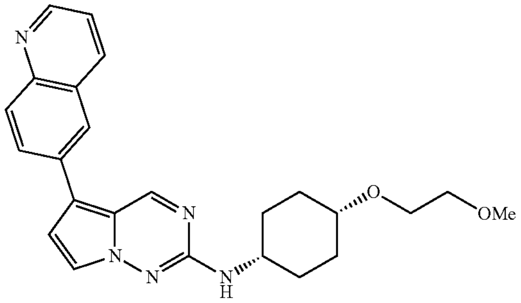 [SMILES: COCCO[C@H]1CC[C@@H](Nc2ncc3c(-c4ccc5ncccc5c4)ccn3n2)CC1]
1330

TABLE 1-continued
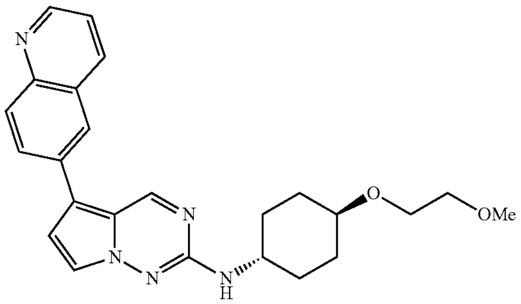 [SMILES: COCCO[C@H]1CC[C@H](Nc2ncc3c(-c4ccc5ncccc5c4)ccn3n2)CC1]
1331
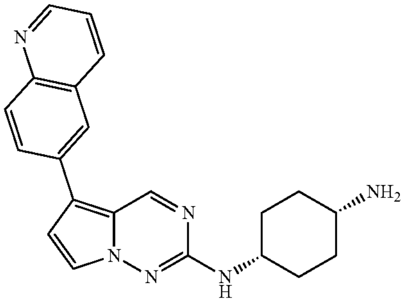 [SMILES: N[C@H]1CC[C@@H](Nc2ncc3c(-c4ccc5ncccc5c4)ccn3n2)CC1]
1332
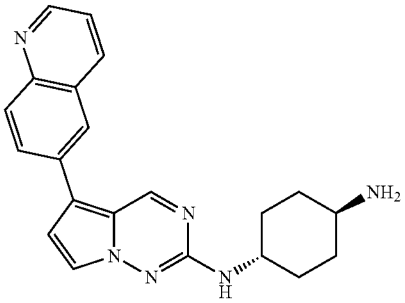 [SMILES: N[C@H]1CC[C@H](Nc2ncc3c(-c4ccc5ncccc5c4)ccn3n2)CC1]
1333
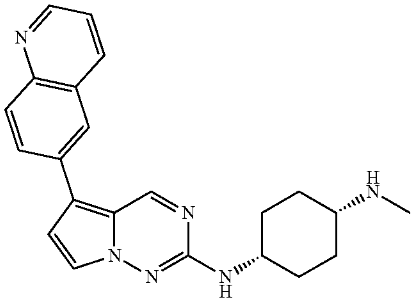 [SMILES: CN[C@H]1CC[C@@H](Nc2ncc3c(-c4ccc5ncccc5c4)ccn3n2)CC1]
1334
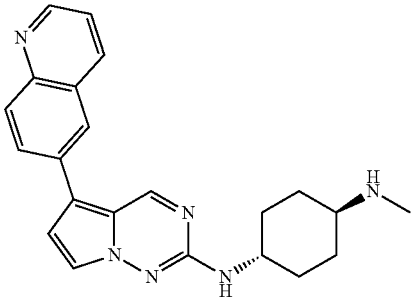 [SMILES: CN[C@H]1CC[C@H](Nc2ncc3c(-c4ccc5ncccc5c4)ccn3n2)CC1]
1335

TABLE 1-continued
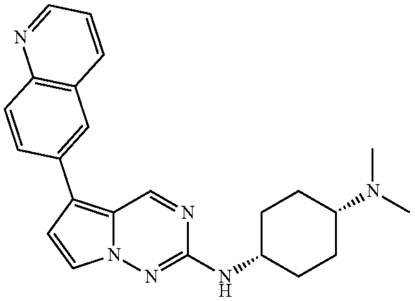 [SMILES: CN(C)[C@H]1CC[C@@H](Nc2ncc3c(-c4ccc5ncccc5c4)ccn3n2)CC1]
1336
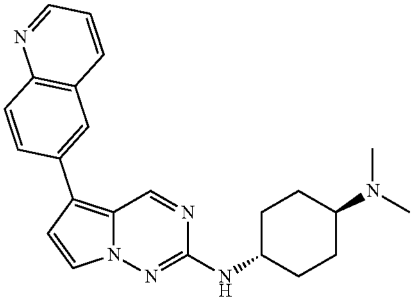 [SMILES: CN(C)[C@H]1CC[C@H](Nc2ncc3c(-c4ccc5ncccc5c4)ccn3n2)CC1]
1337
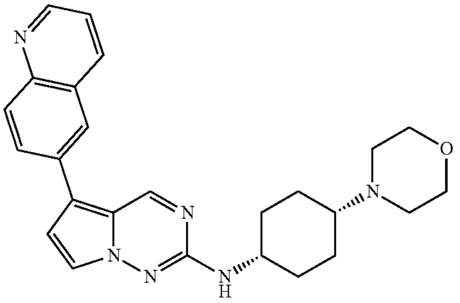 [SMILES: c1cnc2ccc(-c3ccn4nc(N[C@H]5CC[C@@H](N6CCOCC6)CC5)ncc34)cc2c1]
1338
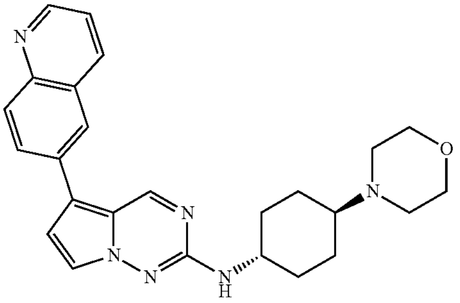 [SMILES: c1cnc2ccc(-c3ccn4nc(N[C@H]5CC[C@H](N6CCOCC6)CC5)ncc34)cc2c1]
1339
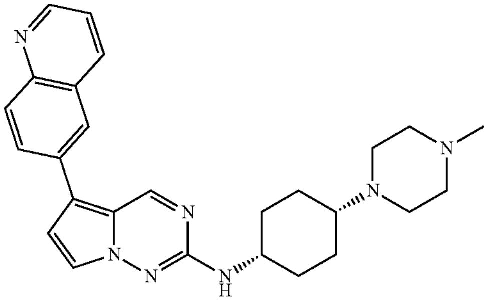 [SMILES: CN1CCN([C@H]2CC[C@@H](Nc3ncc4c(-c5ccc6ncccc6c5)ccn4n3)CC2)CC1]
1340

TABLE 1-continued
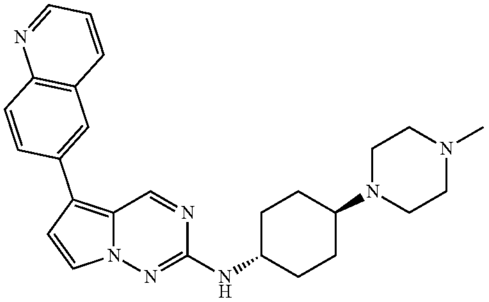 [SMILES: CN1CCN([C@H]2CC[C@H](Nc3ncc4c(-c5ccc6ncccc6c5)ccn4n3)CC2)CC1]
1341
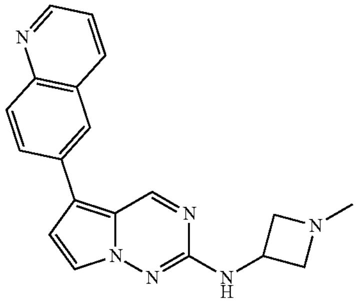 [SMILES: CN1CC(Nc2ncc3c(-c4ccc5ncccc5c4)ccn3n2)C1]
1342
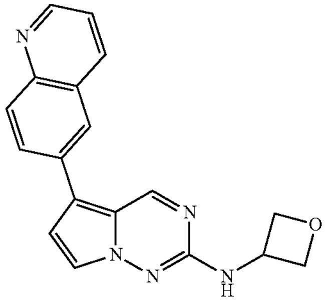 [SMILES: c1cnc2ccc(-c3ccn4nc(NC5COC5)ncc34)cc2c1]
1343
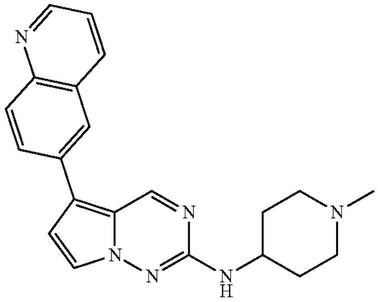 [SMILES: CN1CCC(Nc2ncc3c(-c4ccc5ncccc5c4)ccn3n2)CC1]
1344
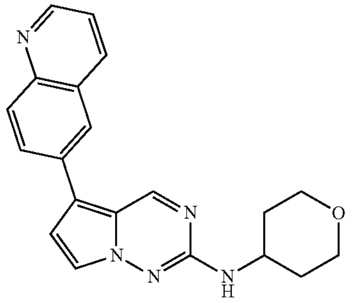 [SMILES: c1cnc2ccc(-c3ccn4nc(NC5CCOCC5)ncc34)cc2c1]
1345

TABLE 1-continued
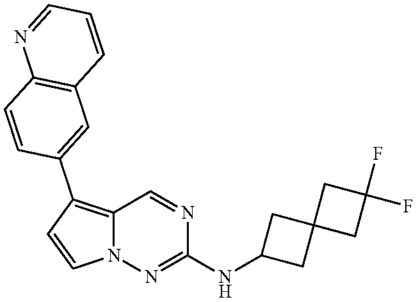 [SMILES: FC1(F)CC2(CC(Nc3ncc4c(-c5ccc6ncccc6c5)ccn4n3)C2)C1]
1346
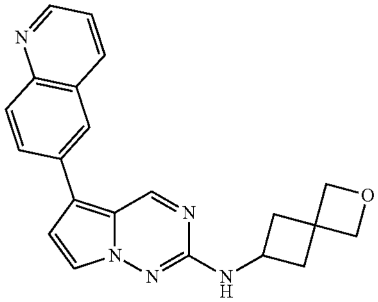 [SMILES: c1cnc2ccc(-c3ccn4nc(NC5CC6(COC6)C5)ncc34)cc2c1]
1347
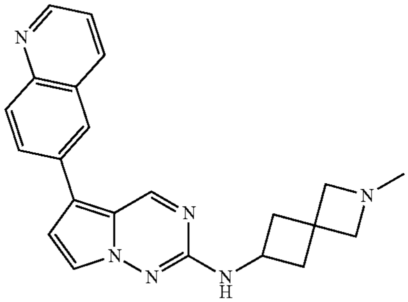 [SMILES: CN1CC2(CC(Nc3ncc4c(-c5ccc6ncccc6c5)ccn4n3)C2)C1]
1348
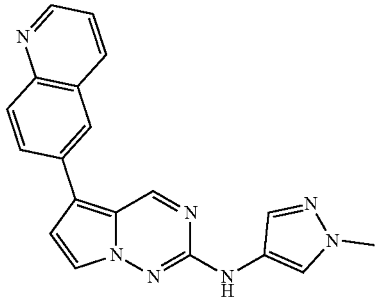 [SMILES: Cn1cc(Nc2ncc3c(-c4ccc5ncccc5c4)ccn3n2)cn1]
1349
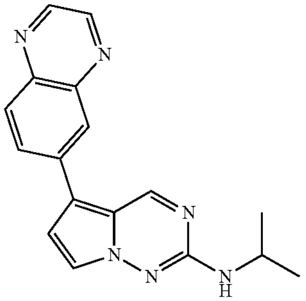 [SMILES: CC(C)Nc1ncc2c(-c3ccc4nccnc4c3)ccn2n1]
1350

TABLE 1-continued
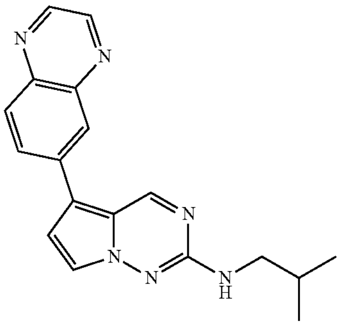 [SMILES: CC(C)CNc1ncc2c(-c3ccc4nccnc4c3)ccn2n1]
1351
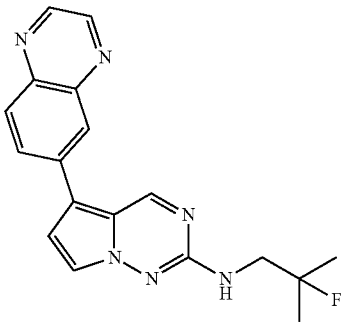 [SMILES: CC(C)(F)CNc1ncc2c(-c3ccc4nccnc4c3)ccn2n1]
1352
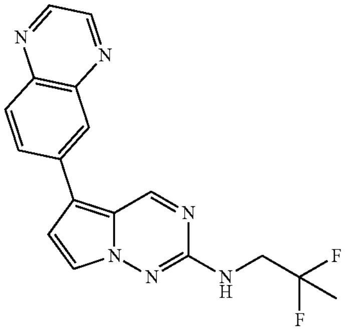
1353
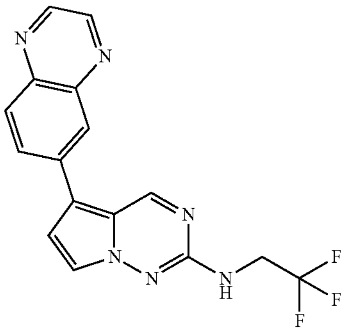 [SMILES: FC(F)(F)CNc1ncc2c(-c3ccc4nccnc4c3)ccn2n1]
1354

TABLE 1-continued
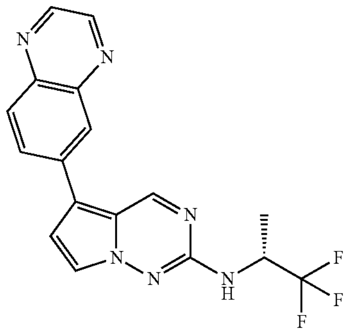 [SMILES: C[C@@H](Nc1ncc2c(-c3ccc4nccnc4c3)ccn2n1)C(F)(F)F]
1355
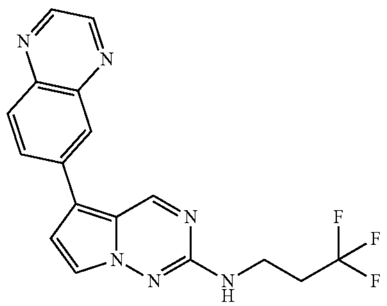 [SMILES: FC(F)(F)CCNc1ncc2c(-c3ccc4nccnc4c3)ccn2n1]
1356
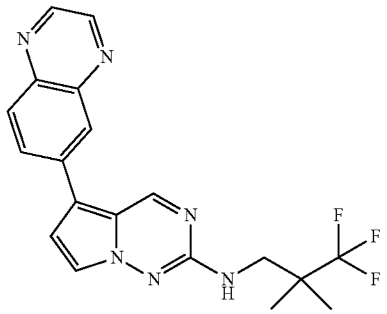 [SMILES: CC(C)(CNc1ncc2c(-c3ccc4nccnc4c3)ccn2n1)C(F)(F)F]
1357
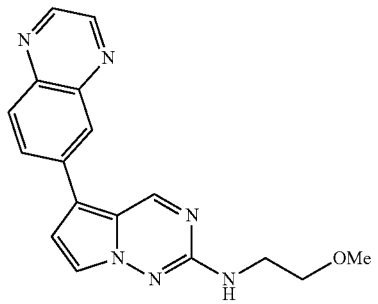 [SMILES: COCCNc1ncc2c(-c3ccc4nccnc4c3)ccn2n1]
1358
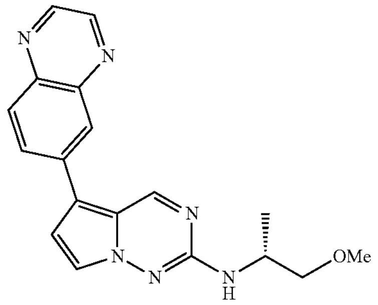 [SMILES: COC[C@@H](C)Nc1ncc2c(-c3ccc4nccnc4c3)ccn2n1]
1359

TABLE 1-continued
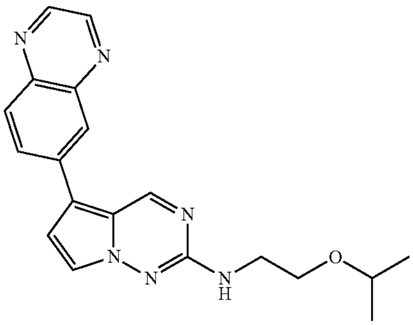 [SMILES: CC(C)OCCNc1ncc2c(-c3ccc4nccnc4c3)ccn2n1]
1360
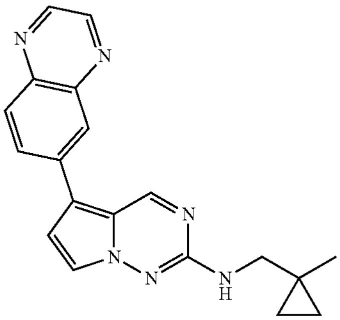 [SMILES: CC1(CNc2ncc3c(-c4ccc5nccnc5c4)ccn3n2)CC1]
1361
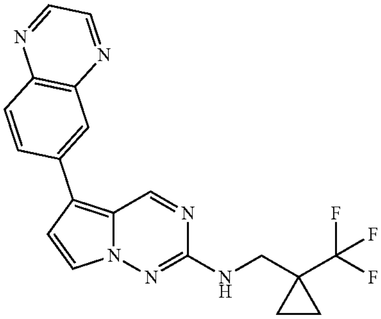 [SMILES: FC(F)(F)C1(CNc2ncc3c(-c4ccc5nccnc5c4)ccn3n2)CC1]
1362
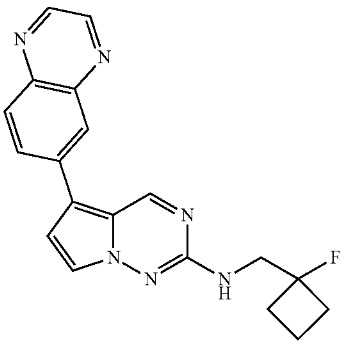 [SMILES: FC1(CNc2ncc3c(-c4ccc5nccnc5c4)ccn3n2)CCC1]
1363

TABLE 1-continued
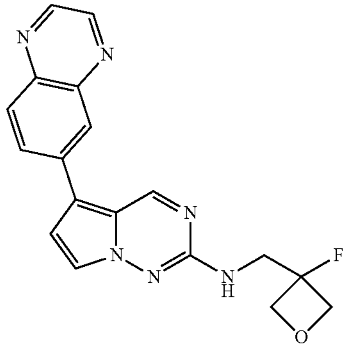 [SMILES: FC1(CNc2ncc3c(-c4ccc5nccnc5c4)ccn3n2)COC1]
1364
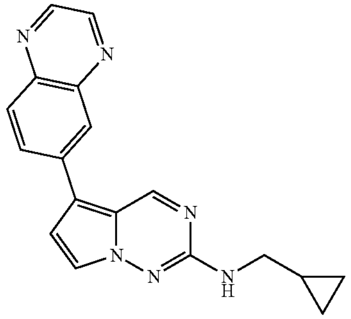 [SMILES: c1cnc2cc(-c3ccn4nc(NCC5CC5)ncc34)ccc2n1]
1365
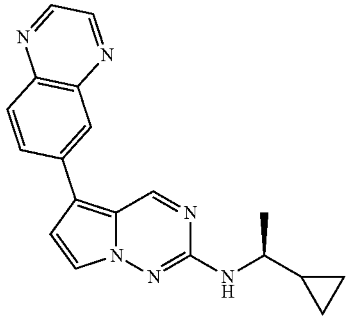 [SMILES: C[C@H](Nc1ncc2c(-c3ccc4nccnc4c3)ccn2n1)C1CC1]
1366
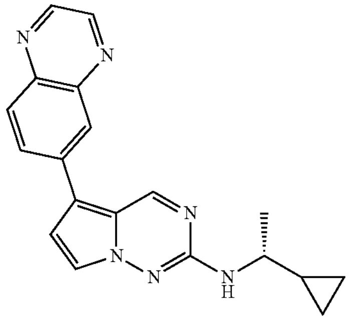 [SMILES: C[C@@H](Nc1ncc2c(-c3ccc4nccnc4c3)ccn2n1)C1CC1]
1367
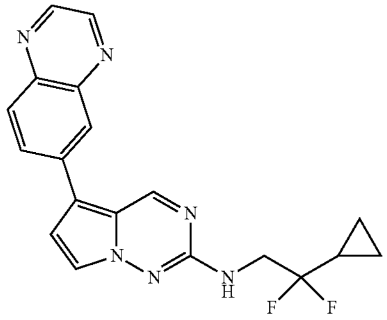
1368

TABLE 1-continued
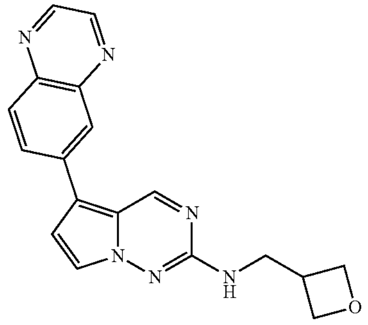
1369
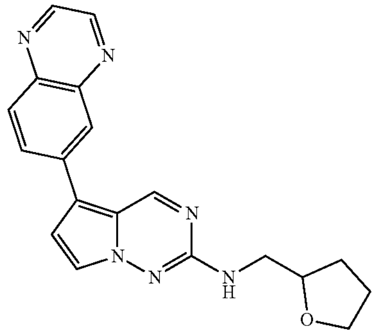 [SMILES: c1cnc2cc(-c3ccn4nc(NCC5CCCO5)ncc34)ccc2n1]
1370
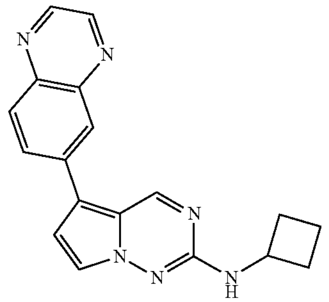 [SMILES: c1cnc2cc(-c3ccn4nc(NC5CCC5)ncc34)ccc2n1]
1371
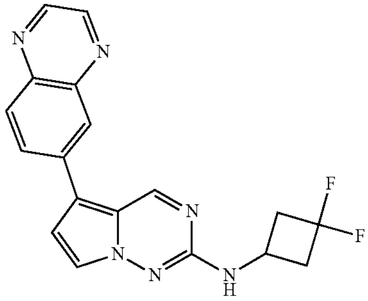 [SMILES: FC1(F)CC(Nc2ncc3c(-c4ccc5nccnc5c4)ccn3n2)C1]
1372
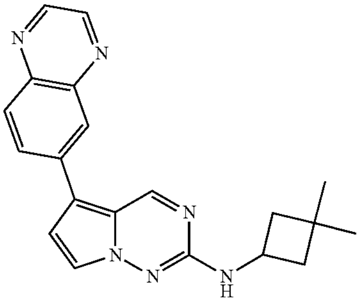 [SMILES: CC1(C)CC(Nc2ncc3c(-c4ccc5nccnc5c4)ccn3n2)C1]
1373

TABLE 1-continued
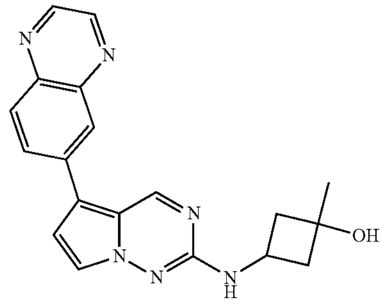 [SMILES: CC1(O)CC(Nc2ncc3c(-c4ccc5nccnc5c4)ccn3n2)C1]
1374
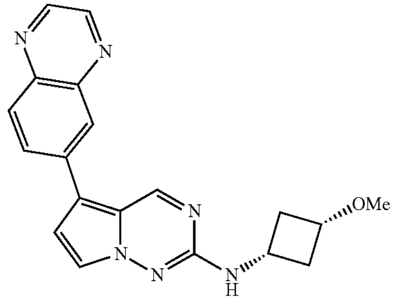 [SMILES: CO[C@H]1C[C@@H](Nc2ncc3c(-c4ccc5nccnc5c4)ccn3n2)C1]
1375
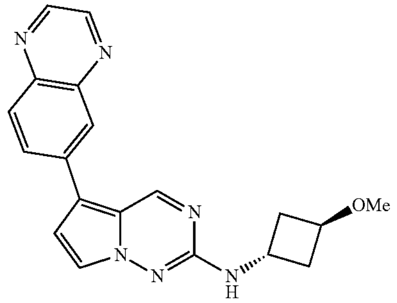 [SMILES: CO[C@H]1C[C@H](Nc2ncc3c(-c4ccc5nccnc5c4)ccn3n2)C1]
1376
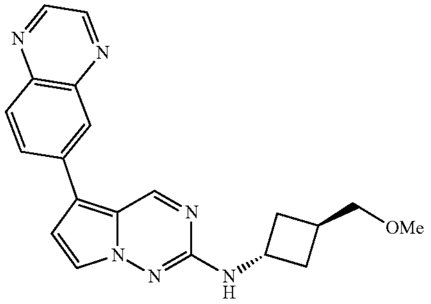 [SMILES: COC[C@H]1C[C@H](Nc2ncc3c(-c4ccc5nccnc5c4)ccn3n2)C1]
1377
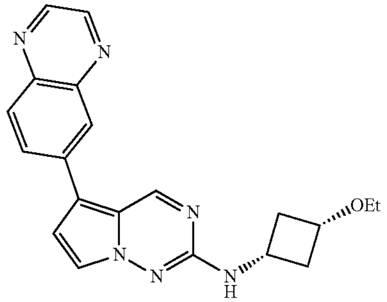 [SMILES: CCO[C@H]1C[C@@H](Nc2ncc3c(-c4ccc5nccnc5c4)ccn3n2)C1]
1378

TABLE 1-continued
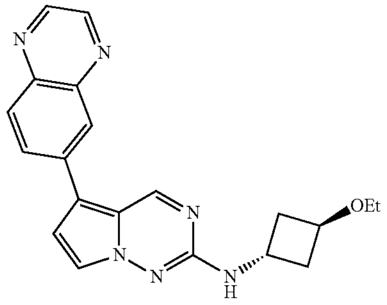 [SMILES: CCO[C@H]1C[C@H](Nc2ncc3c(-c4ccc5nccnc5c4)ccn3n2)C1]
1379
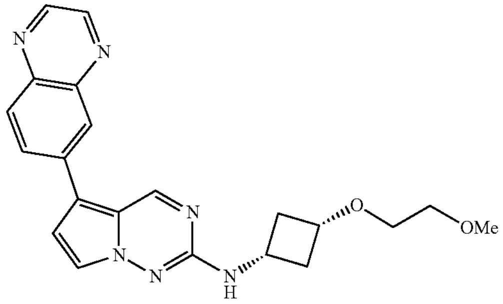 [SMILES: COCCO[C@H]1C[C@@H](Nc2ncc3c(-c4ccc5nccnc5c4)ccn3n2)C1]
1380
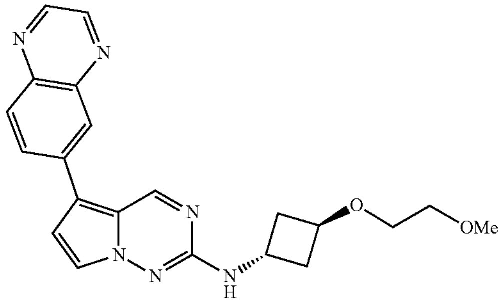 [SMILES: COCCO[C@H]1C[C@H](Nc2ncc3c(-c4ccc5nccnc5c4)ccn3n2)C1]
1381
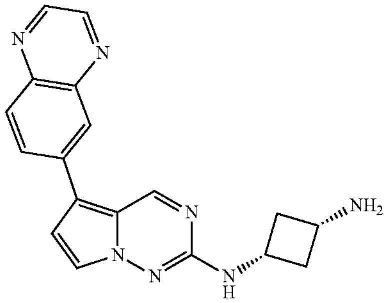 [SMILES: N[C@H]1C[C@@H](Nc2ncc3c(-c4ccc5nccnc5c4)ccn3n2)C1]
1382
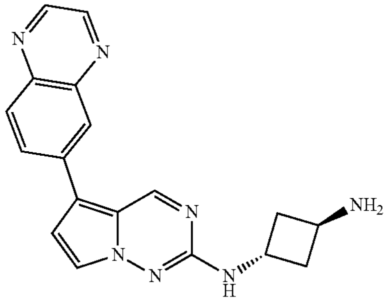 [SMILES: N[C@H]1C[C@H](Nc2ncc3c(-c4ccc5nccnc5c4)ccn3n2)C1]
1383

TABLE 1-continued
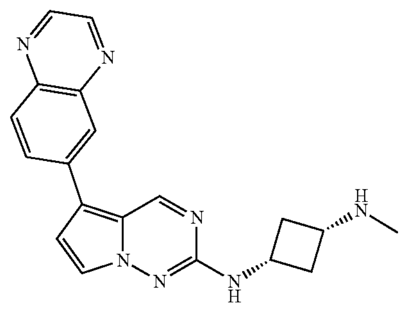 [SMILES: CN[C@H]1C[C@@H](Nc2ncc3c(-c4ccc5nccnc5c4)ccn3n2)C1]
1384
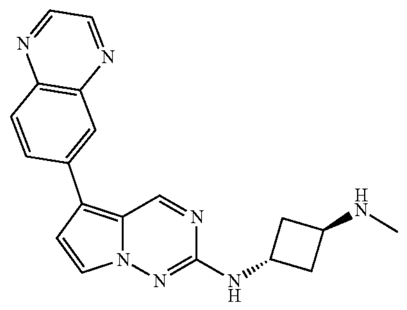 [SMILES: CN[C@H]1C[C@H](Nc2ncc3c(-c4ccc5nccnc5c4)ccn3n2)C1]
1385
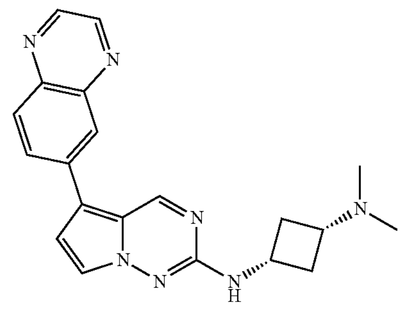 [SMILES: CN(C)[C@H]1C[C@@H](Nc2ncc3c(-c4ccc5nccnc5c4)ccn3n2)C1]
1386
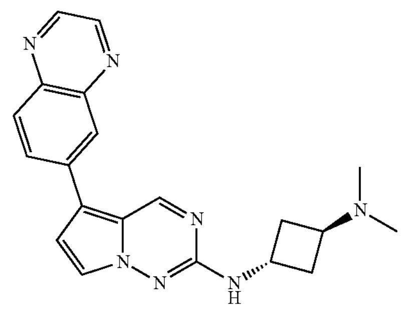 [SMILES: CN(C)[C@H]1C[C@H](Nc2ncc3c(-c4ccc5nccnc5c4)ccn3n2)C1]
1387
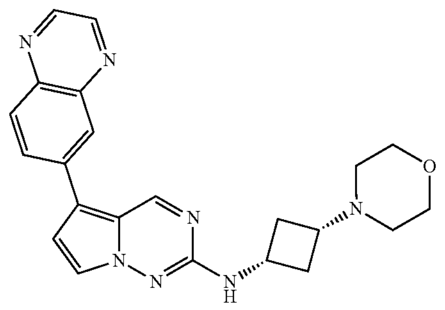 [SMILES: c1cnc2cc(-c3ccn4nc(N[C@H]5C[C@@H](N6CCOCC6)C5)ncc34)ccc2n1]
1388

TABLE 1-continued
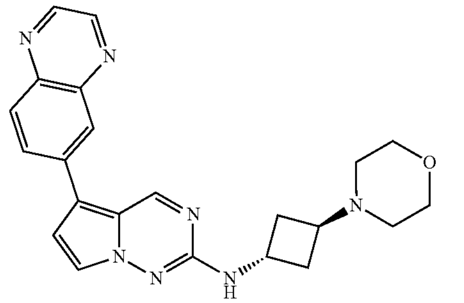 [SMILES: c1cnc2cc(-c3ccn4nc(N[C@H]5C[C@H](N6CCOCC6)C5)ncc34)ccc2n1]
1389
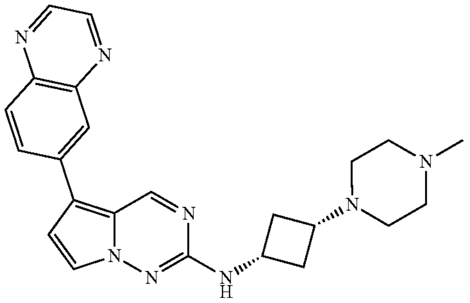 [SMILES: CN1CCN([C@H]2C[C@@H](Nc3ncc4c(-c5ccc6nccnc6c5)ccn4n3)C2)CC1]
1390
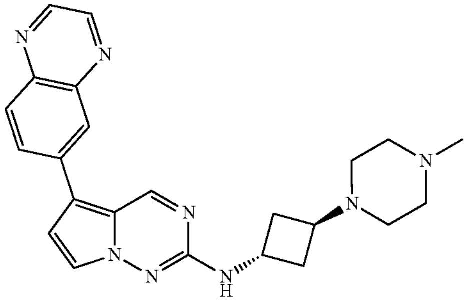 [SMILES: CN1CCN([C@H]2C[C@H](Nc3ncc4c(-c5ccc6nccnc6c5)ccn4n3)C2)CC1]
1391
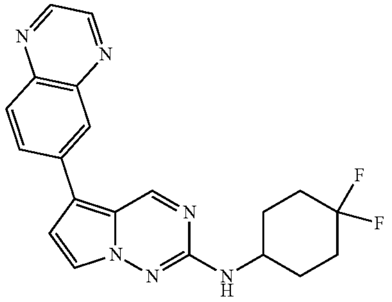 [SMILES: FC1(F)CCC(Nc2ncc3c(-c4ccc5nccnc5c4)ccn3n2)CC1]
1392
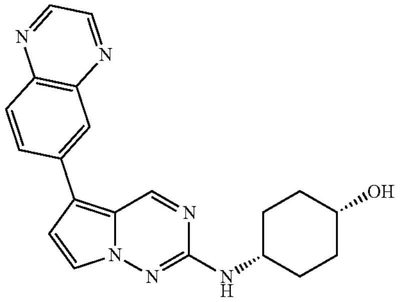
1393

TABLE 1-continued
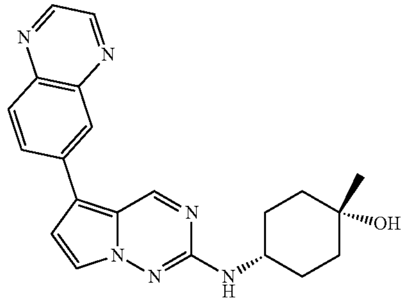 [SMILES: C[C@]1(O)CC[C@@H](Nc2ncc3c(-c4ccc5nccnc5c4)ccn3n2)CC1]
1394
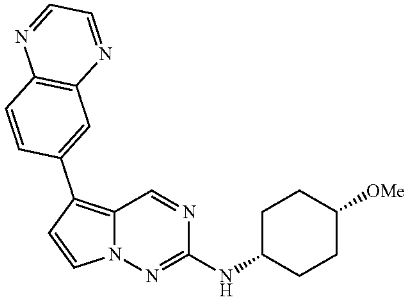 [SMILES: CO[C@H]1CC[C@@H](Nc2ncc3c(-c4ccc5nccnc5c4)ccn3n2)CC1]
1395
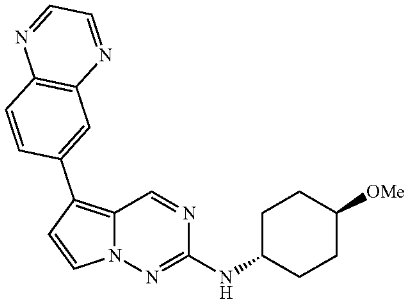 [SMILES: CO[C@H]1CC[C@H](Nc2ncc3c(-c4ccc5nccnc5c4)ccn3n2)CC1]
1396
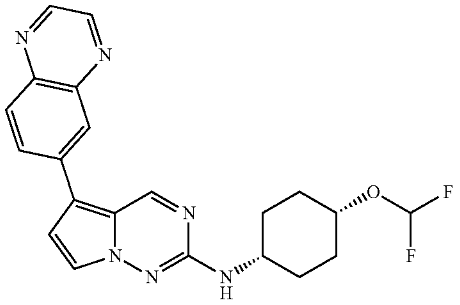 [SMILES: FC(F)O[C@H]1CC[C@@H](Nc2ncc3c(-c4ccc5nccnc5c4)ccn3n2)CC1]
1397
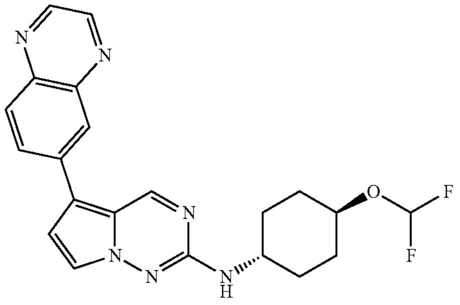 [SMILES: FC(F)O[C@H]1CC[C@H](Nc2ncc3c(-c4ccc5nccnc5c4)ccn3n2)CC1]
1398

TABLE 1-continued
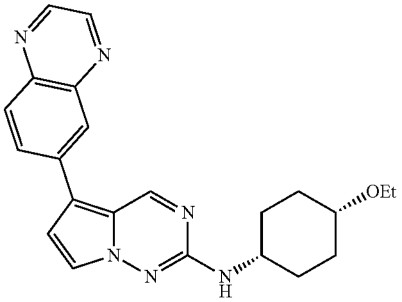 [SMILES: CCO[C@H]1CC[C@@H](Nc2ncc3c(-c4ccc5nccnc5c4)ccn3n2)CC1]
1399
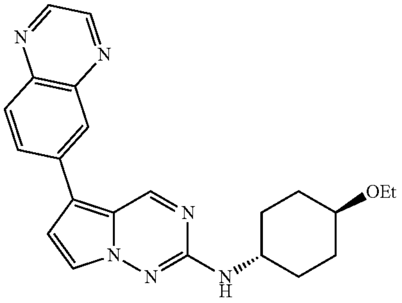
1400
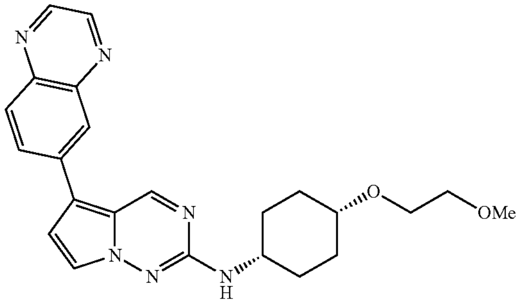 [SMILES: COCCO[C@H]1CC[C@@H](Nc2ncc3c(-c4ccc5nccnc5c4)ccn3n2)CC1]
1401
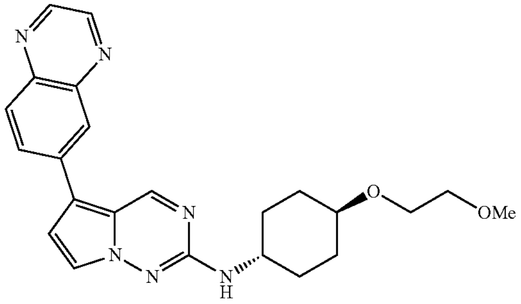 [SMILES: COCCO[C@H]1CC[C@H](Nc2ncc3c(-c4ccc5nccnc5c4)ccn3n2)CC1]
1402
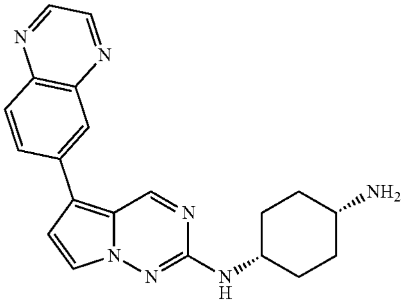 [SMILES: N[C@H]1CC[C@@H](Nc2ncc3c(-c4ccc5nccnc5c4)ccn3n2)CC1]
1403

TABLE 1-continued
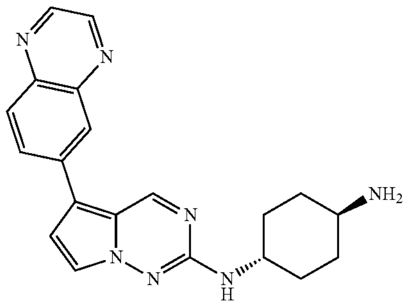 [SMILES: N[C@H]1CC[C@H](Nc2ncc3c(-c4ccc5nccnc5c4)ccn3n2)CC1]
1404
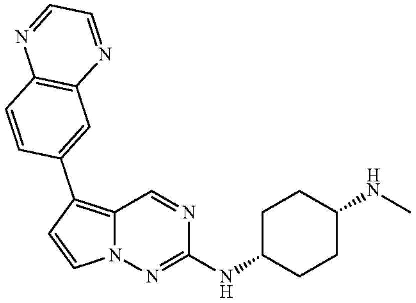 [SMILES: CN[C@H]1CC[C@@H](Nc2ncc3c(-c4ccc5nccnc5c4)ccn3n2)CC1]
1405
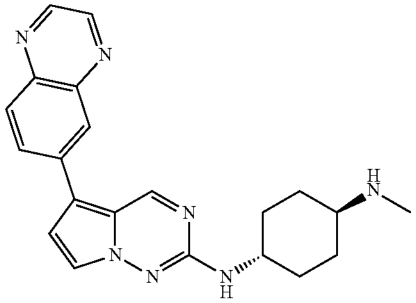 [SMILES: CN[C@H]1CC[C@H](Nc2ncc3c(-c4ccc5nccnc5c4)ccn3n2)CC1]
1406
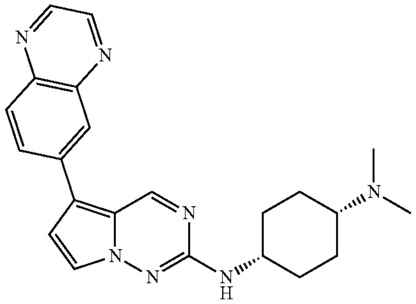 [SMILES: CN(C)[C@H]1CC[C@@H](Nc2ncc3c(-c4ccc5nccnc5c4)ccn3n2)CC1]
1407
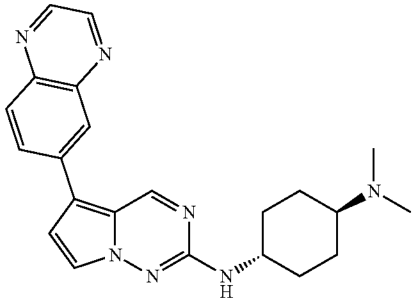 [SMILES: CN(C)[C@H]1CC[C@H](Nc2ncc3c(-c4ccc5nccnc5c4)ccn3n2)CC1]
1408

TABLE 1-continued
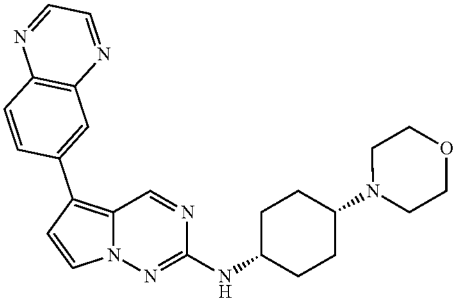 [SMILES: c1cnc2cc(-c3ccn4nc(N[C@H]5CC[C@@H](N6CCOCC6)CC5)ncc34)ccc2n1]
1409
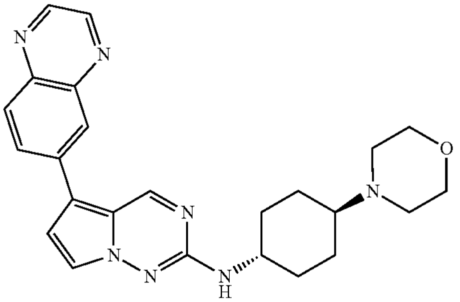 [SMILES: c1cnc2cc(-c3ccn4nc(N[C@H]5CC[C@H](N6CCOCC6)CC5)ncc34)ccc2n1]
1410
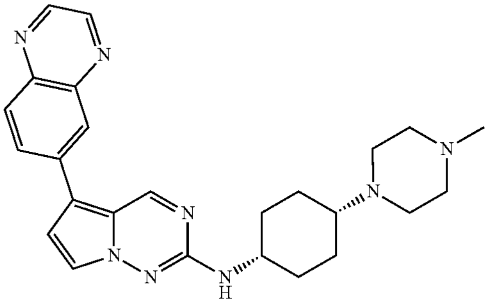 [SMILES: CN1CCN([C@H]2CC[C@@H](Nc3ncc4c(-c5ccc6nccnc6c5)ccn4n3)CC2)CC1]
1411
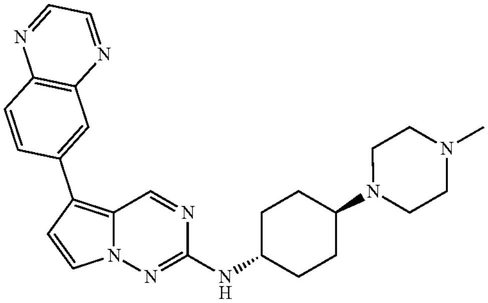 [SMILES: CN1CCN([C@H]2CC[C@H](Nc3ncc4c(-c5ccc6nccnc6c5)ccn4n3)CC2)CC1]
1412
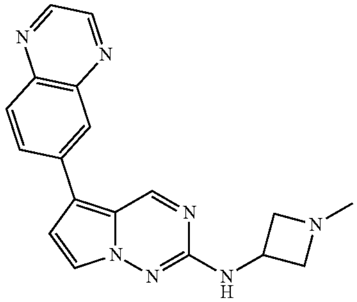 [SMILES: CN1CC(Nc2ncc3c(-c4ccc5nccnc5c4)ccn3n2)C1]
1413

TABLE 1-continued
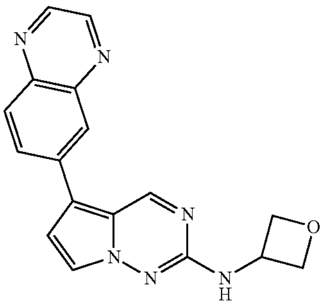 [SMILES: c1cnc2cc(-c3ccn4nc(NC5COC5)ncc34)ccc2n1]
1414
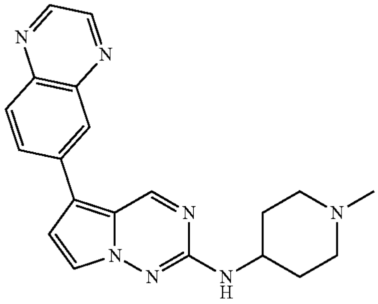 [SMILES: CN1CCC(Nc2ncc3c(-c4ccc5nccnc5c4)ccn3n2)CC1]
1415
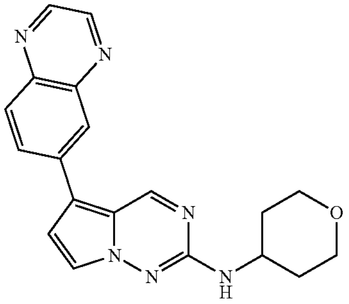 [SMILES: c1cnc2cc(-c3ccn4nc(NC5CCOCC5)ncc34)ccc2n1]
1416
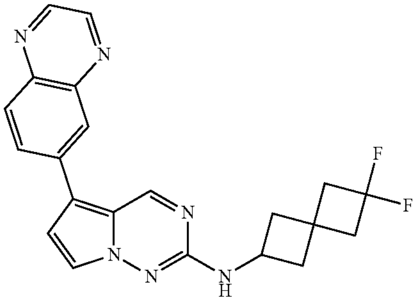 [SMILES: FC1(F)CC2(CC(Nc3ncc4c(-c5ccc6nccnc6c5)ccn4n3)C2)C1]
1417
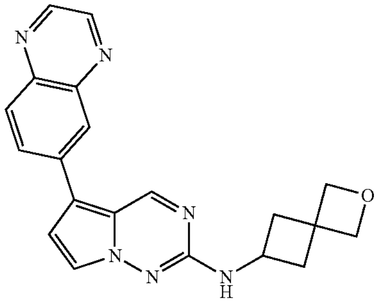 [SMILES: c1cnc2cc(-c3ccn4nc(NC5CC6(COC6)C5)ncc34)ccc2n1]
1418

TABLE 1-continued
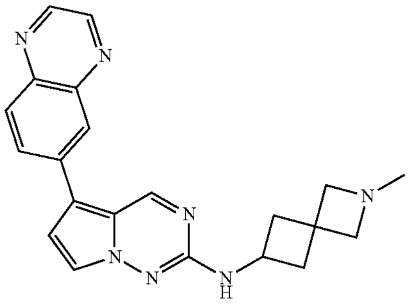 [SMILES: CN1CC2(CC(Nc3ncc4c(-c5ccc6nccnc6c5)ccn4n3)C2)C1]
1419
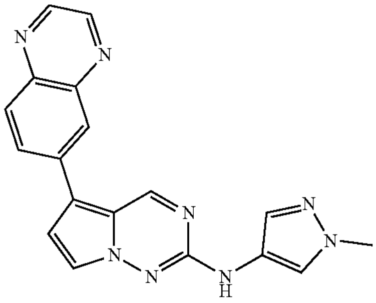 [SMILES: Cn1cc(Nc2ncc3c(-c4ccc5nccnc5c4)ccn3n2)cn1]
1420
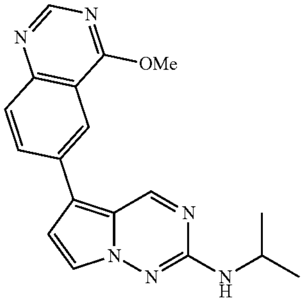 [SMILES: COc1ncnc2ccc(-c3ccn4nc(NC(C)C)ncc34)cc12]
1421
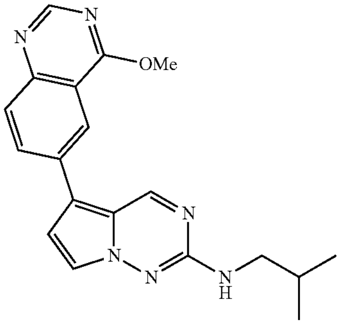 [SMILES: COc1ncnc2ccc(-c3ccn4nc(NCC(C)C)ncc34)cc12]
1422
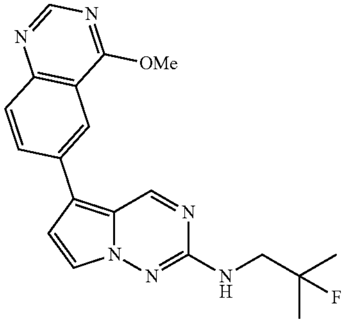 [SMILES: COc1ncnc2ccc(-c3ccn4nc(NCC(C)(C)F)ncc34)cc12]
1423

TABLE 1-continued
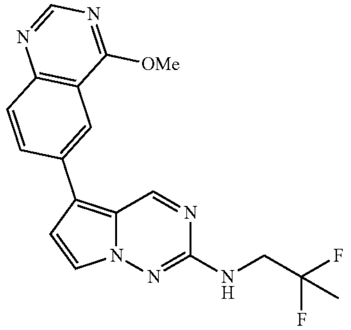 [SMILES: COc1ncnc2ccc(-c3ccn4nc(NCC(C)(F)F)ncc34)cc12]
1424
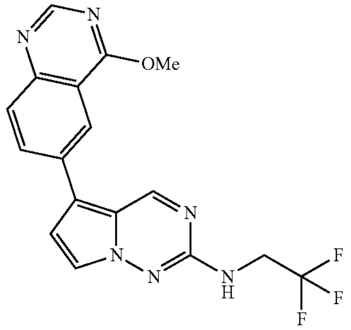
1425
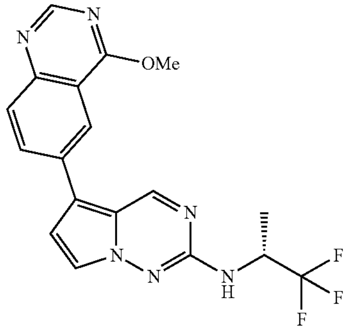 [SMILES: COc1ncnc2ccc(-c3ccn4nc(N[C@H](C)C(F)(F)F)ncc34)cc12]
1426
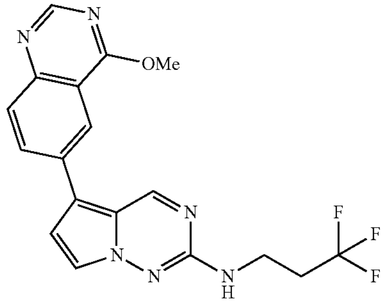 [SMILES: COc1ncnc2ccc(-c3ccn4nc(NCCC(F)(F)F)ncc34)cc12]
1427
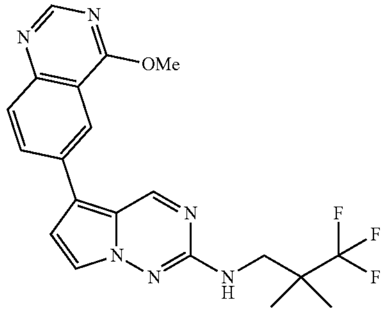 [SMILES: COc1ncnc2ccc(-c3ccn4nc(NCC(C)(C)C(F)(F)F)ncc34)cc12]
1428

TABLE 1-continued
1429
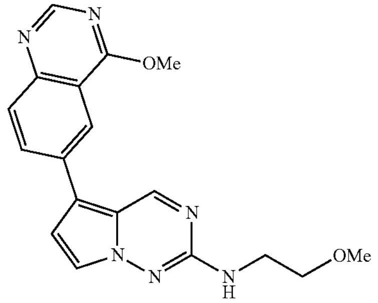 [SMILES: COCCNc1ncc2c(-c3ccc4ncnc(OC)c4c3)ccn2n1]
1430
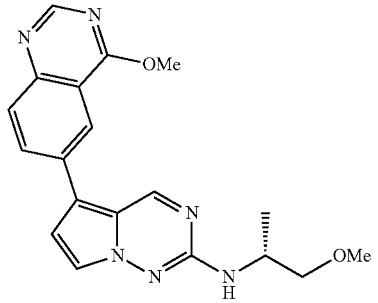 [SMILES: COC[C@@H](C)Nc1ncc2c(-c3ccc4ncnc(OC)c4c3)ccn2n1]
1431
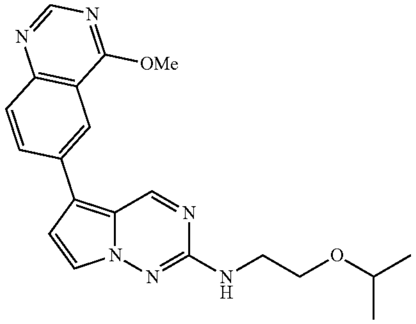 [SMILES: COc1ncnc2ccc(-c3ccn4nc(NCCOC(C)C)ncc34)cc12]
1432
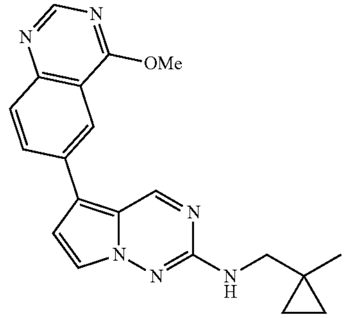 [SMILES: COc1ncnc2ccc(-c3ccn4nc(NCC5(C)CC5)ncc34)cc12]
1433
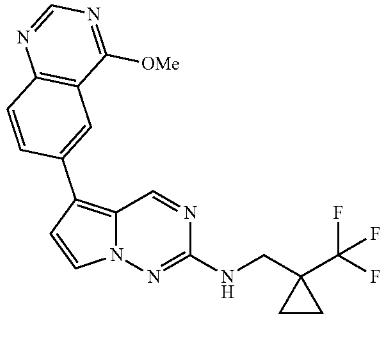 [SMILES: COc1ncnc2ccc(-c3ccn4nc(NCC5(C(F)(F)F)CC5)ncc34)cc12]

TABLE 1-continued
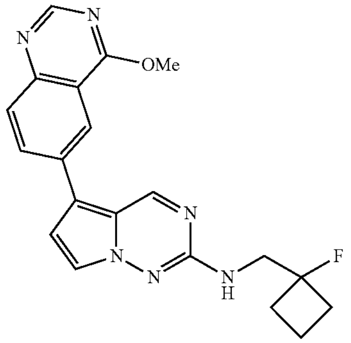 [SMILES: COc1ncnc2ccc(-c3ccn4nc(NCC5(F)CCC5)ncc34)cc12]
1434
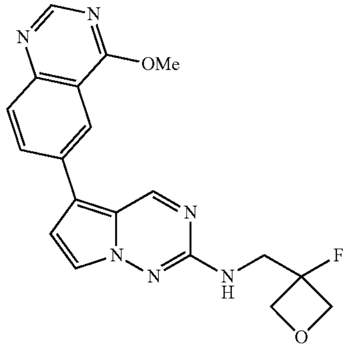 [SMILES: COc1ncnc2ccc(-c3ccn4nc(NCC5(F)COC5)ncc34)cc12]
1435
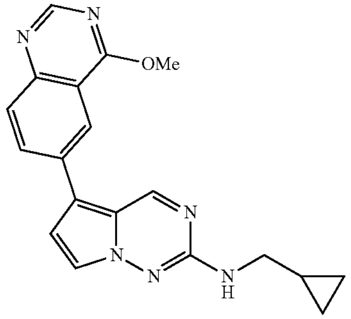 [SMILES: COc1ncnc2ccc(-c3ccn4nc(NCC5CC5)ncc34)cc12]
1436
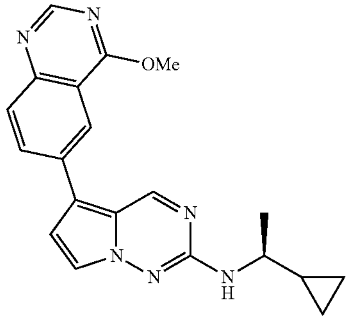 [SMILES: COc1ncnc2ccc(-c3ccn4nc(N[C@@H](C)C5CC5)ncc34)cc12]
1437

TABLE 1-continued
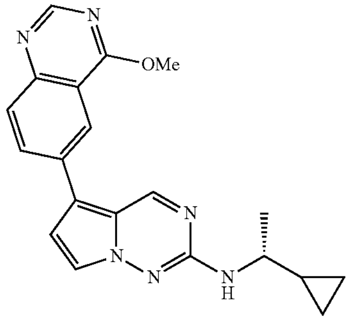 [SMILES: COc1ncnc2ccc(-c3ccn4nc(N[C@H](C)C5CC5)ncc34)cc12]
1438
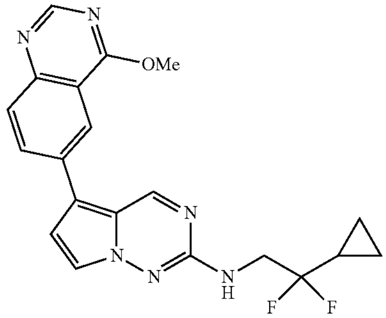 [SMILES: COc1ncnc2ccc(-c3ccn4nc(NCC(F)(F)C5CC5)ncc34)cc12]
1439
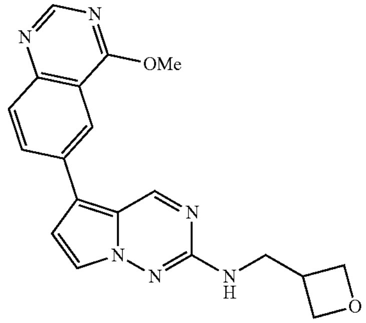 [SMILES: COc1ncnc2ccc(-c3ccn4nc(NCC5COC5)ncc34)cc12]
1440
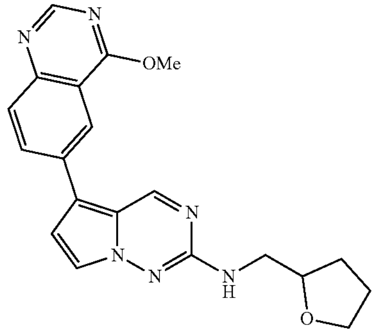 [SMILES: COc1ncnc2ccc(-c3ccn4nc(NCC5CCCO5)ncc34)cc12]
1441
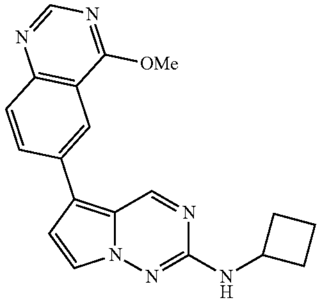 [SMILES: COc1ncnc2ccc(-c3ccn4nc(NC5CCC5)ncc34)cc12]
1442

TABLE 1-continued
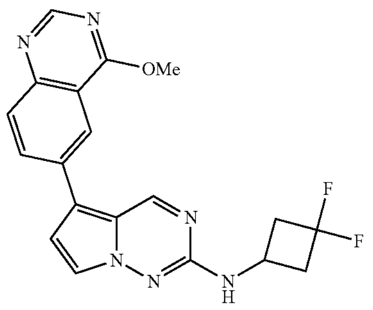 [SMILES: COc1ncnc2ccc(-c3ccn4nc(NC5CC(F)(F)C5)ncc34)cc12]
1443
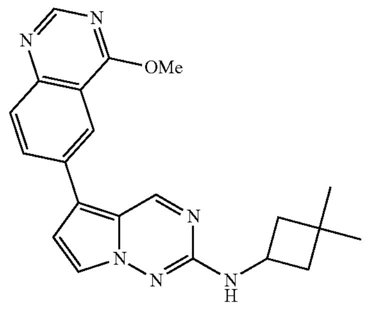 [SMILES: COc1ncnc2ccc(-c3ccn4nc(NC5CC(C)(C)C5)ncc34)cc12]
1444
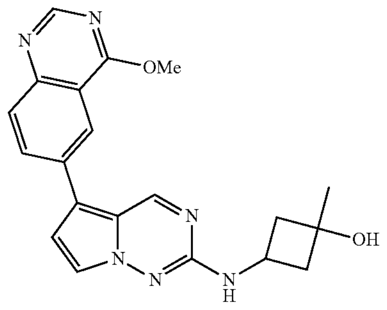 [SMILES: COc1ncnc2ccc(-c3ccn4nc(NC5CC(C)(O)C5)ncc34)cc12]
1445
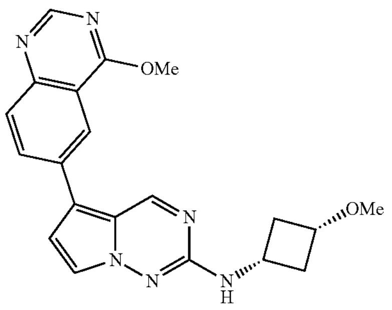 [SMILES: COc1ncnc2ccc(-c3ccn4nc(N[C@H]5C[C@@H](OC)C5)ncc34)cc12]
1446
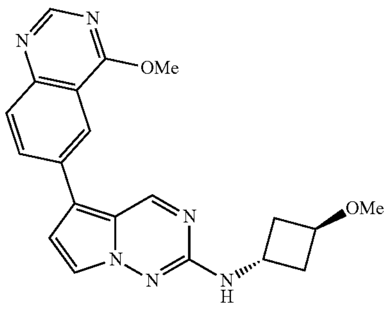 [SMILES: COc1ncnc2ccc(-c3ccn4nc(N[C@H]5C[C@H](OC)C5)ncc34)cc12]
1447

TABLE 1-continued
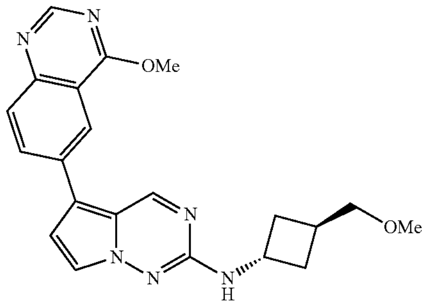 [SMILES: COC[C@H]1C[C@H](Nc2ncc3c(-c4ccc5ncnc(OC)c5c4)ccn3n2)C1]
1448
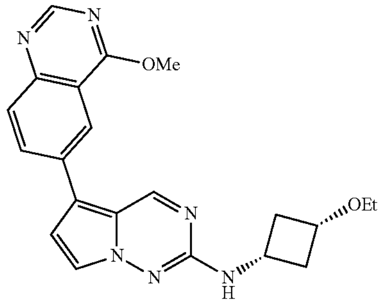 [SMILES: CCO[C@H]1C[C@@H](Nc2ncc3c(-c4ccc5ncnc(OC)c5c4)ccn3n2)C1]
1449
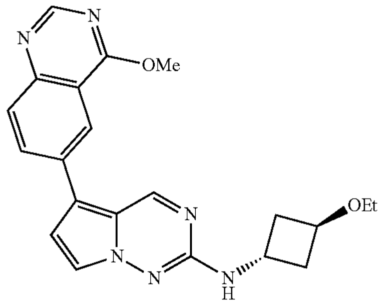 [SMILES: CCO[C@H]1C[C@H](Nc2ncc3c(-c4ccc5ncnc(OC)c5c4)ccn3n2)C1]
1450
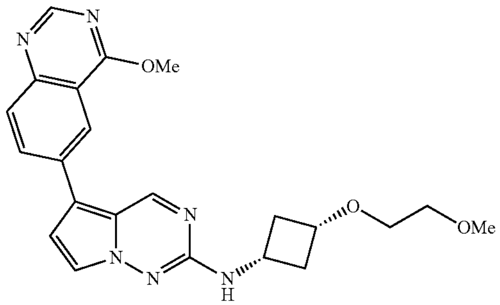 [SMILES: COCCO[C@H]1C[C@@H](Nc2ncc3c(-c4ccc5ncnc(OC)c5c4)ccn3n2)C1]
1451
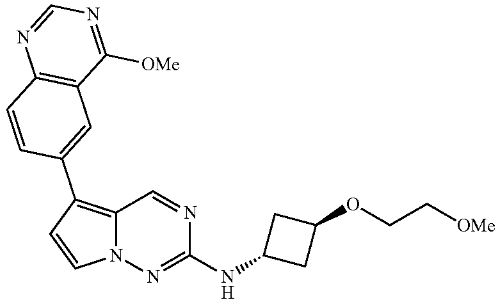 [SMILES: COCCO[C@H]1C[C@H](Nc2ncc3c(-c4ccc5ncnc(OC)c5c4)ccn3n2)C1]
1452

TABLE 1-continued
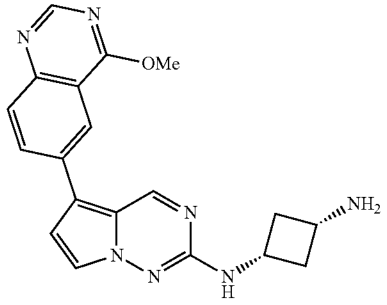 [SMILES: COc1ncnc2ccc(-c3ccn4nc(N[C@H]5C[C@@H](N)C5)ncc34)cc12]
1453
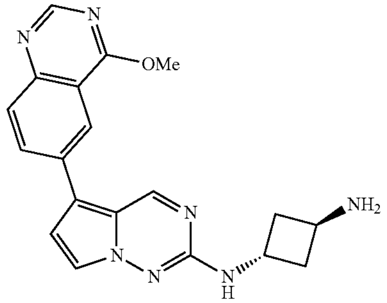 [SMILES: COc1ncnc2ccc(-c3ccn4nc(N[C@H]5C[C@H](N)C5)ncc34)cc12]
1454
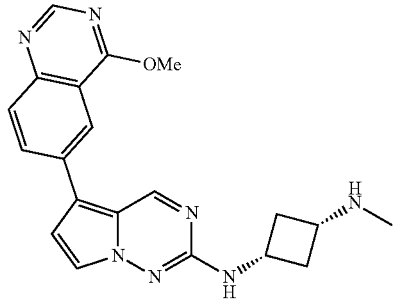 [SMILES: CN[C@H]1C[C@@H](Nc2ncc3c(-c4ccc5ncnc(OC)c5c4)ccn3n2)C1]
1455
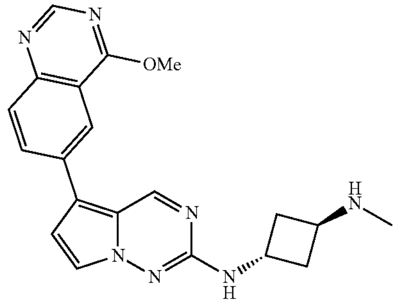 [SMILES: CN[C@H]1C[C@H](Nc2ncc3c(-c4ccc5ncnc(OC)c5c4)ccn3n2)C1]
1456
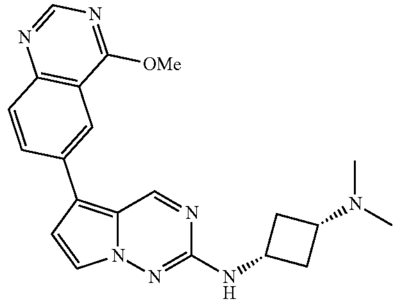 [SMILES: COc1ncnc2ccc(-c3ccn4nc(N[C@H]5C[C@@H](N(C)C)C5)ncc34)cc12]
1457

TABLE 1-continued
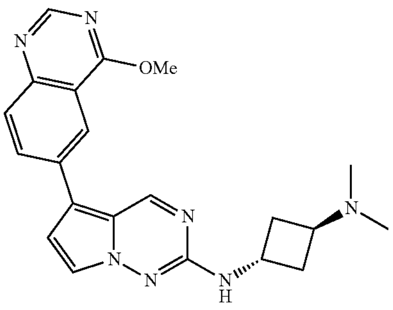 [SMILES: COc1ncnc2ccc(-c3ccn4nc(N[C@H]5C[C@H](N(C)C)C5)ncc34)cc12]
1458
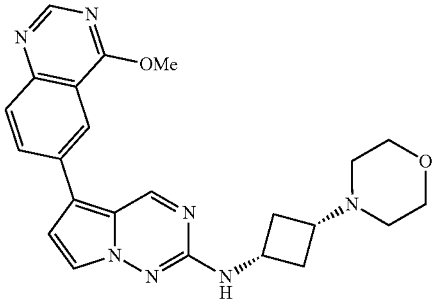 [SMILES: COc1ncnc2ccc(-c3ccn4nc(N[C@H]5C[C@@H](N6CCOCC6)C5)ncc34)cc12]
1459
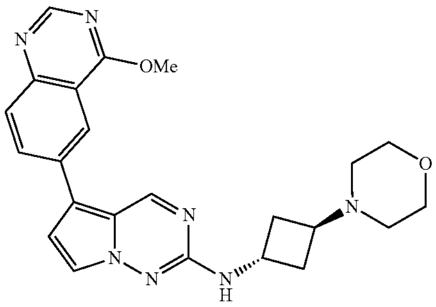 [SMILES: COc1ncnc2ccc(-c3ccn4nc(N[C@H]5C[C@H](N6CCOCC6)C5)ncc34)cc12]
1460
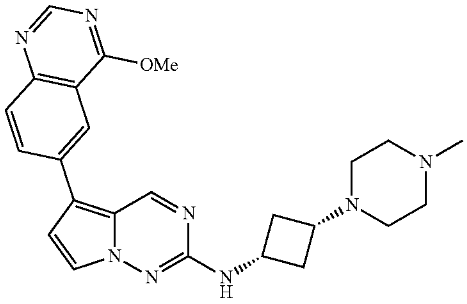 [SMILES: COc1ncnc2ccc(-c3ccn4nc(N[C@H]5C[C@@H](N6CCN(C)CC6)C5)ncc34)cc12]
1461
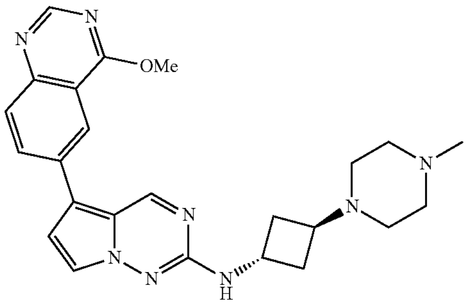 [SMILES: COc1ncnc2ccc(-c3ccn4nc(N[C@H]5C[C@H](N6CCN(C)CC6)C5)ncc34)cc12]
1462

TABLE 1-continued
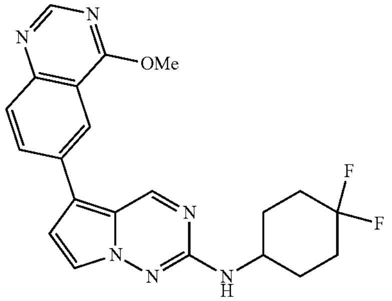 [SMILES: COc1ncnc2ccc(-c3ccn4nc(NC5CCC(F)(F)CC5)ncc34)cc12]
1463
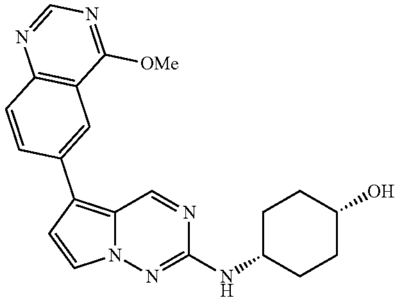 [SMILES: COc1ncnc2ccc(-c3ccn4nc(N[C@H]5CC[C@@H](O)CC5)ncc34)cc12]
1464
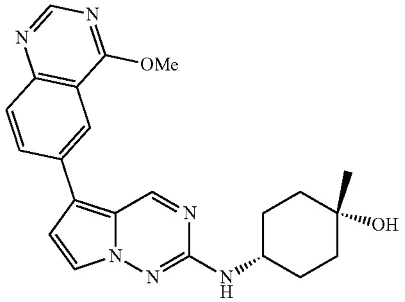 [SMILES: COc1ncnc2ccc(-c3ccn4nc(N[C@H]5CC[C@@](C)(O)CC5)ncc34)cc12]
1465
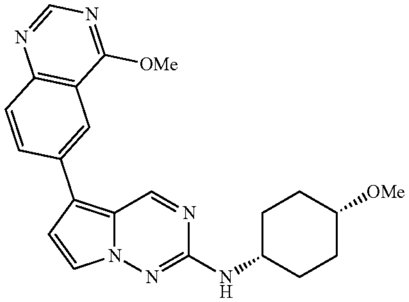 [SMILES: COc1ncnc2ccc(-c3ccn4nc(N[C@H]5CC[C@@H](OC)CC5)ncc34)cc12]
1466
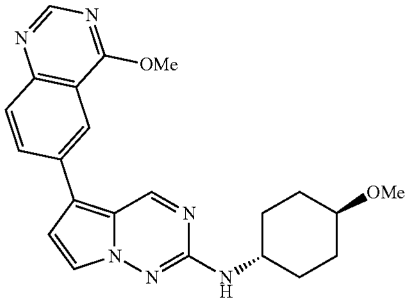 [SMILES: COc1ncnc2ccc(-c3ccn4nc(N[C@H]5CC[C@H](OC)CC5)ncc34)cc12]
1467

TABLE 1-continued
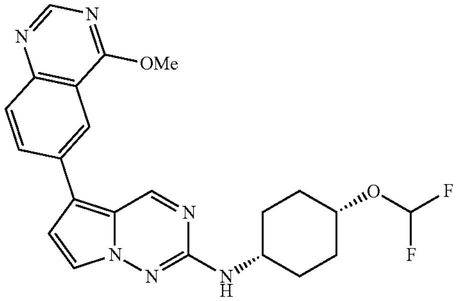 [SMILES: COc1ncnc2ccc(-c3ccn4nc(N[C@H]5CC[C@@H](OC(F)F)CC5)ncc34)cc12]
1468
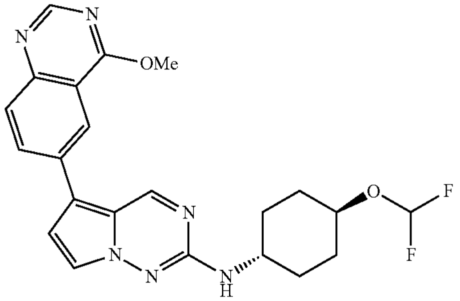 [SMILES: COc1ncnc2ccc(-c3ccn4nc(N[C@H]5CC[C@H](OC(F)F)CC5)ncc34)cc12]
1469
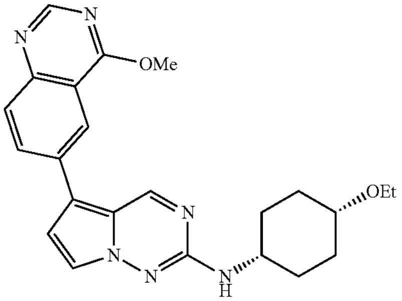 [SMILES: CCO[C@H]1CC[C@@H](Nc2ncc3c(-c4ccc5ncnc(OC)c5c4)ccn3n2)CC1]
1470
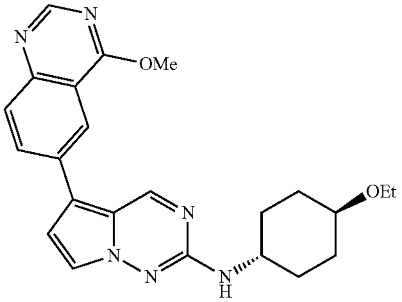 [SMILES: CCO[C@H]1CC[C@H](Nc2ncc3c(-c4ccc5ncnc(OC)c5c4)ccn3n2)CC1]
1471
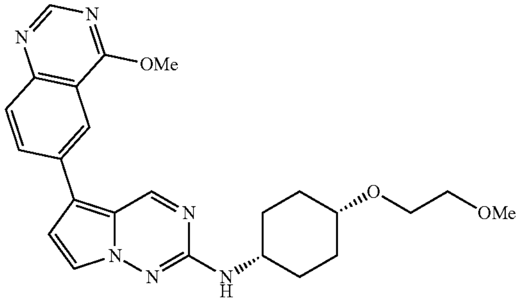 [SMILES: COCCO[C@H]1CC[C@@H](Nc2ncc3c(-c4ccc5ncnc(OC)c5c4)ccn3n2)CC1]
1472

TABLE 1-continued
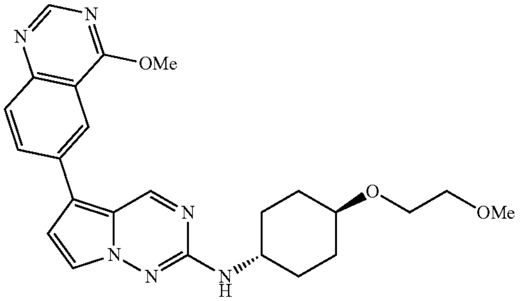 [SMILES: COCCO[C@H]1CC[C@H](Nc2ncc3c(-c4ccc5ncnc(OC)c5c4)ccn3n2)CC1]
1473
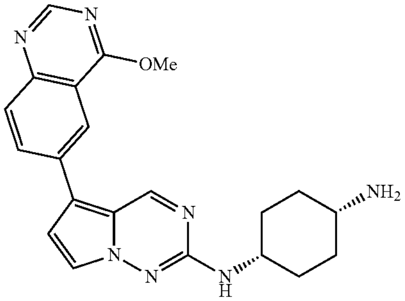 [SMILES: COc1ncnc2ccc(-c3ccn4nc(N[C@H]5CC[C@@H](N)CC5)ncc34)cc12]
1474
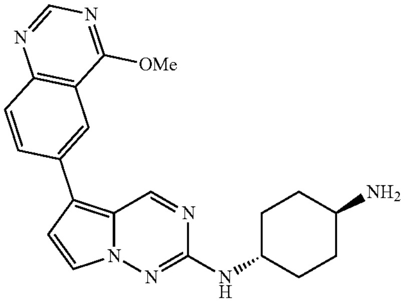 [SMILES: COc1ncnc2ccc(-c3ccn4nc(N[C@H]5CC[C@H](N)CC5)ncc34)cc12]
1475
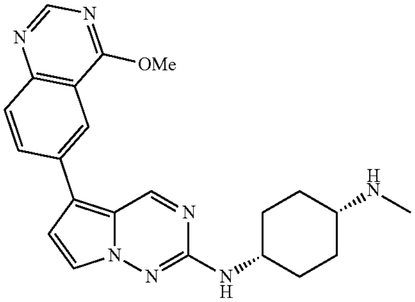 [SMILES: CN[C@H]1CC[C@@H](Nc2ncc3c(-c4ccc5ncnc(OC)c5c4)ccn3n2)CC1]
1476
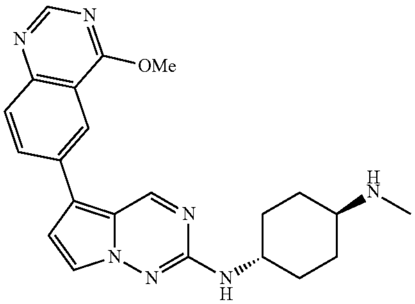 [SMILES: CN[C@H]1CC[C@H](Nc2ncc3c(-c4ccc5ncnc(OC)c5c4)ccn3n2)CC1]
1477

TABLE 1-continued
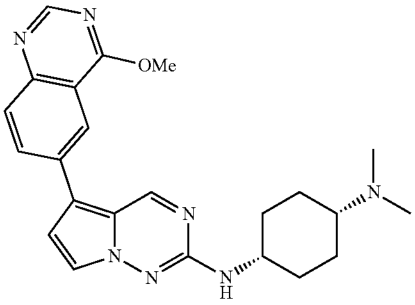 [SMILES: COc1ncnc2ccc(-c3ccn4nc(N[C@H]5CC[C@@H](N(C)C)CC5)ncc34)cc12]
1478
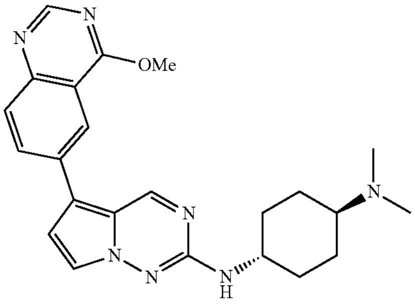 [SMILES: COc1ncnc2ccc(-c3ccn4nc(N[C@H]5CC[C@H](N(C)C)CC5)ncc34)cc12]
1479
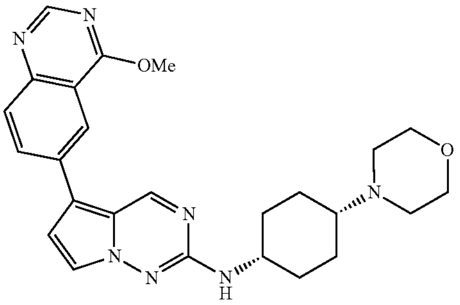 [SMILES: COc1ncnc2ccc(-c3ccn4nc(N[C@H]5CC[C@@H](N6CCOCC6)CC5)ncc34)cc12]
1480
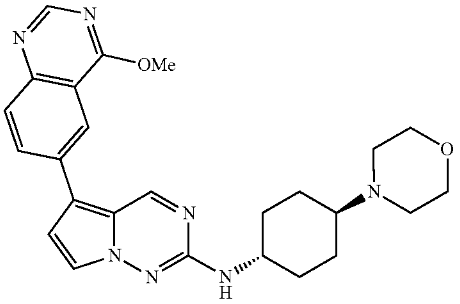 [SMILES: COc1ncnc2ccc(-c3ccn4nc(N[C@H]5CC[C@H](N6CCOCC6)CC5)ncc34)cc12]
1481
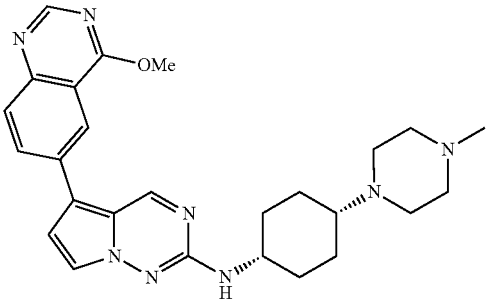 [SMILES: COc1ncnc2ccc(-c3ccn4nc(N[C@H]5CC[C@@H](N6CCN(C)CC6)CC5)ncc34)cc12]
1482

TABLE 1-continued
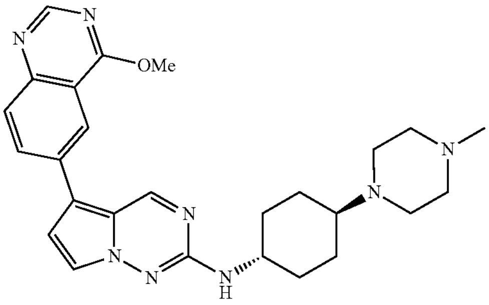 [SMILES: COc1ncnc2ccc(-c3ccn4nc(N[C@H]5CC[C@H](N6CCN(C)CC6)CC5)ncc34)cc12]
1483
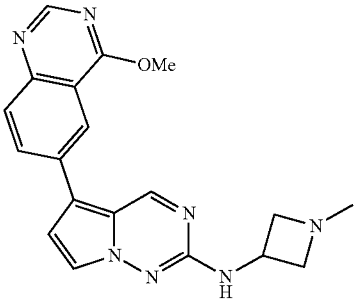 [SMILES: COc1ncnc2ccc(-c3ccn4nc(NC5CN(C)C5)ncc34)cc12]
1484
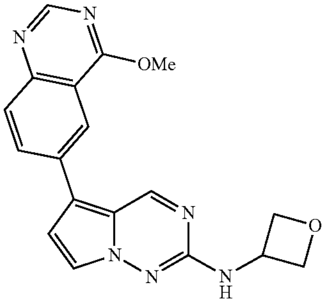 [SMILES: COc1ncnc2ccc(-c3ccn4nc(NC5COC5)ncc34)cc12]
1485
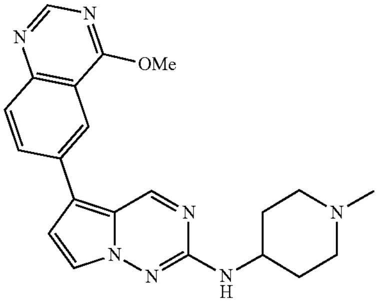 [SMILES: COc1ncnc2ccc(-c3ccn4nc(NC5CCN(C)CC5)ncc34)cc12]
1486
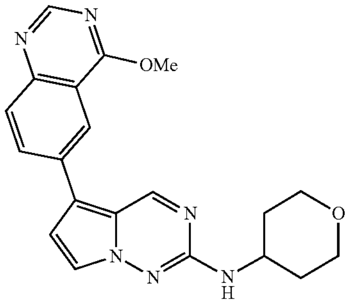 [SMILES: COc1ncnc2ccc(-c3ccn4nc(NC5CCOCC5)ncc34)cc12]
1487

TABLE 1-continued
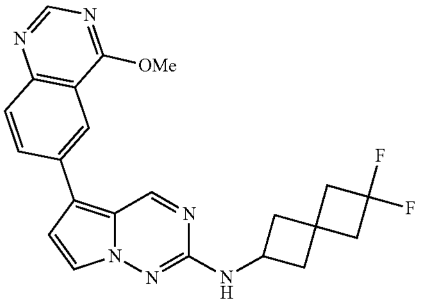 [SMILES: COc1ncnc2ccc(-c3ccn4nc(NC5CC6(C5)CC(F)(F)C6)ncc34)cc12]
1488
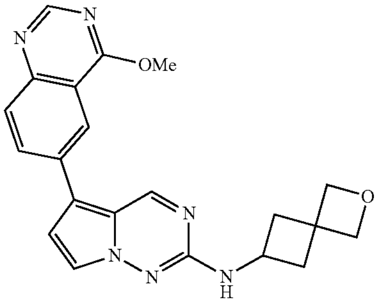 [SMILES: COc1ncnc2ccc(-c3ccn4nc(NC5CC6(COC6)C5)ncc34)cc12]
1489
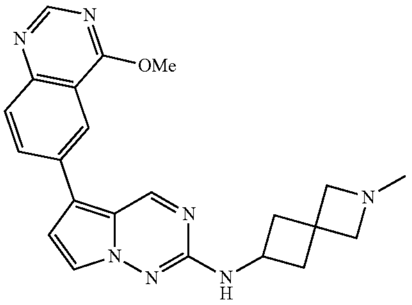 [SMILES: COc1ncnc2ccc(-c3ccn4nc(NC5CC6(C5)CN(C)C6)ncc34)cc12]
1490
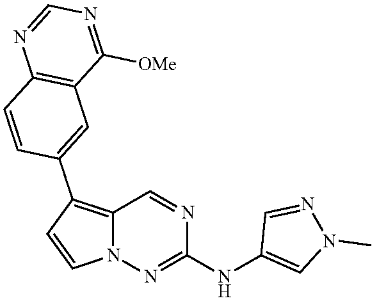 [SMILES: COc1ncnc2ccc(-c3ccn4nc(Nc5cnn(C)c5)ncc34)cc12]
1491
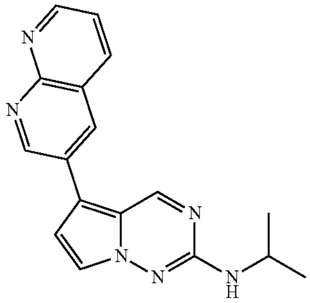 [SMILES: CC(C)Nc1ncc2c(-c3cnc4ncccc4c3)ccn2n1]
1492

TABLE 1-continued
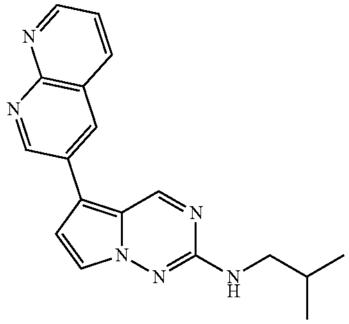 [SMILES: CC(C)CNc1ncc2c(-c3cnc4ncccc4c3)ccn2n1]
1493
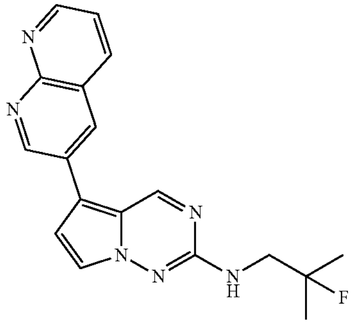 [SMILES: CC(C)(F)CNc1ncc2c(-c3cnc4ncccc4c3)ccn2n1]
1494
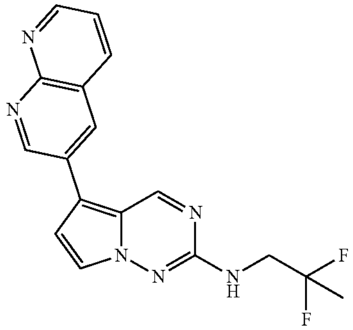 [SMILES: CC(F)(F)CNc1ncc2c(-c3cnc4ncccc4c3)ccn2n1]
1495
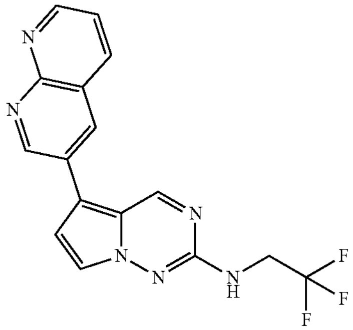 [SMILES: FC(F)(F)CNc1ncc2c(-c3cnc4ncccc4c3)ccn2n1]
1496

TABLE 1-continued
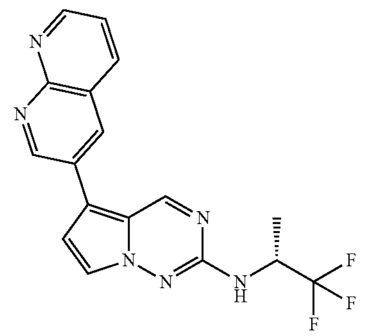 [SMILES: C[C@@H](Nc1ncc2c(-c3cnc4ncccc4c3)ccn2n1)C(F)(F)F]
1497
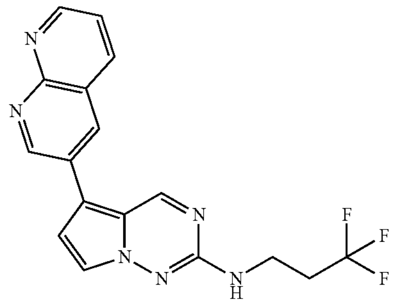 [SMILES: FC(F)(F)CCNc1ncc2c(-c3cnc4ncccc4c3)ccn2n1]
1498
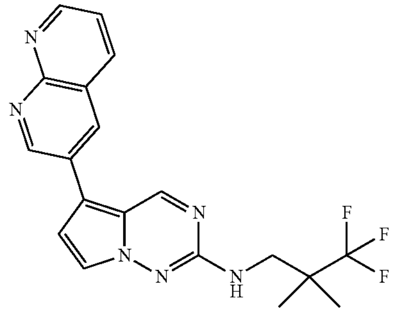 [SMILES: CC(C)(CNc1ncc2c(-c3cnc4ncccc4c3)ccn2n1)C(F)(F)F]
1499
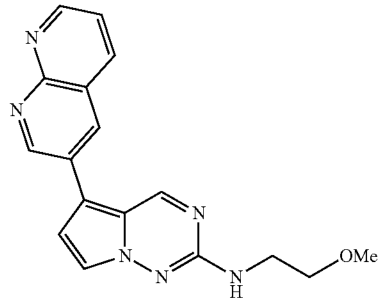 [SMILES: COCCNc1ncc2c(-c3cnc4ncccc4c3)ccn2n1]
1500
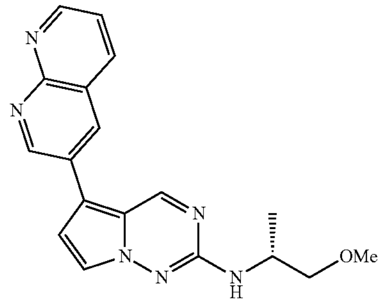 [SMILES: COC[C@@H](C)Nc1ncc2c(-c3cnc4ncccc4c3)ccn2n1]
1501

TABLE 1-continued
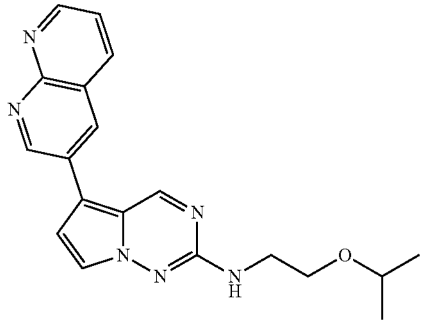 [SMILES: CC(C)OCCNc1ncc2c(-c3cnc4ncccc4c3)ccn2n1]
1502
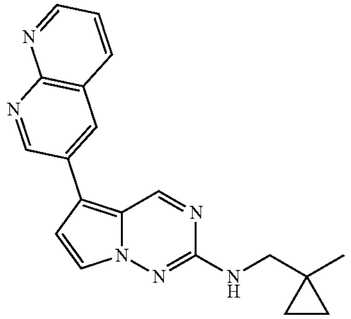 [SMILES: CC1(CNc2ncc3c(-c4cnc5ncccc5c4)ccn3n2)CC1]
1503
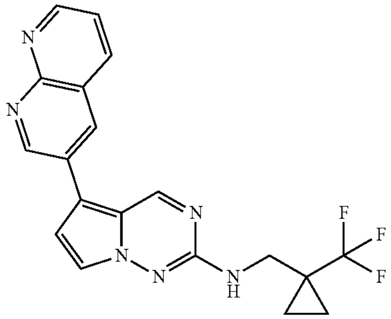 [SMILES: FC(F)(F)C1(CNc2ncc3c(-c4cnc5ncccc5c4)ccn3n2)CC1]
1504
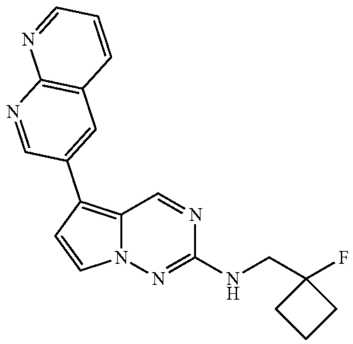 [SMILES: FC1(CNc2ncc3c(-c4cnc5ncccc5c4)ccn3n2)CCC1]
1505

TABLE 1-continued
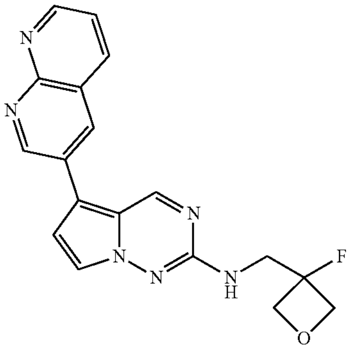 [SMILES: FC1(CNc2ncc3c(-c4cnc5ncccc5c4)ccn3n2)COC1]
1506
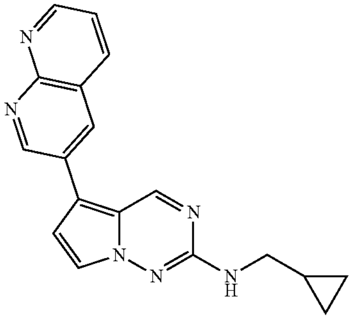 [SMILES: c1cnc2ncc(-c3ccn4nc(NCC5CC5)ncc34)cc2c1]
1507
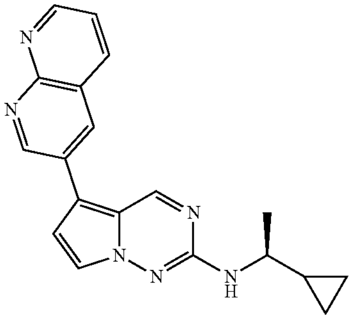 [SMILES: C[C@H](Nc1ncc2c(-c3cnc4ncccc4c3)ccn2n1)C1CC1]
1508
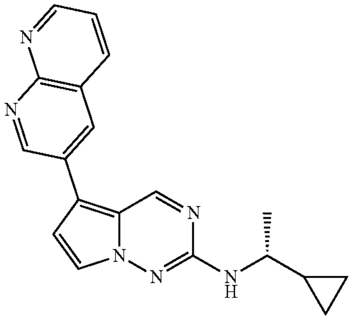 [SMILES: C[C@@H](Nc1ncc2c(-c3cnc4ncccc4c3)ccn2n1)C1CC1]
1509
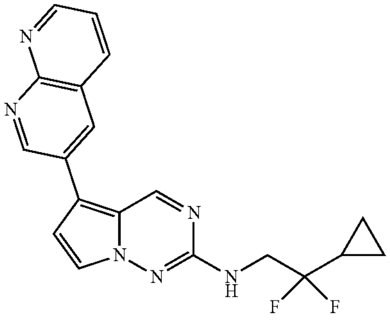 [SMILES: FC(F)(CNc1ncc2c(-c3cnc4ncccc4c3)ccn2n1)C1CC1]
1510

TABLE 1-continued
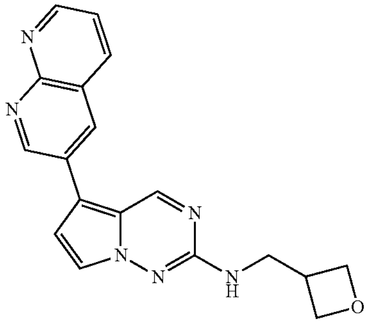 [SMILES: c1cnc2ncc(-c3ccn4nc(NCC5COC5)ncc34)cc2c1]
1511
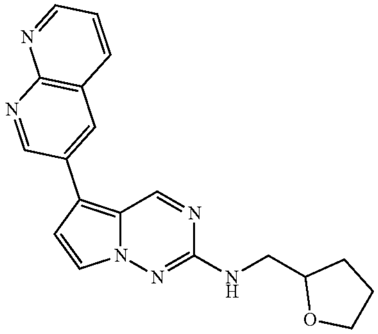 [SMILES: c1cnc2ncc(-c3ccn4nc(NCC5CCCO5)ncc34)cc2c1]
1512
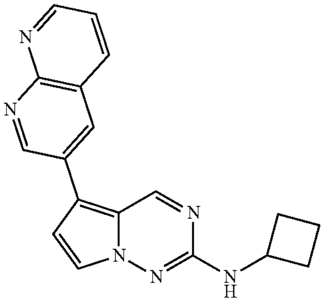 [SMILES: c1cnc2ncc(-c3ccn4nc(NC5CCC5)ncc34)cc2c1]
1513
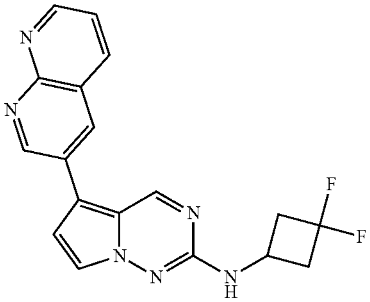 [SMILES: FC1(F)CC(Nc2ncc3c(-c4cnc5ncccc5c4)ccn3n2)C1]
1514
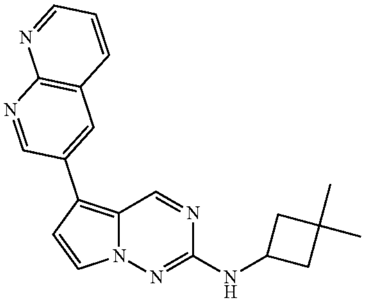 [SMILES: CC1(C)CC(Nc2ncc3c(-c4cnc5ncccc5c4)ccn3n2)C1]
1515

TABLE 1-continued
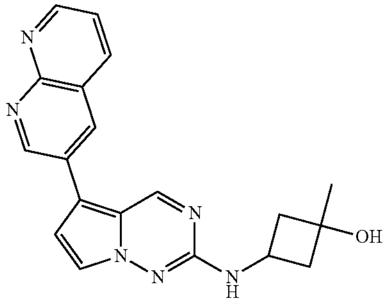 [SMILES: CC1(O)CC(Nc2ncc3c(-c4cnc5ncccc5c4)ccn3n2)C1]
1516
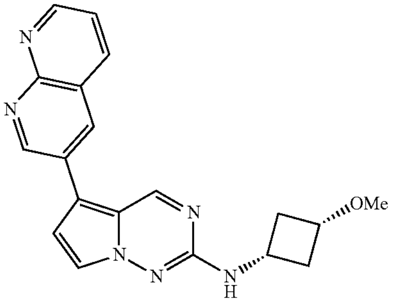 [SMILES: CO[C@H]1C[C@@H](Nc2ncc3c(-c4cnc5ncccc5c4)ccn3n2)C1]
1517
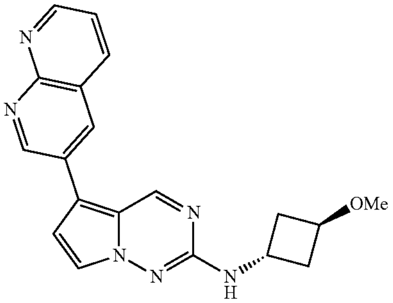 [SMILES: CO[C@H]1C[C@H](Nc2ncc3c(-c4cnc5ncccc5c4)ccn3n2)C1]
1518
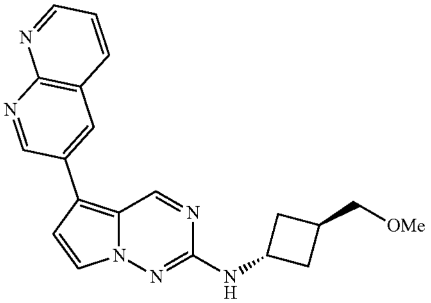
1519
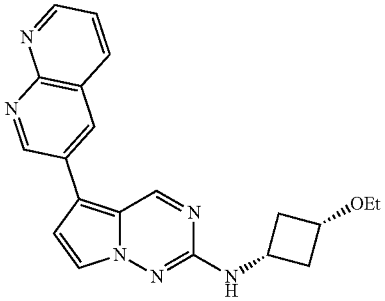 [SMILES: CCO[C@H]1C[C@@H](Nc2ncc3c(-c4cnc5ncccc5c4)ccn3n2)C1]
1520

TABLE 1-continued
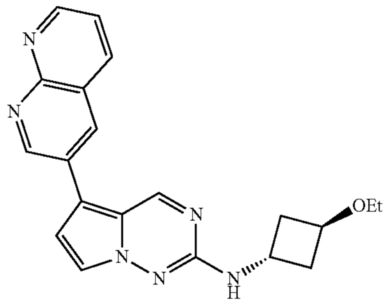 [SMILES: CCO[C@H]1C[C@H](Nc2ncc3c(-c4cnc5ncccc5c4)ccn3n2)C1]
1521
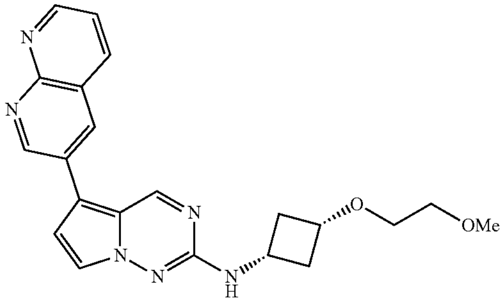 [SMILES: COCCO[C@H]1C[C@@H](Nc2ncc3c(-c4cnc5ncccc5c4)ccn3n2)C1]
1522
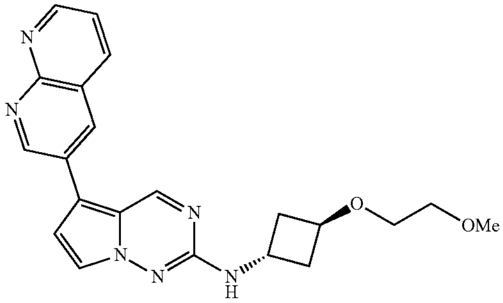 [SMILES: COCCO[C@H]1C[C@H](Nc2ncc3c(-c4cnc5ncccc5c4)ccn3n2)C1]
1523
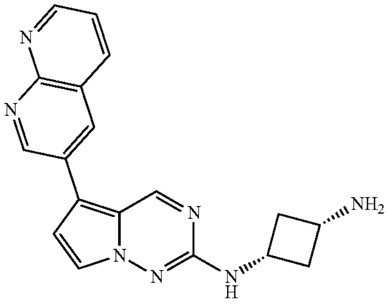 [SMILES: N[C@H]1C[C@@H](Nc2ncc3c(-c4cnc5ncccc5c4)ccn3n2)C1]
1524
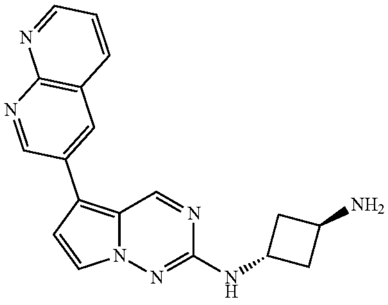 [SMILES: N[C@H]1C[C@H](Nc2ncc3c(-c4cnc5ncccc5c4)ccn3n2)C1]
1525

TABLE 1-continued
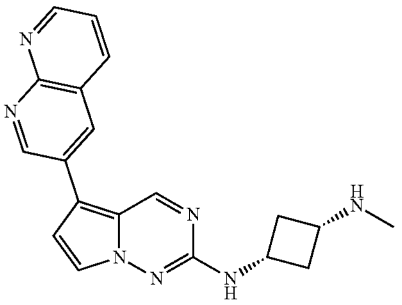 [SMILES: CN[C@H]1C[C@@H](Nc2ncc3c(-c4cnc5ncccc5c4)ccn3n2)C1]
1526
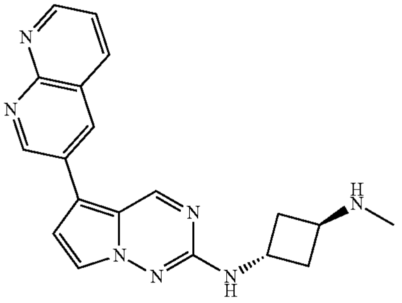 [SMILES: CN[C@H]1C[C@H](Nc2ncc3c(-c4cnc5ncccc5c4)ccn3n2)C1]
1527
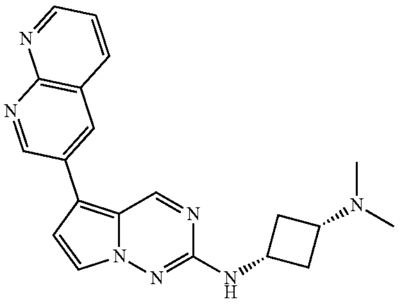 [SMILES: CN(C)[C@H]1C[C@@H](Nc2ncc3c(-c4cnc5ncccc5c4)ccn3n2)C1]
1528
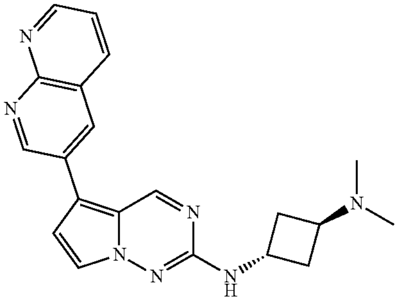 [SMILES: CN(C)[C@H]1C[C@H](Nc2ncc3c(-c4cnc5ncccc5c4)ccn3n2)C1]
1529
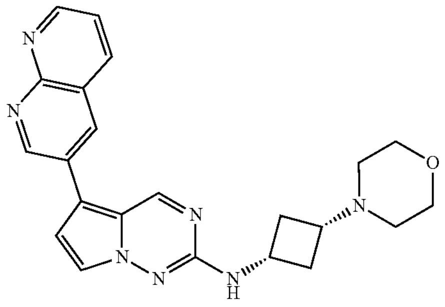 [SMILES: c1cnc2ncc(-c3ccn4nc(N[C@H]5C[C@@H](N6CCOCC6)C5)ncc34)cc2c1]
1530

TABLE 1-continued
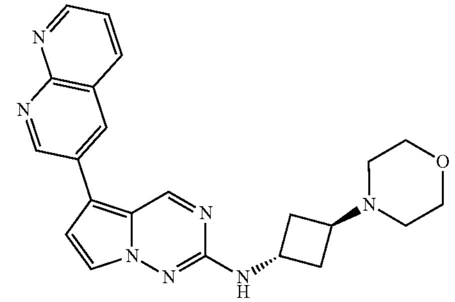 [SMILES: c1cnc2ncc(-c3ccn4nc(N[C@H]5C[C@H](N6CCOCC6)C5)ncc34)cc2c1]
1531
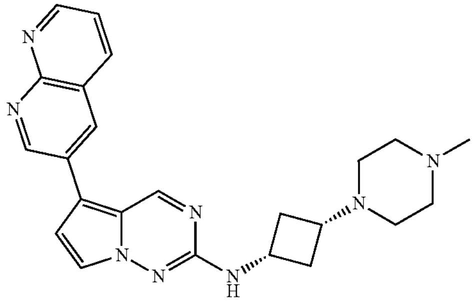 [SMILES: CN1CCN([C@H]2C[C@@H](Nc3ncc4c(-c5cnc6ncccc6c5)ccn4n3)C2)CC1]
1532
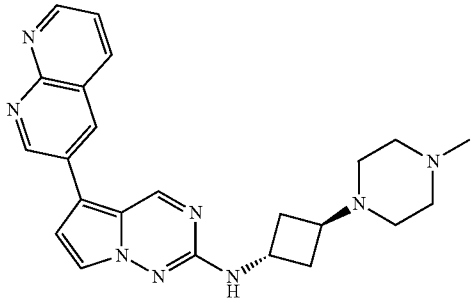 [SMILES: CN1CCN([C@H]2C[C@H](Nc3ncc4c(-c5cnc6ncccc6c5)ccn4n3)C2)CC1]
1533
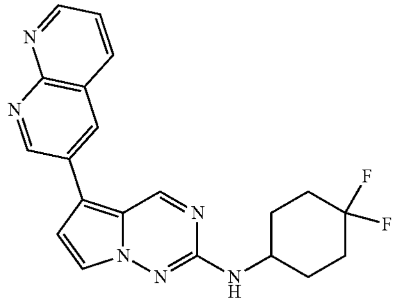 [SMILES: FC1(F)CCC(Nc2ncc3c(-c4cnc5ncccc5c4)ccn3n2)CC1]
1534
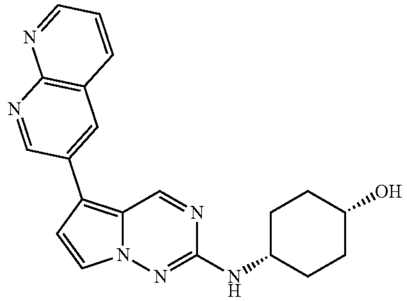 [SMILES: O[C@H]1CC[C@@H](Nc2ncc3c(-c4cnc5ncccc5c4)ccn3n2)CC1]
1535

TABLE 1-continued
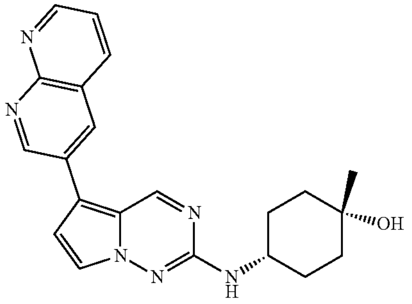 [SMILES: C[C@]1(O)CC[C@@H](Nc2ncc3c(-c4cnc5ncccc5c4)ccn3n2)CC1]
1536
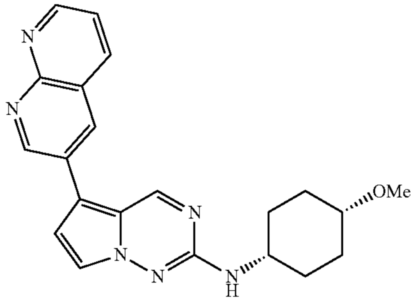 [SMILES: CO[C@H]1CC[C@@H](Nc2ncc3c(-c4cnc5ncccc5c4)ccn3n2)CC1]
1537
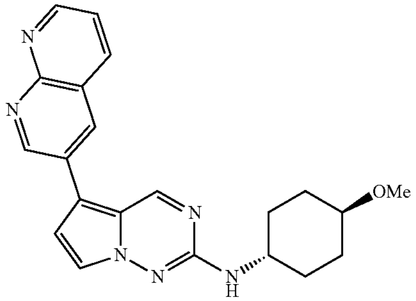 [SMILES: CO[C@H]1CC[C@H](Nc2ncc3c(-c4cnc5ncccc5c4)ccn3n2)CC1]
1538
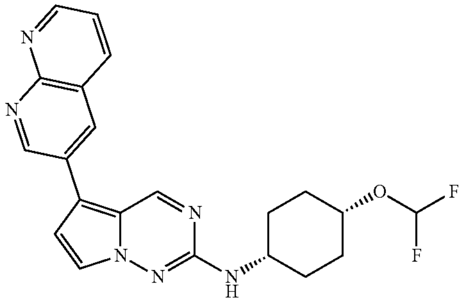 [SMILES: FC(F)O[C@H]1CC[C@@H](Nc2ncc3c(-c4cnc5ncccc5c4)ccn3n2)CC1]
1539
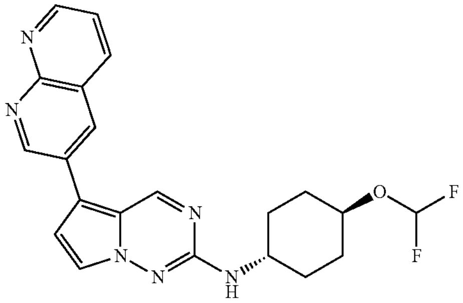 [SMILES: FC(F)O[C@H]1CC[C@H](Nc2ncc3c(-c4cnc5ncccc5c4)ccn3n2)CC1]
1540

TABLE 1-continued
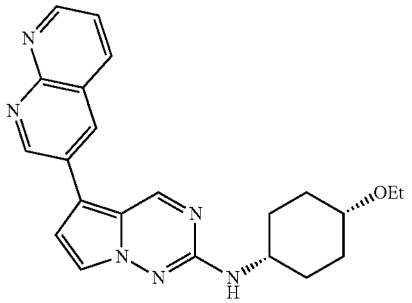 [SMILES: CCO[C@H]1CC[C@@H](Nc2ncc3c(-c4cnc5ncccc5c4)ccn3n2)CC1]
1541
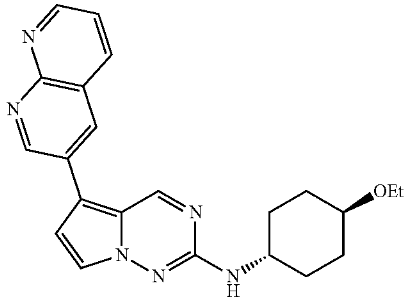 [SMILES: CCO[C@H]1CC[C@H](Nc2ncc3c(-c4cnc5ncccc5c4)ccn3n2)CC1]
1542
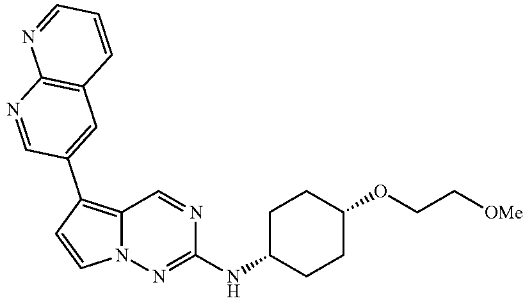
1543
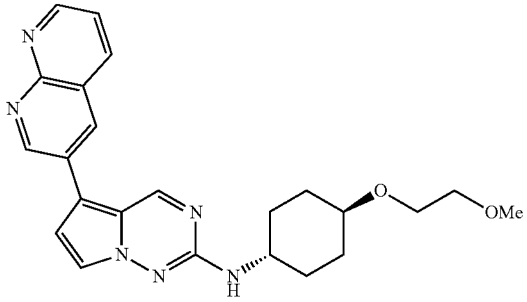 [SMILES: COCCO[C@H]1CC[C@H](Nc2ncc3c(-c4cnc5ncccc5c4)ccn3n2)CC1]
1544
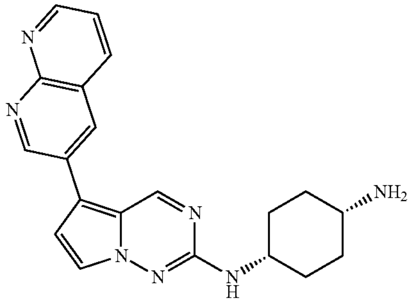 [SMILES: N[C@H]1CC[C@@H](Nc2ncc3c(-c4cnc5ncccc5c4)ccn3n2)CC1]
1545

TABLE 1-continued
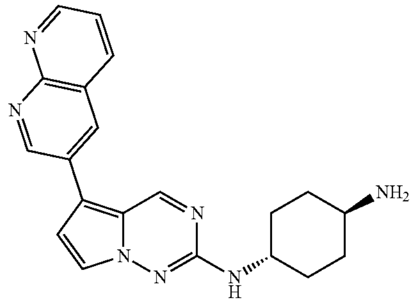 [SMILES: N[C@H]1CC[C@H](Nc2ncc3c(-c4cnc5ncccc5c4)ccn3n2)CC1]
1546
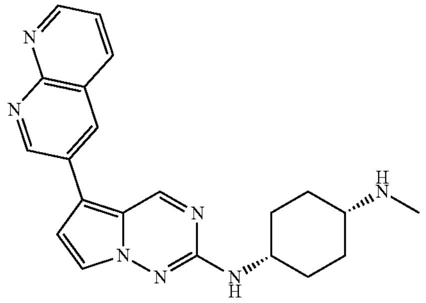 [SMILES: CN[C@H]1CC[C@@H](Nc2ncc3c(-c4cnc5ncccc5c4)ccn3n2)CC1]
1547
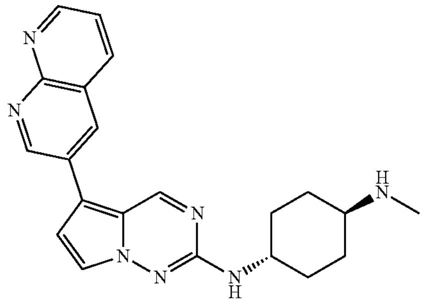 [SMILES: CN[C@H]1CC[C@H](Nc2ncc3c(-c4cnc5ncccc5c4)ccn3n2)CC1]
1548
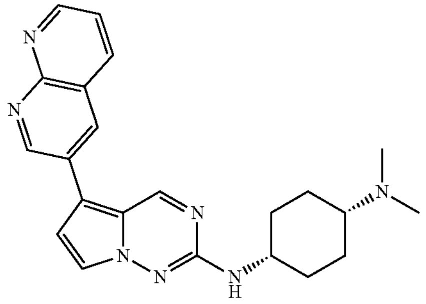 [SMILES: CN(C)[C@H]1CC[C@@H](Nc2ncc3c(-c4cnc5ncccc5c4)ccn3n2)CC1]
1549
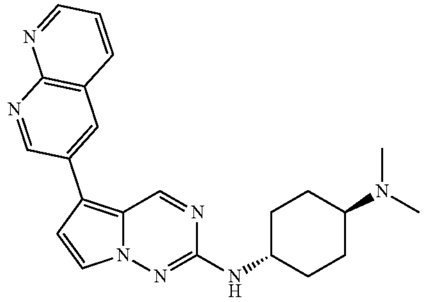 [SMILES: CN(C)[C@H]1CC[C@H](Nc2ncc3c(-c4cnc5ncccc5c4)ccn3n2)CC1]
1550

TABLE 1-continued
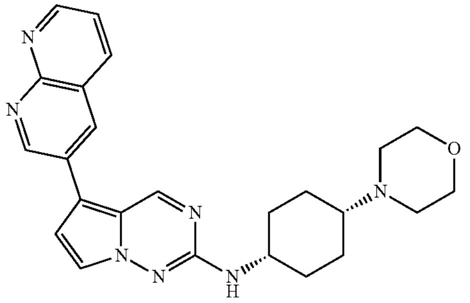 [SMILES: c1cnc2ncc(-c3ccn4nc(N[C@H]5CC[C@@H](N6CCOCC6)CC5)ncc34)cc2c1]
1551
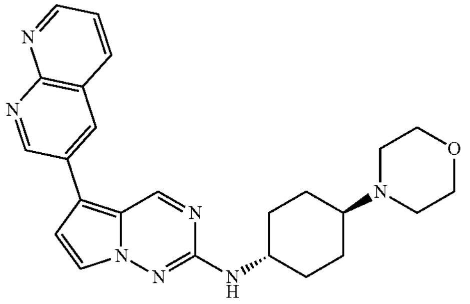 [SMILES: c1cnc2ncc(-c3ccn4nc(N[C@H]5CC[C@H](N6CCOCC6)CC5)ncc34)cc2c1]
1552
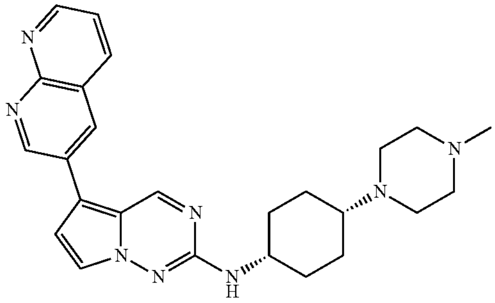 [SMILES: CN1CCN([C@H]2CC[C@@H](Nc3ncc4c(-c5cnc6ncccc6c5)ccn4n3)CC2)CC1]
1553
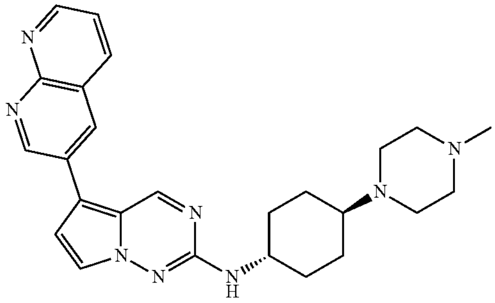 [SMILES: CN1CCN([C@H]2CC[C@H](Nc3ncc4c(-c5cnc6ncccc6c5)ccn4n3)CC2)CC1]
1554
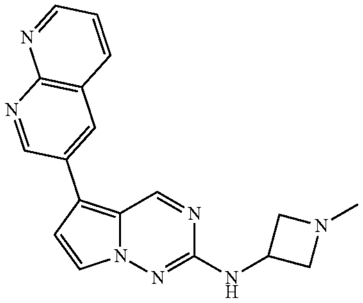 [SMILES: CN1CC(Nc2ncc3c(-c4cnc5ncccc5c4)ccn3n2)C1]
1555

TABLE 1-continued
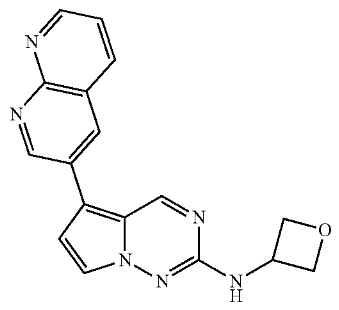 [SMILES: c1cnc2ncc(-c3ccn4nc(NC5COC5)ncc34)cc2c1]
1556
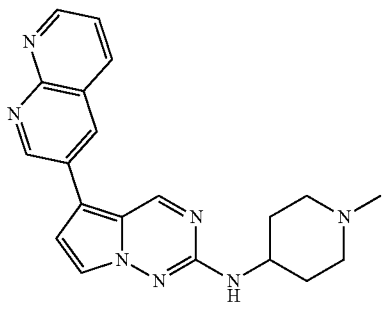 [SMILES: CN1CCC(Nc2ncc3c(-c4cnc5ncccc5c4)ccn3n2)CC1]
1557
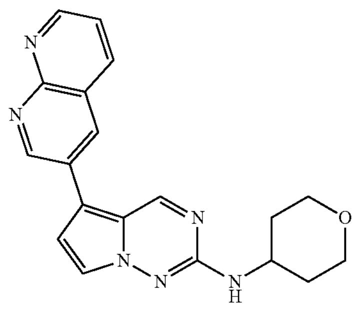 [SMILES: c1cnc2ncc(-c3ccn4nc(NC5CCOCC5)ncc34)cc2c1]
1558
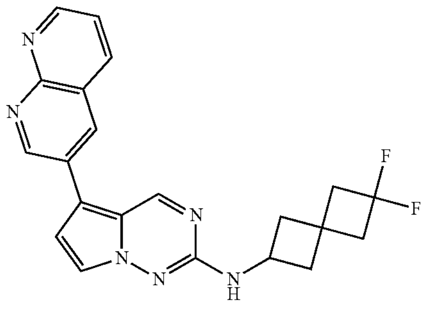 [SMILES: FC1(F)CC2(CC(Nc3ncc4c(-c5cnc6ncccc6c5)ccn4n3)C2)C1]
1559
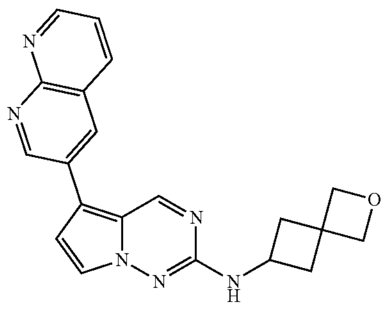 [SMILES: c1cnc2ncc(-c3ccn4nc(NC5CC6(COC6)C5)ncc34)cc2c1]
1560

TABLE 1-continued
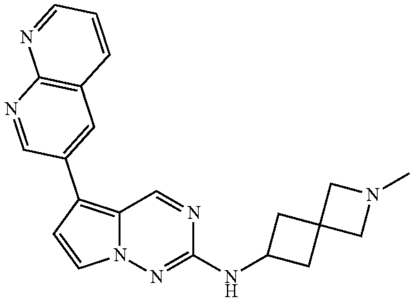 [SMILES: CN1CC2(CC(Nc3ncc4c(-c5cnc6ncccc6c5)ccn4n3)C2)C1]
1561
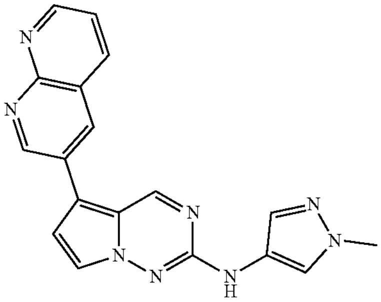 [SMILES: Cn1cc(Nc2ncc3c(-c4cnc5ncccc5c4)ccn3n2)cn1]
1562
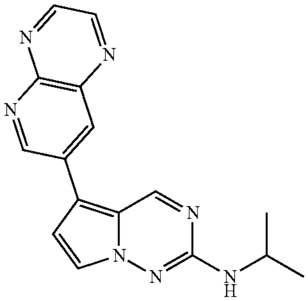 [SMILES: CC(C)Nc1ncc2c(-c3cnc4nccnc4c3)ccn2n1]
1563
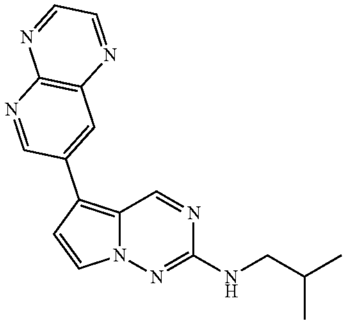 [SMILES: CC(C)CNc1ncc2c(-c3cnc4nccnc4c3)ccn2n1]
1564
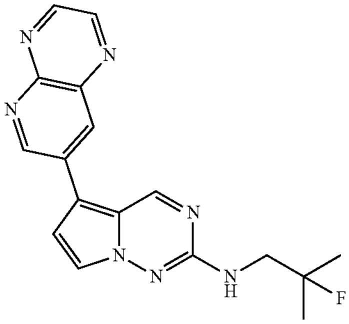
1565

TABLE 1-continued
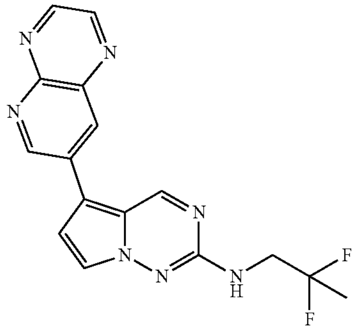 [SMILES: CC(F)(F)CNc1ncc2c(-c3cnc4nccnc4c3)ccn2n1]
1566
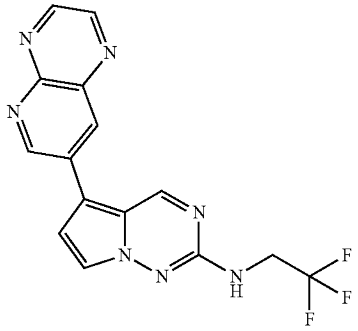 [SMILES: FC(F)(F)CNc1ncc2c(-c3cnc4nccnc4c3)ccn2n1]
1567
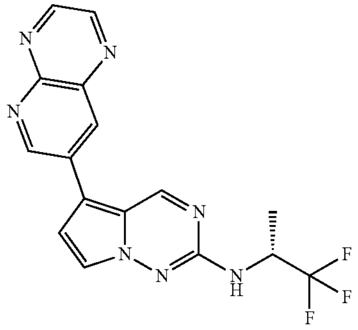 [SMILES: C[C@@H](Nc1ncc2c(-c3cnc4nccnc4c3)ccn2n1)C(F)(F)F]
1568
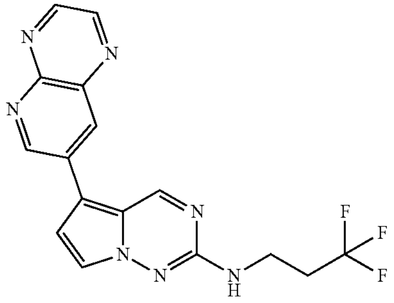 [SMILES: FC(F)(F)CCNc1ncc2c(-c3cnc4nccnc4c3)ccn2n1]
1569
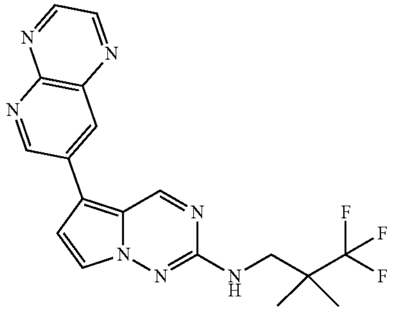 [SMILES: CC(C)(CNc1ncc2c(-c3cnc4nccnc4c3)ccn2n1)C(F)(F)F]
1570

TABLE 1-continued
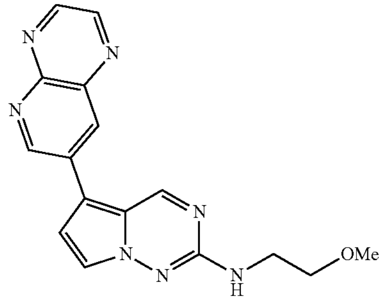 [SMILES: COCCNc1ncc2c(-c3cnc4nccnc4c3)ccn2n1]
1571
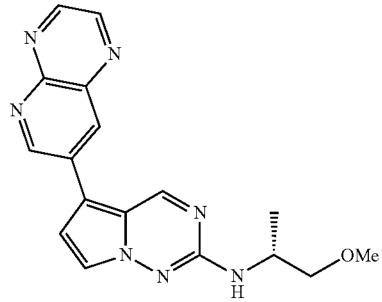 [SMILES: COC[C@@H](C)Nc1ncc2c(-c3cnc4nccnc4c3)ccn2n1]
1572
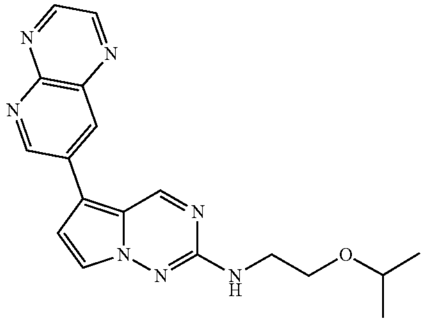 [SMILES: CC(C)OCCNc1ncc2c(-c3cnc4nccnc4c3)ccn2n1]
1573
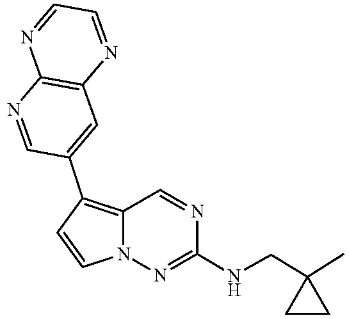 [SMILES: CC1(CNc2ncc3c(-c4cnc5nccnc5c4)ccn3n2)CC1]
1574
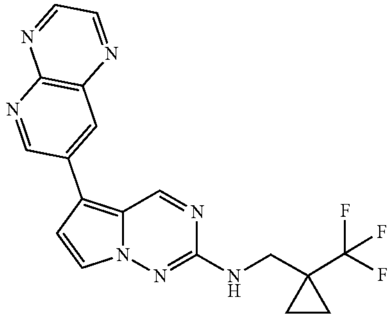 [SMILES: FC(F)(F)C1(CNc2ncc3c(-c4cnc5nccnc5c4)ccn3n2)CC1]
1575

TABLE 1-continued
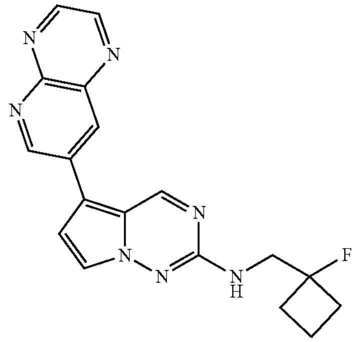 [SMILES: FC1(CNc2ncc3c(-c4cnc5nccnc5c4)ccn3n2)CCC1]
1576
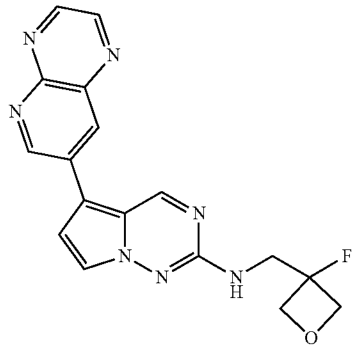 [SMILES: FC1(CNc2ncc3c(-c4cnc5nccnc5c4)ccn3n2)COC1]
1577
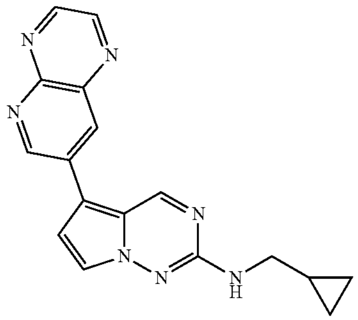 [SMILES: c1cnc2ncc(-c3ccn4nc(NCC5CC5)ncc34)cc2n1]
1578
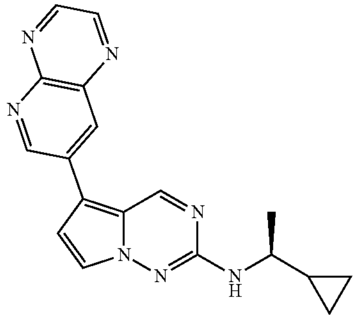 [SMILES: C[C@H](Nc1ncc2c(-c3cnc4nccnc4c3)ccn2n1)C1CC1]
1579

TABLE 1-continued
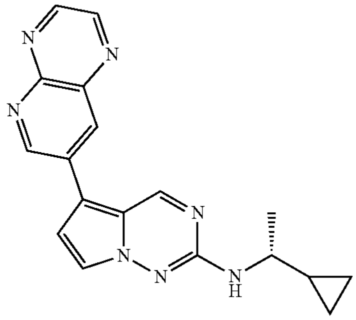 [SMILES: C[C@@H](Nc1ncc2c(-c3cnc4nccnc4c3)ccn2n1)C1CC1]
1580
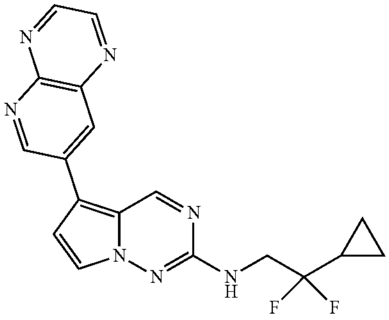 [SMILES: FC(F)(CNc1ncc2c(-c3cnc4nccnc4c3)ccn2n1)C1CC1]
1581
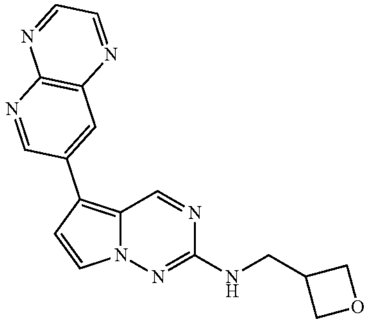 [SMILES: c1cnc2ncc(-c3ccn4nc(NCC5COC5)ncc34)cc2n1]
1582
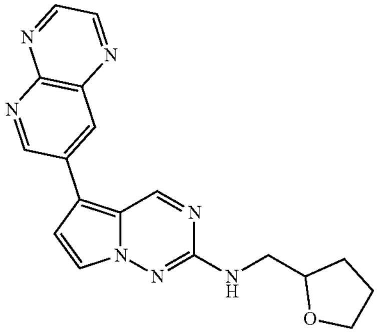
1583
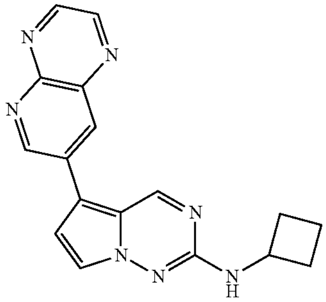 [SMILES: c1cnc2ncc(-c3ccn4nc(NC5CCC5)ncc34)cc2n1]
1584

TABLE 1-continued
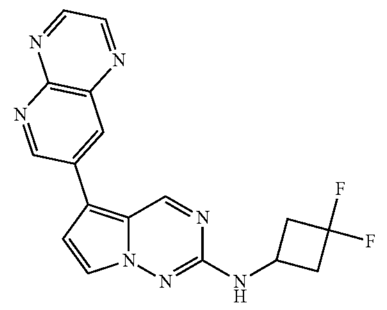 [SMILES: FC1(F)CC(Nc2ncc3c(-c4cnc5nccnc5c4)ccn3n2)C1]
1585
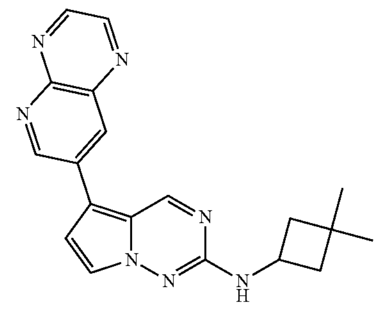 [SMILES: CC1(C)CC(Nc2ncc3c(-c4cnc5nccnc5c4)ccn3n2)C1]
1586
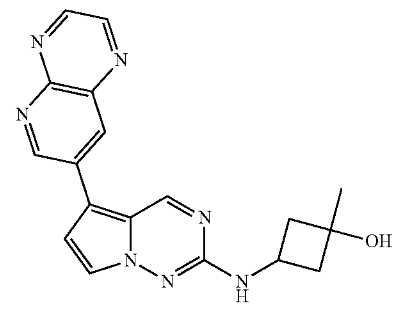
1587
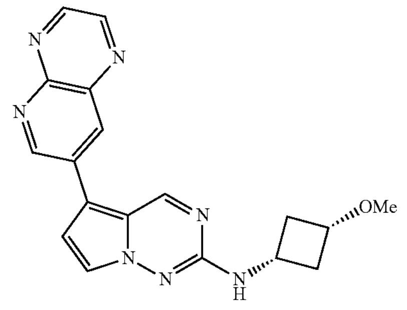 [SMILES: CO[C@H]1C[C@@H](Nc2ncc3c(-c4cnc5nccnc5c4)ccn3n2)C1]
1588
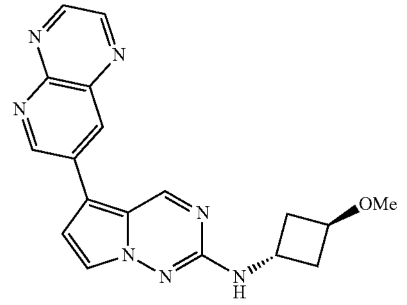 [SMILES: CO[C@H]1C[C@H](Nc2ncc3c(-c4cnc5nccnc5c4)ccn3n2)C1]
1589

TABLE 1-continued
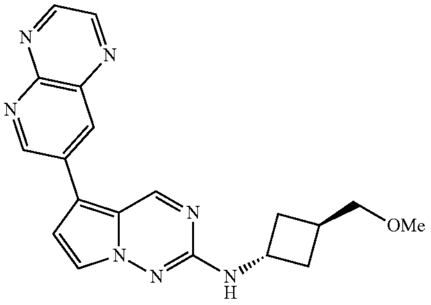 [SMILES: COC[C@H]1C[C@H](Nc2ncc3c(-c4cnc5nccnc5c4)ccn3n2)C1]
1590
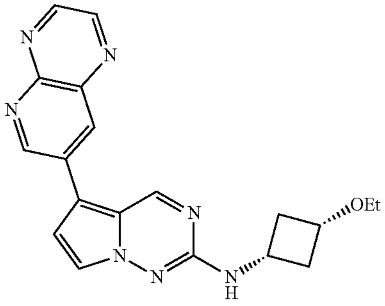 [SMILES: CCO[C@H]1C[C@@H](Nc2ncc3c(-c4cnc5nccnc5c4)ccn3n2)C1]
1591
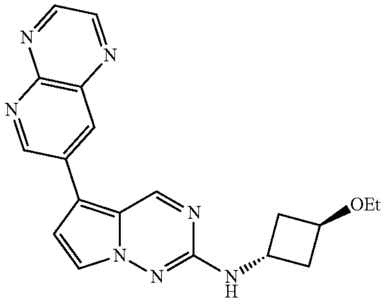 [SMILES: CCO[C@H]1C[C@H](Nc2ncc3c(-c4cnc5nccnc5c4)ccn3n2)C1]
1592
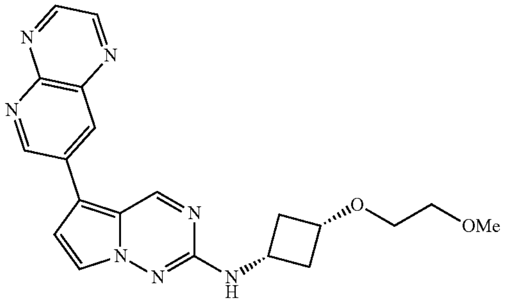
1593
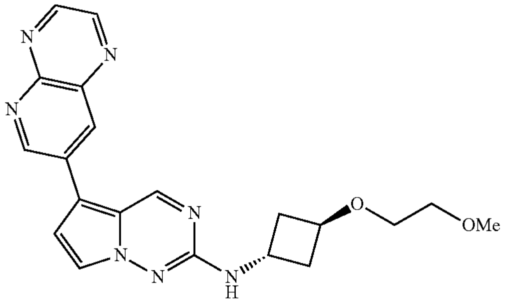 [SMILES: COCCO[C@H]1C[C@H](Nc2ncc3c(-c4cnc5nccnc5c4)ccn3n2)C1]
1594

TABLE 1-continued
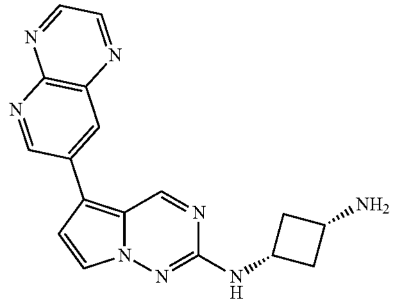 [SMILES: N[C@H]1C[C@@H](Nc2ncc3c(-c4cnc5nccnc5c4)ccn3n2)C1]
1595
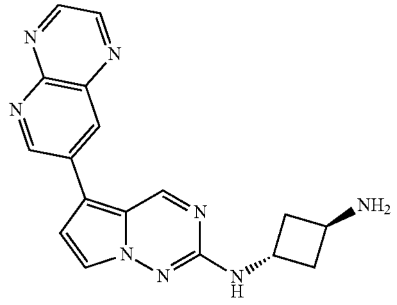 [SMILES: N[C@H]1C[C@H](Nc2ncc3c(-c4cnc5nccnc5c4)ccn3n2)C1]
1596
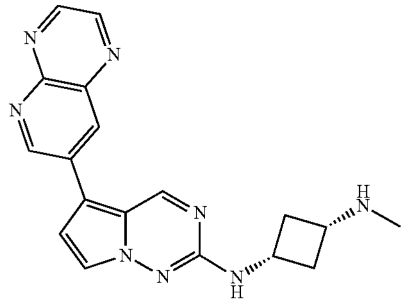 [SMILES: CN[C@H]1C[C@@H](Nc2ncc3c(-c4cnc5nccnc5c4)ccn3n2)C1]
1597
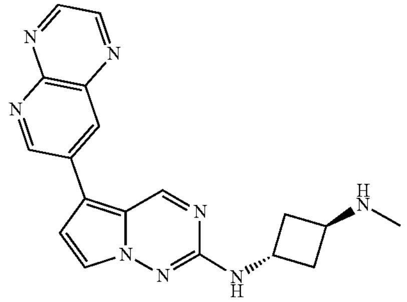 [SMILES: CN[C@H]1C[C@H](Nc2ncc3c(-c4cnc5nccnc5c4)ccn3n2)C1]
1598
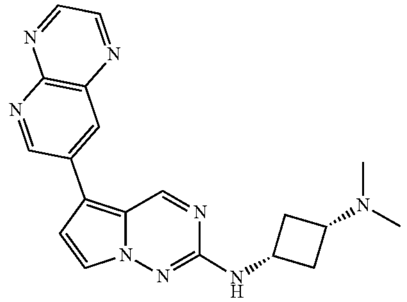 [SMILES: CN(C)[C@H]1C[C@@H](Nc2ncc3c(-c4cnc5nccnc5c4)ccn3n2)C1]
1599

TABLE 1-continued
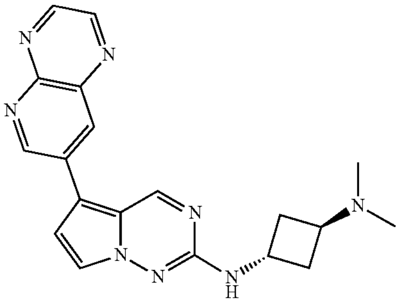 [SMILES: CN(C)[C@H]1C[C@H](Nc2ncc3c(-c4cnc5nccnc5c4)ccn3n2)C1]
1600
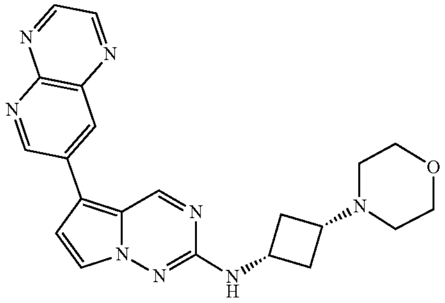 [SMILES: c1cnc2ncc(-c3ccn4nc(N[C@H]5C[C@@H](N6CCOCC6)C5)ncc34)cc2n1]
1601
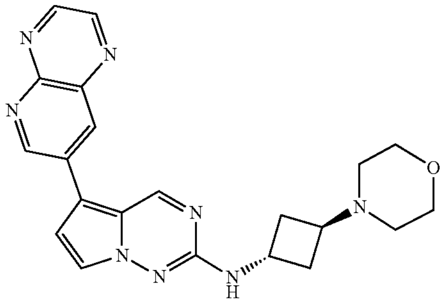 [SMILES: c1cnc2ncc(-c3ccn4nc(N[C@H]5C[C@H](N6CCOCC6)C5)ncc34)cc2n1]
1602
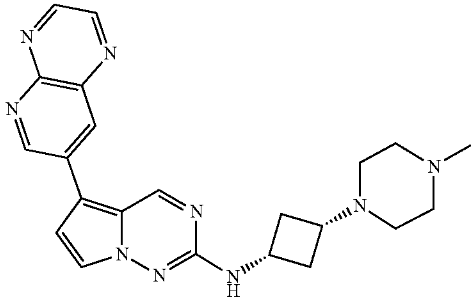 [SMILES: CN1CCN([C@H]2C[C@@H](Nc3ncc4c(-c5cnc6nccnc6c5)ccn4n3)C2)CC1]
1603
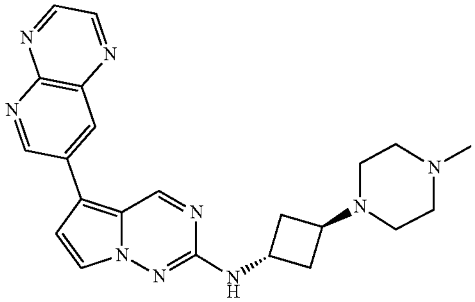 [SMILES: CN1CCN([C@H]2C[C@H](Nc3ncc4c(-c5cnc6nccnc6c5)ccn4n3)C2)CC1]
1604

TABLE 1-continued
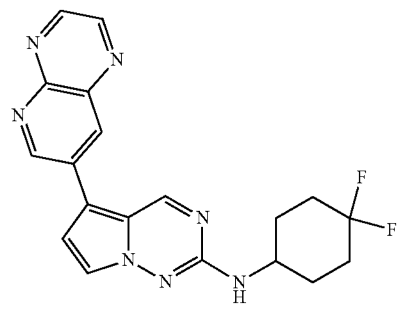 [SMILES: FC1(F)CCC(Nc2ncc3c(-c4cnc5nccnc5c4)ccn3n2)CC1]
1605
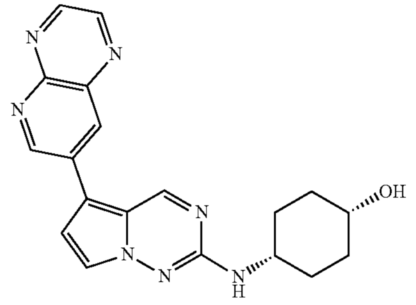 [SMILES: O[C@H]1CC[C@@H](Nc2ncc3c(-c4cnc5nccnc5c4)ccn3n2)CC1]
1606
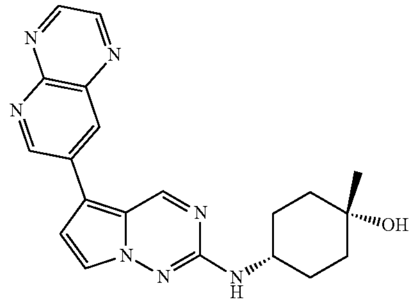 [SMILES: C[C@]1(O)CC[C@@H](Nc2ncc3c(-c4cnc5nccnc5c4)ccn3n2)CC1]
1607
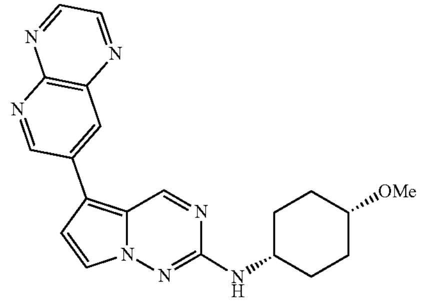 [SMILES: CO[C@H]1CC[C@@H](Nc2ncc3c(-c4cnc5nccnc5c4)ccn3n2)CC1]
1608
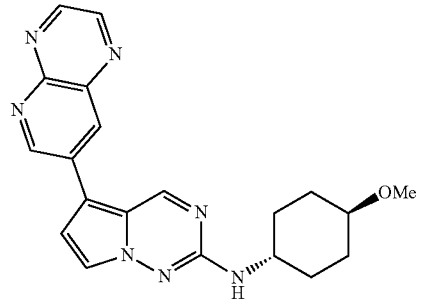 [SMILES: CO[C@H]1CC[C@H](Nc2ncc3c(-c4cnc5nccnc5c4)ccn3n2)CC1]
1609

TABLE 1-continued
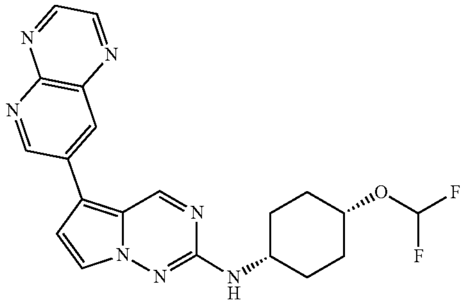 [SMILES: FC(F)O[C@H]1CC[C@@H](Nc2ncc3c(-c4cnc5nccnc5c4)ccn3n2)CC1]
1610
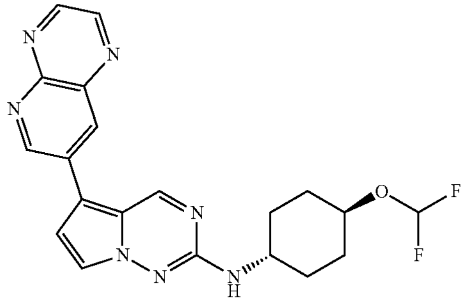 [SMILES: FC(F)O[C@H]1CC[C@H](Nc2ncc3c(-c4cnc5nccnc5c4)ccn3n2)CC1]
1611
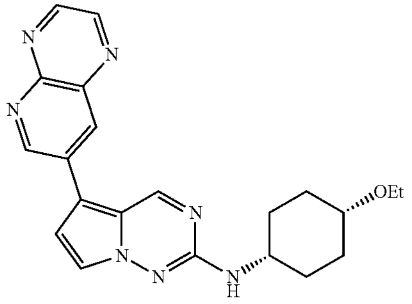 [SMILES: CCO[C@H]1CC[C@@H](Nc2ncc3c(-c4cnc5nccnc5c4)ccn3n2)CC1]
1612
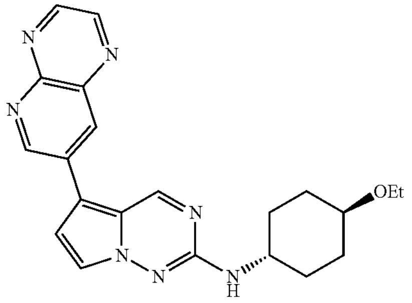 [SMILES: CCO[C@H]1CC[C@H](Nc2ncc3c(-c4cnc5nccnc5c4)ccn3n2)CC1]
1613
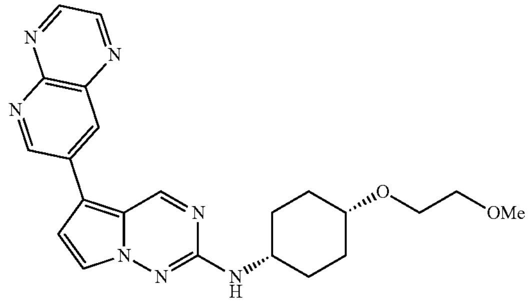 [SMILES: COCCO[C@H]1CC[C@@H](Nc2ncc3c(-c4cnc5nccnc5c4)ccn3n2)CC1]
1614

TABLE 1-continued
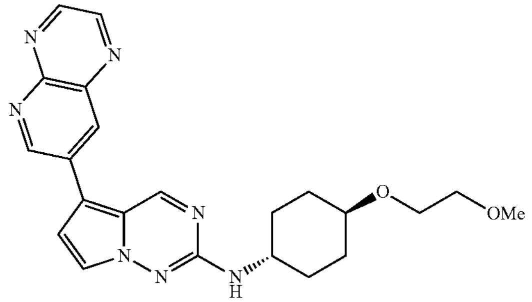 [SMILES: COCCO[C@H]1CC[C@H](Nc2ncc3c(-c4cnc5nccnc5c4)ccn3n2)CC1]
1615
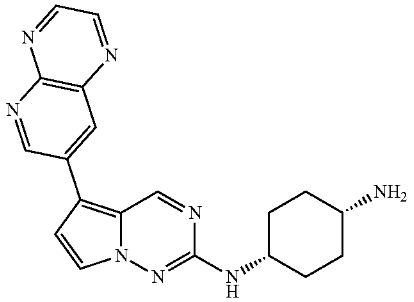 [SMILES: N[C@H]1CC[C@@H](Nc2ncc3c(-c4cnc5nccnc5c4)ccn3n2)CC1]
1616
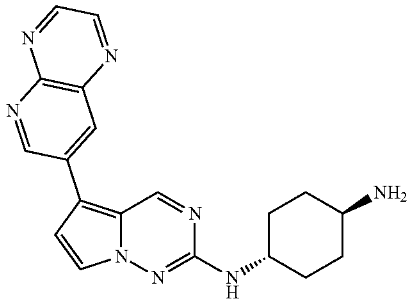 [SMILES: N[C@H]1CC[C@H](Nc2ncc3c(-c4cnc5nccnc5c4)ccn3n2)CC1]
1617
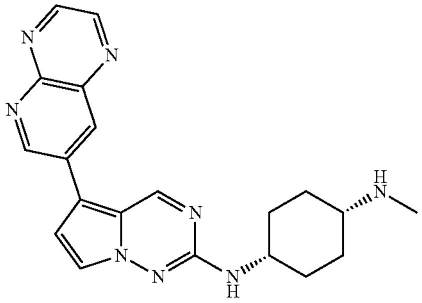 [SMILES: CN[C@H]1CC[C@@H](Nc2ncc3c(-c4cnc5nccnc5c4)ccn3n2)CC1]
1618
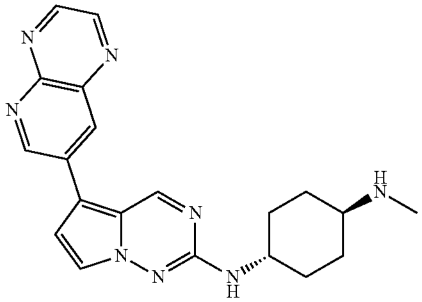 [SMILES: CN[C@H]1CC[C@H](Nc2ncc3c(-c4cnc5nccnc5c4)ccn3n2)CC1]
1619

TABLE 1-continued
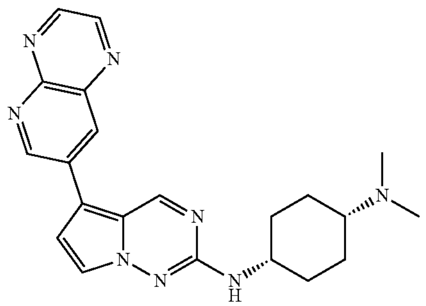 [SMILES: CN(C)[C@H]1CC[C@@H](Nc2ncc3c(-c4cnc5nccnc5c4)ccn3n2)CC1]
1620
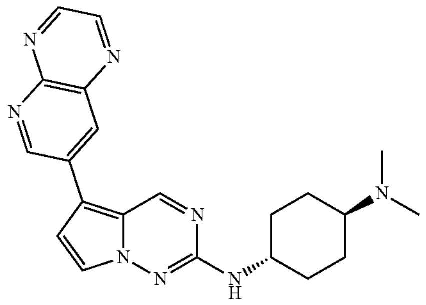 [SMILES: CN(C)[C@H]1CC[C@H](Nc2ncc3c(-c4cnc5nccnc5c4)ccn3n2)CC1]
1621
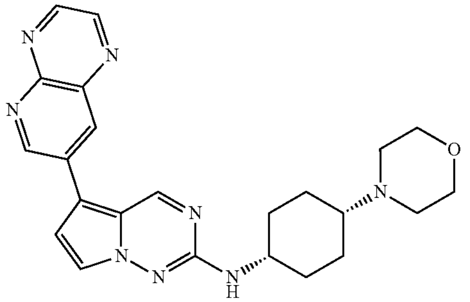 [SMILES: c1cnc2ncc(-c3ccn4nc(N[C@H]5CC[C@@H](N6CCOCC6)CC5)ncc34)cc2n1]
1622
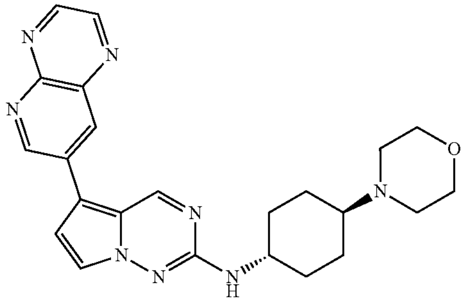
1623
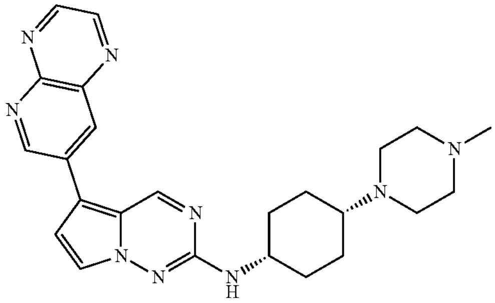 [SMILES: CN1CCN([C@H]2CC[C@@H](Nc3ncc4c(-c5cnc6nccnc6c5)ccn4n3)CC2)CC1]
1624

TABLE 1-continued
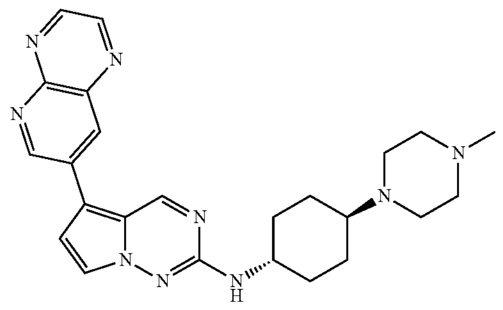 [SMILES: CN1CCN([C@H]2CC[C@H](Nc3ncc4c(-c5cnc6nccnc6c5)ccn4n3)CC2)CC1]
1625
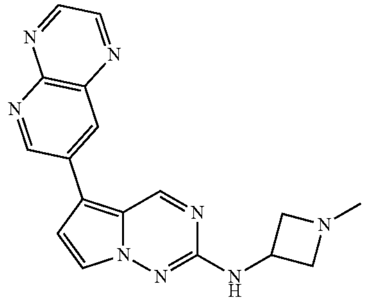 [SMILES: CN1CC(Nc2ncc3c(-c4cnc5nccnc5c4)ccn3n2)C1]
1626
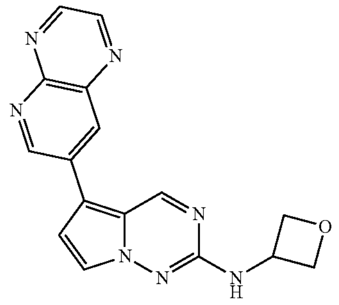 [SMILES: c1cnc2ncc(-c3ccn4nc(NC5COC5)ncc34)cc2n1]
1627
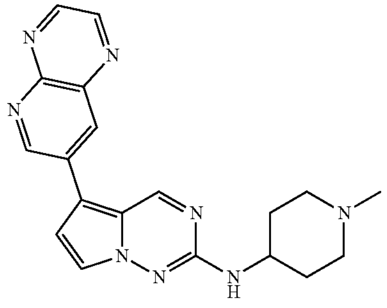 [SMILES: CN1CCC(Nc2ncc3c(-c4cnc5nccnc5c4)ccn3n2)CC1]
1628
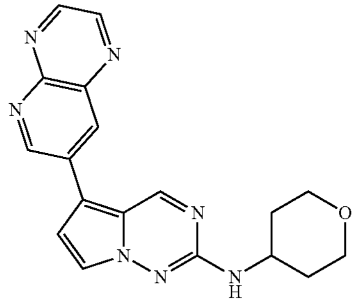 [SMILES: c1cnc2ncc(-c3ccn4nc(NC5CCOCC5)ncc34)cc2n1]
1629

TABLE 1-continued
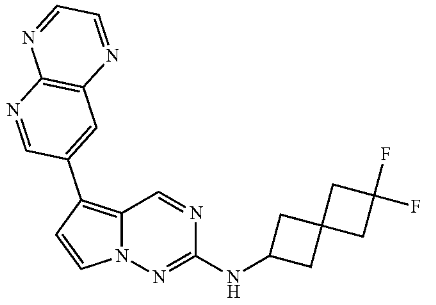 [SMILES: FC1(F)CC2(CC(Nc3ncc4c(-c5cnc6nccnc6c5)ccn4n3)C2)C1]
1630
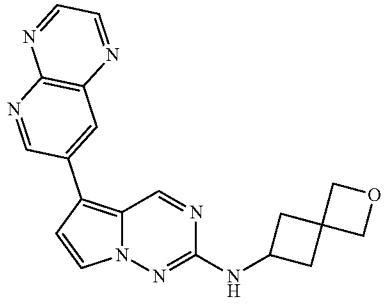 [SMILES: c1cnc2ncc(-c3ccn4nc(NC5CC6(COC6)C5)ncc34)cc2n1]
1631
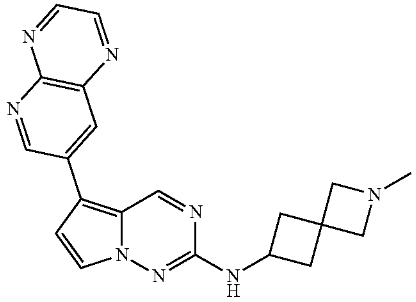 [SMILES: CN1CC2(CC(Nc3ncc4c(-c5cnc6nccnc6c5)ccn4n3)C2)C1]
1632
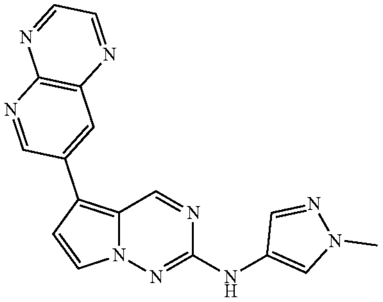
1633
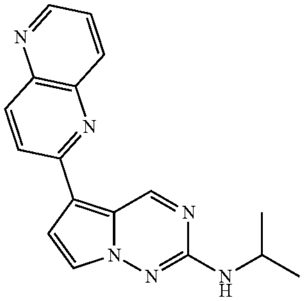 [SMILES: CC(C)Nc1ncc2c(-c3ccc4ncccc4n3)ccn2n1]
1634

TABLE 1-continued
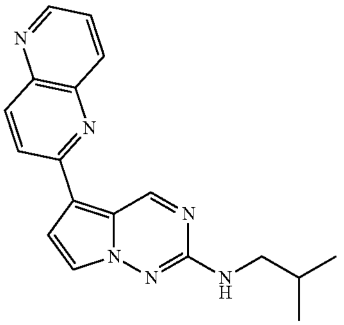 [SMILES: CC(C)CNc1ncc2c(-c3ccc4ncccc4n3)ccn2n1]
1635
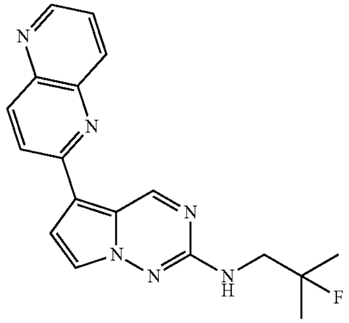 [SMILES: CC(C)(F)CNc1ncc2c(-c3ccc4ncccc4n3)ccn2n1]
1636
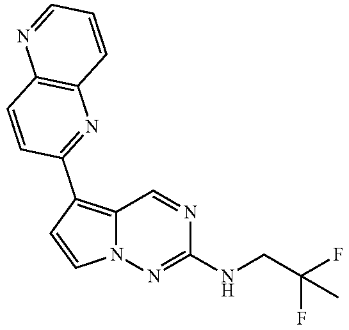 [SMILES: CC(F)(F)CNc1ncc2c(-c3ccc4ncccc4n3)ccn2n1]
1637
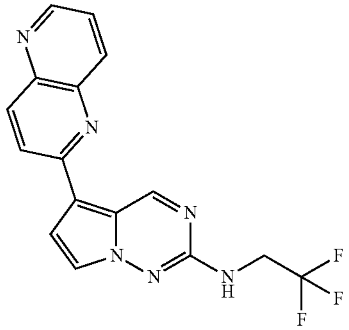
1638

TABLE 1-continued
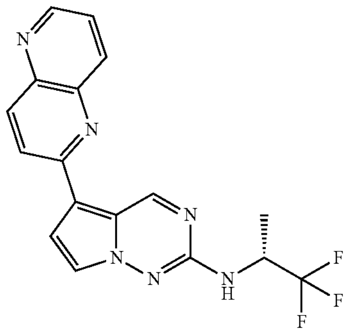 [SMILES: C[C@@H](Nc1ncc2c(-c3ccc4ncccc4n3)ccn2n1)C(F)(F)F]
1639
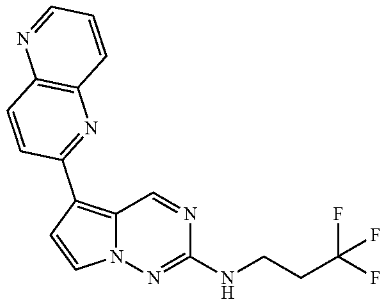 [SMILES: FC(F)(F)CCNc1ncc2c(-c3ccc4ncccc4n3)ccn2n1]
1640
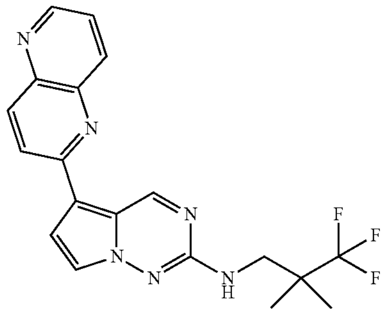 [SMILES: CC(C)(CNc1ncc2c(-c3ccc4ncccc4n3)ccn2n1)C(F)(F)F]
1641
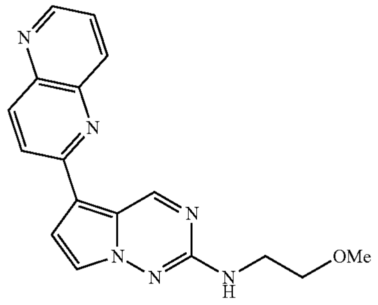 [SMILES: COCCNc1ncc2c(-c3ccc4ncccc4n3)ccn2n1]
1642
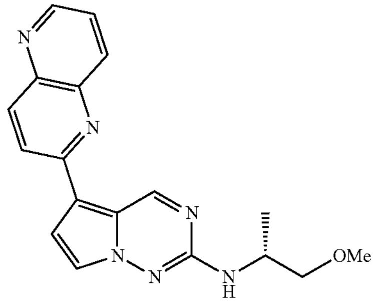
1643

TABLE 1-continued
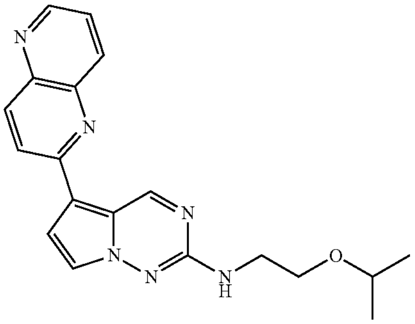 [SMILES: CC(C)OCCNc1ncc2c(-c3ccc4ncccc4n3)ccn2n1]
1644
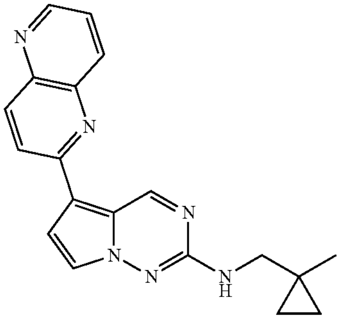
1645
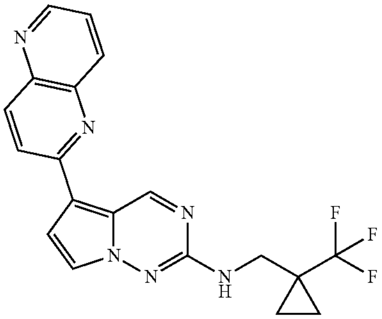 [SMILES: FC(F)(F)C1(CNc2ncc3c(-c4ccc5ncccc5n4)ccn3n2)CC1]
1646
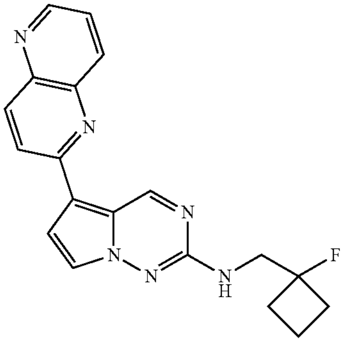 [SMILES: FC1(CNc2ncc3c(-c4ccc5ncccc5n4)ccn3n2)CCC1]
1647

TABLE 1-continued
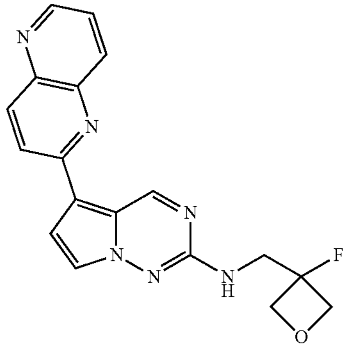 [SMILES: FC1(CNc2ncc3c(-c4ccc5ncccc5n4)ccn3n2)COC1]
1648
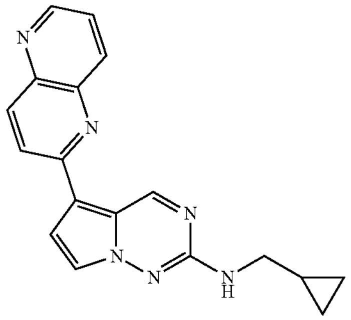 [SMILES: c1cnc2ccc(-c3ccn4nc(NCC5CC5)ncc34)nc2c1]
1649
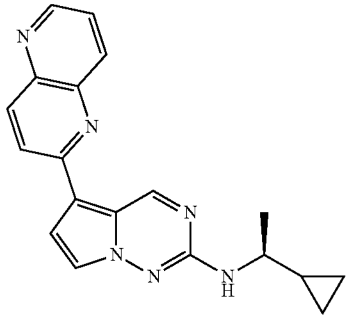 [SMILES: C[C@H](Nc1ncc2c(-c3ccc4ncccc4n3)ccn2n1)C1CC1]
1650
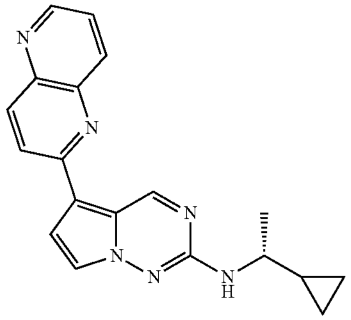 [SMILES: C[C@@H](Nc1ncc2c(-c3ccc4ncccc4n3)ccn2n1)C1CC1]
1651
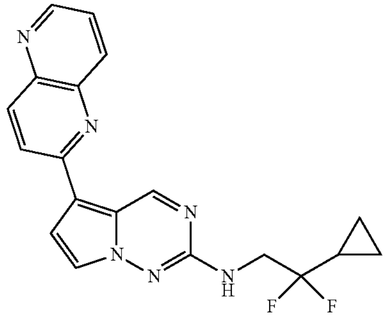
1652

TABLE 1-continued
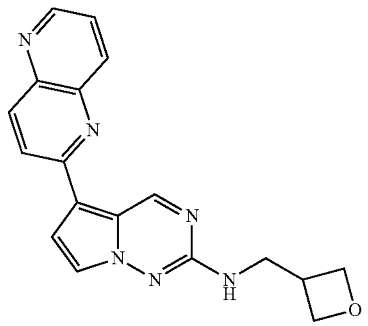 [SMILES: c1cnc2ccc(-c3ccn4nc(NCC5COC5)ncc34)nc2c1]
1653
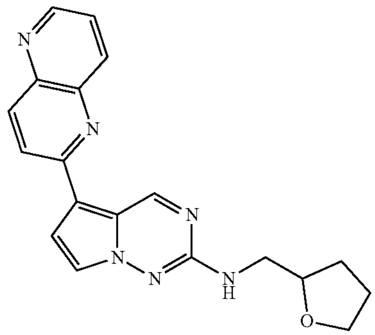 [SMILES: c1cnc2ccc(-c3ccn4nc(NCC5CCCO5)ncc34)nc2c1]
1654
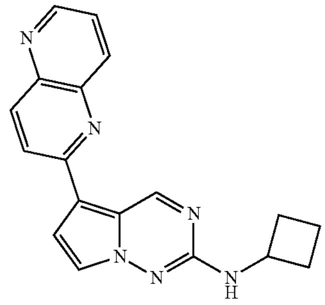 [SMILES: c1cnc2ccc(-c3ccn4nc(NC5CCC5)ncc34)nc2c1]
1655
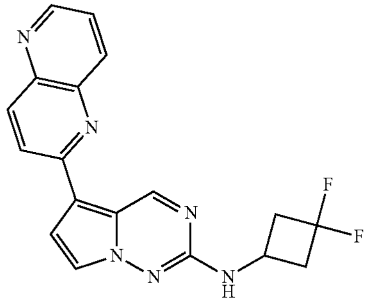 [SMILES: FC1(F)CC(Nc2ncc3c(-c4ccc5ncccc5n4)ccn3n2)C1]
1656
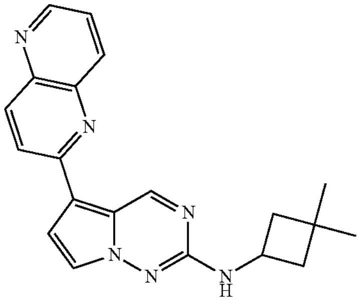 [SMILES: CC1(C)CC(Nc2ncc3c(-c4ccc5ncccc5n4)ccn3n2)C1]
1657

TABLE 1-continued
1658
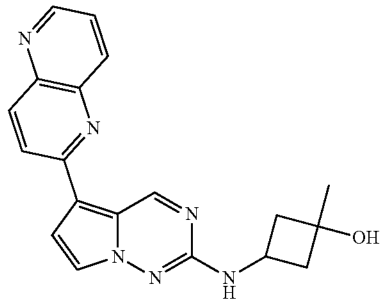 [SMILES: CC1(O)CC(Nc2ncc3c(-c4ccc5ncccc5n4)ccn3n2)C1]
1659
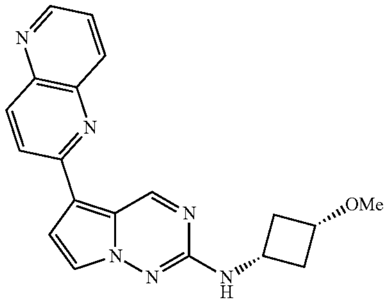 [SMILES: CO[C@H]1C[C@@H](Nc2ncc3c(-c4ccc5ncccc5n4)ccn3n2)C1]
1660
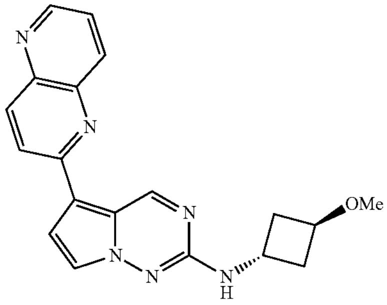 [SMILES: CO[C@H]1C[C@H](Nc2ncc3c(-c4ccc5ncccc5n4)ccn3n2)C1]
1661
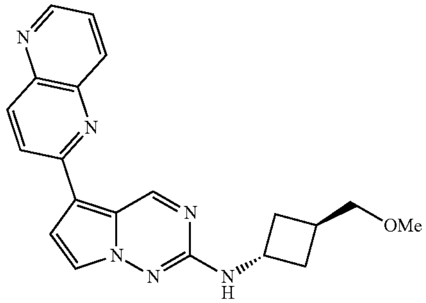 [SMILES: COC[C@H]1C[C@H](Nc2ncc3c(-c4ccc5ncccc5n4)ccn3n2)C1]
1662
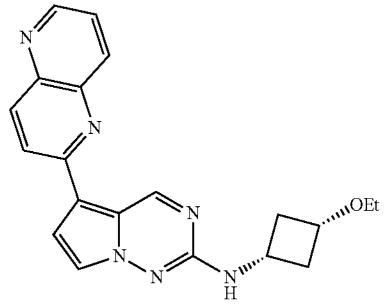 [SMILES: CCO[C@H]1C[C@@H](Nc2ncc3c(-c4ccc5ncccc5n4)ccn3n2)C1]

TABLE 1-continued
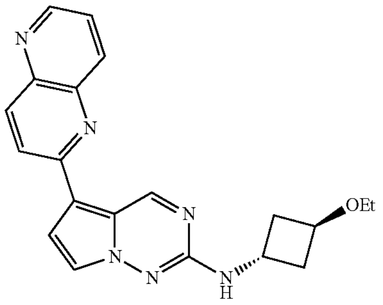 [SMILES: CCO[C@H]1C[C@H](Nc2ncc3c(-c4ccc5ncccc5n4)ccn3n2)C1]
1663
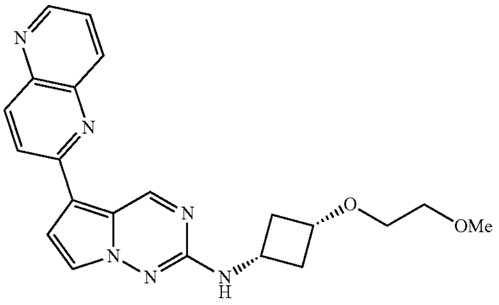 [SMILES: COCCO[C@H]1C[C@@H](Nc2ncc3c(-c4ccc5ncccc5n4)ccn3n2)C1]
1664
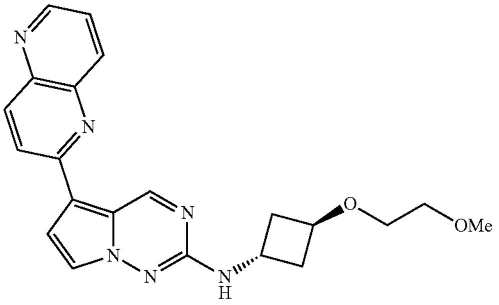 [SMILES: COCCO[C@H]1C[C@H](Nc2ncc3c(-c4ccc5ncccc5n4)ccn3n2)C1]
1665
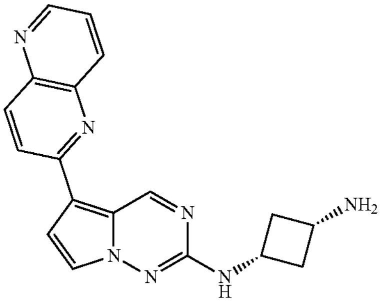 [SMILES: N[C@H]1C[C@@H](Nc2ncc3c(-c4ccc5ncccc5n4)ccn3n2)C1]
1666
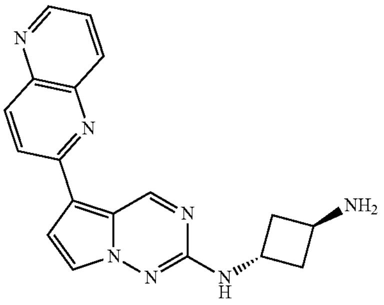 [SMILES: N[C@H]1C[C@H](Nc2ncc3c(-c4ccc5ncccc5n4)ccn3n2)C1]
1667

TABLE 1-continued
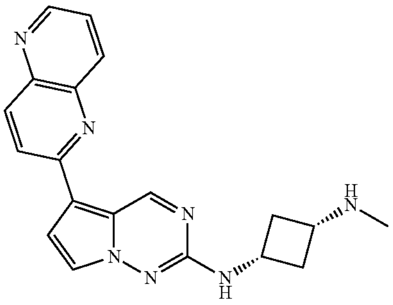 [SMILES: CN[C@H]1C[C@@H](Nc2ncc3c(-c4ccc5ncccc5n4)ccn3n2)C1]
1668
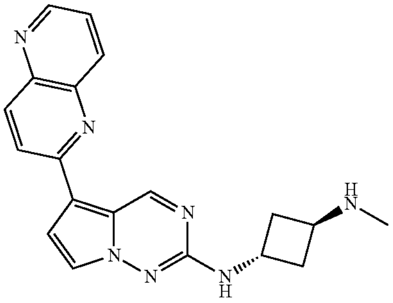 [SMILES: CN[C@H]1C[C@H](Nc2ncc3c(-c4ccc5ncccc5n4)ccn3n2)C1]
1669
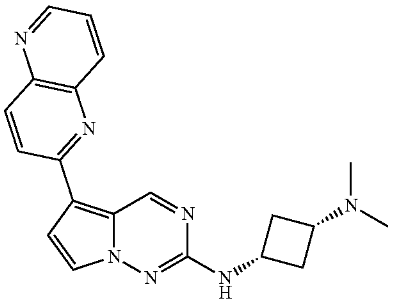
1670
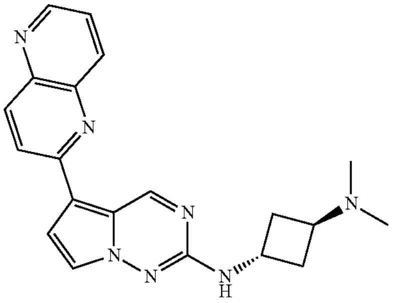 [SMILES: CN(C)[C@H]1C[C@H](Nc2ncc3c(-c4ccc5ncccc5n4)ccn3n2)C1]
1671
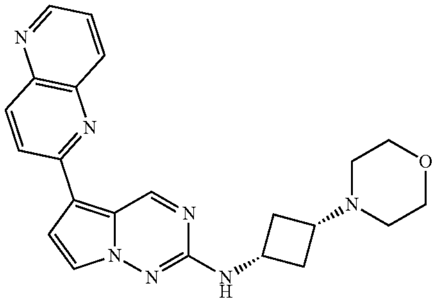 [SMILES: c1cnc2ccc(-c3ccn4nc(N[C@H]5C[C@@H](N6CCOCC6)C5)ncc34)nc2c1]
1672

TABLE 1-continued
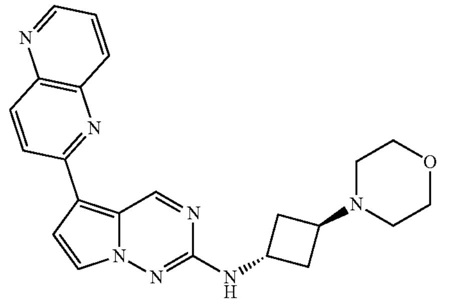 [SMILES: c1cnc2ccc(-c3ccn4nc(N[C@H]5C[C@H](N6CCOCC6)C5)ncc34)nc2c1]
1673
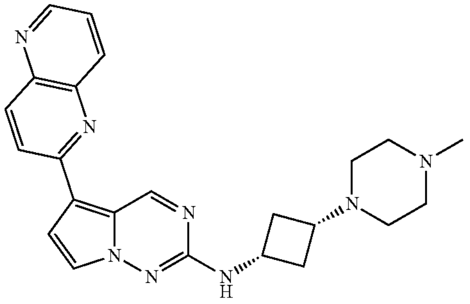 [SMILES: CN1CCN([C@H]2C[C@@H](Nc3ncc4c(-c5ccc6ncccc6n5)ccn4n3)C2)CC1]
1674
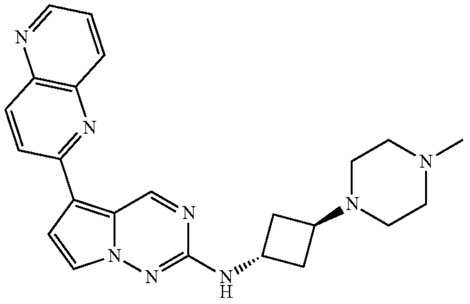 [SMILES: CN1CCN([C@H]2C[C@H](Nc3ncc4c(-c5ccc6ncccc6n5)ccn4n3)C2)CC1]
1675
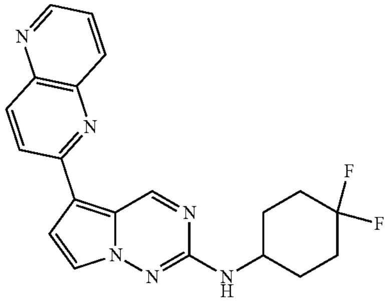 [SMILES: FC1(F)CCC(Nc2ncc3c(-c4ccc5ncccc5n4)ccn3n2)CC1]
1676
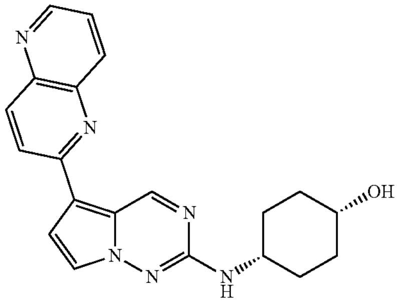 [SMILES: O[C@H]1CC[C@@H](Nc2ncc3c(-c4ccc5ncccc5n4)ccn3n2)CC1]
1677

TABLE 1-continued
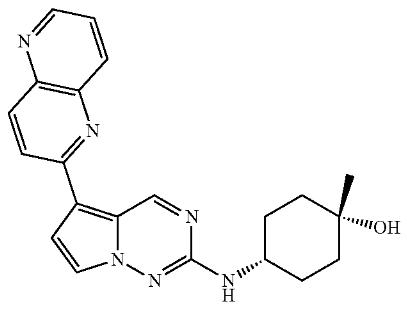 [SMILES: C[C@]1(O)CC[C@@H](Nc2ncc3c(-c4ccc5ncccc5n4)ccn3n2)CC1]
1678
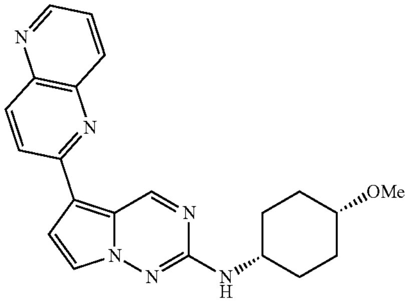 [SMILES: CO[C@H]1CC[C@@H](Nc2ncc3c(-c4ccc5ncccc5n4)ccn3n2)CC1]
1679
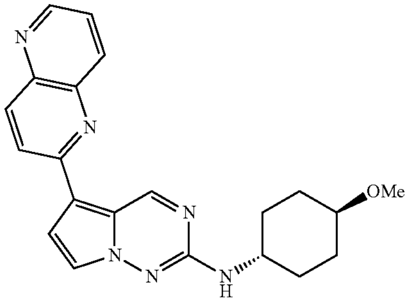 [SMILES: CO[C@H]1CC[C@H](Nc2ncc3c(-c4ccc5ncccc5n4)ccn3n2)CC1]
1680
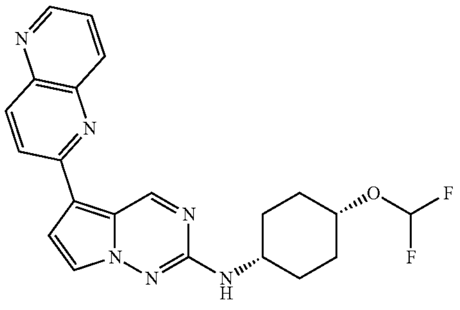 [SMILES: FC(F)O[C@H]1CC[C@@H](Nc2ncc3c(-c4ccc5ncccc5n4)ccn3n2)CC1]
1681
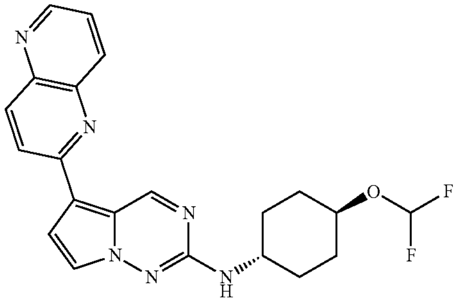 [SMILES: FC(F)O[C@H]1CC[C@H](Nc2ncc3c(-c4ccc5ncccc5n4)ccn3n2)CC1]
1682

TABLE 1-continued
1683
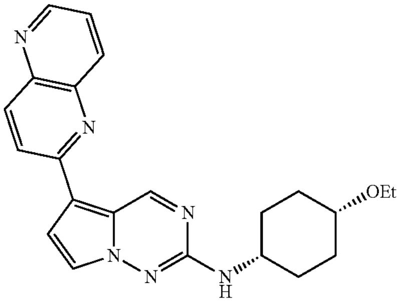 [SMILES: CCO[C@H]1CC[C@@H](Nc2ncc3c(-c4ccc5ncccc5n4)ccn3n2)CC1]
1684
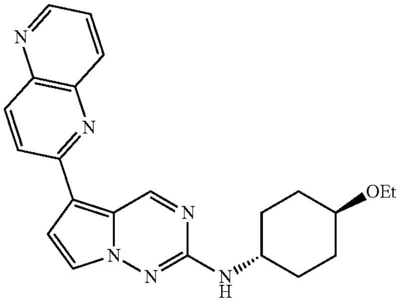 [SMILES: CCO[C@H]1CC[C@H](Nc2ncc3c(-c4ccc5ncccc5n4)ccn3n2)CC1]
1685
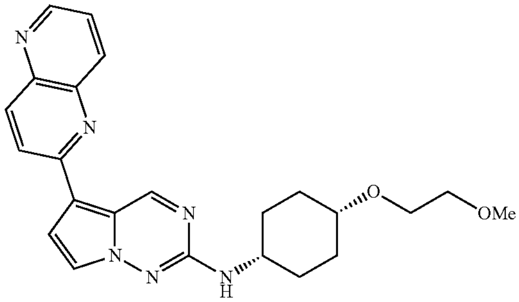 [SMILES: COCCO[C@H]1CC[C@@H](Nc2ncc3c(-c4ccc5ncccc5n4)ccn3n2)CC1]
1686
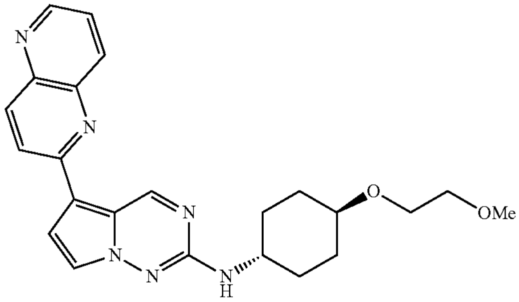 [SMILES: COCCO[C@H]1CC[C@H](Nc2ncc3c(-c4ccc5ncccc5n4)ccn3n2)CC1]
1687
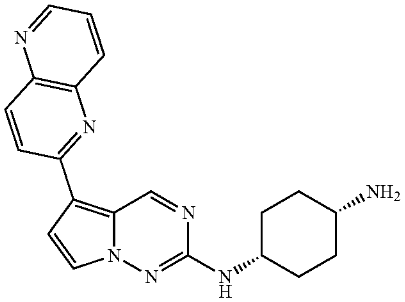

TABLE 1-continued
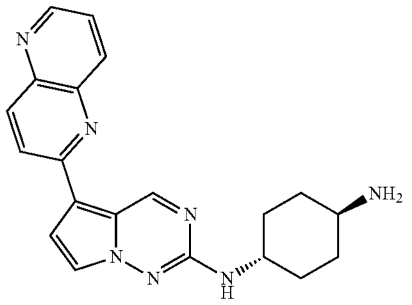 [SMILES: N[C@H]1CC[C@H](Nc2ncc3c(-c4ccc5ncccc5n4)ccn3n2)CC1]
1688
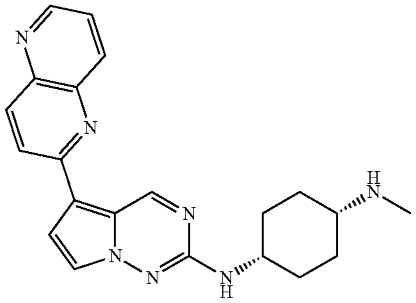 [SMILES: CN[C@H]1CC[C@@H](Nc2ncc3c(-c4ccc5ncccc5n4)ccn3n2)CC1]
1689
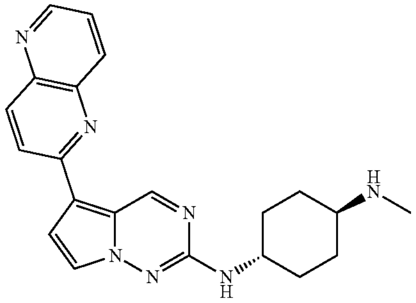 [SMILES: CN[C@H]1CC[C@H](Nc2ncc3c(-c4ccc5ncccc5n4)ccn3n2)CC1]
1690
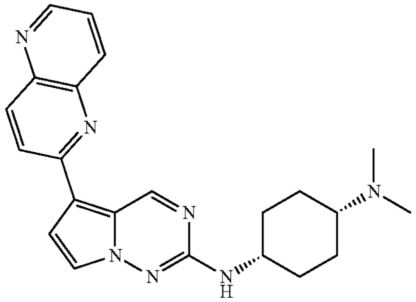 [SMILES: CN(C)[C@H]1CC[C@@H](Nc2ncc3c(-c4ccc5ncccc5n4)ccn3n2)CC1]
1691
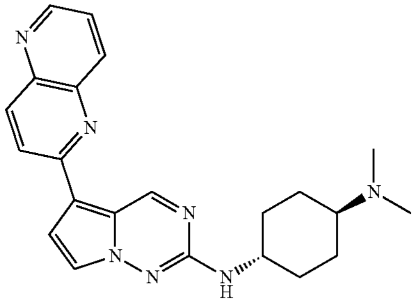 [SMILES: CN(C)[C@H]1CC[C@H](Nc2ncc3c(-c4ccc5ncccc5n4)ccn3n2)CC1]
1692

TABLE 1-continued
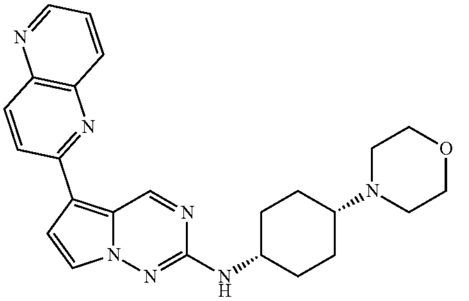 [SMILES: c1cnc2ccc(-c3ccn4nc(N[C@H]5CC[C@@H](N6CCOCC6)CC5)ncc34)nc2c1]
1693
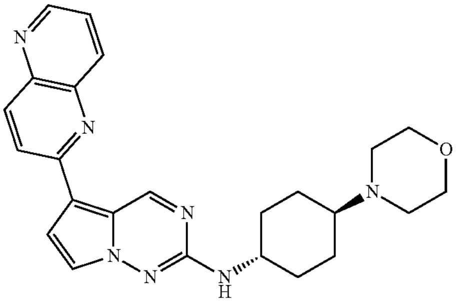 [SMILES: c1cnc2ccc(-c3ccn4nc(N[C@H]5CC[C@H](N6CCOCC6)CC5)ncc34)nc2c1]
1694
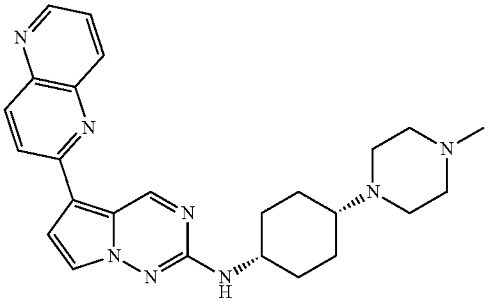 [SMILES: CN1CCN([C@H]2CC[C@@H](Nc3ncc4c(-c5ccc6ncccc6n5)ccn4n3)CC2)CC1]
1695
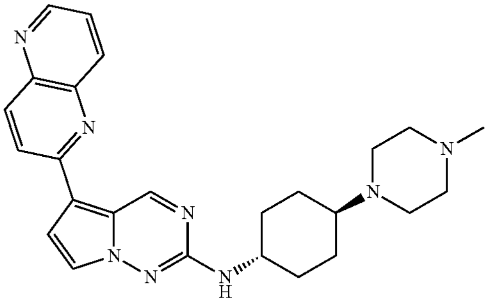 [SMILES: CN1CCN([C@H]2CC[C@H](Nc3ncc4c(-c5ccc6ncccc6n5)ccn4n3)CC2)CC1]
1696
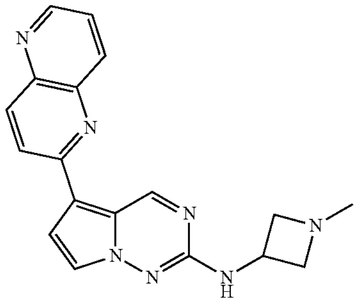 [SMILES: CN1CC(Nc2ncc3c(-c4ccc5ncccc5n4)ccn3n2)C1]
1697

TABLE 1-continued
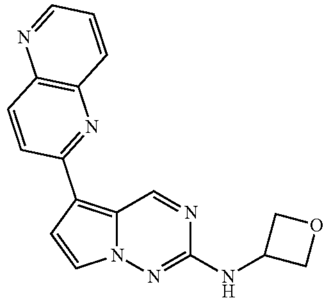 [SMILES: c1cnc2ccc(-c3ccn4nc(NC5COC5)ncc34)nc2c1]
1698
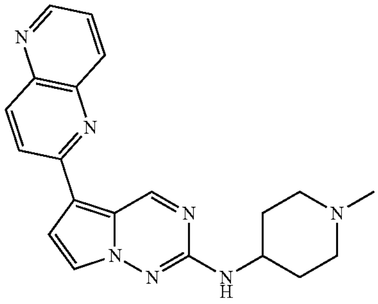
1699
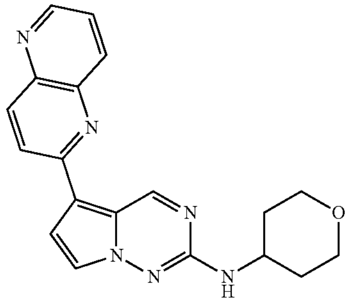 [SMILES: c1cnc2ccc(-c3ccn4nc(NC5CCOCC5)ncc34)nc2c1]
1700
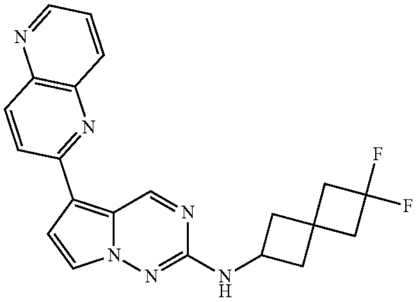 [SMILES: FC1(F)CC2(CC(Nc3ncc4c(-c5ccc6ncccc6n5)ccn4n3)C2)C1]
1701
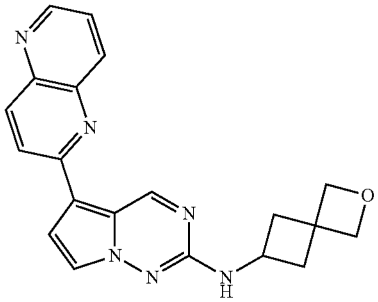 [SMILES: c1cnc2ccc(-c3ccn4nc(NC5CC6(COC6)C5)ncc34)nc2c1]
1702

TABLE 1-continued
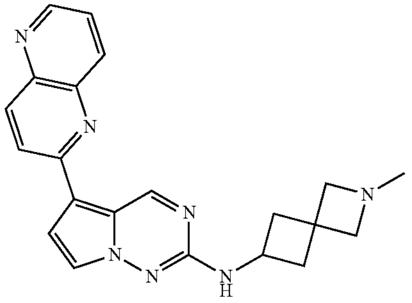 [SMILES: CN1CC2(CC(Nc3ncc4c(-c5ccc6ncccc6n5)ccn4n3)C2)C1]
1703
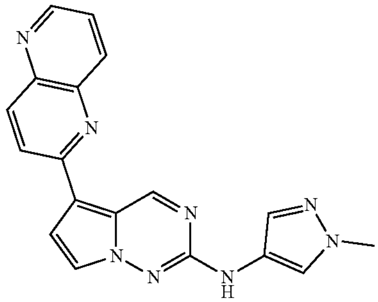 [SMILES: Cn1cc(Nc2ncc3c(-c4ccc5ncccc5n4)ccn3n2)cn1]
1704
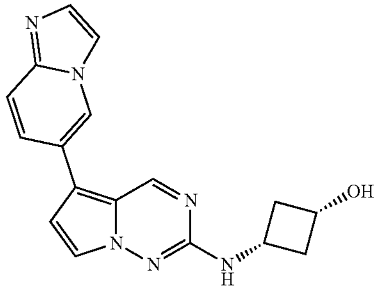 [SMILES: O[C@H]1C[C@@H](Nc2ncc3c(-c4ccc5nccn5c4)ccn3n2)C1]
1705
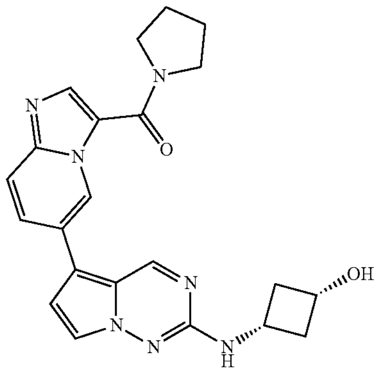 [SMILES: O=C(c1cnc2ccc(-c3ccn4nc(N[C@H]5C[C@@H](O)C5)ncc34)cn12)N1CCCC1]
1706
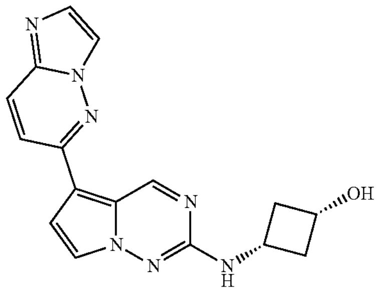 [SMILES: O[C@H]1C[C@@H](Nc2ncc3c(-c4ccc5nccn5n4)ccn3n2)C1]
1707

TABLE 1-continued
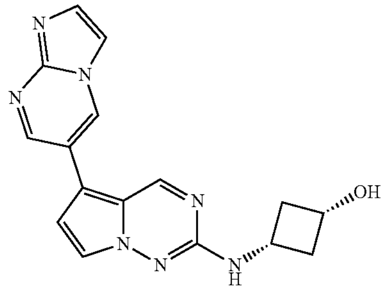 [SMILES: O[C@H]1C[C@@H](Nc2ncc3c(-c4cnc5nccn5c4)ccn3n2)C1]
1708
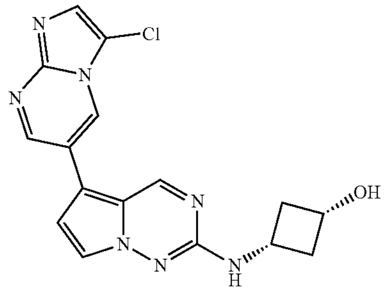 [SMILES: O[C@H]1C[C@@H](Nc2ncc3c(-c4cnc5ncc(Cl)n5c4)ccn3n2)C1]
1709
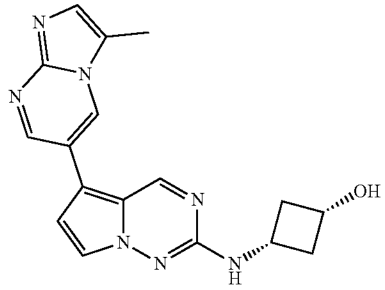 [SMILES: Cc1cnc2ncc(-c3ccn4nc(N[C@H]5C[C@@H](O)C5)ncc34)cn12]
1710
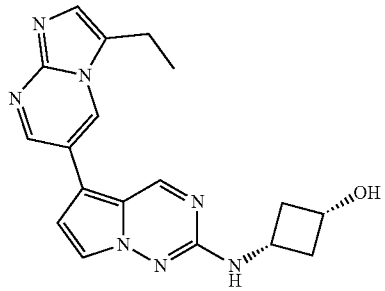 [SMILES: CCc1cnc2ncc(-c3ccn4nc(N[C@H]5C[C@@H](O)C5)ncc34)cn12]
1711
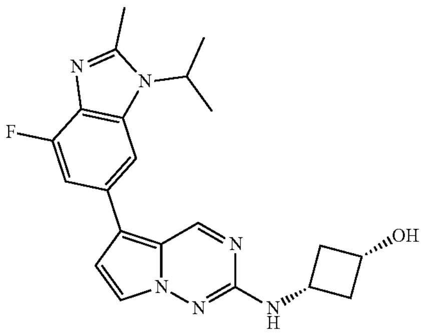 [SMILES: Cc1nc2c(F)cc(-c3ccn4nc(N[C@H]5C[C@@H](O)C5)ncc34)cc2n1C(C)C]
1712

TABLE 1-continued
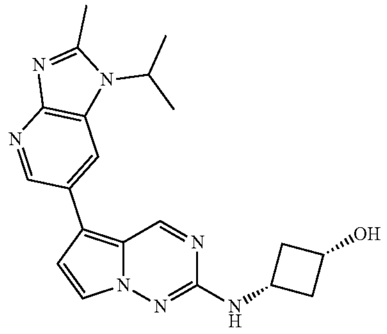 [SMILES: Cc1nc2ncc(-c3ccn4nc(N[C@H]5C[C@@H](O)C5)ncc34)cc2n1C(C)C]
1713
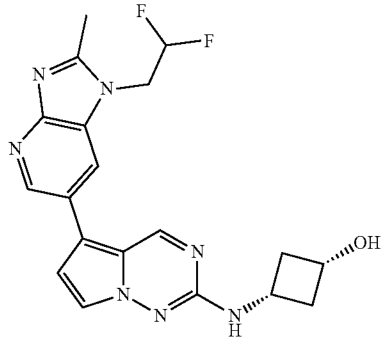 [SMILES: Cc1nc2ncc(-c3ccn4nc(N[C@H]5C[C@@H](O)C5)ncc34)cc2n1CC(F)F]
1714
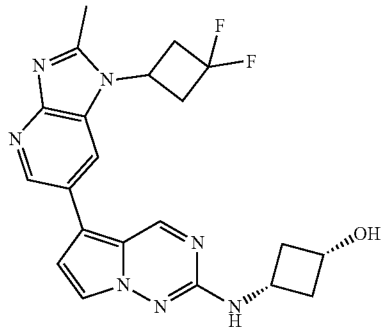 [SMILES: Cc1nc2ncc(-c3ccn4nc(N[C@H]5C[C@@H](O)C5)ncc34)cc2n1C1CC(F)(F)C1]
1715
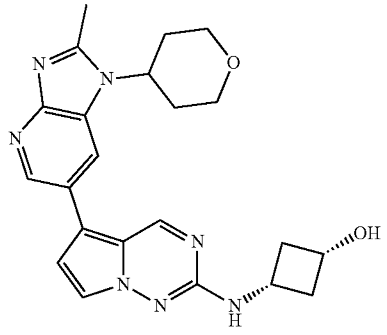 [SMILES: Cc1nc2ncc(-c3ccn4nc(N[C@H]5C[C@@H](O)C5)ncc34)cc2n1C1CCOCC1]
1716

TABLE 1-continued
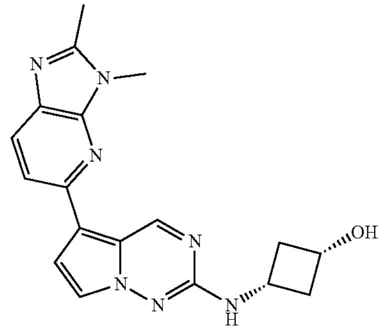 [SMILES: Cc1nc2ccc(-c3ccn4nc(N[C@H]5C[C@@H](O)C5)ncc34)nc2n1C]
1717
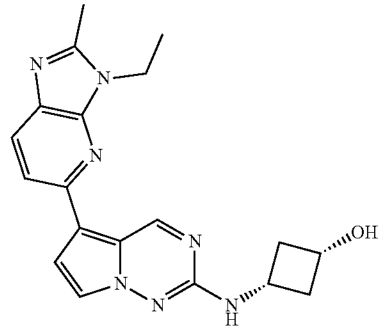 [SMILES: CCn1c(C)nc2ccc(-c3ccn4nc(N[C@H]5C[C@@H](O)C5)ncc34)nc21]
1718
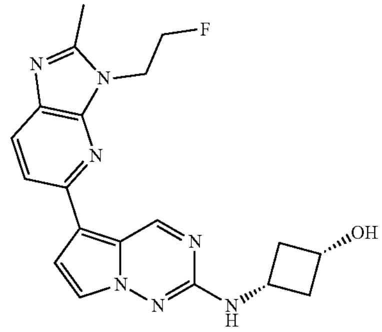 [SMILES: Cc1nc2ccc(-c3ccn4nc(N[C@H]5C[C@@H](O)C5)ncc34)nc2n1CCF]
1719
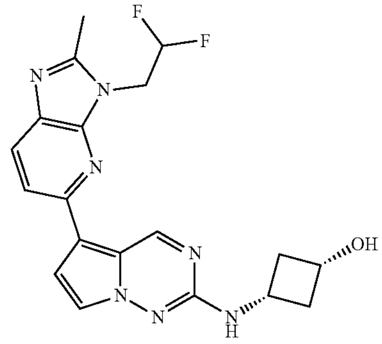 [SMILES: Cc1nc2ccc(-c3ccn4nc(N[C@H]5C[C@@H](O)C5)ncc34)nc2n1CC(F)F]
1720

TABLE 1-continued
1721
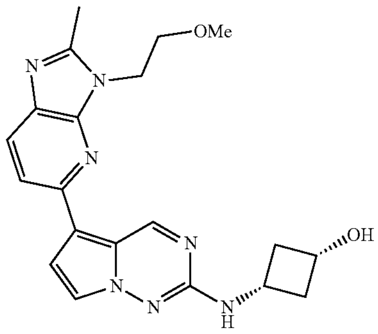 [SMILES: COCCn1c(C)nc2ccc(-c3ccn4nc(N[C@H]5C[C@@H](O)C5)ncc34)nc21]
1722
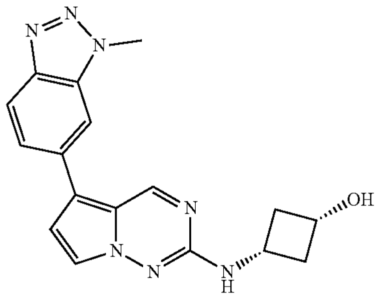 [SMILES: Cn1nnc2ccc(-c3ccn4nc(N[C@H]5C[C@@H](O)C5)ncc34)cc21]
1723
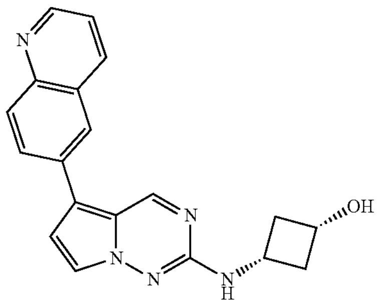 [SMILES: O[C@H]1C[C@@H](Nc2ncc3c(-c4ccc5ncccc5c4)ccn3n2)C1]
1724
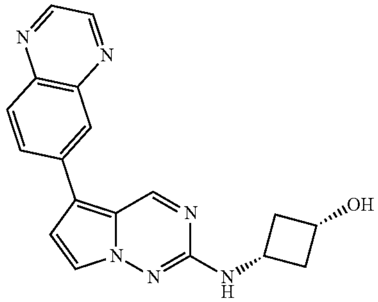 [SMILES: O[C@H]1C[C@@H](Nc2ncc3c(-c4ccc5nccnc5c4)ccn3n2)C1]
1725
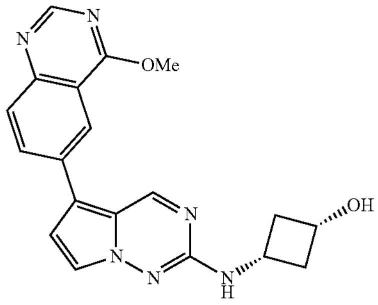 [SMILES: COc1ncnc2ccc(-c3ccn4nc(N[C@H]5C[C@@H](O)C5)ncc34)cc12]

TABLE 1-continued
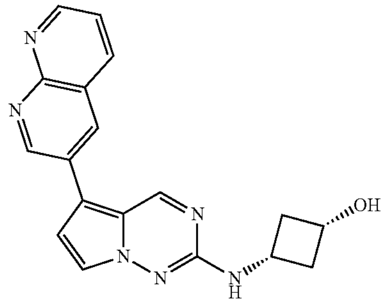 [SMILES: O[C@H]1C[C@@H](Nc2ncc3c(-c4cnc5ncccc5c4)ccn3n2)C1]
1726
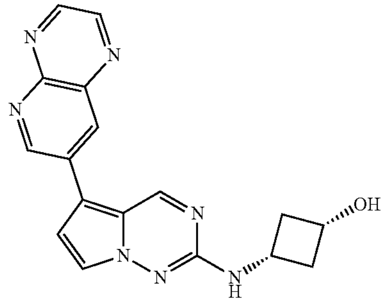 [SMILES: O[C@H]1C[C@@H](Nc2ncc3c(-c4cnc5nccnc5c4)ccn3n2)C1]
1727
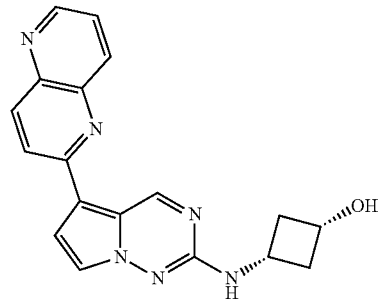 [SMILES: O[C@H]1C[C@@H](Nc2ncc3c(-c4ccc5ncccc5n4)ccn3n2)C1]
1728
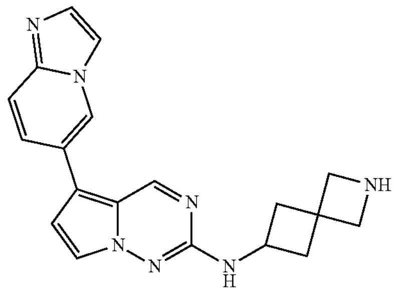 [SMILES: c1cn2cc(-c3ccn4nc(NC5CC6(CNC6)C5)ncc34)ccc2n1]
1729
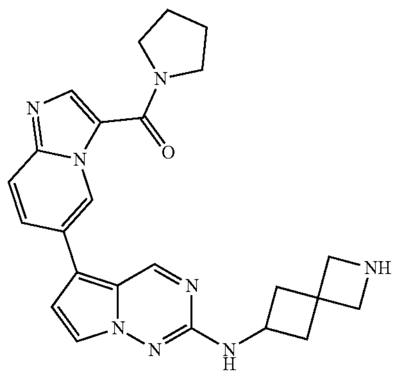 [SMILES: O=C(c1cnc2ccc(-c3ccn4nc(NC5CC6(CNC6)C5)ncc34)cn12)N1CCCC1]
1730

TABLE 1-continued
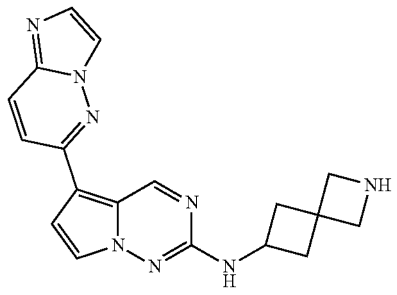 [SMILES: c1cn2nc(-c3ccn4nc(NC5CC6(CNC6)C5)ncc34)ccc2n1]
1731
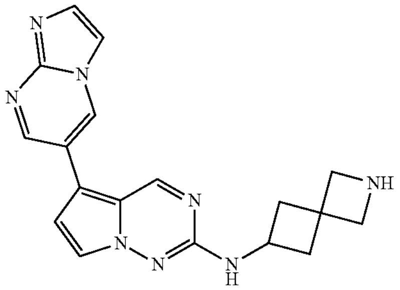 [SMILES: c1cn2cc(-c3ccn4nc(NC5CC6(CNC6)C5)ncc34)cnc2n1]
1732
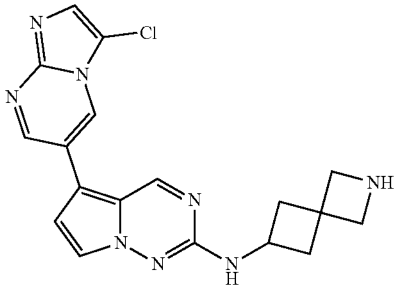 [SMILES: Clc1cnc2ncc(-c3ccn4nc(NC5CC6(CNC6)C5)ncc34)cn12]
1733
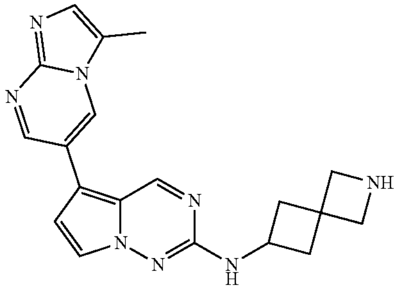 [SMILES: Cc1cnc2ncc(-c3ccn4nc(NC5CC6(CNC6)C5)ncc34)cn12]
1734
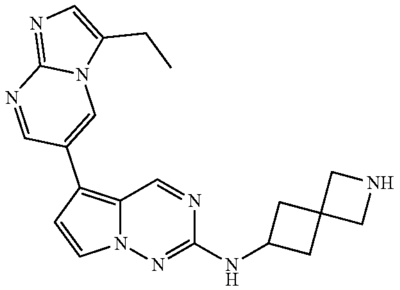 [SMILES: CCc1cnc2ncc(-c3ccn4nc(NC5CC6(CNC6)C5)ncc34)cn12]
1735

TABLE 1-continued
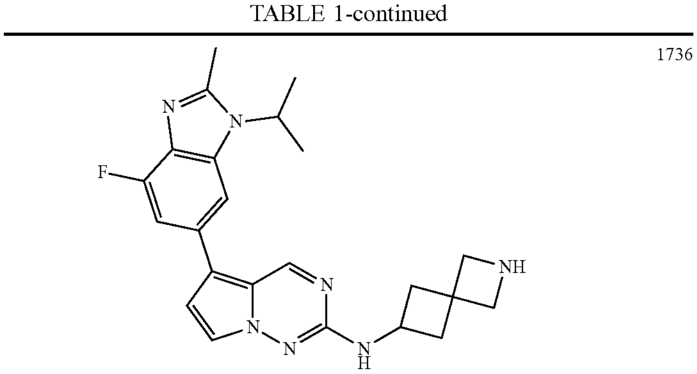
1736
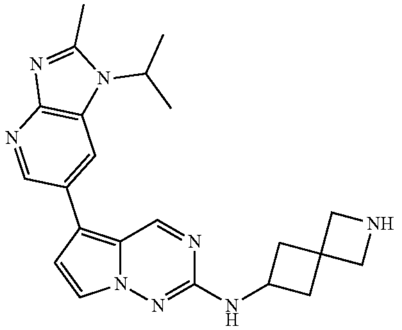 [SMILES: Cc1nc2ncc(-c3ccn4nc(NC5CC6(CNC6)C5)ncc34)cc2n1C(C)C]
1737
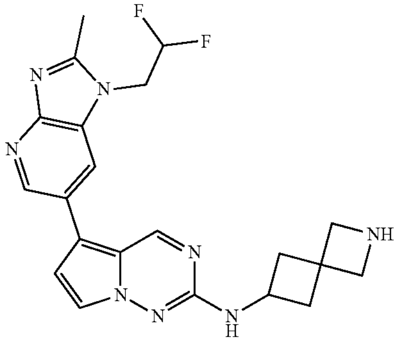 [SMILES: Cc1nc2ncc(-c3ccn4nc(NC5CC6(CNC6)C5)ncc34)cc2n1CC(F)F]
1738
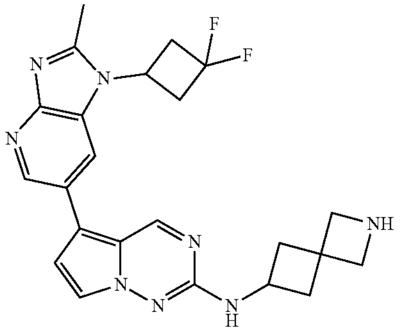 [SMILES: Cc1nc2ncc(-c3ccn4nc(NC5CC6(CNC6)C5)ncc34)cc2n1C1CC(F)(F)C1]
1739

TABLE 1-continued
1740
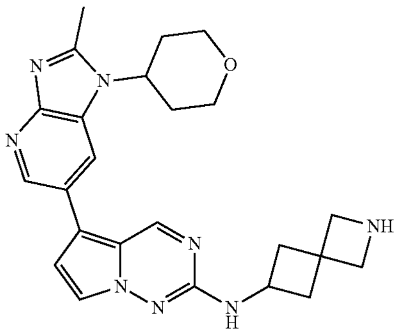 [SMILES: Cc1nc2ncc(-c3ccn4nc(NC5CC6(CNC6)C5)ncc34)cc2n1C1CCOCC1]
1741
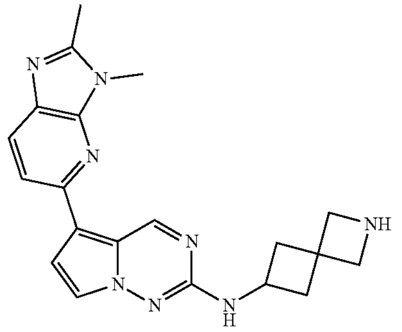 [SMILES: Cc1nc2ccc(-c3ccn4nc(NC5CC6(CNC6)C5)ncc34)nc2n1C]
1742
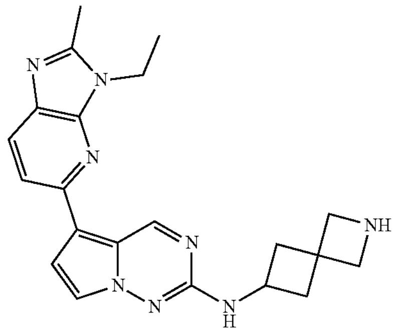 [SMILES: CCn1c(C)nc2ccc(-c3ccn4nc(NC5CC6(CNC6)C5)ncc34)nc21]
1743
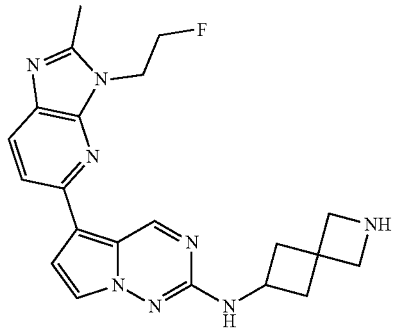 [SMILES: Cc1nc2ccc(-c3ccn4nc(NC5CC6(CNC6)C5)ncc34)nc2n1CCF]

TABLE 1-continued
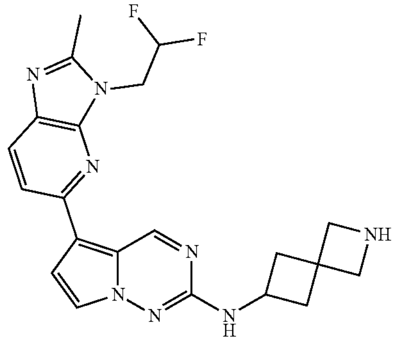 [SMILES: Cc1nc2ccc(-c3ccn4nc(NC5CC6(CNC6)C5)ncc34)nc2n1CC(F)F]
1744
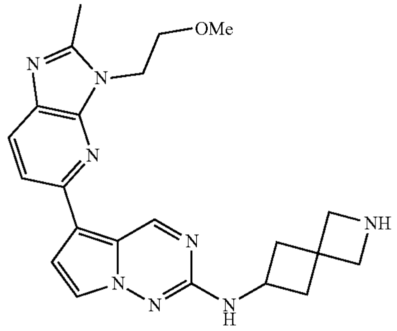 [SMILES: COCCn1c(C)nc2ccc(-c3ccn4nc(NC5CC6(CNC6)C5)ncc34)nc21]
1745
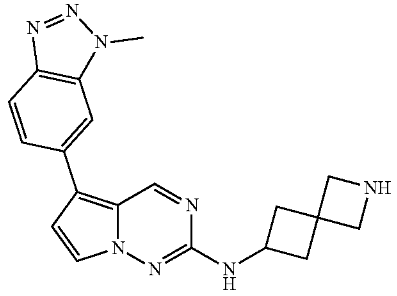 [SMILES: Cn1nnc2ccc(-c3ccn4nc(NC5CC6(CNC6)C5)ncc34)cc21]
1746
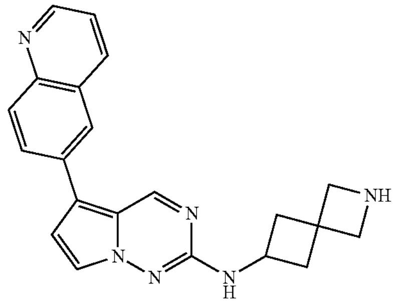 [SMILES: c1cnc2ccc(-c3ccn4nc(NC5CC6(CNC6)C5)ncc34)cc2c1]
1747
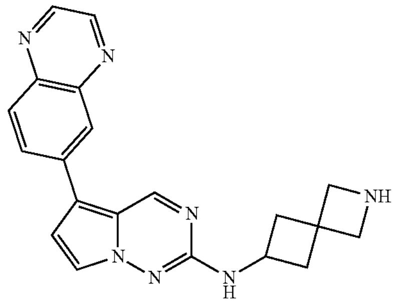 [SMILES: c1cnc2cc(-c3ccn4nc(NC5CC6(CNC6)C5)ncc34)ccc2n1]
1748

TABLE 1-continued
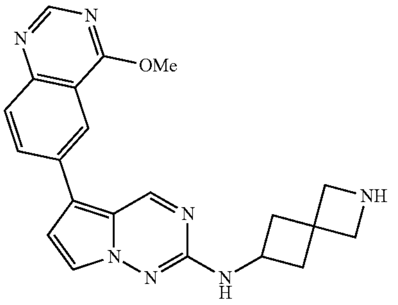 [SMILES: COc1ncnc2ccc(-c3ccn4nc(NC5CC6(CNC6)C5)ncc34)cc12]
1749
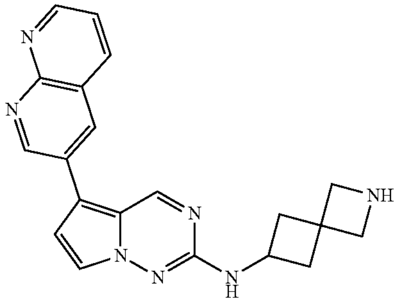 [SMILES: c1cnc2ncc(-c3ccn4nc(NC5CC6(CNC6)C5)ncc34)cc2c1]
1750
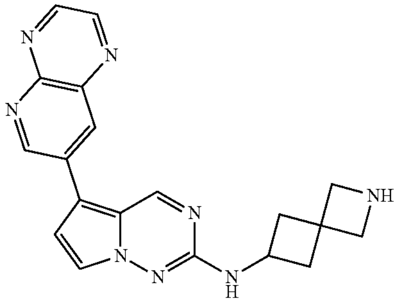 [SMILES: c1cnc2ncc(-c3ccn4nc(NC5CC6(CNC6)C5)ncc34)cc2n1]
1751
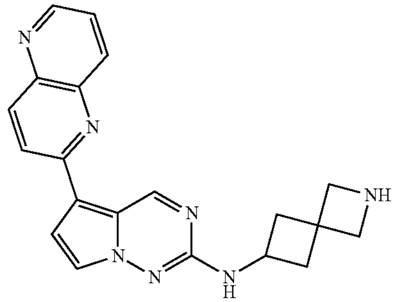 [SMILES: c1cnc2ccc(-c3ccn4nc(NC5CC6(CNC6)C5)ncc34)nc2c1]
1752
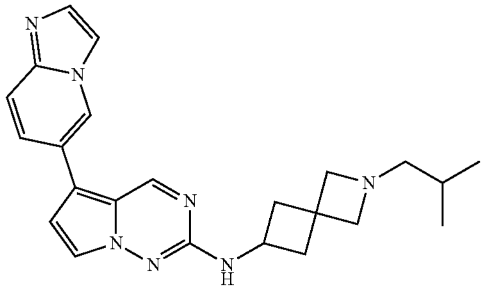 [SMILES: CC(C)CN1CC2(CC(Nc3ncc4c(-c5ccc6nccn6c5)ccn4n3)C2)C1]
1753

TABLE 1-continued
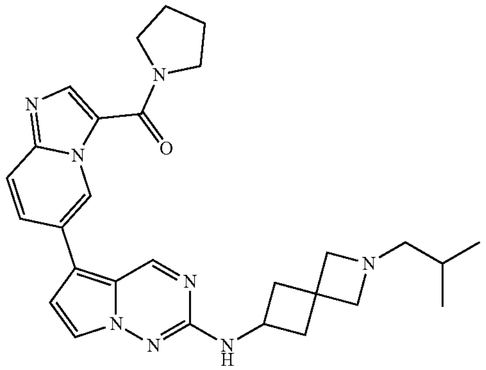 [SMILES: CC(C)CN1CC2(CC(Nc3ncc4c(-c5ccc6ncc(C(=O)N7CCCC7)n6c5)ccn4n3)C2)C1]
1754
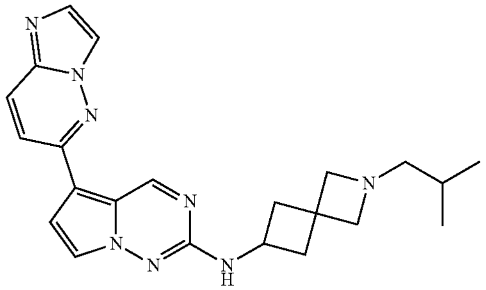 [SMILES: CC(C)CN1CC2(CC(Nc3ncc4c(-c5ccc6nccn6n5)ccn4n3)C2)C1]
1755
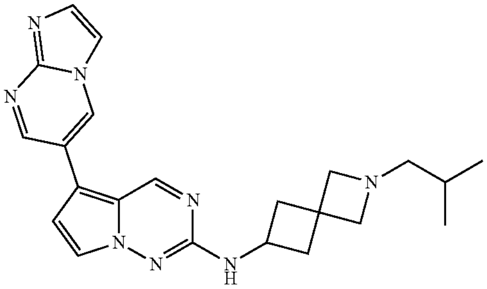 [SMILES: CC(C)CN1CC2(CC(Nc3ncc4c(-c5cnc6nccn6c5)ccn4n3)C2)C1]
1756
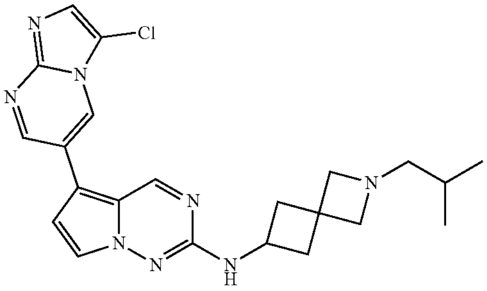 [SMILES: CC(C)CN1CC2(CC(Nc3ncc4c(-c5cnc6ncc(Cl)n6c5)ccn4n3)C2)C1]
1757
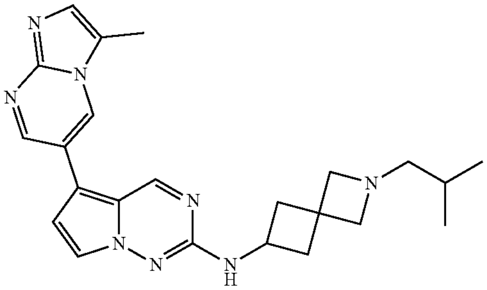 [SMILES: Cc1cnc2ncc(-c3ccn4nc(NC5CC6(C5)CN(CC(C)C)C6)ncc34)cn12]
1758

TABLE 1-continued
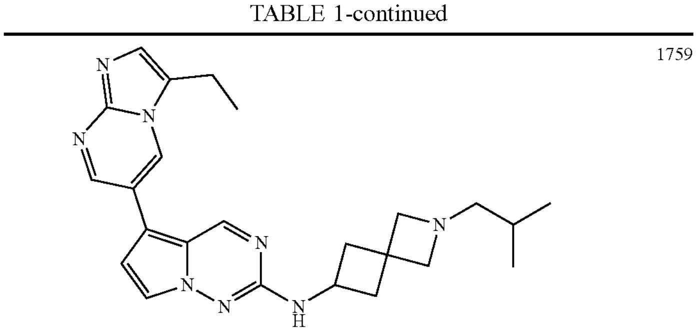
1759
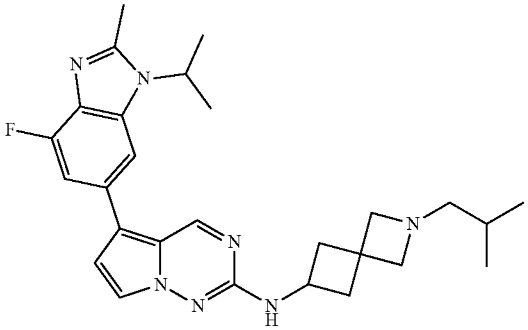 [SMILES: Cc1nc2c(F)cc(-c3ccn4nc(NC5CC6(C5)CN(CC(C)C)C6)ncc34)cc2n1C(C)C]
1760
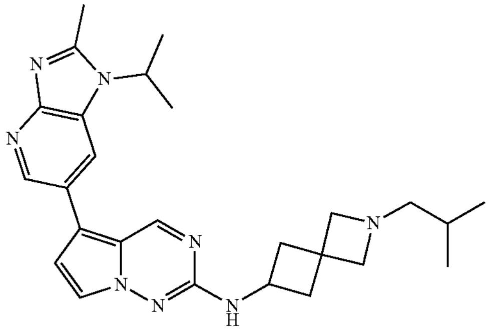 [SMILES: Cc1nc2ncc(-c3ccn4nc(NC5CC6(C5)CN(CC(C)C)C6)ncc34)cc2n1C(C)C]
1761
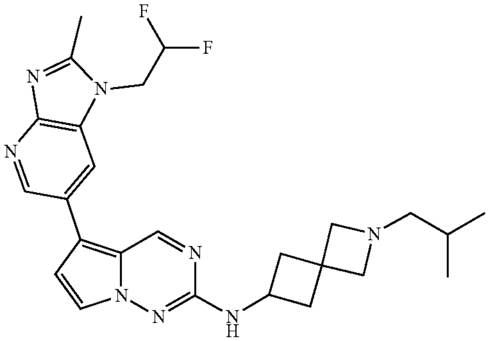 [SMILES: Cc1nc2ncc(-c3ccn4nc(NC5CC6(C5)CN(CC(C)C)C6)ncc34)cc2n1CC(F)F]
1762
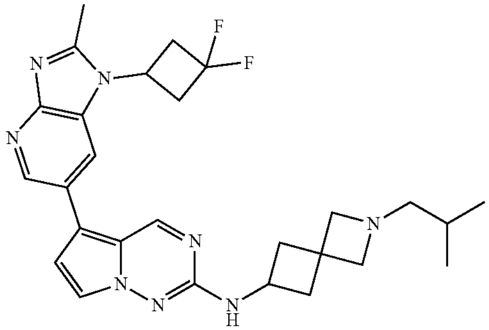 [SMILES: Cc1nc2ncc(-c3ccn4nc(NC5CC6(C5)CN(CC(C)C)C6)ncc34)cc2n1C1CC(F)(F)C1]
1763

TABLE 1-continued
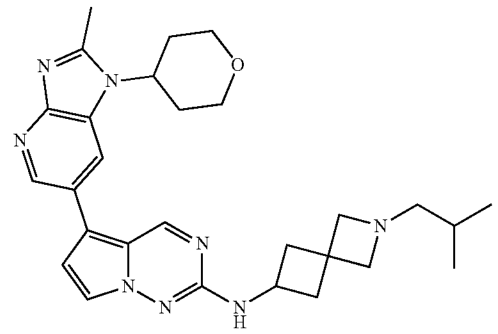 [SMILES: Cc1nc2ncc(-c3ccn4nc(NC5CC6(C5)CN(CC(C)C)C6)ncc34)cc2n1C1CCOCC1]
1764
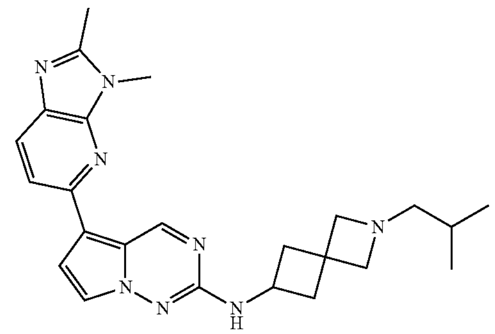 [SMILES: Cc1nc2ccc(-c3ccn4nc(NC5CC6(C5)CN(CC(C)C)C6)ncc34)nc2n1C]
1765
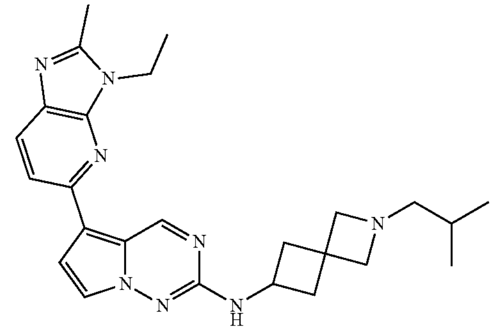 [SMILES: CCn1c(C)nc2ccc(-c3ccn4nc(NC5CC6(C5)CN(CC(C)C)C6)ncc34)nc21]
1766
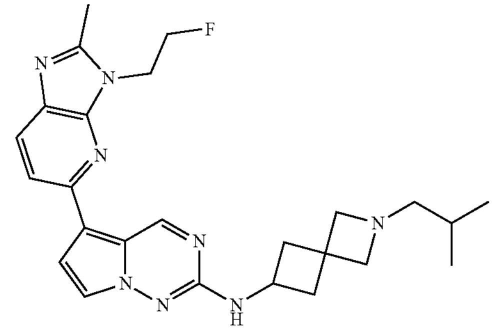 [SMILES: Cc1nc2ccc(-c3ccn4nc(NC5CC6(C5)CN(CC(C)C)C6)ncc34)nc2n1CCF]
1767

TABLE 1-continued
1768
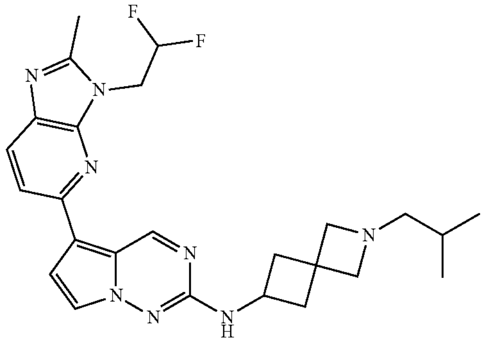 [SMILES: Cc1nc2ccc(-c3ccn4nc(NC5CC6(C5)CN(CC(C)C)C6)ncc34)nc2n1CC(F)F]
1769
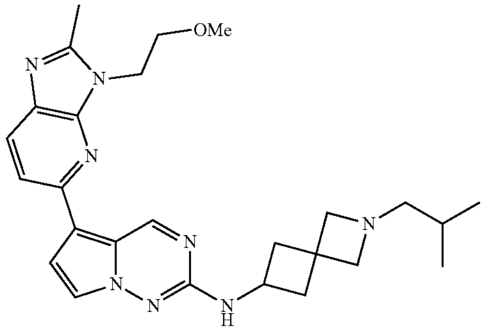 [SMILES: COCCn1c(C)nc2ccc(-c3ccn4nc(NC5CC6(C5)CN(CC(C)C)C6)ncc34)nc21]
1770
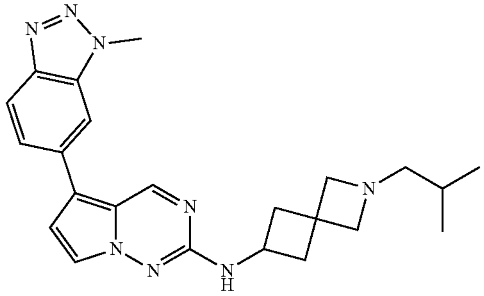 [SMILES: CC(C)CN1CC2(CC(Nc3ncc4c(-c5ccc6nnn(C)c6c5)ccn4n3)C2)C1]
1771
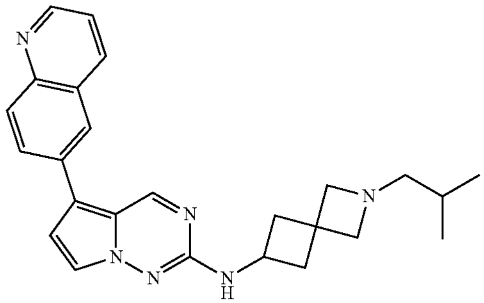
1772
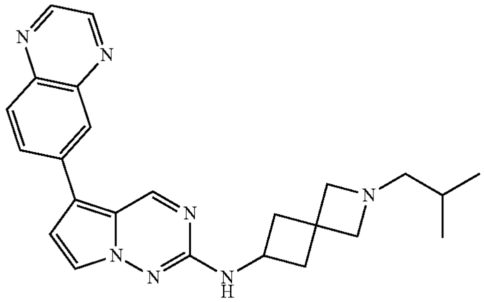 [SMILES: CC(C)CN1CC2(CC(Nc3ncc4c(-c5ccc6nccnc6c5)ccn4n3)C2)C1]

TABLE 1-continued
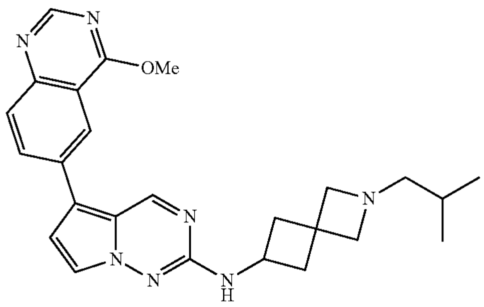 [SMILES: COc1ncnc2ccc(-c3ccn4nc(NC5CC6(C5)CN(CC(C)C)C6)ncc34)cc12]
1773
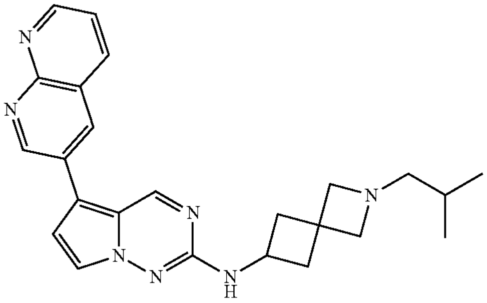 [SMILES: CC(C)CN1CC2(CC(Nc3ncc4c(-c5cnc6ncccc6c5)ccn4n3)C2)C1]
1774
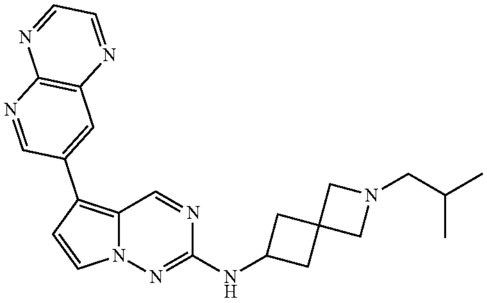 [SMILES: CC(C)CN1CC2(CC(Nc3ncc4c(-c5cnc6nccnc6c5)ccn4n3)C2)C1]
1775
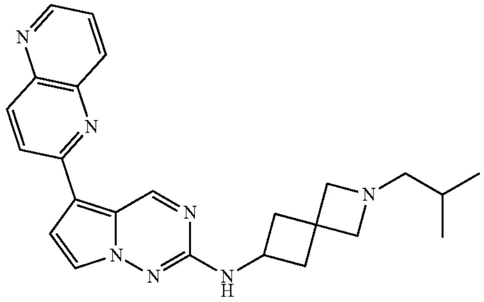 [SMILES: CC(C)CN1CC2(CC(Nc3ncc4c(-c5ccc6ncccc6n5)ccn4n3)C2)C1]
1776
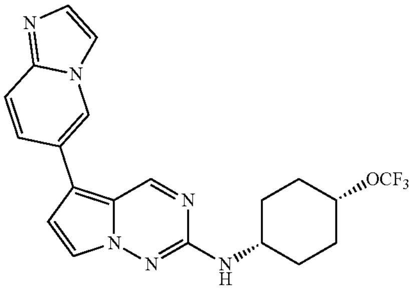 [SMILES: FC(F)(F)O[C@H]1CC[C@@H](Nc2ncc3c(-c4ccc5nccn5c4)ccn3n2)CC1]
1777

TABLE 1-continued
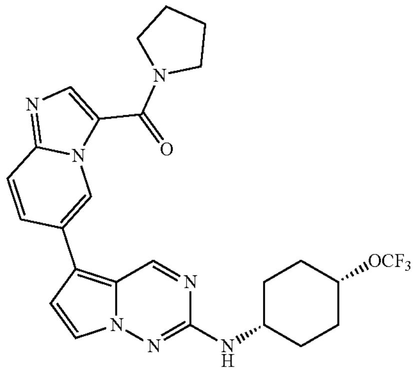 [SMILES: O=C(c1cnc2ccc(-c3ccn4nc(N[C@H]5CC[C@@H](OC(F)(F)F)CC5)ncc34)cn12)N1CCCC1]
1778
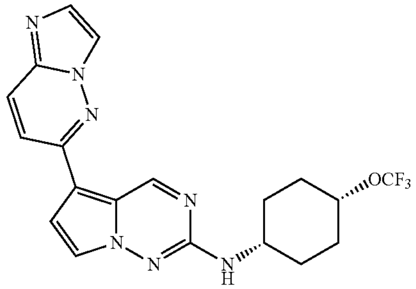 [SMILES: FC(F)(F)O[C@H]1CC[C@@H](Nc2ncc3c(-c4ccc5nccn5n4)ccn3n2)CC1]
1779
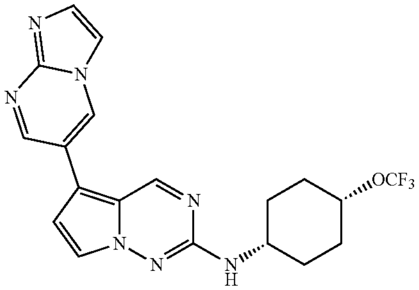 [SMILES: FC(F)(F)O[C@H]1CC[C@@H](Nc2ncc3c(-c4cnc5nccn5c4)ccn3n2)CC1]
1780
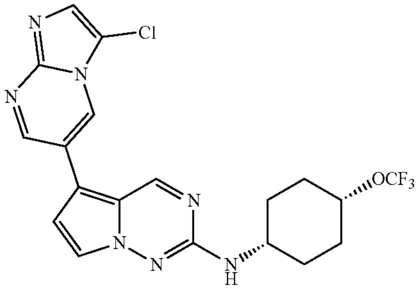 [SMILES: FC(F)(F)O[C@H]1CC[C@@H](Nc2ncc3c(-c4cnc5ncc(Cl)n5c4)ccn3n2)CC1]
1781
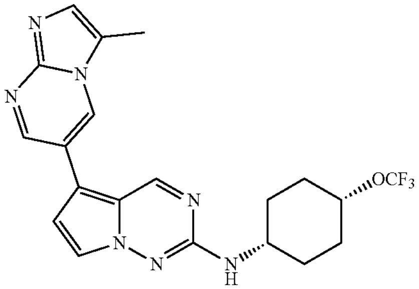 [SMILES: Cc1cnc2ncc(-c3ccn4nc(N[C@H]5CC[C@@H](OC(F)(F)F)CC5)ncc34)cn12]
1782

TABLE 1-continued
1783
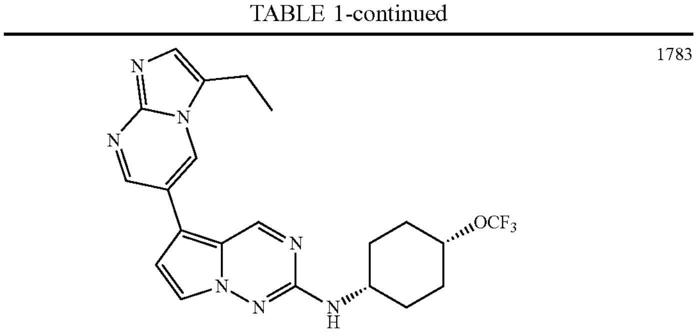
1784
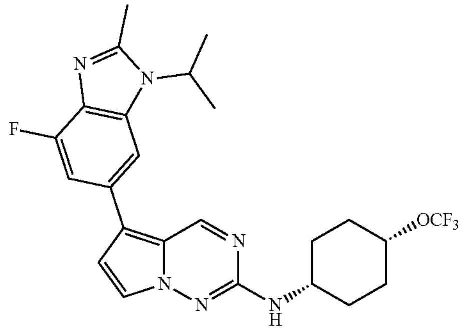 [SMILES: Cc1nc2c(F)cc(-c3ccn4nc(N[C@H]5CC[C@@H](OC(F)(F)F)CC5)ncc34)cc2n1C(C)C]
1785
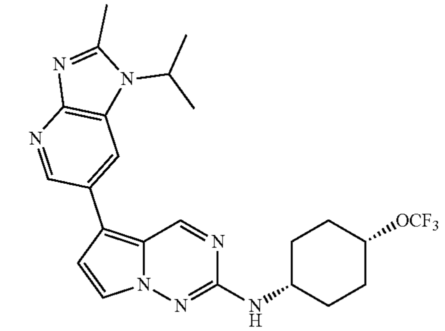 [SMILES: Cc1nc2ncc(-c3ccn4nc(N[C@H]5CC[C@@H](OC(F)(F)F)CC5)ncc34)cc2n1C(C)C]
1786
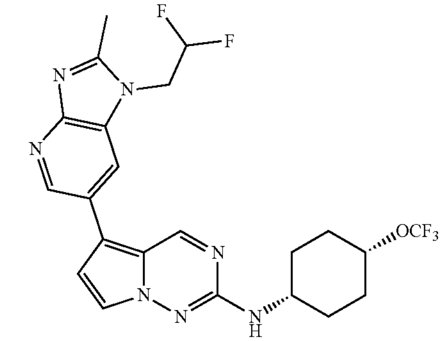 [SMILES: Cc1nc2ncc(-c3ccn4nc(N[C@H]5CC[C@@H](OC(F)(F)F)CC5)ncc34)cc2n1CC(F)F]
1787
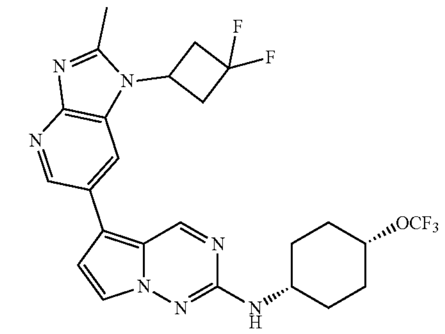 [SMILES: Cc1nc2ncc(-c3ccn4nc(N[C@H]5CC[C@@H](OC(F)(F)F)CC5)ncc34)cc2n1C1CC(F)(F)C1]

TABLE 1-continued
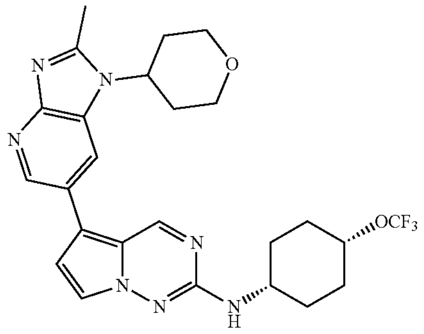 [SMILES: Cc1nc2ncc(-c3ccn4nc(N[C@H]5CC[C@@H](OC(F)(F)F)CC5)ncc34)cc2n1C1CCOCC1]
1788
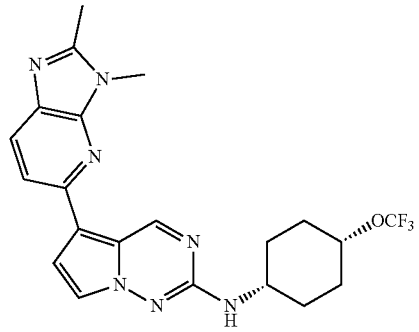 [SMILES: Cc1nc2ccc(-c3ccn4nc(N[C@H]5CC[C@@H](OC(F)(F)F)CC5)ncc34)nc2n1C]
1789
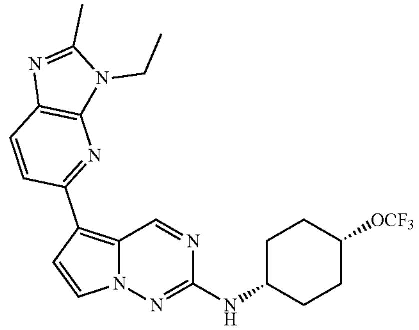 [SMILES: CCn1c(C)nc2ccc(-c3ccn4nc(N[C@H]5CC[C@@H](OC(F)(F)F)CC5)ncc34)nc21]
1790
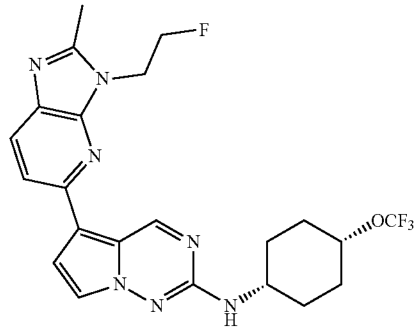 [SMILES: Cc1nc2ccc(-c3ccn4nc(N[C@H]5CC[C@@H](OC(F)(F)F)CC5)ncc34)nc2n1CCF]
1791

TABLE 1-continued
1792
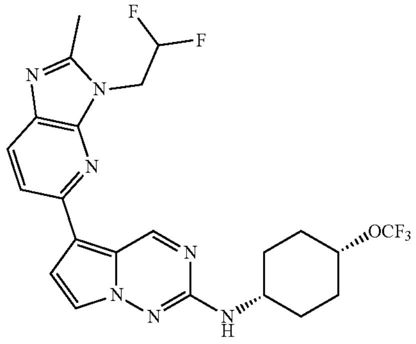 [SMILES: Cc1nc2ccc(-c3ccn4nc(N[C@H]5CC[C@@H](OC(F)(F)F)CC5)ncc34)nc2n1CC(F)F]
1793
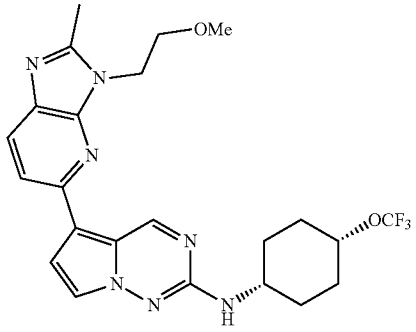 [SMILES: COCCn1c(C)nc2ccc(-c3ccn4nc(N[C@H]5CC[C@@H](OC(F)(F)F)CC5)ncc34)nc21]
1794
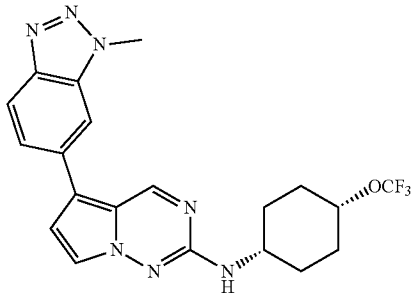 [SMILES: Cn1nnc2ccc(-c3ccn4nc(N[C@H]5CC[C@@H](OC(F)(F)F)CC5)ncc34)cc21]
1795
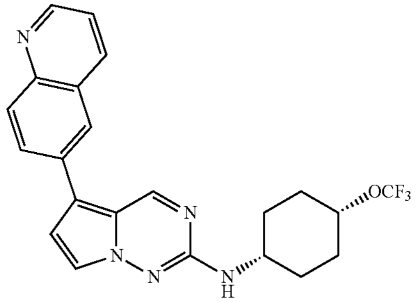 [SMILES: FC(F)(F)O[C@H]1CC[C@@H](Nc2ncc3c(-c4ccc5ncccc5c4)ccn3n2)CC1]
1796
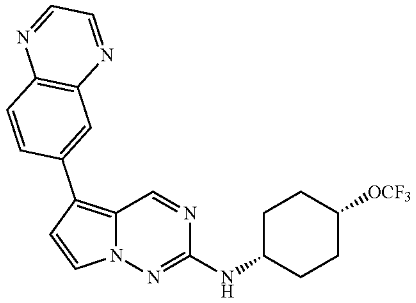 [SMILES: FC(F)(F)O[C@H]1CC[C@@H](Nc2ncc3c(-c4ccc5nccnc5c4)ccn3n2)CC1]

TABLE 1-continued
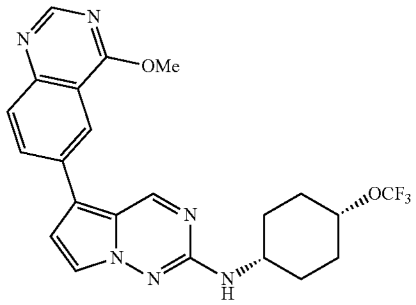 [SMILES: COc1ncnc2ccc(-c3ccn4nc(N[C@H]5CC[C@@H](OC(F)(F)F)CC5)ncc34)cc12]
1797
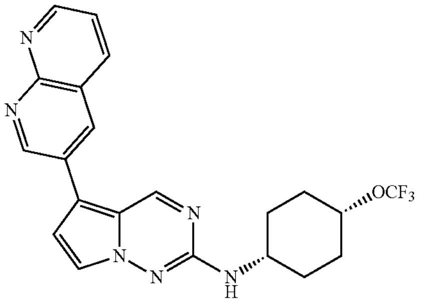 [SMILES: FC(F)(F)O[C@H]1CC[C@@H](Nc2ncc3c(-c4cnc5ncccc5c4)ccn3n2)CC1]
1798
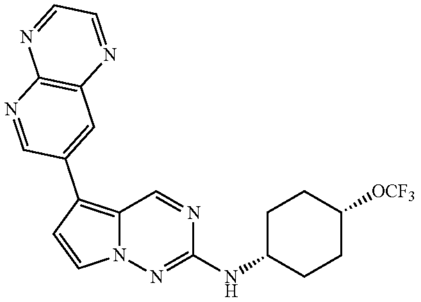 [SMILES: FC(F)(F)O[C@H]1CC[C@@H](Nc2ncc3c(-c4cnc5nccnc5c4)ccn3n2)CC1]
1799
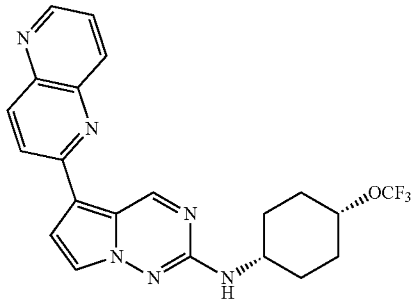 [SMILES: FC(F)(F)O[C@H]1CC[C@@H](Nc2ncc3c(-c4ccc5ncccc5n4)ccn3n2)CC1]
1800
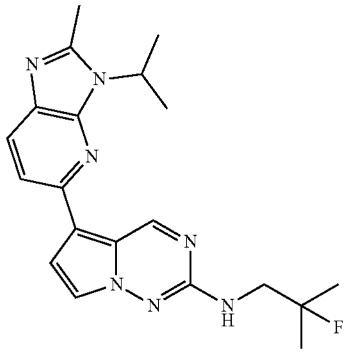 [SMILES: Cc1nc2ccc(-c3ccn4nc(NCC(C)(C)F)ncc34)nc2n1C(C)C]
1801

TABLE 1-continued
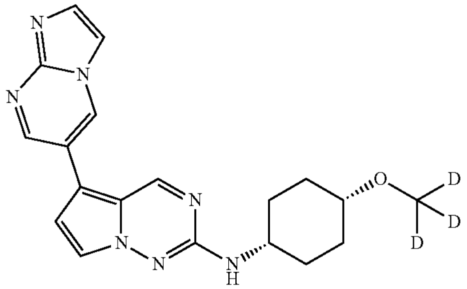 [SMILES: [2H]C([2H])([2H])O[C@H]1CC[C@@H](Nc2ncc3c(-c4cnc5nccn5c4)ccn3n2)CC1]
1802
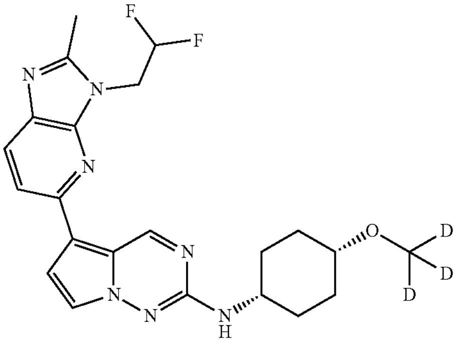 [SMILES: [2H]C([2H])([2H])O[C@H]1CC[C@@H](Nc2ncc3c(-c4ccc5nc(C)n(CC(F)F)c5n4)ccn3n2)CC1]
1803
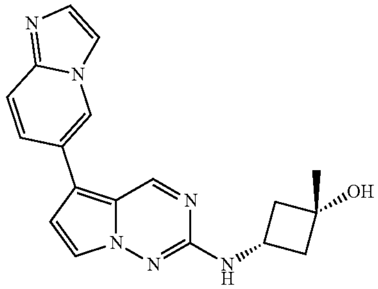 [SMILES: C[C@]1(O)C[C@@H](Nc2ncc3c(-c4ccc5nccn5c4)ccn3n2)C1]
1804
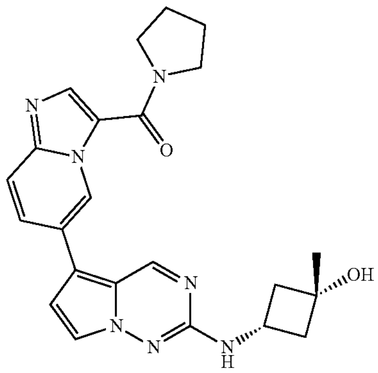 [SMILES: C[C@]1(O)C[C@@H](Nc2ncc3c(-c4ccc5ncc(C(=O)N6CCCC6)n5c4)ccn3n2)C1]
1805
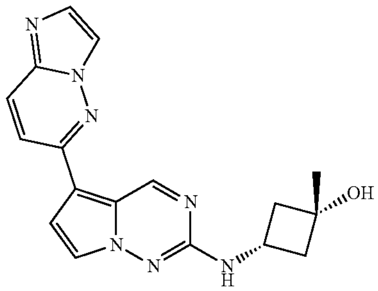
1806

TABLE 1-continued
1807
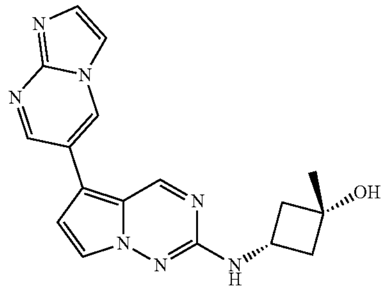 [SMILES: C[C@]1(O)C[C@@H](Nc2ncc3c(-c4cnc5nccn5c4)ccn3n2)C1]
1808
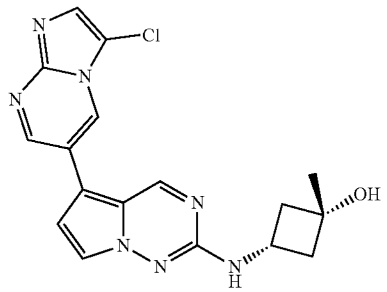 [SMILES: C[C@]1(O)C[C@@H](Nc2ncc3c(-c4cnc5ncc(Cl)n5c4)ccn3n2)C1]
1809
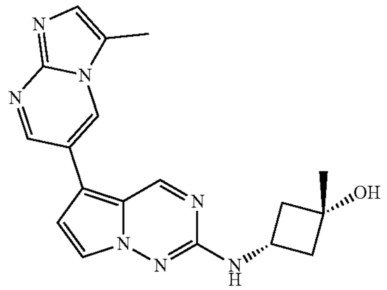 [SMILES: Cc1cnc2ncc(-c3ccn4nc(N[C@H]5C[C@@](C)(O)C5)ncc34)cn12]
1810
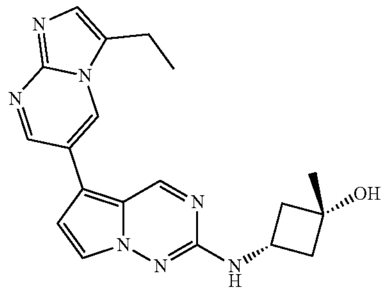 [SMILES: CCc1cnc2ncc(-c3ccn4nc(N[C@H]5C[C@@](C)(O)C5)ncc34)cn12]
1811
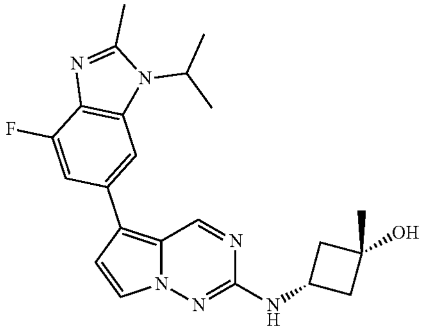 [SMILES: Cc1nc2c(F)cc(-c3ccn4nc(N[C@H]5C[C@@](C)(O)C5)ncc34)cc2n1C(C)C]

TABLE 1-continued
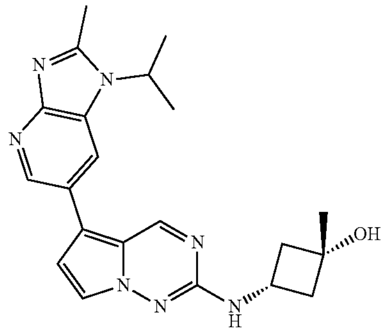 [SMILES: Cc1nc2ncc(-c3ccn4nc(N[C@H]5C[C@@](C)(O)C5)ncc34)cc2n1C(C)C]
1812
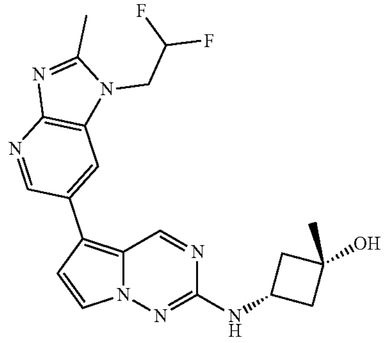 [SMILES: Cc1nc2ncc(-c3ccn4nc(N[C@H]5C[C@@](C)(O)C5)ncc34)cc2n1CC(F)F]
1813
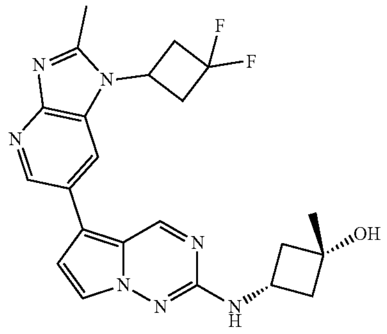 [SMILES: Cc1nc2ncc(-c3ccn4nc(N[C@H]5C[C@@](C)(O)C5)ncc34)cc2n1C1CC(F)(F)C1]
1814
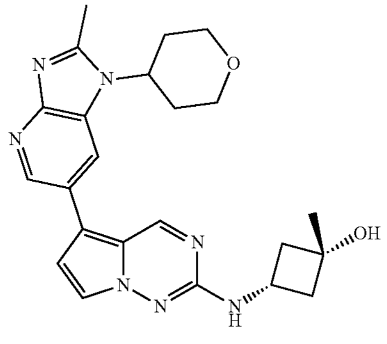 [SMILES: Cc1nc2ncc(-c3ccn4nc(N[C@H]5C[C@@](C)(O)C5)ncc34)cc2n1C1CCOCC1]
1815

TABLE 1-continued
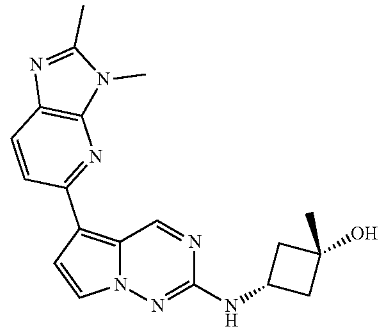 [SMILES: Cc1nc2ccc(-c3ccn4nc(N[C@H]5C[C@@](C)(O)C5)ncc34)nc2n1C]
1816
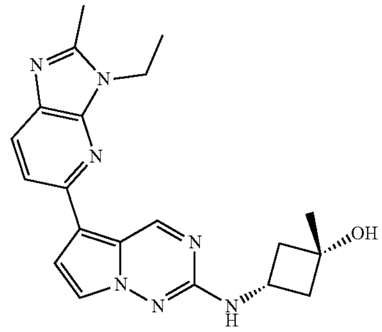 [SMILES: CCn1c(C)nc2ccc(-c3ccn4nc(N[C@H]5C[C@@](C)(O)C5)ncc34)nc21]
1817
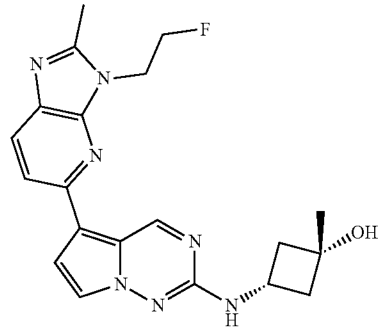 [SMILES: Cc1nc2ccc(-c3ccn4nc(N[C@H]5C[C@@](C)(O)C5)ncc34)nc2n1CCF]
1818
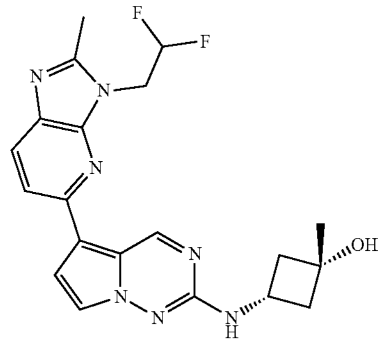 [SMILES: Cc1nc2ccc(-c3ccn4nc(N[C@H]5C[C@@](C)(O)C5)ncc34)nc2n1CC(F)F]
1819

TABLE 1-continued
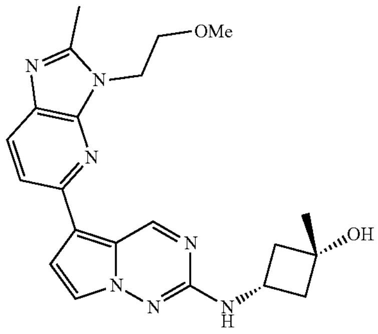 [SMILES: COCCn1c(C)nc2ccc(-c3ccn4nc(N[C@H]5C[C@@](C)(O)C5)ncc34)nc21]
1820
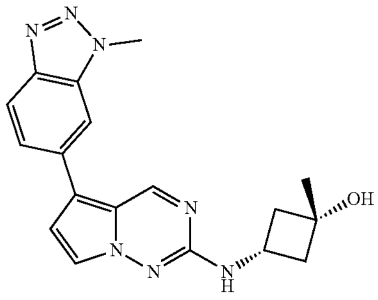 [SMILES: Cn1nnc2ccc(-c3ccn4nc(N[C@H]5C[C@@](C)(O)C5)ncc34)cc21]
1821
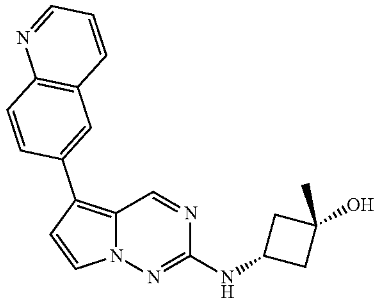 [SMILES: C[C@]1(O)C[C@@H](Nc2ncc3c(-c4ccc5ncccc5c4)ccn3n2)C1]
1822
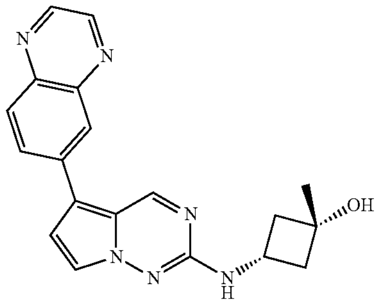 [SMILES: C[C@]1(O)C[C@@H](Nc2ncc3c(-c4ccc5nccnc5c4)ccn3n2)C1]
1823
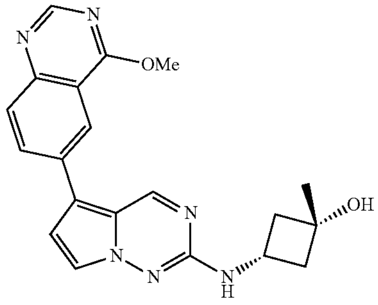 [SMILES: COc1ncnc2ccc(-c3ccn4nc(N[C@H]5C[C@@](C)(O)C5)ncc34)cc12]
1824

TABLE 1-continued
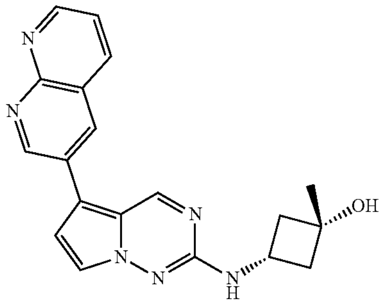 [SMILES: C[C@]1(O)C[C@@H](Nc2ncc3c(-c4cnc5ncccc5c4)ccn3n2)C1]
1825
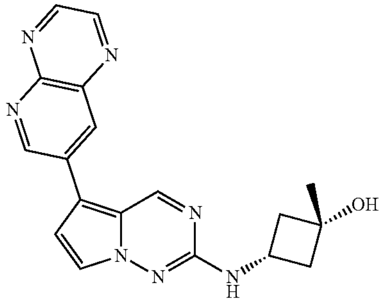 [SMILES: C[C@]1(O)C[C@@H](Nc2ncc3c(-c4cnc5nccnc5c4)ccn3n2)C1]
1826
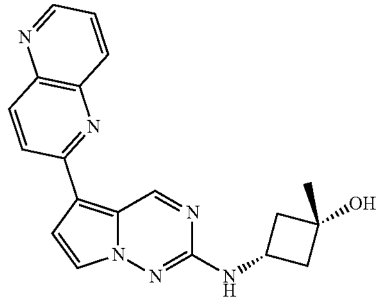 [SMILES: C[C@]1(O)C[C@@H](Nc2ncc3c(-c4ccc5ncccc5n4)ccn3n2)C1]
1827
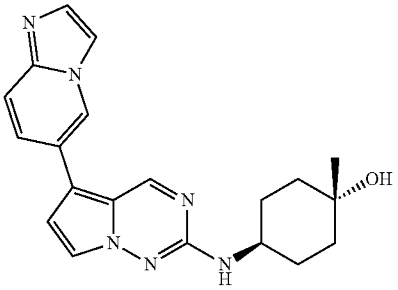 [SMILES: C[C@]1(O)CC[C@H](Nc2ncc3c(-c4ccc5nccn5c4)ccn3n2)CC1]
1828
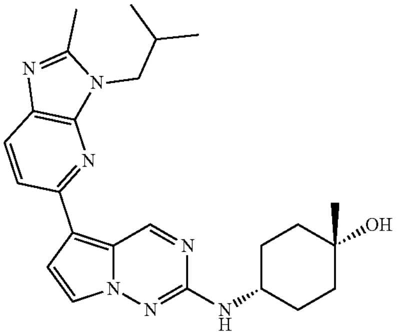 [SMILES: Cc1nc2ccc(-c3ccn4nc(N[C@H]5CC[C@@](C)(O)CC5)ncc34)nc2n1CC(C)C]
1829

TABLE 1-continued
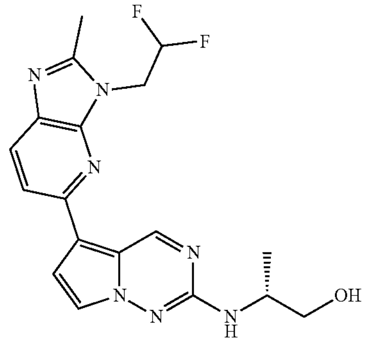 [SMILES: Cc1nc2ccc(-c3ccn4nc(N[C@H](C)CO)ncc34)nc2n1CC(F)F]
1830
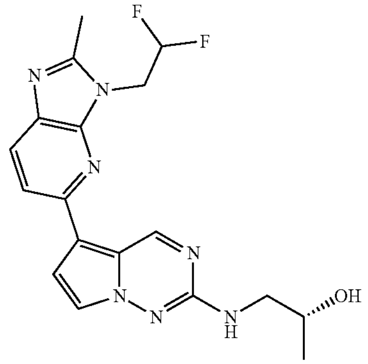 [SMILES: Cc1nc2ccc(-c3ccn4nc(NC[C@@H](C)O)ncc34)nc2n1CC(F)F]
1831
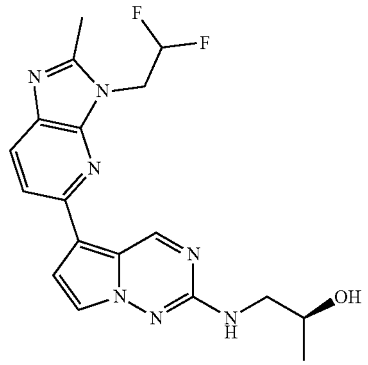 [SMILES: Cc1nc2ccc(-c3ccn4nc(NC[C@H](C)O)ncc34)nc2n1CC(F)F]
1832
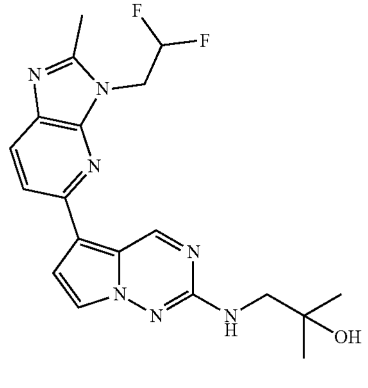 [SMILES: Cc1nc2ccc(-c3ccn4nc(NCC(C)(C)O)ncc34)nc2n1CC(F)F]
1833

TABLE 1-continued
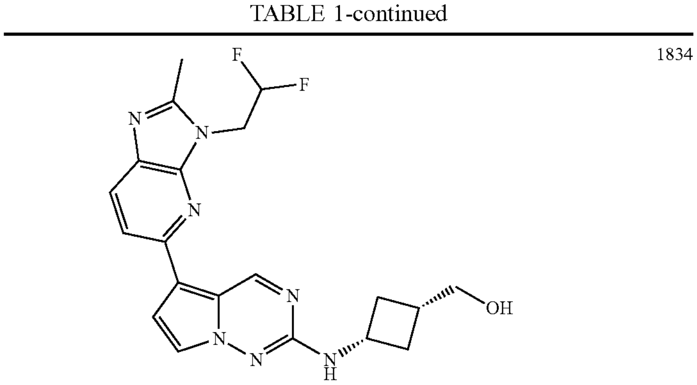
1834
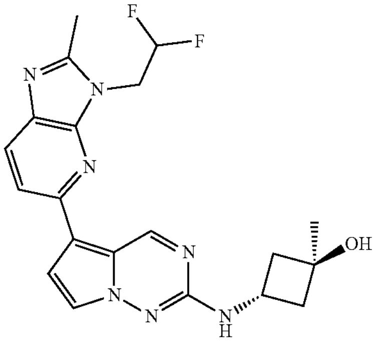 [SMILES: Cc1nc2ccc(-c3ccn4nc(N[C@H]5C[C@](C)(O)C5)ncc34)nc2n1CC(F)F]
1835
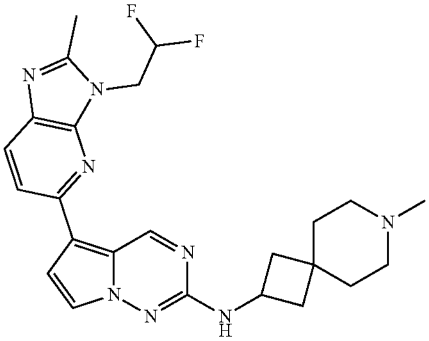 [SMILES: Cc1nc2ccc(-c3ccn4nc(NC5CC6(CCN(C)CC6)C5)ncc34)nc2n1CC(F)F]
1836
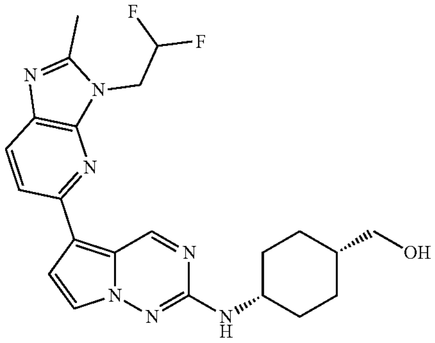 [SMILES: Cc1nc2ccc(-c3ccn4nc(N[C@H]5CC[C@@H](CO)CC5)ncc34)nc2n1CC(F)F]
1837

TABLE 1-continued
1838
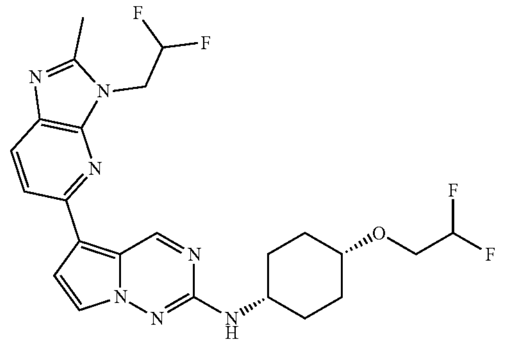 [SMILES: Cc1nc2ccc(-c3ccn4nc(N[C@H]5CC[C@@H](OCC(F)F)CC5)ncc34)nc2n1CC(F)F]
1839
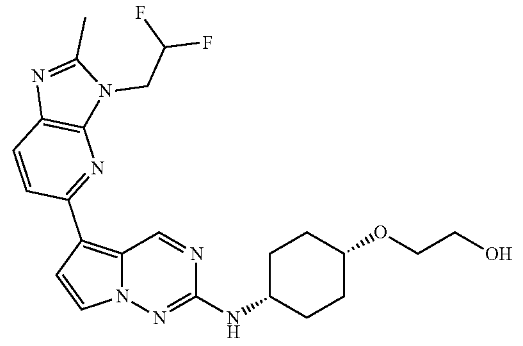 [SMILES: Cc1nc2ccc(-c3ccn4nc(N[C@H]5CC[C@@H](OCCO)CC5)ncc34)nc2n1CC(F)F]
1840
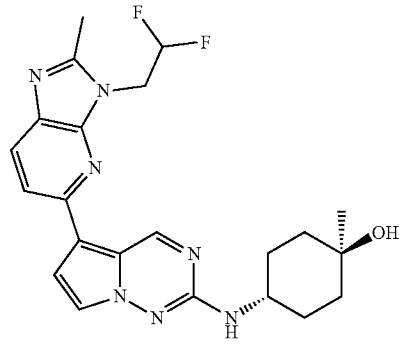 [SMILES: Cc1nc2ccc(-c3ccn4nc(N[C@H]5CC[C@](C)(O)CC5)ncc34)nc2n1CC(F)F]
1841
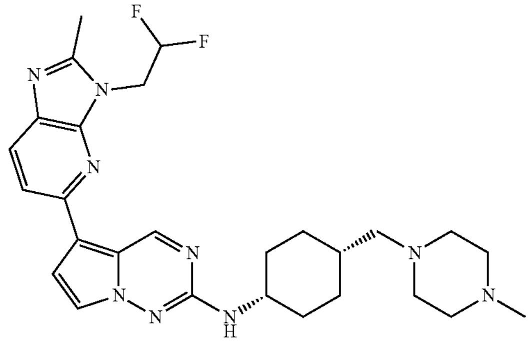 [SMILES: Cc1nc2ccc(-c3ccn4nc(N[C@H]5CC[C@@H](CN6CCN(C)CC6)CC5)ncc34)nc2n1CC(F)F]

TABLE 1-continued
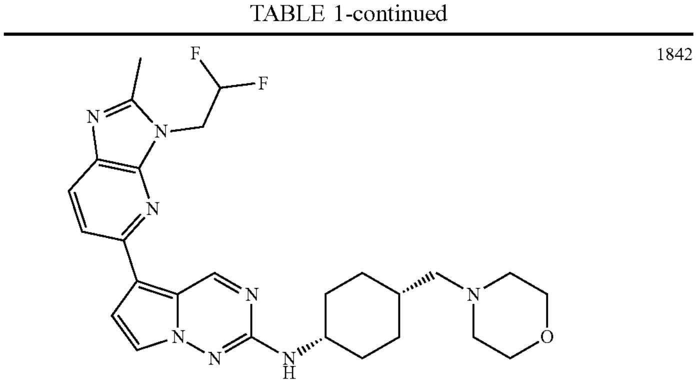
1842
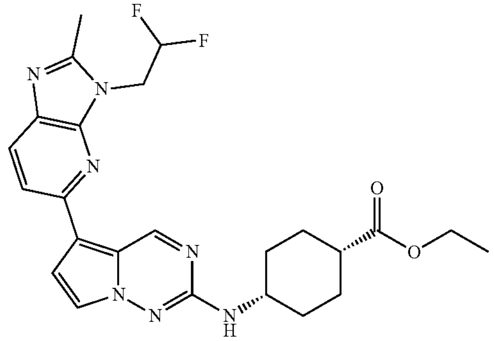 [SMILES: CCOC(=O)[C@H]1CC[C@@H](Nc2ncc3c(-c4ccc5nc(C)n(CC(F)F)c5n4)ccn3n2)CC1]
1843
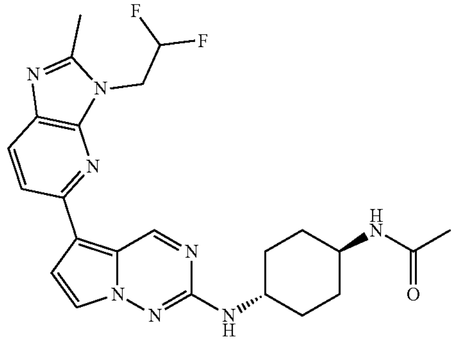 [SMILES: CC(=O)N[C@H]1CC[C@H](Nc2ncc3c(-c4ccc5nc(C)n(CC(F)F)c5n4)ccn3n2)CC1]
1844
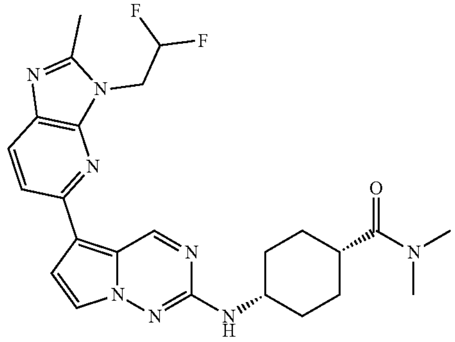 [SMILES: Cc1nc2ccc(-c3ccn4nc(N[C@H]5CC[C@@H](C(=O)N(C)C)CC5)ncc34)nc2n1CC(F)F]
1845

TABLE 1-continued
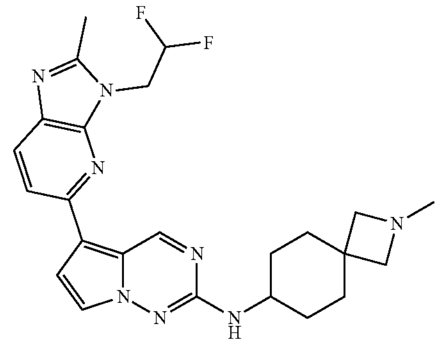 [SMILES: Cc1nc2ccc(-c3ccn4nc(NC5CCC6(CC5)CN(C)C6)ncc34)nc2n1CC(F)F]
1846
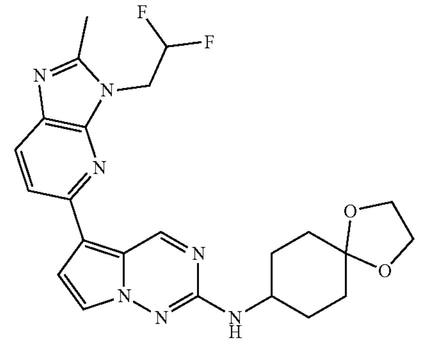 [SMILES: Cc1nc2ccc(-c3ccn4nc(NC5CCC6(CC5)OCCO6)ncc34)nc2n1CC(F)F]
1847
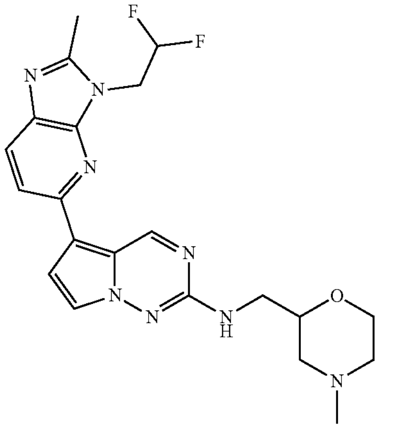 [SMILES: Cc1nc2ccc(-c3ccn4nc(NCC5CN(C)CCO5)ncc34)nc2n1CC(F)F]
1848
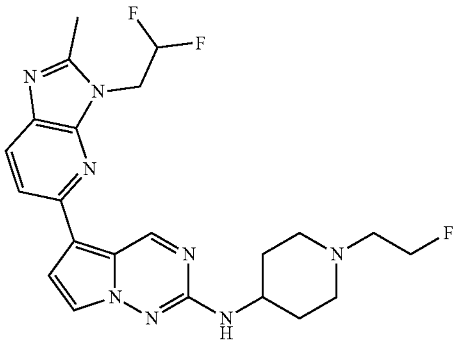 [SMILES: Cc1nc2ccc(-c3ccn4nc(NC5CCN(CCF)CC5)ncc34)nc2n1CC(F)F]
1849

TABLE 1-continued
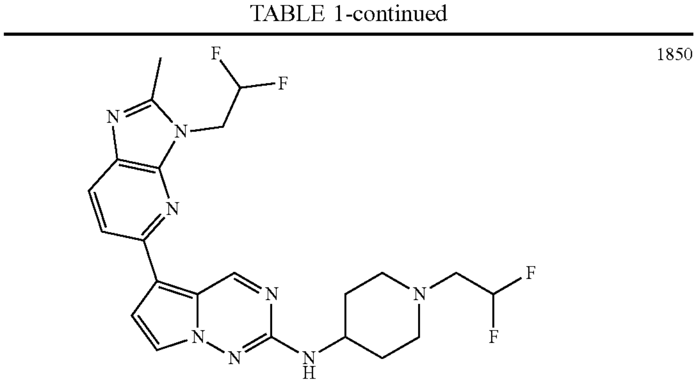
1850
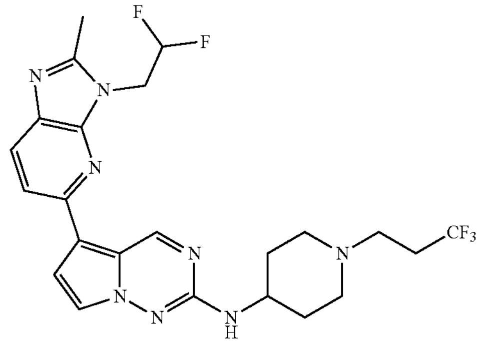 [SMILES: Cc1nc2ccc(-c3ccn4nc(NC5CCN(CCC(F)(F)F)CC5)ncc34)nc2n1CC(F)F]
1851
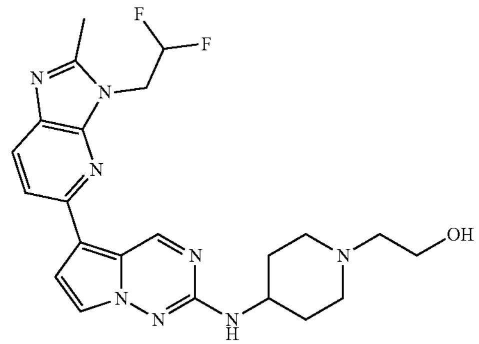 [SMILES: Cc1nc2ccc(-c3ccn4nc(NC5CCN(CCO)CC5)ncc34)nc2n1CC(F)F]
1852
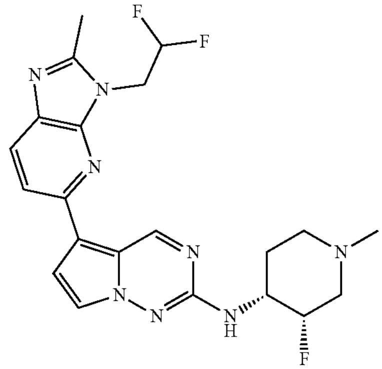 [SMILES: Cc1nc2ccc(-c3ccn4nc(N[C@@H]5CCN(C)C[C@@H]5F)ncc34)nc2n1CC(F)F]
1853

TABLE 1-continued
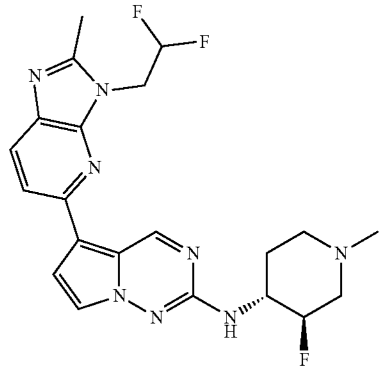 [SMILES: Cc1nc2ccc(-c3ccn4nc(N[C@@H]5CCN(C)C[C@H]5F)ncc34)nc2n1CC(F)F]
1854
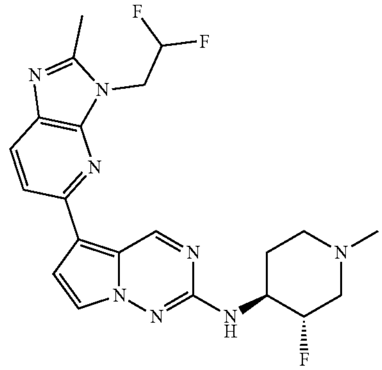 [SMILES: Cc1nc2ccc(-c3ccn4nc(N[C@H]5CCN(C)C[C@@H]5F)ncc34)nc2n1CC(F)F]
1855
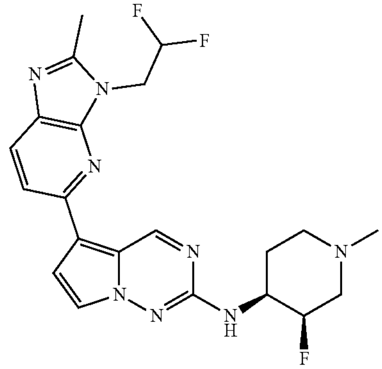 [SMILES: Cc1nc2ccc(-c3ccn4nc(N[C@H]5CCN(C)C[C@H]5F)ncc34)nc2n1CC(F)F]
1856
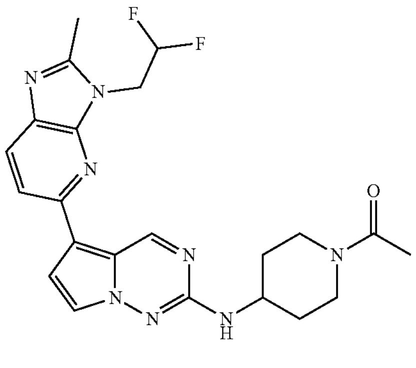 [SMILES: CC(=O)N1CCC(Nc2ncc3c(-c4ccc5nc(C)n(CC(F)F)c5n4)ccn3n2)CC1]
1857

TABLE 1-continued
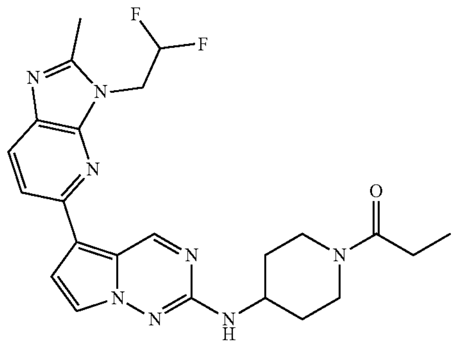 [SMILES: CCC(=O)N1CCC(Nc2ncc3c(-c4ccc5nc(C)n(CC(F)F)c5n4)ccn3n2)CC1]
1858
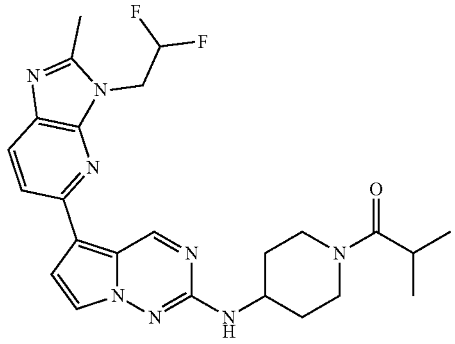 [SMILES: Cc1nc2ccc(-c3ccn4nc(NC5CCN(C(=O)C(C)C)CC5)ncc34)nc2n1CC(F)F]
1859
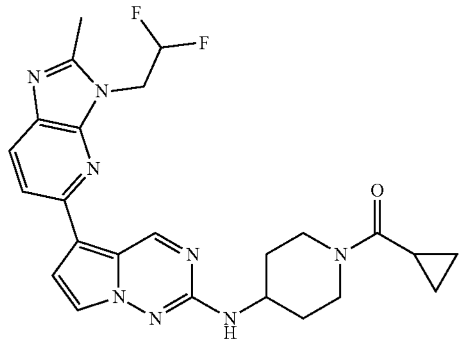 [SMILES: Cc1nc2ccc(-c3ccn4nc(NC5CCN(C(=O)C6CC6)CC5)ncc34)nc2n1CC(F)F]
1860
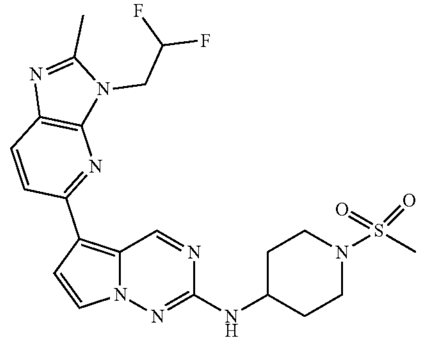 [SMILES: Cc1nc2ccc(-c3ccn4nc(NC5CCN(S(C)(=O)=O)CC5)ncc34)nc2n1CC(F)F]
1861

TABLE 1-continued
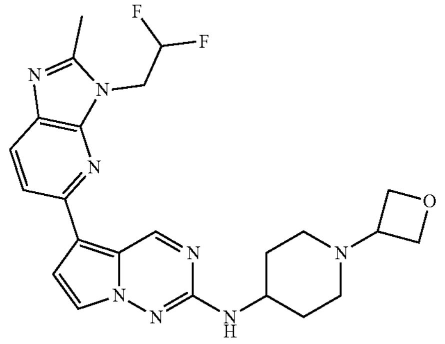 [SMILES: Cc1nc2ccc(-c3ccn4nc(NC5CCN(C6COC6)CC5)ncc34)nc2n1CC(F)F]
1862
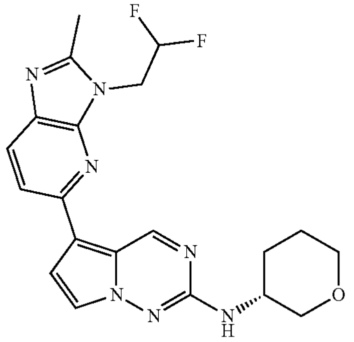 [SMILES: Cc1nc2ccc(-c3ccn4nc(N[C@@H]5CCCOC5)ncc34)nc2n1CC(F)F]
1863
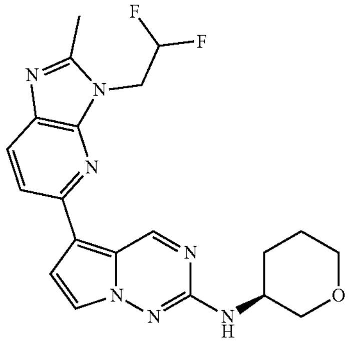 [SMILES: Cc1nc2ccc(-c3ccn4nc(N[C@H]5CCCOC5)ncc34)nc2n1CC(F)F]
1864
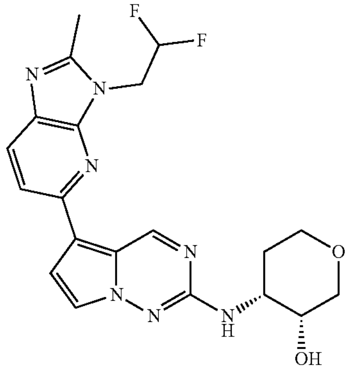 [SMILES: Cc1nc2ccc(-c3ccn4nc(N[C@@H]5CCOC[C@@H]5O)ncc34)nc2n1CC(F)F]
1865

TABLE 1-continued
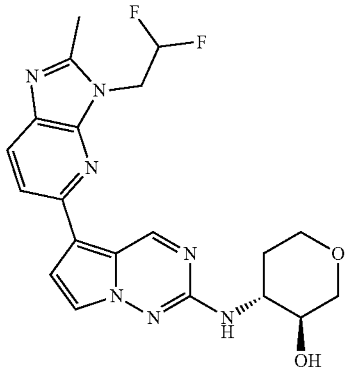 [SMILES: Cc1nc2ccc(-c3ccn4nc(N[C@@H]5CCOC[C@H]5O)ncc34)nc2n1CC(F)F]
1866
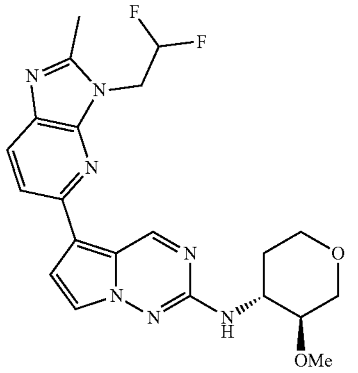 [SMILES: CO[C@@H]1COCC[C@H]1Nc1ncc2c(-c3ccc4nc(C)n(CC(F)F)c4n3)ccn2n1]
1867
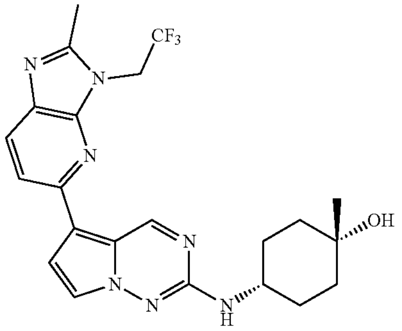 [SMILES: Cc1nc2ccc(-c3ccn4nc(N[C@H]5CC[C@@](C)(O)CC5)ncc34)nc2n1CC(F)(F)F]
1868
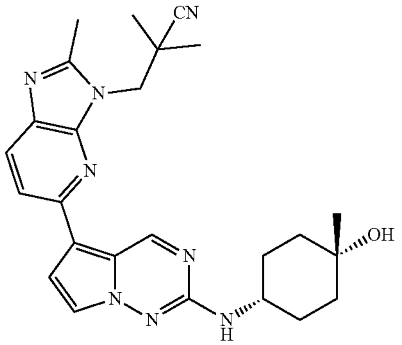 [SMILES: Cc1nc2ccc(-c3ccn4nc(N[C@H]5CC[C@@](C)(O)CC5)ncc34)nc2n1CC(C)(C)C#N]
1869

TABLE 1-continued
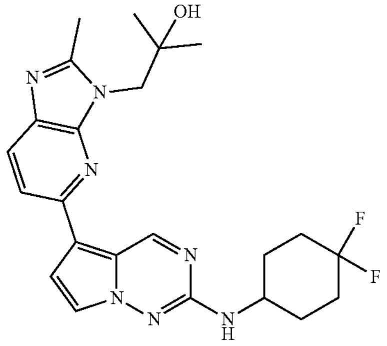 [SMILES: Cc1nc2ccc(-c3ccn4nc(NC5CCC(F)(F)CC5)ncc34)nc2n1CC(C)(C)O]
1870
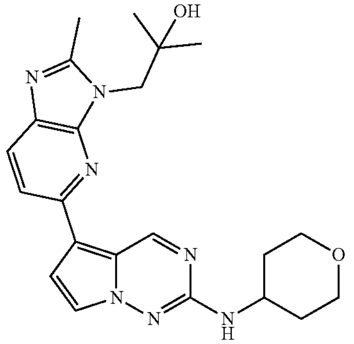 [SMILES: Cc1nc2ccc(-c3ccn4nc(NC5CCOCC5)ncc34)nc2n1CC(C)(C)O]
1871
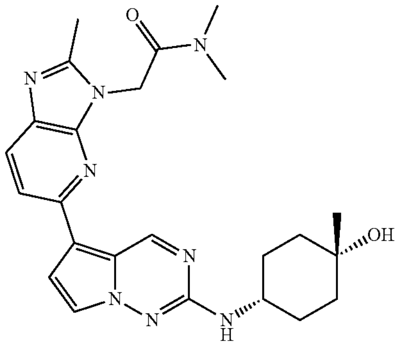 [SMILES: Cc1nc2ccc(-c3ccn4nc(N[C@H]5CC[C@@](C)(O)CC5)ncc34)nc2n1CC(=O)N(C)C]
1872
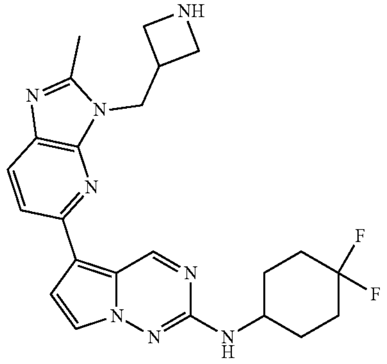 [SMILES: Cc1nc2ccc(-c3ccn4nc(NC5CCC(F)(F)CC5)ncc34)nc2n1CC1CNC1]
1873

TABLE 1-continued
1874
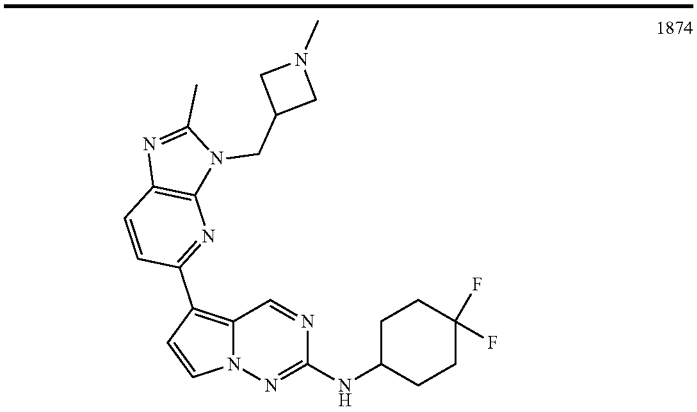
1875
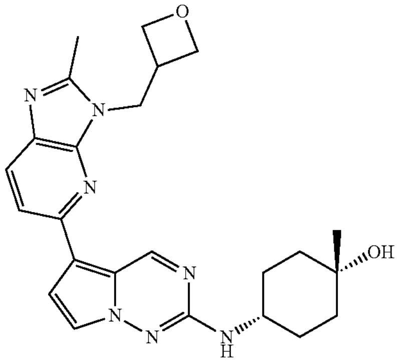 [SMILES: Cc1nc2ccc(-c3ccn4nc(N[C@H]5CC[C@@](C)(O)CC5)ncc34)nc2n1CC1COC1]
1876
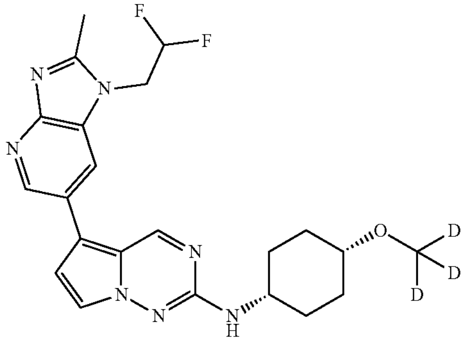 [SMILES: [2H]C([2H])([2H])O[C@H]1CC[C@@H](Nc2ncc3c(-c4cnc5nc(C)n(CC(F)F)c5c4)ccn3n2)CC1]
1877
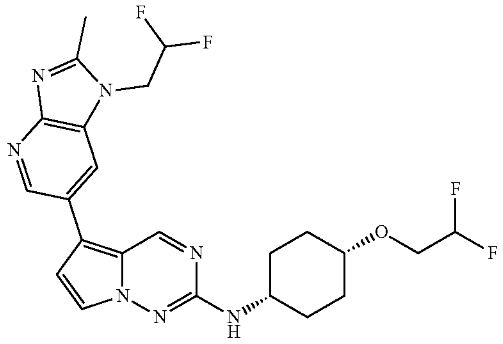 [SMILES: Cc1nc2ncc(-c3ccn4nc(N[C@H]5CC[C@@H](OCC(F)F)CC5)ncc34)cc2n1CC(F)F]

TABLE 1-continued
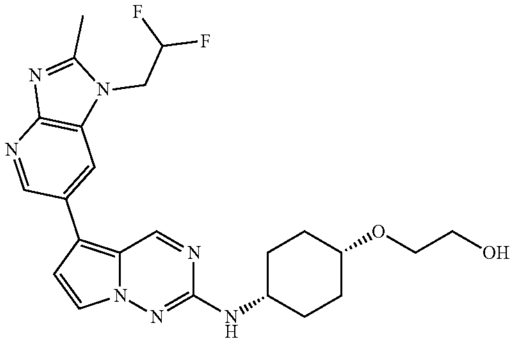 [SMILES: Cc1nc2ncc(-c3ccn4nc(N[C@H]5CC[C@@H](OCCO)CC5)ncc34)cc2n1CC(F)F]
1878
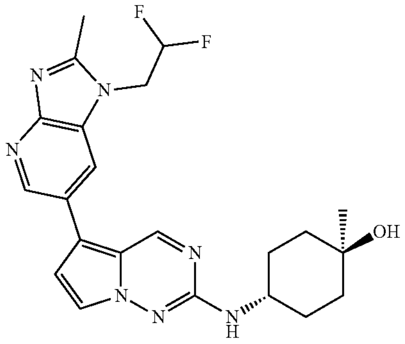 [SMILES: Cc1nc2ncc(-c3ccn4nc(N[C@H]5CC[C@](C)(O)CC5)ncc34)cc2n1CC(F)F]
1879
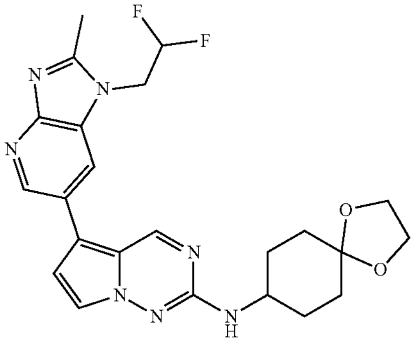 [SMILES: Cc1nc2ncc(-c3ccn4nc(NC5CCC6(CC5)OCCO6)ncc34)cc2n1CC(F)F]
1880
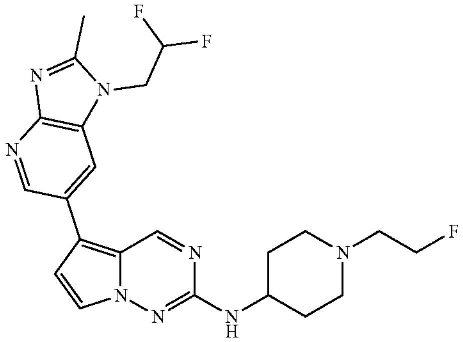 [SMILES: Cc1nc2ncc(-c3ccn4nc(NC5CCN(CCF)CC5)ncc34)cc2n1CC(F)F]
1881

TABLE 1-continued
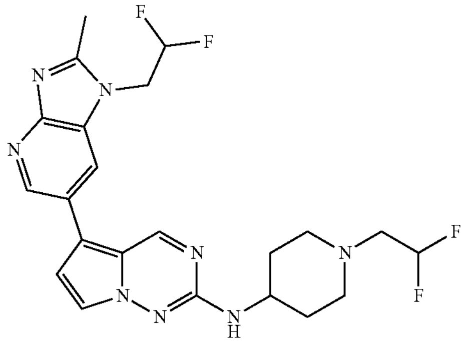 [SMILES: Cc1nc2ncc(-c3ccn4nc(NC5CCN(CC(F)F)CC5)ncc34)cc2n1CC(F)F]
1882
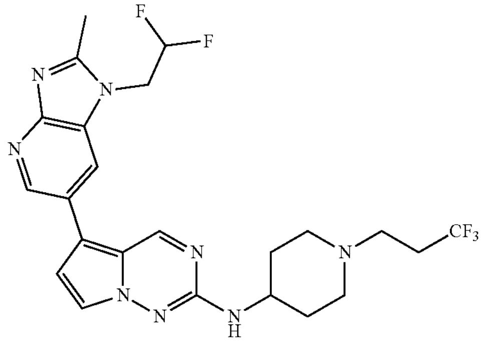 [SMILES: Cc1nc2ncc(-c3ccn4nc(NC5CCN(CCC(F)(F)F)CC5)ncc34)cc2n1CC(F)F]
1883
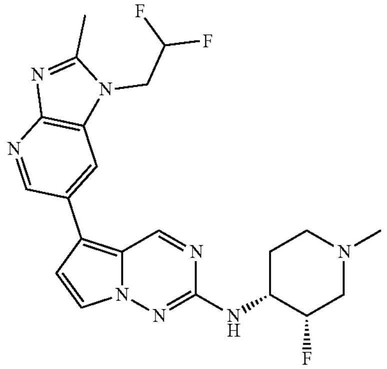 [SMILES: Cc1nc2ncc(-c3ccn4nc(N[C@@H]5CCN(C)C[C@@H]5F)ncc34)cc2n1CC(F)F]
1884
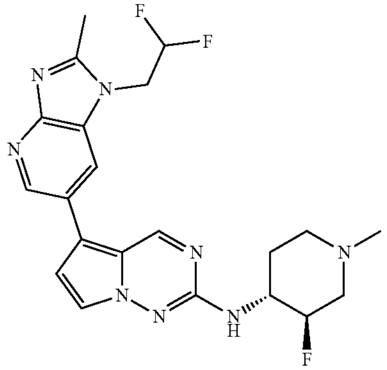 [SMILES: Cc1nc2ncc(-c3ccn4nc(N[C@@H]5CCN(C)C[C@H]5F)ncc34)cc2n1CC(F)F]
1885

TABLE 1-continued
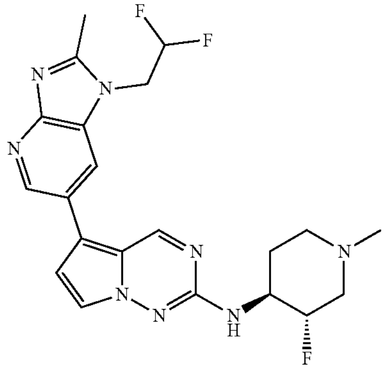 [SMILES: Cc1nc2ncc(-c3ccn4nc(N[C@H]5CCN(C)C[C@@H]5F)ncc34)cc2n1CC(F)F]
1886
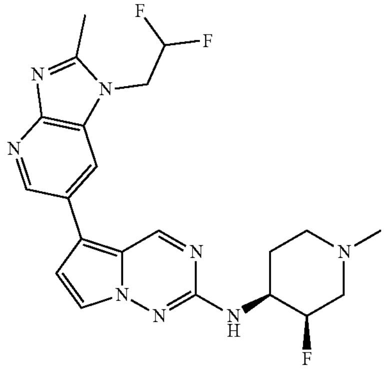 [SMILES: Cc1nc2ncc(-c3ccn4nc(N[C@H]5CCN(C)C[C@H]5F)ncc34)cc2n1CC(F)F]
1887
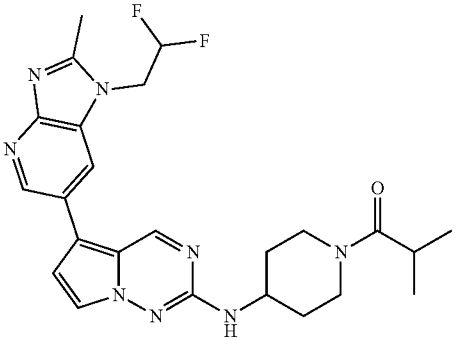 [SMILES: Cc1nc2ncc(-c3ccn4nc(NC5CCN(C(=O)C(C)C)CC5)ncc34)cc2n1CC(F)F]
1888
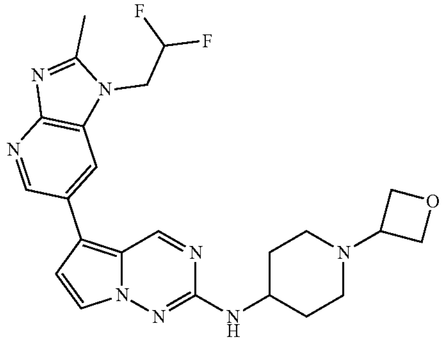 [SMILES: Cc1nc2ncc(-c3ccn4nc(NC5CCN(C6COC6)CC5)ncc34)cc2n1CC(F)F]
1889

TABLE 1-continued
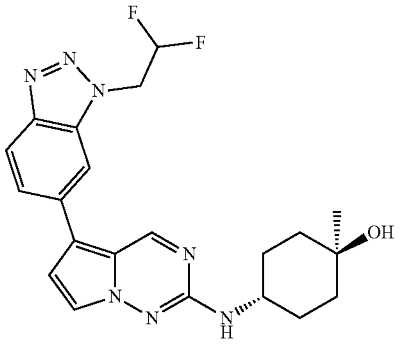 [SMILES: C[C@]1(O)CC[C@H](Nc2ncc3c(-c4ccc5nnn(CC(F)F)c5c4)ccn3n2)CC1]
1890
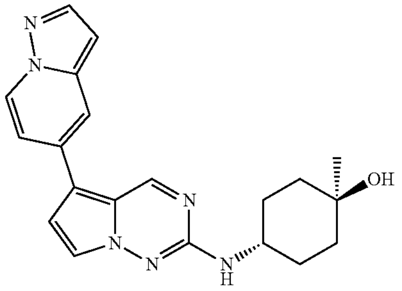 [SMILES: C[C@]1(O)CC[C@H](Nc2ncc3c(-c4ccn5nccc5c4)ccn3n2)CC1]
1891
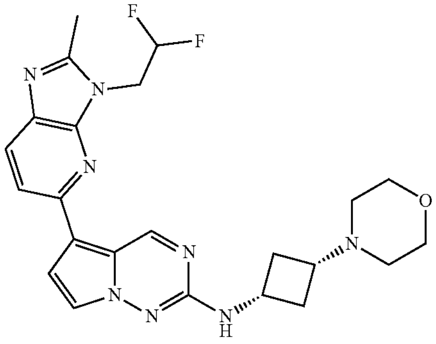 [SMILES: Cc1nc2ccc(-c3ccn4nc(N[C@H]5C[C@@H](N6CCOCC6)C5)ncc34)nc2n1CC(F)F]
1892
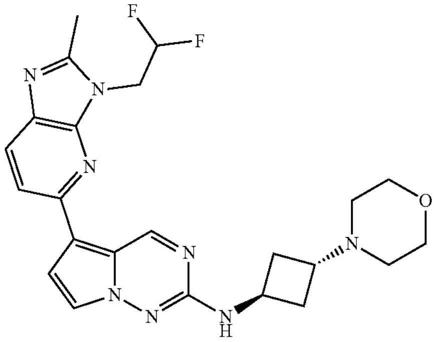 [SMILES: Cc1nc2ccc(-c3ccn4nc(N[C@H]5C[C@H](N6CCOCC6)C5)ncc34)nc2n1CC(F)F]
1893

TABLE 1-continued
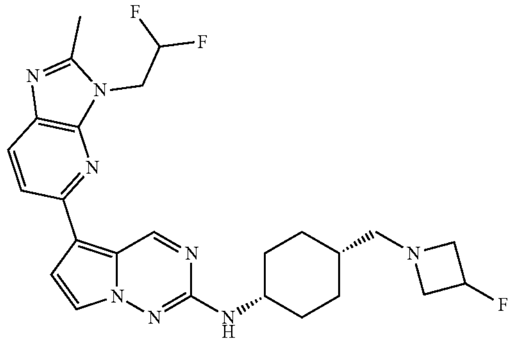 [SMILES: Cc1nc2ccc(-c3ccn4nc(N[C@H]5CC[C@@H](CN6CC(F)C6)CC5)ncc34)nc2n1CC(F)F]
1894
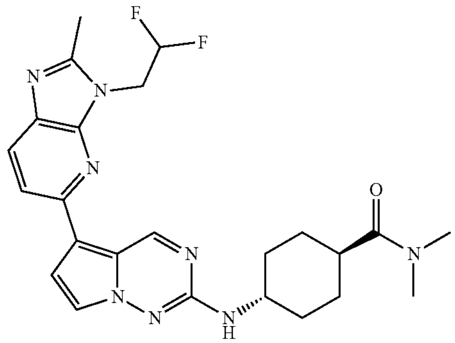 [SMILES: Cc1nc2ccc(-c3ccn4nc(N[C@H]5CC[C@H](C(=O)N(C)C)CC5)ncc34)nc2n1CC(F)F]
1895
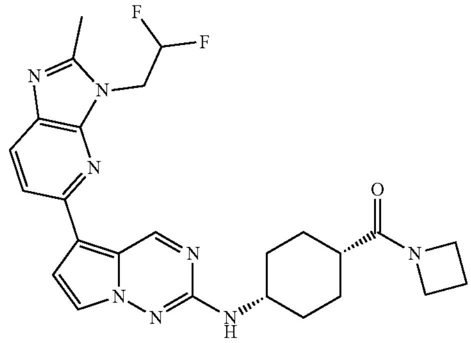 [SMILES: Cc1nc2ccc(-c3ccn4nc(N[C@H]5CC[C@@H](C(=O)N6CCC6)CC5)ncc34)nc2n1CC(F)F]
1896
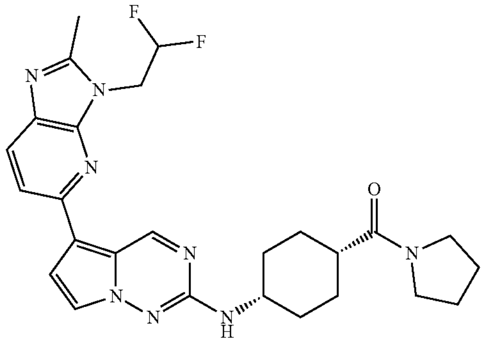 [SMILES: Cc1nc2ccc(-c3ccn4nc(N[C@H]5CC[C@@H](C(=O)N6CCCC6)CC5)ncc34)nc2n1CC(F)F]
1897

TABLE 1-continued
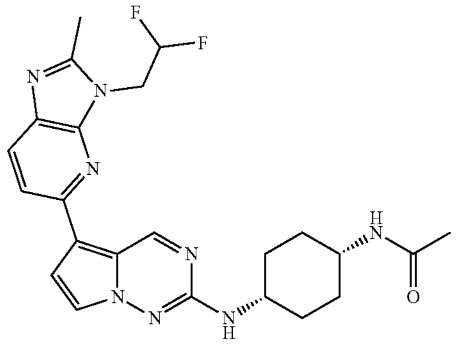 [SMILES: CC(=O)N[C@H]1CC[C@@H](Nc2ncc3c(-c4ccc5nc(C)n(CC(F)F)c5n4)ccn3n2)CC1]
1898
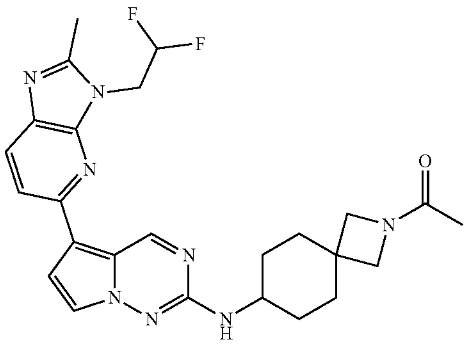 [SMILES: CC(=O)N1CC2(CCC(Nc3ncc4c(-c5ccc6nc(C)n(CC(F)F)c6n5)ccn4n3)CC2)C1]
1899
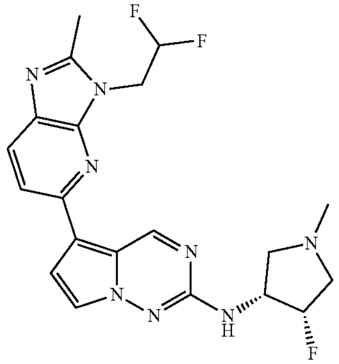 [SMILES: Cc1nc2ccc(-c3ccn4nc(N[C@@H]5CN(C)C[C@@H]5F)ncc34)nc2n1CC(F)F]
1900
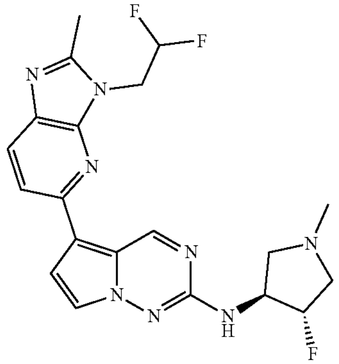 [SMILES: Cc1nc2ccc(-c3ccn4nc(N[C@H]5CN(C)C[C@@H]5F)ncc34)nc2n1CC(F)F]
1901

TABLE 1-continued
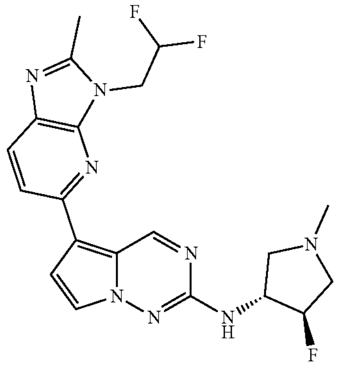 [SMILES: Cc1nc2ccc(-c3ccn4nc(N[C@@H]5CN(C)C[C@H]5F)ncc34)nc2n1CC(F)F]
1902
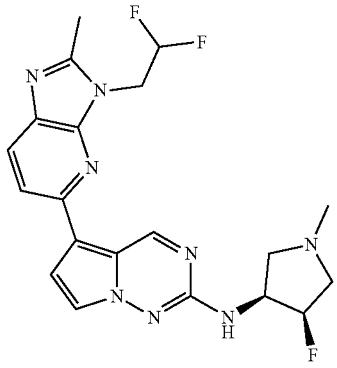 [SMILES: Cc1nc2ccc(-c3ccn4nc(N[C@H]5CN(C)C[C@H]5F)ncc34)nc2n1CC(F)F]
1903
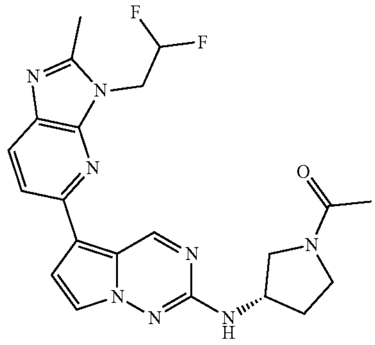 [SMILES: CC(=O)N1CC[C@H](Nc2ncc3c(-c4ccc5nc(C)n(CC(F)F)c5n4)ccn3n2)C1]
1904
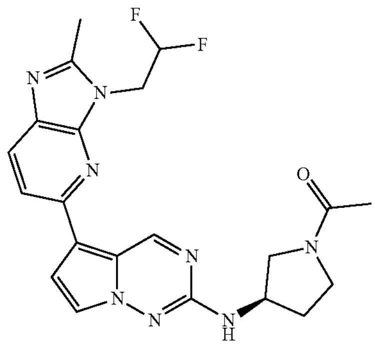 [SMILES: CC(=O)N1CC[C@@H](Nc2ncc3c(-c4ccc5nc(C)n(CC(F)F)c5n4)ccn3n2)C1]
1905

TABLE 1-continued
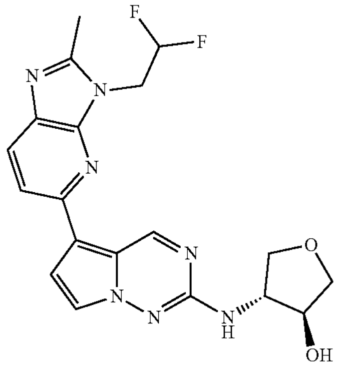 [SMILES: Cc1nc2ccc(-c3ccn4nc(N[C@@H]5COC[C@H]5O)ncc34)nc2n1CC(F)F]
1906
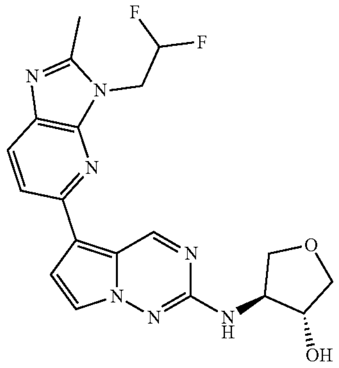 [SMILES: Cc1nc2ccc(-c3ccn4nc(N[C@H]5COC[C@@H]5O)ncc34)nc2n1CC(F)F]
1907
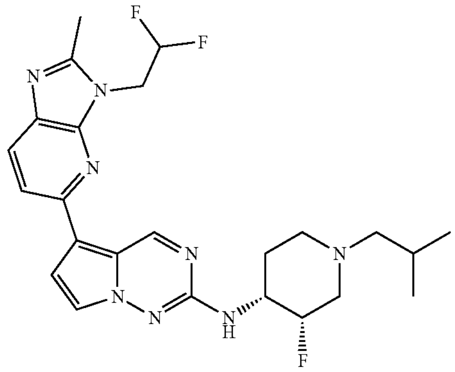 [SMILES: Cc1nc2ccc(-c3ccn4nc(N[C@@H]5CCN(CC(C)C)C[C@@H]5F)ncc34)nc2n1CC(F)F]
1908
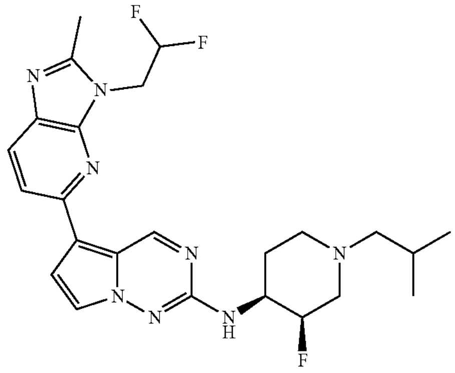 [SMILES: Cc1nc2ccc(-c3ccn4nc(N[C@H]5CCN(CC(C)C)C[C@H]5F)ncc34)nc2n1CC(F)F]
1909

TABLE 1-continued
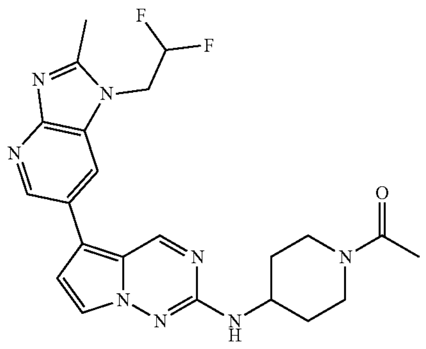 [SMILES: CC(=O)N1CCC(Nc2ncc3c(-c4cnc5nc(C)n(CC(F)F)c5c4)ccn3n2)CC1]
1910
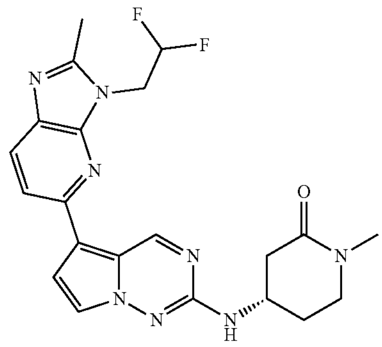 [SMILES: Cc1nc2ccc(-c3ccn4nc(N[C@H]5CCN(C)C(=O)C5)ncc34)nc2n1CC(F)F]
1911
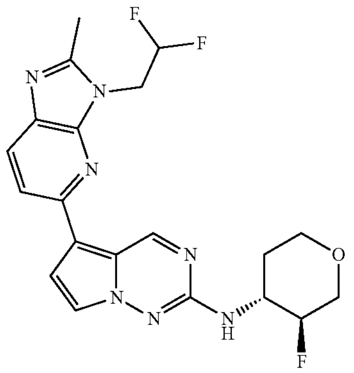 [SMILES: Cc1nc2ccc(-c3ccn4nc(N[C@@H]5CCOC[C@H]5F)ncc34)nc2n1CC(F)F]
1912
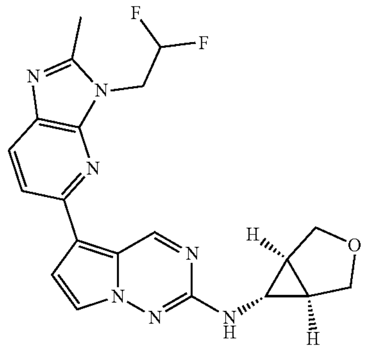 [SMILES: Cc1nc2ccc(-c3ccn4nc(N[C@H]5[C@@H]6COC[C@@H]65)ncc34)nc2n1CC(F)F]
1913

TABLE 1-continued
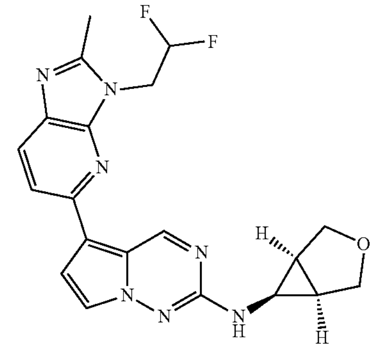 [SMILES: Cc1nc2ccc(-c3ccn4nc(N[C@@H]5[C@@H]6COC[C@@H]65)ncc34)nc2n1CC(F)F]
1914
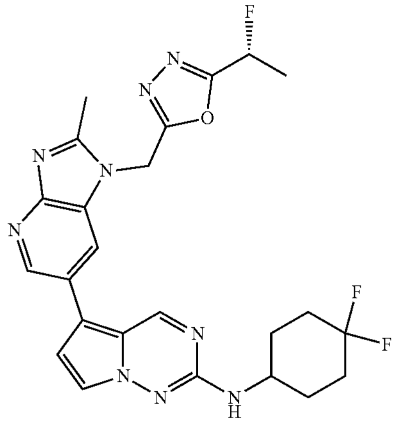 [SMILES: Cc1nc2ncc(-c3ccn4nc(NC5CCC(F)(F)CC5)ncc34)cc2n1Cc1nnc([C@@H](C)F)o1]
1915
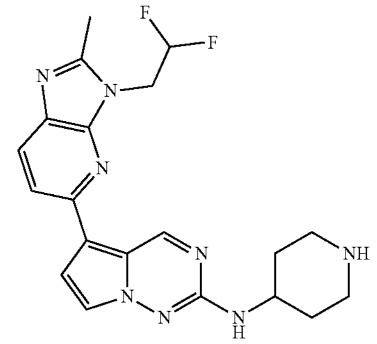 [SMILES: Cc1nc2ccc(-c3ccn4nc(NC5CCNCC5)ncc34)nc2n1CC(F)F]
1916
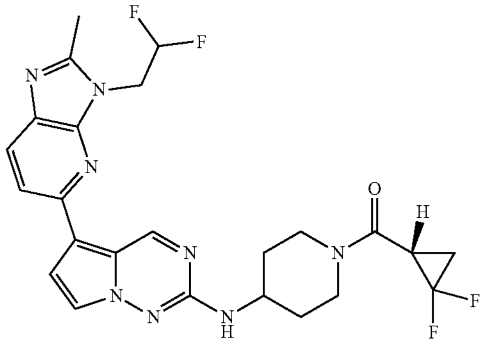 [SMILES: Cc1nc2ccc(-c3ccn4nc(NC5CCN(C(=O)[C@@H]6CC6(F)F)CC5)ncc34)nc2n1CC(F)F]
1917

TABLE 1-continued
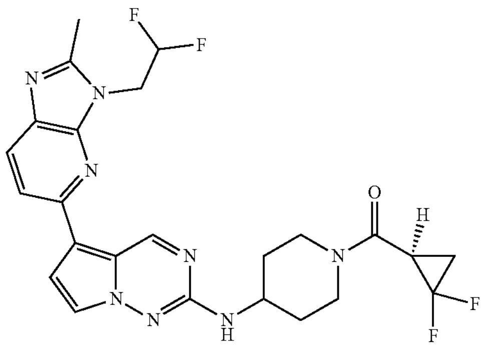 [SMILES: Cc1nc2ccc(-c3ccn4nc(NC5CCN(C(=O)[C@H]6CC6(F)F)CC5)ncc34)nc2n1CC(F)F]
1918
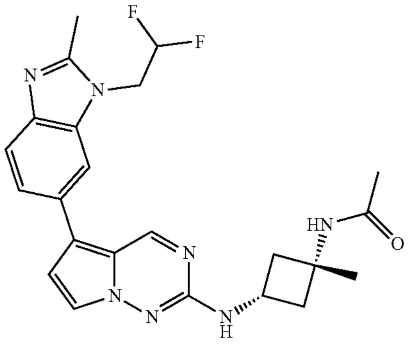 [SMILES: CC(=O)N[C@]1(C)C[C@H](Nc2ncc3c(-c4ccc5nc(C)n(CC(F)F)c5c4)ccn3n2)C1]
1919
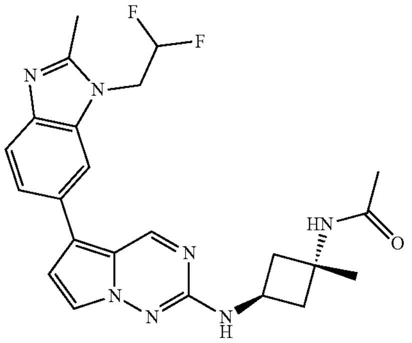 [SMILES: CC(=O)N[C@]1(C)C[C@@H](Nc2ncc3c(-c4ccc5nc(C)n(CC(F)F)c5c4)ccn3n2)C1]
1920
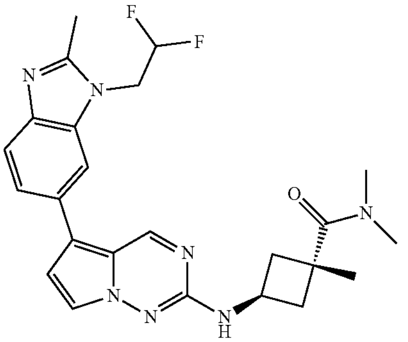 [SMILES: Cc1nc2ccc(-c3ccn4nc(N[C@H]5C[C@](C)(C(=O)N(C)C)C5)ncc34)cc2n1CC(F)F]
1921

TABLE 1-continued
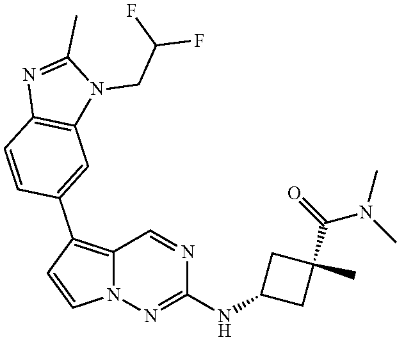 [SMILES: Cc1nc2ccc(-c3ccn4nc(N[C@H]5C[C@@](C)(C(=O)N(C)C)C5)ncc34)cc2n1CC(F)F]
1922
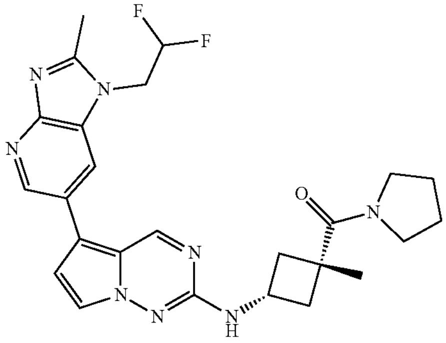 [SMILES: Cc1nc2ncc(-c3ccn4nc(N[C@H]5C[C@@](C)(C(=O)N6CCCC6)C5)ncc34)cc2n1CC(F)F]
1923
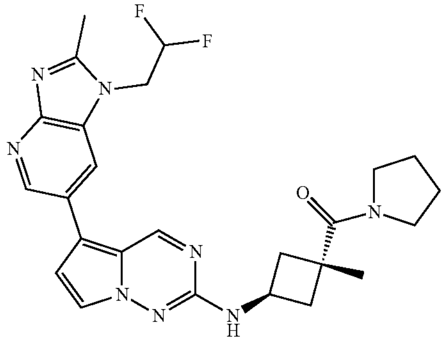 [SMILES: Cc1nc2ncc(-c3ccn4nc(N[C@H]5C[C@](C)(C(=O)N6CCCC6)C5)ncc34)cc2n1CC(F)F]
1924
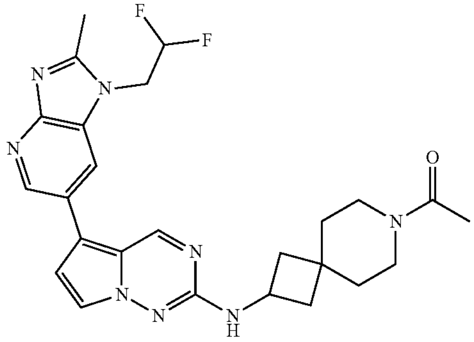 [SMILES: CC(=O)N1CCC2(CC1)CC(Nc1ncc3c(-c4cnc5nc(C)n(CC(F)F)c5c4)ccn3n1)C2]
1925

TABLE 1-continued
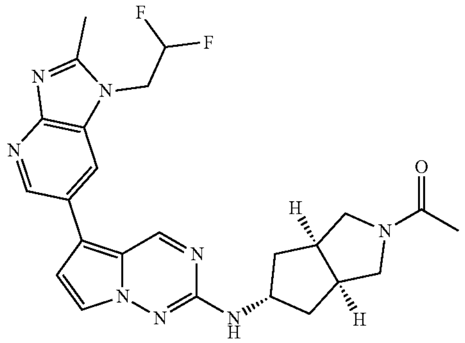 [SMILES: CC(=O)N1C[C@H]2C[C@H](Nc3ncc4c(-c5cnc6nc(C)n(CC(F)F)c6c5)ccn4n3)C[C@H]2C1]
1926
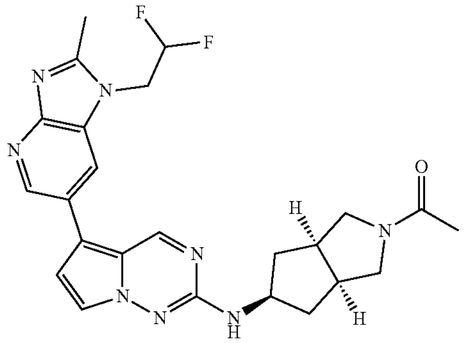 [SMILES: CC(=O)N1C[C@H]2C[C@@H](Nc3ncc4c(-c5cnc6nc(C)n(CC(F)F)c6c5)ccn4n3)C[C@H]2C1]
1927
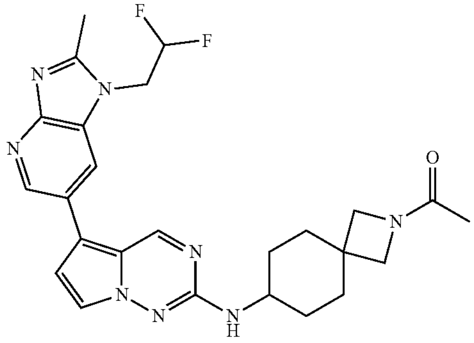
1928
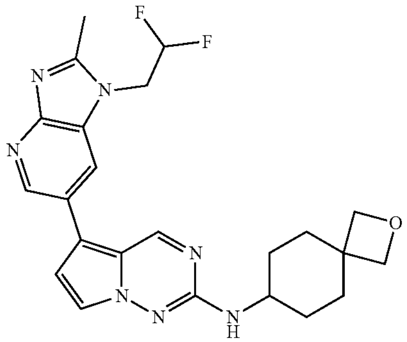 [SMILES: Cc1nc2ncc(-c3ccn4nc(NC5CCC6(CC5)COC6)ncc34)cc2n1CC(F)F]
1929

TABLE 1-continued
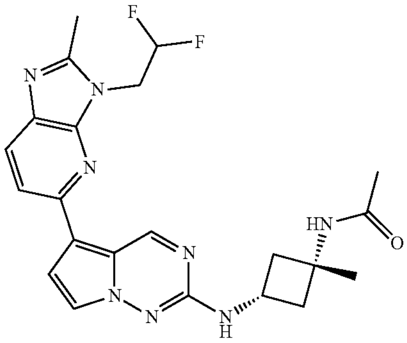 [SMILES: CC(=O)N[C@]1(C)C[C@H](Nc2ncc3c(-c4ccc5nc(C)n(CC(F)F)c5n4)ccn3n2)C1]
1930
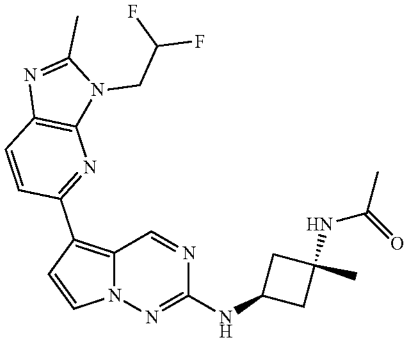
1931
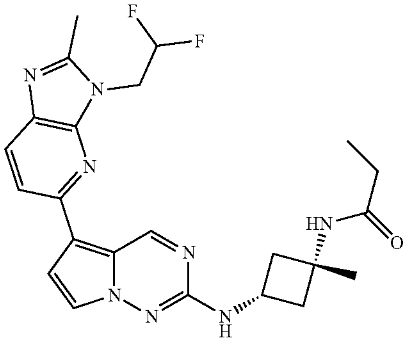 [SMILES: CCC(=O)N[C@]1(C)C[C@H](Nc2ncc3c(-c4ccc5nc(C)n(CC(F)F)c5n4)ccn3n2)C1]
1932
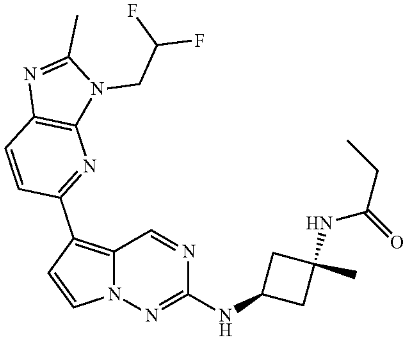 [SMILES: CCC(=O)N[C@]1(C)C[C@@H](Nc2ncc3c(-c4ccc5nc(C)n(CC(F)F)c5n4)ccn3n2)C1]
1933

TABLE 1-continued
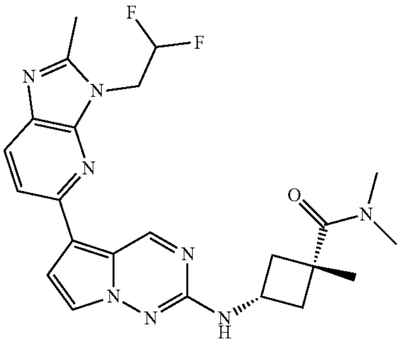 [SMILES: Cc1nc2ccc(-c3ccn4nc(N[C@H]5C[C@@](C)(C(=O)N(C)C)C5)ncc34)nc2n1CC(F)F]
1934
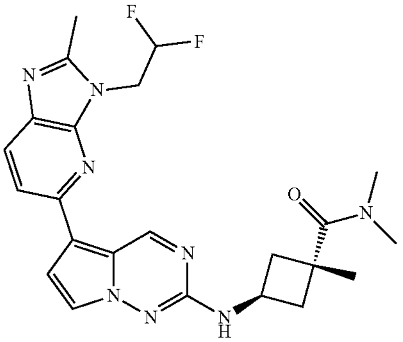 [SMILES: Cc1nc2ccc(-c3ccn4nc(N[C@H]5C[C@](C)(C(=O)N(C)C)C5)ncc34)nc2n1CC(F)F]
1935
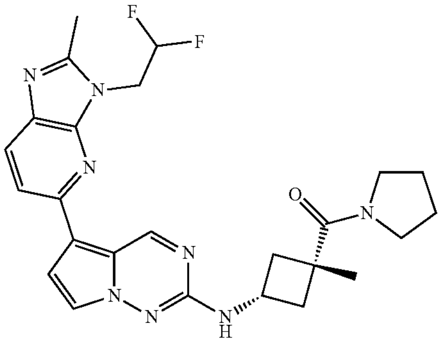 [SMILES: Cc1nc2ccc(-c3ccn4nc(N[C@H]5C[C@@](C)(C(=O)N6CCCC6)C5)ncc34)nc2n1CC(F)F]
1936
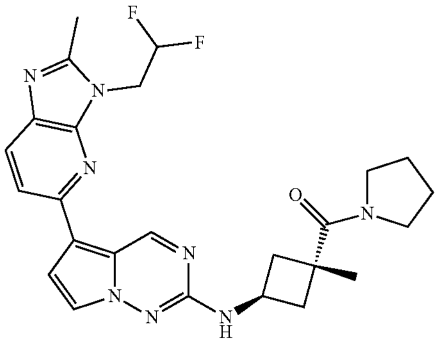 [SMILES: Cc1nc2ccc(-c3ccn4nc(N[C@H]5C[C@](C)(C(=O)N6CCCC6)C5)ncc34)nc2n1CC(F)F]
1937

TABLE 1-continued
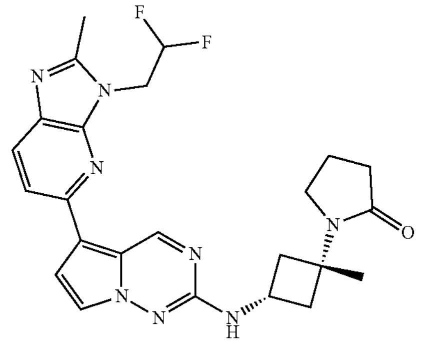 [SMILES: Cc1nc2ccc(-c3ccn4nc(N[C@H]5C[C@@](C)(N6CCCC6=O)C5)ncc34)nc2n1CC(F)F]
1938
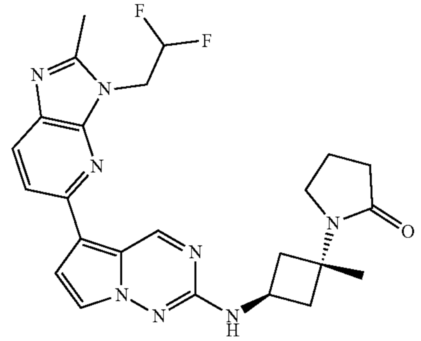 [SMILES: Cc1nc2ccc(-c3ccn4nc(N[C@H]5C[C@](C)(N6CCCC6=O)C5)ncc34)nc2n1CC(F)F]
1939
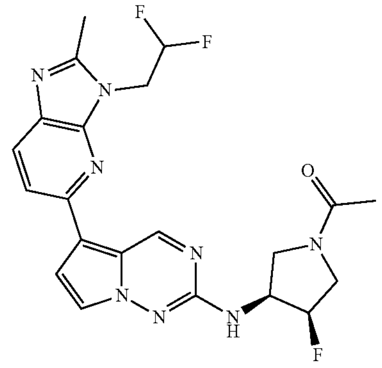 [SMILES: CC(=O)N1C[C@@H](F)[C@@H](Nc2ncc3c(-c4ccc5nc(C)n(CC(F)F)c5n4)ccn3n2)C1]
1940
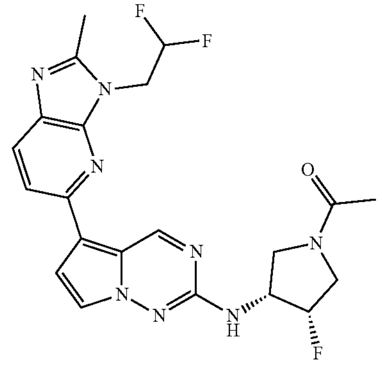 [SMILES: CC(=O)N1C[C@H](F)[C@H](Nc2ncc3c(-c4ccc5nc(C)n(CC(F)F)c5n4)ccn3n2)C1]
1941

TABLE 1-continued
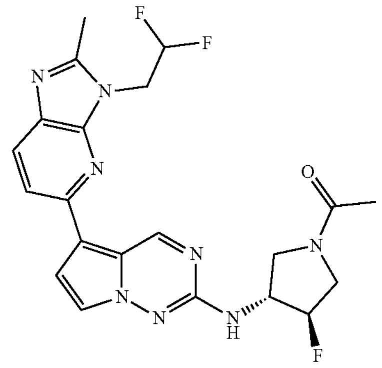 [SMILES: CC(=O)N1C[C@@H](F)[C@H](Nc2ncc3c(-c4ccc5nc(C)n(CC(F)F)c5n4)ccn3n2)C1]
1942
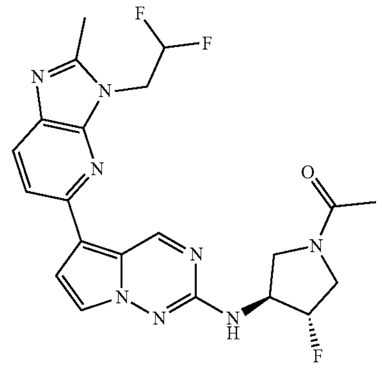 [SMILES: CC(=O)N1C[C@H](Nc2ncc3c(-c4ccc5nc(C)n(CC(F)F)c5n4)ccn3n2)[C@@H](F)C1]
1943
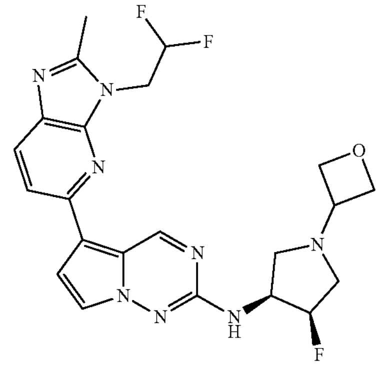 [SMILES: Cc1nc2ccc(-c3ccn4nc(N[C@H]5CN(C6COC6)C[C@H]5F)ncc34)nc2n1CC(F)F]
1944
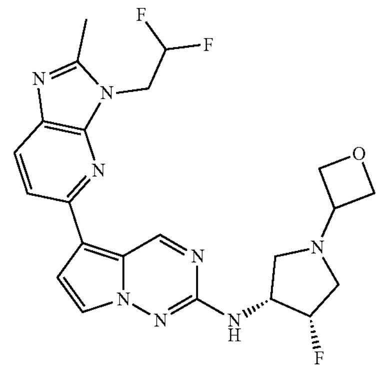 [SMILES: Cc1nc2ccc(-c3ccn4nc(N[C@@H]5CN(C6COC6)C[C@@H]5F)ncc34)nc2n1CC(F)F]
1945

TABLE 1-continued
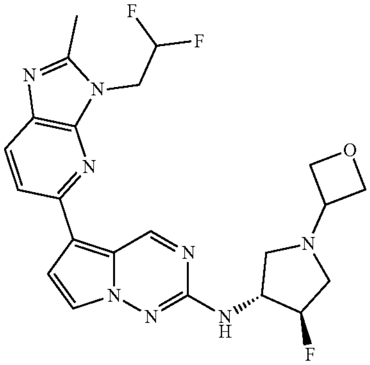 [SMILES: Cc1nc2ccc(-c3ccn4nc(N[C@@H]5CN(C6COC6)C[C@H]5F)ncc34)nc2n1CC(F)F]
1946
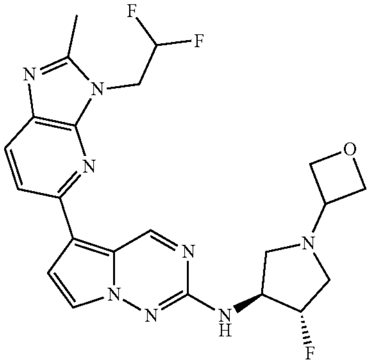 [SMILES: Cc1nc2ccc(-c3ccn4nc(N[C@H]5CN(C6COC6)C[C@@H]5F)ncc34)nc2n1CC(F)F]
1947
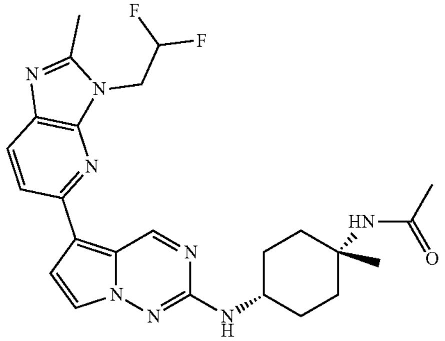 [SMILES: CC(=O)N[C@]1(C)CC[C@H](Nc2ncc3c(-c4ccc5nc(C)n(CC(F)F)c5n4)ccn3n2)CC1]
1948
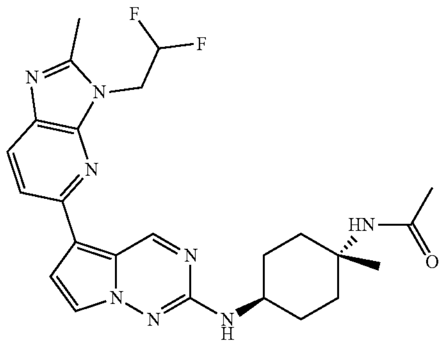 [SMILES: CC(=O)N[C@]1(C)CC[C@@H](Nc2ncc3c(-c4ccc5nc(C)n(CC(F)F)c5n4)ccn3n2)CC1]
1949

TABLE 1-continued
1950
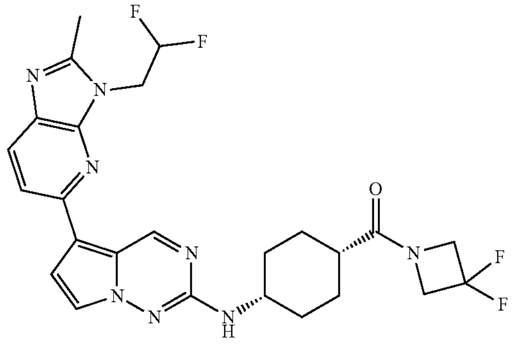 [SMILES: Cc1nc2ccc(-c3ccn4nc(N[C@H]5CC[C@@H](C(=O)N6CC(F)(F)C6)CC5)ncc34)nc2n1CC(F)F]
1951
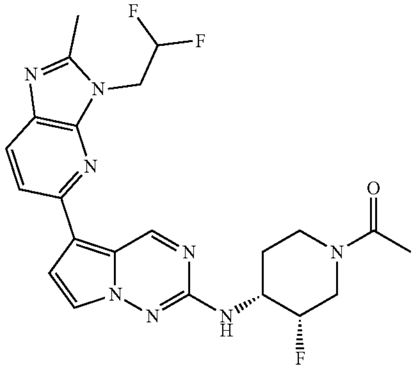 [SMILES: CC(=O)N1CC[C@@H](Nc2ncc3c(-c4ccc5nc(C)n(CC(F)F)c5n4)ccn3n2)[C@@H](F)C1]
1952
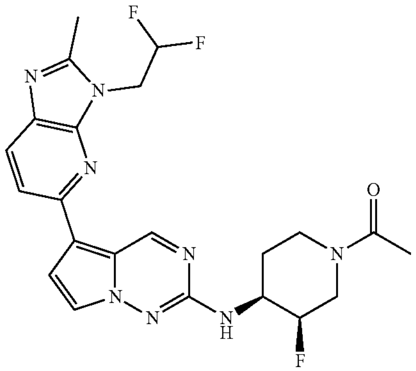 [SMILES: CC(=O)N1CC[C@H](Nc2ncc3c(-c4ccc5nc(C)n(CC(F)F)c5n4)ccn3n2)[C@H](F)C1]
1953
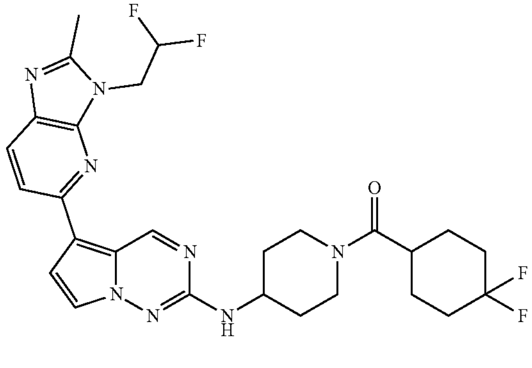 [SMILES: Cc1nc2ccc(-c3ccn4nc(NC5CCN(C(=O)C6CCC(F)(F)CC6)CC5)ncc34)nc2n1CC(F)F]

TABLE 1-continued
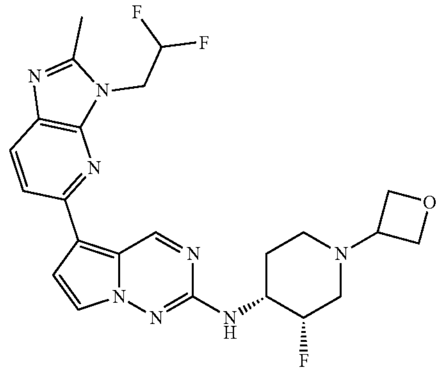 [SMILES: Cc1nc2ccc(-c3ccn4nc(N[C@@H]5CCN(C6COC6)C[C@@H]5F)ncc34)nc2n1CC(F)F]
1954
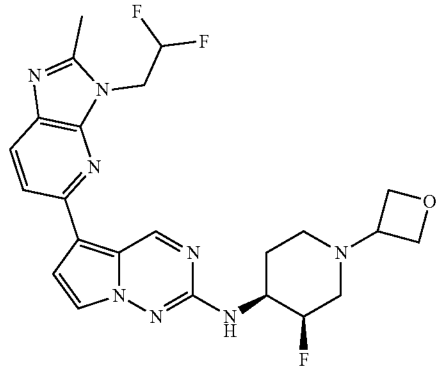 [SMILES: Cc1nc2ccc(-c3ccn4nc(N[C@H]5CCN(C6COC6)C[C@H]5F)ncc34)nc2n1CC(F)F]
1955
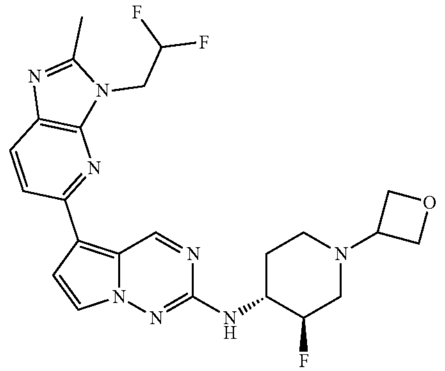 [SMILES: Cc1nc2ccc(-c3ccn4nc(N[C@@H]5CCN(C6COC6)C[C@H]5F)ncc34)nc2n1CC(F)F]
1956
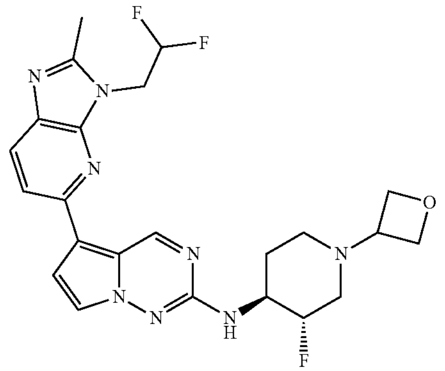 [SMILES: Cc1nc2ccc(-c3ccn4nc(N[C@H]5CCN(C6COC6)C[C@@H]5F)ncc34)nc2n1CC(F)F]
1957

TABLE 1-continued
1958
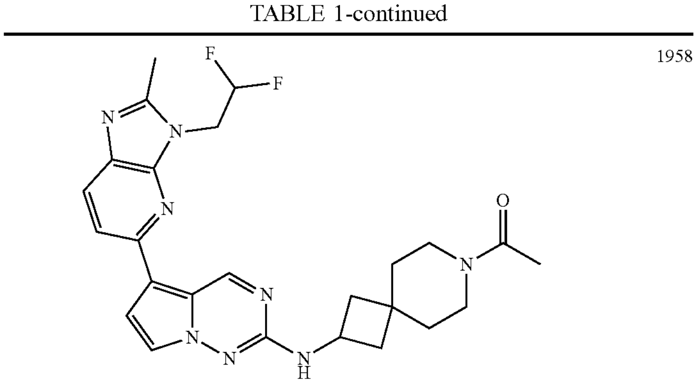
1959
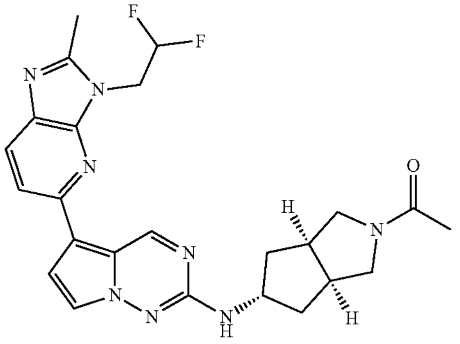 [SMILES: CC(=O)N1C[C@H]2C[C@H](Nc3ncc4c(-c5ccc6nc(C)n(CC(F)F)c6n5)ccn4n3)C[C@H]2C1]
1960
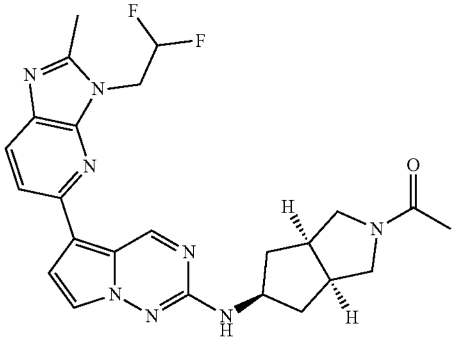 [SMILES: CC(=O)N1C[C@H]2C[C@@H](Nc3ncc4c(-c5ccc6nc(C)n(CC(F)F)c6n5)ccn4n3)C[C@H]2C1]
1961
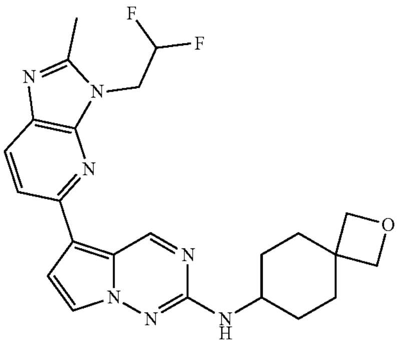 [SMILES: Cc1nc2ccc(-c3ccn4nc(NC5CCC6(CC5)COC6)ncc34)nc2n1CC(F)F]

TABLE 1-continued
1962
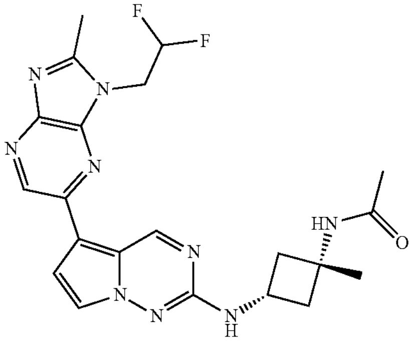 [SMILES: CC(=O)N[C@]1(C)C[C@H](Nc2ncc3c(-c4cnc5nc(C)n(CC(F)F)c5n4)ccn3n2)C1]
1963
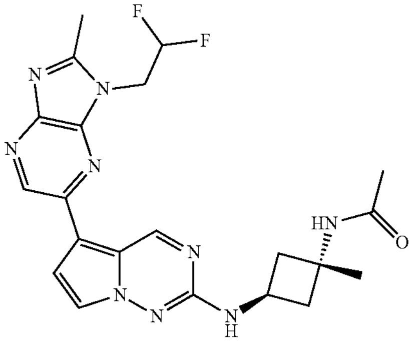 [SMILES: CC(=O)N[C@]1(C)C[C@@H](Nc2ncc3c(-c4cnc5nc(C)n(CC(F)F)c5n4)ccn3n2)C1]
1964
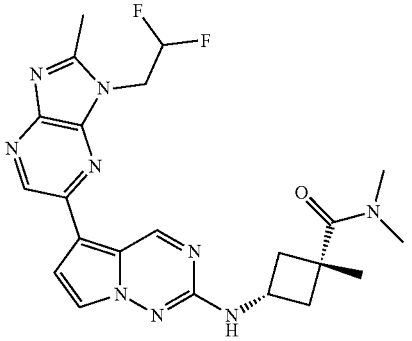 [SMILES: Cc1nc2ncc(-c3ccn4nc(N[C@H]5C[C@@](C)(C(=O)N(C)C)C5)ncc34)nc2n1CC(F)F]
1965
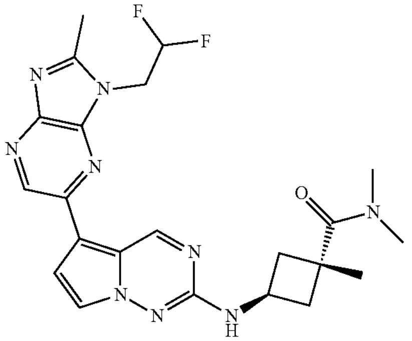 [SMILES: Cc1nc2ncc(-c3ccn4nc(N[C@H]5C[C@](C)(C(=O)N(C)C)C5)ncc34)nc2n1CC(F)F]

TABLE 1-continued
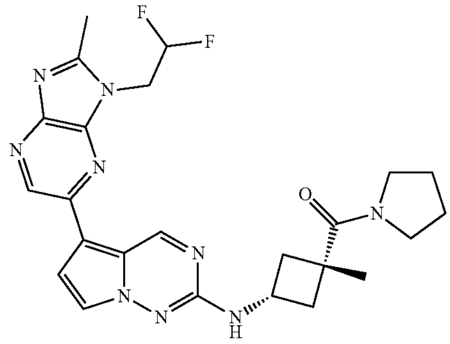 [SMILES: Cc1nc2ncc(-c3ccn4nc(N[C@H]5C[C@@](C)(C(=O)N6CCCC6)C5)ncc34)nc2n1CC(F)F]
1966
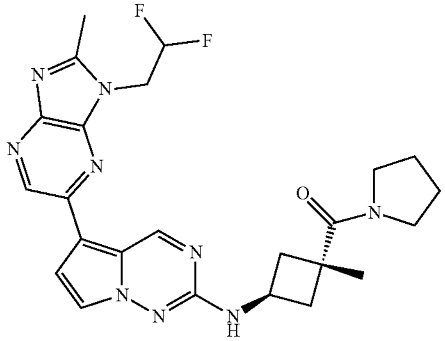
1967
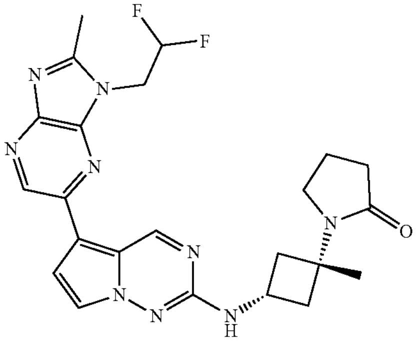 [SMILES: Cc1nc2ncc(-c3ccn4nc(N[C@H]5C[C@@](C)(N6CCCC6=O)C5)ncc34)nc2n1CC(F)F]
1968
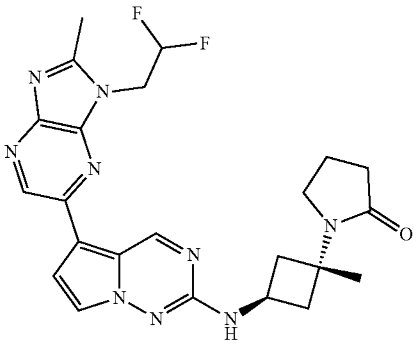 [SMILES: Cc1nc2ncc(-c3ccn4nc(N[C@H]5C[C@](C)(N6CCCC6=O)C5)ncc34)nc2n1CC(F)F]
1969

TABLE 1-continued
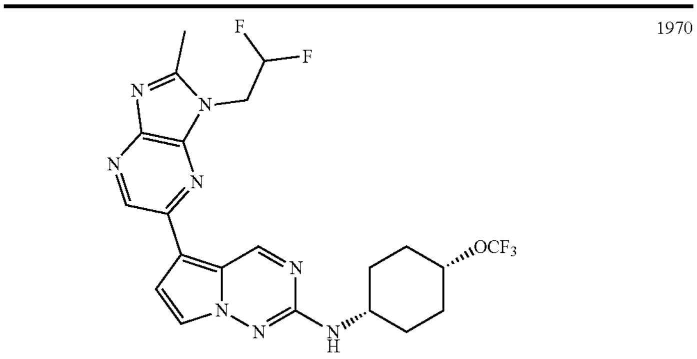
1970
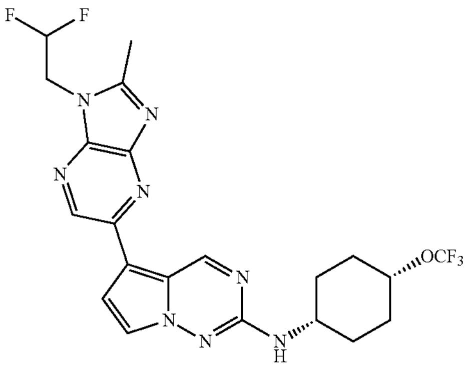 [SMILES: Cc1nc2nc(-c3ccn4nc(N[C@H]5CC[C@@H](OC(F)(F)F)CC5)ncc34)cnc2n1CC(F)F]
1971
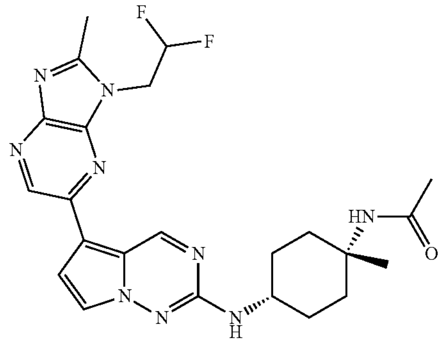 [SMILES: CC(=O)N[C@]1(C)CC[C@H](Nc2ncc3c(-c4cnc5nc(C)n(CC(F)F)c5n4)ccn3n2)CC1]
1972
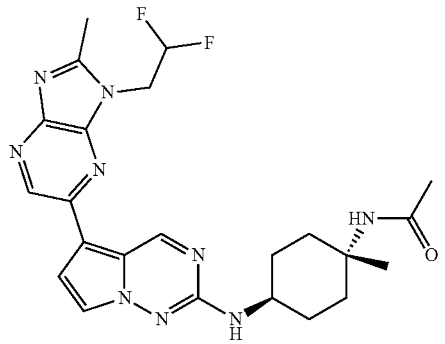 [SMILES: CC(=O)N[C@]1(C)CC[C@@H](Nc2ncc3c(-c4cnc5nc(C)n(CC(F)F)c5n4)ccn3n2)CC1]
1973

TABLE 1-continued
1974
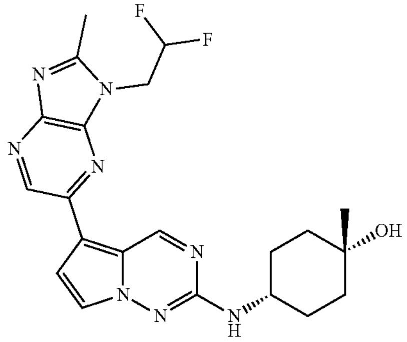 [SMILES: Cc1nc2ncc(-c3ccn4nc(N[C@H]5CC[C@@](C)(O)CC5)ncc34)nc2n1CC(F)F]
1975
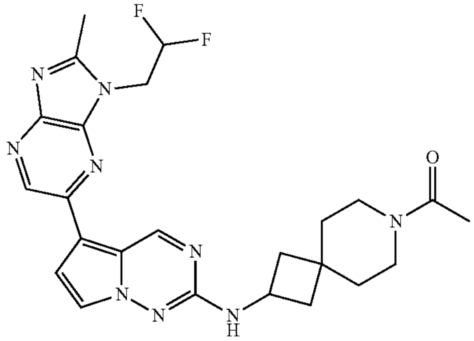 [SMILES: CC(=O)N1CCC2(CC1)CC(Nc1ncc3c(-c4cnc5nc(C)n(CC(F)F)c5n4)ccn3n1)C2]
1976
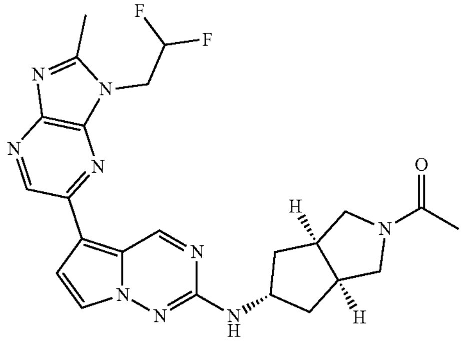 [SMILES: CC(=O)N1C[C@H]2C[C@H](Nc3ncc4c(-c5cnc6nc(C)n(CC(F)F)c6n5)ccn4n3)C[C@H]2C1]
1977
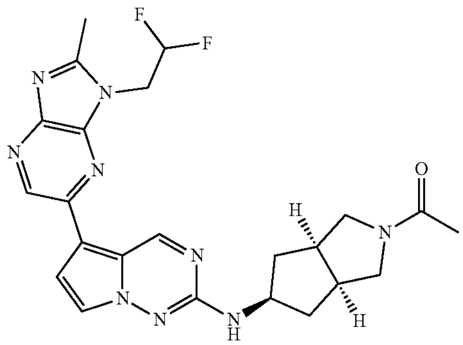

TABLE 1-continued
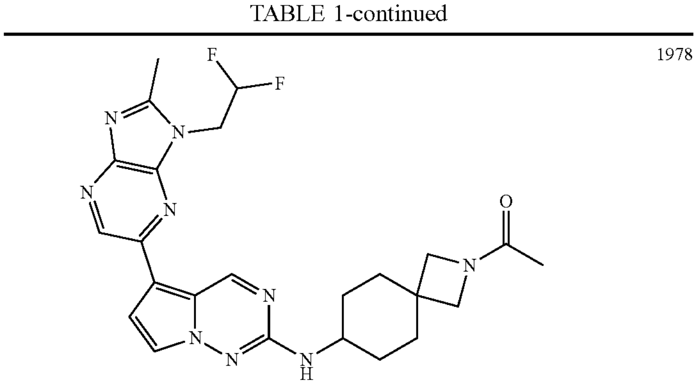
1978
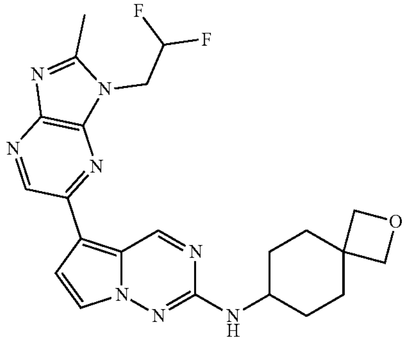
1979
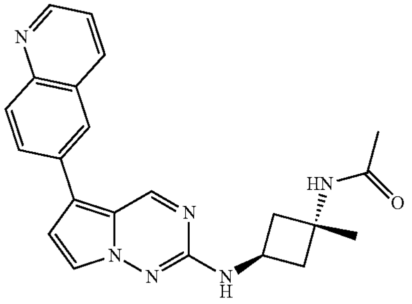 [SMILES: CC(=O)N[C@]1(C)C[C@@H](Nc2ncc3c(-c4ccc5ncccc5c4)ccn3n2)C1]
1980
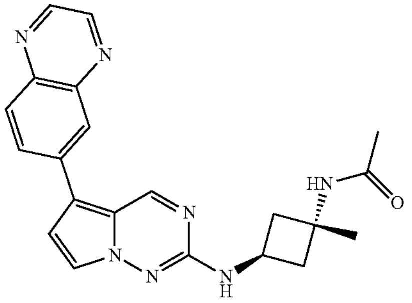 [SMILES: CC(=O)N[C@]1(C)C[C@@H](Nc2ncc3c(-c4ccc5nccnc5c4)ccn3n2)C1]
1981
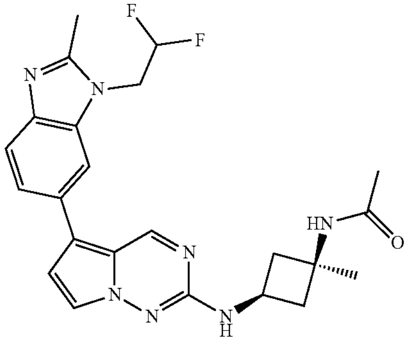 [SMILES: CC(=O)N[C@]1(C)C[C@H](Nc2ncc3c(-c4ccc5nc(C)n(CC(F)F)c5c4)ccn3n2)C1]
1982

TABLE 1-continued

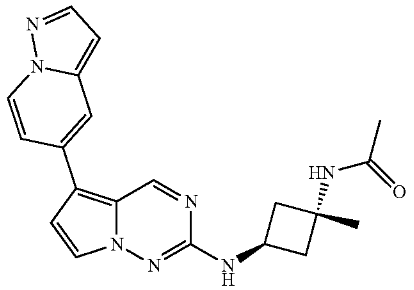 [SMILES: CC(=O)N[C@]1(C)C[C@@H](Nc2ncc3c(-c4ccn5nccc5c4)ccn3n2)C1]

1983

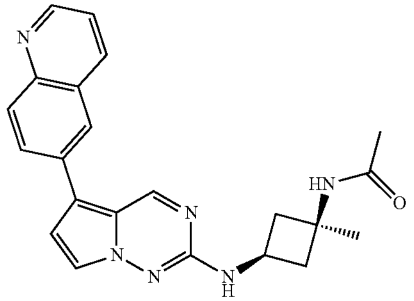 [SMILES: CC(=O)N[C@]1(C)C[C@H](Nc2ncc3c(-c4ccc5ncccc5c4)ccn3n2)C1]

1984

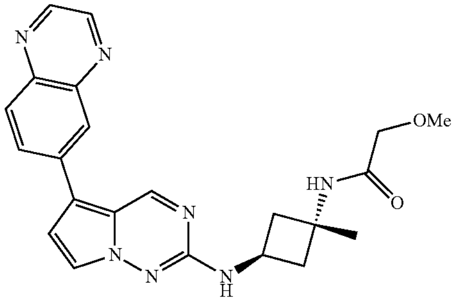 [SMILES: COCC(=O)N[C@]1(C)C[C@@H](Nc2ncc3c(-c4ccc5nccnc5c4)ccn3n2)C1]

1985

Administration and Pharmaceutical Compositions

Some embodiments include pharmaceutical compositions comprising: (a) a therapeutically effective amount of a compound provided herein, or its corresponding enantiomer, diastereoisomer or tautomer, or pharmaceutically acceptable salt; and (b) a pharmaceutically acceptable carrier.

The compounds provided herein may also be useful in combination (administered together or sequentially) with other known agents.

Non-limiting examples of diseases which can be treated with a combination of a compound of Formula (I) and another active agent are colorectal cancer, ovarian cancer, hepatocellular carcinoma, head and neck squamous cell carcinoma, acute lymphoblastic leukemia (ALL), pancreatic cancer, brain tumors, acute megakaryoblastic leukemia (AMKL), and osteoarthritis. For example, a compound of Formula (I) can be combined with one or more chemotherapeutic compounds.

In some embodiments, hepatocellular carcinoma can be treated with a combination of a compound of Formula (I) and one or more of the following drugs/therapies: sorafenib (Nexavar®); regorafenib (Stivarga®, Regonix®), nivolumab (Opdivo®); lenvatinib (Lenvima®); Pembrolizumab (Keytruda®); cabozantinib (Cometriq®, Cabometyx®); 5-fluorouracil (5-FU®); ramucirumab (Cyramza®); combination of gemcitabine and oxaliplatin (GEMOX). Other therapies that can be performed in combination with a compound of Formula (I) are i) transcatheter arterial chemoembolization (TACE) in combination with doxorubicin (DOXIL®), cisplatin, or mitomycin C (Mitosol®, Mutamycin®, Jelmyto®); ii) low-dose brachytherapy.

In some embodiments, head and neck squamous cell carcinoma can be treated with a combination of a compound of Formula (I) and one or more of the following drugs/therapies: TransOral Robotic Surgery (TORS); TORS with radiation therapy; larotrectinib (Vitrakvi®); EGFR inhibitors, e.g., erlotinib (Tarceva®), osimertinib (Tagrisso®), neratinib (Nerlynx®), gefitinib (Iressa®), cetuximab (Erbitux®), panitumumab (Vectibix®), dacomitinib (Vizimpro®), lapatinib (Tykerb®), necitumumab (Portrazza), and vandetanib (Caprelsa®).

In some embodiments, acute lymphoblastic leukemia (ALL) can be treated with a combination of a compound of Formula (I) and one or more of the following drugs/therapies: remission induction therapy; consolidation therapy; nelarabine (Arranon®); Asparaginase *Erwinia Chrysanthemi* (Erwinaze®); Asparaginase *Erwinia Chrysanthemi* (Recombinant)-rywn (Rylaze®); calaspargase Pegol-mknl (Asparlas®); inotuzumab ozogamicin (Besponsa®); blinatumomab (Blincyto®); daunorubicin hydrochloride (Cerubidine®); clofarabine (Clolar®); cyclophosphamide; methotrexate sodium (Trexall®); cytarabine (Cytosar-U®); dasatinib (Sprycel®); dexamethasone; imatinib mesylate (Gleevec®); ponatinib hydrochloride (Iclusig®); mercaptopurine (Purinethol®, Purixan®); tisagenlecleucel (Kymriah®); vincristine sulfate liposome (Marqibo®); pegaspargase (Oncaspar®); prednisone; daunorubicin hydrochloride (Rubidomycin®); and vincristine sulfate.

In some embodiments, pancreatic cancer can be treated with a combination of a compound of Formula (I) and one or more of the following drugs/therapies: ablation and embolization treatment; gemcitabine (Gemzar®); 5-fluorouracil (5-FU®); oxaliplatin (Eloxatin®); albumin-bound paclitaxel (Abraxane®); capecitabine (Xeloda®); cisplatin; irinotecan (Camptosar®); liposomal Irinotecan (Onivyde®); paclitaxel (Taxol®), and docetaxel (Taxotere®).

In some embodiments, brain tumors can be treated with a combination of a compound of Formula (I) and one or more of the following drugs/therapies: carmustine can be administered by way of a gliadel wafer; for glioblastoma and high-grade glioma, radiation therapy with daily low-dose temozolomide (Temodar®) followed by monthly doses of temozolomide after radiation therapy for 6 months to 1 year; lomustine (Gleostine®), procarbazine (Matulane®), and vincristine (Vincasar®), have been used along with radiation therapy; anti-angiogenesis therapy with bevacizumab (Avastin®, Mvasi®); and targeted therapy using larotrectinib (Vitrakvi®).

In some embodiments, acute megakaryoblastic leukemia (AMKL) can be treated with a combination of a compound of Formula (I) and one or more of the following drugs/therapies: cytarabine (Cytosar-U®), etoposide (Vepesid®), and anthracycline drugs. Anthracyclines include daunorubicin (Cerubidine®), idarubicin (Idamycin®), and mitoxantrone (Novantrone®).

In some embodiments, acute myeloid leukemia (AML) can be treated with a combination of a compound of Formula (I) and one or more of the following drugs/therapies: venetoclax and hypomethylating agents (e.g., decitabine, azacitidine), induction chemotherapy (cytarabine and an anthracycline (e.g., daunorubicin or idarubicin), all-trans-retinoic acid (ATRA) and either arsenic trioxide (ATO) monotherapy or an anthracycline), consolidation therapy (cytarabine).

In some embodiments, myelodysplastic syndrome (MDS) can be treated with a combination of a compound of Formula (I) and one or more of the following drugs/therapies: 5-azacytidine, decitabine, lenalidomide, and decitabine/cedazuridine (Ingovi®).

In some embodiments, colorectal cancer can be treated with a combination of a compound of Formula (I) and one or more of the following drugs: 5-Fluorouracil (5-FU), which can be administered with the vitamin-like drug leucovorin (also called folinic acid); capecitabine (XELODA®), irinotecan (CAMPOSTAR®), oxaliplatin (ELOXATIN®). Examples of combinations of these drugs which could be further combined with a compound of Formula (I) are FOLFOX (5-FU, leucovorin, and oxaliplatin), FOLFIRI (5-FU, leucovorin, and irinotecan), FOLFOXIRI (leucovorin, 5-FU, oxaliplatin, and irinotecan) and CapeOx (Capecitabine and oxaliplatin). For rectal cancer, chemo with 5-FU or capecitabine combined with radiation may be given before surgery (neoadjuvant treatment).

In some embodiments, ovarian cancer can be treated with a combination of a compound of Formula (I) and one or more of the following drugs: Topotecan, Liposomal doxorubicin (DOXIL®), Gemcitabine (GEMZAR®), Cyclophosphamide (CYTOXAN®), Vinorelbine (NAVELBINE®), Ifosfamide (IFEX®), Etoposide (VP-16), Altretamine (HEXALEN®), Capecitabine (XELODA®), Irinotecan (CPT-11, CAMPTOSAR®), Melphalan, Pemetrexed (ALIMTA®) and Albumin bound paclitaxel (nab-paclitaxel, ABRAXANE®). Examples of combinations of these drugs which could be further combined with a compound of Formula (I) are TIP (paclitaxel [Taxol], ifosfamide, and cisplatin), VeIP (vinblastine, ifosfamide, and cisplatin) and VIP (etoposide [VP-16], ifosfamide, and cisplatin). Ovarian cancer can also be treated with a combination of a compound of Formula (I) and immune checkpoint blockade (ICB) therapy.

In some embodiments, a compound of Formula (I) can be used to treat cancer in combination with any of the following methods: (a) Hormone therapy such as aromatase inhibitors, LHRH [luteinizing hormone-releasing hormone] analogs and inhibitors, and others; (b) Ablation or embolization procedures such as radiofrequency ablation (RFA), ethanol (alcohol) ablation, microwave thermotherapy and cryosurgery (cryotherapy); (c) Chemotherapy using alkylating agents such as cisplatin and carboplatin, oxaliplatin, mechlorethamine, cyclophosphamide, chlorambucil and ifosfamide; (d) Chemotherapy using anti-metabolites such as azathioprine and mercaptopurine; (e) Chemotherapy using plant alkaloids and terpenoids such as *vinca* alkaloids (i.e. Vincristine, Vinblastine, Vinorelbine and Vindesine) and taxanes; (f) Chemotherapy using podophyllotoxin, etoposide, teniposide and docetaxel; (g) Chemotherapy using topoisomerase inhibitors such as irinotecan, topotecan, amsacrine, etoposide, etoposide phosphate, and teniposide; (h) Chemotherapy using cytotoxic antibiotics such as actinomycin, anthracyclines, doxorubicin, daunorubicin, valrubicin, idarubicin, epirubicin, bleomycin, plicamycin and mitomycin; (i) Chemotherapy using tyrosine-kinase inhibitors such as Imatinib mesylate (GLEEVEC®, also known as STI-571), Gefitinib (Iressa, also known as ZD1839), Erlotinib (marketed as TARCEVA®), Bortezomib (VELCADE®), tamoxifen, tofacitinib, crizotinib, Bcl-2 inhibitors (e.g. obatoclax, navitoclax (ABT-263), oblimersen (G3139), venetoclax (ABT-199), Gossypol), PARP inhibitors (e.g. Iniparib, Olaparib, Rucaparib, Niraparib, Talazoparib), PI3K inhibitors (e.g. perifosine in a phase III trial), VEGF Receptor 2 inhibitors (e.g. Apatinib), AN-152, (AEZS-108), Braf inhibitors (e.g. vemurafenib, dabrafenib and LGX818), MEK inhibitors (e.g. trametinib and MEK162), CDK inhibitors, (e.g. PD-0332991), salinomycin and Sorafenib; (j) Chemotherapy using monoclonal antibodies such as Rituximab (marketed as MABTHERA® or RITUXAN®), Trastuzumab (Herceptin also known as ErbB2), Cetuximab (marketed as ERBITUX®), and Bevacizumab (marketed as AVASTIN®); (k) Chemotherapy using KRAS G12C inhibitors such as sotorasib (Lumakras® and Lumykras®), adagrasib (MRTX849), and ARS-3248 (Wellspring Biosciences); (1) Chemotherapy using checkpoint inhibitor therapy such as Ipilimumab (Yervoy®), Nivolumab (Opdivo®), Pembrolizumab (Keytruda®), Atezolizumab (Tecentriq®), Avelumab (Bavencio), Durvalumab (Imfinzi), Cemiplimab (Libtayo®), and Spartalizumab (PDR001); (m) Chemotherapy using antibody-drug conjugates (ADC) such as Gemtuzumab ozogamicin, Brentuximab vedotin, Trastuzumab emtansine, Inotuzumab ozogamicin, Polatuzumab vedotin, Enfortumab vedotin, Trastuzumab deruxtecan, Sacituzumab govitecan, Belantamab mafodotin, Moxetumomab pasudotox, and Loncastuximab tesirine; (n) Chemotherapy using proteasome inhibitors such as carfilzomib, lactacystin, disulfiram, salinosporamide A (marizomib), oprozomib, delanzomib, epoxomicin, MG132, β-hydroxy β-methylbutyric acid (HMB), bortezomib, ixazomib (alone or in in combination with lenalidomide and dexamethasone); and (o) radiation therapy.

In some embodiments, a compound of Formula I, can be used to treat diabetes mellitus in combination with any of the following methods: (a) injections of insulin; (b) biguanides such as metformin (Glucophage), phenformin (DBI), and buformin; (c) thiazolidinediones (TZDs) such as rosiglitazone (Avandia), pioglitazone (Actos), and yroglitazone (Rezulin); (d) lyn kinase activators such as glimepiride (Amaryl®) and tolimidone (MLR-1023); (e) secretagogues such as sulfonylureas (non-limiting examples are acetohexamide, carbutamide, chlorpropamide, glycyclamide (tolcyclamide), metahexamide, tolazamide, tolbutamide, glibenclamide (glyburide), glibornmuride, gliclazide, glipizide, gliquidone, glisoxepide, glyclopyramide, and glimepiride) and meglitinides (nonlimiting examples are repaglinide (Prandin), nateglinide (Starlix), and mitiglinide (Glufast)); (f) alpha-glucosidase inhibitors such as acarbose (Glucobay, Precose, Prandase), miglitol (Glyset), and voglibose; (g) injectable incretin mimetics such as glucagon-like peptide-1 (GLP-1) and gastric inhibitory peptide (glucose-dependent insulinotropic peptide, GIP), nonlimiting examples of injectable glucagon-like peptide (GLP) analogs and agonists are exenatide (Exendin-4, marketed as Byetta), liraglutide (Victoza, Saxenda), taspoglutide, lixisenatide (Lyxumia), Semaglutide (Ozempic, Rybelsus), dulaglutide (Trulicity), albiglutide (Tanzeum), nonlimiting examples of dipeptidyl peptidase-4 (DPP-4) inhibitors are sitagliptin (Januvia), vildagliptin (Galvus), saxagliptin (Onglyza), linagliptin (Tradjenta), gemigliptin (Zemiglo), anagliptin (Suiny), teneligliptin (Tenelia), alogliptin (Nesina, Vipidia, Kazano, Vipidomet (with metformin), Oseni, Incresync (with pioglitazone)), trelagliptin (Zafatek, Wedica), omarigliptin (MK-3102), evogliptin (Suganon, Evodine), gosogliptin (Saterex), and dutogliptin; (h) injectable amylin analogues such as pramlintide (Symlin); (i) glycosurics (SGLT2 inhibitors) such as canagliflozin (Invokana, Sulisent, Prominad), dapagliflozin (Forxiga, Farxiga, Edistride), empagliflozin (Jardiance, Sciampa-M), ertugliflozin (Steglatro), ipragliflozin (Suglat), luseogliflozin (Lusefi), remogliflozin etabonate (pro-drug of remogliflozin), sergliflozin etabonate (GW869682X), sotagliflozin (Zynquista), and tofogliflozin (CSG452).

In some embodiments, a compound of Formula (I) can be used to treat osteoarthritis in combination with any of the following methods: (d) injections of a Wnt signaling pathway inhibitor (e.g. lorecivivint); (a) Nonsteroidal anti-inflammatory drugs (NSAIDs) such as ibuprofen, naproxen, aspirin and acetaminophen; (b) physical therapy; (c) injections of corticosteroid medications; (d) injections of hyaluronic acid derivatives (e.g. Hyalgan, Synvisc); (e) narcotics, like codeine; (f) in combination with braces and/or shoe inserts or any device that can immobilize or support your joint to help you keep pressure off it (e.g., splints, braces, shoe inserts or other medical devices); (g) realigning bones (osteotomy); (h) joint replacement (arthroplasty); and (i) in combination with a chronic pain class.

In some embodiments, a compound of Formula (I) can be used to treat Alzheimer's disease in combination with aducanumab (Aduhelm™); acetylcholinesterase inhibitors, e.g., tacrine, rivastigmine (Exelon®), galantamine (Razadyne® and GalantaMind™), and donepezil (Aricept®); and memantine (Axura®, Ebixa®, Namenda®).

Administration of the compounds disclosed herein or the pharmaceutically acceptable salts thereof can be via any of the accepted modes of administration, including, but not limited to, orally, subcutaneously, intravenously, intranasally, topically, transdermally, intraperitoneally, intramuscularly, intrapulmonarilly, vaginally, rectally, ontologically, neuro-otologically, intraocularly, subconjuctivally, via anterior eye chamber injection, intravitreally, intraperitoneally, intrathecally, intracystically, intrapleurally, via wound irrigation, intrabuccally, intra-abdominally, intra-articularly, intra-aurally, intrabronchially, intracapsularly, intrameningeally, via inhalation, via endotracheal or endobronchial instillation, via direct instillation into pulmonary cavities, intraspinally, intrasynovially, intrathoracically, via thoracostomy irrigation, epidurally, intratympanically, intracisternally, intravascularly, intraventricularly, intraosseously, via irrigation of infected bone, or via application as part of any admixture with a prosthetic devices. In some embodiments, the administration method includes oral or parenteral administration.

Compounds provided herein intended for pharmaceutical use may be administered as crystalline or amorphous products. Pharmaceutically acceptable compositions may include solid, semi-solid, liquid, solutions, colloidal, liposomes, emulsions, suspensions, complexes, coacervates and aerosols. Dosage forms, such as, e.g., tablets, capsules, powders, liquids, suspensions, suppositories, aerosols, implants, controlled release, or the like. They may be obtained, for example, as solid plugs, powders, or films by methods such as precipitation, crystallization, milling, grinding, supercritical fluid processing, coacervation, complex coacervation, encapsulation, emulsification, complexation, freeze drying, spray drying, or evaporative drying. Microwave or radio frequency drying may be used for this purpose. The compounds can also be administered in sustained or controlled release dosage forms, including depot injections, osmotic pumps, pills (tablets and or capsules), transdermal (including electrotransport) patches, implants, and the like, for prolonged and/or timed, pulsed administration at a predetermined rate.

The compounds can be administered either alone or in combination with a conventional pharmaceutical carrier, excipient, or the like. Pharmaceutically acceptable excipients include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens, poloxamers or other similar polymeric delivery matrices, serum proteins, such as human serum albumin, buffer substances such as phosphates, tris, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium-chloride, zinc salts, colloidal silica, magnesium trisilicate, polyvinyl pyrrolidone, cellulose-based substances, polyethylene glycol, sodium carboxymethyl cellulose, polyacrylates, waxes, polyethylene-polyoxypropylene-block polymers, and wool fat. Cyclodextrins such as α-, β, and γ-cyclodextrin, or chemically modified derivatives such as hydroxyalkylcyclodextrins, including 2- and 3-hydroxypropyl-β-cyclodextrins, or other solubilized derivatives can also be used to enhance delivery of compounds described herein. Dosage forms or compositions containing a compound as described herein in the range of 0.005% to 100% with the balance made up from non-toxic carrier may be prepared. The contemplated compositions may contain 0.001%-100% of a compound provided herein, in one embodiment 0.1-95%, in another embodiment 75-85%, in a further embodiment 20-80%. Actual methods of preparing such dosage forms are known, or will be apparent, to those skilled in this art; for example, see *Remington: The Science and Practice of Pharmacy,* $22^{nd}$ Edition (Pharmaceutical Press, London, U K. 2012).

In one embodiment, the compositions will take the form of a unit dosage form such as a pill or tablet and thus the composition may contain, along with a compound provided herein, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives, or the like. In another solid dosage form, a powder, marume, solution or suspension (e.g., in propylene carbonate, vegetable oils, PEG's, poloxamer 124 or triglycerides) is encapsulated in a capsule (gelatin or cellulose base capsule). Unit dosage forms in which one or more compounds provided herein or additional active agents are physically separated are also contemplated; e.g., capsules with granules (or tablets in a capsule) of each drug; two-layer tablets; two-compartment gel caps, etc. Enteric coated or delayed release oral dosage forms are also contemplated.

Liquid pharmaceutically administrable compositions can, for example, be prepared by dissolving, dispersing, etc. a compound provided herein and optional pharmaceutical adjuvants in a carrier (e.g., water, saline, aqueous dextrose, glycerol, glycols, ethanol, or the like) to form a solution, colloid, liposome, emulsion, complexes, coacervate or suspension. If desired, the pharmaceutical composition can also contain minor amounts of nontoxic auxiliary substances such as wetting agents, emulsifying agents, co-solvents, solubilizing agents, pH buffering agents and the like (e.g., sodium acetate, sodium citrate, cyclodextrin derivatives, sorbitan monolaurate, triethanolamine acetate, triethanolamine oleate, and the like).

In some embodiments, the unit dosage of compounds of Formula (I) is about 0.25 mg/Kg to about 50 mg/Kg in humans.

In some embodiments, the unit dosage of compounds of Formula (I) is about 0.25 mg/Kg to about 20 mg/Kg in humans.

In some embodiments, the unit dosage of compounds of Formula (I) is about 0.50 mg/Kg to about 19 mg/Kg in humans.

In some embodiments, the unit dosage of compounds of Formula (I) is about 0.75 mg/Kg to about 18 mg/Kg in humans.

In some embodiments, the unit dosage of compounds of Formula (I) is about 1.0 mg/Kg to about 17 mg/Kg in humans.

In some embodiments, the unit dosage of compounds of Formula (I) is about 1.25 mg/Kg to about 16 mg/Kg in humans.

In some embodiments, the unit dosage of compounds of Formula (I) is about 1.50 mg/Kg to about 15 mg/Kg in humans.

In some embodiments, the unit dosage of compounds of Formula (I) is about 1.75 mg/Kg to about 14 mg/Kg in humans.

In some embodiments, the unit dosage of compounds of Formula (I) is about 2.0 mg/Kg to about 13 mg/Kg in humans.

In some embodiments, the unit dosage of compounds of Formula (I) is about 3.0 mg/Kg to about 12 mg/Kg in humans.

In some embodiments, the unit dosage of compounds of Formula (I) is about 4.0 mg/Kg to about 11 mg/Kg in humans.

In some embodiments, the unit dosage of compounds of Formula (I) is about 5.0 mg/Kg to about 10 mg/Kg in humans.

In some embodiments, the compositions are provided in unit dosage forms suitable for single administration.

In some embodiments, the compositions are provided in unit dosage forms suitable for twice a day administration.

In some embodiments, the compositions are provided in unit dosage forms suitable for three times a day administration.

Injectables can be prepared in conventional forms, either as liquid solutions, colloid, liposomes, complexes, coacervate or suspensions, as emulsions, or in solid forms suitable for reconstitution in liquid prior to injection. The percentage of a compound provided herein contained in such parenteral compositions is highly dependent on the specific nature thereof, as well as the activity of the compound and the needs of the patient. However, percentages of active ingredient of 0.010% to 10% in solution are employable and could be higher if the composition is a solid or suspension, which could be subsequently diluted to the above percentages.

In some embodiments, the composition comprises about 0.1-10% of the active agent in solution.

In some embodiments, the composition comprises about 0.1-5% of the active agent in solution.

In some embodiments, the composition comprises about 0.1-4% of the active agent in solution.

In some embodiments, the composition comprises about 0.15-3% of the active agent in solution.

In some embodiments, the composition comprises about 0.2-2% of the active agent in solution.

In some embodiments, the compositions are provided in dosage forms suitable for continuous dosage by intravenous infusion over a period of about 1-96 hours.

In some embodiments, the compositions are provided in dosage forms suitable for continuous dosage by intravenous infusion over a period of about 1-72 hours.

In some embodiments, the compositions are provided in dosage forms suitable for continuous dosage by intravenous infusion over a period of about 1-48 hours.

In some embodiments, the compositions are provided in dosage forms suitable for continuous dosage by intravenous infusion over a period of about 1-24 hours.

In some embodiments, the compositions are provided in dosage forms suitable for continuous dosage by intravenous infusion over a period of about 1-12 hours.

In some embodiments, the compositions are provided in dosage forms suitable for continuous dosage by intravenous infusion over a period of about 1-6 hours.

In some embodiments, these compositions can be administered by intravenous infusion to humans at doses of about 5 $mg/m^2$ to about 300 $mg/m^2$.

In some embodiments, these compositions can be administered by intravenous infusion to humans at doses of about 5 $mg/m^2$ to about 200 $mg/m^2$.

In some embodiments, these compositions can be administered by intravenous infusion to humans at doses of about 5 $mg/m^2$ to about 100 $mg/m^2$.

In some embodiments, these compositions can be administered by intravenous infusion to humans at doses of about 10 $mg/m^2$ to about 50 $mg/m^2$.

In some embodiments, these compositions can be administered by intravenous infusion to humans at doses of about 50 $mg/m^2$ to about 200 $mg/m^2$.

In some embodiments, these compositions can be administered by intravenous infusion to humans at doses of about 75 mg/$m^2$ to about 175 mg/$m^2$.

In some embodiments, these compositions can be administered by intravenous infusion to humans at doses of about 100 mg/$m^2$ to about 150 mg/$m^2$.

It is to be noted that concentrations and dosage values may also vary depending on the specific compound and the severity of the condition to be alleviated. It is to be further understood that for any particular patient, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In one embodiment, the compositions can be administered to the respiratory tract (including nasal and pulmonary) e.g., through a nebulizer, metered-dose inhalers, atomizer, mister, aerosol, dry powder inhaler, insufflator, liquid instillation or other suitable device or technique.

In some embodiments, aerosols intended for delivery to the nasal mucosa are provided for inhalation through the nose. For optimal delivery to the nasal cavities, inhaled particle sizes of about 5 to about 100 microns are useful, with particle sizes of about 10 to about 60 microns being preferred. For nasal delivery, a larger inhaled particle size may be desired to maximize impaction on the nasal mucosa and to minimize or prevent pulmonary deposition of the administered formulation. In some embodiments, aerosols intended for delivery to the lung are provided for inhalation through the nose or the mouth. For delivery to the lung, inhaled aerodynamic particle sizes of about less than 10 μm are useful (e.g., about 1 to about 10 microns). Inhaled particles may be defined as liquid droplets containing dissolved drug, liquid droplets containing suspended drug particles (in cases where the drug is insoluble in the suspending medium), dry particles of pure drug substance, drug substance incorporated with excipients, liposomes, emulsions, colloidal systems, coacervates, aggregates of drug nanoparticles, or dry particles of a diluent which contain embedded drug nanoparticles.

In some embodiments, compounds of Formula (I) disclosed herein intended for respiratory delivery (either systemic or local) can be administered as aqueous formulations, as non-aqueous solutions, or suspensions, as suspensions or solutions in halogenated hydrocarbon propellants with or without alcohol, as a colloidal system, as emulsions, coacervates, or as dry powders. Aqueous formulations may be aerosolized by liquid nebulizers employing either hydraulic or ultrasonic atomization or by modified micropump systems (like the soft mist inhalers, the Aerodose® or the AERx® systems). Propellant-based systems may use suitable pressurized metered-dose inhalers (pMDIs). Dry powders may use dry powder inhaler devices (DPIs), which are capable of dispersing the drug substance effectively. A desired particle size and distribution may be obtained by choosing an appropriate device.

In some embodiments, the compositions of Formula (I) disclosed herein can be administered to the ear by various methods. For example, a round window catheter (e.g., U.S. Pat. Nos. 6,440,102 and 6,648,873) can be used.

Alternatively, formulations can be incorporated into a wick for use between the outer and middle ear (e.g., U.S. Pat. No. 6,120,484) or absorbed to collagen sponge or other solid support (e.g., U.S. Pat. No. 4,164,559).

If desired, formulations of the disclosure can be incorporated into a gel formulation (e.g., U.S. Pat. Nos. 4,474,752 and 6,911,211).

In some embodiments, compounds of Formula (I) disclosed herein intended for delivery to the ear can be administered via an implanted pump and delivery system through a needle directly into the middle or inner ear (cochlea) or through a cochlear implant stylet electrode channel or alternative prepared drug delivery channel such as but not limited to a needle through temporal bone into the cochlea.

Other options include delivery via a pump through a thin film coated onto a multichannel electrode or electrode with a specially imbedded drug delivery channel (pathways) carved into the thin film for this purpose. In other embodiments the acidic or basic solid compound of Formula (I) can be delivered from the reservoir of an external or internal implanted pumping system.

Formulations of the disclosure also can be administered to the ear by intratympanic injection into the middle ear, inner ear, or cochlea (e.g., U.S. Pat. No. 6,377,849 and Ser. No. 11/337,815).

Intratympanic injection of therapeutic agents is the technique of injecting a therapeutic agent behind the tympanic membrane into the middle and/or inner ear. In one embodiment, the formulations described herein are administered directly onto the round window membrane via transtympanic injection. In another embodiment, the ion channel modulating agent auris-acceptable formulations described herein are administered onto the round window membrane via a non-transtympanic approach to the inner ear. In additional embodiments, the formulation described herein is administered onto the round window membrane via a surgical approach to the round window membrane comprising modification of the *crista* fenestrae *cochleae*.

In some embodiments, the compounds of Formula (I) are formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, PEG (like PEG ointments), and the like.

Suppositories for rectal administration of the drug (either as a solution, colloid, suspension or a complex) can be prepared by mixing a compound provided herein with a suitable non-irritating excipient that is solid at ordinary temperatures but liquid at the rectal temperature and will therefore melt or erode/dissolve in the rectum and release the compound. Such materials include cocoa butter, glycerinated gelatin, hydrogenated vegetable oils, poloxamers, mixtures of polyethylene glycols of various molecular weights and fatty acid esters of polyethylene glycol. In suppository forms of the compositions, a low-melting wax such as, but not limited to, a mixture of fatty acid glycerides, optionally in combination with cocoa butter, is first melted.

Solid compositions can be provided in various different types of dosage forms, depending on the physicochemical properties of the compound provided herein, the desired dissolution rate, cost considerations, and other criteria. In one of the embodiments, the solid composition is a single unit. This implies that one unit dose of the compound is comprised in a single, physically shaped solid form or article. In other words, the solid composition is coherent, which is in contrast to a multiple unit dosage form, in which the units are incoherent.

Examples of single units which may be used as dosage forms for the solid composition include tablets, such as compressed tablets, film-like units, foil-like units, wafers, lyophilized matrix units, and the like. In one embodiment, the solid composition is a highly porous lyophilized form. Such lyophilizates, sometimes also called wafers or lyophilized tablets, are particularly useful for their rapid disintegration, which also enables the rapid dissolution of the compound.

On the other hand, for some applications the solid composition may also be formed as a multiple unit dosage form as defined above. Examples of multiple units are powders, granules, microparticles, pellets, mini-tablets, beads, lyophilized powders, and the like. In one embodiment, the solid composition is a lyophilized powder. Such a dispersed lyophilized system comprises a multitude of powder particles, and due to the lyophilization process used in the formation of the powder, each particle has an irregular, porous microstructure through which the powder is capable of absorbing water very rapidly, resulting in quick dissolution. Effervescent compositions are also contemplated to aid the quick dispersion and absorption of the compound.

Another type of multiparticulate system which is also capable of achieving rapid drug dissolution is that of powders, granules, or pellets from water-soluble excipients which are coated with a compound provided herein so that the compound is located at the outer surface of the individual particles. In this type of system, the water-soluble low molecular weight excipient may be useful for preparing the cores of such coated particles, which can be subsequently coated with a coating composition comprising the compound and, for example, one or more additional excipients, such as a binder, a pore former, a saccharide, a sugar alcohol, a film-forming polymer, a plasticizer, or other excipients used in pharmaceutical coating compositions.

Also provided herein are kits. Typically, a kit includes one or more compounds or compositions as described herein. In certain embodiments, a kit can include one or more delivery systems, e.g., for delivering or administering a compound as provided herein, and directions for use of the kit (e.g., instructions for treating a patient). In another embodiment, the kit can include a compound or composition as described herein and a label that indicates that the contents are to be administered to a patient with cancer. In another embodiment, the kit can include a compound or composition as described herein and a label that indicates that the contents are to be administered to a patient with one or more of glioblastoma, ovarian, breast, pancreatic cancers, acute lymphoblastic leukemia, acute megakaryoblastic leukemia, chronic myeloid leukemia, Alzheimer's Disease, Amyotrophic Lateral Sclerosis, CDKL5 Deficiency Disorder, Down Syndrome, Frontotemporal Dementia with Parkinsonism-17 (FTDP-17), Lewy body dementia, Parkinson's Disease, Pick's Disease, Autism, Dementia, Epilepsy, Huntington's Disease, and Multiple Sclerosis.

Methods of Treatment

The compounds and compositions provided herein can be used as inhibitors of DYRK1A, and thus can be used to treat a variety of disorders and diseases in which over expression of DYRK1A is implicated, such as cancer and neurological conditions/disorders/diseases. Non-limiting examples of diseases which can be treated with the compounds and compositions provided herein include a variety of cancers, Alzheimer's Disease, Amyotrophic Lateral Sclerosis, CDKL5 Deficiency Disorder, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor, Stroke, tauopathies (e.g., Pick's disease, progressive supranuclear palsy, corticobasal degeneration, argyrophilic grain disease, globular glial tauopathies, primary age-related tauopathy, which includes neurofibrillary tangle dementia, chronic traumatic encephalopathy (CTE), frontotemporal lobar degeneration with tau inclusions (FTLD-tau), and aging-related tau astrogliopathy. Clinical symptoms include frontotemporal dementia, corticobasal syndrome, Richardson syndrome, parkinsonism, pure akinesia with gait freezing and, rarely, motor neuron symptoms or cerebellar ataxia, diabetes, psoriasis, knee osteoarthritis, tendinopathy, human immunodeficiency virus type 1 (HIV-1), human cytomegalovirus (HCMV), hepatitis C virus (HCV), and herpes simplex virus 1 (HSV-1).

The gene encoding DYRK1A is located on chromosome 21, within the Down syndrome critical region (DSCR), the triploidy of which is responsible for most Down syndrome-associated deficiencies (*FEBS Journal* (2011), 278, 246-256). There is considerable genetical and pharmacological evidence showing that the mere 1.5-fold overexpression of DYRK1A is responsible for most cognitive deficits observed in Down syndrome patients (*Pharmacology & Therapeutics* (2019), 194, 199-221 and *Brain Science* (2018), 8(10), 187). Genetical normalization of DYRK1A levels or pharmacological inhibition of its catalytic activity restores cognitive functions. The development of pharmacological inhibitors of DYRK1A is a major avenue for the treatment of cognitive deficits associated with Down syndrome.

DYRK1A and DYRK1B are utilized during human cytomegalovirus (HCMV) placental replication. Inhibition of DYRKs prevent replication of various viruses, including hepatitis C virus (HCV), human cytomegalovirus (HCMV), human immunodeficiency virus type 1 (HIV-1), and herpes simplex virus 1 (HSV-1) (*Journal of Virology* (2020), 94(6) and *PLoS ONE* (2015), 10, e0144229).

There is a growing body of evidence showing that DYRK1A/1B inhibitors induce the proliferation of insulin-producing pancreatic β-cells, making DYRK1A/1B kinases attractive therapeutic targets for β-cell regeneration for both type 1 and type 2 diabetes mellitus and gestational diabetes (*Nature Communications* (2015), 6(8372); *Diabetes* (2016), 65(6), 1660-1671; *JCI Insight* (2020), 5(1), e132594; *Science Translational Medicine* (2020), 12(530); *International Journal of Molecular Sciences* (2021), 22(16), 9083; and *Journal of Medicinal Chemistry* (2021), 64(6), 2901-2922). Other forms of diabetes that may be treated with DYRK inhibitors are maturity onset diabetes of the young (MODY, monogenic diabetes), cases of diabetes that are caused by the body's tissue receptors not responding to insulin, double diabetes (when a type 1 diabetic becomes insulin resistant), diabetes associated with excessive secretion of insulin-antagonistic hormones, malnutrition-related diabetes mellitus (ICD-10 code E12), and diabetes caused by any genetic mutations (autosomal or mitochondrial) that leads to defects in beta cell function.

There is abundant literature linking DYRK1A with solid cancers and leukemias (*Pharmacology & Therapeutics* (2015), 151, 87-98; Cancers (2020), 12(8), 2106; and *Cellular and Molecular Life Sciences* (2021), 78, 603-619). The most prominent examples are pancreatic cancer (Gut (2019), 68(8), 1465-1476 and Gene (2020), 758, 144960), brain tumors, glioblastoma (*Journal of Clinical Investigation* (2013), 123(6), 2475-2487), acute megakaryoblastic leukemia (AMKL) (*Journal of Clinical Investigation* (2012), 122(3), 948-962), and acute lymphoblastic leukemia (ALL)

(*Journal of Clinical Investigation* (2021), 131(1), e135937). Other cancers linked to DYRK1A are ovarian (*Frontiers in Oncology* (2021), 11, 637193), head and neck squamous cell carcinoma (*Scientific Reports* (2016), 6, 36132), hepatocellular carcinoma (*Cell Death & Disease* (2021), 12, 125), DYRK1A regulates DNA damage response (*Scientific Reports* (2019), 9, 6014 and *Scientific Reports* (2019), 9, 6539). In some situations, DYRK1A appears to function as a tumor-suppressor protein (*Molecular & Cellular Oncology* (2015), 2(1), e970048 and *Nature* (2016), 529, 172-177).

Other cancers can also be treated with the compounds and compositions described herein.

More particularly, cancers that may be treated by the compounds, compositions and methods described herein include, but are not limited to, the following:

1) Breast cancers, including, for example $ER^+$ breast cancer, $ER^-$ breast cancer, $her2^-$ breast cancer, $her2^+$ breast cancer, stromal tumors such as fibroadenomas, phyllodes tumors, and sarcomas, and epithelial tumors such as large duct papillomas; carcinomas of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma; chemoresistant breast cancers (TNBC), and miscellaneous malignant neoplasms. Further examples of breast cancers can include luminal A, luminal B, basal A, basal B, and triple negative breast cancer, which is estrogen receptor negative ($ER^-$), progesterone receptor negative, and her2 negative ($her2^-$). In some embodiments, the breast cancer may have a high risk Oncotype score.

2) Cardiac cancers, including, for example sarcoma, e.g., angiosarcoma, fibrosarcoma, rhabdomyosarcoma, and liposarcoma; myxoma; rhabdomyoma; fibroma; lipoma and teratoma.

3) Lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; chemoresistant small cell lung cancer (SCLC), and mesothelioma.

4) Gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; colon cancers with APC gene mutations; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma.

5) Genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma.

6) Liver cancers, including, for example, hepatoma, e.g., hepatocellular carcinoma; cholangiocarcinoma; hepatoblastoma; angiosarcoma; hepatocellular adenoma; and hemangioma.

7) Bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors.

8) Nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, oligodendrocytoma, schwannoma, retinoblastoma, and congenital tumors; and cancers of the spinal cord, e.g., neurofibroma, meningioma, glioma, and sarcoma; pediatric brain cancer, e.g., astrocytoma, medulloblastoma, glioma, ependymoma, germ cell tumors such as germinomas and non-germinomatous tumors such as teratomas, choriocarcinomas, endodermal sinus tumors (yolk sac tumors), embryonal carcinomas, and mixed tumors.

9) Gynecological cancers, including, for example, cancers of the uterus, e.g., endometrial cancers (e.g., carcinoma, endometrioid adenocarcinoma, serous carcinoma, clear cell carcinoma, mucinous carcinomas, mixed or undifferentiated carcinoma (including mixed Müllerian tumor), endometrial stromal sarcoma, squamous cell carcinoma of the endometrium, urothelial carcinoma, endometrial cancer with CTNNB1 mutations); cancers of the cervix, e.g., cervical carcinoma, and pre tumor cervical dysplasia; cancers of the ovaries, e.g., BRCA-mutant ovarian cancer, surface epithelial-stromal tumors (epithelial ovarian cancer (Type 1 (endometroid, mucinous, clear cell, low grade serous) or Type 2 (poorly differentiated, carcinosarcoma, and high grade serous))), ovarian carcinoma, including serous cystadenocarcinoma, mucinous cystadenocarcinoma, endometrioid tumors, small cell ovarian cancer (small cell ovarian cancer of hypercalcemic type, small cell ovarian cancer of pulmonary type) unclassified carcinoma, granulosa theca cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma, primary fallopian tube cancer; Primary peritoneal cancer (also known as serous surface papillary carcinoma, primary peritoneal carcinoma, extra-ovarian serous carcinoma, primary serous papillary carcinoma, and psammomacarcinoma).

10) Hematologic cancers, including, for example, cancers of the blood, e.g., acute myeloid leukemia, chronic myeloid leukemia, myelodysplastic syndromes (refractory cytopenia with unilineage dysplasia (refractory anemia, refractory neutropenia, and refractory thrombocytopenia), refractory anemia with ring sideroblasts, refractory cytopenia with multilineage dysplasia, refractory anemias with excess blasts I and II, refractory cytopenia of childhood), and myeloproliferative neoplasms, acute lymphoblastic leukemia, chronic lymphocytic leukemia, myeloproliferative diseases, multiple myeloma, myelodysplastic syndrome, myelodysplastic-myeloproliferative diseases, Hodgkin's lymphoma, non-Hodgkin's lymphoma (malignant lymphoma) and Waldenstrom's macroglobulinemia.

11) Skin cancers and skin disorders, including, for example, malignant melanoma and metastatic melanoma, basal cell carcinoma, squamous cell carcinoma, Kaposi's sarcoma, moles dysplastic nevi, lipoma, angioma, dermatofibroma, keloids, and scleroderma.

12) Adrenal gland cancers, including, for example, neuroblastoma.

13) Soft-tissue sarcomas (STS) such as fibrosarcoma, malignant fibrous histiocytoma, dermatofibrosarcoma, liposarcoma, rhabdomyosarcoma, leiomyosarcoma, hemangiosarcoma, Kaposi's sarcoma, lymphangiosarcoma, synovial sarcoma, malignant peripheral nerve sheath tumors (also called neurofibrosarcomas, malignant schwannomas, and neurogenic sarcomas), neurofibrosarcoma, extraskeletal chondrosarcoma, extraskeletal osteosarcoma, extraskeletal myxoid chondrosarcoma, extraskeletal mesenchymal, embryonal, alveolar soft part sarcoma, and infantile hemangio-pericytoma.

More particularly, tumors of the central nervous system that may be treated by the compounds, compositions and methods described herein include:

1) Astrocytic tumors, e.g., diffuse astrocytoma (fibrillary, protoplasmic, gemistocytic, mixed), anaplastic (malignant) astrocytoma, glioblastoma multiforme (giant cell glioblastoma and gliosarcoma), pilocytic astrocytoma (pilomyxoid astrocytoma), pleomorphic xanthoastrocytoma, subependymal giant cell astrocytoma, and gliomatosis cerebri.

2) Oligodendroglial tumors, e.g., oligodendroglioma and anaplastic oligodendroglioma.

3) Oligoastrocytic tumors, e.g., oligoastrocytoma and anaplastic oligoastrocytoma.

4) Ependymal tumors, e.g., subependymoma, myxopapillary ependymoma, ependymoma, (cellular, papillary, clear cell, tanycytic), and anaplastic (malignant) ependymoma.

5) Choroid plexus tumors, e.g., choroid plexus papilloma, atypical choroid plexus papilloma, and choroid plexus carcinoma.

6) Neuronal and mixed neuronal-glial tumors, e.g., gangliocytoma, ganglioglioma, dysembryoplastic neuroepithelial tumor (DNET), dysplastic gangliocytoma of the cerebellum (Lhermitte-Duclos), desmoplastic infantile astrocytoma/ganglioglioma, central neurocytoma, anaplastic ganglioglioma, extraventricular neurocytoma, cerebellar liponeurocytoma, Papillary glioneuronal tumor, Rosette-forming glioneuronal tumor of the fourth ventricle, and paraganglioma of the filum *terminale.*

7) Pineal tumors, e.g., pineocytoma, pineoblastoma, papillary tumors ofthe pineal region, and pineal parenchymal tumor of intermediate differentiation.

8) Embryonal tumors, e.g., medulloblastoma (medulloblastoma with extensive nodularity, anaplastic medulloblastoma, desmoplastic, large cell, melanotic, medullomyoblastoma), medulloepithelioma, supratentorial primitive neuroectodermal tumors, and primitive neuroectodermal tumors (PNETs) such as neuroblastoma, ganglioneuroblastoma, ependymoblastoma, and atypical teratoid/rhabdoid tumor.

9) Neuroblastic tumors, e.g., olfactory (esthesioneuroblastoma), olfactory neuroepithelioma, and neuroblastomas of the adrenal gland and sympathetic nervous system.

10) Glial tumors, e.g., astroblastoma, chordoid glioma of the third ventricle, and angiocentric glioma.

11) Tumors of cranial and paraspinal nerves, e.g., schwannoma, neurofibroma Perineurioma, and malignant peripheral nerve sheath tumor.

12) Tumors of the meninges such as tumors of meningothelial cells, e.g., meningioma (atypical meningioma and anaplastic meningioma); mesenchymal tumors, e.g., lipoma, angiolipoma, hibernoma, liposarcoma, solitary fibrous tumor, fibrosarcoma, malignant fibrous histiocytoma, leiomyoma, leiomyosarcoma, rhabdomyoma, rhabdomyosarcoma, chondroma, chondrosarcoma, osteoma, osteosarcoma, osteochondroma, haemangioma, epithelioid hemangioendothelioma, haemangiopericytoma, anaplastic haemangiopericytoma, angiosarcoma, Kaposi Sarcoma, and Ewing Sarcoma; primary melanocytic lesions, e.g., diffuse melanocytosis, melanocytoma, malignant melanoma, meningeal melanomatosis; and hemangioblastomas.

13) Tumors of the hematopoietic system, e.g., malignant Lymphomas, plasmocytoma, and granulocytic sarcoma.

14) Germ cell tumors, e.g., germinoma, embryonal carcinoma, yolk sac tumor, choriocarcinoma, teratoma, and mixed germ cell tumors.

15) Tumors of the sellar region, e.g., craniopharyngioma, granular cell tumor, pituicytoma, and spindle cell oncocytoma of the adenohypophysis.

Cancers may be solid tumors that may or may not be metastatic. Cancers may also occur, as in leukemia, as a diffuse tissue. Thus, the term "tumor cell," as provided herein, includes a cell afflicted by any one of the above identified disorders.

A method of treating cancer using a compound or composition as described herein may be combined with existing methods of treating cancers, for example by chemotherapy, irradiation, or surgery (e.g., oophorectomy). In some embodiments, a compound or composition can be administered before, during, or after another anticancer agent or treatment.

There is mounting evidence for a role of DYRK1A in the onset of Alzheimer's Disease (*Future Medicinal Chemistry* (2016), 8(6), 681-696 and *European Journal of Medicinal Chemistry* (2018), 158, 559-592). DYRK1A phosphorylates key substrates involved in Alzheimer's Disease and dementia: Tau, septin 4, amyloid precursor protein (APP), presenilin 1, neprilysin, Munc18-1, α-synuclein, RCAN1, and β-tubulin. By modulating alternative splicing of Tau exon 10, DYRK1A favors the production of the 3R-Tau splice isoform (characteristic for DS/AD/tauopathy) over the 4R-Tau isoform (*Journal of Biological Chemistry* (2015), 290, 15219-15237).

Genome-wide association studies (GWAS) have revealed that DYRK1A is a risk factor for Parkinson's Disease (*The Lancet Neurology* (2019), 18(12), 1091-1102). DYRK1A phosphorylates key factors for Parkinson's Disease such as parkin, septin 4, and α-synuclein. Upregulation of microRNAs specific for Parkinson's Disease targets DYRK1A expression. There is further evidence that DYRK1A expression is increased in Parkinson's Disease and in Pick's disease (*Neurobiology of Disease* (2005), 20(2), 392-400).

The compounds and compositions provided herein can be used as inhibitors and/or modulators of the enzyme DYRK1A, and thus can be used to treat a variety of disorders and diseases associated with tau protein, including, but not limited to, Alzheimer's disease, amyotrophic lateral sclerosis (ALS), down syndrome, frontotemporal dementia (FTD) including FTD with Parkinsonism-17 (FTDP-17), behavioural variant frontotemporal dementia (bvFTD), FTD in patients with motor neuron disease (MND) (typically amyotrophic lateral sclerosis, also called FTD-ALS), corticobasal degeneration (CBD) (also called corticobasal ganglionic degeneration), progressive supranuclear palsy, primary progressive aphasia (PPA), globular glial tauopathy (GGT), myotonic dystrophy type 1 (DM1) (also called Steinert disease), myotonic dystrophy type 2 (DM2) (also called proximal myotonic myopathy), Guam complex, argyrophilic grain disease, dementia pugilistica, post-encephalitic parkinsonism, Lewy body dementia, Parkinson's disease, Pick's disease, and additional diseases with pronounced neurodegeneration such as autism, dementia, epilepsy, Huntington's disease, multiple sclerosis; diseases and disorders associated with acquired brain injury such as chronic traumatic encephalopathy, traumatic brain injury, tumor, and stroke.

Non-limiting examples of neurological disorders (e.g., neurological conditions and neurological diseases) which can be treated with the compounds and compositions provided herein include Alzheimer's disease, aphasia, apraxia, arachnoiditis, ataxia telangiectasia, attention deficit hyperactivity disorder, auditory processing disorder, autism, alcoholism, Bell's palsy, bipolar disorder, brachial plexus injury, Canavan disease, carpal tunnel syndrome, causalgia, central pain syndrome, central pontine myelinolysis, centronuclear myopathy, cephalic disorder, cerebral aneurysm, cerebral arteriosclerosis, cerebral atrophy, cerebral gigantism, cerebral palsy, cerebral vasculitis, cervical spinal stenosis, Charcot-Marie-Tooth disease, Chiari malformation, chronic fatigue syndrome, chronic inflammatory demyelinating polyneuropathy (CIDP), chronic pain, Coffin-Lowry syndrome, complex regional pain syndrome, compression neuropathy, congenital facial diplegia, corticobasal degeneration, cranial arteritis, craniosynostosis, Creutzfeldt-Jakob disease, cumulative trauma disorder, Cushing's syndrome, cytomegalic inclusion body disease (CIBD), Dandy-Walker syndrome, Dawson disease, De Morsier's syndrome, Dejerine-Klumpke palsy, Dejerine-Sottas disease, delayed sleep phase syndrome, dementia, dermatomyositis, developmental dyspraxia, diabetic neuropathy, diffuse sclerosis, Dravet syndrome, dysautonomia, dyscalculia, dysgraphia, dyslexia, dystonia, empty sella syndrome, encephalitis, encephalocele, encephalotrigeminal angiomatosis, encopresis, epilepsy, Erb's palsy, erythromelalgia, essential tremor, Fabry's disease, Fahr's syndrome, familial spastic paralysis, febrile seizure, Fisher syndrome, Friedreich's ataxia, fibromyalgia, Foville's syndrome, Gaucher's disease, Gerstmann's syndrome, giant cell arteritis, giant cell inclusion disease, globoid cell leukodystrophy, gray matter heterotopia, Guillain-Barré syndrome, HTLV-1 associated myelopathy, Hallervorden-Spatz disease, hemifacial spasm, hereditary spastic paraplegia, heredopathia atactica polyneuritiformis, herpes zoster oticus, herpes zoster, Hirayama syndrome, holoprosencephaly, Huntington's disease, hydranencephaly, hydrocephalus, hypercortisolism, hypoxia, immune-mediated encephalomyelitis, inclusion body myositis, incontinentia pigmenti, infantile phytanic acid storage disease, infantile Refsum disease, infantile spasms, inflammatory myopathy, intracranial cyst, intracranial hypertension, Joubert syndrome, Karak syndrome, Kearns-Sayre syndrome, Kennedy disease, Kinsbourne syndrome, Klippel Feil syndrome, Krabbe disease, Kugelberg-Welander disease, kuru, Lafora disease, Lambert-Eaton myasthenic syndrome, Landau-Kleffner syndrome, lateral medullary (Wallenberg) syndrome, Leigh's disease, Lennox-Gastaut syndrome, Lesch-Nyhan syndrome, leukodystrophy, Lewy body dementia, lissencephaly, locked-in syndrome, Lou Gehrig's disease, lumbar disc disease, lumbar spinal stenosis, Lyme disease, Machado-Joseph disease (Spinocerebellar ataxia type 3), macrencephaly, macropsia, megalencephaly, Melkersson-Rosenthal syndrome, Meniere's disease, meningitis, Menkes disease, metachromatic leukodystrophy, microcephaly, micropsia, Miller Fisher syndrome, misophonia, mitochondrial myopathy, Mobius syndrome, monomelic amyotrophy, motor neuron disease, motor skills disorder, Moyamoya disease, mucopolysaccharidoses, multi-infarct dementia, multifocal motor neuropathy, multiple sclerosis, multiple system atrophy, muscular dystrophy, myalgic encephalomyelitis, myasthenia gravis, myelinoclastic diffuse sclerosis, myoclonic Encephalopathy of infants, myoclonus, myopathy, myotubular myopathy, myotonia congenital, narcolepsy, neurofibromatosis, neuroleptic malignant syndrome, lupus erythematosus, neuromyotonia, neuronal ceroid lipofuscinosis, Niemann-Pick disease, O'Sullivan-McLeod syndrome, occipital Neuralgia, occult Spinal Dysraphism Sequence, Ohtahara syndrome, olivopontocerebellar atrophy, opsoclonus myoclonus syndrome, optic neuritis, orthostatic hypotension, palinopsia, paresthesia, Parkinson's disease, paramyotonia Congenita, paraneoplastic diseases, paroxysmal attacks, Parry-Romberg syndrome, Pelizaeus-Merzbacher disease, periodic paralyses, peripheral neuropathy, photic sneeze reflex, phytanic acid storage disease, Pick's disease, polymicrogyria (PMG), polymyositis, porencephaly, post-polio syndrome, postherpetic neuralgia (PHN), postural hypotension, Prader-Willi syndrome, primary lateral sclerosis, prion diseases, progressive hemifacial atrophy, progressive multifocal leukoencephalopathy, progressive supranuclear palsy, pseudotumor cerebri, Ramsay Hunt syndrome type I, Ramsay Hunt syndrome type II, Ramsay Hunt syndrome type III, Rasmussen's encephalitis, reflex neurovascular dystrophy, Refsum disease, restless legs syndrome, retrovirus-associated myelopathy, Rett syndrome, Reye's syndrome, rhythmic movement disorder, Romberg syndrome, Saint Vitus dance, Sandhoff disease, schizophrenia, Schilder's disease, schizencephaly, sensory integration dysfunction, septo-optic dysplasia, Shy-Drager syndrome, Sjögren's syndrome, snatiation, Sotos syndrome, spasticity, spina *bifida*, spinal cord tumors, spinal muscular atrophy, spinocerebellar ataxia, Steele-Richardson-Olszewski syndrome, Stiff-person syndrome, stroke, Sturge-Weber syndrome, subacute sclerosing panencephalitis, subcortical arteriosclerotic encephalopathy, superficial siderosis, Sydenham's chorea, syncope, synesthesia, syringomyelia, tarsal tunnel syndrome, tardive dyskinesia, tardive dysphrenia, Tarlov cyst, Tay-Sachs disease, temporal arteritis, tetanus, tethered spinal cord syndrome, Thomsen disease, thoracic outlet syndrome, tic douloureux, Todd's paralysis, Tourette syndrome, toxic encephalopathy, transient ischemic attack, transmissible spongiform encephalopathies, transverse myelitis, tremor, trigeminal neuralgia, tropical spastic paraparesis, trypanosomiasis, tuberous sclerosis, ubisiosis, Von Hippel-Lindau disease (VHL), Viliuisk Encephalomyelitis (VE), Wallenberg's syndrome, Werdnig, Hoffman disease, west syndrome, Williams syndrome, Wilson's disease, and Zellweger syndrome.

The compounds and compositions may also be useful in the inhibition of the development of invasive cancer, tumor angiogenesis and metastasis.

In some embodiments, the pharmaceutical composition comprises a therapeutically effective amount of a compound of Formula (I), or a pharmaceutically acceptable salt thereof, and a pharmaceutically acceptable excipient.

In some embodiments, the disorder or disease is cancer.

In some embodiments, the disorder or disease is metastatic melanoma.

In some embodiments, the disorder or disease is tendon regeneration.

In some embodiments, the disorder or disease is diabetes.

In some embodiments, the disorder or disease is degenerative disc disease.

In some embodiments, the disorder or disease is osteoarthritis.

In some embodiments, the disorder or disease is a viral infection.

In some embodiments, the disorder or disease is a neurological disorder.

In some embodiments, the disorder or disease is Alzheimer's disease.

In some embodiments, the disorder or disease is osteoarthritis.

In some embodiments, the patient is a human.

In some embodiments, the cancer is chosen from: hepatocellular carcinoma, colon cancer, breast cancer, pancreatic cancer, chronic myeloid leukemia (CML), chronic myelomonocytic leukemia, chronic lymphocytic leukemia (CLL), acute myeloid leukemia, acute lymphocytic leukemia, Hodgkin lymphoma, lymphoma, sarcoma, and ovarian cancer.

In some embodiments, the cancer is chosen from: lung cancer—non-small cell, lung cancer—small cell, multiple myeloma, nasopharyngeal cancer, neuroblastoma, osteosarcoma, penile cancer, pituitary tumors, prostate cancer, retinoblastoma, synovial sarcoma, rhabdomyosarcoma, salivary gland cancer, skin cancer—basal and squamous cell, skin cancer—melanoma, small intestine cancer, stomach (gastric) cancers, testicular cancer, thymus cancer, thyroid cancer, uterine sarcoma, vaginal cancer, vulvar cancer, laryngeal or hypopharyngeal cancer, kidney cancer, Kaposi sarcoma, gestational trophoblastic disease, gastrointestinal stromal tumor, gastrointestinal carcinoid tumor, gallbladder cancer, eye cancer (melanoma and lymphoma), Ewing tumor, esophagus cancer, endometrial cancer, colorectal cancer, cervical cancer, brain or spinal cord tumor, bone metastasis, bone cancer, bladder cancer, bile duct cancer, anal cancer and adrenal cortical cancer.

In some embodiments, the cancer is hepatocellular carcinoma; in some embodiments, the cancer is colon cancer; in some embodiments, the cancer is colorectal cancer; in some embodiments, the cancer is breast cancer; in some embodiments, the cancer is pancreatic cancer; in some embodiments, the cancer is chronic myeloid leukemia (CML); in some embodiments, the cancer is chronic myelomonocytic leukemia; in some embodiments, the cancer is chronic lymphocytic leukemia (CLL); in some embodiments, the cancer is acute myeloid leukemia; in some embodiments, the cancer is acute lymphocytic leukemia; in some embodiments, the cancer is Hodgkin lymphoma; in some embodiments, the cancer is lymphoma; in some embodiments, the cancer is sarcoma; in some embodiments, the cancer is ovarian cancer; in some embodiments, the cancer is lung cancer—non-small cell; in some embodiments, the cancer is lung cancer—small cell; in some embodiments, the cancer is multiple myeloma; in some embodiments, the cancer is nasopharyngeal cancer; in some embodiments, the cancer is neuroblastoma; in some embodiments, the cancer is osteosarcoma; in some embodiments, the cancer is penile cancer; in some embodiments, the cancer is pituitary tumors; in some embodiments, the cancer is prostate cancer; in some embodiments, the cancer is retinoblastoma; in some embodiments, the cancer is rhabdomyosarcoma; in some embodiments, the cancer is salivary gland cancer; in some embodiments, the cancer is skin cancer—basal and squamous cell; in some embodiments, the cancer is skin cancer—melanoma; in some embodiments, the cancer is small intestine cancer; in some embodiments, the cancer is stomach (gastric) cancers; in some embodiments, the cancer is testicular cancer; in some embodiments, the cancer is thymus cancer; in some embodiments, the cancer is thyroid cancer; in some embodiments, the cancer is uterine sarcoma; in some embodiments, the cancer is vaginal cancer; in some embodiments, the cancer is vulvar cancer; in some embodiments, the cancer is Wilms tumor; in some embodiments, the cancer is laryngeal or hypopharyngeal cancer; in some embodiments, the cancer is kidney cancer; in some embodiments, the cancer is Kaposi sarcoma; in some embodiments, the cancer is gestational trophoblastic disease; in some embodiments, the cancer is gastrointestinal stromal tumor; in some embodiments, the cancer is gastrointestinal carcinoid tumor; in some embodiments, the cancer is gallbladder cancer; in some embodiments, the cancer is eye cancer (melanoma and lymphoma); in some embodiments, the cancer is Ewing tumor; in some embodiments, the cancer is esophagus cancer; in some embodiments, the cancer is endometrial cancer; in some embodiments, the cancer is colorectal cancer; in some embodiments, the cancer is cervical cancer; in some embodiments, the cancer is brain or spinal cord tumor; in some embodiments, the cancer is bone metastasis; in some embodiments, the cancer is bone cancer; in some embodiments, the cancer is bladder cancer; in some embodiments, the cancer is bile duct cancer; in some embodiments, the cancer is anal cancer; and in some embodiments, the cancer is adrenal cortical cancer.

In some embodiments, the disorder or disease is a neurological condition, disorder, or disease, wherein the neurological disease is selected from: Alzheimer's disease, frontotemporal dementias, Parkinson's disease, Huntington's disease, progressive supranuclear palsy, corticobasal degeneration, multiple system atrophy, amyotrophic lateral sclerosis (ALS), inclusion body myositis, autism, degenerative myopathies.

In some embodiments, the disorder or disease is selected from the group consisting of: Alzheimer's Disease, Amyotrophic Lateral Sclerosis, Down Syndrome, Frontotemporal Dementia with Parkinsonism-17 (FTDP-17), Lewy body dementia, Parkinson's Disease, Pick's Disease, and additional diseases with pronounced neurodegeneration such as Autism, Dementia, Epilepsy, Huntington's Disease, Multiple Sclerosis; diseases and disorders associated with acquired brain injury such as Chronic Traumatic Encephalopathy, Traumatic Brain Injury, Tumor, and Stroke.

In some embodiments, a compound of Formula (I) inhibits DYRK1A.

In some embodiments, the method treats a disease or disorder mediated by kinase activity in a patient, the method comprises administering to the patient a therapeutically effective amount of a compound (or compounds) of Formula (I), or a pharmaceutically acceptable salt thereof.

In some embodiments, the disease or disorder comprises tumor growth, cell proliferation, or angiogenesis.

In some embodiments, the method inhibits the activity of a protein kinase receptor, the method comprises contacting the receptor with an effective amount of a compound (or compounds) of Formula (I), or a pharmaceutically acceptable salt thereof.

In some embodiments, the method treats a disease or disorder associated with aberrant cellular proliferation in a patient; the method comprises administering to the patient a therapeutically effective amount of a compound (or compounds) of Formula (I), or a pharmaceutically acceptable salt thereof.

In some embodiments, the method prevents or reduces abnormal cellular proliferation in a patient; the method comprises administering to the patient a therapeutically effective amount of a compound (or compounds) of Formula (I), or a pharmaceutically acceptable salt thereof.

In some embodiments, the method treats a disease or disorder associated with aberrant cellular proliferation in a patient, the method comprises administering to the patient a pharmaceutical composition comprising one or more of the compounds of claim 1 in combination with a pharmaceutically acceptable carrier and one or more other agents.

Evaluation of Biological Activity

The biological activity of the compounds described herein can be tested using any suitable assay known to those of skill in the art. For example, the activity of a compound may be tested using one or more of the test methods outlined below.

For example, in vitro assays for DYRK1A biological activity may be used, e.g., regulation of microtubule-associated protein tau (MAPT/Tau) phosphorylation in neuronal cell lines such as the human SH-SY5Y neuroblastoma cell line. Assays for DYRK1A-regulated level of phosphorylation can include monitoring levels of basal pSer396 Tau, which can be measured, for example, by serial dilutions of a candidate inhibitor composition using a ten micromolar top concentration and detected by ELISA or Western Blotting. An exemplary assay for DYRK-1A-regulated phosphorylation uses the SH-SY5Y cells cultured in a 96 well plate format for a period of time sufficient to stabilize microtubules and Tau phosphorylation, usually at least 2 days, then treated with a ⅓ serial dilution of compounds overnight and lysed. The cell lysate is resolved by SDS PAGE, then transferred to nitrocellulose and probed with an antibody specific for pSer396 Tau. The chemiluminescence signal for HRP-linked antibodies used in western blotting is detected using a Carestream Image Station and blot densitometry for pSer396 and beta-actin are analyzed using ImageJ (NIH).

In a further example, the activity of a candidate compound can be measured by phosphoTau (Thr212) AlphaLISA by adding the lysate mentioned above onto total Tau-coated plates and detected with a specific pThr212Tau antibody. Colorimetric detection of AlphaLISA signal is performed by EnVision Multilabel Plate Reader (Perkin Elmer).

To further illustrate this disclosure, the following examples are included. The examples should not, of course, be construed as specifically limiting the disclosure. Variations of these examples within the scope of the claims are within the purview of one skilled in the art and are considered to fall within the scope of the disclosure as described and claimed herein. The reader will recognize that the skilled artisan, armed with the present disclosure, and skill in the art is able to prepare and use the disclosure without exhaustive examples.

EXAMPLES

Compound Preparation

The starting materials used in preparing the compounds of the disclosure are known, made by known methods, or are commercially available. It will be apparent to the skilled artisan that methods for preparing precursors and functionality related to the compounds claimed herein are generally described in the literature. The skilled artisan given the literature and this disclosure is well equipped to prepare any of the compounds.

It is recognized that the skilled artisan in the art of organic chemistry can readily carry out manipulations without further direction, that is, it is well within the scope and practice of the skilled artisan to carry out these manipulations. These include reduction of carbonyl compounds to their corresponding alcohols, oxidations, acylations, aromatic substitutions, both electrophilic and nucleophilic, etherifications, esterification and saponification and the like. These manipulations are discussed in standard texts such as *March's Advanced Organic Chemistry: Reactions, Mechanisms, and Structure* $7^{th}$ Ed., John Wiley & Sons (2013), Carey and Sundberg, *Advanced Organic Chemistry* $5^{th}$ Ed., Springer (2007), *Comprehensive Organic Transformations: A Guide to Functional Group Transformations,* $2^{nd}$ Ed., John Wiley & Sons (1999) (incorporated herein by reference in its entirety) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in P. Wuts *Greene's Protective Groups in Organic Synthesis,* 5th Ed., John Wiley & Sons (2014), incorporated herein by reference in its entirety.

Trademarks used herein are examples only and reflect illustrative materials used at the time of the disclosure. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the disclosure.

($^1H$) nuclear magnetic resonance spectra (NMR) were measured in the indicated solvents on a Bruker NMR spectrometer (Avance™ DRX300, 300 MHz for $^1H$ or Avance™ DRX500, 500 MHz for $^1H$) or Varian NMR spectrometer (Mercury 400BB, 400 MHz for $^1H$). Peak positions are expressed in parts per million (ppm) downfield from tetramethylsilane. The peak multiplicities are denoted as follows, s, singlet; d, doublet; t, triplet; q, quartet; ABq, AB quartet; quin, quintet; sex, sextet; sep, septet; non, nonet; dd, doublet of doublets; ddd, doublet of doublets of doublets; d/ABq, doublet of AB quartet; dt, doublet of triplets; td, triplet of doublets; dq, doublet of quartets; m, multiplet.

The following abbreviations have the indicated meanings:

$Ac_2O$=acetic anhydride
brine=saturated aqueous sodium chloride
tBuOK=potassium tert-butoxide
$CDCl_3$=deuterated chloroform
m-CPBA=meta-chloroperoxybenzoic acid
$Cs_2CO_3$=cesium carbonate
DCE=dichloroethane
DCM=dichloromethane
DIPEA=N,N-diisopropylethylamine
DME=dimethoxyethane, or glyme, or monoglyme
DMF=N,N-dimethylformamide
DMPU=N,N'-dimethylpropyleneurea
DMSO-$d_6$=deuterated dimethylsulfoxide
ESIMS=electron spray mass spectrometry
EtOAc=ethyl acetate
HATU=1-[Bis(dimethylamino)methylene]-1H-1,2,3-triazolo[4,5-b]pyridinium 3-oxid hexafluorophosphate HCl=hydrochloric acid
HOAc=acetic acid
ISCO=Teledyne ISCO, Inc brand CombiFlash® Rf 200
KOAc=potassium acetate
LC/MS=Liquid chromatography-mass spectrometry
MeCN=acetonitrile
MeOH=methanol
$MgSO_4$=magnesium sulfate
monoglyme=1,2-dimethoxyethane
MsC1=mesyl chloride or methanesulfonyl chloride
MW=microwave irradiation
$NaHCO_3$=sodium bicarbonate
$Na(OAc)_3BH$=Sodium triacetoxyborohydride
$Na_2SO_4$=sodium sulfate
NMR=nuclear magnetic resonance
ON=overnight
$PCy_3$=tricyclohexylphosphine
Pd/C=palladium on carbon
$Pd_2(dba)_3$=tris(dibenzylideneacetone)dipalladium(0)
$Pd(dppf)Cl_2$=1,1'-bis(diphenylphosphino)ferrocene-palladium(II)dichloride
$Pd(OH)_2/C$=palladium hydroxide on carbon
prep-TLC=preparative thin layer chromatography
r.t.=room temperature
SM=starting material
T3P=propanephosphonic acid anhydride
TEA=triethylamine
TFA=trifluoroacetic acid
THF=tetrahydrofuran
TLC=thin layer chromatography The following example schemes are provided for the guidance of the reader, and collectively represent an example method for making the compounds provided herein. Furthermore, other methods for preparing compounds of the disclosure will be readily apparent to the person of ordinary skill in the art in light of the following reaction schemes and examples. The skilled artisan is thoroughly equipped to prepare these compounds by those methods given the literature and this disclosure. The compound numberings used in the synthetic schemes depicted below are meant for those specific schemes only and should not be construed as or confused with same numberings in other sections of the application. Unless otherwise indicated, all variables are as defined above.

General Procedures

Compounds of Formula I of the present disclosure can be prepared as depicted in Scheme 1.

Scheme 1

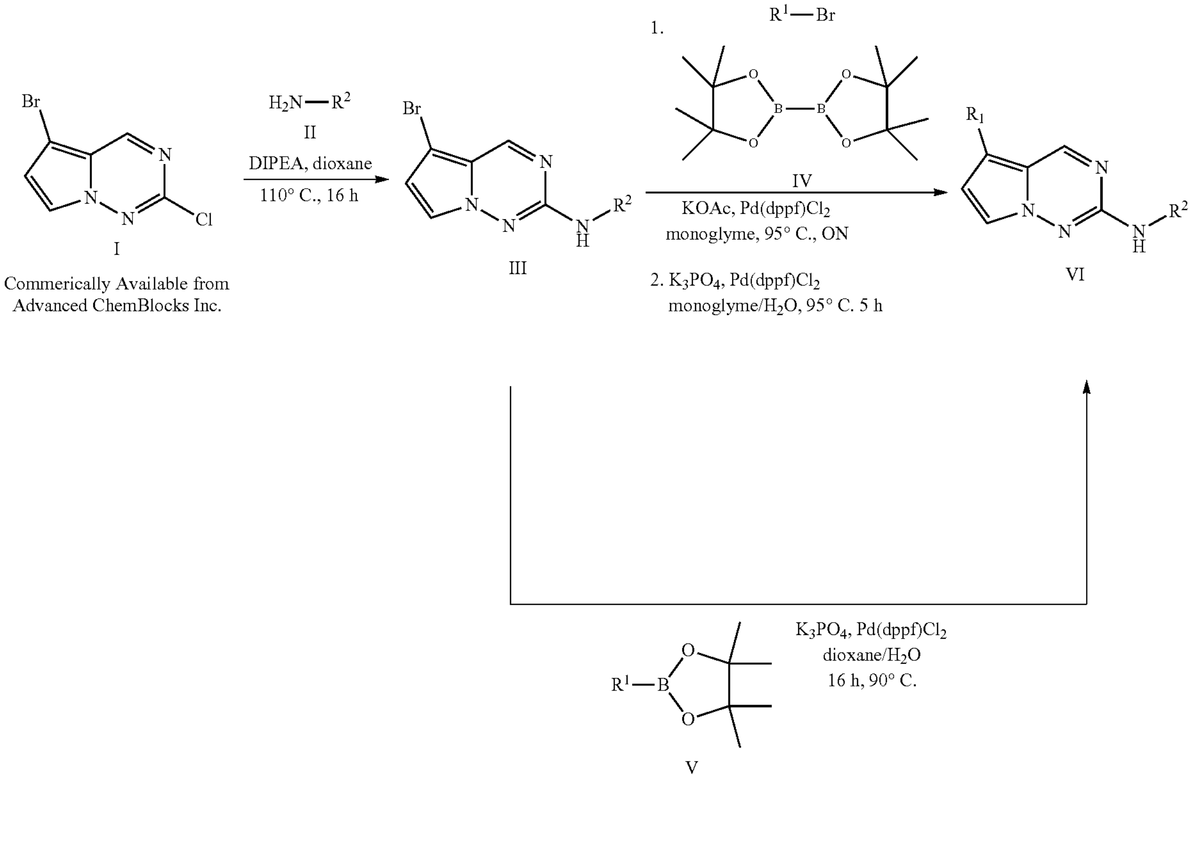

Scheme 1 describes a method for preparation of pyrrolo[2,1-f][1,2,4]triazine derivatives (VI) by first coupling the chloride (I) with a variety of amines (II) to produce bromo pyrrolo[2,1-f][1,2,4]triazine III. Formation of a variety of boronic acid pinacol esters by reacting various bromides (IV) with bis(pinacolato)diboron followed by Suzuki coupling with bromide (IV) produces the final pyrrolo[2,1-f][1,2,4]triazine (VI). Alternatively, a variety of commercial boronic acid pinacol esters (V) can be directly coupled with bromide (III) to produce the final pyrrolo[2,1-f][1,2,4]triazine (VI).

Compounds of Formula I of the present disclosure can also be prepared as depicted in Scheme 2.

Scheme 2

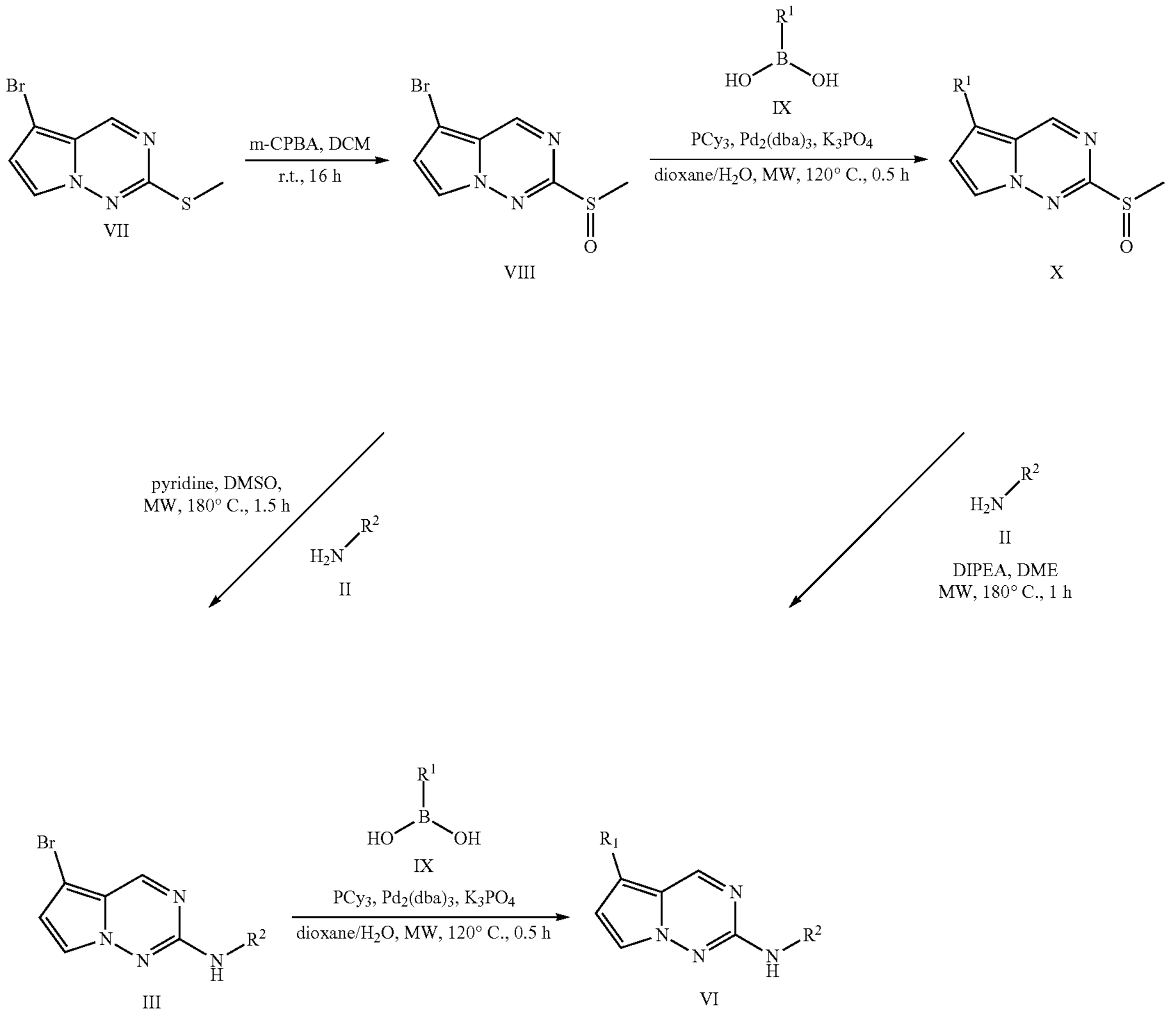

Scheme 2 describes a method for preparation of pyrrolo [2,1-f][1,2,4]triazine derivatives (VI) by oxidizing sulfide VII to the sulfone VIII. Sulfone VIII can then be coupled with a variety of amines (II) to produce bromo pyrrolo[2, 1-f][1,2,4]triazine III followed by Suzuki coupling with a variety of boronic acids (IX) to produce the final pyrrolo[2, 1-f][1,2,4]triazine (VI). Alternatively, a variety of boronic acids (IX) can coupled with sulfone VIII followed by coupling with a variety of amines (II) to produce the final pyrrolo[2,1-f][1,2,4]triazine (VI).

Illustrative Compound Examples

Preparation of intermediate 6-bromo-1-(2,2-difluoroethyl)-2-methyl-1H-imidazo[4,5-b]pyridine (XV) is depicted below in Scheme 3.

Scheme 3

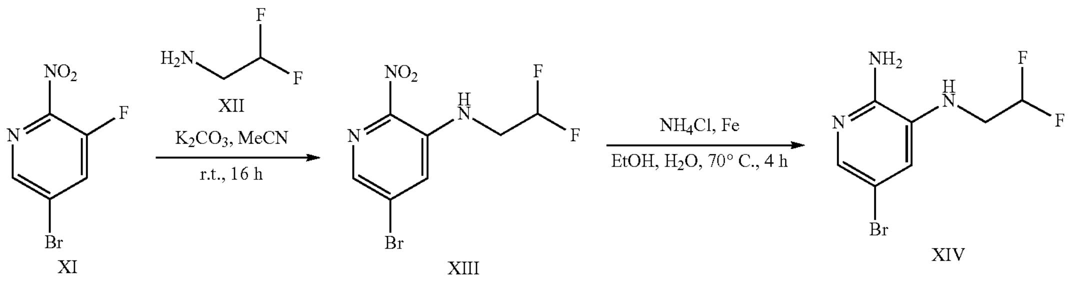

-continued

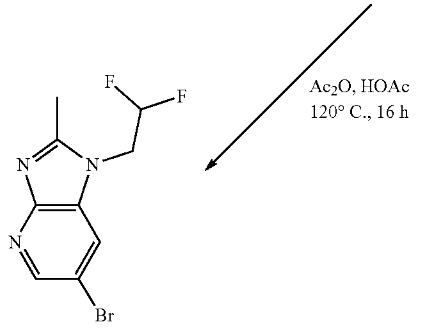

XV

Step 1

A mixture of 2,2-difluoroethan-1-amine (XII) (410 mg, 5.02 mmol), 5-bromo-3-fluoro-2-nitropyridine (XI) (commercially available from Ark Pharma Scientific Limited) (1.0 g, 4.53 mmol) and $K_2CO_3$ (1.38 g, 9.95 mmol) in MeCN (20 mL) was stirred at room temperature for 16 h. The reaction was filtered and concentrated under high vacuum. The residue was taken up in water, stirred for 1 hour and the solids were collected by filtration and dried in vacuo to obtain 5-bromo-N-(2,2-difluoroethyl)-2-nitropyridin-3-amine (XIII) (1.066 g, 3.780 mmol, 83.5% yield) as a yellow solid which was used for next step without purification. ESIMS found for $C_7H_6BrF_2N_3O_2$ m/z 282.0 ($^{79}$BrM+H).

Step 2

A mixture of 5-bromo-N-(2,2-difluoroethyl)-2-nitropyridin-3-amine (XIII) (1.32 g, 4.69 mmol), Fe (3.07 g, 46.95 mmol) and $NH_4Cl$ (3.77 g, 70.48 mmol) was taken in a mixture of EtOH (18 mL), and water (6 mL) and the mixture was heated to 70° C. for 4 h. The reaction mixture was cooled and filtered through Celite®. The filtrates were taken up in EtOAc, washed with water and brine, dried over anhydrous $Na_2SO_4$, filtered, and concentrated under reduced pressure to obtain 5-bromo-$N^3$-(2,2-difluoroethyl)pyridine-2,3-diamine (XIV) (630 mg, 2.499 mmol, 53.2% yield) as a grey solid which was used for next reaction without further purification. ESIMS found for $C_7H_8BrF_2N_3$ m/z 252.0 ($^{79}$BrM+H).

Step 3

A solution of 5-bromo-$N^3$-(2,2-difluoroethyl)pyridine-2,3-diamine (XIV) (630 mg, 2.5 mmol) and acetic anhydride (0.28 mL, 2.97 mmol) in HOAc (15 mL) was heated to 120° C. for 16 h. The reaction mixture was concentrated, the residue partitioned between EtOAc/1 N NaOH, organics separated, and washed with water and brine. The organics were dried over anhydrous $Na_2SO_4$, solvents and concentrated under high vacuum. The residue was triturated with diethyl ether, sonicated and the solids were collected by filtration and dried under high vacuo to obtain 6-bromo-1-(2,2-difluoroethyl)-2-methylimidazo[4,5-b]pyridine (XV) (325 mg, 1.177 mmol, 47.1% yield) as a grey solid which was used for next step without purification. ESIMS found for $C_9H_8BrF_2N_3$ m/z 276.0 ($^{79}$BrM+H).

The following intermediates were prepared in accordance with the procedure described in the above Scheme 3.

XVI

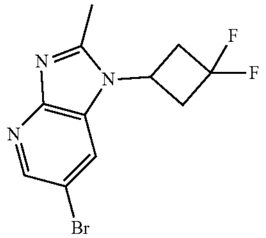

6-Bromo-1-(3,3-difluorocyclobutyl)-2-methyl-1H-imidazo[4,5-b] pyridine (XVI): Grey solid (1.57 g, 6.178 mmol, 68.3% yield). ESIMS found $C_{11}H_{10}BrF_2N_3$ m/z 302.1 (M+H).

XVII

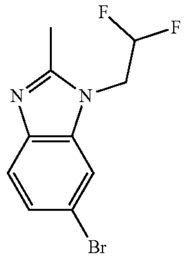

6-Bromo-1-(2,2-difluoroethyl)-2-methyl-1H-benzo[d] imidazole (XVII): Beige solid (970 mg, 3.526 mmol, 79.0% yield). ESIMS found $C_{10}H_9BrF_2N_2$ m/z 275.0 (M+H).

Preparation of intermediate 6-bromo-1-isopropyl-2-methyl-1H-imidazo[4,5-b]pyridine (XXII) is depicted below in Scheme 4.

Scheme 4

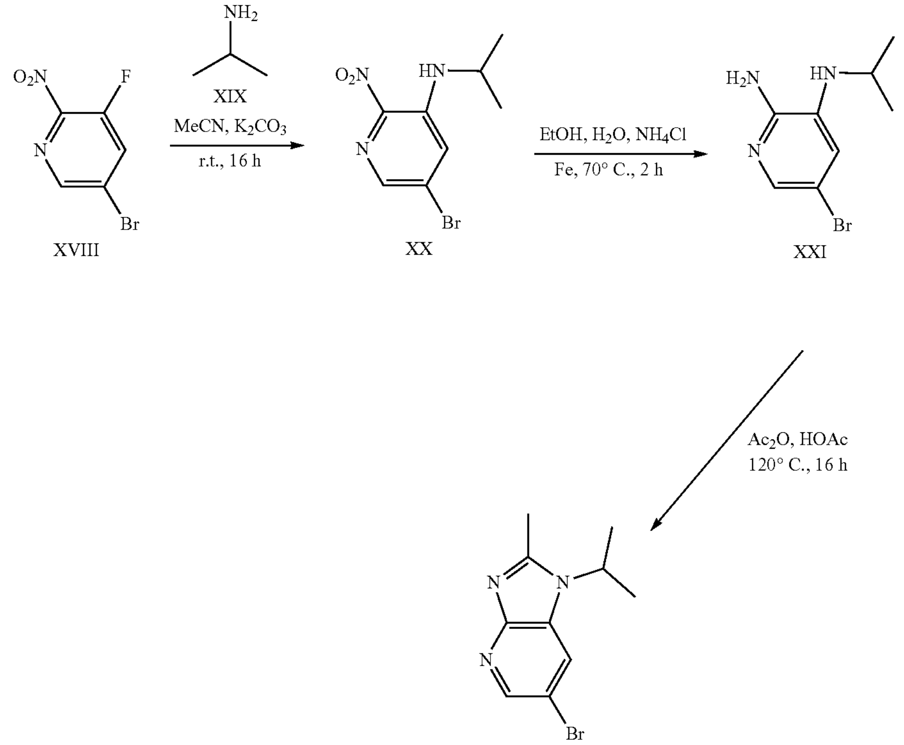

XVIII XX XXI XXII

Step 1

A mixture of 2-aminopropane (XIX) (0.86 mL, 9.96 mmol), 5-bromo-3-fluoro-2-nitropyridine (XVIII) (2 g, 9.05 mmol) and $K_2CO_3$ (2.5 g, 18.1 mmol) in MeCN (40 mL) was stirred at room temperature for 16 h. The reaction mixture was added to water (200 mL), stirred for 1 h and the resulting solids were collected by filtration and dried under high vacuo to obtain 5-bromo-N-isopropyl-2-nitropyridin-3-amine (XX) (2.36 g, 9.074 mmol, 100.3% yield) as a yellow solid which was used for next step without purification. ESIMS found for $C_8H_{10}BrN_3O_2$ m/z 260.0 (M+H).

Step 2

A mixture of 5-bromo-N-isopropyl-2-nitropyridin-3-amine (XX) (2.35 g, 9.04 mmol) Fe (5.91 g, 90.35 mmol) and $NH_4Cl$ (7.25 g, 135.53 mmol) was taken in a mixture of EtOH (30 mL) and water (10 mL) and the mixture was heated to 70° C. for 2 h. The reaction mixture was cooled, filtered through Celite®, filtrates were taken into EtOAc, washed with water then brine, dried over anhydrous $Na_2SO_4$, filtered, and concentrated under reduced pressure to obtain 5-bromo-$N^3$-isopropylpyridine-2,3-diamine (XXI) (2.2 g, 9.561 mmol, 105.8% yield) as a dark brown solid which was used for next step without purification. ESIMS found for $C_8H_{12}BrN_3$ m/z 230.05 (M+H).

Step 3

A solution of 5-bromo-$N^3$-isopropylpyridine-2,3-diamine (XXI) (2.08 g, 9.04 mmol) and $Ac_2O$ (1.05 mL, 10.84 mmol) in HOAc (20 mL) was heated to 120° C. for 16 h. The reaction mixture was concentrated, the residue partitioned between EtOAc/1 N NaOH, organics separated, washed with water and brine. The organics were dried over anhydrous $Na_2SO_4$, solvents concentrated and dried under high vacuo to give 6-bromo-1-isopropyl-2-methyl-1H-imidazo[4,5-b]pyridine (XXII) (1.57 g, 6.178 mmol, 68.3% yield) as a dark brown solid which was used for next step without purification. ESIMS found for $C_{10}H_{12}BrN_3$ m/z 254.0 (M+H).

The following intermediates were prepared in accordance with the procedure described in the above Scheme 4.

XXIII

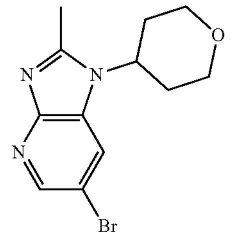

6-Bromo-2-methyl-1-(tetrahydro-2H-pyran-4-yl)-1H-imidazo[4,5-b]pyridine (XXIII): Grey solid (722 mg, 2.438 mmol, 66.3% yield). ESIMS found $C_{12}H_{14}BrN_3O$ m/z 296.0 (M+H).

XXIV

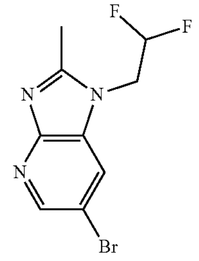

6-Bromo-1-(2,2-difluoroethyl)-2-methyl-1H-imidazo[4,5-b]pyridine (XXIV): Grey solid (325 mg, 1.177 mmol, 47.1% yield). ESIMS found $C_9HgBrF_2N_3$ m/z 276.0 (M+H).

Preparation of intermediate (R)-2-((6-bromo-2-methyl-1H-imidazo[4,5-b]pyridin-1-yl)methyl)-5-(1-fluoroethyl)-1,3,4-oxadiazole (XXXI) is depicted below in Scheme 5.

Step 1

A mixture of $^tBuOK$ (2.1 g, 18.71 mmol) and 6-bromo-2-methyl-3H-imidazo[4,5-b]pyridine (XXV) (4 g, 18.86 mmol) in THF (40 mL) was stirred at 50° C. for 20 minutes. Methyl bromoacetate (XXVI) (1.98 mL, 20.92 mmol) was added to the mixture. The mixture was stirred at 50° C. for 1 h. The reaction was stopped with HOAc/water (1/10, 10 mL) at 0° C., and the mixture was diluted with EtOAc (20 mL) and a saturated aqueous $NaHCO_3$ (20 mL). The mixture was concentrated, and the precipitate collected by filtration, and the obtained solid was washed with water and small amount of EtOAc to obtain a light brown compound with two products. The aqueous phase was extracted with $CHCl_3$ (3*50 mL) and combined with the solid and purified by silica gel column chromatography (0→40% 1.7 N $NH_3$ in MeOH) to produce two sets of fractions containing the correct molecular weight by LC/MS. The least polar fractions were isolated as the byproduct, methyl 2-(6-bromo-2-methyl-3H-imidazo[4,5-b]pyridin-3-yl)acetate (XXVII)

Scheme 5

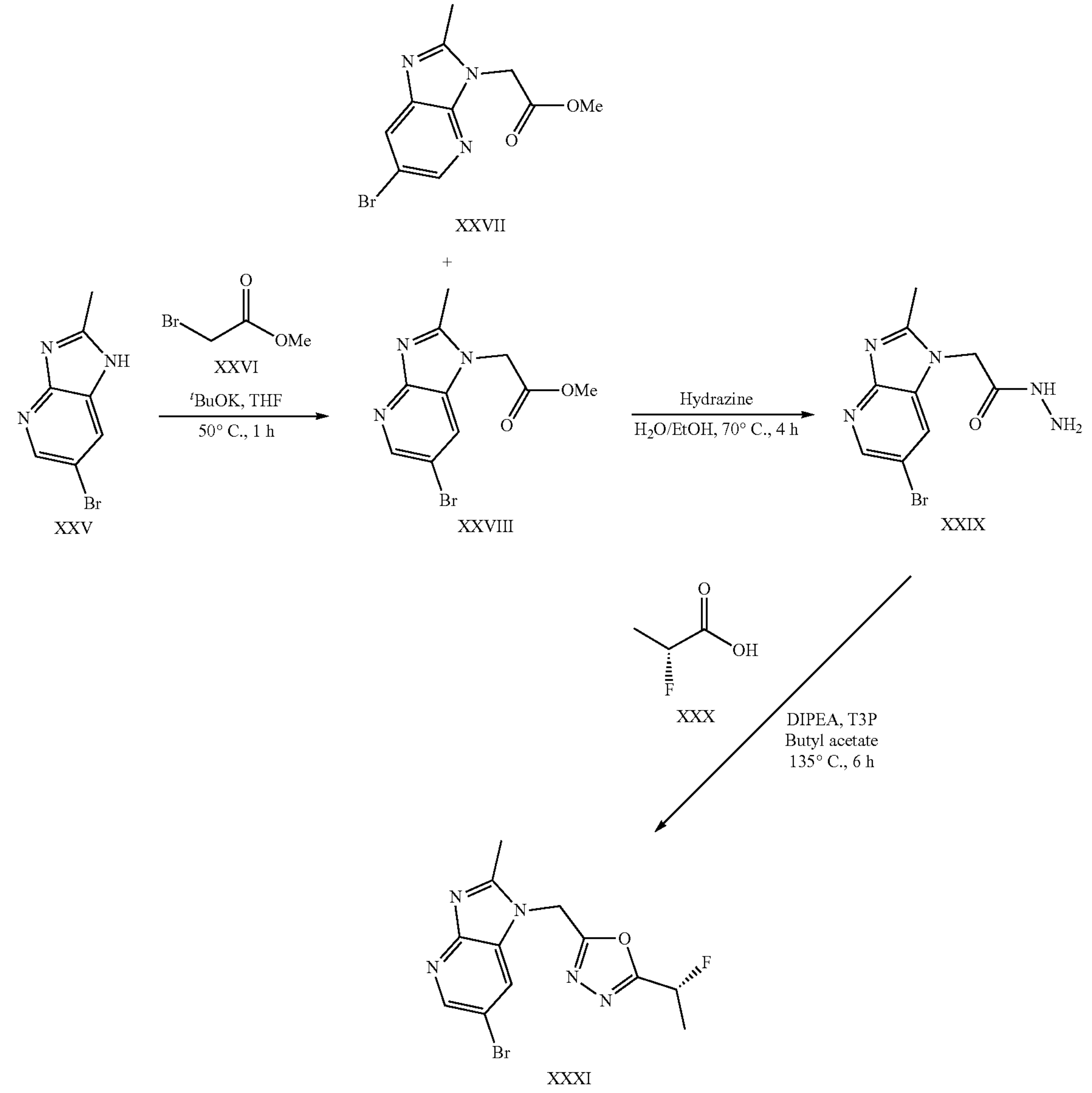

methyl (1.48 g, 5.209 mmol, 27.6% yield). $^1$H NMR (500 MHz, DMSO-$d_6$) δ ppm 2.54 (3H, s), 3.71 (3H, s), 5.18 (2H, s), 8.25 (1H, d, J=1.65 Hz), 8.36 (1H, d, J=1.37 Hz); ESIMS found for $C_{10}H_{10}BrN_3O_2$ m/z 284.0 (M+H). The more polar fractions were isolated as the desired product, methyl 2-(6-bromo-2-methyl-1H-imidazo[4,5-b]pyridin-1-yl)acetate (XXVIII) (2.43 g, 8.55 mmol, 45.3% yield) as an off-white solid. $^1$H NMR (499 MHz, DMSO-$d_6$) δ ppm 2.51 (3H, s), 3.72 (3H, s), 5.27 (2H, s), 8.33 (1H, d, J=2.19 Hz), 8.41 (1H, d, J=2.19 Hz); ESIMS found for $C_{10}H_{10}BrN_3O_2$ m/z 284.0 (M+H).

Step 2

A suspension of methyl 2-(6-bromo-2-methylimidazo[4,5-b]pyridin-1-yl)acetate (XXVIII) (2.35 g, 8.27 mmol)) in EtOH (26 mL)/water (1.3 mL) was stirred at 70° C. for 10 min (clear yellow solution). Hydrazine hydrate (3.6 mL, 73.86 mmol) was added to the mixture, and the mixture was stirred at 70° C. for 4 h (off-white ppt forms). The reaction was cooled to room temperature and concentrated. The precipitate was collected by filtration and washed with EtOH to obtain 2-(6-bromo-2-methylimidazo[4,5-b]pyridin-1-yl)acetohydrazide (XXIX) (1.94 g, 6.828 mmol, 82.6% yield) as an off-white solid. $^1$H NMR (499 MHz, DMSO-$d_6$) δ ppm 2.53 (3H, s), 4.36 (2H, br s), 4.87 (2H, s), 8.22 (1H, d, J=2.19 Hz), 8.39 (1H, d, J=2.19 Hz), 9.48 (1H, br s); ESIMS found for $C_9H_{10}BrN_5O$ m/z 284.0 (M+H).

Step 3

(2R)-2-Fluoropropanoic acid (XXX) (0.16 g, 1.76 mmol), 2-(6-bromo-2-methylimidazo[4,5-b]pyridin-1-yl)acetohydrazide (XXIX) (0.5 g, 1.76 mmol), T3P in EtOAc (1.2 mL, 2.06 mmol) and DIPEA (0.89 mL, 5.11 mmol) were added to butyl acetate (11 mL) at room temperature in a microwave vial. The vial was sealed, and the mixture was stirred at 50° C. for 30 minutes, a 2$^{nd}$ a batch of T3P in EtOAc (1.2 mL, 2.06 mmol) was added to the mixture, and the resulting mixture was heated to 135° C. for 3 h. The reaction was still not complete. A 3$^{rd}$ batch of T3P in EtOAc (0.58 mL, 1 mmol) was added and the mixture was stirred at 135° C. for another 3 h. The mixture was cooled, a saturated aqueous $NaHCO_3$ (30 mL) was then added to the mixture. The liquid layer was extracted with EtOAc (75 mL*3), the organic layer was washed with water and a saturated brine and dried over $Na_2SO_4$. The organic layer was purified by silica gel column chromatography (0→5% MeOH/$CHCl_3$) to produce (R)-2-((6-bromo-2-methyl-1H-imidazo[4,5-b]pyridin-1-yl)methyl)-5-(1-fluoroethyl)-1,3,4-oxadiazole (XXXI) (430 mg, 1.264 mmol, 71.8% yield) as an off-white solid. $^1$H NMR (499 MHz, DMSO-$d_6$) δ ppm 1.71 (3H, dd, J=24.40, 6.60 Hz), 2.62 (3H, s), 5.99 (1H, dq, J=47.20, 6.60 Hz), 5.95 (2H, s), 8.38 (1H, d, J=2.19 Hz), 8.45 (1H, d, J=2.19 Hz); ESIMS found for $C_{12}H_{11}BrFN_5O$ m/z 340.0 (M+H).

Preparation of intermediate 5-chloro-3-ethyl-2-methyl-3H-imidazo[4,5-b]pyridine (XXXIII) is depicted below in Scheme 6.

Scheme 6

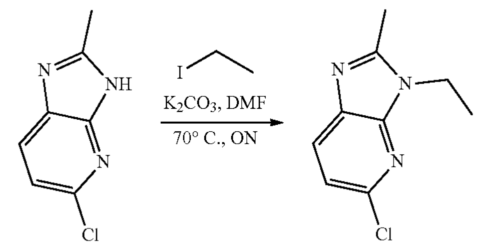

XXXII XXXIII

Step 1

A mixture of 5-chloro-2-methyl-3H-imidazo[4,5-b]pyridine (XXXII) (commercially available from eNovation Chemicals, LLC) (500 mg, 2.98 mmol), iodoethane (560 mg, 3.58 mmol) and $K_2CO_3$ (830 mg, 5.97 mmol) in DMF (10 mL) was heated to 70° C. overnight. The reaction mixture was cooled, solvents concentrated, the residue partitioned between EtOAc/water, the organic layers were separated, washed with brine, dried over anhydrous $MgSO_4$ and the solvents were concentrated under vacuo and dried to obtain 5-chloro-3-ethyl-2-methylimidazo[4,5-b]pyridine (XXXIII) (466 mg, 2.382 mmol, 79.8% yield) as a dark brown solid which was used for next step without purification. ESIMS found for $C_9H_{10}ClN_3$ m/z 196.05 (M+H).

The following intermediates were prepared in accordance with the procedure described in the above Scheme 6.

XXXIV

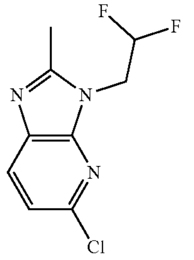

5-Chloro-3-(2,2-difluoroethyl)-2-methyl-3H-imidazo[4,5-b]pyridine (XXXIV): Beige solid (830 mg, 3.583 mmol, 60.1% yield). ESIMS found $C_9H_8ClF_2N_3$ m/z 232.0 (M+H).

XXXV

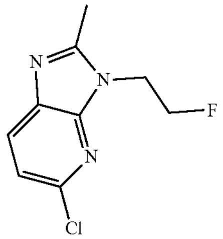

5-Chloro-3-(2-fluoroethyl)-2-methyl-3H-imidazo[4,5-b]pyridine (XXXV): Beige solid (220 mg, 1.030 mmol, 57.5% yield). ESIMS found $C_9H_9ClFN_3$ m/z 214.05 (M+H).

XXXVI

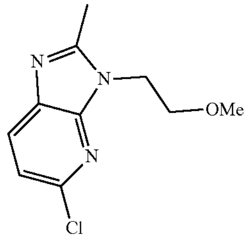

5-Chloro-3-(2-methoxyethyl)-2-methyl-3H-imidazo[4,5-b]pyridine (XXXVI): Beige solid (195 mg, 0.864 mmol, 48.3% yield). ESIMS found $C_{10}H_{12}ClN_3O$ m/z 226.1 (M+H).

XXXVII

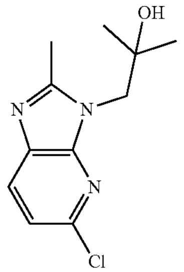

1-(5-Chloro-2-methyl-3H-imidazo[4,5-b]pyridin-3-yl)-2-methylpropan-2-ol (XXXVII): White solid (229.9 mg, 0.959 mmol, 39.7% yield). $^1H$ NMR (499 MHz, DMSO-$d_6$) δ ppm 1.13 (6H, s), 2.63 (3H, s), 4.11 (2H, s), 4.80 (1H, s), 7.25 (1H, d, J=8.21 Hz), 7.96 (1H, d, J=8.21 Hz); ESIMS found $C_{11}H_{14}ClN_3O$ m/z 240.1 (M+H).

XXXVIII

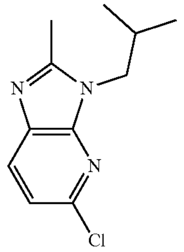

5-Chloro-3-isobutyl-2-methyl-3H-imidazo[4,5-b]pyridine (XXXVIII): White solid (206.8 mg, 0.925 mmol, 38.7% yield). $^1H$ NMR (499 MHz, DMSO-$d_6$) δ ppm 0.87 (6H, d, J=6.57 Hz), 2.22 (1H, dquin, J=13.89, 7.07, 7.07, 7.07, 7.07 Hz), 2.58 (3H, s), 4.01 (2H, d, J=7.67 Hz), 7.26 (1H, d, J=8.21 Hz), 7.98 (1H, d, J=8.21 Hz); ESIMS found $C_{11}H_{14}ClN_3$ m/z 224.1 (M+H).

XXXIX

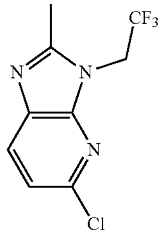

5-Chloro-2-methyl-3-(2,2,2-trifluoroethyl)-3H-imidazo[4,5-b]pyridine (XXXIX): Beige solid (372 mg, 1.490 mmol, 50.0% yield). ESIMS found $C_9H_7ClF_3N_3$ m/z 250.0 (M+H).

XL

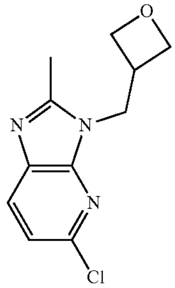

5-Chloro-2-methyl-3-(oxetan-3-ylmethyl)-3H-imidazo[4,5-b]pyridine (XL): Light brown solid (289.7 mg, 1.219 mmol, 40.4% yield). $^1H$ NMR (499 MHz, DMSO-$d_6$) δ ppm 2.59 (3H, s), 3.43-3.56 (1H, m), 4.47 (2H, t, J=6.02 Hz), 4.52 (2H, d, J=7.67 Hz), 4.62 (2H, dd, J=7.67, 6.02 Hz), 7.27 (1H, d, J=8.21 Hz), 7.98 (1H, d, J=8.21 Hz); ESIMS found $C_{11}H_{12}ClN_3O$ m/z 238.1 (M+H).

XLI

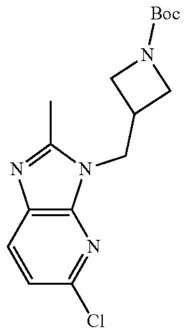

tert-Butyl 3-((5-chloro-2-methyl-3H-imidazo[4,5-b]pyridin-3-yl)methyl)azetidine-1-carboxylate (XLI): Off-white amorphous solid (532.6 mg, 1.581 mmol, 52.1% yield). ESIMS found $C_{16}H_{21}ClN_4O_2$ m/z 337.1 (M+H).

XLII

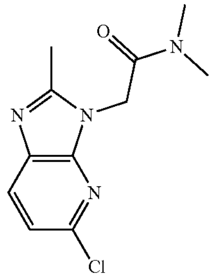

2-(5-Chloro-2-methyl-3H-imidazo[4,5-b]pyridin-3-yl)-N,N-dimethylacetamide (XLII): Off-white solid (474.4 mg, 1.877 mmol, 62.6% yield). ESIMS found $C_{11}H_{13}ClN_4O$ m/z 253.1 (M+H).

XLIII

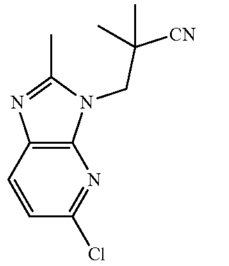

3-(5-Chloro-2-methyl-3H-imidazo[4,5-b]pyridin-3-yl)-2,2-dimethylpropanenitrile (XLIII): Off-white amorphous solid (59.1 mg, 0.238 mmol, 7.9% yield). ESIMS found $C_{12}H_{13}ClN_4$ m/z 249.1 (M+H).

XLIV

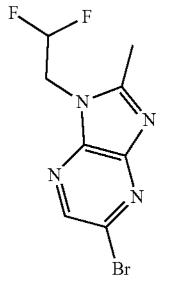

XLV

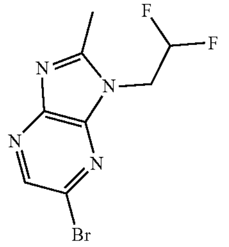

An inseparable mixture of 5-bromo-1-(2,2-difluoroethyl)-2-methylimidazo[4,5-b]pyrazine (XLIV) and 5-bromo-3-(2,2-difluoroethyl)-2-methylimidazo[4,5-b]pyrazine (XLV) (556 mg, 2.007 mmol, 40.7% yield) as a brown solid. ESIMS found $C_8H_7BrF_2N_4$ m/z 277.0 (M+H). Used as a mixture of the synthesis of compounds 1970 and 1971. Final compounds were separated by chiral supercritical fluid chromatography (SFC).

Preparation of intermediate 6-bromo-1-(2,2-difluoroethyl)-1H-benzo[d][1,2,3]triazole (XLIX) is depicted below in Scheme 7.

Scheme 7

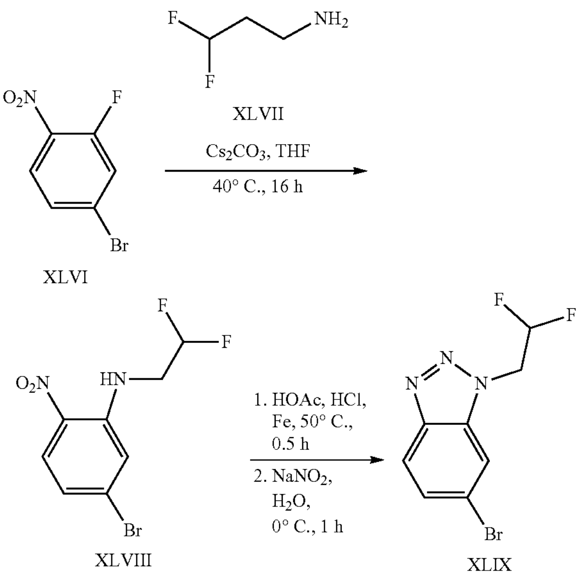

Step 1

A solution of 4-bromo-2-fluoro-1-nitrobenzene (XLVI) (20.0 g, 98.03 mmol) in THF (500.0 mL) was cooled to 0° C. $Cs_2CO_3$ (63.9 g, 196.06 mmol) was added, 2,2-difluoroethan-1-amine (XLVII) (36.6 g, 183.81 mmol) was added at 0° C. The reaction was warmed to 40° C. for 16 h. The reaction mixture was extracted with EtOAc (500 L×3). The combined organics were washed with brine (500 mL×3). The combined organic layers were dried with $Na_2SO_4$, filtered, and concentrated to give the crude product. The crude was purified by column chromatography on silica gel (10-20% EtOAc/petroleum ether) to give 5-bromo-N-(2,2-difluoroethyl)-2-nitroaniline (XLVIII) (23 g, 81.83 mmol, 83.5% yield) as a yellow solid. $^1H$ NMR (400 MHz, DMSO-$d_6$) δ 3.99 (tdd, J=15.6, 6.6, 3.8 Hz, 2H), 6.29 (tt, J=55.4, 3.7 Hz, 1H), 6.96 (dd, J=9.2, 2.0 Hz, 1H), 7.51 (d, J=1.6 Hz, 1H), 8.05 (d, J=9.2 Hz, 1H), 8.33 (t, J=6.4 Hz, 1H); ESIMS found for $C_8H_7BrF_2N_2O_2$ m/z 280.9 (M+H).

Step 2

To a solution of 5-bromo-N-(2,2-difluoroethyl)-2-nitroaniline (XLVIII) (12.0 g, 42.86 mmol) in HOAc/HCl (500/50 mL) was added Fe (30.0 g, 428.62 mmol). The reaction mixture was stirred at 50° C. for 30 minutes, then cooled to room temperature and filtered. $NaNO_2$ (3.0 g, 53.58 mmol) in water (20 mL) was then added dropwise into above acid solution at 0° C. The reaction solution was stirred for 1 h at 0° C. The reaction mixture was concentrated to dryness, the reaction mixture was poured into EtOAc (300 mL) and $H_2O$ (300 mL). The pH was adjusted >7 with $NaHCO_3$. The reaction mixture was extracted with EtOAc (500 mL×3).

The combined organics were washed with brine (500 mL×3). The organic layers was concentrated, dried over $Na_2SO_4$, filtered, and concentrated to give the crude. The crude was purified by column chromatography on silica gel (10→50% EtOAc/petroleum ether) to give 6-bromo-1-(2,2-difluoroethyl)-1H-benzo[d][1,2,3]triazole (XLIX) (5 g, 19.08 mmol, 44.5%) as a brown solid. $^1H$ NMR (400 MHz, DMSO-$d_6$) δ 5.41-5.29 (m, 2H), 6.61 (tt, J=54.2, 3.2 Hz, 1H), 7.60 (dd, J=8.8, 1.7 Hz, 1H), 8.08 (d, J=8.8 Hz, 1H), 8.31 (d, J=1.0 Hz, 1H); ESIMS found for $C_8H_6BrF_2N_3$ m/z 261.9 (M+H).

Preparation of intermediate (6-bromoimidazo[1,2-a]pyridin-3-yl)(pyrrolidin-1-yl)methanone (LII) is depicted below in Scheme 8.

Scheme 8

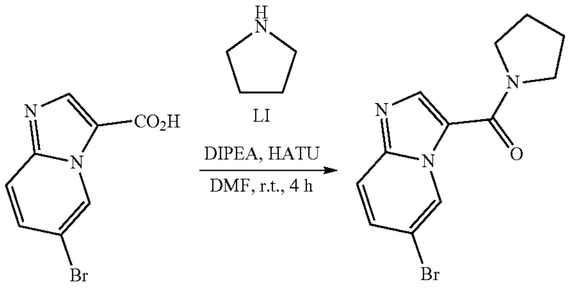

L LII

Step 1

A mixture of 6-bromoimidazo[1,2-a]pyridine-3-carboxylic acid (L) (0.5 g, 2.07 mmol), DIPEA (0.9 mL, 5.17 mmol) and HATU (0.79 g, 2.07 mmol) in DMF (4 mL) was stirred for 5 min. Pyrrolidine (LI) (0.32 mL, 3.18 mmol) was then added, and the reaction mixture was continued to stir at room temperature for 4 h. The solvent were concentrated, the residue partitioned between EtOAc and saturated aqueous $NaHCO_3$, the organic layer was separated, washed with water and brine. The organic layer was dried over anhydrous $Na_2SO_4$, concentrated and dried under high vacuo to obtain (6-bromoimidazo[1,2-a]pyridin-3-yl)-pyrrolidin-1-ylmethanone (LII) (577 mg, 1.962 mmol, 94.6% yield) as a beige solid. ESIMS found for $C_{12}H_{12}BrN_3O$ m/z 294.0 (M+H).

Preparation of intermediate imidazo[1,2-a]pyrimidin-6-ylboronic acid (LV) is depicted below in Scheme 9.

Scheme 9

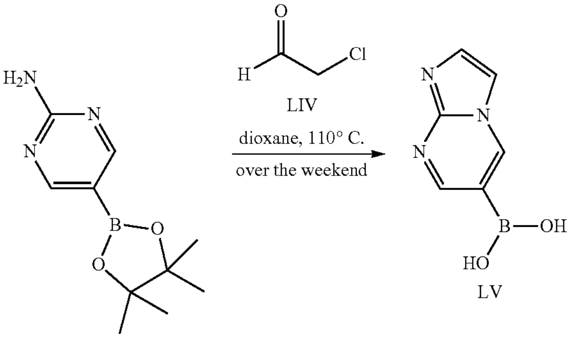

LV

LIII

Step 1

A mixture of 5-(4,4,5,5-tetramethyl-1,3,2-dioxaborolan-2-yl)pyrimidin-2-amine (LIII) (1 g, 4.52 mmol) and chloroacetaldehyde (LIV) (0.92 mL, 5.39 mmol) was dissolved in 1,4-dioxane (20 mL) and heated to 110° C. over the weekend. The reaction mixture was cooled, and the solids were collected by filtration and dried under high vacuo to obtain imidazo[1,2-a]pyrimidin-6-ylboronic acid (LV) (650 mg, 3.989 mmol, 88.2% yield) as a brown solid which was used for next step without purification. ESIMS found for $C_6H_6BN_3O_2$ m/z 164.1 (M+H).

Preparation of intermediate 6-bromo-3-methylimidazo[1,2-a]pyrimidine (LX) is depicted below in Scheme 10.

Scheme 10

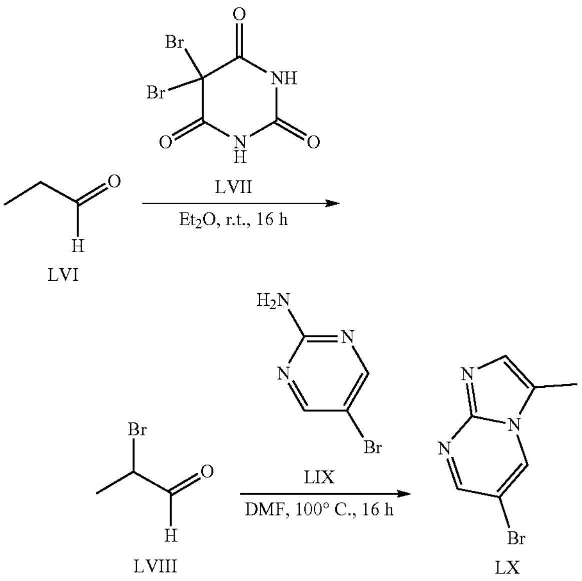

Step 1

To a mixture of propionaldehyde (LVI) (5 g, 70 mmol) in $Et_2O$ (150 mL) was added 5,5-dibromopyrimidine-2,4,6(1H,3H,5H)-trione (LVII) (9.91 g, 35 mmol) and the resulting mixture was stirred at room temperature for 16 h. After completion, the mixture was washed by petroleum ether (80 mL×2). The organic layer was filtered and concentrated to give 2-bromopropanal (LVIII) (2.0 g, 14.6 mmol, 20.9% yield) as a yellow oil.

Step 2

To a solution of 2-bromopropanal (LVIII) (0.7 g, 5.11 mol) in DMF (20 mL) was added 5-bromopyrimidin-2-amine (LIX) (0.97 g, 5.56 mmol) at room temperature under Ar. The mixture was stirred at 100° C. for 16 h. After completion, the mixture was diluted with EtOAc and washed with brine (20 mL×3). The organic layer was dried over anhydrous $Na_2SO_4$, filtered and concentrated. The crude residue was purified by silica gel column chromatography (0%→20% EtOAc/petroleum ether) to give 6-bromo-3-methylimidazo[1,2-a]pyrimidine (LX) (80 mg, 0.377 mmol, 7.4% yield) as a white solid. ESIMS found for $C_7H_6BrN_3$ m/z 212.1 (M+H).

The following intermediate was prepared in accordance with the procedure described in the above Scheme 10.

LXI

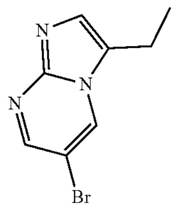

6-Bromo-3-ethylimidazo[1,2-a]pyrimidine (LXI): White solid (200 mg, 0.885 mmol, 19.1% yield). ESIMS found $C_8H_8BrN_3$ m/z 226.0 (M+H).

Preparation of intermediate cis-4-(methoxy-$d_3$)cyclohexan-1-amine (LXVII) is depicted below in Scheme 11.

Scheme 11

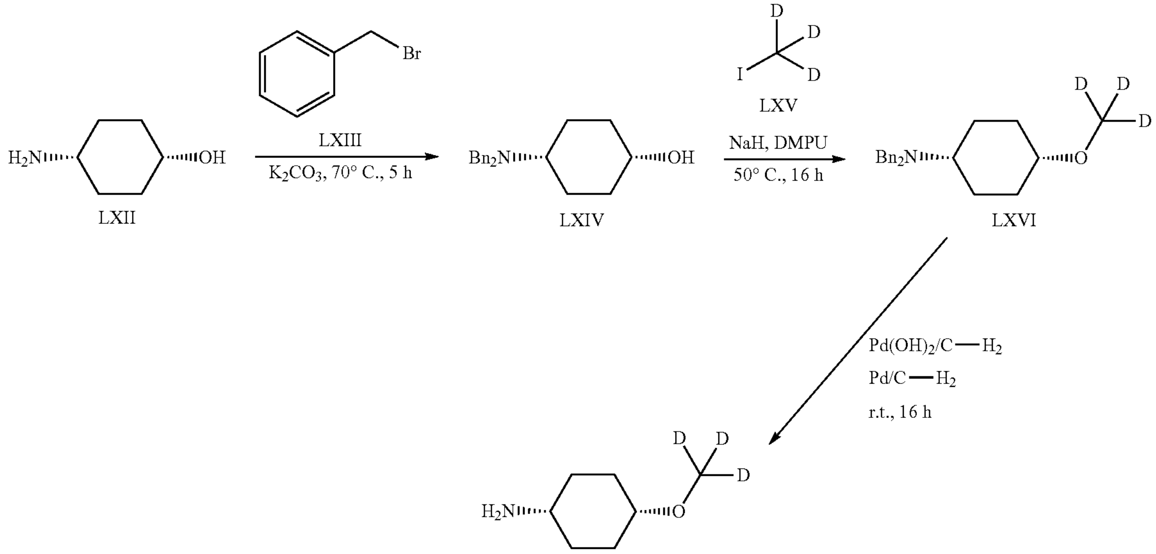

Step 1

To a solution of cis-4-aminocyclohexan-1-ol (LXII) (5 g, 32.9 mmol), (bromomethyl)benzene (LXIII) (11.25 g, 65.8 mmol) in MeCN (80 mL) was added $K_2CO_3$ (13.64 g, 98.7 mmol). The mixture was stirred at 70° C. for 5 h. The reaction mixture was concentrated under reduced pressure to remove MeCN. The mixture was diluted with EtOAc and then extracted with EtOAc (100 mL×3) and $H_2O$. The combined organic layers were concentrated, and the crude residue was purified by silica gel column chromatography (0%→30% EtOAc/petroleum ether) to give the cis-4-(dibenzylamino)cyclohexan-1-ol (LIV) (8.0 g, 27.08 mmol, 82.3% yield) as a white solid. ESIMS found for $C_{20}H_{25}NO$ m/z 296.4 (M+H).

Step 2

To a solution of cis-4-(dibenzylamino)cyclohexan-1-ol (LIV) (8.0 g, 27.08 mmol) in DMPU (80 mL) was added slowly NaH (5.98 g, 149.7 mmol) under nitrogen atmosphere with continuous stirring. The reaction mixture was stirred at room temperature for 1 h. Then iodomethane-$d_3$ (LXV) (10.85 g, 74.86 mmol) was added at room temperature over a period of 10 min. After complete addition, the reaction mixture was stirred at 50° C. for 16 h. The reaction mixture was then quenched with saturated aqueous $NH_4Cl$ (300 mL) and stirred for 10 min. The mixture was diluted with EtOAc and then extracted with EtOAc (300 mL×3) and $H_2O$. The crude residue was purified by silica gel column chromatography (0%-20% EtOAc/petroleum ether) to yield cis-N,N-dibenzyl-4-(methoxy-$d_3$)cyclohexan-1-amine (LXVI) (6 g, 19.202 mmol, 70.9% yield) as a colorless oil. ESIMS found for $C_{21}H_{24}D_3NO$ m/z 313.0 (M+H).

Step 3

To a solution of cis-N,N-dibenzyl-4-(methoxy-$d_3$)cyclohexan-1-amine (LXVI) (200 mg, 0.64 mmol) in EtOH (5 mL) was added $Pd(OH)_2/C$ (50 mg) and Pd/C (50 mg). The mixture was stirred at room temperature for 16 h. The mixture was filtered through Celite® and washed with EtOH. The reaction mixture was concentrated under reduced pressure to give the cis-4-(methoxy-$d_3$)cyclohexan-1-amine (LXVII) (76.4 mg, 0.578 mmol, 90.3% yield) as a colorless oil. $^1H$ NMR (400 MHz, DMSO-$d_6$) δ ppm 1.51-1.40 (m, 4H), 1.67-1.56 (m, 4H), 1.86 (td, J=9.8, 4.6 Hz, 2H), 2.71 (tt, J=10.8, 5.4 Hz, 1H), 3.34 (td, J=4.8, 2.4 Hz, 1H); ESIMS found for $C_7H_{12}D_3NO$ m/z 133.0 (M+H).

The following intermediates were prepared in accordance with the procedure described in the above Scheme 11.

LXVIII

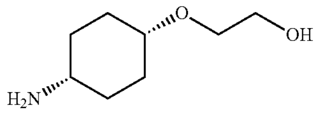

2-((cis-4-Aminocyclohexyl)oxy)ethan-1-ol (LXVIII): Colorless oil (0.5 g, 3.14 mmol, 67.4% yield). ESIMS found for $C_8H_{17}NO_2$ m/z 160. (M+H).

LXIX

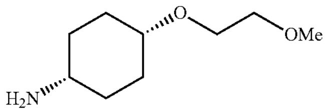

cis-4-(2-Methoxyethoxy)cyclohexan-1-amine (LXIX): Colorless oil (1.5 g, 8.65 mmol, 76.6% yield). ESIMS found for $C_9H_{19}NO_2$ m/z 174.1 (M+H).

LXX

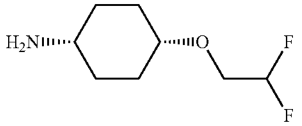

cis-4-(2,2-Difluoroethoxy)cyclohexan-1-amine (LXX): White solid (1.352 g, 7.54 mmol, 90.3% yield). ESIMS found for $C_8H_{15}F_2NO$ m/z 180.1 (M+H).

LXXI

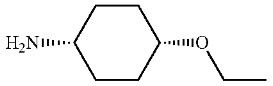

cis-4-Ethoxycyclohexan-1-amine (LXXI): Colorless oil (2 g, 13.96 mmol, 64.4% yield). $^1$H NMR (400 MHz, $CDCl_3$) δ 1.19 (t, J=7.0 Hz, 3H), 1.49-1.44 (m, 6H), 1.62-1.55 (m, 2H), 1.86-1.79 (m, 2H), 2.4-2.723 (m, 1H), 3.49-3.41 (m, 3H).

LXXII

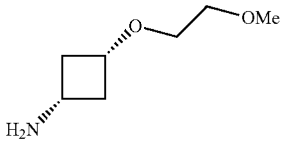

cis-3-(2-Methoxyethoxy)cyclobutan-1-amine (LXXII): Colorless oil. $^1$H NMR (400 MHz, DMSO-$d_6$) δ 1.51 (dd, J=13.4, 5.2 Hz, 2H), 2.49-2.40 (m, 2H), 2.89-2.75 (m, 1H), 3.23 (s, 3H), 3.37-3.35 (m, 3H), 3.47 (s, 2H), 3.54-3.48 (m, 1H).

Preparation of intermediate cis-4-(difluoromethoxy)cyclohexan-1-amine (LXXV) is depicted below in Scheme 12.

Scheme 12

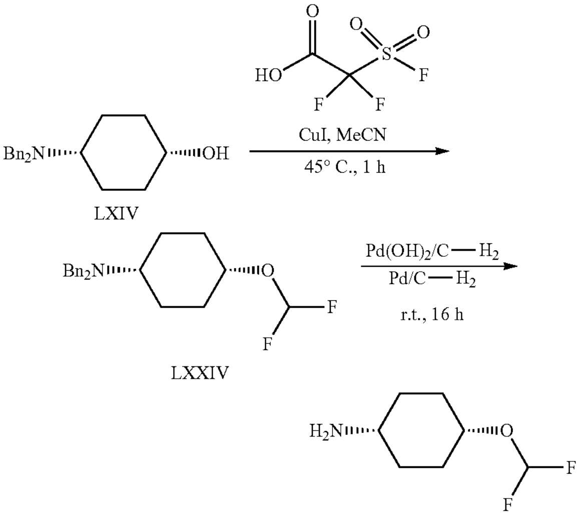

LXIV

LXXIV

LXXV

Step 1

To a solution of cis-4-(dibenzylamino)cyclohexan-1-ol (LXIV) (50 mg, 0.170 mmol), CuI (6.5 mg, 0.034 mmol) in MeCN (5 mL) and heated to 45° C. under nitrogen atmosphere for 5 min. To this mixture was added a solution of 2,2-difluoro-2-(fluorosulfonyl)acetic acid (LXXIII) (60 mg, 0.339 mmol) in (2 mL) MeCN over 10 min. Then the mixture was stirred at 45° C. for 1 h. Volatile components were then removed via evaporation and the residue was diluted with EtOAc (100 mL) and 100 mL of a 1:1 mixture of water and saturated aqueous $NaHCO_3$. The resulting biphasic mixture containing solids was filtered through a sintered glass Buchner funnel. The filtrate layers were separated, and the aqueous layer was extracted with EtOAc (50 mL). The combined EtOAc layers were washed with 50 mL of a 1:1 mixture of brine and water, dried over anhydrous $MgSO_4$, filtered, and concentrated to an oil. The crude oil was purified by silica gel chromatography (0-30% EtOAc/hexanes). Product containing fractions were combined and concentrated to afford the cis-N,N-dibenzyl-4-(difluoromethoxy)cyclohexan-1-amine (LXXIV) (25 mg, 0.072 mmol, 42.3% yield) as an oil that solidified to an off-white solid. ESIMS found for $C_{21}H_{25}F_2NO$ m/z 346.1 (M+H).

Step 2

To a solution of cis-N,N-dibenzyl-4-(difluoromethoxy)cyclohexan-1-amine (LXXIV) (2.8 g, 8.11 mmol) in THF (60 mL) was added Pd $(OH)_2$/C (1.4 g) and Pd/C (1.4 g). The mixture was stirred at room temperature for 16 h. The mixture was filtered through Celite® and washed with THF. The reaction mixture was concentrated under reduced pressure to afford cis-4-(difluoromethoxy)cyclohexan-1-amine (LXXV) (1.05 g, 6.36 mmol, 78.4% yield) as a colorless oil. ESIMS found for $C_7H_{13}F_2NO$ m/z 166.1 (M+H).

Preparation of intermediate 1-(3,3,3-trifluoropropyl)piperidin-4-amine (LXXIX) is depicted below in Scheme 13.

Scheme 13

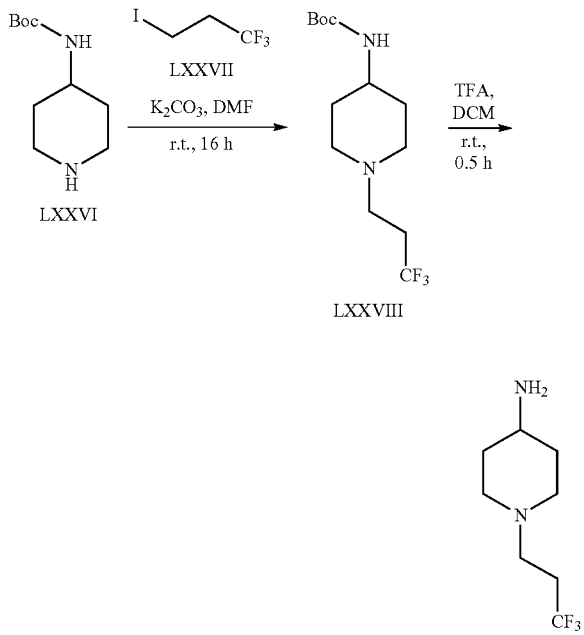

LXXVI LXXVII LXXVIII LXXIX

Step 1 tert-Butyl piperidin-4-ylcarbamate (LXXVI) (Commercially available from Combi-Blocks Inc.) (1 g, 4.99 mmol) and $K_2CO_3$ (1.73 g, 12.52 mmol) were dissolved in DMF (15 mL) and 1-iodo-3,3,3-trifluoropropane (LXXVII) (878 µL, 7.49 mmol) was added and the reaction was stirred at room temperature for 16 h. The reaction mixture was poured in EtOAc, and the aqueous layer was separated. The aqueous layer was extracted with EtOAc (x3) and then the combined organic layers were acidified to pH 4.5 with 1 M citric acid. The organic layer was washed three times with small volumes of water to remove unreacted SM. Sufficient amounts of the product remained in the organic layer which was dried using anhydrous $MgSO_4$ and reduced in vacuo to give the product tert-butyl N-[1-(3,3,3-trifluoropropyl)piperidin-4-yl]carbamate (LXXVIII) (861 mg, 2.906 mmol, 58.2% yield) as a white solid. ESIMS found for $C_{13}H_{23}F_3N_2O_2$ m/z 297.2 (M+H).

Step 2 tert-Butyl N-[1-(3,3,3-trifluoropropyl)piperidin-4-yl]carbamate (LXXVIII) (200 mg, 0.670 mmol) was dissolved in DCE (3.2 mL) and TFA (800 µL, 10.38 mmol) was added and the reaction was stirred at room temperature for 30 m. The reaction mixture was blown dry and excess TFA removed by high vacuum to give the crude intermediate 1-(3,3,3-trifluoropropyl)piperidin-4-amine (LXXIX) (209 mg, 0.674 mmol, 99.8% yield) as a white semi-solid which was used without further purification. ESIMS found for $C_8H_{15}F_3N_2$ m/z 197.1 (M+H).

Preparation of intermediate N-(trans-4-aminocyclohexyl) acetamide (LXXXII) is depicted below in Scheme 14.

Scheme 14

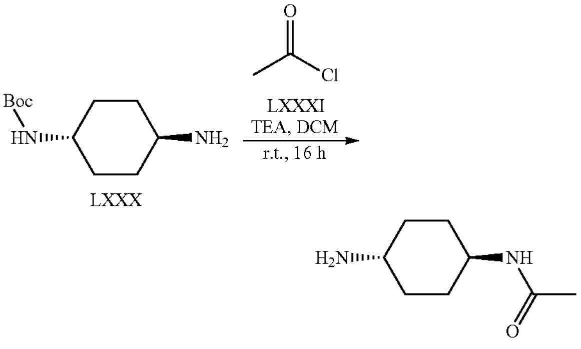

LXXXI LXXX LXXXII

Step 1

To a stirring solution of tert-butyl N-(4-aminocyclohexyl) carbamate (LXXX) (Commercially available from Combi-Blocks Inc.) (0.6 g, 2.8 mmol) in DCM (6 mL) was added TEA (1.2 mL, 8.61 mmol). Acetyl chloride (LXXXI) (0.22 mL, 3.09 mmol) was then slowly, and the reaction mixture was stirred at room temperature for 16 h. The solvent was removed, and the crude material was dissolved in EtOAc, washed with 1 M NaOH, brine, and dried over anhydrous $MgSO_4$ and finally concentrated. The product was dissolved in EtOH (2 mL) and 4 M HCl (1 mL). The solution was stirred at room temperature for 2 h before evaporating to dryness to give the HCl salt of N-(4-aminocyclohexyl) acetamide (LXXXII) (480 mg, 2.49 mmol, 89.0% yield) as a white solid. ESIMS found for $C_8H_{16}N_2O$ m/z 157.05 (M+H).

Preparation of intermediate cis-4-amino-N,N-dimethylcyclohexane-1-carboxamide (LXXXIV) is depicted below in Scheme 15.

Scheme 15

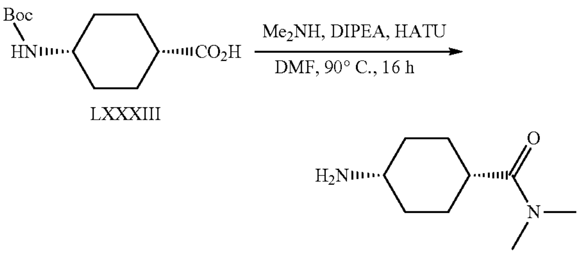

LXXXIII LXXXIV

Step 1

To a stirring solution of 4-(tert-butoxycarbonylamino) cyclohexanecarboxylic acid (LXXXIII) (Commercially available from Combi-Blocks Inc.) (0.3 g, 1.23 mmol) in DMF (6 mL) was added DIPEA (0.65 mL, 3.73 mmol) and HATU (0.7 g, 1.85 mmol). Reaction was stirred for 5 min at room temperature. Dimethylamine (0.92 mL, 1.84 mmol) was added, and reaction was heated to 90 C for 16 h. The reaction was concentrated and dissolved in EtOH (2 mL) and 4 M HCl in dioxane (1 mL). The mixture was stirred for 2 h at room temperature, concentrated under vacuum to yield the HCl salt of 4-amino-N,N-dimethylcyclohexane-1-carboxamide (LXXXIV) (280 mg, 1.355 mmol, 109.9% yield) as a light brown viscous solid. ESIMS found for $C_9H_{18}N_2O$ m/z 171.15 (M+H).

The following intermediate was prepared in accordance with the procedure described in the above Scheme 15.

LXXXV

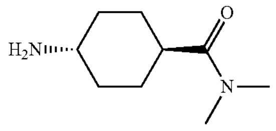

trans-4-Amino-N,N-dimethylcyclohexane-1-carboxamide (LXXXV): Light brown viscous solid (290 mg, 1.403 mmol, 113.8% yield). ESIMS found for $C_9H_{18}N_2O$ m/z 171.1 (M+H).

Example 1

Preparation of N-(cyclopropylmethyl)-5-(imidazo[1,2-a]pyridin-6-yl)pyrrolo[2,1-f][1,2,4]triazin-2-amine (16) is depicted below in Scheme 16.

Step 1

To a solution of 5-bromo-2-(methylthio)pyrrolo[2,1-f][1,2,4]triazine (VII) (commercially available from Combi-Blocks Inc.) (4.0 g, 15.59 mmol) in DCM (80 mL) was added m-CPBA (3.22 g, 18.66 mmol) at 0° C. The mixture was stirred at room temperature for 16 h. The reaction mixture was quenched with saturated aqueous $NaS_2O_3$ at 0° C., diluted with $H_2O$ (50 mL) and extracted with EtOAc (200 mL). The combined organic layers were concentrated to give the residue. The aqueous phase was concentrated, washed with DCM/MeOH (200 mL/10 mL), filtered to give a residue. The combined residue was purified by reverse phase chromatography (C18-I, Regular C18 20-40 μm, 120 g, 40→45% MeCN/0.1% formic acid in $H_2O$) to afford 5-bromo-2-(methylsulfinyl)pyrrolo[2,1-f][1,2,4]triazine (VIII) (1.5 g, 5.767 mmol, 37%) as a yellow solid. $^1H$ NMR (400 MHz, $CDCl_3$) δ 3.01 (s, 3H), 7.10 (d, J=2.8 Hz, 1H), 7.97 (d, J=2.7 Hz, 1H), 8.93 (s, 1H); ESIMS found for $C_7H_6BrN_3OS$ m/z 261.9 ($^{81}$BrM+H).

Step 2

A solution of 5-bromo-2-(methylsulfinyl)pyrrolo[2,1-f][1,2,4]triazine (VIII) (400 mg, 1.55 mmol), imidazo[1,2-a]

Scheme 16

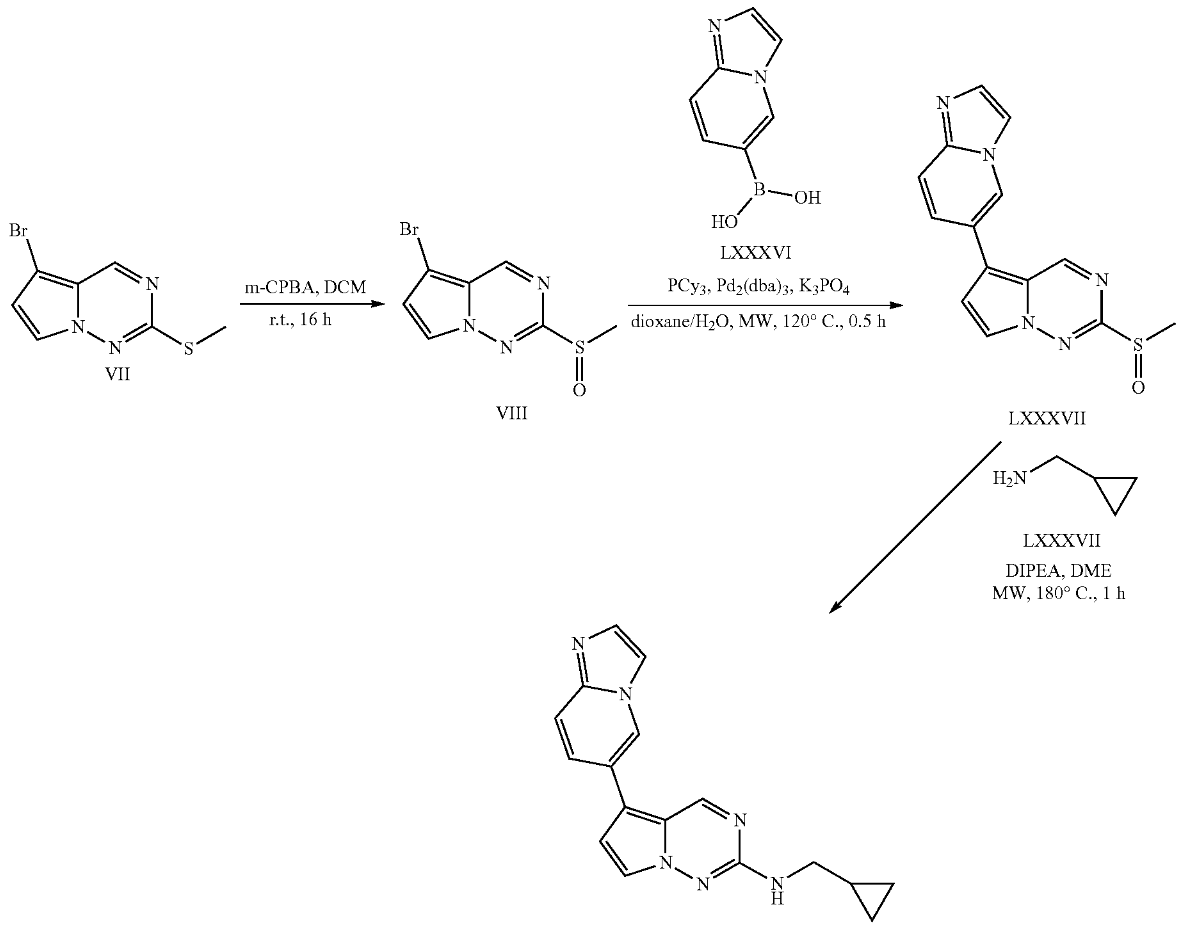

16 pyridin-6-ylboronic acid (LXXXVI) (commercially available from Synthonix Corporation) (301.2 mg, 1.86 mmol), $PCy_3$ (86.8 mg, 0.31 mmol), $Pd_2(dba)_3$ (141.8 mg, 0.155 mmol) and $K_3PO_4$ (657.2 mg, 3.1 mmol) in 1,4-dioxane/$H_2O$ (6 mL/2 mL) was irradiated with microwave at 120° C. for 0.5 h under $N_2$. The reaction mixture was diluted with $H_2O$ (30 mL) and extracted with EtOAc (60 mL). The combined organic layers were concentrated to give the residue. The residue was purified by reverse phase chromatography (C18-I, Regular C18, 20-40 μm, 120 g, 50% MeCN/0.1% formic acid in $H_2O$) to afford the product 5-(imidazo[1,2-a]pyridin-6-yl)-2-(methylsulfinyl)pyrrolo[2,1-f][1,2,4]triazine (LXXXVII) (240 mg, 0.807 mmol, 52.1% yield) as a yellow solid. ESIMS found for $C_{14}H_{11}N_5OS$ m/z 298. (M+H).

Step 3

A solution of 5-(imidazo[1,2-a]pyridin-6-yl)-2-(methylsulfinyl)pyrrolo[2,1-f][1,2,4]triazine (LXXXVII) (58 mg, 0.185 mmol), cyclopropylmethanamine (LXXXVIII) (40.0 mg, 0.555 mmol) and DIPEA (71.8 mg, 0.555 mmol) in DME (2 mL) was irradiated with microwave at 180° C. for 1 h. The reaction mixture was diluted with $H_2O$ (30 mL) and extracted with EtOAc (60 mL). The combined organic layers were concentrated to give the residue. The residue was purified by preparative HPLC (Sunfire C18 21.2*250 mm*10 μm, 18→20% MeCN/0.1% formic acid in $H_2O$) to afford N-(cyclopropylmethyl)-5-(imidazo[1,2-a]pyridin-6-yl)pyrrolo[2,1-f][1,2,4] triazin-2-amine (16) (5.16 mg, 0.017 mmol, 9.2% yield) as a yellow solid. H NMR (400 MHz, DMSO-$d_6$) δ ppm 0.19-0.28 (2H, m), 0.40-0.50 (2H, m), 1.07-1.17 (1H, m), 3.09 (2H, t, J=6.24 Hz), 6.96 (1H, d, J=2.57 Hz), 7.04 (1H, t, J=5.81 Hz), 7.53-7.65 (2H, m), 7.58 (1H, d, J=1.10 Hz), 7.71 (1H, dd, J=2.45, 0.61 Hz), 7.95 (1H, s), 8.92 (1H, dd, J=1.65, 1.04 Hz), 9.12 (1H, s); ESIMS found for $C_{17}H_{16}N_6$ m/z 305.3 (M+1).

Example 2

Preparation of (R)-5-(imidazo[1,2-a]pyrimidin-6-yl)-N-(1,1,1-trifluoropropan-2-yl)pyrrolo[2,1-f][1,2,4]triazin-2-amine (219) is depicted below in Scheme 17.

Scheme 17

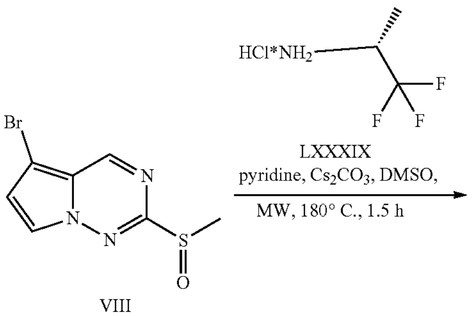

LXXXIX

VIII

-continued

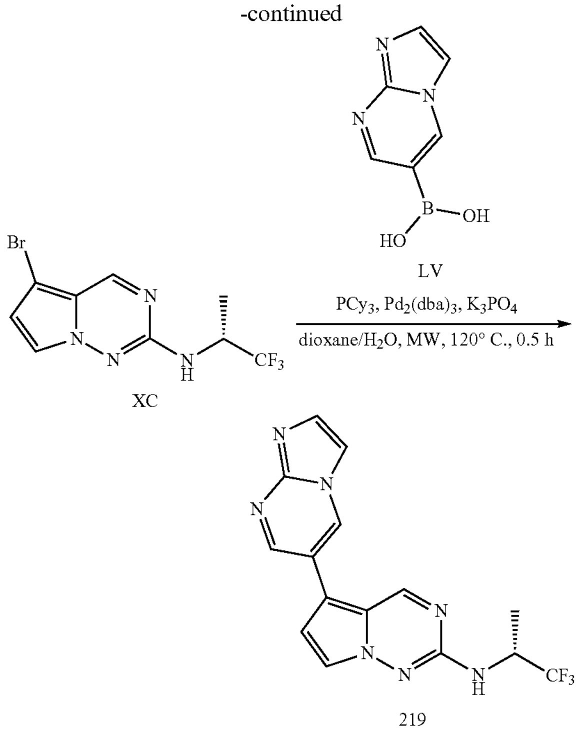

LV

XC

219

Step 1

(R)-1,1,1-Trifluoropropan-2-amine (LXXXIX) (433.7 mg, 0.29 mmol) and $Cs_2CO_3$ (945.4 mg, 2.9 mmol) were dissolved in DMSO (2 mL) and stirred for 30 min. To this mixture was added 5-bromo-2-(methylsulfinyl)pyrrolo[2,1-f][1,2,4]triazine (VIII) (150 mg, 0.58 mmol) and pyridine (229.39 mg, 2.9 mmol). The resulting mixture was sealed and irradiated with microwave at 180° C. for 1.5 h. The reaction mixture was then cooled to room temperature and diluted with EtOAc (30 mL). The solution was washed with water (30 mL), and the aqueous portion was extracted with EtOAc (30 mL). The combined organic extracts were washed with brine (30 mL) and dried over anhydrous $MgSO_4$, filtrated, and concentrated in vacuo to afford the crude product which was purified by pre-TLC (16.7% EtOAc/petroleum ether) to give (R)-5-bromo-N-(1,1,1-trifluoropropan-2-yl)pyrrolo[2,1-f][1,2,4]triazin-2-amine (XC) (58 mg, 0.187 mmol, 64.5% yield) as a yellow solid. ESIMS found for $C_9H_8BrF_3N_4$ m/z 309.0 ($^{79}$BrM+H).

Step 2

Performed using procedure shown in Example 3, Scheme 18, Step 2 to yield (R)-5-(Imidazo[1,2-a]pyrimidin-6-yl)-N-(1,1,1-trifluoropropan-2-yl)pyrrolo [2,1-f][1,2,4]triazin-2-amine (219) (20.91 mg, 0.060 mmol) as a yellow solid. $^1$H NMR (400 MHz, DMSO-$d_6$) δ ppm 1.37 (3H, d, J=7.00 Hz), 4.66-4.82 (1H, m), 7.15 (1H, d, J=2.50 Hz), 7.60 (1H, d, J=9.13 Hz), 7.75 (1H, d, J=1.13 Hz), 7.84 (1H, d, J=2.63 Hz), 7.90 (1H, d, J=1.25 Hz), 8.90 (1H, d, J=2.50 Hz), 9.24 (1H, s), 9.33 (1H, d, J=2.50 Hz); ESIMS found for $C_{15}H_{12}F_3N_7$ m/z 348.1 (M+1).

Example 3

Preparation of 5-(imidazo[1,2-a]pyrimidin-6-yl)-N-(tetrahydro-2H-pyran-4-yl)pyrrolo[2,1-f][1,2,4]triazin-2-amine (280) is depicted below in Scheme 18.

Scheme 18

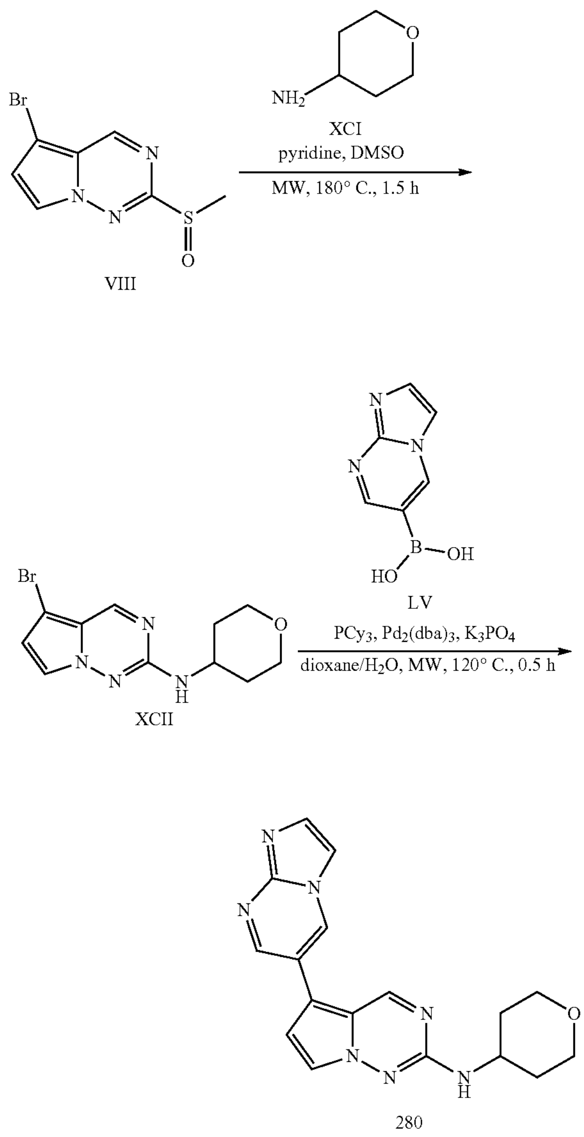

Step 1

A solution of 5-bromo-2-(methylsulfinyl)pyrrolo[2,1-f][1,2,4]triazine (VIII) (150 mg, 0.58 mmol), tetrahydro-2H-pyran-4-amine (XCI) (293.3 mg, 2.9 mmol), and pyridine (225 μL, 2.9 mmol) in DMSO (3 mL) was sealed and irradiated with microwave at 180° C. for 1.5 h. The reaction mixture was then cooled to room temperature and diluted with EtOAc (30 mL). The solution was washed with water (30x3 mL), and the aqueous portion was extracted with EtOAc (30x3 mL). The combined organic extracts were washed with brine (30x3 mL) and dried over anhydrous $Na_2SO_4$, filtrated, and concentrated in vacuo to afford the crude residue. The residue was purified by pre-TLC (20% EtOAc/petroleum ether) to afford 5-bromo-N-(tetrahydro-2H-pyran-4-yl)pyrrolo[2,1-f][1,2,4]triazin-2-amine (XCII) (220 mg, 0.740 mmol, >100% yield) as a yellow solid. ESIMS found for $C_{11}H_{13}BrN_4O$ m/z 297.0 ($^{79}$BrM+H).

Step 2

A solution of 5-bromo-N-(tetrahydro-2H-pyran-4-yl)pyrrolo[2,1-f][1,2,4]triazin-2-amine (XCII) (190 mg, 0.64 mmol), imidazo[1,2-a]pyrimidin-6-ylboronic acid (LV) (1.04 g, 6.4 mmol), $PCy_3$ (71.8 mg, 0.26 mmol), $Pd_2(dba)_3$ (117.1 mg, 0.13 mmol) and $K_3PO_4$ (407.6 mg, 1.92 mmol) in dioxane/water (12 mL, 3:1 ratio) was sealed and irradiated with microwave at 120° C. for 30 min. The reaction mixture was then cooled to room temperature and diluted with EtOAc (30x3 mL). The solution was washed with water (30x3 mL), and the aqueous portion was extracted with EtOAc (30x3 mL). The combined organic extracts were washed with brine (30x3 mL) and dried over anhydrous $Na_2SO_4$, filtrated, and concentrated in vacuo to afford the crude which was purified by pre-TLC (6.25% MeOH/DCM→50% EtOAc/petroleum ether) to produce 5-(imidazo[1,2-a]pyrimidin-6-yl)-N-(tetrahydro-2H-pyran-4-yl)pyrrolo[2,1-f][1,2,4]triazin-2-amine (280) (25.1 mg, 0.075 mmol, 11.7% yield) as a yellow solid. $^1$H NMR (400 MHz, DMSO-$d_6$) δ ppm 1.45-1.61 (2H, m), 1.90 (2H, br dd, J=12.51, 2.00 Hz), 3.35-3.43 (2H, m), 3.72-3.83 (1H, m), 3.84-3.93 (2H, m), 7.01 (1H, d, J=7.75 Hz), 7.06 (1H, d, J=2.50 Hz), 7.74 (2H, dd, J=4.13, 1.88 Hz), 7.89 (1H, d, J=1.25 Hz), 8.88 (1H, d, J=2.50 Hz), 9.16 (1H, s), 9.29 (1H, d, J=2.50 Hz); ESIMS found for $C_{17}H_{17}N_7O$ m/z 336.1 (M+1).

Example 4

Preparation of 5-(1-(2,2-difluoroethyl)-2-methyl-1H-imidazo[4,5-b]pyridin-6-yl)-N-(2-fluoro-2-methylpropyl)pyrrolo[2,1-f][1,2,4]triazin-2-amine (642) is depicted below in Scheme 19.

Scheme 19

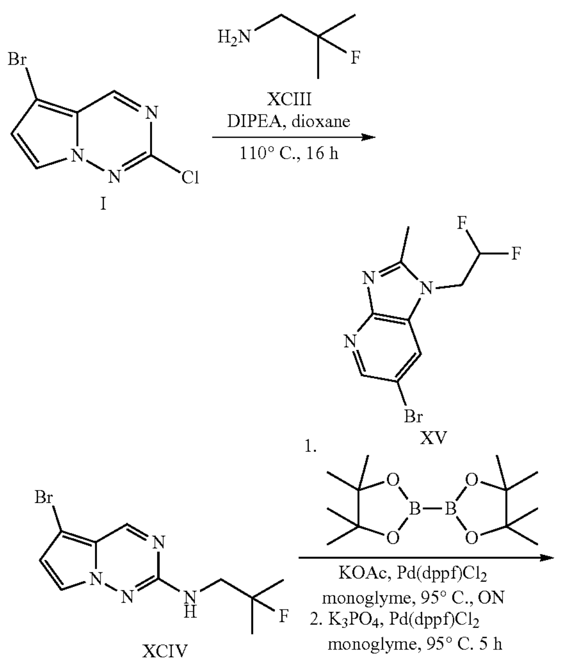

-continued

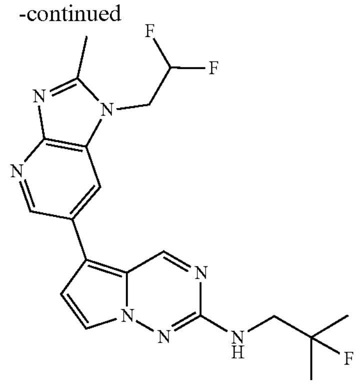

642

Step 1

A mixture of 2-fluoro-2-methylpropan-1-amine hydrochloride (XCIII) (290 mg, 2.26 mmol), 5-bromo-2-chloropyrrolo[2,1-f][1,2,4]triazine (I) (commercially available from Advanced ChemBlocks Inc.) (350 mg, 1.51 mmol) and DIPEA (1.2 mL, 6.89 mmol) in 1,4-dioxane (4 mL) was heated to 110° C. for 16 h. The reaction mixture was concentrated, the residue partitioned between $CHCl_3$/water, the organic layer was separated, washed with brine solution, dried over anhydrous $Na_2SO_4$, and the solvents concentrated and dried under high vacuo to obtain crude 5-bromo-N-(2-fluoro-2-methylpropyl)pyrrolo[2,1-f][1,2,4]triazin-2-amine (XCIV) (435 mg, 1.52 mmol, 100.6% yield) which was used for next step without purification. ESIMS found for $C_{10}H_{12}BrFN_4$ m/z 287.0 ($^{79}$BrM+H).

Steps 2-3

A mixture of 6-bromo-1-(2,2-difluoroethyl)-2-methyl-1H-imidazo[4,5-b]pyridine (XV) (100 mg, 0.370 mmol), bis(pinacolato)diboron (100 mg, 0.400 mmol), KOAc (110 mg, 1.1 mmol) and Pd(dppf)$Cl_2$ (100 mg, 0.020 mmol) was taken in monoglyme (1.5 mL) and $N_2$ was purged into the mixture for 2 min and the vial was sealed and heated to 95° C. overnight. LCMS showed the completion of reaction and the formation of boronic acid.

To the mixture was added 5-bromo-N-(2-fluoro-2-methylpropyl)pyrrolo[2,1-f][1,2,4]triazin-2-amine (XCIV) (70 mg, 0.240 mmol), Pd(dppf)$Cl_2$ (100 mg, 0.020 mmol) and 2 N solution of $K_3PO_4$ (0.37 mL, 0.750 mmol), $N_2$ was purged for 2 min and the mixture was heated to 95° C. for 5 h. The organics were separated, absorbed on silica gel, and was purified by ISCO (0→6% 7 N $NH_3$ MeOH/$CHCl_3$). The pure fractions were combined, triturated with diethyl ether, sonicated and the solids were collected by filtration to obtain 5-(1-(2,2-difluoroethyl)-2-methyl-1H-imidazo[4,5-b]pyridin-6-yl)-N-(2-fluoro-2-methylpropyl)pyrrolo[2,1-f][1,2,4]triazin-2-amine (642) (37 mg, 0.092 mmol, 37.6% yield) as a yellow solid. $^1$H NMR (499 MHz, DMSO-$d_6$) δ ppm 1.38 (6H, d, J=21.40 Hz), 2.63 (3H, s), 3.49 (2H, dd, J=19.30, 6.43 Hz), 4.91 (2H, td, J=15.88, 3.01 Hz), 6.53 (1H, tt, J=54.40, 3.20 Hz), 7.01 (1H, d, J=2.74 Hz), 7.03 (1H, t, J=6.43 Hz), 7.73 (1H, d, J=2.46 Hz), 8.25 (1H, d, J=1.92 Hz), 8.67 (1H, d, J=1.92 Hz), 9.14 (1H, s); ESIMS found for $C_{19}H_{20}F_3N_7$ m/z 404.2 (M+1).

Example 5

Preparation of N-(2-isobutyl-2-azaspiro[3.3]heptan-6-yl)-5-(quinolin-6-yl)pyrrolo[2,1-f][1,2,4]triazin-2-amine (1771) is depicted below in Scheme 20.

Scheme 20

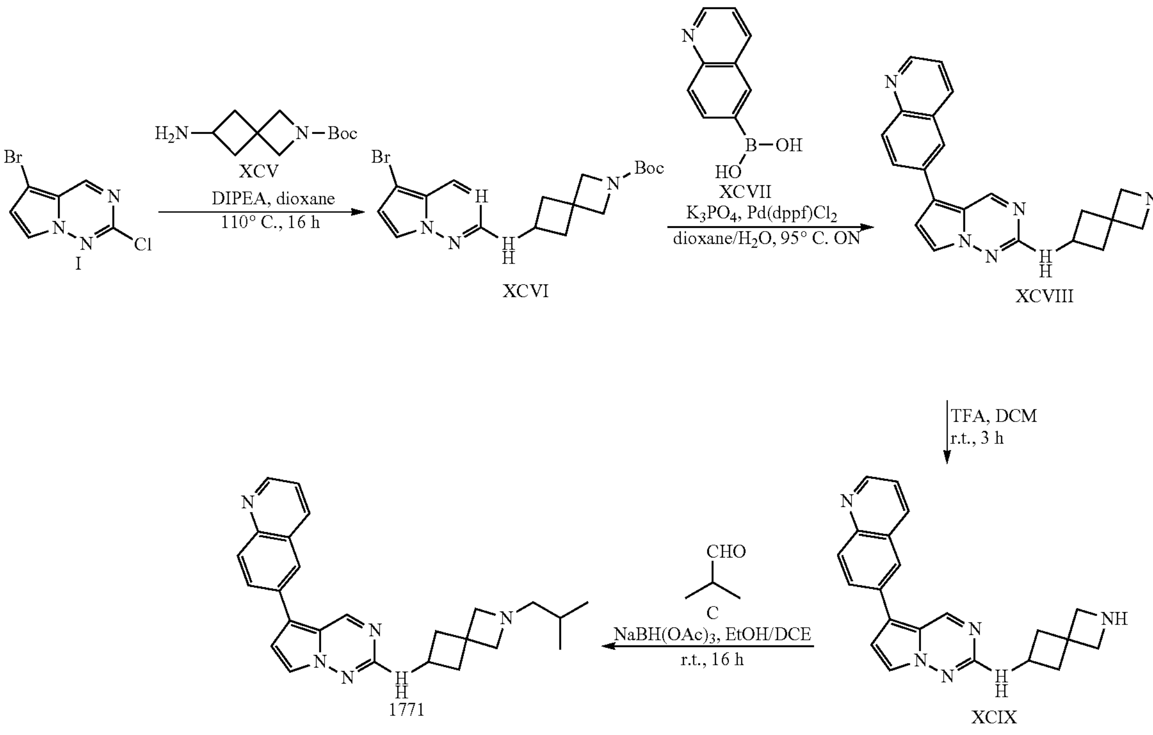

Step 1

A mixture of DIPEA (0.79 mL, 4.52 mmol), 5-bromo-2-chloropyrrolo[2,1-f][1,2,4]triazine (I) (commercially available from Advanced ChemBlocks Inc.) (350 mg, 1.51 mmol) and tert-butyl 6-amino-2-azaspiro[3.3]heptane-2-carboxylate (XCV) (480 mg, 2.26 mmol) in 1,4-dioxane (4 mL) was heated to 110° C. for 16 h. The reaction mixture was concentrated, the residue partitioned between DCM/water, organic layer separated, washed with brine solution, dried over anhydrous $Na_2SO_4$, solvents concentrated and dried under high vacuo to obtain crude tert-butyl 6-((5-bromopyrrolo[2,1-f][1,2,4]triazin-2-yl)amino)-2-azaspiro[3.3]heptane-2-carboxylate (XCVI) (630 mg, 1.54 mmol, 102.5% yield) which was used in the next step without purification. ESIMS found for $C_{17}H_{22}BrN_5O_2$ m/z 352.1 (M+H-$^t$Bu).

Step 2

A mixture of tert-butyl 6-((5-bromopyrrolo[2,1-f][1,2,4]triazin-2-yl)amino)-2-azaspiro[3.3]heptane-2-carboxylate (XCVI) (620 mg, 1.51 mmol), 2 N aqueous solution of $K_3PO_4$ (4.44 mL, 8.88 mmol), and Pd(dppf)$Cl_2$ (60 g, 0.080 mmol) was taken in 1,4-dioxane (8 mL) and quinoline-6-boronic acid (XCVII) (520 mg, 3.01 mmol) was added. The reaction mixture was purged with $N_2$ gas for 5 min, the vial was sealed and heated at 95° C. overnight. The solvents were added to saturated aqueous $NaHCO_3$, solids were collected by filtration and the crude was purified by ISCO (4% 7 N $NH_3$ MeOH in $CHCl_3$) to produce tert-butyl 6-((5-(quinolin-6-yl)pyrrolo[2,1-f][1,2,4]triazin-2-yl)amino)-2-azaspiro[3.3]heptane-2-carboxylate (XCVIII) (588 mg, 1.29 mmol, 85.5% yield) as a yellow solid. ESIMS found for $C_{26}H_{28}N_6O_2$ m/z 457.3 (M+H).

Step 3

To a stirred solution of tert-butyl 6-((5-(quinolin-6-yl)pyrrolo[2,1-f][1,2,4]triazin-2-yl)amino)-2-azaspiro[3.3]heptane-2-carboxylate (XCVIII) (590 mg, 1.29 mmol) in DCM (10 mL) was added TFA (3.8 mL, 49.3 mmol) and the mixture was stirred at room temperature for 3 h. The mixture was concentrated and basified with 2 N $NH_3$ solution in MeOH and purified via column chromatography (0→8% 7 N $NH_3$ in MeOH/$CHCl_3$) to yield 5-(quinolin-6-yl)-N-(2-azaspiro[3.3]heptan-6-yl)pyrrolo[2,1-f][1,2,4]triazin-2-amine (XCIX) (410 mg, 1.15 mmol, 89.3% yield) as a yellow solid. ESIMS found for $C_{21}H_{20}N_6$ m/z 357.2 (M+H).

Step 4

To a stirring solution of 5-(quinolin-6-yl)-N-(2-azaspiro[3.3]heptan-6-yl)pyrrolo[2,1-f][1,2,4]triazin-2-amine (XCIX) (100 mg, 0.280 mmol) in DCE (1 mL) and EtOH (0.125 mL) was added isobutyraldehyde (C) (0.26 mL, 2.81 mmol). Reaction mixture was allowed to stir for 30 min and NaBH$(OAc)_3$ (150 mg, 0.700 mmol) was added. Reaction mixture was allowed to stir at room temperature for 16 h. Quenched reaction with saturated aqueous $NaHCO_3$. Extracted with DCM. Washed organics with brine and dried over $MgSO_4$. Concentrated. Purified via column chromatography. (100% $CHCl_3$=>6% 7 N $NH_3$ in MeOH/$CHCl_3$) to afford 5-(imidazo[1,2-a]pyrimidin-6-yl)-N-(cis-4-(trifluoromethoxy) cyclohexyl)pyrrolo[2,1-f][1,2,4]triazin-2-amine (1771) (20 mg, 0.048 mmol, 18.2% yield) as a brown solid. $^1$H NMR (499 MHz, DMSO-$d_6$) δ ppm 1.62-1.71 (2H, m), 1.71-1.80 (2H, m), 1.80-1.88 (2H, m), 1.95 (2H, br dd, J=9.03, 4.65 Hz), 3.65-3.77 (1H, m), 4.57-4.65 (1H, m), 7.02 (1H, d, J=7.12 Hz), 7.07 (1H, d, J=2.74 Hz), 7.73-7.76 (2H, m), 7.89 (1H, d, J=1.09 Hz), 8.88 (1H, d, J=2.74 Hz), 9.16 (1H, s), 9.30 (1H, d, J=2.74 Hz); ESIMS found for $C_{19}H_{18}F_3N_7O$ m/z 418.2 (M+1).

Example 6

Preparation of 5-(3-(2,2-difluoroethyl)-2-methyl-3H-imidazo[4,5-b]pyridin-5-yl)-N-(cis-4-(morpholinomethyl)cyclohexyl)pyrrolo[2,1-f][1,2,4]triazin-2-amine (1842) is depicted below in Scheme 21.

Scheme 21

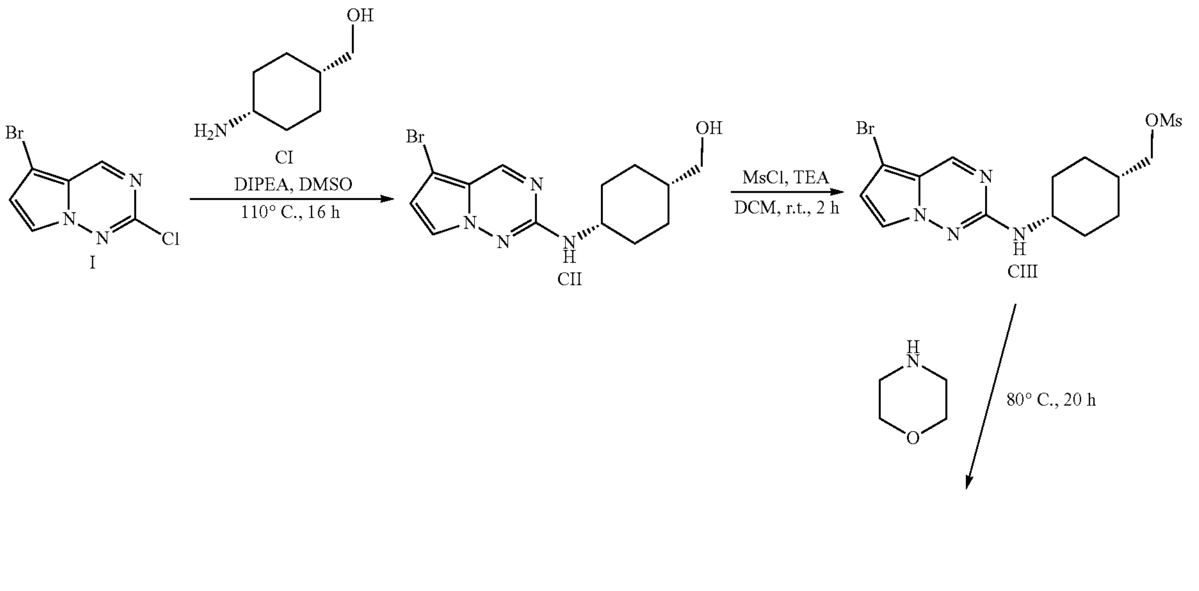

I
CI
CII
CIII

-continued

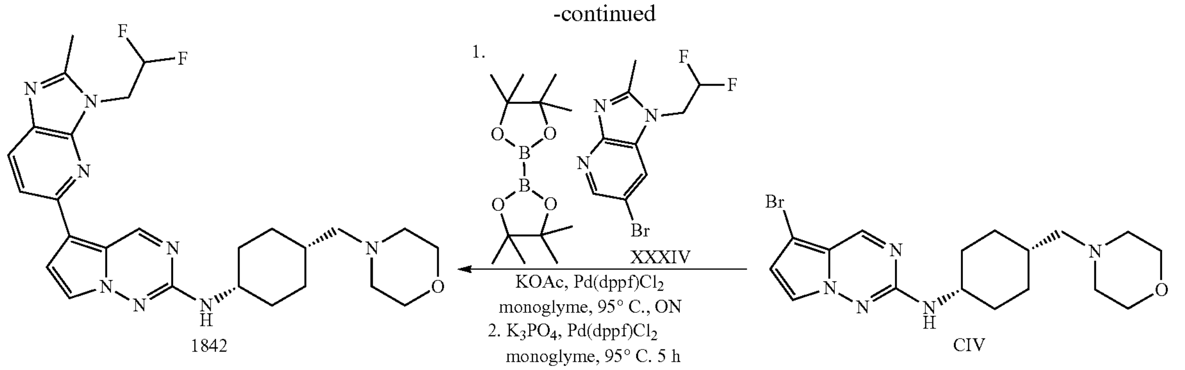

1842 CIV

Step 1

A mixture of 5-bromo-2-chloropyrrolo[2,1-f][1,2,4]triazine (I) (commercially available from Advanced ChemBlocks Inc.) (200 mg, 0.860 mmol), (cis-4-aminocyclohexyl)methanol HCl salt (CI) (commercially available from Combi-Blocks Inc.) (215 mg, 1.3 mmol) and DIPEA (0.44 mL, 2.53 mmol) in DMSO (1 mL) was heated to 110° C. for 16 h. The reaction mixture was concentrated. The residue was purified by silica gel column chromatography (0→00% EtOAc/Hexanes) to produce (cis-4-((5-bromopyrrolo[2,1-f][1,2,4]triazin-2-yl)amino)cyclohexyl)methanol (CII) (203.9 mg, 0.627 mmol, 72.9% yield) as a tan solid. $^1H$ NMR (499 MHz, DMSO-$d_6$) δ ppm 1.42-1.51 (5H, m), 1.53-1.60 (2H, m), 1.66-1.74 (2H, m), 3.30 (2H, t, J=5.75 Hz), 3.70-3.80 (1H, m), 4.37 (1H, t, J=5.34 Hz), 6.73 (1H, d, J=2.46 Hz), 6.82 (1H, d, J=7.12 Hz), 7.66 (1H, d, J=2.74 Hz), 8.69 (1H, s); ESIMS found for $C_{13}H_{17}BrN_4O$ m/z 325.0 (M+H).

Step 2

To a solution of (cis-4-((5-bromopyrrolo[2,1-f][1,2,4]triazin-2-yl)amino)cyclohexyl) methanol (CII) (180 mg, 0.550 mmol) in DCM (4 mL) at 0° C. was added MsCl (43 uL, 0.560 mmol) and TEA (231 μL, 1.66 mmol). The reaction was allowed to warm to room temperature and stir for 2 h. The reaction evaporated onto Celite® and purified by silica gel column chromatography (0→100% EtOAc/Hexanes) to produce ((cis-4-((5-bromopyrrolo[2,1-f][1,2,4]triazin-2-yl)amino)cyclohexyl)methyl methanesulfonate (CIII) (182 mg, 0.451 mmol, 81.5% yield) as an off-white solid. $^1H$ NMR (499 MHz, DMSO-$d_6$) δ ppm 1.53 (4H, q, J=5.75 Hz), 1.56-1.64 (2H, m), 1.77 (2H, br dd, J=12.73, 5.06 Hz), 1.80-1.86 (1H, m), 3.17 (3H, s), 3.75-3.85 (1H, m), 4.10 (2H, d, J=7.12 Hz), 6.74 (1H, d, J=2.74 Hz), 6.87 (1H, d, J=7.12 Hz), 7.63-7.70 (1H, m), 8.71 (1H, s); ESIMS found for $C_{14}H_{19}BrN_4O_3S$ m/z 403.1 (M+H).

Step 3

A solution of ((cis-4-((5-bromopyrrolo[2,1-f][1,2,4]triazin-2-yl)amino)cyclohexyl) methyl methanesulfonate (CIII) (60 mg, 0.150 mmol) in morpholine (1 mL, 11.59 mmol) was heated to 80° C. for 20 h. The solvent was removed under reduced pressure and the residue was purified by silica gel column chromatography (0 to 5% MeOH/$CHCl_3$) to produce 5-bromo-N-(cis-4-(morpholinomethyl)cyclohexyl)pyrrolo[2,1-f][1,2,4]triazin-2-amine (CIV) (73 mg, 0.185 mmol, 124.4% yield) as an off-white solid. ESIMS found for $C_{17}H_{24}BrN_5O$ m/z 394.1 (M+H).

Steps 4-5

5-Chloro-3-(2,2-difluoroethyl)-2-methylimidazo[4,5-b]pyridine (XXXIV) (50 mg, 0.220 mmol), Pd(dppf)$Cl_2$ (17 mg, 0.020 mmol), bis(pinacolato)diboron (82 mg, 0.320 mmol) and KOAc (63 mg, 0.640 mmol) were suspended in dioxane (4 mL). The reaction was degassed with $N_2$ before stirred at 90° C. for 5 h. The reaction was cooled to room temperature before adding 5-bromo-N-(cis-4-(morpholinomethyl)cyclohexyl)pyrrolo[2,1-f][1,2,4]triazin-2-amine (CIV) (73 mg, 0.190 mmol), an aqueous solution of $Na_2CO_3$ (0.69 mL, 0.650 mmol), Pd(dppf)$Cl_2$ (17 mg, 0.020 mmol), and monoglyme (4 mL). The reaction was heated to 90° C. for 16 h. The reaction evaporated onto Celite® and purified by silica gel column chromatography (0→50% MeOH/$CHCl_3$) to afford 5-(3-(2,2-difluoroethyl)-2-methyl-3H-imidazo[4,5-b]pyridin-5-yl)-N-(cis-4-(morpholinomethyl)cyclohexyl)pyrrolo[2,1-f][1,2,4]triazin-2-amine (1842) (38 mg, 0.074 mmol, 34.5% yield) as a light brown solid. $^1H$ NMR (499 MHz, DMSO-$d_6$) δ ppm 1.42-1.56 (4H, m), 1.56-1.65 (2H, m), 1.65-1.76 (3H, m), 2.18 (2H, br d, J=7.12 Hz), 2.32 (4H, br s), 2.61 (3H, s), 3.57 (4H, br t, J=4.24 Hz), 3.76-3.85 (1H, m), 4.83 (2H, td, J=15.81, 2.33 Hz), 6.55 (1H, tt, J=54.60, 3.00 Hz), 6.67 (1H, d, J=7.39 Hz), 7.22 (1H, d, J=2.46 Hz), 7.64 (1H, d, J=2.74 Hz), 7.72 (1H, d, J=8.49 Hz), 7.95 (1H, d, J=8.49 Hz), 9.70 (1H, s); ESIMS found for $C_{26}H_{32}F_2N_8O$ m/z 511.3 (M+1).

Example 7

Preparation of azetidin-1-yl(cis-4-((5-(3-(2,2-difluoroethyl)-2-methyl-3H-imidazo[4,5-b]pyridin-5-yl)pyrrolo[2,1-f][1,2,4]triazin-2-yl)amino)cyclohexyl)methanone (1896) is depicted below in Scheme 22.

Scheme 22

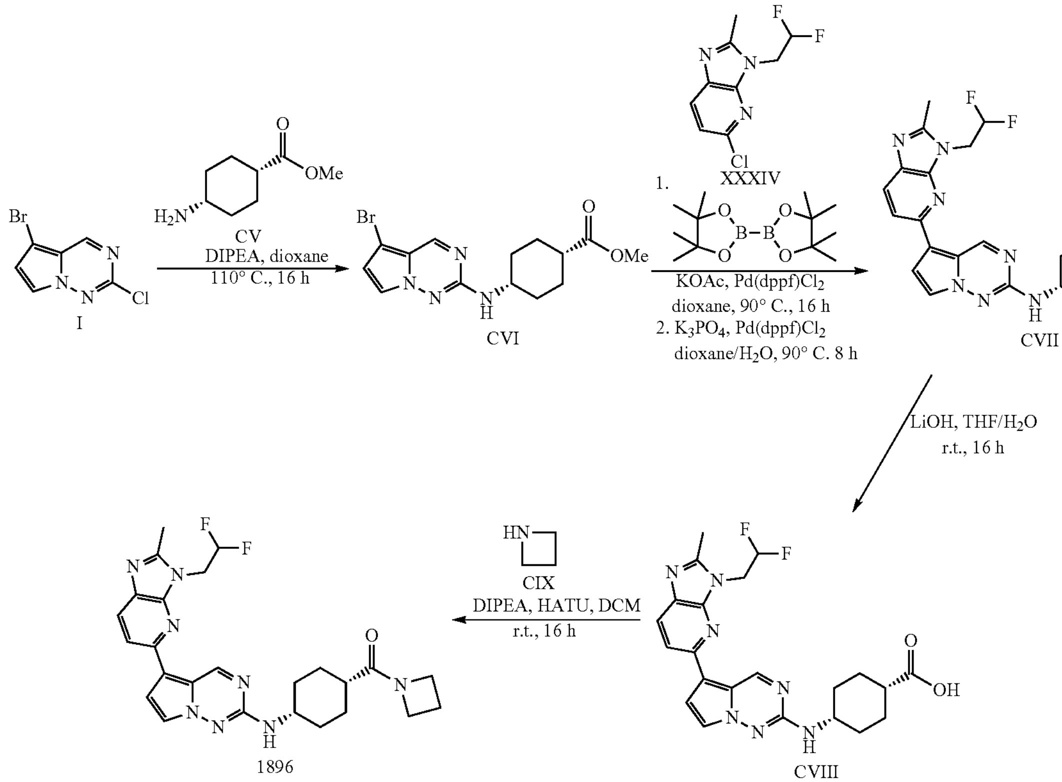

I CVI CVII CVIII 1896

Step 1

A mixture of DIPEA (1.35 mL, 7.75 mmol), 5-bromo-2-chloropyrrolo[2,1-f][1,2,4]triazine (I) (commercially available from Advanced ChemBlocks Inc.) (600 mg, 2.58 mmol) and methyl 4-aminocyclohexane-1-carboxylate (CV) (commercially available from Combi-Blocks Inc.) (490 mg, 3.1 mmol) in 1,4-dioxane (10 mL) was heated to 110° C. for 16 h. The reaction was concentrated and purified via column chromatography (0→2% MeOH/$CHCl_3$) (12 g of silica gel) to yield methyl 4-[(5-bromopyrrolo[2,1-f][1,2,4]triazin-2-yl)amino]cyclohexane-1-carboxylate (CVI) (729 mg, 2.064 mmol, 80.0% yield) as a light brown viscous solid. ESIMS found for $C_{14}H_{17}BrN_4O_2$ m/z 353.1 (M-$^t$Bu+H).

Steps 2-3

To a microwave vial was added 5-chloro-3-(2,2-difluoroethyl)-2-methylimidazo[4,5-b]pyridine (XXXIV) (720 mg, 3.1 mmol), bis(pinacolato)diboron (1.05 g, 4.13 mmol), KOAc (0.91 g, 9.29 mmol), and Pd(dppf)$Cl_2$ (0.13 g, 0.15 mmol) in 1,4-dioxane (15 mL). The reaction mixture was heated to 90° C. for 16 h before adding methyl 4-[(5-bromopyrrolo[2,1-f][1,2,4]triazin-2-yl)amino]cyclohexane-1-carboxylate (CVI) (730 mg, 2.06 mmol), a 2 N aqueous solution of $K_3PO_4$ (3.3 mL, 6.6 mmol), and Pd(dppf)$Cl_2$ (130 mg, 0.15 mmol). The reaction was stirred at 90° C. for an additional 8 h. The reaction was concentrated and purified via column chromatography (0→8% MeOH/$CHCl_3$) (24 g of silica gel) to give methyl 4-[[5-[3-(2,2-difluoroethyl)-2-methylimidazo[4,5-b]pyridin-5-yl]pyrrolo[2,1-f][1,2,4]triazin-2-yl]amino]cyclohexane-1-carboxylate (CVII) (765 mg, 1.629 mmol, 78.9% yield) as an amber viscous solid. ESIMS found for $C_{23}H_{25}F_2N_7O_2$ m/z 470.2 (M+H).

Step 4

Methyl 4-[[5-[3-(2,2-difluoroethyl)-2-methylimidazo[4,5-b]pyridin-5-yl]pyrrolo[2,1-f][1,2,4]triazin-2-yl]amino]cyclohexane-1-carboxylate (CVII) (729 mg, 1.55 mmol) to a mixture of water (3 mL) and THF (12 mL) followed by LiOH (1.4 mL, 2.8 mmol). The reaction was stirred at room temperature for 16 h. Concentrated HCl (2.9 mL, 2.9 mmol) was added to neutralize the reaction. The reaction mixture was stripped evaporated onto Celite®, and the sample was purified by reverse phase C18 silica gel (0-20% MeCN/water (containing 0.1% formic acid)). The fractions containing compound were lyophilized (frozen at −78° C.) to produce 4-[[5-[3-(2,2-difluoroethyl)-2-methylimidazo[4,5-b]pyridin-5-yl]pyrrolo[2,1-f][1,2,4]triazin-2-yl]amino]cyclohexane-1-carboxylic acid (CVIII) (450 mg, 0.988 mmol, 63.6% yield) as an orange-brown solid. ESIMS found for $C_{22}H_{23}F_2N_7O_2$ m/z 456.2 (M+H).

Step 5

To a stirring solution of 4-[[5-[3-(2,2-difluoroethyl)-2-methylimidazo[4,5-b]pyridin-5-yl]pyrrolo[2,1-f][1,2,4]triazin-2-yl]amino]cyclohexane-1-carboxylic acid (CVIII) (50 mg, 0.1 mmol) in DCM (1 mL) was added DIPEA (0.07 mL, 0.4 mmol) and HATU (60 mg, 0.15 mmol). The reaction was stirred at room temperature for 5 min. Azetidine hydrochloride (CIX) (20 mg, 0.2 mmol) was then added and the reaction was stirred at room temperature for 16 h. The reaction was concentrated and purified via column chromatography (0→8% 7 N $NH_3$ in MeOH/Chloroform) (8 g of silica gel) to afford azetidin-1-yl(cis-4-((5-(3-(2,2-difluoroethyl)-2-methyl-3H-imidazo[4,5-b]pyridin-5-yl)pyrrolo[2,1-f][1,2,4]triazin-2-yl)amino)cyclohexyl)methanone (1896) (7 mg, 0.014 mmol, 14.3% yield) as a yellow solid. $^1$H NMR (499 MHz, DMSO-$d_6$) δ ppm 1.42-1.50 (2H, m), 1.57-1.66 (2H, m), 1.73-1.83 (2H, m), 1.92 (2H, dt, J=6.64, 3.39 Hz), 2.13-2.22 (2H, m), 2.31 (1H, tt, J=8.62, 4.11 Hz), 2.61 (3H, s), 3.75-3.80 (1H, m), 3.82 (2H, t, J=7.67 Hz), 4.15 (2H, t, J=7.53 Hz), 4.83 (2H, td, J=15.95, 2.60 Hz), 6.55 (1H, tt, J=54.60, 3.00 Hz), 6.77 (1H, d, J=6.30 Hz), 7.22 (1H, d, J=2.74 Hz), 7.64 (1 H, d, J=2.46 Hz), 7.72 (1H, d, J=8.21 Hz), 7.95 (1H, d, J=8.21 Hz), 9.70 (1H, s); ESIMS found for $C_{23}H_{26}F_2N_8O$ m/z 495.3 (M+1).

Example 8

Preparation of 1-(7-((5-(3-(2,2-difluoroethyl)-2-methyl-3H-imidazo[4,5-b]pyridin-5-yl)pyrrolo[2,1-f][1,2,4]triazin-2-yl)amino)-2-azaspiro[3.5]nonan-2-yl)ethan-1-one (1899) is depicted below in Scheme 23.

Scheme 23
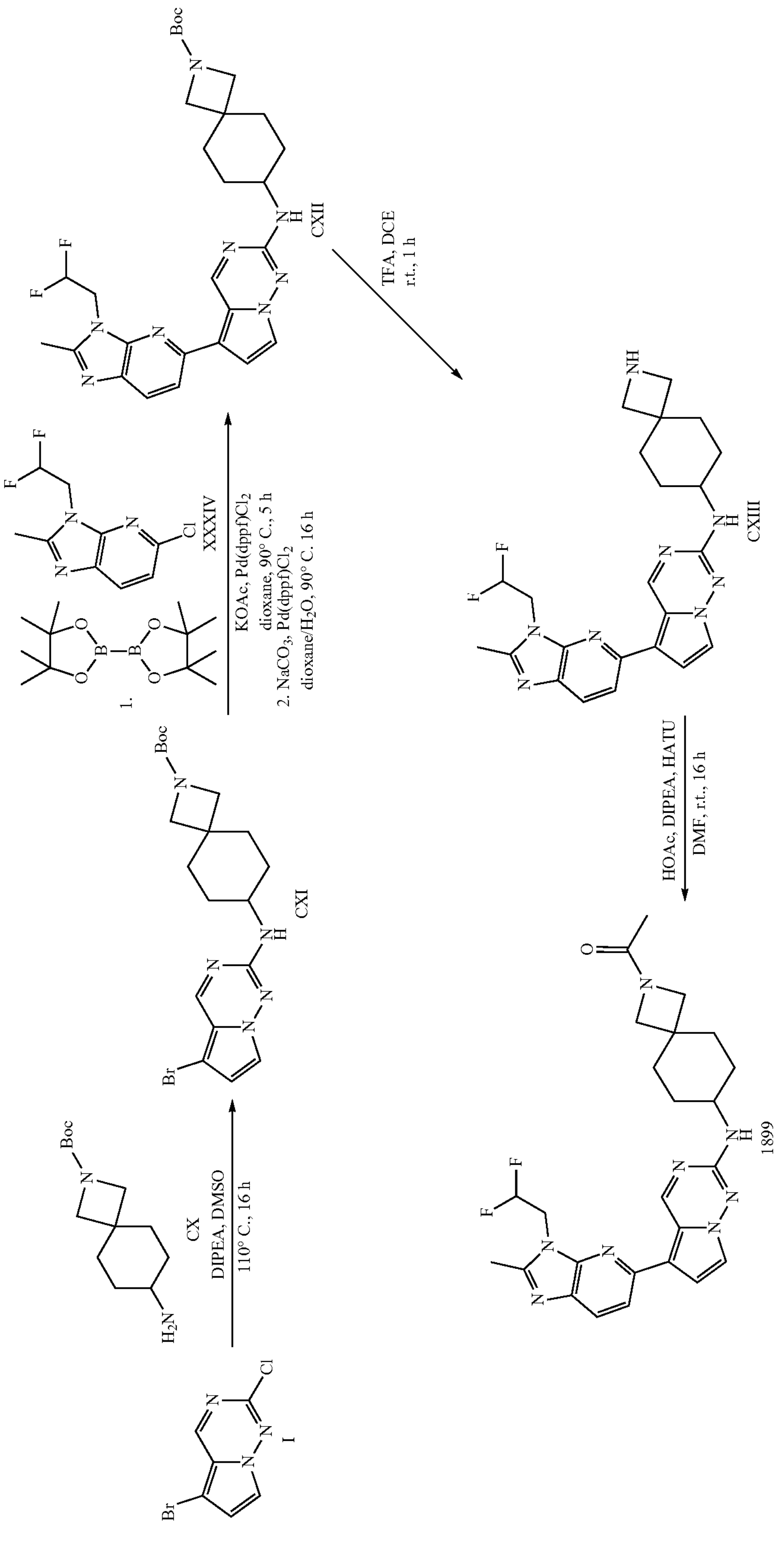

Step 1

A mixture of 5-bromo-2-chloropyrrolo[2,1-f][1,2,4]triazine (I) (commercially available from Advanced ChemBlocks Inc.) (200 mg, 0.860 mmol), tert-butyl 7-amino-2-azaspiro[3.5]nonane-2-carboxylate (CX) (commercially available from A2B Chem LLC) (311.9 mg, 1.3 mmol) and DIPEA (0.44 mL, 2.53 mmol) in DMSO (1 mL) was heated to 110° C. for 16 h. The reaction mixture was concentrated under high vacuum. The residue was purified by silica gel column chromatography (0→100% EtOAc/hexanes) to produce tert-butyl 7-((5-bromopyrrolo[2,1-f][1,2,4]triazin-2-yl)amino)-2-azaspiro[3.5]nonane-2-carboxylate (CXI) (2.185 mg, 0.501 mmol, 58.2% yield) as a tan solid. ESIMS found for $C_{19}H_{26}BrN_5O_2$ m/z 380.1 (M-$^t$Bu+H).

Steps 2-3

5-Chloro-3-(2,2-difluoroethyl)-2-methylimidazo[4,5-b]pyridine (XXXVI) (100 mg, 0.430 mmol), Pd(dppf)$Cl_2$ (35 mg, 0.040 mmol), bis(pinacolato)diboron (164 mg, 0.650 mmol), and KOAc (127 mg, 1.29 mmol) were suspended in dioxane (4 mL). The reaction was degassed with $N_2$ before stirred at 90° C. for 5 h. The reaction was cooled to room temperature before adding tert-butyl 7-((5-bromopyrrolo[2,1-f][1,2,4]triazin-2-yl)amino)-2-azaspiro[3.5]nonane-2-carboxylate (CXI) (124 mg, 0.280 mmol), an aqueous solution of $Na_2CO_3$ (1.3 mL, 1.3 mmol), Pd(dppf)$Cl_2$ (35 mg, 0.040 mmol), and DME (4 mL), The reaction was heated to 90° C. for 16 h. The reaction evaporated onto Celite® and purified by silica gel column chromatography (0→50% MeOH/$CHCl_3$) to yield tert-butyl 7-((5-(3-(2,2-difluoroethyl)-2-methyl-3H-imidazo[4,5-b]pyridin-5-yl)pyrrolo[2,1-f][1,2,4]triazin-2-yl)amino)-2-azaspiro[3.5]nonane-2-carboxylate (CXII) (133 mg, 0.241 mmol, 55.7% yield) as a yellow solid. ESIMS found for $C_{28}H_{34}F_2N_8O_2$ m/z 553.3 (M+H).

Step 4 tert-Butyl 7-((5-(3-(2,2-difluoroethyl)-2-methyl-3H-imidazo[4,5-b]pyridin-5-yl)pyrrolo[2,1-f][1,2,4]triazin-2-yl)amino)-2-azaspiro[3.5]nonane-2-carboxylate (CXII) (133 mg, 0.240 mmol) was added to TFA (1 mL, 12.98 mmol) in DCE (4 mL) and stirred at room temperature for 1 h. The solvent was removed, and the residue was purified by silica gel column chromatography (0→10% 7 N $NH_3$ in MeOH/$CHCl_3$) to produce 5-(3-(2,2-difluoroethyl)-2-methyl-3H-imidazo[4,5-b]pyridin-5-yl)-N-(2-azaspiro[3.5]nonan-7-yl)pyrrolo[2,1-f][1,2,4]triazin-2-amine (CXIII) (112 mg, 0.248 mmol, 102.8% yield) as a light-yellow solid. ESIMS found for $C_{23}H_{26}F_2N_8$ m/z 453.2 (M+H).

Step 5

To a solution of 5-(3-(2,2-difluoroethyl)-2-methyl-3H-imidazo[4,5-b]pyridin-5-yl)-N-(2-azaspiro[3.5]nonan-7-yl)pyrrolo[2,1-f][1,2,4]triazin-2-amine (CXIII) (55 mg, 0.120 mmol) in DMF (1.2 mL) was added HOAc (8 μL, 0.140 mmol) followed by HATU (60 mg, 0.160 mmol) and DIPEA (64 μL, 0.370 mmol). The solution was stirred at room temperature for 16 h. Water (40 mL) was added, and the solution was extracted with EtOAc. The reaction evaporated onto Celite® and purified by silica gel column chromatography (0-100% EtOAc/hexanes). The compound was still not pure by NMR. The crude product was dissolved in DCM and washed with saturated aqueous $NaHCO_3$ and then re-purified using silica gel column chromatography (0→100% EtOAc/hexanes) to afford 1-(7-((5-(3-(2,2-difluoroethyl)-2-methyl-3H-imidazo[4,5-b]pyridin-5-yl)pyrrolo[2,1-f][1,2,4]triazin-2-yl)amino)-2-azaspiro[3.5]nonan-2-yl)ethan-1-one (1899) (33 mg, 0.067 mmol, 54.9% yield) as a yellow solid. $^1$H NMR (499 MHz, DMSO-$d_6$) δ ppm 1.27-1.41 (2H, m), 1.50-1.62 (2H, m), 1.73-1.79 (3H, m), 1.88 (4H, br d, J=10.13 Hz), 2.60 (3H, s), 3.45-3.55 (2H, m), 3.55-3.66 (1H, m), 3.70-3.85 (2H, in), 4.77-4.90 (2H, in), 6.55 (1H, tt, J=54.60, 3.00 Hz), 6.74 (1H, dd, J=12.05, 7.94 Hz), 7.23 (1H, d, J=2.74 Hz), 7.65 (1H, t, J=3.01 Hz), 7.72 (1H, d, J=8.21 Hz), 7.95 (1H, d, J=8.21 Hz), 9.69 (1H, s); ESIMS found for $C_{25}H_{28}F_2N_8O$ m/z 495.25 (M+1).

Example 9

Preparation of 5-(3-(2,2-difluoroethyl)-2-methyl-3H-imidazo[4,5-b]pyridin-5-yl)-N-((3R,4S)-3-fluoro-1-isobutylpiperidin-4-yl)pyrrolo[2,1-f][1,2,4]triazin-2-amine (1909) is depicted below in Scheme 24.

Scheme 24

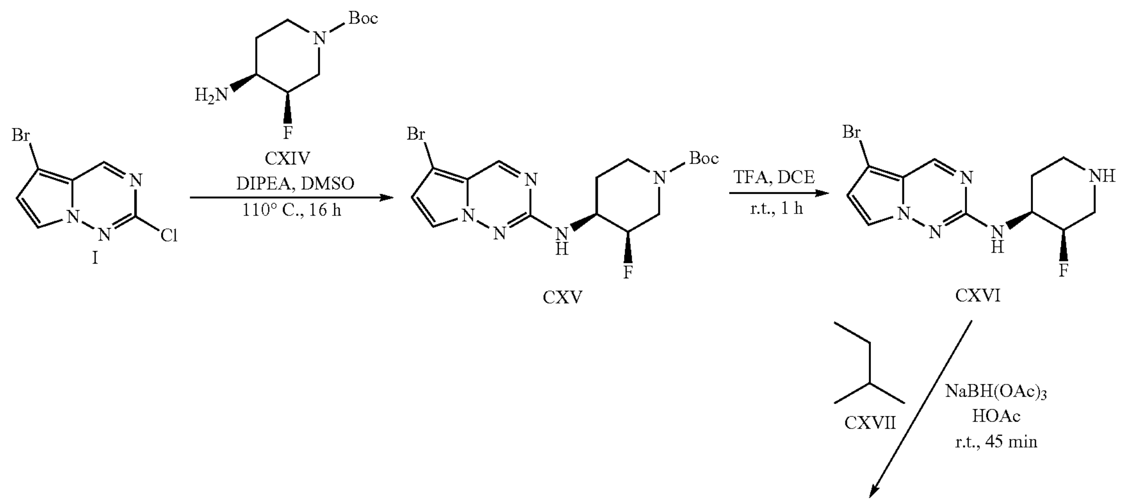

-continued

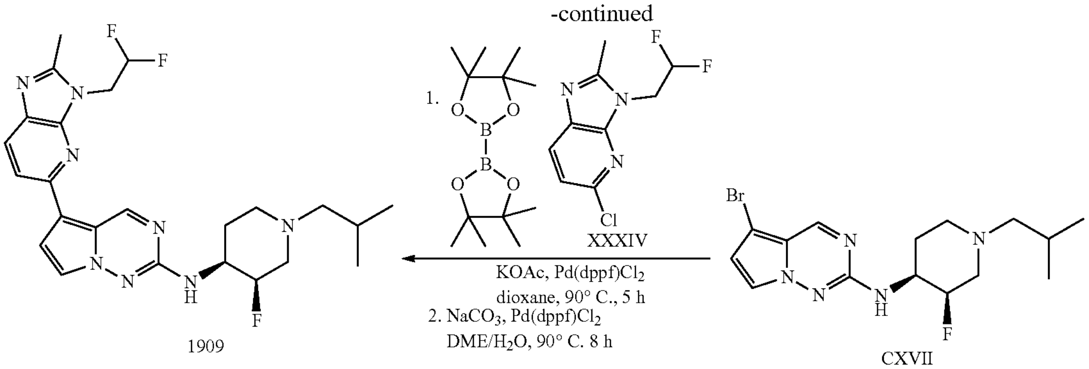

1909

CXVII

Step 1

To a solution of 5-bromo-2-chloropyrrolo[2,1-f][1,2,4]triazine (I) (commercially available from Advanced ChemBlocks Inc.) (200 mg, 0.860 mmol) and tert-butyl (3R,4S)-4-amino-3-fluoropiperidine-1-carboxylate (CXIV) (commercially available from Sunshine Chemlab, Inc.) (282 mg, 1.29 mmol) in DMSO (1 mL) was added DIPEA (450 μL, 2.58 mmol). The reaction was stirred at 120° C. for 16 h. The reaction mixture was then added to water and EtOAc and the organic layer was separated. The aqueous layer was extracted with EtOAc (x3) and the combined organic layers were washed with brine, dried ($MgSO_4$), and reduced in vacuo to give the crude product tert-butyl (3R,4S)-4-((5-bromopyrrolo[2,1-f][1,2,4]triazin-2-yl)amino)-3-fluoropiperidine-1-carboxylate (CXV) (457 mg, 1.103 mmol, 128% yield) as a fluffy brown solid which was used without further purification. ESIMS found for $C_{16}H_{21}BrFN_5O_2$ m/z 358.1 (M-$^t$Bu+H).

Step 2

To a solution of tert-butyl (3R,4S)-4-((5-bromopyrrolo[2,1-f][1,2,4]triazin-2-yl)amino)-3-fluoropiperidine-1-carboxylate (CXV) (356 mg, 0.860 mmol) in DCE (2.7 mL) was added TFA (300 μL, 3.89 mmol). The reaction was stirred at room temperature for 3 h. The reaction mixture was blown dry and excess TFA removed by high vacuum to give the crude intermediate 5-bromo-N-((3R,4S)-3-fluoropiperidin-4-yl)pyrrolo[2,1-f][1,2,4]triazin-2-amine (CXVI) (270 mg, 0.859 mmol, 100% yield) as a brown semi-solid which was used without further purification. ESIMS found for $C_{11}H_{13}BrFN_5$ m/z 314.0 (M+H).

Step 3

To a solution of 5-bromo-N-((3R,4S)-3-fluoropiperidin-4-yl)pyrrolo[2,1-f][1,2,4]triazin-2-amine (CXVI) (135 mg, 0.430 mmol) in MeOH (3 mL) was added HOAc (50 μL, 0.870 mmol) and isobutyraldehyde (CXVII) (78 μL, 0.850 mmol). The reaction was stirred at room temperature for 20 minutes. NaBH(OAc)$_3$ (228 mg, 1.08 mmol) was added, and the reaction was stirred for 10 minutes. LCMS showed partial conversion therefore NaBH(OAc)$_3$ (228 mg, 1.08 mmol) was added in 5 minutes intervals until LCMS confirmed completion (3 additions). The reaction evaporated onto Celite® and purified by reverse phase chromatography (0→20% MeCN/0.1% formic acid in $H_2O$) to give 5-bromo-N-((3R,4S)-3-fluoro-1-isobutylpiperidin-4-yl)pyrrolo[2,1-f][1,2,4]triazin-2-amine (CXVIII) (33 mg, 0.089 mmol, 20.7% yield) as a brown semi-solid. ESIMS found for $C_{15}H_{21}BrFN_5$ m/z 370.1 (M+H).

Step 4

5-Chloro-3-(2,2-difluoroethyl)-2-methylimidazo[4,5-b]pyridine (XXXIV) (1 g, 4.32 mmol), bis(pinacolato)diboron (1.75 g, 6.89 mmol), Pd(dppf)Cl$_2$ (176 mg, 0.220 mmol) and KOAc (1.28 g, 13.04 mmol) were dissolved in dry DMF (30 mL) and the reaction was sonicated and degassed with Ar for 5 minutes. The reaction was stirred at 100° C. for 16 h. The reaction mixture was cooled and reduced in vacuo to give a black solid. The crude product was purified by a C18Aq reverse phase column chromatography (0→11% MeCN/0.1% formic acid in $H_2O$). Appropriate fractions were collected and evaporated under high vacuum to produce (3-(2,2-difluoroethyl)-2-methyl-3H-imidazo[4,5-b]pyridin-5-yl)boronic acid (CXIX) (543 mg, 2.253 mmol, 52.2% yield) as a fluffy yellow solid which was stored in −20° C. ESIMS found for $C_9H_{10}BF_2N_3O_2$ m/z 242.1 (M+H).

Step 5

To a suspension of 5-Bromo-N-((3R,4S)-3-fluoro-1-isobutylpiperidin-4-yl)pyrrolo[2,1-f][1,2,4]triazin-2-amine (CXVIII) (32 mg, 0.090 mmol), (3-(2,2-difluoroethyl)-2-methyl-3H-imidazo[4,5-b]pyridin-5-yl)boronic acid (CXIX) (31 mg, 0.130 mmol) and Pd(dppf)Cl$_2$ (3 mg, 0 mmol) in dioxane (1.5 mL) was added an aqueous solution of $Na_2CO_3$ (274 μL, 0.260 mmol). The reaction was sonicated and degassed for 5 minutes with Ar and then heated 100° C. for 16 h. The reaction mixture was purified by column chromatography (0→10% 7.0 M $NH_3$ in MeOH/$CHCl_3$). The compound was further purified by reverse phase chromatography (0→17% MeCN/0.1% formic acid in $H_2O$). Appropriate fractions were collected and added to saturated aqueous $NaHCO_3$ and extracted with DCM (x3). The combined organic layers were washed with brine, dried ($MgSO_4$) and reduced in vacuo to afford 5-(3-(2,2-difluoroethyl)-2-methyl-3H-imidazo[4,5-b]pyridin-5-yl)-N-((3R,4S)-3-fluoro-1-isobutylpiperidin-4-yl)pyrrolo[2,1-f][1,2,4]triazin-2-amine (1909) (15 mg, 0.031 mmol, 35.7% yield) as a yellow solid. $^1H$ NMR (500 MHz, DMSO-d$_6$) δ ppm 0.86 (6H, br d, J=6.31 Hz), 1.66-1.82 (2H, m), 1.88-1.99 (1H, m), 2.00-2.11 (3H, m), 2.12-2.27 (1H, m), 2.61 (3H, s), 2.80-2.91 (1H, m), 3.05-3.17 (1H, m), 3.73-3.92 (1H, m), 4.84 (2H, td, J=15.85, 2.61 Hz), 4.94 (1H, br s), 6.55 (1H, tt, J=54.60, 3.00 Hz), 6.86 (1H, br d, J=7.68 Hz), 7.26 (1H, d, J=2.47 Hz), 7.66 (1H, d, J=2.47 Hz), 7.74 (1H, d, J=8.51

Hz), 7.96 (1H, d, J=8.51 Hz), 9.73 (1H, s); ESIMS found for $C_{24}H_{29}F_3N_8$ m/z 487.3 (M+1).

Example 10

Preparation of 5-(3-(2,2-difluoroethyl)-2-methyl-3H-imidazo[4,5-b]pyridin-5-yl)-N-((3S,4R)-4-fluoro-1-(oxetan-3-yl)pyrrolidin-3-yl)pyrrolo[2,1-f][1,2,4]triazin-2-amine (1944) is depicted below in Scheme 25.

Scheme 25

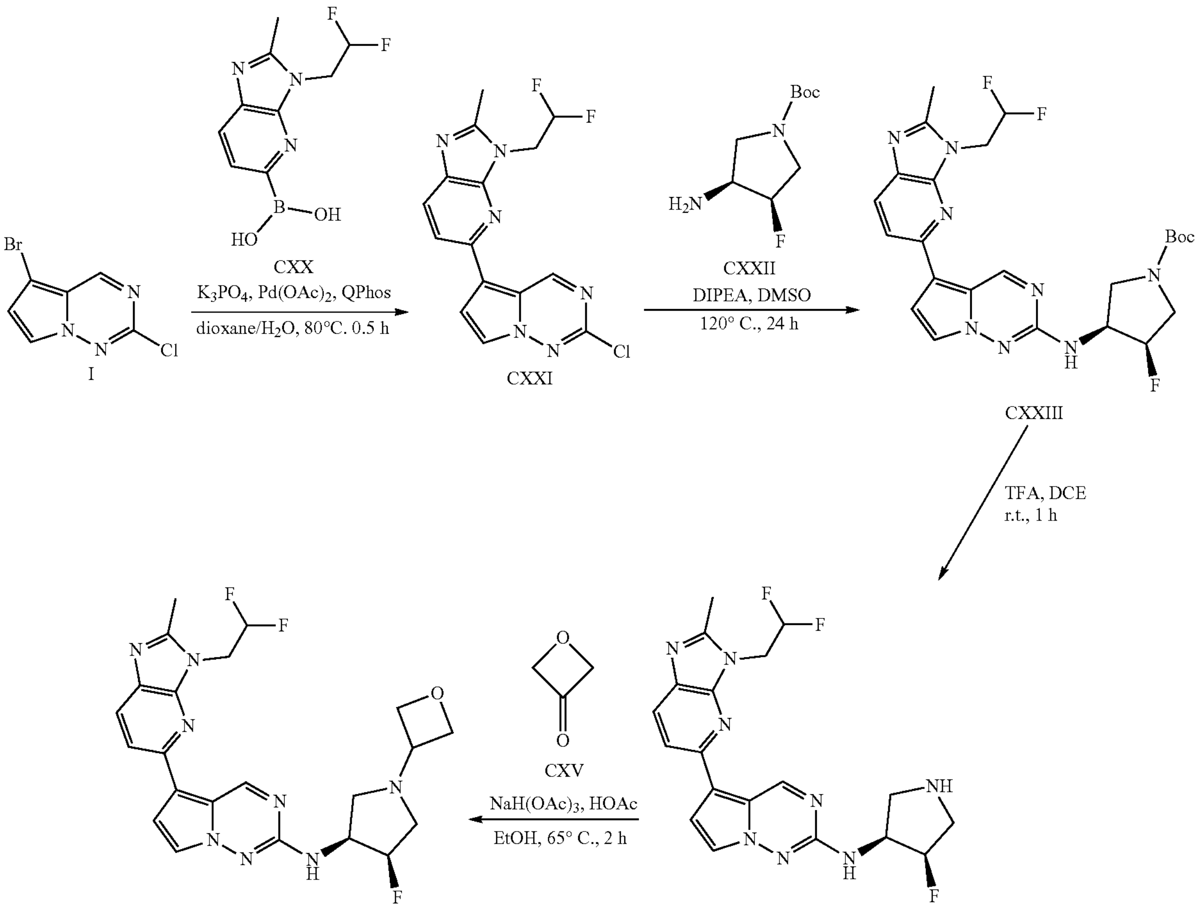

I, CXXI, CXXIII, CXXIV, 1944

Step 1

5-bromo-2-chloropyrrolo[2,1-f][1,2,4]triazine (I) (commercially available from Advanced ChemBlocks Inc.) (1.5 g, 6.45 mmol), [3-(2,2-difluoroethyl)-2-methylimidazo[4,5-b]pyridin-5-yl]boronic acid (CXX) (1.63 g, 6.78 mmol), $Pd(OAc)_2$ (45 mg, 0.2 mmol) and QPhos (270 mg, 0.38 mmol) were dissolved in dry 1,4-dioxane (35 mL) and purged with Ar for 5 min. A 2 N aqueous solution of $K_3PO_4$ (6.45 mL, 12.9 mmol) was added and the reaction was purged with Ar for a further 2 min. The reaction was then heated to 80° C. for 30 min. To the reaction mixture was added to DCM and aqueous saturated $NH_4Cl$ solution was added, and the organic layer was separated. The aqueous layer was extracted with DCM (×3), and the combined organic layers were dried (anhydrous $MgSO_4$) and reduced in vacuo to give an orange solid. The crude product was purified by column chromatography (0→100% EtOAc/hexanes) followed by (0→6% 7.0 M $NH_3$ in $MeOH/CHCl_3$). Appropriate fractions were combined and reduced in vacuo to give an orange solid. The solid was triturated with MeOH and filtered, washing with MeOH. The product 5-(2-chloropyrrolo[2,1-f][1,2,4]triazin-5-yl)-3-(2,2-difluoroethyl)-2-methylimidazo[4,5-b]pyridine (1.79 g, 5.133 mmol, 79.5% yield) was collected as a yellow solid. The filtrate was reduced in vacuo to give additional 5-(2-chloropyrrolo[2,1-f][1,2,4]triazin-5-yl)-3-(2,2-difluoroethyl)-2-methylimidazo[4,5-b]pyridine (CXXI) (481 mg, 1.379 mmol, 21.4% yield) as an orange solid (60% pure) and was used without further purification. ESIMS found for $C_{15}H_{11}ClF_2N_6$ m/z 349.1 (M+H).

Step 2

5-(2-chloropyrrolo[2,1-f][1,2,4]triazin-5-yl)-3-(2,2-difluoroethyl)-2-methylimidazo [4,5-b]pyridine (CXXI) (150 mg, 0.43 mmol) and tert-butyl (3S,4R)-3-amino-4-fluoropyrrolidine-1-carboxylate (CXXII) (114 mg, 0.56 mmol) were dissolved in DMSO (1 mL) and DIPEA (150 μL, 0.86 mmol) was added and the reaction was stirred at 120° C. for 24 h. The reaction mixture was added to water and EtOAc and the organic layer was separated. The aqueous layer was extracted with EtOAc (×3) and the combined organic layers were washed with brine, dried (anhydrous $MgSO_4$), and reduced in vacuo to give the crude product tert-butyl (3S, 4R)-3-((5-(3-(2,2-difluoroethyl)-2-methyl-3H-imidazo[4,5-b]pyridin-5-yl)pyrrolo[2,1-f][1,2,4]triazin-2-yl)amino)-4-fluoropyrrolidine-1-carboxylate (CXXIII) (222 mg, 0.430 mmol, 99.9% yield), assuming quantitative yield, as a brown semi-solid which was used without further purification. ESIMS found for $C_{24}H_{27}F_3N_8O_2$ m/z 517.3 (M+H).

Step 3 tert-Butyl (3S,4R)-3-((5-(3-(2,2-difluoroethyl)-2-methyl-3H-imidazo[4,5-b]pyridin-5-yl)pyrrolo[2,1-f][1,2,4]triazin-2-yl)amino)-4-fluoropyrrolidine-1-carboxylate (CXXIII) (222 mg, 0.43 mmol) was dissolved in DCE (4.5 mL) and the reaction was cooled to 0° C. TFA (0.50 mL) was added and the reaction was stirred at room temperature for 16 h. The reaction mixture was evaporated, and the crude product was purified by column chromatography (0→2% 7.0 M $NH_3$ in MeOH/$CHCl_3$) to give 5-(3-(2,2-difluoroethyl)-2-methyl-3H-imidazo[4,5-b]pyridin-5-yl)-N-((3S,4R)-4-fluoropyrrolidin-3-yl)pyrrolo[2,1-f][1,2,4]triazin-2-amine (CXXIV) (138 mg, 0.331 mmol, 77.1% yield) as a yellow semi-solid. ESIMS found for $C_{19}H_{19}F_3N_8$ m/z 417.2 (M+H).

Step 4

In a solution of 5-(3-(2,2-difluoroethyl)-2-methyl-3H-imidazo[4,5-b]pyridin-5-yl)-N-((3S,4R)-4-fluoropyrrolidin-3-yl)pyrrolo[2,1-f][1,2,4]triazin-2-amine (CXXIV) (138 mg, 0.33 mmol) in EtOH (3 mL) was added HOAc (95 μL, 1.66 mmol) and oxetan-3-one (CXXV) (97 μL, 1.66 mmol). The reaction was stirred at room temperature for 10 min. $NaH(OAc)_2$ (105 mg, 0.5 mmol) was added and the reaction was stirred at room temperature for another 20 min. LCMS showed minor product formation, therefore, the reaction was heated to 65° C. for 30 min. LCMS showed more conversion. Additional oxetan-3-one (CXXV) (97 μL, 1.66 mmol) and HOAc (95 μL, 1.66 mmol) were added and stirred at room temperature for 5 min. $NaH(OAc)_2$ (105 mg, 0.5 mmol) was added and stirred at 65° C. for 1 h. Subsequent rounds of reagents were added until no more conversion was observed (~90%) and therefore the reaction was stopped. The reaction mixture was loaded on Celite® and purified by column chromatography (0→6% 7.0 M $NH_3$ in MeOH/$CHCl_3$). The product was further purified by HPLC (0→35% MeCN/$H_2O$ (containing 0.1% formic acid)). Appropriate fractions were collected and neutralized with aqueous saturated $NaHCO_3$ and extracted with DCM (×2). The combined organic layers were dried (anhydrous $MgSO_4$) and reduced in vacuo to afford 5-(3-(2,2-difluoroethyl)-2-methyl-3H-imidazo[4,5-b]pyridin-5-yl)-N-((3S, 4R)-4-fluoro-1-(oxetan-3-yl)pyrrolidin-3-yl)pyrrolo[2,1-f][1,2,4]triazin-2-amine (1944) (80 mg, 0.169 mmol, 51.1% yield) as a yellow solid. $^1H$ NMR (499 MHz, DMSO-$d_6$) δ ppm 2.61 (3H, s), 2.71 (1H, t, J=9.17 Hz), 2.80 (1H, dd, J=28.50, 11.20 Hz), 3.04 (1H, t, J=8.21 Hz), 3.17 (1H, ddd, J=33.45, 12.05, 4.40 Hz), 3.80 (1H, quin, J=6.16 Hz), 4.23-4.40 (1H, m), 4.48 (2H, t, J=5.89 Hz), 4.60 (2H, t, J=6.57 Hz), 4.84 (2H, td, J=16.02, 2.74 Hz), 5.26 (1H, dt, J=56.25, 3.55 Hz), 6.56 (1H, tt, J=54.50, 3.00 Hz), 7.06 (1H, d, J=7.94 Hz), 7.28 (1H, d, J=2.74 Hz), 7.69 (1H, d, J=2.46 Hz), 7.75 (1H, d, J=8.49 Hz), 7.96 (1H, d, J=8.21 Hz), 9.74 (1H, s); ESIMS found for $C_{22}H_{23}F_3N_8O$ m/z 473.3 (M+1).

Example 11

Preparation of 5-(3-(2,2-difluoroethyl)-2-methyl-3H-imidazo[4,5-b]pyridin-5-yl)-N-(piperidin-4-yl)pyrrolo[2,1-f][1,2,4]triazin-2-amine (1916) and (4,4-difluorocyclohexyl)(4-((5-(3-(2,2-difluoroethyl)-2-methyl-3H-imidazo[4,5-b]pyridin-5-yl)pyrrolo[2,1-f][1,2,4]triazin-2-yl)amino)piperidin-1-yl)methanone (1953) is depicted below in Scheme 26.

Scheme 26

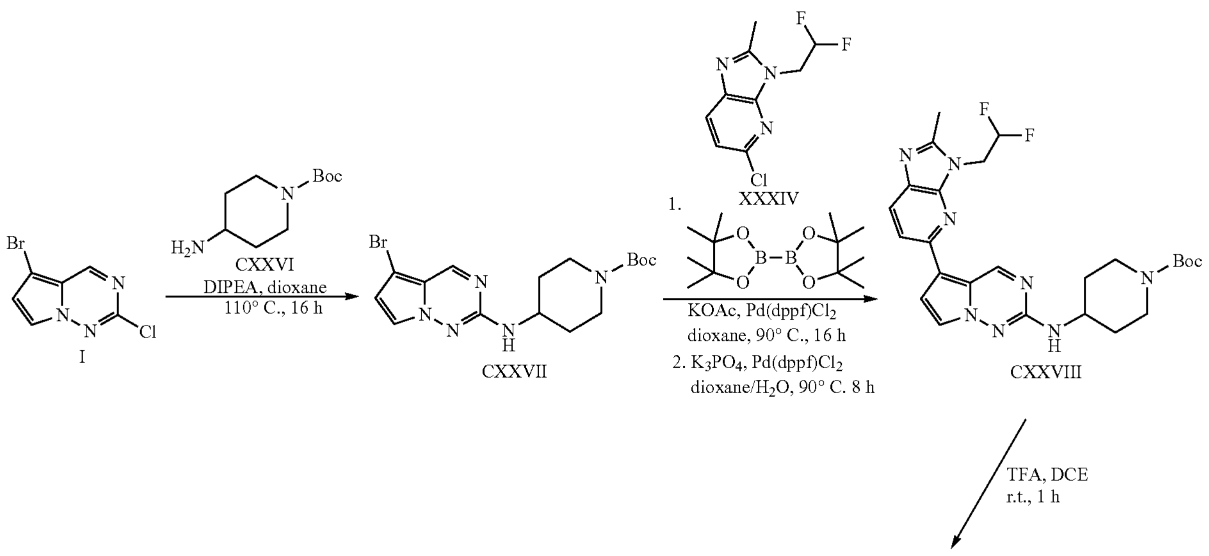

-continued

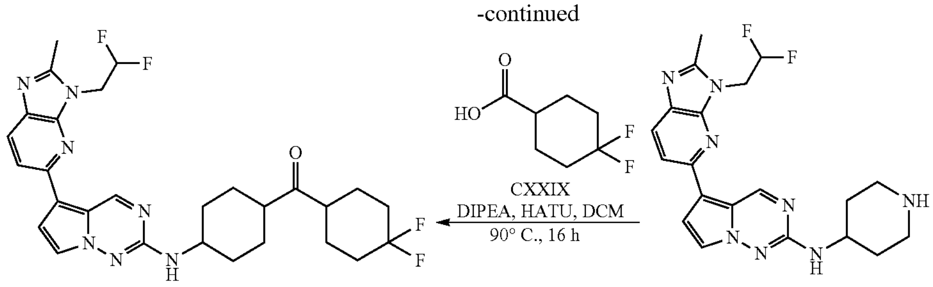

1953 1916

Step 1

A mixture of DIPEA (1.6 mL, 9.19 mmol), 5-bromo-2-chloropyrrolo[2,1-f][1,2,4]triazine (I) (commercially available from Advanced ChemBlocks Inc.) (530 mg, 2.26 mmol) and 4-amino-1-Boc-piperidine (CXXVI) (commercially available from Combi-Blocks Inc.) (540 mg, 2.71 mmol) in 1,4-dioxane (10 mL) was heated to 110° C. for 16 h. The reaction was concentrated and dissolved in DCM, washed with water, brine. dried over anhydrous $MgSO_4$, filtered, and concentrated to produce tert-butyl 4-[(5-bromopyrrolo[2,1-f][1,2,4]triazin-2-yl)amino]piperidine-1-carboxylate (CXXVII) (940 mg, 2.372 mmol, 105.0% yield) as a light brown viscous solid. Carried forward to the next step without further purification. ESIMS found for $C_{16}H_{22}BrN_5O_2$ m/z 396.1 (M+H).

Steps 2-3

To a microwave vial was added 5-chloro-3-(2,2-difluoroethyl)-2-methylimidazo[4,5-b]pyridine (XXXIV) (350 mg, 1.51 mmol), bis(pinacolato)diboron (510 mg, 2.02 mmol), KOAc (450 mg, 4.54 mmol), and Pd(dppf)$Cl_2$ (60 mg, 0.08 mmol) in 1,4-dioxane (5 mL). The reaction mixture was heated to 90° C. for 16 h. tert-Butyl 4-[(5-bromopyrrolo[2,1-f][1,2,4]triazin-2-yl)amino]piperidine-1-carboxylate (CXXVII) (400 mg, 1.01 mmol), a 2 N aqueous solution of $K_3PO_4$ (1.6 mL, 3.2 mmol), and Pd(dppf)$Cl_2$ (60 mg, 0.08 mmol) was added and stirred for 90° C. for an additional 8 h. The reaction was concentrated and purified via column chromatography. (0→8% MeOH/$CHCl_3$) (12 g of silica gel) to yield tert-butyl 4-[[5-[3-(2,2-difluoroethyl)-2-methylimidazo [4,5-b]pyridin-5-yl]pyrrolo[2,1-f][1,2,4]triazin-2-yl] amino]piperidine-1-carboxylate (CXXVIII) (470 mg, 0.917 mmol, 90.8% yield) as an amber viscous solid. ESIMS found for $C_{25}H_{30}F_2N_8O_2$ m/z 513.3 (M+H).

Step 4

To a solution of tert-butyl 4-[[5-[3-(2,2-difluoroethyl)-2-methylimidazo[4,5-b]pyridin-5-yl]pyrrolo[2,1-f][1,2,4]triazin-2-yl]amino]piperidine-1-carboxylate (CXXVIII) (470 mg, 0.92 mmol) in DCM (5 mL) was added TFA (0.7 mL, 9.09 mmol). The reaction mixture was stirred at room temperature for 3 h. The reaction was concentrated and basified with a $NH_4$ solution (7 N) in MeOH and then purified via column chromatography (0→10% 7 N $NH_3$ in MeOH/$CHCl_3$) (12 g of silica gel) to give 5-(3-(2,2-difluoroethyl)-2-methyl-3H-imidazo[4,5-b]pyridin-5-yl)-N-(piperidin-4-yl)pyrrolo[2,1-f][1,2,4]triazin-2-amine (1916) (220 mg, 0.533 mmol, 58.2% yield) as a yellow solid. $^1$H NMR (499 MHz, DMSO-$d_6$) δ ppm 1.36 (2H, qd, J=11.59, 3.83 Hz), 1.88 (2H, br d, J=9.86 Hz), 2.51-2.55 (2H, m), 2.60 (3H, s), 2.96 (2H, br d, J=12.32 Hz), 3.59-3.72 (1H, m), 4.83 (2H, td, J=15.95, 2.60 Hz), 6.55 (1H, tt, J=54.60, 3.00 Hz), 6.80 (1H, d, J=7.94 Hz), 7.22 (1H, d, J=2.74 Hz), 7.64 (1H, d, J=2.46 Hz), 7.72 (1H, d, J=8.49 Hz), 7.95 (1H, d, J=8.21 Hz), 9.69 (1H, s); ESIMS found for $C_{20}H_{22}F_2N_8$ m/z 413.2 (M+1).

Step 5

To a solution of 5-[3-(2,2-difluoroethyl)-2-methylimidazo [4,5-b]pyridin-5-yl]-N-piperidin-4-ylpyrrolo[2,1-f][1,2,4] triazin-2-amine (1916) (30 mg, 0.07 mmol) in DCM (1 mL) was added DIPEA (40 µL, 0.24 mmol) and HATU (40 mg, 0.11 mmol). The reaction was allowed to stir at room temperature for 5 min. 4,4-Difluorocyclohexanecarboxylic acid (CXXIX) (10 mg, 0.09 mmol) was then added and reaction was heated to 90° C. for 16 h. The reaction was concentrated and purified via column chromatography (0→8% 7 N $NH_3$ in MeOH/$CHCl_3$) (8 g of silica gel) to afford (4,4-difluorocyclohexyl)(4-((5-(3-(2,2-difluoroethyl)-2-methyl-3H-imidazo[4,5-b]pyridin-5-yl)pyrrolo[2,1-f][1,2,4]triazin-2-yl)amino)piperidin-1-yl)methanone (1953) (18 mg, 0.032 mmol, 44.3% yield) as a yellow solid. $^1$H NMR (499 MHz, DMSO-$d_6$) δ ppm 1.30-1.39 (1H, m), 1.41-1.51 (1H, m), 1.53-1.67 (2H, m), 1.73 (2H, br d, J=13.14 Hz), 1.81-1.92 (1H, m), 1.92-1.98 (2H, m), 1.98-2.12 (3H, m), 2.61 (3H, s), 2.74-2.81 (1H, m), 2.84 (1H, brt, J=11.23 Hz), 3.20 (1H, brt, J=11.91 Hz), 3.82-3.94 (1H, m), 3.99 (1H, brd, J=13.42 Hz), 4.31 (1H, br d, J=12.59 Hz), 4.83 (2H, td, J=16.02, 2.74 Hz), 6.55 (1H, tt, J=54.50, 3.00 Hz), 6.91 (1H, d, J=7.94 Hz), 7.24 (1H, d, J=2.74 Hz), 7.66 (1H, d, J=2.74 Hz), 7.73 (1H, d, J=8.49 Hz), 7.95 (1H, d, J=8.49 Hz), 9.71 (1H, s); ESIMS found for $C_{27}H_{30}F_4N_8O$ m/z 559.3 (M+1).

Example 12

Preparation of N-((1r,3r)-1-methyl-3-((5-(quinoxalin-6-yl)pyrrolo[2,1-f][1,2,4]triazin-2-yl)amino)cyclobutyl)acetamide (1981) is depicted below in Scheme 27.

Scheme 27

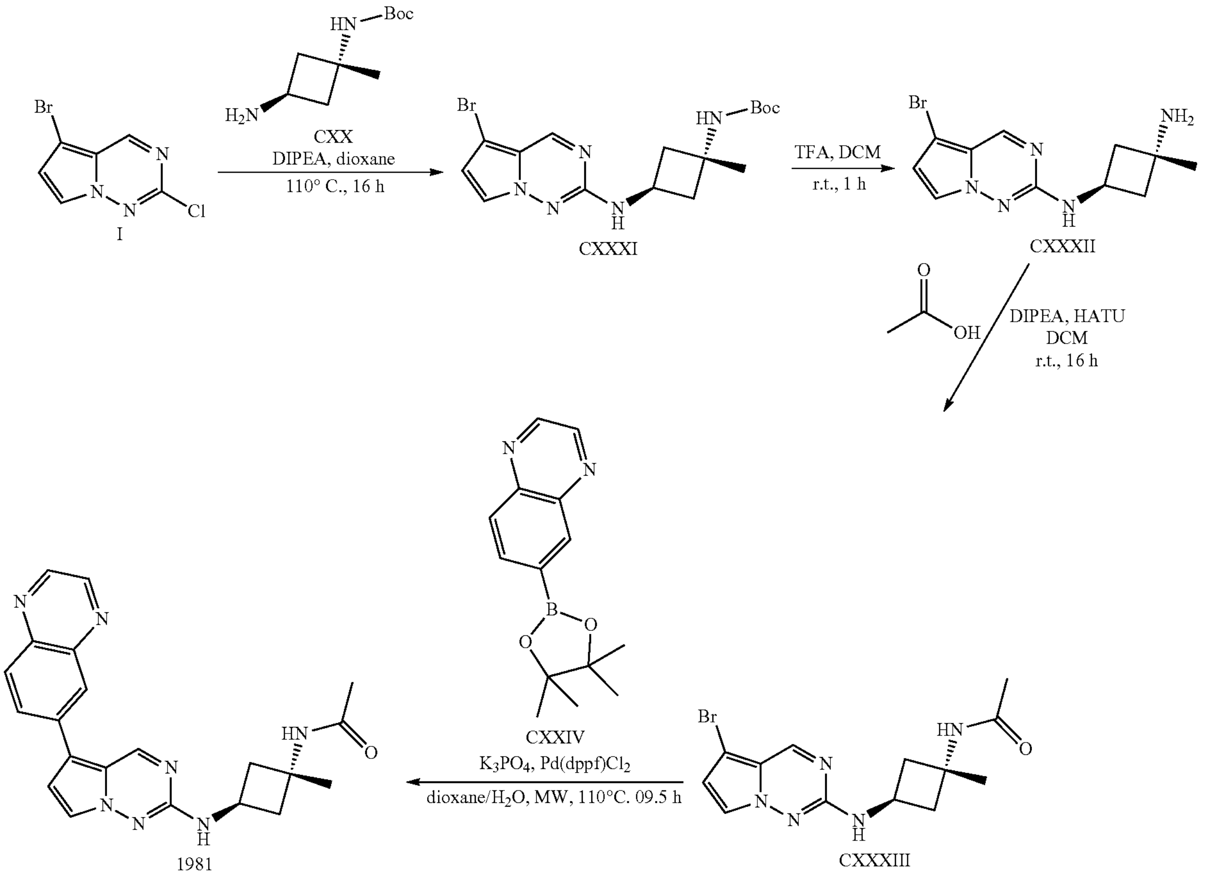

Step 1

To a microwave vial of 5-bromo-2-chloropyrrolo[2,1-f][1,2,4]triazine (I) (commercially available from Advanced ChemBlocks Inc.) (500 mg, 2.15 mmol) in 1,4-dioxane (10 mL) was added DIPEA (1.12 mL, 6.43 mmol) and trans-tert-butyl N-(3-amino-1-methylcyclobutyl)carbamate (CXXX) (commercially available from PharmaBlock (USA), Inc.) (544 mg, 2.72 mmol). Reaction vial was capped and heated to 110° C. for 16 h. The reaction was concentrated and purified via column chromatography (0→8% 7 N $NH_3$ in MeOH/$CHCl_3$) (8 g of silica gel) to give tert-butyl N-[3-[(5-bromopyrrolo[2,1-f][1,2,4]triazin-2-yl)amino]-1-methylcyclobutyl]carbamate (CXXXI) (266 mg, 0.671 mmol, 31.2% yield) as a light-yellow solid. ESIMS found for $C_{16}H_{22}BrN_5O_2$ m/z 396.1 (M-$^t$Bu+H).

Steps 2

To a stirred solution of tert-butyl N-[3-[(5-bromopyrrolo[2,1-f][1,2,4]triazin-2-yl)amino]-1-methylcyclobutyl]carbamate (CXXXI) (266 mg, 0.67 mmol) in DCM (1 mL) was added TFA (1.6 mL, 20.77 mmol). The mixture was stirred at room temperature for 1 h, concentrated and the residue was purified by ISCO (0→8% 7 N $NH_3$ MeOH/$CHCl_3$). The pure fractions were collected, concentrated under reduced pressure, and dried under high vacuo to obtain 3-N-(5-bromopyrrolo[2,1-f][1,2,4]triazin-2-yl)-1-methylcyclobutane-1,3-diamine (CXXXII) (126 mg, 0.425 mmol, 63.4% yield) as a dark yellow solid. ESIMS found for $C_{11}H_{14}BrN_5$ m/z 296.05 (M+H).

Step 3

To a solution of HOAc (37 μL, 0.65 mmol), HATU (243 mg, 0.64 mmol) in DMF (200 μL) was added DIPEA (220 μL, 1.26 mmol). The mixture was stirred for 5 min then, 3-N-(5-bromopyrrolo[2,1-f][1,2,4]triazin-2-yl)-1-methylcyclobutane-1,3-diamine (CXXXII) (146 mg, 0.49 mmol) in DMF (300 μL) was added and the reaction mixture was stirred at room temperature for 16 h. Water (10 mL) was added, and the solution was extracted with EtOAc. The organics were separated, concentrated, absorbed on silica gel, and purified by ISCO (0→100% 7 N $NH_3$ in MeOH/$CHCl_3$). The pure fractions were concentrated and dried under high vacuo to obtain N-[3-[(5-bromopyrrolo[2,1-f][1,2,4]triazin-2-yl)amino]-1-methylcyclobutyl]acetamide (CXXXIII) (130 mg, 0.384 mmol, 78.0% yield) as a dark yellow solid. ESIMS found for $C_{13}H_{16}BrN_5O$ m/z 338.1 (M+H).

Step 4

A mixture of trans-N-[3-[(5-bromopyrrolo[2,1-f][1,2,4]triazin-2-yl)amino]-1-methylcyclobutyl]acetamide (CXXXIII) (30 mg, 0.09 mmol), 6-(4,4,5,5-tetramethyl-1,3,2-dioxaborolan-2-yl)quinoxaline (CXXXIV) (commercially available from AmBeed, Inc.) (27.3 mg, 0.11 mmol), Pd(dppf)$Cl_2$ (3.7 mg, 0.0045 mmol), and a 2 N aqueous solution of $K_3PO_4$ (130 μL, 0.26 mmol), in 1,4-dioxane (5 mL) was purged with $N_2$ gas for 5 min. The mixture was stirred and irradiated with microwave at 110° C. for 30 min. The reaction mixture was cooled, and organic layer was separated, concentrated and purified via column chromatography (0-7% 7 N $NH_3$ in MeOH/$CHCl_3$) (8 g of silica gel) to afford N-((1r,3r)-1-methyl-3-((5-(quinoxalin-6-yl)pyrrolo[2,1-f][1,2,4]triazin-2-yl)amino)cyclobutyl)acetamide (1981) (14 mg, 0.036 mmol, 40.7% yield) as a yellow solid. $^1$H NMR (499 MHz, DMSO-$d_6$) δ ppm 1.37 (3H, s), 1.82 (3H, s), 1.90-2.01 (2H, m), 2.66 (2H, ddd, J=10.27, 7.94, 2.60 Hz), 4.20 (1H, sxt, J=7.72 Hz), 7.19 (1H, d, J=2.74 Hz), 7.36 (1H, d, J=7.12 Hz), 7.75 (1H, d, J=2.46 Hz), 7.96 (1H, s), 8.13 (1H, d, J=8.76 Hz), 8.23 (1H, dd, J=8.76, 1.92 Hz), 8.31 (1H, d, J=2.19 Hz), 8.90 (1H, d, J=1.92 Hz), 8.95 (1H, d, J=1.92 Hz), 9.19 (1H, s); ESIMS found for $C_{21}H_{21}N_7O$ m/z 388.2 (M+1).

The following compounds were prepared in accordance with the procedures described in the above Schemes 1-27.

2

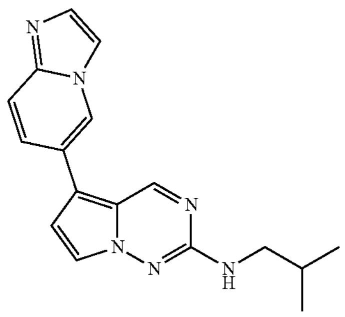

5-(Imidazo[1,2-a]pyridin-6-yl)-N-isobutylpyrrolo[2,1-f][1,2,4]triazin-2-amine 2

Yellow solid (40.14 mg, 0.131 mmol). $^1$H NMR (400 MHz, DMSO-$d_6$) δ ppm 0.92 (6H, d, J=6.60 Hz), 1.95 (1H, dquin, J=13.49, 6.75, 6.75, 6.75, 6.75 Hz), 3.03 (2H, dd, J=6.85, 5.99 Hz), 6.94 (1H, d, J=2.57 Hz), 7.00 (1H, t, J=5.75 Hz), 7.53-7.58 (1H, m), 7.58 (1H, d, J=1.22 Hz), 7.60-7.65 (1H, m), 7.70 (1H, dd, J=2.57, 0.61 Hz), 7.94 (1H, d, J=0.73 Hz), 8.91 (1H, dd, J=1.71, 1.10 Hz), 9.10 (1H, s); ESIMS found for $C_{17}H_{18}N_6$ m/z 307.2 (M+1).

3

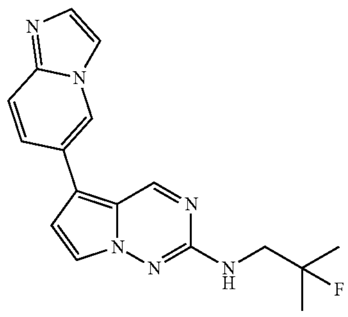

N-(2-Fluoro-2-methylpropyl)-5-(imidazo[1,2-a]pyridin-6-yl)pyrrolo[2,1-f][1,2,4]triazin-2-amine 3

Pale yellow solid (16 mg, 0.049 mmol, 38.3% yield). $^1$H NMR (499 MHz, DMSO-$d_6$) δ ppm 1.37 (6H, d, J=21.40 Hz), 3.48 (2H, dd, J=19.16, 6.57 Hz), 6.98 (1H, d, J=2.46 Hz), 7.05 (1H, t, J=6.43 Hz), 7.54-7.58 (1H, m), 7.59 (1H, d, J=1.09 Hz), 7.61-7.64 (1H, m), 7.72 (1H, d, J=2.46 Hz), 7.95 (1H, s), 8.89-8.96 (1H, m), 9.14 (1H, s); ESIMS found for $C_{17}H_{17}FN_6$ m/z 325.2 (M+1).

4

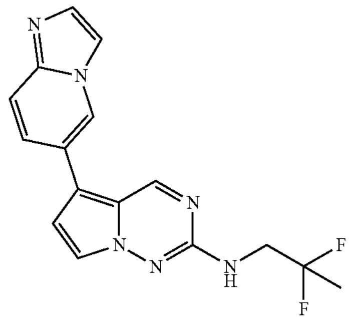

N-(2,2-Difluoropropyl)-5-(imidazo[1,2-a]pyridin-6-yl)pyrrolo[2,14][1,2,4]triazin-2-amine 4

Yellow solid (9.31 mg, 0.028 mmol). $^1$H NMR (400 MHz, DMSO-$d_6$) δ ppm 1.66 (3H, t, J=19.01 Hz), 3.72 (2H, td, J=13.75, 6.72 Hz), 7.01 (1H, d, J=2.57 Hz), 7.33 (1H, t, J=6.66 Hz), 7.55-7.66 (2H, m), 7.59 (1H, s), 7.76 (1H, d, J=2.45 Hz), 7.95 (1H, s), 8.93 (1H, s), 9.17 (1H, s); ESIMS found for $C_{16}H_{14}F_2N_6$ m/z 329.1 (M+1).

9

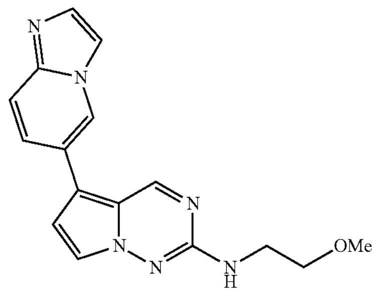

5-(Imidazo[1,2-a]pyridin-6-yl)-N-(2-methoxyethyl)pyrrolo[2,1-f][1,2,4]triazin-2-amine 9

Yellow solid (55.95 mg, 0.181 mmol). $^1$H NMR (400 MHz, DMSO-$d_6$) δ ppm 3.28 (3H, s), 3.36-3.38 (2H, m), 3.50-3.54 (2H, m), 6.91 (1H, brt, J=5.69 Hz), 6.96 (1H, d, J=2.57 Hz), 7.54-7.65 (2H, m), 7.58 (1H, s), 7.72 (1H, d, J=2.32 Hz), 7.94 (1H, s), 8.91 (1H, s), 9.12 (1H, s); ESIMS found for $C_{16}H_{16}N_6O$ m/z 309.1 (M+1).

11

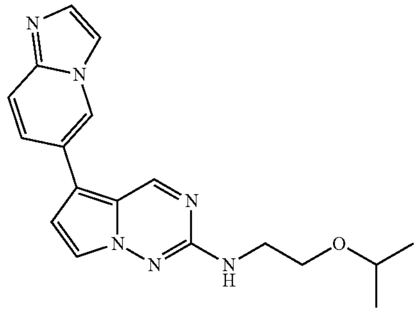

5-(Imidazo[1,2-a]pyridin-6-yl)-N-(2-isopropoxy-ethyl)pyrrolo[2,1-f][1,2,4]triazin-2-amine 11

Yellow solid (30.8 mg, 0.092 mmol). $^1$H NMR (400 MHz, DMSO-$d_6$) δ ppm 1.10 (6H, d, J=6.13 Hz), 3.34-3.38 (2H, m), 3.55 (2H, t, J=6.19 Hz), 3.57-3.63 (1H, m), 6.84 (1H, t, J=5.75 Hz), 6.97 (1H, d, J=2.50 Hz), 7.53-7.65 (2H, m), 7.58 (1H, d, J=1.00 Hz), 7.73 (1H, d, J=2.50 Hz), 7.94 (1H, s), 8.92 (1H, s), 9.12 (1H, s); ESIMS found for $C_{18}H_{20}N_6O$ m/z 337.1 (M+1).

12

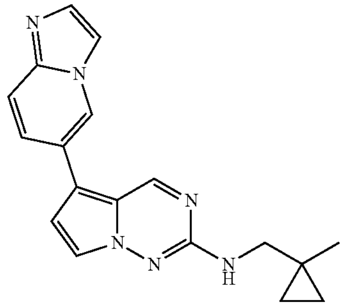

5-(Imidazo[1,2-a]pyridin-6-yl)-N-((1-methylcyclo-propyl)methyl)pyrrolo[2,1-f][1,2,4]triazin-2-amine 12

Yellow solid (13.6 mg, 0.043 mmol). $^1$H NMR (400 MHz, DMSO-$d_6$) δ ppm 0.22-0.30 (2H, m), 0.48-0.54 (2H, m), 1.11 (3H, s), 3.17 (2H, d, J=5.88 Hz), 6.91-6.99 (2H, m), 7.53-7.64 (2H, m), 7.58 (1H, d, J=0.88 Hz), 7.69 (1H, d, J=2.50 Hz), 7.94 (1H, s), 8.92 (1H, s), 9.12 (1H, s); ESIMS found for $C_{18}H_{18}N_6$ m/z 319.1 (M+1).

16

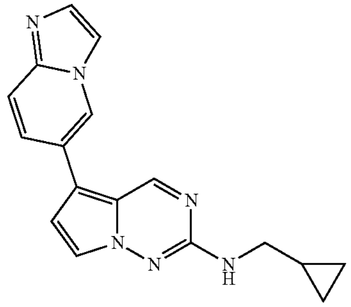

N-(Cyclopropylmethyl)-5-(imidazo[1,2-a]pyridin-6-yl)pyrrolo[2,1-f][1,2,4]triazin-2-amine 16

Yellow solid (5.16 mg, 0.017 mmol). $^1$H NMR (400 MHz, DMSO-$d_6$) δ ppm 0.19-0.28 (2H, m), 0.40-0.50 (2H, m), 1.07-1.17 (1H, m), 3.09 (2H, t, J=6.24 Hz), 6.96 (1H, d, J=2.57 Hz), 7.04 (1H, t, J=5.81 Hz), 7.53-7.65 (2H, m), 7.58 (1H, d, J=1.10 Hz), 7.71 (1H, dd, J=2.45, 0.61 Hz), 7.95 (1H, s), 8.92 (1H, dd, J=1.65, 1.04 Hz), 9.12 (1H, s); ESIMS found for $C_{17}H_{16}N_6$ m/z 305.3 (M+1).

20

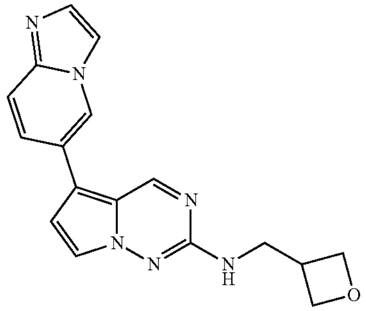

5-(Imidazo[1,2-a]pyridin-6-yl)-N-(oxetan-3-ylm-ethyl)pyrrolo[2,1-f][1,2,4]triazin-2-amine 20

Yellow solid (14.48 mg, 0.045 mmol). $^1$H NMR (400 MHz, DMSO-$d_6$) δ ppm 3.26 (1H, br s), 3.51 (2H, br s), 4.36 (2H, br s), 4.66 (2H, br s), 6.96 (1H, br s), 7.16 (1H, br s), 7.59 (3H, br d, J=8.31 Hz), 7.73 (1H, br s), 7.94 (1H, br s), 8.91 (1H, br s), 9.12 (1H, br s); ESIMS found for $C_{17}H_{16}N_6O$ m/z 321.0 (M+1).

21

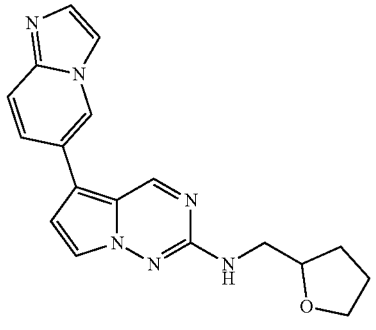

5-(Imidazo[1,2-a]pyridin-6-yl)-N-((tetrahydrofuran-2-yl)methyl)pyrrolo[2,1-f][1,2,4]triazin-2-amine 21

Yellow solid (36.87 mg, 0.110 mmol). $^1$H NMR (400 MHz, DMSO-$d_6$) δ ppm 1.56-1.70 (1H, m), 1.74-1.89 (2H, m), 1.90-2.01 (1H, m), 3.15-3.26 (1H, m), 3.29-3.38 (1H, m), 3.58-3.70 (1H, m), 3.74-3.85 (1H, m), 4.08 (1H, quin, J=6.36 Hz), 6.92 (1H, t, J=5.99 Hz), 6.96 (1H, d, J=2.57 Hz), 7.54-7.64 (2H, m), 7.58 (1H, d, J=0.98 Hz), 7.72 (1H, d, J=2.45 Hz), 7.94 (1H, s), 8.92 (1H, s), 9.12 (1H, s); ESIMS found for $C_{18}H_{18}N_6O$ m/z 335.4 (M+1).

23

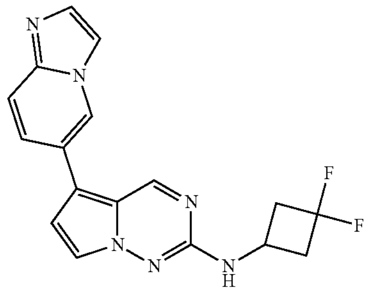

N-(3,3-Difluorocyclobutyl)-5-(imidazo[1,2-a]pyridin-6-yl)pyrrolo[2,1-f][1,2,4]triazin-2-amine 23

Yellow solid (4.61 mg, 0.014 mmol). $^1H$ NMR (400 MHz, DMSO-$d_6$) δ ppm 2.57-2.77 (2H, m), 2.91-3.07 (2H, m), 3.99-4.13 (1H, m), 7.00 (1H, d, J=2.57 Hz), 7.52-7.65 (3H, m), 7.59 (1H, d, J=1.10 Hz), 7.76 (1H, d, J=2.57 Hz), 7.95 (1H, s), 8.93 (1H, s), 9.17 (1H, s); ESIMS found for $C_{17}H_{14}F_2N_6$ m/z 341.0 (M+1).

26

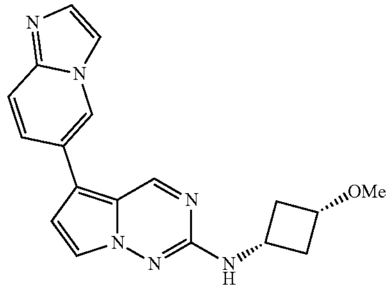

5-(Imidazo[1,2-a]pyridin-6-yl)-N-(cis-3-methoxycyclobutyl)pyrrolo[2,1-f][1,2,4]triazin-2-amine 26

Yellow solid (37.9 mg, 0.113 mmol). $^1H$ NMR (400 MHz, DMSO-$d_6$) δ ppm 1.78-1.91 (2H, m), 2.60-2.72 (2H, m), 3.14 (3H, s), 3.62 (1H, quin, J=7.09 Hz), 3.78 (1H, sxt, J=7.85 Hz), 6.96 (1H, d, J=2.45 Hz), 7.28 (1H, d, J=7.34 Hz), 7.53-7.64 (3H, m), 7.70 (1H, d, J=2.57 Hz), 7.94 (1H, s), 8.92 (1H, s), 9.12 (1H, s); ESIMS found for $C_{18}H_{18}N_6O$ m/z 335.4 (M+1).

43

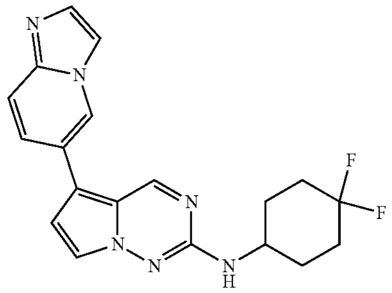

N-(4,4-Difluorocyclohexyl)-5-(imidazo[1,2-a]pyridin-6-yl)pyrrolo[2,1-f][1,2,4]triazin-2-amine 43

Yellow solid (52.2 mg, 0.142 mmol). $^1H$ NMR (400 MHz, DMSO-$d_6$) δ ppm 1.64 (2H, q, J=11.25 Hz), 1.82-2.03 (4H, m), 2.04-2.17 (2H, m), 3.72-3.88 (1H, m), 6.97 (1H, d, J=2.57 Hz), 7.02 (1H, d, J=7.58 Hz), 7.54-7.65 (2H, m), 7.59 (1H, s), 7.72 (1H, d, J=2.45 Hz), 7.95 (1H, s), 8.92 (1H, s), 9.13 (1H, s); ESIMS found for $C_{19}H_{18}F_2N_6$ m/z 369.1 (M+1).

64

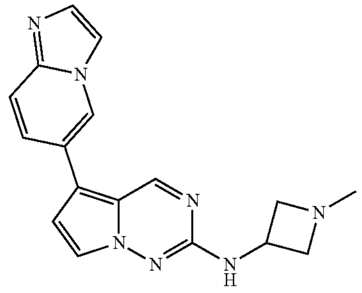

5-(Imidazo[1,2-a]pyridin-6-yl)-N-(1-methylazetidin-3-yl)pyrrolo[2,1-f][1,2,4]triazin-2-amine 64

Yellow solid (1.93 mg, 0.006 mmol). $^1H$ NMR (400 MHz, DMSO-$d_6$) δ ppm 2.25 (3H, s), 2.91 (2H, t, J=7.21 Hz), 3.57-3.64 (2H, m), 4.22 (1H, sxt, J=6.80 Hz), 6.97 (1H, d, J=2.57 Hz), 7.43 (1H, d, J=6.85 Hz), 7.54-7.64 (2H, m), 7.58 (1H, d, J=0.98 Hz), 7.72 (1H, d, J=2.08 Hz), 7.94 (1H, s), 8.92 (1H, s), 9.14 (1H, s); ESIMS found for $C_{17}H_{17}N_7$ m/z 320.0 (M+1).

65

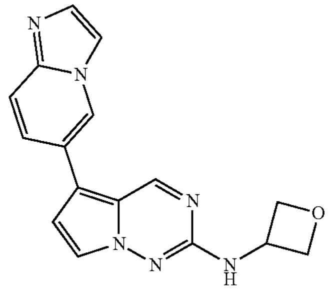

5-(Imidazo[1,2-a]pyridin-6-yl)-N-(oxetan-3-yl)pyrrolo[2,1-f][1,2,4]triazin-2-amine 65

Yellow solid (28.58 mg, 0.093 mmol). $^1H$ NMR (400 MHz, DMSO-$d_6$) δ ppm 4.55 (2H, s), 4.74-4.85 (3H, m), 6.99 (1H, d, J=2.50 Hz), 7.54-7.65 (2H, m), 7.59 (1H, s), 7.72 (1H, d, J=2.50 Hz), 7.76 (1H, br d, J=5.38 Hz), 7.94 (1H, s), 8.93 (1H, s), 9.17 (1H, s); ESIMS found for $C_{16}H_{14}N_6O$ m/z 307.2 (M+1).

66

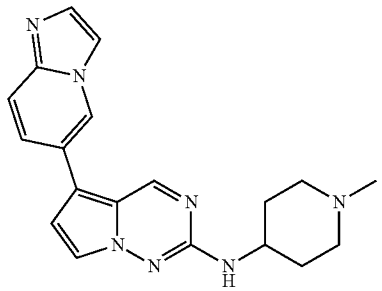

5-(Imidazo[1,2-a]pyridin-6-yl)-N-(1-methylpiperidin-4-yl)pyrrolo[2,1-f][1,2,4]triazin-2-amine 66

Yellow solid (38.32 mg, 0.110 mmol). H NMR (400 MHz, DMSO-$d_6$) δ ppm 1.53 (2H, qd, J=11.59, 3.61 Hz), 1.86-2.00 (4H, m), 2.16 (3H, s), 2.75 (2H, br d, J=11.62 Hz), 3.47-3.61 (1H, m), 6.85 (1H, d, J=7.83 Hz), 6.95 (1H, d, J=2.57 Hz), 7.53-7.64 (2H, m), 7.58 (1H, d, J=1.10 Hz), 7.71 (1H, d, J=2.08 Hz), 7.94 (1H, s), 8.88-8.94 (1H, m), 9.12 (1H, s); ESIMS found for $C_{19}H_{21}N_7$ m/z 348.1 (M+1).

67

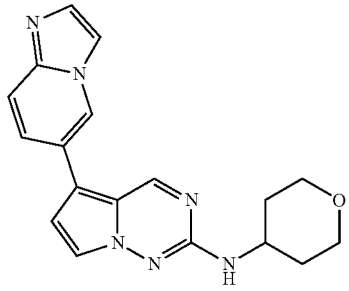

5-(Imidazo[1,2-a]pyridin-6-yl)-N-(tetrahydro-2H-pyran-4-yl)pyrrolo[2,1-f][1,2,4]triazin-2-amine 67

Yellow solid (7.97 mg, 0.024 mmol). $^1$H NMR (400 MHz, DMSO-$d_6$) δ ppm 1.46-1.63 (2H, m), 1.91 (2H, br d, J=11.13 Hz), 3.40 (2H, br t, J=10.82 Hz), 3.73-3.84 (1H, m), 3.89 (2H, br d, J=11.37 Hz), 6.91-7.01 (2H, m), 7.54-7.66 (3H, m), 7.71 (1H, d, J=2.20 Hz), 7.95 (1H, s), 8.91 (1H, s), 9.13 (1H, s); ESIMS found for $C_{18}H_{18}N_6O$ m/z 335.1 (M+1).

74

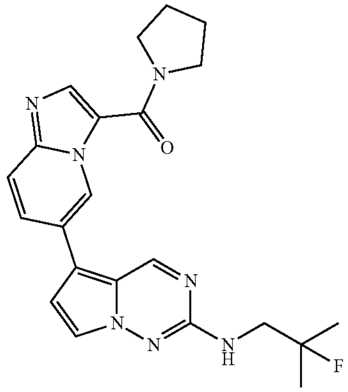

(6-(2-((2-Fluoro-2-methylpropyl)amino)pyrrolo[2,1-f][1,2,4]triazin-5-yl) imidazo[1,2-a]pyridin-3-yl)(pyrrolidin-1-yl)methanone 74

Yellow solid (21 mg, 0.050 mmol, 22.0% yield). $^1$H NMR (499 MHz, DMSO-$d_6$) δ ppm 1.38 (6H, d, J=21.40 Hz), 1.91 (2H, br s), 1.95 (2H, br s), 3.49 (2H, dd, J=19.16, 6.30 Hz), 3.58 (2H, br s), 3.81 (2H, br s), 6.99 (1H, d, J=2.46 Hz), 7.08 (1H, t, J=6.43 Hz), 7.74 (1H, d, J=2.46 Hz), 7.77-7.86 (2H, m), 8.22 (1H, s), 9.03 (1H, s), 9.65 (1H, t, J=1.37 Hz); ESIMS found for $C_{22}H_{24}FN_7O$ m/z 422.2 (M+1).

145

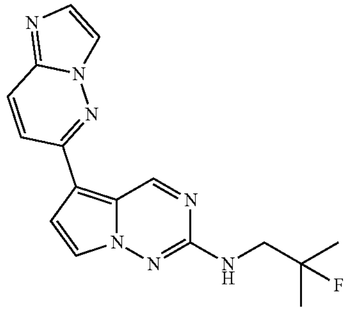

N-(2-Fluoro-2-methylpropyl)-5-(imidazo[1,2-b]pyridazin-6-yl)pyrrolo[2,1-f][1,2,4]triazin-2-amine 145

Light brown solid (18 mg, 0.055 mmol, 21.2% yield). $^1$H NMR (499 MHz, DMSO-$d_6$) δ ppm 1.38 (6H, d, J=21.40 Hz), 3.49 (2H, dd, J=19.03, 6.43 Hz), 7.25 (1H, t, J=6.43 Hz), 7.41 (1H, d, J=2.74 Hz), 7.73-7.78 (3H, m), 8.13 (1H, d, J=9.58 Hz), 8.35 (1H, s), 9.58 (1H, s); ESIMS found for $C_{16}H_{16}FN_7$ m/z 326.1 (M+1).

214

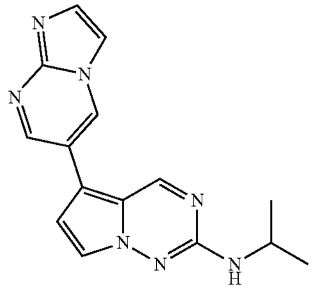

5-(Imidazo[1,2-a]pyrimidin-6-yl)-N-isopropylpyrrolo[2,1-f][1,2,4]triazin-2-amine 214

Yellow solid (12.01 mg, 0.041 mmol). $^{1}$H NMR (400 MHz, DMSO-$d_6$) δ ppm 1.19 (6H, d, J=6.50 Hz), 3.82-3.97 (1H, m), 6.84 (1H, d, J=7.88 Hz), 7.05 (1H, d, J=2.63 Hz), 7.74 (2H, d, J=1.50 Hz), 7.89 (1H, d, J=1.13 Hz), 8.88 (1H, d, J=2.50 Hz), 9.14 (1H, s), 9.29 (1H, d, J=2.38 Hz); ESIMS found for $C_{15}H_{15}N_7$ m/z 294.1 (M+1).

215

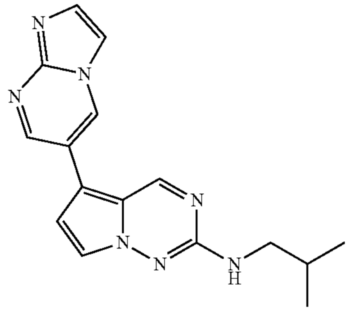

5-(Imidazo[1,2-a]pyrimidin-6-yl)-N-isobutylpyrrolo[2,1-f][1,2,4]triazin-2-amine 215

Yellow solid (25.06 mg, 0.082 mmol). $^{1}$H NMR (400 MHz, DMSO-$d_6$) δ ppm 0.92 (6H, d, J=6.50 Hz), 1.95 (1H, dquin, J=13.30, 6.65, 6.65, 6.65, 6.65 Hz), 3.03 (2H, br t, J=6.25 Hz), 7.00-7.09 (2H, m), 7.74 (2H, br s), 7.89 (1H, s), 8.88 (1H, s), 9.14 (1H, s), 9.29 (1H, s); ESIMS found for $C_{16}H_{17}N_7$ m/z 308.0 (M+1).

216

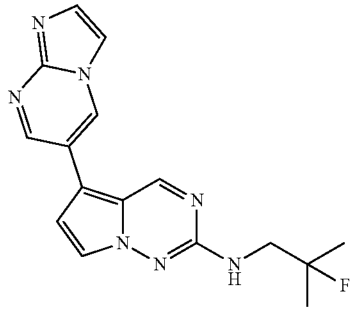

N-(2-Fluoro-2-methylpropyl)-5-(imidazo[1,2-a]pyrimidin-6-yl)pyrrolo[2,1-f][1,2,4]triazin-2-amine 216

Yellow solid (102 mg, 0.314 mmol, 20.0% yield). $^{1}$H NMR (500 MHz, DMSO-$d_6$) δ ppm 1.37 (6H, d, J=21.40 Hz), 3.48 (2H, dd, J=18.94, 6.31 Hz), 7.09 (1H, d, J=2.74 Hz), 7.11 (1H, t, J=6.45 Hz), 7.74 (1H, d, J=1.37 Hz), 7.75-7.77 (1H, m), 7.89 (1H, d, J=1.37 Hz), 8.89 (1H, d, J=2.47 Hz), 9.18 (1H, d, J=0.82 Hz), 9.31 (1H, d, J=2.74 Hz); ESIMS found for $C_{16}H_{16}FN_7$ m/z 326.1 (M+1).

218

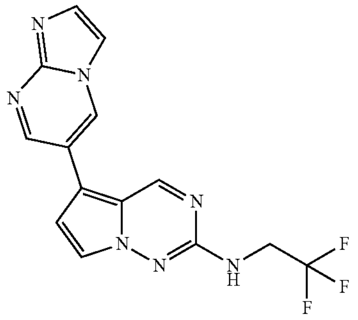

5-(Imidazo[1,2-a]pyrimidin-6-yl)-N-(2,2,2-trifluoroethyl)pyrrolo[2,1-f][1,2,4]triazin-2-amine 218

Yellow solid (8.99 mg, 0.027 mmol). $^{1}$H NMR (400 MHz, DMSO-$d_6$) δ ppm 4.03-4.17 (2H, m), 7.16 (1H, d, J=2.63 Hz), 7.65 (1H, t, J=7.00 Hz), 7.75 (1H, d, J=1.25 Hz), 7.86 (1H, d, J=2.63 Hz), 7.90 (1H, d, J=1.25 Hz), 8.90 (1H, d, J=2.50 Hz), 9.25 (1H, s), 9.33 (1H, d, J=2.63 Hz); ESIMS found for $C_{14}H_{10}F_3N_7$ m/z 334.1 (M+1).

219

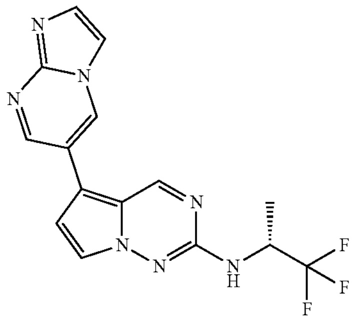

(R)-5-(Imidazo[1,2-a]pyrimidin-6-yl)-N-(1,1,1-trifluoropropan-2-yl)pyrrolo [2,1-f][1,2,4]triazin-2-amine 219

Yellow solid (20.91 mg, 0.060 mmol). $^{1}$H NMR (400 MHz, DMSO-$d_6$) δ ppm 1.37 (3H, d, J=7.00 Hz), 4.66-4.82 (1H, m), 7.15 (1H, d, J=2.50 Hz), 7.60 (1H, d, J=9.13 Hz), 7.75 (1H, d, J=1.13 Hz), 7.84 (1H, d, J=2.63 Hz), 7.90 (1H, d, J=1.25 Hz), 8.90 (1H, d, J=2.50 Hz), 9.24 (1H, s), 9.33 (1H, d, J=2.50 Hz); ESIMS found for $C_{15}H_{12}F_3N_7$ m/z 348.1 (M+1).

220

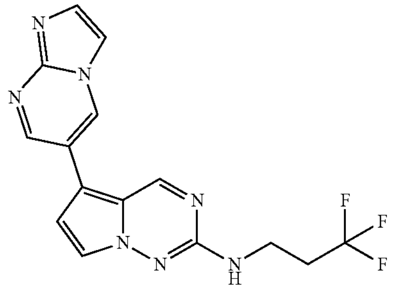

5-(Imidazo[1,2-a]pyrimidin-6-yl)-N-(3,3,3-trifluoro-propyl)pyrrolo[2,1-f][1,2,4]triazin-2-amine 220

Yellow solid (12.8 mg, 0.037 mmol $^1$H NMR (400 MHz, DMSO-$d_6$) δ ppm 2.55-2.71 (2H, m), 3.47 (2H, q, J=6.70 Hz), 7.10 (1H, d, J=2.63 Hz), 7.19 (1H, t, J=5.69 Hz), 7.74 (1H, s), 7.80 (1H, d, J=2.50 Hz), 7.89 (1H, d, J=0.88 Hz), 8.89 (1H, d, J=2.50 Hz), 9.18 (1H, s), 9.31 (1H, d, J=2.50 Hz); ESIMS found for $C_{15}H_{12}F_3N_7$ m/z 348.0 (M+1).

221

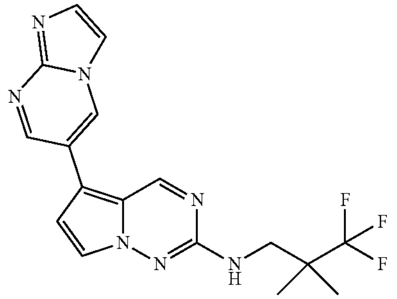

5-(Imidazo[1,2-a]pyrimidin-6-yl)-N-(3,3,3-trifluoro-2,2-dimethylpropyl) pyrrolo[2,1-f][1,2,4]triazin-2-amine 221

Pale yellow solid (29 mg, 0.077 mmol, 26.0% yield). $^1$H NMR (499 MHz, DMSO-$d_6$) δ ppm 1.16 (6H, s), 3.48 (2H, d, J=6.57 Hz), 7.10 (1H, d, J=2.74 Hz), 7.13 (1H, t, J=6.57 Hz), 7.75 (1H, d, J=1.09 Hz), 7.78 (1H, d, J=2.74 Hz), 7.90 (1H, d, J=1.09 Hz), 8.89 (1H, d, J=2.19 Hz), 9.20 (1H, s), 9.31 (1H, d, J=2.19 Hz); ESIMS found for $C_{17}H_{16}F_3N_7$ m/z 376.2 (M+1).

223

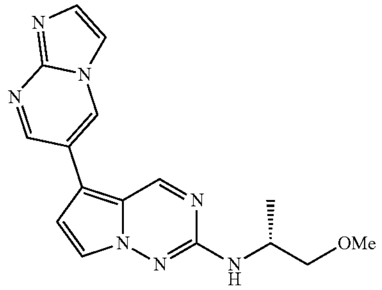

(R)-5-(Imidazo[1,2-a]pyrimidin-6-yl)-N-(1-methoxypropan-2-yl)pyrrolo[2,1-f][1,2,4]triazin-2-amine 223

Yellow solid (28.36 mg, 0.088 mmol). $^1$H NMR (400 MHz, DMSO-$d_6$) δ ppm 1.17 (3H, d, J=6.63 Hz), 3.26-3.32 (1H, m), 3.28 (3H, s), 3.43-3.48 (1H, m), 3.94-4.09 (1H, m), 6.79 (1H, d, J=8.25 Hz), 7.07 (1H, d, J=2.50 Hz), 7.74 (1H, br s), 7.75 (1H, d, J=2.50 Hz), 7.89 (1H, s), 8.88 (1H, d, J=2.50 Hz), 9.16 (1H, s), 9.30 (1H, d, J=2.38 Hz); ESIMS found for $C_{16}H_{17}N_7O$ m/z 324.0 (M+1).

225

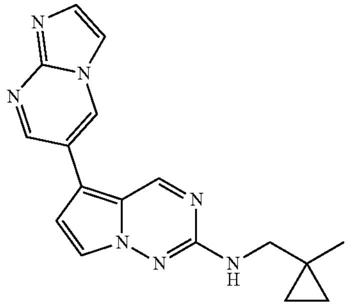

5-(Imidazo[1,2-a]pyrimidin-6-yl)-N-((1-methylcy-clopropyl)methyl)pyrrolo [2,1-f][1,2,4]triazin-2-amine 225

Pale yellow solid (43 mg, 0.135 mmol, 37.9% yield). $^1$H NMR (499 MHz, DMSO-$d_6$) δ ppm 0.23-0.30 (2H, m), 0.47-0.54 (2H, m), 1.11 (3H, s), 3.17 (2H, d, J=6.02 Hz), 7.00 (1H, t, J=5.75 Hz), 7.06 (1H, d, J=2.74 Hz), 7.73 (1H, d, J=2.19 Hz), 7.74 (1H, d, J=1.10 Hz), 7.89 (1H, d, J=1.10 Hz), 8.88 (1H, d, J=2.19 Hz), 9.16 (1H, s), 9.30 (1H, d, J=2.74 Hz); ESIMS found for $C_{17}H_{17}N_7$ m/z 3202. (M+1).

226

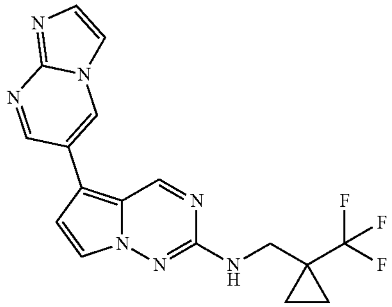

5-(Imidazo[1,2-a]pyrimidin-6-yl)-N-((1-(trifluorom-ethyl)cyclopropyl) methyl)pyrrolo[2,1-f][1,2,4]tri-azin-2-amine 226

Pale yellow solid (27 mg, 0.072 mmol, 24.2% yield). $^1$H NMR (499 MHz, DMSO-$d_6$) δ ppm 0.88-0.94 (2H, m), 0.94-1.01 (2H, m), 3.63 (2H, d, J=6.57 Hz), 7.10 (1H, d, J=2.74 Hz), 7.14 (1H, t, J=6.30 Hz), 7.74 (1H, d, J=1.09 Hz), 7.78 (1H, d, J=2.19 Hz), 7.89 (1H, d, J=1.64 Hz), 8.89 (1H, d, J=2.74 Hz), 9.19 (1H, s), 9.31 (1H, d, J=2.74 Hz); ESIMS found for $C_{17}H_{14}F_3N_7$ m/z 374.1 (M+1).

227

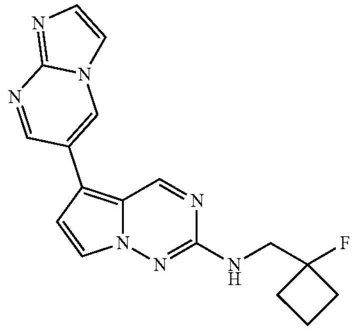

N-((1-Fluorocyclobutyl)methyl)-5-(imidazo[1,2-a]pyrimidin-6-yl)pyrrolo [2,1-f][1,2,4]triazin-2-amine 227

Pale yellow solid (30 mg, 0.089 mmol, 26.6% yield). $^1$H NMR (499 MHz, DMSO-$d_6$) δ ppm 1.48-1.63 (1H, m), 1.71-1.84 (1H, m), 2.14-2.24 (2H, m), 2.25-2.32 (2H, m), 3.57-3.68 (2H, m), 7.09 (1H, d, J=2.74 Hz), 7.16 (1H, t, J=6.30 Hz), 7.74 (1H, d, J=1.64 Hz), 7.77 (1H, d, J=2.74 Hz), 7.89 (1H, d, J=1.09 Hz), 8.89 (1H, d, J=2.74 Hz), 9.19 (1H, s), 9.31 (1H, d, J=2.74 Hz); ESIMS found for $C_{17}H_{16}FN_7$ m/z 338.2 (M+1).

228

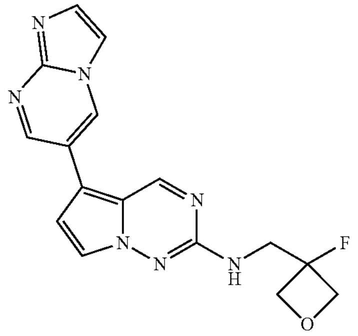

N-((3-Fluorooxetan-3-yl)methyl)-5-(imidazo[1,2-a]pyrimidin-6-yl)pyrrolo [2,1-f][1,2,4]triazin-2-amine 228

Yellow solid (26 mg, 0.077 mmol, 33.0% yield). $^1$H NMR (499 MHz, DMSO-$d_6$) δ ppm 3.80 (2H, dd, J=19.71, 6.02 Hz), 4.61-4.77 (4H, m), 7.11 (1H, d, J=2.19 Hz), 7.37 (1H, t, J=6.30 Hz), 7.75 (1H, d, J=1.10 Hz), 7.80 (1H, d, J=2.19 Hz), 7.90 (1H, d, J=1.10 Hz), 8.89 (1H, d, J=2.74 Hz), 9.20 (1H, s), 9.32 (1H, d, J=2.74 Hz); ESIMS found for $C_{16}H_{14}FN_7O$ m/z 340.1 (M+1).

229

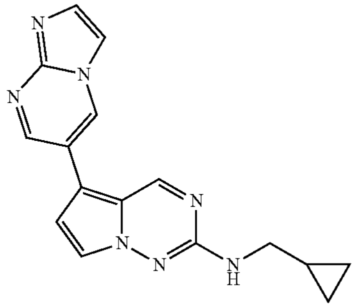

N-(Cyclopropylmethyl)-5-(imidazo[1,2-a]pyrimidin-6-yl)pyrrolo[2,1-f][1,2,4]triazin-2-amine 229

Yellow solid (11.82 mg, 0.039 mmol). $^1$H NMR (400 MHz, DMSO-$d_6$) δ ppm 0.21-0.29 (2H, m), 0.41-0.50 (2H, m), 1.08-1.21 (1H, m), 3.10 (2H, t, J=6.25 Hz), 7.05-7.11 (2H, m), 7.75 (2H, dd, J=3.56, 1.94 Hz), 7.89 (1H, d, J=1.13 Hz), 8.88 (1H, d, J=2.50 Hz), 9.16 (1H, s), 9.30 (1H, d, J=2.50 Hz); ESIMS found for $C_{16}H_{15}N_7$ m/z 306.1 (M+1).

230

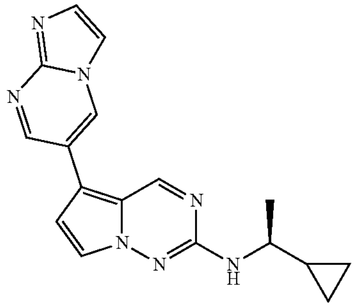

(S)—N-(1-Cyclopropylethyl)-5-(imidazo[1,2-a]pyrimidin-6-yl)pyrrolo[2,1-f][1,2,4]triazin-2-amine 230

Yellow solid (28.31 mg, 0.089 mmol). $^1$H NMR (400 MHz, DMSO-$d_6$) δ ppm 0.15-0.24 (1H, m), 0.31-0.51 (3H, m), 0.97-1.09 (1H, m), 1.24 (3H, d, J=6.63 Hz), 3.35 (1H, br d, J=4.38 Hz), 7.05 (1H, br d, J=3.25 Hz), 7.18 (1H, d, J=2.63 Hz), 7.78 (1H, d, J=2.50 Hz), 8.17 (1H, d, J=2.25 Hz), 8.25 (1H, d, J=2.13 Hz), 9.22 (1H, s), 9.37 (1H, d, J=2.25 Hz), 9.61 (1H, d, J=2.38 Hz); ESIMS found for $C_{17}H_{17}N_7$ m/z 320.2 (M+1).

231

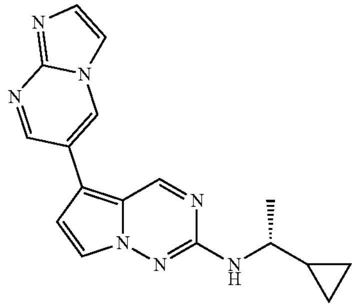

(R)—N-(1-Cyclopropylethyl)-5-(imidazo[1,2-a]pyrimidin-6-yl)pyrrolo[2,1-f][1,2,4]triazin-2-amine 231

Yellow solid (21.29 mg, 0.067 mmol). $^1$H NMR (400 MHz, DMSO-$d_6$) δ ppm 0.14-0.24 (1H, m), 0.31-0.50 (3H, m), 0.96-1.08 (1H, m), 1.23 (3H, d, J=6.50 Hz), 6.90 (1H, d, J=8.38 Hz), 7.05 (1H, d, J=2.50 Hz), 7.71 (1H, d, J=2.38 Hz), 7.74 (1H, s), 7.89 (1H, s), 8.88 (1H, d, J=2.50 Hz), 9.14 (1H, s), 9.29 (1H, d, J=2.50 Hz); ESIMS found for $C_{17}H_{17}N_7$ m/z 320.1 (M+1).

232

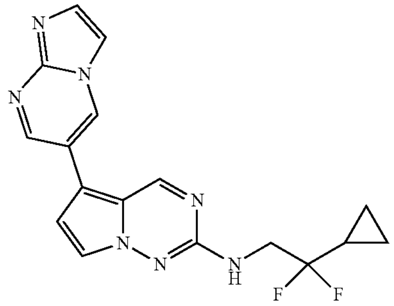

N-(2-Cyclopropyl-2,2-difluoroethyl)-5-(imidazo[1,2-a]pyrimidin-6-yl) pyrrolo[2,1-f][1,2,4]triazin-2-amine 232

Yellow solid (3 mg, 0.008 mmol, 4.1% yield). $^1$H NMR (499 MHz, DMSO-$d_6$) δ ppm 0.55-0.60 (4H, m), 1.41-1.55 (1H, m), 3.82 (2H, td, J=13.96, 6.57 Hz), 7.12 (1H, d, J=2.19 Hz), 7.36 (1H, t, J=6.57 Hz), 7.75 (1H, d, J=1.10 Hz), 7.80 (1H, d, J=2.19 Hz), 7.89 (1H, d, J=1.64 Hz), 8.90 (1H, d, J=2.74 Hz), 9.21 (1H, s), 9.32 (1H, d, J=2.74 Hz); ESIMS found for $C_{17}H_{15}F_2N_7$ m/z 356.1 (M+1).

235

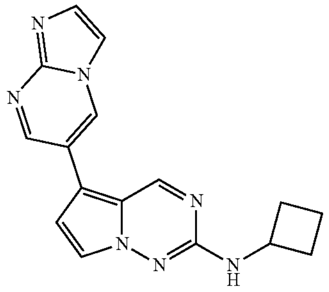

N-Cyclobutyl-5-(imidazo[1,2-a]pyrimidin-6-yl)pyrrolo[2,1-f][1,2,4]triazin-2-amine 235

Yellow solid (11.92 mg, 0.039 mmol). $^1$H NMR (400 MHz, DMSO-$d_6$) δ ppm 1.60-1.76 (2H, m), 1.92-2.06 (2H, m), 2.22-2.35 (2H, m), 4.18 (1H, dt, J=15.99, 7.96 Hz), 7.23 (1H, d, J=2.57 Hz), 7.81 (1H, d, J=2.57 Hz), 8.28-8.35 (2H, m), 9.29 (1H, s), 9.44 (1H, d, J=2.32 Hz), 9.82 (1H, d, J=2.20 Hz); ESIMS found for $C_{16}H_{15}N_7$ m/z 306.2 (M+1).

236

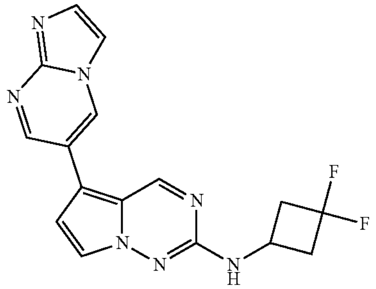

N-(3,3-Difluorocyclobutyl)-5-(imidazo[1,2-a]pyrimidin-6-yl)pyrrolo[2,1-f][1,2,4]triazin-2-amine 236

Yellow solid (10.03 mg, 0.029 mmol). $^1$H NMR (400 MHz, DMSO-$d_6$) δ ppm 2.58-2.75 (2H, m), 2.92-3.06 (2H, m), 4.01-4.13 (1H, m), 7.11 (1H, d, J=2.38 Hz), 7.58 (1H, d, J=6.25 Hz), 7.74 (1H, s), 7.79 (1H, d, J=2.38 Hz), 7.89 (1H, s), 8.88 (1H, d, J=2.25 Hz), 9.20 (1H, s), 9.31 (1H, d, J=2.25 Hz); ESIMS found for $C_{16}H_{13}F_2N_7$ m/z 342.0 (M+1).

237

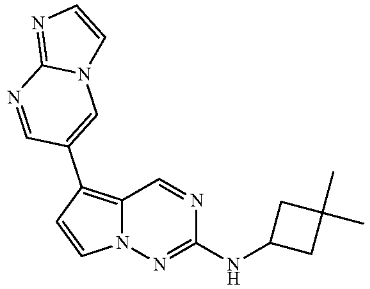

N-(3,3-Dimethylcyclobutyl)-5-(imidazo[1,2-a]pyrimidin-6-yl)pyrrolo[2,1-f][1,2,4]triazin-2-amine 237

Yellow solid (9.7 mg, 0.029 mmol). $^1$H NMR (400 MHz, DMSO-$d_6$) δ ppm 1.11 (3H, s), 1.16 (3H, s), 1.77-1.89 (2H, m), 2.16 (2H, ddd, J=9.14, 7.92, 2.51 Hz), 4.16 (1H, dt, J=16.11, 8.02 Hz), 7.22 (1H, d, J=2.69 Hz), 7.83 (1H, d, J=2.57 Hz), 8.27 (1H, d, J=2.20 Hz), 8.32 (1H, d, J=2.20 Hz), 9.26 (1H, s), 9.43 (1H, d, J=2.32 Hz), 9.76 (1H, d, J=2.20 Hz); ESIMS found for $C_{18}H_{19}N_7$ m/z 334.2 (M+1).

239

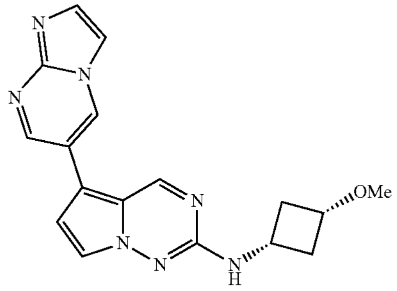

5-(Imidazo[1,2-a]pyrimidin-6-yl)-N-(cis-3-methoxycyclobutyl)pyrrolo[2,1-f][1,2,4]triazin-2-amine 239

Yellow solid (3.11 mg, 0.009 mmol). $^1$H NMR (400 MHz, DMSO-$d_6$) δ ppm 1.78-1.90 (2H, m), 2.66 (2H, dtd, J=9.06, 6.66, 6.66, 2.81 Hz), 3.14 (3H, s), 3.56-3.68 (1H, m), 3.78 (1H, dq, J=15.59, 7.93 Hz), 7.08 (1H, d, J=2.57 Hz), 7.32 (1H, d, J=7.34 Hz), 7.69-7.77 (2H, m), 7.89 (1H, d, J=1.34 Hz), 8.88 (1H, d, J=2.45 Hz), 9.16 (1H, s), 9.30 (1H, d, J=2.57 Hz); ESIMS found for $C_{17}H_{17}N_7O$ m/z 336.1 (M+1).

240

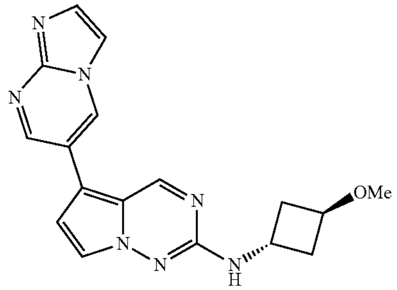

5-(Imidazo[1,2-a]pyrimidin-6-yl)-N-(trans-3-methoxycyclobutyl)pyrrolo [2,1-f][1,2,4]triazin-2-amine 240

Yellow solid (9.17 mg, 0.027 mmol). $^1$H NMR (400 MHz, DMSO-$d_6$) δ ppm 2.18-2.34 (4H, m), 3.16 (3H, s), 3.98-4.03 (1H, m), 4.15-4.25 (1H, m), 7.17 (1H, d, J=2.63 Hz), 7.47 (1H, br d, J=6.00 Hz), 7.81 (1H, d, J=2.50 Hz), 8.10-8.14 (2H, m), 9.21 (1H, s), 9.25 (1H, d, J=2.25 Hz), 9.54 (1H, d, J=2.38 Hz); ESIMS found for $C_{17}H_{17}N_7O$ m/z 336.1 (M+1).

242

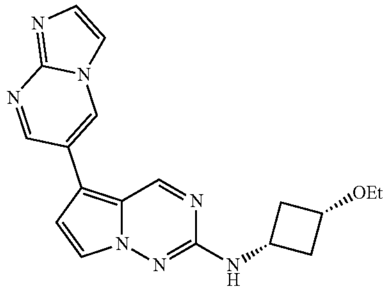

N-(cis-3-Ethoxycyclobutyl)-5-(imidazo[1,2-a]pyrimidin-6-yl)pyrrolo[2,1-f][1,2,4]triazin-2-amine 242

Brown solid (20 mg, 0.057 mmol, 11.9% yield). $^1$H NMR (499 MHz, DMSO-$d_6$) δ ppm 1.10 (3H, t, J=6.84 Hz), 1.80-1.92 (2H, m), 2.66 (2H, dtd, J=8.90, 6.78, 6.78, 2.74 Hz), 3.33-3.38 (2H, m), 3.66-3.73 (1H, m), 3.73-3.83 (1H, m), 7.07 (1H, d, J=2.74 Hz), 7.31 (1H, d, J=7.12 Hz), 7.72-7.75 (2H, m), 7.89 (1H, d, J=1.10 Hz), 8.88 (1H, d, J=2.19 Hz), 9.15 (1H, s), 9.30 (1H, d, J=2.19 Hz); ESIMS found for $C_{18}H_{19}N_7O$ m/z 350.15 (M+1).

244

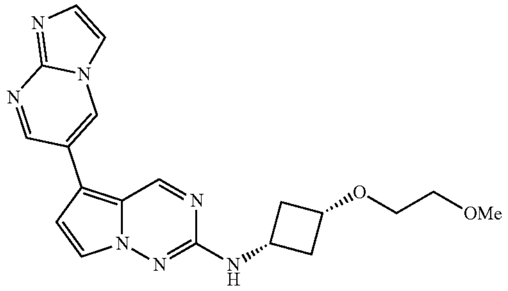

5-(Imidazo[1,2-a]pyrimidin-6-yl)-N-(cis-3-(2-methoxyethoxy)cyclobutyl) pyrrolo[2,1-f][1,2,4]triazin-2-amine 244

Tan solid (12 mg, 0.032 mmol, 5.4% yield). $^1$H NMR (499 MHz, DMSO-$d_6$) δ ppm 1.82-1.93 (2H, m), 2.62-2.71 (2H, m), 3.25 (3H, s), 3.42 (4H, s), 3.68-3.84 (2H, m), 7.07 (1H, d, J=2.19 Hz), 7.32 (1H, d, J=7.12 Hz), 7.74 (1H, d, J=4.38 Hz), 7.74 (1H, s), 7.89 (1H, d, J=1.64 Hz), 8.88 (1H, d, J=2.19 Hz), 9.16 (1H, s), 9.30 (1H, d, J=2.74 Hz); ESIMS found for $C_{19}H_{21}N_7O_2$ m/z 380.2 (M+1).

256

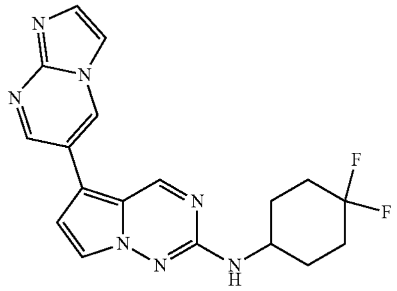

N-(4,4-Difluorocyclohexyl)-5-(imidazo[1,2-a]pyrimidin-6-yl)pyrrolo[2,1-f][1,2,4]triazin-2-amine 256

Pale yellow solid (67 mg, 0.1814 mmol, 23.3% yield). $^1$H NMR (499 MHz, DMSO-$d_6$) δ ppm 1.57-1.71 (2H, m), 1.85-2.04 (4H, m), 2.04-2.15 (2H, m), 3.74-3.86 (1H, m), 7.06 (1H, d, J=8.21 Hz), 7.08 (1H, d, J=2.74 Hz), 7.74 (1H, d, J=1.64 Hz), 7.76 (1H, d, J=2.74 Hz), 7.89 (1H, d, J=1.64 Hz), 8.89 (1H, d, J=2.19 Hz), 9.17 (1H, s), 9.30 (1H, d, J=2.74 Hz); ESIMS found for $C_{18}H_{17}F_2N_7$ m/z 370.1 (M+1).

258

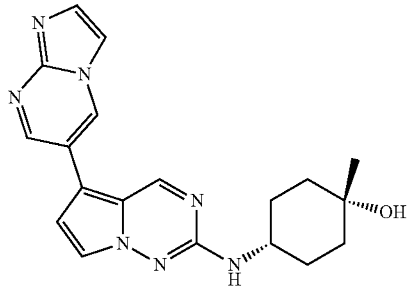

(1s,4s)-4-((5-(Imidazo[1,2-a]pyrimidin-6-yl)pyrrolo[2,1-f][1,2,4]triazin-2-yl)amino)-1-methylcyclohexan-1-ol 258

Yellow solid (37 mg, 0.102 mmol, 33.1% yield). $^1$H NMR (499 MHz, DMSO-$d_6$) δ ppm 1.12 (3H, s), 1.37 (2H, td, J=13.00, 4.11 Hz), 1.58 (2H, br d, J=12.05 Hz), 1.61-1.69 (2H, m), 1.69-1.75 (2H, m), 3.45-3.57 (1H, m), 4.02 (1H, s), 6.84 (1H, d, J=8.21 Hz), 7.04 (1H, d, J=2.74 Hz), 7.73 (1H, d, J=2.74 Hz), 7.74 (1H, d, J=1.10 Hz), 7.89 (1H, d, J=1.10 Hz), 8.88 (1H, d, J=2.19 Hz), 9.14 (1H, s), 9.29 (1H, d, J=2.74 Hz); ESIMS found for $C_{19}H_{21}N_7O$ m/z 364.2 (M+1).

259

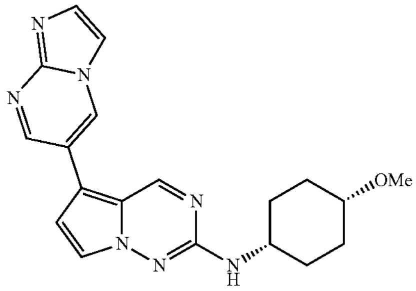

5-(Imidazo[1,2-a]pyrimidin-6-yl)-N-(cis-4-methoxycyclohexyl)pyrrolo[2,1-f][1,2,4]triazin-2-amine 259

Beige solid (5 mg, 0.014 mmol, 4.5% yield). $^1$H NMR (499 MHz, DMSO-$d_6$) δ ppm 1.42-1.55 (2H, m), 1.56-1.65 (2H, m), 1.66-1.76 (2H, m), 1.80-1.91 (2H, m), 3.22 (3H, s), 3.33-3.37 (1H, m), 3.59-3.68 (1H, m), 6.89 (1H, d, J=7.67 Hz), 7.05 (1H, q, J=2.19 Hz), 7.71-7.75 (2H, m), 7.89 (1H, d, J=1.64 Hz), 8.88 (1H, d, J=2.19 Hz), 9.14 (1H, s), 9.29 (1H, d, J=2.19 Hz); ESIMS found for $C_{19}H_{21}N_7O$ m/z 364.2 (M+1).

260

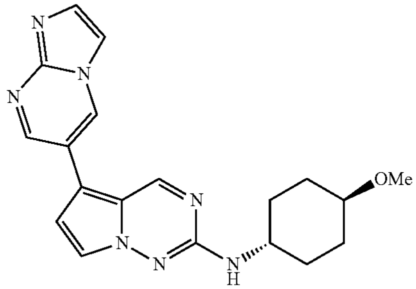

5-(Imidazo[1,2-a]pyrimidin-6-yl)-N-(trans-4-methoxycyclohexyl)pyrrolo [2,1-f][1,2,4]triazin-2-amine 260

Yellow solid (16.56 mg, 0.046 mmol). $^1$H NMR (400 MHz, DMSO-$d_6$) δ ppm 1.14-1.27 (2H, m), 1.27-1.41 (2H, m), 1.95-2.08 (4H, m), 3.13 (1H, tt, J=10.06, 3.45 Hz), 3.24 (3H, s), 3.51-3.63 (1H, m), 6.88 (1H, d, J=7.95 Hz), 7.06 (1H, d, J=2.57 Hz), 7.74 (1H, d, J=1.34 Hz), 7.76 (1H, d, J=2.08 Hz), 7.89 (1H, d, J=1.34 Hz), 8.88 (1H, d, J=2.57 Hz), 9.15 (1H, s), 9.29 (1H, d, J=2.45 Hz); ESIMS found for $C_{19}H_{21}N_7O$ m/z 364.2 (M+1).

263

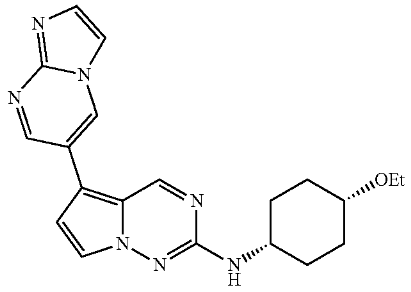

N-(cis-4-Ethoxycyclohexyl)-5-(imidazo[1,2-a]pyrimidin-6-yl)pyrrolo[2,1-f][1,2,4]triazin-2-amine 263

Tan solid (44 mg, 0.117 mmol, 26.4% yield). $^1$H NMR (499 MHz, DMSO-$d_6$) δ ppm 1.12 (3H, t, J=7.12 Hz), 1.43-1.56 (2H, m), 1.58-1.75 (4H, m), 1.77-1.87 (2H, m), 3.42 (2H, q, J=7.12 Hz), 3.44-3.47 (1H, m), 3.59-3.69 (1H, m), 6.88 (1H, d, J=7.67 Hz), 7.05 (1H, d, J=2.74 Hz), 7.74 (1H, d, J=3.85 Hz), 7.74 (1H, s), 7.89 (1H, d, J=1.64 Hz), 8.88 (1H, d, J=2.19 Hz), 9.14 (1H, s), 9.29 (1H, d, J=2.19 Hz); ESIMS found for $C_{20}H_{23}N_7O$ m/z 378.2 (M+1).

265

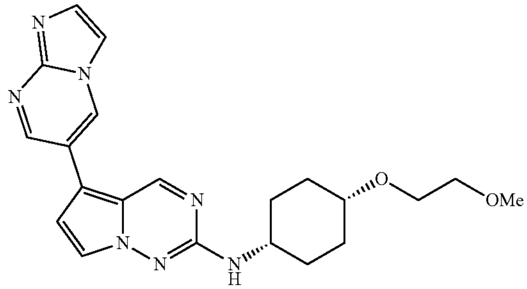

5-(Imidazo[1,2-a]pyrimidin-6-yl)-N-(cis-4-(2-methoxyethoxy)cyclohexyl) pyrrolo[2,1-f][1,2,4]triazin-2-amine 265

Yellow solid (18 mg, 0.044 mmol, 12.8% yield). $^1$H NMR (499 MHz, DMSO-$d_6$) δ ppm 1.44-1.57 (2H, m), 1.60-1.75 (4H, m), 1.78-1.88 (2H, m), 3.27 (3H, s), 3.43-3.46 (2H, m), 3.46-3.49 (1H, m), 3.49-3.52 (2H, m), 3.58-3.69 (1H, m), 6.91 (1H, d, J=7.67 Hz), 7.05 (1H, d, J=2.74 Hz), 7.73-7.75 (2H, m), 7.89 (1H, d, J=1.10 Hz), 8.88 (1H, d, J=2.74 Hz), 9.15 (1H, s), 9.29 (1H, d, J=2.74 Hz); ESIMS found for $C_{21}H_{25}N_7O_2$ m/z 408.2 (M+1).

279

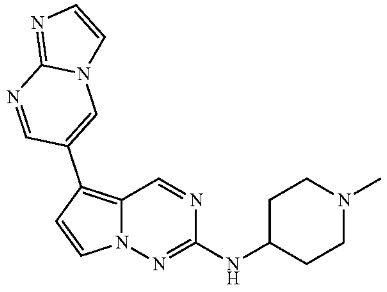

5-(Imidazo[1,2-a]pyrimidin-6-yl)-N-(1-methylpiperidin-4-yl)pyrrolo[2,1-f][1,2,4]triazin-2-amine 279

Yellow solid (18 mg, 0.052 mmol, 16.0% yield). $^1$H NMR (499 MHz, DMSO-$d_6$) δ ppm 1.47-1.60 (2H, m), 1.90 (2H, br d, J=9.86 Hz), 1.96 (2H, br t, J=11.50 Hz), 2.17 (3H, s), 2.75 (2H, br d, J=12.05 Hz), 3.48-3.59 (1H, m), 6.90 (1H, d, J=7.67 Hz), 7.06 (1H, d, J=2.74 Hz), 7.74 (1H, d, J=1.64 Hz), 7.75 (1H, d, J=2.19 Hz), 7.89 (1H, d, J=1.64 Hz), 8.88 (1H, d, J=2.74 Hz), 9.16 (1H, s), 9.30 (1H, d, J=2.74 Hz); ESIMS found for $C_{19}H_{20}N_8$ m/z 349.2 (M+1).

280

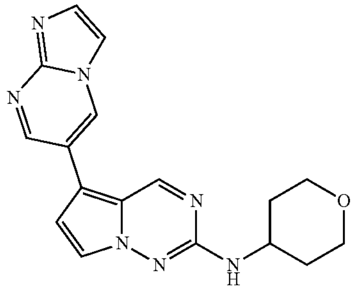

5-(Imidazo[1,2-a]pyrimidin-6-yl)-N-(tetrahydro-2H-pyran-4-yl)pyrrolo[2,1-f][1,2,4]triazin-2-amine 280

Yellow solid (54.78 mg, 0.163 mmol). $^1$H NMR (400 MHz, DMSO-$d_6$) δ ppm 1.45-1.61 (2H, m), 1.90 (2H, br dd, J=12.51, 2.00 Hz), 3.35-3.43 (2H, m), 3.72-3.83 (1H, m), 3.84-3.93 (2H, m), 7.01 (1H, d, J=7.75 Hz), 7.06 (1H, d, J=2.50 Hz), 7.74 (2H, dd, J=4.13, 1.88 Hz), 7.89 (1H, d, J=1.25 Hz), 8.88 (1H, d, J=2.50 Hz), 9.16 (1H, s), 9.29 (1H, d, J=2.50 Hz); ESIMS found for $C_{17}H_{17}N_7O$ m/z 336.1 (M+1).

281

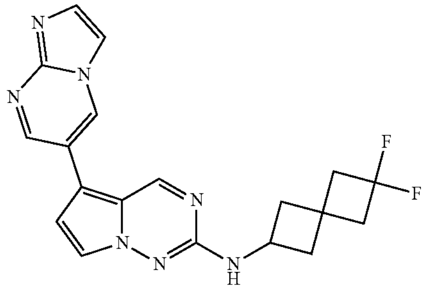

N-(6,6-Difluorospiro[3.3]heptan-2-yl)-5-(imidazo[1,2-a]pyrimidin-6-yl) pyrrolo[2,1-f][1,2,4]triazin-2-amine 281

Beige solid (33 mg, 0.087 mmol, 29.7% yield). $^1$H NMR (499 MHz, DMSO-$d_6$) δ ppm 2.12-2.21 (2H, m), 2.45-2.49 (2H, m), 2.58 (2H, brt, J=12.59 Hz), 2.65-2.76 (2H, m), 4.13 (1H, sxt, J=7.78 Hz), 7.07 (1H, d, J=2.74 Hz), 7.34 (1H, d, J=7.12 Hz), 7.74 (1H, d, J=1.64 Hz), 7.76 (1H, d, J=2.74 Hz), 7.89 (1H, d, J=1.10 Hz), 8.88 (1H, d, J=2.19 Hz), 9.16 (1H, s), 9.30 (1H, d, J=2.74 Hz); ESIMS found for $C_{19}H_{17}F_2N_7$ m/z 382.2 (M+1).

282

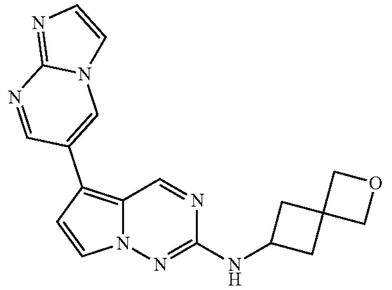

5-(Imidazo[1,2-a]pyrimidin-6-yl)-N-(2-oxaspiro[3.3]heptan-6-yl)pyrrolo[2,1-f][1,2,4]triazin-2-amine 282

Light brown solid (11 mg, 0.032 mmol, 10.9% yield). $^1$H NMR (499 MHz, DMSO-$d_6$) δ ppm 2.12-2.22 (2H, m), 2.58-2.67 (2H, m), 3.99 (1H, sxt, J=7.67 Hz), 4.52 (2H, s), 4.64 (2H, s), 7.07 (1H, d, J=2.74 Hz), 7.29 (1H, d, J=6.57 Hz), 7.72-7.76 (2H, m), 7.89 (1H, d, J=1.64 Hz), 8.88 (1H, d, J=2.74 Hz), 9.15 (1H, s), 9.30 (1H, d, J=2.19 Hz); ESIMS found for $C_{18}H_{17}N_7O$ m/z 348.2 (M+1).

283

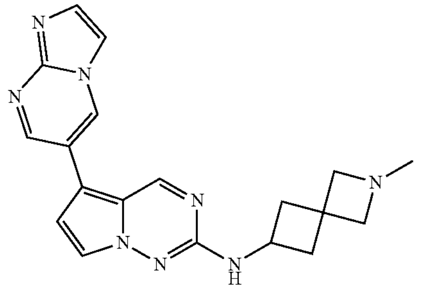

5-(Imidazo[1,2-a]pyrimidin-6-yl)-N-(2-methyl-2-azaspiro[3.3]heptan-6-yl)pyrrolo[2,1-f][1,2,4]triazin-2-amine 283

Yellow solid (5 mg, 0.014 mmol, 12.0% yield). $^1$H NMR (499 MHz, DMSO-$d_6$) δ ppm 2.03-2.10 (2H, m), 2.16 (3H, s), 2.45 (2H, ddd, J=9.72, 7.26, 2.74 Hz), 3.04 (2H, s), 3.16 (2H, s), 4.03 (1H, sxt, J=7.67 Hz), 7.07 (1H, d, J=2.74 Hz), 7.27 (1H, d, J=7.12 Hz), 7.74 (1H, d, J=1.64 Hz), 7.75 (1H, d, J=2.74 Hz), 7.89 (1H, d, J=1.09 Hz), 8.88 (1H, d, J=2.74 Hz), 9.14 (1H, s), 9.29 (1H, d, J=2.19 Hz); ESIMS found for $C_{19}H_{20}N_8$ m/z 361.2 (M+1).

287

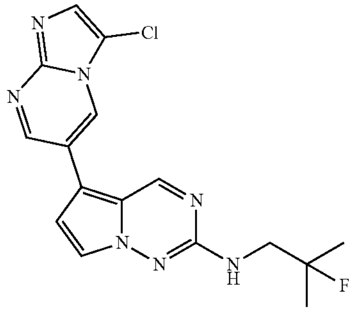

5-(3-Chloroimidazo[1,2-a]pyrimidin-6-yl)-N-(2-fluoro-2-methylpropyl) pyrrolo[2,1-f][1,2,4]triazin-2-amine 287

Yellow solid (16 mg, 0.045 mmol, 18.2% yield). $^1$H NMR (499 MHz, DMSO-$d_6$) δ ppm 1.38 (6H, d, J=21.40 Hz), 3.49 (2H, dd, J=19.16, 6.30 Hz), 7.11-7.15 (2H, m), 7.77 (1H, d, J=2.19 Hz), 7.89 (1H, s), 8.95 (2H, q, J=2.28 Hz), 9.15 (1H, s); ESIMS found for $C_{16}H_{15}ClFN_7$ m/z 360.1 (M+1).

358

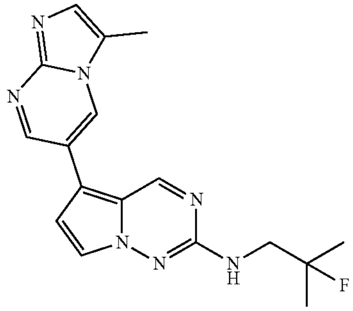

N-(2-Fluoro-2-methylpropyl)-5-(3-methylimidazo[1,2-a]pyrimidin-6-yl) pyrrolo[2,1-f][1,2,4]triazin-2-amine 358

Yellow solid (10.71 mg, 0.032 mmol). $^1$H NMR (400 MHz, DMSO-$d_6$) δ ppm 1.33 (6H, d, J=21.40 Hz), 2.46 (2H, br s), 3.44 (2H, dd, J=19.20, 6.32 Hz), 6.98-7.08 (2H, m), 7.49 (1H, s), 7.71 (1H, d, J=2.50 Hz), 8.77 (1H, d, J=2.25 Hz), 8.86 (1H, d, J=2.13 Hz), 9.14 (1H, s); ESIMS found for $C_{17}H_{18}FN_7$ m/z 340.1 (M+1).

398

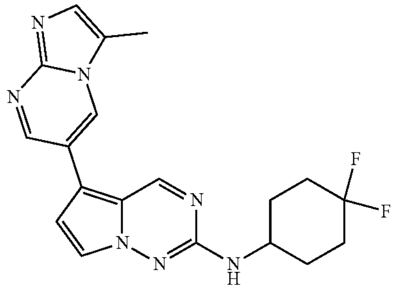

N-(4,4-Difluorocyclohexyl)-5-(3-methylimidazo[1,2-a]pyrimidin-6-yl) pyrrolo[2,1-f][1,2,4]triazin-2-amine 398

Yellow solid (2.1 mg, 0.005 mmol). $^1$H NMR (400 MHz, DMSO-$d_6$) δ ppm 1.58-1.72 (2H, m), 1.86-2.04 (4H, m), 2.09 (2H, br d, J=7.38 Hz), 2.54 (3H, s), 3.76-3.89 (1H, m), 7.01 (1H, br d, J=7.63 Hz), 7.07 (1H, d, J=2.38 Hz), 7.53 (1H, s), 7.75 (1H, d, J=2.38 Hz), 8.81 (1H, d, J=2.25 Hz), 8.89 (1H, d, J=2.13 Hz), 9.18 (1H, s); ESIMS found for $C_{19}H_{19}F_2N_7$ m/z 384.2 (M+1).

429

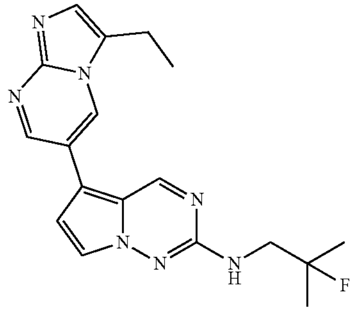

5-(3-Ethylimidazo[1,2-a]pyrimidin-6-yl)-N-(2-fluoro-2-methylpropyl) pyrrolo[2,1-f][1,2,4]triazin-2-amine 429

Yellow solid (11.07 mg, 0.031 mmol). $^1$H NMR (400 MHz, DMSO-$d_6$) δ ppm 1.31-1.37 (3H, m), 1.37 (6H, d, J=21.40 Hz), 2.98 (2H, q, J=7.50 Hz), 3.49 (2H, br dd, J=19.20, 6.32 Hz), 7.03-7.12 (2H, m), 7.55 (1H, s), 7.76 (1H, d, J=2.25 Hz), 8.82 (1H, d, J=2.25 Hz), 8.94 (1H, d, J=2.38 Hz), 9.15 (1H, s); ESIMS found for $C_{19}H_{20}FN_7$ m/z 354.3 (M+1).

500

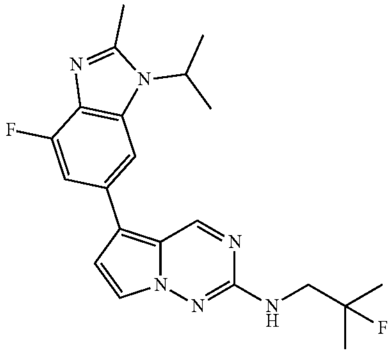

5-(4-Fluoro-1-isopropyl-2-methyl-1H-benzo[d]imidazol-6-yl)-N-(2-fluoro-2-methylpropyl)pyrrolo[2,1-f][1,2,4]triazin-2-amine 500

Yellow solid (34 mg, 0.085 mmol, 49.0% yield). $^1$H NMR (499 MHz, DMSO-$d_6$) δ ppm 1.37 (6H, d, J=21.40 Hz), 1.59 (6H, d, J=6.84 Hz), 2.60 (3H, s), 3.48 (2H, dd, J=19.16, 6.57 Hz), 4.83 (1H, dt, J=13.89, 6.88 Hz), 6.96-7.01 (2H, m), 7.24 (1H, dd, J=11.77, 1.10 Hz), 7.63 (1H, d, J=1.10 Hz), 7.68 (1H, d, J=2.46 Hz), 8.98 (1H, s); ESIMS found for $C_{21}H_{24}F_2N_6$ m/z 399.2 (M+1).

571

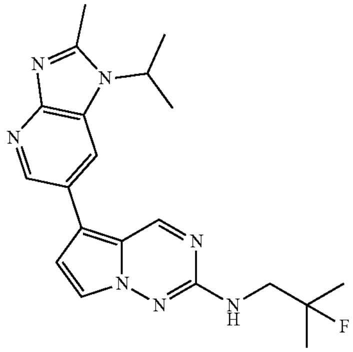

N-(2-Fluoro-2-methylpropyl)-5-(1-isopropyl-2-methyl-1H-imidazo[4,5-b]pyridin-6-yl)pyrrolo[2,1-f][1,2,4]triazin-2-amine 571

Yellow solid (39 mg, 0.102 mmol, 39.1% yield). $^1$H NMR (499 MHz, DMSO-$d_6$) δ ppm 1.38 (6H, d, J=21.40 Hz), 1.60 (6H, d, J=6.84 Hz), 2.64 (3H, s), 3.49 (2H, dd, J=19.30, 6.43 Hz), 4.76-4.90 (1H, m), 6.99-7.04 (2H, m), 7.72 (1H, d, J=2.46 Hz), 8.22 (1H, d, J=1.92 Hz), 8.60 (1H, d, J=2.19 Hz), 8.99 (1H, s); ESIMS found for $C_{20}H_{24}FN_7$ m/z 382.2 (M+1).

642

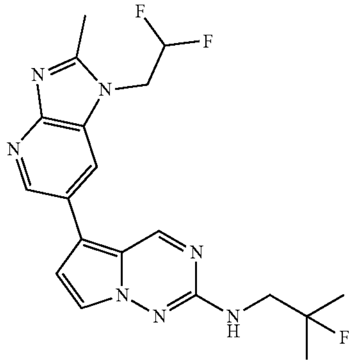

5-(1-(2,2-Difluoroethyl)-2-methyl-1H-imidazo[4,5-b]pyridin-6-yl)-N-(2-fluoro-2-methylpropyl)pyrrolo[2,1-f][1,2,4]triazin-2-amine 642

Yellow solid (37 mg, 0.092 mmol, 37.6% yield). $^1$H NMR (499 MHz, DMSO-$d_6$) δ ppm 1.38 (6H, d, J=21.40 Hz), 2.63 (3H, s), 3.49 (2H, dd, J=19.30, 6.43 Hz), 4.91 (2H, td, J=15.88, 3.01 Hz), 6.53 (1H, tt, J=54.40, 3.20 Hz), 7.01 (1H, d, J=2.74 Hz), 7.03 (1H, t, J=6.43 Hz), 7.73 (1H, d, J=2.46 Hz), 8.25 (1H, d, J=1.92 Hz), 8.67 (1H, d, J=1.92 Hz), 9.14 (1H, s); ESIMS found for $C_{19}H_{20}F_3N_7$ m/z 404.2 (M+1).

682

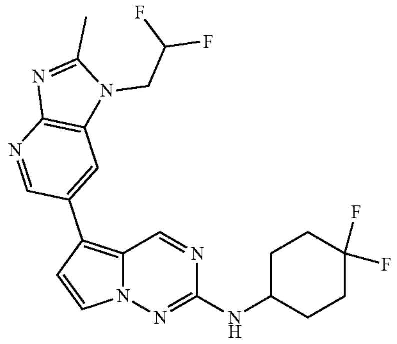

N-(4,4-Difluorocyclohexyl)-5-(1-(2,2-difluoroethyl)-2-methyl-1H-imidazo[4,5-b]pyridin-6-yl)pyrrolo[2,1-f][1,2,4]triazin-2-amine 682

Yellowish brown solid (8 mg, 0.018 mmol, 5.9% yield). $^1$H NMR (499 MHz, DMSO-$d_6$) δ ppm 1.56-1.70 (2H, m), 1.87-2.03 (4H, m), 2.03-2.16 (2H, m), 2.63 (3H, s), 3.76-3.86 (1H, m), 4.90 (2H, td, J=15.88, 2.74 Hz), 6.53 (1H, tt, J=54.60, 3.00 Hz), 6.98 (1H, d, J=8.21 Hz), 7.00 (1H, d, J=2.74 Hz), 7.73 (1H, d, J=2.74 Hz), 8.24 (1H, d, J=2.19 Hz), 8.66 (1H, d, J=2.19 Hz), 9.13 (1H, s); ESIMS found for $C_{21}H_{21}F_4N_7$ m/z 448.2 (M+1).

684

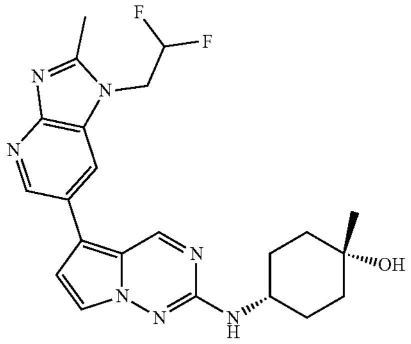

cis-4-((5-(1-(2,2-Difluoroethyl)-2-methyl-1H-imidazo[4,5-b]pyridin-6-yl)pyrrolo[2,1-f][1,2,4]triazin-2-yl)amino)-1-methylcyclohexan-1-ol 684

Dark yellow solid (16 mg, 0.036 mmol, 11.8% yield). $^1$H NMR (499 MHz, DMSO-$d_6$) δ ppm 1.13 (3H, s), 1.37 (2H, td, J=13.14, 4.38 Hz), 1.59 (2H, br d, J=12.05 Hz), 1.62-1.70 (2H, m), 1.70-1.76 (2H, m), 2.62 (3H, s), 3.47-3.60 (1H, m), 4.01 (1H, s), 4.90 (2H, td, J=15.74, 3.01 Hz), 6.52 (1H, tt, J=54.40, 3.00 Hz), 6.74 (1H, d, J=7.67 Hz), 6.96 (1H, d, J=2.74 Hz), 7.69 (1H, d, J=2.74 Hz), 8.22 (1H, d, J=2.19 Hz), 8.65 (1H, d, J=2.19 Hz), 9.09 (1H, s); ESIMS found for $C_{22}H_{25}F_2N_7O$ m/z 442.2 (M+1).

683

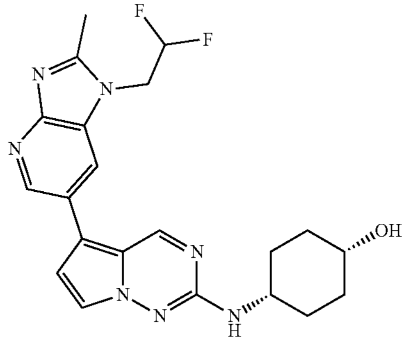

cis-4-((5-(1-(2,2-Difluoroethyl)-2-methyl-1H-imidazo[4,5-b]pyridin-6-yl)pyrrolo[2,1-f][1,2,4]triazin-2-yl)amino)cyclohexan-1-ol 683

Light brown solid (6 mg, 0.014 mmol, 4.4% yield). $^1$H NMR (499 MHz, DMSO-$d_6$) δ ppm 1.45-1.57 (2H, m), 1.61-1.69 (4H, m), 1.70-1.81 (2H, m), 2.62 (3H, s), 3.57-3.68 (1H, m), 3.74 (1H, br d, J=2.46 Hz), 4.35 (1H, d, J=3.01 Hz), 4.90 (2H, td, J=15.95, 2.87 Hz), 6.53 (1H, tt, J=54.60, 3.00 Hz), 6.76 (1H, d, J=7.67 Hz), 6.97 (1H, d, J=2.46 Hz), 7.71 (1H, d, J=2.46 Hz), 8.23 (1H, d, J=2.19 Hz), 8.66 (1H, d, J=1.92 Hz), 9.10 (1H, s); ESIMS found for $C_{21}H_{23}F_2N_7O$ m/z 428.2 (M+1).

685

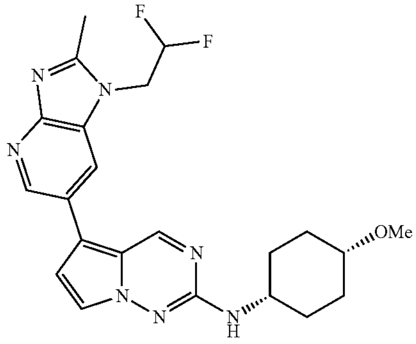

5-(1-(2,2-Difluoroethyl)-2-methyl-1H-imidazo[4,5-b]pyridin-6-yl)-N-(cis-4-methoxycyclohexyl)pyrrolo[2,1-f][1,2,4]triazin-2-amine 685

Light brown solid (46 mg, 0.104 mmol, 33.9% yield). $^1$H NMR (499 MHz, DMSO-$d_6$) δ ppm 1.44-1.53 (2H, m), 1.55-1.65 (2H, m), 1.66-1.74 (2H, m), 1.82-1.90 (2H, m), 2.62 (3H, s), 3.22 (3H, s), 3.35 (1H, br d, J=2.19 Hz), 3.60-3.72 (1H, m), 4.90 (2H, td, J=15.88, 2.74 Hz), 6.52 (1H, tt, J=54.60, 3.00 Hz), 6.80 (1H, d, J=7.94 Hz), 6.97 (1H, d, J=2.74 Hz), 7.71 (1H, d, J=2.19 Hz), 8.23 (1H, d, J=1.92 Hz), 8.66 (1H, d, J=2.19 Hz), 9.10 (1H, s); ESIMS found for $C_{22}H_{25}F_2N_7O$ m/z 442.2 (M+1).

686

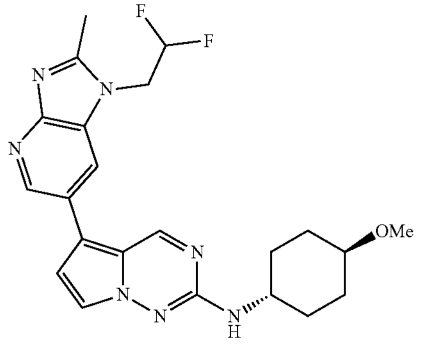

5-(1-(2,2-Difluoroethyl)-2-methyl-1H-imidazo[4,5-b]pyridin-6-yl)-N-(trans-4-methoxycyclohexyl)pyrrolo[2,1-f][1,2,4]triazin-2-amine 686

Light brown solid (42 mg, 0.095 mmol, 30.9% yield). $^1$H NMR (499 MHz, DMSO-$d_6$) δ ppm 1.14-1.26 (2H, m), 1.27-1.38 (2H, m), 1.95-2.09 (4H, m), 2.62 (3H, s), 3.13 (1H, tt, J=10.13, 3.42 Hz), 3.25 (3H, s), 3.51-3.64 (1H, m), 4.90 (2H, td, J=15.81, 2.60 Hz), 6.52 (1H, tt, J=54.60, 3.00 Hz), 6.79 (1H, d, J=8.21 Hz), 6.98 (1H, d, J=2.46 Hz), 7.73 (1 H, d, J=2.46 Hz), 8.23 (1H, d, J=1.64 Hz), 8.66 (1H, d, J=1.92 Hz), 9.11 (1H, s); ESIMS found for $C_{22}H_{25}F_2N_7O$ m/z 442.2 (M+1).

687

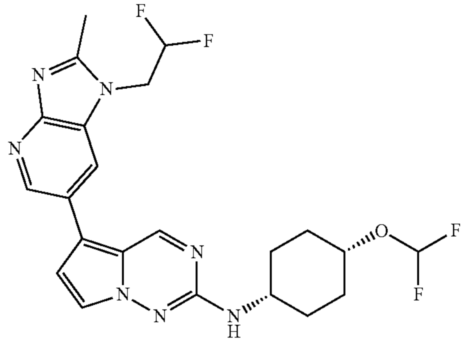

5-(1-(2,2-Difluoroethyl)-2-methyl-1H-imidazo[4,5-b]pyridin-6-yl)-N-(cis-4-(difluoromethoxy)cyclohexyl)pyrrolo[2,1-f][1,2,4]triazin-2-amine 687

Light brown solid (7 mg, 0.015 mmol, 5.3% yield). $^1$H NMR (499 MHz, DMSO-$d_6$) δ ppm 1.60-1.72 (4H, m), 1.73-1.82 (2H, m), 1.88 (2H, dt, J=9.31, 4.65 Hz), 2.63 (3H, s), 3.64-3.76 (1H, m), 4.29 (1H, br s), 4.90 (2H, td, J=15.88, 2.74 Hz), 6.53 (1H, tt, J=54.60, 3.00 Hz), 6.73 (1H, t, J=76.80 Hz), 6.90 (1H, d, J=7.67 Hz), 6.98 (1H, d, J=2.19 Hz), 7.71 (1H, d, J=2.19 Hz), 8.23 (1H, d, J=2.19 Hz), 8.66 (1H, d, J=2.19 Hz), 9.11 (1H, s); ESIMS found for $C_{22}H_{23}F_4N_7O$ m/z 478.2 (M+1).

691

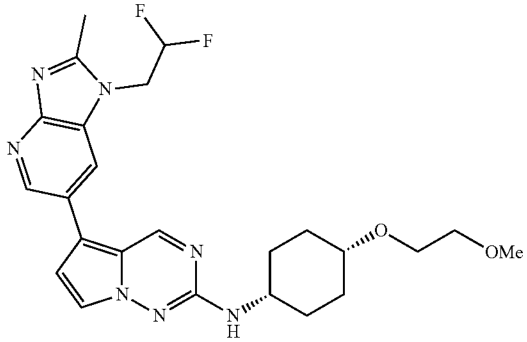

5-(1-(2,2-Difluoroethyl)-2-methyl-1H-imidazo[4,5-b]pyridin-6-yl)-N-(cis-4-(2-methoxyethoxy)cyclohexyl)pyrrolo[2,1-f][1,2,4]triazin-2-amine 691

Yellow solid (23 mg, 0.047 mmol, 17.5% yield). $^1$H NMR (499 MHz, DMSO-$d_6$) δ ppm 1.45-1.57 (2H, m), 1.59-1.75 (4H, m), 1.79-1.89 (2H, m), 2.62 (3H, s), 3.27 (3H, s), 3.43-3.47 (2H, m), 3.47-3.49 (1H, m), 3.49-3.52 (2H, m), 3.59-3.70 (1H, m), 4.90 (2H, td, J=15.81, 2.87 Hz), 6.53 (1H, tt, J=54.60, 3.00 Hz), 6.81 (1H, d, J=7.67 Hz), 6.97 (1H, d, J=2.46 Hz), 7.71 (1H, d, J=2.46 Hz), 8.23 (1H, d, J=1.92 Hz), 8.66 (1H, d, J=2.19 Hz), 9.10 (1H, s); ESIMS found for $C_{24}H_{29}F_2N_7O_2$ m/z 486.2 (M+1).

692

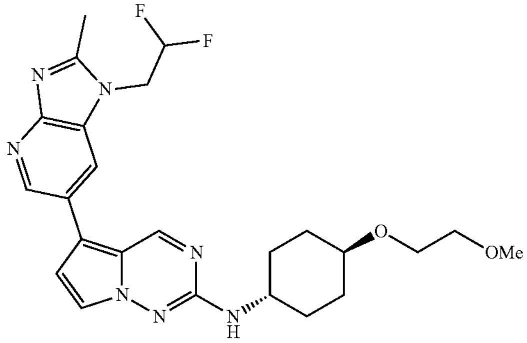

5-(1-(2,2-Difluoroethyl)-2-methyl-1H-imidazo[4,5-b]pyridin-6-yl)-N-(trans-4-(2-methoxyethoxy)cyclohexyl)pyrrolo[2,1-f][1,2,4]triazin-2-amine 692

Dark yellow solid (25 mg, 0.052 mmol, 19.0% yield). $^1$H NMR (499 MHz, DMSO-$d_6$) δ ppm 1.18-1.39 (4H, m), 2.01 (4H, br dd, J=10.40, 2.20 Hz), 2.62 (3H, s), 3.21-3.28 (1H, m), 3.25 (2H, s), 3.42 (2H, t, J=4.90 Hz), 3.54 (2H, t, J=4.90 Hz), 3.55-3.62 (1H, m), 4.84-4.97 (2H, m), 6.52 (1H, tt, J=54.60, 3.00 Hz), 6.77 (1H, d, J=8.21 Hz), 6.98 (1H, d, J=2.74 Hz), 7.73 (1H, d, J=2.74 Hz), 8.23 (1H, d, J=1.64 Hz), 8.66 (1H, d, J=2.19 Hz), 9.11 (1H, s); ESIMS found for $C_{24}H_{29}F_2N_7O_2$ m/z 486.2 (M+1).

706

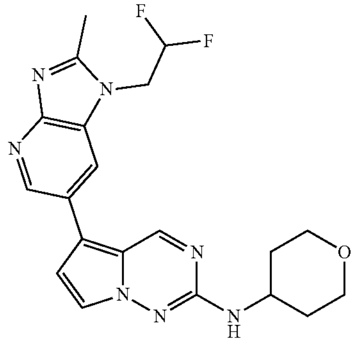

5-(1-(2,2-Difluoroethyl)-2-methyl-1H-imidazo[4,5-b]pyridin-6-yl)-N-(tetrahydro-2H-pyran-4-yl)pyrrolo[2,1-f][1,2,4]triazin-2-amine 706

Light brown solid (8 mg, 0.019 mmol, 5.8% yield). $^1$H NMR (499 MHz, DMSO-$d_6$) δ ppm 1.45-1.59 (2H, m), 1.91 (2H, br dd, J=12.59, 2.19 Hz), 2.63 (3H, s), 3.41 (2H, td, J=11.64, 1.92 Hz), 3.75-3.85 (1H, m), 3.86-3.94 (2H, m), 4.90 (2H, td, J=15.88, 2.74 Hz), 6.52 (1H, tt, J=54.60, 3.00 Hz), 6.91 (1H, d, J=7.67 Hz), 6.99 (1H, d, J=2.74 Hz), 7.73 (1H, d, J=2.19 Hz), 8.23 (1H, d, J=2.19 Hz), 8.66 (1H, d, J=1.64 Hz), 9.12 (1H, s); ESIMS found for $C_{20}H_{21}F_2N_7O$ m/z 414.2 (M+1).

713

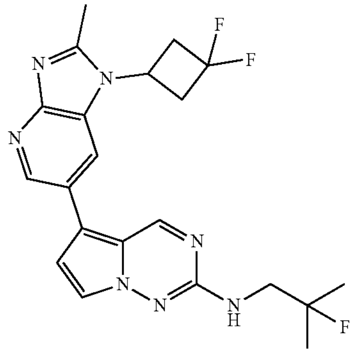

5-(1-(3,3-Difluorocyclobutyl)-2-methyl-1H-imidazo[4,5-b]pyridin-6-yl)-N-(2-fluoro-2-methylpropyl)pyrrolo[2,1-f][1,2,4]triazin-2-amine 713

Yellow solid (45 mg, 0.105 mmol, 43.0% yield). $^1$H NMR (499 MHz, DMSO-$d_6$) δ ppm 1.38 (6H, d, J=21.40 Hz), 2.64 (3H, s), 3.35-3.43 (2H, m), 3.48 (2H, dd, J=19.30, 6.43 Hz), 3.53-3.64 (2H, m), 5.04-5.17 (1H, m), 6.99-7.06 (2H, m), 7.73 (1H, d, J=2.46 Hz), 8.04 (1H, d, J=1.92 Hz), 8.66 (1H, d, J=1.92 Hz), 9.10 (1H, s); ESIMS found for $C_{21}H_{22}F_3N_7$ m/z 430.2 (M+1).

784

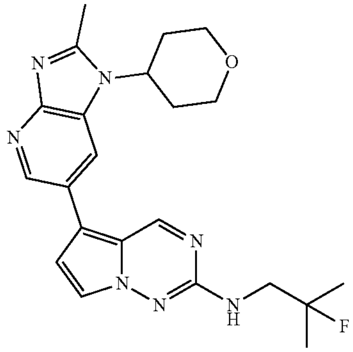

N-(2-Fluoro-2-methylpropyl)-5-(2-methyl-1-(tetrahydro-2H-pyran-4-yl)-1H-imidazo[4,5-b]pyridin-6-yl)pyrrolo[2,1-f][1,2,4]triazin-2-amine 784

Yellow solid (19 mg, 0.045 mmol, 19.8% yield). $^1$H NMR (499 MHz, DMSO-$d_6$) δ ppm 1.38 (6H, d, J=21.40 Hz), 1.87 (2H, br dd, J=12.32, 2.46 Hz), 2.44 (2H, qd, J=12.37, 4.52 Hz), 2.68 (3H, s), 3.49 (2H, dd, J=19.30, 6.43 Hz), 3.54-3.62 (2H, m), 4.04 (2H, br dd, J=11.23, 4.11 Hz), 4.68 (1H, tt, J=12.22, 4.21 Hz), 7.01 (1H, t, J=6.43 Hz), 7.04 (1H, d, J=2.46 Hz), 7.73 (1H, d, J=2.46 Hz), 8.18 (1H, d, J=1.92 Hz), 8.61 (1H, d, J=1.92 Hz), 9.01 (1H, s); ESIMS found for $C_{22}H_{26}FN_7O$ m/z 424.2 (M+1).

855

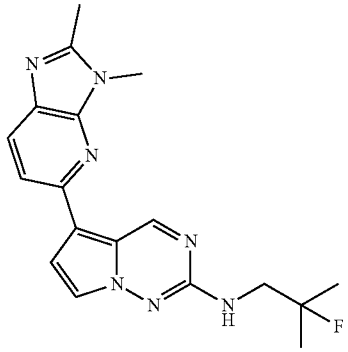

5-(2,3-Dimethyl-3H-imidazo[4,5-b]pyridin-5-yl)-N-(2-fluoro-2-methylpropyl)pyrrolo[2,1-f][1,2,4]triazin-2-amine 855

Yellow solid ((16 mg, 0.045 mmol, 18.6% yield). $^1$H NMR (500 MHz, DMSO-$d_6$) δ ppm 1.38 (6H, d, J=21.40 Hz), 2.58 (3H, s), 3.49 (2H, dd, J=19.35, 6.45 Hz), 3.82 (3H, s), 7.02 (1H, t, J=6.45 Hz), 7.24 (1H, d, J=2.74 Hz), 7.65 (1H, d, J=2.74 Hz), 7.69 (1H, d, J=8.51 Hz), 7.90 (1H, d, J=8.23 Hz), 9.76 (1H, s); ESIMS found for $C_{18}H_{20}FN_7$ m/z 354.2 (M+1).

926

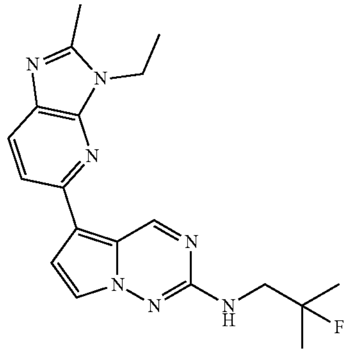

5-(3-Ethyl-2-methyl-3H-imidazo[4,5-b]pyridin-5-yl)-N-(2-fluoro-2-methylpropyl)pyrrolo[2,1-f][1,2,4]triazin-2-amine 926

Yellow solid (13 mg, 0.035 mmol, 13.5% yield). $^1$H NMR (499 MHz, DMSO-$d_6$) δ ppm 1.38 (6H, d, J=21.40 Hz), 1.41 (3H, t, J=7.10 Hz), 2.60 (3H, s), 3.49 (2H, dd, J=19.71, 6.57 Hz), 4.33 (2H, q, J=7.12 Hz), 7.01 (1H, t, J=6.30 Hz), 7.24 (1H, d, J=2.74 Hz), 7.66 (1H, d, J=2.19 Hz), 7.69 (1H, d, J=8.21 Hz), 7.91 (1H, d, J=8.21 Hz), 9.71 (1H, s); ESIMS found for $C_{19}H_{22}FN_7$ m/z 368.2 (M+1).

1068

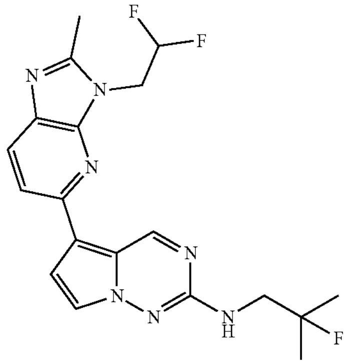

N-(2-Fluoro-2-methylpropyl)-5-(3-(2,2-difluoroethyl)-2-methyl-3H-imidazo[4,5-b]pyridin-5-yl)pyrrolo[2,1-f][1,2,4]triazin-2-amine 1068

Yellow solid (86 mg, 0.213 mmol, 38.3% yield). $^1$H NMR (499 MHz, DMSO-$d_6$) δ ppm 1.38 (6H, d, J=21.40 Hz), 2.61 (3H, s), 3.50 (2H, dd, J=19.44, 6.30 Hz), 4.84 (2H, td, J=16.02, 3.01 Hz), 6.56 (1H, tt, J=54.90, 3.20 Hz), 7.01 (1H, t, J=6.30 Hz), 7.25 (1H, d, J=2.74 Hz), 7.65 (1H, d, J=2.74 Hz), 7.73 (1H, d, J=8.21 Hz), 7.95 (1H, d, J=8.21 Hz), 9.72 (1H, s); ESIMS found for $C_{19}H_{20}F_3N_7$ m/z 404.2 (M+1).

1037

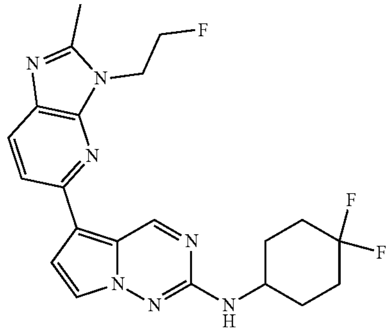

N-(4,4-Difluorocyclohexyl)-5-(3-(2-fluoroethyl)-2-methyl-3H-imidazo[4,5-b]pyridin-5-yl)pyrrolo[2,1-f][1,2,4]triazin-2-amine 1037

Yellow solid (19 mg, 0.044 mmol, 19.5% yield). $^1$H NMR (499 MHz, DMSO-$d_6$) δ ppm 1.58-1.72 (2H, m), 1.86-2.03 (4H, m), 2.03-2.16 (2H, m), 2.59 (3H, s), 3.76-3.90 (1H, m), 4.66 (2H, dt, J=27.40, 4.80 Hz), 4.87 (2H, dt, J=47.20, 4.90 Hz), 6.92 (1H, d, J=7.67 Hz), 7.23 (1H, d, J=2.74 Hz), 7.65 (1H, d, J=2.74 Hz), 7.71 (1H, d, J=8.21 Hz), 7.93 (1H, d, J=8.21 Hz), 9.67 (1H, s); ESIMS found for $C_{21}H_{22}F_3N_7$ m/z 430.2 (M+1).

1088

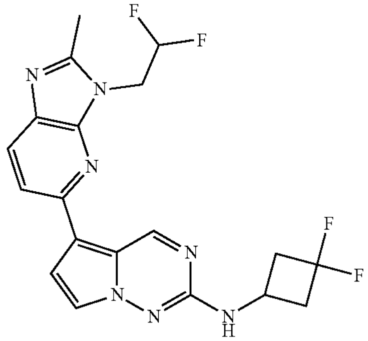

N-(3,3-Difluorocyclobutyl)-5-(3-(2,2-difluoroethyl)-2-methyl-3H-imidazo [4,5-b]pyridin-5-yl)pyrrolo[2,1-f][1,2,4]triazin-2-amine 1088

Yellow solid (13 mg, 0.031 mmol, 12.5% yield). $^1$H NMR (499 MHz, DMSO-$d_6$) δ ppm 2.61 (3H, s), 2.63-2.74 (2H, m), 2.95-3.04 (2H, m), 4.02-4.15 (1H, m), 4.84 (2H, td, J=16.02, 3.01 Hz), 6.55 (1H, tt, J=54.40, 2.90 Hz), 7.28 (1H, d, J=2.74 Hz), 7.46 (1H, d, J=6.02 Hz), 7.70 (1H, d, J=2.74 Hz), 7.74 (1H, d, J=8.21 Hz), 7.96 (1H, d, J=8.21 Hz), 9.74 (1H, s); ESIMS found for $C_{19}H_{17}F_4N_7$ m/z 420.15 (M+1).

1091

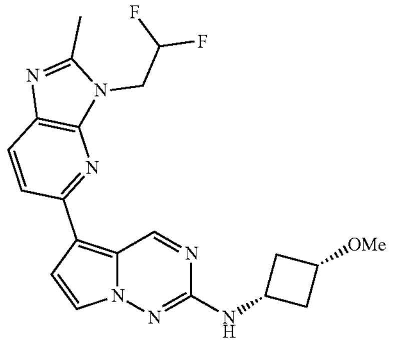

5-(3-(2,2-Difluoroethyl)-2-methyl-3H-imidazo[4,5-b]pyridin-5-yl)-N-(cis-3-methoxycyclobutyl)pyrrolo[2,1-f][1,2,4]triazin-2-amine 1091

Yellow solid (5 mg, 0.012 mmol, 4.8% yield). $^1$H NMR (499 MHz, DMSO-$d_6$) δ ppm 1.80-1.94 (2H, m), 2.62-2.72 (2H, m), 3.15 (3H, s), 3.59-3.67 (1H, m), 3.76-3.88 (1H, m), 4.83 (2H, td, J=16.02, 3.01 Hz), 6.55 (1H, tt, J=54.50, 3.10 Hz), 7.20 (1H, d, J=7.12 Hz), 7.24 (1H, d, J=2.74 Hz), 7.63 (1H, d, J=2.74 Hz), 7.73 (1H, d, J=8.21 Hz), 7.95 (1H, d, J=8.21 Hz), 9.70 (1H, s); ESIMS found for $C_{20}H_{21}F_2N_7O$ m/z 414.2 (M+1).

1108

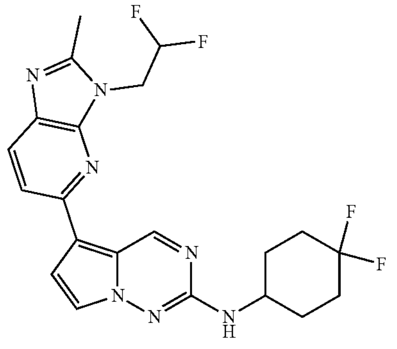

N-(4,4-Difluorocyclohexyl)-5-(3-(2,2-difluoroethyl)-2-methyl-3H-imidazo [4,5-b]pyridin-5-yl)pyrrolo[2,1-f][1,2,4]triazin-2-amine 1108

Yellow solid (35 mg, 0.078 mmol, 25.8% yield). $^1$H NMR (499 MHz, DMSO-$d_6$) δ ppm 1.57-1.72 (2H, m), 1.86-2.03 (4H, m), 2.03-2.15 (2H, m), 3.77-3.88 (1H, m), 4.83 (2H, td, J=16.02, 3.01 Hz), 6.55 (1H, tt, J=54.90, 3.30 Hz), 6.95 (1H, d, J=7.67 Hz), 7.24 (1H, d, J=2.74 Hz), 7.65 (1H, d, J=2.74 Hz), 7.73 (1H, d, J=8.76 Hz), 7.95 (1H, d, J=8.21 Hz), 9.71 (1H, s); ESIMS found for $C_{21}H_{21}F_4N_7$ m/z 448.2 (M+1).

1109

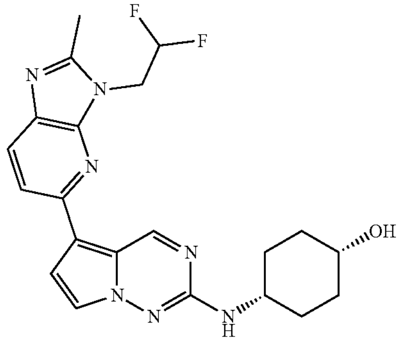

cis-4-((5-(3-(2,2-Difluoroethyl)-2-methyl-3H-imidazo[4,5-b]pyridin-5-yl)pyrrolo[2,1-f][1,2,4]triazin-2-yl)amino)cyclohexan-1-ol 1109

Yellow solid (9 mg, 0.021 mmol, 6.5% yield). $^1$H NMR (499 MHz, DMSO-$d_6$) δ ppm 1.47-1.56 (2H, m), 1.61-1.70 (4H, m), 1.71-1.80 (2H, m), 2.61 (3H, s), 3.56-3.69 (1H, m), 3.74 (1H, br d, J=1.64 Hz), 4.36 (1H, d, J=2.74 Hz), 4.83 (2H, td, J=16.02, 3.01 Hz), 6.55 (1H, tt, J=54.50, 3.00 Hz), 6.74 (1H, d, J=7.67 Hz), 7.21 (1H, d, J=2.74 Hz), 7.63 (1H, d, J=2.74 Hz), 7.72 (1H, d, J=8.76 Hz), 7.95 (1H, d, J=8.21 Hz), 9.69 (1H, s); ESIMS found for $C_{21}H_{23}F_2N_7O$ m/z 428.2 (M+1).

1110

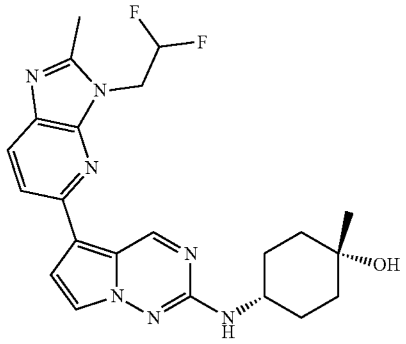

(1s,4s)-4-((5-(3-(2,2-Difluoroethyl)-2-methyl-3H-imidazo[4,5-b]pyridin-5-yl)pyrrolo[2,1-f][1,2,4] triazin-2-yl)amino)-1-methylcyclohexan-1-ol 1110

Pale yellow solid (70 mg, 0.159 mmol, 51.6% yield). $^1$H NMR (499 MHz, DMSO-$d_6$) δ ppm 1.13 (3H, s), 1.37 (2H, td, J=13.00, 4.65 Hz), 1.59 (2H, br d, J=12.59 Hz), 1.63-1.76 (4H, m), 2.60 (3H, s), 3.48-3.60 (1H, m), 4.02 (1H, s), 4.83 (2H, td, J=16.02, 3.01 Hz), 6.55 (1H, tt, J=54.85, 3.30 Hz), 6.72 (1H, d, J=8.21 Hz), 7.21 (1H, d, J=2.74 Hz), 7.62 (1H, d, J=2.19 Hz), 7.72 (1H, d, J=8.21 Hz), 7.94 (1H, d, J=8.21 Hz), 9.69 (1H, s); ESIMS found for $C_{22}H_{25}F_2N_7O$ m/z 442.2 (M+1).

1111

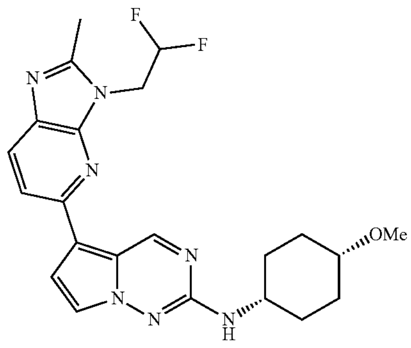

5-(3-(2,2-Difluoroethyl)-2-methyl-3H-imidazo[4,5-b]pyridin-5-yl)-N-(cis-4-methoxycyclohexyl)pyrrolo[2,1-f][1,2,4]triazin-2-amine 1111

Pale yellow solid (50 mg, 0.113 mmol, 36.8% yield). $^{1}$H NMR (499 MHz, DMSO-$d_6$) δ ppm 1.45-1.55 (2H, m), 1.56-1.66 (2H, m), 1.66-1.74 (2H, m), 1.80-1.91 (2H, m), 2.61 (3H, s), 3.23 (3H, s), 3.33-3.39 (1H, m), 3.60-3.72 (1H, m), 4.83 (2H, td, J=16.15, 2.74 Hz), 6.55 (1H, tt, J=54.50, 3.30 Hz), 6.76 (1H, d, J=8.21 Hz), 7.21 (1H, d, J=2.74 Hz), 7.63 (1H, d, J=2.74 Hz), 7.72 (1H, d, J=8.21 Hz), 7.94 (1H, d, J=8.21 Hz), 9.69 (1H, s); ESIMS found for $C_{22}H_{25}F_2N_7O$ m/z 442.2 (M+1).

1113

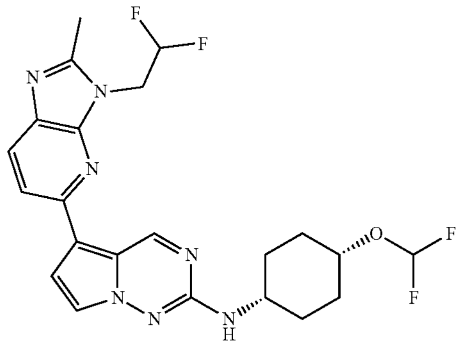

N-(cis-4-(Difluoromethoxy)cyclohexyl)-5-(3-(2,2-difluoroethyl)-2-methyl-3H-imidazo[4,5-b]pyridin-5-yl)pyrrolo[2,1-f][1,2,4]triazin-2-amine 1113

Yellow solid (32 mg, 0.067 mmol, 24.2% yield). $^{1}$H NMR (499 MHz, DMSO-$d_6$) δ ppm 1.59-1.73 (4H, m), 1.74-1.83 (2H, m), 1.88 (2H, dt, J=9.38, 4.76 Hz), 2.61 (3H, s), 3.71 (1H, dt, J=7.80, 3.76 Hz), 4.30 (1H, br s), 4.83 (2H, td, J=15.95, 2.87 Hz), 6.55 (1H, tt, J=54.60, 3.00 Hz), 6.73 (1H, t, J=77.05 Hz), 6.88 (2H, d, J=7.12 Hz), 7.22 (1H, d, J=2.46 Hz), 7.64 (1H, d, J=2.46 Hz), 7.72 (1H, d, J=8.21 Hz), 7.95 (1H, d, J=8.49 Hz), 9.70 (1H, s); ESIMS found for $C_{22}H_{23}F_4N_7O$ m/z 478.2 (M+1).

1115

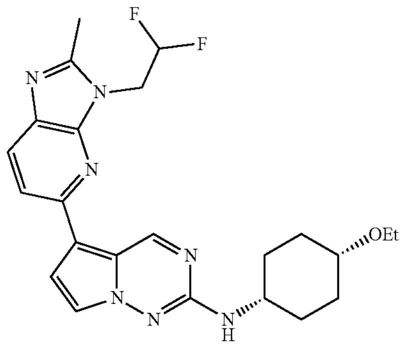

N-(cis-4-Ethoxycyclohexyl)-5-(3-(2,2-difluoroethyl)-2-methyl-3H-imidazo [4,5-b]pyridin-5-yl) pyrrolo[2,1-f][1,2,4]triazin-2-amine 1115

Yellow solid (54 mg, 0.119 mmol, 53.6% yield). $^{1}$H NMR (499 MHz, DMSO-$d_6$) δ ppm 1.13 (3H, t, J=6.84 Hz), 1.45-1.57 (2H, m), 1.59-1.75 (4H, m), 1.78-1.88 (2H, m), 2.60 (3H, s), 3.42 (2H, q, J=7.12 Hz), 3.45-3.48 (1H, m), 3.62-3.72 (1H, m), 4.83 (2H, td, J=16.02, 3.01 Hz), 6.55 (1H, tt, J=54.85, 2.75 Hz), 6.77 (1H, d, J=7.67 Hz), 7.21 (1H, d, J=2.74 Hz), 7.63 (1H, d, J=2.74 Hz), 7.72 (1H, d, J=8.21 Hz), 7.94 (1H, d, J=8.21 Hz), 9.69 (1H, s); ESIMS found for $C_{23}H_{27}F_2N_7O$ m/z 456.25 (M+1).

1117

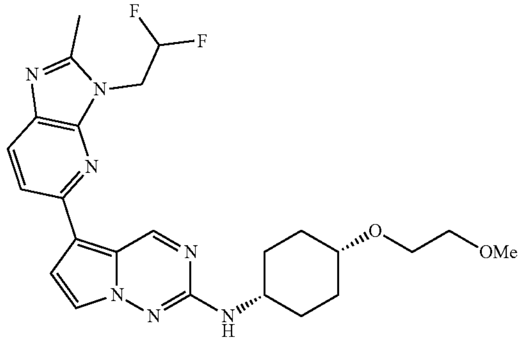

5-(3-(2,2-Difluoroethyl)-2-methyl-3H-imidazo[4,5-b]pyridin-5-yl)-N-(cis-4-(2-methoxyethoxy)cyclohexyl)pyrrolo[2,1-f][1,2,4]triazin-2-amine 1117

Yellow solid (44 mg, 0.091 mmol, 44.6% yield). $^{1}$H NMR (499 MHz, DMSO-$d_6$) δ ppm 1.46-1.57 (2H, m), 1.59-1.75 (4H, m), 1.79-1.88 (2H, m), 2.61 (3H, s), 3.27 (3H, s), 3.44-3.47 (2H, m), 3.47-3.49 (1H, m), 3.49-3.52 (2H, m), 3.61-3.71 (1H, m), 4.83 (2H, td, J=16.02, 3.01 Hz), 6.55 (1H, tt, J=54.90, 3.30 Hz), 6.79 (1H, d, J=7.67 Hz), 7.22 (1H, d, J=2.74 Hz), 7.63 (1H, d, J=2.74 Hz), 7.72 (1H, d, J=8.21 Hz), 7.95 (1H, d, J=8.21 Hz), 9.69 (1H, s); ESIMS found for $C_{24}H_{29}F_2N_7O_2$ m/z 486.2 (M+1).

1118

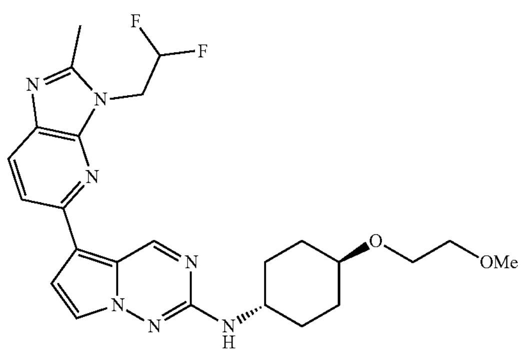

5-(3-(2,2-Difluoroethyl)-2-methyl-3H-imidazo[4,5-b]pyridin-5-yl)-N-(trans-4-(2-methoxyethoxy)cyclohexyl)pyrrolo[2,1-f][1,2,4]triazin-2-amine 1118

Yellow solid (12 mg, 0.025 mmol, 12.2% yield). $^1$H NMR (499 MHz, DMSO-$d_6$) δ ppm 1.17-1.41 (4H, m), 2.01 (4H, br dd, J=9.58, 2.46 Hz), 2.61 (3H, s), 3.22-3.29 (1H, m), 3.25 (3H, s), 3.41-3.44 (2H, m), 3.52-3.55 (2H, m), 3.56-3.63 (1H, m), 4.83 (2H, td, J=16.02, 3.01 Hz), 6.55 (1H, tt, J=54.60, 3.00 Hz), 6.75 (1H, d, J=8.21 Hz), 7.22 (1H, d, J=2.74 Hz), 7.66 (1H, d, J=2.74 Hz), 7.72 (1H, d, J=8.21 Hz), 7.95 (1H, d, J=8.21 Hz), 9.69 (1H, s); ESIMS found for $C_{24}H_{29}F_2N_7O_2$ m/z 486.2 (M+1).

1125

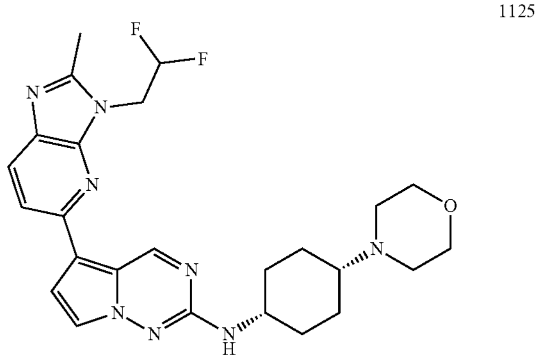 [SMILES: Cc1nc2ccc(-c3ccn4nc(N[C@H]5CC[C@@H](N6CCOCC6)CC5)ncc34)nc2n1CC(F)F]

5-(3-(2,2-Difluoroethyl)-2-methyl-3H-imidazo[4,5-b]pyridin-5-yl)-N-(cis-4-morpholinocyclohexyl)pyrrolo[2,1-f][1,2,4]triazin-2-amine 1125

Brown solid (65.0 mg, 0.131 mmol, 30.3% yield). $^1$H NMR (499 MHz, DMSO-$d_6$) δ ppm 1.46-1.55 (2H, m), 1.55-1.63 (2H, m), 1.74-1.89 (4H, m), 2.14-2.21 (1H, m), 2.44 (4H, br s), 2.61 (3H, s), 3.58 (4H, t, J=4.52 Hz), 3.75-3.83 (1H, m), 4.83 (2H, td, J=16.02, 3.01 Hz), 6.55 (1H, tt, J=54.60, 3.30 Hz), 6.81 (1H, d, J=7.12 Hz), 7.22 (1H, d, J=2.74 Hz), 7.64 (1H, d, J=2.46 Hz), 7.72 (1H, d, J=8.49 Hz), 7.95 (1H, d, J=8.21 Hz), 9.70 (1H, s); ESIMS found for $C_{25}H_{30}F_2N_8O$ m/z 497.3 (M+1).

1131

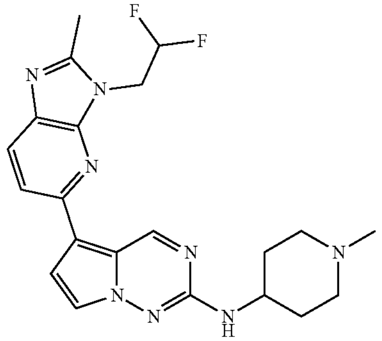

5-(3-(2,2-Difluoroethyl)-2-methyl-3H-imidazo[4,5-b]pyridin-5-yl)-N-(1-methylpiperidin-4-yl)pyrrolo[2,1-f][1,2,4]triazin-2-amine 1131

Yellow solid (62 mg, 0.145 mmol, 45.1% yield). $^1$H NMR (499 MHz, DMSO-$d_6$) δ ppm 1.50-1.66 (2H, m), 1.88-1.99 (2H, m), 2.10 (2H, br t, J=10.95 Hz), 2.23 (3H, s), 2.61 (3H, s), 2.83 (2H, br d, J=12.05 Hz), 3.54-3.65 (1H, m), 4.83 (2H, td, J=16.02, 3.01 Hz), 6.55 (1H, tt, J=54.60, 3.00 Hz), 6.82 (1H, d, J=7.67 Hz), 7.23 (1H, d, J=2.74 Hz), 7.65 (1H, d, J=2.19 Hz), 7.72 (1H, d, J=8.21 Hz), 7.95 (1H, d, J=8.21 Hz), 9.70 (1H, s); ESIMS found for $C_{21}H_{24}F_2N_8$ m/z 427.2 (M+1).

1132

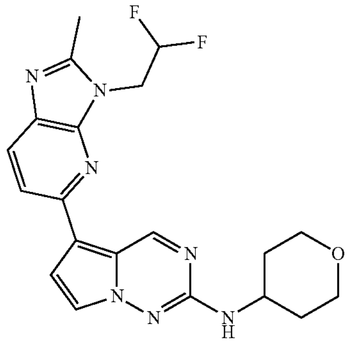

5-(3-(2,2-Difluoroethyl)-2-methyl-3H-imidazo[4,5-b]pyridin-5-yl)-N-(tetrahydro-2H-pyran-4-yl)pyrrolo[2,1-f][1,2,4]triazin-2-amine 1132

Yellow solid (46.0 mg, 0.111 mmol, 33.1% yield). $^1$H NMR (499 MHz, DMSO-$d_6$) δ ppm 1.47-1.62 (2H, m), 1.91 (2H, br dd, J=12.59, 2.19 Hz), 2.61 (3H, s), 3.41 (2H, td, J=11.64, 1.92 Hz), 3.76-3.85 (1H, m), 3.86-3.93 (2H, m), 4.83 (2H, td, J=16.02, 3.01 Hz), 6.55 (1H, tt, J=54.40, 3.20 Hz), 6.89 (1H, d, J=8.21 Hz), 7.23 (1H, d, J=2.74 Hz), 7.66 (1H, d, J=2.74 Hz), 7.73 (1H, d, J=8.76 Hz), 7.95 (1H, d, J=8.21 Hz), 9.71 (1H, s); ESIMS found for $C_{20}H_{21}F_2N_7O$ m/z 414.2 (M+1).

1179

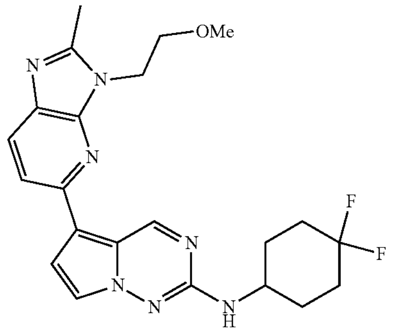

N-(4,4-Difluorocyclohexyl)-5-(3-(2-methoxyethyl)-2-methyl-3H-imidazo [4,5-b]pyridin-5-yl)pyrrolo[2,1-f][1,2,4]triazin-2-amine 1179

Yellow solid (20 mg, 0.045 mmol, 20.0% yield). $^1$H NMR (499 MHz, DMSO-$d_6$) δ ppm 1.56-1.73 (2H, m), 1.87-2.04 (4H, m), 2.04-2.15 (2H, m), 2.59 (3H, s), 3.25 (3H, s), 3.77 (2H, t, J=5.48 Hz), 3.80-3.88 (1H, m), 4.47 (2H, t, J=5.48 Hz), 6.95 (1H, d, J=7.67 Hz), 7.23 (1H, d, J=2.74 Hz), 7.65 (1H, d, J=2.74 Hz), 7.69 (1H, d, J=8.21 Hz), 7.91 (1H, d, J=8.76 Hz), 9.70 (1H, s); ESIMS found for $C_{22}H_{25}F_2N_7O$ m/z 442.2 (M+1).

1210

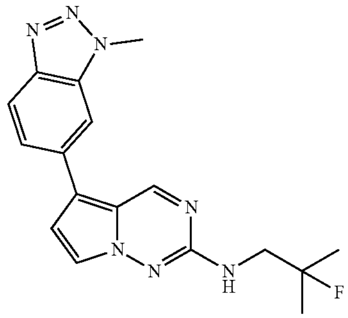

N-(2-Fluoro-2-methylpropyl)-5-(1-methyl-1H-benzo [d][1,2,3]triazol-6-yl) pyrrolo[2,1-f][1,2,4]triazin-2-amine 1210

Yellow solid (47 mg, 0.139 mmol, 53.0% yield). $^1$H NMR (499 MHz, DMSO-$d_6$) δ ppm 1.38 (6H, d, J=21.40 Hz), 3.49 (2H, dd, J=19.16, 6.30 Hz), 4.36 (3H, s), 7.08 (1H, s), 7.06 (1H, d, J=2.46 Hz), 7.70-7.75 (2H, m), 8.05 (1H, d, J=8.76 Hz), 8.07 (1H, s), 9.23 (1H, s); ESIMS found for $C_{17}H_{18}FN_7$ m/z 340.15 (M+1).

1281

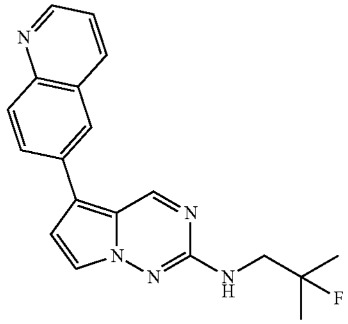

N-(2-Fluoro-2-methylpropyl)-5-(quinolin-6-yl)pyrrolo[2,1-f][1,2,4]triazin-2-amine 1281

Yellow solid (19.6 mg, 0.058 mmol). $^1$H NMR (400 MHz, DMSO-$d_6$) δ ppm 1.39 (6H, d, J=21.40 Hz), 3.49 (2H, dd, J=19.20, 6.32 Hz), 7.07 (1H, t, J=6.38 Hz), 7.11 (1H, d, J=2.63 Hz), 7.54 (1H, dd, J=8.25, 4.13 Hz), 7.74 (1H, d, J=2.50 Hz), 8.03-8.13 (2H, m), 8.30 (1H, d, J=1.75 Hz), 8.40-8.47 (1H, m), 8.86 (1H, dd, J=4.19, 1.56 Hz), 9.25 (1H, s); ESIMS found for $C_{19}H_{18}FN_5$ m/z 336.2 (M+1).

1309

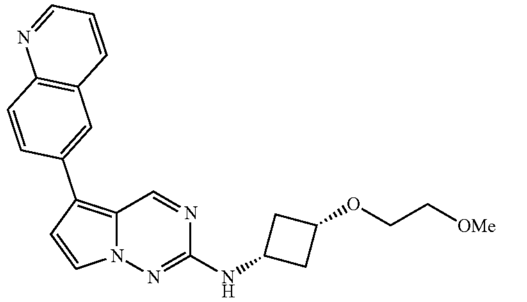

N-(cis-3-(2-Methoxyethoxy)cyclobutyl)-5-(quinolin-6-yl)pyrrolo[2,1-f][1,2,4]triazin-2-amine 1309

Yellow solid (48.0 mg, 0.123 mmol, 35.0% yield). $^1$H NMR (499 MHz, DMSO-$d_6$) δ ppm 1.81-1.94 (2H, m), 2.61-2.73 (2H, m), 3.25 (3H, s), 3.40-3.45 (4H, m), 3.69-3.76 (1H, m), 3.76-3.84 (1H, m), 7.09 (1H, d, J=2.74 Hz), 7.30 (1H, d, J=7.67 Hz), 7.54 (1H, dd, J=8.49, 4.11 Hz), 7.72 (1H, d, J=2.19 Hz), 8.03-8.07 (1H, m), 8.08-8.12 (1H, m), 8.28 (1H, d, J=2.19 Hz), 8.43 (1H, dd, J=8.21, 1.64 Hz), 8.86 (1H, dd, J=4.38, 1.64 Hz), 9.23 (1H, s); ESIMS found for $C_{22}H_{23}N_5O_2$ m/z 390.2 (M+1).

1322

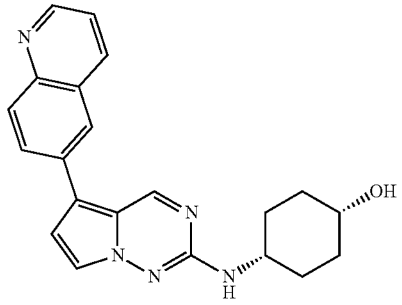

cis-4-((5-(Quinolin-6-yl)pyrrolo[2,1-f][1,2,4]triazin-2-yl)amino)cyclohexan-1-ol 1322

Tan solid (11 mg, 0.031 mmol, 9.5% yield). $^1$H NMR (499 MHz, DMSO-$d_6$) δ ppm 1.45-1.57 (2H, m), 1.61-1.71 (4H, m), 1.71-1.82 (2H, m), 3.57-3.67 (1H, m), 3.74 (1H, br d, J=2.19 Hz), 4.36 (1H, d, J=2.74 Hz), 6.82 (1H, d, J=7.67 Hz), 7.07 (1H, d, J=2.19 Hz), 7.54 (1H, dd, J=8.49, 4.11 Hz), 7.72 (1H, d, J=2.19 Hz), 8.03-8.07 (1H, m), 8.08-8.12 (1H, m), 8.28 (1H, d, J=2.19 Hz), 8.39-8.46 (1H, m), 8.85 (1H, dd, J=4.38, 1.64 Hz), 9.22 (1H, s); ESIMS found for $C_{21}H_{21}N_5O$ m/z 360.2 (M+1).

1323

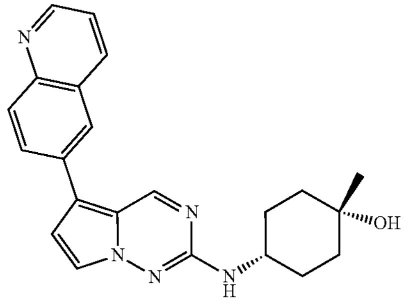

(1s,4s)-1-Methyl-4-((5-(quinolin-6-yl)pyrrolo[2,1-f][1,2,4]triazin-2-yl) amino)cyclohexan-1-ol 1323.

Yellow solid (8 mg, 0.021 mmol, 5.1% yield). $^1$H NMR (499 MHz, DMSO-$d_6$) δ ppm 1.13 (3H, s), 1.37 (2H, td, J=13.14, 4.38 Hz), 1.59 (2H, br d, J=12.05 Hz), 1.63-1.76 (4H, m), 3.46-3.59 (1H, m), 4.01 (1H, s), 6.80 (1H, d, J=7.67 Hz), 7.07 (1H, d, J=2.74 Hz), 7.49-7.58 (1H, m), 7.71 (1H, d, J=2.19 Hz), 8.03-8.07 (1H, m), 8.08-8.12 (1H, m), 8.28 (1H, d, J=2.19 Hz), 8.42 (1H, dd, J=8.49, 1.37 Hz), 8.85 (1H, dd, J=3.83, 1.64 Hz), 9.21 (1H, s); ESIMS found for $C_{22}H_{23}N_5O$ m/z 374.2 (M+1).

1332

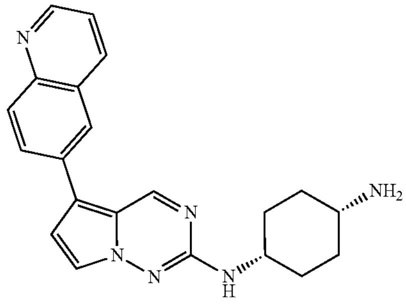

cis-Ni-(5-(Quinolin-6-yl)pyrrolo[2,1-f][1,2,4]triazin-2-yl)cyclohexane-1,4-diamine 1332

Yellow solid (335 mg, 0.935 mmol, 79.7% yield). $^1$H NMR (499 MHz, DMSO-$d_6$) δ ppm 1.48-1.56 (4H, m), 1.58-1.66 (2H, m), 1.74-1.88 (2H, m), 2.79-2.89 (1H, m), 3.68 (1H, tq, J=7.39, 3.65 Hz), 6.72 (1H, d, J=7.12 Hz), 7.08 (1H, d, J=2.19 Hz), 7.54 (1H, dd, J=8.21, 4.38 Hz), 7.73 (1H, d, J=2.19 Hz), 8.03-8.07 (1H, m), 8.08-8.12 (1H, m), 8.28 (1H, d, J=2.19 Hz), 8.43 (1H, dd, J=8.49, 1.37 Hz), 8.86 (1H, dd, J=4.38, 1.64 Hz), 9.22 (1H, s); ESIMS found for $C_{21}H_{22}N_6$ m/z 359.2 (M+1).

1336

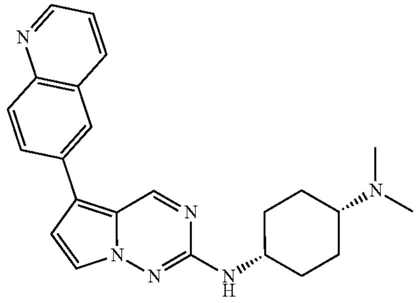

cis-$N^1$,$N^1$-Dimethyl-$N^4$-(5-(quinolin-6-yl)pyrrolo[2,1-f][1,2,4]triazin-2-yl) cyclohexane-1,4-diamine 1336

Yellow solid (22 mg, 0.057 mmol, 35.2% yield). $^1$H NMR (499 MHz, DMSO-$d_6$) δ ppm 1.48 (2H, td, J=8.35, 4.11 Hz), 1.60 (2H, ddd, J=12.46, 8.35, 3.83 Hz), 1.71-1.89 (4H, m), 2.02-2.11 (1H, m), 2.17 (6H, s), 3.72-3.83 (1H, m), 6.86 (1H, d, J=7.12 Hz), 7.07 (1H, d, J=2.19 Hz), 7.54 (1H, dd, J=8.21, 3.83 Hz), 7.73 (1H, d, J=2.74 Hz), 8.04-8.07 (1H, m), 8.08-8.12 (1H, m), 8.28 (1H, d, J=2.19 Hz), 8.39-8.47 (1H, m), 8.86 (1H, dd, J=3.83, 1.64 Hz), 9.22 (1H, s); ESIMS found for $C_{23}H_{26}N_6$ m/z 387.3 (M+1).

1348

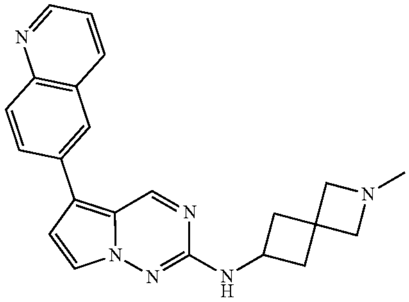

N-(2-Methyl-2-azaspiro[3.3]heptan-6-yl)-5-(quinolin-6-yl)pyrrolo[2,1-f][1,2,4]triazin-2-amine 1348

Yellow solid (19 mg, 0.051 mmol, 18.3% yield). $^1$H NMR (499 MHz, DMSO-$d_6$) δ ppm 2.03-2.12 (2H, m), 2.16 (3H, s), 2.42-2.49 (2H, m), 3.06 (2H, s), 3.17 (2H, s), 4.05 (1H, sxt, J=7.78 Hz), 7.09 (1H, d, J=2.19 Hz), 7.24 (1H, d, J=7.12 Hz), 7.54 (1H, dd, J=8.21, 4.38 Hz), 7.74 (1H, d, J=2.19 Hz), 8.03-8.06 (1H, m), 8.08-8.11 (1H, m), 8.28 (1H, d, J=2.19 Hz), 8.42 (1H, dd, J=8.49, 1.37 Hz), 8.86 (1H, dd, J=3.83, 1.64 Hz), 9.22 (1H, s); ESIMS found for $C_{22}H_{22}N_6$ m/z 371.1 (M+1).

1352

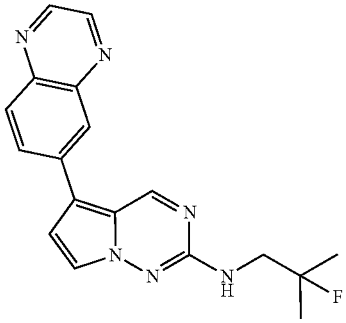

N-(2-Fluoro-2-methylpropyl)-5-(quinoxalin-6-yl)pyrrolo[2,1-f][1,2,4]triazin-2-amine 1352

Yellow solid (38.22 mg, 0.114 mmol). $^1$H NMR (400 MHz, DMSO-$d_6$) δ ppm 1.39 (6H, d, J=21.40 Hz), 3.49 (2H, dd, J=19.20, 6.44 Hz), 7.14 (1H, t, J=6.44 Hz), 7.20 (1H, d, J=2.50 Hz), 7.77 (1H, d, J=2.38 Hz), 8.14 (1H, d, J=8.76 Hz), 8.24 (1H, dd, J=8.82, 1.69 Hz), 8.32 (1H, d, J=1.75 Hz), 8.90 (1H, d, J=1.63 Hz), 8.96 (1H, d, J=1.50 Hz), 9.22 (1H, s); ESIMS found for $C_{18}H_{17}FN_6$ m/z 337.1 (M+1).

1375

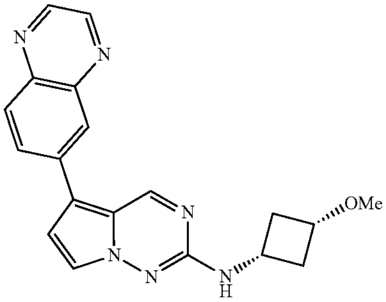

N-(cis-3-Methoxycyclobutyl)-5-(quinoxalin-6-yl)pyrrolo[2,1-f][1,2,4]triazin-2-amine 1375

Yellow solid (32 mg, 0.092 mmol, 36.6% yield). $^1$H NMR (499 MHz, DMSO-$d_6$) δ ppm 1.80-1.91 (2H, m), 2.61-2.72 (2H, m), 3.15 (3H, s), 3.58-3.69 (1H, m), 3.73-3.86 (1H, m), 7.19 (1H, d, J=2.74 Hz), 7.36 (1H, d, J=7.67 Hz), 7.75 (1H, d, J=1.64 Hz), 8.13 (1H, d, J=8.76 Hz), 8.23 (1H, dd, J=8.76, 1.64 Hz), 8.31 (1H, d, J=1.64 Hz), 8.90 (1H, d, J=1.64 Hz), 8.95 (1H, d, J=1.64 Hz), 9.19 (1H, s); ESIMS found for $C_{19}H_8N_6O$ m/z 347.2 (M+1).

1376

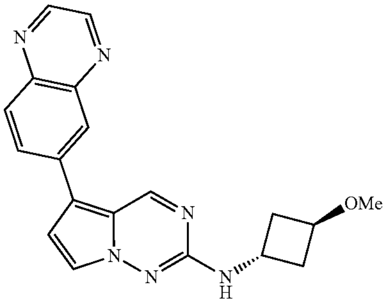

N-(trans-3-Methoxycyclobutyl)-5-(quinoxalin-6-yl)pyrrolo[2,1-f][1,2,4]triazin-2-amine 1376

Yellow solid (28.54 mg, 0.082 mmol, % yield). $^1$H NMR (400 MHz, DMSO-$d_6$) δ ppm 2.18-2.35 (4H, m), 3.16 (3H, s), 3.96-4.07 (1H, m), 4.16-4.27 (1H, m), 7.19 (1H, d, J=2.57 Hz), 7.78 (1H, d, J=2.57 Hz), 8.09-8.17 (1H, m), 8.19-8.26 (1H, m), 8.30 (1H, d, J=1.71 Hz), 8.89 (1H, d, J=1.71 Hz), 8.95 (1H, d, J=1.71 Hz), 9.20 (1H, s); ESIMS found for $C_{19}H_8N_6O$ m/z 347.1 (M+1).

1377

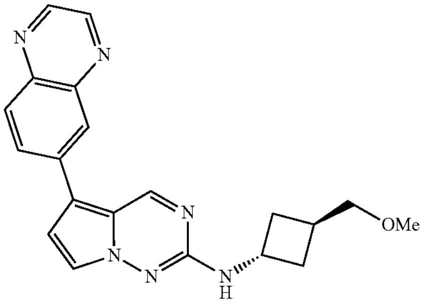

N-(trans-3-(Methoxymethyl)cyclobutyl)-5-(quinoxalin-6-yl)pyrrolo[2,1-f][1,2,4]triazin-2-amine 1377

Yellow solid (37 mg, 0.103 mmol, 42.6% yield). $^1$H NMR (499 MHz, DMSO-$d_6$) δ ppm 2.07-2.18 (4H, m), 2.39-2.47 (1H, m), 3.29 (3H, s), 3.41 (2H, d, J=7.12 Hz), 4.25 (1H, sxt, J=7.34 Hz), 7.18 (1H, d, J=2.74 Hz), 7.39 (1H, d, J=7.12 Hz), 7.77 (1H, d, J=2.19 Hz), 8.13 (1H, d, J=8.76 Hz), 8.23 (1H, dd, J=8.49, 1.92 Hz), 8.31 (1H, d, J=2.19 Hz), 8.89 (1H, d, J=2.19 Hz), 8.95 (1H, d, J=1.64 Hz), 9.19 (1H, s); ESIMS found for $C_{20}H_{20}N_6O$ m/z 361.2 (M+1).

1392

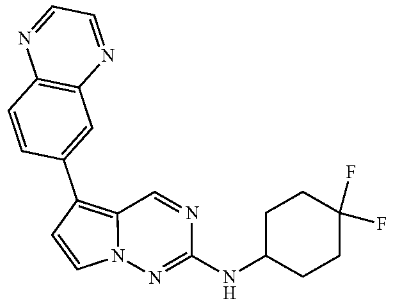

N-(4,4-Difluorocyclohexyl)-5-(quinoxalin-6-yl)pyrrolo[2,1-f][1,2,4]triazin-2-amine 1392

Yellow solid (26 mg, 0.068 mmol, 30.2% yield). $^1$H NMR (499 MHz, DMSO-$d_6$) δ ppm 1.59-1.71 (2H, m), 1.86-2.04 (4H, m), 2.04-2.16 (2H, m), 3.76-3.88 (1H, m), 7.11 (1H, d, J=7.67 Hz), 7.19 (1H, d, J=2.74 Hz), 7.77 (1H, d, J=2.19 Hz), 8.13 (1H, d, J=8.76 Hz), 8.23 (1H, dd, J=8.76, 2.19 Hz), 8.32 (1H, d, J=2.19 Hz), 8.90 (1H, d, J=1.64 Hz), 8.95 (1H, d, J=1.64 Hz), 9.21 (1H, s); ESIMS found for $C_{20}H_{18}F_2N_6$ m/z 381.2 (M+1).

1393

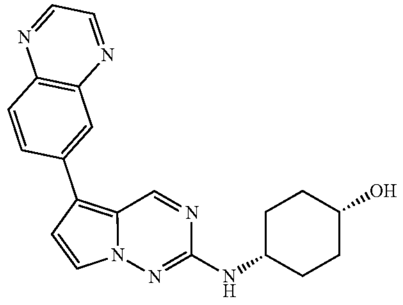

cis-4-((5-(Quinoxalin-6-yl)pyrrolo[2,1-f][1,2,4]triazin-2-yl)amino) cyclohexan-1-ol 1393

Beige solid (7 mg, 0.019 mmol, 6.0% yield). $^1$H NMR (499 MHz, DMSO-$d_6$) δ ppm 1.44-1.56 (2H, m), 1.61-1.71 (4H, m), 1.71-1.82 (2H, m), 3.57-3.67 (1H, m), 3.74 (1H, br d, J=2.19 Hz), 4.36 (1H, d, J=2.74 Hz), 6.89 (1H, d, J=7.67 Hz), 7.17 (1H, d, J=2.74 Hz), 7.75 (1H, d, J=2.74 Hz), 8.13 (1H, d, J=8.76 Hz), 8.23 (1H, dd, J=8.76, 2.19 Hz), 8.31 (1H, d, J=2.19 Hz), 8.89 (1H, d, J=2.19 Hz), 8.95 (1H, d, J=1.64 Hz), 9.18 (1H, s); ESIMS found for $C_{20}H_{20}N_6O$ m/z 361.2 (M+1).

1394

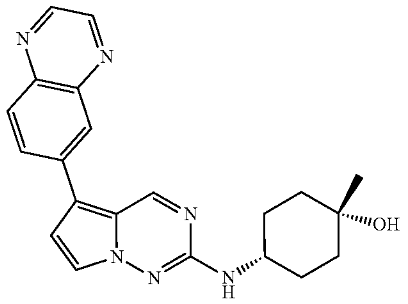

(1s,4s)-1-Methyl-4-((5-(quinoxalin-6-yl)pyrrolo[2,1-f][1,2,4]triazin-2-yl) amino)cyclohexan-1-ol 1394

Yellow solid (30 mg, 0.080 mmol, 19.0% yield). $^1$H NMR (499 MHz, DMSO-$d_6$) δ ppm 1.13 (3H, s), 1.37 (2H, td, J=12.87, 4.38 Hz), 1.59 (2H, br d, J=12.05 Hz), 1.63-1.76 (4H, m), 3.46-3.59 (1H, m), 4.02 (1H, s), 6.87 (1H, d, J=8.21 Hz), 7.16 (1H, d, J=2.74 Hz), 7.74 (1H, d, J=2.74 Hz), 8.12 (1H, d, J=8.76 Hz), 8.22 (1H, dd, J=8.76, 2.19 Hz), 8.30 (1H, d, J=1.64 Hz), 8.89 (1H, d, J=1.64 Hz), 8.95 (1H, d, J=1.64 Hz), 9.17 (1H, s); ESIMS found for $C_{21}H_{22}N_6O$ m/z 375.2 (M+1).

1395

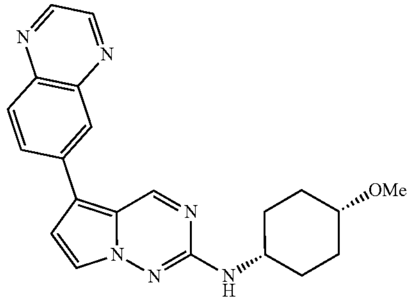

N-(cis-4-Methoxycyclohexyl)-5-(quinoxalin-6-yl) pyrrolo[2,1-f][1,2,4]triazin-2-amine 1395

Yellow solid (62 mg, 0.166 mmol, 39.9% yield). $^1$H NMR (499 MHz, DMSO-$d_6$) δ ppm 1.46-1.55 (2H, m), 1.56-1.67 (2H, m), 1.67-1.75 (2H, m), 1.81-1.90 (2H, m), 3.23 (3H, s), 3.33-3.37 (1H, m), 3.59-3.71 (1H, m), 6.93 (1H, d, J=7.67 Hz), 7.17 (1H, d, J=2.74 Hz), 7.75 (1H, d, J=2.74 Hz), 8.13 (1H, d, J=8.76 Hz), 8.23 (1H, dd, J=8.76, 2.19 Hz), 8.31 (1H, d, J=1.64 Hz), 8.89 (1H, d, J=2.19 Hz), 8.95 (1H, d, J=1.64 Hz), 9.18 (1H, s); ESIMS found for $C_{21}H_{22}N_6O$ m/z 375.2 (M+1).

1418

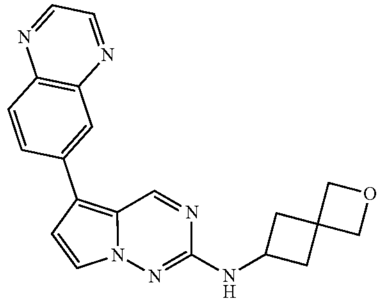

5-(Quinoxalin-6-yl)-N-(2-oxaspiro[3.3]heptan-6-yl) pyrrolo[2,1-f][1,2,4]triazin-2-amine 1418

Pale yellow solid (26 mg, 0.073 mmol, 24.9% yield). $^1$H NMR (499 MHz, DMSO-$d_6$) δ ppm 2.13-2.23 (2H, m), 2.59-2.68 (2H, m), 4.01 (1H, sxt, J=7.67 Hz), 4.52 (2H, s), 4.64 (2H, s), 7.19 (1H, d, J=2.19 Hz), 7.33 (1H, d, J=7.12 Hz), 7.76 (1H, d, J=2.19 Hz), 8.13 (1H, d, J=8.76 Hz), 8.20-8.26 (1H, m), 8.31 (1H, d, J=2.19 Hz), 8.90 (1H, d, J=1.64 Hz), 8.95 (1H, d, J=2.19 Hz), 9.19 (1H, s); ESIMS found for $C_{20}H_{18}N_6O$ m/z 359.2 (M+1).

1423

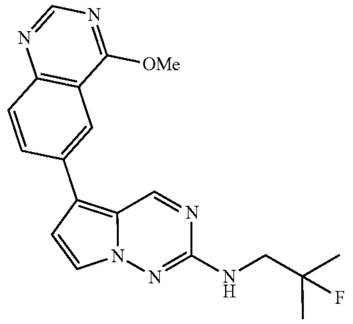

N-(2-Fluoro-2-methylpropyl)-5-(4-methoxyquinazolin-6-yl)pyrrolo[2,1-f][1,2,4]triazin-2-amine 1423

Yellow solid (52.33 mg, 0.143 mmol). $^1$H NMR (400 MHz, DMSO-$d_6$) δ ppm 1.38 (6H, d, J=21.40 Hz), 3.49 (2H, dd, J=19.20, 6.40 Hz), 4.18 (3H, s), 7.10-7.14 (1H, m), 7.11 (1H, d, J=2.63 Hz), 7.75 (1H, d, J=2.50 Hz), 7.97 (1H, d, J=9.63 Hz), 8.27-8.31 (1H, m), 8.28 (1H, s), 8.79 (1H, s), 9.11 (1H, s); ESIMS found for $C_{19}H_{19}FN_6O$ m/z 367.2 (M+1).

1520

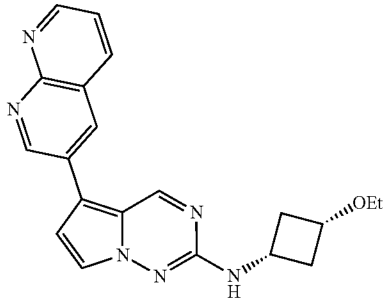

N-(cis-3-Ethoxycyclobutyl)-5-(1,8-naphthyridin-3-yl)pyrrolo[2,1-f][1,2,4]triazin-2-amine 1520

Beige solid (62 mg, 0.172 mmol, 53.5% yield). $^1$H NMR (499 MHz, DMSO-$d_6$) δ ppm 1.11 (3H, t, J=6.84 Hz), 1.81-1.95 (2H, m), 2.61-2.73 (2H, m), 3.35 (2H, q, J=7.12 Hz), 3.66-3.74 (1H, m), 3.75-3.85 (1H, m), 7.24 (1H, d, J=2.74 Hz), 7.35 (1H, d, J=7.67 Hz), 7.66 (1H, dd, J=8.21, 4.38 Hz), 7.77 (1H, d, J=2.74 Hz), 8.52 (1H, dd, J=8.21, 2.19 Hz), 8.74 (1H, d, J=2.19 Hz), 9.03 (1H, dd, J=4.11, 1.92 Hz), 9.29 (1H, s), 9.45 (1H, d, J=2.74 Hz); ESIMS found for $C_{20}H_{20}N_6O$ m/z 361.2 (M+1).

1522

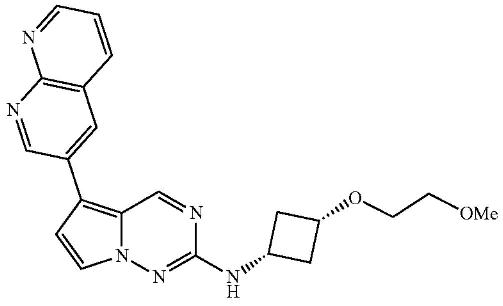

N-(cis-3-(2-Methoxyethoxy)cyclobutyl)-5-(1,8-naphthyridin-3-yl)pyrrolo [2,1-f][1,2,4]triazin-2-amine 1522

Light brown solid (51 mg, 0.131 mmol, 44.6% yield). $^1$H NMR (499 MHz, DMSO-$d_6$) δ ppm 1.81-1.94 (2H, m), 2.61-2.73 (2H, m), 3.25 (3H, s), 3.40-3.46 (1H, m), 3.43 (3H, s), 3.70-3.76 (1H, m), 3.76-3.83 (1H, m), 7.24 (1H, d, J=2.74 Hz), 7.36 (1H, d, J=7.67 Hz), 7.64-7.70 (1H, m), 7.77 (1H, d, J=2.74 Hz), 8.52 (1H, dd, J=8.21, 1.64 Hz), 8.74 (1H, d, J=2.74 Hz), 9.00-9.07 (1H, m), 9.29 (1H, s), 9.45 (1H, d, J=2.19 Hz); ESIMS found for $C_{21}H_{22}N_6O_2$ m/z 391.2 (M+1).

1535

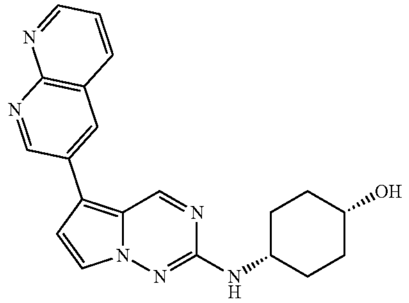

cis-4-((5-(1,8-Naphthyridin-3-yl)pyrrolo[2,1-f][1,2,4]triazin-2-yl)amino) cyclohexan-1-ol 1535

Light orange solid (4.0 mg, 0.011 mmol, 62.5% yield). $^1$H NMR (499 MHz, DMSO-$d_6$) δ ppm 1.44-1.58 (2H, m), 1.62-1.71 (4H, m), 1.71-1.81 (2H, m), 3.56-3.69 (2H, m), 3.75 (1H, br s), 4.36 (1H, br s), 6.90 (1H, d, J=7.67 Hz), 7.22 (1H, d, J=2.74 Hz), 7.61-7.71 (1H, m), 7.77 (1H, d, J=2.74 Hz), 8.52 (1H, dd, J=8.21, 2.19 Hz), 8.74 (1H, d, J=2.74 Hz), 9.03 (1H, dd, J=4.38, 2.19 Hz), 9.28 (1H, s), 9.45 (1H, d, J=2.74 Hz); ESIMS found for $C_{20}H_{20}N_6O$ m/z 361.1 (M+1).

1536

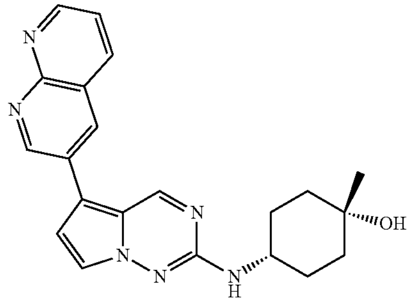

(1s,4s)-4-((5-(1,8-Naphthyridin-3-yl)pyrrolo[2,1-f][1,2,4]triazin-2-yl)amino)-1-methylcyclohexan-1-ol 1536

Beige solid (7 mg, 0.019 mmol, 4.1% yield). $^1$H NMR (499 MHz, DMSO-$d_6$) δ ppm 1.13 (3H, s), 1.37 (2H, td, J=12.87, 4.38 Hz), 1.59 (2H, br d, J=12.05 Hz), 1.63-1.76 (4H, m), 3.46-3.59 (1H, m), 4.02 (1H, s), 6.88 (1H, d, J=7.67 Hz), 7.21 (1H, d, J=2.74 Hz), 7.65 (1H, dd, J=7.94, 4.11 Hz), 7.76 (1H, d, J=2.74 Hz), 8.51 (1H, dd, J=8.21, 1.64 Hz), 8.73 (1H, d, J=2.74 Hz), 9.03 (1H, dd, J=4.11, 1.92 Hz), 9.27 (1H, s), 9.45 (1H, d, J=2.74 Hz); ESIMS found for $C_{21}H_{22}N_6O$ m/z 375.2 (M+1).

1537

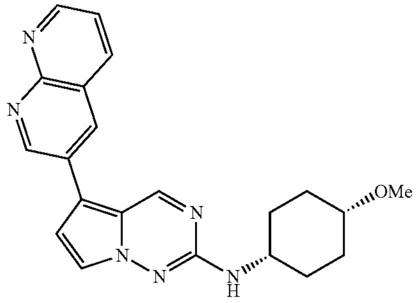

N-(cis-4-Methoxycyclohexyl)-5-(1,8-naphthyridin-3-yl)pyrrolo[2,1-f][1,2,4]triazin-2-amine 1537

Pale yellow solid (18 mg, 0.048 mmol, 15.6% yield). $^1$H NMR (499 MHz, DMSO-$d_6$) δ ppm 1.46-1.56 (2H, m), 1.57-1.67 (2H, m), 1.67-1.76 (2H, m), 1.81-1.91 (2H, m), 3.23 (3H, s), 3.34-3.39 (1H, m), 3.60-3.72 (1H, m), 6.93 (1H, d, J=7.67 Hz), 7.22 (1H, d, J=2.74 Hz), 7.66 (1H, dd, J=7.94, 4.11 Hz), 7.77 (1H, d, J=2.74 Hz), 8.52 (1H, dd, J=7.94, 1.92 Hz), 8.74 (1H, d, J=2.74 Hz), 9.03 (1H, dd, J=4.11, 1.92 Hz), 9.28 (1H, s), 9.45 (1H, d, J=2.74 Hz); ESIMS found for $C_{21}H_{22}N_6O$ m/z 375.2 (M+1).

1541

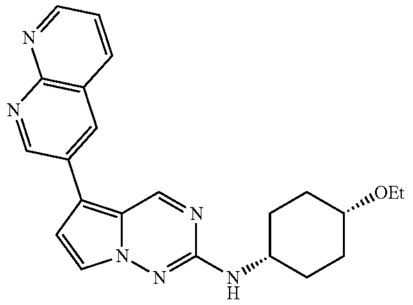

N-(cis-4-Ethoxycyclohexyl)-5-(1,8-naphthyridin-3-yl)pyrrolo[2,1-f][1,2,4]triazin-2-amine 1541

Light brown solid (61 mg, 0.157 mmol, 61.2% yield). $^1$H NMR (499 MHz, DMSO-$d_6$) δ ppm 1.13 (3H, t, J=6.84 Hz), 1.44-1.57 (2H, m), 1.60-1.75 (4H, m), 1.78-1.88 (2H, m), 3.42 (2H, q, J=6.75 Hz), 3.45-3.48 (1H, m), 3.58-3.71 (1H, m), 6.93 (1H, d, J=7.67 Hz), 7.22 (1H, d, J=2.74 Hz), 7.65 (1H, dd, J=7.94, 4.11 Hz), 7.77 (1H, d, J=2.74 Hz), 8.51 (1H, dd, J=8.21, 1.64 Hz), 8.73 (1H, d, J=2.74 Hz), 9.03 (1H, dd, J=4.11, 1.92 Hz), 9.28 (1H, s), 9.45 (1H, d, J=2.74 Hz); ESIMS found for $C_{22}H_{24}N_6O$ m/z 389.2 (M+1).

1543

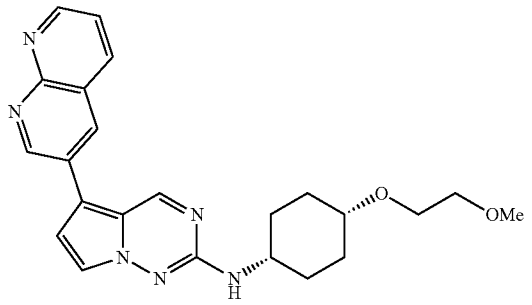

N-(cis-4-(2-Methoxyethoxy)cyclohexyl)-5-(1,8-naphthyridin-3-yl)pyrrolo [2,1-f][1,2,4]triazin-2-amine 1543

Dark yellow solid (85 mg, 0.203 mmol, 50.0% yield). $^1$H NMR (499 MHz, DMSO-$d_6$) δ ppm 1.45-1.57 (2H, m), 1.59-1.76 (4H, m), 1.79-1.90 (2H, m), 3.27 (3H, s), 3.44-3.46 (2H, m), 3.47-3.49 (1H, m), 3.49-3.52 (2H, m), 3.65 (1H, qt, J=8.53, 4.45 Hz), 6.94 (1H, d, J=7.67 Hz), 7.22 (1H, d, J=2.74 Hz), 7.65 (1H, dd, J=8.21, 4.38 Hz), 7.77 (1H, d, J=2.74 Hz), 8.51 (1H, dd, J=8.21, 1.64 Hz), 8.73 (1H, d, J=2.74 Hz), 9.03 (1H, dd, J=4.11, 1.92 Hz), 9.28 (1H, s), 9.45 (1H, d, J=2.74 Hz); ESIMS found for $C_{23}H_{26}N_6O_2$ m/z 419.2 (M+1).

1544

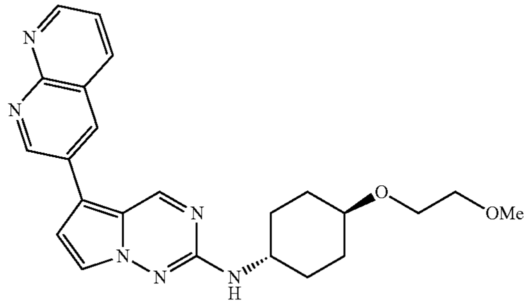

N-(trans-4-(2-Methoxyethoxy)cyclohexyl)-5-(1,8-naphthyridin-3-yl)pyrrolo [2,1-f][1,2,4]triazin-2-amine 1544

Light brown solid (16 mg, 0.038 mmol, 23.5% yield). $^1$H NMR (499 MHz, DMSO-$d_6$) δ ppm 1.17-1.40 (4H, m), 2.02 (4H, br d, J=9.31 Hz), 3.22-3.28 (1H, m), 3.25 (3H, s), 3.43 (2H, dd, J=5.75, 4.11 Hz), 3.54 (2H, dd, J=5.48, 3.83 Hz), 3.56-3.62 (1H, m), 6.92 (1H, d, J=7.67 Hz), 7.23 (1H, d, J=2.74 Hz), 7.61-7.69 (1H, m), 7.80 (1H, d, J=2.74 Hz), 8.52 (1H, dd, J=8.21, 2.19 Hz), 8.74 (1H, d, J=2.19 Hz), 9.03 (1H, dd, J=4.11, 1.92 Hz), 9.29 (1H, s), 9.45 (1H, d, J=2.19 Hz); ESIMS found for $C_{23}H_{26}N_6O_2$ m/z 419.3 (M+1).

1551

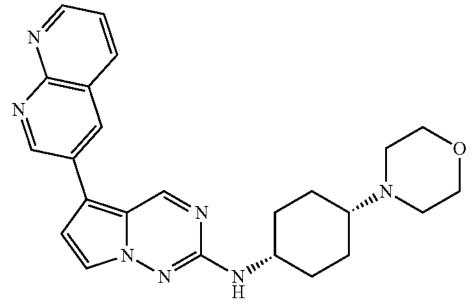

N-(cis-4-Morpholinocyclohexyl)-5-(1,8-naphthyridin-3-yl)pyrrolo[2,1-f][1,2,4]triazin-2-amine 1551

Yellow solid (25 mg, 0.058 mmol, 41.8% yield). $^1$H NMR (499 MHz, DMSO-$d_6$) δ ppm 1.47-1.56 (2H, m), 1.56-1.64 (2H, m), 1.75-1.82 (2H, m), 1.82-1.90 (2H, m), 2.12-2.23 (1H, m), 2.45 (4H, br s), 3.59 (4H, t, J=4.38 Hz), 3.76-3.85 (1H, m), 6.95 (1H, d, J=7.12 Hz), 7.22 (1H, d, J=2.74 Hz), 7.66 (1H, dd, J=7.94, 4.11 Hz), 7.78 (1H, d, J=2.74 Hz), 8.52 (1H, dd, J=7.94, 1.92 Hz), 8.74 (1H, d, J=2.74 Hz), 9.03 (1H, dd, J=4.11, 1.92 Hz), 9.29 (1H, s), 9.46 (1H, d, J=2.74 Hz); ESIMS found for $C_{24}H_{27}N_7O$ m/z 430.3 (M+1).

1557

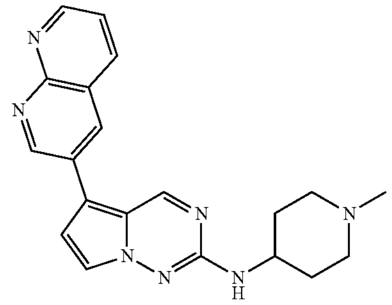

N-(1-Methylpiperidin-4-yl)-5-(1,8-naphthyridin-3-yl)pyrrolo[2,1-f][1,2,4]triazin-2-amine 1557

Light brown solid (50 mg, 0.139 mmol, 28.8% yield). $^1$H NMR (499 MHz, DMSO-$d_6$) δ ppm 1.13 (3H, t, J=6.84 Hz), 1.44-1.57 (2H, m), 1.60-1.75 (4H, m), 1.78-1.88 (2H, m), 3.42 (2H, q, J=6.75 Hz), 3.45-3.48 (1H, m), 3.58-3.71 (1H, m), 6.93 (1H, d, J=7.67 Hz), 7.22 (1H, d, J=2.74 Hz), 7.65 (1H, dd, J=7.94, 4.11 Hz), 7.77 (1H, d, J=2.74 Hz), 8.51 (1H, dd, J=8.21, 1.64 Hz), 8.73 (1H, d, J=2.74 Hz), 9.03 (1H, dd, J=4.11, 1.92 Hz), 9.28 (1H, s), 9.45 (1H, d, J=2.74 Hz); ESIMS found for $C_{20}H_{21}N_7$ m/z 360.2 (M+1).

1720

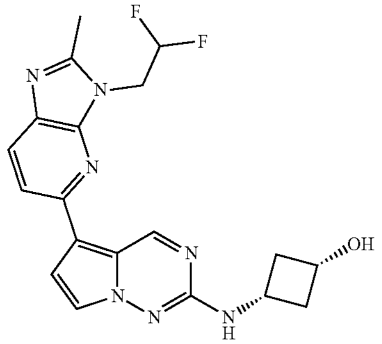

cis-3-((5-(3-(2,2-Difluoroethyl)-2-methyl-3H-imidazo[4,5-b]pyridin-5-yl)pyrrolo[2,1-f][1,2,4]triazin-2-yl)amino)cyclobutan-1-ol 1720

Pale yellow solid (43 mg, 0.108 mmol, 44.2% yield). $^1$H NMR (499 MHz, DMSO-$d_6$) δ ppm 1.79-1.89 (2H, m), 2.59-2.66 (2H, m), 2.62 (3H, s), 3.67 (1H, dq, J=14.89, 7.54 Hz), 3.82-3.92 (1H, m), 4.85 (2H, td, J=15.88, 2.46 Hz), 6.55 (1H, tt, J=54.60, 3.00 Hz), 7.16 (1H, br d, J=7.12 Hz), 7.24 (1H, d, J=2.74 Hz), 7.63 (1H, d, J=2.46 Hz), 7.74 (1H, d, J=8.49 Hz), 7.96 (1H, d, J=8.21 Hz), 9.69 (1H, s); ESIMS found for $C_{19}H_{19}F_2N_7O$ m/z 400.2 (M+1).

1723

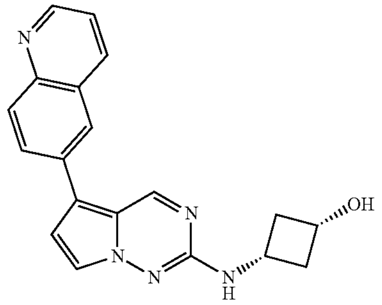

cis-3-((5-(Quinolin-6-yl)pyrrolo[2,1-f][1,2,4]triazin-2-yl)amino)cyclobutan-1-ol 1723

Yellow solid (14 mg, 0.042 mmol, 11.4% yield). $^1$H NMR (499 MHz, DMSO-$d_6$) δ ppm 1.79-1.90 (2H, m), 2.58-2.68 (2H, m), 3.60-3.72 (1H, m), 3.8-3.93 (1H, m), 5.06 (1H, br d, J=4.38 Hz), 7.09 (1H, d, J=2.74 Hz), 7.24 (1H, d, J=7.12 Hz), 7.54 (1H, dd, J=8.21, 4.38 Hz), 7.71 (1H, d, J=2.19 Hz), 8.03-8.07 (1H, m), 8.08-8.12 (1H, m), 8.28 (1H, d, J=2.19 Hz), 8.43 (1H, dd, J=8.49, 1.37 Hz), 8.86 (1H, dd, J=4.38, 1.64 Hz), 9.22 (1H, s); ESIMS found for $C_{19}H_{17}N_5O$ m/z 332.2 (M+1).

1724

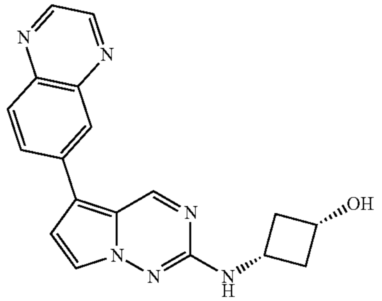

cis-3-((5-(Quinoxalin-6-yl)pyrrolo[2,1-f][1,2,4]triazin-2-yl)amino) cyclobutan-1-ol 1724

Yellow solid (16 mg, 0.048 mmol, 13.0% yield). $^1$H NMR (499 MHz, DMSO-$d_6$) δ ppm 1.79-1.89 (2H, m), 2.58-2.69 (2H, m), 3.61-3.72 (1H, m), 3.82-3.93 (1H, m), 5.06 (1H, d, J=6.02 Hz), 7.18 (1H, d, J=2.74 Hz), 7.30 (1H, d, J=7.12 Hz), 7.74 (1H, d, J=2.74 Hz), 8.13 (1H, d, J=8.76 Hz), 8.23 (1H, dd, J=8.76, 2.19 Hz), 8.31 (1H, d, J=1.64 Hz), 8.90 (1H, d, J=1.64 Hz), 8.95 (1H, d, J=2.19 Hz), 9.19 (1H, s); ESIMS found for $C_{18}H_6N_6O$ m/z 333.2 (M+1).

1732

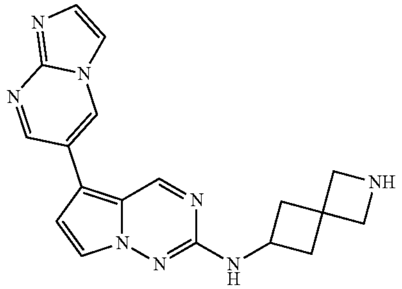

5-(Imidazo[1,2-a]pyrimidin-6-yl)-N-(2-azaspiro[3.3]heptan-6-yl)pyrrolo[2,1-f][1,2,4]triazin-2-amine 1732

Light yellow solid (90 mg, 0.260 mmol, 71.2% yield). $^1$H NMR (499 MHz, DMSO-$d_6$) δ ppm 2.17-2.27 (2H, m), 2.60-2.70 (2H, m), 3.95 (2H, s), 4.00-4.10 (1H, m), 4.05 (2H, br s), 7.09 (1H, d, J=2.74 Hz), 7.33 (1H, d, J=6.57 Hz), 7.73 (1H, d, J=2.19 Hz), 7.75 (1H, d, J=1.10 Hz), 7.90 (1H, d, J=1.10 Hz), 8.89 (1H, d, J=2.74 Hz), 9.17 (1H, s), 9.31 (1H, d, J=2.74 Hz); ESIMS found for $C_{18}H_{18}N_8$ m/z 347.2 (M+1).

1747

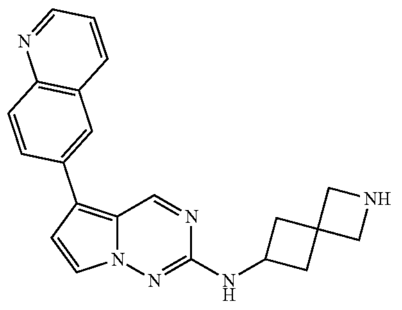

5-(Quinolin-6-yl)-N-(2-azaspiro[3.3]heptan-6-yl) pyrrolo[2,1-f][1,2,4]triazin-2-amine 1747

Yellow solid (45 mg, 0.126 mmol, 25.1% yield). $^1$H NMR (499 MHz, DMSO-$d_6$) δ ppm 2.17-2.28 (2H, m), 2.60-2.70 (2H, m), 3.94 (2H, s), 4.05-4.11 (1H, m), 7.11 (1H, d, J=2.74 Hz), 7.31 (1H, d, J=7.12 Hz), 7.54 (1H, dd, J=8.21, 3.83 Hz), 7.71 (1H, d, J=2.74 Hz), 8.04-8.07 (1H, m), 8.08-8.12 (1H, m), 8.28 (1H, d, J=1.64 Hz), 8.43 (1H, dd, J=8.21, 1.09 Hz), 8.86 (1H, dd, J=4.38, 1.64 Hz), 9.23 (1H, s); ESIMS found for $C_{21}H_{20}N_6$ m/z 357.2 (M+1).

1756

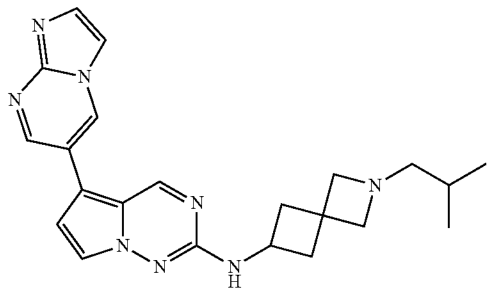

5-(Imidazo[1,2-a]pyrimidin-6-yl)-N-(2-isobutyl-2-azaspiro[3.3]heptan-6-yl)pyrrolo[2,1-f][1,2,4]triazin-2-amine 1756

Yellow solid (20 mg, 0.050 mmol, 43.0% yield). $^1$H NMR (499 MHz, DMSO-$d_6$) δ ppm 0.82 (6H, d, J=6.57 Hz), 1.48 (1H, dquin, J=13.48, 6.76, 6.76, 6.76, 6.76 Hz), 1.57-1.58 (1H, m), 2.04-2.11 (2H, m), 2.11 (2H, d, J=7.12 Hz), 2.45 (2H, ddd, J=9.72, 7.26, 2.74 Hz), 3.03 (2H, s), 3.15 (2H, s), 4.04 (1H, sxt, J=7.67 Hz), 7.07 (1H, d, J=2.19 Hz), 7.27 (1H, d, J=7.12 Hz), 7.74 (1H, d, J=1.64 Hz), 7.75 (1H, d, J=2.74 Hz), 7.89 (1H, d, J=1.09 Hz), 8.88 (1H, d, J=2.74 Hz), 9.14 (1H, s), 9.29 (1H, d, J=2.74 Hz); ESIMS found for $C_{22}H_{26}N_8$ m/z 403.2 (M+1).

1771

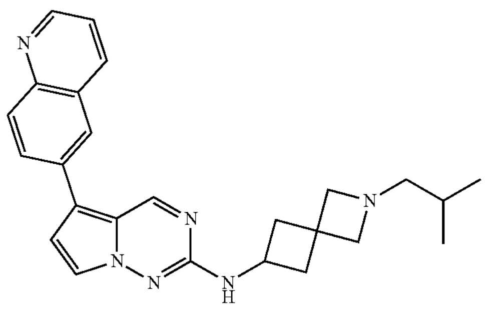

N-(2-Isobutyl-2-azaspiro[3.3]heptan-6-yl)-5-(quinolin-6-yl)pyrrolo[2,1-f][1,2,4]triazin-2-amine 1771

Yellow solid (60 mg, 0.145 mmol, 51.8% yield). $^1$H NMR (499 MHz, DMSO-$d_6$) δ ppm 0.82 (6H, d, J=7.12 Hz), 1.48 (1H, dquin, J=13.48, 6.62, 6.62, 6.62, 6.62 Hz), 2.06-2.10 (2H, m), 2.11 (2H, d, J=6.57 Hz), 2.46 (2H, ddd, J=9.72, 7.26, 2.74 Hz), 3.03 (2H, s), 3.15 (2H, s), 4.05 (1H, sxt, J=7.78 Hz), 7.09 (1H, d, J=2.74 Hz), 7.24 (1H, d, J=7.12 Hz), 7.50-7.58 (1H, m), 7.73 (1H, d, J=2.19 Hz), 8.03-8.06 (1H, m), 8.08-8.12 (1H, m), 8.28 (1H, d, J=2.19 Hz), 8.42 (1H, dd, J=8.49, 1.37 Hz), 8.85 (1H, dd, J=4.38, 1.64 Hz), 9.22 (1H, s); ESIMS found for $C_{25}H_{28}N_6$ m/z 413.25 (M+1).

1780

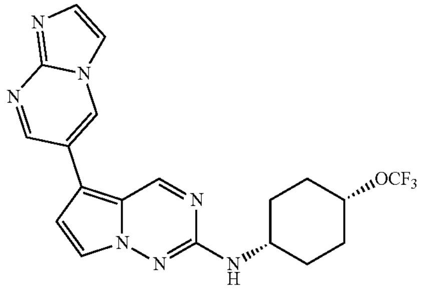

5-(Imidazo[1,2-a]pyrimidin-6-yl)-N-(cis-4-(trifluoromethoxy)cyclohexyl) pyrrolo[2,1-f][1,2,4]triazin-2-amine 1780

Brown solid (20 mg, 0.048 mmol, 18.2% yield). $^1$H NMR (499 MHz, DMSO-$d_6$) δ ppm 1.62-1.71 (2H, m), 1.71-1.80 (2H, m), 1.80-1.88 (2H, m), 1.95 (2H, br dd, J=9.03, 4.65 Hz), 3.65-3.77 (1H, m), 4.57-4.65 (1H, m), 7.02 (1H, d, J=7.12 Hz), 7.07 (1H, d, J=2.74 Hz), 7.73-7.76 (2H, m), 7.89 (1H, d, J=1.09 Hz), 8.88 (1H, d, J=2.74 Hz), 9.16 (1H, s), 9.30 (1H, d, J=2.74 Hz); ESIMS found for $C_{19}H_{18}F_3N_7O$ m/z 418.2 (M+1).

1786

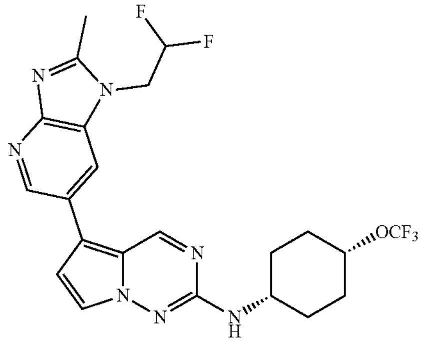

5-(1-(2,2-Difluoroethyl)-2-methyl-1H-imidazo[4,5-b]pyridin-6-yl)-N-(cis-4-(trifluoromethoxy) cyclohexyl)pyrrolo[2,1-f][1,2,4]triazin-2-amine 1786

Light brown solid (35 mg, 0.071 mmol, 26.8% yield). $^1$H NMR (499 MHz, DMSO-$d_6$) δ ppm 1.62-1.71 (2H, m), 1.72-1.80 (2H, m), 1.81-1.88 (2H, m), 1.91-2.01 (2H, m), 2.63 (3H, s), 3.67-3.79 (1H, m), 4.56-4.66 (1H, m), 4.90 (2H, td, J=15.81, 2.87 Hz), 6.53 (1H, tt, J=54.60, 3.00 Hz), 6.93 (1H, d, J=7.94 Hz), 6.98 (1H, d, J=2.46 Hz), 7.71 (1H, d, J=2.46 Hz), 8.23 (1H, d, J=1.92 Hz), 8.66 (1H, d, J=2.19 Hz), 9.12 (1H, s); ESIMS found for $C_{22}H_{22}F_5N_7O$ m/z 496.2 (M+1).

1792

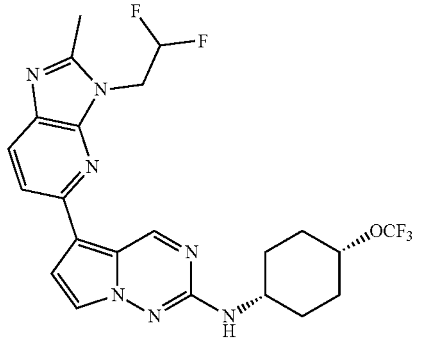

5-(3-(2,2-Difluoroethyl)-2-methyl-3H-imidazo[4,5-b]pyridin-5-yl)-N-(cis-4-(trifluoromethoxy)cyclohexyl)pyrrolo[2,1-f][1,2,4]triazin-2-amine 1792

Pale yellow solid (33 mg, 0.067 mmol, 21.7% yield). $^1$H NMR (499 MHz, DMSO-$d_6$) δ ppm 1.61-1.71 (2H, m), 1.72-1.80 (2H, m), 1.81-1.88 (2H, m), 1.92-2.00 (2H, m), 2.61 (3H, s), 3.67-3.81 (1H, m), 4.56-4.66 (1H, m), 4.83 (2H, td, J=16.02, 3.01 Hz), 6.55 (1H, tt, J=54.85, 3.30 Hz), 6.90 (1H, d, J=7.67 Hz), 7.23 (1H, d, J=2.19 Hz), 7.64 (1H, d, J=2.74 Hz), 7.73 (1H, d, J=8.21 Hz), 7.95 (1H, d, J=8.21 Hz), 9.71 (1H, s); ESIMS found for $C_{22}H_{22}F_5N_7O$ m/z 496.2 (M+1).

1798

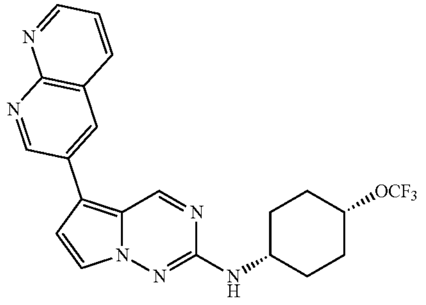

5-(1,8-Naphthyridin-3-yl)-N-(cis-4-(trifluoromethoxy)cyclohexyl)pyrrolo [2,1-f][1,2,4]triazin-2-amine 1798

Yellow solid (13 mg, 0.030 mmol, 9.2% yield). $^1$H NMR (499 MHz, DMSO-$d_6$) δ ppm 1.62-1.72 (2H, m), 1.73-1.81 (2H, m), 1.81-1.89 (2H, m), 1.96 (2H, br dd, J=9.03, 4.65 Hz), 3.66-3.79 (1H, m), 4.56-4.66 (1H, m), 7.06 (1H, d, J=7.67 Hz), 7.23 (1H, d, J=2.74 Hz), 7.66 (1H, dd, J=7.94, 4.11 Hz), 7.78 (1H, d, J=2.19 Hz), 8.52 (1H, dd, J=8.21, 2.19 Hz), 8.74 (1H, d, J=2.74 Hz), 9.03 (1H, dd, J=4.38, 2.19 Hz), 9.30 (1H, s), 9.45 (1H, d, J=2.74 Hz); ESIMS found for $C_{21}H_{19}F_3N_6O$ m/z 429.15 (M+1).

1801

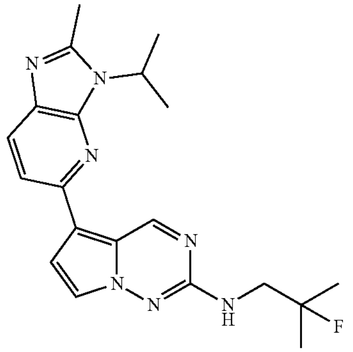

N-(2-Fluoro-2-methylpropyl)-5-(3-isopropyl-2-methyl-3H-imidazo[4,5-b]pyridin-5-yl)pyrrolo [2,1-f][1,2,4]triazin-2-amine 1801

Yellow solid (24 mg, 0.063 mmol, 21.3% yield). $^1$H NMR (499 MHz, DMSO-$d_6$) δ ppm 1.38 (6H, d, J=21.20 Hz), 1.72 (6H, d, J=6.84 Hz), 2.61 (3H, s), 3.49 (2H, dd, J=19.30, 6.43 Hz), 4.84 (1H, spt, J=6.80 Hz), 7.02 (1H, t, J=6.30 Hz), 7.24 (1H, d, J=2.74 Hz), 7.66 (1H, d, J=2.74 Hz), 7.69 (1H, d, J=8.49 Hz), 7.89 (1H, d, J=8.21 Hz), 9.66 (1H, s); ESIMS found for $C_{20}H_{24}FN_7$ m/z 382.2 (M+1).

1802

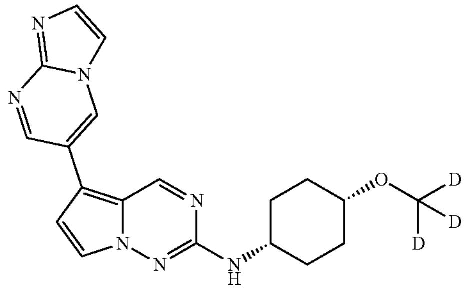

5-(Imidazo[1,2-a]pyrimidin-6-yl)-N-(cis-4-(methoxy-$d_3$)cyclohexyl)pyrrolo [2,1-f][1,2,4] triazin-2-amine 1802

Pale yellow solid (61 mg, 0.167 mmol, 54.6% yield). $^1$H NMR (499 MHz, DMSO-$d_6$) δ ppm 1.45-1.54 (2H, m), 1.56-1.65 (2H, m), 1.66-1.74 (2H, m), 1.80-1.88 (2H, m), 3.33-3.36 (1H, m), 3.58-3.69 (1H, m), 6.89 (1H, d, J=7.67 Hz), 7.05 (1H, d, J=2.74 Hz), 7.69-7.78 (2H, m), 7.89 (1H, d, J=1.64 Hz), 8.88 (1H, d, J=2.74 Hz), 9.14 (1H, s), 9.29 (1H, d, J=2.74 Hz); ESIMS found for $C_{19}H_{18}[2H_3]N_7O$ m/z 367.2 (M+1).

1803

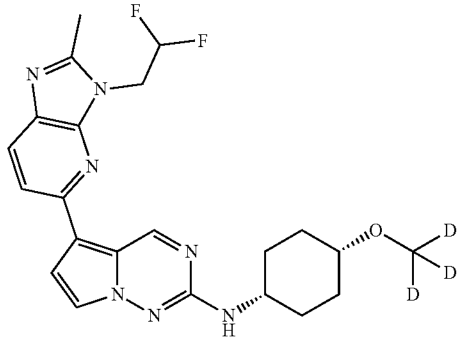

5-(3-(2,2-Difluoroethyl)-2-methyl-3H-imidazo[4,5-b]pyridin-5-yl)-N-(cis-4-(methoxy-$d_3$) cyclohexyl) pyrrolo[2,1-f][1,2,4]triazin-2-amine 1803

Pale yellow solid (50 mg, 0.113 mmol, 36.9% yield). $^{11}$H NMR (499 MHz, DMSO-$d_6$) δ ppm 1.45-1.55 (2H, m), 1.56-1.66 (2H, m), 1.66-1.74 (2H, m), 1.81-1.89 (2H, m), 2.60 (3H, s), 3.33-3.37 (1H, m), 3.59-3.74 (1H, m), 4.83 (2H, td, J=16.02, 3.01 Hz), 6.55 (1H, tt, J=54.85, 3.30 Hz), 6.77 (1H, d, J=7.67 Hz), 7.21 (1H, d, J=2.74 Hz), 7.63 (1H, d, J=2.19 Hz), 7.72 (1H, d, J=8.21 Hz), 7.94 (1H, d, J=8.76 Hz), 9.69 (1H, s); ESIMS found for $C_{22}H_{22}[2H_3]F_2N_7O$ m/z 445.2 (M+1).

1813

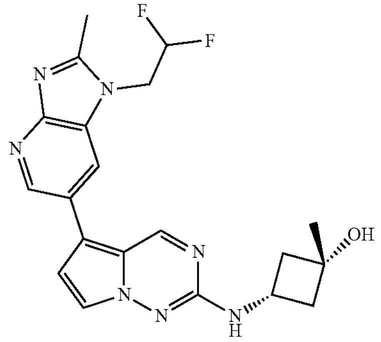

cis-3-((5-(1-(2,2-Difluoroethyl)-2-methyl-1H-imidazo[4,5-b]pyridin-6-yl)pyrrolo[2,1-f][1,2,4]triazin-2-yl)amino)-1-methylcyclobutan-1-ol 1813

Olive green solid (8 mg, 0.019 mmol, 5.8% yield). $^1$H NMR (499 MHz, DMSO-$d_6$) δ ppm 1.28 (3H, s), 1.97-2.08 (2H, m), 2.32-2.43 (2H, m), 2.62 (3H, s), 3.73 (1H, dq, J=15.06, 7.57 Hz), 4.85-4.95 (2H, m), 4.94 (1H, s), 6.52 (1H, tt, J=54.60, 3.00 Hz), 6.98 (1H, d, J=2.19 Hz), 7.17 (1H, br d, J=6.57 Hz), 7.73 (1H, d, J=2.19 Hz), 8.23 (1H, d, J=1.64 Hz), 8.65 (1H, d, J=1.64 Hz), 9.10 (1H, s); ESIMS found for $C_{20}H_{21}F_2N_7O$ m/z 414.2 (M+1).

1819

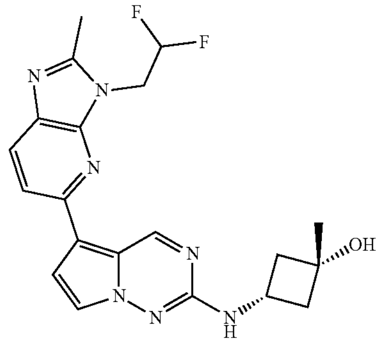

cis-3-((5-(3-(2,2-Difluoroethyl)-2-methyl-3H-imidazo[4,5-b]pyridin-5-yl)pyrrolo[2,1-f][1,2,4]triazin-2-yl)amino)-1-methylcyclobutan-1-ol 1819

Olive green solid (13 mg, 0.031 mmol, 12.5% yield). $^1$H NMR (499 MHz, DMSO-$d_6$) δ ppm 1.28 (3H, s), 2.03 (2H, td, J=9.03, 2.19 Hz), 2.33-2.42 (2H, m), 2.61 (3H, s), 3.74 (1H, dq, J=15.33, 7.67 Hz), 4.83 (2H, td, J=15.88, 2.74 Hz), 4.95 (1H, s), 6.55 (1H, tt, J=54.60, 3.00 Hz), 7.14 (1H, d, J=7.12 Hz), 7.23 (1H, d, J=2.74 Hz), 7.65 (1H, d, J=2.74 Hz), 7.72 (1H, d, J=8.21 Hz), 7.95 (1H, d, J=8.21 Hz), 9.69 (1H, s); ESIMS found for $C_{20}H_{21}F_2N_7O$ m/z 414.2 (M+1).

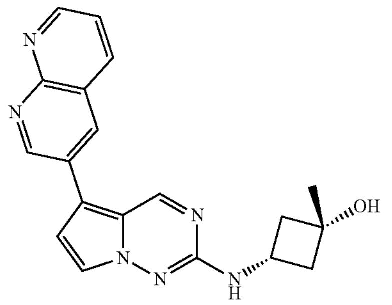

1825 cis-3-((5-(1,8-Naphthyridin-3-yl)pyrrolo[2,1-f][1,2,4]triazin-2-yl)amino)-1-methylcyclobutan-1-ol 1825

Brownish orange solid (6 mg, 0.017 mmol, 5.1% yield). $^1$H NMR (499 MHz, DMSO-$d_6$) δ ppm 1.28 (3H, s), 1.98-2.09 (2H, m), 2.33-2.43 (2H, m), 3.68-3.80 (1H, m), 4.95 (1H, br s), 7.23 (1H, d, J=2.74 Hz), 7.31 (1H, d, J=6.57 Hz), 7.66 (1H, dd, J=8.21, 4.38 Hz), 7.79 (1H, d, J=2.74 Hz), 8.52 (1H, dd, J=8.21, 1.64 Hz), 8.74 (1H, d, J=2.74 Hz), 9.03 (1 H, dd, J=4.38, 2.19 Hz), 9.28 (1H, s), 9.45 (1H, d, J=2.74 Hz); ESIMS found for $C_{19}H_{18}N_6O$ m/z 347. (M+1).

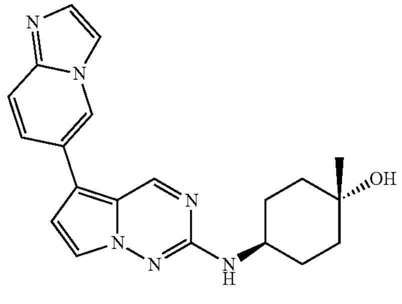

1828 trans-4-((5-(Imidazo[1,2-a]pyridin-6-yl)pyrrolo[2,1-f][1,2,4]triazin-2-yl)amino)-1-methylcyclohexan-1-ol 1828

Beige solid (22 mg, 0.061 mmol, 24.7% yield). $^1$H NMR (499 MHz, DMSO-$d_6$) δ ppm 1.14 (3H, s), 1.36-1.53 (4H, m), 1.57-1.66 (2H, m), 1.81-1.95 (2H, m), 3.64 (1H, br dd, J=7.80, 3.97 Hz), 4.24 (1H, br s), 6.77 (1H, d, J=7.94 Hz), 6.94 (1H, d, J=2.46 Hz), 7.54-7.57 (1H, m), 7.58 (1H, d, J=0.82 Hz), 7.60-7.64 (1H, m), 7.72 (1H, d, J=2.46 Hz), 7.94 (1H, s), 8.91 (1H, s), 9.11 (1H, s); ESIMS found for $C_{20}H_{22}N_6O$ m/z 363.2 (M+1).

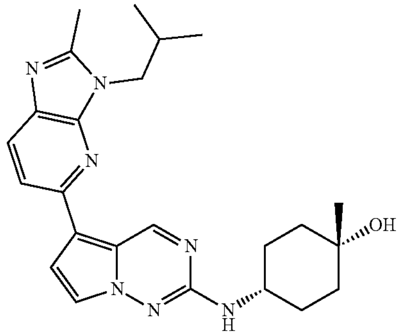

1829 cis-4-((5-(3-Isobutyl-2-methyl-3H-imidazo[4,5-b]pyridin-5-yl)pyrrolo[2,1-f][1,2,4]triazin-2-yl)amino)-1-methylcyclohexan-1-ol 1829

Yellow solid (18.4 mg, 0.042 mmol, 21.6% yield). $^1$H NMR (499 MHz, DMSO-$d_6$) δ ppm 0.95 (6H, d, J=6.57 Hz), 1.13 (3H, s), 1.37 (2H, td, J=12.87, 3.83 Hz), 1.58 (2H, br d, J=12.05 Hz), 1.63-1.68 (2H, m), 1.69-1.76 (2H, m), 2.25-2.39 (1H, m), 2.58 (3H, s), 3.45-3.58 (2H, m), 4.01 (1H, s), 4.10 (2H, br d, J=7.67 Hz), 6.81 (1H, br d, J=7.67 Hz), 7.20 (1H, d, J=2.74 Hz), 7.62 (1H, d, J=2.74 Hz), 7.68 (1H, d, J=8.21 Hz), 7.90 (1H, d, J=8.76 Hz), 9.70 (1H, s); ESIMS found for $C_{24}H_{31}N_7O$ m/z 434.3 (M+1).

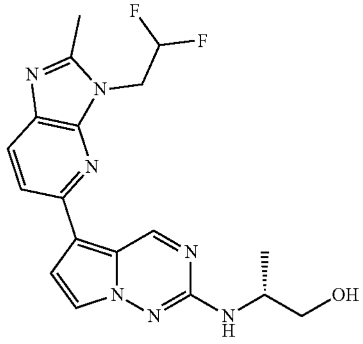

1830

(R)-2-((5-(3-(2,2-Difluoroethyl)-2-methyl-3H-imidazo[4,5-b]pyridin-5-yl)pyrrolo[2,1-f][1,2,4]triazin-2-yl)amino)propan-1-ol 1830

Pale yellow solid (30 mg, 0.077 mmol, 37.5% yield). $^1$H NMR (499 MHz, DMSO-$d_6$) δ ppm 1.17 (3H, d, J=6.57 Hz), 2.61 (3H, s), 3.37 (1H, dt, J=10.54, 6.09 Hz), 3.52 (1H, dt, J=10.47, 5.30 Hz), 3.78-3.92 (1H, m), 4.71 (1H, t, J=5.61 Hz), 4.83 (2H, td, J=16.02, 2.74 Hz), 6.55 (1H, tt, J=54.60, 3.00 Hz), 6.53 (1H, d, J=8.21 Hz), 7.23 (1H, d, J=2.46 Hz), 7.64 (1H, d, J=2.46 Hz), 7.73 (1H, d, J=8.49 Hz), 7.95 (1H, d, J=8.21 Hz), 9.70 (1H, s); ESIMS found for $C_{18}H_{19}F_2N_7O$ m/z 388.2 (M+1). F

1831

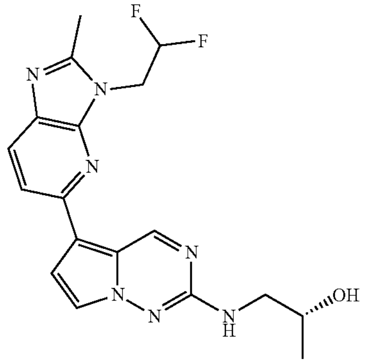

(R)-1-((5-(3-(2,2-Difluoroethyl)-2-methyl-3H-imidazo[4,5-b]pyridin-5-yl)pyrrolo[2,1-f][1,2,4]triazin-2-yl)amino)propan-2-ol 1831

Light yellow solid (54 mg, 0.139 mmol, 46.7% yield). $^1$H NMR (499 MHz, DMSO-$d_6$) δ ppm 1.11 (3H, d, J=6.30 Hz), 2.61 (3H, s), 3.18 (2H, t, J=6.02 Hz), 3.83-3.95 (1H, m), 4.72 (1H, d, J=4.65 Hz), 4.84 (2H, td, J=16.08, 2.87 Hz), 6.55 (1H, tt, J=54.60, 3.00 Hz), 6.71 (1H, t, J=5.89 Hz), 7.24 (1H, d, J=2.46 Hz), 7.65 (1H, d, J=2.46 Hz), 7.73 (1H, d, J=8.21 Hz), 7.95 (1H, d, J=8.21 Hz), 9.70 (1H, s); ESIMS found for $C_{18}H_{19}F_2N_7O$ m/z 388.2 (M+1).

1832

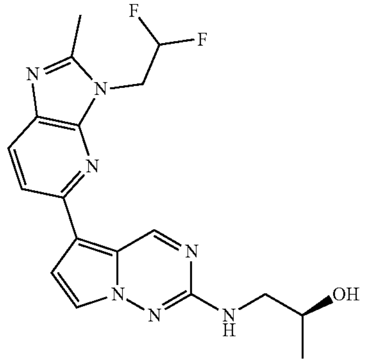

(S)-1-((5-(3-(2,2-Difluoroethyl)-2-methyl-3H-imidazo[4,5-b]pyridin-5-yl)pyrrolo[2,1-f][1,2,4]triazin-2-yl)amino)propan-2-ol 1832

Light yellow solid (48 mg, 0.124 mmol, 38.6% yield). $^1$H NMR (499 MHz, DMSO-$d_6$) δ ppm 1.11 (3H, d, J=6.30 Hz), 2.61 (3H, s), 3.17 (2H, t, J=6.16 Hz), 3.83-3.95 (1H, m), 4.72 (1H, d, J=4.93 Hz), 4.84 (2H, td, J=16.02, 2.74 Hz), 6.55 (1H, tt, J=54.60, 3.00 Hz), 6.71 (1H, t, J=5.89 Hz), 7.24 (1H, d, J=2.74 Hz), 7.65 (1H, d, J=2.46 Hz), 7.73 (1H, d, J=8.21 Hz), 7.95 (1H, d, J=8.21 Hz), 9.70 (1H, s); ESIMS found for $C_{18}H_{19}F_2N_7O$ m/z 388.15 (M+1).

1833

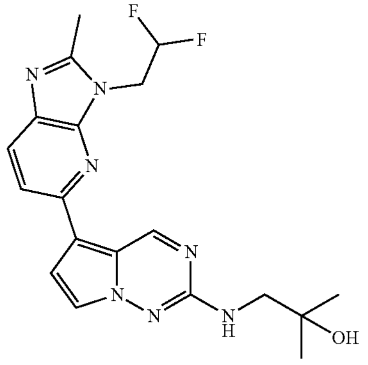

1-((5-(3-(2,2-Difluoroethyl)-2-methyl-3H-imidazo[4,5-b]pyridin-5-yl)pyrrolo[2,1-f][1,2,4]triazin-2-yl)amino)-2-methylpropan-2-ol 1833

Light yellow solid (43 mg, 0.107 mmol, 30.9% yield). $^1$H NMR (499 MHz, DMSO-$d_6$) δ ppm 1.17 (6H, s), 2.61 (3H, s), 3.24 (2H, d, J=6.02 Hz), 4.56 (1H, s), 4.84 (2H, td, J=15.95, 2.87 Hz), 6.43 (1H, t, J=6.02 Hz), 6.55 (1H, tt, J=54.60, 3.00 Hz), 7.24 (1H, d, J=2.46 Hz), 7.65 (1H, d, J=2.46 Hz), 7.73 (1H, d, J=8.49 Hz), 7.95 (1H, d, J=8.21 Hz), 9.71 (1H, s); ESIMS found for $C_{19}H_{21}F_2N_7O$ m/z 402.2 (M+1).

1834

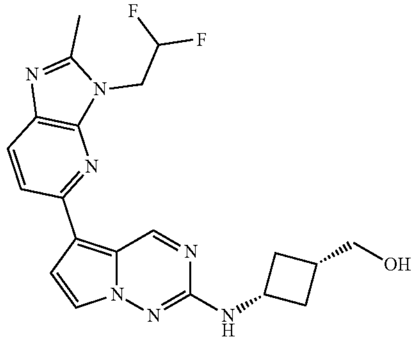

(cis-3-((5-(3-(2,2-Difluoroethyl)-2-methyl-3H-imidazo[4,5-b]pyridin-5-yl)pyrrolo[2,1-f][1,2,4]triazin-2-yl)amino)cyclobutyl)methanol 1834

Light yellow solid (50 mg, 0.121 mmol, 44.9% yield). $^1$H NMR (499 MHz, DMSO-$d_6$) δ ppm 1.66-1.76 (2H, m), 2.03-2.15 (1H, m), 2.30-2.40 (2H, m), 2.60 (3H, s), 3.38 (2H, t, J=5.61 Hz), 4.02-4.11 (1H, m), 4.48 (1H, t, J=5.34 Hz), 4.83 (2H, td, J=15.95, 2.87 Hz), 6.55 (1H, tt, J=54.60, 3.00 Hz), 7.11 (1H, d, J=7.39 Hz), 7.23 (1H, d, J=2.74 Hz), 7.63 (1H, d, J=2.46 Hz), 7.72 (1H, d, J=8.21 Hz), 7.95 (1H, d, J=8.49 Hz), 9.69 (1H, s); ESIMS found for $C_{20}H_{21}F_2N_7O$ m/z 414.2 (M+1).

1835

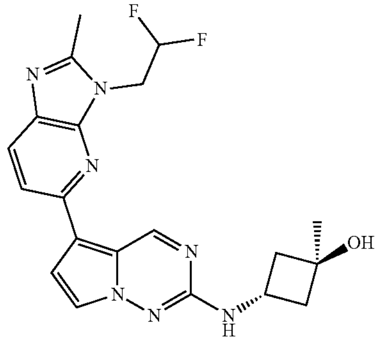

trans-3-((5-(3-(2,2-Difluoroethyl)-2-methyl-3H-imidazo[4,5-b]pyridin-5-yl)pyrrolo[2,1-f][1,2,4]triazin-2-yl)amino)-1-methylcyclobutan-1-ol 1835

Light yellow solid (40 mg, 0.097 mmol, 45.6% yield). $^1$H NMR (499 MHz, DMSO-$d_6$) δ ppm 1.29 (3H, s), 1.96-2.04 (2H, m), 2.30-2.38 (2H, m), 2.61 (3H, s), 3.07 (1H, s), 4.26 (1H, sxt, J=7.39 Hz), 4.83 (2H, td, J=15.88, 2.74 Hz), 6.55 (1H, tt, J=54.60, 3.00 Hz), 7.15 (1H, d, J=6.84 Hz), 7.23 (1H, d, J=2.74 Hz), 7.65 (1H, d, J=2.46 Hz), 7.73 (1H, d, J=8.49 Hz), 7.95 (1H, d, J=8.49 Hz), 9.69 (1H, s); ESIMS found for $C_{20}H_{21}F_2N_7O$ m/z 414.2 (M+1).

1836

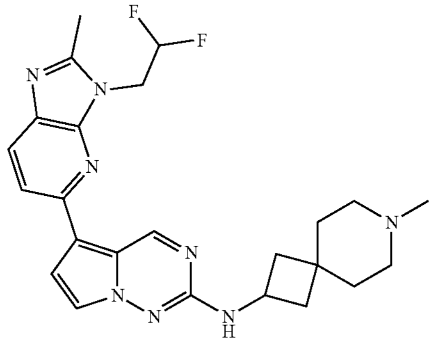

5-(3-(2,2-Difluoroethyl)-2-methyl-3H-imidazo[4,5-b]pyridin-5-yl)-N-(7-methyl-7-azaspiro[3.5]nonan-2-yl)pyrrolo[2,1-f][1,2,4]triazin-2-amine 1836

Yellow solid (44 mg, 0.086 mmol, 97.1% yield). $^1$H NMR (499 MHz, DMSO-$d_6$) δ ppm 1.54 (2H, t, J=5.48 Hz), 1.61 (2H, br t, J=5.20 Hz), 1.74 (2H, br dd, J=11.50, 8.21 Hz), 2.16 (3H, s), 2.13-2.39 (4H, m), 2.23 (2H, brt, J=9.86 Hz), 2.60 (3H, s), 4.16 (1H, dq, J=15.50, 7.79 Hz), 4.83 (2H, td, J=16.02, 2.74 Hz), 6.55 (1H, tt, J=54.60, 3.00 Hz), 7.17 (1H, d, J=7.39 Hz), 7.23 (1H, d, J=2.46 Hz), 7.65 (1H, d, J=2.46 Hz), 7.72 (1H, d, J=8.49 Hz), 7.95 (1H, d, J=8.49 Hz), 9.69 (1H, s); ESIMS found for $C_{24}H_{28}F_2N_8$ m/z 467.25 (M+1).

1837

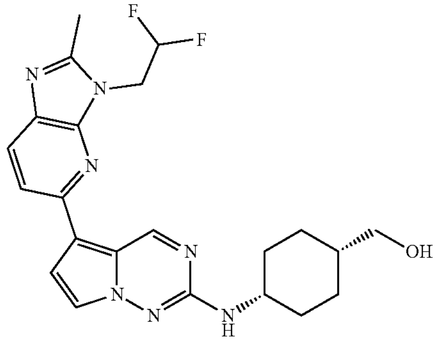

(cis-4-((5-(3-(2,2-Difluoroethyl)-2-methyl-3H-imidazo[4,5-b]pyridin-5-yl)pyrrolo[2,1-f][1,2,4]triazin-2-yl)amino)cyclohexyl)methanol 1837

Light yellow solid (226 mg, 0.512 mmol, 59.3% yield). $^1$H NMR (499 MHz, DMSO-$d_6$) δ ppm 1.43-1.55 (5H, m), 1.56-1.65 (2H, m), 1.68-1.78 (2H, m), 2.61 (3H, s), 3.29-3.33 (2H, m), 3.76-3.86 (1H, m), 4.39 (1H, t, J=5.34 Hz), 4.82 (2H, td, J=15.95, 2.87 Hz), 6.55 (1H, tt, J=54.60, 3.00 Hz), 6.68 (1H, d, J=7.39 Hz), 7.22 (1H, d, J=2.46 Hz), 7.64 (1H, d, J=2.46 Hz), 7.72 (1H, d, J=8.21 Hz), 7.95 (1H, d, J=8.21 Hz), 9.70 (1H, s); ESIMS found for $C_{22}H_{25}F_2N_7O$ m/z 442.2 (M+1).

1838

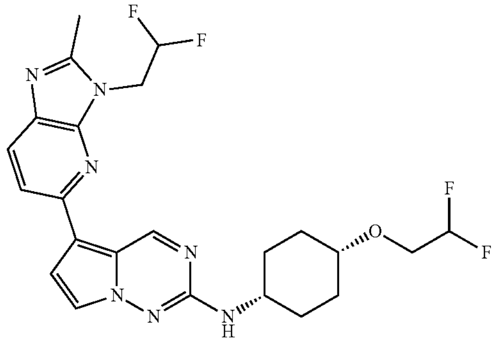

N-(cis-4-(2,2-Difluoroethoxy)cyclohexyl)-5-(3-(2,2-difluoroethyl)-2-methyl-3H-imidazo[4,5-b]pyridin-5-yl)pyrrolo[2,1-f][1,2,4]triazin-2-amine 1838

Yellow solid (20 mg, 0.041 mmol, 20.4% yield). $^1$H NMR (499 MHz, DMSO-$d_6$) δ ppm 1.51-1.60 (2H, m), 1.60-1.68 (2H, m), 1.68-1.75 (2H, m), 1.81-1.92 (2H, m), 2.61 (3H, s), 3.57-3.62 (1H, m), 3.63-3.71 (1H, m), 3.67 (2H, td, J=15.33, 3.83 Hz), 4.83 (2H, td, J=16.02, 3.01 Hz), 6.13 (1H, tt, J=55.12, 3.85 Hz), 6.55 (1H, tt, J=54.60, 3.00 Hz), 6.81 (1H, d, J=7.67 Hz), 7.22 (1H, d, J=2.19 Hz), 7.63 (1H, d, J=2.74 Hz), 7.72 (1H, d, J=8.21 Hz), 7.95 (1H, d, J=8.21 Hz), 9.70 (1H, s); ESIMS found for $C_{23}H_{25}F_4N_7O$ m/z 492.2 (M+1).

1839

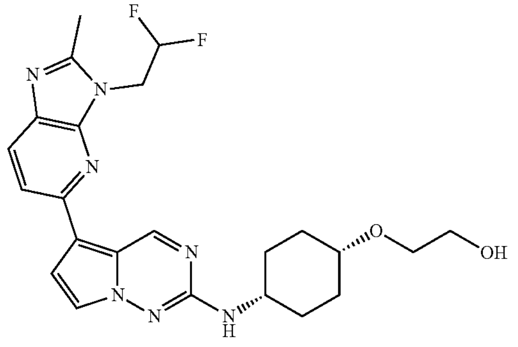

2-((cis-4-((5-(3-(2,2-difluoroethyl)-2-methyl-3H-imidazo[4,5-b]pyridin-5-yl)pyrrolo[2,1-f][1,2,4]triazin-2-yl)amino)cyclohexyl)oxy)ethan-1-ol 1839

Yellow solid (4 mg, 0.009 mmol, 4.0% yield). $^1H$ NMR (499 MHz, DMSO-$d_6$) δ ppm 1.47-1.56 (2H, m), 1.62-1.73 (4H, m), 1.80-1.88 (2H, m), 2.61 (3H, s), 3.41 (2H, t, J=5.48 Hz), 3.49 (1H, br d, J=2.74 Hz), 3.51 (2H, t, J=5.50 Hz), 3.66 (1H, td, J=8.21, 4.38 Hz), 4.52 (1H, br s), 4.77-4.91 (2H, m), 6.55 (2H, tt, J=54.60, 3.00 Hz), 6.76 (1H, d, J=7.67 Hz), 7.22 (1H, d, J=2.74 Hz), 7.63 (1H, d, J=2.74 Hz), 7.72 (1H, d, J=8.21 Hz), 7.95 (1H, d, J=8.21 Hz), 9.69 (1H, s); ESIMS found for $C_{23}H_{27}F_2N_7O_2$ m/z 472.2 (M+1).

1840

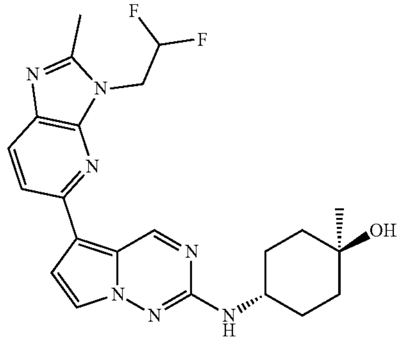

trans-4-((5-(3-(2,2-Difluoroethyl)-2-methyl-3H-imidazo[4,5-b]pyridin-5-yl)pyrrolo[2,1-f][1,2,4]triazin-2-yl)amino)-1-methylcyclohexan-1-ol 1840

Brownish orange solid (9 mg, 0.020 mmol, 6.6% yield). $^1H$ NMR (499 MHz, DMSO-$d_6$) δ ppm 1.15 (3H, s), 1.38-1.54 (4H, m), 1.57-1.66 (2H, m), 1.84-1.94 (2H, m), 2.61 (3H, s), 3.66 (1H, dt, J=7.87, 3.87 Hz), 4.23 (1H, s), 4.83 (2H, td, J=15.95, 2.87 Hz), 6.55 (2H, tt, J=54.60, 3.00 Hz), 6.71 (1H, d, J=7.94 Hz), 7.22 (1H, d, J=2.74 Hz), 7.65 (1H, d, J=2.46 Hz), 7.72 (1H, d, J=8.49 Hz), 7.95 (1H, d, J=8.49 Hz), 9.69 (1H, s); ESIMS found for $C_{22}H_{25}F_2N_7O$ m/z 442.2 (M+1).

1841

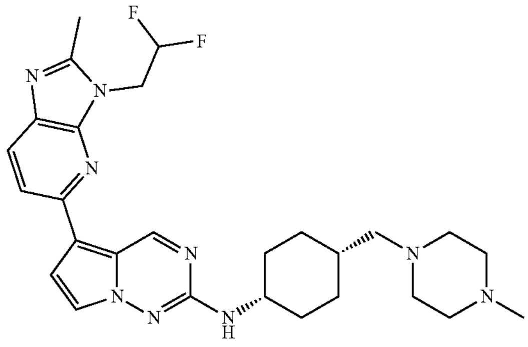

5-(3-(2,2-Difluoroethyl)-2-methyl-3H-imidazo[4,5-b]pyridin-5-yl)-N-(cis-4-((4-methylpiperazin-1-yl)methyl)cyclohexyl)pyrrolo[2,1-f][1,2,4]triazin-2-amine 1841

Light brown solid (24 mg, 0.046 mmol, 21.2% yield). $^1H$ NMR (499 MHz, DMSO-$d_6$) δ ppm 1.40-1.54 (4H, m), 1.55-1.63 (2H, m), 1.64-1.75 (3H, m), 2.14 (3H, s), 2.17 (2H, d, J=7.39 Hz), 2.19-2.44 (8H, m), 2.61 (3H, s), 3.81 (1H, br d, J=2.74 Hz), 4.82 (2H, td, J=15.88, 2.74 Hz), 6.55 (1H, tt, J=54.60, 3.00 Hz), 6.66 (1H, d, J=7.39 Hz), 7.22 (1H, d, J=2.74 Hz), 7.64 (1H, d, J=2.74 Hz), 7.72 (1H, d, J=8.49 Hz), 7.95 (1H, d, J=8.21 Hz), 9.70 (1H, s); ESIMS found for $C_{27}H_{35}F_2N_9$ m/z 524.35 (M+1).

1842

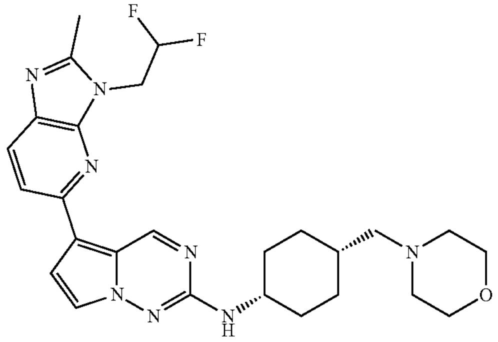

5-(3-(2,2-Difluoroethyl)-2-methyl-3H-imidazo[4,5-b]pyridin-5-yl)-N-(cis-4-(morpholinomethyl)cyclohexyl)pyrrolo[2,1-f][1,2,4]triazin-2-amine 1842

Light brown solid (38 mg, 0.074 mmol, 34.5% yield). $^1H$ NMR (499 MHz, DMSO-$d_6$) δ ppm 1.42-1.56 (4H, m), 1.56-1.65 (2H, m), 1.65-1.76 (3H, m), 2.18 (2H, br d, J=7.12 Hz), 2.32 (4H, br s), 2.61 (3H, s), 3.57 (4H, br t, J=4.24 Hz), 3.76-3.85 (1H, m), 4.83 (2H, td, J=15.81, 2.33 Hz), 6.55 (1H, tt, J=54.60, 3.00 Hz), 6.67 (1H, d, J=7.39 Hz), 7.22 (1H, d, J=2.46 Hz), 7.64 (1H, d, J=2.74 Hz), 7.72 (1H, d, J=8.49 Hz), 7.95 (1H, d, J=8.49 Hz), 9.70 (1H, s); ESIMS found for $C_{26}H_{32}F_2N_8O$ m/z 511.3 (M+1).

1843

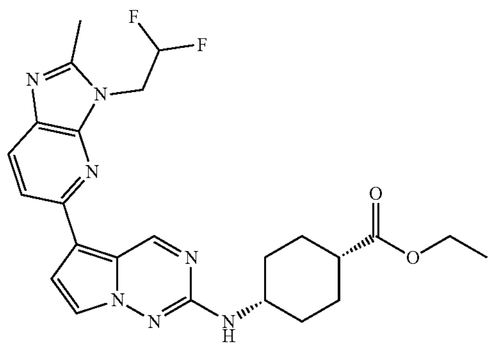

Ethyl cis-4-((5-(3-(2,2-difluoroethyl)-2-methyl-3H-imidazo[4,5-b]pyridin-5-yl)pyrrolo[2,1-f][1,2,4]triazin-2-yl)amino)cyclohexane-1-carboxylate 1843

Yellow solid (22 mg, 0.046 mmol, 8.6% yield). $^1$H NMR (499 MHz, DMSO-$d_6$) δ ppm 1.20 (3H, t, J=7.12 Hz), 1.55-1.68 (4H, m), 1.71-1.80 (2H, m), 1.92-2.04 (2H, m), 2.51-2.56 (1H, m), 2.61 (3H, s), 3.72 (1H, br s), 4.09 (2H, q, J=7.12 Hz), 4.83 (2H, td, J=15.95, 2.87 Hz), 6.55 (1H, tt, J=54.60, 3.00 Hz), 6.80 (1H, d, J=7.39 Hz), 7.22 (1H, d, J=2.74 Hz), 7.64 (1H, d, J=2.46 Hz), 7.72 (1H, d, J=8.49 Hz), 7.95 (1H, d, J=8.49 Hz), 9.70 (1H, s); ESIMS found for $C_{24}H_{27}F_2N_7O_2$ m/z 484.2 (M+1).

1844

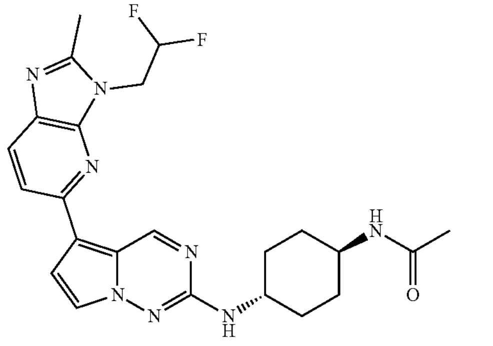

N-(trans-4-((5-(3-(2,2-Difluoroethyl)-2-methyl-3H-imidazo[4,5-b]pyridin-5-yl)pyrrolo[2,1-f][1,2,4]triazin-2-yl)amino)cyclohexyl)acetamide 1844

Yellow solid (7 mg, 0.015 mmol, 8.1% yield). $^1$H NMR (499 MHz, DMSO-$d_6$) δ ppm 1.20-1.30 (2H, m), 1.31-1.42 (2H, m), 1.79 (3H, s), 1.83 (2H, br d, J=10.95 Hz), 2.01 (2H, br d, J=11.23 Hz), 2.61 (3H, s), 3.46-3.53 (1H, m), 3.54-3.61 (1H, m), 4.83 (2H, br t, J=15.74 Hz), 6.55 (1H, tt, J=54.60, 3.00 Hz), 6.76 (1H, d, J=7.94 Hz), 7.22 (1H, d, J=2.46 Hz), 7.66 (1H, d, J=2.19 Hz), 7.70-7.77 (2H, m), 7.95 (1H, d, J=8.49 Hz), 9.69 (1H, s); ESIMS found for $C_{23}H_{26}F_2N_8O$ m/z 469.2 (M+1).

1845

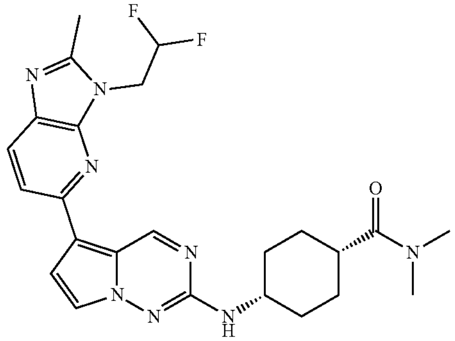

cis-4-((5-(3-(2,2-Difluoroethyl)-2-methyl-3H-imidazo[4,5-b]pyridin-5-yl)pyrrolo[2,1-f][1,2,4]triazin-2-yl)amino)-N,N-dimethylcyclohexane-1-carboxamide 1845

Yellow solid (55 mg, 0.114 mmol, 41.7% yield). $^1$H NMR (499 MHz, DMSO-$d_6$) δ ppm 1.43-1.53 (2H, m), 1.59-1.69 (2H, m), 1.72-1.86 (2H, m), 1.92-2.04 (2H, m), 2.61 (3H, s), 2.65-2.73 (1H, m), 2.81 (3H, s), 3.01 (3H, s), 3.83 (1H, br d, J=4.11 Hz), 4.75-4.91 (2H, m), 6.55 (1H, tt, J=54.60, 3.00 Hz), 6.76 (1H, d, J=6.02 Hz), 7.22 (1H, d, J=2.46 Hz), 7.64 (1H, d, J=2.46 Hz), 7.72 (1H, d, J=8.49 Hz), 7.95 (1H, d, J=8.21 Hz), 9.71 (1H, s); ESIMS found for $C_{24}H_{28}F_2N_8O$ m/z 483.3 (M+1).

1846

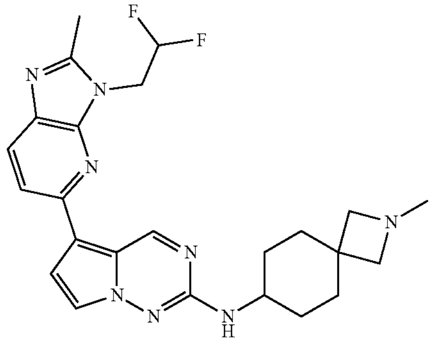

5-(3-(2,2-Difluoroethyl)-2-methyl-3H-imidazo[4,5-b]pyridin-5-yl)-N-(2-methyl-2-azaspiro[3.5]nonan-7-yl)pyrrolo[2,1-f][1,2,4]triazin-2-amine 1846

Yellow solid (35 mg, 0.075 mmol, 61.7% yield). $^1$H NMR (499 MHz, DMSO-$d_6$) δ ppm 1.23-1.36 (2H, m), 1.41-1.52 (2H, m), 1.81-1.90 (4H, m), 2.23 (3H, s), 2.60 (3H, s), 2.87 (2H, s), 2.94 (2H, s), 3.50-3.60 (1H, m), 4.83 (2H, td, J=16.02, 3.01 Hz), 6.55 (1H, tt, J=54.60, 3.00 Hz), 6.69 (1H, d, J=7.94 Hz), 7.22 (1H, d, J=2.74 Hz), 7.64 (1H, d, J=2.46 Hz), 7.72 (1H, d, J=8.49 Hz), 7.94 (1H, d, J=8.21 Hz), 9.69 (1H, s); ESIMS found for $C_{24}H_{28}F_2N_8$ m/z 467.2 (M+1).

1847

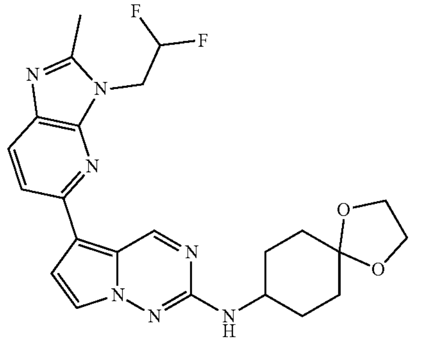

5-(3-(2,2-Difluoroethyl)-2-methyl-3H-imidazo[4,5-b]pyridin-5-yl)-N-(1,4-dioxaspiro[4.5]decan-8-yl)pyrrolo[2,1-f][1,2,4]triazin-2-amine 1847

Yellow solid (78 mg, 0.166 mmol, 48.9% yield). $^1$H NMR (499 MHz, DMSO-$d_6$) δ ppm 1.52-1.66 (4H, m), 1.69-1.77 (2H, m), 1.89-1.96 (2H, m), 2.60 (3H, s), 3.64-3.75 (1H, m), 3.83-3.90 (4H, m), 4.83 (2H, td, J=15.88, 2.74 Hz), 6.55 (1H, tt, J=54.60, 3.00 Hz), 6.84 (1H, d, J=7.94 Hz), 7.22 (1H, d, J=2.46 Hz), 7.65 (1H, d, J=2.74 Hz), 7.72 (1H, d, J=8.49 Hz), 7.95 (1H, d, J=8.21 Hz), 9.69 (1H, s); ESIMS found for $C_{23}H_{25}F_2N_7O_2$ m/z 470.25 (M+1).

1848

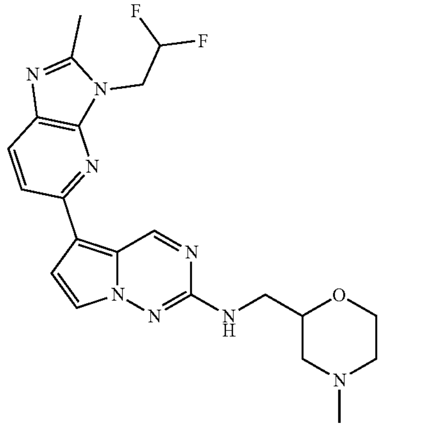

5-(3-(2,2-Difluoroethyl)-2-methyl-3H-imidazo[4,5-b]pyridin-5-yl)-N-((4-methylmorpholin-2-yl)methyl)pyrrolo[2,1-f][1,2,4]triazin-2-amine 1848

Dark yellow solid (46 mg, 0.104 mmol, 44.6% yield). $^1$H NMR (499 MHz, DMSO-$d_6$) δ ppm 1.71-1.81 (1H, m), 1.98 (1H, td, J=11.23, 3.29 Hz), 2.17 (3H, s), 2.55-2.59 (1H, m), 2.61 (3H, s), 2.77 (1H, br d, J=11.23 Hz), 3.18-3.27 (1H, m), 3.30-3.37 (1H, m), 3.50 (1H, td, J=11.16, 2.33 Hz), 3.67-3.75 (1H, m), 3.79 (1H, dt, J=9.72, 1.44 Hz), 4.84 (2H, td, J=16.08, 2.87 Hz), 6.55 (1H, tt, J=54.60, 3.00 Hz), 6.91 (1H, t, J=6.02 Hz), 7.25 (1H, d, J=2.74 Hz), 7.67 (1H, d, J=2.74 Hz), 7.73 (1H, d, J=8.49 Hz), 7.95 (1H, d, J=8.21 Hz), 9.71 (1H, s); ESIMS found for $C_{21}H_{24}F_2N_8O$ m/z 443.2 (M+1).

1849

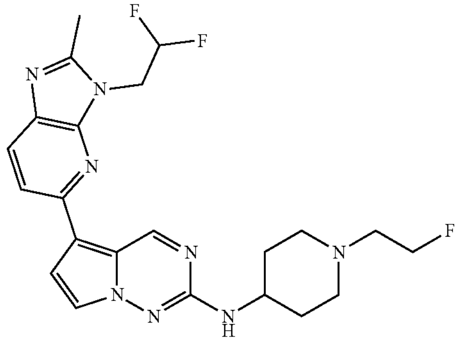

5-(3-(2,2-Difluoroethyl)-2-methyl-3H-imidazo[4,5-b]pyridin-5-yl)-N-(1-(2-fluoroethyl)piperidin-4-yl)pyrrolo[2,1-f][1,2,4]triazin-2-amine 1849

Yellow solid (2.4 mg, 0.005 mmol, 2.4% yield). $^1$H NMR (499 MHz, DMSO-$d_6$) δ ppm 1.47-1.62 (2H, m), 1.92 (2H, br d, J=10.95 Hz), 2.07-2.19 (2H, m), 2.62 (2H, dt, J=28.25, 4.90 Hz), 2.61 (3H, s), 2.89 (2H, br d, J=11.77 Hz), 3.54-3.67 (1H, m), 4.53 (2H, dt, J=48.00, 5.00 Hz), 4.83 (2H, td, J=15.95, 2.60 Hz), 6.55 (1H, tt, J=54.60, 3.00 Hz), 6.82 (1H, d, J=7.94 Hz), 7.23 (1H, d, J=2.74 Hz), 7.65 (1H, d, J=2.46 Hz), 7.73 (1H, d, J=8.21 Hz), 7.95 (1H, d, J=8.49 Hz), 9.70 (1H, s); ESIMS found for $C_{22}H_{25}F_3N_8$ m/z 459.3 (M+1).

1850

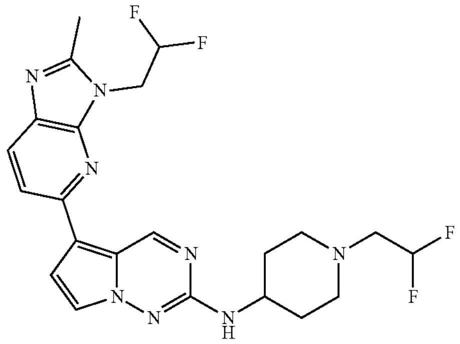

5-(3-(2,2-Difluoroethyl)-2-methyl-3H-imidazo[4,5-b]pyridin-5-yl)-N-(1-(2,2-difluoroethyl)piperidin-4-yl)pyrrolo[2,1-f][1,2,4]triazin-2-amine 1850

Yellow solid (32 mg, 0.067 mmol, 28.1% yield). $^1$H NMR (499 MHz, DMSO-$d_6$) δ ppm 1.49-1.62 (2H, m), 1.91 (2H, br d, J=10.68 Hz), 2.27 (2H, br t, J=10.13 Hz), 2.61 (3H, s), 2.68-2.81 (2H, m), 2.91 (2H, br d, J=8.76 Hz), 3.60 (1H, br d, J=4.11 Hz), 4.83 (2H, td, J=16.02, 2.74 Hz), 6.14 (1H, tt, J=55.12, 3.85 Hz), 6.55 (1H, tt, J=54.60, 3.00 Hz), 6.57-6.63 (1H, m), 6.82 (1H, br d, J=6.84 Hz), 7.23 (1H, d, J=2.46 Hz), 7.65 (1H, d, J=2.74 Hz), 7.73 (1H, d, J=8.21 Hz), 7.95 (1H, d, J=8.49 Hz), 9.70 (1H, s); ESIMS found for $C_{22}H_{24}F_4N_8$ m/z 477.2 (M+1).

1851

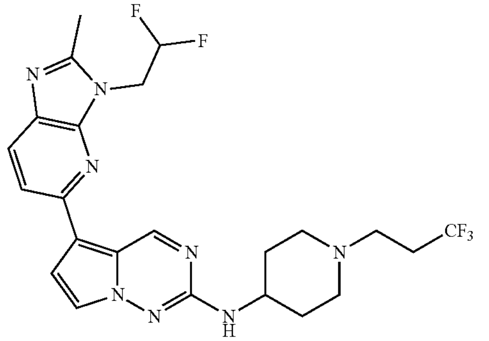

5-(3-(2,2-Difluoroethyl)-2-methyl-3H-imidazo[4,5-b]pyridin-5-yl)-N-(1-(3,3,3-trifluoropropyl)piperidin-4-yl)pyrrolo[2,1-f][1,2,4]triazin-2-amine 1851

Yellow solid (7 mg, 0.014 mmol, 10.8% yield). $^1$H NMR (499 MHz, DMSO-$d_6$) δ ppm 1.46-1.60 (2H, m), 1.87-1.97 (2H, m), 2.02-2.12 (2H, m), 2.40-2.48 (2H, m), 2.51-2.56 (2H, m), 2.61 (3H, s), 2.88 (2H, br d, J=11.50 Hz), 3.55-3.67 (1H, m), 4.83 (2H, td, J=16.02, 2.74 Hz), 6.55 (1H, tt, J=54.60, 3.00 Hz), 6.82 (1H, d, J=7.94 Hz), 7.23 (1H, d, J=2.74 Hz), 7.65 (1H, d, J=2.46 Hz), 7.72 (1H, d, J=8.49 Hz), 7.95 (1H, d, J=8.21 Hz), 9.70 (1H, s); ESIMS found for $C_{23}H_{25}F_5N_8$ m/z 509.2 (M+1).

1852

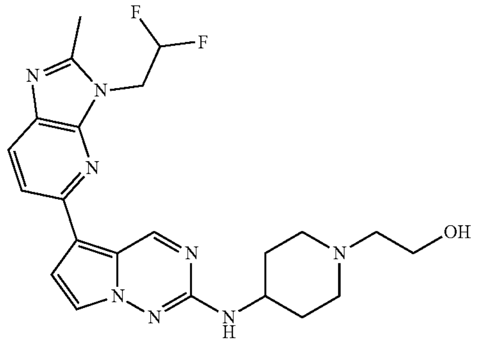

2-(4-((5-(3-(2,2-Difluoroethyl)-2-methyl-3H-imidazo[4,5-b]pyridin-5-yl)pyrrolo[2,1-f][1,2,4]triazin-2-yl)amino)piperidin-1-yl)ethan-1-ol 1852

Light brown solid (13 mg, 0.029 mmol, 12.9% yield). $^1$H NMR (499 MHz, DMSO-$d_6$) δ ppm 1.47-1.61 (2H, m), 1.91 (2H, br d, J=10.95 Hz), 2.08 (2H, br s), 2.33-2.44 (2H, m), 2.61 (3H, s), 2.88 (2H, br d, J=10.68 Hz), 3.44-3.53 (2H, m), 3.54-3.66 (1H, m), 4.38 (1H, br s), 4.83 (2H, td, J=15.95, 2.87 Hz), 6.55 (1H, tt, J=54.60, 3.00 Hz), 6.81 (1H, br d, J=7.94 Hz), 7.23 (1H, d, J=2.74 Hz), 7.65 (1H, d, J=2.74 Hz), 7.72 (1H, d, J=8.49 Hz), 7.95 (1H, d, J=8.21 Hz), 9.69 (1H, s); ESIMS found for $C_{22}H_{26}F_2N_8O$ m/z 457.2 (M+1).

1853

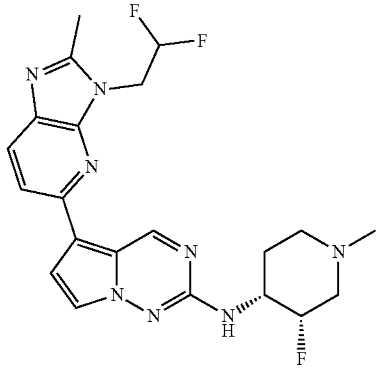

5-(3-(2,2-Difluoroethyl)-2-methyl-3H-imidazo[4,5-b]pyridin-5-yl)-N-((3S,4R)-3-fluoro-1-methylpiperidin-4-yl)pyrrolo[2,1-f][1,2,4]triazin-2-amine 1853

Yellow solid (2 mg, 0.005 mmol, 3.7% yield). $^1$H NMR (499 MHz, DMSO-$d_6$) δ ppm 1.68-1.75 (1H, m), 1.93 (1H, qd, J=12.14, 3.56 Hz), 2.03-2.10 (1H, m), 2.12-2.25 (1H, m), 2.19 (3H, s), 2.61 (3H, s), 2.81 (1H, brd, J=12.32 Hz), 3.01-3.10 (1H, m), 3.70-3.87 (1H, m), 4.79-4.97 (2H, m), 4.84 (1H, br d, J=3.01 Hz), 6.55 (1H, tt, J=54.60, 3.00 Hz), 6.86 (1H, d, J=7.94 Hz), 7.26 (1H, d, J=2.74 Hz), 7.66 (1H, d, J=2.74 Hz), 7.74 (1H, d, J=8.49 Hz), 7.95 (1H, d, J=8.49 Hz), 9.73 (1H, s); ESIMS found for $C_{21}H_{23}F_3N_8$ m/z 445.2 (M+1).

1854

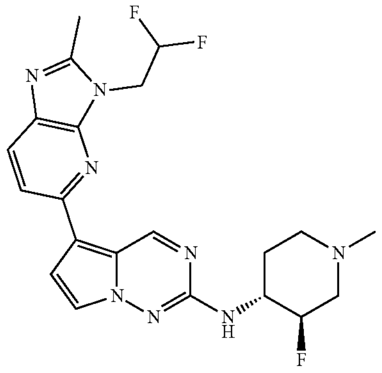

5-(3-(2,2-Difluoroethyl)-2-methyl-3H-imidazo[4,5-b]pyridin-5-yl)-N-((3R,4R)-3-fluoro-1-methylpiperidin-4-yl)pyrrolo[2,1-f][1,2,4]triazin-2-amine 1854

Yellow solid (2.5 mg, 0.006 mmol, 4.6% yield). $^1$H NMR (499 MHz, DMSO-$d_6$) δ ppm 1.48-1.62 (1H, m), 1.94-2.05 (2H, m), 2.08 (1H, dt, J=9.92, 5.03 Hz), 2.24 (3H, s), 2.61 (3H, s), 2.71 (1H, brd, J=11.22 Hz), 3.05-3.12 (1H, m), 3.77-3.92 (1H, m), 4.59 (1H, dtd, J=49.90, 9.24, 9.24, 4.52 Hz), 4.84 (2H, td, J=16.02, 2.74 Hz), 6.55 (1H, tt, J=54.60, 3.00 Hz), 7.04 (1H, d, J=8.76 Hz), 7.25 (1H, d, J=2.46 Hz), 7.67 (1H, d, J=2.74 Hz), 7.74 (1H, d, J=8.49 Hz), 7.95 (1H, d, J=8.49 Hz), 9.71 (1H, s); ESIMS found for $C_{21}H_{23}F_3N_8$ m/z 445.2 (M+1).

1855

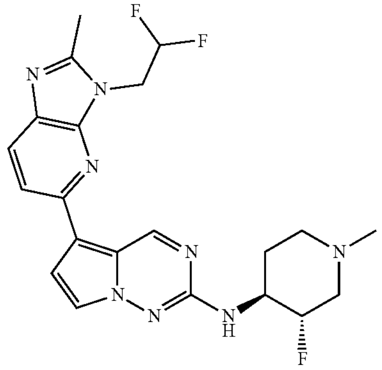

5-(3-(2,2-Difluoroethyl)-2-methyl-3H-imidazo[4,5-b]pyridin-5-yl)-N-((3S,4S)-3-fluoro-1-methylpiperidin-4-yl)pyrrolo[2,1-f][1,2,4]triazin-2-amine 1855

Yellow solid (4 mg, 0.009 mmol, 7.4% yield). $^1$H NMR (499 MHz, DMSO-d$_6$) δ ppm 1.49-1.62 (1H, m), 1.94-2.05 (2H, m), 2.05-2.12 (1H, m), 2.24 (3H, s), 2.61 (3H, s), 2.71 (1H, br d, J=11.22 Hz), 3.06-3.11 (1H, m), 3.78-3.91 (1H, m), 4.59 (1H, dtd, J=49.65, 9.31, 9.31, 4.65 Hz), 4.84 (2H, td, J=16.02, 2.74 Hz), 6.55 (1H, tt, J=54.60, 3.00 Hz), 7.03 (1H, d, J=8.49 Hz), 7.25 (1H, d, J=2.74 Hz), 7.67 (1H, d, J=2.46 Hz), 7.73 (1H, d, J=8.21 Hz), 7.95 (1H, d, J=8.21 Hz), 9.71 (1H, s); ESIMS found for $C_{21}H_{23}F_3N_8$ m/z 445.2 (M+1).

1856

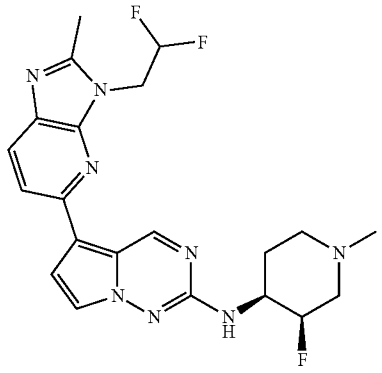

5-(3-(2,2-Difluoroethyl)-2-methyl-3H-imidazo[4,5-b]pyridin-5-yl)-N-((3R,4S)-3-fluoro-1-methylpiperidin-4-yl)pyrrolo[2,1-f][1,2,4]triazin-2-amine 1856

Yellow solid (4 mg, 0.009 mmol, 8.4% yield). $^1$H NMR (499 MHz, DMSO-d$_6$) δ ppm 1.67-1.78 (1H, m), 1.93 (1H, qd, J=12.18, 3.70 Hz), 2.04-2.12 (1H, m), 2.13-2.26 (1H, m), 2.20 (3H, s), 2.61 (3H, s), 2.81 (1H, brd,J=11.23 Hz), 3.01-3.12 (1H, m), 3.71-3.89 (1H, m), 4.80-4.97 (2H, m), 4.84 (1H, d, J=3.01 Hz), 6.55 (1H, tt, J=54.60, 3.00 Hz), 6.86 (1H, d, J=7.94 Hz), 7.26 (1H, d, J=2.74 Hz), 7.66 (1H, d, J=2.46 Hz), 7.74 (1H, d, J=8.49 Hz), 7.96 (1H, d, J=8.21 Hz), 9.73 (1H, s); ESIMS found for $C_{21}H_{23}F_3N_8$ m/z 445.2 (M+1).

1857

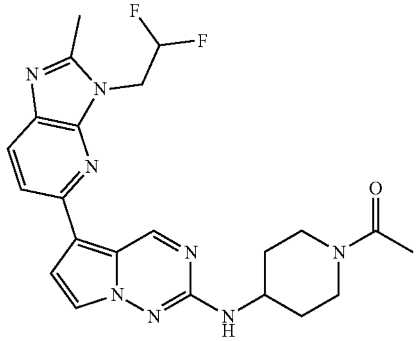

1-(4-((5-(3-(2,2-Difluoroethyl)-2-methyl-3H-imidazo[4,5-b]pyridin-5-yl)pyrrolo[2,1-f][1,2,4]triazin-2-yl)amino)piperidin-1-yl)ethan-1-one 1857

Yellow solid (5 mg, 0.011 mmol, 3.7% yield). $^1$H NMR (499 MHz, DMSO-d$_6$) δ ppm 1.30-1.40 (1H, m), 1.41-1.52 (1H, m), 1.89-1.96 (1H, m), 1.99 (1H, br d, J=12.87 Hz), 2.02 (3H, s), 2.61 (3H, s), 2.73-2.84 (1H, m), 3.12-3.23 (1H, m), 3.79-3.84 (1H, m), 3.84-3.90 (1H, m), 4.28 (1H, br d, J=13.96 Hz), 4.83 (2H, td, J=16.02, 3.01 Hz), 6.55 (2H, tt, J=54.60, 3.00 Hz), 6.91 (1H, d, J=7.94 Hz), 7.24 (1H, d, J=2.74 Hz), 7.66 (1H, d, J=2.74 Hz), 7.73 (1H, d, J=8.49 Hz), 7.95 (1H, d, J=8.21 Hz), 9.71 (1H, s); ESIMS found for $C_{22}H_{24}F_2N_8O$ m/z 455.2 (M+1).

1858

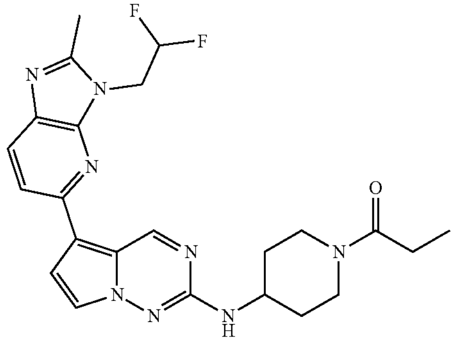

1-(4-((5-(3-(2,2-Difluoroethyl)-2-methyl-3H-imidazo[4,5-b]pyridin-5-yl)pyrrolo[2,1-f][1,2,4]triazin-2-yl)amino)piperidin-1-yl)propan-1-one 1858

Light orange solid (5 mg, 0.011 mmol, 37.2% yield). $^1$H NMR (499 MHz, DMSO-d$_6$) δ ppm 1.00 (3H, t, J=7.39 Hz), 1.30-1.39 (1H, m), 1.39-1.49 (1H, m), 1.88-2.03 (2H, m), 2.33 (2H, q, J=7.39 Hz), 2.61 (3H, s), 2.77 (1H, br t, J=11.23 Hz), 3.14 (1H, br t, J=11.64 Hz), 3.81-3.91 (2H, m), 4.30 (1H, br d, J=12.59 Hz), 4.83 (2H, td, J=15.95, 2.87 Hz), 6.55 (1H, tt, J=54.60, 3.00 Hz), 6.90 (1H, d, J=7.94 Hz), 7.24 (1H, d, J=2.74 Hz), 7.66 (1H, d, J=2.74 Hz), 7.73 (1H, d, J=8.21 Hz), 7.95 (1H, d, J=8.49 Hz), 9.71 (1H, s); ESIMS found for $C_{23}H_{26}F_2N_8O$ m/z 469.2 (M+1).

1859

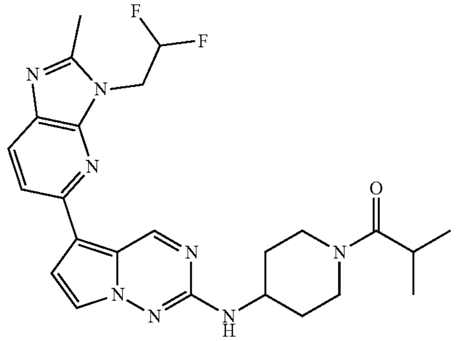

1-(4-((5-(3-(2,2-Difluoroethyl)-2-methyl-3H-imidazo[4,5-b]pyridin-5-yl)pyrrolo[2,1-f][1,2,4]triazin-2-yl)amino)piperidin-1-yl)-2-methylpropan-1-one 1859

Yellow solid (5 mg, 0.010 mmol, 5.1% yield). $^1$H NMR (499 MHz, DMSO-$d_6$) δ ppm 0.98-1.04 (6H, m), 1.28-1.39 (1H, m), 1.40-1.50 (1H, m), 1.94 (1H, br d, J=10.95 Hz), 2.01 (1H, br d, J=11.50 Hz), 2.61 (3H, s), 2.72-2.80 (1H, m), 2.87-2.94 (1H, m), 3.18 (1H, br t, J=11.64 Hz), 3.81-3.90 (1H, m), 3.95 (1H, br d, J=13.96 Hz), 4.28-4.39 (1H, m), 4.83 (2H, td, J=15.95, 2.60 Hz), 6.55 (2H, tt, J=54.60, 3.00 Hz), 6.89 (1H, d, J=7.94 Hz), 7.24 (1H, d, J=2.74 Hz), 7.66 (1H, d, J=2.74 Hz), 7.73 (1H, d, J=8.21 Hz), 7.95 (1H, d, J=8.21 Hz), 9.71 (1H, s); ESIMS found for $C_{24}H_{28}F_2N_8O$ m/z 483.2 (M+1).

1860

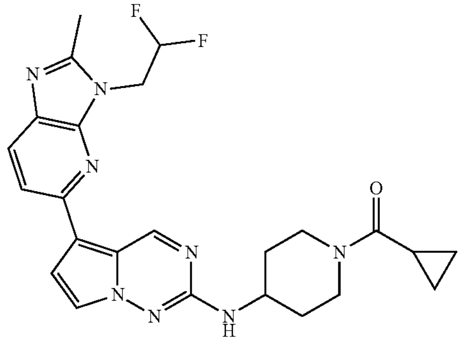

Cyclopropyl(4-((5-(3-(2,2-difluoroethyl)-2-methyl-3H-imidazo[4,5-b]pyridin-5-yl)pyrrolo[2,1-f][1,2,4]triazin-2-yl)amino)piperidin-1-yl)methanone 1860

Yellow solid (19 mg, 0.040 mmol, 14.4% yield). $^1$H NMR (499 MHz, DMSO-$d_6$) δ ppm 0.65-0.78 (4H, m), 1.30-1.41 (1H, m), 1.43-1.54 (1H, m), 1.90-1.97 (1H, m), 1.97-2.07 (2H, m), 2.61 (3H, s), 2.75-2.86 (1H, m), 3.21-3.29 (1H, m), 3.84-3.97 (1H, m), 4.18-4.34 (2H, m), 4.83 (2H, td, J=15.95, 3.15 Hz), 6.55 (1H, tt, J=54.60, 3.00 Hz), 6.91 (1H, d, J=7.94 Hz), 7.24 (1H, d, J=2.74 Hz), 7.67 (1H, d, J=2.46 Hz), 7.73 (1H, d, J=8.21 Hz), 7.95 (1H, d, J=8.21 Hz), 9.71 (1H, s); ESIMS found for $C_{24}H_{26}F_2N_8O$ m/z 481.2 (M+1).

1861

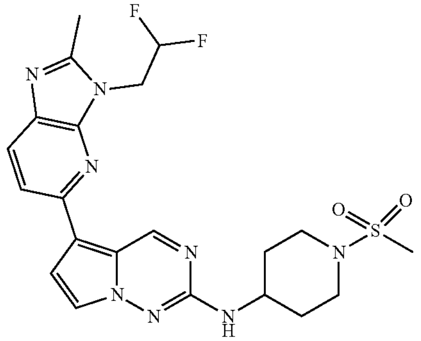

5-(3-(2,2-Difluoroethyl)-2-methyl-3H-imidazo[4,5-b]pyridin-5-yl)-N-(1-(methylsulfonyl)piperidin-4-yl)pyrrolo[2,1-f][1,2,4]triazin-2-amine 1861

Off-white solid (58 mg, 0.118 mmol, 55.3% yield). $^1$H NMR (499 MHz, DMSO-$d_6$) δ ppm 1.53-1.67 (2H, m), 1.98-2.09 (2H, m), 2.61 (3H, s), 2.87-2.94 (2H, m), 2.89 (3H, s), 3.51-3.59 (2H, m), 3.72-3.83 (1H, m), 4.83 (2H, td, J=16.08, 2.87 Hz), 6.55 (2H, tt, J=54.60, 3.00 Hz), 6.97 (1H, d, J=7.94 Hz), 7.25 (1H, d, J=2.46 Hz), 7.65 (1H, d, J=2.74 Hz), 7.74 (1H, d, J=8.21 Hz), 7.95 (1H, d, J=8.21 Hz), 9.72 (1H, s); ESIMS found for $C_{21}H_{24}F_2N_8O_2S$ m/z 491.2 (M+1).

1862

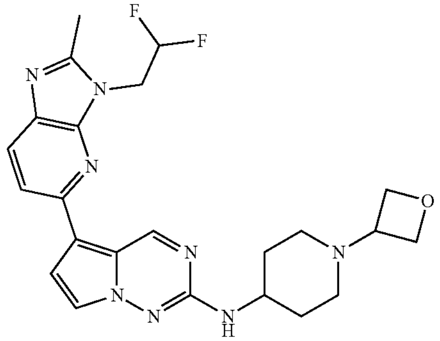

5-(3-(2,2-Difluoroethyl)-2-methyl-3H-imidazo[4,5-b]pyridin-5-yl)-N-(1-(oxetan-3-yl)piperidin-4-yl)pyrrolo[2,1-f][1,2,4]triazin-2-amine 1862

Yellow solid (31 mg, 0.066 mmol, 28.8% yield). $^1$H NMR (499 MHz, DMSO-$d_6$) δ ppm 1.49-1.62 (2H, m), 1.88 (2H, br t, J=11.64 Hz), 1.93 (2H, br d, J=12.32 Hz), 2.61 (3H, s), 2.69 (2H, br d, J=11.22 Hz), 3.39 (1H, quin, J=6.43 Hz), 3.55-3.68 (1H, m), 4.42 (2H, t, J=6.02 Hz), 4.53 (2H, t, J=6.57 Hz), 4.83 (2H, td, J=15.95, 2.87 Hz), 6.55 (1H, tt, J=54.60, 3.00 Hz), 6.85 (1H, d, J=7.94 Hz), 7.23 (1H, d, J=2.74 Hz), 7.65 (1H, d, J=2.46 Hz), 7.72 (1H, d, J=8.49 Hz), 7.95 (1H, d, J=8.49 Hz), 9.70 (1H, s); ESIMS found for $C_{23}H_{26}F_2N_8O$ m/z 469.25 (M+1).

1863

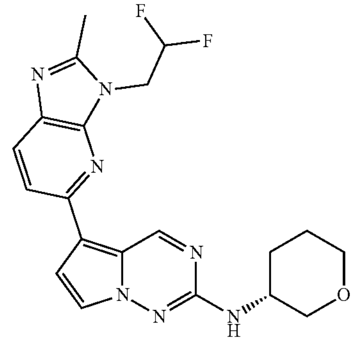

(R)-5-(3-(2,2-Difluoroethyl)-2-methyl-3H-imidazo[4,5-b]pyridin-5-yl)-N-(tetrahydro-2H-pyran-3-yl)pyrrolo[2,1-f][1,2,4]triazin-2-amine 1863

Off-white solid (48 mg, 0.116 mmol, 53.1% yield). $^1$H NMR (499 MHz, DMSO-$d_6$) δ ppm 1.50-1.65 (2H, m), 1.67-1.78 (1H, m), 1.95-2.05 (1H, m), 2.61 (3H, s), 3.14 (1H, dd, J=10.40, 9.31 Hz), 3.27-3.32 (1H, m), 3.72-3.83 (2H, m), 3.90-4.01 (1H, m), 4.83 (2H, td, J=16.08, 2.87 Hz), 6.55 (1H, tt, J=54.60, 3.00 Hz), 6.81 (1H, d, J=7.94 Hz), 7.25 (1H, d, J=2.74 Hz), 7.68 (1H, d, J=2.46 Hz), 7.73 (1H, d, J=8.49 Hz), 7.95 (1H, d, J=8.49 Hz), 9.71 (1H, s); ESIMS found for $C_{20}H_{21}F_2N_7O$ m/z 414.2 (M+1).

1864

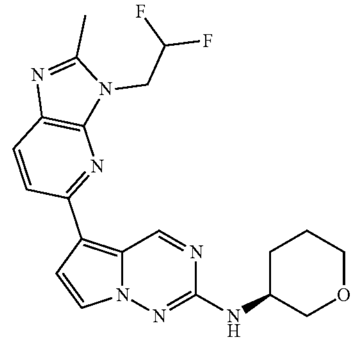

(S)-5-(3-(2,2-Difluoroethyl)-2-methyl-3H-imidazo[4,5-b]pyridin-5-yl)-N-(tetrahydro-2H-pyran-3-yl)pyrrolo[2,1-f][1,2,4]triazin-2-amine 1864

Off-white solid (59 mg, 0.143 mmol, 77.1% yield). $^1$H NMR (499 MHz, DMSO-$d_6$) δ ppm 1.50-1.64 (2H, m), 1.68-1.77 (1H, m), 1.96-2.05 (1H, m), 2.61 (3H, s), 3.14 (1H, dd, J=10.68, 9.31 Hz), 3.27-3.32 (1H, m), 3.71-3.82 (2H, m), 3.90-3.99 (1H, m), 4.83 (2H, td, J=16.02, 3.01 Hz), 6.55 (1H, tt, J=54.60, 3.00 Hz), 6.81 (1H, d, J=7.94 Hz), 7.25 (1H, d, J=2.74 Hz), 7.67 (1H, d, J=2.46 Hz), 7.73 (1H, d, J=8.49 Hz), 7.95 (1H, d, J=8.21 Hz), 9.71 (1H, s); ESIMS found for $C_{20}H_{21}F_2N_7O$ m/z 414.2 (M+1).

1865

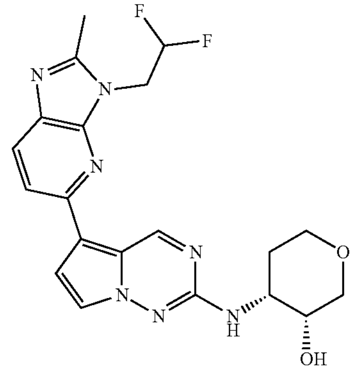

(3R,4R)-4-((5-(3-(2,2-Difluoroethyl)-2-methyl-3H-imidazo[4,5-b]pyridin-5-yl)pyrrolo[2,1-f][1,2,4]triazin-2-yl)amino)tetrahydro-2H-pyran-3-ol 1865

Yellow solid (116 mg, 0.270 mmol, 84.6% yield). $^1$H NMR (499 MHz, DMSO-$d_6$) δ ppm 1.67 (1H, br dd, J=13.28, 3.15 Hz), 1.84-2.00 (1H, m), 2.61 (3H, s), 3.42 (1H, td, J=11.36, 2.19 Hz), 3.49 (1H, dd, J=11.77, 1.37 Hz), 3.76 (1H, dd, J=11.77, 3.01 Hz), 3.79-3.85 (2H, m), 3.89 (1H, ddt, J=11.05, 7.43, 3.90, 3.90 Hz), 4.84 (2H, td, J=15.95, 2.87 Hz), 4.95 (1H, d, J=4.93 Hz), 6.20 (1H, d, J=7.94 Hz), 6.55 (1H, tt, J=54.60, 3.00 Hz), 7.25 (1H, d, J=2.74 Hz), 7.67 (1H, d, J=2.46 Hz), 7.73 (1H, d, J=8.21 Hz), 7.95 (1H, d, J=8.21 Hz), 9.73 (1H, s); ESIMS found for $C_{20}H_{21}F_2N_7O_2$ m/z 430.2 (M+1).

1866

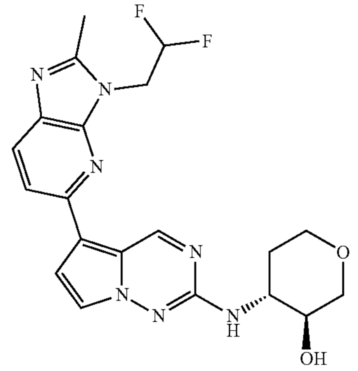

(3S,4R)-4-((5-(3-(2,2-Difluoroethyl)-2-methyl-3H-imidazo[4,5-b]pyridin-5-yl)pyrrolo[2,1-f][1,2,4]triazin-2-yl)amino)tetrahydro-2H-pyran-3-ol 1866

Yellow solid (70 mg, 0.163 mmol, 78.5% yield). $^1$H NMR (499 MHz, DMSO-$d_6$) δ ppm 1.44-1.58 (1H, m), 1.98-2.09 (1H, m), 2.61 (3H, s), 3.07 (1H, dd, J=10.95, 9.86 Hz), 3.34-3.39 (1H, m), 3.45-3.58 (1H, m), 3.64-3.75 (1H, m), 3.78-3.88 (2H, m), 4.84 (2H, td, J=16.08, 2.87 Hz), 4.96 (1H, d, J=5.48 Hz), 6.55 (1H, tt, J=54.60, 3.00 Hz), 6.76 (1H, d, J=7.94 Hz), 7.23 (1H, d, J=2.74 Hz), 7.65 (1H, d, J=2.74 Hz), 7.73 (1H, d, J=8.49 Hz), 7.95 (1H, d, J=8.21 Hz), 9.71 (1H, s); ESIMS found for $C_{20}H_{21}F_2N_7O_2$ m/z 430.2 (M+1).

1867

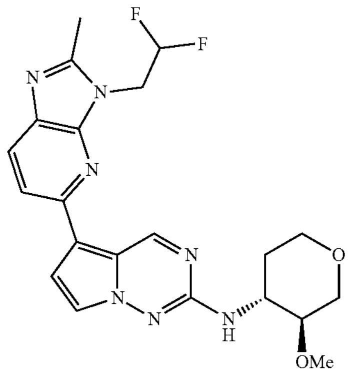

5-(3-(2,2-Difluoroethyl)-2-methyl-3H-imidazo[4,5-b]pyridin-5-yl)-N-((3S,4R)-3-methoxytetrahydro-2H-pyran-4-yl)pyrrolo[2,1-f][1,2,4]triazin-2-amine 1867

Off-white solid (69 mg, 0.156 mmol, 75.0% yield). $^1$H NMR (499 MHz, DMSO-$d_6$) δ ppm 1.47-1.61 (1H, m), 1.96-2.06 (1H, m), 2.61 (3H, s), 3.11 (1H, dd, J=11.23, 9.03 Hz), 3.28 (1H, td, J=8.90, 4.38 Hz), 3.34 (3H, s), 3.38 (1H, td, J=11.29, 2.33 Hz), 3.78-3.91 (2H, m), 4.03 (1H, dd, J=11.23, 4.38 Hz), 4.84 (2H, td, J=16.02, 3.01 Hz), 6.55 (1H, tt, J=54.60, 3.00 Hz), 6.99 (1H, d, J=8.21 Hz), 7.24 (1H, d, J=2.74 Hz), 7.65 (1H, d, J=2.74 Hz), 7.73 (1H, d, J=8.21 Hz), 7.95 (1H, d, J=8.21 Hz), 9.71 (1H, s); ESIMS found for $C_{21}H_{23}F_2N_7O_2$ m/z 444.2 (M+1).

1868

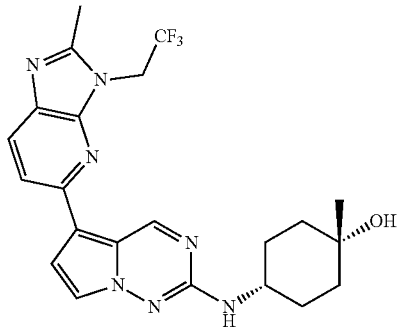

cis-1-Methyl-4-((5-(2-methyl-3-(2,2,2-trifluoroethyl)-3H-imidazo[4,5-b]pyridin-5-yl)pyrrolo[2,1-f][1,2,4]triazin-2-yl)amino)cyclohexan-1-ol 1868

Yellow solid (12.1 mg, 0.026 mmol, 13.7% yield). $^1$H NMR (499 MHz, DMSO-$d_6$) δ ppm 1.13 (3H, s), 1.32-1.42 (2H, m), 1.59 (2H, br d, J=12.59 Hz), 1.63-1.77 (4H, m), 2.63 (3H, s), 3.48-3.61 (1H, m), 4.02 (1H, s), 5.30-5.39 (2H, m), 6.75 (1H, brd, J=7.67 Hz), 7.23 (1H, br s), 7.63 (1H, br s), 7.76 (1H, br d, J=8.21 Hz), 7.97 (1H, br d, J=8.21 Hz), 9.71 (1H, s); ESIMS found for $C_{22}H_{24}F_3N_7O$ m/z 460.2 (M+1).

1869

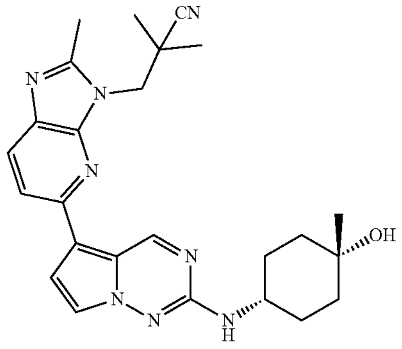

3-(5-(2-((cis-4-Hydroxy-4-methylcyclohexyl)amino)pyrrolo[2,1-f][1,2,4]triazin-5-yl)-2-methyl-3H-imidazo[4,5-b]pyridin-3-yl)-2,2-dimethylpropanenitrile 1869

Yellow solid (17.2 mg, 0.038 mmol, 15.8% yield). $^1$H NMR (499 MHz, DMSO-$d_6$) δ ppm 1.13 (3H, s), 1.37 (2H, td, J=13.07, 4.24 Hz), 1.50 (6H, s), 1.58 (2H, br d, J=12.05 Hz), 1.61-1.69 (2H, m), 1.69-1.75 (2H, m), 2.69 (3H, s), 3.46-3.59 (1H, m), 4.02 (1H, br s), 4.57 (2H, s), 6.78 (1H, d, J=7.94 Hz), 7.22 (1H, d, J=2.74 Hz), 7.63 (1H, d, J=2.74 Hz), 7.74 (1H, d, J=8.21 Hz), 7.94 (1H, d, J=8.21 Hz), 9.79 (1H, s); ESIMS found for $C_{25}H_{30}N_8O$ m/z 459.3 (M+1).

1870

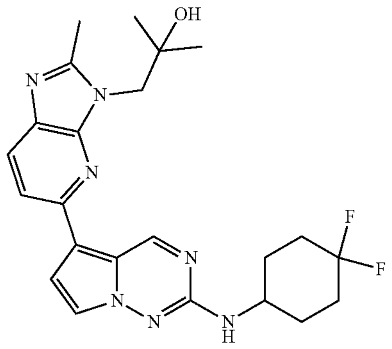

1-(5-(2-((4,4-Difluorocyclohexyl)amino)pyrrolo[2,1-f][1,2,4]triazin-5-yl)-2-methyl-3H-imidazo[4,5-b]pyridin-3-yl)-2-methylpropan-2-ol 1870

Yellow solid (12.2 mg, 0.027 mmol, 13.7% yield). $^1$H NMR (499 MHz, DMSO-$d_6$) δ ppm 1.19 (6H, s), 1.57-1.71 (2H, m), 1.87-2.03 (4H, m), 2.04-2.16 (2H, m), 2.64 (3H, s), 3.74-3.88 (1H, m), 4.23 (2H, s), 4.86 (1H, br s), 7.00 (1H, d, J=7.67 Hz), 7.23 (1H, d, J=2.19 Hz), 7.65 (1H, d, J=2.74 Hz), 7.69 (1H, d, J=8.76 Hz), 7.90 (1H, d, J=8.21 Hz), 9.77 (1H, s); ESIMS found for $C_{23}H_{27}F_2N_7O$ m/z 456.3 (M+1).

1871

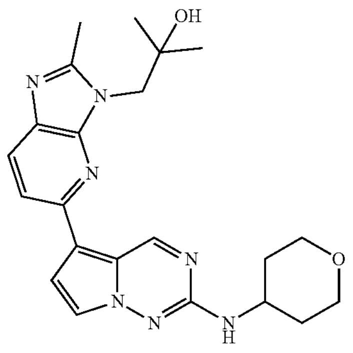

2-Methyl-1-(2-methyl-5-(2-((tetrahydro-2H-pyran-4-yl)amino)pyrrolo[2,1-f][1,2,4]triazin-5-yl)-3H-imidazo[4,5-b]pyridin-3-yl)propan-2-ol 1871

Yellow solid (15.9 mg, 0.038 mmol, 17.3% yield). $^1$H NMR (499 MHz, DMSO-$d_6$) δ ppm 1.19 (6H, s), 1.46-1.60 (2H, m), 1.91 (2H, br dd, J=12.59, 2.19 Hz), 2.64 (3H, s), 3.41 (2H, td, J=11.50, 2.19 Hz), 3.72-3.85 (1H, m), 3.85-3.94 (2H, m), 4.23 (2H, s), 4.86 (1H, s), 6.95 (1H, d, J=8.21 Hz), 7.22 (1H, d, J=2.74 Hz), 7.65 (1H, d, J=2.19 Hz), 7.68 (1 H, d, J=8.21 Hz), 7.89 (1H, d, J=8.21 Hz), 9.76 (1H, s); ESIMS found for $C_{22}H_{27}N_7O_2$ m/z 422.2 (M+1).

1872

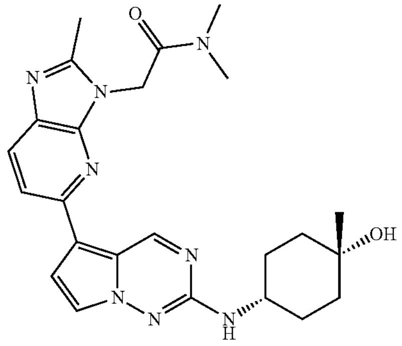

2-(5-(2-((cis-4-Hydroxy-4-methylcyclohexyl)amino)pyrrolo[2,1-f][1,2,4]triazin-5-yl)-2-methyl-3H-imidazo[4,5-b]pyridin-3-yl)-N,N-dimethylacetamide 1872

Yellow solid (23.9 mg, 0.052 mmol, 25.5% yield). $^1$H NMR (499 MHz, DMSO-$d_6$) δ ppm 1.13 (3H, s), 1.37 (2H, td, J=13.07, 4.24 Hz), 1.58 (2H, br d, J=12.32 Hz), 1.62-1.69 (2H, m), 1.69-1.75 (2H, m), 2.47 (3H, s), 2.89 (3H, s), 3.23 (3H, s), 3.46-3.58 (1H, m), 4.01 (1H, s), 5.27 (2H, s), 6.77 (1H, d, J=7.94 Hz), 7.18 (1H, d, J=2.74 Hz), 7.61 (1H, d, J=2.46 Hz), 7.67 (1H, d, J=8.49 Hz), 7.91 (1H, d, J=8.21 Hz), 9.59 (1H, s); ESIMS found for $C_{24}H_{30}N_8O_2$ m/z 463.3 (M+1).

1873

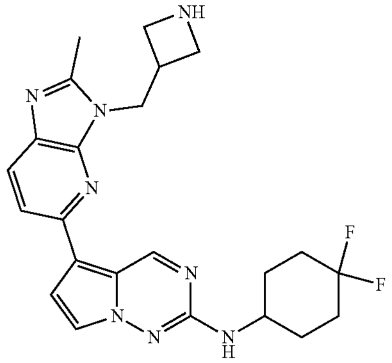

5-(3-(Azetidin-3-ylmethyl)-2-methyl-3H-imidazo[4,5-b]pyridin-5-yl)-N-(4,4-difluorocyclohexyl)pyrrolo[2,1-f][1,2,4]triazin-2-amine 1873

Yellow solid (18.0 mg, 0.040 mmol, 34.3% yield). $^1$H NMR (499 MHz, DMSO-$d_6$) δ ppm 1.57-1.71 (2H, m), 1.86-2.03 (4H, m), 2.05-2.16 (2H, m), 2.59 (3H, s), 3.07-3.19 (2H, m), 3.36-3.46 (1H, m), 3.49 (2H, brt, J=7.39 Hz), 3.78-3.90 (1H, m), 4.54 (2H, br d, J=7.39 Hz), 7.01 (1H, d, J=7.67 Hz), 7.24 (1H, d, J=2.46 Hz), 7.66 (1H, d, J=2.74 Hz), 7.70 (1H, d, J=8.21 Hz), 7.90 (1H, d, J=8.49 Hz), 9.79 (1H, s); ESIMS found for $C_{23}H_{26}F_2N_8$ m/z 453.2 (M+1).

1875

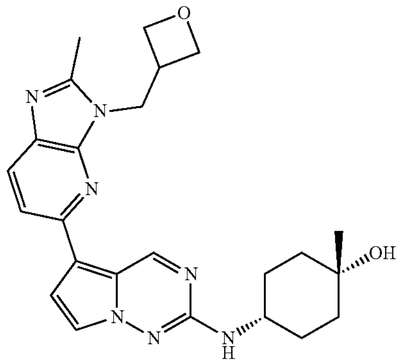

cis-1-Methyl-4-((5-(2-methyl-3-(oxetan-3-ylmethyl)-3H-imidazo[4,5-b]pyridin-5-yl)pyrrolo[2,1-f][1,2,4]triazin-2-yl)amino)cyclohexan-1-ol 1875

Off-white solid (19.9 mg, 0.045 mmol, 19.8% yield). $^1$H NMR (499 MHz, DMSO-$d_6$) δ ppm 1.13 (3H, s), 1.37 (2H, td, J=13.00, 4.38 Hz), 1.59 (2H, br d, J=12.05 Hz), 1.62-1.69 (2H, m), 1.70-1.75 (2H, m), 2.59 (3H, s), 3.47-3.60 (2H, m), 4.02 (1H, br s), 4.53 (2H, t, J=5.89 Hz), 4.62-4.67 (4H, m), 6.78 (1H, d, J=7.94 Hz), 7.21 (1H, d, J=2.74 Hz), 7.63 (1H, d, J=2.46 Hz), 7.69 (1H, d, J=8.49 Hz), 7.90 (1H, d, J=8.21 Hz), 9.74 (1H, s); ESIMS found for $C_{24}H_{29}N_7O_2$ m/z 448.3 (M+1).

1876

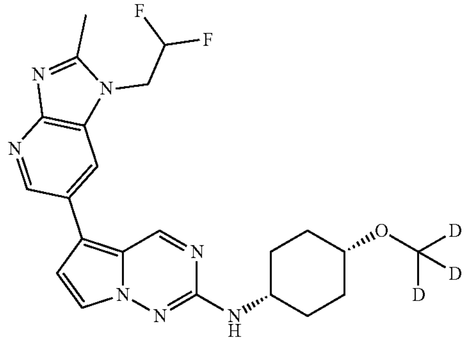

5-(1-(2,2-Difluoroethyl)-2-methyl-1H-imidazo[4,5-b]pyridin-6-yl)-N-(cis-4-(methoxy-$d_3$)cyclohexyl) pyrrolo[2,1-f][1,2,4]triazin-2-amine 1876

Light brown solid (62 mg, 0.140 mmol, 41.6% yield). $^1H$ NMR (499 MHz, DMSO-$d_6$) δ ppm 1.44-1.55 (2H, m), 1.55-1.66 (2H, m), 1.66-1.75 (2H, m), 1.80-1.90 (2H, m), 2.62 (3H, s), 3.33-3.37 (1H, m), 3.59-3.70 (1H, m), 4.90 (2H, td, J=15.95, 2.87 Hz), 6.52 (1H, tt, J=54.60, 3.00 Hz), 6.80 (1H, d, J=7.94 Hz), 6.97 (1H, d, J=2.46 Hz), 7.71 (1H, d, J=2.46 Hz), 8.23 (1H, d, J=1.92 Hz), 8.66 (1H, d, J=2.19 Hz), 9.10 (1H, s); ESIMS found for $C_{22}H_{22}[2H_3]F_2N_7O$ m/z 445.1 (M+1).

1877

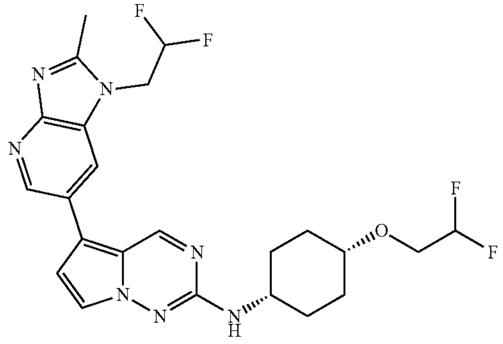

N-(cis-4-(2,2-Difluoroethoxy)cyclohexyl)-5-(1-(2,2-difluoroethyl)-2-methyl-1H-imidazo[4,5-b]pyridin-6-yl)pyrrolo[2,1-f][1,2,4]triazin-2-amine 1877

Yellow solid (27 mg, 0.055 mmol, 20.6% yield). $^1H$ NMR (499 MHz, DMSO-$d_6$) δ ppm 1.50-1.60 (2H, m), 1.60-1.68 (2H, m), 1.69-1.75 (2H, m), 1.82-1.92 (2H, m), 2.62 (3H, s), 3.59 (1H, br s), 3.62-3.69 (1H, m), 3.67 (2H, td, J=15.06, 3.83 Hz), 4.90 (2H, td, J=15.88, 2.74 Hz), 6.13 (1H, tt, J=55.12, 3.85 Hz), 6.52 (1H, tt, J=54.60, 3.00 Hz), 6.83 (1H, d, J=7.67 Hz), 6.97 (1H, d, J=2.74 Hz), 7.71 (1H, d, J=2.19 Hz), 8.23 (1H, d, J=1.64 Hz), 8.66 (1H, d, J=1.64 Hz), 9.10 (1H, s); ESIMS found for $C_{23}H_{25}F_4N_7O$ m/z 492.2 (M+1).

1878

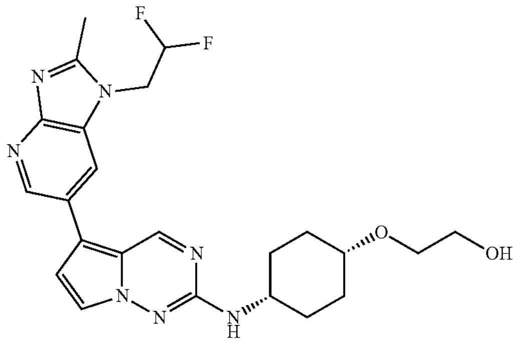

2-((cis-4-((5-(1-(2,2-Difluoroethyl)-2-methyl-1H-imidazo[4,5-b]pyridin-6-yl)pyrrolo[2,1-f][1,2,4]triazin-2-yl)amino)cyclohexyl)oxy)ethan-1-ol 1878

Olive green solid (19 mg, 0.040 mmol, 20.5% yield). $^1H$ NMR (499 MHz, DMSO-$d_6$) δ ppm 1.45-1.57 (2H, m), 1.60-1.75 (4H, m), 1.79-1.89 (2H, m), 2.62 (3H, s), 3.39-3.42 (2H, m), 3.46-3.52 (1H, m), 3.50-3.53 (2H, m), 3.59-3.71 (1H, m), 4.51 (1H, t, J=5.48 Hz), 4.90 (2H, td, J=15.88, 2.74 Hz), 6.52 (1H, tt, J=54.60, 3.00 Hz), 6.78 (1H, d, J=7.67 Hz), 6.97 (1H, d, J=2.74 Hz), 7.71 (1H, d, J=2.74 Hz), 8.23 (1H, d, J=2.19 Hz), 8.66 (1H, d, J=2.19 Hz), 9.10 (1H, s); ESIMS found for $C_{23}H_{27}F_2N_7O_2$ m/z 472.2 (M+1).

1879

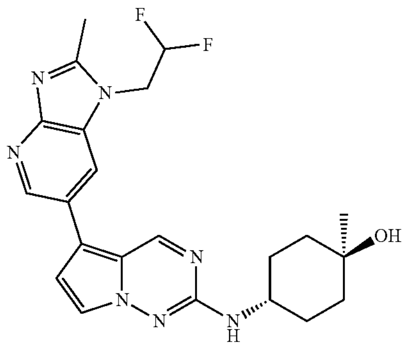

trans-4-((5-(1-(2,2-Difluoroethyl)-2-methyl-1H-imidazo[4,5-b]pyridin-6-yl)pyrrolo[2,1-f][1,2,4]triazin-2-yl)amino)-1-methylcyclohexan-1-ol 1879

Olive green solid (38 mg, 0.086 mmol, 28.0% yield). $^1H$ NMR (499 MHz, DMSO-$d_6$) δ ppm 1.15 (3H, s), 1.39-1.52 (4H, m), 1.58-1.66 (2H, m), 1.84-1.94 (2H, m), 2.62 (3H, s), 3.61-3.71 (1H, m), 4.23 (1H, s), 4.83-4.96 (2H, m), 6.52 (1H, tt, J=54.60, 3.00 Hz), 6.72 (1H, d, J=7.67 Hz), 6.97 (1H, d, J=2.19 Hz), 7.72 (1H, d, J=2.19 Hz), 8.23 (1H, d, J=1.64 Hz), 8.66 (1H, d, J=2.19 Hz), 9.10 (1H, s); ESIMS found for $C_{22}H_{25}F_2N_7O$ m/z 442.2 (M+1).

1880

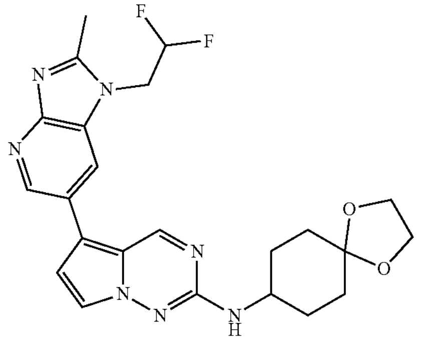

5-(1-(2,2-Difluoroethyl)-2-methyl-1H-imidazo[4,5-b]pyridin-6-yl)-N-(1,4-dioxaspiro[4.5]decan-8-yl)pyrrolo[2,1-f][1,2,4]triazin-2-amine 1880

Light yellow solid (36 mg, 0.077 mmol, 26.6% yield). $^1$H NMR (499 MHz, DMSO-$d_6$) δ ppm 1.51-1.67 (4H, m), 1.70-1.78 (2H, m), 1.88-1.97 (2H, m), 2.62 (3H, s), 3.61-3.75 (1H, m), 3.81-3.92 (4H, m), 4.90 (2H, td, J=15.81, 2.87 Hz), 6.52 (1H, tt, J=54.60, 3.00 Hz), 6.86 (1H, d, J=7.94 Hz), 6.97 (1H, d, J=2.46 Hz), 7.72 (1H, d, J=2.19 Hz), 8.23 (1H, d, J=1.92 Hz), 8.66 (1H, d, J=2.19 Hz), 9.10 (1H, s); ESIMS found for $C_{23}H_{25}F_2N_7O_2$ m/z 470.2 (M+1).

1881

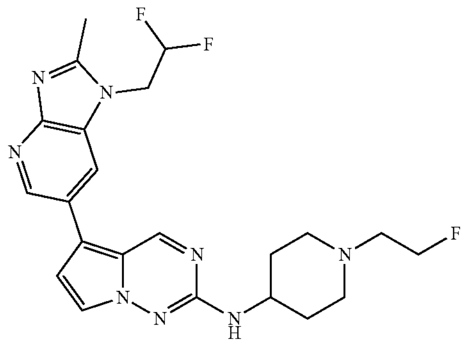

5-(1-(2,2-Difluoroethyl)-2-methyl-1H-imidazo[4,5-b]pyridin-6-yl)-N-(1-(2-fluoroethyl)piperidin-4-yl)pyrrolo[2,1-f][1,2,4]triazin-2-amine 1881

Yellow solid (7 mg, 0.015 mmol, 13.1% yield). $^1$H NMR (499 MHz, DMSO-$d_6$) δ ppm 1.48-1.60 (2H, m), 1.91 (2H, br d, J=13.42 Hz), 2.12 (2H, br t, J=10.95 Hz), 2.62 (2H, dt, J=28.52, 4.93 Hz), 2.62 (3H, s), 2.89 (2H, br d, J=11.77 Hz), 3.53-3.65 (1H, m), 4.53 (2H, dt, J=47.65, 4.95 Hz), 4.90 (2H, td, J=15.81, 2.33 Hz), 6.53 (1H, tt, J=54.40, 3.00 Hz), 6.84 (1H, d, J=7.94 Hz), 6.98 (1H, d, J=2.46 Hz), 7.72 (1H, d, J=2.46 Hz), 8.23 (1H, d, J=1.64 Hz), 8.66 (1H, d, J=1.92 Hz), 9.12 (1H, s); ESIMS found for $C_{22}H_{25}F_3N_8$ m/z 459.2 (M+1).

1882

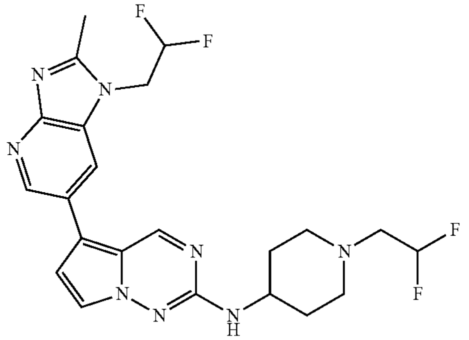

5-(1-(2,2-Difluoroethyl)-2-methyl-1H-imidazo[4,5-b]pyridin-6-yl)-N-(1-(2,2-difluoroethyl)piperidin-4-yl)pyrrolo[2,1-f][1,2,4]triazin-2-amine 1882

Yellow solid (18 mg, 0.038 mmol, 34.0% yield). $^1$H NMR (499 MHz, DMSO-$d_6$) δ ppm 1.48-1.62 (2H, m), 1.90 (2H, br d, J=13.14 Hz), 2.22-2.32 (2H, m), 2.62 (3H, s), 2.73 (2H, td, J=15.61, 4.38 Hz), 2.91 (2H, br d, J=11.77 Hz), 3.53-3.65 (1H, m), 4.85-4.97 (2H, m), 6.14 (1H, tt, J=55.95, 4.10 Hz), 6.53 (1H, tt, J=54.60, 3.00 Hz), 6.85 (1H, d, J=7.94 Hz), 6.98 (1H, d, J=2.46 Hz), 7.72 (1H, d, J=2.46 Hz), 8.23 (1H, d, J=1.64 Hz), 8.66 (1H, d, J=1.92 Hz), 9.12 (1H, s); ESIMS found for $C_{22}H_{24}F_4N_8$ m/z 477.2 (M+1).

1883

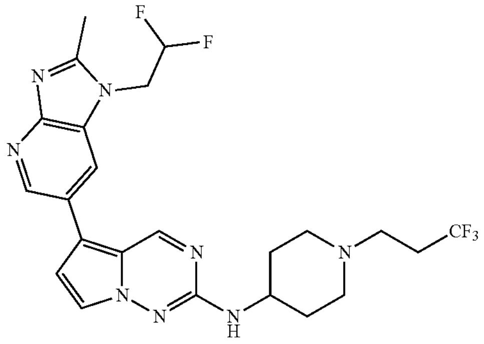

5-(1-(2,2-Difluoroethyl)-2-methyl-1H-imidazo[4,5-b]pyridin-6-yl)-N-(1-(3,3,3-trifluoropropyl)piperidin-4-yl)pyrrolo[2,1-f][1,2,4]triazin-2-amine 1883

Dark yellow solid (13 mg, 0.026 mmol, 16.7% yield). $^1$H NMR (499 MHz, DMSO-$d_6$) δ ppm 1.45-1.59 (2H, m), 1.87-1.96 (2H, m), 2.01-2.10 (2H, m), 2.41-2.48 (2H, m), 2.52-2.56 (2H, m), 2.62 (3H, s), 2.88 (2H, br d, J=11.50 Hz), 3.52-3.65 (1H, m), 4.84-4.97 (2H, m), 6.53 (1H, tt, J=54.60, 3.00 Hz), 6.84 (1H, d, J=7.94 Hz), 6.98 (1H, d, J=2.74 Hz), 7.72 (1H, d, J=2.46 Hz), 8.23 (1H, d, J=1.64 Hz), 8.66 (1H, d, J=1.92 Hz), 9.11 (1H, s); ESIMS found for $C_{23}H_{25}F_5N_8$ m/z 509.2 (M+1).

1884

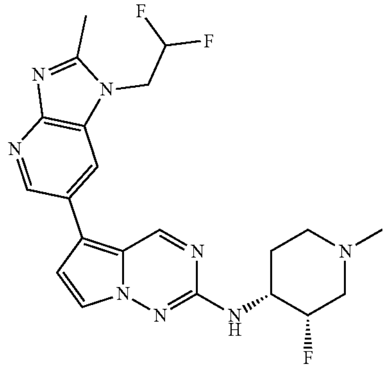

5-(1-(2,2-Difluoroethyl)-2-methyl-1H-imidazo[4,5-b]pyridin-6-yl)-N-((3S,4R)-3-fluoro-1-methylpiperidin-4-yl)pyrrolo[2,1-f][1,2,4]triazin-2-amine 1884

Dark yellow solid (16 mg, 0.036 mmol, 29.5% yield). $^1$H NMR (499 MHz, DMSO-$d_6$) δ ppm 1.74 (1H, br d, J=11.77 Hz), 1.91-2.03 (1H, m), 2.07-2.35 (2H, m), 2.25 (3H, br s), 2.63 (3H, s), 2.87 (1H, br d, J=2.74 Hz), 3.09-3.23 (1H, m), 3.73-3.92 (1H, m), 4.86-5.02 (2H, m), 4.91 (1H, br d, J=2.74 Hz), 6.53 (1H, tt, J=54.60, 3.00 Hz), 6.93 (1H, br d, J=5.20 Hz), 7.02 (1H, d, J=2.46 Hz), 7.73 (1H, d, J=2.46 Hz), 8.24 (1H, d, J=1.92 Hz), 8.67 (1H, d, J=1.92 Hz), 9.15 (1H, s); ESIMS found for $C_{21}H_{23}F_3N_8$ m/z 445.2 (M+1).

1885

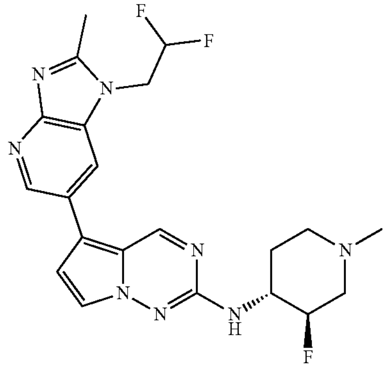

5-(1-(2,2-Difluoroethyl)-2-methyl-1H-imidazo[4,5-b]pyridin-6-yl)-N-((3R,4R)-3-fluoro-1-methylpiperidin-4-yl)pyrrolo[2,1-f][1,2,4]triazin-2-amine 1885

Dark yellow solid (16 mg, 0.036 mmol, 29.5% yield). $^1$H NMR (499 MHz, DMSO-$d_6$) δ ppm 1.46-1.66 (1H, m), 1.94-2.16 (3H, m), 2.26 (3H, br s), 2.63 (3H, s), 2.69-2.83 (1H, m), 3.08-3.19 (1H, m), 3.78-3.93 (1H, m), 4.50-4.74 (1H, m), 4.85-4.95 (2H, m), 6.53 (1H, tt, J=54.60, 3.00 Hz), 7.01 (1H, d, J=2.46 Hz), 7.08 (1H, br d, J=7.94 Hz), 7.75 (1H, d, J=2.46 Hz), 8.24 (1H, d, J=1.64 Hz), 8.67 (1H, d, J=1.92 Hz), 9.14 (1H, s); ESIMS found for $C_{21}H_{23}F_3N_8$ m/z 445.2 (M+1).

1886

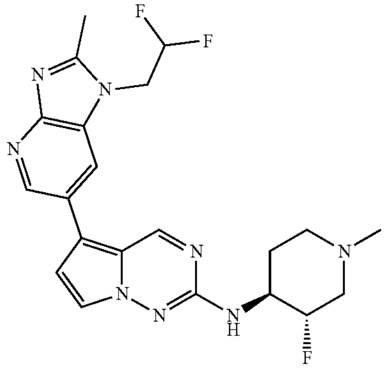

5-(1-(2,2-Difluoroethyl)-2-methyl-1H-imidazo[4,5-b]pyridin-6-yl)-N-((3S,4S)-3-fluoro-1-methylpiperidin-4-yl)pyrrolo[2,1-f][1,2,4]triazin-2-amine 1886

Dark yellow solid (19 mg, 0.043 mmol, 35.1% yield). $^1$H NMR (499 MHz, DMSO-$d_6$) δ ppm 1.47-1.66 (1H, m), 1.93-2.16 (3H, m), 2.26 (3H, br s), 2.63 (3H, s), 2.67-2.81 (1H, m), 3.08-3.17 (1H, m), 3.76-3.90 (1H, m), 4.50-4.73 (1H, m), 4.91 (2H, td, J=15.88, 2.74 Hz), 6.53 (1H, tt, J=54.60, 3.00 Hz), 7.01 (1H, d, J=2.46 Hz), 7.08 (1H, br d, J=7.67 Hz), 7.75 (1H, d, J=2.46 Hz), 8.24 (1H, d, J=1.92 Hz), 8.67 (1H, d, J=1.92 Hz), 9.14 (1H, s); ESIMS found for $C_{21}H_{23}F_3N_8$ m/z 445.2 (M+1).

1887

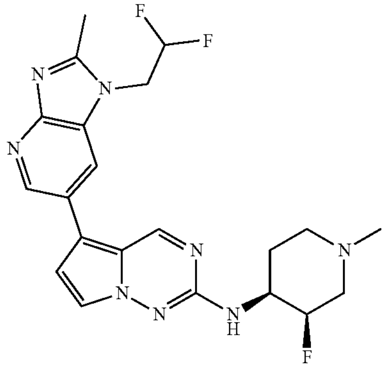

5-(1-(2,2-Difluoroethyl)-2-methyl-1H-imidazo[4,5-b]pyridin-6-yl)-N-((3R,4S)-3-fluoro-1-methylpiperidin-4-yl)pyrrolo[2,1-f][1,2,4]triazin-2-amine 1887

Dark yellow solid (16 mg, 0.036 mmol, 33.8% yield). $^1$H NMR (499 MHz, DMSO-$d_6$) δ ppm 1.71 (1H, br dd, J=8.49, 3.83 Hz), 1.93 (1H, qd, J=12.14, 3.56 Hz), 2.02-2.11 (1H, m), 2.12-2.26 (1H, m), 2.20 (3H, s), 2.63 (3H, s), 2.81 (1H, br d, J=11.22 Hz), 3.00-3.12 (1H, m), 3.70-3.86 (1H, m), 4.87 (1H, br d, J=3.29 Hz), 4.89-4.98 (2H, m), 6.53 (1H, tt, J=54.60, 3.00 Hz), 6.89 (1H, d, J=7.94 Hz), 7.01 (1H, d, J=2.74 Hz), 7.73 (1H, d, J=2.46 Hz), 8.24 (1H, d, J=1.92 Hz), 8.67 (1H, d, J=2.19 Hz), 9.15 (1H, s); ESIMS found for $C_{21}H_{23}F_3N_8$ m/z 445.2 (M+1).

1888

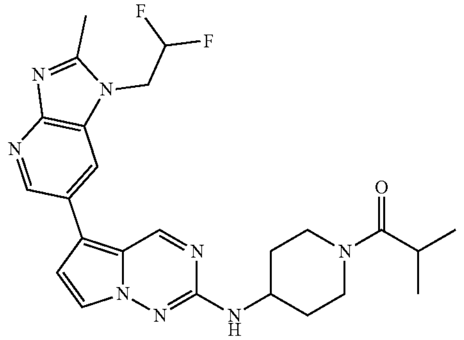

1-(4-((5-(1-(2,2-Difluoroethyl)-2-methyl-1H-imidazo[4,5-b]pyridin-6-yl)pyrrolo[2,1-f][1,2,4]triazin-2-yl)amino)piperidin-1-yl)-2-methylpropan-1-one 1888

Light brown solid (5 mg, 0.010 mmol, 5.1% yield). $^1$H NMR (499 MHz, DMSO-$d_6$) δ ppm 0.94-1.06 (6H, m), 1.34 (1H, q, J=10.22 Hz), 1.44 (1H, q, J=10.31 Hz), 1.94 (1H, br d, J=12.32 Hz), 2.01 (1H, br d, J=11.77 Hz), 2.63 (3H, s), 2.71-2.81 (1H, m), 2.90 (1H, spt, J=6.71 Hz), 3.17 (1H, br t, J=12.05 Hz), 3.79-3.91 (1H, m), 3.95 (1H, br d, J=12.87 Hz), 4.32 (1H, br d, J=12.59 Hz), 4.91 (2H, td, J=15.74, 2.46 Hz), 6.53 (1H, tt, J=54.60, 3.00 Hz), 6.92 (1H, d, J=7.94 Hz), 7.00 (1H, d, J=2.46 Hz), 7.74 (1H, d, J=2.46 Hz), 8.24 (1H, d, J=1.92 Hz), 8.66 (1H, d, J=2.19 Hz), 9.13 (1H, s); ESIMS found for $C_{24}H_{28}F_2N_8O$ m/z 483.2 (M+1).

1889

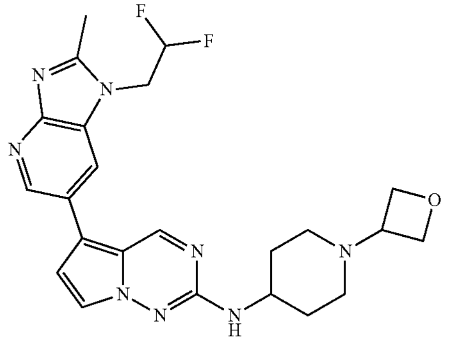

5-(1-(2,2-Difluoroethyl)-2-methyl-1H-imidazo[4,5-b]pyridin-6-yl)-N-(1-(oxetan-3-yl)piperidin-4-yl)pyrrolo[2,1-f][1,2,4]triazin-2-amine 1889

Dark yellow solid (29 mg, 0.062 mmol, 54.5% yield). $^1$H NMR (499 MHz, DMSO-$d_6$) δ ppm 1.47-1.61 (2H, m), 1.87 (2H, br t, J=11.36 Hz), 1.93 (2H, br d, J=10.95 Hz), 2.62 (3H, s), 2.69 (2H, br d, J=10.13 Hz), 3.35-3.43 (1H, m), 3.54-3.67 (1H, m), 4.43 (2H, br t, J=5.89 Hz), 4.53 (2H, t, J=6.43 Hz), 4.84-4.97 (2H, m), 6.53 (1H, tt, J=54.60, 3.00 Hz), 6.88 (1H, br d, J=7.67 Hz), 6.98 (1H, d, J=2.46 Hz), 7.72 (1H, d, J=2.46 Hz), 8.23 (1H, d, J=1.64 Hz), 8.66 (1H, d, J=2.19 Hz), 9.12 (1H, s); ESIMS found for $C_{23}H_{26}F_2N_8O$ m/z 469.3 (M+1).

1890

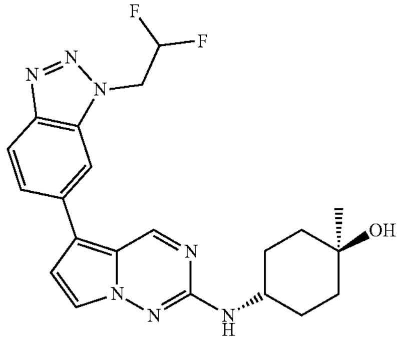

trans-4-((5-(1-(2,2-Difluoroethyl)-1H-benzo[d][1,2,3]triazol-6-yl)pyrrolo [2,1-f][1,2,4]triazin-2-yl)amino)-1-methylcyclohexan-1-ol 1890

Yellow solid (5 mg, 0.012 mmol, 8.9% yield). $^1$H NMR (499 MHz, DMSO-$d_6$) δ ppm 1.15 (3H, s), 1.39-1.53 (4H, m), 1.57-1.66 (2H, m), 1.84-1.93 (2H, m), 3.65 (1H, br dd, J=8.35, 3.97 Hz), 4.24 (1H, s), 5.38 (2H, td, J=15.54, 3.15 Hz), 6.62 (1H, tt, J=54.30, 3.15 Hz), 6.79 (1H, d, J=7.94 Hz), 7.03 (1H, d, J=2.74 Hz), 7.73-7.78 (2H, m), 8.10 (1H, d, J=8.49 Hz), 8.14 (1H, s), 9.19 (1H, s); ESIMS found for $C_{21}H_{23}F_2N_7O$ m/z 428.2 (M+1).

1891

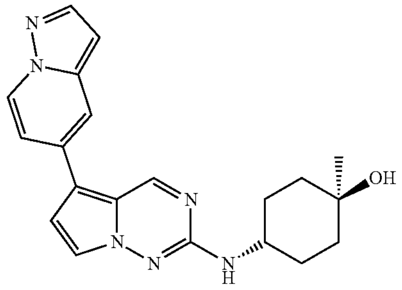

trans-1-Methyl-4-((5-(pyrazolo[1,5-a]pyridin-5-yl)pyrrolo[2,1-f][1,2,4]triazin-2-yl)amino)cyclohexan-1-ol 1891

Yellow solid (80 mg, 0.221 mmol, 71.8% yield). $^1$H NMR (499 MHz, DMSO-$d_6$) δ ppm 1.14 (3H, s), 1.36-1.52 (4H, m), 1.57-1.66 (2H, m), 1.82-1.94 (2H, m), 3.64 (1H, br dd, J=7.67, 3.56 Hz), 4.24 (1H, s), 6.59 (1H, d, J=1.92 Hz), 6.83 (1H, d, J=7.94 Hz), 7.05 (1H, d, J=2.46 Hz), 7.21 (1H, dd, J=7.26, 1.78 Hz), 7.72 (1H, d, J=2.46 Hz), 7.98 (1H, s), 7.98 (1H, s), 8.67 (1H, d, J=7.12 Hz), 9.16 (1H, s); ESIMS found for $C_{20}H_{22}N_6O$ m/z 363.2 (M+1).

1892

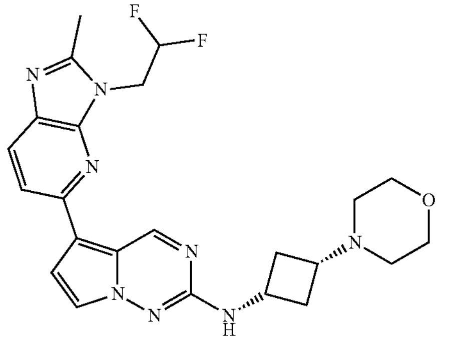

5-(3-(2,2-Difluoroethyl)-2-methyl-3H-imidazo[4,5-b] pyridin-5-yl)-N-(cis-3-morpholinocyclobutyl)pyrrolo[2,1-f] [1,2,4]triazin-2-amine 1893.

Yellow solid (37 mg, 0.079 mmol, 11.4% yield). $^1$H NMR (499 MHz, DMSO-$d_6$) δ ppm 2.02-2.13 (2H, m), 2.18-2.35 (6H, m), 2.61 (3H, s), 2.79-2.87 (1H, m), 3.60 (4H, br s), 4.12-4.21 (1H, m), 4.84 (2H, td, J=15.95, 2.87 Hz), 6.55 (1H, tt, J=54.60, 3.00 Hz), 7.23 (1H, d, J=2.74 Hz), 7.29 (1H, br d, J=6.57 Hz), 7.66 (1H, d, J=2.74 Hz), 7.73 (1H, d, J=8.49 Hz), 7.95 (1H, d, J=8.21 Hz), 9.70 (1H, s); ESIMS found for $C_{23}H_{26}F_2N_8O$ m/z 469.2 (M+1).

1893

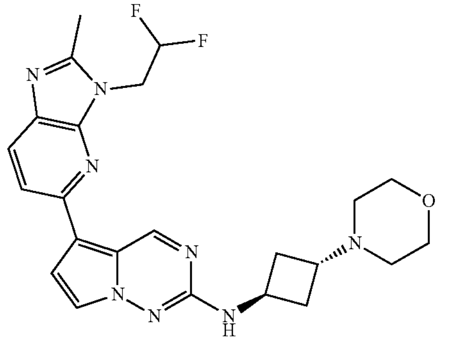

5-(3-(2,2-Difluoroethyl)-2-methyl-3H-imidazo[4,5-b]pyridin-5-yl)-N-(trans-3-morpholinocyclobutyl) pyrrolo[2,1-f][1,2,4]triazin-2-amine 1893

Yellow solid (32 mg, 0.068 mmol, 9.9% yield). $^1$H NMR (499 MHz, DMSO-$d_6$) δ ppm 1.75-1.86 (2H, m), 2.26 (4H, br s), 2.40-2.48 (3H, m), 2.60 (3H, s), 3.54-3.63 (4H, m), 3.89-4.00 (1H, m), 4.84 (2H, td, J=16.08, 2.87 Hz), 6.55 (1H, tt, J=54.60, 3.00 Hz), 7.18 (1H, s), 7.24 (1H, d, J=2.74 Hz), 7.63 (1H, d, J=2.46 Hz), 7.73 (1H, d, J=8.21 Hz), 7.95 (1H, d, J=8.21 Hz), 9.70 (1H, s); ESIMS found for $C_{23}H_{26}F_2N_8O$ m/z 469.2 (M+1).

1894

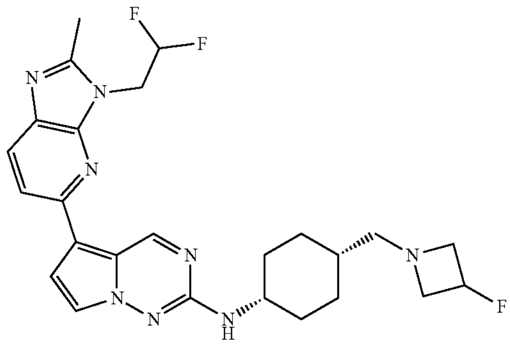

5-(3-(2,2-Difluoroethyl)-2-methyl-3H-imidazo[4,5-b] pyridin-5-yl)-N-(cis-4-((3-fluoroazetidin-1-yl)methyl)cyclohexyl)pyrrolo[2,1-f][1,2,4]triazin-2-amine 1894.

Yellow solid (5.7 mg, 0.011 mmol, 22.1% yield). $^1$H NMR (499 MHz, DMSO-$d_6$) δ ppm 1.48 (5H, br s), 1.53-1.63 (2H, m), 1.68 (2H, br s), 2.37-2.44 (1H, m), 2.51-2.53 (1H, m), 2.61 (3H, s), 2.93-3.12 (2H, m), 3.47-3.63 (2H, m), 3.79 (1H, br d, J=3.29 Hz), 4.82 (2H, td, J=15.95, 2.87 Hz), 5.05-5.28 (1H, m), 6.55 (1H, tt, J=54.60, 3.00 Hz), 6.69 (1H, br d, J=7.12 Hz), 7.22 (1H, d, J=2.74 Hz), 7.64 (1H, d, J=2.74 Hz), 7.72 (1H, d, J=8.21 Hz), 7.95 (1H, d, J=8.21 Hz), 9.70 (1H, s); ESIMS found for $C_{25}H_{29}F_3N_8$ m/z 250.2 (M/2+1).

1895

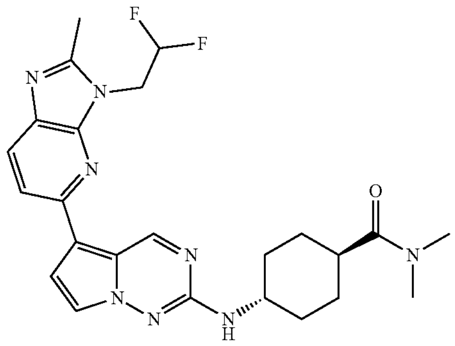

trans-4-((5-(3-(2,2-Difluoroethyl)-2-methyl-3H-imidazo[4,5-b]pyridin-5-yl)pyrrolo[2,1-f][1,2,4]triazin-2-yl)amino)-N,N-dimethylcyclohexane-1-carboxamide 1895

Yellow solid (8 mg, 0.017 mmol, 6.1% yield). $^1$H NMR (499 MHz, DMSO-$d_6$) δ ppm 1.29-1.40 (2H, m), 1.34-1.34 (2H, m), 1.40-1.51 (2H, m), 1.74 (2H, br d, J=12.05 Hz), 2.05 (2H, br dd, J=12.18, 2.60 Hz), 2.56 (1H, tt, J=11.64, 3.42 Hz), 2.61 (3H, s), 2.81 (3H, s), 3.02 (3H, s), 3.51-3.65 (1H, m), 4.83 (2H, td, J=15.95, 2.87 Hz), 6.55 (1H, tt, J=54.60, 3.00 Hz), 6.81 (1H, d, J=7.94 Hz), 7.22 (1H, d, J=2.74 Hz), 7.66 (1H, d, J=2.46 Hz), 7.72 (1H, d, J=8.21 Hz), 7.95 (1H, d, J=8.21 Hz), 9.69 (1H, s); ESIMS found for $C_{24}H_{28}F_2N_8O$ m/z 483.2 (M+1).

1896

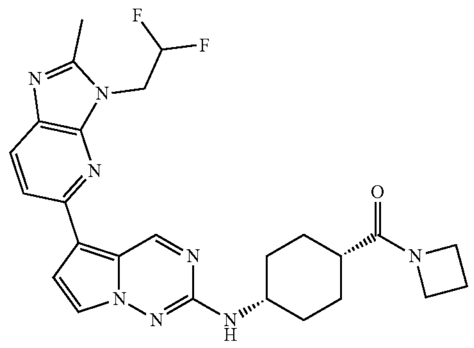

Azetidin-1-yl(cis-4-((5-(3-(2,2-difluoroethyl)-2-methyl-3H-imidazo[4,5-b]pyridin-5-yl)pyrrolo[2,1-f][1,2,4]triazin-2-yl)amino)cyclohexyl)methanone 1896

Yellow solid (7 mg, 0.014 mmol, 14.3% yield). $^1$H NMR (499 MHz, DMSO-$d_6$) δ ppm 1.42-1.50 (2H, m), 1.57-1.66 (2H, m), 1.73-1.83 (2H, m), 1.92 (2H, dt, J=6.64, 3.39 Hz), 2.13-2.22 (2H, m), 2.31 (1H, tt, J=8.62, 4.11 Hz), 2.61 (3H, s), 3.75-3.80 (1H, m), 3.82 (2H, t, J=7.67 Hz), 4.15 (2H, t, J=7.53 Hz), 4.83 (2H, td, J=15.95, 2.60 Hz), 6.55 (1H, tt, J=54.60, 3.00 Hz), 6.77 (1H, d, J=6.30 Hz), 7.22 (1H, d, J=2.74 Hz), 7.64 (1H, d, J=2.46 Hz), 7.72 (1H, d, J=8.21 Hz), 7.95 (1H, d, J=8.21 Hz), 9.70 (1H, s); ESIMS found for $C_{23}H_{26}F_2N_8O$ m/z 495.3 (M+1).

1898

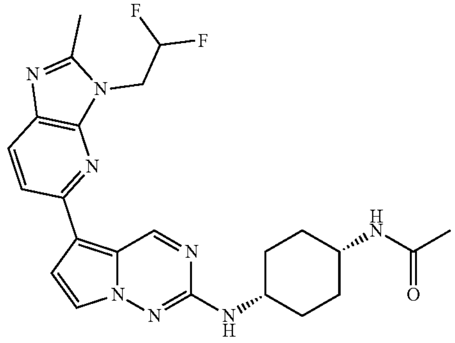

N-(cis-4-((5-(3-(2,2-Difluoroethyl)-2-methyl-3H-imidazo[4,5-b]pyridin-5-yl)pyrrolo[2,1-f][1,2,4]triazin-2-yl)amino)cyclohexyl)acetamide 1898

Yellow solid (60 mg, 0.128 mmol, 72.8% yield). $^1$H NMR (499 MHz, DMSO-$d_6$) δ ppm 1.52-1.59 (2H, m), 1.61-1.73 (4H, m), 1.74-1.80 (2H, m), 1.82 (3H, s), 2.61 (3H, s), 3.68 (2H, br d, J=3.29 Hz), 4.83 (2H, td, J=15.95, 2.87 Hz), 6.55 (1H, tt, J=54.60, 3.00 Hz), 6.72 (1H, d, J=6.57 Hz), 7.23 (1H, d, J=2.74 Hz), 7.65 (1H, d, J=2.46 Hz), 7.71-7.75 (1H, m), 7.73 (1H, d, J=8.21 Hz), 7.95 (1H, d, J=8.21 Hz), 9.71 (1H, s); ESIMS found for $C_{25}H_{28}F_2N_8O$ m/z 469.2 (M+1).

1899

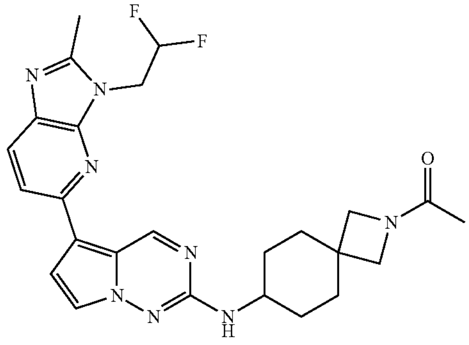

1-(7-((5-(3-(2,2-Difluoroethyl)-2-methyl-3H-imidazo[4,5-b]pyridin-5-yl)pyrrolo[2,1-f][1,2,4]triazin-2-yl)amino)-2-azaspiro[3.5]nonan-2-yl)ethan-1-one 1899

Yellow solid (33 mg, 0.067 mmol, 54.9% yield). $^1$H NMR (499 MHz, DMSO-$d_6$) δ ppm 1.27-1.41 (2H, m), 1.50-1.62 (2H, m), 1.73-1.79 (3H, m), 1.88 (4H, br d, J=10.13 Hz), 2.60 (3H, s), 3.45-3.55 (2H, m), 3.55-3.66 (1H, m), 3.70-3.85 (2H, m), 4.77-4.90 (2H, m), 6.55 (1H, tt, J=54.60, 3.00 Hz), 6.74 (1H, dd, J=12.05, 7.94 Hz), 7.23 (1H, d, J=2.74 Hz), 7.65 (1H, t, J=3.01 Hz), 7.72 (1H, d, J=8.21 Hz), 7.95 (1H, d, J=8.21 Hz), 9.69 (1H, s); ESIMS found for $C_{25}H_{28}F_2N_8O$ m/z 495.25 (M+1).

1900

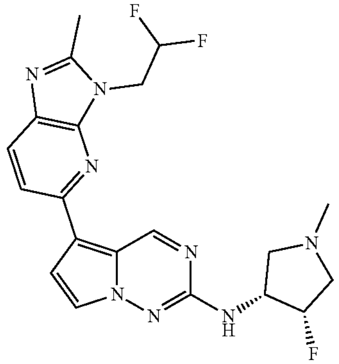

5-(3-(2,2-Difluoroethyl)-2-methyl-3H-imidazo[4,5-b]pyridin-5-yl)-N-((3R,4S)-4-fluoro-1-methylpyrrolidin-3-yl)pyrrolo[2,1-f][1,2,4]triazin-2-amine 1900

Yellow solid (36 mg, 0.084 mmol, 26.3% yield). $^1$H NMR (499 MHz, DMSO-$d_6$) δ ppm 2.33 (3H, s), 2.61 (3H, s), 2.62-2.72 (2H, m), 2.95 (1H, br t, J=8.21 Hz), 3.15 (1H, ddd, J=30.20, 11.77, 4.65 Hz), 4.23-4.37 (1H, m), 4.84 (2H, td, J=16.02, 2.74 Hz), 5.22 (1H, dtd, J=55.70, 4.86, 4.86, 2.05 Hz), 6.56 (1H, tt, J=54.60, 3.00 Hz), 7.01 (1H, d, J=7.94 Hz), 7.28 (1H, d, J=2.74 Hz), 7.68 (1H, d, J=2.46 Hz), 7.75 (1H, d, J=8.49 Hz), 7.96 (1H, d, J=8.21 Hz), 9.74 (1H, s); ESIMS found for $C_{20}H_{21}F_3N_8$ m/z 431.2 (M+1).

1901

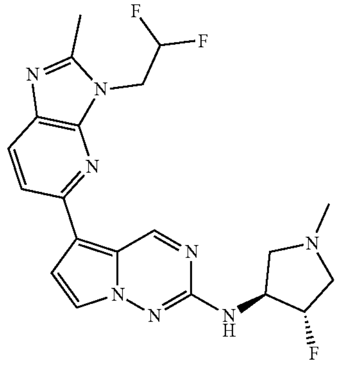

5-(3-(2,2-Difluoroethyl)-2-methyl-3H-imidazo[4,5-b]pyridin-5-yl)-N-((3S,4S)-4-fluoro-1-methylpyrrolidin-3-yl)pyrrolo[2,1-f][1,2,4]triazin-2-amine 1901

Yellow solid (34 mg, 0.079 mmol, 24.8% yield). $^1$H NMR (499 MHz, DMSO-$d_6$) δ ppm 2.24-2.30 (1H, m), 2.32 (3H, s), 2.61 (3H, s), 2.62-2.75 (1H, m), 2.88-3.01 (1H, m), 3.24-3.30 (1H, m), 4.24-4.35 (1H, m), 4.84 (2H, td, J=16.02, 3.01 Hz), 5.09 (1H, dd, J=53.20, 4.70 Hz), 6.55 (1H, tt, J=54.60, 3.00 Hz), 7.22 (1H, d, J=7.12 Hz), 7.28 (1H, d, J=2.74 Hz), 7.70 (1H, d, J=2.46 Hz), 7.75 (1H, d, J=8.21 Hz), 7.96 (1H, d, J=8.21 Hz), 9.73 (1H, s); ESIMS found for $C_{20}H_{21}F_3N_8$ m/z 431.2 (M+1).

1902

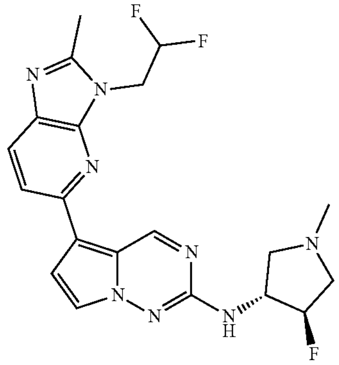

5-(3-(2,2-Difluoroethyl)-2-methyl-3H-imidazo[4,5-b]pyridin-5-yl)-N-((3R,4R)-4-fluoro-1-methylpyrrolidin-3-yl)pyrrolo[2,1-f][1,2,4]triazin-2-amine 1902

Yellow solid (28 mg, 0.065 mmol, 20.4% yield). $^1$H NMR (499 MHz, DMSO-$d_6$) δ ppm 2.34 (4H, br s), 2.61 (3H, s), 2.66-2.80 (1H, m), 2.91-3.05 (1H, m), 3.28-3.31 (1H, m), 4.24-4.38 (1H, m), 4.84 (2H, td, J=16.08, 2.87 Hz), 5.10 (1H, dd, J=53.20, 4.25 Hz), 6.55 (1H, tt, J=54.60, 3.00 Hz), 7.22 (1H, d, J=7.12 Hz), 7.28 (1H, d, J=2.74 Hz), 7.71 (1H, d, J=2.74 Hz), 7.75 (1H, d, J=8.49 Hz), 7.96 (1H, d, J=8.21 Hz), 9.74 (1H, s); ESIMS found for $C_{20}H_{21}F_3N_8$ m/z 431.2 (M+1).

1903

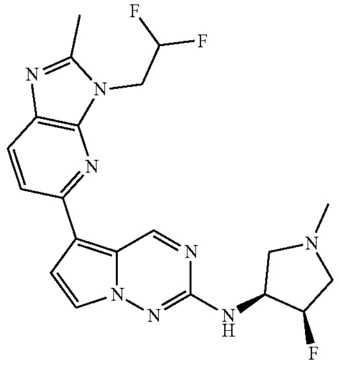

5-(3-(2,2-Difluoroethyl)-2-methyl-3H-imidazo[4,5-b]pyridin-5-yl)-N-((3S,4R)-4-fluoro-1-methylpyrrolidin-3-yl)pyrrolo[2,1-f][1,2,4]triazin-2-amine 1903

Yellow solid (35 mg, 0.081 mmol, 25.5% yield). $^1$H NMR (499 MHz, DMSO-$d_6$) δ ppm 2.33 (3H, s), 2.61 (3H, s), 2.63-2.73 (2H, m), 2.95 (1H, t, J=8.21 Hz), 3.16 (1H, ddd, J=30.20, 11.77, 4.65 Hz), 4.23-4.37 (1H, m), 4.84 (2H, td, J=15.95, 2.87 Hz), 5.22 (1H, dtd, J=55.65, 4.77, 4.77, 1.64 Hz), 6.56 (1H, tt, J=54.60, 3.00 Hz), 7.01 (1H, d, J=7.67 Hz), 7.28 (1H, d, J=2.74 Hz), 7.68 (1H, d, J=2.46 Hz), 7.75 (1H, d, J=8.21 Hz), 7.96 (1H, d, J=8.21 Hz), 9.74 (1H, s); ESIMS found for $C_{20}H_{21}F_3N_8$ m/z 431.2 (M+1).

1906

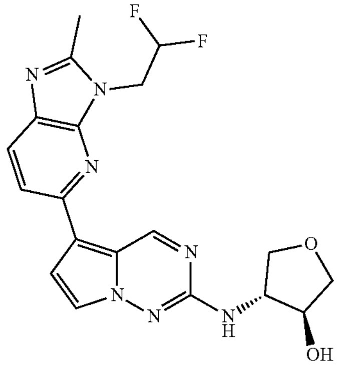

(3S,4R)-4-((5-(3-(2,2-Difluoroethyl)-2-methyl-3H-imidazo[4,5-b]pyridin-5-yl)pyrrolo[2,1-f][1,2,4]triazin-2-yl)amino)tetrahydrofuran-3-ol 1906

Yellow solid (80 mg, 0.193 mmol, 57.6% yield). $^1$H NMR (499 MHz, DMSO-$d_6$) δ ppm 2.61 (3H, s), 3.55 (1H, dd, J=9.31, 2.19 Hz), 3.64-3.73 (1H, m), 3.92 (1H, dd, J=9.31, 4.38 Hz), 4.00-4.07 (2H, m), 4.26 (1H, td, J=4.04, 2.05 Hz), 4.84 (2H, td, J=16.08, 2.87 Hz), 5.21 (1H, d, J=4.11 Hz), 6.55 (1H, tt, J=54.50, 3.00 Hz), 7.13 (1H, d, J=6.02 Hz), 7.26 (1H, d, J=2.74 Hz), 7.68 (1H, d, J=2.46 Hz), 7.74 (1H, d, J=8.49 Hz), 7.95 (1H, d, J=8.21 Hz), 9.72 (1H, s); ESIMS found for $C_{19}H_{19}F_2N_7O_2$ m/z 416.2 (M+1).

1908

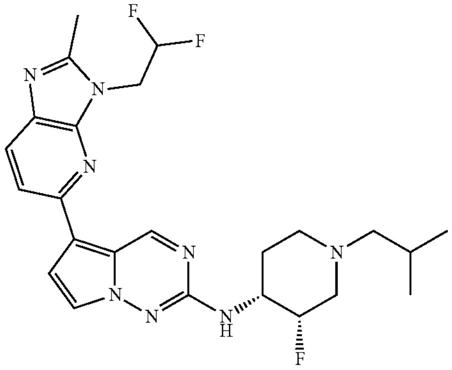

5-(3-(2,2-Difluoroethyl)-2-methyl-3H-imidazo[4,5-b]pyridin-5-yl)-N-((3S,4R)-3-fluoro-1-isobutylpiperidin-4-yl)pyrrolo[2,1-f][1,2,4]triazin-2-amine 1908

Yellow solid (22 mg, 0.045 mmol, 55.8% yield). $^{1}$H NMR (500 MHz, DMSO-$d_6$) δ ppm 0.86 (6H, br d, J=6.31 Hz), 1.65-1.83 (2H, m), 1.86-1.99 (1H, m), 2.02-2.11 (3H, m), 2.12-2.26 (1H, m), 2.61 (3H, s), 2.85 (1H, br d, J=10.70 Hz), 3.05-3.17 (1H, m), 3.74-3.94 (1H, m), 4.84 (2H, td, J=16.05, 2.47 Hz), 4.83-4.96 (1H, m), 6.55 (1H, tt, J=54.60, 3.00 Hz), 6.85 (1H, br d, J=7.96 Hz), 7.26 (1H, br s), 7.66 (1H, d, J=2.47 Hz), 7.74 (1H, d, J=8.23 Hz), 7.96 (1H, d, J=8.23 Hz), 9.73 (1H, s); ESIMS found for $C_{24}H_{29}F_3N_8$ m/z 487.3 (M+1).

1909

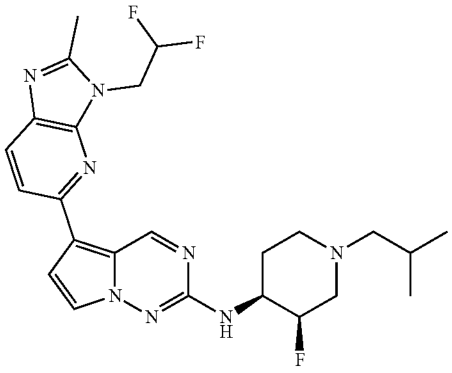

5-(3-(2,2-Difluoroethyl)-2-methyl-3H-imidazo[4,5-b]pyridin-5-yl)-N-((3R,4S)-3-fluoro-1-isobutylpiperidin-4-yl)pyrrolo[2,1-f][1,2,4]triazin-2-amine 1909

Yellow solid (15 mg, 0.031 mmol, 35.7% yield). $^{1}$H NMR (500 MHz, DMSO-$d_6$) δ ppm 0.86 (6H, br d, J=6.31 Hz), 1.66-1.82 (2H, m), 1.88-1.99 (1H, m), 2.00-2.11 (3H, m), 2.12-2.27 (1H, m), 2.61 (3H, s), 2.80-2.91 (1H, m), 3.05-3.17 (1H, m), 3.73-3.92 (1H, m), 4.84 (2H, td, J=15.85, 2.61 Hz), 4.94 (1H, br s), 6.55 (1H, tt, J=54.60, 3.00 Hz), 6.86 (1H, br d, J=7.68 Hz), 7.26 (1H, d, J=2.47 Hz), 7.66 (1H, d, J=2.47 Hz), 7.74 (1H, d, J=8.51 Hz), 7.96 (1H, d, J=8.51 Hz), 9.73 (1H, s); ESIMS found for $C_{24}H_{29}F_3N_8$ m/z 487.3 (M+1).

1910

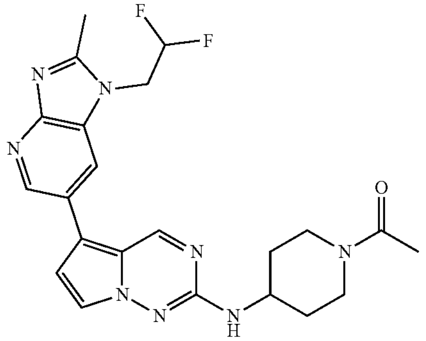

1-(4-((5-(1-(2,2-Difluoroethyl)-2-methyl-1H-imidazo[4,5-b]pyridin-6-yl)pyrrolo[2,1-f][1,2,4]triazin-2-yl)amino)piperidin-1-yl)ethan-1-one 1910

Light brown solid (8 mg, 0.0178 mmol, 3.4% yield). $^{1}$H NMR (499 MHz, DMSO-$d_6$) δ ppm 1.29-1.39 (1H, m), 1.40-1.53 (1H, m), 1.90-2.00 (2H, m), 2.01 (3H, s), 2.63 (3H, s), 2.71-2.81 (1H, m), 3.13-3.23 (1H, m), 3.78-3.89 (2H, m), 4.28 (1H, br dd, J=13.42, 1.37 Hz), 4.91 (2H, td, J=15.88, 2.74 Hz), 6.53 (1H, tt, J=54.60, 3.00 Hz), 6.95 (1H, d, J=7.94 Hz), 6.99 (1H, d, J=2.74 Hz), 7.74 (1H, d, J=2.46 Hz), 8.24 (1H, d, J=1.92 Hz), 8.66 (1H, d, J=1.92 Hz), 9.13 (1H, s) ESIMS found for $C_{22}H_{24}F_2N_8O$ m/z 455.2 (M+1).

1911

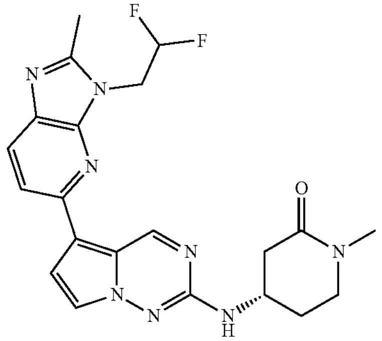

(S)-4-((5-(3-(2,2-Difluoroethyl)-2-methyl-3H-imidazo[4,5-b]pyridin-5-yl)pyrrolo[2,1-f][1,2,4]triazin-2-yl)amino)-1-methylpiperidin-2-one 1911

Yellow solid (12 mg, 0.027 mmol, 67.9% yield). $^{1}$H NMR (499 MHz, DMSO-$d_6$) δ ppm 1.90-1.97 (1H, m), 1.98-2.06 (1H, m), 2.28-2.44 (2H, m), 2.61 (3H, s), 2.81 (3H, s), 3.26 (1H, dd, J=12.05, 7.94 Hz), 3.58 (1H, dd, J=11.77, 4.93 Hz), 4.05-4.16 (1H, m), 4.84 (2H, td, J=15.95, 2.60 Hz), 6.55 (1H, tt, J=54.60, 3.00 Hz), 7.13 (1H, d, J=7.12 Hz), 7.27 (1H, d, J=2.46 Hz), 7.70 (1H, d, J=2.74 Hz), 7.74 (1H, d, J=8.49 Hz), 7.96 (1H, d, J=8.21 Hz), 9.73 (1H, s); ESIMS found for $C_{21}H_{22}F_2N_8O$ m/z 441.2 (M+1).

1912

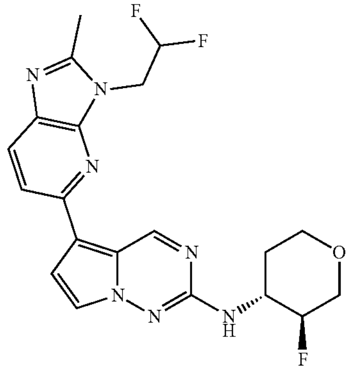

5-(3-(2,2-Difluoroethyl)-2-methyl-3H-imidazo[4,5-b]pyridin-5-yl)-N-((3S,4R)-3-fluorotetrahydro-2H-pyran-4-yl)pyrrolo[2,1-f][1,2,4]triazin-2-amine 1912

Yellow solid (17 mg, 0.039 mmol, 62.0% yield). $^1$H NMR (499 MHz, DMSO-$d_6$) δ ppm 1.57-1.67 (1H, m), 2.05-2.12 (1H, m), 2.61 (3H, s), 3.43 (1H, ddd, J=11.43, 8.15, 6.16 Hz), 3.46-3.52 (1H, m), 3.79-3.87 (1H, m), 3.97-4.05 (1H, m), 4.06-4.16 (1H, m), 4.49-4.66 (1H, m), 4.84 (2H, td, J=15.95, 2.87 Hz), 6.55 (1H, tt, J=54.60, 3.00 Hz), 7.17 (1H, d, J=8.21 Hz), 7.27 (1H, d, J=2.46 Hz), 7.69 (1H, d, J=2.74 Hz), 7.74 (1H, d, J=8.49 Hz), 7.96 (1H, d, J=8.21 Hz), 9.73 (1H, s); ESIMS found for $C_{20}H_{20}F_3N_7O$ m/z 432.2 (M+1).

1914

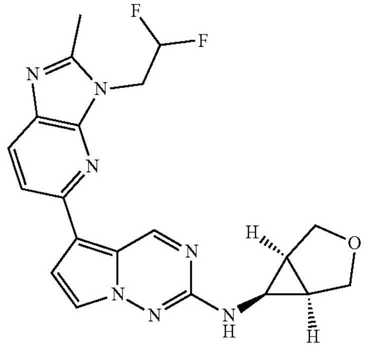

N-((1R,5S,6s)-3-Oxabicyclo[3.1.0]hexan-6-yl)-5-(3-(2,2-difluoroethyl)-2-methyl-3H-imidazo[4,5-b]pyridin-5-yl)pyrrolo[2,1-f][1,2,4]triazin-2-amine 1914

Yellow solid (58 mg, 0.141 mmol, 80.0% yield). $^1$H NMR (499 MHz, DMSO-$d_6$) δ ppm 2.03 (2H, d, J=6.84 Hz), 2.61 (3H, s), 2.89 (1H, td, J=6.78, 3.42 Hz), 3.84 (4H, s), 4.83 (2H, td, J=15.95, 2.87 Hz), 6.55 (1H, tt, J=54.60, 3.00 Hz), 6.57 (1H, d, J=3.29 Hz), 7.26 (1H, d, J=2.74 Hz), 7.69 (1H, d, J=2.46 Hz), 7.74 (1H, d, J=8.21 Hz), 7.96 (1H, d, J=8.21 Hz), 9.71 (1H, s); ESIMS found for $C_{20}H_{19}F_2N_7O$ m/z 412.2 (M+1).

1915

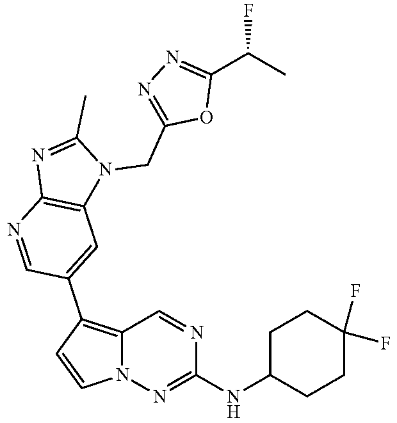

(R)—N-(4,4-Difluorocyclohexyl)-5-(1-((5-(1-fluoroethyl)-1,3,4-oxadiazol-2-yl)methyl)-2-methyl-1H-imidazo[4,5-b]pyridin-6-yl)pyrrolo[2,1-f][1,2,4]triazin-2-amine 1915

Beige solid (15 mg, 0.029 mmol, 16.6% yield). $^1$H NMR (499 MHz, DMSO-$d_6$) δ ppm 1.59-1.68 (2H, m), 1.70 (3H, dd, J=24.10, 6.55 Hz), 1.86-2.03 (4H, m), 2.03-2.15 (2H, m), 2.65 (3H, s), 3.80 (1H, br d, J=8.21 Hz), 5.97 (1H, dq, J=47.15, 6.60 Hz), 6.04 (2H, s), 6.96-7.01 (2H, m), 7.72 (1H, d, J=2.19 Hz), 8.28 (1H, d, J=2.19 Hz), 8.69 (1H, d, J=2.19 Hz), 9.13 (1H, s); ESIMS found for $C_{24}H_{24}F_3N_9O$ m/z 512.2 (M+1).

1916

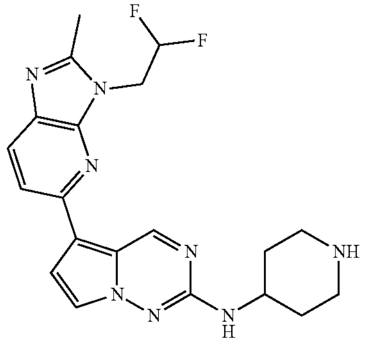

5-(3-(2,2-Difluoroethyl)-2-methyl-3H-imidazo[4,5-b]pyridin-5-yl)-N-(piperidin-4-yl)pyrrolo[2,1-f][1,2,4]triazin-2-amine 1916

Yellow solid (220 mg, 0.533 mmol, 58.2% yield). $^1$H NMR (499 MHz, DMSO-$d_6$) δ ppm 1.36 (2H, qd, J=11.59, 3.83 Hz), 1.88 (2H, br d, J=9.86 Hz), 2.51-2.55 (2H, m), 2.60 (3H, s), 2.96 (2H, br d, J=12.32 Hz), 3.59-3.72 (1H, m), 4.83 (2H, td, J=15.95, 2.60 Hz), 6.55 (1H, tt, J=54.60, 3.00 Hz), 6.80 (1H, d, J=7.94 Hz), 7.22 (1H, d, J=2.74 Hz), 7.64 (1H, d, J=2.46 Hz), 7.72 (1H, d, J=8.49 Hz), 7.95 (1H, d, J=8.21 Hz), 9.69 (1H, s); ESIMS found for $C_{20}H_{22}F_2N_8$ m/z 413.2 (M+1).

1917

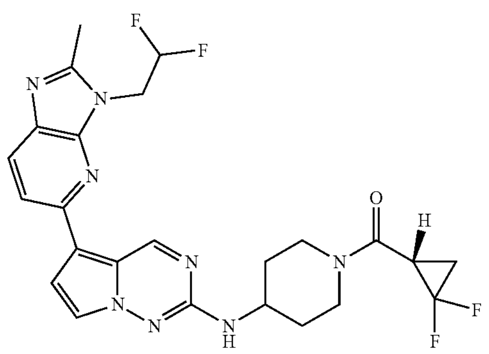

(S)-(2,2-Difluorocyclopropyl)(4-((5-(3-(2,2-difluoroethyl)-2-methyl-3H-imidazo[4,5-b]pyridin-5-yl)pyrrolo[2,1-f][1,2,4]triazin-2-yl)amino)piperidin-1-yl)methanone 1917

Yellow solid (9 mg, 0.017 mmol, 14.4% yield). $^1$H NMR (499 MHz, DMSO-$d_6$) δ ppm 1.30-1.62 (2H, m), 1.78-1.87 (1H, m), 1.87-1.94 (1H, m), 1.97 (1H, br d, J=13.42 Hz), 1.99-2.12 (1H, m), 2.61 (3H, s), 2.86-2.98 (1H, m), 3.10-3.30 (2H, m), 3.85-3.97 (1H, m), 3.99-4.14 (1H, m), 4.22-4.34 (1H, m), 4.77-4.91 (2H, m), 6.55 (1H, tt, J=54.60, 3.00 Hz), 6.97 (1H, dd, J=7.80, 4.24 Hz), 7.25 (1H, d, J=2.46 Hz), 7.67 (1H, dd, J=5.34, 2.60 Hz), 7.73 (1H, d, J=8.49 Hz), 7.95 (1H, d, J=8.49 Hz), 9.72 (1H, d, J=1.37 Hz); ESIMS found for $C_{24}H_{24}F_4N_8O$ m/z 517.2 (M+1).

1918

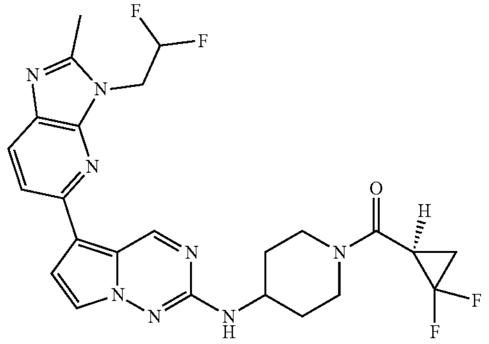

(R)-(2,2-Difluorocyclopropyl)(4-((5-(3-(2,2-difluoroethyl)-2-methyl-3H-imidazo[4,5-b]pyridin-5-yl)pyrrolo[2,1-f][1,2,4]triazin-2-yl)amino)piperidin-1-yl)methanone 1918

Yellow solid (14 mg, 0.027 mmol, 22.4% yield). $^1$H NMR (499 MHz, DMSO-$d_6$) δ ppm 1.29-1.62 (2H, m), 1.78-1.86 (1H, m), 1.87-1.94 (1H, m), 1.97 (1H, br d, J=13.42 Hz), 1.99-2.12 (1H, m), 2.61 (3H, s), 2.85-2.98 (1H, m), 3.10-3.31 (2H, m), 3.86-3.97 (1H, m), 3.99-4.13 (1H, m), 4.28 (1H, br t, J=12.32 Hz), 4.77-4.91 (2H, m), 6.55 (1H, tt, J=54.60, 3.00 Hz), 6.97 (1H, dd, J=7.94, 4.11 Hz), 7.25 (1H, d, J=2.46 Hz), 7.67 (1H, dd, J=5.48, 2.74 Hz), 7.73 (1H, d, J=8.21 Hz), 7.95 (1H, d, J=8.49 Hz), 9.72 (1H, d, J=1.37 Hz); ESIMS found for $C_{24}H_{24}F_4N_8O$ m/z 517.2 (M+1).

1920

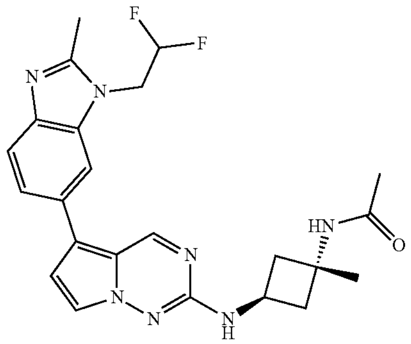

N-((1r,3r)-3-((5-(1-(2,2-Difluoroethyl)-2-methyl-1H-benzo[d]imidazol-6-yl)pyrrolo[2,1-f][1,2,4]triazin-2-yl)amino)-1-methylcyclobutyl)acetamide 1920

Yellow solid (23 mg, 0.051 mmol, 24.5% yield). $^1$H NMR (499 MHz, DMSO-$d_6$) δ ppm 1.37 (3H, s), 1.82 (3H, s), 1.90-2.01 (2H, m), 2.56 (3H, s), 2.65 (2H, ddd, J=10.20, 7.87, 2.74 Hz), 4.19 (1H, sxt, J=7.83 Hz), 4.85 (2H, td, J=15.88, 2.46 Hz), 6.49 (1H, tt, J=54.50, 3.00 Hz), 6.89 (1H, d, J=2.46 Hz), 7.16 (1H, d, J=7.12 Hz), 7.45 (1H, dd, J=8.35, 1.51 Hz), 7.57 (1H, d, J=8.21 Hz), 7.66 (1H, d, J=2.46 Hz), 7.80 (1H, s), 7.95 (1H, s), 9.06 (1H, s); ESIMS found for $C_{23}H_{25}F_2N_7O$ m/z 454.2 (M+1).

1940

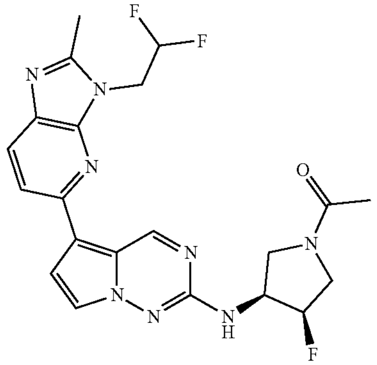

1-((3S,4R)-3-((5-(3-(2,2-Difluoroethyl)-2-methyl-3H-imidazo[4,5-b]pyridin-5-yl)pyrrolo[2,1-f][1,2,4]triazin-2-yl)amino)-4-fluoropyrrolidin-1-yl)ethan-1-one 1940

Yellow solid (9 mg, 0.020 mmol, 45.4% yield). $^1$H NMR (499 MHz, DMSO-$d_6$) δ ppm 1.93-2.03 (3H, m), 2.61 (3H, s), 3.47-3.78 (2H, m), 3.81 (0.5H, s), 3.84-3.92 (1H, m), 3.97 (0.5H, t, J=9.03 Hz), 4.31-4.62 (1H, m), 4.77-4.92 (2H, m), 5.23-5.51 (1H, m), 6.56 (1H, tt, J=54.50, 3.00 Hz), 7.26-7.32 (2H, m), 7.70 (1H, dd, J=4.65, 2.74 Hz), 7.76 (1H, dd, J=8.35, 0.96 Hz), 7.96 (1H, d, J=8.21 Hz), 9.76 (1H, d, J=3.83 Hz); ESIMS found for $C_{21}H_{21}F_3N_8O$ m/z 459.2 (M+1).

1941

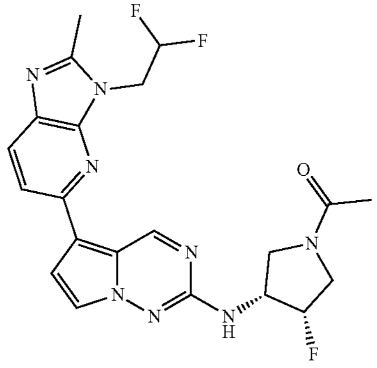

1-((3R,4S)-3-((5-(3-(2,2-Difluoroethyl)-2-methyl-3H-imidazo[4,5-b]pyridin-5-yl)pyrrolo[2,1-f][1,2,4]triazin-2-yl)amino)-4-fluoropyrrolidin-1-yl)ethan-1-one 1941

Yellow solid (8 mg, 0.018 mmol, 22.7% yield). $^1$H NMR (499 MHz, DMSO-d$_6$) δ ppm 1.94-2.01 (3H, m), 2.61 (3H, s), 3.48-3.76 (2H, m), 3.81 (0.5H, s), 3.84-3.91 (1H, m), 3.97 (0.5H, t, J=9.03 Hz), 4.33-4.60 (1H, m), 4.79-4.90 (2H, m), 5.27-5.48 (1H, m), 6.56 (1H, tt, J=54.50, 3.00 Hz), 7.27-7.32 (2H, m), 7.70 (1H, dd, J=4.65, 2.46 Hz), 7.76 (1H, dd, J=8.35, 0.96 Hz), 7.97 (1H, d, J=8.49 Hz), 9.76 (1H, d, J=4.11 Hz); ESIMS found for $C_{21}H_{21}F_3N_8O$ m/z 459.2 (M+1).

1944

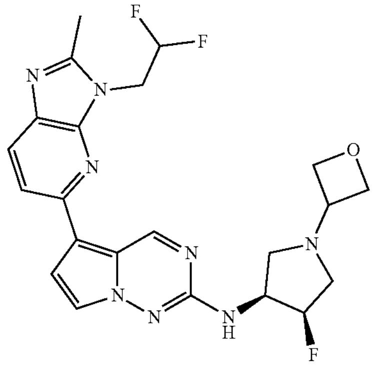

5-(3-(2,2-Difluoroethyl)-2-methyl-3H-imidazo[4,5-b]pyridin-5-yl)-N-((3S,4R)-4-fluoro-1-(oxetan-3-yl)pyrrolidin-3-yl)pyrrolo[2,1-f][1,2,4]triazin-2-amine 1944

Yellow solid (80 mg, 0.169 mmol, 51.1% yield). $^1$H NMR (499 MHz, DMSO-d$_6$) δ ppm 2.61 (3H, s), 2.71 (1H, t, J=9.17 Hz), 2.80 (1H, dd, J=28.50, 11.20 Hz), 3.04 (1H, t, J=8.21 Hz), 3.17 (1H, ddd, J=33.45, 12.05, 4.40 Hz), 3.80 (1H, quin, J=6.16 Hz), 4.23-4.40 (1H, m), 4.48 (2H, t, J=5.89 Hz), 4.60 (2H, t, J=6.57 Hz), 4.84 (2H, td, J=16.02, 2.74 Hz), 5.26 (1H, dt, J=56.25, 3.55 Hz), 6.56 (1H, tt, J=54.50, 3.00 Hz), 7.06 (1H, d, J=7.94 Hz), 7.28 (1H, d, J=2.74 Hz), 7.69 (1H, d, J=2.46 Hz), 7.75 (1H, d, J=8.49 Hz), 7.96 (1H, d, J=8.21 Hz), 9.74 (1H, s); ESIMS found for $C_{22}H_{23}F_3N_8O$ m/z 473.3 (M+1).

1945

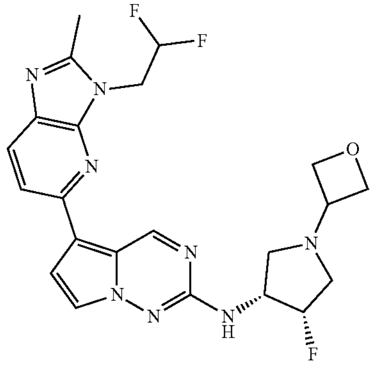

5-(3-(2,2-Difluoroethyl)-2-methyl-3H-imidazo[4,5-b]pyridin-5-yl)-N-((3R,4S)-4-fluoro-1-(oxetan-3-yl)pyrrolidin-3-yl)pyrrolo[2,1-f][1,2,4]triazin-2-amine 1945

Yellow solid (59 mg, 0.125 mmol, 38.5% yield). $^1$H NMR (499 MHz, DMSO-d$_6$) δ ppm 2.61 (3H, s), 2.71 (1H, br t, J=9.17 Hz), 2.80 (1H, dd, J=29.65, 11.80 Hz), 3.04 (1H, br t, J=8.21 Hz), 3.17 (1H, ddd, J=33.45, 12.05, 4.10 Hz), 3.81 (1H, quin, J=5.95 Hz), 4.26-4.40 (1H, m), 4.48 (2H, t, J=5.89 Hz), 4.60 (2H, t, J=6.57 Hz), 4.84 (2H, td, J=15.95, 2.87 Hz), 5.26 (1H, dt, J=56.40, 3.55 Hz), 6.56 (1H, tt, J=54.50, 3.00 Hz), 7.06 (1H, br d, J=7.67 Hz), 7.28 (1H, d, J=2.74 Hz), 7.69 (1H, d, J=2.46 Hz), 7.75 (1H, d, J=8.49 Hz), 7.96 (1H, d, J=8.21 Hz), 9.74 (1H, s); ESIMS found for $C_{22}H_{23}F_3N_8O$ m/z 473.2 (M+1).

1950

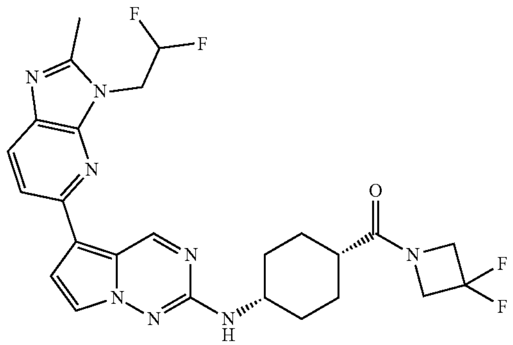

(3,3-Difluoroazetidin-1-yl)(cis-4-((5-(3-(2,2-difluoroethyl)-2-methyl-3H-imidazo[4,5-b]pyridin-5-yl)pyrrolo[2,1-f][1,2,4]triazin-2-yl)amino)cyclohexyl)methanone 1950

Yellow solid (10 mg, 0.019 mmol, 19.1% yield). $^1$H NMR (499 MHz, DMSO-d$_6$) δ ppm 1.49-1.57 (2H, m), 1.60-1.68 (2H, m), 1.77-1.85 (2H, m), 1.86-1.94 (2H, m), 2.44 (1H, tt, J=8.38, 4.07 Hz), 2.61 (3H, s), 3.79 (1H, br d, J=5.48 Hz), 4.46 (4H, dt, J=195.00, 12.35 Hz), 4.83 (2H, td, J=15.95, 2.87 Hz), 6.55 (1H, tt, J=54.60, 3.00 Hz), 6.81 (1H, d, J=6.57 Hz), 7.22 (1H, d, J=2.46 Hz), 7.64 (1H, d, J=2.46 Hz), 7.72 (1H, d, J=8.21 Hz), 7.95 (1H, d, J=8.49 Hz), 9.70 (1H, s); ESIMS found for $C_{25}H_{26}F_4N_8O$ m/z 531.2 (M+1).

1951

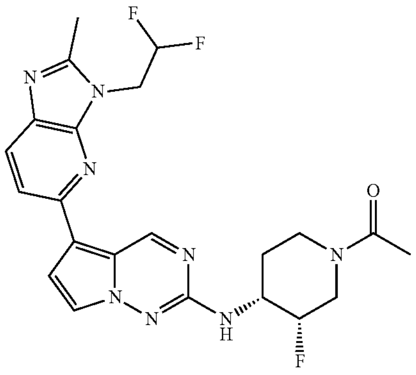

1-((3S,4R)-4-((5-(3-(2,2-Difluoroethyl)-2-methyl-3H-imidazo[4,5-b]pyridin-5-yl)pyrrolo[2,1-f][1,2,4]triazin-2-yl)amino)-3-fluoropiperidin-1-yl)ethan-1-one 1951

Yellow solid (31 mg, 0.066 mmol, 58.8% yield). $^{1}$H NMR (499 MHz, DMSO-$d_6$) δ ppm 1.67-1.90 (2H, m), 1.98-2.07 (3H, m), 2.61 (3H, s), 2.67-2.77 (0.5H, m), 2.84-2.99 (0.5H, m), 3.18-3.27 (0.5H, m), 3.38-3.52 (0.5H, m), 3.91 (0.5H, brd, J=13.14 Hz), 3.98-4.06 (0.5H, m), 4.07-4.18 (1H, m), 4.41-4.49 (0.5H, m), 4.66-4.76 (0.5H, m), 4.84 (2H, td, J=15.95, 2.33 Hz), 4.90-5.06 (1H, m), 6.55 (1H, tt, J=54.50, 3.00 Hz), 7.00 (1H, br d, J=7.94 Hz), 7.27 (1H, d, J=2.74 Hz), 7.66 (1H, d, J=2.74 Hz), 7.74 (1H, d, J=8.21 Hz), 7.96 (1H, d, J=8.21 Hz), 9.74 (1H, s); ESIMS found for $C_{22}H_{23}F_{3}N_{8}O$ m/z 473.25 (M+1).

1952

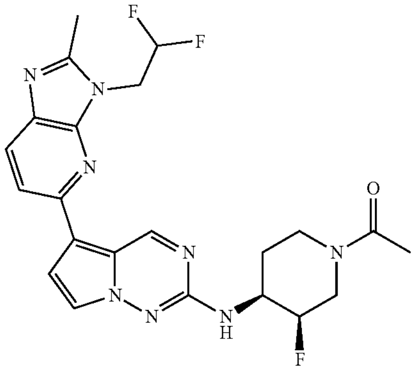

1-((3R,4S)-4-((5-(3-(2,2-Difluoroethyl)-2-methyl-3H-imidazo[4,5-b]pyridin-5-yl)pyrrolo[2,1-f][1,2,4]triazin-2-yl)amino)-3-fluoropiperidin-1-yl)ethan-1-one 1952

Yellow solid (30 mg, 0.064 mmol, 51.6% yield). $^{1}$H NMR (499 MHz, DMSO-$d_6$) δ ppm 1.65-1.75 (1H, m), 1.80 (0.5H, ddd, J=13.21, 9.51, 4.11 Hz), 1.86 (0.5H, dd, J=12.46, 3.97 Hz), 1.98-2.07 (3H, m), 2.61 (3H, s), 2.68-2.76 (0.5H, m), 2.84-2.98 (0.5H, m), 3.18-3.26 (0.5H, m), 3.38-3.51 (0.5H, m), 3.91 (0.5H, br d, J=14.78 Hz), 3.98-4.06 (0.5H, m), 4.06-4.17 (1H, m), 4.40-4.50 (0.5H, m), 4.64-4.75 (0.5H, m), 4.84 (2H, td, J=16.02, 2.74 Hz), 4.91-5.07 (1H, m), 6.55 (1H, tt, J=54.50, 3.00 Hz), 7.00 (1H, d, J=7.94 Hz), 7.27 (1H, d, J=2.74 Hz), 7.66 (1H, d, J=2.74 Hz), 7.74 (1H, d, J=8.49 Hz), 7.96 (1H, d, J=8.49 Hz), 9.74 (1H, s); ESIMS found for $C_{22}H_{23}F_{3}N_{8}O$ m/z 473.2 (M+1).

1953

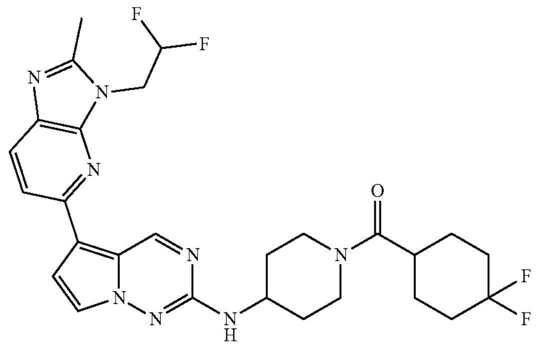

(4,4-Difluorocyclohexyl)(4-((5-(3-(2,2-difluoroethyl)-2-methyl-3H-imidazo[4,5-b]pyridin-5-yl)pyrrolo[2,1-f][1,2,4]triazin-2-yl)amino)piperidin-1-yl)methanone 1953

Yellow solid (18 mg, 0.032 mmol, 44.3% yield). $^{1}$H NMR (499 MHz, DMSO-$d_6$) δ ppm 1.30-1.39 (1H, m), 1.41-1.51 (1H, m), 1.53-1.67 (2H, m), 1.73 (2H, br d, J=13.14 Hz), 1.81-1.92 (1H, m), 1.92-1.98 (2H, m), 1.98-2.12 (3H, m), 2.61 (3H, s), 2.74-2.81 (1H, m), 2.84 (1H, brt, J=11.23 Hz), 3.20 (1H, brt, J=11.91 Hz), 3.82-3.94 (1H, m), 3.99 (1H, br d, J=13.42 Hz), 4.31 (1H, br d, J=12.59 Hz), 4.83 (2H, td, J=16.02, 2.74 Hz), 6.55 (1H, tt, J=54.50, 3.00 Hz), 6.91 (1H, d, J=7.94 Hz), 7.24 (1H, d, J=2.74 Hz), 7.66 (1H, d, J=2.74 Hz), 7.73 (1H, d, J=8.49 Hz), 7.95 (1H, d, J=8.49 Hz), 9.71 (1H, s); ESIMS found for $C_{27}H_{30}F_{4}N_{8}O$ m/z 559.3 (M+1).

1954

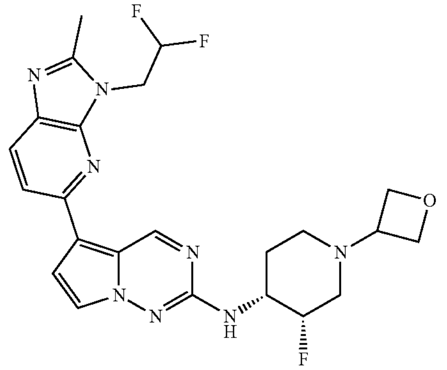

5-(3-(2,2-Difluoroethyl)-2-methyl-3H-imidazo[4,5-b]pyridin-5-yl)-N-((3S,4R)-3-fluoro-1-(oxetan-3-yl)piperidin-4-yl)pyrrolo[2,1-f][1,2,4]triazin-2-amine 1954

Yellow solid (67 mg, 0.138 mmol, 38.0% yield). $^{1}$H NMR (499 MHz, DMSO-$d_6$) δ ppm 1.75 (1H, br d, J=9.86 Hz), 1.92 (1H, qd, J=12.09, 3.42 Hz), 1.99-2.08 (1H, m), 2.17 (1H, dd, J=37.05, 12.90 Hz), 2.61 (3H, s), 2.76 (1H, br d, J=9.31 Hz), 2.99 (1H, br t, J=10.13 Hz), 3.50 (1H, quin, J=6.37 Hz), 3.77-3.94 (1H, m), 4.41 (1H, t, J=6.16 Hz), 4.46 (1H, t, J=6.16 Hz), 4.54 (2H, td, J=6.57, 3.01 Hz), 4.79-4.87 (2H, m), 4.92 (1H, d, J=52.65 Hz), 6.55 (1H, tt, J=54.50, 3.00 Hz), 6.92 (1H, d, J=7.94 Hz), 7.26 (1H, d, J=2.74 Hz), 7.66 (1H, d, J=2.46 Hz), 7.74 (1H, d, J=8.49 Hz), 7.95 (1H, d, J=8.21 Hz), 9.73 (1H, s); ESIMS found for $C_{23}H_{25}F_3N_8O$ m/z 487.3 (M+1).

1955

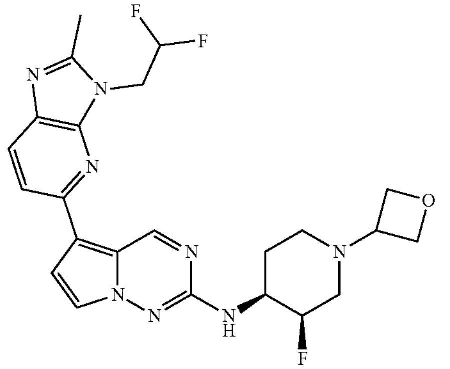

5-(3-(2,2-Difluoroethyl)-2-methyl-3H-imidazo[4,5-b]pyridin-5-yl)-N-((3R,4S)-3-fluoro-1-(oxetan-3-yl)piperidin-4-yl)pyrrolo[2,1-f][1,2,4]triazin-2-amine 1955

Yellow solid (69 mg, 0.142 mmol, 40.7% yield). $^1$H NMR (499 MHz, DMSO-$d_6$) δ ppm 1.71-1.79 (1H, m), 1.92 (1H, qd, J=12.00, 3.70 Hz), 1.99-2.07 (1H, m), 2.17 (1H, dd, J=37.00, 12.90 Hz), 2.61 (3H, s), 2.76 (1H, br d, J=10.68 Hz), 2.95-3.04 (1H, m), 3.50 (1H, quin, J=6.37 Hz), 3.79-3.93 (1H, m), 4.41 (1H, t, J=6.16 Hz), 4.46 (1H, t, J=6.02 Hz), 4.54 (2H, td, J=6.43, 3.01 Hz), 4.79-4.87 (2H, m), 4.93 (1H, d, J=52.65 Hz), 6.55 (1H, tt, J=54.50, 3.00 Hz), 6.92 (1H, d, J=7.94 Hz), 7.26 (1H, d, J=2.74 Hz), 7.66 (1H, d, J=2.74 Hz), 7.74 (1H, d, J=8.49 Hz), 7.96 (1H, d, J=8.21 Hz), 9.73 (1H, s); ESIMS found for $C_{23}H_{25}F_3N_8O$ m/z 487.3 (M+1).

1961

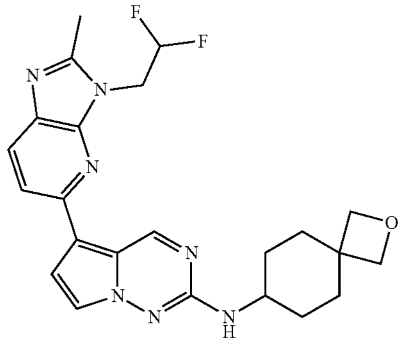

5-(3-(2,2-Difluoroethyl)-2-methyl-3H-imidazo[4,5-b]pyridin-5-yl)-N-(2-oxaspiro[3.5]nonan-7-yl)pyrrolo[2,1-f][1,2,4]triazin-2-amine 1961

Yellow solid (60 mg, 0.132 mmol, 38.5% yield). $^1$H NMR (499 MHz, DMSO-$d_6$) δ ppm 1.21-1.33 (2H, m), 1.53 (2H, td, J=12.87, 3.29 Hz), 1.88 (2H, br dd, J=13.14, 3.29 Hz), 2.07 (2H, br d, J=12.87 Hz), 2.60 (3H, s), 3.50-3.63 (1H, m), 4.24 (2H, s), 4.33 (2H, s), 4.83 (2H, td, J=15.95, 2.87 Hz), 6.55 (1H, tt, J=54.50, 3.00 Hz), 6.71 (1H, d, J=7.94 Hz), 7.22 (1 H, d, J=2.74 Hz), 7.64 (1H, d, J=2.46 Hz), 7.72 (1H, d, J=8.21 Hz), 7.95 (1H, d, J=8.21 Hz), 9.69 (1H, s); ESIMS found for $C_{23}H_{25}F_2N_7O$ m/z 454.25 (M+1).

1970

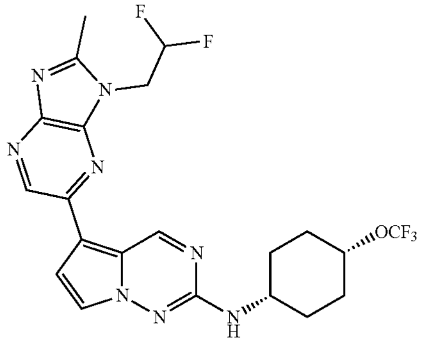

5-(1-(2,2-Difluoroethyl)-2-methyl-1H-imidazo[4,5-b]pyrazin-6-yl)-N-(cis-4-(trifluoromethoxy)cyclohexyl)pyrrolo[2,1-f][1,2,4]triazin-2-amine 1970

White solid (6.52 mg, 0.013 mmol, 10.0% yield). $^1$H NMR (400 MHz, DMSO-$d_6$) δ ppm 1.60-1.80 (4H, m), 1.81-1.89 (2H, m), 1.95 (2H, br dd, J=9.05, 3.91 Hz), 2.68 (3H, s), 3.67-3.80 (1H, m), 4.62 (1H, br d, J=2.69 Hz), 4.84-4.99 (2H, m), 6.56 (1H, tt, J=54.60, 3.00 Hz), 6.98 (1H, d, J=7.95 Hz), 7.39 (1H, d, J=2.69 Hz), 7.70 (1H, d, J=2.32 Hz), 8.97 (1H, s), 9.65 (1H, s); ESIMS found for $C_{21}H_{21}F_5N_8O$ m/z 497.1 (M+1).

1971

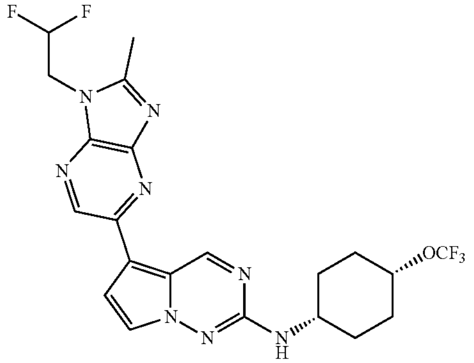

5-(1-(2,2-Difluoroethyl)-2-methyl-1H-imidazo[4,5-b]pyrazin-5-yl)-N-(cis-4-(trifluoromethoxy)cyclohexyl)pyrrolo[2,1-f][1,2,4]triazin-2-amine 1971

White solid (6.75 mg, 0.014 mmol, 10.3% yield). $^1$H NMR (400 MHz, DMSO-$d_6$) δ ppm 1.62-1.80 (4H, m), 1.81-1.89 (2H, m), 1.91-2.02 (2H, m), 2.69 (3H, s), 3.66-3.78 (1H, m), 4.60 (1H, br s), 4.74-4.91 (2H, m), 6.51 (1H, tt, J=54.08, 3.00 Hz), 7.09 (1H, d, J=7.58 Hz), 7.36 (1H, d, J=2.81 Hz), 7.70 (1H, d, J=2.69 Hz), 8.87 (1H, s), 9.57 (1H, s); ESIMS found for $C_{21}H_{21}F_5N_8O$ m/z 497.1 (M+1).

1974

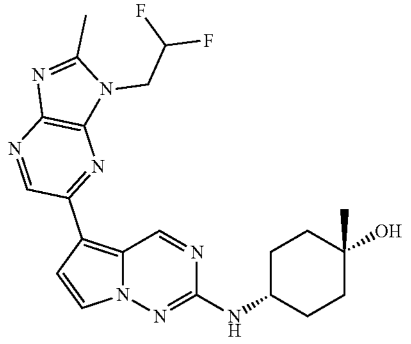

cis-4-((5-(1-(2,2-difluoroethyl)-2-methyl-1H-imidazo[4,5-b]pyrazin-6-yl)pyrrolo[2,1-f][1,2,4]triazin-2-yl)amino)-1-methylcyclohexan-1-ol 1974

Yellow fluffy solid (27 mg, 0.06 mmol, 24.8% yield). $^1$H NMR (400 MHz, DMSO-$d_6$) δ ppm 1.13 (3H, s), 1.31-1.44 (2H, m), 1.54-1.62 (2H, m), 1.64-1.75 (4H, m), 2.68 (3H, s), 3.47-3.62 (1H, m), 4.03 (1H, s), 4.83-4.97 (2H, m), 6.56 (1H, tt, J=54.30, 3.00 Hz), 6.81 (1H, d, J=8.07 Hz), 7.37 (1H, d, J=2.69 Hz), 7.68 (1H, d, J=2.57 Hz), 8.97 (1H, s), 9.63 (1H, s); ESIMS found for $C_{21}H_{24}F_2N_8O$ m/z 443.2 (M+1).

1981

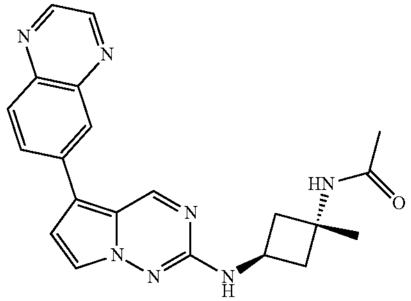

N-((1r,3r)-1-Methyl-3-((5-(quinoxalin-6-yl)pyrrolo[2,1-f][1,2,4]triazin-2-yl)amino)cyclobutyl)acetamide 1981

Yellow solid (14 mg, 0.036 mmol, 40.7% yield). $^1$H NMR (499 MHz, DMSO-$d_6$) δ ppm 1.37 (3H, s), 1.82 (3H, s), 1.90-2.01 (2H, m), 2.66 (2H, ddd, J=10.27, 7.94, 2.60 Hz), 4.20 (1H, sxt, J=7.72 Hz), 7.19 (1H, d, J=2.74 Hz), 7.36 (1H, d, J=7.12 Hz), 7.75 (1H, d, J=2.46 Hz), 7.96 (1H, s), 8.13 (1H, d, J=8.76 Hz), 8.23 (1H, dd, J=8.76, 1.92 Hz), 8.31 (1H, d, J=2.19 Hz), 8.90 (1H, d, J=1.92 Hz), 8.95 (1H, d, J=1.92 Hz), 9.19 (1H, s); ESIMS found for $C_{21}H_{21}N_7O$ m/z 388.2 (M+1).

1980

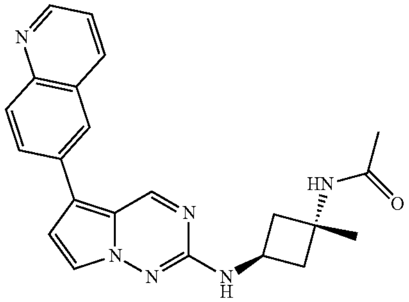

N-((1r,3r)-1-Methyl-3-((5-(quinolin-6-yl)pyrrolo[2,1-f][1,2,4]triazin-2-yl)amino)cyclobutyl)acetamide 1980

Yellow solid (4 mg, 0.010 mmol, 11.7% yield). $^1$H NMR (499 MHz, DMSO-$d_6$) δ ppm 1.37 (3H, s), 1.82 (3H, s), 1.91-2.02 (2H, m), 2.60-2.71 (2H, m), 4.20 (1H, sxt, J=7.72 Hz), 7.09 (1H, d, J=2.74 Hz), 7.30 (1H, d, J=7.12 Hz), 7.54 (1H, dd, J=8.35, 4.24 Hz), 7.73 (1H, d, J=2.46 Hz), 7.95 (1H, s), 8.03-8.07 (1H, m), 8.08-8.12 (1H, m), 8.29 (1H, d, J=1.92 Hz), 8.43 (1H, dd, J=8.35, 1.23 Hz), 8.86 (1H, dd, J=4.24, 1.78 Hz), 9.23 (1H, s); ESIMS found for $C_{22}H_{22}N_6O$ m/z 387.2 (M+1).

1983

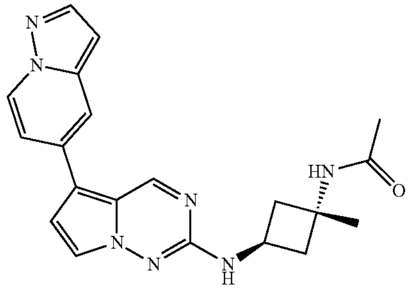

N-(trans-1-Methyl-3-((5-(pyrazolo[1,5-a]pyridin-5-yl)pyrrolo[2,1-f][1,2,4]triazin-2-yl)amino)cyclobutyl)acetamide 1983

Yellow solid (10 mg, 0.027 mmol, 22.5% yield). $^1$H NMR (499 MHz, DMSO-$d_6$) δ ppm 1.36 (3H, s), 1.82 (3H, s), 1.91-2.02 (2H, m), 2.60-2.71 (2H, m), 4.12-4.26 (1H, m), 6.59 (1H, d, J=1.64 Hz), 7.06 (1H, d, J=2.46 Hz), 7.21 (1H, dd, J=7.26, 2.05 Hz), 7.32 (1H, d, J=7.39 Hz), 7.70 (1H, d, J=2.19 Hz), 7.95 (1H, s), 7.98-8.00 (2H, m), 8.67 (1H, d, J=7.12 Hz), 9.17 (1H, s); ESIMS found for $C_{20}H_{21}N_7O$ m/z 376.2 (M+1).

1985

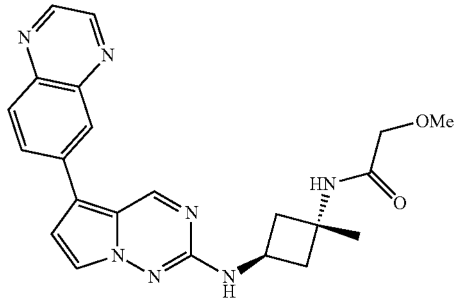

2-Methoxy-N-(trans-1-methyl-3-((5-(quinoxalin-6-yl)pyrrolo[2,1-f][1,2,4]triazin-2-yl)amino)cyclobutyl)acetamide 1985

Yellow solid (8 mg, 0.019 mmol, 14.7% yield). $^1$H NMR (499 MHz, DMSO-$d_6$) δ ppm 1.40 (3H, s), 1.94-2.06 (2H, m), 2.69-2.81 (2H, m), 3.33 (3H, s), 3.79 (2H, s), 4.19 (1H, sxt, J=7.67 Hz), 7.19 (1H, d, J=2.46 Hz), 7.37 (1H, d, J=7.12 Hz), 7.74 (1H, s), 7.76 (1H, d, J=2.46 Hz), 8.13 (1H, d, J=8.76 Hz), 8.23 (1H, dd, J=8.76, 1.92 Hz), 8.31 (1H, d, J=1.92 Hz), 8.90 (1H, d, J=1.92 Hz), 8.95 (1H, d, J=1.64 Hz), 9.19 (1H, s); ESIMS found for $C_{22}H_{23}N_7O_2$ m/z 418.2 (M+1).

Example 13

Representative compounds were screened using the assay procedure for DYRK1A kinase activity as described below.

Each compound was dissolved in DMSO as a 10 mM stock and used to prepare compound source plates. Serial dilution (1:3, 11-point dose-response curves from 10 μM to 0.00016 μM) and compound transfer was performed using the ECHO 550 (Labcyte, Sunnyvale, CA) into 1536-well black-walled round bottom plates (Corning).

The DYRK1A kinase assay was run using the Ser/Thr 18 peptide Z-lyte assay kit according to manufacturer's instructions (Life Technologies-a Division of Thermo-Fisher). This is a non-radioactive assay using fluorescence resonance energy transfer (FRET) between coumarin and fluorescein to detect kinase activity which is represented as a ratio of coumarin emission/fluorescein emission.

Briefly, recombinant DYRK1A kinase, ATP and Ser/Thr peptide 18 were prepared in 1× Kinase buffer to final concentrations of 0.25 μg/mL, 15 μM, and 4 μM respectively. The mixture was allowed to incubate with the representative compounds for one hour at room temperature. All reactions were performed in duplicate. Unphosphorylated ("0% Control") and phosphorylated ("100% control") forms of Ser/Thr 18 served as control reactions. Additionally, an 11-point dose-response curve of Staurosporine (1 uM top) was run to serve as a positive compound control.

After incubation, Development Reagent A was diluted in Development Buffer then added to the reaction and allowed to further incubate for one hour at room temperature. The plate was read at Ex 400 Em 455 to detect the coumarin signal and Ex 400 Em 520 to measure the signal (EnVision Multilabel Plate Reader, PerkinElmer).

The Emission ratio (Em) was calculated as a ratio of the coumarin (C) emission signal (at 445 nm)/Fluorescein (F) emission signal (at 520 nm). The percent phosphorylation was then calculated using the following formula: $[1-((\text{Em ratio}\times F_{100\%})-C_{100\%})/((C_{0\%}-C_{100\%})+(\text{Em ratio}\times(F_{100\%}-F_{0\%})))]$. Dose-response curves were generated, and inhibitory concentration ($IC_{50}$) values were calculated using non-linear regression curve fit in the Dotmatics' Studies Software (Bishops Stortford, UK).

TABLE 2 shows the measured activity for representative compounds of Formula I as described herein.

| Compound | $EC_{50}$ (μM) | Compound | $EC_{50}$ (μM) | Compound | $EC_{50}$ (μM) | Compound | $EC_{50}$ (μM) |
|---|---|---|---|---|---|---|---|
| 2 | 0.041 | 683 | 0.006 | 1747 | 0.003 | 1876 | 0.002 |
| 3 | 0.023 | 684 | 0.004 | 1756 | 0.018 | 1877 | 0.002 |
| 4 | 0.073 | 685 | 0.003 | 1771 | 0.005 | 1878 | 0.002 |
| 9 | 0.081 | 686 | 0.005 | 1780 | 0.007 | 1879 | 0.002 |
| 11 | 0.116 | 687 | 0.002 | 1786 | 0.005 | 1880 | 0.003 |
| 12 | 0.045 | 691 | 0.003 | 1792 | 0.026 | 1881 | 0.002 |
| 16 | 0.048 | 692 | 0.028 | 1798 | 0.004 | 1882 | 0.004 |
| 20 | 0.067 | 706 | 0.005 | 1801 | 0.005 | 1883 | 0.009 |
| 21 | 0.061 | 713 | 0.011 | 1802 | 0.005 | 1884 | 0.007 |
| 23 | 0.028 | 784 | 0.011 | 1803 | 0.003 | 1885 | 0.006 |
| 26 | 0.011 | 855 | 0.043 | 1813 | 0.004 | 1886 | 0.003 |
| 43 | 0.019 | 926 | 0.027 | 1819 | 0.003 | 1887 | 0.031 |
| 64 | 0.192 | 1037 | 0.020 | 1825 | 0.005 | 1888 | 0.003 |
| 65 | 0.025 | 1068 | 0.004 | 1828 | 0.010 | 1889 | 0.007 |
| 66 | 0.264 | 1088 | 0.004 | 1829 | 0.033 | 1890 | 0.014 |
| 67 | 0.040 | 1091 | 3.335 | 1830 | 0.016 | 1891 | 0.011 |
| 74 | 5.100 | 1108 | 0.008 | 1831 | 0.007 | 1892 | 0.002 |
| 145 | 0.045 | 1109 | 0.006 | 1832 | 0.006 | 1893 | 0.005 |
| 214 | 0.033 | 1110 | 0.003 | 1833 | 0.008 | 1894 | 0.011 |
| 215 | 0.006 | 1111 | 0.003 | 1834 | 0.003 | 1895 | 0.003 |
| 216 | 0.012 | 1113 | 0.007 | 1835 | 0.003 | 1896 | 0.003 |
| 218 | 0.013 | 1115 | 0.003 | 1836 | 0.003 | 1898 | 0.003 |
| 219 | 0.014 | 1117 | 0.004 | 1837 | 0.006 | 1899 | 0.001 |
| 220 | 0.014 | 1118 | 0.005 | 1838 | 0.006 | 1900 | 0.005 |
| 221 | 0.029 | 1125 | 0.018 | 1839 | 0.004 | 1901 | 0.004 |
| 223 | 0.101 | 1131 | 0.016 | 1840 | 0.003 | 1902 | 0.006 |
| 225 | 0.011 | 1132 | 0.005 | 1841 | 0.006 | 1903 | 0.012 |
| 226 | 0.011 | 1179 | 0.026 | 1842 | 0.005 | 1906 | 0.004 |
| 227 | 0.004 | 1210 | 0.066 | 1843 | 0.033 | 1908 | 0.007 |
| 228 | 0.013 | 1281 | 0.015 | 1844 | 0.003 | 1909 | 0.005 |
| 229 | 0.009 | 1309 | 0.003 | 1845 | 0.004 | 1910 | 0.004 |
| 230 | 0.058 | 1322 | 0.393 | 1846 | 0.004 | 1911 | 0.004 |
| 231 | 0.028 | 1323 | 0.007 | 1847 | 0.005 | 1912 | 0.007 |
| 232 | 0.009 | 1332 | 0.020 | 1848 | 0.005 | 1914 | 0.005 |
| 235 | 0.377 | 1336 | 0.025 | 1849 | 0.007 | 1915 | 0.009 |
| 236 | 0.009 | 1348 | 0.005 | 1850 | 0.008 | 1916 | 0.005 |
| 237 | 0.003 | 1352 | 0.027 | 1851 | 0.011 | 1917 | 0.009 |
| 239 | 0.006 | 1375 | 0.006 | 1852 | 0.009 | 1918 | 0.007 |
| 240 | 0.014 | 1376 | 0.014 | 1853 | 0.005 | 1920 | 0.001 |
| 242 | 0.005 | 1377 | 0.008 | 1854 | 0.008 | 1940 | 0.007 |
| 244 | 0.005 | 1392 | 0.529 | 1855 | 0.006 | 1941 | 0.004 |
| 256 | 0.005 | 1393 | 0.023 | 1856 | 0.006 | 1944 | 0.013 |
| 258 | 0.010 | 1394 | 0.014 | 1857 | 0.003 | 1945 | 0.001 |
| 259 | 0.007 | 1395 | 0.011 | 1858 | 0.007 | 1950 | 0.003 |
| 260 | 0.009 | 1418 | 0.011 | 1859 | 0.008 | 1951 | 0.005 |
| 263 | 0.006 | 1423 | 0.149 | 1860 | 0.005 | 1952 | 0.004 |
| 265 | 0.006 | 1520 | 0.963 | 1861 | 0.007 | 1953 | 0.007 |
| 279 | 0.049 | 1522 | 0.003 | 1862 | 0.006 | 1954 | 0.006 |
| 280 | 0.015 | 1535 | 0.007 | 1863 | 0.008 | 1955 | 0.004 |
| 281 | 0.003 | 1536 | 0.005 | 1864 | 0.003 | 1961 | 0.003 |
| 282 | 0.007 | 1537 | 0.003 | 1865 | 0.020 | 1970 | 0.007 |
| 283 | 0.020 | 1541 | 0.003 | 1866 | 0.033 | 1971 | 0.379 |
| 287 | 0.170 | 1543 | 0.002 | 1867 | 0.032 | 1974 | 0.002 |
| 358 | 0.025 | 1544 | 0.005 | 1868 | 0.009 | 1980 | 0.001 |
| 398 | 0.012 | 1551 | 0.038 | 1869 | 0.016 | 1981 | 0.002 |
| 429 | 0.654 | 1557 | 0.018 | 1870 | 0.078 | 1983 | 0.001 |
| 500 | 0.044 | 1720 | 0.005 | 1871 | 0.072 | 1985 | 0.003 |
| 571 | 0.011 | 1723 | 0.004 | 1872 | 0.498 | | |
| 642 | 0.004 | 1724 | 0.011 | 1873 | 0.131 | | |
| 682 | 0.004 | 1732 | 0.013 | 1875 | 0.014 | | |

Example 14

Representative compounds were screened using the assay procedure for tau phosphorylation activity described below.

HEK293T cells (ATCC, CRL3216) cultured in DMEM (Thermo Fisher Scientific, 10566024) supplemented with 10% FBS (Corning, 35-011-CV) and Penicillin/Streptomycin (Thermo Fisher Scientific, 15140163) were seeded in a 75 $cm^2$ flask at $8.1\times10^6$ cells/flask. The HEK293T cells were then transiently transfected with 5 μg DYRK1A (NM_001396) human untagged clone (OriGene, SC314641) and 2.5 μg MAPT (441 a.a. Tau gene) (NM_005910) human untagged clone (OriGene, TP313312) using Lipofectamine 3000 (Thermo Fisher Scientific, L30000015) and incubated for 20-30 hours in a humidified incubator at 37° C. and 5% $CO^2$. Post-incubation, HEK293T cells transfected with the DYRK1A and MAPT expression vectors were harvested and seeded in BioCoat poly-D lysine coated 96-well plates (Corning, 354461) at $3\times10^4$ cells/well.

The above synthesized compounds were screened using the cell assay procedure to assess decreased Tau phosphorylation at Thr212 (pThr212) described below.

Each compound was dissolved in DMSO (Sigma-Aldrich, D8418-100 mL) as a 10 mM stock. 10 mM stocks were serially diluted 1:3, 10-point dose-response curve and added to the cells with a final concentration ranging from 20 μM to 1.1 nM. Cells were treated with compounds in duplicate and incubated for 18-24 hours in a humidified incubator at 37° C. and 5% $CO^2$.

Following the overnight compound treatment, cells were lysed with 1× Alpha Surefire Ultra Lysis Buffer (Perkin Elmer, ALSU-LB-100ML) complemented with 1× Halt Phosphatase Inhibitor Cocktail (Thermo Fisher Scientific, 78427) and 1× Halt Protease Inhibitor Cocktail (Thermo Fisher Scientific, 78438). Lysates were spun down at 12,000 g for 10 min to remove any cellular debris and 5 μL of lysates were dispensed into a 384-well Opti-Plate (Perkin Elmer, 6007290) for the measurement of Tau phosphorylation in the phosphoTau (Thr212) AlphaLISA assay. Donor antibody, biotinylated HT7Tau (Thermo Fisher Scientific, MN1000B), and acceptor antibody, pThr212Tau (Thermo Fisher Scientific, 44740G) were both added to the cell lysates at a final concentration of 3 nM and incubated for 1 hour at room temperature. Following incubation of the lysates with the donor and acceptor antibodies, anti-rabbit IgG (Fc specific) AlphaLISA acceptor beads (Perkin Elmer, AL104C) were added at a 10 ug/mL final concentration and incubated for 1 hour at room temperature protected from light. Lastly, AlphaScreen streptavidin donor beads (PerkinElmer, 6760002) were added at 40 ug/mL final concentration and incubated for 1 hour at room temperature protected from light. Plates were read at Ex=665 nm, and Em=615 nm on the EnVision Multilabel Plate Reader (Perkin Elmer)

phospho-Tau (Thr212) AlphaLISA signal was used to plot, draw the curve fitting, and determine each compound's $EC_{50}$ in Prism (GraphPad).

TABLE 3 shows the activity of representative compounds as provided herein.

| Compound | pTau (Thr212) $EC_{50}$ (μM) | Compound | pTau (Thr212) $EC_{50}$ (μM) | Compound | pTau (Thr212) $EC_{50}$ (μM) | Compound | pTau (Thr212) $EC_{50}$ (μM) |
|---|---|---|---|---|---|---|---|
| 3 | 1.841 | 256 | 0.220 | 1068 | 0.159 | 1395 | 0.380 |
| 23 | 0.794 | 259 | 0.150 | 1108 | 0.126 | 1418 | 0.212 |
| 26 | 0.238 | 281 | 0.070 | 1111 | 0.071 | 1724 | 0.305 |
| 43 | 0.504 | 282 | 0.172 | 1179 | 0.470 | 1801 | 0.152 |
| 65 | 0.828 | 571 | 0.725 | 1332 | 0.524 | | |
| 216 | 0.455 | 784 | 0.516 | 1393 | 0.718 | | |
| 228 | 0.292 | 1037 | 0.403 | 1394 | 0.709 | | |

What is claimed is:

1. A compound, or a pharmaceutically acceptable salt thereof, of Formula I:

I

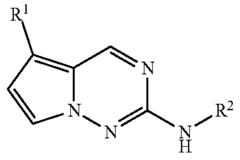

wherein:

$R^1$ is heteroaryl optionally substituted with 1-10 $R^3$; wherein the heteroaryl is selected from the group consisting of:

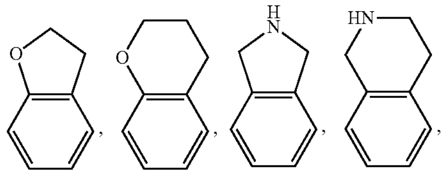

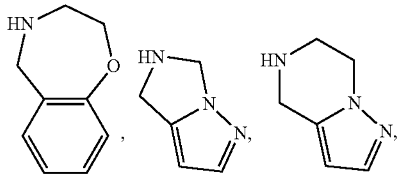

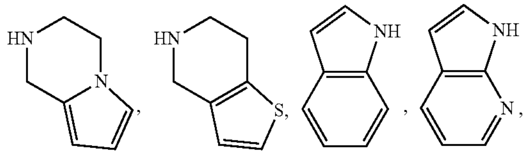

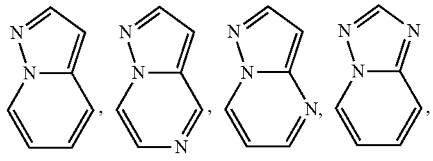

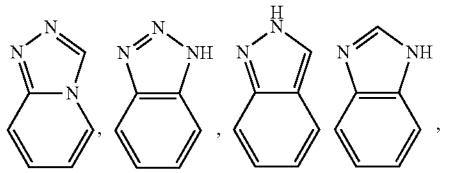

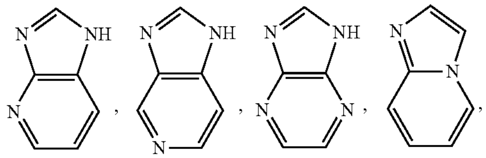

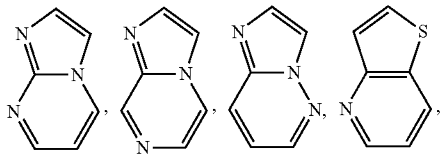

-continued

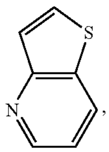, 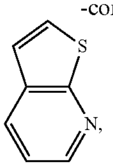, 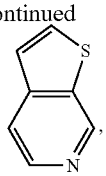, 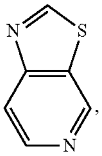,

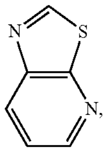, 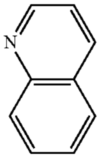, 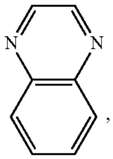, 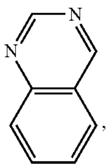,

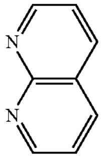, 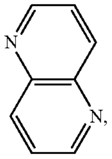, and 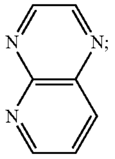;

$R^2$ is selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$OR$^4$, —($C_{1-5}$ alkylene)$_p$heterocyclyl optionally substituted with 1-10 $R^5$, -heteroaryl optionally substituted with 1-10 $R^6$, and —($C_{1-5}$ alkylene)$_p$carbocyclyl optionally substituted with 1-12 $R^7$, wherein each —($C_{1-5}$ alkylene) is, independently, optionally substituted with 1-5 halide and/or 1-3 unsubstituted —($C_{1-3}$ alkyl);

each $R^3$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$-OR$^B$, —($C_{1-5}$ alkylene)CN, —($C_{1-5}$ alkylene)$_p$heterocyclyl optionally substituted with 1-10 $R^9$, -carbocyclyl optionally substituted with 1-12 $R^{10}$, —($C_{1-5}$ alkylene)$_p$ heteroaryl optionally substituted with 1-10 $R^{19}$, —($C_{1-5}$ alkylene)$_p$C(=O)N($R^{11}$)$_2$, and —C(=O)$R^{12}$, wherein each —($C_{1-5}$ alkylene) is, independently, optionally substituted with 1-5 halide and/or 1-3 unsubstituted —($C_{1-3}$ alkyl);

each $R^4$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^5$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), -heterocyclyl optionally substituted with 1-10 $R^{15}$, —($C_{1-5}$ alkylene)$_p$OR$^{20}$, —SO$_2$R$^{22}$, and —C(=O)$R^{23}$, wherein the —($C_{1-5}$ alkylene) is optionally substituted with 1-5 halide and/or 1-3 unsubstituted —($C_{1-3}$ alkyl);

alternatively, two $R^5$ attached to the same carbon atom are taken together to form a carbonyl group;

each $R^6$ is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —OMe;

each R is independently selected from the group consisting of halide, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —N($R^{13}$)$_2$, —($C_{1-5}$ alkylene)$_p$OR$^{14}$, —($C_{1-5}$ alkylene)$_p$heterocyclyl optionally substituted with 1-10 $R^{15}$, —C(=O)$R^{21}$, and —NH(=O)$R^{22}$, wherein each —($C_{1-5}$ alkylene) is, independently, optionally substituted with 1-5 halide and/or 1-3 unsubstituted —($C_{1-3}$ alkyl);

each $R^8$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^9$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{10}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{11}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), —($C_{1-5}$ alkylene)$_p$-carbocyclyl optionally substituted with 1-12 $R^{16}$, -heterocyclyl optionally substituted with 1-10 $R^{17}$, and -heteroaryl optionally substituted with 1-10 $R^{18}$, wherein the —($C_{1-5}$ alkylene) is optionally substituted with 1-5 halide and/or 1-3 unsubstituted —($C_{1-3}$ alkyl);

each $R^{12}$ is -heterocyclyl optionally substituted with 1-10 $R^{17}$;

each $R^{13}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{14}$ is independently selected from the group consisting of H, unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —($C_{1-5}$ alkylene)$_p$OR$^{20}$;

each $R^{15}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

alternatively, two $R^{15}$ attached to the same carbon atom are taken together to form a carbonyl group;

each $R^{16}$ is independently selected from the group consisting of halide, —OMe, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{17}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{18}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{19}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{20}$ is independently selected from the group consisting of H, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each $R^{21}$ is independently selected from the group consisting of -heterocyclyl optionally substituted with 1-10 $R^{17}$, —N($R^{11}$)$_2$ and —OR$^{20}$;

each $R^{22}$ is independently selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and —($C_{1-5}$ alkylene)$_p$OR$^{20}$;

each $R^{23}$ is independently selected from the group consisting of unsubstituted —($C_{1-9}$ alkyl), unsubstituted —($C_{2-9}$ alkenyl), unsubstituted —($C_{2-9}$ alkynyl), unsubstituted —($C_{1-9}$ haloalkyl), and -carbocyclyl optionally substituted with 1-12 $R^{24}$;

each $R^{24}$ is independently selected from the group consisting of halide, unsubstituted —($C_{1-9}$ alkyl), unsubstituted —($C_{2-9}$ alkenyl), unsubstituted —($C_{2-9}$ alkynyl), and unsubstituted —($C_{1-9}$ haloalkyl);

each p is independently 0 or 1; and wherein each H atom is optionally, independently replaced by $^2$H (D) (deuterium).

2. The compound of claim 1, wherein $R^1$ is selected from the group consisting of:

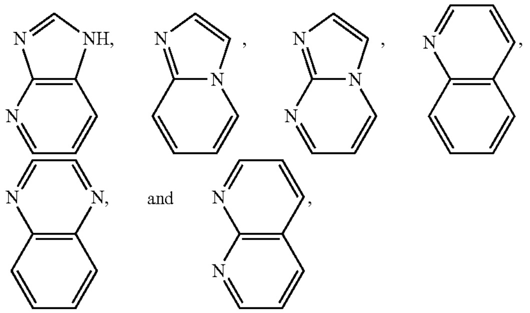
and optionally substituted with 1-10 $R^3$.

3. The compound of claim 2, wherein $R^1$ is selected from the group consisting of:

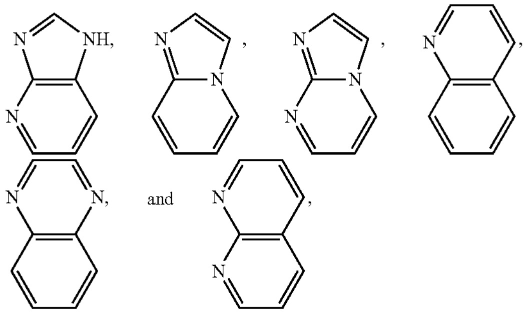
and optionally substituted with 1-3 $R^3$.

4. The compound of claim 3, wherein $R^1$ is selected from the group consisting of:

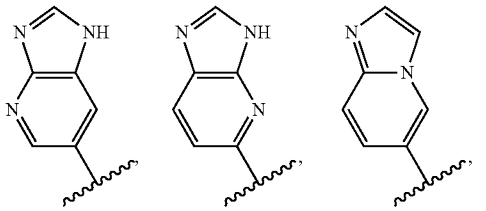

-continued

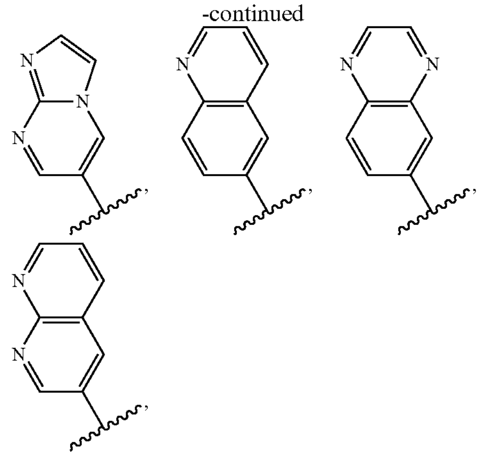
and optionally substituted with 1-3 $R^3$.

5. The compound of claim 3, wherein $R^1$ is selected from the group consisting of:

unsubstituted

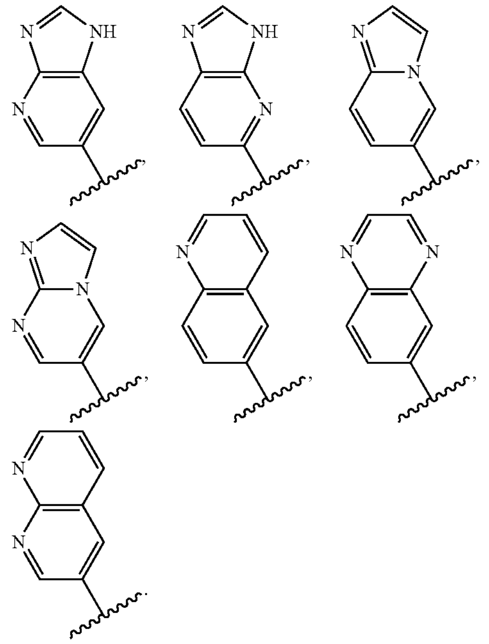
and

6. The compound of claim 4, wherein $R^3$ is selected from the group consisting of halide, unsubstituted —($C_{1-4}$ alkyl), unsubstituted —($C_{1-4}$ haloalkyl), -heterocyclyl optionally substituted with 1-3 $R^9$, and -carbocyclyl optionally substituted with 1-3 $R^{10}$.

7. The compound of claim 1, wherein $R^2$ is selected from the group consisting of unsubstituted —($C_{1-5}$ alkyl), unsubstituted —($C_{1-5}$ haloalkyl), —($C_{1-2}$ alkylene)$_p$heterocyclyl optionally substituted with 1-3 $R^5$, and —($C_{1-2}$ alkylene)$_p$carbocyclyl optionally substituted with 1-3 $R^7$, wherein each —($C_{1-5}$ alkylene) is, independently, optionally substituted with 1-2 halide.

8. The compound of claim 1, wherein the compound of Formula I is selected from the group consisting of 5-(imidazo[1,2-a]pyridin-6-yl)-N-isopropylpyrrolo[2,1-f][1,2,4]triazin-2-amine [1];

5-(imidazo[1,2-a]pyridin-6-yl)-N-isobutylpyrrolo[2,1-f][1,2,4]triazin-2-amine [2];

N-(2-fluoro-2-methylpropyl)-5-(imidazo[1,2-a]pyridin-6-yl)pyrrolo[2,1-f][1,2,4]triazin-2-amine [3];

N-(2,2-difluoropropyl)-5-(imidazo[1,2-a]pyridin-6-yl)pyrrolo[2,1-f][1,2,4]triazin-2-amine [4];

5-(imidazo[1,2-a]pyridin-6-yl)-N-(2,2,2-trifluoroethyl)pyrrolo[2,1-f][1,2,4]triazin-2-amine [5];

(R)-5-(imidazo[1,2-a]pyridin-6-yl)-N-(1,1,1-trifluoropropan-2-yl)pyrrolo[2,1-f][1,2,4]triazin-2-amine [6];

5-(imidazo[1,2-a]pyridin-6-yl)-N-(3,3,3-trifluoropropyl)pyrrolo[2,1-f][1,2,4]triazin-2-amine [7];

5-(imidazo[1,2-a]pyridin-6-yl)-N-(3,3,3-trifluoro-2,2-dimethylpropyl)pyrrolo[2,1-f][1,2,4]triazin-2-amine [8];

5-(imidazo[1,2-a]pyridin-6-yl)-N-(2-methoxyethyl)pyrrolo[2,1-f][1,2,4]triazin-2-amine [9];

(R)-5-(imidazo[1,2-a]pyridin-6-yl)-N-(1-methoxypropan-2-yl)pyrrolo[2,1-f][1,2,4]triazin-2-amine [10];

5-(imidazo[1,2-a]pyridin-6-yl)-N-(2-isopropoxyethyl)pyrrolo[2,1-f][1,2,4]triazin-2-amine [11];

5-(imidazo[1,2-a]pyridin-6-yl)-N-((1-methylcyclopropyl)methyl)pyrrolo[2,1-f][1,2,4]triazin-2-amine [12];

5-(imidazo[1,2-a]pyridin-6-yl)-N-((1-(trifluoromethyl)cyclopropyl)methyl)pyrrolo[2,1-f][1,2,4]triazin-2-amine [13];

N-((1-fluorocyclobutyl)methyl)-5-(imidazo[1,2-a]pyridin-6-yl)pyrrolo[2,1-f][1,2,4]triazin-2-amine [14];

N-((3-fluorooxetan-3-yl)methyl)-5-(imidazo[1,2-a]pyridin-6-yl)pyrrolo[2,1-f][1,2,4]triazin-2-amine [15];

N-(cyclopropylmethyl)-5-(imidazo[1,2-a]pyridin-6-yl)pyrrolo[2,1-f][1,2,4]triazin-2-amine [16];

(S)—N-(1-cyclopropylethyl)-5-(imidazo[1,2-a]pyridin-6-yl)pyrrolo[2,1-f][1,2,4]triazin-2-amine [17];

(R)—N-(1-cyclopropylethyl)-5-(imidazo[1,2-a]pyridin-6-yl)pyrrolo[2,1-f][1,2,4]triazin-2-amine [18];

N-(2-cyclopropyl-2,2-difluoroethyl)-5-(imidazo[1,2-a]pyridin-6-yl)pyrrolo[2,1-f][1,2,4]triazin-2-amine [19];

5-(imidazo[1,2-a]pyridin-6-yl)-N-(oxetan-3-ylmethyl)pyrrolo[2,1-f][1,2,4]triazin-2-amine [20];

5-(imidazo[1,2-a]pyridin-6-yl)-N-((tetrahydrofuran-2-yl)methyl)pyrrolo[2,1-f][1,2,4]triazin-2-amine [21];

N-cyclobutyl-5-(imidazo[1,2-a]pyridin-6-yl)pyrrolo[2,1-f][1,2,4]triazin-2-amine [22];

N-(3,3-difluorocyclobutyl)-5-(imidazo[1,2-a]pyridin-6-yl)pyrrolo[2,1-f][1,2,4]triazin-2-amine [23];

N-(3,3-dimethylcyclobutyl)-5-(imidazo[1,2-a]pyridin-6-yl)pyrrolo[2,1-f][1,2,4]triazin-2-amine [24];

3-((5-(imidazo[1,2-a]pyridin-6-yl)pyrrolo[2,1-f][1,2,4]triazin-2-yl)amino)-1-methylcyclobutan-1-ol [25];

5-(imidazo[1,2-a]pyridin-6-yl)-N-(cis-3-methoxycyclobutyl)pyrrolo[2,1-f][1,2,4]triazin-2-amine [26];

5-(imidazo[1,2-a]pyridin-6-yl)-N-(trans-3-methoxycyclobutyl)pyrrolo[2,1-f][1,2,4]triazin-2-amine [27];

5-(imidazo[1,2-a]pyridin-6-yl)-N-(trans-3-(methoxymethyl)cyclobutyl)pyrrolo[2,1-f][1,2,4]triazin-2-amine [28];

N-(cis-3-ethoxycyclobutyl)-5-(imidazo[1,2-a]pyridin-6-yl)pyrrolo[2,1-f][1,2,4]triazin-2-amine [29];

N-(trans-3-ethoxycyclobutyl)-5-(imidazo[1,2-a]pyridin-6-yl)pyrrolo[2,1-f][1,2,4]triazin-2-amine [30];

5-(imidazo[1,2-a]pyridin-6-yl)-N-(cis-3-(2-methoxyethoxy)cyclobutyl)pyrrolo[2,1-f][1,2,4]triazin-2-amine [31];

5-(imidazo[1,2-a]pyridin-6-yl)-N-(trans-3-(2-methoxyethoxy)cyclobutyl)pyrrolo[2,1-f][1,2,4]triazin-2-amine [32];

cis-$N^1$-(5-(imidazo[1,2-a]pyridin-6-yl)pyrrolo[2,1-f][1,2,4]triazin-2-yl)cyclobutane-1,3-diamine [33];

trans-$N^1$-(5-(imidazo[1,2-a]pyridin-6-yl)pyrrolo[2,1-f][1,2,4]triazin-2-yl)cyclobutane-1,3-diamine [34];

cis-$N^1$-(5-(imidazo[1,2-a]pyridin-6-yl)pyrrolo[2,1-f][1,2,4]triazin-2-yl)-$N^3$-methylcyclobutane-1,3-diamine [35];

trans-$N^1$-(5-(imidazo[1,2-a]pyridin-6-yl)pyrrolo[2,1-f][1,2,4]triazin-2-yl)-$N^3$-methylcyclobutane-1,3-diamine [36];

cis-$N^1$-(5-(imidazo[1,2-a]pyridin-6-yl)pyrrolo[2,1-f][1,2,4]triazin-2-yl)-$N^3$,$N^3$-dimethylcyclobutane-1,3-diamine [37];

trans-$N^1$-(5-(imidazo[1,2-a]pyridin-6-yl)pyrrolo[2,1-f][1,2,4]triazin-2-yl)-$N^3$,$N^3$-dimethylcyclobutane-1,3-diamine [38];

5-(imidazo[1,2-a]pyridin-6-yl)-N-(cis-3-morpholinocyclobutyl)pyrrolo[2,1-f][1,2,4]triazin-2-amine [39];

5-(imidazo[1,2-a]pyridin-6-yl)-N-(trans-3-morpholinocyclobutyl)pyrrolo[2,1-f][1,2,4]triazin-2-amine [40];

5-(imidazo[1,2-a]pyridin-6-yl)-N-(cis-3-(4-methylpiperazin-1-yl)cyclobutyl)pyrrolo[2,1-f][1,2,4]triazin-2-amine [41];

5-(imidazo[1,2-a]pyridin-6-yl)-N-(trans-3-(4-methylpiperazin-1-yl)cyclobutyl)pyrrolo[2,1-f][1,2,4]triazin-2-amine [42];

N-(4,4-difluorocyclohexyl)-5-(imidazo[1,2-a]pyridin-6-yl)pyrrolo[2,1-f][1,2,4]triazin-2-amine [43];

cis-4-((5-(imidazo[1,2-a]pyridin-6-yl)pyrrolo[2,1-f][1,2,4]triazin-2-yl)amino)cyclohexan-1-ol [44];

(1s,4s)-4-((5-(imidazo[1,2-a]pyridin-6-yl)pyrrolo[2,1-f][1,2,4]triazin-2-yl)amino)-1-methylcyclohexan-1-ol [45];

5-(imidazo[1,2-a]pyridin-6-yl)-N-(cis-4-methoxycyclohexyl)pyrrolo[2,1-f][1,2,4]triazin-2-amine [46];

5-(imidazo[1,2-a]pyridin-6-yl)-N-(trans-4-methoxycyclohexyl)pyrrolo[2,1-f][1,2,4]triazin-2-amine [47];

N-(cis-4-(difluoromethoxy)cyclohexyl)-5-(imidazo[1,2-a]pyridin-6-yl)pyrrolo[2,1-f][1,2,4]triazin-2-amine [48];

N-(trans-4-(difluoromethoxy)cyclohexyl)-5-(imidazo[1,2-a]pyridin-6-yl)pyrrolo[2,1-f][1,2,4]triazin-2-amine [49];

N-(cis-4-ethoxycyclohexyl)-5-(imidazo[1,2-a]pyridin-6-yl)pyrrolo[2,1-f][1,2,4]triazin-2-amine [50];

N-(trans-4-ethoxycyclohexyl)-5-(imidazo[1,2-a]pyridin-6-yl)pyrrolo[2,1-f][1,2,4]triazin-2-amine [51];

5-(imidazo[1,2-a]pyridin-6-yl)-N-(cis-4-(2-methoxyethoxy)cyclohexyl)pyrrolo[2,1-f][1,2,4]triazin-2-amine [52];

5-(imidazo[1,2-a]pyridin-6-yl)-N-(trans-4-(2-methoxyethoxy)cyclohexyl)pyrrolo[2,1-f][1,2,4]triazin-2-amine [53];

cis-$N^1$-(5-(imidazo[1,2-a]pyridin-6-yl)pyrrolo[2,1-f][1,2,4]triazin-2-yl)cyclohexane-1,4-diamine [54];

trans-$N^1$-(5-(imidazo[1,2-a]pyridin-6-yl)pyrrolo[2,1-f][1,2,4]triazin-2-yl)cyclohexane-1,4-diamine [55];

cis-$N^1$-(5-(imidazo[1,2-a]pyridin-6-yl)pyrrolo[2,1-f][1,2,4]triazin-2-yl)-$N^4$-methylcyclohexane-1,4-diamine [56];

trans-$N^1$-(5-(imidazo[1,2-a]pyridin-6-yl)pyrrolo[2,1-f][1,2,4]triazin-2-yl)-$N^4$-methylcyclohexane-1,4-diamine [57];

cis-$N^1$-(5-(imidazo[1,2-a]pyridin-6-yl)pyrrolo[2,1-f][1,2,4]triazin-2-yl)-$N^4$,$N^4$-dimethylcyclohexane-1,4-diamine [58];

trans-$N^1$-(5-(imidazo[1,2-a]pyridin-6-yl)pyrrolo[2,1-f][1,2,4]triazin-2-yl)-$N^4$,$N^4$-dimethylcyclohexane-1,4-diamine [59];

5-(imidazo[1,2-a]pyridin-6-yl)-N-(cis-4-morpholinocyclohexyl)pyrrolo[2,1-f][1,2,4]triazin-2-amine [60];

5-(imidazo[1,2-a]pyridin-6-yl)-N-(trans-4-morpholinocyclohexyl)pyrrolo[2,1-f][1,2,4]triazin-2-amine [61];

5-(imidazo[1,2-a]pyridin-6-yl)-N-(cis-4-(4-methylpiperazin-1-yl)cyclohexyl)pyrrolo[2,1-f][1,2,4]triazin-2-amine [62];

5-(imidazo[1,2-a]pyridin-6-yl)-N-(trans-4-(4-methylpiperazin-1-yl)cyclohexyl)pyrrolo[2,1-f][1,2,4]triazin-2-amine [63];

5-(imidazo[1,2-a]pyridin-6-yl)-N-(1-methylazetidin-3-yl)pyrrolo[2,1-f][1,2,4]triazin-2-amine [64];

5-(imidazo[1,2-a]pyridin-6-yl)-N-(oxetan-3-yl)pyrrolo[2,1-f][1,2,4]triazin-2-amine [65];

5-(imidazo[1,2-a]pyridin-6-yl)-N-(1-methylpiperidin-4-yl)pyrrolo[2,1-f][1,2,4]triazin-2-amine [66];

5-(imidazo[1,2-a]pyridin-6-yl)-N-(tetrahydro-2H-pyran-4-yl)pyrrolo[2,1-f][1,2,4]triazin-2-amine [67];

N-(6,6-difluorospiro[3.3]heptan-2-yl)-5-(imidazo[1,2-a]pyridin-6-yl)pyrrolo[2,1-f][1,2,4]triazin-2-amine [68];

5-(imidazo[1,2-a]pyridin-6-yl)-N-(2-oxaspiro[3.3]heptan-6-yl)pyrrolo[2,1-f][1,2,4]triazin-2-amine [69];

5-(imidazo[1,2-a]pyridin-6-yl)-N-(2-methyl-2-azaspiro[3.3]heptan-6-yl)pyrrolo[2,1-f][1,2,4]triazin-2-amine [70];

5-(imidazo[1,2-a]pyridin-6-yl)-N-(1-methyl-1H-pyrazol-4-yl)pyrrolo[2,1-f][1,2,4]triazin-2-amine [71];

(6-(2-(isopropylamino)pyrrolo[2,1-f][1,2,4]triazin-5-yl)imidazo[1,2-a]pyridin-3-yl)(pyrrolidin-1-yl)methanone [72];

(6-(2-(isobutylamino)pyrrolo[2,1-f][1,2,4]triazin-5-yl)imidazo[1,2-a]pyridin-3-yl)(pyrrolidin-1-yl)methanone [73];

(6-(2-((2-fluoro-2-methylpropyl)amino)pyrrolo[2,1-f][1,2,4]triazin-5-yl)imidazo[1,2-a]pyridin-3-yl)(pyrrolidin-1-yl)methanone [74];

(6-(2-((2,2-difluoropropyl)amino)pyrrolo[2,1-f][1,2,4]triazin-5-yl)imidazo[1,2-a]pyridin-3-yl)(pyrrolidin-1-yl)methanone [75];

pyrrolidin-1-yl(6-(2-((2,2,2-trifluoroethyl)amino)pyrrolo[2,1-f][1,2,4]triazin-5-yl)imidazo[1,2-a]pyridin-3-yl)methanone [76];

(R)-pyrrolidin-1-yl(6-(2-((1,1,1-trifluoropropan-2-yl)amino)pyrrolo[2,1-f][1,2,4]triazin-5-yl)imidazo[1,2-a]pyridin-3-yl)methanone [77];

pyrrolidin-1-yl(6-(2-((3,3,3-trifluoropropyl)amino)pyrrolo[2,1-f][1,2,4]triazin-5-yl)imidazo[1,2-a]pyridin-3-yl)methanone [78];

pyrrolidin-1-yl(6-(2-((3,3,3-trifluoro-2,2-dimethylpropyl)amino)pyrrolo[2,1-f][1,2,4]triazin-5-yl)imidazo[1,2-a]pyridin-3-yl)methanone [79];

(6-(2-((2-methoxyethyl)amino)pyrrolo[2,1-f][1,2,4]triazin-5-yl)imidazo[1,2-a]pyridin-3-yl)(pyrrolidin-1-yl)methanone [80];

(R)-(6-(2-((1-methoxypropan-2-yl)amino)pyrrolo[2,1-f][1,2,4]triazin-5-yl)imidazo[1,2-a]pyridin-3-yl)(pyrrolidin-1-yl)methanone [81];

(6-(2-((2-isopropoxyethyl)amino)pyrrolo[2,1-f][1,2,4]triazin-5-yl)imidazo[1,2-a]pyridin-3-yl)(pyrrolidin-1-yl)methanone [82];

(6-(2-(((1-methylcyclopropyl)methyl)amino)pyrrolo[2,1-f][1,2,4]triazin-5-yl)imidazo[1,2-a]pyridin-3-yl)(pyrrolidin-1-yl)methanone [83];

pyrrolidin-1-yl(6-(2-(((1-(trifluoromethyl)cyclopropyl)methyl)amino)pyrrolo[2,1-f][1,2,4]triazin-5-yl)imidazo[1,2-a]pyridin-3-yl)methanone [84];

(6-(2-(((1-fluorocyclobutyl)methyl)amino)pyrrolo[2,1-f][1,2,4]triazin-5-yl)imidazo[1,2-a]pyridin-3-yl)(pyrrolidin-1-yl)methanone [85];

(6-(2-(((3-fluorooxetan-3-yl)methyl)amino)pyrrolo[2,1-f][1,2,4]triazin-5-yl)imidazo[1,2-a]pyridin-3-yl)(pyrrolidin-1-yl)methanone [86];

(6-(2-((cyclopropylmethyl)amino)pyrrolo[2,1-f][1,2,4]triazin-5-yl)imidazo[1,2-a]pyridin-3-yl)(pyrrolidin-1-yl)methanone [87];

(S)-(6-(2-((1-cyclopropylethyl)amino)pyrrolo[2,1-f][1,2,4]triazin-5-yl)imidazo[1,2-a]pyridin-3-yl)(pyrrolidin-1-yl)methanone [88];

(R)-(6-(2-((1-cyclopropylethyl)amino)pyrrolo[2,1-f][1,2,4]triazin-5-yl)imidazo[1,2-a]pyridin-3-yl)(pyrrolidin-1-yl)methanone [89];

(6-(2-((2-cyclopropyl-2,2-difluoroethyl)amino)pyrrolo[2,1-f][1,2,4]triazin-5-yl)imidazo[1,2-a]pyridin-3-yl)(pyrrolidin-1-yl)methanone [90];

(6-(2-((oxetan-3-ylmethyl)amino)pyrrolo[2,1-f][1,2,4]triazin-5-yl)imidazo[1,2-a]pyridin-3-yl)(pyrrolidin-1-yl)methanone [91];

pyrrolidin-1-yl(6-(2-(((tetrahydrofuran-2-yl)methyl)amino)pyrrolo[2,1-f][1,2,4]triazin-5-yl)imidazo[1,2-a]pyridin-3-yl)methanone [92];

(6-(2-(cyclobutylamino)pyrrolo[2,1-f][1,2,4]triazin-5-yl)imidazo[1,2-a]pyridin-3-yl)(pyrrolidin-1-yl)methanone [93];

(6-(2-((3,3-difluorocyclobutyl)amino)pyrrolo[2,1-f][1,2,4]triazin-5-yl)imidazo[1,2-a]pyridin-3-yl)(pyrrolidin-1-yl)methanone [94];

(6-(2-((3,3-dimethylcyclobutyl)amino)pyrrolo[2,1-f][1,2,4]triazin-5-yl)imidazo[1,2-a]pyridin-3-yl)(pyrrolidin-1-yl)methanone [95];

(6-(2-((3-hydroxy-3-methylcyclobutyl)amino)pyrrolo[2,1-f][1,2,4]triazin-5-yl)imidazo[1,2-a]pyridin-3-yl)(pyrrolidin-1-yl)methanone [96];

(6-(2-((cis-3-methoxycyclobutyl)amino)pyrrolo[2,1-f][1,2,4]triazin-5-yl)imidazo[1,2-a]pyridin-3-yl)(pyrrolidin-1-yl)methanone [97];

(6-(2-((trans-3-methoxycyclobutyl)amino)pyrrolo[2,1-f][1,2,4]triazin-5-yl)imidazo[1,2-a]pyridin-3-yl)(pyrrolidin-1-yl)methanone [98];

(6-(2-((trans-3-(methoxymethyl)cyclobutyl)amino)pyrrolo[2,1-f][1,2,4]triazin-5-yl)imidazo[1,2-a]pyridin-3-yl)(pyrrolidin-1-yl)methanone [99];

(6-(2-((cis-3-ethoxycyclobutyl)amino)pyrrolo[2,1-f][1,2,4]triazin-5-yl)imidazo[1,2-a]pyridin-3-yl)(pyrrolidin-1-yl)methanone [100];

(6-(2-((trans-3-ethoxycyclobutyl)amino)pyrrolo[2,1-f][1,2,4]triazin-5-yl)imidazo[1,2-a]pyridin-3-yl)(pyrrolidin-1-yl)methanone [101];

(6-(2-((cis-3-(2-methoxyethoxy)cyclobutyl)amino)pyrrolo[2,1-f][1,2,4]triazin-5-yl)imidazo[1,2-a]pyridin-3-yl)(pyrrolidin-1-yl)methanone [102];

(6-(2-((trans-3-(2-methoxyethoxy)cyclobutyl)amino)pyrrolo[2,1-f][1,2,4]triazin-5-yl)imidazo[1,2-a]pyridin-3-yl)(pyrrolidin-1-yl)methanone [103];

(6-(2-((cis-3-aminocyclobutyl)amino)pyrrolo[2,1-f][1,2,4]triazin-5-yl)imidazo[1,2-a]pyridin-3-yl)(pyrrolidin-1-yl)methanone [104];

(6-(2-((trans-3-aminocyclobutyl)amino)pyrrolo[2,1-f][1,2,4]triazin-5-yl)imidazo[1,2-a]pyridin-3-yl)(pyrrolidin-1-yl)methanone [105];

(6-(2-((cis-3-(methylamino)cyclobutyl)amino)pyrrolo[2,1-f][1,2,4]triazin-5-yl)imidazo[1,2-a]pyridin-3-yl)(pyrrolidin-1-yl)methanone [106];

(6-(2-((trans-3-(methylamino)cyclobutyl)amino)pyrrolo[2,1-f][1,2,4]triazin-5-yl)imidazo[1,2-a]pyridin-3-yl)(pyrrolidin-1-yl)methanone [107];

(6-(2-((cis-3-(dimethylamino)cyclobutyl)amino)pyrrolo[2,1-f][1,2,4]triazin-5-yl)imidazo[1,2-a]pyridin-3-yl)(pyrrolidin-1-yl)methanone [108];

(6-(2-((trans-3-(dimethylamino)cyclobutyl)amino)pyrrolo[2,1-f][1,2,4]triazin-5-yl)imidazo[1,2-a]pyridin-3-yl)(pyrrolidin-1-yl)methanone [109];

(6-(2-((cis-3-morpholinocyclobutyl)amino)pyrrolo[2,1-f][1,2,4]triazin-5-yl)imidazo[1,2-a]pyridin-3-yl)(pyrrolidin-1-yl)methanone [110];

(6-(2-((trans-3-morpholinocyclobutyl)amino)pyrrolo[2,1-f][1,2,4]triazin-5-yl)imidazo[1,2-a]pyridin-3-yl)(pyrrolidin-1-yl)methanone [111];

(6-(2-((cis-3-(4-methylpiperazin-1-yl)cyclobutyl)amino)pyrrolo[2,1-f][1,2,4]triazin-5-yl)imidazo[1,2-a]pyridin-3-yl)(pyrrolidin-1-yl)methanone [112];

(6-(2-((trans-3-(4-methylpiperazin-1-yl)cyclobutyl)amino)pyrrolo[2,1-f][1,2,4]triazin-5-yl)imidazo[1,2-a]pyridin-3-yl)(pyrrolidin-1-yl)methanone [113];

(6-(2-((4,4-difluorocyclohexyl)amino)pyrrolo[2,1-f][1,2,4]triazin-5-yl)imidazo[1,2-a]pyridin-3-yl)(pyrrolidin-1-yl)methanone [114];

(6-(2-((cis-4-hydroxycyclohexyl)amino)pyrrolo[2,1-f][1,2,4]triazin-5-yl)imidazo[1,2-a]pyridin-3-yl)(pyrrolidin-1-yl)methanone [115];

(6-(2-(((1s,4s)-4-hydroxy-4-methylcyclohexyl)amino)pyrrolo[2,1-f][1,2,4]triazin-5-yl)imidazo[1,2-a]pyridin-3-yl)(pyrrolidin-1-yl)methanone [116];

(6-(2-((cis-4-methoxycyclohexyl)amino)pyrrolo[2,1-f][1,2,4]triazin-5-yl)imidazo[1,2-a]pyridin-3-yl)(pyrrolidin-1-yl)methanone [117];

(6-(2-((trans-4-methoxycyclohexyl)amino)pyrrolo[2,1-f][1,2,4]triazin-5-yl)imidazo[1,2-a]pyridin-3-yl)(pyrrolidin-1-yl)methanone [118];

(6-(2-((cis-4-(difluoromethoxy)cyclohexyl)amino)pyrrolo[2,1-f][1,2,4]triazin-5-yl)imidazo[1,2-a]pyridin-3-yl)(pyrrolidin-1-yl)methanone [119];

(6-(2-((trans-4-(difluoromethoxy)cyclohexyl)amino)pyrrolo[2,1-f][1,2,4]triazin-5-yl)imidazo[1,2-a]pyridin-3-yl)(pyrrolidin-1-yl)methanone [120];

(6-(2-((cis-4-ethoxycyclohexyl)amino)pyrrolo[2,1-f][1,2,4]triazin-5-yl)imidazo[1,2-a]pyridin-3-yl)(pyrrolidin-1-yl)methanone [121];

(6-(2-((trans-4-ethoxycyclohexyl)amino)pyrrolo[2,1-f][1,2,4]triazin-5-yl)imidazo[1,2-a]pyridin-3-yl)(pyrrolidin-1-yl)methanone [122];

(6-(2-((cis-4-(2-methoxyethoxy)cyclohexyl)amino)pyrrolo[2,1-f][1,2,4]triazin-5-yl)imidazo[1,2-a]pyridin-3-yl)(pyrrolidin-1-yl)methanone [123];

(6-(2-((trans-4-(2-methoxyethoxy)cyclohexyl)amino)pyrrolo[2,1-f][1,2,4]triazin-5-yl)imidazo[1,2-a]pyridin-3-yl)(pyrrolidin-1-yl)methanone [124];

(6-(2-((cis-4-aminocyclohexyl)amino)pyrrolo[2,1-f][1,2,4]triazin-5-yl)imidazo[1,2-a]pyridin-3-yl)(pyrrolidin-1-yl)methanone [125];

(6-(2-((trans-4-aminocyclohexyl)amino)pyrrolo[2,1-f][1,2,4]triazin-5-yl)imidazo[1,2-a]pyridin-3-yl)(pyrrolidin-1-yl)methanone [126];

(6-(2-((cis-4-(methylamino)cyclohexyl)amino)pyrrolo[2,1-f][1,2,4]triazin-5-yl)imidazo[1,2-a]pyridin-3-yl)(pyrrolidin-1-yl)methanone [127];

(6-(2-((trans-4-(methylamino)cyclohexyl)amino)pyrrolo[2,1-f][1,2,4]triazin-5-yl)imidazo[1,2-a]pyridin-3-yl)(pyrrolidin-1-yl)methanone [128];

(6-(2-((cis-4-(dimethylamino)cyclohexyl)amino)pyrrolo[2,1-f][1,2,4]triazin-5-yl)imidazo[1,2-a]pyridin-3-yl)(pyrrolidin-1-yl)methanone [129];

(6-(2-((trans-4-(dimethylamino)cyclohexyl)amino)pyrrolo[2,1-f][1,2,4]triazin-5-yl)imidazo[1,2-a]pyridin-3-yl)(pyrrolidin-1-yl)methanone [130];

(6-(2-((cis-4-morpholinocyclohexyl)amino)pyrrolo[2,1-f][1,2,4]triazin-5-yl)imidazo[1,2-a]pyridin-3-yl)(pyrrolidin-1-yl)methanone [131];

(6-(2-((trans-4-morpholinocyclohexyl)amino)pyrrolo[2,1-f][1,2,4]triazin-5-yl)imidazo[1,2-a]pyridin-3-yl)(pyrrolidin-1-yl)methanone [132];

(6-(2-((cis-4-(4-methylpiperazin-1-yl)cyclohexyl)amino)pyrrolo[2,1-f][1,2,4]triazin-5-yl)imidazo[1,2-a]pyridin-3-yl)(pyrrolidin-1-yl)methanone [133];

(6-(2-((trans-4-(4-methylpiperazin-1-yl)cyclohexyl)amino)pyrrolo[2,1-f][1,2,4]triazin-5-yl)imidazo[1,2-a]pyridin-3-yl)(pyrrolidin-1-yl)methanone [134];

(6-(2-((1-methylazetidin-3-yl)amino)pyrrolo[2,1-f][1,2,4]triazin-5-yl)imidazo[1,2-a]pyridin-3-yl)(pyrrolidin-1-yl)methanone [135];

(6-(2-(oxetan-3-ylamino)pyrrolo[2,1-f][1,2,4]triazin-5-yl)imidazo[1,2-a]pyridin-3-yl)(pyrrolidin-1-yl)methanone [136];

(6-(2-((1-methylpiperidin-4-yl)amino)pyrrolo[2,1-f][1,2,4]triazin-5-yl)imidazo[1,2-a]pyridin-3-yl)(pyrrolidin-1-yl)methanone [137];

pyrrolidin-1-yl(6-(2-((tetrahydro-2H-pyran-4-yl)amino)pyrrolo[2,1-f][1,2,4]triazin-5-yl)imidazo[1,2-a]pyridin-3-yl)methanone [138];

(6-(2-((6,6-difluorospiro[3.3]heptan-2-yl)amino)pyrrolo[2,1-f][1,2,4]triazin-5-yl)imidazo[1,2-a]pyridin-3-yl)(pyrrolidin-1-yl)methanone [139];

(6-(2-((2-oxaspiro[3.3]heptan-6-yl)amino)pyrrolo[2,1-f][1,2,4]triazin-5-yl)imidazo[1,2-a]pyridin-3-yl)(pyrrolidin-1-yl)methanone [140];

(6-(2-((2-methyl-2-azaspiro[3.3]heptan-6-yl)amino)pyrrolo[2,1-f][1,2,4]triazin-5-yl)imidazo[1,2-a]pyridin-3-yl)(pyrrolidin-1-yl)methanone [141];

(6-(2-((1-methyl-1H-pyrazol-4-yl)amino)pyrrolo[2,1-f][1,2,4]triazin-5-yl)imidazo[1,2-a]pyridin-3-yl)(pyrrolidin-1-yl)methanone [142];

5-(imidazo[1,2-b]pyridazin-6-yl)-N-isopropylpyrrolo[2,1-f][1,2,4]triazin-2-amine [143];

5-(imidazo[1,2-b]pyridazin-6-yl)-N-isobutylpyrrolo[2,1-f][1,2,4]triazin-2-amine [144];

N-(2-fluoro-2-methylpropyl)-5-(imidazo[1,2-b]pyridazin-6-yl)pyrrolo[2,1-f][1,2,4]triazin-2-amine [145];

N-(2,2-difluoropropyl)-5-(imidazo[1,2-b]pyridazin-6-yl)pyrrolo[2,1-f][1,2,4]triazin-2-amine [146];

5-(imidazo[1,2-b]pyridazin-6-yl)-N-(2,2,2-trifluoroethyl)pyrrolo[2,1-f][1,2,4]triazin-2-amine [147];

(R)-5-(imidazo[1,2-b]pyridazin-6-yl)-N-(1,1,1-trifluoropropan-2-yl)pyrrolo[2,1-f][1,2,4]triazin-2-amine [148];

5-(imidazo[1,2-b]pyridazin-6-yl)-N-(3,3,3-trifluoropropyl)pyrrolo[2,1-f][1,2,4]triazin-2-amine [149];

5-(imidazo[1,2-b]pyridazin-6-yl)-N-(3,3,3-trifluoro-2,2-dimethylpropyl)pyrrolo[2,1-f][1,2,4]triazin-2-amine [150];

5-(imidazo[1,2-b]pyridazin-6-yl)-N-(2-methoxyethyl)pyrrolo[2,1-f][1,2,4]triazin-2-amine [151];

(R)-5-(imidazo[1,2-b]pyridazin-6-yl)-N-(1-methoxypropan-2-yl)pyrrolo[2,1-f][1,2,4]triazin-2-amine [152];

5-(imidazo[1,2-b]pyridazin-6-yl)-N-(2-isopropoxyethyl)pyrrolo[2,1-f][1,2,4]triazin-2-amine [153];

5-(imidazo[1,2-b]pyridazin-6-yl)-N-((1-methylcyclopropyl)methyl)pyrrolo[2,1-f][1,2,4]triazin-2-amine [154];

5-(imidazo[1,2-b]pyridazin-6-yl)-N-((1-(trifluoromethyl)cyclopropyl)methyl)pyrrolo[2,1-f][1,2,4]triazin-2-amine [155];

N-((1-fluorocyclobutyl)methyl)-5-(imidazo[1,2-b]pyridazin-6-yl)pyrrolo[2,1-f][1,2,4]triazin-2-amine [156];

N-((3-fluorooxetan-3-yl)methyl)-5-(imidazo[1,2-b]pyridazin-6-yl)pyrrolo[2,1-f][1,2,4]triazin-2-amine [157];

N-(cyclopropylmethyl)-5-(imidazo[1,2-b]pyridazin-6-yl)pyrrolo[2,1-f][1,2,4]triazin-2-amine [158];

(S)—N-(1-cyclopropylethyl)-5-(imidazo[1,2-b]pyridazin-6-yl)pyrrolo[2,1-f][1,2,4]triazin-2-amine [159];

(R)—N-(1-cyclopropylethyl)-5-(imidazo[1,2-b]pyridazin-6-yl)pyrrolo[2,1-f][1,2,4]triazin-2-amine [160];

N-(2-cyclopropyl-2,2-difluoroethyl)-5-(imidazo[1,2-b]pyridazin-6-yl)pyrrolo[2,1-f][1,2,4]triazin-2-amine [161];

5-(imidazo[1,2-b]pyridazin-6-yl)-N-(oxetan-3-ylmethyl)pyrrolo[2,1-f][1,2,4]triazin-2-amine [162];

5-(imidazo[1,2-b]pyridazin-6-yl)-N-((tetrahydrofuran-2-yl)methyl)pyrrolo[2,1-f][1,2,4]triazin-2-amine [163];

N-cyclobutyl-5-(imidazo[1,2-b]pyridazin-6-yl)pyrrolo[2,1-f][1,2,4]triazin-2-amine [164];

N-(3,3-difluorocyclobutyl)-5-(imidazo[1,2-b]pyridazin-6-yl)pyrrolo[2,1-f][1,2,4]triazin-2-amine [165];

N-(3,3-dimethylcyclobutyl)-5-(imidazo[1,2-b]pyridazin-6-yl)pyrrolo[2,1-f][1,2,4]triazin-2-amine [166];

3-((5-(imidazo[1,2-b]pyridazin-6-yl)pyrrolo[2,1-f][1,2,4]triazin-2-yl)amino)-1-methylcyclobutan-1-ol [167];

5-(imidazo[1,2-b]pyridazin-6-yl)-N-(cis-3-methoxycyclobutyl)pyrrolo[2,1-f][1,2,4]triazin-2-amine [168];

5-(imidazo[1,2-b]pyridazin-6-yl)-N-(trans-3-methoxycyclobutyl)pyrrolo[2,1-f][1,2,4]triazin-2-amine [169];

5-(imidazo[1,2-b]pyridazin-6-yl)-N-(trans-3-(methoxymethyl)cyclobutyl)pyrrolo[2,1-f][1,2,4]triazin-2-amine [170];

N-(cis-3-ethoxycyclobutyl)-5-(imidazo[1,2-b]pyridazin-6-yl)pyrrolo[2,1-f][1,2,4]triazin-2-amine [171];

N-(trans-3-ethoxycyclobutyl)-5-(imidazo[1,2-b]pyridazin-6-yl)pyrrolo[2,1-f][1,2,4]triazin-2-amine [172];

5-(imidazo[1,2-b]pyridazin-6-yl)-N-(cis-3-(2-methoxyethoxy)cyclobutyl)pyrrolo[2,1-f][1,2,4]triazin-2-amine [173];

5-(imidazo[1,2-b]pyridazin-6-yl)-N-(trans-3-(2-methoxyethoxy)cyclobutyl)pyrrolo[2,1-f][1,2,4]triazin-2-amine [174];

cis-$N^1$-(5-(imidazo[1,2-b]pyridazin-6-yl)pyrrolo[2,1-f][1,2,4]triazin-2-yl)cyclobutane-1,3-diamine [175];

trans-$N^1$-(5-(imidazo[1,2-b]pyridazin-6-yl)pyrrolo[2,1-f][1,2,4]triazin-2-yl)cyclobutane-1,3-diamine [176];

cis-$N^1$-(5-(imidazo[1,2-b]pyridazin-6-yl)pyrrolo[2,1-f][1,2,4]triazin-2-yl)-$N^3$-methylcyclobutane-1,3-diamine [177];

trans-$N^1$-(5-(imidazo[1,2-b]pyridazin-6-yl)pyrrolo[2,1-f][1,2,4]triazin-2-yl)-$N^3$-methylcyclobutane-1,3-diamine [178];

cis-$N^1$-(5-(imidazo[1,2-b]pyridazin-6-yl)pyrrolo[2,1-f][1,2,4]triazin-2-yl)-$N^3$,$N^3$-dimethylcyclobutane-1,3-diamine [179];

trans-$N^1$-(5-(imidazo[1,2-b]pyridazin-6-yl)pyrrolo[2,1-f][1,2,4]triazin-2-yl)-$N^3$,$N^3$-dimethylcyclobutane-1,3-diamine [180];

5-(imidazo[1,2-b]pyridazin-6-yl)-N-(cis-3-morpholinocyclobutyl)pyrrolo[2,1-f][1,2,4]triazin-2-amine [181];

5-(imidazo[1,2-b]pyridazin-6-yl)-N-(trans-3-morpholinocyclobutyl)pyrrolo[2,1-f][1,2,4]triazin-2-amine [182];

5-(imidazo[1,2-b]pyridazin-6-yl)-N-(cis-3-(4-methylpiperazin-1-yl)cyclobutyl)pyrrolo[2,1-f][1,2,4]triazin-2-amine [183];

5-(imidazo[1,2-b]pyridazin-6-yl)-N-(trans-3-(4-methylpiperazin-1-yl)cyclobutyl)pyrrolo[2,1-f][1,2,4]triazin-2-amine [184];

N-(4,4-difluorocyclohexyl)-5-(imidazo[1,2-b]pyridazin-6-yl)pyrrolo[2,1-f][1,2,4]triazin-2-amine [185];

cis-4-((5-(imidazo[1,2-b]pyridazin-6-yl)pyrrolo[2,1-f][1,2,4]triazin-2-yl)amino)cyclohexan-1-ol [186];

(1s,4s)-4-((5-(imidazo[1,2-b]pyridazin-6-yl)pyrrolo[2,1-f][1,2,4]triazin-2-yl)amino)-1-methylcyclohexan-1-ol [187];

5-(imidazo[1,2-b]pyridazin-6-yl)-N-(cis-4-methoxycyclohexyl)pyrrolo[2,1-f][1,2,4]triazin-2-amine [188];

5-(imidazo[1,2-b]pyridazin-6-yl)-N-(trans-4-methoxycyclohexyl)pyrrolo[2,1-f][1,2,4]triazin-2-amine [189];

N-(cis-4-(difluoromethoxy)cyclohexyl)-5-(imidazo[1,2-b]pyridazin-6-yl)pyrrolo[2,1-f][1,2,4]triazin-2-amine [190];

N-(trans-4-(difluoromethoxy)cyclohexyl)-5-(imidazo[1,2-b]pyridazin-6-yl)pyrrolo[2,1-f][1,2,4]triazin-2-amine [191];

N-(cis-4-ethoxycyclohexyl)-5-(imidazo[1,2-b]pyridazin-6-yl)pyrrolo[2,1-f][1,2,4]triazin-2-amine [192];

N-(trans-4-ethoxycyclohexyl)-5-(imidazo[1,2-b]pyridazin-6-yl)pyrrolo[2,1-f][1,2,4]triazin-2-amine [193];

5-(imidazo[1,2-b]pyridazin-6-yl)-N-(cis-4-(2-methoxyethoxy)cyclohexyl)pyrrolo[2,1-f][1,2,4]triazin-2-amine [194];

5-(imidazo[1,2-b]pyridazin-6-yl)-N-(trans-4-(2-methoxyethoxy)cyclohexyl)pyrrolo[2,1-f][1,2,4]triazin-2-amine [195];

cis-$N^1$-(5-(imidazo[1,2-b]pyridazin-6-yl)pyrrolo[2,1-f][1,2,4]triazin-2-yl)cyclohexane-1,4-diamine [196];

trans-$N^1$-(5-(imidazo[1,2-b]pyridazin-6-yl)pyrrolo[2,1-f][1,2,4]triazin-2-yl)cyclohexane-1,4-diamine [197];

cis-$N^1$-(5-(imidazo[1,2-b]pyridazin-6-yl)pyrrolo[2,1-f][1,2,4]triazin-2-yl)-$N^4$-methylcyclohexane-1,4-diamine [198];

trans-$N^1$-(5-(imidazo[1,2-b]pyridazin-6-yl)pyrrolo[2,1-f][1,2,4]triazin-2-yl)-$N^4$-methylcyclohexane-1,4-diamine [199];

cis-$N^1$-(5-(imidazo[1,2-b]pyridazin-6-yl)pyrrolo[2,1-f][1,2,4]triazin-2-yl)-$N^4$,$N^4$-dimethylcyclohexane-1,4-diamine [200];

trans-$N^1$-(5-(imidazo[1,2-b]pyridazin-6-yl)pyrrolo[2,1-f][1,2,4]triazin-2-yl)-$N^4$,$N^4$-dimethylcyclohexane-1,4-diamine [201];

5-(imidazo[1,2-b]pyridazin-6-yl)-N-(cis-4-morpholinocyclohexyl)pyrrolo[2,1-f][1,2,4]triazin-2-amine [202];

5-(imidazo[1,2-b]pyridazin-6-yl)-N-(trans-4-morpholinocyclohexyl)pyrrolo[2,1-f][1,2,4]triazin-2-amine [203];

5-(imidazo[1,2-b]pyridazin-6-yl)-N-(cis-4-(4-methylpiperazin-1-yl)cyclohexyl)pyrrolo[2,1-f][1,2,4]triazin-2-amine [204];

5-(imidazo[1,2-b]pyridazin-6-yl)-N-(trans-4-(4-methylpiperazin-1-yl)cyclohexyl)pyrrolo[2,1-f][1,2,4]triazin-2-amine [205];

5-(imidazo[1,2-b]pyridazin-6-yl)-N-(1-methylazetidin-3-yl)pyrrolo[2,1-f][1,2,4]triazin-2-amine [206];

5-(imidazo[1,2-b]pyridazin-6-yl)-N-(oxetan-3-yl)pyrrolo[2,1-f][1,2,4]triazin-2-amine [207];

5-(imidazo[1,2-b]pyridazin-6-yl)-N-(1-methylpiperidin-4-yl)pyrrolo[2,1-f][1,2,4]triazin-2-amine [208];

5-(imidazo[1,2-b]pyridazin-6-yl)-N-(tetrahydro-2H-pyran-4-yl)pyrrolo[2,1-f][1,2,4]triazin-2-amine [209];

N-(6,6-difluorospiro[3.3]heptan-2-yl)-5-(imidazo[1,2-b]pyridazin-6-yl)pyrrolo[2,1-f][1,2,4]triazin-2-amine [210];

5-(imidazo[1,2-b]pyridazin-6-yl)-N-(2-oxaspiro[3.3]heptan-6-yl)pyrrolo[2,1-f][1,2,4]triazin-2-amine [211];

5-(imidazo[1,2-b]pyridazin-6-yl)-N-(2-methyl-2-azaspiro[3.3]heptan-6-yl)pyrrolo[2,1-f][1,2,4]triazin-2-amine [212];

5-(imidazo[1,2-b]pyridazin-6-yl)-N-(1-methyl-1H-pyrazol-4-yl)pyrrolo[2,1-f][1,2,4]triazin-2-amine [213];

5-(imidazo[1,2-a]pyrimidin-6-yl)-N-isopropylpyrrolo[2,1-f][1,2,4]triazin-2-amine [214];

5-(imidazo[1,2-a]pyrimidin-6-yl)-N-isobutylpyrrolo[2,1-f][1,2,4]triazin-2-amine [215];

N-(2-fluoro-2-methylpropyl)-5-(imidazo[1,2-a]pyrimidin-6-yl)pyrrolo[2,1-f][1,2,4]triazin-2-amine [216];

N-(2,2-difluoropropyl)-5-(imidazo[1,2-a]pyrimidin-6-yl)pyrrolo[2,1-f][1,2,4]triazin-2-amine [217];

5-(imidazo[1,2-a]pyrimidin-6-yl)-N-(2,2,2-trifluoroethyl)pyrrolo[2,1-f][1,2,4]triazin-2-amine [218];

(R)-5-(imidazo[1,2-a]pyrimidin-6-yl)-N-(1,1,1-trifluoropropan-2-yl)pyrrolo[2,1-f][1,2,4]triazin-2-amine [219];

5-(imidazo[1,2-a]pyrimidin-6-yl)-N-(3,3,3-trifluoropropyl)pyrrolo[2,1-f][1,2,4]triazin-2-amine [220];

5-(imidazo[1,2-a]pyrimidin-6-yl)-N-(3,3,3-trifluoro-2,2-dimethylpropyl)pyrrolo[2,1-f][1,2,4]triazin-2-amine [221];

5-(imidazo[1,2-a]pyrimidin-6-yl)-N-(2-methoxyethyl)pyrrolo[2,1-f][1,2,4]triazin-2-amine [222];

(R)-5-(imidazo[1,2-a]pyrimidin-6-yl)-N-(1-methoxypropan-2-yl)pyrrolo[2,1-f][1,2,4]triazin-2-amine [223];

5-(imidazo[1,2-a]pyrimidin-6-yl)-N-(2-isopropoxyethyl)pyrrolo[2,1-f][1,2,4]triazin-2-amine [224];

5-(imidazo[1,2-a]pyrimidin-6-yl)-N-((1-methylcyclopropyl)methyl)pyrrolo[2,1-f][1,2,4]triazin-2-amine [225];

5-(imidazo[1,2-a]pyrimidin-6-yl)-N-((1-(trifluoromethyl)cyclopropyl)methyl)pyrrolo[2,1-f][1,2,4]triazin-2-amine [226];

N-((1-fluorocyclobutyl)methyl)-5-(imidazo[1,2-a]pyrimidin-6-yl)pyrrolo[2,1-f][1,2,4]triazin-2-amine [227];

N-((3-fluorooxetan-3-yl)methyl)-5-(imidazo[1,2-a]pyrimidin-6-yl)pyrrolo[2,1-f][1,2,4]triazin-2-amine [228];

N-(cyclopropylmethyl)-5-(imidazo[1,2-a]pyrimidin-6-yl)pyrrolo[2,1-f][1,2,4]triazin-2-amine [229];

(S)—N-(1-cyclopropylethyl)-5-(imidazo[1,2-a]pyrimidin-6-yl)pyrrolo[2,1-f][1,2,4]triazin-2-amine [230];

(R)—N-(1-cyclopropylethyl)-5-(imidazo[1,2-a]pyrimidin-6-yl)pyrrolo[2,1-f][1,2,4]triazin-2-amine [231];

N-(2-cyclopropyl-2,2-difluoroethyl)-5-(imidazo[1,2-a]pyrimidin-6-yl)pyrrolo[2,1-f][1,2,4]triazin-2-amine [232];

5-(imidazo[1,2-a]pyrimidin-6-yl)-N-(oxetan-3-ylmethyl)pyrrolo[2,1-f][1,2,4]triazin-2-amine [233];

5-(imidazo[1,2-a]pyrimidin-6-yl)-N-((tetrahydrofuran-2-yl)methyl)pyrrolo[2,1-f][1,2,4]triazin-2-amine [234];

N-cyclobutyl-5-(imidazo[1,2-a]pyrimidin-6-yl)pyrrolo[2,1-f][1,2,4]triazin-2-amine [235];

N-(3,3-difluorocyclobutyl)-5-(imidazo[1,2-a]pyrimidin-6-yl)pyrrolo[2,1-f][1,2,4]triazin-2-amine [236];

N-(3,3-dimethylcyclobutyl)-5-(imidazo[1,2-a]pyrimidin-6-yl)pyrrolo[2,1-f][1,2,4]triazin-2-amine [237];

3-((5-(imidazo[1,2-a]pyrimidin-6-yl)pyrrolo[2,1-f][1,2,4]triazin-2-yl)amino)-1-methylcyclobutan-1-ol [238];

5-(imidazo[1,2-a]pyrimidin-6-yl)-N-(cis-3-methoxycyclobutyl)pyrrolo[2,1-f][1,2,4]triazin-2-amine [239];

5-(imidazo[1,2-a]pyrimidin-6-yl)-N-(trans-3-methoxycyclobutyl)pyrrolo[2,1-f][1,2,4]triazin-2-amine [240];

5-(imidazo[1,2-a]pyrimidin-6-yl)-N-(trans-3-(methoxymethyl)cyclobutyl)pyrrolo[2,1-f][1,2,4]triazin-2-amine [241];

N-(cis-3-ethoxycyclobutyl)-5-(imidazo[1,2-a]pyrimidin-6-yl)pyrrolo[2,1-f][1,2,4]triazin-2-amine [242];

N-(trans-3-ethoxycyclobutyl)-5-(imidazo[1,2-a]pyrimidin-6-yl)pyrrolo[2,1-f][1,2,4]triazin-2-amine [243];

5-(imidazo[1,2-a]pyrimidin-6-yl)-N-(cis-3-(2-methoxyethoxy)cyclobutyl)pyrrolo[2,1-f][1,2,4]triazin-2-amine [244];

5-(imidazo[1,2-a]pyrimidin-6-yl)-N-(trans-3-(2-methoxyethoxy)cyclobutyl)pyrrolo[2,1-f][1,2,4]triazin-2-amine [245];

cis-$N^1$-(5-(imidazo[1,2-a]pyrimidin-6-yl)pyrrolo[2,1-f][1,2,4]triazin-2-yl)cyclobutane-1,3-diamine [246];

trans-$N^1$-(5-(imidazo[1,2-a]pyrimidin-6-yl)pyrrolo[2,1-f][1,2,4]triazin-2-yl)cyclobutane-1,3-diamine [247];

cis-$N^1$-(5-(imidazo[1,2-a]pyrimidin-6-yl)pyrrolo[2,1-f][1,2,4]triazin-2-yl)-$N^3$-methylcyclobutane-1,3-diamine [248];

trans-$N^1$-(5-(imidazo[1,2-a]pyrimidin-6-yl)pyrrolo[2,1-f][1,2,4]triazin-2-yl)-$N^3$-methylcyclobutane-1,3-diamine [249];

cis-$N^1$-(5-(imidazo[1,2-a]pyrimidin-6-yl)pyrrolo[2,1-f][1,2,4]triazin-2-yl)-$N^3$,$N^3$-dimethylcyclobutane-1,3-diamine [250];

trans-$N^1$-(5-(imidazo[1,2-a]pyrimidin-6-yl)pyrrolo[2,1-f][1,2,4]triazin-2-yl)-$N_3$,$N^3$-dimethylcyclobutane-1,3-diamine [251];

5-(imidazo[1,2-a]pyrimidin-6-yl)-N-(cis-3-morpholinocyclobutyl)pyrrolo[2,1-f][1,2,4]triazin-2-amine [252];

5-(imidazo[1,2-a]pyrimidin-6-yl)-N-(trans-3-morpholinocyclobutyl)pyrrolo[2,1-f][1,2,4]triazin-2-amine [253];

5-(imidazo[1,2-a]pyrimidin-6-yl)-N-(cis-3-(4-methylpiperazin-1-yl)cyclobutyl)pyrrolo[2,1-f][1,2,4]triazin-2-amine [254];

5-(imidazo[1,2-a]pyrimidin-6-yl)-N-(trans-3-(4-methylpiperazin-1-yl)cyclobutyl)pyrrolo[2,1-f][1,2,4]triazin-2-amine [255];

N-(4,4-difluorocyclohexyl)-5-(imidazo[1,2-a]pyrimidin-6-yl)pyrrolo[2,1-f][1,2,4]triazin-2-amine [256];

cis-4-((5-(imidazo[1,2-a]pyrimidin-6-yl)pyrrolo[2,1-f][1,2,4]triazin-2-yl)amino)cyclohexan-1-ol [257];

(1s,4s)-4-((5-(imidazo[1,2-a]pyrimidin-6-yl)pyrrolo[2,1-f][1,2,4]triazin-2-yl)amino)-1-methylcyclohexan-1-ol [258];

5-(imidazo[1,2-a]pyrimidin-6-yl)-N-(cis-4-methoxycyclohexyl)pyrrolo[2,1-f][1,2,4]triazin-2-amine [259];

5-(imidazo[1,2-a]pyrimidin-6-yl)-N-(trans-4-methoxycyclohexyl)pyrrolo[2,1-f][1,2,4]triazin-2-amine [260];

N-(cis-4-(difluoromethoxy)cyclohexyl)-5-(imidazo[1,2-a]pyrimidin-6-yl)pyrrolo[2,1-f][1,2,4]triazin-2-amine [261];

N-(trans-4-(difluoromethoxy)cyclohexyl)-5-(imidazo[1,2-a]pyrimidin-6-yl)pyrrolo[2,1-f][1,2,4]triazin-2-amine [262];

N-(cis-4-ethoxycyclohexyl)-5-(imidazo[1,2-a]pyrimidin-6-yl)pyrrolo[2,1-f][1,2,4]triazin-2-amine [263];

N-(trans-4-ethoxycyclohexyl)-5-(imidazo[1,2-a]pyrimidin-6-yl)pyrrolo[2,1-f][1,2,4]triazin-2-amine [264];

5-(imidazo[1,2-a]pyrimidin-6-yl)-N-(cis-4-(2-methoxyethoxy)cyclohexyl)pyrrolo[2,1-f][1,2,4]triazin-2-amine [265];

5-(imidazo[1,2-a]pyrimidin-6-yl)-N-(trans-4-(2-methoxyethoxy)cyclohexyl)pyrrolo[2,1-f][1,2,4]triazin-2-amine [266];

cis-$N^1$-(5-(imidazo[1,2-a]pyrimidin-6-yl)pyrrolo[2,1-f][1,2,4]triazin-2-yl)cyclohexane-1,4-diamine [267];

trans-$N^1$-(5-(imidazo[1,2-a]pyrimidin-6-yl)pyrrolo[2,1-f][1,2,4]triazin-2-yl)cyclohexane-1,4-diamine [268];

cis-$N^1$-(5-(imidazo[1,2-a]pyrimidin-6-yl)pyrrolo[2,1-f][1,2,4]triazin-2-yl)-$N^4$-methylcyclohexane-1,4-diamine [269];

trans-$N^1$-(5-(imidazo[1,2-a]pyrimidin-6-yl)pyrrolo[2,1-f][1,2,4]triazin-2-yl)-$N^4$-methylcyclohexane-1,4-diamine [270];

cis-$N^1$-(5-(imidazo[1,2-a]pyrimidin-6-yl)pyrrolo[2,1-f][1,2,4]triazin-2-yl)-$N^4$,$N^4$-dimethylcyclohexane-1,4-diamine [271];

trans-$N^1$-(5-(imidazo[1,2-a]pyrimidin-6-yl)pyrrolo[2,1-f][1,2,4]triazin-2-yl)-$N^4$,$N^4$-dimethylcyclohexane-1,4-diamine [272];

5-(imidazo[1,2-a]pyrimidin-6-yl)-N-(cis-4-morpholinocyclohexyl)pyrrolo[2,1-f][1,2,4]triazin-2-amine [273];

5-(imidazo[1,2-a]pyrimidin-6-yl)-N-(trans-4-morpholinocyclohexyl)pyrrolo[2,1-f][1,2,4]triazin-2-amine [274];

5-(imidazo[1,2-a]pyrimidin-6-yl)-N-(cis-4-(4-methylpiperazin-1-yl)cyclohexyl)pyrrolo[2,1-f][1,2,4]triazin-2-amine [275];

5-(imidazo[1,2-a]pyrimidin-6-yl)-N-(trans-4-(4-methylpiperazin-1-yl)cyclohexyl)pyrrolo[2,1-f][1,2,4]triazin-2-amine [276];

5-(imidazo[1,2-a]pyrimidin-6-yl)-N-(1-methylazetidin-3-yl)pyrrolo[2,1-f][1,2,4]triazin-2-amine [277];

5-(imidazo[1,2-a]pyrimidin-6-yl)-N-(oxetan-3-yl)pyrrolo[2,1-f][1,2,4]triazin-2-amine [278];

5-(imidazo[1,2-a]pyrimidin-6-yl)-N-(1-methylpiperidin-4-yl)pyrrolo[2,1-f][1,2,4]triazin-2-amine [279];

5-(imidazo[1,2-a]pyrimidin-6-yl)-N-(tetrahydro-2H-pyran-4-yl)pyrrolo[2,1-f][1,2,4]triazin-2-amine [280];

N-(6,6-difluorospiro[3.3]heptan-2-yl)-5-(imidazo[1,2-a]pyrimidin-6-yl)pyrrolo[2,1-f][1,2,4]triazin-2-amine [281];

5-(imidazo[1,2-a]pyrimidin-6-yl)-N-(2-oxaspiro[3.3]heptan-6-yl)pyrrolo[2,1-f][1,2,4]triazin-2-amine [282];

5-(imidazo[1,2-a]pyrimidin-6-yl)-N-(2-methyl-2-azaspiro[3.3]heptan-6-yl)pyrrolo[2,1-f][1,2,4]triazin-2-amine [283];

5-(imidazo[1,2-a]pyrimidin-6-yl)-N-(1-methyl-1H-pyrazol-4-yl)pyrrolo[2,1-f][1,2,4]triazin-2-amine [284];

5-(3-chloroimidazo[1,2-a]pyrimidin-6-yl)-N-isopropylpyrrolo[2,1-f][1,2,4]triazin-2-amine [285];

5-(3-chloroimidazo[1,2-a]pyrimidin-6-yl)-N-isobutylpyrrolo[2,1-f][1,2,4]triazin-2-amine [286];

5-(3-chloroimidazo[1,2-a]pyrimidin-6-yl)-N-(2-fluoro-2-methylpropyl)pyrrolo[2,1-f][1,2,4]triazin-2-amine [287];

5-(3-chloroimidazo[1,2-a]pyrimidin-6-yl)-N-(2,2-difluoropropyl)pyrrolo[2,1-f][1,2,4]triazin-2-amine [288];

5-(3-chloroimidazo[1,2-a]pyrimidin-6-yl)-N-(2,2,2-trifluoroethyl)pyrrolo[2,1-f][1,2,4]triazin-2-amine [289];

(R)-5-(3-chloroimidazo[1,2-a]pyrimidin-6-yl)-N-(1,1,1-trifluoropropan-2-yl)pyrrolo[2,1-f][1,2,4]triazin-2-amine [290];

5-(3-chloroimidazo[1,2-a]pyrimidin-6-yl)-N-(3,3,3-trifluoropropyl)pyrrolo[2,1-f][1,2,4]triazin-2-amine [291];

5-(3-chloroimidazo[1,2-a]pyrimidin-6-yl)-N-(3,3,3-trifluoro-2,2-dimethylpropyl)pyrrolo[2,1-f][1,2,4]triazin-2-amine [292];

5-(3-chloroimidazo[1,2-a]pyrimidin-6-yl)-N-(2-methoxyethyl)pyrrolo[2,1-f][1,2,4]triazin-2-amine [293];

(R)-5-(3-chloroimidazo[1,2-a]pyrimidin-6-yl)-N-(1-methoxypropan-2-yl)pyrrolo[2,1-f][1,2,4]triazin-2-amine [294];

5-(3-chloroimidazo[1,2-a]pyrimidin-6-yl)-N-(2-isopropoxyethyl)pyrrolo[2,1-f][1,2,4]triazin-2-amine [295];

5-(3-chloroimidazo[1,2-a]pyrimidin-6-yl)-N-((1-methylcyclopropyl)methyl)pyrrolo[2,1-f][1,2,4]triazin-2-amine [296];

5-(3-chloroimidazo[1,2-a]pyrimidin-6-yl)-N-((1-(trifluoromethyl)cyclopropyl)methyl)pyrrolo[2,1-f][1,2,4]triazin-2-amine [297];

5-(3-chloroimidazo[1,2-a]pyrimidin-6-yl)-N-((1-fluorocyclobutyl)methyl)pyrrolo[2,1-f][1,2,4]triazin-2-amine [298];

5-(3-chloroimidazo[1,2-a]pyrimidin-6-yl)-N-((3-fluorooxetan-3-yl)methyl)pyrrolo[2,1-f][1,2,4]triazin-2-amine [299];

5-(3-chloroimidazo[1,2-a]pyrimidin-6-yl)-N-(cyclopropylmethyl)pyrrolo[2,1-f][1,2,4]triazin-2-amine [300];

(S)-5-(3-chloroimidazo[1,2-a]pyrimidin-6-yl)-N-(1-cyclopropylethyl)pyrrolo[2,1-f][1,2,4]triazin-2-amine [301];

(R)-5-(3-chloroimidazo[1,2-a]pyrimidin-6-yl)-N-(1-cyclopropylethyl)pyrrolo[2,1-f][1,2,4]triazin-2-amine [302];

5-(3-chloroimidazo[1,2-a]pyrimidin-6-yl)-N-(2-cyclopropyl-2,2-difluoroethyl)pyrrolo[2,1-f][1,2,4]triazin-2-amine [303];

5-(3-chloroimidazo[1,2-a]pyrimidin-6-yl)-N-(oxetan-3-ylmethyl)pyrrolo[2,1-f][1,2,4]triazin-2-amine [304];

5-(3-chloroimidazo[1,2-a]pyrimidin-6-yl)-N-((tetrahydrofuran-2-yl)methyl)pyrrolo[2,1-f][1,2,4]triazin-2-amine [305];

5-(3-chloroimidazo[1,2-a]pyrimidin-6-yl)-N-cyclobutylpyrrolo[2,1-f][1,2,4]triazin-2-amine [306];

5-(3-chloroimidazo[1,2-a]pyrimidin-6-yl)-N-(3,3-difluorocyclobutyl)pyrrolo[2,1-f][1,2,4]triazin-2-amine [307];

5-(3-chloroimidazo[1,2-a]pyrimidin-6-yl)-N-(3,3-dimethylcyclobutyl)pyrrolo[2,1-f][1,2,4]triazin-2-amine [308];

3-((5-(3-chloroimidazo[1,2-a]pyrimidin-6-yl)pyrrolo[2,1-f][1,2,4]triazin-2-yl)amino)-1-methylcyclobutan-1-ol [309];

5-(3-chloroimidazo[1,2-a]pyrimidin-6-yl)-N-(cis-3-methoxycyclobutyl)pyrrolo[2,1-f][1,2,4]triazin-2-amine [310];

5-(3-chloroimidazo[1,2-a]pyrimidin-6-yl)-N-(trans-3-methoxycyclobutyl)pyrrolo[2,1-f][1,2,4]triazin-2-amine [311];

5-(3-chloroimidazo[1,2-a]pyrimidin-6-yl)-N-(trans-3-(methoxymethyl)cyclobutyl)pyrrolo[2,1-f][1,2,4]triazin-2-amine [312];

5-(3-chloroimidazo[1,2-a]pyrimidin-6-yl)-N-(cis-3-ethoxycyclobutyl)pyrrolo[2,1-f][1,2,4]triazin-2-amine [313];

5-(3-chloroimidazo[1,2-a]pyrimidin-6-yl)-N-(trans-3-ethoxycyclobutyl)pyrrolo[2,1-f][1,2,4]triazin-2-amine [314];

5-(3-chloroimidazo[1,2-a]pyrimidin-6-yl)-N-(cis-3-(2-methoxyethoxy)cyclobutyl)pyrrolo[2,1-f][1,2,4]triazin-2-amine [315];

5-(3-chloroimidazo[1,2-a]pyrimidin-6-yl)-N-(trans-3-(2-methoxyethoxy)cyclobutyl)pyrrolo[2,1-f][1,2,4]triazin-2-amine [316];

cis-$N^1$-(5-(3-chloroimidazo[1,2-a]pyrimidin-6-yl)pyrrolo[2,1-f][1,2,4]triazin-2-yl)cyclobutane-1,3-diamine [317];

trans-$N^1$-(5-(3-chloroimidazo[1,2-a]pyrimidin-6-yl)pyrrolo[2,1-f][1,2,4]triazin-2-yl)cyclobutane-1,3-diamine [318];

cis-$N^1$-(5-(3-chloroimidazo[1,2-a]pyrimidin-6-yl)pyrrolo[2,1-f][1,2,4]triazin-2-yl)-$N^3$-methylcyclobutane-1,3-diamine [319];

trans-$N^1$-(5-(3-chloroimidazo[1,2-a]pyrimidin-6-yl)pyrrolo[2,1-f][1,2,4]triazin-2-yl)-$N^3$-methylcyclobutane-1,3-diamine [320];

cis-$N^1$-(5-(3-chloroimidazo[1,2-a]pyrimidin-6-yl)pyrrolo[2,1-f][1,2,4]triazin-2-yl)-$N_3$,$N^3$-dimethylcyclobutane-1,3-diamine [321];

trans-$N^1$-(5-(3-chloroimidazo[1,2-a]pyrimidin-6-yl)pyrrolo[2,1-f][1,2,4]triazin-2-yl)-$N_3$,$N^3$-dimethylcyclobutane-1,3-diamine [322];

5-(3-chloroimidazo[1,2-a]pyrimidin-6-yl)-N-(cis-3-morpholinocyclobutyl)pyrrolo[2,1-f][1,2,4]triazin-2-amine [323];

5-(3-chloroimidazo[1,2-a]pyrimidin-6-yl)-N-(trans-3-morpholinocyclobutyl)pyrrolo[2,1-f][1,2,4]triazin-2-amine [324];

5-(3-chloroimidazo[1,2-a]pyrimidin-6-yl)-N-(cis-3-(4-methylpiperazin-1-yl)cyclobutyl)pyrrolo[2,1-f][1,2,4]triazin-2-amine [325];

5-(3-chloroimidazo[1,2-a]pyrimidin-6-yl)-N-(trans-3-(4-methylpiperazin-1-yl)cyclobutyl)pyrrolo[2,1-f][1,2,4]triazin-2-amine [326];

5-(3-chloroimidazo[1,2-a]pyrimidin-6-yl)-N-(4,4-difluorocyclohexyl)pyrrolo[2,1-f][1,2,4]triazin-2-amine [327];

cis-4-((5-(3-chloroimidazo[1,2-a]pyrimidin-6-yl)pyrrolo[2,1-f][1,2,4]triazin-2-yl)amino)cyclohexan-1-ol [328];

(1s,4s)-4-((5-(3-chloroimidazo[1,2-a]pyrimidin-6-yl)pyrrolo[2,1-f][1,2,4]triazin-2-yl)amino)-1-methylcyclohexan-1-ol [329];

5-(3-chloroimidazo[1,2-a]pyrimidin-6-yl)-N-(cis-4-methoxycyclohexyl)pyrrolo[2,1-f][1,2,4]triazin-2-amine [330];

5-(3-chloroimidazo[1,2-a]pyrimidin-6-yl)-N-(trans-4-methoxycyclohexyl)pyrrolo[2,1-f][1,2,4]triazin-2-amine [331];

5-(3-chloroimidazo[1,2-a]pyrimidin-6-yl)-N-(cis-4-(difluoromethoxy)cyclohexyl)pyrrolo[2,1-f][1,2,4]triazin-2-amine [332];

5-(3-chloroimidazo[1,2-a]pyrimidin-6-yl)-N-(trans-4-(difluoromethoxy)cyclohexyl)pyrrolo[2,1-f][1,2,4]triazin-2-amine [333];

5-(3-chloroimidazo[1,2-a]pyrimidin-6-yl)-N-(cis-4-ethoxycyclohexyl)pyrrolo[2,1-f][1,2,4]triazin-2-amine [334];

5-(3-chloroimidazo[1,2-a]pyrimidin-6-yl)-N-(trans-4-ethoxycyclohexyl)pyrrolo [2,1-f][1,2,4]triazin-2-amine [335];

5-(3-chloroimidazo[1,2-a]pyrimidin-6-yl)-N-(cis-4-(2-methoxyethoxy)cyclohexyl)pyrrolo[2,1-f][1,2,4]triazin-2-amine [336];

5-(3-chloroimidazo[1,2-a]pyrimidin-6-yl)-N-(trans-4-(2-methoxyethoxy)cyclohexyl)pyrrolo[2,1-f][1,2,4]triazin-2-amine [337];

cis-$N^1$-(5-(3-chloroimidazo[1,2-a]pyrimidin-6-yl)pyrrolo[2,1-f][1,2,4]triazin-2-yl)cyclohexane-1,4-diamine [338];

trans-$N^1$-(5-(3-chloroimidazo[1,2-a]pyrimidin-6-yl)pyrrolo[2,1-f][1,2,4]triazin-2-yl)cyclohexane-1,4-diamine [339];

cis-$N^1$-(5-(3-chloroimidazo[1,2-a]pyrimidin-6-yl)pyrrolo[2,1-f][1,2,4]triazin-2-yl)-$N^4$-methylcyclohexane-1,4-diamine [340];

trans-$N^1$-(5-(3-chloroimidazo[1,2-a]pyrimidin-6-yl)pyrrolo[2,1-f][1,2,4]triazin-2-yl)-$N^4$-methylcyclohexane-1,4-diamine [341];

cis-$N^1$-(5-(3-chloroimidazo[1,2-a]pyrimidin-6-yl)pyrrolo[2,1-f][1,2,4]triazin-2-yl)-$N^4$,$N^4$-dimethylcyclohexane-1,4-diamine [342];

trans-$N^1$-(5-(3-chloroimidazo[1,2-a]pyrimidin-6-yl)pyrrolo[2,1-f][1,2,4]triazin-2-yl)-$N^4$,$N^4$-dimethylcyclohexane-1,4-diamine [343];

5-(3-chloroimidazo[1,2-a]pyrimidin-6-yl)-N-(cis-4-morpholinocyclohexyl)pyrrolo[2,1-f][1,2,4]triazin-2-amine [344];

5-(3-chloroimidazo[1,2-a]pyrimidin-6-yl)-N-(trans-4-(4-methylpiperazin-1-yl)cyclohexyl)pyrrolo[2,1-f][1,2,4]triazin-2-amine [345];

5-(3-chloroimidazo[1,2-a]pyrimidin-6-yl)-N-(cis-4-(4-methylpiperazin-1-yl)cyclohexyl)pyrrolo[2,1-f][1,2,4]triazin-2-amine [346];

5-(3-chloroimidazo[1,2-a]pyrimidin-6-yl)-N-(trans-4-(4-methylpiperazin-1-yl)cyclohexyl)pyrrolo[2,1-f][1,2,4]triazin-2-amine [347];

5-(3-chloroimidazo[1,2-a]pyrimidin-6-yl)-N-(1-methylazetidin-3-yl)pyrrolo[2,1-f][1,2,4]triazin-2-amine [348];

5-(3-chloroimidazo[1,2-a]pyrimidin-6-yl)-N-(oxetan-3-yl)pyrrolo[2,1-f][1,2,4]triazin-2-amine [349];

5-(3-chloroimidazo[1,2-a]pyrimidin-6-yl)-N-(1-methylpiperidin-4-yl)pyrrolo[2,1-f][1,2,4]triazin-2-amine [350];

5-(3-chloroimidazo[1,2-a]pyrimidin-6-yl)-N-(tetrahydro-2H-pyran-4-yl)pyrrolo[2,1-f][1,2,4]triazin-2-amine [351];

5-(3-chloroimidazo[1,2-a]pyrimidin-6-yl)-N-(6,6-difluorospiro[3.3]heptan-2-yl)pyrrolo[2,1-f][1,2,4]triazin-2-amine [352];

5-(3-chloroimidazo[1,2-a]pyrimidin-6-yl)-N-(2-oxaspiro[3.3]heptan-6-yl)pyrrolo[2,1-f][1,2,4]triazin-2-amine [353];

5-(3-chloroimidazo[1,2-a]pyrimidin-6-yl)-N-(2-methyl-2-azaspiro[3.3]heptan-6-yl)pyrrolo[2,1-f][1,2,4]triazin-2-amine [354];

5-(3-chloroimidazo[1,2-a]pyrimidin-6-yl)-N-(1-methyl-1H-pyrazol-4-yl)pyrrolo[2,1-f][1,2,4]triazin-2-amine [355];

N-isopropyl-5-(3-methylimidazo[1,2-a]pyrimidin-6-yl)pyrrolo[2,1-f][1,2,4]triazin-2-amine [356];

N-isobutyl-5-(3-methylimidazo[1,2-a]pyrimidin-6-yl)pyrrolo[2,1-f][1,2,4]triazin-2-amine [357];

N-(2-fluoro-2-methylpropyl)-5-(3-methylimidazo[1,2-a]pyrimidin-6-yl)pyrrolo[2,1-f][1,2,4]triazin-2-amine [358];

N-(2,2-difluoropropyl)-5-(3-methylimidazo[1,2-a]pyrimidin-6-yl)pyrrolo[2,1-f][1,2,4]triazin-2-amine [359];

5-(3-methylimidazo[1,2-a]pyrimidin-6-yl)-N-(2,2,2-trifluoroethyl)pyrrolo[2,1-f][1,2,4]triazin-2-amine [360];

(R)-5-(3-methylimidazo[1,2-a]pyrimidin-6-yl)-N-(1,1,1-trifluoropropan-2-yl)pyrrolo[2,1-f][1,2,4]triazin-2-amine [361];

5-(3-methylimidazo[1,2-a]pyrimidin-6-yl)-N-(3,3,3-trifluoropropyl)pyrrolo[2,1-f][1,2,4]triazin-2-amine [362];

5-(3-methylimidazo[1,2-a]pyrimidin-6-yl)-N-(3,3,3-trifluoro-2,2-dimethylpropyl)pyrrolo[2,1-f][1,2,4]triazin-2-amine [363];

N-(2-methoxyethyl)-5-(3-methylimidazo[1,2-a]pyrimidin-6-yl)pyrrolo[2,1-f][1,2,4]triazin-2-amine [364];

(R)—N-(1-methoxypropan-2-yl)-5-(3-methylimidazo[1,2-a]pyrimidin-6-yl)pyrrolo[2,1-f][1,2,4]triazin-2-amine [365];

N-(2-isopropoxyethyl)-5-(3-methylimidazo[1,2-a]pyrimidin-6-yl)pyrrolo[2,1-f][1,2,4]triazin-2-amine [366];

N-((1-methylcyclopropyl)methyl)-5-(3-methylimidazo[1,2-a]pyrimidin-6-yl)pyrrolo[2,1-f][1,2,4]triazin-2-amine [367];

5-(3-methylimidazo[1,2-a]pyrimidin-6-yl)-N-((1-(trifluoromethyl)cyclopropyl)methyl)pyrrolo[2,1-f][1,2,4]triazin-2-amine [368];

N-((1-fluorocyclobutyl)methyl)-5-(3-methylimidazo[1,2-a]pyrimidin-6-yl)pyrrolo[2,1-f][1,2,4]triazin-2-amine [369];

N-((3-fluorooxetan-3-yl)methyl)-5-(3-methylimidazo[1,2-a]pyrimidin-6-yl)pyrrolo[2,1-f][1,2,4]triazin-2-amine [370];

N-(cyclopropylmethyl)-5-(3-methylimidazo[1,2-a]pyrimidin-6-yl)pyrrolo[2,1-f][1,2,4]triazin-2-amine [371];

(S)—N-(1-cyclopropylethyl)-5-(3-methylimidazo[1,2-a]pyrimidin-6-yl)pyrrolo[2,1-f][1,2,4]triazin-2-amine [372];

(R)—N-(1-cyclopropylethyl)-5-(3-methylimidazo[1,2-a]pyrimidin-6-yl)pyrrolo[2,1-f][1,2,4]triazin-2-amine [373];

N-(2-cyclopropyl-2,2-difluoroethyl)-5-(3-methylimidazo[1,2-a]pyrimidin-6-yl)pyrrolo[2,1-f][1,2,4]triazin-2-amine [374];

5-(3-methylimidazo[1,2-a]pyrimidin-6-yl)-N-(oxetan-3-ylmethyl)pyrrolo[2,1-f][1,2,4]triazin-2-amine [375];

5-(3-methylimidazo[1,2-a]pyrimidin-6-yl)-N-((tetrahydrofuran-2-yl)methyl)pyrrolo[2,1-f][1,2,4]triazin-2-amine [376];

N-cyclobutyl-5-(3-methylimidazo[1,2-a]pyrimidin-6-yl)pyrrolo[2,1-f][1,2,4]triazin-2-amine [377];

N-(3,3-difluorocyclobutyl)-5-(3-methylimidazo[1,2-a]pyrimidin-6-yl)pyrrolo[2,1-f][1,2,4]triazin-2-amine [378];

N-(3,3-dimethylcyclobutyl)-5-(3-methylimidazo[1,2-a]pyrimidin-6-yl)pyrrolo[2,1-f][1,2,4]triazin-2-amine [379];

1-methyl-3-((5-(3-methylimidazo[1,2-a]pyrimidin-6-yl)pyrrolo[2,1-f][1,2,4]triazin-2-yl)amino)cyclobutan-1-ol [380];

N-(cis-3-methoxycyclobutyl)-5-(3-methylimidazo[1,2-a]pyrimidin-6-yl)pyrrolo[2,1-f][1,2,4]triazin-2-amine [381];

N-(trans-3-methoxycyclobutyl)-5-(3-methylimidazo[1,2-a]pyrimidin-6-yl)pyrrolo[2,1-f][1,2,4]triazin-2-amine [382];

N-(trans-3-(methoxymethyl)cyclobutyl)-5-(3-methylimidazo[1,2-a]pyrimidin-6-yl)pyrrolo[2,1-f][1,2,4]triazin-2-amine [383];

N-(cis-3-ethoxycyclobutyl)-5-(3-methylimidazo[1,2-a]pyrimidin-6-yl)pyrrolo[2,1-f][1,2,4]triazin-2-amine [384];

N-(trans-3-ethoxycyclobutyl)-5-(3-methylimidazo[1,2-a]pyrimidin-6-yl)pyrrolo[2,1-f][1,2,4]triazin-2-amine [385];

N-(cis-3-(2-methoxyethoxy)cyclobutyl)-5-(3-methylimidazo[1,2-a]pyrimidin-6-yl)pyrrolo[2,1-f][1,2,4]triazin-2-amine [386];

N-(trans-3-(2-methoxyethoxy)cyclobutyl)-5-(3-methylimidazo[1,2-a]pyrimidin-6-yl)pyrrolo[2,1-f][1,2,4]triazin-2-amine [387];

cis-$N^1$-(5-(3-methylimidazo[1,2-a]pyrimidin-6-yl)pyrrolo[2,1-f][1,2,4]triazin-2-yl)cyclobutane-1,3-diamine [388];

trans-$N^1$-(5-(3-methylimidazo[1,2-a]pyrimidin-6-yl)pyrrolo[2,1-f][1,2,4]triazin-2-yl)cyclobutane-1,3-diamine [389];

cis-$N^1$-methyl-$N^3$-(5-(3-methylimidazo[1,2-a]pyrimidin-6-yl)pyrrolo[2,1-f][1,2,4]triazin-2-yl)cyclobutane-1,3-diamine [390];

trans-$N^1$-methyl-$N^3$-(5-(3-methylimidazo[1,2-a]pyrimidin-6-yl)pyrrolo[2,1-f][1,2,4]triazin-2-yl)cyclobutane-1,3-diamine [391];

cis-$N^1$,$N^1$-dimethyl-$N^3$-(5-(3-methylimidazo[1,2-a]pyrimidin-6-yl)pyrrolo[2,1-f][1,2,4]triazin-2-yl)cyclobutane-1,3-diamine [392];

trans-$N^1$,$N^1$-dimethyl-$N^3$-(5-(3-methylimidazo[1,2-a]pyrimidin-6-yl)pyrrolo[2,1-f][1,2,4]triazin-2-yl)cyclobutane-1,3-diamine [393];

5-(3-methylimidazo[1,2-a]pyrimidin-6-yl)-N-(cis-3-morpholinocyclobutyl)pyrrolo[2,1-f][1,2,4]triazin-2-amine [394];

5-(3-methylimidazo[1,2-a]pyrimidin-6-yl)-N-(trans-3-morpholinocyclobutyl)pyrrolo[2,1-f][1,2,4]triazin-2-amine [395];

5-(3-methylimidazo[1,2-a]pyrimidin-6-yl)-N-(cis-3-(4-methylpiperazin-1-yl)cyclobutyl)pyrrolo[2,1-f][1,2,4]triazin-2-amine [396];

5-(3-methylimidazo[1,2-a]pyrimidin-6-yl)-N-(trans-3-(4-methylpiperazin-1-yl)cyclobutyl)pyrrolo[2,1-f][1,2,4]triazin-2-amine [397];

N-(4,4-difluorocyclohexyl)-5-(3-methylimidazo[1,2-a]pyrimidin-6-yl)pyrrolo[2,1-f][1,2,4]triazin-2-amine [398];

cis-4-((5-(3-methylimidazo[1,2-a]pyrimidin-6-yl)pyrrolo[2,1-f][1,2,4]triazin-2-yl)amino)cyclohexan-1-ol [399];

(1s,4s)-1-methyl-4-((5-(3-methylimidazo[1,2-a]pyrimidin-6-yl)pyrrolo[2,1-f][1,2,4]triazin-2-yl)amino)cyclohexan-1-ol [400];

N-(cis-4-methoxycyclohexyl)-5-(3-methylimidazo[1,2-a]pyrimidin-6-yl)pyrrolo[2,1-f][1,2,4]triazin-2-amine [401];

N-(trans-4-methoxycyclohexyl)-5-(3-methylimidazo[1,2-a]pyrimidin-6-yl)pyrrolo[2,1-f][1,2,4]triazin-2-amine [402];

N-(cis-4-(difluoromethoxy)cyclohexyl)-5-(3-methylimidazo[1,2-a]pyrimidin-6-yl)pyrrolo[2,1-f][1,2,4]triazin-2-amine [403];

N-(trans-4-(difluoromethoxy)cyclohexyl)-5-(3-methylimidazo[1,2-a]pyrimidin-6-yl)pyrrolo[2,1-f][1,2,4]triazin-2-amine [404];

N-(cis-4-ethoxycyclohexyl)-5-(3-methylimidazo[1,2-a]pyrimidin-6-yl)pyrrolo[2,1-f][1,2,4]triazin-2-amine [405];

N-(trans-4-ethoxycyclohexyl)-5-(3-methylimidazo[1,2-a]pyrimidin-6-yl)pyrrolo[2,1-f][1,2,4]triazin-2-amine [406];

N-(cis-4-(2-methoxyethoxy)cyclohexyl)-5-(3-methylimidazo[1,2-a]pyrimidin-6-yl)pyrrolo[2,1-f][1,2,4]triazin-2-amine [407];

N-(trans-4-(2-methoxyethoxy)cyclohexyl)-5-(3-methylimidazo[1,2-a]pyrimidin-6-yl)pyrrolo[2,1-f][1,2,4]triazin-2-amine [408];

cis-$N^1$-(5-(3-methylimidazo[1,2-a]pyrimidin-6-yl)pyrrolo[2,1-f][1,2,4]triazin-2-yl)cyclohexane-1,4-diamine [409];

trans-$N^1$-(5-(3-methylimidazo[1,2-a]pyrimidin-6-yl)pyrrolo[2,1-f][1,2,4]triazin-2-yl)cyclohexane-1,4-diamine [410];

cis-$N^1$-methyl-$N^4$-(5-(3-methylimidazo[1,2-a]pyrimidin-6-yl)pyrrolo[2,1-f][1,2,4]triazin-2-yl)cyclohexane-1,4-diamine [411];

trans-$N^1$-methyl-$N^4$-(5-(3-methylimidazo[1,2-a]pyrimidin-6-yl)pyrrolo[2,1-f][1,2,4]triazin-2-yl)cyclohexane-1,4-diamine [412];

cis-$N^1$,$N^1$-dimethyl-$N^4$-(5-(3-methylimidazo[1,2-a]pyrimidin-6-yl)pyrrolo[2,1-f][1,2,4]triazin-2-yl)cyclohexane-1,4-diamine [413];

trans-$N^1$,$N^1$-dimethyl-$N^4$-(5-(3-methylimidazo[1,2-a]pyrimidin-6-yl)pyrrolo[2,1-f][1,2,4]triazin-2-yl)cyclohexane-1,4-diamine [414];

5-(3-methylimidazo[1,2-a]pyrimidin-6-yl)-N-(cis-4-morpholinocyclohexyl)pyrrolo[2,1-f][1,2,4]triazin-2-amine [415];

5-(3-methylimidazo[1,2-a]pyrimidin-6-yl)-N-(trans-4-morpholinocyclohexyl)pyrrolo[2,1-f][1,2,4]triazin-2-amine [416];

5-(3-methylimidazo[1,2-a]pyrimidin-6-yl)-N-(cis-4-(4-methylpiperazin-1-yl)cyclohexyl)pyrrolo[2,1-f][1,2,4]triazin-2-amine [417];

5-(3-methylimidazo[1,2-a]pyrimidin-6-yl)-N-(trans-4-(4-methylpiperazin-1-yl)cyclohexyl)pyrrolo[2,1-f][1,2,4]triazin-2-amine [418];

N-(1-methylazetidin-3-yl)-5-(3-methylimidazo[1,2-a]pyrimidin-6-yl)pyrrolo[2,1-f][1,2,4]triazin-2-amine [419];

5-(3-methylimidazo[1,2-a]pyrimidin-6-yl)-N-(oxetan-3-yl)pyrrolo[2,1-f][1,2,4]triazin-2-amine [420];

5-(3-methylimidazo[1,2-a]pyrimidin-6-yl)-N-(1-methylpiperidin-4-yl)pyrrolo[2,1-f][1,2,4]triazin-2-amine [421];

5-(3-methylimidazo[1,2-a]pyrimidin-6-yl)-N-(tetrahydro-2H-pyran-4-yl)pyrrolo[2,1-f][1,2,4]triazin-2-amine [422];

N-(6,6-difluorospiro[3.3]heptan-2-yl)-5-(3-methylimidazo[1,2-a]pyrimidin-6-yl)pyrrolo[2,1-f][1,2,4]triazin-2-amine [423];

5-(3-methylimidazo[1,2-a]pyrimidin-6-yl)-N-(2-oxaspiro[3.3]heptan-6-yl)pyrrolo[2,1-f][1,2,4]triazin-2-amine [424];

N-(2-methyl-2-azaspiro[3.3]heptan-6-yl)-5-(3-methylimidazo[1,2-a]pyrimidin-6-yl)pyrrolo[2,1-f][1,2,4]triazin-2-amine [425];

N-(1-methyl-1H-pyrazol-4-yl)-5-(3-methylimidazo[1,2-a]pyrimidin-6-yl)pyrrolo[2,1-f][1,2,4]triazin-2-amine [426];

5-(3-ethylimidazo[1,2-a]pyrimidin-6-yl)-N-isopropylpyrrolo[2,1-f][1,2,4]triazin-2-amine [427];

5-(3-ethylimidazo[1,2-a]pyrimidin-6-yl)-N-isobutylpyrrolo[2,1-f][1,2,4]triazin-2-amine [428];

5-(3-ethylimidazo[1,2-a]pyrimidin-6-yl)-N-(2-fluoro-2-methylpropyl)pyrrolo[2,1-f][1,2,4]triazin-2-amine [429];

N-(2,2-difluoropropyl)-5-(3-ethylimidazo[1,2-a]pyrimidin-6-yl)pyrrolo[2,1-f][1,2,4]triazin-2-amine [430];

5-(3-ethylimidazo[1,2-a]pyrimidin-6-yl)-N-(2,2,2-trifluoroethyl)pyrrolo[2,1-f][1,2,4]triazin-2-amine [431];

(R)-5-(3-ethylimidazo[1,2-a]pyrimidin-6-yl)-N-(1,1,1-trifluoropropan-2-yl)pyrrolo[2,1-f][1,2,4]triazin-2-amine [432];

5-(3-ethylimidazo[1,2-a]pyrimidin-6-yl)-N-(3,3,3-trifluoropropyl)pyrrolo[2,1-f][1,2,4]triazin-2-amine [433];

5-(3-ethylimidazo[1,2-a]pyrimidin-6-yl)-N-(3,3,3-trifluoro-2,2-dimethylpropyl)pyrrolo[2,1-f][1,2,4]triazin-2-amine [434];

5-(3-ethylimidazo[1,2-a]pyrimidin-6-yl)-N-(2-methoxyethyl)pyrrolo[2,1-f][1,2,4]triazin-2-amine [435];

(R)-5-(3-ethylimidazo[1,2-a]pyrimidin-6-yl)-N-(1-methoxypropan-2-yl)pyrrolo[2,1-f][1,2,4]triazin-2-amine [436];

5-(3-ethylimidazo[1,2-a]pyrimidin-6-yl)-N-(2-isopropoxyethyl)pyrrolo[2,1-f][1,2,4]triazin-2-amine [437];

5-(3-ethylimidazo[1,2-a]pyrimidin-6-yl)-N-((1-methylcyclopropyl)methyl)pyrrolo[2,1-f][1,2,4]triazin-2-amine [438];

5-(3-ethylimidazo[1,2-a]pyrimidin-6-yl)-N-((1-(trifluoromethyl)cyclopropyl)methyl)pyrrolo[2,1-f][1,2,4]triazin-2-amine [439];

5-(3-ethylimidazo[1,2-a]pyrimidin-6-yl)-N-((1-fluorocyclobutyl)methyl)pyrrolo[2,1-f][1,2,4]triazin-2-amine [440];

5-(3-ethylimidazo[1,2-a]pyrimidin-6-yl)-N-((3-fluorooxetan-3-yl)methyl)pyrrolo[2,1-f][1,2,4]triazin-2-amine [441];

N-(cyclopropylmethyl)-5-(3-ethylimidazo[1,2-a]pyrimidin-6-yl)pyrrolo[2,1-f][1,2,4]triazin-2-amine [442];

(S)—N-(1-cyclopropylethyl)-5-(3-ethylimidazo[1,2-a]pyrimidin-6-yl)pyrrolo[2,1-f][1,2,4]triazin-2-amine [443];

(R)—N-(1-cyclopropylethyl)-5-(3-ethylimidazo[1,2-a]pyrimidin-6-yl)pyrrolo[2,1-f][1,2,4]triazin-2-amine [444];

N-(2-cyclopropyl-2,2-difluoroethyl)-5-(3-ethylimidazo[1,2-a]pyrimidin-6-yl)pyrrolo[2,1-f][1,2,4]triazin-2-amine [445];

5-(3-ethylimidazo[1,2-a]pyrimidin-6-yl)-N-(oxetan-3-ylmethyl)pyrrolo[2,1-f][1,2,4]triazin-2-amine [446];

5-(3-ethylimidazo[1,2-a]pyrimidin-6-yl)-N-((tetrahydrofuran-2-yl)methyl)pyrrolo[2,1-f][1,2,4]triazin-2-amine [447];

N-cyclobutyl-5-(3-ethylimidazo[1,2-a]pyrimidin-6-yl)pyrrolo[2,1-f][1,2,4]triazin-2-amine [448];

N-(3,3-difluorocyclobutyl)-5-(3-ethylimidazo[1,2-a]pyrimidin-6-yl)pyrrolo[2,1-f][1,2,4]triazin-2-amine [449];

N-(3,3-dimethylcyclobutyl)-5-(3-ethylimidazo[1,2-a]pyrimidin-6-yl)pyrrolo[2,1-f][1,2,4]triazin-2-amine [450];

3-((5-(3-ethylimidazo[1,2-a]pyrimidin-6-yl)pyrrolo[2,1-f][1,2,4]triazin-2-yl)amino)-1-methylcyclobutan-1-ol [451];

5-(3-ethylimidazo[1,2-a]pyrimidin-6-yl)-N-(cis-3-methoxycyclobutyl)pyrrolo[2,1-f][1,2,4]triazin-2-amine [452];

5-(3-ethylimidazo[1,2-a]pyrimidin-6-yl)-N-(trans-3-methoxycyclobutyl)pyrrolo[2,1-f][1,2,4]triazin-2-amine [453];

5-(3-ethylimidazo[1,2-a]pyrimidin-6-yl)-N-(trans-3-(methoxymethyl)cyclobutyl)pyrrolo[2,1-f][1,2,4]triazin-2-amine [454];

N-(cis-3-ethoxycyclobutyl)-5-(3-ethylimidazo[1,2-a]pyrimidin-6-yl)pyrrolo[2,1-f][1,2,4]triazin-2-amine [455];

N-(trans-3-ethoxycyclobutyl)-5-(3-ethylimidazo[1,2-a]pyrimidin-6-yl)pyrrolo[2,1-f][1,2,4]triazin-2-amine [456];

5-(3-ethylimidazo[1,2-a]pyrimidin-6-yl)-N-(cis-3-(2-methoxyethoxy)cyclobutyl)pyrrolo[2,1-f][1,2,4]triazin-2-amine [457];

5-(3-ethylimidazo[1,2-a]pyrimidin-6-yl)-N-(trans-3-(2-methoxyethoxy)cyclobutyl)pyrrolo[2,1-f][1,2,4]triazin-2-amine [458];

cis-$N^1$-(5-(3-ethylimidazo[1,2-a]pyrimidin-6-yl)pyrrolo[2,1-f][1,2,4]triazin-2-yl)cyclobutane-1,3-diamine [459];

trans-$N^1$-(5-(3-ethylimidazo[1,2-a]pyrimidin-6-yl)pyrrolo[2,1-f][1,2,4]triazin-2-yl)cyclobutane-1,3-diamine [460];

cis-$N^1$-(5-(3-ethylimidazo[1,2-a]pyrimidin-6-yl)pyrrolo[2,1-f][1,2,4]triazin-2-yl)-$N^3$-methylcyclobutane-1,3-diamine [461];

trans-$N^1$-(5-(3-ethylimidazo[1,2-a]pyrimidin-6-yl)pyrrolo[2,1-f][1,2,4]triazin-2-yl)-$N^3$-methylcyclobutane-1,3-diamine [462];

cis-$N^1$-(5-(3-ethylimidazo[1,2-a]pyrimidin-6-yl)pyrrolo[2,1-f][1,2,4]triazin-2-yl)-$N^3$,$N^3$-dimethylcyclobutane-1,3-diamine [463];

trans-$N^1$-(5-(3-ethylimidazo[1,2-a]pyrimidin-6-yl)pyrrolo[2,1-f][1,2,4]triazin-2-yl)-$N^3$,$N^3$-dimethylcyclobutane-1,3-diamine [464];

5-(3-ethylimidazo[1,2-a]pyrimidin-6-yl)-N-(cis-3-morpholinocyclobutyl)pyrrolo[2,1-f][1,2,4]triazin-2-amine [465];

5-(3-ethylimidazo[1,2-a]pyrimidin-6-yl)-N-(trans-3-morpholinocyclobutyl)pyrrolo[2,1-f][1,2,4]triazin-2-amine [466];

5-(3-ethylimidazo[1,2-a]pyrimidin-6-yl)-N-(cis-3-(4-methylpiperazin-1-yl)cyclobutyl)pyrrolo[2,1-f][1,2,4]triazin-2-amine [467];

5-(3-ethylimidazo[1,2-a]pyrimidin-6-yl)-N-(trans-3-(4-methylpiperazin-1-yl)cyclobutyl)pyrrolo[2,1-f][1,2,4]triazin-2-amine [468];

N-(4,4-difluorocyclohexyl)-5-(3-ethylimidazo[1,2-a]pyrimidin-6-yl)pyrrolo[2,1-f][1,2,4]triazin-2-amine [469];

cis-4-((5-(3-ethylimidazo[1,2-a]pyrimidin-6-yl)pyrrolo[2,1-f][1,2,4]triazin-2-yl)amino)cyclohexan-1-ol [470];

(1s,4s)-4-((5-(3-ethylimidazo[1,2-a]pyrimidin-6-yl)pyrrolo[2,1-f][1,2,4]triazin-2-yl)amino)-1-methylcyclohexan-1-ol [471];

5-(3-ethylimidazo[1,2-a]pyrimidin-6-yl)-N-(cis-4-methoxycyclohexyl)pyrrolo[2,1-f][1,2,4]triazin-2-amine [472];

5-(3-ethylimidazo[1,2-a]pyrimidin-6-yl)-N-(trans-4-methoxycyclohexyl)pyrrolo[2,1-f][1,2,4]triazin-2-amine [473];

N-(cis-4-(difluoromethoxy)cyclohexyl)-5-(3-ethylimidazo[1,2-a]pyrimidin-6-yl)pyrrolo[2,1-f][1,2,4]triazin-2-amine [474];

N-(trans-4-(difluoromethoxy)cyclohexyl)-5-(3-ethylimidazo[1,2-a]pyrimidin-6-yl)pyrrolo[2,1-f][1,2,4]triazin-2-amine [475];

N-(cis-4-ethoxycyclohexyl)-5-(3-ethylimidazo[1,2-a]pyrimidin-6-yl)pyrrolo[2,1-f][1,2,4]triazin-2-amine [476];

N-(trans-4-ethoxycyclohexyl)-5-(3-ethylimidazo[1,2-a]pyrimidin-6-yl)pyrrolo[2,1-f][1,2,4]triazin-2-amine [477];

5-(3-ethylimidazo[1,2-a]pyrimidin-6-yl)-N-(cis-4-(2-methoxyethoxy)cyclohexyl)pyrrolo[2,1-f][1,2,4]triazin-2-amine [478];

5-(3-ethylimidazo[1,2-a]pyrimidin-6-yl)-N-(trans-4-(2-methoxyethoxy)cyclohexyl)pyrrolo[2,1-f][1,2,4]triazin-2-amine [479];

cis-$N^1$-(5-(3-ethylimidazo[1,2-a]pyrimidin-6-yl)pyrrolo[2,1-f][1,2,4]triazin-2-yl)cyclohexane-1,4-diamine [480];

trans-$N^1$-(5-(3-ethylimidazo[1,2-a]pyrimidin-6-yl)pyrrolo[2,1-f][1,2,4]triazin-2-yl)cyclohexane-1,4-diamine [481];

cis-$N^1$-(5-(3-ethylimidazo[1,2-a]pyrimidin-6-yl)pyrrolo[2,1-f][1,2,4]triazin-2-yl)-$N^4$-methylcyclohexane-1,4-diamine [482];

trans-$N^1$-(5-(3-ethylimidazo[1,2-a]pyrimidin-6-yl)pyrrolo[2,1-f][1,2,4]triazin-2-yl)-$N^4$-methylcyclohexane-1,4-diamine [483];

cis-$N^1$-(5-(3-ethylimidazo[1,2-a]pyrimidin-6-yl)pyrrolo[2,1-f][1,2,4]triazin-2-yl)-$N^4$,$N^4$-dimethylcyclohexane-1,4-diamine [484];

trans-$N^1$-(5-(3-ethylimidazo[1,2-a]pyrimidin-6-yl)pyrrolo[2,1-f][1,2,4]triazin-2-yl)-$N^4$,$N^4$-dimethylcyclohexane-1,4-diamine [485];

5-(3-ethylimidazo[1,2-a]pyrimidin-6-yl)-N-(cis-4-morpholinocyclohexyl)pyrrolo[2,1-f][1,2,4]triazin-2-amine [486];

5-(3-ethylimidazo[1,2-a]pyrimidin-6-yl)-N-(trans-4-morpholinocyclohexyl)pyrrolo[2,1-f][1,2,4]triazin-2-amine [487];

5-(3-ethylimidazo[1,2-a]pyrimidin-6-yl)-N-(cis-4-(4-methylpiperazin-1-yl)cyclohexyl)pyrrolo[2,1-f][1,2,4]triazin-2-amine [488];

5-(3-ethylimidazo[1,2-a]pyrimidin-6-yl)-N-(trans-4-(4-methylpiperazin-1-yl)cyclohexyl)pyrrolo[2,1-f][1,2,4]triazin-2-amine [489];

5-(3-ethylimidazo[1,2-a]pyrimidin-6-yl)-N-(1-methylazetidin-3-yl)pyrrolo[2,1-f][1,2,4]triazin-2-amine [490];

5-(3-ethylimidazo[1,2-a]pyrimidin-6-yl)-N-(oxetan-3-yl)pyrrolo[2,1-f][1,2,4]triazin-2-amine [491];

5-(3-ethylimidazo[1,2-a]pyrimidin-6-yl)-N-(1-methylpiperidin-4-yl)pyrrolo[2,1-f][1,2,4]triazin-2-amine [492];

5-(3-ethylimidazo[1,2-a]pyrimidin-6-yl)-N-(tetrahydro-2H-pyran-4-yl)pyrrolo[2,1-f][1,2,4]triazin-2-amine [493];

N-(6,6-difluorospiro[3.3]heptan-2-yl)-5-(3-ethylimidazo[1,2-a]pyrimidin-6-yl)pyrrolo[2,1-f][1,2,4]triazin-2-amine [494];

5-(3-ethylimidazo[1,2-a]pyrimidin-6-yl)-N-(2-oxaspiro[3.3]heptan-6-yl)pyrrolo[2,1-f][1,2,4]triazin-2-amine [495];

5-(3-ethylimidazo[1,2-a]pyrimidin-6-yl)-N-(2-methyl-2-azaspiro[3.3]heptan-6-yl)pyrrolo[2,1-f][1,2,4]triazin-2-amine [496];

5-(3-ethylimidazo[1,2-a]pyrimidin-6-yl)-N-(1-methyl-1H-pyrazol-4-yl)pyrrolo[2,1-f][1,2,4]triazin-2-amine [497];

5-(4-fluoro-1-isopropyl-2-methyl-1H-benzo[d]imidazol-6-yl)-N-isopropylpyrrolo[2,1-f][1,2,4]triazin-2-amine [498];

5-(4-fluoro-1-isopropyl-2-methyl-1H-benzo[d]imidazol-6-yl)-N-isobutylpyrrolo[2,1-f][1,2,4]triazin-2-amine [499]; and 5-(4-fluoro-1-isopropyl-2-methyl-1H-benzo[d]imidazol-6-yl)-N-(2-fluoro-2-methylpropyl)pyrrolo[2,1-f][1,2,4]triazin-2-amine [500]; or a pharmaceutically acceptable salt thereof.

9. The compound of claim 1, wherein the compound of Formula I is selected from the group consisting of:

N-(2,2-difluoropropyl)-5-(4-fluoro-1-isopropyl-2-methyl-1H-benzo[d]imidazol-6-yl)pyrrolo[2,1-f][1,2,4]triazin-2-amine [501];

5-(4-fluoro-1-isopropyl-2-methyl-1H-benzo[d]imidazol-6-yl)-N-(2,2,2-trifluoroethyl)pyrrolo[2,1-f][1,2,4]triazin-2-amine [502];

(R)-5-(4-fluoro-1-isopropyl-2-methyl-1H-benzo[d]imidazol-6-yl)-N-(1,1,1-trifluoropropan-2-yl)pyrrolo[2,1-f][1,2,4]triazin-2-amine [503];

5-(4-fluoro-1-isopropyl-2-methyl-1H-benzo[d]imidazol-6-yl)-N-(3,3,3-trifluoropropyl)pyrrolo[2,1-f][1,2,4]triazin-2-amine [504];

5-(4-fluoro-1-isopropyl-2-methyl-1H-benzo[d]imidazol-6-yl)-N-(3,3,3-trifluoro-2,2-dimethylpropyl)pyrrolo[2,1-f][1,2,4]triazin-2-amine [505];

5-(4-fluoro-1-isopropyl-2-methyl-1H-benzo[d]imidazol-6-yl)-N-(2-methoxyethyl)pyrrolo[2,1-f][1,2,4]triazin-2-amine [506];

(R)-5-(4-fluoro-1-isopropyl-2-methyl-1H-benzo[d]imidazol-6-yl)-N-(1-methoxypropan-2-yl)pyrrolo[2,1-f][1,2,4]triazin-2-amine [507];

5-(4-fluoro-1-isopropyl-2-methyl-1H-benzo[d]imidazol-6-yl)-N-(2-isopropoxyethyl)pyrrolo[2,1-f][1,2,4]triazin-2-amine [508];

5-(4-fluoro-1-isopropyl-2-methyl-1H-benzo[d]imidazol-6-yl)-N-((1-methylcyclopropyl)methyl)pyrrolo[2,1-f][1,2,4]triazin-2-amine [509];

5-(4-fluoro-1-isopropyl-2-methyl-1H-benzo[d]imidazol-6-yl)-N-((1-(trifluoromethyl)cyclopropyl)methyl)pyrrolo[2,1-f][1,2,4]triazin-2-amine [510];

5-(4-fluoro-1-isopropyl-2-methyl-1H-benzo[d]imidazol-6-yl)-N-((1-fluorocyclobutyl)methyl)pyrrolo[2,1-f][1,2,4]triazin-2-amine [511];

5-(4-fluoro-1-isopropyl-2-methyl-1H-benzo[d]imidazol-6-yl)-N-((3-fluorooxetan-3-yl)methyl)pyrrolo[2,1-f][1,2,4]triazin-2-amine [512];

N-(cyclopropylmethyl)-5-(4-fluoro-1-isopropyl-2-methyl-1H-benzo[d]imidazol-6-yl)pyrrolo[2,1-f][1,2,4]triazin-2-amine [513];

(S)—N-(1-cyclopropylethyl)-5-(4-fluoro-1-isopropyl-2-methyl-1H-benzo[d]imidazol-6-yl)pyrrolo[2,1-f][1,2,4]triazin-2-amine [514];

(R)—N-(1-cyclopropylethyl)-5-(4-fluoro-1-isopropyl-2-methyl-1H-benzo[d]imidazol-6-yl)pyrrolo[2,1-f][1,2,4]triazin-2-amine [515];

N-(2-cyclopropyl-2,2-difluoroethyl)-5-(4-fluoro-1-isopropyl-2-methyl-1H-benzo[d]imidazol-6-yl)pyrrolo[2,1-f][1,2,4]triazin-2-amine [516];

5-(4-fluoro-1-isopropyl-2-methyl-1H-benzo[d]imidazol-6-yl)-N-(oxetan-3-ylmethyl)pyrrolo[2,1-f][1,2,4]triazin-2-amine [517];

5-(4-fluoro-1-isopropyl-2-methyl-1H-benzo[d]imidazol-6-yl)-N-((tetrahydrofuran-2-yl)methyl)pyrrolo[2,1-f][1,2,4]triazin-2-amine [518];

N-cyclobutyl-5-(4-fluoro-1-isopropyl-2-methyl-1H-benzo[d]imidazol-6-yl)pyrrolo[2,1-f][1,2,4]triazin-2-amine [519];

N-(3,3-difluorocyclobutyl)-5-(4-fluoro-1-isopropyl-2-methyl-1H-benzo[d]imidazol-6-yl)pyrrolo[2,1-f][1,2,4]triazin-2-amine [520];

N-(3,3-dimethylcyclobutyl)-5-(4-fluoro-1-isopropyl-2-methyl-1H-benzo[d]imidazol-6-yl)pyrrolo[2,1-f][1,2,4]triazin-2-amine [521];

3-((5-(4-fluoro-1-isopropyl-2-methyl-1H-benzo[d]imidazol-6-yl)pyrrolo[2,1-f][1,2,4]triazin-2-yl)amino)-1-methylcyclobutan-1-ol [522];

5-(4-fluoro-1-isopropyl-2-methyl-1H-benzo[d]imidazol-6-yl)-N-(cis-3-methoxycyclobutyl)pyrrolo[2,1-f][1,2,4]triazin-2-amine [523];

5-(4-fluoro-1-isopropyl-2-methyl-1H-benzo[d]imidazol-6-yl)-N-(trans-3-methoxycyclobutyl)pyrrolo[2,1-f][1,2,4]triazin-2-amine [524];

5-(4-fluoro-1-isopropyl-2-methyl-1H-benzo[d]imidazol-6-yl)-N-(trans-3-(methoxymethyl)cyclobutyl)pyrrolo[2,1-f][1,2,4]triazin-2-amine [525];

N-(cis-3-ethoxycyclobutyl)-5-(4-fluoro-1-isopropyl-2-methyl-1H-benzo[d]imidazol-6-yl)pyrrolo[2,1-f][1,2,4]triazin-2-amine [526];

N-(trans-3-ethoxycyclobutyl)-5-(4-fluoro-1-isopropyl-2-methyl-1H-benzo[d]imidazol-6-yl)pyrrolo[2,1-f][1,2,4]triazin-2-amine [527];

5-(4-fluoro-1-isopropyl-2-methyl-1H-benzo[d]imidazol-6-yl)-N-(cis-3-(2-methoxyethoxy)cyclobutyl)pyrrolo[2,1-f][1,2,4]triazin-2-amine [528];

5-(4-fluoro-1-isopropyl-2-methyl-1H-benzo[d]imidazol-6-yl)-N-(trans-3-(2-methoxyethoxy)cyclobutyl)pyrrolo[2,1-f][1,2,4]triazin-2-amine [529];

cis-$N^1$-(5-(4-fluoro-1-isopropyl-2-methyl-1H-benzo[d]imidazol-6-yl)pyrrolo[2,1-f][1,2,4]triazin-2-yl)cyclobutane-1,3-diamine [530];

trans-$N^1$-(5-(4-fluoro-1-isopropyl-2-methyl-1H-benzo[d]imidazol-6-yl)pyrrolo[2,1-f][1,2,4]triazin-2-yl)cyclobutane-1,3-diamine [531];

cis-$N^1$-(5-(4-fluoro-1-isopropyl-2-methyl-1H-benzo[d]imidazol-6-yl)pyrrolo[2,1-f][1,2,4]triazin-2-yl)-$N^3$-methylcyclobutane-1,3-diamine [532];

trans-$N^1$-(5-(4-fluoro-1-isopropyl-2-methyl-1H-benzo[d]imidazol-6-yl)pyrrolo[2,1-f][1,2,4]triazin-2-yl)-$N^3$-methylcyclobutane-1,3-diamine [533];

cis-$N^1$-(5-(4-fluoro-1-isopropyl-2-methyl-1H-benzo[d]imidazol-6-yl)pyrrolo[2,1-f][1,2,4]triazin-2-yl)-$N^3$,$N^3$-dimethylcyclobutane-1,3-diamine [534];

trans-$N^1$-(5-(4-fluoro-1-isopropyl-2-methyl-1H-benzo[d]imidazol-6-yl)pyrrolo[2,1-f][1,2,4]triazin-2-yl)-$N^3$,$N^3$-dimethylcyclobutane-1,3-diamine [535];

5-(4-fluoro-1-isopropyl-2-methyl-1H-benzo[d]imidazol-6-yl)-N-(cis-3-morpholinocyclobutyl)pyrrolo[2,1-f][1,2,4]triazin-2-amine [536];

5-(4-fluoro-1-isopropyl-2-methyl-1H-benzo[d]imidazol-6-yl)-N-(trans-3-morpholinocyclobutyl)pyrrolo[2,1-f][1,2,4]triazin-2-amine [537];

5-(4-fluoro-1-isopropyl-2-methyl-1H-benzo[d]imidazol-6-yl)-N-(cis-3-(4-methylpiperazin-1-yl)cyclobutyl)pyrrolo[2,1-f][1,2,4]triazin-2-amine [538];

5-(4-fluoro-1-isopropyl-2-methyl-1H-benzo[d]imidazol-6-yl)-N-(trans-3-(4-methylpiperazin-1-yl)cyclobutyl)pyrrolo[2,1-f][1,2,4]triazin-2-amine [539];

N-(4,4-difluorocyclohexyl)-5-(4-fluoro-1-isopropyl-2-methyl-1H-benzo[d]imidazol-6-yl)pyrrolo[2,1-f][1,2,4]triazin-2-amine [540];

cis-4-((5-(4-fluoro-1-isopropyl-2-methyl-1H-benzo[d]imidazol-6-yl)pyrrolo[2,1-f][1,2,4]triazin-2-yl)amino)cyclohexan-1-ol [541];

(1s,4s)-4-((5-(4-fluoro-1-isopropyl-2-methyl-1H-benzo[d]imidazol-6-yl)pyrrolo[2,1-f][1,2,4] triazin-2-yl)amino)-1-methylcyclohexan-1-ol [542];

5-(4-fluoro-1-isopropyl-2-methyl-1H-benzo[d]imidazol-6-yl)-N-(cis-4-methoxycyclohexyl)pyrrolo[2,1-f][1,2,4]triazin-2-amine [543];

5-(4-fluoro-1-isopropyl-2-methyl-1H-benzo[d]imidazol-6-yl)-N-(trans-4-methoxycyclohexyl)pyrrolo[2,1-f][1,2,4]triazin-2-amine [544];

N-(cis-4-(difluoromethoxy)cyclohexyl)-5-(4-fluoro-1-isopropyl-2-methyl-1H-benzo[d]imidazol-6-yl)pyrrolo[2,1-f][1,2,4]triazin-2-amine [545];

N-(trans-4-(difluoromethoxy)cyclohexyl)-5-(4-fluoro-1-isopropyl-2-methyl-1H-benzo[d]imidazol-6-yl)pyrrolo[2,1-f][1,2,4]triazin-2-amine [546];

N-(cis-4-ethoxycyclohexyl)-5-(4-fluoro-1-isopropyl-2-methyl-1H-benzo[d]imidazol-6-yl)pyrrolo[2,1-f][1,2,4]triazin-2-amine [547];

N-(trans-4-ethoxycyclohexyl)-5-(4-fluoro-1-isopropyl-2-methyl-1H-benzo[d]imidazol-6-yl)pyrrolo[2,1-f][1,2,4]triazin-2-amine [548];

5-(4-fluoro-1-isopropyl-2-methyl-1H-benzo[d]imidazol-6-yl)-N-(cis-4-(2-methoxyethoxy)cyclohexyl)pyrrolo[2,1-f][1,2,4]triazin-2-amine [549];

5-(4-fluoro-1-isopropyl-2-methyl-1H-benzo[d]imidazol-6-yl)-N-(trans-4-(2-methoxyethoxy)cyclohexyl)pyrrolo[2,1-f][1,2,4]triazin-2-amine [550];

cis-$N^1$-(5-(4-fluoro-1-isopropyl-2-methyl-1H-benzo[d]imidazol-6-yl)pyrrolo[2,1-f][1,2,4]triazin-2-yl)cyclohexane-1,4-diamine [551];

trans-$N^1$-(5-(4-fluoro-1-isopropyl-2-methyl-1H-benzo[d]imidazol-6-yl)pyrrolo[2,1-f][1,2,4]triazin-2-yl)cyclohexane-1,4-diamine [552];

cis-$N^1$-(5-(4-fluoro-1-isopropyl-2-methyl-1H-benzo[d]imidazol-6-yl)pyrrolo[2,1-f][1,2,4]triazin-2-yl)-$N^4$-methylcyclohexane-1,4-diamine [553];

trans-$N^1$-(5-(4-fluoro-1-isopropyl-2-methyl-1H-benzo[d]imidazol-6-yl)pyrrolo[2,1-f][1,2,4]triazin-2-yl)-$N^4$-methylcyclohexane-1,4-diamine [554];

cis-$N^1$-(5-(4-fluoro-1-isopropyl-2-methyl-1H-benzo[d]imidazol-6-yl)pyrrolo[2,1-f][1,2,4]triazin-2-yl)-$N^4$,$N^4$-dimethylcyclohexane-1,4-diamine [555];

trans-$N^1$-(5-(4-fluoro-1-isopropyl-2-methyl-1H-benzo[d]imidazol-6-yl)pyrrolo[2,1-f][1,2,4]triazin-2-yl)-$N^4$,$N^4$-dimethylcyclohexane-1,4-diamine [556];

5-(4-fluoro-1-isopropyl-2-methyl-1H-benzo[d]imidazol-6-yl)-N-(cis-4-morpholinocyclohexyl)pyrrolo[2,1-f][1,2,4]triazin-2-amine [557];

5-(4-fluoro-1-isopropyl-2-methyl-1H-benzo[d]imidazol-6-yl)-N-(trans-4-morpholinocyclohexyl)pyrrolo[2,1-f][1,2,4]triazin-2-amine [558];

5-(4-fluoro-1-isopropyl-2-methyl-1H-benzo[d]imidazol-6-yl)-N-(cis-4-(4-methylpiperazin-1-yl)cyclohexyl)pyrrolo[2,1-f][1,2,4]triazin-2-amine [559];

5-(4-fluoro-1-isopropyl-2-methyl-1H-benzo[d]imidazol-6-yl)-N-(trans-4-(4-methylpiperazin-1-yl)cyclohexyl)pyrrolo[2,1-f][1,2,4]triazin-2-amine [560];

5-(4-fluoro-1-isopropyl-2-methyl-1H-benzo[d]imidazol-6-yl)-N-(1-methylazetidin-3-yl)pyrrolo[2,1-f][1,2,4]triazin-2-amine [561];

5-(4-fluoro-1-isopropyl-2-methyl-1H-benzo[d]imidazol-6-yl)-N-(oxetan-3-yl)pyrrolo[2,1-f][1,2,4]triazin-2-amine [562];

5-(4-fluoro-1-isopropyl-2-methyl-1H-benzo[d]imidazol-6-yl)-N-(1-methylpiperidin-4-yl)pyrrolo[2,1-f][1,2,4]triazin-2-amine [563];

5-(4-fluoro-1-isopropyl-2-methyl-1H-benzo[d]imidazol-6-yl)-N-(tetrahydro-2H-pyran-4-yl)pyrrolo[2,1-f][1,2,4]triazin-2-amine [564];

N-(6,6-difluorospiro[3.3]heptan-2-yl)-5-(4-fluoro-1-isopropyl-2-methyl-1H-benzo[d]imidazol-6-yl)pyrrolo[2,1-f][1,2,4]triazin-2-amine [565];

5-(4-fluoro-1-isopropyl-2-methyl-1H-benzo[d]imidazol-6-yl)-N-(2-oxaspiro[3.3]heptan-6-yl)pyrrolo[2,1-f][1,2,4]triazin-2-amine [566];

5-(4-fluoro-1-isopropyl-2-methyl-1H-benzo[d]imidazol-6-yl)-N-(2-methyl-2-azaspiro[3.3]heptan-6-yl)pyrrolo[2,1-f][1,2,4]triazin-2-amine [567];

5-(4-fluoro-1-isopropyl-2-methyl-1H-benzo[d]imidazol-6-yl)-N-(1-methyl-1H-pyrazol-4-yl)pyrrolo[2,1-f][1,2,4]triazin-2-amine [568];

N-isopropyl-5-(1-isopropyl-2-methyl-1H-imidazo[4,5-b]pyridin-6-yl)pyrrolo[2,1-f][1,2,4]triazin-2-amine [569];

N-isobutyl-5-(1-isopropyl-2-methyl-1H-imidazo[4,5-b]pyridin-6-yl)pyrrolo[2,1-f][1,2,4]triazin-2-amine [570];

N-(2-fluoro-2-methylpropyl)-5-(1-isopropyl-2-methyl-1H-imidazo[4,5-b]pyridin-6-yl)pyrrolo[2,1-f][1,2,4]triazin-2-amine [571];

N-(2,2-difluoropropyl)-5-(1-isopropyl-2-methyl-1H-imidazo[4,5-b]pyridin-6-yl)pyrrolo[2,1-f][1,2,4]triazin-2-amine [572];

5-(1-isopropyl-2-methyl-1H-imidazo[4,5-b]pyridin-6-yl)-N-(2,2,2-trifluoroethyl)pyrrolo[2,1-f][1,2,4]triazin-2-amine [573];

(R)-5-(1-isopropyl-2-methyl-1H-imidazo[4,5-b]pyridin-6-yl)-N-(1,1,1-trifluoropropan-2-yl)pyrrolo[2,1-f][1,2,4]triazin-2-amine [574];

5-(1-isopropyl-2-methyl-1H-imidazo[4,5-b]pyridin-6-yl)-N-(3,3,3-trifluoropropyl)pyrrolo[2,1-f][1,2,4]triazin-2-amine [575];

5-(1-isopropyl-2-methyl-1H-imidazo[4,5-b]pyridin-6-yl)-N-(3,3,3-trifluoro-2,2-dimethylpropyl)pyrrolo[2,1-f][1,2,4]triazin-2-amine [576];

5-(1-isopropyl-2-methyl-1H-imidazo[4,5-b]pyridin-6-yl)-N-(2-methoxyethyl)pyrrolo[2,1-f][1,2,4]triazin-2-amine [577];

(R)-5-(1-isopropyl-2-methyl-1H-imidazo[4,5-b]pyridin-6-yl)-N-(1-methoxypropan-2-yl)pyrrolo[2,1-f][1,2,4]triazin-2-amine [578];

N-(2-isopropoxyethyl)-5-(1-isopropyl-2-methyl-1H-imidazo[4,5-b]pyridin-6-yl)pyrrolo[2,1-f][1,2,4]triazin-2-amine [579];

5-(1-isopropyl-2-methyl-1H-imidazo[4,5-b]pyridin-6-yl)-N-((1-methylcyclopropyl)methyl)pyrrolo[2,1-f][1,2,4]triazin-2-amine [580];

5-(1-isopropyl-2-methyl-1H-imidazo[4,5-b]pyridin-6-yl)-N-((1-(trifluoromethyl)cyclopropyl)methyl)pyrrolo[2,1-f][1,2,4]triazin-2-amine [581];

N-((1-fluorocyclobutyl)methyl)-5-(1-isopropyl-2-methyl-1H-imidazo[4,5-b]pyridin-6-yl)pyrrolo[2,1-f][1,2,4]triazin-2-amine [582];

N-((3-fluorooxetan-3-yl)methyl)-5-(1-isopropyl-2-methyl-1H-imidazo[4,5-b]pyridin-6-yl)pyrrolo[2,1-f][1,2,4]triazin-2-amine [583];

N-(cyclopropylmethyl)-5-(1-isopropyl-2-methyl-1H-imidazo[4,5-b]pyridin-6-yl)pyrrolo[2,1-f][1,2,4]triazin-2-amine [584];

(S)—N-(1-cyclopropylethyl)-5-(1-isopropyl-2-methyl-1H-imidazo[4,5-b]pyridin-6-yl)pyrrolo[2,1-f][1,2,4]triazin-2-amine [585];

(R)—N-(1-cyclopropylethyl)-5-(1-isopropyl-2-methyl-1H-imidazo[4,5-b]pyridin-6-yl)pyrrolo[2,1-f][1,2,4]triazin-2-amine [586];

N-(2-cyclopropyl-2,2-difluoroethyl)-5-(1-isopropyl-2-methyl-1H-imidazo[4,5-b]pyridin-6-yl)pyrrolo[2,1-f][1,2,4]triazin-2-amine [587];

5-(1-isopropyl-2-methyl-1H-imidazo[4,5-b]pyridin-6-yl)-N-(oxetan-3-ylmethyl)pyrrolo[2,1-f][1,2,4]triazin-2-amine [588];

5-(1-isopropyl-2-methyl-1H-imidazo[4,5-b]pyridin-6-yl)-N-((tetrahydrofuran-2-yl)methyl)pyrrolo[2,1-f][1,2,4]triazin-2-amine [589];

N-cyclobutyl-5-(1-isopropyl-2-methyl-1H-imidazo[4,5-b]pyridin-6-yl)pyrrolo[2,1-f][1,2,4]triazin-2-amine [590];

N-(3,3-difluorocyclobutyl)-5-(1-isopropyl-2-methyl-1H-imidazo[4,5-b]pyridin-6-yl)pyrrolo[2,1-f][1,2,4]triazin-2-amine [591];

N-(3,3-dimethylcyclobutyl)-5-(1-isopropyl-2-methyl-1H-imidazo[4,5-b]pyridin-6-yl)pyrrolo[2,1-f][1,2,4]triazin-2-amine [592];

3-((5-(1-isopropyl-2-methyl-1H-imidazo[4,5-b]pyridin-6-yl)pyrrolo[2,1-f][1,2,4]triazin-2-yl)amino)-1-methylcyclobutan-1-ol [593];

5-(1-isopropyl-2-methyl-1H-imidazo[4,5-b]pyridin-6-yl)-N-(cis-3-methoxycyclobutyl)pyrrolo[2,1-f][1,2,4]triazin-2-amine [594];

5-(1-isopropyl-2-methyl-1H-imidazo[4,5-b]pyridin-6-yl)-N-(trans-3-methoxycyclobutyl)pyrrolo[2,1-f][1,2,4]triazin-2-amine [595];

5-(1-isopropyl-2-methyl-1H-imidazo[4,5-b]pyridin-6-yl)-N-(trans-3-(methoxymethyl)cyclobutyl)pyrrolo[2,1-f][1,2,4]triazin-2-amine [596];

N-(cis-3-ethoxycyclobutyl)-5-(1-isopropyl-2-methyl-1H-imidazo[4,5-b]pyridin-6-yl)pyrrolo[2,1-f][1,2,4]triazin-2-amine [597];

N-(trans-3-ethoxycyclobutyl)-5-(1-isopropyl-2-methyl-1H-imidazo[4,5-b]pyridin-6-yl)pyrrolo[2,1-f][1,2,4]triazin-2-amine [598];

5-(1-isopropyl-2-methyl-1H-imidazo[4,5-b]pyridin-6-yl)-N-(cis-3-(2-methoxyethoxy)cyclobutyl)pyrrolo[2,1-f][1,2,4]triazin-2-amine [599];

5-(1-isopropyl-2-methyl-1H-imidazo[4,5-b]pyridin-6-yl)-N-(trans-3-(2-methoxyethoxy)cyclobutyl)pyrrolo[2,1-f][1,2,4]triazin-2-amine [600];

cis-$N^1$-(5-(1-isopropyl-2-methyl-1H-imidazo[4,5-b]pyridin-6-yl)pyrrolo[2,1-f][1,2,4]triazin-2-yl)cyclobutane-1,3-diamine [601];

trans-$N^1$-(5-(1-isopropyl-2-methyl-1H-imidazo[4,5-b]pyridin-6-yl)pyrrolo[2,1-f][1,2,4]triazin-2-yl)cyclobutane-1,3-diamine [602];

cis-$N^1$-(5-(1-isopropyl-2-methyl-1H-imidazo[4,5-b]pyridin-6-yl)pyrrolo[2,1-f][1,2,4]triazin-2-yl)-N-methylcyclobutane-1,3-diamine [603];

trans-$N^1$-(5-(1-isopropyl-2-methyl-1H-imidazo[4,5-b]pyridin-6-yl)pyrrolo[2,1-f][1,2,4]triazin-2-yl)-$N^3$-methylcyclobutane-1,3-diamine [604];

cis-$N^1$-(5-(1-isopropyl-2-methyl-1H-imidazo[4,5-b]pyridin-6-yl)pyrrolo[2,1-f][1,2,4]triazin-2-yl)-$N_3$,$N^3$-dimethylcyclobutane-1,3-diamine [605];

trans-$N^1$-(5-(1-isopropyl-2-methyl-1H-imidazo[4,5-b]pyridin-6-yl)pyrrolo[2,1-f][1,2,4]triazin-2-yl)-$N^3$,$N^3$-dimethylcyclobutane-1,3-diamine [606];

5-(1-isopropyl-2-methyl-1H-imidazo[4,5-b]pyridin-6-yl)-N-(cis-3-morpholinocyclobutyl)pyrrolo[2,1-f][1,2,4]triazin-2-amine [607];

5-(1-isopropyl-2-methyl-1H-imidazo[4,5-b]pyridin-6-yl)-N-(trans-3-morpholinocyclobutyl)pyrrolo[2,1-f][1,2,4]triazin-2-amine [608];

5-(1-isopropyl-2-methyl-1H-imidazo[4,5-b]pyridin-6-yl)-N-(cis-3-(4-methylpiperazin-1-yl)cyclobutyl)pyrrolo[2,1-f][1,2,4]triazin-2-amine [609];

5-(1-isopropyl-2-methyl-1H-imidazo[4,5-b]pyridin-6-yl)-N-(trans-3-(4-methylpiperazin-1-yl)cyclobutyl)pyrrolo[2,1-f][1,2,4]triazin-2-amine [610];

N-(4,4-difluorocyclohexyl)-5-(1-isopropyl-2-methyl-1H-imidazo[4,5-b]pyridin-6-yl)pyrrolo[2,1-f][1,2,4]triazin-2-amine [611];

cis-4-((5-(1-isopropyl-2-methyl-1H-imidazo[4,5-b]pyridin-6-yl)pyrrolo[2,1-f][1,2,4]triazin-2-yl)amino)cyclohexan-1-ol [612];

(1s,4s)-4-((5-(1-isopropyl-2-methyl-1H-imidazo[4,5-b]pyridin-6-yl)pyrrolo[2,1-f][1,2,4]triazin-2-yl)amino)-1-methylcyclohexan-1-ol [613];

5-(1-isopropyl-2-methyl-1H-imidazo[4,5-b]pyridin-6-yl)-N-(cis-4-methoxycyclohexyl)pyrrolo[2,1-f][1,2,4]triazin-2-amine [614];

5-(1-isopropyl-2-methyl-1H-imidazo[4,5-b]pyridin-6-yl)-N-(trans-4-methoxycyclohexyl)pyrrolo[2,1-f][1,2,4]triazin-2-amine [615];

N-(cis-4-(difluoromethoxy)cyclohexyl)-5-(1-isopropyl-2-methyl-1H-imidazo[4,5-b]pyridin-6-yl)pyrrolo[2,1-f][1,2,4]triazin-2-amine [616];

N-(trans-4-(difluoromethoxy)cyclohexyl)-5-(1-isopropyl-2-methyl-1H-imidazo[4,5-b]pyridin-6-yl)pyrrolo[2,1-f][1,2,4]triazin-2-amine [617];

N-(cis-4-ethoxycyclohexyl)-5-(1-isopropyl-2-methyl-1H-imidazo[4,5-b]pyridin-6-yl)pyrrolo[2,1-f][1,2,4]triazin-2-amine [618];

N-(trans-4-ethoxycyclohexyl)-5-(1-isopropyl-2-methyl-1H-imidazo[4,5-b]pyridin-6-yl)pyrrolo[2,1-f][1,2,4]triazin-2-amine [619];

5-(1-isopropyl-2-methyl-1H-imidazo[4,5-b]pyridin-6-yl)-N-(cis-4-(2-methoxyethoxy)cyclohexyl)pyrrolo[2,1-f][1,2,4]triazin-2-amine [620];

5-(1-isopropyl-2-methyl-1H-imidazo[4,5-b]pyridin-6-yl)-N-(trans-4-(2-methoxyethoxy)cyclohexyl)pyrrolo[2,1-f][1,2,4]triazin-2-amine [621];

cis-$N^1$-(5-(1-isopropyl-2-methyl-1H-imidazo[4,5-b]pyridin-6-yl)pyrrolo[2,1-f][1,2,4]triazin-2-yl)cyclohexane-1,4-diamine [622];

trans-$N^1$-(5-(1-isopropyl-2-methyl-1H-imidazo[4,5-b]pyridin-6-yl)pyrrolo[2,1-f][1,2,4]triazin-2-yl)cyclohexane-1,4-diamine [623];

cis-$N^1$-(5-(1-isopropyl-2-methyl-1H-imidazo[4,5-b]pyridin-6-yl)pyrrolo[2,1-f][1,2,4]triazin-2-yl)-$N^4$-methylcyclohexane-1,4-diamine [624];

trans-$N^1$-(5-(1-isopropyl-2-methyl-1H-imidazo[4,5-b]pyridin-6-yl)pyrrolo[2,1-f][1,2,4]triazin-2-yl)-$N^4$-methylcyclohexane-1,4-diamine [625];

cis-$N^1$-(5-(1-isopropyl-2-methyl-1H-imidazo[4,5-b]pyridin-6-yl)pyrrolo[2,1-f][1,2,4]triazin-2-yl)-$N^4$,$N^4$-dimethylcyclohexane-1,4-diamine [626];

trans-$N^1$-(5-(1-isopropyl-2-methyl-1H-imidazo[4,5-b]pyridin-6-yl)pyrrolo[2,1-f][1,2,4]triazin-2-yl)-$N^4$,$N^4$-dimethylcyclohexane-1,4-diamine [627];

5-(1-isopropyl-2-methyl-1H-imidazo[4,5-b]pyridin-6-yl)-N-(cis-4-morpholinocyclohexyl)pyrrolo[2,1-f][1,2,4]triazin-2-amine [628];

5-(1-isopropyl-2-methyl-1H-imidazo[4,5-b]pyridin-6-yl)-N-(trans-4-morpholinocyclohexyl)pyrrolo[2,1-f][1,2,4]triazin-2-amine [629];

5-(1-isopropyl-2-methyl-1H-imidazo[4,5-b]pyridin-6-yl)-N-(cis-4-(4-methylpiperazin-1-yl)cyclohexyl)pyrrolo[2,1-f][1,2,4]triazin-2-amine [630];

5-(1-isopropyl-2-methyl-1H-imidazo[4,5-b]pyridin-6-yl)-N-(trans-4-(4-methylpiperazin-1-yl)cyclohexyl)pyrrolo[2,1-f][1,2,4]triazin-2-amine [631];

5-(1-isopropyl-2-methyl-1H-imidazo[4,5-b]pyridin-6-yl)-N-(1-methylazetidin-3-yl)pyrrolo[2,1-f][1,2,4]triazin-2-amine [632];

5-(1-isopropyl-2-methyl-1H-imidazo[4,5-b]pyridin-6-yl)-N-(oxetan-3-yl)pyrrolo[2,1-f][1,2,4]triazin-2-amine [633];

5-(1-isopropyl-2-methyl-1H-imidazo[4,5-b]pyridin-6-yl)-N-(1-methylpiperidin-4-yl)pyrrolo[2,1-f][1,2,4]triazin-2-amine [634];

5-(1-isopropyl-2-methyl-1H-imidazo[4,5-b]pyridin-6-yl)-N-(tetrahydro-2H-pyran-4-yl)pyrrolo[2,1-f][1,2,4]triazin-2-amine [635];

N-(6,6-difluorospiro[3.3]heptan-2-yl)-5-(1-isopropyl-2-methyl-1H-imidazo[4,5-b]pyridin-6-yl)pyrrolo[2,1-f][1,2,4]triazin-2-amine [636];

5-(1-isopropyl-2-methyl-1H-imidazo[4,5-b]pyridin-6-yl)-N-(2-oxaspiro[3.3]heptan-6-yl)pyrrolo[2,1-f][1,2,4]triazin-2-amine [637];

5-(1-isopropyl-2-methyl-1H-imidazo[4,5-b]pyridin-6-yl)-N-(2-methyl-2-azaspiro[3.3]heptan-6-yl)pyrrolo[2,1-f][1,2,4]triazin-2-amine [638];

5-(1-isopropyl-2-methyl-1H-imidazo[4,5-b]pyridin-6-yl)-N-(1-methyl-1H-pyrazol-4-yl)pyrrolo[2,1-f][1,2,4]triazin-2-amine [639];

5-(1-(2,2-difluoroethyl)-2-methyl-1H-imidazo[4,5-b]pyridin-6-yl)-N-isopropylpyrrolo[2,1-f][1,2,4]triazin-2-amine [640];

5-(1-(2,2-difluoroethyl)-2-methyl-1H-imidazo[4,5-b]pyridin-6-yl)-N-isobutylpyrrolo[2,1-f][1,2,4]triazin-2-amine [641];

5-(1-(2,2-difluoroethyl)-2-methyl-1H-imidazo[4,5-b]pyridin-6-yl)-N-(2-fluoro-2-methylpropyl)pyrrolo[2,1-f][1,2,4]triazin-2-amine [642];

5-(1-(2,2-difluoroethyl)-2-methyl-1H-imidazo[4,5-b]pyridin-6-yl)-N-(2,2-difluoropropyl)pyrrolo[2,1-f][1,2,4]triazin-2-amine [643];

5-(1-(2,2-difluoroethyl)-2-methyl-1H-imidazo[4,5-b]pyridin-6-yl)-N-(2,2,2-trifluoroethyl)pyrrolo[2,1-f][1,2,4]triazin-2-amine [644];

(R)-5-(1-(2,2-difluoroethyl)-2-methyl-1H-imidazo[4,5-b]pyridin-6-yl)-N-(1,1,1-trifluoropropan-2-yl)pyrrolo[2,1-f][1,2,4]triazin-2-amine [645];

5-(1-(2,2-difluoroethyl)-2-methyl-1H-imidazo[4,5-b]pyridin-6-yl)-N-(3,3,3-trifluoropropyl)pyrrolo[2,1-f][1,2,4]triazin-2-amine [646];

5-(1-(2,2-difluoroethyl)-2-methyl-1H-imidazo[4,5-b]pyridin-6-yl)-N-(3,3,3-trifluoro-2,2-dimethylpropyl)pyrrolo[2,1-f][1,2,4]triazin-2-amine [647];

5-(1-(2,2-difluoroethyl)-2-methyl-1H-imidazo[4,5-b]pyridin-6-yl)-N-(2-methoxyethyl)pyrrolo[2,1-f][1,2,4]triazin-2-amine [648];

(R)-5-(1-(2,2-difluoroethyl)-2-methyl-1H-imidazo[4,5-b]pyridin-6-yl)-N-(1-methoxypropan-2-yl)pyrrolo[2,1-f][1,2,4]triazin-2-amine [649];

5-(1-(2,2-difluoroethyl)-2-methyl-1H-imidazo[4,5-b]pyridin-6-yl)-N-(2-isopropoxyethyl)pyrrolo[2,1-f][1,2,4]triazin-2-amine [650];

5-(1-(2,2-difluoroethyl)-2-methyl-1H-imidazo[4,5-b]pyridin-6-yl)-N-((1-methylcyclopropyl)methyl)pyrrolo[2,1-f][1,2,4]triazin-2-amine [651];

5-(1-(2,2-difluoroethyl)-2-methyl-1H-imidazo[4,5-b]pyridin-6-yl)-N-((1-(trifluoromethyl)cyclopropyl)methyl)pyrrolo[2,1-f][1,2,4]triazin-2-amine [652];

5-(1-(2,2-difluoroethyl)-2-methyl-1H-imidazo[4,5-b]pyridin-6-yl)-N-((1-fluorocyclobutyl)methyl)pyrrolo[2,1-f][1,2,4]triazin-2-amine [653];

5-(1-(2,2-difluoroethyl)-2-methyl-1H-imidazo[4,5-b]pyridin-6-yl)-N-((3-fluorooxetan-3-yl)methyl)pyrrolo[2,1-f][1,2,4]triazin-2-amine [654];

N-(cyclopropylmethyl)-5-(1-(2,2-difluoroethyl)-2-methyl-1H-imidazo[4,5-b]pyridin-6-yl)pyrrolo[2,1-f][1,2,4]triazin-2-amine [655];

(S)—N-(1-cyclopropylethyl)-5-(1-(2,2-difluoroethyl)-2-methyl-1H-imidazo[4,5-b]pyridin-6-yl)pyrrolo[2,1-f][1,2,4]triazin-2-amine [656];

(R)—N-(1-cyclopropylethyl)-5-(1-(2,2-difluoroethyl)-2-methyl-1H-imidazo[4,5-b]pyridin-6-yl)pyrrolo[2,1-f][1,2,4]triazin-2-amine [657];

N-(2-cyclopropyl-2,2-difluoroethyl)-5-(1-(2,2-difluoroethyl)-2-methyl-1H-imidazo[4,5-b]pyridin-6-yl)pyrrolo[2,1-f][1,2,4]triazin-2-amine [658];

5-(1-(2,2-difluoroethyl)-2-methyl-1H-imidazo[4,5-b]pyridin-6-yl)-N-(oxetan-3-ylmethyl)pyrrolo[2,1-f][1,2,4]triazin-2-amine [659];

5-(1-(2,2-difluoroethyl)-2-methyl-1H-imidazo[4,5-b]pyridin-6-yl)-N-((tetrahydrofuran-2-yl)methyl)pyrrolo[2,1-f][1,2,4]triazin-2-amine [660];

N-cyclobutyl-5-(1-(2,2-difluoroethyl)-2-methyl-1H-imidazo[4,5-b]pyridin-6-yl)pyrrolo[2,1-f][1,2,4]triazin-2-amine [661];

N-(3,3-difluorocyclobutyl)-5-(1-(2,2-difluoroethyl)-2-methyl-1H-imidazo[4,5-b]pyridin-6-yl)pyrrolo[2,1-f][1,2,4]triazin-2-amine [662];

5-(1-(2,2-difluoroethyl)-2-methyl-1H-imidazo[4,5-b]pyridin-6-yl)-N-(3,3-dimethylcyclobutyl)pyrrolo[2,1-f][1,2,4]triazin-2-amine [663];

3-((5-(1-(2,2-difluoroethyl)-2-methyl-1H-imidazo[4,5-b]pyridin-6-yl)pyrrolo[2,1-f][1,2,4]triazin-2-yl)amino)-1-methylcyclobutan-1-ol [664];

5-(1-(2,2-difluoroethyl)-2-methyl-1H-imidazo[4,5-b]pyridin-6-yl)-N-(cis-3-methoxycyclobutyl)pyrrolo[2,1-f][1,2,4]triazin-2-amine [665];

5-(1-(2,2-difluoroethyl)-2-methyl-1H-imidazo[4,5-b]pyridin-6-yl)-N-(trans-3-methoxycyclobutyl)pyrrolo[2,1-f][1,2,4]triazin-2-amine [666];

5-(1-(2,2-difluoroethyl)-2-methyl-1H-imidazo[4,5-b]pyridin-6-yl)-N-(trans-3-(methoxymethyl)cyclobutyl)pyrrolo[2,1-f][1,2,4]triazin-2-amine [667];

5-(1-(2,2-difluoroethyl)-2-methyl-1H-imidazo[4,5-b]pyridin-6-yl)-N-(cis-3-ethoxycyclobutyl)pyrrolo[2,1-f][1,2,4]triazin-2-amine [668];

5-(1-(2,2-difluoroethyl)-2-methyl-1H-imidazo[4,5-b]pyridin-6-yl)-N-(trans-3-ethoxycyclobutyl)pyrrolo[2,1-f][1,2,4]triazin-2-amine [669];

5-(1-(2,2-difluoroethyl)-2-methyl-1H-imidazo[4,5-b]pyridin-6-yl)-N-(cis-3-(2-methoxyethoxy)cyclobutyl)pyrrolo[2,1-f][1,2,4]triazin-2-amine [670];

5-(1-(2,2-difluoroethyl)-2-methyl-1H-imidazo[4,5-b]pyridin-6-yl)-N-(trans-3-(2-methoxyethoxy)cyclobutyl)pyrrolo[2,1-f][1,2,4]triazin-2-amine [671];

cis-$N^1$-(5-(1-(2,2-difluoroethyl)-2-methyl-1H-imidazo[4,5-b]pyridin-6-yl)pyrrolo[2,1-f][1,2,4]triazin-2-yl)cyclobutane-1,3-diamine [672];

trans-$N^1$-(5-(1-(2,2-difluoroethyl)-2-methyl-1H-imidazo[4,5-b]pyridin-6-yl)pyrrolo[2,1-f][1,2,4]triazin-2-yl)cyclobutane-1,3-diamine [673];

cis-$N^1$-(5-(1-(2,2-difluoroethyl)-2-methyl-1H-imidazo[4,5-b]pyridin-6-yl)pyrrolo[2,1-f][1,2,4]triazin-2-yl)-$N^3$-methylcyclobutane-1,3-diamine [674];

trans-$N^1$-(5-(1-(2,2-difluoroethyl)-2-methyl-1H-imidazo[4,5-b]pyridin-6-yl)pyrrolo[2,1-f][1,2,4]triazin-2-yl)-$N^3$-methylcyclobutane-1,3-diamine [675];

cis-$N^1$-(5-(1-(2,2-difluoroethyl)-2-methyl-1H-imidazo[4,5-b]pyridin-6-yl)pyrrolo[2,1-f][1,2,4]triazin-2-yl)-$N^3$,$N^3$-dimethylcyclobutane-1,3-diamine [676];

trans-$N^1$-(5-(1-(2,2-difluoroethyl)-2-methyl-1H-imidazo[4,5-b]pyridin-6-yl)pyrrolo[2,1-f][1,2,4]triazin-2-yl)-$N^3$,$N^3$-dimethylcyclobutane-1,3-diamine [677];

5-(1-(2,2-difluoroethyl)-2-methyl-1H-imidazo[4,5-b]pyridin-6-yl)-N-(cis-3-morpholinocyclobutyl)pyrrolo[2,1-f][1,2,4]triazin-2-amine [678];

5-(1-(2,2-difluoroethyl)-2-methyl-1H-imidazo[4,5-b]pyridin-6-yl)-N-(trans-3-morpholinocyclobutyl)pyrrolo[2,1-f][1,2,4]triazin-2-amine [679];

5-(1-(2,2-difluoroethyl)-2-methyl-1H-imidazo[4,5-b]pyridin-6-yl)-N-(cis-3-(4-methylpiperazin-1-yl)cyclobutyl)pyrrolo[2,1-f][1,2,4]triazin-2-amine [680];

5-(1-(2,2-difluoroethyl)-2-methyl-1H-imidazo[4,5-b]pyridin-6-yl)-N-(trans-3-(4-methylpiperazin-1-yl)cyclobutyl)pyrrolo[2,1-f][1,2,4]triazin-2-amine [681];

N-(4,4-difluorocyclohexyl)-5-(1-(2,2-difluoroethyl)-2-methyl-1H-imidazo[4,5-b]pyridin-6-yl)pyrrolo[2,1-f][1,2,4]triazin-2-amine [682];

cis-4-((5-(1-(2,2-difluoroethyl)-2-methyl-1H-imidazo[4,5-b]pyridin-6-yl)pyrrolo[2,1-f][1,2,4]triazin-2-yl)amino)cyclohexan-1-ol [683];

(1s,4s)-4-((5-(1-(2,2-difluoroethyl)-2-methyl-1H-imidazo[4,5-b]pyridin-6-yl)pyrrolo[2,1-f][1,2,4]triazin-2-yl)amino)-1-methylcyclohexan-1-ol [684];

5-(1-(2,2-difluoroethyl)-2-methyl-1H-imidazo[4,5-b]pyridin-6-yl)-N-(cis-4-methoxycyclohexyl)pyrrolo[2,1-f][1,2,4]triazin-2-amine [685];

5-(1-(2,2-difluoroethyl)-2-methyl-1H-imidazo[4,5-b]pyridin-6-yl)-N-(trans-4-methoxycyclohexyl)pyrrolo[2,1-f][1,2,4]triazin-2-amine [686];

5-(1-(2,2-difluoroethyl)-2-methyl-1H-imidazo[4,5-b]pyridin-6-yl)-N-(cis-4-(difluoromethoxy)cyclohexyl)pyrrolo[2,1-f][1,2,4]triazin-2-amine [687];

5-(1-(2,2-difluoroethyl)-2-methyl-1H-imidazo[4,5-b]pyridin-6-yl)-N-(trans-4-(difluoromethoxy)cyclohexyl)pyrrolo[2,1-f][1,2,4]triazin-2-amine [688];

5-(1-(2,2-difluoroethyl)-2-methyl-1H-imidazo[4,5-b]pyridin-6-yl)-N-(cis-4-ethoxycyclohexyl)pyrrolo[2,1-f][1,2,4]triazin-2-amine [689];

5-(1-(2,2-difluoroethyl)-2-methyl-1H-imidazo[4,5-b]pyridin-6-yl)-N-(trans-4-ethoxycyclohexyl)pyrrolo[2,1-f][1,2,4]triazin-2-amine [690];

5-(1-(2,2-difluoroethyl)-2-methyl-1H-imidazo[4,5-b]pyridin-6-yl)-N-(cis-4-(2-methoxyethoxy)cyclohexyl)pyrrolo[2,1-f][1,2,4]triazin-2-amine [691];

5-(1-(2,2-difluoroethyl)-2-methyl-1H-imidazo[4,5-b]pyridin-6-yl)-N-(trans-4-(2-methoxyethoxy)cyclohexyl)pyrrolo[2,1-f][1,2,4]triazin-2-amine [692];

cis-$N^1$-(5-(1-(2,2-difluoroethyl)-2-methyl-1H-imidazo[4,5-b]pyridin-6-yl)pyrrolo[2,1-f][1,2,4]triazin-2-yl)cyclohexane-1,4-diamine [693];

trans-$N^1$-(5-(1-(2,2-difluoroethyl)-2-methyl-1H-imidazo[4,5-b]pyridin-6-yl)pyrrolo[2,1-f][1,2,4]triazin-2-yl)cyclohexane-1,4-diamine [694];

cis-$N^1$-(5-(1-(2,2-difluoroethyl)-2-methyl-1H-imidazo[4,5-b]pyridin-6-yl)pyrrolo[2,1-f][1,2,4]triazin-2-yl)-$N^4$-methylcyclohexane-1,4-diamine [695];

trans-$N^1$-(5-(1-(2,2-difluoroethyl)-2-methyl-1H-imidazo[4,5-b]pyridin-6-yl)pyrrolo[2,1-f][1,2,4]triazin-2-yl)-$N^4$-methylcyclohexane-1,4-diamine [696];

cis-$N^1$-(5-(1-(2,2-difluoroethyl)-2-methyl-1H-imidazo[4,5-b]pyridin-6-yl)pyrrolo[2,1-f][1,2,4]triazin-2-yl)-$N^4$,$N^4$-dimethylcyclohexane-1,4-diamine [697];

trans-$N^1$-(5-(1-(2,2-difluoroethyl)-2-methyl-1H-imidazo[4,5-b]pyridin-6-yl)pyrrolo[2,1-f][1,2,4]triazin-2-yl)-$N^4$,$N^4$-dimethylcyclohexane-1,4-diamine [698];

5-(1-(2,2-difluoroethyl)-2-methyl-1H-imidazo[4,5-b]pyridin-6-yl)-N-(cis-4-morpholinocyclohexyl)pyrrolo[2,1-f][1,2,4]triazin-2-amine [699];

5-(1-(2,2-difluoroethyl)-2-methyl-1H-imidazo[4,5-b]pyridin-6-yl)-N-(trans-4-morpholinocyclohexyl)pyrrolo[2,1-f][1,2,4]triazin-2-amine [700];

5-(1-(2,2-difluoroethyl)-2-methyl-1H-imidazo[4,5-b]pyridin-6-yl)-N-(cis-4-(4-methylpiperazin-1-yl)cyclohexyl)pyrrolo[2,1-f][1,2,4]triazin-2-amine [701];

5-(1-(2,2-difluoroethyl)-2-methyl-1H-imidazo[4,5-b]pyridin-6-yl)-N-(trans-4-(4-methylpiperazin-1-yl)cyclohexyl)pyrrolo[2,1-f][1,2,4]triazin-2-amine [702];

5-(1-(2,2-difluoroethyl)-2-methyl-1H-imidazo[4,5-b]pyridin-6-yl)-N-(1-methylazetidin-3-yl)pyrrolo[2,1-f][1,2,4]triazin-2-amine [703];

5-(1-(2,2-difluoroethyl)-2-methyl-1H-imidazo[4,5-b]pyridin-6-yl)-N-(oxetan-3-yl)pyrrolo[2,1-f][1,2,4]triazin-2-amine [704];

5-(1-(2,2-difluoroethyl)-2-methyl-1H-imidazo[4,5-b]pyridin-6-yl)-N-(1-methylpiperidin-4-yl)pyrrolo[2,1-f][1,2,4]triazin-2-amine [705];

5-(1-(2,2-difluoroethyl)-2-methyl-1H-imidazo[4,5-b]pyridin-6-yl)-N-(tetrahydro-2H-pyran-4-yl)pyrrolo[2,1-f][1,2,4]triazin-2-amine [706];

5-(1-(2,2-difluoroethyl)-2-methyl-1H-imidazo[4,5-b]pyridin-6-yl)-N-(6,6-difluorospiro[3.3]heptan-2-yl)pyrrolo[2,1-f][1,2,4]triazin-2-amine [707];

5-(1-(2,2-difluoroethyl)-2-methyl-1H-imidazo[4,5-b]pyridin-6-yl)-N-(2-oxaspiro[3.3]heptan-6-yl)pyrrolo[2,1-f][1,2,4]triazin-2-amine [708];

5-(1-(2,2-difluoroethyl)-2-methyl-1H-imidazo[4,5-b]pyridin-6-yl)-N-(2-methyl-2-azaspiro[3.3]heptan-6-yl)pyrrolo[2,1-f][1,2,4]triazin-2-amine [709];

5-(1-(2,2-difluoroethyl)-2-methyl-1H-imidazo[4,5-b]pyridin-6-yl)-N-(1-methyl-1H-pyrazol-4-yl)pyrrolo[2,1-f][1,2,4]triazin-2-amine [710];

5-(1-(3,3-difluorocyclobutyl)-2-methyl-1H-imidazo[4,5-b]pyridin-6-yl)-N-isopropylpyrrolo[2,1-f][1,2,4]triazin-2-amine [711];

5-(1-(3,3-difluorocyclobutyl)-2-methyl-1H-imidazo[4,5-b]pyridin-6-yl)-N-isobutylpyrrolo[2,1-f][1,2,4]triazin-2-amine [712];

5-(1-(3,3-difluorocyclobutyl)-2-methyl-1H-imidazo[4,5-b]pyridin-6-yl)-N-(2-fluoro-2-methylpropyl)pyrrolo[2,1-f][1,2,4]triazin-2-amine [713];

5-(1-(3,3-difluorocyclobutyl)-2-methyl-1H-imidazo[4,5-b]pyridin-6-yl)-N-(2,2-difluoropropyl)pyrrolo[2,1-f][1,2,4]triazin-2-amine [714];

5-(1-(3,3-difluorocyclobutyl)-2-methyl-1H-imidazo[4,5-b]pyridin-6-yl)-N-(2,2,2-trifluoroethyl)pyrrolo[2,1-f][1,2,4]triazin-2-amine [715];

(R)-5-(1-(3,3-difluorocyclobutyl)-2-methyl-1H-imidazo[4,5-b]pyridin-6-yl)-N-(1,1,1-trifluoropropan-2-yl)pyrrolo[2,1-f][1,2,4]triazin-2-amine [716];

5-(1-(3,3-difluorocyclobutyl)-2-methyl-1H-imidazo[4,5-b]pyridin-6-yl)-N-(3,3,3-trifluoropropyl)pyrrolo[2,1-f][1,2,4]triazin-2-amine [717];

5-(1-(3,3-difluorocyclobutyl)-2-methyl-1H-imidazo[4,5-b]pyridin-6-yl)-N-(3,3,3-trifluoro-2,2-dimethylpropyl)pyrrolo[2,1-f][1,2,4]triazin-2-amine [718];

5-(1-(3,3-difluorocyclobutyl)-2-methyl-1H-imidazo[4,5-b]pyridin-6-yl)-N-(2-methoxyethyl)pyrrolo[2,1-f][1,2,4]triazin-2-amine [719];

(R)-5-(1-(3,3-difluorocyclobutyl)-2-methyl-1H-imidazo[4,5-b]pyridin-6-yl)-N-(1-methoxypropan-2-yl)pyrrolo[2,1-f][1,2,4]triazin-2-amine [720];

5-(1-(3,3-difluorocyclobutyl)-2-methyl-1H-imidazo[4,5-b]pyridin-6-yl)-N-(2-isopropoxyethyl)pyrrolo[2,1-f][1,2,4]triazin-2-amine [721];

5-(1-(3,3-difluorocyclobutyl)-2-methyl-1H-imidazo[4,5-b]pyridin-6-yl)-N-((1-methylcyclopropyl)methyl)pyrrolo[2,1-f][1,2,4]triazin-2-amine [722];

5-(1-(3,3-difluorocyclobutyl)-2-methyl-1H-imidazo[4,5-b]pyridin-6-yl)-N-((1-(trifluoromethyl)cyclopropyl)methyl)pyrrolo[2,1-f][1,2,4]triazin-2-amine [723];

5-(1-(3,3-difluorocyclobutyl)-2-methyl-1H-imidazo[4,5-b]pyridin-6-yl)-N-((1-fluorocyclobutyl)methyl)pyrrolo[2,1-f][1,2,4]triazin-2-amine [724];

5-(1-(3,3-difluorocyclobutyl)-2-methyl-1H-imidazo[4,5-b]pyridin-6-yl)-N-((3-fluorooxetan-3-yl)methyl)pyrrolo[2,1-f][1,2,4]triazin-2-amine [725];

N-(cyclopropylmethyl)-5-(1-(3,3-difluorocyclobutyl)-2-methyl-1H-imidazo[4,5-b]pyridin-6-yl)pyrrolo[2,1-f][1,2,4]triazin-2-amine [726];

(S)—N-(1-cyclopropylethyl)-5-(1-(3,3-difluorocyclobutyl)-2-methyl-1H-imidazo[4,5-b]pyridin-6-yl)pyrrolo[2,1-f][1,2,4]triazin-2-amine [727];

(R)—N-(1-cyclopropylethyl)-5-(1-(3,3-difluorocyclobutyl)-2-methyl-1H-imidazo[4,5-b]pyridin-6-yl)pyrrolo[2,1-f][1,2,4]triazin-2-amine [728];

N-(2-cyclopropyl-2,2-difluoroethyl)-5-(1-(3,3-difluorocyclobutyl)-2-methyl-1H-imidazo[4,5-b]pyridin-6-yl)pyrrolo[2,1-f][1,2,4]triazin-2-amine [729];

5-(1-(3,3-difluorocyclobutyl)-2-methyl-1H-imidazo[4,5-b]pyridin-6-yl)-N-(oxetan-3-ylmethyl)pyrrolo[2,1-f][1,2,4]triazin-2-amine [730];

5-(1-(3,3-difluorocyclobutyl)-2-methyl-1H-imidazo[4,5-b]pyridin-6-yl)-N-((tetrahydrofuran-2-yl)methyl)pyrrolo[2,1-f][1,2,4]triazin-2-amine [731];

N-cyclobutyl-5-(1-(3,3-difluorocyclobutyl)-2-methyl-1H-imidazo[4,5-b]pyridin-6-yl)pyrrolo[2,1-f][1,2,4]triazin-2-amine [732];

N-(3,3-difluorocyclobutyl)-5-(1-(3,3-difluorocyclobutyl)-2-methyl-1H-imidazo[4,5-b]pyridin-6-yl)pyrrolo[2,1-f][1,2,4]triazin-2-amine [733];

5-(1-(3,3-difluorocyclobutyl)-2-methyl-1H-imidazo[4,5-b]pyridin-6-yl)-N-(3,3-dimethylcyclobutyl)pyrrolo[2,1-f][1,2,4]triazin-2-amine [734];

3-((5-(1-(3,3-difluorocyclobutyl)-2-methyl-1H-imidazo[4,5-b]pyridin-6-yl)pyrrolo[2,1-f][1,2,4]triazin-2-yl)amino)-1-methylcyclobutan-1-ol [735];

5-(1-(3,3-difluorocyclobutyl)-2-methyl-1H-imidazo[4,5-b]pyridin-6-yl)-N-(cis-3-methoxycyclobutyl)pyrrolo[2,1-f][1,2,4]triazin-2-amine [736];

5-(1-(3,3-difluorocyclobutyl)-2-methyl-1H-imidazo[4,5-b]pyridin-6-yl)-N-(trans-3-methoxycyclobutyl)pyrrolo[2,1-f][1,2,4]triazin-2-amine [737];

5-(1-(3,3-difluorocyclobutyl)-2-methyl-1H-imidazo[4,5-b]pyridin-6-yl)-N-(trans-3-(methoxymethyl)cyclobutyl)pyrrolo[2,1-f][1,2,4]triazin-2-amine [738];

5-(1-(3,3-difluorocyclobutyl)-2-methyl-1H-imidazo[4,5-b]pyridin-6-yl)-N-(cis-3-ethoxycyclobutyl)pyrrolo[2,1-f][1,2,4]triazin-2-amine [739];

5-(1-(3,3-difluorocyclobutyl)-2-methyl-1H-imidazo[4,5-b]pyridin-6-yl)-N-(trans-3-ethoxycyclobutyl)pyrrolo[2,1-f][1,2,4]triazin-2-amine [740];

5-(1-(3,3-difluorocyclobutyl)-2-methyl-1H-imidazo[4,5-b]pyridin-6-yl)-N-(cis-3-(2-methoxyethoxy)cyclobutyl)pyrrolo[2,1-f][1,2,4]triazin-2-amine [741];

5-(1-(3,3-difluorocyclobutyl)-2-methyl-1H-imidazo[4,5-b]pyridin-6-yl)-N-(trans-3-(2-methoxyethoxy)cyclobutyl)pyrrolo[2,1-f][1,2,4]triazin-2-amine [742];

cis-$N^1$-(5-(1-(3,3-difluorocyclobutyl)-2-methyl-1H-imidazo[4,5-b]pyridin-6-yl)pyrrolo[2,1-f][1,2,4]triazin-2-yl)cyclobutane-1,3-diamine [743];

trans-$N^1$-(5-(1-(3,3-difluorocyclobutyl)-2-methyl-1H-imidazo[4,5-b]pyridin-6-yl)pyrrolo[2,1-f][1,2,4]triazin-2-yl)cyclobutane-1,3-diamine [744];

cis-$N^1$-(5-(1-(3,3-difluorocyclobutyl)-2-methyl-1H-imidazo[4,5-b]pyridin-6-yl)pyrrolo[2,1-f][1,2,4]triazin-2-yl)-$N^3$-methylcyclobutane-1,3-diamine [745];

trans-$N^1$-(5-(1-(3,3-difluorocyclobutyl)-2-methyl-1H-imidazo[4,5-b]pyridin-6-yl)pyrrolo[2,1-f][1,2,4]triazin-2-yl)-$N^3$-methylcyclobutane-1,3-diamine [746];

cis-$N^1$-(5-(1-(3,3-difluorocyclobutyl)-2-methyl-1H-imidazo[4,5-b]pyridin-6-yl)pyrrolo[2,1-f][1,2,4]triazin-2-yl)-$N^3$,$N^3$-dimethylcyclobutane-1,3-diamine [747];

trans-$N^1$-(5-(1-(3,3-difluorocyclobutyl)-2-methyl-1H-imidazo[4,5-b]pyridin-6-yl)pyrrolo[2,1-f][1,2,4]triazin-2-yl)-$N^3$,$N^3$-dimethylcyclobutane-1,3-diamine [748];

5-(1-(3,3-difluorocyclobutyl)-2-methyl-1H-imidazo[4,5-b]pyridin-6-yl)-N-(cis-3-morpholinocyclobutyl)pyrrolo[2,1-f][1,2,4]triazin-2-amine [749];

5-(1-(3,3-difluorocyclobutyl)-2-methyl-1H-imidazo[4,5-b]pyridin-6-yl)-N-(trans-3-morpholinocyclobutyl)pyrrolo[2,1-f][1,2,4]triazin-2-amine [750];

5-(1-(3,3-difluorocyclobutyl)-2-methyl-1H-imidazo[4,5-b]pyridin-6-yl)-N-(cis-3-(4-methylpiperazin-1-yl)cyclobutyl)pyrrolo[2,1-f][1,2,4]triazin-2-amine [751];

5-(1-(3,3-difluorocyclobutyl)-2-methyl-1H-imidazo[4,5-b]pyridin-6-yl)-N-(trans-3-(4-methylpiperazin-1-yl)cyclobutyl)pyrrolo[2,1-f][1,2,4]triazin-2-amine [752];

5-(1-(3,3-difluorocyclobutyl)-2-methyl-1H-imidazo[4,5-b]pyridin-6-yl)-N-(4,4-difluorocyclohexyl)pyrrolo[2,1-f][1,2,4]triazin-2-amine [753];

cis-4-((5-(1-(3,3-difluorocyclobutyl)-2-methyl-1H-imidazo[4,5-b]pyridin-6-yl)pyrrolo[2,1-f][1,2,4]triazin-2-yl)amino)cyclohexan-1-ol [754];

(1s,4s)-4-((5-(1-(3,3-difluorocyclobutyl)-2-methyl-1H-imidazo[4,5-b]pyridin-6-yl)pyrrolo[2,1-f][1,2,4]triazin-2-yl)amino)-1-methylcyclohexan-1-ol [755];

5-(1-(3,3-difluorocyclobutyl)-2-methyl-1H-imidazo[4,5-b]pyridin-6-yl)-N-(cis-4-methoxycyclohexyl)pyrrolo[2,1-f][1,2,4]triazin-2-amine [756];

5-(1-(3,3-difluorocyclobutyl)-2-methyl-1H-imidazo[4,5-b]pyridin-6-yl)-N-(trans-4-methoxycyclohexyl)pyrrolo[2,1-f][1,2,4]triazin-2-amine [757];

5-(1-(3,3-difluorocyclobutyl)-2-methyl-1H-imidazo[4,5-b]pyridin-6-yl)-N-(cis-4-(difluoromethoxy)cyclohexyl)pyrrolo[2,1-f][1,2,4]triazin-2-amine [758];

5-(1-(3,3-difluorocyclobutyl)-2-methyl-1H-imidazo[4,5-b]pyridin-6-yl)-N-(trans-4-(difluoromethoxy)cyclohexyl)pyrrolo[2,1-f][1,2,4]triazin-2-amine [759];

5-(1-(3,3-difluorocyclobutyl)-2-methyl-1H-imidazo[4,5-b]pyridin-6-yl)-N-(cis-4-ethoxycyclohexyl)pyrrolo[2,1-f][1,2,4]triazin-2-amine [760];

5-(1-(3,3-difluorocyclobutyl)-2-methyl-1H-imidazo[4,5-b]pyridin-6-yl)-N-(trans-4-ethoxycyclohexyl)pyrrolo[2,1-f][1,2,4]triazin-2-amine [761];

5-(1-(3,3-difluorocyclobutyl)-2-methyl-1H-imidazo[4,5-b]pyridin-6-yl)-N-(cis-4-(2-methoxyethoxy)cyclohexyl)pyrrolo[2,1-f][1,2,4]triazin-2-amine [762];

5-(1-(3,3-difluorocyclobutyl)-2-methyl-1H-imidazo[4,5-b]pyridin-6-yl)-N-(trans-4-(2-methoxyethoxy)cyclohexyl)pyrrolo[2,1-f][1,2,4]triazin-2-amine [763];

cis-$N^1$-(5-(1-(3,3-difluorocyclobutyl)-2-methyl-1H-imidazo[4,5-b]pyridin-6-yl)pyrrolo[2,1-f][1,2,4]triazin-2-yl)cyclohexane-1,4-diamine [764];

trans-$N^1$-(5-(1-(3,3-difluorocyclobutyl)-2-methyl-1H-imidazo[4,5-b]pyridin-6-yl)pyrrolo[2,1-f][1,2,4]triazin-2-yl)cyclohexane-1,4-diamine [765];

cis-$N^1$-(5-(1-(3,3-difluorocyclobutyl)-2-methyl-1H-imidazo[4,5-b]pyridin-6-yl)pyrrolo[2,1-f][1,2,4]triazin-2-yl)-$N^4$-methylcyclohexane-1,4-diamine [766];

trans-$N^1$-(5-(1-(3,3-difluorocyclobutyl)-2-methyl-1H-imidazo[4,5-b]pyridin-6-yl)pyrrolo[2,1-f][1,2,4]triazin-2-yl)-$N^4$-methylcyclohexane-1,4-diamine [767];

cis-$N^1$-(5-(1-(3,3-difluorocyclobutyl)-2-methyl-1H-imidazo[4,5-b]pyridin-6-yl)pyrrolo[2,1-f][1,2,4]triazin-2-yl)-$N^4$,$N^4$-dimethylcyclohexane-1,4-diamine [768];

trans-$N^1$-(5-(1-(3,3-difluorocyclobutyl)-2-methyl-1H-imidazo[4,5-b]pyridin-6-yl)pyrrolo[2,1-f][1,2,4]triazin-2-yl)-$N^4$,$N^4$-dimethylcyclohexane-1,4-diamine [769];

5-(1-(3,3-difluorocyclobutyl)-2-methyl-1H-imidazo[4,5-b]pyridin-6-yl)-N-(cis-4-morpholinocyclohexyl)pyrrolo[2,1-f][1,2,4]triazin-2-amine [770];

5-(1-(3,3-difluorocyclobutyl)-2-methyl-1H-imidazo[4,5-b]pyridin-6-yl)-N-(trans-4-morpholinocyclohexyl)pyrrolo[2,1-f][1,2,4]triazin-2-amine [771];

5-(1-(3,3-difluorocyclobutyl)-2-methyl-1H-imidazo[4,5-b]pyridin-6-yl)-N-(cis-4-(4-methylpiperazin-1-yl)cyclohexyl)pyrrolo[2,1-f][1,2,4]triazin-2-amine [772];

5-(1-(3,3-difluorocyclobutyl)-2-methyl-1H-imidazo[4,5-b]pyridin-6-yl)-N-(trans-4-(4-methylpiperazin-1-yl)cyclohexyl)pyrrolo[2,1-f][1,2,4]triazin-2-amine [773];

5-(1-(3,3-difluorocyclobutyl)-2-methyl-1H-imidazo[4,5-b]pyridin-6-yl)-N-(1-methylazetidin-3-yl)pyrrolo[2,1-f][1,2,4]triazin-2-amine [774];

5-(1-(3,3-difluorocyclobutyl)-2-methyl-1H-imidazo[4,5-b]pyridin-6-yl)-N-(oxetan-3-yl)pyrrolo[2,1-f][1,2,4]triazin-2-amine [775];

5-(1-(3,3-difluorocyclobutyl)-2-methyl-1H-imidazo[4,5-b]pyridin-6-yl)-N-(1-methylpiperidin-4-yl)pyrrolo[2,1-f][1,2,4]triazin-2-amine [776];

5-(1-(3,3-difluorocyclobutyl)-2-methyl-1H-imidazo[4,5-b]pyridin-6-yl)-N-(tetrahydro-2H-pyran-4-yl)pyrrolo[2,1-f][1,2,4]triazin-2-amine [777];

5-(1-(3,3-difluorocyclobutyl)-2-methyl-1H-imidazo[4,5-b]pyridin-6-yl)-N-(6,6-difluorospiro[3.3]heptan-2-yl)pyrrolo[2,1-f][1,2,4]triazin-2-amine [778];

5-(1-(3,3-difluorocyclobutyl)-2-methyl-1H-imidazo[4,5-b]pyridin-6-yl)-N-(2-oxaspiro[3.3]heptan-6-yl)pyrrolo[2,1-f][1,2,4]triazin-2-amine [779];

5-(1-(3,3-difluorocyclobutyl)-2-methyl-1H-imidazo[4,5-b]pyridin-6-yl)-N-(2-methyl-2-azaspiro[3.3]heptan-6-yl)pyrrolo[2,1-f][1,2,4]triazin-2-amine [780];

5-(1-(3,3-difluorocyclobutyl)-2-methyl-1H-imidazo[4,5-b]pyridin-6-yl)-N-(1-methyl-1H-pyrazol-4-yl)pyrrolo[2,1-f][1,2,4]triazin-2-amine [781];

N-isopropyl-5-(2-methyl-1-(tetrahydro-2H-pyran-4-yl)-1H-imidazo[4,5-b]pyridin-6-yl)pyrrolo[2,1-f][1,2,4]triazin-2-amine [782];

N-isobutyl-5-(2-methyl-1-(tetrahydro-2H-pyran-4-yl)-1H-imidazo[4,5-b]pyridin-6-yl)pyrrolo[2,1-f][1,2,4]triazin-2-amine [783];

N-(2-fluoro-2-methylpropyl)-5-(2-methyl-1-(tetrahydro-2H-pyran-4-yl)-1H-imidazo[4,5-b]pyridin-6-yl)pyrrolo[2,1-f][1,2,4]triazin-2-amine [784];

N-(2,2-difluoropropyl)-5-(2-methyl-1-(tetrahydro-2H-pyran-4-yl)-1H-imidazo[4,5-b]pyridin-6-yl)pyrrolo[2,1-f][1,2,4]triazin-2-amine [785];

5-(2-methyl-1-(tetrahydro-2H-pyran-4-yl)-1H-imidazo[4,5-b]pyridin-6-yl)-N-(2,2,2-trifluoroethyl)pyrrolo[2,1-f][1,2,4]triazin-2-amine [786];

(R)-5-(2-methyl-1-(tetrahydro-2H-pyran-4-yl)-1H-imidazo[4,5-b]pyridin-6-yl)-N-(1,1,1-trifluoropropan-2-yl)pyrrolo[2,1-f][1,2,4]triazin-2-amine [787];

5-(2-methyl-1-(tetrahydro-2H-pyran-4-yl)-1H-imidazo[4,5-b]pyridin-6-yl)-N-(3,3,3-trifluoropropyl)pyrrolo[2,1-f][1,2,4]triazin-2-amine [788];

5-(2-methyl-1-(tetrahydro-2H-pyran-4-yl)-1H-imidazo[4,5-b]pyridin-6-yl)-N-(3,3,3-trifluoro-2,2-dimethylpropyl)pyrrolo[2,1-f][1,2,4]triazin-2-amine [789];

N-(2-methoxyethyl)-5-(2-methyl-1-(tetrahydro-2H-pyran-4-yl)-1H-imidazo[4,5-b]pyridin-6-yl)pyrrolo[2,1-f][1,2,4]triazin-2-amine [790];

(R)—N-(1-methoxypropan-2-yl)-5-(2-methyl-1-(tetrahydro-2H-pyran-4-yl)-1H-imidazo[4,5-b]pyridin-6-yl)pyrrolo[2,1-f][1,2,4]triazin-2-amine [791];

N-(2-isopropoxyethyl)-5-(2-methyl-1-(tetrahydro-2H-pyran-4-yl)-1H-imidazo[4,5-b]pyridin-6-yl)pyrrolo[2,1-f][1,2,4]triazin-2-amine [792];

5-(2-methyl-1-(tetrahydro-2H-pyran-4-yl)-1H-imidazo[4,5-b]pyridin-6-yl)-N-((1-methylcyclopropyl)methyl)pyrrolo[2,1-f][1,2,4]triazin-2-amine [793];

5-(2-methyl-1-(tetrahydro-2H-pyran-4-yl)-1H-imidazo[4,5-b]pyridin-6-yl)-N-((1-(trifluoromethyl)cyclopropyl)methyl)pyrrolo[2,1-f][1,2,4]triazin-2-amine [794];

N-((1-fluorocyclobutyl)methyl)-5-(2-methyl-1-(tetrahydro-2H-pyran-4-yl)-1H-imidazo[4,5-b]pyridin-6-yl)pyrrolo[2,1-f][1,2,4]triazin-2-amine [795];

N-((3-fluorooxetan-3-yl)methyl)-5-(2-methyl-1-(tetrahydro-2H-pyran-4-yl)-1H-imidazo[4,5-b]pyridin-6-yl)pyrrolo[2,1-f][1,2,4]triazin-2-amine [796];

N-(cyclopropylmethyl)-5-(2-methyl-1-(tetrahydro-2H-pyran-4-yl)-1H-imidazo[4,5-b]pyridin-6-yl)pyrrolo[2,1-f][1,2,4]triazin-2-amine [797];

(S)—N-(1-cyclopropylethyl)-5-(2-methyl-1-(tetrahydro-2H-pyran-4-yl)-1H-imidazo[4,5-b]pyridin-6-yl)pyrrolo[2,1-f][1,2,4]triazin-2-amine [798];

(R)—N-(1-cyclopropylethyl)-5-(2-methyl-1-(tetrahydro-2H-pyran-4-yl)-1H-imidazo[4,5-b]pyridin-6-yl)pyrrolo[2,1-f][1,2,4]triazin-2-amine [799];

N-(2-cyclopropyl-2,2-difluoroethyl)-5-(2-methyl-1-(tetrahydro-2H-pyran-4-yl)-1H-imidazo[4,5-b]pyridin-6-yl)pyrrolo[2,1-f][1,2,4]triazin-2-amine [800];

5-(2-methyl-1-(tetrahydro-2H-pyran-4-yl)-1H-imidazo[4,5-b]pyridin-6-yl)-N-(oxetan-3-ylmethyl)pyrrolo[2,1-f][1,2,4]triazin-2-amine [801];

5-(2-methyl-1-(tetrahydro-2H-pyran-4-yl)-1H-imidazo[4,5-b]pyridin-6-yl)-N-((tetrahydrofuran-2-yl)methyl)pyrrolo[2,1-f][1,2,4]triazin-2-amine [802];

N-cyclobutyl-5-(2-methyl-1-(tetrahydro-2H-pyran-4-yl)-1H-imidazo[4,5-b]pyridin-6-yl)pyrrolo[2,1-f][1,2,4]triazin-2-amine [803];

N-(3,3-difluorocyclobutyl)-5-(2-methyl-1-(tetrahydro-2H-pyran-4-yl)-1H-imidazo[4,5-b]pyridin-6-yl)pyrrolo[2,1-f][1,2,4]triazin-2-amine [804];

N-(3,3-dimethylcyclobutyl)-5-(2-methyl-1-(tetrahydro-2H-pyran-4-yl)-1H-imidazo[4,5-b]pyridin-6-yl)pyrrolo[2,1-f][1,2,4]triazin-2-amine [805];

1-methyl-3-((5-(2-methyl-1-(tetrahydro-2H-pyran-4-yl)-1H-imidazo[4,5-b]pyridin-6-yl)pyrrolo[2,1-f][1,2,4]triazin-2-yl)amino)cyclobutan-1-ol [806];

N-(cis-3-methoxycyclobutyl)-5-(2-methyl-1-(tetrahydro-2H-pyran-4-yl)-1H-imidazo[4,5-b]pyridin-6-yl)pyrrolo[2,1-f][1,2,4]triazin-2-amine [807];

N-(trans-3-methoxycyclobutyl)-5-(2-methyl-1-(tetrahydro-2H-pyran-4-yl)-1H-imidazo[4,5-b]pyridin-6-yl)pyrrolo[2,1-f][1,2,4]triazin-2-amine [808];

N-(trans-3-(methoxymethyl)cyclobutyl)-5-(2-methyl-1-(tetrahydro-2H-pyran-4-yl)-1H-imidazo[4,5-b]pyridin-6-yl)pyrrolo[2,1-f][1,2,4]triazin-2-amine [809];

N-(cis-3-ethoxycyclobutyl)-5-(2-methyl-1-(tetrahydro-2H-pyran-4-yl)-1H-imidazo[4,5-b]pyridin-6-yl)pyrrolo[2,1-f][1,2,4]triazin-2-amine [810];

N-(trans-3-ethoxycyclobutyl)-5-(2-methyl-1-(tetrahydro-2H-pyran-4-yl)-1H-imidazo[4,5-b]pyridin-6-yl)pyrrolo[2,1-f][1,2,4]triazin-2-amine [811];

N-(cis-3-(2-methoxyethoxy)cyclobutyl)-5-(2-methyl-1-(tetrahydro-2H-pyran-4-yl)-1H-imidazo[4,5-b]pyridin-6-yl)pyrrolo[2,1-f][1,2,4]triazin-2-amine [812];

N-(trans-3-(2-methoxyethoxy)cyclobutyl)-5-(2-methyl-1-(tetrahydro-2H-pyran-4-yl)-1H-imidazo[4,5-b]pyridin-6-yl)pyrrolo[2,1-f][1,2,4]triazin-2-amine [813];

cis-$N^1$-(5-(2-methyl-1-(tetrahydro-2H-pyran-4-yl)-1H-imidazo[4,5-b]pyridin-6-yl)pyrrolo[2,1-f][1,2,4]triazin-2-yl)cyclobutane-1,3-diamine [814];

trans-$N^1$-(5-(2-methyl-1-(tetrahydro-2H-pyran-4-yl)-1H-imidazo[4,5-b]pyridin-6-yl)pyrrolo[2,1-f][1,2,4]triazin-2-yl)cyclobutane-1,3-diamine [815];

cis-$N^1$-methyl-$N^3$-(5-(2-methyl-1-(tetrahydro-2H-pyran-4-yl)-1H-imidazo[4,5-b]pyridin-6-yl)pyrrolo[2,1-f][1,2,4]triazin-2-yl)cyclobutane-1,3-diamine [816];

trans-$N^1$-methyl-$N^3$-(5-(2-methyl-1-(tetrahydro-2H-pyran-4-yl)-1H-imidazo[4,5-b]pyridin-6-yl)pyrrolo[2,1-f][1,2,4]triazin-2-yl)cyclobutane-1,3-diamine [817];

cis-$N^1$,$N^1$-dimethyl-$N^3$-(5-(2-methyl-1-(tetrahydro-2H-pyran-4-yl)-1H-imidazo[4,5-b]pyridin-6-yl)pyrrolo[2,1-f][1,2,4]triazin-2-yl)cyclobutane-1,3-diamine [818];

trans-$N^1$,$N^1$-dimethyl-$N^3$-(5-(2-methyl-1-(tetrahydro-2H-pyran-4-yl)-1H-imidazo[4,5-b]pyridin-6-yl)pyrrolo[2,1-f][1,2,4]triazin-2-yl)cyclobutane-1,3-diamine [819];

5-(2-methyl-1-(tetrahydro-2H-pyran-4-yl)-1H-imidazo[4,5-b]pyridin-6-yl)-N-(cis-3-morpholinocyclobutyl)pyrrolo[2,1-f][1,2,4]triazin-2-amine [820];

5-(2-methyl-1-(tetrahydro-2H-pyran-4-yl)-1H-imidazo[4,5-b]pyridin-6-yl)-N-(trans-3-morpholinocyclobutyl)pyrrolo[2,1-f][1,2,4]triazin-2-amine [821];

5-(2-methyl-1-(tetrahydro-2H-pyran-4-yl)-1H-imidazo[4,5-b]pyridin-6-yl)-N-(cis-3-(4-methylpiperazin-1-yl)cyclobutyl)pyrrolo[2,1-f][1,2,4]triazin-2-amine [822];

5-(2-methyl-1-(tetrahydro-2H-pyran-4-yl)-1H-imidazo[4,5-b]pyridin-6-yl)-N-(trans-3-(4-methylpiperazin-1-yl)cyclobutyl)pyrrolo[2,1-f][1,2,4]triazin-2-amine [823];

N-(4,4-difluorocyclohexyl)-5-(2-methyl-1-(tetrahydro-2H-pyran-4-yl)-1H-imidazo[4,5-b]pyridin-6-yl)pyrrolo[2,1-f][1,2,4]triazin-2-amine [824];

cis-4-((5-(2-methyl-1-(tetrahydro-2H-pyran-4-yl)-1H-imidazo[4,5-b]pyridin-6-yl)pyrrolo[2,1-f][1,2,4]triazin-2-yl)amino)cyclohexan-1-ol [825];

(1s,4s)-1-methyl-4-((5-(2-methyl-1-(tetrahydro-2H-pyran-4-yl)-1H-imidazo[4,5-b]pyridin-6-yl)pyrrolo[2,1-f][1,2,4]triazin-2-yl)amino)cyclohexan-1-ol [826];

N-(cis-4-methoxycyclohexyl)-5-(2-methyl-1-(tetrahydro-2H-pyran-4-yl)-1H-imidazo[4,5-b]pyridin-6-yl)pyrrolo[2,1-f][1,2,4]triazin-2-amine [827];

N-(trans-4-methoxycyclohexyl)-5-(2-methyl-1-(tetrahydro-2H-pyran-4-yl)-1H-imidazo[4,5-b]pyridin-6-yl)pyrrolo[2,1-f][1,2,4]triazin-2-amine [828];

N-(cis-4-(difluoromethoxy)cyclohexyl)-5-(2-methyl-1-(tetrahydro-2H-pyran-4-yl)-1H-imidazo[4,5-b]pyridin-6-yl)pyrrolo[2,1-f][1,2,4]triazin-2-amine [829];

N-(trans-4-(difluoromethoxy)cyclohexyl)-5-(2-methyl-1-(tetrahydro-2H-pyran-4-yl)-1H-imidazo[4,5-b]pyridin-6-yl)pyrrolo[2,1-f][1,2,4]triazin-2-amine [830];

N-(cis-4-ethoxycyclohexyl)-5-(2-methyl-1-(tetrahydro-2H-pyran-4-yl)-1H-imidazo[4,5-b]pyridin-6-yl)pyrrolo[2,1-f][1,2,4]triazin-2-amine [831];

N-(trans-4-ethoxycyclohexyl)-5-(2-methyl-1-(tetrahydro-2H-pyran-4-yl)-1H-imidazo[4,5-b]pyridin-6-yl)pyrrolo[2,1-f][1,2,4]triazin-2-amine [832];

N-(cis-4-(2-methoxyethoxy)cyclohexyl)-5-(2-methyl-1-(tetrahydro-2H-pyran-4-yl)-1H-imidazo[4,5-b]pyridin-6-yl)pyrrolo[2,1-f][1,2,4]triazin-2-amine [833];

N-(trans-4-(2-methoxyethoxy)cyclohexyl)-5-(2-methyl-1-(tetrahydro-2H-pyran-4-yl)-1H-imidazo[4,5-b]pyridin-6-yl)pyrrolo[2,1-f][1,2,4]triazin-2-amine [834];

cis-$N^1$-(5-(2-methyl-1-(tetrahydro-2H-pyran-4-yl)-1H-imidazo[4,5-b]pyridin-6-yl)pyrrolo[2,1-f][1,2,4]triazin-2-yl)cyclohexane-1,4-diamine [835];

trans-$N^1$-(5-(2-methyl-1-(tetrahydro-2H-pyran-4-yl)-1H-imidazo[4,5-b]pyridin-6-yl)pyrrolo[2,1-f][1,2,4]triazin-2-yl)cyclohexane-1,4-diamine [836];

cis-$N^1$-methyl-$N^4$-(5-(2-methyl-1-(tetrahydro-2H-pyran-4-yl)-1H-imidazo[4,5-b]pyridin-6-yl)pyrrolo[2,1-f][1,2,4]triazin-2-yl)cyclohexane-1,4-diamine [837];

trans-$N^1$-methyl-$N^4$-(5-(2-methyl-1-(tetrahydro-2H-pyran-4-yl)-1H-imidazo[4,5-b]pyridin-6-yl)pyrrolo[2,1-f][1,2,4]triazin-2-yl)cyclohexane-1,4-diamine [838];

cis-$N^1$,$N^1$-dimethyl-$N^4$-(5-(2-methyl-1-(tetrahydro-2H-pyran-4-yl)-1H-imidazo[4,5-b]pyridin-6-yl)pyrrolo[2,1-f][1,2,4]triazin-2-yl)cyclohexane-1,4-diamine [839];

trans-$N^1$,$N^1$-dimethyl-$N^4$-(5-(2-methyl-1-(tetrahydro-2H-pyran-4-yl)-1H-imidazo[4,5-b]pyridin-6-yl)pyrrolo[2,1-f][1,2,4]triazin-2-yl)cyclohexane-1,4-diamine [840];

5-(2-methyl-1-(tetrahydro-2H-pyran-4-yl)-1H-imidazo[4,5-b]pyridin-6-yl)-N-(cis-4-morpholinocyclohexyl)pyrrolo[2,1-f][1,2,4]triazin-2-amine [841];

5-(2-methyl-1-(tetrahydro-2H-pyran-4-yl)-1H-imidazo[4,5-b]pyridin-6-yl)-N-(trans-4-morpholinocyclohexyl)pyrrolo[2,1-f][1,2,4]triazin-2-amine [842];

5-(2-methyl-1-(tetrahydro-2H-pyran-4-yl)-1H-imidazo[4,5-b]pyridin-6-yl)-N-(cis-4-(4-methylpiperazin-1-yl)cyclohexyl)pyrrolo[2,1-f][1,2,4]triazin-2-amine [843];

5-(2-methyl-1-(tetrahydro-2H-pyran-4-yl)-1H-imidazo[4,5-b]pyridin-6-yl)-N-(trans-4-(4-methylpiperazin-1-yl)cyclohexyl)pyrrolo[2,1-f][1,2,4]triazin-2-amine [844];

5-(2-methyl-1-(tetrahydro-2H-pyran-4-yl)-1H-imidazo[4,5-b]pyridin-6-yl)-N-(1-methylazetidin-3-yl)pyrrolo[2,1-f][1,2,4]triazin-2-amine [845];

5-(2-methyl-1-(tetrahydro-2H-pyran-4-yl)-1H-imidazo[4,5-b]pyridin-6-yl)-N-(oxetan-3-yl)pyrrolo[2,1-f][1,2,4]triazin-2-amine [846];

5-(2-methyl-1-(tetrahydro-2H-pyran-4-yl)-1H-imidazo[4,5-b]pyridin-6-yl)-N-(1-methylpiperidin-4-yl)pyrrolo[2,1-f][1,2,4]triazin-2-amine [847];

5-(2-methyl-1-(tetrahydro-2H-pyran-4-yl)-1H-imidazo[4,5-b]pyridin-6-yl)-N-(tetrahydro-2H-pyran-4-yl)pyrrolo[2,1-f][1,2,4]triazin-2-amine [848];

N-(6,6-difluorospiro[3.3]heptan-2-yl)-5-(2-methyl-1-(tetrahydro-2H-pyran-4-yl)-1H-imidazo[4,5-b]pyridin-6-yl)pyrrolo[2,1-f][1,2,4]triazin-2-amine [849];

5-(2-methyl-1-(tetrahydro-2H-pyran-4-yl)-1H-imidazo[4,5-b]pyridin-6-yl)-N-(2-oxaspiro[3.3]heptan-6-yl)pyrrolo[2,1-f][1,2,4]triazin-2-amine [850];

5-(2-methyl-1-(tetrahydro-2H-pyran-4-yl)-1H-imidazo[4,5-b]pyridin-6-yl)-N-(2-methyl-2-azaspiro[3.3]heptan-6-yl)pyrrolo[2,1-f][1,2,4]triazin-2-amine [851];

5-(2-methyl-1-(tetrahydro-2H-pyran-4-yl)-1H-imidazo[4,5-b]pyridin-6-yl)-N-(1-methyl-1H-pyrazol-4-yl)pyrrolo[2,1-f][1,2,4]triazin-2-amine [852];

5-(2,3-dimethyl-3H-imidazo[4,5-b]pyridin-5-yl)-N-isopropylpyrrolo[2,1-f][1,2,4]triazin-2-amine [853];

5-(2,3-dimethyl-3H-imidazo[4,5-b]pyridin-5-yl)-N-isobutylpyrrolo[2,1-f][1,2,4]triazin-2-amine [854];

5-(2,3-dimethyl-3H-imidazo[4,5-b]pyridin-5-yl)-N-(2-fluoro-2-methylpropyl)pyrrolo[2,1-f][1,2,4]triazin-2-amine [855];

N-(2,2-difluoropropyl)-5-(2,3-dimethyl-3H-imidazo[4,5-b]pyridin-5-yl)pyrrolo[2,1-f][1,2,4]triazin-2-amine [856];

5-(2,3-dimethyl-3H-imidazo[4,5-b]pyridin-5-yl)-N-(2,2,2-trifluoroethyl)pyrrolo[2,1-f][1,2,4]triazin-2-amine [857];

(R)-5-(2,3-dimethyl-3H-imidazo[4,5-b]pyridin-5-yl)-N-(1,1,1-trifluoropropan-2-yl)pyrrolo[2,1-f][1,2,4]triazin-2-amine [858];

5-(2,3-dimethyl-3H-imidazo[4,5-b]pyridin-5-yl)-N-(3,3,3-trifluoropropyl)pyrrolo[2,1-f][1,2,4]triazin-2-amine [859];

5-(2,3-dimethyl-3H-imidazo[4,5-b]pyridin-5-yl)-N-(3,3,3-trifluoro-2,2-dimethylpropyl)pyrrolo[2,1-f][1,2,4]triazin-2-amine [860];

5-(2,3-dimethyl-3H-imidazo[4,5-b]pyridin-5-yl)-N-(2-methoxyethyl)pyrrolo[2,1-f][1,2,4]triazin-2-amine [861];

(R)-5-(2,3-dimethyl-3H-imidazo[4,5-b]pyridin-5-yl)-N-(1-methoxypropan-2-yl)pyrrolo[2,1-f][1,2,4]triazin-2-amine [862];

5-(2,3-dimethyl-3H-imidazo[4,5-b]pyridin-5-yl)-N-(2-isopropoxyethyl)pyrrolo[2,1-f][1,2,4]triazin-2-amine [863];

5-(2,3-dimethyl-3H-imidazo[4,5-b]pyridin-5-yl)-N-((1-methylcyclopropyl)methyl)pyrrolo[2,1-f][1,2,4]triazin-2-amine [864];

5-(2,3-dimethyl-3H-imidazo[4,5-b]pyridin-5-yl)-N-((1-(trifluoromethyl)cyclopropyl)methyl)pyrrolo[2,1-f][1,2,4]triazin-2-amine [865];

5-(2,3-dimethyl-3H-imidazo[4,5-b]pyridin-5-yl)-N-((1-fluorocyclobutyl)methyl)pyrrolo[2,1-f][1,2,4]triazin-2-amine [866];

5-(2,3-dimethyl-3H-imidazo[4,5-b]pyridin-5-yl)-N-((3-fluorooxetan-3-yl)methyl)pyrrolo[2,1-f][1,2,4]triazin-2-amine [867];

N-(cyclopropylmethyl)-5-(2,3-dimethyl-3H-imidazo[4,5-b]pyridin-5-yl)pyrrolo[2,1-f][1,2,4]triazin-2-amine [868];

(S)—N-(1-cyclopropylethyl)-5-(2,3-dimethyl-3H-imidazo[4,5-b]pyridin-5-yl)pyrrolo[2,1-f][1,2,4]triazin-2-amine [869];

(R)—N-(1-cyclopropylethyl)-5-(2,3-dimethyl-3H-imidazo[4,5-b]pyridin-5-yl)pyrrolo[2,1-f][1,2,4]triazin-2-amine [870];

N-(2-cyclopropyl-2,2-difluoroethyl)-5-(2,3-dimethyl-3H-imidazo[4,5-b]pyridin-5-yl)pyrrolo[2,1-f][1,2,4]triazin-2-amine [871];

5-(2,3-dimethyl-3H-imidazo[4,5-b]pyridin-5-yl)-N-(oxetan-3-ylmethyl)pyrrolo[2,1-f][1,2,4]triazin-2-amine [872];

5-(2,3-dimethyl-3H-imidazo[4,5-b]pyridin-5-yl)-N-((tetrahydrofuran-2-yl)methyl)pyrrolo[2,1-f][1,2,4]triazin-2-amine [873];

N-cyclobutyl-5-(2,3-dimethyl-3H-imidazo[4,5-b]pyridin-5-yl)pyrrolo[2,1-f][1,2,4]triazin-2-amine [874];

N-(3,3-difluorocyclobutyl)-5-(2,3-dimethyl-3H-imidazo[4,5-b]pyridin-5-yl)pyrrolo[2,1-f][1,2,4]triazin-2-amine [875];

5-(2,3-dimethyl-3H-imidazo[4,5-b]pyridin-5-yl)-N-(3,3-dimethylcyclobutyl)pyrrolo[2,1-f][1,2,4]triazin-2-amine [876];

3-((5-(2,3-dimethyl-3H-imidazo[4,5-b]pyridin-5-yl)pyrrolo[2,1-f][1,2,4]triazin-2-yl)amino)-1-methylcyclobutan-1-ol [877];

5-(2,3-dimethyl-3H-imidazo[4,5-b]pyridin-5-yl)-N-(cis-3-methoxycyclobutyl)pyrrolo[2,1-f][1,2,4]triazin-2-amine [878];

5-(2,3-dimethyl-3H-imidazo[4,5-b]pyridin-5-yl)-N-(trans-3-methoxycyclobutyl)pyrrolo[2,1-f][1,2,4]triazin-2-amine [879];

5-(2,3-dimethyl-3H-imidazo[4,5-b]pyridin-5-yl)-N-(trans-3-(methoxymethyl)cyclobutyl)pyrrolo[2,1-f][1,2,4]triazin-2-amine [880];

5-(2,3-dimethyl-3H-imidazo[4,5-b]pyridin-5-yl)-N-(cis-3-ethoxycyclobutyl)pyrrolo[2,1-f][1,2,4]triazin-2-amine [881];

5-(2,3-dimethyl-3H-imidazo[4,5-b]pyridin-5-yl)-N-(trans-3-ethoxycyclobutyl)pyrrolo[2,1-f][1,2,4]triazin-2-amine [882];

5-(2,3-dimethyl-3H-imidazo[4,5-b]pyridin-5-yl)-N-(cis-3-(2-methoxyethoxy)cyclobutyl)pyrrolo[2,1-f][1,2,4]triazin-2-amine [883];

5-(2,3-dimethyl-3H-imidazo[4,5-b]pyridin-5-yl)-N-(trans-3-(2-methoxyethoxy)cyclobutyl)pyrrolo[2,1-f][1,2,4]triazin-2-amine [884];

cis-$N^1$-(5-(2,3-dimethyl-3H-imidazo[4,5-b]pyridin-5-yl)pyrrolo[2,1-f][1,2,4]triazin-2-yl)cyclobutane-1,3-diamine [885];

trans-$N^1$-(5-(2,3-dimethyl-3H-imidazo[4,5-b]pyridin-5-yl)pyrrolo[2,1-f][1,2,4]triazin-2-yl)cyclobutane-1,3-diamine [886];

cis-$N^1$-(5-(2,3-dimethyl-3H-imidazo[4,5-b]pyridin-5-yl)pyrrolo[2,1-f][1,2,4]triazin-2-yl)-$N^3$-methylcyclobutane-1,3-diamine [887];

trans-$N^1$-(5-(2,3-dimethyl-3H-imidazo[4,5-b]pyridin-5-yl)pyrrolo[2,1-f][1,2,4]triazin-2-yl)-$N^3$-methylcyclobutane-1,3-diamine [888];

cis-$N^1$-(5-(2,3-dimethyl-3H-imidazo[4,5-b]pyridin-5-yl)pyrrolo[2,1-f][1,2,4]triazin-2-yl)-$N^3$,$N^3$-dimethylcyclobutane-1,3-diamine [889];

trans-$N^1$-(5-(2,3-dimethyl-3H-imidazo[4,5-b]pyridin-5-yl)pyrrolo[2,1-f][1,2,4]triazin-2-yl)-$N_3$,$N^3$-dimethylcyclobutane-1,3-diamine [890];

5-(2,3-dimethyl-3H-imidazo[4,5-b]pyridin-5-yl)-N-(cis-3-morpholinocyclobutyl)pyrrolo[2,1-f][1,2,4]triazin-2-amine [891];

5-(2,3-dimethyl-3H-imidazo[4,5-b]pyridin-5-yl)-N-(trans-3-morpholinocyclobutyl)pyrrolo[2,1-f][1,2,4]triazin-2-amine [892];

5-(2,3-dimethyl-3H-imidazo[4,5-b]pyridin-5-yl)-N-(cis-3-(4-methylpiperazin-1-yl)cyclobutyl)pyrrolo[2,1-f][1,2,4]triazin-2-amine [893];

5-(2,3-dimethyl-3H-imidazo[4,5-b]pyridin-5-yl)-N-(trans-3-(4-methylpiperazin-1-yl)cyclobutyl)pyrrolo[2,1-f][1,2,4]triazin-2-amine [894];

N-(4,4-difluorocyclohexyl)-5-(2,3-dimethyl-3H-imidazo[4,5-b]pyridin-5-yl)pyrrolo[2,1-f][1,2,4]triazin-2-amine [895];

cis-4-((5-(2,3-dimethyl-3H-imidazo[4,5-b]pyridin-5-yl)pyrrolo[2,1-f][1,2,4]triazin-2-yl)amino)cyclohexan-1-ol [896];

(1s,4s)-4-((5-(2,3-dimethyl-3H-imidazo[4,5-b]pyridin-5-yl)pyrrolo[2,1-f][1,2,4]triazin-2-yl)amino)-1-methylcyclohexan-1-ol [897];

5-(2,3-dimethyl-3H-imidazo[4,5-b]pyridin-5-yl)-N-(cis-4-methoxycyclohexyl)pyrrolo[2,1-f][1,2,4]triazin-2-amine [898];

5-(2,3-dimethyl-3H-imidazo[4,5-b]pyridin-5-yl)-N-(trans-4-methoxycyclohexyl)pyrrolo[2,1-f][1,2,4]triazin-2-amine [899];

N-(cis-4-(difluoromethoxy)cyclohexyl)-5-(2,3-dimethyl-3H-imidazo[4,5-b]pyridin-5-yl)pyrrolo[2,1-f][1,2,4]triazin-2-amine [900];

N-(trans-4-(difluoromethoxy)cyclohexyl)-5-(2,3-dimethyl-3H-imidazo[4,5-b]pyridin-5-yl)pyrrolo[2,1-f][1,2,4]triazin-2-amine [901];

5-(2,3-dimethyl-3H-imidazo[4,5-b]pyridin-5-yl)-N-(cis-4-ethoxycyclohexyl)pyrrolo[2,1-f][1,2,4]triazin-2-amine [902];

5-(2,3-dimethyl-3H-imidazo[4,5-b]pyridin-5-yl)-N-(trans-4-ethoxycyclohexyl)pyrrolo[2,1-f][1,2,4]triazin-2-amine [903];

5-(2,3-dimethyl-3H-imidazo[4,5-b]pyridin-5-yl)-N-(cis-4-(2-methoxyethoxy)cyclohexyl)pyrrolo[2,1-f][1,2,4]triazin-2-amine [904];

5-(2,3-dimethyl-3H-imidazo[4,5-b]pyridin-5-yl)-N-(trans-4-(2-methoxyethoxy)cyclohexyl)pyrrolo[2,1-f][1,2,4]triazin-2-amine [905];

cis-$N^1$-(5-(2,3-dimethyl-3H-imidazo[4,5-b]pyridin-5-yl)pyrrolo[2,1-f][1,2,4]triazin-2-yl)cyclohexane-1,4-diamine [906];

trans-$N^1$-(5-(2,3-dimethyl-3H-imidazo[4,5-b]pyridin-5-yl)pyrrolo[2,1-f][1,2,4]triazin-2-yl)cyclohexane-1,4-diamine [907];

cis-$N^1$-(5-(2,3-dimethyl-3H-imidazo[4,5-b]pyridin-5-yl)pyrrolo[2,1-f][1,2,4]triazin-2-yl)-$N^4$-methylcyclohexane-1,4-diamine [908];

trans-$N^1$-(5-(2,3-dimethyl-3H-imidazo[4,5-b]pyridin-5-yl)pyrrolo[2,1-f][1,2,4]triazin-2-yl)-$N^4$-methylcyclohexane-1,4-diamine [909];

cis-$N^1$-(5-(2,3-dimethyl-3H-imidazo[4,5-b]pyridin-5-yl)pyrrolo[2,1-f][1,2,4]triazin-2-yl)-$N^4$,$N^4$-dimethylcyclohexane-1,4-diamine [910];

trans-$N^1$-(5-(2,3-dimethyl-3H-imidazo[4,5-b]pyridin-5-yl)pyrrolo[2,1-f][1,2,4]triazin-2-yl)-$N^4$,$N^4$-dimethylcyclohexane-1,4-diamine [911];

5-(2,3-dimethyl-3H-imidazo[4,5-b]pyridin-5-yl)-N-(cis-4-morpholinocyclohexyl)pyrrolo[2,1-f][1,2,4]triazin-2-amine [912];

5-(2,3-dimethyl-3H-imidazo[4,5-b]pyridin-5-yl)-N-(trans-4-morpholinocyclohexyl)pyrrolo[2,1-f][1,2,4]triazin-2-amine [913];

5-(2,3-dimethyl-3H-imidazo[4,5-b]pyridin-5-yl)-N-(cis-4-(4-methylpiperazin-1-yl)cyclohexyl)pyrrolo[2,1-f][1,2,4]triazin-2-amine [914];

5-(2,3-dimethyl-3H-imidazo[4,5-b]pyridin-5-yl)-N-(trans-4-(4-methylpiperazin-1-yl)cyclohexyl)pyrrolo[2,1-f][1,2,4]triazin-2-amine [915];

5-(2,3-dimethyl-3H-imidazo[4,5-b]pyridin-5-yl)-N-(1-methylazetidin-3-yl)pyrrolo[2,1-f][1,2,4]triazin-2-amine [916];

5-(2,3-dimethyl-3H-imidazo[4,5-b]pyridin-5-yl)-N-(oxetan-3-yl)pyrrolo[2,1-f][1,2,4]triazin-2-amine [917];

5-(2,3-dimethyl-3H-imidazo[4,5-b]pyridin-5-yl)-N-(1-methylpiperidin-4-yl)pyrrolo[2,1-f][1,2,4]triazin-2-amine [918];

5-(2,3-dimethyl-3H-imidazo[4,5-b]pyridin-5-yl)-N-(tetrahydro-2H-pyran-4-yl)pyrrolo[2,1-f][1,2,4]triazin-2-amine [919];

N-(6,6-difluorospiro[3.3]heptan-2-yl)-5-(2,3-dimethyl-3H-imidazo[4,5-b]pyridin-5-yl)pyrrolo[2,1-f][1,2,4]triazin-2-amine [920];

5-(2,3-dimethyl-3H-imidazo[4,5-b]pyridin-5-yl)-N-(2-oxaspiro[3.3]heptan-6-yl)pyrrolo[2,1-f][1,2,4]triazin-2-amine [921];

5-(2,3-dimethyl-3H-imidazo[4,5-b]pyridin-5-yl)-N-(2-methyl-2-azaspiro[3.3]heptan-6-yl)pyrrolo[2,1-f][1,2,4]triazin-2-amine [922];

5-(2,3-dimethyl-3H-imidazo[4,5-b]pyridin-5-yl)-N-(1-methyl-1H-pyrazol-4-yl)pyrrolo[2,1-f][1,2,4]triazin-2-amine [923];

5-(3-ethyl-2-methyl-3H-imidazo[4,5-b]pyridin-5-yl)-N-isopropylpyrrolo[2,1-f][1,2,4]triazin-2-amine [924];

5-(3-ethyl-2-methyl-3H-imidazo[4,5-b]pyridin-5-yl)-N-isobutylpyrrolo[2,1-f][1,2,4]triazin-2-amine [925];

5-(3-ethyl-2-methyl-3H-imidazo[4,5-b]pyridin-5-yl)-N-(2-fluoro-2-methylpropyl)pyrrolo[2,1-f][1,2,4]triazin-2-amine [926];

N-(2,2-difluoropropyl)-5-(3-ethyl-2-methyl-3H-imidazo[4,5-b]pyridin-5-yl)pyrrolo[2,1-f][1,2,4]triazin-2-amine [927];

5-(3-ethyl-2-methyl-3H-imidazo[4,5-b]pyridin-5-yl)-N-(2,2,2-trifluoroethyl)pyrrolo[2,1-f][1,2,4]triazin-2-amine [928];

(R)-5-(3-ethyl-2-methyl-3H-imidazo[4,5-b]pyridin-5-yl)-N-(1,1,1-trifluoropropan-2-yl)pyrrolo[2,1-f][1,2,4]triazin-2-amine [929];

5-(3-ethyl-2-methyl-3H-imidazo[4,5-b]pyridin-5-yl)-N-(3,3,3-trifluoropropyl)pyrrolo[2,1-f][1,2,4]triazin-2-amine [930];

5-(3-ethyl-2-methyl-3H-imidazo[4,5-b]pyridin-5-yl)-N-(3,3,3-trifluoro-2,2-dimethylpropyl)pyrrolo[2,1-f][1,2,4]triazin-2-amine [931];

5-(3-ethyl-2-methyl-3H-imidazo[4,5-b]pyridin-5-yl)-N-(2-methoxyethyl)pyrrolo[2,1-f][1,2,4]triazin-2-amine [932];

(R)-5-(3-ethyl-2-methyl-3H-imidazo[4,5-b]pyridin-5-yl)-N-(1-methoxypropan-2-yl)pyrrolo[2,1-f][1,2,4]triazin-2-amine [933];

5-(3-ethyl-2-methyl-3H-imidazo[4,5-b]pyridin-5-yl)-N-(2-isopropoxyethyl)pyrrolo[2,1-f][1,2,4]triazin-2-amine [934];

5-(3-ethyl-2-methyl-3H-imidazo[4,5-b]pyridin-5-yl)-N-((1-methylcyclopropyl)methyl)pyrrolo[2,1-f][1,2,4]triazin-2-amine [935];

5-(3-ethyl-2-methyl-3H-imidazo[4,5-b]pyridin-5-yl)-N-((1-(trifluoromethyl)cyclopropyl)methyl)pyrrolo[2,1-f][1,2,4]triazin-2-amine [936];

5-(3-ethyl-2-methyl-3H-imidazo[4,5-b]pyridin-5-yl)-N-((1-fluorocyclobutyl)methyl)pyrrolo[2,1-f][1,2,4]triazin-2-amine [937];

5-(3-ethyl-2-methyl-3H-imidazo[4,5-b]pyridin-5-yl)-N-((3-fluorooxetan-3-yl)methyl)pyrrolo[2,1-f][1,2,4]triazin-2-amine [938];

N-(cyclopropylmethyl)-5-(3-ethyl-2-methyl-3H-imidazo[4,5-b]pyridin-5-yl)pyrrolo[2,1-f][1,2,4]triazin-2-amine [939];

(S)—N-(1-cyclopropylethyl)-5-(3-ethyl-2-methyl-3H-imidazo[4,5-b]pyridin-5-yl)pyrrolo[2,1-f][1,2,4]triazin-2-amine [940];

(R)—N-(1-cyclopropylethyl)-5-(3-ethyl-2-methyl-3H-imidazo[4,5-b]pyridin-5-yl)pyrrolo[2,1-f][1,2,4]triazin-2-amine [941];

N-(2-cyclopropyl-2,2-difluoroethyl)-5-(3-ethyl-2-methyl-3H-imidazo[4,5-b]pyridin-5-yl)pyrrolo[2,1-f][1,2,4]triazin-2-amine [942];

5-(3-ethyl-2-methyl-3H-imidazo[4,5-b]pyridin-5-yl)-N-(oxetan-3-ylmethyl)pyrrolo[2,1-f][1,2,4]triazin-2-amine [943];

5-(3-ethyl-2-methyl-3H-imidazo[4,5-b]pyridin-5-yl)-N-((tetrahydrofuran-2-yl)methyl)pyrrolo[2,1-f][1,2,4]triazin-2-amine [944];

N-cyclobutyl-5-(3-ethyl-2-methyl-3H-imidazo[4,5-b]pyridin-5-yl)pyrrolo[2,1-f][1,2,4]triazin-2-amine [945];

N-(3,3-difluorocyclobutyl)-5-(3-ethyl-2-methyl-3H-imidazo[4,5-b]pyridin-5-yl)pyrrolo[2,1-f][1,2,4]triazin-2-amine [946];

N-(3,3-dimethylcyclobutyl)-5-(3-ethyl-2-methyl-3H-imidazo[4,5-b]pyridin-5-yl)pyrrolo[2,1-f][1,2,4]triazin-2-amine [947];

3-((5-(3-ethyl-2-methyl-3H-imidazo[4,5-b]pyridin-5-yl)pyrrolo[2,1-f][1,2,4]triazin-2-yl)amino)-1-methylcyclobutan-1-ol [948];

5-(3-ethyl-2-methyl-3H-imidazo[4,5-b]pyridin-5-yl)-N-(cis-3-methoxycyclobutyl)pyrrolo[2,1-f][1,2,4]triazin-2-amine [949];

5-(3-ethyl-2-methyl-3H-imidazo[4,5-b]pyridin-5-yl)-N-(trans-3-methoxycyclobutyl)pyrrolo[2,1-f][1,2,4]triazin-2-amine [950];

5-(3-ethyl-2-methyl-3H-imidazo[4,5-b]pyridin-5-yl)-N-(trans-3-(methoxymethyl)cyclobutyl)pyrrolo[2,1-f][1,2,4]triazin-2-amine [951];

N-(cis-3-ethoxycyclobutyl)-5-(3-ethyl-2-methyl-3H-imidazo[4,5-b]pyridin-5-yl)pyrrolo[2,1-f][1,2,4]triazin-2-amine [952];

N-(trans-3-ethoxycyclobutyl)-5-(3-ethyl-2-methyl-3H-imidazo[4,5-b]pyridin-5-yl)pyrrolo[2,1-f][1,2,4]triazin-2-amine [953];

5-(3-ethyl-2-methyl-3H-imidazo[4,5-b]pyridin-5-yl)-N-(cis-3-(2-methoxyethoxy)cyclobutyl)pyrrolo[2,1-f][1,2,4]triazin-2-amine [954];

5-(3-ethyl-2-methyl-3H-imidazo[4,5-b]pyridin-5-yl)-N-(trans-3-(2-methoxyethoxy)cyclobutyl)pyrrolo[2,1-f][1,2,4]triazin-2-amine [955];

cis-$N^1$-(5-(3-ethyl-2-methyl-3H-imidazo[4,5-b]pyridin-5-yl)pyrrolo[2,1-f][1,2,4]triazin-2-yl)cyclobutane-1,3-diamine [956];

trans-$N^1$-(5-(3-ethyl-2-methyl-3H-imidazo[4,5-b]pyridin-5-yl)pyrrolo[2,1-f][1,2,4]triazin-2-yl)cyclobutane-1,3-diamine [957];

cis-$N^1$-(5-(3-ethyl-2-methyl-3H-imidazo[4,5-b]pyridin-5-yl)pyrrolo[2,1-f][1,2,4]triazin-2-yl)-$N^3$-methylcyclobutane-1,3-diamine [958];

trans-$N^1$-(5-(3-ethyl-2-methyl-3H-imidazo[4,5-b]pyridin-5-yl)pyrrolo[2,1-f][1,2,4]triazin-2-yl)-$N^3$-methylcyclobutane-1,3-diamine [959];

cis-$N^1$-(5-(3-ethyl-2-methyl-3H-imidazo[4,5-b]pyridin-5-yl)pyrrolo[2,1-f][1,2,4]triazin-2-yl)-$N^3$,$N^3$-dimethylcyclobutane-1,3-diamine [960];

trans-$N^1$-(5-(3-ethyl-2-methyl-3H-imidazo[4,5-b]pyridin-5-yl)pyrrolo[2,1-f][1,2,4]triazin-2-yl)-$N_3$,$N^3$-dimethylcyclobutane-1,3-diamine [961];

5-(3-ethyl-2-methyl-3H-imidazo[4,5-b]pyridin-5-yl)-N-(cis-3-morpholinocyclobutyl)pyrrolo[2,1-f][1,2,4]triazin-2-amine [962];

5-(3-ethyl-2-methyl-3H-imidazo[4,5-b]pyridin-5-yl)-N-(trans-3-morpholinocyclobutyl)pyrrolo[2,1-f][1,2,4]triazin-2-amine [963];

5-(3-ethyl-2-methyl-3H-imidazo[4,5-b]pyridin-5-yl)-N-(cis-3-(4-methylpiperazin-1-yl)cyclobutyl)pyrrolo[2,1-f][1,2,4]triazin-2-amine [964];

5-(3-ethyl-2-methyl-3H-imidazo[4,5-b]pyridin-5-yl)-N-(trans-3-(4-methylpiperazin-1-yl)cyclobutyl)pyrrolo[2,1-f][1,2,4]triazin-2-amine [965];

N-(4,4-difluorocyclohexyl)-5-(3-ethyl-2-methyl-3H-imidazo[4,5-b]pyridin-5-yl)pyrrolo[2,1-f][1,2,4]triazin-2-amine [966];

cis-4-((5-(3-ethyl-2-methyl-3H-imidazo[4,5-b]pyridin-5-yl)pyrrolo[2,1-f][1,2,4]triazin-2-yl)amino)cyclohexan-1-ol [967];

(1s,4s)-4-((5-(3-ethyl-2-methyl-3H-imidazo[4,5-b]pyridin-5-yl)pyrrolo[2,1-f][1,2,4]triazin-2-yl)amino)-1-methylcyclohexan-1-ol [968];

5-(3-ethyl-2-methyl-3H-imidazo[4,5-b]pyridin-5-yl)-N-(cis-4-methoxycyclohexyl)pyrrolo[2,1-f][1,2,4]triazin-2-amine [969];

5-(3-ethyl-2-methyl-3H-imidazo[4,5-b]pyridin-5-yl)-N-(trans-4-methoxycyclohexyl)pyrrolo[2,1-f][1,2,4]triazin-2-amine [970];

N-(cis-4-(difluoromethoxy)cyclohexyl)-5-(3-ethyl-2-methyl-3H-imidazo[4,5-b]pyridin-5-yl)pyrrolo[2,1-f][1,2,4]triazin-2-amine [971];

N-(trans-4-(difluoromethoxy)cyclohexyl)-5-(3-ethyl-2-methyl-3H-imidazo[4,5-b]pyridin-5-yl)pyrrolo[2,1-f][1,2,4]triazin-2-amine [972];

N-(cis-4-ethoxycyclohexyl)-5-(3-ethyl-2-methyl-3H-imidazo[4,5-b]pyridin-5-yl)pyrrolo[2,1-f][1,2,4]triazin-2-amine [973];

N-(trans-4-ethoxycyclohexyl)-5-(3-ethyl-2-methyl-3H-imidazo[4,5-b]pyridin-5-yl)pyrrolo[2,1-f][1,2,4]triazin-2-amine [974];

5-(3-ethyl-2-methyl-3H-imidazo[4,5-b]pyridin-5-yl)-N-(cis-4-(2-methoxyethoxy)cyclohexyl)pyrrolo[2,1-f][1,2,4]triazin-2-amine [975];

5-(3-ethyl-2-methyl-3H-imidazo[4,5-b]pyridin-5-yl)-N-(trans-4-(2-methoxyethoxy)cyclohexyl)pyrrolo[2,1-f][1,2,4]triazin-2-amine [976];

cis-$N^1$-(5-(3-ethyl-2-methyl-3H-imidazo[4,5-b]pyridin-5-yl)pyrrolo[2,1-f][1,2,4]triazin-2-yl)cyclohexane-1,4-diamine [977];

trans-$N^1$-(5-(3-ethyl-2-methyl-3H-imidazo[4,5-b]pyridin-5-yl)pyrrolo[2,1-f][1,2,4]triazin-2-yl)cyclohexane-1,4-diamine [978];

cis-$N^1$-(5-(3-ethyl-2-methyl-3H-imidazo[4,5-b]pyridin-5-yl)pyrrolo[2,1-f][1,2,4]triazin-2-yl)-$N^4$-methylcyclohexane-1,4-diamine [979];

trans-$N^1$-(5-(3-ethyl-2-methyl-3H-imidazo[4,5-b]pyridin-5-yl)pyrrolo[2,1-f][1,2,4]triazin-2-yl)-$N^4$-methylcyclohexane-1,4-diamine [980];

cis-$N^1$-(5-(3-ethyl-2-methyl-3H-imidazo[4,5-b]pyridin-5-yl)pyrrolo[2,1-f][1,2,4]triazin-2-yl)-$N^4$,$N^4$-dimethylcyclohexane-1,4-diamine [981];

trans-$N^1$-(5-(3-ethyl-2-methyl-3H-imidazo[4,5-b]pyridin-5-yl)pyrrolo[2,1-f][1,2,4]triazin-2-yl)-$N^4$,$N^4$-dimethylcyclohexane-1,4-diamine [982];

5-(3-ethyl-2-methyl-3H-imidazo[4,5-b]pyridin-5-yl)-N-(cis-4-morpholinocyclohexyl)pyrrolo[2,1-f][1,2,4]triazin-2-amine [983];

5-(3-ethyl-2-methyl-3H-imidazo[4,5-b]pyridin-5-yl)-N-(trans-4-morpholinocyclohexyl)pyrrolo[2,1-f][1,2,4]triazin-2-amine [984];

5-(3-ethyl-2-methyl-3H-imidazo[4,5-b]pyridin-5-yl)-N-(cis-4-(4-methylpiperazin-1-yl)cyclohexyl)pyrrolo[2,1-f][1,2,4]triazin-2-amine [985];

5-(3-ethyl-2-methyl-3H-imidazo[4,5-b]pyridin-5-yl)-N-(trans-4-(4-methylpiperazin-1-yl)cyclohexyl)pyrrolo[2,1-f][1,2,4]triazin-2-amine [986];

5-(3-ethyl-2-methyl-3H-imidazo[4,5-b]pyridin-5-yl)-N-(1-methylazetidin-3-yl)pyrrolo[2,1-f][1,2,4]triazin-2-amine [987];

5-(3-ethyl-2-methyl-3H-imidazo[4,5-b]pyridin-5-yl)-N-(oxetan-3-yl)pyrrolo[2,1-f][1,2,4]triazin-2-amine [988];

5-(3-ethyl-2-methyl-3H-imidazo[4,5-b]pyridin-5-yl)-N-(1-methylpiperidin-4-yl)pyrrolo[2,1-f][1,2,4]triazin-2-amine [989];

5-(3-ethyl-2-methyl-3H-imidazo[4,5-b]pyridin-5-yl)-N-(tetrahydro-2H-pyran-4-yl)pyrrolo[2,1-f][1,2,4]triazin-2-amine [990];

N-(6,6-difluorospiro[3.3]heptan-2-yl)-5-(3-ethyl-2-methyl-3H-imidazo[4,5-b]pyridin-5-yl)pyrrolo[2,1-f][1,2,4]triazin-2-amine [991];

5-(3-ethyl-2-methyl-3H-imidazo[4,5-b]pyridin-5-yl)-N-(2-oxaspiro[3.3]heptan-6-yl)pyrrolo[2,1-f][1,2,4]triazin-2-amine [992];

5-(3-ethyl-2-methyl-3H-imidazo[4,5-b]pyridin-5-yl)-N-(2-methyl-2-azaspiro[3.3]heptan-6-yl)pyrrolo[2,1-f][1,2,4]triazin-2-amine [993];

5-(3-ethyl-2-methyl-3H-imidazo[4,5-b]pyridin-5-yl)-N-(1-methyl-1H-pyrazol-4-yl)pyrrolo[2,1-f][1,2,4]triazin-2-amine [994];

5-(3-(2-fluoroethyl)-2-methyl-3H-imidazo[4,5-b]pyridin-5-yl)-N-isopropylpyrrolo[2,1-f][1,2,4]triazin-2-amine [995];

5-(3-(2-fluoroethyl)-2-methyl-3H-imidazo[4,5-b]pyridin-5-yl)-N-isobutylpyrrolo[2,1-f][1,2,4]triazin-2-amine [996];

N-(2-fluoro-2-methylpropyl)-5-(3-(2-fluoroethyl)-2-methyl-3H-imidazo[4,5-b]pyridin-5-yl)pyrrolo[2,1-f][1,2,4]triazin-2-amine [997];

N-(2,2-difluoropropyl)-5-(3-(2-fluoroethyl)-2-methyl-3H-imidazo[4,5-b]pyridin-5-yl)pyrrolo[2,1-f][1,2,4]triazin-2-amine [998];

5-(3-(2-fluoroethyl)-2-methyl-3H-imidazo[4,5-b]pyridin-5-yl)-N-(2,2,2-trifluoroethyl)pyrrolo[2,1-f][1,2,4]triazin-2-amine [999]; and (R)-5-(3-(2-fluoroethyl)-2-methyl-3H-imidazo[4,5-b]pyridin-5-yl)-N-(1,1,1-trifluoropropan-2-yl)pyrrolo[2,1-f][1,2,4]triazin-2-amine [1000]; or a pharmaceutically acceptable salt thereof.

10. The compound of claim 1, wherein the compound of Formula I is selected from the group consisting of 5-(3-(2-fluoroethyl)-2-methyl-3H-imidazo[4,5-b]pyridin-5-yl)-N-(3,3,3-trifluoropropyl)pyrrolo[2,1-f][1,2,4]triazin-2-amine [1001];

5-(3-(2-fluoroethyl)-2-methyl-3H-imidazo[4,5-b]pyridin-5-yl)-N-(3,3,3-trifluoro-2,2-dimethylpropyl)pyrrolo[2,1-f][1,2,4]triazin-2-amine [1002];

5-(3-(2-fluoroethyl)-2-methyl-3H-imidazo[4,5-b]pyridin-5-yl)-N-(2-methoxyethyl)pyrrolo[2,1-f][1,2,4]triazin-2-amine [1003];

(R)-5-(3-(2-fluoroethyl)-2-methyl-3H-imidazo[4,5-b]pyridin-5-yl)-N-(1-methoxypropan-2-yl)pyrrolo[2,1-f][1,2,4]triazin-2-amine [1004];

5-(3-(2-fluoroethyl)-2-methyl-3H-imidazo[4,5-b]pyridin-5-yl)-N-(2-isopropoxyethyl)pyrrolo[2,1-f][1,2,4]triazin-2-amine [1005];

5-(3-(2-fluoroethyl)-2-methyl-3H-imidazo[4,5-b]pyridin-5-yl)-N-((1-methylcyclopropyl)methyl)pyrrolo[2,1-f][1,2,4]triazin-2-amine [1006];

5-(3-(2-fluoroethyl)-2-methyl-3H-imidazo[4,5-b]pyridin-5-yl)-N-((1-(trifluoromethyl)cyclopropyl)methyl)pyrrolo[2,1-f][1,2,4]triazin-2-amine [1007];

N-((1-fluorocyclobutyl)methyl)-5-(3-(2-fluoroethyl)-2-methyl-3H-imidazo[4,5-b]pyridin-5-yl)pyrrolo[2,1-f][1,2,4]triazin-2-amine [1008];

5-(3-(2-fluoroethyl)-2-methyl-3H-imidazo[4,5-b]pyridin-5-yl)-N-((3-fluorooxetan-3-yl)methyl)pyrrolo[2,1-f][1,2,4]triazin-2-amine [1009];

N-(cyclopropylmethyl)-5-(3-(2-fluoroethyl)-2-methyl-3H-imidazo[4,5-b]pyridin-5-yl)pyrrolo[2,1-f][1,2,4]triazin-2-amine [1010];

(S)—N-(1-cyclopropylethyl)-5-(3-(2-fluoroethyl)-2-methyl-3H-imidazo[4,5-b]pyridin-5-yl)pyrrolo[2,1-f][1,2,4]triazin-2-amine [1011];

(R)—N-(1-cyclopropylethyl)-5-(3-(2-fluoroethyl)-2-methyl-3H-imidazo[4,5-b]pyridin-5-yl)pyrrolo[2,1-f][1,2,4]triazin-2-amine [1012];

N-(2-cyclopropyl-2,2-difluoroethyl)-5-(3-(2-fluoroethyl)-2-methyl-3H-imidazo[4,5-b]pyridin-5-yl)pyrrolo[2,1-f][1,2,4]triazin-2-amine [1013];

5-(3-(2-fluoroethyl)-2-methyl-3H-imidazo[4,5-b]pyridin-5-yl)-N-(oxetan-3-ylmethyl)pyrrolo[2,1-f][1,2,4]triazin-2-amine [1014];

5-(3-(2-fluoroethyl)-2-methyl-3H-imidazo[4,5-b]pyridin-5-yl)-N-((tetrahydrofuran-2-yl)methyl)pyrrolo[2,1-f][1,2,4]triazin-2-amine [1015];

N-cyclobutyl-5-(3-(2-fluoroethyl)-2-methyl-3H-imidazo[4,5-b]pyridin-5-yl)pyrrolo[2,1-f][1,2,4]triazin-2-amine [1016];

N-(3,3-difluorocyclobutyl)-5-(3-(2-fluoroethyl)-2-methyl-3H-imidazo[4,5-b]pyridin-5-yl)pyrrolo[2,1-f][1,2,4]triazin-2-amine [1017];

N-(3,3-dimethylcyclobutyl)-5-(3-(2-fluoroethyl)-2-methyl-3H-imidazo[4,5-b]pyridin-5-yl)pyrrolo[2,1-f][1,2,4]triazin-2-amine [1018];

3-((5-(3-(2-fluoroethyl)-2-methyl-3H-imidazo[4,5-b]pyridin-5-yl)pyrrolo[2,1-f][1,2,4]triazin-2-yl)amino)-1-methylcyclobutan-1-ol [1019];

5-(3-(2-fluoroethyl)-2-methyl-3H-imidazo[4,5-b]pyridin-5-yl)-N-(cis-3-methoxycyclobutyl)pyrrolo[2,1-f][1,2,4]triazin-2-amine [1020];

5-(3-(2-fluoroethyl)-2-methyl-3H-imidazo[4,5-b]pyridin-5-yl)-N-(trans-3-methoxycyclobutyl)pyrrolo[2,1-f][1,2,4]triazin-2-amine [1021];

5-(3-(2-fluoroethyl)-2-methyl-3H-imidazo[4,5-b]pyridin-5-yl)-N-(trans-3-(methoxymethyl)cyclobutyl)pyrrolo[2,1-f][1,2,4]triazin-2-amine [1022];

N-(cis-3-ethoxycyclobutyl)-5-(3-(2-fluoroethyl)-2-methyl-3H-imidazo[4,5-b]pyridin-5-yl)pyrrolo[2,1-f][1,2,4]triazin-2-amine [1023];

N-(trans-3-ethoxycyclobutyl)-5-(3-(2-fluoroethyl)-2-methyl-3H-imidazo[4,5-b]pyridin-5-yl)pyrrolo[2,1-f][1,2,4]triazin-2-amine [1024];

5-(3-(2-fluoroethyl)-2-methyl-3H-imidazo[4,5-b]pyridin-5-yl)-N-(cis-3-(2-methoxyethoxy)cyclobutyl)pyrrolo[2,1-f][1,2,4]triazin-2-amine [1025];

5-(3-(2-fluoroethyl)-2-methyl-3H-imidazo[4,5-b]pyridin-5-yl)-N-(trans-3-(2-methoxyethoxy)cyclobutyl)pyrrolo[2,1-f][1,2,4]triazin-2-amine [1026];

cis-$N^1$-(5-(3-(2-fluoroethyl)-2-methyl-3H-imidazo[4,5-b]pyridin-5-yl)pyrrolo[2,1-f][1,2,4]triazin-2-yl)cyclobutane-1,3-diamine [1027];

trans-$N^1$-(5-(3-(2-fluoroethyl)-2-methyl-3H-imidazo[4,5-b]pyridin-5-yl)pyrrolo[2,1-f][1,2,4]triazin-2-yl)cyclobutane-1,3-diamine [1028];

cis-$N^1$-(5-(3-(2-fluoroethyl)-2-methyl-3H-imidazo[4,5-b]pyridin-5-yl)pyrrolo[2,1-f][1,2,4]triazin-2-yl)-$N^3$-methylcyclobutane-1,3-diamine [1029];

trans-$N^1$-(5-(3-(2-fluoroethyl)-2-methyl-3H-imidazo[4,5-b]pyridin-5-yl)pyrrolo[2,1-f][1,2,4]triazin-2-yl)-$N^3$-methylcyclobutane-1,3-diamine [1030];

cis-$N^1$-(5-(3-(2-fluoroethyl)-2-methyl-3H-imidazo[4,5-b]pyridin-5-yl)pyrrolo[2,1-f][1,2,4]triazin-2-yl)-$N^3$,$N^3$-dimethylcyclobutane-1,3-diamine [1031];

trans-$N^1$-(5-(3-(2-fluoroethyl)-2-methyl-3H-imidazo[4,5-b]pyridin-5-yl)pyrrolo[2,1-f][1,2,4]triazin-2-yl)-$N^3$,$N^3$-dimethylcyclobutane-1,3-diamine [1032];

5-(3-(2-fluoroethyl)-2-methyl-3H-imidazo[4,5-b]pyridin-5-yl)-N-(cis-3-morpholinocyclobutyl)pyrrolo[2,1-f][1,2,4]triazin-2-amine [1033];

5-(3-(2-fluoroethyl)-2-methyl-3H-imidazo[4,5-b]pyridin-5-yl)-N-(trans-3-morpholinocyclobutyl)pyrrolo[2,1-f][1,2,4]triazin-2-amine [1034];

5-(3-(2-fluoroethyl)-2-methyl-3H-imidazo[4,5-b]pyridin-5-yl)-N-(cis-3-(4-methylpiperazin-1-yl)cyclobutyl)pyrrolo[2,1-f][1,2,4]triazin-2-amine [1035];

5-(3-(2-fluoroethyl)-2-methyl-3H-imidazo[4,5-b]pyridin-5-yl)-N-(trans-3-(4-methylpiperazin-1-yl)cyclobutyl)pyrrolo[2,1-f][1,2,4]triazin-2-amine [1036];

N-(4,4-difluorocyclohexyl)-5-(3-(2-fluoroethyl)-2-methyl-3H-imidazo[4,5-b]pyridin-5-yl)pyrrolo[2,1-f][1,2,4]triazin-2-amine [1037];

cis-4-((5-(3-(2-fluoroethyl)-2-methyl-3H-imidazo[4,5-b]pyridin-5-yl)pyrrolo[2,1-f][1,2,4]triazin-2-yl)amino)cyclohexan-1-ol [1038];

(1s,4s)-4-((5-(3-(2-fluoroethyl)-2-methyl-3H-imidazo[4,5-b]pyridin-5-yl)pyrrolo[2,1-f][1,2,4] triazin-2-yl)amino)-1-methylcyclohexan-1-ol [1039];

5-(3-(2-fluoroethyl)-2-methyl-3H-imidazo[4,5-b]pyridin-5-yl)-N-(cis-4-methoxycyclohexyl)pyrrolo[2,1-f][1,2,4]triazin-2-amine [1040];

5-(3-(2-fluoroethyl)-2-methyl-3H-imidazo[4,5-b]pyridin-5-yl)-N-(trans-4-methoxycyclohexyl)pyrrolo[2,1-f][1,2,4]triazin-2-amine [1041];

N-(cis-4-(difluoromethoxy)cyclohexyl)-5-(3-(2-fluoroethyl)-2-methyl-3H-imidazo[4,5-b]pyridin-5-yl)pyrrolo[2,1-f][1,2,4]triazin-2-amine [1042];

N-(trans-4-(difluoromethoxy)cyclohexyl)-5-(3-(2-fluoroethyl)-2-methyl-3H-imidazo[4,5-b]pyridin-5-yl)pyrrolo[2,1-f][1,2,4]triazin-2-amine [1043];

N-(cis-4-ethoxycyclohexyl)-5-(3-(2-fluoroethyl)-2-methyl-3H-imidazo[4,5-b]pyridin-5-yl)pyrrolo[2,1-f][1,2,4]triazin-2-amine [1044];

N-(trans-4-ethoxycyclohexyl)-5-(3-(2-fluoroethyl)-2-methyl-3H-imidazo[4,5-b]pyridin-5-yl)pyrrolo[2,1-f][1,2,4]triazin-2-amine [1045];

5-(3-(2-fluoroethyl)-2-methyl-3H-imidazo[4,5-b]pyridin-5-yl)-N-(cis-4-(2-methoxyethoxy)cyclohexyl)pyrrolo[2,1-f][1,2,4]triazin-2-amine [1046];

5-(3-(2-fluoroethyl)-2-methyl-3H-imidazo[4,5-b]pyridin-5-yl)-N-(trans-4-(2-methoxyethoxy)cyclohexyl)pyrrolo[2,1-f][1,2,4]triazin-2-amine [1047];

cis-$N^1$-(5-(3-(2-fluoroethyl)-2-methyl-3H-imidazo[4,5-b]pyridin-5-yl)pyrrolo[2,1-f][1,2,4]triazin-2-yl)cyclohexane-1,4-diamine [1048];

trans-$N^1$-(5-(3-(2-fluoroethyl)-2-methyl-3H-imidazo[4,5-b]pyridin-5-yl)pyrrolo[2,1-f][1,2,4]triazin-2-yl)cyclohexane-1,4-diamine [1049];

cis-$N^1$-(5-(3-(2-fluoroethyl)-2-methyl-3H-imidazo[4,5-b]pyridin-5-yl)pyrrolo[2,1-f][1,2,4]triazin-2-yl)-$N^4$-methylcyclohexane-1,4-diamine [1050];

trans-$N^1$-(5-(3-(2-fluoroethyl)-2-methyl-3H-imidazo[4,5-b]pyridin-5-yl)pyrrolo[2,1-f][1,2,4]triazin-2-yl)-$N^4$-methylcyclohexane-1,4-diamine [1051];

cis-$N^1$-(5-(3-(2-fluoroethyl)-2-methyl-3H-imidazo[4,5-b]pyridin-5-yl)pyrrolo[2,1-f][1,2,4]triazin-2-yl)-$N^4$,$N^4$-dimethylcyclohexane-1,4-diamine [1052];

trans-$N^1$-(5-(3-(2-fluoroethyl)-2-methyl-3H-imidazo[4,5-b]pyridin-5-yl)pyrrolo[2,1-f][1,2,4]triazin-2-yl)-$N^4$,$N^4$-dimethylcyclohexane-1,4-diamine [1053];

5-(3-(2-fluoroethyl)-2-methyl-3H-imidazo[4,5-b]pyridin-5-yl)-N-(cis-4-morpholinocyclohexyl)pyrrolo[2,1-f][1,2,4]triazin-2-amine [1054];

5-(3-(2-fluoroethyl)-2-methyl-3H-imidazo[4,5-b]pyridin-5-yl)-N-(trans-4-morpholinocyclohexyl)pyrrolo[2,1-f][1,2,4]triazin-2-amine [1055];

5-(3-(2-fluoroethyl)-2-methyl-3H-imidazo[4,5-b]pyridin-5-yl)-N-(cis-4-(4-methylpiperazin-1-yl)cyclohexyl)pyrrolo[2,1-f][1,2,4]triazin-2-amine [1056];

5-(3-(2-fluoroethyl)-2-methyl-3H-imidazo[4,5-b]pyridin-5-yl)-N-(trans-4-(4-methylpiperazin-1-yl)cyclohexyl)pyrrolo[2,1-f][1,2,4]triazin-2-amine [1057];

5-(3-(2-fluoroethyl)-2-methyl-3H-imidazo[4,5-b]pyridin-5-yl)-N-(1-methylazetidin-3-yl)pyrrolo[2,1-f][1,2,4]triazin-2-amine [1058];

5-(3-(2-fluoroethyl)-2-methyl-3H-imidazo[4,5-b]pyridin-5-yl)-N-(oxetan-3-yl)pyrrolo[2,1-f][1,2,4]triazin-2-amine [1059];

5-(3-(2-fluoroethyl)-2-methyl-3H-imidazo[4,5-b]pyridin-5-yl)-N-(1-methylpiperidin-4-yl)pyrrolo[2,1-f][1,2,4]triazin-2-amine [1060];

5-(3-(2-fluoroethyl)-2-methyl-3H-imidazo[4,5-b]pyridin-5-yl)-N-(tetrahydro-2H-pyran-4-yl)pyrrolo[2,1-f][1,2,4]triazin-2-amine [1061];

N-(6,6-difluorospiro[3.3]heptan-2-yl)-5-(3-(2-fluoroethyl)-2-methyl-3H-imidazo[4,5-b]pyridin-5-yl)pyrrolo[2,1-f][1,2,4]triazin-2-amine [1062];

5-(3-(2-fluoroethyl)-2-methyl-3H-imidazo[4,5-b]pyridin-5-yl)-N-(2-oxaspiro[3.3]heptan-6-yl)pyrrolo[2,1-f][1,2,4]triazin-2-amine [1063];

5-(3-(2-fluoroethyl)-2-methyl-3H-imidazo[4,5-b]pyridin-5-yl)-N-(2-methyl-2-azaspiro[3.3]heptan-6-yl)pyrrolo[2,1-f][1,2,4]triazin-2-amine [1064];

5-(3-(2-fluoroethyl)-2-methyl-3H-imidazo[4,5-b]pyridin-5-yl)-N-(1-methyl-1H-pyrazol-4-yl)pyrrolo[2,1-f][1,2,4]triazin-2-amine [1065];

5-(3-(2,2-difluoroethyl)-2-methyl-3H-imidazo[4,5-b]pyridin-5-yl)-N-isopropylpyrrolo[2,1-f][1,2,4]triazin-2-amine [1066];

5-(3-(2,2-difluoroethyl)-2-methyl-3H-imidazo[4,5-b]pyridin-5-yl)-N-isobutylpyrrolo[2,1-f][1,2,4]triazin-2-amine [1067];

N-(2-fluoro-2-methylpropyl)-5-(3-(2,2-difluoroethyl)-2-methyl-3H-imidazo[4,5-b]pyridin-5-yl)pyrrolo[2,1-f][1,2,4]triazin-2-amine [1068];

N-(2,2-difluoropropyl)-5-(3-(2,2-difluoroethyl)-2-methyl-3H-imidazo[4,5-b]pyridin-5-yl)pyrrolo[2,1-f][1,2,4]triazin-2-amine [1069];

5-(3-(2,2-difluoroethyl)-2-methyl-3H-imidazo[4,5-b]pyridin-5-yl)-N-(2,2,2-trifluoroethyl)pyrrolo[2,1-f][1,2,4]triazin-2-amine [1070];

(R)-5-(3-(2,2-difluoroethyl)-2-methyl-3H-imidazo[4,5-b]pyridin-5-yl)-N-(1,1,1-trifluoropropan-2-yl)pyrrolo[2,1-f][1,2,4]triazin-2-amine [1071];

5-(3-(2,2-difluoroethyl)-2-methyl-3H-imidazo[4,5-b]pyridin-5-yl)-N-(3,3,3-trifluoropropyl)pyrrolo[2,1-f][1,2,4]triazin-2-amine [1072];

5-(3-(2,2-difluoroethyl)-2-methyl-3H-imidazo[4,5-b]pyridin-5-yl)-N-(3,3,3-trifluoro-2,2-dimethylpropyl)pyrrolo[2,1-f][1,2,4]triazin-2-amine [1073];

5-(3-(2,2-difluoroethyl)-2-methyl-3H-imidazo[4,5-b]pyridin-5-yl)-N-(2-methoxyethyl)pyrrolo[2,1-f][1,2,4]triazin-2-amine [1074];

(R)-5-(3-(2,2-difluoroethyl)-2-methyl-3H-imidazo[4,5-b]pyridin-5-yl)-N-(1-methoxypropan-2-yl)pyrrolo[2,1-f][1,2,4]triazin-2-amine [1075];

5-(3-(2,2-difluoroethyl)-2-methyl-3H-imidazo[4,5-b]pyridin-5-yl)-N-(2-isopropoxyethyl)pyrrolo[2,1-f][1,2,4]triazin-2-amine [1076];

5-(3-(2,2-difluoroethyl)-2-methyl-3H-imidazo[4,5-b]pyridin-5-yl)-N-((1-methylcyclopropyl)methyl)pyrrolo[2,1-f][1,2,4]triazin-2-amine [1077];

5-(3-(2,2-difluoroethyl)-2-methyl-3H-imidazo[4,5-b]pyridin-5-yl)-N-((1-(trifluoromethyl)cyclopropyl)methyl)pyrrolo[2,1-f][1,2,4]triazin-2-amine [1078];

N-((1-fluorocyclobutyl)methyl)-5-(3-(2,2-difluoroethyl)-2-methyl-3H-imidazo[4,5-b]pyridin-5-yl)pyrrolo[2,1-f][1,2,4]triazin-2-amine [1079];

5-(3-(2,2-difluoroethyl)-2-methyl-3H-imidazo[4,5-b]pyridin-5-yl)-N-((3-fluorooxetan-3-yl)methyl)pyrrolo[2,1-f][1,2,4]triazin-2-amine [1080];

N-(cyclopropylmethyl)-5-(3-(2,2-difluoroethyl)-2-methyl-3H-imidazo[4,5-b]pyridin-5-yl)pyrrolo[2,1-f][1,2,4]triazin-2-amine [1081];

(S)—N-(1-cyclopropylethyl)-5-(3-(2,2-difluoroethyl)-2-methyl-3H-imidazo[4,5-b]pyridin-5-yl)pyrrolo[2,1-f][1,2,4]triazin-2-amine [1082];

(R)—N-(1-cyclopropylethyl)-5-(3-(2,2-difluoroethyl)-2-methyl-3H-imidazo[4,5-b]pyridin-5-yl)pyrrolo[2,1-f][1,2,4]triazin-2-amine [1083];

N-(2-cyclopropyl-2,2-difluoroethyl)-5-(3-(2,2-difluoroethyl)-2-methyl-3H-imidazo[4,5-b]pyridin-5-yl)pyrrolo[2,1-f][1,2,4]triazin-2-amine [1084];

5-(3-(2,2-difluoroethyl)-2-methyl-3H-imidazo[4,5-b]pyridin-5-yl)-N-(oxetan-3-ylmethyl)pyrrolo[2,1-f][1,2,4]triazin-2-amine [1085];

5-(3-(2,2-difluoroethyl)-2-methyl-3H-imidazo[4,5-b]pyridin-5-yl)-N-((tetrahydrofuran-2-yl)methyl)pyrrolo[2,1-f][1,2,4]triazin-2-amine [1086];

N-cyclobutyl-5-(3-(2,2-difluoroethyl)-2-methyl-3H-imidazo[4,5-b]pyridin-5-yl)pyrrolo[2,1-f][1,2,4]triazin-2-amine [1087];

N-(3,3-difluorocyclobutyl)-5-(3-(2,2-difluoroethyl)-2-methyl-3H-imidazo[4,5-b]pyridin-5-yl)pyrrolo[2,1-f][1,2,4]triazin-2-amine [1088];

N-(3,3-dimethylcyclobutyl)-5-(3-(2,2-difluoroethyl)-2-methyl-3H-imidazo[4,5-b]pyridin-5-yl)pyrrolo[2,1-f][1,2,4]triazin-2-amine [1089];

3-((5-(3-(2,2-difluoroethyl)-2-methyl-3H-imidazo[4,5-b]pyridin-5-yl)pyrrolo[2,1-f][1,2,4]triazin-2-yl)amino)-1-methylcyclobutan-1-ol [1090];

5-(3-(2,2-difluoroethyl)-2-methyl-3H-imidazo[4,5-b]pyridin-5-yl)-N-(cis-3-methoxycyclobutyl)pyrrolo[2,1-f][1,2,4]triazin-2-amine [1091];

5-(3-(2,2-difluoroethyl)-2-methyl-3H-imidazo[4,5-b]pyridin-5-yl)-N-(trans-3-methoxycyclobutyl)pyrrolo[2,1-f][1,2,4]triazin-2-amine [1092];

5-(3-(2,2-difluoroethyl)-2-methyl-3H-imidazo[4,5-b]pyridin-5-yl)-N-(trans-3-(methoxymethyl)cyclobutyl)pyrrolo[2,1-f][1,2,4]triazin-2-amine [1093];

N-(cis-3-ethoxycyclobutyl)-5-(3-(2,2-difluoroethyl)-2-methyl-3H-imidazo[4,5-b]pyridin-5-yl)pyrrolo[2,1-f][1,2,4]triazin-2-amine [1094];

N-(trans-3-ethoxycyclobutyl)-5-(3-(2,2-difluoroethyl)-2-methyl-3H-imidazo[4,5-b]pyridin-5-yl)pyrrolo[2,1-f][1,2,4]triazin-2-amine [1095];

5-(3-(2,2-difluoroethyl)-2-methyl-3H-imidazo[4,5-b]pyridin-5-yl)-N-(cis-3-(2-methoxyethoxy)cyclobutyl)pyrrolo[2,1-f][1,2,4]triazin-2-amine [1096];

5-(3-(2,2-difluoroethyl)-2-methyl-3H-imidazo[4,5-b]pyridin-5-yl)-N-(trans-3-(2-methoxyethoxy)cyclobutyl)pyrrolo[2,1-f][1,2,4]triazin-2-amine [1097];

cis-$N^1$-(5-(3-(2,2-difluoroethyl)-2-methyl-3H-imidazo[4,5-b]pyridin-5-yl)pyrrolo[2,1-f][1,2,4]triazin-2-yl)cyclobutane-1,3-diamine [1098];

trans-$N^1$-(5-(3-(2,2-difluoroethyl)-2-methyl-3H-imidazo[4,5-b]pyridin-5-yl)pyrrolo[2,1-f][1,2,4]triazin-2-yl)cyclobutane-1,3-diamine [1099];

cis-$N^1$-(5-(3-(2,2-difluoroethyl)-2-methyl-3H-imidazo[4,5-b]pyridin-5-yl)pyrrolo[2,1-f][1,2,4]triazin-2-yl)-$N^3$-methylcyclobutane-1,3-diamine [1100];

trans-$N^1$-(5-(3-(2,2-difluoroethyl)-2-methyl-3H-imidazo[4,5-b]pyridin-5-yl)pyrrolo[2,1-f][1,2,4]triazin-2-yl)-$N^3$-methylcyclobutane-1,3-diamine [1101];

cis-$N^1$-(5-(3-(2,2-difluoroethyl)-2-methyl-3H-imidazo[4,5-b]pyridin-5-yl)pyrrolo[2,1-f][1,2,4]triazin-2-yl)-$N^3$,$N^3$-dimethylcyclobutane-1,3-diamine [1102];

trans-$N^1$-(5-(3-(2,2-difluoroethyl)-2-methyl-3H-imidazo[4,5-b]pyridin-5-yl)pyrrolo[2,1-f][1,2,4]triazin-2-yl)-$N^3$,$N^3$-dimethylcyclobutane-1,3-diamine [1103];

5-(3-(2,2-difluoroethyl)-2-methyl-3H-imidazo[4,5-b]pyridin-5-yl)-N-(cis-3-morpholinocyclobutyl)pyrrolo[2,1-f][1,2,4]triazin-2-amine [1104];

5-(3-(2,2-difluoroethyl)-2-methyl-3H-imidazo[4,5-b]pyridin-5-yl)-N-(trans-3-morpholinocyclobutyl)pyrrolo[2,1-f][1,2,4]triazin-2-amine [1105];

5-(3-(2,2-difluoroethyl)-2-methyl-3H-imidazo[4,5-b]pyridin-5-yl)-N-(cis-3-(4-methylpiperazin-1-yl)cyclobutyl)pyrrolo[2,1-f][1,2,4]triazin-2-amine [1106];

5-(3-(2,2-difluoroethyl)-2-methyl-3H-imidazo[4,5-b]pyridin-5-yl)-N-(trans-3-(4-methylpiperazin-1-yl)cyclobutyl)pyrrolo[2,1-f][1,2,4]triazin-2-amine [1107];

N-(4,4-difluorocyclohexyl)-5-(3-(2,2-difluoroethyl)-2-methyl-3H-imidazo[4,5-b]pyridin-5-yl)pyrrolo[2,1-f][1,2,4]triazin-2-amine [1108];

cis-4-((5-(3-(2,2-difluoroethyl)-2-methyl-3H-imidazo[4,5-b]pyridin-5-yl)pyrrolo[2,1-f][1,2,4]triazin-2-yl)amino)cyclohexan-1-ol [1109];

(1s,4s)-4-((5-(3-(2,2-difluoroethyl)-2-methyl-3H-imidazo[4,5-b]pyridin-5-yl)pyrrolo[2,1-f][1,2,4] triazin-2-yl)amino)-1-methylcyclohexan-1-ol [1110];

5-(3-(2,2-difluoroethyl)-2-methyl-3H-imidazo[4,5-b]pyridin-5-yl)-N-(cis-4-methoxycyclohexyl)pyrrolo[2,1-f][1,2,4]triazin-2-amine [1111];

5-(3-(2,2-difluoroethyl)-2-methyl-3H-imidazo[4,5-b]pyridin-5-yl)-N-(trans-4-methoxycyclohexyl)pyrrolo[2,1-f][1,2,4]triazin-2-amine [1112];

N-(cis-4-(difluoromethoxy)cyclohexyl)-5-(3-(2,2-difluoroethyl)-2-methyl-3H-imidazo[4,5-b]pyridin-5-yl)pyrrolo[2,1-f][1,2,4]triazin-2-amine [1113];

N-(trans-4-(difluoromethoxy)cyclohexyl)-5-(3-(2,2-difluoroethyl)-2-methyl-3H-imidazo[4,5-b]pyridin-5-yl)pyrrolo[2,1-f][1,2,4]triazin-2-amine [1114];

N-(cis-4-ethoxycyclohexyl)-5-(3-(2,2-difluoroethyl)-2-methyl-3H-imidazo[4,5-b]pyridin-5-yl)pyrrolo[2,1-f][1,2,4]triazin-2-amine [1115];

N-(trans-4-ethoxycyclohexyl)-5-(3-(2,2-difluoroethyl)-2-methyl-3H-imidazo[4,5-b]pyridin-5-yl)pyrrolo[2,1-f][1,2,4]triazin-2-amine [1116];

5-(3-(2,2-difluoroethyl)-2-methyl-3H-imidazo[4,5-b]pyridin-5-yl)-N-(cis-4-(2-methoxyethoxy)cyclohexyl)pyrrolo[2,1-f][1,2,4]triazin-2-amine [1117];

5-(3-(2,2-difluoroethyl)-2-methyl-3H-imidazo[4,5-b]pyridin-5-yl)-N-(trans-4-(2-methoxyethoxy)cyclohexyl)pyrrolo[2,1-f][1,2,4]triazin-2-amine [1118];

cis-$N^1$-(5-(3-(2,2-difluoroethyl)-2-methyl-3H-imidazo[4,5-b]pyridin-5-yl)pyrrolo[2,1-f][1,2,4]triazin-2-yl)cyclohexane-1,4-diamine [1119];

trans-$N^1$-(5-(3-(2,2-difluoroethyl)-2-methyl-3H-imidazo[4,5-b]pyridin-5-yl)pyrrolo[2,1-f][1,2,4]triazin-2-yl)cyclohexane-1,4-diamine [1120];

cis-$N^1$-(5-(3-(2,2-difluoroethyl)-2-methyl-3H-imidazo[4,5-b]pyridin-5-yl)pyrrolo[2,1-f][1,2,4]triazin-2-yl)-$N^4$-methylcyclohexane-1,4-diamine [1121];

trans-$N^1$-(5-(3-(2,2-difluoroethyl)-2-methyl-3H-imidazo[4,5-b]pyridin-5-yl)pyrrolo[2,1-f][1,2,4]triazin-2-yl)-$N^4$-methylcyclohexane-1,4-diamine [1122];

cis-$N^1$-(5-(3-(2,2-difluoroethyl)-2-methyl-3H-imidazo[4,5-b]pyridin-5-yl)pyrrolo[2,1-f][1,2,4]triazin-2-yl)-$N^4$,$N^4$-dimethylcyclohexane-1,4-diamine [1123];

trans-$N^1$-(5-(3-(2,2-difluoroethyl)-2-methyl-3H-imidazo[4,5-b]pyridin-5-yl)pyrrolo[2,1-f][1,2,4]triazin-2-yl)-$N^4$,$N^4$-dimethylcyclohexane-1,4-diamine [1124];

5-(3-(2,2-difluoroethyl)-2-methyl-3H-imidazo[4,5-b]pyridin-5-yl)-N-(cis-4-morpholinocyclohexyl)pyrrolo[2,1-f][1,2,4]triazin-2-amine [1125];

5-(3-(2,2-difluoroethyl)-2-methyl-3H-imidazo[4,5-b]pyridin-5-yl)-N-(trans-4-morpholinocyclohexyl)pyrrolo[2,1-f][1,2,4]triazin-2-amine [1126];

5-(3-(2,2-difluoroethyl)-2-methyl-3H-imidazo[4,5-b]pyridin-5-yl)-N-(cis-4-(4-methylpiperazin-1-yl)cyclohexyl)pyrrolo[2,1-f][1,2,4]triazin-2-amine [1127];

5-(3-(2,2-difluoroethyl)-2-methyl-3H-imidazo[4,5-b]pyridin-5-yl)-N-(trans-4-(4-methylpiperazin-1-yl)cyclohexyl)pyrrolo[2,1-f][1,2,4]triazin-2-amine [1128];

5-(3-(2,2-difluoroethyl)-2-methyl-3H-imidazo[4,5-b]pyridin-5-yl)-N-(1-methylazetidin-3-yl)pyrrolo[2,1-f][1,2,4]triazin-2-amine [1129];

5-(3-(2,2-difluoroethyl)-2-methyl-3H-imidazo[4,5-b]pyridin-5-yl)-N-(oxetan-3-yl)pyrrolo[2,1-f][1,2,4]triazin-2-amine [1130];

5-(3-(2,2-difluoroethyl)-2-methyl-3H-imidazo[4,5-b]pyridin-5-yl)-N-(1-methylpiperidin-4-yl)pyrrolo[2,1-f][1,2,4]triazin-2-amine [1131];

5-(3-(2,2-difluoroethyl)-2-methyl-3H-imidazo[4,5-b]pyridin-5-yl)-N-(tetrahydro-2H-pyran-4-yl)pyrrolo[2,1-f][1,2,4]triazin-2-amine [1132];

N-(6,6-difluorospiro[3.3]heptan-2-yl)-5-(3-(2,2-difluoroethyl)-2-methyl-3H-imidazo[4,5-b]pyridin-5-yl)pyrrolo[2,1-f][1,2,4]triazin-2-amine [1133];

5-(3-(2,2-difluoroethyl)-2-methyl-3H-imidazo[4,5-b]pyridin-5-yl)-N-(2-oxaspiro[3.3]heptan-6-yl)pyrrolo[2,1-f][1,2,4]triazin-2-amine [1134];

5-(3-(2,2-difluoroethyl)-2-methyl-3H-imidazo[4,5-b]pyridin-5-yl)-N-(2-methyl-2-azaspiro[3.3]heptan-6-yl)pyrrolo[2,1-f][1,2,4]triazin-2-amine [1135];

5-(3-(2,2-difluoroethyl)-2-methyl-3H-imidazo[4,5-b]pyridin-5-yl)-N-(1-methyl-1H-pyrazol-4-yl)pyrrolo[2,1-f][1,2,4]triazin-2-amine [1136];

N-isopropyl-5-(3-(2-methoxyethyl)-2-methyl-3H-imidazo[4,5-b]pyridin-5-yl)pyrrolo[2,1-f][1,2,4]triazin-2-amine [1137];

N-isobutyl-5-(3-(2-methoxyethyl)-2-methyl-3H-imidazo[4,5-b]pyridin-5-yl)pyrrolo[2,1-f][1,2,4]triazin-2-amine [1138];

N-(2-fluoro-2-methylpropyl)-5-(3-(2-methoxyethyl)-2-methyl-3H-imidazo[4,5-b]pyridin-5-yl)pyrrolo[2,1-f][1,2,4]triazin-2-amine [1139];

N-(2,2-difluoropropyl)-5-(3-(2-methoxyethyl)-2-methyl-3H-imidazo[4,5-b]pyridin-5-yl)pyrrolo[2,1-f][1,2,4]triazin-2-amine [1140];

5-(3-(2-methoxyethyl)-2-methyl-3H-imidazo[4,5-b]pyridin-5-yl)-N-(2,2,2-trifluoroethyl)pyrrolo[2,1-f][1,2,4]triazin-2-amine [1141];

(R)-5-(3-(2-methoxyethyl)-2-methyl-3H-imidazo[4,5-b]pyridin-5-yl)-N-(1,1,1-trifluoropropan-2-yl)pyrrolo[2,1-f][1,2,4]triazin-2-amine [1142];

5-(3-(2-methoxyethyl)-2-methyl-3H-imidazo[4,5-b]pyridin-5-yl)-N-(3,3,3-trifluoropropyl)pyrrolo[2,1-f][1,2,4]triazin-2-amine [1143];

5-(3-(2-methoxyethyl)-2-methyl-3H-imidazo[4,5-b]pyridin-5-yl)-N-(3,3,3-trifluoro-2,2-dimethylpropyl)pyrrolo[2,1-f][1,2,4]triazin-2-amine [1144];

N-(2-methoxyethyl)-5-(3-(2-methoxyethyl)-2-methyl-3H-imidazo[4,5-b]pyridin-5-yl)pyrrolo[2,1-f][1,2,4]triazin-2-amine [1145];

(R)-5-(3-(2-methoxyethyl)-2-methyl-3H-imidazo[4,5-b]pyridin-5-yl)-N-(1-methoxypropan-2-yl)pyrrolo[2,1-f][1,2,4]triazin-2-amine [1146];

N-(2-isopropoxyethyl)-5-(3-(2-methoxyethyl)-2-methyl-3H-imidazo[4,5-b]pyridin-5-yl)pyrrolo[2,1-f][1,2,4]triazin-2-amine [1147];

5-(3-(2-methoxyethyl)-2-methyl-3H-imidazo[4,5-b]pyridin-5-yl)-N-((1-methylcyclopropyl)methyl)pyrrolo[2,1-f][1,2,4]triazin-2-amine [1148];

5-(3-(2-methoxyethyl)-2-methyl-3H-imidazo[4,5-b]pyridin-5-yl)-N-((1-(trifluoromethyl)cyclopropyl)methyl) pyrrolo[2,1-f][1,2,4]triazin-2-amine [1149];

N-((1-fluorocyclobutyl)methyl)-5-(3-(2-methoxyethyl)-2-methyl-3H-imidazo[4,5-b]pyridin-5-yl)pyrrolo[2,1-f][1,2,4]triazin-2-amine [1150];

N-((3-fluorooxetan-3-yl)methyl)-5-(3-(2-methoxyethyl)-2-methyl-3H-imidazo[4,5-b]pyridin-5-yl)pyrrolo[2,1-f][1,2,4]triazin-2-amine [1151];

N-(cyclopropylmethyl)-5-(3-(2-methoxyethyl)-2-methyl-3H-imidazo[4,5-b]pyridin-5-yl)pyrrolo[2,1-f][1,2,4] triazin-2-amine [1152];

(S)—N-(1-cyclopropylethyl)-5-(3-(2-methoxyethyl)-2-methyl-3H-imidazo[4,5-b]pyridin-5-yl)pyrrolo[2,1-f] [1,2,4]triazin-2-amine [1153];

(R)—N-(1-cyclopropylethyl)-5-(3-(2-methoxyethyl)-2-methyl-3H-imidazo[4,5-b]pyridin-5-yl)pyrrolo[2,1-f] [1,2,4]triazin-2-amine [1154];

N-(2-cyclopropyl-2,2-difluoroethyl)-5-(3-(2-methoxyethyl)-2-methyl-3H-imidazo[4,5-b]pyridin-5-yl)pyrrolo[2,1-f][1,2,4]triazin-2-amine [1155];

5-(3-(2-methoxyethyl)-2-methyl-3H-imidazo[4,5-b]pyridin-5-yl)-N-(oxetan-3-ylmethyl)pyrrolo[2,1-f][1,2,4] triazin-2-amine [1156];

5-(3-(2-methoxyethyl)-2-methyl-3H-imidazo[4,5-b]pyridin-5-yl)-N-((tetrahydrofuran-2-yl)methyl)pyrrolo[2,1-f][1,2,4]triazin-2-amine [1157];

N-cyclobutyl-5-(3-(2-methoxyethyl)-2-methyl-3H-imidazo[4,5-b]pyridin-5-yl)pyrrolo[2,1-f][1,2,4]triazin-2-amine [1158];

N-(3,3-difluorocyclobutyl)-5-(3-(2-methoxyethyl)-2-methyl-3H-imidazo[4,5-b]pyridin-5-yl)pyrrolo[2,1-f] [1,2,4]triazin-2-amine [1159];

N-(3,3-dimethylcyclobutyl)-5-(3-(2-methoxyethyl)-2-methyl-3H-imidazo[4,5-b]pyridin-5-yl)pyrrolo[2,1-f] [1,2,4]triazin-2-amine [1160];

3-((5-(3-(2-methoxyethyl)-2-methyl-3H-imidazo[4,5-b] pyridin-5-yl)pyrrolo[2,1-f][1,2,4]triazin-2-yl)amino)-1-methylcyclobutan-1-ol [1161];

N-(cis-3-methoxycyclobutyl)-5-(3-(2-methoxyethyl)-2-methyl-3H-imidazo[4,5-b]pyridin-5-yl)pyrrolo[2,1-f] [1,2,4]triazin-2-amine [1162];

N-(trans-3-methoxycyclobutyl)-5-(3-(2-methoxyethyl)-2-methyl-3H-imidazo[4,5-b]pyridin-5-yl)pyrrolo[2,1-f][1,2,4]triazin-2-amine [1163];

5-(3-(2-methoxyethyl)-2-methyl-3H-imidazo[4,5-b]pyridin-5-yl)-N-(trans-3-(methoxymethyl)cyclobutyl)pyrrolo[2,1-f][1,2,4]triazin-2-amine [1164];

N-(cis-3-ethoxycyclobutyl)-5-(3-(2-methoxyethyl)-2-methyl-3H-imidazo[4,5-b]pyridin-5-yl)pyrrolo[2,1-f] [1,2,4]triazin-2-amine [1165];

N-(trans-3-ethoxycyclobutyl)-5-(3-(2-methoxyethyl)-2-methyl-3H-imidazo[4,5-b]pyridin-5-yl)pyrrolo[2,1-f] [1,2,4]triazin-2-amine [1166];

N-(cis-3-(2-methoxyethoxy)cyclobutyl)-5-(3-(2-methoxyethyl)-2-methyl-3H-imidazo[4,5-b]pyridin-5-yl)pyrrolo[2,1-f][1,2,4]triazin-2-amine [1167];

N-(trans-3-(2-methoxyethoxy)cyclobutyl)-5-(3-(2-methoxyethyl)-2-methyl-3H-imidazo[4,5-b]pyridin-5-yl)pyrrolo[2,1-f][1,2,4]triazin-2-amine [1168];

cis-$N^1$-(5-(3-(2-methoxyethyl)-2-methyl-3H-imidazo[4,5-b]pyridin-5-yl)pyrrolo[2,1-f][1,2,4]triazin-2-yl)cyclobutane-1,3-diamine [1169];

trans-$N^1$-(5-(3-(2-methoxyethyl)-2-methyl-3H-imidazo [4,5-b]pyridin-5-yl)pyrrolo[2,1-f][1,2,4]triazin-2-yl) cyclobutane-1,3-diamine [1170];

cis-$N^1$-(5-(3-(2-methoxyethyl)-2-methyl-3H-imidazo[4,5-b]pyridin-5-yl)pyrrolo[2,1-f][1,2,4]triazin-2-yl)-$N^3$-methylcyclobutane-1,3-diamine [1171];

trans-$N^1$-(5-(3-(2-methoxyethyl)-2-methyl-3H-imidazo [4,5-b]pyridin-5-yl)pyrrolo[2,1-f][1,2,4]triazin-2-yl)-$N^3$-methylcyclobutane-1,3-diamine [1172];

cis-$N^1$-(5-(3-(2-methoxyethyl)-2-methyl-3H-imidazo[4,5-b]pyridin-5-yl)pyrrolo[2,1-f][1,2,4]triazin-2-yl)-$N^3$,$N^3$-dimethylcyclobutane-1,3-diamine [1173];

trans-$N^1$-(5-(3-(2-methoxyethyl)-2-methyl-3H-imidazo [4,5-b]pyridin-5-yl)pyrrolo[2,1-f][1,2,4]triazin-2-yl)-$N^3$,$N^3$-dimethylcyclobutane-1,3-diamine [1174];

5-(3-(2-methoxyethyl)-2-methyl-3H-imidazo[4,5-b]pyridin-5-yl)-N-(cis-3-morpholinocyclobutyl)pyrrolo[2,1-f][1,2,4]triazin-2-amine [1175];

5-(3-(2-methoxyethyl)-2-methyl-3H-imidazo[4,5-b]pyridin-5-yl)-N-(trans-3-morpholinocyclobutyl)pyrrolo[2,1-f][1,2,4]triazin-2-amine [1176];

5-(3-(2-methoxyethyl)-2-methyl-3H-imidazo[4,5-b]pyridin-5-yl)-N-(cis-3-(4-methylpiperazin-1-yl)cyclobutyl)pyrrolo[2,1-f][1,2,4]triazin-2-amine [1177];

5-(3-(2-methoxyethyl)-2-methyl-3H-imidazo[4,5-b]pyridin-5-yl)-N-(trans-3-(4-methylpiperazin-1-yl)cyclobutyl)pyrrolo[2,1-f][1,2,4]triazin-2-amine [1178];

N-(4,4-difluorocyclohexyl)-5-(3-(2-methoxyethyl)-2-methyl-3H-imidazo[4,5-b]pyridin-5-yl)pyrrolo[2,1-f] [1,2,4]triazin-2-amine [1179];

cis-4-((5-(3-(2-methoxyethyl)-2-methyl-3H-imidazo[4,5-b]pyridin-5-yl)pyrrolo[2,1-f][1,2,4]triazin-2-yl)amino) cyclohexan-1-ol [1180];

(1s,4s)-4-((5-(3-(2-methoxyethyl)-2-methyl-3H-imidazo [4,5-b]pyridin-5-yl)pyrrolo[2,1-f][1,2,4] triazin-2-yl) amino)-1-methylcyclohexan-1-ol [1181];

N-(cis-4-methoxycyclohexyl)-5-(3-(2-methoxyethyl)-2-methyl-3H-imidazo[4,5-b]pyridin-5-yl)pyrrolo[2,1-f] [1,2,4]triazin-2-amine [1182];

N-(trans-4-methoxycyclohexyl)-5-(3-(2-methoxyethyl)-2-methyl-3H-imidazo[4,5-b]pyridin-5-yl)pyrrolo[2,1-f][1,2,4]triazin-2-amine [1183];

N-(cis-4-(difluoromethoxy)cyclohexyl)-5-(3-(2-methoxyethyl)-2-methyl-3H-imidazo[4,5-b]pyridin-5-yl)pyrrolo[2,1-f][1,2,4]triazin-2-amine [1184];

N-(trans-4-(difluoromethoxy)cyclohexyl)-5-(3-(2-methoxyethyl)-2-methyl-3H-imidazo[4,5-b]pyridin-5-yl)pyrrolo[2,1-f][1,2,4]triazin-2-amine [1185];

N-(cis-4-ethoxycyclohexyl)-5-(3-(2-methoxyethyl)-2-methyl-3H-imidazo[4,5-b]pyridin-5-yl)pyrrolo[2,1-f] [1,2,4]triazin-2-amine [1186];

N-(trans-4-ethoxycyclohexyl)-5-(3-(2-methoxyethyl)-2-methyl-3H-imidazo[4,5-b]pyridin-5-yl)pyrrolo[2,1-f] [1,2,4]triazin-2-amine [1187];

N-(cis-4-(2-methoxyethoxy)cyclohexyl)-5-(3-(2-methoxyethyl)-2-methyl-3H-imidazo[4,5-b]pyridin-5-yl)pyrrolo[2,1-f][1,2,4]triazin-2-amine [1188];

N-(trans-4-(2-methoxyethoxy)cyclohexyl)-5-(3-(2-methoxyethyl)-2-methyl-3H-imidazo[4,5-b]pyridin-5-yl)pyrrolo[2,1-f][1,2,4]triazin-2-amine [1189];

cis-$N^1$-(5-(3-(2-methoxyethyl)-2-methyl-3H-imidazo[4,5-b]pyridin-5-yl)pyrrolo[2,1-f][1,2,4]triazin-2-yl)cyclohexane-1,4-diamine [1190];

trans-$N^1$-(5-(3-(2-methoxyethyl)-2-methyl-3H-imidazo [4,5-b]pyridin-5-yl)pyrrolo[2,1-f][1,2,4]triazin-2-yl) cyclohexane-1,4-diamine [1191];

cis-$N^1$-(5-(3-(2-methoxyethyl)-2-methyl-3H-imidazo[4,5-b]pyridin-5-yl)pyrrolo[2,1-f][1,2,4]triazin-2-yl)-$N^4$-methylcyclohexane-1,4-diamine [1192];

trans-$N^1$-(5-(3-(2-methoxyethyl)-2-methyl-3H-imidazo[4,5-b]pyridin-5-yl)pyrrolo[2,1-f][1,2,4]triazin-2-yl)-$N^4$-methylcyclohexane-1,4-diamine [1193];

cis-$N^1$-(5-(3-(2-methoxyethyl)-2-methyl-3H-imidazo[4,5-b]pyridin-5-yl)pyrrolo[2,1-f][1,2,4]triazin-2-yl)-$N^4$,$N^4$-dimethylcyclohexane-1,4-diamine [1194];

trans-$N^1$-(5-(3-(2-methoxyethyl)-2-methyl-3H-imidazo[4,5-b]pyridin-5-yl)pyrrolo[2,1-f][1,2,4]triazin-2-yl)-$N^4$,$N^4$-dimethylcyclohexane-1,4-diamine [1195];

5-(3-(2-methoxyethyl)-2-methyl-3H-imidazo[4,5-b]pyridin-5-yl)-N-(cis-4-morpholinocyclohexyl)pyrrolo[2,1-f][1,2,4]triazin-2-amine [1196];

5-(3-(2-methoxyethyl)-2-methyl-3H-imidazo[4,5-b]pyridin-5-yl)-N-(trans-4-morpholinocyclohexyl)pyrrolo[2,1-f][1,2,4]triazin-2-amine [1197];

5-(3-(2-methoxyethyl)-2-methyl-3H-imidazo[4,5-b]pyridin-5-yl)-N-(cis-4-(4-methylpiperazin-1-yl)cyclohexyl)pyrrolo[2,1-f][1,2,4]triazin-2-amine [1198];

5-(3-(2-methoxyethyl)-2-methyl-3H-imidazo[4,5-b]pyridin-5-yl)-N-(trans-4-(4-methylpiperazin-1-yl)cyclohexyl)pyrrolo[2,1-f][1,2,4]triazin-2-amine [1199];

5-(3-(2-methoxyethyl)-2-methyl-3H-imidazo[4,5-b]pyridin-5-yl)-N-(1-methylazetidin-3-yl)pyrrolo[2,1-f][1,2,4]triazin-2-amine [1200];

5-(3-(2-methoxyethyl)-2-methyl-3H-imidazo[4,5-b]pyridin-5-yl)-N-(oxetan-3-yl)pyrrolo[2,1-f][1,2,4]triazin-2-amine [1201];

5-(3-(2-methoxyethyl)-2-methyl-3H-imidazo[4,5-b]pyridin-5-yl)-N-(1-methylpiperidin-4-yl)pyrrolo[2,1-f][1,2,4]triazin-2-amine [1202];

5-(3-(2-methoxyethyl)-2-methyl-3H-imidazo[4,5-b]pyridin-5-yl)-N-(tetrahydro-2H-pyran-4-yl)pyrrolo[2,1-f][1,2,4]triazin-2-amine [1203];

N-(6,6-difluorospiro[3.3]heptan-2-yl)-5-(3-(2-methoxyethyl)-2-methyl-3H-imidazo[4,5-b]pyridin-5-yl)pyrrolo[2,1-f][1,2,4]triazin-2-amine [1204];

5-(3-(2-methoxyethyl)-2-methyl-3H-imidazo[4,5-b]pyridin-5-yl)-N-(2-oxaspiro[3.3]heptan-6-yl)pyrrolo[2,1-f][1,2,4]triazin-2-amine [1205];

5-(3-(2-methoxyethyl)-2-methyl-3H-imidazo[4,5-b]pyridin-5-yl)-N-(2-methyl-2-azaspiro[3.3]heptan-6-yl)pyrrolo[2,1-f][1,2,4]triazin-2-amine [1206];

5-(3-(2-methoxyethyl)-2-methyl-3H-imidazo[4,5-b]pyridin-5-yl)-N-(1-methyl-1H-pyrazol-4-yl)pyrrolo[2,1-f][1,2,4]triazin-2-amine [1207];

N-isopropyl-5-(1-methyl-1H-benzo[d][1,2,3]triazol-6-yl)pyrrolo[2,1-f][1,2,4]triazin-2-amine [1208];

N-isobutyl-5-(1-methyl-1H-benzo[d][1,2,3]triazol-6-yl)pyrrolo[2,1-f][1,2,4]triazin-2-amine [1209];

N-(2-fluoro-2-methylpropyl)-5-(1-methyl-1H-benzo[d][1,2,3]triazol-6-yl)pyrrolo[2,1-f][1,2,4]triazin-2-amine [1210];

N-(2,2-difluoropropyl)-5-(1-methyl-1H-benzo[d][1,2,3]triazol-6-yl)pyrrolo[2,1-f][1,2,4]triazin-2-amine [1211];

5-(1-methyl-1H-benzo[d][1,2,3]triazol-6-yl)-N-(2,2,2-trifluoroethyl)pyrrolo[2,1-f][1,2,4]triazin-2-amine [1212];

(R)-5-(1-methyl-1H-benzo[d][1,2,3]triazol-6-yl)-N-(1,1,1-trifluoropropan-2-yl)pyrrolo[2,1-f][1,2,4]triazin-2-amine [1213];

5-(1-methyl-1H-benzo[d][1,2,3]triazol-6-yl)-N-(3,3,3-trifluoropropyl)pyrrolo[2,1-f][1,2,4]triazin-2-amine [1214];

5-(1-methyl-1H-benzo[d][1,2,3]triazol-6-yl)-N-(3,3,3-trifluoro-2,2-dimethylpropyl)pyrrolo[2,1-f][1,2,4]triazin-2-amine [1215];

N-(2-methoxyethyl)-5-(1-methyl-1H-benzo[d][1,2,3]triazol-6-yl)pyrrolo[2,1-f][1,2,4]triazin-2-amine [1216];

(R)—N-(1-methoxypropan-2-yl)-5-(1-methyl-1H-benzo[d][1,2,3]triazol-6-yl)pyrrolo[2,1-f][1,2,4] triazin-2-amine [1217];

N-(2-isopropoxyethyl)-5-(1-methyl-1H-benzo[d][1,2,3]triazol-6-yl)pyrrolo[2,1-f][1,2,4]triazin-2-amine [1218];

5-(1-methyl-1H-benzo[d][1,2,3]triazol-6-yl)-N-((1-methylcyclopropyl)methyl)pyrrolo[2,1-f][1,2,4]triazin-2-amine [1219];

5-(1-methyl-1H-benzo[d][1,2,3]triazol-6-yl)-N-((1-(trifluoromethyl)cyclopropyl)methyl)pyrrolo [2,1-f][1,2,4]triazin-2-amine [1220];

N-((1-fluorocyclobutyl)methyl)-5-(1-methyl-1H-benzo[d][1,2,3]triazol-6-yl)pyrrolo[2,1-f][1,2,4]triazin-2-amine [1221];

N-((3-fluorooxetan-3-yl)methyl)-5-(1-methyl-1H-benzo[d][1,2,3]triazol-6-yl)pyrrolo[2,1-f][1,2,4]triazin-2-amine [1222];

N-(cyclopropylmethyl)-5-(1-methyl-1H-benzo[d][1,2,3]triazol-6-yl)pyrrolo[2,1-f][1,2,4]triazin-2-amine [1223];

(S)—N-(1-cyclopropylethyl)-5-(1-methyl-1H-benzo[d][1,2,3]triazol-6-yl)pyrrolo[2,1-f][1,2,4] triazin-2-amine [1224];

(R)—N-(1-cyclopropylethyl)-5-(1-methyl-1H-benzo[d][1,2,3]triazol-6-yl)pyrrolo[2,1-f][1,2,4] triazin-2-amine [1225];

N-(2-cyclopropyl-2,2-difluoroethyl)-5-(1-methyl-1H-benzo[d][1,2,3]triazol-6-yl)pyrrolo[2,1-f][1,2,4]triazin-2-amine [1226];

5-(1-methyl-1H-benzo[d][1,2,3]triazol-6-yl)-N-(oxetan-3-ylmethyl)pyrrolo[2,1-f][1,2,4]triazin-2-amine [1227];

5-(1-methyl-1H-benzo[d][1,2,3]triazol-6-yl)-N-((tetrahydrofuran-2-yl)methyl)pyrrolo[2,1-f][1,2,4]triazin-2-amine [1228];

N-cyclobutyl-5-(1-methyl-1H-benzo[d][1,2,3]triazol-6-yl)pyrrolo[2,1-f][1,2,4]triazin-2-amine [1229];

N-(3,3-difluorocyclobutyl)-5-(1-methyl-1H-benzo[d][1,2,3]triazol-6-yl)pyrrolo[2,1-f][1,2,4] triazin-2-amine [1230];

N-(3,3-dimethylcyclobutyl)-5-(1-methyl-1H-benzo[d][1,2,3]triazol-6-yl)pyrrolo[2,1-f][1,2,4]triazin-2-amine [1231];

1-methyl-3-((5-(1-methyl-1H-benzo[d][1,2,3]triazol-6-yl)pyrrolo[2,1-f][1,2,4]triazin-2-yl)amino)cyclobutan-1-ol [1232];

N-(cis-3-methoxycyclobutyl)-5-(1-methyl-1H-benzo[d][1,2,3]triazol-6-yl)pyrrolo[2,1-f][1,2,4]triazin-2-amine [1233];

N-(trans-3-methoxycyclobutyl)-5-(1-methyl-1H-benzo[d][1,2,3]triazol-6-yl)pyrrolo[2,1-f][1,2,4]triazin-2-amine [1234];

N-(trans-3-(methoxymethyl)cyclobutyl)-5-(1-methyl-1H-benzo[d][1,2,3]triazol-6-yl)pyrrolo[2,1-f][1,2,4]triazin-2-amine [1235];

N-(cis-3-ethoxycyclobutyl)-5-(1-methyl-1H-benzo[d][1,2,3]triazol-6-yl)pyrrolo[2,1-f][1,2,4]triazin-2-amine [1236];

N-(trans-3-ethoxycyclobutyl)-5-(1-methyl-1H-benzo[d][1,2,3]triazol-6-yl)pyrrolo[2,1-f][1,2,4]triazin-2-amine [1237];

N-(cis-3-(2-methoxyethoxy)cyclobutyl)-5-(1-methyl-1H-benzo[d][1,2,3]triazol-6-yl)pyrrolo[2,1-f][1,2,4]triazin-2-amine [1238];

N-(trans-3-(2-methoxyethoxy)cyclobutyl)-5-(1-methyl-1H-benzo[d][1,2,3]triazol-6-yl)pyrrolo[2,1-f][1,2,4]triazin-2-amine [1239];

cis-$N^1$-(5-(1-methyl-1H-benzo[d][1,2,3]triazol-6-yl)pyrrolo[2,1-f][1,2,4]triazin-2-yl)cyclobutane-1,3-diamine [1240];

trans-$N^1$-(5-(1-methyl-1H-benzo[d][1,2,3]triazol-6-yl)pyrrolo[2,1-f][1,2,4]triazin-2-yl)cyclobutane-1,3-diamine [1241];

cis-$N^1$-methyl-$N^3$-(5-(1-methyl-1H-benzo[d][1,2,3]triazol-6-yl)pyrrolo[2,1-f][1,2,4]triazin-2-yl)cyclobutane-1,3-diamine [1242];

trans-$N^1$-methyl-$N^3$-(5-(1-methyl-1H-benzo[d][1,2,3]triazol-6-yl)pyrrolo[2,1-f][1,2,4]triazin-2-yl)cyclobutane-1,3-diamine [1243];

cis-$N^1$,$N^1$-dimethyl-$N^3$-(5-(1-methyl-1H-benzo[d][1,2,3]triazol-6-yl)pyrrolo[2,1-f][1,2,4]triazin-2-yl)cyclobutane-1,3-diamine [1244];

trans-$N^1$,$N^1$-dimethyl-$N^3$-(5-(1-methyl-1H-benzo[d][1,2,3]triazol-6-yl)pyrrolo[2,1-f][1,2,4] triazin-2-yl)cyclobutane-1,3-diamine [1245];

5-(1-methyl-1H-benzo[d][1,2,3]triazol-6-yl)-N-(cis-3-morpholinocyclobutyl)pyrrolo[2,1-f][1,2,4]triazin-2-amine [1246];

5-(1-methyl-1H-benzo[d][1,2,3]triazol-6-yl)-N-(trans-3-morpholinocyclobutyl)pyrrolo[2,1-f][1,2,4]triazin-2-amine [1247];

5-(1-methyl-1H-benzo[d][1,2,3]triazol-6-yl)-N-(cis-3-(4-methylpiperazin-1-yl)cyclobutyl)pyrrolo [2,1-f][1,2,4]triazin-2-amine [1248];

5-(1-methyl-1H-benzo[d][1,2,3]triazol-6-yl)-N-(trans-3-(4-methylpiperazin-1-yl)cyclobutyl) pyrrolo[2,1-f][1,2,4]triazin-2-amine [1249];

N-(4,4-difluorocyclohexyl)-5-(1-methyl-1H-benzo[d][1,2,3]triazol-6-yl)pyrrolo[2,1-f][1,2,4] triazin-2-amine [1250];

cis-4-((5-(1-methyl-1H-benzo[d][1,2,3]triazol-6-yl)pyrrolo[2,1-f][1,2,4]triazin-2-yl)amino) cyclohexan-1-ol [1251];

(1s,4s)-1-methyl-4-((5-(1-methyl-1H-benzo[d][1,2,3]triazol-6-yl)pyrrolo[2,1-f][1,2,4]triazin-2-yl)amino)cyclohexan-1-ol [1252];

N-(cis-4-methoxycyclohexyl)-5-(1-methyl-1H-benzo[d][1,2,3]triazol-6-yl)pyrrolo[2,1-f][1,2,4] triazin-2-amine [1253];

N-(trans-4-methoxycyclohexyl)-5-(1-methyl-1H-benzo[d][1,2,3]triazol-6-yl)pyrrolo[2,1-f][1,2,4] triazin-2-amine [1254];

N-(cis-4-(difluoromethoxy)cyclohexyl)-5-(1-methyl-1H-benzo[d][1,2,3]triazol-6-yl)pyrrolo[2,1-f][1,2,4]triazin-2-amine [1255];

N-(trans-4-(difluoromethoxy)cyclohexyl)-5-(1-methyl-1H-benzo[d][1,2,3]triazol-6-yl)pyrrolo [2,1-f][1,2,4]triazin-2-amine [1256];

N-(cis-4-ethoxycyclohexyl)-5-(1-methyl-1H-benzo[d][1,2,3]triazol-6-yl)pyrrolo[2,1-f][1,2,4] triazin-2-amine [1257];

N-(trans-4-ethoxycyclohexyl)-5-(1-methyl-1H-benzo[d][1,2,3]triazol-6-yl)pyrrolo[2,1-f][1,2,4] triazin-2-amine [1258];

N-(cis-4-(2-methoxyethoxy)cyclohexyl)-5-(1-methyl-1H-benzo[d][1,2,3]triazol-6-yl)pyrrolo[2,1-f][1,2,4]triazin-2-amine [1259];

N-(trans-4-(2-methoxyethoxy)cyclohexyl)-5-(1-methyl-1H-benzo[d][1,2,3]triazol-6-yl)pyrrolo [2,1-f][1,2,4]triazin-2-amine [1260];

cis-$N^1$-(5-(1-methyl-1H-benzo[d][1,2,3]triazol-6-yl)pyrrolo[2,1-f][1,2,4]triazin-2-yl)cyclohexane-1,4-diamine [1261];

trans-$N^1$-(5-(1-methyl-1H-benzo[d][1,2,3]triazol-6-yl)pyrrolo[2,1-f][1,2,4]triazin-2-yl) cyclohexane-1,4-diamine [1262];

cis-$N^1$-methyl-$N^4$-(5-(1-methyl-1H-benzo[d][1,2,3]triazol-6-yl)pyrrolo[2,1-f][1,2,4]triazin-2-yl) cyclohexane-1,4-diamine [1263];

trans-$N^1$-methyl-$N^4$-(5-(1-methyl-1H-benzo[d][1,2,3]triazol-6-yl)pyrrolo[2,1-f][1,2,4]triazin-2-yl)cyclohexane-1,4-diamine [1264];

cis-$N^1$,$N^1$-dimethyl-$N^4$-(5-(1-methyl-1H-benzo[d][1,2,3]triazol-6-yl)pyrrolo[2,1-f][1,2,4]triazin-2-yl)cyclohexane-1,4-diamine [1265];

trans-$N^1$,$N^1$-dimethyl-$N^4$-(5-(1-methyl-1H-benzo[d][1,2,3]triazol-6-yl)pyrrolo[2,1-f][1,2,4] triazin-2-yl)cyclohexane-1,4-diamine [1266];

5-(1-methyl-1H-benzo[d][1,2,3]triazol-6-yl)-N-(cis-4-morpholinocyclohexyl)pyrrolo[2,1-f][1,2,4]triazin-2-amine [1267];

5-(1-methyl-1H-benzo[d][1,2,3]triazol-6-yl)-N-(trans-4-morpholinocyclohexyl)pyrrolo[2,1-f][1,2,4]triazin-2-amine [1268];

5-(1-methyl-1H-benzo[d][1,2,3]triazol-6-yl)-N-(cis-4-(4-methylpiperazin-1-yl)cyclohexyl)pyrrolo [2,1-f][1,2,4]triazin-2-amine [1269];

5-(1-methyl-1H-benzo[d][1,2,3]triazol-6-yl)-N-(trans-4-(4-methylpiperazin-1-yl)cyclohexyl) pyrrolo[2,1-f][1,2,4]triazin-2-amine [1270];

5-(1-methyl-1H-benzo[d][1,2,3]triazol-6-yl)-N-(1-methylazetidin-3-yl)pyrrolo[2,1-f][1,2,4] triazin-2-amine [1271];

5-(1-methyl-1H-benzo[d][1,2,3]triazol-6-yl)-N-(oxetan-3-yl)pyrrolo[2,1-f][1,2,4]triazin-2-amine [1272];

5-(1-methyl-1H-benzo[d][1,2,3]triazol-6-yl)-N-(1-methylpiperidin-4-yl)pyrrolo[2,1-f][1,2,4] triazin-2-amine [1273];

5-(1-methyl-1H-benzo[d][1,2,3]triazol-6-yl)-N-(tetrahydro-2H-pyran-4-yl)pyrrolo[2,1-f][1,2,4] triazin-2-amine [1274];

N-(6,6-difluorospiro[3.3]heptan-2-yl)-5-(1-methyl-1H-benzo[d][1,2,3]triazol-6-yl)pyrrolo[2,1-f][1,2,4]triazin-2-amine [1275];

5-(1-methyl-1H-benzo[d][1,2,3]triazol-6-yl)-N-(2-oxaspiro[3.3]heptan-6-yl)pyrrolo[2,1-f][1,2,4] triazin-2-amine [1276];

5-(1-methyl-1H-benzo[d][1,2,3]triazol-6-yl)-N-(2-methyl-2-azaspiro[3.3]heptan-6-yl)pyrrolo[2,1-f][1,2,4]triazin-2-amine [1277];

5-(1-methyl-1H-benzo[d][1,2,3]triazol-6-yl)-N-(1-methyl-1H-pyrazol-4-yl)pyrrolo[2,1-f][1,2,4] triazin-2-amine [1278];

N-isopropyl-5-(quinolin-6-yl)pyrrolo[2,1-f][1,2,4]triazin-2-amine [1279];

N-isobutyl-5-(quinolin-6-yl)pyrrolo[2,1-f][1,2,4]triazin-2-amine [1280];

N-(2-fluoro-2-methylpropyl)-5-(quinolin-6-yl)pyrrolo[2,1-f][1,2,4]triazin-2-amine [1281];

N-(2,2-difluoropropyl)-5-(quinolin-6-yl)pyrrolo[2,1-f][1,2,4]triazin-2-amine [1282];

5-(quinolin-6-yl)-N-(2,2,2-trifluoroethyl)pyrrolo[2,1-f][1,2,4]triazin-2-amine [1283];

(R)-5-(quinolin-6-yl)-N-(1,1,1-trifluoropropan-2-yl)pyrrolo[2,1-f][1,2,4]triazin-2-amine [1284];

5-(quinolin-6-yl)-N-(3,3,3-trifluoropropyl)pyrrolo[2,1-f][1,2,4]triazin-2-amine [1285];

5-(quinolin-6-yl)-N-(3,3,3-trifluoro-2,2-dimethylpropyl)pyrrolo[2,1-f][1,2,4]triazin-2-amine [1286];

N-(2-methoxyethyl)-5-(quinolin-6-yl)pyrrolo[2,1-f][1,2,4]triazin-2-amine [1287];

(R)—N-(1-methoxypropan-2-yl)-5-(quinolin-6-yl)pyrrolo[2,1-f][1,2,4]triazin-2-amine [1288];

N-(2-isopropoxyethyl)-5-(quinolin-6-yl)pyrrolo[2,1-f][1,2,4]triazin-2-amine [1289];

N-((1-methylcyclopropyl)methyl)-5-(quinolin-6-yl)pyrrolo[2,1-f][1,2,4]triazin-2-amine [1290];

5-(quinolin-6-yl)-N-((1-(trifluoromethyl)cyclopropyl)methyl)pyrrolo[2,1-f][1,2,4]triazin-2-amine [1291];

N-((1-fluorocyclobutyl)methyl)-5-(quinolin-6-yl)pyrrolo[2,1-f][1,2,4]triazin-2-amine [1292];

N-((3-fluorooxetan-3-yl)methyl)-5-(quinolin-6-yl)pyrrolo[2,1-f][1,2,4]triazin-2-amine [1293];

N-(cyclopropylmethyl)-5-(quinolin-6-yl)pyrrolo[2,1-f][1,2,4]triazin-2-amine [1294];

(S)—N-(1-cyclopropylethyl)-5-(quinolin-6-yl)pyrrolo[2,1-f][1,2,4]triazin-2-amine [1295];

(R)—N-(1-cyclopropylethyl)-5-(quinolin-6-yl)pyrrolo[2,1-f][1,2,4]triazin-2-amine [1296];

N-(2-cyclopropyl-2,2-difluoroethyl)-5-(quinolin-6-yl)pyrrolo[2,1-f][1,2,4]triazin-2-amine [1297];

N-(oxetan-3-ylmethyl)-5-(quinolin-6-yl)pyrrolo[2,1-f][1,2,4]triazin-2-amine [1298];

5-(quinolin-6-yl)-N-((tetrahydrofuran-2-yl)methyl)pyrrolo[2,1-f][1,2,4]triazin-2-amine [1299];

N-cyclobutyl-5-(quinolin-6-yl)pyrrolo[2,1-f][1,2,4]triazin-2-amine [1300];

N-(3,3-difluorocyclobutyl)-5-(quinolin-6-yl)pyrrolo[2,1-f][1,2,4]triazin-2-amine [1301];

N-(3,3-dimethylcyclobutyl)-5-(quinolin-6-yl)pyrrolo[2,1-f][1,2,4]triazin-2-amine [1302];

1-methyl-3-((5-(quinolin-6-yl)pyrrolo[2,1-f][1,2,4]triazin-2-yl)amino)cyclobutan-1-ol [1303];

N-(cis-3-methoxycyclobutyl)-5-(quinolin-6-yl)pyrrolo[2,1-f][1,2,4]triazin-2-amine [1304];

N-(trans-3-methoxycyclobutyl)-5-(quinolin-6-yl)pyrrolo[2,1-f][1,2,4]triazin-2-amine [1305];

N-(trans-3-(methoxymethyl)cyclobutyl)-5-(quinolin-6-yl)pyrrolo[2,1-f][1,2,4]triazin-2-amine [1306];

N-(cis-3-ethoxycyclobutyl)-5-(quinolin-6-yl)pyrrolo[2,1-f][1,2,4]triazin-2-amine [1307];

N-(trans-3-ethoxycyclobutyl)-5-(quinolin-6-yl)pyrrolo[2,1-f][1,2,4]triazin-2-amine [1308];

N-(cis-3-(2-methoxyethoxy)cyclobutyl)-5-(quinolin-6-yl)pyrrolo[2,1-f][1,2,4]triazin-2-amine [1309];

N-(trans-3-(2-methoxyethoxy)cyclobutyl)-5-(quinolin-6-yl)pyrrolo[2,1-f][1,2,4]triazin-2-amine [1310];

cis-$N^1$-(5-(quinolin-6-yl)pyrrolo[2,1-f][1,2,4]triazin-2-yl)cyclobutane-1,3-diamine [1311];

trans-$N^1$-(5-(quinolin-6-yl)pyrrolo[2,1-f][1,2,4]triazin-2-yl)cyclobutane-1,3-diamine [1312];

cis-$N^1$-methyl-$N^3$-(5-(quinolin-6-yl)pyrrolo[2,1-f][1,2,4]triazin-2-yl)cyclobutane-1,3-diamine [1313];

trans-$N^1$-methyl-$N^3$-(5-(quinolin-6-yl)pyrrolo[2,1-f][1,2,4]triazin-2-yl)cyclobutane-1,3-diamine [1314];

cis-$N^1$,$N^1$-dimethyl-$N^3$-(5-(quinolin-6-yl)pyrrolo[2,1-f][1,2,4]triazin-2-yl)cyclobutane-1,3-diamine [1315];

trans-$N^1$,$N^1$-dimethyl-$N^3$-(5-(quinolin-6-yl)pyrrolo[2,1-f][1,2,4]triazin-2-yl)cyclobutane-1,3-diamine [1316];

N-(cis-3-morpholinocyclobutyl)-5-(quinolin-6-yl)pyrrolo[2,1-f][1,2,4]triazin-2-amine [1317];

N-(trans-3-morpholinocyclobutyl)-5-(quinolin-6-yl)pyrrolo[2,1-f][1,2,4]triazin-2-amine [1318];

N-(cis-3-(4-methylpiperazin-1-yl)cyclobutyl)-5-(quinolin-6-yl)pyrrolo[2,1-f][1,2,4]triazin-2-amine [1319];

N-(trans-3-(4-methylpiperazin-1-yl)cyclobutyl)-5-(quinolin-6-yl)pyrrolo[2,1-f][1,2,4]triazin-2-amine [1320];

N-(4,4-difluorocyclohexyl)-5-(quinolin-6-yl)pyrrolo[2,1-f][1,2,4]triazin-2-amine [1321];

cis-4-((5-(quinolin-6-yl)pyrrolo[2,1-f][1,2,4]triazin-2-yl)amino)cyclohexan-1-ol [1322];

(1s,4s)-1-methyl-4-((5-(quinolin-6-yl)pyrrolo[2,1-f][1,2,4]triazin-2-yl)amino)cyclohexan-1-ol [1323];

N-(cis-4-methoxycyclohexyl)-5-(quinolin-6-yl)pyrrolo[2,1-f][1,2,4]triazin-2-amine [1324];

N-(trans-4-methoxycyclohexyl)-5-(quinolin-6-yl)pyrrolo[2,1-f][1,2,4]triazin-2-amine [1325];

N-(cis-4-(difluoromethoxy)cyclohexyl)-5-(quinolin-6-yl)pyrrolo[2,1-f][1,2,4]triazin-2-amine [1326];

N-(trans-4-(difluoromethoxy)cyclohexyl)-5-(quinolin-6-yl)pyrrolo[2,1-f][1,2,4]triazin-2-amine [1327];

N-(cis-4-ethoxycyclohexyl)-5-(quinolin-6-yl)pyrrolo[2,1-f][1,2,4]triazin-2-amine [1328];

N-(trans-4-ethoxycyclohexyl)-5-(quinolin-6-yl)pyrrolo[2,1-f][1,2,4]triazin-2-amine [1329];

N-(cis-4-(2-methoxyethoxy)cyclohexyl)-5-(quinolin-6-yl)pyrrolo[2,1-f][1,2,4]triazin-2-amine [1330];

N-(trans-4-(2-methoxyethoxy)cyclohexyl)-5-(quinolin-6-yl)pyrrolo[2,1-f][1,2,4]triazin-2-amine [1331];

cis-$N^1$-(5-(quinolin-6-yl)pyrrolo[2,1-f][1,2,4]triazin-2-yl)cyclohexane-1,4-diamine [1332];

trans-$N^1$-(5-(quinolin-6-yl)pyrrolo[2,1-f][1,2,4]triazin-2-yl)cyclohexane-1,4-diamine [1333];

cis-$N^1$-methyl-$N^4$-(5-(quinolin-6-yl)pyrrolo[2,1-f][1,2,4]triazin-2-yl)cyclohexane-1,4-diamine [1334];

trans-$N^1$-methyl-$N^4$-(5-(quinolin-6-yl)pyrrolo[2,1-f][1,2,4]triazin-2-yl)cyclohexane-1,4-diamine [1335];

cis-$N^1$,$N^1$-dimethyl-$N^4$-(5-(quinolin-6-yl)pyrrolo[2,1-f][1,2,4]triazin-2-yl)cyclohexane-1,4-diamine [1336];

trans-$N^1$,$N^1$-dimethyl-$N^4$-(5-(quinolin-6-yl)pyrrolo[2,1-f][1,2,4]triazin-2-yl)cyclohexane-1,4-diamine [1337];

N-(cis-4-morpholinocyclohexyl)-5-(quinolin-6-yl)pyrrolo[2,1-f][1,2,4]triazin-2-amine [1338];

N-(trans-4-morpholinocyclohexyl)-5-(quinolin-6-yl)pyrrolo[2,1-f][1,2,4]triazin-2-amine [1339];

N-(cis-4-(4-methylpiperazin-1-yl)cyclohexyl)-5-(quinolin-6-yl)pyrrolo[2,1-f][1,2,4]triazin-2-amine [1340];

N-(trans-4-(4-methylpiperazin-1-yl)cyclohexyl)-5-(quinolin-6-yl)pyrrolo[2,1-f][1,2,4]triazin-2-amine [1341];

N-(1-methylazetidin-3-yl)-5-(quinolin-6-yl)pyrrolo[2,1-f][1,2,4]triazin-2-amine [1342];

N-(oxetan-3-yl)-5-(quinolin-6-yl)pyrrolo[2,1-f][1,2,4]triazin-2-amine [1343];

N-(1-methylpiperidin-4-yl)-5-(quinolin-6-yl)pyrrolo[2,1-f][1,2,4]triazin-2-amine [1344];

5-(quinolin-6-yl)-N-(tetrahydro-2H-pyran-4-yl)pyrrolo[2,1-f][1,2,4]triazin-2-amine [1345];

N-(6,6-difluorospiro[3.3]heptan-2-yl)-5-(quinolin-6-yl)pyrrolo[2,1-f][1,2,4]triazin-2-amine [1346];

5-(quinolin-6-yl)-N-(2-oxaspiro[3.3]heptan-6-yl)pyrrolo[2,1-f][1,2,4]triazin-2-amine [1347];

N-(2-methyl-2-azaspiro[3.3]heptan-6-yl)-5-(quinolin-6-yl)pyrrolo[2,1-f][1,2,4]triazin-2-amine [1348];

N-(1-methyl-1H-pyrazol-4-yl)-5-(quinolin-6-yl)pyrrolo[2,1-f][1,2,4]triazin-2-amine [1349];

N-isopropyl-5-(quinoxalin-6-yl)pyrrolo[2,1-f][1,2,4]triazin-2-amine [1350];

N-isobutyl-5-(quinoxalin-6-yl)pyrrolo[2,1-f][1,2,4]triazin-2-amine [1351];

N-(2-fluoro-2-methylpropyl)-5-(quinoxalin-6-yl)pyrrolo[2,1-f][1,2,4]triazin-2-amine [1352];
N-(2,2-difluoropropyl)-5-(quinoxalin-6-yl)pyrrolo[2,1-f][1,2,4]triazin-2-amine [1353];
5-(quinoxalin-6-yl)-N-(2,2,2-trifluoroethyl)pyrrolo[2,1-f][1,2,4]triazin-2-amine [1354];
(R)-5-(quinoxalin-6-yl)-N-(1,1,1-trifluoropropan-2-yl)pyrrolo[2,1-f][1,2,4]triazin-2-amine [1355];
5-(quinoxalin-6-yl)-N-(3,3,3-trifluoropropyl)pyrrolo[2,1-f][1,2,4]triazin-2-amine [1356];
5-(quinoxalin-6-yl)-N-(3,3,3-trifluoro-2,2-dimethylpropyl)pyrrolo[2,1-f][1,2,4]triazin-2-amine [1357];
N-(2-methoxyethyl)-5-(quinoxalin-6-yl)pyrrolo[2,1-f][1,2,4]triazin-2-amine [1358];
(R)—N-(1-methoxypropan-2-yl)-5-(quinoxalin-6-yl)pyrrolo[2,1-f][1,2,4]triazin-2-amine [1359];
N-(2-isopropoxyethyl)-5-(quinoxalin-6-yl)pyrrolo[2,1-f][1,2,4]triazin-2-amine [1360];
N-((1-methylcyclopropyl)methyl)-5-(quinoxalin-6-yl)pyrrolo[2,1-f][1,2,4]triazin-2-amine [1361];
5-(quinoxalin-6-yl)-N-((1-(trifluoromethyl)cyclopropyl)methyl)pyrrolo[2,1-f][1,2,4]triazin-2-amine [1362];
N-((1-fluorocyclobutyl)methyl)-5-(quinoxalin-6-yl)pyrrolo[2,1-f][1,2,4]triazin-2-amine [1363];
N-((3-fluorooxetan-3-yl)methyl)-5-(quinoxalin-6-yl)pyrrolo[2,1-f][1,2,4]triazin-2-amine [1364];
N-(cyclopropylmethyl)-5-(quinoxalin-6-yl)pyrrolo[2,1-f][1,2,4]triazin-2-amine [1365];
(S)—N-(1-cyclopropylethyl)-5-(quinoxalin-6-yl)pyrrolo[2,1-f][1,2,4]triazin-2-amine [1366];
(R)—N-(1-cyclopropylethyl)-5-(quinoxalin-6-yl)pyrrolo[2,1-f][1,2,4]triazin-2-amine [1367];
N-(2-cyclopropyl-2,2-difluoroethyl)-5-(quinoxalin-6-yl)pyrrolo[2,1-f][1,2,4]triazin-2-amine [1368];
N-(oxetan-3-ylmethyl)-5-(quinoxalin-6-yl)pyrrolo[2,1-f][1,2,4]triazin-2-amine [1369];
5-(quinoxalin-6-yl)-N-((tetrahydrofuran-2-yl)methyl)pyrrolo[2,1-f][1,2,4]triazin-2-amine [1370];
N-cyclobutyl-5-(quinoxalin-6-yl)pyrrolo[2,1-f][1,2,4]triazin-2-amine [1371];
N-(3,3-difluorocyclobutyl)-5-(quinoxalin-6-yl)pyrrolo[2,1-f][1,2,4]triazin-2-amine [1372];
N-(3,3-dimethylcyclobutyl)-5-(quinoxalin-6-yl)pyrrolo[2,1-f][1,2,4]triazin-2-amine [1373];
1-methyl-3-((5-(quinoxalin-6-yl)pyrrolo[2,1-f][1,2,4]triazin-2-yl)amino)cyclobutan-1-ol [1374];
N-(cis-3-methoxycyclobutyl)-5-(quinoxalin-6-yl)pyrrolo[2,1-f][1,2,4]triazin-2-amine [1375];
N-(trans-3-methoxycyclobutyl)-5-(quinoxalin-6-yl)pyrrolo[2,1-f][1,2,4]triazin-2-amine [1376];
N-(trans-3-(methoxymethyl)cyclobutyl)-5-(quinoxalin-6-yl)pyrrolo[2,1-f][1,2,4]triazin-2-amine [1377];
N-(cis-3-ethoxycyclobutyl)-5-(quinoxalin-6-yl)pyrrolo[2,1-f][1,2,4]triazin-2-amine [1378];
N-(trans-3-ethoxycyclobutyl)-5-(quinoxalin-6-yl)pyrrolo[2,1-f][1,2,4]triazin-2-amine [1379];
N-(cis-3-(2-methoxyethoxy)cyclobutyl)-5-(quinoxalin-6-yl)pyrrolo[2,1-f][1,2,4]triazin-2-amine [1380];
N-(trans-3-(2-methoxyethoxy)cyclobutyl)-5-(quinoxalin-6-yl)pyrrolo[2,1-f][1,2,4]triazin-2-amine [1381];
cis-$N^1$-(5-(quinoxalin-6-yl)pyrrolo[2,1-f][1,2,4]triazin-2-yl)cyclobutane-1,3-diamine [1382];
trans-$N^1$-(5-(quinoxalin-6-yl)pyrrolo[2,1-f][1,2,4]triazin-2-yl)cyclobutane-1,3-diamine [1383];
cis-$N^1$-methyl-$N^3$-(5-(quinoxalin-6-yl)pyrrolo[2,1-f][1,2,4]triazin-2-yl)cyclobutane-1,3-diamine [1384];
trans-$N^1$-methyl-$N^3$-(5-(quinoxalin-6-yl)pyrrolo[2,1-f][1,2,4]triazin-2-yl)cyclobutane-1,3-diamine [1385];
cis-$N^1$,$N^1$-dimethyl-$N^3$-(5-(quinoxalin-6-yl)pyrrolo[2,1-f][1,2,4]triazin-2-yl)cyclobutane-1,3-diamine [1386];
trans-$N^1$,$N^1$-dimethyl-$N^3$-(5-(quinoxalin-6-yl)pyrrolo[2,1-f][1,2,4]triazin-2-yl)cyclobutane-1,3-diamine [1387];
N-(cis-3-morpholinocyclobutyl)-5-(quinoxalin-6-yl)pyrrolo[2,1-f][1,2,4]triazin-2-amine [1388];
N-(trans-3-morpholinocyclobutyl)-5-(quinoxalin-6-yl)pyrrolo[2,1-f][1,2,4]triazin-2-amine [1389];
N-(cis-3-(4-methylpiperazin-1-yl)cyclobutyl)-5-(quinoxalin-6-yl)pyrrolo[2,1-f][1,2,4]triazin-2-amine [1390];
N-(trans-3-(4-methylpiperazin-1-yl)cyclobutyl)-5-(quinoxalin-6-yl)pyrrolo[2,1-f][1,2,4]triazin-2-amine [1391];
N-(4,4-difluorocyclohexyl)-5-(quinoxalin-6-yl)pyrrolo[2,1-f][1,2,4]triazin-2-amine [1392];
cis-4-((5-(quinoxalin-6-yl)pyrrolo[2,1-f][1,2,4]triazin-2-yl)amino)cyclohexan-1-ol [1393];
(1s,4s)-1-methyl-4-((5-(quinoxalin-6-yl)pyrrolo[2,1-f][1,2,4]triazin-2-yl)amino)cyclohexan-1-ol [1394];
N-(cis-4-methoxycyclohexyl)-5-(quinoxalin-6-yl)pyrrolo[2,1-f][1,2,4]triazin-2-amine [1395];
N-(trans-4-methoxycyclohexyl)-5-(quinoxalin-6-yl)pyrrolo[2,1-f][1,2,4]triazin-2-amine [1396];
N-(cis-4-(difluoromethoxy)cyclohexyl)-5-(quinoxalin-6-yl)pyrrolo[2,1-f][1,2,4]triazin-2-amine [1397];
N-(trans-4-(difluoromethoxy)cyclohexyl)-5-(quinoxalin-6-yl)pyrrolo[2,1-f][1,2,4]triazin-2-amine [1398];
N-(cis-4-ethoxycyclohexyl)-5-(quinoxalin-6-yl)pyrrolo[2,1-f][1,2,4]triazin-2-amine [1399];
N-(trans-4-ethoxycyclohexyl)-5-(quinoxalin-6-yl)pyrrolo[2,1-f][1,2,4]triazin-2-amine [1400];
N-(cis-4-(2-methoxyethoxy)cyclohexyl)-5-(quinoxalin-6-yl)pyrrolo[2,1-f][1,2,4]triazin-2-amine [1401];
N-(trans-4-(2-methoxyethoxy)cyclohexyl)-5-(quinoxalin-6-yl)pyrrolo[2,1-f][1,2,4]triazin-2-amine [1402];
cis-$N^1$-(5-(quinoxalin-6-yl)pyrrolo[2,1-f][1,2,4]triazin-2-yl)cyclohexane-1,4-diamine [1403];
trans-$N^1$-(5-(quinoxalin-6-yl)pyrrolo[2,1-f][1,2,4]triazin-2-yl)cyclohexane-1,4-diamine [1404];
cis-$N^1$-methyl-$N^4$-(5-(quinoxalin-6-yl)pyrrolo[2,1-f][1,2,4]triazin-2-yl)cyclohexane-1,4-diamine [1405];
trans-$N^1$-methyl-$N^4$-(5-(quinoxalin-6-yl)pyrrolo[2,1-f][1,2,4]triazin-2-yl)cyclohexane-1,4-diamine [1406];
cis-$N^1$,$N^1$-dimethyl-$N^4$-(5-(quinoxalin-6-yl)pyrrolo[2,1-f][1,2,4]triazin-2-yl)cyclohexane-1,4-diamine [1407];
trans-$N^1$,$N^1$-dimethyl-$N^4$-(5-(quinoxalin-6-yl)pyrrolo[2,1-f][1,2,4]triazin-2-yl)cyclohexane-1,4-diamine [1408];
N-(cis-4-morpholinocyclohexyl)-5-(quinoxalin-6-yl)pyrrolo[2,1-f][1,2,4]triazin-2-amine [1409];
N-(trans-4-morpholinocyclohexyl)-5-(quinoxalin-6-yl)pyrrolo[2,1-f][1,2,4]triazin-2-amine [1410];
N-(cis-4-(4-methylpiperazin-1-yl)cyclohexyl)-5-(quinoxalin-6-yl)pyrrolo[2,1-f][1,2,4]triazin-2-amine [1411];
N-(trans-4-(4-methylpiperazin-1-yl)cyclohexyl)-5-(quinoxalin-6-yl)pyrrolo[2,1-f][1,2,4]triazin-2-amine [1412];
N-(1-methylazetidin-3-yl)-5-(quinoxalin-6-yl)pyrrolo[2,1-f][1,2,4]triazin-2-amine [1413];
N-(oxetan-3-yl)-5-(quinoxalin-6-yl)pyrrolo[2,1-f][1,2,4]triazin-2-amine [1414];

N-(1-methylpiperidin-4-yl)-5-(quinoxalin-6-yl)pyrrolo[2,1-f][1,2,4]triazin-2-amine [1415];
5-(quinoxalin-6-yl)-N-(tetrahydro-2H-pyran-4-yl)pyrrolo[2,1-f][1,2,4]triazin-2-amine [1416];
N-(6,6-difluorospiro[3.3]heptan-2-yl)-5-(quinoxalin-6-yl)pyrrolo[2,1-f][1,2,4]triazin-2-amine [1417];
5-(quinoxalin-6-yl)-N-(2-oxaspiro[3.3]heptan-6-yl)pyrrolo[2,1-f][1,2,4]triazin-2-amine [1418];
N-(2-methyl-2-azaspiro[3.3]heptan-6-yl)-5-(quinoxalin-6-yl)pyrrolo[2,1-f][1,2,4]triazin-2-amine [1419];
N-(1-methyl-1H-pyrazol-4-yl)-5-(quinoxalin-6-yl)pyrrolo[2,1-f][1,2,4]triazin-2-amine [1420];
N-isopropyl-5-(4-methoxyquinazolin-6-yl)pyrrolo[2,1-f][1,2,4]triazin-2-amine [1421];
N-isobutyl-5-(4-methoxyquinazolin-6-yl)pyrrolo[2,1-f][1,2,4]triazin-2-amine [1422];
N-(2-fluoro-2-methylpropyl)-5-(4-methoxyquinazolin-6-yl)pyrrolo[2,1-f][1,2,4]triazin-2-amine [1423];
N-(2,2-difluoropropyl)-5-(4-methoxyquinazolin-6-yl)pyrrolo[2,1-f][1,2,4]triazin-2-amine [1424];
5-(4-methoxyquinazolin-6-yl)-N-(2,2,2-trifluoroethyl)pyrrolo[2,1-f][1,2,4]triazin-2-amine [1425];
(R)-5-(4-methoxyquinazolin-6-yl)-N-(1,1,1-trifluoropropan-2-yl)pyrrolo[2,1-f][1,2,4]triazin-2-amine [1426];
5-(4-methoxyquinazolin-6-yl)-N-(3,3,3-trifluoropropyl)pyrrolo[2,1-f][1,2,4]triazin-2-amine [1427];
5-(4-methoxyquinazolin-6-yl)-N-(3,3,3-trifluoro-2,2-dimethylpropyl)pyrrolo[2,1-f][1,2,4]triazin-2-amine [1428];
N-(2-methoxyethyl)-5-(4-methoxyquinazolin-6-yl)pyrrolo[2,1-f][1,2,4]triazin-2-amine [1429];
(R)—N-(1-methoxypropan-2-yl)-5-(4-methoxyquinazolin-6-yl)pyrrolo[2,1-f][1,2,4]triazin-2-amine [1430];
N-(2-isopropoxyethyl)-5-(4-methoxyquinazolin-6-yl)pyrrolo[2,1-f][1,2,4]triazin-2-amine [1431];
5-(4-methoxyquinazolin-6-yl)-N-((1-methylcyclopropyl)methyl)pyrrolo[2,1-f][1,2,4]triazin-2-amine [1432];
5-(4-methoxyquinazolin-6-yl)-N-((1-(trifluoromethyl)cyclopropyl)methyl)pyrrolo[2,1-f][1,2,4]triazin-2-amine [1433];
N-((1-fluorocyclobutyl)methyl)-5-(4-methoxyquinazolin-6-yl)pyrrolo[2,1-f][1,2,4]triazin-2-amine [1434];
N-((3-fluorooxetan-3-yl)methyl)-5-(4-methoxyquinazolin-6-yl)pyrrolo[2,1-f][1,2,4]triazin-2-amine [1435];
N-(cyclopropylmethyl)-5-(4-methoxyquinazolin-6-yl)pyrrolo[2,1-f][1,2,4]triazin-2-amine [1436];
(S)—N-(1-cyclopropylethyl)-5-(4-methoxyquinazolin-6-yl)pyrrolo[2,1-f][1,2,4]triazin-2-amine [1437];
(R)—N-(1-cyclopropylethyl)-5-(4-methoxyquinazolin-6-yl)pyrrolo[2,1-f][1,2,4]triazin-2-amine [1438];
N-(2-cyclopropyl-2,2-difluoroethyl)-5-(4-methoxyquinazolin-6-yl)pyrrolo[2,1-f][1,2,4]triazin-2-amine [1439];
5-(4-methoxyquinazolin-6-yl)-N-(oxetan-3-ylmethyl)pyrrolo[2,1-f][1,2,4]triazin-2-amine [1440];
5-(4-methoxyquinazolin-6-yl)-N-((tetrahydrofuran-2-yl)methyl)pyrrolo[2,1-f][1,2,4]triazin-2-amine [1441];
N-cyclobutyl-5-(4-methoxyquinazolin-6-yl)pyrrolo[2,1-f][1,2,4]triazin-2-amine [1442];
N-(3,3-difluorocyclobutyl)-5-(4-methoxyquinazolin-6-yl)pyrrolo[2,1-f][1,2,4]triazin-2-amine [1443];
N-(3,3-dimethylcyclobutyl)-5-(4-methoxyquinazolin-6-yl)pyrrolo[2,1-f][1,2,4]triazin-2-amine [1444];
3-((5-(4-methoxyquinazolin-6-yl)pyrrolo[2,1-f][1,2,4]triazin-2-yl)amino)-1-methylcyclobutan-1-ol [1445];
N-(cis-3-methoxycyclobutyl)-5-(4-methoxyquinazolin-6-yl)pyrrolo[2,1-f][1,2,4]triazin-2-amine [1446];
N-(trans-3-methoxycyclobutyl)-5-(4-methoxyquinazolin-6-yl)pyrrolo[2,1-f][1,2,4]triazin-2-amine [1447];
N-(trans-3-(methoxymethyl)cyclobutyl)-5-(4-methoxyquinazolin-6-yl)pyrrolo[2,1-f][1,2,4] triazin-2-amine [1448];
N-(cis-3-ethoxycyclobutyl)-5-(4-methoxyquinazolin-6-yl)pyrrolo[2,1-f][1,2,4]triazin-2-amine [1449];
N-(trans-3-ethoxycyclobutyl)-5-(4-methoxyquinazolin-6-yl)pyrrolo[2,1-f][1,2,4]triazin-2-amine [1450];
N-(cis-3-(2-methoxyethoxy)cyclobutyl)-5-(4-methoxyquinazolin-6-yl)pyrrolo[2,1-f][1,2,4] triazin-2-amine [1451];
N-(trans-3-(2-methoxyethoxy)cyclobutyl)-5-(4-methoxyquinazolin-6-yl)pyrrolo[2,1-f][1,2,4] triazin-2-amine [1452];
cis-$N^1$-(5-(4-methoxyquinazolin-6-yl)pyrrolo[2,1-f][1,2,4]triazin-2-yl)cyclobutane-1,3-diamine [1453];
trans-$N^1$-(5-(4-methoxyquinazolin-6-yl)pyrrolo[2,1-f][1,2,4]triazin-2-yl)cyclobutane-1,3-diamine [1454];
cis-$N^1$-(5-(4-methoxyquinazolin-6-yl)pyrrolo[2,1-f][1,2,4]triazin-2-yl)-$N^3$-methylcyclobutane-1,3-diamine [1455];
trans-$N^1$-(5-(4-methoxyquinazolin-6-yl)pyrrolo[2,1-f][1,2,4]triazin-2-yl)-$N^3$-methylcyclobutane-1,3-diamine [1456];
cis-$N^1$-(5-(4-methoxyquinazolin-6-yl)pyrrolo[2,1-f][1,2,4]triazin-2-yl)-$N^3$,$N^3$-dimethylcyclobutane-1,3-diamine [1457];
trans-$N^1$-(5-(4-methoxyquinazolin-6-yl)pyrrolo[2,1-f][1,2,4]triazin-2-yl)-$N_3$,$N^3$-dimethylcyclobutane-1,3-diamine [1458];
5-(4-methoxyquinazolin-6-yl)-N-(cis-3-morpholinocyclobutyl)pyrrolo[2,1-f][1,2,4]triazin-2-amine [1459];
5-(4-methoxyquinazolin-6-yl)-N-(trans-3-morpholinocyclobutyl)pyrrolo[2,1-f][1,2,4]triazin-2-amine [1460];
5-(4-methoxyquinazolin-6-yl)-N-(cis-3-(4-methylpiperazin-1-yl)cyclobutyl)pyrrolo[2,1-f][1,2,4] triazin-2-amine [1461];
5-(4-methoxyquinazolin-6-yl)-N-(trans-3-(4-methylpiperazin-1-yl)cyclobutyl)pyrrolo[2,1-f][1,2,4]triazin-2-amine [1462];
N-(4,4-difluorocyclohexyl)-5-(4-methoxyquinazolin-6-yl)pyrrolo[2,1-f][1,2,4]triazin-2-amine [1463];
cis-4-((5-(4-methoxyquinazolin-6-yl)pyrrolo[2,1-f][1,2,4]triazin-2-yl)amino)cyclohexan-1-ol [1464];
(1s,4s)-4-((5-(4-methoxyquinazolin-6-yl)pyrrolo[2,1-f][1,2,4]triazin-2-yl)amino)-1-methylcyclohexan-1-ol [1465];
N-(cis-4-methoxycyclohexyl)-5-(4-methoxyquinazolin-6-yl)pyrrolo[2,1-f][1,2,4]triazin-2-amine [1466];
N-(trans-4-methoxycyclohexyl)-5-(4-methoxyquinazolin-6-yl)pyrrolo[2,1-f][1,2,4]triazin-2-amine [1467];
N-(cis-4-(difluoromethoxy)cyclohexyl)-5-(4-methoxyquinazolin-6-yl)pyrrolo[2,1-f][1,2,4]triazin-2-amine [1468];
N-(trans-4-(difluoromethoxy)cyclohexyl)-5-(4-methoxyquinazolin-6-yl)pyrrolo[2,1-f][1,2,4] triazin-2-amine [1469];
N-(cis-4-ethoxycyclohexyl)-5-(4-methoxyquinazolin-6-yl)pyrrolo[2,1-f][1,2,4]triazin-2-amine [1470];
N-(trans-4-ethoxycyclohexyl)-5-(4-methoxyquinazolin-6-yl)pyrrolo[2,1-f][1,2,4]triazin-2-amine [1471];
N-(cis-4-(2-methoxyethoxy)cyclohexyl)-5-(4-methoxyquinazolin-6-yl)pyrrolo[2,1-f][1,2,4] triazin-2-amine [1472];

N-(trans-4-(2-methoxyethoxy)cyclohexyl)-5-(4-methoxyquinazolin-6-yl)pyrrolo[2,1-f][1,2,4] triazin-2-amine [1473];

cis-$N^1$-(5-(4-methoxyquinazolin-6-yl)pyrrolo[2,1-f][1,2,4]triazin-2-yl)cyclohexane-1,4-diamine [1474];

trans-$N^1$-(5-(4-methoxyquinazolin-6-yl)pyrrolo[2,1-f][1,2,4]triazin-2-yl)cyclohexane-1,4-diamine [1475];

cis-$N^1$-(5-(4-methoxyquinazolin-6-yl)pyrrolo[2,1-f][1,2,4]triazin-2-yl)-$N^4$-methylcyclohexane-1,4-diamine [1476];

trans-$N^1$-(5-(4-methoxyquinazolin-6-yl)pyrrolo[2,1-f][1,2,4]triazin-2-yl)-$N^4$-methylcyclohexane-1,4-diamine [1477];

cis-$N^1$-(5-(4-methoxyquinazolin-6-yl)pyrrolo[2,1-f][1,2,4]triazin-2-yl)-$N^4$,$N^4$-dimethylcyclohexane-1,4-diamine [1478];

trans-$N^1$-(5-(4-methoxyquinazolin-6-yl)pyrrolo[2,1-f][1,2,4]triazin-2-yl)-$N^4$,$N^4$-dimethylcyclohexane-1,4-diamine [1479];

5-(4-methoxyquinazolin-6-yl)-N-(cis-4-morpholinocyclohexyl)pyrrolo[2,1-f][1,2,4]triazin-2-amine [1480];

5-(4-methoxyquinazolin-6-yl)-N-(trans-4-morpholinocyclohexyl)pyrrolo[2,1-f][1,2,4]triazin-2-amine [1481];

5-(4-methoxyquinazolin-6-yl)-N-(cis-4-(4-methylpiperazin-1-yl)cyclohexyl)pyrrolo[2,1-f][1,2,4] triazin-2-amine [1482];

5-(4-methoxyquinazolin-6-yl)-N-(trans-4-(4-methylpiperazin-1-yl)cyclohexyl)pyrrolo[2,1-f][1,2,4]triazin-2-amine [1483];

5-(4-methoxyquinazolin-6-yl)-N-(1-methylazetidin-3-yl)pyrrolo[2,1-f][1,2,4]triazin-2-amine [1484];

5-(4-methoxyquinazolin-6-yl)-N-(oxetan-3-yl)pyrrolo[2,1-f][1,2,4]triazin-2-amine [1485];

5-(4-methoxyquinazolin-6-yl)-N-(1-methylpiperidin-4-yl)pyrrolo[2,1-f][1,2,4]triazin-2-amine [1486];

5-(4-methoxyquinazolin-6-yl)-N-(tetrahydro-2H-pyran-4-yl)pyrrolo[2,1-f][1,2,4]triazin-2-amine [1487];

N-(6,6-difluorospiro[3.3]heptan-2-yl)-5-(4-methoxyquinazolin-6-yl)pyrrolo[2,1-f][1,2,4]triazin-2-amine [1488];

5-(4-methoxyquinazolin-6-yl)-N-(2-oxaspiro[3.3]heptan-6-yl)pyrrolo[2,1-f][1,2,4]triazin-2-amine [1489];

5-(4-methoxyquinazolin-6-yl)-N-(2-methyl-2-azaspiro[3.3]heptan-6-yl)pyrrolo[2,1-f][1,2,4] triazin-2-amine [1490];

5-(4-methoxyquinazolin-6-yl)-N-(1-methyl-1H-pyrazol-4-yl)pyrrolo[2,1-f][1,2,4]triazin-2-amine [1491];

N-isopropyl-5-(1,8-naphthyridin-3-yl)pyrrolo[2,1-f][1,2,4]triazin-2-amine [1492];

N-isobutyl-5-(1,8-naphthyridin-3-yl)pyrrolo[2,1-f][1,2,4]triazin-2-amine [1493];

N-(2-fluoro-2-methylpropyl)-5-(1,8-naphthyridin-3-yl)pyrrolo[2,1-f][1,2,4]triazin-2-amine [1494];

N-(2,2-difluoropropyl)-5-(1,8-naphthyridin-3-yl)pyrrolo[2,1-f][1,2,4]triazin-2-amine [1495];

5-(1,8-naphthyridin-3-yl)-N-(2,2,2-trifluoroethyl)pyrrolo[2,1-f][1,2,4]triazin-2-amine [1496];

(R)-5-(1,8-naphthyridin-3-yl)-N-(1,1,1-trifluoropropan-2-yl)pyrrolo[2,1-f][1,2,4]triazin-2-amine [1497];

5-(1,8-naphthyridin-3-yl)-N-(3,3,3-trifluoropropyl)pyrrolo[2,1-f][1,2,4]triazin-2-amine [1498];

5-(1,8-naphthyridin-3-yl)-N-(3,3,3-trifluoro-2,2-dimethylpropyl)pyrrolo[2,1-f][1,2,4]triazin-2-amine [1499]; and N-(2-methoxyethyl)-5-(1,8-naphthyridin-3-yl)pyrrolo[2,1-f][1,2,4]triazin-2-amine [1500]; or a pharmaceutically acceptable salt thereof.

11. The compound of claim 1, wherein the compound of Formula I is selected from the group consisting of (R)—N-(1-methoxypropan-2-yl)-5-(1,8-naphthyridin-3-yl)pyrrolo[2,1-f][1,2,4]triazin-2-amine [1501];

N-(2-isopropoxyethyl)-5-(1,8-naphthyridin-3-yl)pyrrolo[2,1-f][1,2,4]triazin-2-amine [1502];

N-((1-methylcyclopropyl)methyl)-5-(1,8-naphthyridin-3-yl)pyrrolo[2,1-f][1,2,4]triazin-2-amine [1503];

5-(1,8-naphthyridin-3-yl)-N-((1-(trifluoromethyl)cyclopropyl)methyl)pyrrolo[2,1-f][1,2,4]triazin-2-amine [1504];

N-((1-fluorocyclobutyl)methyl)-5-(1,8-naphthyridin-3-yl)pyrrolo[2,1-f][1,2,4]triazin-2-amine [1505];

N-((3-fluorooxetan-3-yl)methyl)-5-(1,8-naphthyridin-3-yl)pyrrolo[2,1-f][1,2,4]triazin-2-amine [1506];

N-(cyclopropylmethyl)-5-(1,8-naphthyridin-3-yl)pyrrolo[2,1-f][1,2,4]triazin-2-amine [1507];

(S)—N-(1-cyclopropylethyl)-5-(1,8-naphthyridin-3-yl)pyrrolo[2,1-f][1,2,4]triazin-2-amine [1508];

(R)—N-(1-cyclopropylethyl)-5-(1,8-naphthyridin-3-yl)pyrrolo[2,1-f][1,2,4]triazin-2-amine [1509];

N-(2-cyclopropyl-2,2-difluoroethyl)-5-(1,8-naphthyridin-3-yl)pyrrolo[2,1-f][1,2,4]triazin-2-amine [1510];

5-(1,8-naphthyridin-3-yl)-N-(oxetan-3-ylmethyl)pyrrolo[2,1-f][1,2,4]triazin-2-amine [1511];

5-(1,8-naphthyridin-3-yl)-N-((tetrahydrofuran-2-yl)methyl)pyrrolo[2,1-f][1,2,4]triazin-2-amine [1512];

N-cyclobutyl-5-(1,8-naphthyridin-3-yl)pyrrolo[2,1-f][1,2,4]triazin-2-amine [1513];

N-(3,3-difluorocyclobutyl)-5-(1,8-naphthyridin-3-yl)pyrrolo[2,1-f][1,2,4]triazin-2-amine [1514];

N-(3,3-dimethylcyclobutyl)-5-(1,8-naphthyridin-3-yl)pyrrolo[2,1-f][1,2,4]triazin-2-amine [1515];

3-((5-(1,8-naphthyridin-3-yl)pyrrolo[2,1-f][1,2,4]triazin-2-yl)amino)-1-methylcyclobutan-1-ol [1516];

N-(cis-3-methoxycyclobutyl)-5-(1,8-naphthyridin-3-yl)pyrrolo[2,1-f][1,2,4]triazin-2-amine [1517];

N-(trans-3-methoxycyclobutyl)-5-(1,8-naphthyridin-3-yl)pyrrolo[2,1-f][1,2,4]triazin-2-amine [1518];

N-(trans-3-(methoxymethyl)cyclobutyl)-5-(1,8-naphthyridin-3-yl)pyrrolo[2,1-f][1,2,4]triazin-2-amine [1519];

N-(cis-3-ethoxycyclobutyl)-5-(1,8-naphthyridin-3-yl)pyrrolo[2,1-f][1,2,4]triazin-2-amine [1520];

N-(trans-3-ethoxycyclobutyl)-5-(1,8-naphthyridin-3-yl)pyrrolo[2,1-f][1,2,4]triazin-2-amine [1521];

N-(cis-3-(2-methoxyethoxy)cyclobutyl)-5-(1,8-naphthyridin-3-yl)pyrrolo[2,1-f][1,2,4]triazin-2-amine [1522];

N-(trans-3-(2-methoxyethoxy)cyclobutyl)-5-(1,8-naphthyridin-3-yl)pyrrolo[2,1-f][1,2,4]triazin-2-amine [1523];

cis-$N^1$-(5-(1,8-naphthyridin-3-yl)pyrrolo[2,1-f][1,2,4]triazin-2-yl)cyclobutane-1,3-diamine [1524];

trans-$N^1$-(5-(1,8-naphthyridin-3-yl)pyrrolo[2,1-f][1,2,4]triazin-2-yl)cyclobutane-1,3-diamine [1525];

cis-$N^1$-(5-(1,8-naphthyridin-3-yl)pyrrolo[2,1-f][1,2,4]triazin-2-yl)-$N^3$-methylcyclobutane-1,3-diamine [1526];

trans-$N^1$-(5-(1,8-naphthyridin-3-yl)pyrrolo[2,1-f][1,2,4]triazin-2-yl)-$N^3$-methylcyclobutane-1,3-diamine [1527];

cis-$N^1$-(5-(1,8-naphthyridin-3-yl)pyrrolo[2,1-f][1,2,4]triazin-2-yl)-$N_3$,$N^3$-dimethylcyclobutane-1,3-diamine [1528];

trans-$N^1$-(5-(1,8-naphthyridin-3-yl)pyrrolo[2,1-f][1,2,4]triazin-2-yl)-$N^3$,$N^3$-dimethylcyclobutane-1,3-diamine [1529];

N-(cis-3-morpholinocyclobutyl)-5-(1,8-naphthyridin-3-yl)pyrrolo[2,1-f][1,2,4]triazin-2-amine [1530];

N-(trans-3-morpholinocyclobutyl)-5-(1,8-naphthyridin-3-yl)pyrrolo[2,1-f][1,2,4]triazin-2-amine [1531];
N-(cis-3-(4-methylpiperazin-1-yl)cyclobutyl)-5-(1,8-naphthyridin-3-yl)pyrrolo[2,1-f][1,2,4] triazin-2-amine [1532];
N-(trans-3-(4-methylpiperazin-1-yl)cyclobutyl)-5-(1,8-naphthyridin-3-yl)pyrrolo[2,1-f][1,2,4] triazin-2-amine [1533];
N-(4,4-difluorocyclohexyl)-5-(1,8-naphthyridin-3-yl)pyrrolo[2,1-f][1,2,4]triazin-2-amine [1534];
cis-4-((5-(1,8-naphthyridin-3-yl)pyrrolo[2,1-f][1,2,4]triazin-2-yl)amino)cyclohexan-1-ol [1535];
(1s,4s)-4-((5-(1,8-naphthyridin-3-yl)pyrrolo[2,1-f][1,2,4]triazin-2-yl)amino)-1-methylcyclohexan-1-ol [1536];
N-(cis-4-methoxycyclohexyl)-5-(1,8-naphthyridin-3-yl)pyrrolo[2,1-f][1,2,4]triazin-2-amine [1537];
N-(trans-4-methoxycyclohexyl)-5-(1,8-naphthyridin-3-yl)pyrrolo[2,1-f][1,2,4]triazin-2-amine [1538];
N-(cis-4-(difluoromethoxy)cyclohexyl)-5-(1,8-naphthyridin-3-yl)pyrrolo[2,1-f][1,2,4]triazin-2-amine [1539];
N-(trans-4-(difluoromethoxy)cyclohexyl)-5-(1,8-naphthyridin-3-yl)pyrrolo[2,1-f][1,2,4]triazin-2-amine [1540];
N-(cis-4-ethoxycyclohexyl)-5-(1,8-naphthyridin-3-yl)pyrrolo[2,1-f][1,2,4]triazin-2-amine [1541];
N-(trans-4-ethoxycyclohexyl)-5-(1,8-naphthyridin-3-yl)pyrrolo[2,1-f][1,2,4]triazin-2-amine [1542];
N-(cis-4-(2-methoxyethoxy)cyclohexyl)-5-(1,8-naphthyridin-3-yl)pyrrolo[2,1-f][1,2,4]triazin-2-amine [1543];
N-(trans-4-(2-methoxyethoxy)cyclohexyl)-5-(1,8-naphthyridin-3-yl)pyrrolo[2,1-f][1,2,4]triazin-2-amine [1544];
cis-$N^1$-(5-(1,8-naphthyridin-3-yl)pyrrolo[2,1-f][1,2,4]triazin-2-yl)cyclohexane-1,4-diamine [1545];
trans-$N^1$-(5-(1,8-naphthyridin-3-yl)pyrrolo[2,1-f][1,2,4]triazin-2-yl)cyclohexane-1,4-diamine [1546];
cis-$N^1$-(5-(1,8-naphthyridin-3-yl)pyrrolo[2,1-f][1,2,4]triazin-2-yl)-$N^4$-methylcyclohexane-1,4-diamine [1547];
trans-$N^1$-(5-(1,8-naphthyridin-3-yl)pyrrolo[2,1-f][1,2,4]triazin-2-yl)-$N^4$-methylcyclohexane-1,4-diamine [1548];
cis-$N^1$-(5-(1,8-naphthyridin-3-yl)pyrrolo[2,1-f][1,2,4]triazin-2-yl)-$N^4$,$N^4$-dimethylcyclohexane-1,4-diamine [1549];
trans-$N^1$-(5-(1,8-naphthyridin-3-yl)pyrrolo[2,1-f][1,2,4]triazin-2-yl)-$N^4$,$N^4$-dimethylcyclohexane-1,4-diamine [1550];
N-(cis-4-morpholinocyclohexyl)-5-(1,8-naphthyridin-3-yl)pyrrolo[2,1-f][1,2,4]triazin-2-amine [1551];
N-(trans-4-morpholinocyclohexyl)-5-(1,8-naphthyridin-3-yl)pyrrolo[2,1-f][1,2,4]triazin-2-amine [1552];
N-(cis-4-(4-methylpiperazin-1-yl)cyclohexyl)-5-(1,8-naphthyridin-3-yl)pyrrolo[2,1-f][1,2,4] triazin-2-amine [1553];
N-(trans-4-(4-methylpiperazin-1-yl)cyclohexyl)-5-(1,8-naphthyridin-3-yl)pyrrolo[2,1-f][1,2,4] triazin-2-amine [1554];
N-(1-methylazetidin-3-yl)-5-(1,8-naphthyridin-3-yl)pyrrolo[2,1-f][1,2,4]triazin-2-amine [1555];
5-(1,8-naphthyridin-3-yl)-N-(oxetan-3-yl)pyrrolo[2,1-f][1,2,4]triazin-2-amine [1556];
N-(1-methylpiperidin-4-yl)-5-(1,8-naphthyridin-3-yl)pyrrolo[2,1-f][1,2,4]triazin-2-amine [1557];
5-(1,8-naphthyridin-3-yl)-N-(tetrahydro-2H-pyran-4-yl)pyrrolo[2,1-f][1,2,4]triazin-2-amine [1558];
N-(6,6-difluorospiro[3.3]heptan-2-yl)-5-(1,8-naphthyridin-3-yl)pyrrolo[2,1-f][1,2,4]triazin-2-amine [1559];
5-(1,8-naphthyridin-3-yl)-N-(2-oxaspiro[3.3]heptan-6-yl)pyrrolo[2,1-f][1,2,4]triazin-2-amine [1560];
N-(2-methyl-2-azaspiro[3.3]heptan-6-yl)-5-(1,8-naphthyridin-3-yl)pyrrolo[2,1-f][1,2,4]triazin-2-amine [1561];
N-(1-methyl-1H-pyrazol-4-yl)-5-(1,8-naphthyridin-3-yl)pyrrolo[2,1-f][1,2,4]triazin-2-amine [1562];
N-isopropyl-5-(pyrido[2,3-b]pyrazin-7-yl)pyrrolo[2,1-f][1,2,4]triazin-2-amine [1563];
N-isobutyl-5-(pyrido[2,3-b]pyrazin-7-yl)pyrrolo[2,1-f][1,2,4]triazin-2-amine [1564];
N-(2-fluoro-2-methylpropyl)-5-(pyrido[2,3-b]pyrazin-7-yl)pyrrolo[2,1-f][1,2,4]triazin-2-amine [1565];
N-(2,2-difluoropropyl)-5-(pyrido[2,3-b]pyrazin-7-yl)pyrrolo[2,1-f][1,2,4]triazin-2-amine [1566];
5-(pyrido[2,3-b]pyrazin-7-yl)-N-(2,2,2-trifluoroethyl)pyrrolo[2,1-f][1,2,4]triazin-2-amine [1567];
(R)-5-(pyrido[2,3-b]pyrazin-7-yl)-N-(1,1,1-trifluoropropan-2-yl)pyrrolo[2,1-f][1,2,4]triazin-2-amine [1568];
5-(pyrido[2,3-b]pyrazin-7-yl)-N-(3,3,3-trifluoropropyl)pyrrolo[2,1-f][1,2,4]triazin-2-amine [1569];
5-(pyrido[2,3-b]pyrazin-7-yl)-N-(3,3,3-trifluoro-2,2-dimethylpropyl)pyrrolo[2,1-f][1,2,4]triazin-2-amine [1570];
N-(2-methoxyethyl)-5-(pyrido[2,3-b]pyrazin-7-yl)pyrrolo[2,1-f][1,2,4]triazin-2-amine [1571];
(R)—N-(1-methoxypropan-2-yl)-5-(pyrido[2,3-b]pyrazin-7-yl)pyrrolo[2,1-f][1,2,4]triazin-2-amine [1572];
N-(2-isopropoxyethyl)-5-(pyrido[2,3-b]pyrazin-7-yl)pyrrolo[2,1-f][1,2,4]triazin-2-amine [1573];
N-((1-methylcyclopropyl)methyl)-5-(pyrido[2,3-b]pyrazin-7-yl)pyrrolo[2,1-f][1,2,4]triazin-2-amine [1574];
5-(pyrido[2,3-b]pyrazin-7-yl)-N-((1-(trifluoromethyl)cyclopropyl)methyl)pyrrolo[2,1-f][1,2,4] triazin-2-amine compound with methane (1:1) [1575];
N-((1-fluorocyclobutyl)methyl)-5-(pyrido[2,3-b]pyrazin-7-yl)pyrrolo[2,1-f][1,2,4]triazin-2-amine [1576];
N-((3-fluorooxetan-3-yl)methyl)-5-(pyrido[2,3-b]pyrazin-7-yl)pyrrolo[2,1-f][1,2,4]triazin-2-amine [1577];
N-(cyclopropylmethyl)-5-(pyrido[2,3-b]pyrazin-7-yl)pyrrolo[2,1-f][1,2,4]triazin-2-amine [1578];
(S)—N-(1-cyclopropylethyl)-5-(pyrido[2,3-b]pyrazin-7-yl)pyrrolo[2,1-f][1,2,4]triazin-2-amine [1579];
(R)—N-(1-cyclopropylethyl)-5-(pyrido[2,3-b]pyrazin-7-yl)pyrrolo[2,1-f][1,2,4]triazin-2-amine [1580];
N-(2-cyclopropyl-2,2-difluoroethyl)-5-(pyrido[2,3-b]pyrazin-7-yl)pyrrolo[2,1-f][1,2,4]triazin-2-amine [1581];
N-(oxetan-3-ylmethyl)-5-(pyrido[2,3-b]pyrazin-7-yl)pyrrolo[2,1-f][1,2,4]triazin-2-amine [1582];
5-(pyrido[2,3-b]pyrazin-7-yl)-N-((tetrahydrofuran-2-yl)methyl)pyrrolo[2,1-f][1,2,4]triazin-2-amine [1583];
N-cyclobutyl-5-(pyrido[2,3-b]pyrazin-7-yl)pyrrolo[2,1-f][1,2,4]triazin-2-amine [1584];
N-(3,3-difluorocyclobutyl)-5-(pyrido[2,3-b]pyrazin-7-yl)pyrrolo[2,1-f][1,2,4]triazin-2-amine [1585];
N-(3,3-dimethylcyclobutyl)-5-(pyrido[2,3-b]pyrazin-7-yl)pyrrolo[2,1-f][1,2,4]triazin-2-amine [1586];
1-methyl-3-((5-(pyrido[2,3-b]pyrazin-7-yl)pyrrolo[2,1-f][1,2,4]triazin-2-yl)amino)cyclobutan-1-ol [1587];
N-(cis-3-methoxycyclobutyl)-5-(pyrido[2,3-b]pyrazin-7-yl)pyrrolo[2,1-f][1,2,4]triazin-2-amine [1588];
N-(trans-3-methoxycyclobutyl)-5-(pyrido[2,3-b]pyrazin-7-yl)pyrrolo[2,1-f][1,2,4]triazin-2-amine [1589];

N-(trans-3-(methoxymethyl)cyclobutyl)-5-(pyrido[2,3-b]pyrazin-7-yl)pyrrolo[2,1-f][1,2,4] triazin-2-amine [1590];

N-(cis-3-ethoxycyclobutyl)-5-(pyrido[2,3-b]pyrazin-7-yl)pyrrolo[2,1-f][1,2,4]triazin-2-amine [1591];

N-(trans-3-ethoxycyclobutyl)-5-(pyrido[2,3-b]pyrazin-7-yl)pyrrolo[2,1-f][1,2,4]triazin-2-amine [1592];

N-(cis-3-(2-methoxyethoxy)cyclobutyl)-5-(pyrido[2,3-b]pyrazin-7-yl)pyrrolo[2,1-f][1,2,4]triazin-2-amine [1593];

N-(trans-3-(2-methoxyethoxy)cyclobutyl)-5-(pyrido[2,3-b]pyrazin-7-yl)pyrrolo[2,1-f][1,2,4] triazin-2-amine [1594];

cis-$N^1$-(5-(pyrido[2,3-b]pyrazin-7-yl)pyrrolo[2,1-f][1,2,4]triazin-2-yl)cyclobutane-1,3-diamine [1595];

trans-$N^1$-(5-(pyrido[2,3-b]pyrazin-7-yl)pyrrolo[2,1-f][1,2,4]triazin-2-yl)cyclobutane-1,3-diamine [1596];

cis-$N^1$-methyl-$N^3$-(5-(pyrido[2,3-b]pyrazin-7-yl)pyrrolo[2,1-f][1,2,4]triazin-2-yl)cyclobutane-1,3-diamine [1597];

trans-$N^1$-methyl-$N^3$-(5-(pyrido[2,3-b]pyrazin-7-yl)pyrrolo[2,1-f][1,2,4]triazin-2-yl)cyclobutane-1,3-diamine [1598];

cis-$N^1$,$N^1$-dimethyl-$N^3$-(5-(pyrido[2,3-b]pyrazin-7-yl)pyrrolo[2,1-f][1,2,4]triazin-2-yl) cyclobutane-1,3-diamine [1599];

trans-$N^1$,$N^1$-dimethyl-$N^3$-(5-(pyrido[2,3-b]pyrazin-7-yl)pyrrolo[2,1-f][1,2,4]triazin-2-yl) cyclobutane-1,3-diamine [1600];

N-(cis-3-morpholinocyclobutyl)-5-(pyrido[2,3-b]pyrazin-7-yl)pyrrolo[2,1-f][1,2,4]triazin-2-amine [1601];

N-(trans-3-morpholinocyclobutyl)-5-(pyrido[2,3-b]pyrazin-7-yl)pyrrolo[2,1-f][1,2,4]triazin-2-amine [1602];

N-(cis-3-(4-methylpiperazin-1-yl)cyclobutyl)-5-(pyrido[2,3-b]pyrazin-7-yl)pyrrolo[2,1-f][1,2,4] triazin-2-amine [1603];

N-(trans-3-(4-methylpiperazin-1-yl)cyclobutyl)-5-(pyrido[2,3-b]pyrazin-7-yl)pyrrolo[2,1-f][1,2,4]triazin-2-amine [1604];

N-(4,4-difluorocyclohexyl)-5-(pyrido[2,3-b]pyrazin-7-yl)pyrrolo[2,1-f][1,2,4]triazin-2-amine [1605];

cis-4-((5-(pyrido[2,3-b]pyrazin-7-yl)pyrrolo[2,1-f][1,2,4]triazin-2-yl)amino)cyclohexan-1-ol [1606];

(1s,4s)-1-methyl-4-((5-(pyrido[2,3-b]pyrazin-7-yl)pyrrolo[2,1-f][1,2,4]triazin-2-yl)amino) cyclohexan-1-ol [1607];

N-(cis-4-methoxycyclohexyl)-5-(pyrido[2,3-b]pyrazin-7-yl)pyrrolo[2,1-f][1,2,4]triazin-2-amine [1608];

N-(trans-4-methoxycyclohexyl)-5-(pyrido[2,3-b]pyrazin-7-yl)pyrrolo[2,1-f][1,2,4]triazin-2-amine [1609];

N-(cis-4-(difluoromethoxy)cyclohexyl)-5-(pyrido[2,3-b]pyrazin-7-yl)pyrrolo[2,1-f][1,2,4]triazin-2-amine [1610];

N-(trans-4-(difluoromethoxy)cyclohexyl)-5-(pyrido[2,3-b]pyrazin-7-yl)pyrrolo[2,1-f][1,2,4] triazin-2-amine [1611];

N-(cis-4-ethoxycyclohexyl)-5-(pyrido[2,3-b]pyrazin-7-yl)pyrrolo[2,1-f][1,2,4]triazin-2-amine [1612];

N-(trans-4-ethoxycyclohexyl)-5-(pyrido[2,3-b]pyrazin-7-yl)pyrrolo[2,1-f][1,2,4]triazin-2-amine [1613];

N-(cis-4-(2-methoxyethoxy)cyclohexyl)-5-(pyrido[2,3-b]pyrazin-7-yl)pyrrolo[2,1-f][1,2,4]triazin-2-amine [1614];

N-(trans-4-(2-methoxyethoxy)cyclohexyl)-5-(pyrido[2,3-b]pyrazin-7-yl)pyrrolo[2,1-f][1,2,4] triazin-2-amine [1615];

cis-$N^1$-(5-(pyrido[2,3-b]pyrazin-7-yl)pyrrolo[2,1-f][1,2,4]triazin-2-yl)cyclohexane-1,4-diamine [1616];

trans-$N^1$-(5-(pyrido[2,3-b]pyrazin-7-yl)pyrrolo[2,1-f][1,2,4]triazin-2-yl)cyclohexane-1,4-diamine [1617];

cis-$N^1$-methyl-$N^4$-(5-(pyrido[2,3-b]pyrazin-7-yl)pyrrolo[2,1-f][1,2,4]triazin-2-yl)cyclohexane-1,4-diamine [1618];

trans-$N^1$-methyl-$N^4$-(5-(pyrido[2,3-b]pyrazin-7-yl)pyrrolo[2,1-f][1,2,4]triazin-2-yl)cyclohexane-1,4-diamine [1619];

cis-$N^1$,$N^1$-dimethyl-$N^4$-(5-(pyrido[2,3-b]pyrazin-7-yl)pyrrolo[2,1-f][1,2,4]triazin-2-yl) cyclohexane-1,4-diamine [1620];

trans-$N^1$,$N^1$-dimethyl-$N^4$-(5-(pyrido[2,3-b]pyrazin-7-yl)pyrrolo[2,1-f][1,2,4]triazin-2-yl) cyclohexane-1,4-diamine [1621];

N-(cis-4-morpholinocyclohexyl)-5-(pyrido[2,3-b]pyrazin-7-yl)pyrrolo[2,1-f][1,2,4]triazin-2-amine [1622];

N-(trans-4-morpholinocyclohexyl)-5-(pyrido[2,3-b]pyrazin-7-yl)pyrrolo[2,1-f][1,2,4]triazin-2-amine [1623];

N-(cis-4-(4-methylpiperazin-1-yl)cyclohexyl)-5-(pyrido[2,3-b]pyrazin-7-yl)pyrrolo[2,1-f][1,2,4] triazin-2-amine [1624];

N-(trans-4-(4-methylpiperazin-1-yl)cyclohexyl)-5-(pyrido[2,3-b]pyrazin-7-yl)pyrrolo[2,1-f][1,2,4]triazin-2-amine [1625];

N-(1-methylazetidin-3-yl)-5-(pyrido[2,3-b]pyrazin-7-yl)pyrrolo[2,1-f][1,2,4]triazin-2-amine [1626];

N-(oxetan-3-yl)-5-(pyrido[2,3-b]pyrazin-7-yl)pyrrolo[2,1-f][1,2,4]triazin-2-amine [1627];

N-(1-methylpiperidin-4-yl)-5-(pyrido[2,3-b]pyrazin-7-yl)pyrrolo[2,1-f][1,2,4]triazin-2-amine [1628];

5-(pyrido[2,3-b]pyrazin-7-yl)-N-(tetrahydro-2H-pyran-4-yl)pyrrolo[2,1-f][1,2,4]triazin-2-amine [1629];

N-(6,6-difluorospiro[3.3]heptan-2-yl)-5-(pyrido[2,3-b]pyrazin-7-yl)pyrrolo[2,1-f][1,2,4]triazin-2-amine [1630];

5-(pyrido[2,3-b]pyrazin-7-yl)-N-(2-oxaspiro[3.3]heptan-6-yl)pyrrolo[2,1-f][1,2,4]triazin-2-amine [1631];

N-(2-methyl-2-azaspiro[3.3]heptan-6-yl)-5-(pyrido[2,3-b]pyrazin-7-yl)pyrrolo[2,1-f][1,2,4] triazin-2-amine [1632];

N-(1-methyl-1H-pyrazol-4-yl)-5-(pyrido[2,3-b]pyrazin-7-yl)pyrrolo[2,1-f][1,2,4]triazin-2-amine [1633];

N-isopropyl-5-(1,5-naphthyridin-2-yl)pyrrolo[2,1-f][1,2,4]triazin-2-amine [1634];

N-isobutyl-5-(1,5-naphthyridin-2-yl)pyrrolo[2,1-f][1,2,4]triazin-2-amine [1635];

N-(2-fluoro-2-methylpropyl)-5-(1,5-naphthyridin-2-yl)pyrrolo[2,1-f][1,2,4]triazin-2-amine [1636];

N-(2,2-difluoropropyl)-5-(1,5-naphthyridin-2-yl)pyrrolo[2,1-f][1,2,4]triazin-2-amine [1637];

5-(1,5-naphthyridin-2-yl)-N-(2,2,2-trifluoroethyl)pyrrolo[2,1-f][1,2,4]triazin-2-amine [1638];

(R)-5-(1,5-naphthyridin-2-yl)-N-(1,1,1-trifluoropropan-2-yl)pyrrolo[2,1-f][1,2,4]triazin-2-amine [1639];

5-(1,5-naphthyridin-2-yl)-N-(3,3,3-trifluoropropyl)pyrrolo[2,1-f][1,2,4]triazin-2-amine [1640];

5-(1,5-naphthyridin-2-yl)-N-(3,3,3-trifluoro-2,2-dimethylpropyl)pyrrolo[2,1-f][1,2,4]triazin-2-amine [1641];

N-(2-methoxyethyl)-5-(1,5-naphthyridin-2-yl)pyrrolo[2,1-f][1,2,4]triazin-2-amine [1642];

(R)—N-(1-methoxypropan-2-yl)-5-(1,5-naphthyridin-2-yl)pyrrolo[2,1-f][1,2,4]triazin-2-amine [1643];

N-(2-isopropoxyethyl)-5-(1,5-naphthyridin-2-yl)pyrrolo[2,1-f][1,2,4]triazin-2-amine [1644];

N-((1-methylcyclopropyl)methyl)-5-(1,5-naphthyridin-2-yl)pyrrolo[2,1-f][1,2,4]triazin-2-amine [1645];

5-(1,5-naphthyridin-2-yl)-N-((1-(trifluoromethyl)cyclopropyl)methyl)pyrrolo[2,1-f][1,2,4] triazin-2-amine [1646];

N-((1-fluorocyclobutyl)methyl)-5-(1,5-naphthyridin-2-yl)pyrrolo[2,1-f][1,2,4]triazin-2-amine [1647];

N-((3-fluorooxetan-3-yl)methyl)-5-(1,5-naphthyridin-2-yl)pyrrolo[2,1-f][1,2,4]triazin-2-amine [1648];

N-(cyclopropylmethyl)-5-(1,5-naphthyridin-2-yl)pyrrolo[2,1-f][1,2,4]triazin-2-amine [1649];

(S)—N-(1-cyclopropylethyl)-5-(1,5-naphthyridin-2-yl)pyrrolo[2,1-f][1,2,4]triazin-2-amine [1650];

(R)—N-(1-cyclopropylethyl)-5-(1,5-naphthyridin-2-yl)pyrrolo[2,1-f][1,2,4]triazin-2-amine [1651];

N-(2-cyclopropyl-2,2-difluoroethyl)-5-(1,5-naphthyridin-2-yl)pyrrolo[2,1-f][1,2,4]triazin-2-amine [1652];

5-(1,5-naphthyridin-2-yl)-N-(oxetan-3-ylmethyl)pyrrolo[2,1-f][1,2,4]triazin-2-amine [1653];

5-(1,5-naphthyridin-2-yl)-N-((tetrahydrofuran-2-yl)methyl)pyrrolo[2,1-f][1,2,4]triazin-2-amine [1654];

N-cyclobutyl-5-(1,5-naphthyridin-2-yl)pyrrolo[2,1-f][1,2,4]triazin-2-amine [1655];

N-(3,3-difluorocyclobutyl)-5-(1,5-naphthyridin-2-yl)pyrrolo[2,1-f][1,2,4]triazin-2-amine [1656];

N-(3,3-dimethylcyclobutyl)-5-(1,5-naphthyridin-2-yl)pyrrolo[2,1-f][1,2,4]triazin-2-amine [1657];

3-((5-(1,5-naphthyridin-2-yl)pyrrolo[2,1-f][1,2,4]triazin-2-yl)amino)-1-methylcyclobutan-1-ol [1658];

N-(cis-3-methoxycyclobutyl)-5-(1,5-naphthyridin-2-yl)pyrrolo[2,1-f][1,2,4]triazin-2-amine [1659];

N-(trans-3-methoxycyclobutyl)-5-(1,5-naphthyridin-2-yl)pyrrolo[2,1-f][1,2,4]triazin-2-amine [1660];

N-(trans-3-(methoxymethyl)cyclobutyl)-5-(1,5-naphthyridin-2-yl)pyrrolo[2,1-f][1,2,4]triazin-2-amine [1661];

N-(cis-3-ethoxycyclobutyl)-5-(1,5-naphthyridin-2-yl)pyrrolo[2,1-f][1,2,4]triazin-2-amine [1662];

N-(trans-3-ethoxycyclobutyl)-5-(1,5-naphthyridin-2-yl)pyrrolo[2,1-f][1,2,4]triazin-2-amine [1663];

N-(cis-3-(2-methoxyethoxy)cyclobutyl)-5-(1,5-naphthyridin-2-yl)pyrrolo[2,1-f][1,2,4]triazin-2-amine [1664];

N-(trans-3-(2-methoxyethoxy)cyclobutyl)-5-(1,5-naphthyridin-2-yl)pyrrolo[2,1-f][1,2,4]triazin-2-amine [1665];

cis-$N^1$-(5-(1,5-naphthyridin-2-yl)pyrrolo[2,1-f][1,2,4]triazin-2-yl)cyclobutane-1,3-diamine [1666];

trans-$N^1$-(5-(1,5-naphthyridin-2-yl)pyrrolo[2,1-f][1,2,4]triazin-2-yl)cyclobutane-1,3-diamine [1667];

cis-$N^1$-(5-(1,5-naphthyridin-2-yl)pyrrolo[2,1-f][1,2,4]triazin-2-yl)-$N^3$-methylcyclobutane-1,3-diamine [1668];

trans-$N^1$-(5-(1,5-naphthyridin-2-yl)pyrrolo[2,1-f][1,2,4]triazin-2-yl)-$N^3$-methylcyclobutane-1,3-diamine [1669];

cis-$N^1$-(5-(1,5-naphthyridin-2-yl)pyrrolo[2,1-f][1,2,4]triazin-2-yl)-$N^3$,$N^3$-dimethylcyclobutane-1,3-diamine [1670];

trans-$N^1$-(5-(1,5-naphthyridin-2-yl)pyrrolo[2,1-f][1,2,4]triazin-2-yl)-$N^3$,$N^3$-dimethylcyclobutane-1,3-diamine [1671];

N-(cis-3-morpholinocyclobutyl)-5-(1,5-naphthyridin-2-yl)pyrrolo[2,1-f][1,2,4]triazin-2-amine [1672];

N-(trans-3-morpholinocyclobutyl)-5-(1,5-naphthyridin-2-yl)pyrrolo[2,1-f][1,2,4]triazin-2-amine [1673];

N-(cis-3-(4-methylpiperazin-1-yl)cyclobutyl)-5-(1,5-naphthyridin-2-yl)pyrrolo[2,1-f][1,2,4] triazin-2-amine [1674];

N-(trans-3-(4-methylpiperazin-1-yl)cyclobutyl)-5-(1,5-naphthyridin-2-yl)pyrrolo[2,1-f][1,2,4] triazin-2-amine [1675];

N-(4,4-difluorocyclohexyl)-5-(1,5-naphthyridin-2-yl)pyrrolo[2,1-f][1,2,4]triazin-2-amine [1676];

cis-4-((5-(1,5-naphthyridin-2-yl)pyrrolo[2,1-f][1,2,4]triazin-2-yl)amino)cyclohexan-1-ol [1677];

(1s,4s)-4-((5-(1,5-naphthyridin-2-yl)pyrrolo[2,1-f][1,2,4]triazin-2-yl)amino)-1-methylcyclohexan-1-ol [1678];

N-(cis-4-methoxycyclohexyl)-5-(1,5-naphthyridin-2-yl)pyrrolo[2,1-f][1,2,4]triazin-2-amine [1679];

N-(trans-4-methoxycyclohexyl)-5-(1,5-naphthyridin-2-yl)pyrrolo[2,1-f][1,2,4]triazin-2-amine [1680];

N-(cis-4-(difluoromethoxy)cyclohexyl)-5-(1,5-naphthyridin-2-yl)pyrrolo[2,1-f][1,2,4]triazin-2-amine [1681];

N-(trans-4-(difluoromethoxy)cyclohexyl)-5-(1,5-naphthyridin-2-yl)pyrrolo[2,1-f][1,2,4]triazin-2-amine [1682];

N-(cis-4-ethoxycyclohexyl)-5-(1,5-naphthyridin-2-yl)pyrrolo[2,1-f][1,2,4]triazin-2-amine [1683];

N-(trans-4-ethoxycyclohexyl)-5-(1,5-naphthyridin-2-yl)pyrrolo[2,1-f][1,2,4]triazin-2-amine [1684];

N-(cis-4-(2-methoxyethoxy)cyclohexyl)-5-(1,5-naphthyridin-2-yl)pyrrolo[2,1-f][1,2,4]triazin-2-amine [1685];

N-(trans-4-(2-methoxyethoxy)cyclohexyl)-5-(1,5-naphthyridin-2-yl)pyrrolo[2,1-f][1,2,4]triazin-2-amine [1686];

cis-$N^1$-(5-(1,5-naphthyridin-2-yl)pyrrolo[2,1-f][1,2,4]triazin-2-yl)cyclohexane-1,4-diamine [1687];

trans-$N^1$-(5-(1,5-naphthyridin-2-yl)pyrrolo[2,1-f][1,2,4]triazin-2-yl)cyclohexane-1,4-diamine [1688];

cis-$N^1$-(5-(1,5-naphthyridin-2-yl)pyrrolo[2,1-f][1,2,4]triazin-2-yl)-$N^4$-methylcyclohexane-1,4-diamine [1689];

trans-$N^1$-(5-(1,5-naphthyridin-2-yl)pyrrolo[2,1-f][1,2,4]triazin-2-yl)-$N^4$-methylcyclohexane-1,4-diamine [1690];

cis-$N^1$-(5-(1,5-naphthyridin-2-yl)pyrrolo[2,1-f][1,2,4]triazin-2-yl)-$N^4$,$N^4$-dimethylcyclohexane-1,4-diamine [1691];

trans-$N^1$-(5-(1,5-naphthyridin-2-yl)pyrrolo[2,1-f][1,2,4]triazin-2-yl)-$N^4$,$N^4$-dimethylcyclohexane-1,4-diamine [1692];

N-(cis-4-morpholinocyclohexyl)-5-(1,5-naphthyridin-2-yl)pyrrolo[2,1-f][1,2,4]triazin-2-amine [1693];

N-(trans-4-morpholinocyclohexyl)-5-(1,5-naphthyridin-2-yl)pyrrolo[2,1-f][1,2,4]triazin-2-amine [1694];

N-(cis-4-(4-methylpiperazin-1-yl)cyclohexyl)-5-(1,5-naphthyridin-2-yl)pyrrolo[2,1-f][1,2,4] triazin-2-amine [1695];

N-(trans-4-(4-methylpiperazin-1-yl)cyclohexyl)-5-(1,5-naphthyridin-2-yl)pyrrolo[2,1-f][1,2,4] triazin-2-amine [1696];

N-(1-methylazetidin-3-yl)-5-(1,5-naphthyridin-2-yl)pyrrolo[2,1-f][1,2,4]triazin-2-amine [1697];

5-(1,5-naphthyridin-2-yl)-N-(oxetan-3-yl)pyrrolo[2,1-f][1,2,4]triazin-2-amine [1698];

N-(1-methylpiperidin-4-yl)-5-(1,5-naphthyridin-2-yl)pyrrolo[2,1-f][1,2,4]triazin-2-amine [1699];

5-(1,5-naphthyridin-2-yl)-N-(tetrahydro-2H-pyran-4-yl)pyrrolo[2,1-f][1,2,4]triazin-2-amine [1700];

N-(6,6-difluorospiro[3.3]heptan-2-yl)-5-(1,5-naphthyridin-2-yl)pyrrolo[2,1-f][1,2,4]triazin-2-amine [1701];

5-(1,5-naphthyridin-2-yl)-N-(2-oxaspiro[3.3]heptan-6-yl)pyrrolo[2,1-f][1,2,4]triazin-2-amine [1702];

N-(2-methyl-2-azaspiro[3.3]heptan-6-yl)-5-(1,5-naphthyridin-2-yl)pyrrolo[2,1-f][1,2,4]triazin-2-amine [1703];

N-(1-methyl-1H-pyrazol-4-yl)-5-(1,5-naphthyridin-2-yl)pyrrolo[2,1-f][1,2,4]triazin-2-amine [1704];

cis-3-((5-(imidazo[1,2-a]pyridin-6-yl)pyrrolo[2,1-f][1,2,4]triazin-2-yl)amino)cyclobutan-1-ol [1705];

(6-(2-((cis-3-hydroxycyclobutyl)amino)pyrrolo[2,1-f][1,2,4]triazin-5-yl)imidazo[1,2-a]pyridin-3-yl)(pyrrolidin-1-yl)methanone [1706];

cis-3-((5-(imidazo[1,2-b]pyridazin-6-yl)pyrrolo[2,1-f][1,2,4]triazin-2-yl)amino)cyclobutan-1-ol [1707];

cis-3-((5-(imidazo[1,2-a]pyrimidin-6-yl)pyrrolo[2,1-f][1,2,4]triazin-2-yl)amino)cyclobutan-1-ol [1708];

cis-3-((5-(3-chloroimidazo[1,2-a]pyrimidin-6-yl)pyrrolo[2,1-f][1,2,4]triazin-2-yl)amino) cyclobutan-1-ol [1709];

cis-3-((5-(3-methylimidazo[1,2-a]pyrimidin-6-yl)pyrrolo[2,1-f][1,2,4]triazin-2-yl)amino) cyclobutan-1-ol [1710];

cis-3-((5-(3-ethylimidazo[1,2-a]pyrimidin-6-yl)pyrrolo[2,1-f][1,2,4]triazin-2-yl)amino) cyclobutan-1-ol [1711];

cis-3-((5-(4-fluoro-1-isopropyl-2-methyl-1H-benzo[d]imidazol-6-yl)pyrrolo[2,1-f][1,2,4]triazin-2-yl)amino)cyclobutan-1-ol [1712];

cis-3-((5-(1-isopropyl-2-methyl-1H-imidazo[4,5-b]pyridin-6-yl)pyrrolo[2,1-f][1,2,4]triazin-2-yl)amino)cyclobutan-1-ol [1713];

cis-3-((5-(1-(2,2-difluoroethyl)-2-methyl-1H-imidazo[4,5-b]pyridin-6-yl)pyrrolo[2,1-f][1,2,4]triazin-2-yl)amino)cyclobutan-1-ol [1714];

cis-3-((5-(1-(3,3-difluorocyclobutyl)-2-methyl-1H-imidazo[4,5-b]pyridin-6-yl)pyrrolo[2,1-f][1,2,4]triazin-2-yl)amino)cyclobutan-1-ol [1715];

cis-3-((5-(2-methyl-1-(tetrahydro-2H-pyran-4-yl)-1H-imidazo[4,5-b]pyridin-6-yl)pyrrolo[2,1-f][1,2,4]triazin-2-yl)amino)cyclobutan-1-ol [1716];

cis-3-((5-(2,3-dimethyl-3H-imidazo[4,5-b]pyridin-5-yl)pyrrolo[2,1-f][1,2,4]triazin-2-yl)amino)cyclobutan-1-ol [1717];

cis-3-((5-(3-ethyl-2-methyl-3H-imidazo[4,5-b]pyridin-5-yl)pyrrolo[2,1-f][1,2,4]triazin-2-yl)amino)cyclobutan-1-ol [1718];

cis-3-((5-(3-(2-fluoroethyl)-2-methyl-3H-imidazo[4,5-b]pyridin-5-yl)pyrrolo[2,1-f][1,2,4]triazin-2-yl)amino)cyclobutan-1-ol [1719];

cis-3-((5-(3-(2,2-difluoroethyl)-2-methyl-3H-imidazo[4,5-b]pyridin-5-yl)pyrrolo[2,1-f][1,2,4]triazin-2-yl)amino)cyclobutan-1-ol [1720];

cis-3-((5-(3-(2-methoxyethyl)-2-methyl-3H-imidazo[4,5-b]pyridin-5-yl)pyrrolo[2,1-f][1,2,4]triazin-2-yl)amino)cyclobutan-1-ol [1721];

cis-3-((5-(1-methyl-1H-benzo[d][1,2,3]triazol-6-yl)pyrrolo[2,1-f][1,2,4]triazin-2-yl)amino) cyclobutan-1-ol [1722];

cis-3-((5-(quinolin-6-yl)pyrrolo[2,1-f][1,2,4]triazin-2-yl)amino)cyclobutan-1-ol [1723];

cis-3-((5-(quinoxalin-6-yl)pyrrolo[2,1-f][1,2,4]triazin-2-yl)amino)cyclobutan-1-ol [1724];

cis-3-((5-(4-methoxyquinazolin-6-yl)pyrrolo[2,1-f][1,2,4]triazin-2-yl)amino)cyclobutan-1-ol [1725];

cis-3-((5-(1,8-naphthyridin-3-yl)pyrrolo[2,1-f][1,2,4]triazin-2-yl)amino)cyclobutan-1-ol [1726];

cis-3-((5-(pyrido[2,3-b]pyrazin-7-yl)pyrrolo[2,1-f][1,2,4]triazin-2-yl)amino)cyclobutan-1-ol [1727];

cis-3-((5-(1,5-naphthyridin-2-yl)pyrrolo[2,1-f][1,2,4]triazin-2-yl)amino)cyclobutan-1-ol [1728];

5-(imidazo[1,2-a]pyridin-6-yl)-N-(2-azaspiro[3.3]heptan-6-yl)pyrrolo[2,1-f][1,2,4]triazin-2-amine [1729];

(6-(2-((2-azaspiro[3.3]heptan-6-yl)amino)pyrrolo[2,1-f][1,2,4]triazin-5-yl)imidazo[1,2-a]pyridin-3-yl)(pyrrolidin-1-yl)methanone [1730];

5-(imidazo[1,2-b]pyridazin-6-yl)-N-(2-azaspiro[3.3]heptan-6-yl)pyrrolo[2,1-f][1,2,4]triazin-2-amine [1731];

5-(imidazo[1,2-a]pyrimidin-6-yl)-N-(2-azaspiro[3.3]heptan-6-yl)pyrrolo[2,1-f][1,2,4]triazin-2-amine [1732];

5-(3-chloroimidazo[1,2-a]pyrimidin-6-yl)-N-(2-azaspiro[3.3]heptan-6-yl)pyrrolo[2,1-f][1,2,4]triazin-2-amine [1733];

5-(3-methylimidazo[1,2-a]pyrimidin-6-yl)-N-(2-azaspiro[3.3]heptan-6-yl)pyrrolo[2,1-f][1,2,4]triazin-2-amine [1734];

5-(3-ethylimidazo[1,2-a]pyrimidin-6-yl)-N-(2-azaspiro[3.3]heptan-6-yl)pyrrolo[2,1-f][1,2,4]triazin-2-amine [1735];

5-(4-fluoro-1-isopropyl-2-methyl-1H-benzo[d]imidazol-6-yl)-N-(2-azaspiro[3.3]heptan-6-yl)pyrrolo[2,1-f][1,2,4]triazin-2-amine [1736];

5-(1-isopropyl-2-methyl-1H-imidazo[4,5-b]pyridin-6-yl)-N-(2-azaspiro[3.3]heptan-6-yl)pyrrolo[2,1-f][1,2,4]triazin-2-amine [1737];

5-(1-(2,2-difluoroethyl)-2-methyl-1H-imidazo[4,5-b]pyridin-6-yl)-N-(2-azaspiro[3.3]heptan-6-yl)pyrrolo[2,1-f][1,2,4]triazin-2-amine [1738];

5-(1-(3,3-difluorocyclobutyl)-2-methyl-1H-imidazo[4,5-b]pyridin-6-yl)-N-(2-azaspiro[3.3]heptan-6-yl)pyrrolo[2,1-f][1,2,4]triazin-2-amine [1739];

5-(2-methyl-1-(tetrahydro-2H-pyran-4-yl)-1H-imidazo[4,5-b]pyridin-6-yl)-N-(2-azaspiro[3.3]heptan-6-yl)pyrrolo[2,1-f][1,2,4]triazin-2-amine [1740];

5-(2,3-dimethyl-3H-imidazo[4,5-b]pyridin-5-yl)-N-(2-azaspiro[3.3]heptan-6-yl)pyrrolo[2,1-f][1,2,4]triazin-2-amine [1741];

5-(3-ethyl-2-methyl-3H-imidazo[4,5-b]pyridin-5-yl)-N-(2-azaspiro[3.3]heptan-6-yl)pyrrolo[2,1-f][1,2,4]triazin-2-amine [1742];

5-(3-(2-fluoroethyl)-2-methyl-3H-imidazo[4,5-b]pyridin-5-yl)-N-(2-azaspiro[3.3]heptan-6-yl)pyrrolo[2,1-f][1,2,4]triazin-2-amine [1743];

5-(3-(2,2-difluoroethyl)-2-methyl-3H-imidazo[4,5-b]pyridin-5-yl)-N-(2-azaspiro[3.3]heptan-6-yl)pyrrolo[2,1-f][1,2,4]triazin-2-amine [1744];

5-(3-(2-methoxyethyl)-2-methyl-3H-imidazo[4,5-b]pyridin-5-yl)-N-(2-azaspiro[3.3]heptan-6-yl)pyrrolo[2,1-f][1,2,4]triazin-2-amine [1745];

5-(1-methyl-1H-benzo[d][1,2,3]triazol-6-yl)-N-(2-azaspiro[3.3]heptan-6-yl)pyrrolo[2,1-f][1,2,4]triazin-2-amine [1746];

5-(quinolin-6-yl)-N-(2-azaspiro[3.3]heptan-6-yl)pyrrolo[2,1-f][1,2,4]triazin-2-amine [1747];

5-(quinoxalin-6-yl)-N-(2-azaspiro[3.3]heptan-6-yl)pyrrolo[2,1-f][1,2,4]triazin-2-amine [1748];

5-(4-methoxyquinazolin-6-yl)-N-(2-azaspiro[3.3]heptan-6-yl)pyrrolo[2,1-f][1,2,4]triazin-2-amine [1749];

5-(1,8-naphthyridin-3-yl)-N-(2-azaspiro[3.3]heptan-6-yl)pyrrolo[2,1-f][1,2,4]triazin-2-amine [1750];

5-(pyrido[2,3-b]pyrazin-7-yl)-N-(2-azaspiro[3.3]heptan-6-yl)pyrrolo[2,1-f][1,2,4]triazin-2-amine [1751];

5-(1,5-naphthyridin-2-yl)-N-(2-azaspiro[3.3]heptan-6-yl)pyrrolo[2,1-f][1,2,4]triazin-2-amine [1752];

5-(imidazo[1,2-a]pyridin-6-yl)-N-(2-isobutyl-2-azaspiro[3.3]heptan-6-yl)pyrrolo[2,1-f][1,2,4]triazin-2-amine [1753];

(6-(2-((2-isobutyl-2-azaspiro[3.3]heptan-6-yl)amino)pyrrolo[2,1-f][1,2,4]triazin-5-yl)imidazo[1,2-a]pyridin-3-yl)(pyrrolidin-1-yl)methanone [1754];

5-(imidazo[1,2-b]pyridazin-6-yl)-N-(2-isobutyl-2-azaspiro[3.3]heptan-6-yl)pyrrolo[2,1-f][1,2,4]triazin-2-amine [1755];

5-(imidazo[1,2-a]pyrimidin-6-yl)-N-(2-isobutyl-2-azaspiro[3.3]heptan-6-yl)pyrrolo[2,1-f][1,2,4]triazin-2-amine [1756];

5-(3-chloroimidazo[1,2-a]pyrimidin-6-yl)-N-(2-isobutyl-2-azaspiro[3.3]heptan-6-yl)pyrrolo[2,1-f][1,2,4]triazin-2-amine [1757];

N-(2-isobutyl-2-azaspiro[3.3]heptan-6-yl)-5-(3-methylimidazo[1,2-a]pyrimidin-6-yl)pyrrolo[2,1-f][1,2,4]triazin-2-amine [1758];

5-(3-ethylimidazo[1,2-a]pyrimidin-6-yl)-N-(2-isobutyl-2-azaspiro[3.3]heptan-6-yl)pyrrolo[2,1-f][1,2,4]triazin-2-amine [1759];

5-(4-fluoro-1-isopropyl-2-methyl-1H-benzo[d]imidazol-6-yl)-N-(2-isobutyl-2-azaspiro[3.3]heptan-6-yl)pyrrolo[2,1-f][1,2,4]triazin-2-amine [1760];

N-(2-isobutyl-2-azaspiro[3.3]heptan-6-yl)-5-(1-isopropyl-2-methyl-1H-imidazo[4,5-b]pyridin-6-yl)pyrrolo[2,1-f][1,2,4]triazin-2-amine [1761];

5-(1-(2,2-difluoroethyl)-2-methyl-1H-imidazo[4,5-b]pyridin-6-yl)-N-(2-isobutyl-2-azaspiro[3.3]heptan-6-yl)pyrrolo[2,1-f][1,2,4]triazin-2-amine [1762];

5-(1-(3,3-difluorocyclobutyl)-2-methyl-1H-imidazo[4,5-b]pyridin-6-yl)-N-(2-isobutyl-2-azaspiro[3.3]heptan-6-yl)pyrrolo[2,1-f][1,2,4]triazin-2-amine [1763];

N-(2-isobutyl-2-azaspiro[3.3]heptan-6-yl)-5-(2-methyl-1-(tetrahydro-2H-pyran-4-yl)-1H-imidazo[4,5-b]pyridin-6-yl)pyrrolo[2,1-f][1,2,4]triazin-2-amine [1764];

5-(2,3-dimethyl-3H-imidazo[4,5-b]pyridin-5-yl)-N-(2-isobutyl-2-azaspiro[3.3]heptan-6-yl)pyrrolo[2,1-f][1,2,4]triazin-2-amine [1765];

5-(3-ethyl-2-methyl-3H-imidazo[4,5-b]pyridin-5-yl)-N-(2-isobutyl-2-azaspiro[3.3]heptan-6-yl)pyrrolo[2,1-f][1,2,4]triazin-2-amine [1766];

5-(3-(2-fluoroethyl)-2-methyl-3H-imidazo[4,5-b]pyridin-5-yl)-N-(2-isobutyl-2-azaspiro[3.3]heptan-6-yl)pyrrolo[2,1-f][1,2,4]triazin-2-amine [1767];

5-(3-(2,2-difluoroethyl)-2-methyl-3H-imidazo[4,5-b]pyridin-5-yl)-N-(2-isobutyl-2-azaspiro[3.3]heptan-6-yl)pyrrolo[2,1-f][1,2,4]triazin-2-amine [1768];

N-(2-isobutyl-2-azaspiro[3.3]heptan-6-yl)-5-(3-(2-methoxyethyl)-2-methyl-3H-imidazo[4,5-b]pyridin-5-yl)pyrrolo[2,1-f][1,2,4]triazin-2-amine [1769];

N-(2-isobutyl-2-azaspiro[3.3]heptan-6-yl)-5-(1-methyl-1H-benzo[d][1,2,3]triazol-6-yl)pyrrolo[2,1-f][1,2,4]triazin-2-amine [1770];

N-(2-isobutyl-2-azaspiro[3.3]heptan-6-yl)-5-(quinolin-6-yl)pyrrolo[2,1-f][1,2,4]triazin-2-amine [1771];

N-(2-isobutyl-2-azaspiro[3.3]heptan-6-yl)-5-(quinoxalin-6-yl)pyrrolo[2,1-f][1,2,4]triazin-2-amine [1772];

N-(2-isobutyl-2-azaspiro[3.3]heptan-6-yl)-5-(4-methoxyquinazolin-6-yl)pyrrolo[2,1-f][1,2,4]triazin-2-amine [1773];

N-(2-isobutyl-2-azaspiro[3.3]heptan-6-yl)-5-(1,8-naphthyridin-3-yl)pyrrolo[2,1-f][1,2,4]triazin-2-amine [1774];

N-(2-isobutyl-2-azaspiro[3.3]heptan-6-yl)-5-(pyrido[2,3-b]pyrazin-7-yl)pyrrolo[2,1-f][1,2,4]triazin-2-amine [1775];

N-(2-isobutyl-2-azaspiro[3.3]heptan-6-yl)-5-(1,5-naphthyridin-2-yl)pyrrolo[2,1-f][1,2,4]triazin-2-amine [1776];

5-(imidazo[1,2-a]pyridin-6-yl)-N-(cis-4-(trifluoromethoxy)cyclohexyl)pyrrolo[2,1-f][1,2,4]triazin-2-amine [1777];

pyrrolidin-1-yl(6-(2-((cis-4-(trifluoromethoxy)cyclohexyl)amino)pyrrolo[2,1-f][1,2,4]triazin-5-yl)imidazo[1,2-a]pyridin-3-yl)methanone [1778];

5-(imidazo[1,2-b]pyridazin-6-yl)-N-(cis-4-(trifluoromethoxy)cyclohexyl)pyrrolo[2,1-f][1,2,4]triazin-2-amine [1779];

5-(imidazo[1,2-a]pyrimidin-6-yl)-N-(cis-4-(trifluoromethoxy)cyclohexyl)pyrrolo[2,1-f][1,2,4]triazin-2-amine [1780];

5-(3-chloroimidazo[1,2-a]pyrimidin-6-yl)-N-(cis-4-(trifluoromethoxy)cyclohexyl)pyrrolo [2,1-f][1,2,4]triazin-2-amine [1781];

5-(3-methylimidazo[1,2-a]pyrimidin-6-yl)-N-(cis-4-(trifluoromethoxy)cyclohexyl)pyrrolo [2,1-f][1,2,4]triazin-2-amine [1782];

5-(3-ethylimidazo[1,2-a]pyrimidin-6-yl)-N-(cis-4-(trifluoromethoxy)cyclohexyl)pyrrolo[2,1-f][1,2,4]triazin-2-amine [1783];

5-(4-fluoro-1-isopropyl-2-methyl-1H-benzo[d]imidazol-6-yl)-N-(cis-4-(trifluoromethoxy) cyclohexyl)pyrrolo[2,1-f][1,2,4]triazin-2-amine [1784];

5-(1-isopropyl-2-methyl-1H-imidazo[4,5-b]pyridin-6-yl)-N-(cis-4-(trifluoromethoxy) cyclohexyl)pyrrolo[2,1-f][1,2,4]triazin-2-amine [1785];

5-(1-(2,2-difluoroethyl)-2-methyl-1H-imidazo[4,5-b]pyridin-6-yl)-N-(cis-4-(trifluoromethoxy) cyclohexyl)pyrrolo[2,1-f][1,2,4]triazin-2-amine [1786];

5-(1-(3,3-difluorocyclobutyl)-2-methyl-1H-imidazo[4,5-b]pyridin-6-yl)-N-(cis-4-(trifluoromethoxy)cyclohexyl)pyrrolo[2,1-f][1,2,4]triazin-2-amine [1787];

5-(2-methyl-1-(tetrahydro-2H-pyran-4-yl)-1H-imidazo[4,5-b]pyridin-6-yl)-N-(cis-4-(trifluoromethoxy)cyclohexyl)pyrrolo[2,1-f][1,2,4]triazin-2-amine [1788];

5-(2,3-dimethyl-3H-imidazo[4,5-b]pyridin-5-yl)-N-(cis-4-(trifluoromethoxy)cyclohexyl) pyrrolo[2,1-f][1,2,4]triazin-2-amine [1789];

5-(3-ethyl-2-methyl-3H-imidazo[4,5-b]pyridin-5-yl)-N-(cis-4-(trifluoromethoxy)cyclohexyl) pyrrolo[2,1-f][1,2,4]triazin-2-amine [1790];

5-(3-(2-fluoroethyl)-2-methyl-3H-imidazo[4,5-b]pyridin-5-yl)-N-(cis-4-(trifluoromethoxy) cyclohexyl)pyrrolo[2,1-f][1,2,4]triazin-2-amine [1791];

5-(3-(2,2-difluoroethyl)-2-methyl-3H-imidazo[4,5-b]pyridin-5-yl)-N-(cis-4-(trifluoromethoxy)cyclohexyl)pyrrolo[2,1-f][1,2,4]triazin-2-amine [1792];

5-(3-(2-methoxyethyl)-2-methyl-3H-imidazo[4,5-b]pyridin-5-yl)-N-(cis-4-(trifluoromethoxy) cyclohexyl)pyrrolo[2,1-f][1,2,4]triazin-2-amine [1793];

5-(1-methyl-1H-benzo[d][1,2,3]triazol-6-yl)-N-(cis-4-(trifluoromethoxy)cyclohexyl)pyrrolo [2,1-f][1,2,4]triazin-2-amine [1794];

5-(quinolin-6-yl)-N-(cis-4-(trifluoromethoxy)cyclohexyl)pyrrolo[2,1-f][1,2,4]triazin-2-amine [1795];

5-(quinoxalin-6-yl)-N-(cis-4-(trifluoromethoxy)cyclohexyl)pyrrolo[2,1-f][1,2,4]triazin-2-amine [1796];

5-(4-methoxyquinazolin-6-yl)-N-(cis-4-(trifluoromethoxy)cyclohexyl)pyrrolo[2,1-f][1,2,4] triazin-2-amine [1797];

5-(1,8-naphthyridin-3-yl)-N-(cis-4-(trifluoromethoxy)cyclohexyl)pyrrolo[2,1-f][1,2,4]triazin-2-amine [1798];

5-(pyrido[2,3-b]pyrazin-7-yl)-N-(cis-4-(trifluoromethoxy)cyclohexyl)pyrrolo[2,1-f][1,2,4] triazin-2-amine [1799];

5-(1,5-naphthyridin-2-yl)-N-(cis-4-(trifluoromethoxy)cyclohexyl)pyrrolo[2,1-f][1,2,4]triazin-2-amine [1800];

N-(2-fluoro-2-methylpropyl)-5-(3-isopropyl-2-methyl-3H-imidazo[4,5-b]pyridin-5-yl)pyrrolo [2,1-f][1,2,4]triazin-2-amine [1801];

5-(imidazo[1,2-a]pyrimidin-6-yl)-N-(cis-4-(methoxy-$d_3$)cyclohexyl)pyrrolo[2,1-f][1,2,4] triazin-2-amine [1802];

5-(3-(2,2-difluoroethyl)-2-methyl-3H-imidazo[4,5-b]pyridin-5-yl)-N-(cis-4-(methoxy-$d_3$) cyclohexyl)pyrrolo[2,1-f][1,2,4]triazin-2-amine [1803];

cis-3-((5-(imidazo[1,2-a]pyridin-6-yl)pyrrolo[2,1-f][1,2,4]triazin-2-yl)amino)-1-methylcyclobutan-1-ol [1804];

(6-(2-((cis-3-hydroxy-3-methylcyclobutyl)amino)pyrrolo[2,1-f][1,2,4]triazin-5-yl)imidazo[1,2-a]pyridin-3-yl)(pyrrolidin-1-yl)methanone [1805];

cis-3-((5-(imidazo[1,2-b]pyridazin-6-yl)pyrrolo[2,1-f][1,2,4]triazin-2-yl)amino)-1-methylcyclobutan-1-ol [1806];

cis-3-((5-(imidazo[1,2-a]pyrimidin-6-yl)pyrrolo[2,1-f][1,2,4]triazin-2-yl)amino)-1-methylcyclobutan-1-ol [1807];

cis-3-((5-(3-chloroimidazo[1,2-a]pyrimidin-6-yl)pyrrolo[2,1-f][1,2,4]triazin-2-yl)amino)-1-methylcyclobutan-1-ol [1808];

cis-1-methyl-3-((5-(3-methylimidazo[1,2-a]pyrimidin-6-yl)pyrrolo[2,1-f][1,2,4]triazin-2-yl)amino)cyclobutan-1-ol [1809];

cis-3-((5-(3-ethylimidazo[1,2-a]pyrimidin-6-yl)pyrrolo[2,1-f][1,2,4]triazin-2-yl)amino)-1-methylcyclobutan-1-ol [1810];

cis-3-((5-(4-fluoro-1-isopropyl-2-methyl-1H-benzo[d]imidazol-6-yl)pyrrolo[2,1-f][1,2,4]triazin-2-yl)amino)-1-methylcyclobutan-1-ol [1811];

cis-3-((5-(1-isopropyl-2-methyl-1H-imidazo[4,5-b]pyridin-6-yl)pyrrolo[2,1-f][1,2,4]triazin-2-yl)amino)-1-methylcyclobutan-1-ol [1812];

cis-3-((5-(1-(2,2-difluoroethyl)-2-methyl-1H-imidazo[4,5-b]pyridin-6-yl)pyrrolo[2,1-f][1,2,4]triazin-2-yl)amino)-1-methylcyclobutan-1-ol [1813];

cis-3-((5-(1-(3,3-difluorocyclobutyl)-2-methyl-1H-imidazo[4,5-b]pyridin-6-yl)pyrrolo[2,1-f][1,2,4]triazin-2-yl)amino)-1-methylcyclobutan-1-ol [1814];

cis-1-methyl-3-((5-(2-methyl-1-(tetrahydro-2H-pyran-4-yl)-1H-imidazo[4,5-b]pyridin-6-yl)pyrrolo[2,1-f][1,2,4]triazin-2-yl)amino)cyclobutan-1-ol [1815];

cis-3-((5-(2,3-dimethyl-3H-imidazo[4,5-b]pyridin-5-yl)pyrrolo[2,1-f][1,2,4]triazin-2-yl)amino)-1-methylcyclobutan-1-ol [1816];

cis-3-((5-(3-ethyl-2-methyl-3H-imidazo[4,5-b]pyridin-5-yl)pyrrolo[2,1-f][1,2,4]triazin-2-yl)amino)-1-methylcyclobutan-1-ol [1817];

cis-3-((5-(3-(2-fluoroethyl)-2-methyl-3H-imidazo[4,5-b]pyridin-5-yl)pyrrolo[2,1-f][1,2,4]triazin-2-yl)amino)-1-methylcyclobutan-1-ol [1818];

cis-3-((5-(3-(2,2-difluoroethyl)-2-methyl-3H-imidazo[4,5-b]pyridin-5-yl)pyrrolo[2,1-f][1,2,4]triazin-2-yl)amino)-1-methylcyclobutan-1-ol [1819];

cis-3-((5-(3-(2-methoxyethyl)-2-methyl-3H-imidazo[4,5-b]pyridin-5-yl)pyrrolo[2,1-f][1,2,4]triazin-2-yl)amino)-1-methylcyclobutan-1-ol [1820];

cis-1-methyl-3-((5-(1-methyl-1H-benzo[d][1,2,3]triazol-6-yl)pyrrolo[2,1-f][1,2,4]triazin-2-yl)amino)cyclobutan-1-ol [1821];

cis-1-methyl-3-((5-(quinolin-6-yl)pyrrolo[2,1-f][1,2,4]triazin-2-yl)amino)cyclobutan-1-ol [1822];

cis-1-methyl-3-((5-(quinoxalin-6-yl)pyrrolo[2,1-f][1,2,4]triazin-2-yl)amino)cyclobutan-1-ol [1823];

cis-3-((5-(4-methoxyquinazolin-6-yl)pyrrolo[2,1-f][1,2,4]triazin-2-yl)amino)-1-methylcyclobutan-1-ol [1824];

cis-3-((5-(1,8-naphthyridin-3-yl)pyrrolo[2,1-f][1,2,4]triazin-2-yl)amino)-1-methylcyclobutan-1-ol [1825];

cis-1-methyl-3-((5-(pyrido[2,3-b]pyrazin-7-yl)pyrrolo[2,1-f][1,2,4]triazin-2-yl)amino)cyclobutan-1-ol [1826];

cis-3-((5-(1,5-naphthyridin-2-yl)pyrrolo[2,1-f][1,2,4]triazin-2-yl)amino)-1-methylcyclobutan-1-ol [1827];

trans-4-((5-(imidazo[1,2-a]pyridin-6-yl)pyrrolo[2,1-f][1,2,4]triazin-2-yl)amino)-1-methylcyclohexan-1-ol [1828];

cis-4-((5-(3-isobutyl-2-methyl-3H-imidazo[4,5-b]pyridin-5-yl)pyrrolo[2,1-f][1,2,4]triazin-2-yl)amino)-1-methylcyclohexan-1-ol [1829];

(R)-2-((5-(3-(2,2-difluoroethyl)-2-methyl-3H-imidazo[4,5-b]pyridin-5-yl)pyrrolo[2,1-f][1,2,4]triazin-2-yl)amino)propan-1-ol [1830];

(R)-1-((5-(3-(2,2-difluoroethyl)-2-methyl-3H-imidazo[4,5-b]pyridin-5-yl)pyrrolo[2,1-f][1,2,4]triazin-2-yl)amino)propan-2-ol [1831];

(S)-1-((5-(3-(2,2-difluoroethyl)-2-methyl-3H-imidazo[4,5-b]pyridin-5-yl)pyrrolo[2,1-f][1,2,4]triazin-2-yl)amino)propan-2-ol [1832];

1-((5-(3-(2,2-difluoroethyl)-2-methyl-3H-imidazo[4,5-b]pyridin-5-yl)pyrrolo[2,1-f][1,2,4]triazin-2-yl)amino)-2-methylpropan-2-ol [1833];

(cis-3-((5-(3-(2,2-difluoroethyl)-2-methyl-3H-imidazo[4,5-b]pyridin-5-yl)pyrrolo[2,1-f][1,2,4]triazin-2-yl)amino)cyclobutyl)methanol [1834];

trans-3-((5-(3-(2,2-difluoroethyl)-2-methyl-3H-imidazo[4,5-b]pyridin-5-yl)pyrrolo[2,1-f][1,2,4]triazin-2-yl)amino)-1-methylcyclobutan-1-ol [1835];

5-(3-(2,2-difluoroethyl)-2-methyl-3H-imidazo[4,5-b]pyridin-5-yl)-N-(7-methyl-7-azaspiro[3.5]nonan-2-yl)pyrrolo[2,1-f][1,2,4]triazin-2-amine [1836];

(cis-4-((5-(3-(2,2-difluoroethyl)-2-methyl-3H-imidazo[4,5-b]pyridin-5-yl)pyrrolo[2,1-f][1,2,4]triazin-2-yl)amino)cyclohexyl)methanol [1837];

N-(cis-4-(2,2-difluoroethoxy)cyclohexyl)-5-(3-(2,2-difluoroethyl)-2-methyl-3H-imidazo[4,5-b]pyridin-5-yl)pyrrolo[2,1-f][1,2,4]triazin-2-amine [1838];

2-((cis-4-((5-(3-(2,2-difluoroethyl)-2-methyl-3H-imidazo[4,5-b]pyridin-5-yl)pyrrolo[2,1-f][1,2,4]triazin-2-yl)amino)cyclohexyl)oxy)ethan-1-ol [1839];

trans-4-((5-(3-(2,2-difluoroethyl)-2-methyl-3H-imidazo[4,5-b]pyridin-5-yl)pyrrolo[2,1-f][1,2,4]triazin-2-yl)amino)-1-methylcyclohexan-1-ol [1840];

5-(3-(2,2-difluoroethyl)-2-methyl-3H-imidazo[4,5-b]pyridin-5-yl)-N-(cis-4-((4-methylpiperazin-1-yl)methyl)cyclohexyl)pyrrolo[2,1-f][1,2,4]triazin-2-amine [1841];

5-(3-(2,2-difluoroethyl)-2-methyl-3H-imidazo[4,5-b]pyridin-5-yl)-N-(cis-4-(morpholinomethyl)cyclohexyl)pyrrolo[2,1-f][1,2,4]triazin-2-amine [1842];

ethyl cis-4-((5-(3-(2,2-difluoroethyl)-2-methyl-3H-imidazo[4,5-b]pyridin-5-yl)pyrrolo[2,1-f][1,2,4]triazin-2-yl)amino)cyclohexane-1-carboxylate [1843];

N-(trans-4-((5-(3-(2,2-difluoroethyl)-2-methyl-3H-imidazo[4,5-b]pyridin-5-yl)pyrrolo[2,1-f][1,2,4]triazin-2-yl)amino)cyclohexyl)acetamide [1844];

cis-4-((5-(3-(2,2-difluoroethyl)-2-methyl-3H-imidazo[4,5-b]pyridin-5-yl)pyrrolo[2,1-f][1,2,4]triazin-2-yl)amino)-N,N-dimethylcyclohexane-1-carboxamide [1845];

5-(3-(2,2-difluoroethyl)-2-methyl-3H-imidazo[4,5-b]pyridin-5-yl)-N-(2-methyl-2-azaspiro[3.5]nonan-7-yl)pyrrolo[2,1-f][1,2,4]triazin-2-amine [1846];

5-(3-(2,2-difluoroethyl)-2-methyl-3H-imidazo[4,5-b]pyridin-5-yl)-N-(1,4-dioxaspiro[4.5]decan-8-yl)pyrrolo[2,1-f][1,2,4]triazin-2-amine [1847];

5-(3-(2,2-difluoroethyl)-2-methyl-3H-imidazo[4,5-b]pyridin-5-yl)-N-((4-methylmorpholin-2-yl)methyl)pyrrolo[2,1-f][1,2,4]triazin-2-amine [1848];

5-(3-(2,2-difluoroethyl)-2-methyl-3H-imidazo[4,5-b]pyridin-5-yl)-N-(1-(2-fluoroethyl)piperidin-4-yl)pyrrolo[2,1-f][1,2,4]triazin-2-amine [1849];

5-(3-(2,2-difluoroethyl)-2-methyl-3H-imidazo[4,5-b]pyridin-5-yl)-N-(1-(2,2-difluoroethyl)piperidin-4-yl)pyrrolo[2,1-f][1,2,4]triazin-2-amine [1850];

5-(3-(2,2-difluoroethyl)-2-methyl-3H-imidazo[4,5-b]pyridin-5-yl)-N-(1-(3,3,3-trifluoropropyl)piperidin-4-yl)pyrrolo[2,1-f][1,2,4]triazin-2-amine [1851];

2-(4-((5-(3-(2,2-difluoroethyl)-2-methyl-3H-imidazo[4,5-b]pyridin-5-yl)pyrrolo[2,1-f][1,2,4]triazin-2-yl)amino)piperidin-1-yl)ethan-1-ol [1852];

5-(3-(2,2-difluoroethyl)-2-methyl-3H-imidazo[4,5-b]pyridin-5-yl)-N-((3S,4R)-3-fluoro-1-methylpiperidin-4-yl)pyrrolo[2,1-f][1,2,4]triazin-2-amine [1853];

5-(3-(2,2-difluoroethyl)-2-methyl-3H-imidazo[4,5-b]pyridin-5-yl)-N-((3R,4R)-3-fluoro-1-methylpiperidin-4-yl)pyrrolo[2,1-f][1,2,4]triazin-2-amine [1854];

5-(3-(2,2-difluoroethyl)-2-methyl-3H-imidazo[4,5-b]pyridin-5-yl)-N-((3S,4S)-3-fluoro-1-methylpiperidin-4-yl)pyrrolo[2,1-f][1,2,4]triazin-2-amine [1855];

5-(3-(2,2-difluoroethyl)-2-methyl-3H-imidazo[4,5-b]pyridin-5-yl)-N-((3R,4S)-3-fluoro-1-methylpiperidin-4-yl)pyrrolo[2,1-f][1,2,4]triazin-2-amine [1856];

1-(4-((5-(3-(2,2-difluoroethyl)-2-methyl-3H-imidazo[4,5-b]pyridin-5-yl)pyrrolo[2,1-f][1,2,4]triazin-2-yl)amino)piperidin-1-yl)ethan-1-one [1857];

1-(4-((5-(3-(2,2-difluoroethyl)-2-methyl-3H-imidazo[4,5-b]pyridin-5-yl)pyrrolo[2,1-f][1,2,4]triazin-2-yl)amino)piperidin-1-yl)propan-1-one [1858];

1-(4-((5-(3-(2,2-difluoroethyl)-2-methyl-3H-imidazo[4,5-b]pyridin-5-yl)pyrrolo[2,1-f][1,2,4]triazin-2-yl)amino)piperidin-1-yl)-2-methylpropan-1-one [1859];

cyclopropyl(4-((5-(3-(2,2-difluoroethyl)-2-methyl-3H-imidazo[4,5-b]pyridin-5-yl)pyrrolo[2,1-f][1,2,4]triazin-2-yl)amino)piperidin-1-yl)methanone [1860];

5-(3-(2,2-difluoroethyl)-2-methyl-3H-imidazo[4,5-b]pyridin-5-yl)-N-(1-(methylsulfonyl)piperidin-4-yl)pyrrolo[2,1-f][1,2,4]triazin-2-amine [1861];

5-(3-(2,2-difluoroethyl)-2-methyl-3H-imidazo[4,5-b]pyridin-5-yl)-N-(1-(oxetan-3-yl)piperidin-4-yl)pyrrolo[2,1-f][1,2,4]triazin-2-amine [1862];

(R)-5-(3-(2,2-difluoroethyl)-2-methyl-3H-imidazo[4,5-b]pyridin-5-yl)-N-(tetrahydro-2H-pyran-3-yl)pyrrolo[2,1-f][1,2,4]triazin-2-amine [1863];

(S)-5-(3-(2,2-difluoroethyl)-2-methyl-3H-imidazo[4,5-b]pyridin-5-yl)-N-(tetrahydro-2H-pyran-3-yl)pyrrolo[2,1-f][1,2,4]triazin-2-amine [1864];

(3R,4R)-4-((5-(3-(2,2-difluoroethyl)-2-methyl-3H-imidazo[4,5-b]pyridin-5-yl)pyrrolo[2,1-f][1,2,4]triazin-2-yl)amino)tetrahydro-2H-pyran-3-ol [1865];

(3S,4R)-4-((5-(3-(2,2-difluoroethyl)-2-methyl-3H-imidazo[4,5-b]pyridin-5-yl)pyrrolo[2,1-f][1,2,4]triazin-2-yl)amino)tetrahydro-2H-pyran-3-ol [1866];

5-(3-(2,2-difluoroethyl)-2-methyl-3H-imidazo[4,5-b]pyridin-5-yl)-N-((3S,4R)-3-methoxytetrahydro-2H-pyran-4-yl)pyrrolo[2,1-f][1,2,4]triazin-2-amine [1867];

cis-1-methyl-4-((5-(2-methyl-3-(2,2,2-trifluoroethyl)-3H-imidazo[4,5-b]pyridin-5-yl)pyrrolo[2,1-f][1,2,4]triazin-2-yl)amino)cyclohexan-1-ol [1868];

3-(5-(2-((cis-4-hydroxy-4-methylcyclohexyl)amino)pyrrolo[2,1-f][1,2,4]triazin-5-yl)-2-methyl-3H-imidazo[4,5-b]pyridin-3-yl)-2,2-dimethylpropanenitrile [1869];

1-(5-(2-((4,4-difluorocyclohexyl)amino)pyrrolo[2,1-f][1,2,4]triazin-5-yl)-2-methyl-3H-imidazo[4,5-b]pyridin-3-yl)-2-methylpropan-2-ol [1870];

2-methyl-1-(2-methyl-5-(2-((tetrahydro-2H-pyran-4-yl)amino)pyrrolo[2,1-f][1,2,4]triazin-5-yl)-3H-imidazo[4,5-b]pyridin-3-yl)propan-2-ol [1871];

2-(5-(2-((cis-4-hydroxy-4-methylcyclohexyl)amino)pyrrolo[2,1-f][1,2,4]triazin-5-yl)-2-methyl-3H-imidazo[4,5-b]pyridin-3-yl)-N,N-dimethylacetamide [1872];

5-(3-(azetidin-3-ylmethyl)-2-methyl-3H-imidazo[4,5-b]pyridin-5-yl)-N-(4,4-difluorocyclohexyl)pyrrolo[2,1-f][1,2,4]triazin-2-amine [1873];

N-(4,4-difluorocyclohexyl)-5-(2-methyl-3-((1-methylazetidin-3-yl)methyl)-3H-imidazo[4,5-b]pyridin-5-yl)pyrrolo[2,1-f][1,2,4]triazin-2-amine [1874];

cis-1-methyl-4-((5-(2-methyl-3-(oxetan-3-ylmethyl)-3H-imidazo[4,5-b]pyridin-5-yl)pyrrolo[2,1-f][1,2,4]triazin-2-yl)amino)cyclohexan-1-ol [1875];

5-(1-(2,2-difluoroethyl)-2-methyl-1H-imidazo[4,5-b]pyridin-6-yl)-N-(cis-4-(methoxy-$d_3$)cyclohexyl)pyrrolo[2,1-f][1,2,4]triazin-2-amine [1876];

N-(cis-4-(2,2-difluoroethoxy)cyclohexyl)-5-(1-(2,2-difluoroethyl)-2-methyl-1H-imidazo[4,5-b]pyridin-6-yl)pyrrolo[2,1-f][1,2,4]triazin-2-amine [1877];

2-((cis-4-((5-(1-(2,2-difluoroethyl)-2-methyl-1H-imidazo[4,5-b]pyridin-6-yl)pyrrolo[2,1-f][1,2,4]triazin-2-yl)amino)cyclohexyl)oxy)ethan-1-ol [1878];

trans-4-((5-(1-(2,2-difluoroethyl)-2-methyl-1H-imidazo[4,5-b]pyridin-6-yl)pyrrolo[2,1-f][1,2,4]triazin-2-yl)amino)-1-methylcyclohexan-1-ol [1879];

5-(1-(2,2-difluoroethyl)-2-methyl-1H-imidazo[4,5-b]pyridin-6-yl)-N-(1,4-dioxaspiro[4.5]decan-8-yl)pyrrolo[2,1-f][1,2,4]triazin-2-amine [1880];

5-(1-(2,2-difluoroethyl)-2-methyl-1H-imidazo[4,5-b]pyridin-6-yl)-N-(1-(2-fluoroethyl)piperidin-4-yl)pyrrolo[2,1-f][1,2,4]triazin-2-amine [1881];

5-(1-(2,2-difluoroethyl)-2-methyl-1H-imidazo[4,5-b]pyridin-6-yl)-N-(1-(2,2-difluoroethyl)piperidin-4-yl)pyrrolo[2,1-f][1,2,4]triazin-2-amine [1882];

5-(1-(2,2-difluoroethyl)-2-methyl-1H-imidazo[4,5-b]pyridin-6-yl)-N-(1-(3,3,3-trifluoropropyl)piperidin-4-yl)pyrrolo[2,1-f][1,2,4]triazin-2-amine [1883];

5-(1-(2,2-difluoroethyl)-2-methyl-1H-imidazo[4,5-b]pyridin-6-yl)-N-((3S,4R)-3-fluoro-1-methylpiperidin-4-yl)pyrrolo[2,1-f][1,2,4]triazin-2-amine [1884];

5-(1-(2,2-difluoroethyl)-2-methyl-1H-imidazo[4,5-b]pyridin-6-yl)-N-((3R,4R)-3-fluoro-1-methylpiperidin-4-yl)pyrrolo[2,1-f][1,2,4]triazin-2-amine [1885];

5-(1-(2,2-difluoroethyl)-2-methyl-1H-imidazo[4,5-b]pyridin-6-yl)-N-((3S,4S)-3-fluoro-1-methylpiperidin-4-yl)pyrrolo[2,1-f][1,2,4]triazin-2-amine [1886];

5-(1-(2,2-difluoroethyl)-2-methyl-1H-imidazo[4,5-b]pyridin-6-yl)-N-((3R,4S)-3-fluoro-1-methylpiperidin-4-yl)pyrrolo[2,1-f][1,2,4]triazin-2-amine [1887];

1-(4-((5-(1-(2,2-difluoroethyl)-2-methyl-1H-imidazo[4,5-b]pyridin-6-yl)pyrrolo[2,1-f][1,2,4]triazin-2-yl)amino)piperidin-1-yl)-2-methylpropan-1-one [1888];

5-(1-(2,2-difluoroethyl)-2-methyl-1H-imidazo[4,5-b]pyridin-6-yl)-N-(1-(oxetan-3-yl)piperidin-4-yl)pyrrolo[2,1-f][1,2,4]triazin-2-amine [1889];

trans-4-((5-(1-(2,2-difluoroethyl)-1H-benzo[d][1,2,3]triazol-6-yl)pyrrolo[2,1-f][1,2,4]triazin-2-yl)amino)-1-methylcyclohexan-1-ol [1890];

trans-1-methyl-4-((5-(pyrazolo[1,5-a]pyridin-5-yl)pyrrolo[2,1-f][1,2,4]triazin-2-yl)amino)cyclohexan-1-ol [1891];

5-(3-(2,2-difluoroethyl)-2-methyl-3H-imidazo[4,5-b]pyridin-5-yl)-N-(cis-3-morpholinocyclobutyl)pyrrolo[2,1-f][1,2,4]triazin-2-amine [1892];

5-(3-(2,2-difluoroethyl)-2-methyl-3H-imidazo[4,5-b]pyridin-5-yl)-N-(trans-3-morpholinocyclobutyl)pyrrolo[2,1-f][1,2,4]triazin-2-amine [1893];

5-(3-(2,2-difluoroethyl)-2-methyl-3H-imidazo[4,5-b]pyridin-5-yl)-N-(cis-4-((3-fluoroazetidin-1-yl)methyl)cyclohexyl)pyrrolo[2,1-f][1,2,4]triazin-2-amine [1894];

trans-4-((5-(3-(2,2-difluoroethyl)-2-methyl-3H-imidazo[4,5-b]pyridin-5-yl)pyrrolo[2,1-f][1,2,4]triazin-2-yl)amino)-N,N-dimethylcyclohexane-1-carboxamide [1895];

azetidin-1-yl(cis-4-((5-(3-(2,2-difluoroethyl)-2-methyl-3H-imidazo[4,5-b]pyridin-5-yl)pyrrolo[2,1-f][1,2,4]triazin-2-yl)amino)cyclohexyl)methanone [1896];

(cis-4-((5-(3-(2,2-difluoroethyl)-2-methyl-3H-imidazo[4,5-b]pyridin-5-yl)pyrrolo[2,1-f][1,2,4]triazin-2-yl)amino)cyclohexyl)(pyrrolidin-1-yl)methanone [1897];

N-(cis-4-((5-(3-(2,2-difluoroethyl)-2-methyl-3H-imidazo[4,5-b]pyridin-5-yl)pyrrolo[2,1-f][1,2,4]triazin-2-yl)amino)cyclohexyl)acetamide [1898];

1-(7-((5-(3-(2,2-difluoroethyl)-2-methyl-3H-imidazo[4,5-b]pyridin-5-yl)pyrrolo[2,1-f][1,2,4]triazin-2-yl)amino)-2-azaspiro[3.5]nonan-2-yl)ethan-1-one [1899];

5-(3-(2,2-difluoroethyl)-2-methyl-3H-imidazo[4,5-b]pyridin-5-yl)-N-((3R,4S)-4-fluoro-1-methylpyrrolidin-3-yl)pyrrolo[2,1-f][1,2,4]triazin-2-amine [1900];

5-(3-(2,2-difluoroethyl)-2-methyl-3H-imidazo[4,5-b]pyridin-5-yl)-N-((3S,4S)-4-fluoro-1-methylpyrrolidin-3-yl)pyrrolo[2,1-f][1,2,4]triazin-2-amine [1901];

5-(3-(2,2-difluoroethyl)-2-methyl-3H-imidazo[4,5-b]pyridin-5-yl)-N-((3R,4R)-4-fluoro-1-methylpyrrolidin-3-yl)pyrrolo[2,1-f][1,2,4]triazin-2-amine [1902];

5-(3-(2,2-difluoroethyl)-2-methyl-3H-imidazo[4,5-b]pyridin-5-yl)-N-((3S,4R)-4-fluoro-1-methylpyrrolidin-3-yl)pyrrolo[2,1-f][1,2,4]triazin-2-amine [1903];

(S)-1-(3-((5-(3-(2,2-difluoroethyl)-2-methyl-3H-imidazo[4,5-b]pyridin-5-yl)pyrrolo[2,1-f][1,2,4]triazin-2-yl)amino)pyrrolidin-1-yl)ethan-1-one [1904];

(R)-1-(3-((5-(3-(2,2-difluoroethyl)-2-methyl-3H-imidazo[4,5-b]pyridin-5-yl)pyrrolo[2,1-f][1,2,4]triazin-2-yl)amino)pyrrolidin-1-yl)ethan-1-one [1905];

(3S,4R)-4-((5-(3-(2,2-difluoroethyl)-2-methyl-3H-imidazo[4,5-b]pyridin-5-yl)pyrrolo[2,1-f][1,2,4]triazin-2-yl)amino)tetrahydrofuran-3-ol [1906];

(3R,4S)-4-((5-(3-(2,2-difluoroethyl)-2-methyl-3H-imidazo[4,5-b]pyridin-5-yl)pyrrolo[2,1-f][1,2,4]triazin-2-yl)amino)tetrahydrofuran-3-ol [1907];

5-(3-(2,2-difluoroethyl)-2-methyl-3H-imidazo[4,5-b]pyridin-5-yl)-N-((3S,4R)-3-fluoro-1-isobutylpiperidin-4-yl)pyrrolo[2,1-f][1,2,4]triazin-2-amine [1908];

5-(3-(2,2-difluoroethyl)-2-methyl-3H-imidazo[4,5-b]pyridin-5-yl)-N-((3R,4S)-3-fluoro-1-isobutylpiperidin-4-yl)pyrrolo[2,1-f][1,2,4]triazin-2-amine [1909];

1-(4-((5-(1-(2,2-difluoroethyl)-2-methyl-1H-imidazo[4,5-b]pyridin-6-yl)pyrrolo[2,1-f][1,2,4]triazin-2-yl)amino)piperidin-1-yl)ethan-1-one [1910];

(S)-4-((5-(3-(2,2-difluoroethyl)-2-methyl-3H-imidazo[4,5-b]pyridin-5-yl)pyrrolo[2,1-f][1,2,4]triazin-2-yl)amino)-1-methylpiperidin-2-one [1911];

5-(3-(2,2-difluoroethyl)-2-methyl-3H-imidazo[4,5-b]pyridin-5-yl)-N-((3S,4R)-3-fluorotetrahydro-2H-pyran-4-yl)pyrrolo[2,1-f][1,2,4]triazin-2-amine [1912];

N-((1R,5S,6r)-3-Oxabicyclo[3.1.0]hexan-6-yl)-5-(3-(2,2-difluoroethyl)-2-methyl-3H-imidazo[4,5-b]pyridin-5-yl)pyrrolo[2,1-f][1,2,4]triazin-2-amine [1913];

N-((1R,5S,6s)-3-Oxabicyclo[3.1.0]hexan-6-yl)-5-(3-(2,2-difluoroethyl)-2-methyl-3H-imidazo[4,5-b]pyridin-5-yl)pyrrolo[2,1-f][1,2,4]triazin-2-amine [1914];

(R)—N-(4,4-difluorocyclohexyl)-5-(1-((5-(1-fluoroethyl)-1,3,4-oxadiazol-2-yl)methyl)-2-methyl-1H-imidazo[4,5-b]pyridin-6-yl)pyrrolo[2,1-f][1,2,4]triazin-2-amine [1915];

5-(3-(2,2-difluoroethyl)-2-methyl-3H-imidazo[4,5-b]pyridin-5-yl)-N-(piperidin-4-yl)pyrrolo[2,1-f][1,2,4]triazin-2-amine [1916];

(S)-(2,2-difluorocyclopropyl)(4-((5-(3-(2,2-difluoroethyl)-2-methyl-3H-imidazo[4,5-b]pyridin-5-yl)pyrrolo[2,1-f][1,2,4]triazin-2-yl)amino)piperidin-1-yl)methanone [1917];

(R)-(2,2-difluorocyclopropyl)(4-((5-(3-(2,2-difluoroethyl)-2-methyl-3H-imidazo[4,5-b]pyridin-5-yl)pyrrolo[2,1-f][1,2,4]triazin-2-yl)amino)piperidin-1-yl)methanone [1918];

N-((1s,3s)-3-((5-(1-(2,2-difluoroethyl)-2-methyl-1H-benzo[d]imidazol-6-yl)pyrrolo[2,1-f][1,2,4]triazin-2-yl)amino)-1-methylcyclobutyl)acetamide [1919];

N-((1r,3r)-3-((5-(1-(2,2-difluoroethyl)-2-methyl-1H-benzo[d]imidazol-6-yl)pyrrolo[2,1-f][1,2,4]triazin-2-yl)amino)-1-methylcyclobutyl)acetamide [1920];

(1r,3r)-3-((5-(1-(2,2-difluoroethyl)-2-methyl-1H-benzo[d]imidazol-6-yl)pyrrolo[2,1-f][1,2,4]triazin-2-yl)amino)-N,N,1-trimethylcyclobutane-1-carboxamide [1921];

(1s,3s)-3-((5-(1-(2,2-difluoroethyl)-2-methyl-1H-benzo[d]imidazol-6-yl)pyrrolo[2,1-f][1,2,4]triazin-2-yl)amino)-N,N,1-trimethylcyclobutane-1-carboxamide [1922];

((1s,3s)-3-((5-(1-(2,2-difluoroethyl)-2-methyl-1H-imidazo[4,5-b]pyridin-6-yl)pyrrolo[2,1-f][1,2,4]triazin-2-yl)amino)-1-methylcyclobutyl)(pyrrolidin-1-yl)methanone [1923];

((1r,3r)-3-((5-(1-(2,2-difluoroethyl)-2-methyl-1H-imidazo[4,5-b]pyridin-6-yl)pyrrolo[2,1-f][1,2,4]triazin-2-yl)amino)-1-methylcyclobutyl)(pyrrolidin-1-yl)methanone [1924];

1-(2-((5-(1-(2,2-difluoroethyl)-2-methyl-1H-imidazo[4,5-b]pyridin-6-yl)pyrrolo[2,1-f][1,2,4] triazin-2-yl)amino)-7-azaspiro[3.5]nonan-7-yl)ethan-1-one [1925];

1-((3aR,5s,6aS)-5-((5-(1-(2,2-difluoroethyl)-2-methyl-1H-imidazo[4,5-b]pyridin-6-yl)pyrrolo [2,1-f][1,2,4]triazin-2-yl)amino)hexahydrocyclopenta[c]pyrrol-2(1H)-yl)ethan-1-one [1926];

1-((3aR,5r,6aS)-5-((5-(1-(2,2-difluoroethyl)-2-methyl-1H-imidazo[4,5-b]pyridin-6-yl)pyrrolo [2,1-f][1,2,4]triazin-2-yl)amino)hexahydrocyclopenta[c]pyrrol-2(1H)-yl)ethan-1-one [1927];

1-(7-((5-(1-(2,2-difluoroethyl)-2-methyl-1H-imidazo[4,5-b]pyridin-6-yl)pyrrolo[2,1-f][1,2,4] triazin-2-yl)amino)-2-azaspiro[3.5]nonan-2-yl)ethan-1-one [1928];

5-(1-(2,2-difluoroethyl)-2-methyl-1H-imidazo[4,5-b]pyridin-6-yl)-N-(2-oxaspiro[3.5]nonan-7-yl)pyrrolo[2,1-f][1,2,4]triazin-2-amine [1929];

N-((1s,3s)-3-((5-(3-(2,2-difluoroethyl)-2-methyl-3H-imidazo[4,5-b]pyridin-5-yl)pyrrolo[2,1-f][1,2,4]triazin-2-yl)amino)-1-methylcyclobutyl)acetamide [1930];

N-((1r,3r)-3-((5-(3-(2,2-difluoroethyl)-2-methyl-3H-imidazo[4,5-b]pyridin-5-yl)pyrrolo[2,1-f][1,2,4]triazin-2-yl)amino)-1-methylcyclobutyl)acetamide [1931];

N-((1s,3s)-3-((5-(3-(2,2-difluoroethyl)-2-methyl-3H-imidazo[4,5-b]pyridin-5-yl)pyrrolo[2,1-f][1,2,4]triazin-2-yl)amino)-1-methylcyclobutyl)propionamide [1932];

N-((1r,3r)-3-((5-(3-(2,2-difluoroethyl)-2-methyl-3H-imidazo[4,5-b]pyridin-5-yl)pyrrolo[2,1-f][1,2,4]triazin-2-yl)amino)-1-methylcyclobutyl)propionamide [1933];

(1s,3s)-3-((5-(3-(2,2-difluoroethyl)-2-methyl-3H-imidazo[4,5-b]pyridin-5-yl)pyrrolo[2,1-f][1,2,4]triazin-2-yl)amino)-N,N,1-trimethylcyclobutane-1-carboxamide [1934];

(1r,3r)-3-((5-(3-(2,2-difluoroethyl)-2-methyl-3H-imidazo[4,5-b]pyridin-5-yl)pyrrolo[2,1-f][1,2,4]triazin-2-yl)amino)-N,N,1-trimethylcyclobutane-1-carboxamide [1935];

((1s,3s)-3-((5-(3-(2,2-difluoroethyl)-2-methyl-3H-imidazo[4,5-b]pyridin-5-yl)pyrrolo[2,1-f][1,2,4]triazin-2-yl)amino)-1-methylcyclobutyl)(pyrrolidin-1-yl)methanone [1936];

((1r,3r)-3-((5-(3-(2,2-difluoroethyl)-2-methyl-3H-imidazo[4,5-b]pyridin-5-yl)pyrrolo[2,1-f][1,2,4]triazin-2-yl)amino)-1-methylcyclobutyl)(pyrrolidin-1-yl)methanone [1937];

1-((1s,3s)-3-((5-(3-(2,2-difluoroethyl)-2-methyl-3H-imidazo[4,5-b]pyridin-5-yl)pyrrolo[2,1-f][1,2,4]triazin-2-yl)amino)-1-methylcyclobutyl)pyrrolidin-2-one [1938];

1-((1r,3r)-3-((5-(3-(2,2-difluoroethyl)-2-methyl-3H-imidazo[4,5-b]pyridin-5-yl)pyrrolo[2,1-f][1,2,4]triazin-2-yl)amino)-1-methylcyclobutyl)pyrrolidin-2-one [1939];

1-((3S,4R)-3-((5-(3-(2,2-difluoroethyl)-2-methyl-3H-imidazo[4,5-b]pyridin-5-yl)pyrrolo[2,1-f][1,2,4]triazin-2-yl)amino)-4-fluoropyrrolidin-1-yl)ethan-1-one [1940];

1-((3R,4S)-3-((5-(3-(2,2-difluoroethyl)-2-methyl-3H-imidazo[4,5-b]pyridin-5-yl)pyrrolo[2,1-f][1,2,4]triazin-2-yl)amino)-4-fluoropyrrolidin-1-yl)ethan-1-one [1941];

1-((3R,4R)-3-((5-(3-(2,2-difluoroethyl)-2-methyl-3H-imidazo[4,5-b]pyridin-5-yl)pyrrolo[2,1-f][1,2,4]triazin-2-yl)amino)-4-fluoropyrrolidin-1-yl)ethan-1-one [1942];

1-((3S,4S)-3-((5-(3-(2,2-difluoroethyl)-2-methyl-3H-imidazo[4,5-b]pyridin-5-yl)pyrrolo[2,1-f][1,2,4]triazin-2-yl)amino)-4-fluoropyrrolidin-1-yl)ethan-1-one [1943];

5-(3-(2,2-difluoroethyl)-2-methyl-3H-imidazo[4,5-b]pyridin-5-yl)-N-((3S,4R)-4-fluoro-1-(oxetan-3-yl)pyrrolidin-3-yl)pyrrolo[2,1-f][1,2,4]triazin-2-amine [1944];

5-(3-(2,2-difluoroethyl)-2-methyl-3H-imidazo[4,5-b]pyridin-5-yl)-N-((3R,4S)-4-fluoro-1-(oxetan-3-yl)pyrrolidin-3-yl)pyrrolo[2,1-f][1,2,4]triazin-2-amine [1945];

5-(3-(2,2-difluoroethyl)-2-methyl-3H-imidazo[4,5-b]pyridin-5-yl)-N-((3R,4R)-4-fluoro-1-(oxetan-3-yl)pyrrolidin-3-yl)pyrrolo[2,1-f][1,2,4]triazin-2-amine [1946];

5-(3-(2,2-difluoroethyl)-2-methyl-3H-imidazo[4,5-b]pyridin-5-yl)-N-((3S,4S)-4-fluoro-1-(oxetan-3-yl)pyrrolidin-3-yl)pyrrolo[2,1-f][1,2,4]triazin-2-amine [1947];

N-((1s,4s)-4-((5-(3-(2,2-difluoroethyl)-2-methyl-3H-imidazo[4,5-b]pyridin-5-yl)pyrrolo[2,1-f][1,2,4]triazin-2-yl)amino)-1-methylcyclohexyl)acetamide [1948];

N-((1r,4r)-4-((5-(3-(2,2-difluoroethyl)-2-methyl-3H-imidazo[4,5-b]pyridin-5-yl)pyrrolo[2,1-f][1,2,4]triazin-2-yl)amino)-1-methylcyclohexyl)acetamide [1949];

(3,3-difluoroazetidin-1-yl)((1s,4s)-4-((5-(3-(2,2-difluoroethyl)-2-methyl-3H-imidazo[4,5-b]pyridin-5-yl)pyrrolo[2,1-f][1,2,4]triazin-2-yl)amino)cyclohexyl)methanone [1950];

1-((3S,4R)-4-((5-(3-(2,2-difluoroethyl)-2-methyl-3H-imidazo[4,5-b]pyridin-5-yl)pyrrolo[2,1-f][1,2,4]triazin-2-yl)amino)-3-fluoropiperidin-1-yl)ethan-1-one [1951];

1-((3R,4S)-4-((5-(3-(2,2-difluoroethyl)-2-methyl-3H-imidazo[4,5-b]pyridin-5-yl)pyrrolo[2,1-f][1,2,4]triazin-2-yl)amino)-3-fluoropiperidin-1-yl)ethan-1-one [1952];

(4,4-difluorocyclohexyl)(4-((5-(3-(2,2-difluoroethyl)-2-methyl-3H-imidazo[4,5-b]pyridin-5-yl)pyrrolo[2,1-f][1,2,4]triazin-2-yl)amino)piperidin-1-yl)methanone [1953];

5-(3-(2,2-difluoroethyl)-2-methyl-3H-imidazo[4,5-b]pyridin-5-yl)-N-((3S,4R)-3-fluoro-1-(oxetan-3-yl)piperidin-4-yl)pyrrolo[2,1-f][1,2,4]triazin-2-amine [1954];

5-(3-(2,2-difluoroethyl)-2-methyl-3H-imidazo[4,5-b]pyridin-5-yl)-N-((3R,4S)-3-fluoro-1-(oxetan-3-yl)piperidin-4-yl)pyrrolo[2,1-f][1,2,4]triazin-2-amine [1955];

5-(3-(2,2-difluoroethyl)-2-methyl-3H-imidazo[4,5-b]pyridin-5-yl)-N-((3R,4R)-3-fluoro-1-(oxetan-3-yl)piperidin-4-yl)pyrrolo[2,1-f][1,2,4]triazin-2-amine [1956];

5-(3-(2,2-difluoroethyl)-2-methyl-3H-imidazo[4,5-b]pyridin-5-yl)-N-((3S,4S)-3-fluoro-1-(oxetan-3-yl)piperidin-4-yl)pyrrolo[2,1-f][1,2,4]triazin-2-amine [1957];

1-(2-((5-(3-(2,2-difluoroethyl)-2-methyl-3H-imidazo[4,5-b]pyridin-5-yl)pyrrolo[2,1-f][1,2,4] triazin-2-yl)amino)-7-azaspiro[3.5]nonan-7-yl)ethan-1-one [1958];

1-((3aR,5s,6aS)-5-((5-(3-(2,2-difluoroethyl)-2-methyl-3H-imidazo[4,5-b]pyridin-5-yl)pyrrolo [2,1-f][1,2,4]triazin-2-yl)amino)hexahydrocyclopenta[c]pyrrol-2(1H)-yl)ethan-1-one [1959];

1-((3aR,5r,6aS)-5-((5-(3-(2,2-difluoroethyl)-2-methyl-3H-imidazo[4,5-b]pyridin-5-yl)pyrrolo [2,1-f][1,2,4]triazin-2-yl)amino)hexahydrocyclopenta[c]pyrrol-2(1H)-yl)ethan-1-one [1960];

5-(3-(2,2-difluoroethyl)-2-methyl-3H-imidazo[4,5-b]pyridin-5-yl)-N-(2-oxaspiro[3.5]nonan-7-yl)pyrrolo[2,1-f][1,2,4]triazin-2-amine [1961];

N-((1s,3s)-3-((5-(1-(2,2-difluoroethyl)-2-methyl-1H-imidazo[4,5-b]pyrazin-6-yl)pyrrolo[2,1-f][1,2,4]triazin-2-yl)amino)-1-methylcyclobutyl)acetamide [1962];

N-((1r,3r)-3-((5-(1-(2,2-difluoroethyl)-2-methyl-1H-imidazo[4,5-b]pyrazin-6-yl)pyrrolo[2,1-f][1,2,4]triazin-2-yl)amino)-1-methylcyclobutyl)acetamide [1963];

(1s,3s)-3-((5-(1-(2,2-difluoroethyl)-2-methyl-1H-imidazo[4,5-b]pyrazin-6-yl)pyrrolo[2,1-f][1,2,4]triazin-2-yl)amino)-N,N,1-trimethylcyclobutane-1-carboxamide [1964];

(1r,3r)-3-((5-(1-(2,2-difluoroethyl)-2-methyl-1H-imidazo[4,5-b]pyrazin-6-yl)pyrrolo[2,1-f][1,2,4]triazin-2-yl)amino)-N,N,1-trimethylcyclobutane-1-carboxamide [1965];

((1s,3s)-3-((5-(1-(2,2-difluoroethyl)-2-methyl-1H-imidazo[4,5-b]pyrazin-6-yl)pyrrolo[2,1-f][1,2,4]triazin-2-yl)amino)-1-methylcyclobutyl)(pyrrolidin-1-yl)methanone [1966];

((1r,3r)-3-((5-(1-(2,2-difluoroethyl)-2-methyl-1H-imidazo[4,5-b]pyrazin-6-yl)pyrrolo[2,1-f][1,2,4]triazin-2-yl)amino)-1-methylcyclobutyl)(pyrrolidin-1-yl)methanone [1967];

1-((1s,3s)-3-((5-(1-(2,2-difluoroethyl)-2-methyl-1H-imidazo[4,5-b]pyrazin-6-yl)pyrrolo[2,1-f][1,2,4]triazin-2-yl)amino)-1-methylcyclobutyl)pyrrolidin-2-one [1968];

1-((1r,3r)-3-((5-(1-(2,2-difluoroethyl)-2-methyl-1H-imidazo[4,5-b]pyrazin-6-yl)pyrrolo[2,1-f][1,2,4]triazin-2-yl)amino)-1-methylcyclobutyl)pyrrolidin-2-one [1969];

5-(1-(2,2-difluoroethyl)-2-methyl-1H-imidazo[4,5-b]pyrazin-6-yl)-N-(cis-4-(trifluoromethoxy) cyclohexyl)pyrrolo[2,1-f][1,2,4]triazin-2-amine [1970];

5-(1-(2,2-difluoroethyl)-2-methyl-1H-imidazo[4,5-b]pyrazin-5-yl)-N-(cis-4-(trifluoromethoxy) cyclohexyl)pyrrolo[2,1-f][1,2,4]triazin-2-amine [1971];

N-((1s,4s)-4-((5-(1-(2,2-difluoroethyl)-2-methyl-1H-imidazo[4,5-b]pyrazin-6-yl)pyrrolo[2,1-f][1,2,4]triazin-2-yl)amino)-1-methylcyclohexyl)acetamide [1972];

N-((1r,4r)-4-((5-(1-(2,2-difluoroethyl)-2-methyl-1H-imidazo[4,5-b]pyrazin-6-yl)pyrrolo[2,1-f][1,2,4]triazin-2-yl)amino)-1-methylcyclohexyl)acetamide [1973];

(1s,4s)-4-((5-(1-(2,2-difluoroethyl)-2-methyl-1H-imidazo[4,5-b]pyrazin-6-yl)pyrrolo[2,1-f][1,2,4]triazin-2-yl)amino)-1-methylcyclohexan-1-ol [1974];

1-(2-((5-(1-(2,2-difluoroethyl)-2-methyl-1H-imidazo[4,5-b]pyrazin-6-yl)pyrrolo[2,1-f][1,2,4]triazin-2-yl)amino)-7-azaspiro[3.5]nonan-7-yl)ethan-1-one [1975];

1-((3aR,5s,6aS)-5-((5-(1-(2,2-difluoroethyl)-2-methyl-1H-imidazo[4,5-b]pyrazin-6-yl)pyrrolo [2,1-f][1,2,4]triazin-2-yl)amino)hexahydrocyclopenta[c]pyrrol-2(1H)-yl)ethan-1-one [1976];

1-((3aR,5r,6aS)-5-((5-(1-(2,2-difluoroethyl)-2-methyl-1H-imidazo[4,5-b]pyrazin-6-yl)pyrrolo [2,1-f][1,2,4]triazin-2-yl)amino)hexahydrocyclopenta[c]pyrrol-2(1H)-yl)ethan-1-one [1977];

1-(7-((5-(1-(2,2-difluoroethyl)-2-methyl-1H-imidazo[4,5-b]pyrazin-6-yl)pyrrolo[2,1-f][1,2,4] triazin-2-yl)amino)-2-azaspiro[3.5]nonan-2-yl)ethan-1-one [1978];

5-(1-(2,2-difluoroethyl)-2-methyl-1H-imidazo[4,5-b]pyrazin-6-yl)-N-(2-oxaspiro[3.5]nonan-7-yl)pyrrolo[2,1-f][1,2,4]triazin-2-amine [1979];

N-((1r,3r)-1-methyl-3-((5-(quinolin-6-yl)pyrrolo[2,1-f][1,2,4]triazin-2-yl)amino)cyclobutyl) acetamide [1980];

N-((1r,3r)-1-methyl-3-((5-(quinoxalin-6-yl)pyrrolo[2,1-f][1,2,4]triazin-2-yl)amino)cyclobutyl) acetamide [1981];

N-(cis-3-((5-(1-(2,2-difluoroethyl)-2-methyl-1H-benzo[d]imidazol-6-yl)pyrrolo[2,1-f][1,2,4] triazin-2-yl)amino)-1-methylcyclobutyl)acetamide [1982];

N-(trans-1-methyl-3-((5-(pyrazolo[1,5-a]pyridin-5-yl)pyrrolo[2,1-f][1,2,4]triazin-2-yl)amino) cyclobutyl)acetamide [1983];

N-(cis-1-methyl-3-((5-(quinolin-6-yl)pyrrolo[2,1-f][1,2,4]triazin-2-yl)amino)cyclobutyl) acetamide [1984];

2-methoxy-N-(trans-1-methyl-3-((5-(quinoxalin-6-yl)pyrrolo[2,1-f][1,2,4]triazin-2-yl)amino) cyclobutyl)acetamide [1985]; or a pharmaceutically acceptable salt thereof.

12. A pharmaceutical composition comprising a therapeutically effective amount of a compound of claim 1, or a pharmaceutically acceptable salt thereof, and a pharmaceutically acceptable excipient.

* * * * *